United States Patent
Senger et al.

(10) Patent No.: US 11,613,761 B1
(45) Date of Patent: Mar. 28, 2023

(54) MATERIALS AND METHODS FOR PUFA PRODUCTION, AND PUFA-CONTAINING COMPOSITIONS

(71) Applicants: BASF PLANT SCIENCE COMPANY GMBH, Ludwigshafen (DE); BIORIGINAL FOOD & SCIENCE CORPORATION, Saskatoon (CA)

(72) Inventors: Toralf Senger, Durham, NC (US); Laurent Marty, Heidelberg (DE); Irene Kunze, Gatersleben (DE); Heiko Haertel, Berlin (DE); Steven Craig Bremmer, Apex, NC (US); Steven D. Breazeale, Apex, NC (US); Joerg Bauer, Durham, NC (US); Patricia Vrinten, Saskatoon (CA); Sten Stymne, Landskrona (SE); Jenny Lindberg Yilmaz, Bfarred (SE); John A. McElver, Roxboro, NC (US); Dietrich Rein, Berlin (DE); Carl Andre, Raleigh, NC (US)

(73) Assignees: Bioriginal Food & Science Corporation, Saskatoon (CA); BASF Plant Science Company GmbH, Ludwigshafen (DE)

( * ) Notice: Subject to any disclaimer, the term of this patent is extended or adjusted under 35 U.S.C. 154(b) by 106 days.

(21) Appl. No.: 15/526,550

(22) PCT Filed: Nov. 13, 2015

(86) PCT No.: PCT/EP2015/076631
§ 371 (c)(1),
(2) Date: May 12, 2017

(87) PCT Pub. No.: WO2016/075326
PCT Pub. Date: May 19, 2016

Related U.S. Application Data

(60) Provisional application No. 62/079,622, filed on Nov. 14, 2014, provisional application No. 62/234,373, filed on Sep. 29, 2015.

(51) Int. Cl.
*C12N 15/82* (2006.01)
*C12N 9/02* (2006.01)

(52) U.S. Cl.
CPC ........ *C12N 15/8247* (2013.01); *C12N 9/0071* (2013.01); *C12Y 114/19* (2013.01)

(58) Field of Classification Search
None
See application file for complete search history.

(56) References Cited

U.S. PATENT DOCUMENTS

| | | | |
|---|---|---|---|
| 5,827,289 A | 10/1998 | Reiley et al. | |
| 6,303,849 B1 | 10/2001 | Potts et al. | |
| 6,462,258 B1 | 10/2002 | Fincher et al. | |
| 6,689,880 B2 | 2/2004 | Chen et al. | |
| 6,733,974 B1 | 5/2004 | Feazel | |
| 6,740,488 B2 | 5/2004 | Rangwala et al. | |
| 6,818,807 B2 | 11/2004 | Trolinder et al. | |
| 6,825,400 B2 | 11/2004 | Behr et al. | |
| 6,893,826 B1 | 5/2005 | Hillyard et al. | |
| 6,900,014 B1 | 5/2005 | Weston et al. | |
| 7,371,930 B1 | 5/2008 | Knerr | |
| 7,423,198 B2 | 9/2008 | Yao et al. | |
| 8,999,411 B2 | 4/2015 | Froman et al. | |
| 10,035,989 B2 | 7/2018 | Cirpus et al. | |
| 10,760,089 B2 | 9/2020 | Andre | |
| 10,829,775 B2 | 11/2020 | Andre | |
| 11,033,593 B2 | 6/2021 | Senger et al. | |
| 2006/0051847 A1* | 3/2006 | Gunnarsson | A61K 8/361 435/134 |
| 2013/0288377 A1 | 10/2013 | Champagne et al. | |
| 2014/0220215 A1 | 8/2014 | Iassonova et al. | |
| 2015/0299676 A1 | 10/2015 | Walsh et al. | |
| 2016/0369290 A1 | 12/2016 | Cirpus et al. | |

FOREIGN PATENT DOCUMENTS

| | | |
|---|---|---|
| AU | 2011289381 A1 | 1/2013 |
| CN | 101400798 A | 4/2009 |
| JP | 2007527716 A | 10/2007 |
| WO | WO-93/10241 A1 | 5/1993 |
| WO | WO-94/13814 A1 | 6/1994 |
| WO | WO-95/27791 A1 | 10/1995 |
| WO | WO-96/24674 A1 | 8/1996 |

(Continued)

OTHER PUBLICATIONS

Abedi et al (Long-chain polyunsaturated fatty acid sources and evaluation of their nutritional and functional properties. Food Science & Nutrition. 2(5): 443-463, 2014) (Year: 2014).*

Dubois et al (Fatty acid profiles of 80 vegetable oils with regard to their nutritional potential. Eur. J. Lipid Sci. Technol. 109:710-732, 2007) (Year: 2007).*

Wu et al (Stepwise engineering to produce high yields of very long-chain polyunsaturated fatty acids in plants. Nature Biotech. 8: 1013-1017, 2005). (Year: 2006).*

Chen et al (MISSA Is a Highly Efficient in Vivo DNA Assembly Method for Plant Multiple-Gene Transformation. Plant Physiology, vol. 153, pp. 41-51, May 2010). (Year: 2010).*

Wu et al. (Stepwise engineering to produce high yields of very long-chain polyunsaturated fatty acids in plants. Nature Biotech. 8: 1013-1017, 2005) (Year: 2005).*

(Continued)

*Primary Examiner* — Charles Logsdon
*Assistant Examiner* — Wayne Zhong
(74) *Attorney, Agent, or Firm* — Marshall, Gerstein & Borun LLP

(57) ABSTRACT

T-DNA for expression of a target gene in a plant, wherein the T-DNA comprises a left and a right border element and at least one expression cassette comprising a promoter, operatively linked thereto a target gene, and downstream thereof a terminator, wherein the length of the T-DNA, measured from left to right border element and comprising the target gene, has a length of at least 30000 bp.

12 Claims, 93 Drawing Sheets

Specification includes a Sequence Listing.

(56) References Cited

FOREIGN PATENT DOCUMENTS

| | | | |
|---|---|---|---|
| WO | WO-98/55631 A1 | 12/1998 | |
| WO | WO-98/55632 A1 | 12/1998 | |
| WO | WO-99/64616 A2 | 12/1999 | |
| WO | WO-00/18889 A2 | 4/2000 | |
| WO | WO-01/059128 A2 | 8/2001 | |
| WO | WO-02/26946 A2 | 4/2002 | |
| WO | WO-2002/052024 A2 | 7/2002 | |
| WO | WO-02/102970 A2 | 12/2002 | |
| WO | WO-2003/078639 A2 | 9/2003 | |
| WO | WO-2003/089452 A2 | 10/2003 | |
| WO | WO-2003/093482 A2 | 11/2003 | |
| WO | WO-2004/071467 A2 | 8/2004 | |
| WO | WO-2004/087902 A2 | 10/2004 | |
| WO | WO-2004/090123 A2 | 10/2004 | |
| WO | WO-2005/007845 A2 | 1/2005 | |
| WO | WO-2005/012316 A2 | 2/2005 | |
| WO | WO-2005/083053 A2 | 9/2005 | |
| WO | WO-2005/083093 A2 | 9/2005 | |
| WO | WO-2005118814 A2 * | 12/2005 | C11B 1/00 |
| WO | WO-2006/008099 A2 | 1/2006 | |
| WO | WO-2006/012325 A1 | 2/2006 | |
| WO | WO-2006/024509 A2 | 3/2006 | |
| WO | WO-2006/069710 A1 | 7/2006 | |
| WO | WO-2006/100241 A2 | 9/2006 | |
| WO | WO-2007/096387 A1 | 8/2007 | |
| WO | WO-2008/022963 A2 | 2/2008 | |
| WO | WO-2008022963 A2 * | 2/2008 | A61K 31/202 |
| WO | WO-2009/111263 A1 | 9/2009 | |
| WO | WO-2009130291 A2 * | 10/2009 | A61P 3/02 |
| WO | WO-2010/023202 A2 | 3/2010 | |
| WO | WO-201 0/066703 A2 | 6/2010 | |
| WO | WO-2011/006948 A1 | 1/2011 | |
| WO | WO-2011006948 A1 * | 1/2011 | C12N 9/1029 |
| WO | WO-2011/161093 A1 | 12/2011 | |
| WO | WO-2013/049227 A2 | 4/2013 | |
| WO | WO-2013/153404 A1 | 10/2013 | |
| WO | WO-2013153404 A1 * | 10/2013 | A61K 31/202 |
| WO | WO-2013/185184 A2 | 12/2013 | |
| WO | WO-2015/089587 A1 | 6/2015 | |

OTHER PUBLICATIONS

Chen et al (MISSA Is a Highly Efficient in Vivo DNA Assembly Method for Plant Multiple-Gene Transformation. Plant Physiology, vol. 153, pp. 41-51, 2010). (Year: 2010).*
Hamilton et al (Metabolic engineering of Phaeodactylum tricornutum for the enhanced accumulation of omega-3 long chain polyunsaturated fatty acids. Metabolic Engineering 22: 3-9, published online Dec. 2013) (Year: 2013).*
Abidi et al., "Effect of Genetic Modification on the Distribution of Minor Constituents in Canola Oil", Journal of the American Oil Chemists' Society, vol. 76, Issue 4, pp. 463-467 (Apr. 1999).
Akermoun et al., Complex lipid biosynthesis: phospholipid synthesis, Biochemical Society Transactions 28: 713-5 (2000).
Arondel, et al., "Map-based Cloning of a Gene Controlling Omega-3 Fatty Acid Desaturation in Arabidopsisc", Science vol. 258, Issue 5086, Nov. 20, 1992, pp. 1353-1355.
Bafor et al., Ricinoleic acid biosynthesis and triacylglycerol assembly in microsomal preparations from developing castor-bean (*Ricinus communis*) endosperm, Biochem. J., 280(Pt.2):507-14 (Dec. 1991).
Bai, et al., "X-ray Structure of a Mammalian Stearoyl-CoA Desaturase", Nature, Aug. 2015, vol. 524, pp. 252-256.
Banas et al., Biosynthesis of an Acetylenic Fatty Acid in Microsomal Preparations from Developing Seeds of *Crepis alpina*. In: *Physiology, Biochemistry and Molecular Biology of Plant Lipids* (Williams et al. eds.) pp. 57-59. Kluwer Academic Press, Dordrecht (1997).
Bates et al., Acyl Editing and Headgroup Exchange Are the Major Mechanisms That Direct Polyunsaturated Fatty Acid Flux into Triacylglycerols. Plant Physiology 160: 1530-1539 (2012).
Bernert et al., Analysis of Partial Reactions in the Overall Chain Elongation of Saturated and Unsaturated Fatty Acids by Rat Liver Microsomes. J. Biol. Chem. 252, 6736-6744 (1977).

Bligh, et al., "A Rapid Method of Total Lipid Extraction and Purification", Canadian Journal of Biochemistry and Physiology, vol. 37, Issue 1, 1959, pp. 911-917.
Blombach et al., Acetohydroxyacid synthase, a novel target for improvement of L-lysine production by Corynebacterium glutamicum, Appl. Environ. Microbiol., 75(2):419-27 (Jan. 2009).
Broadwater et al., Desaturation and hydroxylation. Residues 148 and 324 of *Arabidopsis* FAD2, in addition to substrate chain length, exert a major influence in partitioning of catalytic specificity, J. Biol. Chem., 277(18):15613-20 (May 2002).
Broun et al., Catalytic plasticity of fatty acid modification enzymes underlying chemical diversity of plant lipids, Science, 282(5392):1315-7 (Nov. 1998).
Brown et al., Synthetic promoters for CHO cell engineering, Biotechnol. Bioeng., 111(8):1638-47 (Aug. 2014).
Browse et al., Fatty acid composition of leaf lipids determined after combined digestion and fatty acid methyl ester formation from fresh tissue, Anal. Biochem., 152(1):141-5 (1986).
Cahoon et al., Biosynthetic origin of conjugated double bonds: production of fatty acid components of high-value drying oils in transgenic soybean embryos, Proc. Natl. Acad. Sci. USA, 96(22):12935-40 (1999).
Calvo et al., Genetic connection between fatty acid metabolism and sporulation in Aspergillus nidulans, J. Biol. Chem., 276(28):25766-74 (Jul. 2001).
Certik et al., Desaturase-defective fungal mutants: useful tools for the regulation and overproduction of polyunsaturated fatty acids, Trends in Biotechnology, vol. 16, No. 12, Dec. 1, 1998, pp. 500-505.
Cutler, et al., "Abscisic Acid: Emergence of a Core Signaling Network", Annual Review of Plant Biology, vol. 61, 2010, pp. 651-679.
Database EMBL [Online] 5, "Rattus Norvegicus clone CH230-506F12, Working Draft Sequence, Unordered Pieces.", XP002754369, retrieved from EBI accession No. EM_HTG:AC142370 (Mar. 29, 2003).
Database EMBL [Online], "Mus Musculus Domesticus DNA, Bag Clone: B6Ng01-175K07, 3' End.", XP002754370, retrieved from EBI accession No. EM_GSS:GA003396, created Feb. 6, 2011).
Datar et al. Cell and Cell Debris Removal: Centrifugation and Crossflow Filtration, pp. 472-503 IN: Rehm et al. (eds.), Biotechnology, Second, Completely Revised Edition, vol. 3 (Bioprocessing) edited by Stephanopoulos, Weinheim, Germany: VCH (1993).
De Block, et al., "Transformation of *Brassica napus* and *Brassica oleracea* Using Agrobacterium Tumefaciens and the Expression of the Bar and Neo Genes in the Transgenic Plants", Plant Physiol., v.91(2):694-701 (1989).
Deal et al., Histone variants and modifications in plant gene regulation, Curr. Opin. Plant Biol., 14(2):116-22 (Apr. 2011).
Demeke et al., Influence of DNA extraction methods, PCR inhibitors and quantification methods on real-time PCR assay of biotechnology-derived traits, Anal. Bioanal. Chem., 396(6):1977-90 (Mar. 2010).
Denic et al., A molecular caliper mechanism for determining very long-chain fatty acid length, Cell, 130(4):663-77 (Aug. 2007).
Dolde et al., "Tocopherols in Breeding Lines and Effects of Planting Location, Fatty Acid Composition, and Temperature During Development", JAOCS, 76:349-55 (Mar. 1999).
Domergue et al., Acyl Carriers Used as Substrates by the Desaturases and Elongases Involved in Very Long-chain Polyunsaturated Fatty Acids Biosynthesis Reconstituted in Yeast, J. Biol. Chem., 278(37):35115-26 (2003).
Domergue et al., "In Vivo Characterization of the First Acyl-CoA Δ6-Desaturase from a Member of the Plant Kingdom, the Microalga Ostreococcus Tauri", Biochem. J., 389(Pt. 2):483-90 (2005).
Dubos et al., "Integrating Bioinformatic Resources to Predict Transcription Factors Interacting with Cis-Sequences Conserved in Co-Regulated Genes", BMC Genomics, 15:317 (2014).
Focks et al., "Wrinkled1: A Novel, Low-Seed-Oil Mutant of *Arabidopsis* with a Deficiency in the Seed-Specific Regulation of Carbohydrate Metabolism", Plant Physiol., 118(1):91-101 (1998).
Fraser et al., Partial purification and photoaffinity labelling of sunflower acyl-CoA:lysophosphatidylcholine acyltransferase, Biochem. Soc. Trans., 28(6):715-8 (Dec. 2000).

(56) References Cited

OTHER PUBLICATIONS

Fujiwara et al., Seed-specific repression of GUS activity in tobacco plants by antisense RNA, Plant Mol. Biol., 20(6):1059-69 (1992).
Fukuda, Characterization of matrix attachment sites in the upstream region of a tobacco chitinase gene, Plant Mol. Biol., 39(5):1051-62 (Mar. 1999).
Giusto et al., Lipid metabolism in vertebrate retinal rod outer segments, Prog. Lipid Res., 39(4):315-91 (Jul. 2000).
Griffiths, et al., Delta 6- and Delta 12-desaturase Activities and Phosphatidic Acid Formation in Microsomal Preparations from the Developing Cotyledons of Common Borage (*Borango officinalis*), Biochem. J., 252(3):641-7 (1988).
Hamilton, A binary-BAC system for plant transformation with high-molecular-weight DNA, Gene, 200(1-2):107-16 (Oct. 1997).
Hattori et al., Experimentally determined sequence requirement of ACGT-containing abscisic acid response element, Plant Cell Physiol., 43(1):136-40 (Jan. 2002).
He et al., Agrobacterium-Mediated Transformation of Large DNA Fragments Using a BIBAC Vector System in Rice, Plant Molecular Biology Reporter, vol. 28, No. 4, Mar. 2, 2010, pp. 613-619.
Higo et al., Plant cis-acting regulatory DNA elements (PLACE) database: 1999, Nucleic Acids Res., 27(1):297-300 (Jan. 1999).
Hinnebusch, The scanning mechanism of eukaryotic translation initiation, Annu. Rev. Biochem., 83:779-812 (2014).
Horrocks et al., Health benefits of Docosahexaenoic acid (DHA), Pharmacol. Res., 40(3):211-25 (Sep. 1999).
Hull et al., Analysis of the promoter of an abscisic acid responsive late embryogenesis abundant gene of *Arabidopsis thaliana*, Plant Sci., 14:181-92 (1996).
International Preliminary Report on Patentability, International Application No. PCT/EP2015/076596, dated May 16, 2017.
International Preliminary Report on Patentability, International Application No. PCT/EP2015/076630, dated May 16, 2017.
International Preliminary Report on Patentability, PCT Application No. PCT/EP2015/076608, completed Feb. 28, 2017.
International Preliminary Report on Patentability, PCT application No. PCT/EP2015/076605, dated May 16, 2017.
International Search Report and Written Opinion for PCT Patent Application No. PCT/EP2015/076596, dated Mar. 11, 2016, 15 pages.
International Search Report and Written Opinion for PCT Patent Application No. PCT/EP2015/076605, dated Feb. 24, 2016, 13 pages.
International Search Report and Written Opinion for PCT Patent Application No. PCT/EP2015/076608, dated Mar. 9, 2016, 13 pages.
International Search Report and Written Opinion, International Application No. PCT/EP2015/076630, dated Mar. 7, 2016.
Jain, et al., "Identification of a Novel Lysophospholipid Acyltransferase in *Saccharomyces cerevisiae*", J. Biol. Chem., 282(42):30562-9 (2007).
Kargiotidou, et al., "Low Temperature and Light Regulate Delta 12 Fatty Acid Desaturases (FAD2) at a Transcriptional Level in Cotton (*Gossypium hirsutum*)", J. Exp. Bot., 49(8):2043-56 (2008).
Keller et al., Crystal structure of a bZIP/DNA complex at 2.2 A: determinants of DNA specific recognition, J. Mol. Biol., 254(4):657-67 (Dec. 1995).
Kim et al., Transcription factors that directly regulate the expression of CSLA9 encoding mannan synthase in *Arabidopsis thaliana*, Plant Mol. Biol., 84(4-5):577-87 (Mar. 2014).
Knutzon, et al., "Identification of Delta5-dehydratase from Mortierella Alpina by Heterologous Expression in Bakers' Yeast and Canola", J. Biol. Chem., 273(45):29360-6 (1998).
Komori et al., Current status of binary vectors and superbinary vectors, Plant Physiol., 145(4):1155-60 (Dec. 2007).
Kong et al., Expression levels of domestic cDNA cassettes integrated in the nuclear genomes of various Chlamydomonas reinhardtii strains, J. Biosci. Bioeng., 117(5):613-6 (May 2014).
Kozak, Initiation of translation in prokaryotes and eukaryotes, Gene, 234(2):187-208 (Jul. 1999).

Li, et al., "Correlations between Tocopherol and Fatty Acid Components in Germplasm Collections of *Brassica* Oilseeds", Journal of Agricultural and Food Chemistry, 61:34-40 (2013).
Livak et al., Analysis of relative gene expression data using real-time quantitative PCR and the 2(-Delta Delta C(T)) Method, Methods, 25(4):402-8 (2001).
Lopez et al., Identification of novel motif patterns to decipher the promoter architecture of co-expressed genes in *Arabidopsis thaliana*, BMC Syst. Biol., 7 Suppl 3:S10 (Oct. 2013).
Lowenthal et al., Quantitative bottom-up proteomics depends on digestion conditions, Anal. Chem., 86(1):551-8 (Jan. 2014).
Machens et al., Identification of a novel type of WRKY transcription factor binding site in elicitor-responsive cis-sequences from *Arabidopsis thaliana*, Plant Mol. Biol., 84(4-5):371-85 (2014).
Makriyannis et al., Design and study of peptide-ligand affinity chromatography adsorbents: application to the case of trypsin purification from bovine pancreas, Biotechnol. Bioeng., 53(1):49-57 (Jan. 1997).
Mantle et al., Differentiation of Claviceps purpurea in axenic culture, J. Gen. Microbiol., 93(2):321-34 (Apr. 1976).
Meesapyodsuk, et al., "The Front-end Desaturase: Structure, Function, Evolution and Biotechnological Use", Lipids, vol. 47, Issue 3, Mar. 2012, pp. 227-237.
Meggendorfer et al., Functional nuclear topography of transcriptionally inducible extra-chromosomal transgene clusters, CHromosome Res., 18(4):401-17 (Jun. 2010).
Mendel, *Versuche über Pflanzenhybriden* Verhandlungen des naturforschenden Vereines in Brünn, Bd. IV für das Jahr, 1865 Abhandlungen:3-47 (1866).
Mey et al., The biotrophic, non-appressorium-forming grass pathogen Claviceps purpurea needs a Fus3/Pmk1 homologous mitogen-activated protein kinase for colonization of rye ovarian tissue, Mol. Plant Microbe Interact., 15(4):303-12 (Apr. 2002).
Muino et al., Structural determinants of DNA recognition by plant MADS-domain transcription factors, Nucleic Acids Res., 42(4):2138-46 (Feb. 2014).
Murashige et al., A Revised Medium for Rapid Growth and Bio Assays with Tobacco Tissue Cultures. Physiologia Plantarum 15, 3:473-497 (1962).
Nakagawa et al., Diversity of preferred nucleotide sequences around the translation initiation codon in eukaryote genomes, Nucleic Acids Res., 36(3):861-71 (Feb. 2008).
Nishikata et al., Database construction for PromoterCAD: synthetic promoter design for mammals and plants, ACS Synth. Biol., 3(3):192-6 (Mar. 2014).
O'Malley, et al., "An Adapter Ligation-Mediated Pcr Method for High-Throughput Mapping of T-DNA Inserts in the *Arabidopsis* Genome", Nature Protocols, vol. 2, Issue 11, 2007, pp. 2910-2917.
Okayasu, et al., "Purification and Partial Characterization of Linoleoyl-CoA Desaturase from Rat Liver Microsomes", Archives of Biochemistry and Biophysics, 206(1):21-8 (1981).
Okuley, et al., "*Arabidopsis* FAD2 Gene Encodes the Enzyme that is Essential for Polyunsaturated Lipid Synthesis", The Plant Cell Online, vol. 6, Issue 1, Jan. 1994, pp. 147-158.
Parker et al., Local DNA topography correlates with functional noncoding regions of the human genome, Science, 324(5925):389-92 (Apr. 2009).
Paul, et al., "Members of the *Arabidopsis* FAE1-like 3-Ketoacyl-CoA Synthase Gene Family Substitute for the Elop Proteins of *Saccharomyces cerevisiae*", J. Biol. Chem., 281(14):9018-29 (2006).
Petrie et al., Metabolic engineering Camelina sativa with fish oil-like levels of DHA, PLoS One, 9(1):e85061 (Jan. 2014).
Potts et al., Inheritance of fatty acid composition in *Brassica juncea*, Proceedings of the 10th International Rapeseed Congress, Sep. 26, 1999.
Proc et al., A quantitative study of the effects of chaotropic agents, surfactants, and solvents on the digestion efficiency of human plasma proteins by trypsin, J> Proteome Res., 9(10):5422-37 (Oct. 2010).
Qi, et al., "Production of Very Long Chain Polyunsaturated Omega-3 and Omega-6 Fatty Acids in Plants", Nature Biotechnology, vol. 22, Issue 6, Jun. 2004, pp. 739-745.

(56) References Cited

OTHER PUBLICATIONS

Quek, et al., "Commercial Extraction of Vitamin E from Food Sources" The Encyclopedia of Vitamin E, Eds. Preedy, et al., CABI Publishers, Oxford, U.K., 2007, pp. 140-152.
Ramamoorthy et al., Length and sequence dependent accumulation of simple sequence repeats in vertebrates: potential role in genome organization and regulation, Gene, 551(2):167-75 (Nov. 2014).
Riekhof, et al., "Lysophosphatidylcholine Metabolism in *Saccharomyces cerevisiae* The Role of P-Type Atpases in Transport and in Broad Specificity Acyltransferase in Acylation", J. Biol. Chem., 282(51):36853-61 (2007).
Ruiz-Lopez, et al., "Successful High-level Accumulation of Fish Oil Omega-3 Long-Chain Polyunsaturated Fatty Acids in a Transgenic Oilseed Crop", Plant J., 77(2):198-208 (2014).
Ruuska, et al., "Contrapuntal Networks of Gene Expression during *Arabidopsis* Seed Filling", The Plant Cell Online, vol. 14, Issue 6, Jun. 2002, pp. 1191-1206.
Rychlik, et al., "A computer program for choosing optimal oligonudeotides for filter hybridization, sequencing and in vitro amplification of DNA", Nucleic Acids Research, 17(21):8543-51 (1989).
Sarkar, et al., "Specificity Determinants for the Abscisic Acid Response Element", FEBS Open Bio, vol. 3, Issue 1, Jan. 1, 2013, pp. 101-105.
Shanklin, et al., "Desaturation and Related Modifications of Fatty Acids1", Annual Review of Plant Physiology and Plant Molecular Biology, vol. 49, Jun. 1998, pp. 611-641.
Shanklin, et al., "Stearoyl-acyl-carrier-protein desaturase from Higher Plants is Structurally Unrelated to the Animal and Fungal Homologs", Proc. Natl. Acad. Sci. USA, 88(6):2510-4 (1991).
Smith et al., Measurement of protein using bicinchoninic acid, Anal. Biochem., 150(1):76-85 (Oct. 1985).
Spector, Essentiality of fatty acids, Lipids, 34 Suppl: S1-3 (1999).
Strittmatter et al., "Purification and Properties of Rat Liver Microsomal Stearyl Coenzyme A Desaturase", Proc. Natl. Acad. Sci. USA, 71(11):4565-9 (1974).
Stymne et al., Evidence for the reversibility of the acyl-CoA:lysophosphatidylcholine acyltransferase in microsomal preparations from developing safflower (*Carthamus tinctorius* L.) cotyledons and rat liver, Biochem. J., 233(2):305-14 (1984).
Stymne, et al., "Biosynthesis of γ-linolenic Acid in Cotyledons and Microsomal Preparations of the Developing Seeds of Common Borage (*Borago officinalis*)", Biochem. J., 240(2):385-93 (1986).
Sánchez-García et al., Differential temperature regulation of three sunflower microsomal oleate desaturase (FAD2) isoforms overexpressed in *Saccharomyces cerevisia*, Eur. J. Lipid Sci. Tech., 106:583-590 (2004).
Tamaki, et al., "LPT1 Encodes a Membrane-bound O-Acyltransferase Involved in the Acylation of Lysophospholipids in the Yeast *Saccharomyces cerevisiae*", J. Biol. Chem., 282(47):34288-98 (2007).
Tang, et al., "Oleate Desaturase Enzymes of Soybean: Evidence of Regulation Through Differential Stability and Phosphorylation", Plant J., 44(3):433-46 (2005).
Tudzynski et al., Biotechnology and genetics of ergot alkaloids, Appl. Microbiol. Biotechnol., 57(5-6):593-605 (Dec. 2001).
Tumaney et al., Synthesis of azidophospholipids and labeling of lysophosphatidylcholine acyltransferase from developing soybean cotyledons, Biochim. Biophys. Acta, 1439(1):47-56 (Jul. 1999).
Vilardell et al., Regulation of the rab17 gene promoter in transgenic *Arabidopsis* wild-type, ABA-deficient and ABA-insensitive mutants, Plant Mol. Biol., 24(4):561-9 (1994).
Wachter et al., Synthetic CpG islands reveal DNA sequence determinants of chromatin structure, Elife, 3:e03397 (Sep. 2014).
Wang, et al., "Crystal Structure of Human Stearoyl-Coenzyme a Desaturase in Complex with Substrate", Nature Structural & Molecular Biology, vol. 22, 2015, pp. 581-585.
Wijesundra, The influence of triacylglycerol structure on the oxidative stability of polyunsaturated oils, Lipid Technology, 20:199-202 (2008).
Wu, et al., "Stepwise Engineering to Produce High Yields of Very Long-Chain Polyunsaturated Fatty Acids in Plants", Nature Biotechnology, vol. 23, Issue 8, 2005, pp. 1013-1017.
Xiao, et al., "Characterization of the Promoter and 5'-UTR Intron of Oleic Acid Desaturase (FAD2) Gene in *Brassica napus*", Gene, vol. 545, Issue 1, Jul. 2014, pp. 45-55.
Yamashita et al., ATP-independent fatty acyl-coenzyme A synthesis from phospholipid: coenzyme A-dependent transacylation activity toward lysophosphatidic acid catalyzed by acyl-coenzyme A:lysophosphatidic acid acyltransferase, J. Biol. Chem., 276(29):26745-52 (Jul. 2001).
Schwender et al., "Rubisco without the Calvin cycle improves the carbon efficiency of developing green seeds", Nature, 432:779-82 (2004).
Eiamsa-ard et al., Two novel Physcomitrella patens fatty acid elongases (ELOs): identification and functional characterization, Appl. Microbiol. Biotechnol., 97:3485-3497 (2013).
Goffman, et al., "Genetic variation of tocopherol content in a germplasm collection of *Brassica napus* L.", Euphytica, vol. 125, May 2002, pp. 189-196.
Meyer et al., Novel fatty acid elongases and their use for the reconstitution of docosahexaenoic acid biosynthesis, Journal of Lipid Research, 45:1899-1909 (2004).
Shrestha et al., Int. J. Mol. Sci., Comparison of the substrate preferences of ω3 fatty acid desaturases for long chain polyunsaturated fatty acids, 20:3058 (2019).
Wang et al., ω3 fatty acid desaturases from microorganisms: structure, function, evolution, and biotechnological use, App. Microbiol., 97:10255-62 (2013).
Bahrani et al., Relationship of seed quality traits for greenhouse-grown versus field-grown high erucic acid rapeseed: is seed quality trait selection for greenhouse-grown seed worthwhile? Can. J. Plant Sci., 88:419-23 (2008).
Barret et al., A rapeseed FAE1 gene is linked to the E1 locus associated with variation in the content of erucic acid, Theor. Appl. Genet., 96:177-86 (1998).
Batista et al., Nutritional and nutraceutical potential of rape (*Brassica napus* L. var. *napus*) and "tronchuda" cabbage (*Brassica oleraceae* L. var. *costata*) inflorescences, Food Chem. Toxicol., 49(6):1208-14(2011).
Bork et al., Go hunting in sequence databases but watch out for the traps, Trends Genet., 12(10):425-7 (1996).
Del Villar et al., Amino acid substitutions that convert the protein substrate specificity of farnesyltransferase to that of geranylgeranyltransferase type I, J. Biol. Chem., 272(1):680-7 (1997).
Doerks et al., Protein annotation: detective work for function prediction, Trends Genet., 14(6):248-50(1998).
Guo et al., Protein tolerance to random amino acid change, Proc. Natl. Acad. Sci. USA, 101(25):9205-10 (2004).
Hanzawa et al., A single amino acid converts a repressor to an activator of flowering, Proc. Natl. Acad. Sci. USA, 102(21):7748-53 (2005).
Keskin et al., A new, structurally nonredundant, diverse data set of protein-protein interfaces and its implications, Protein Sci., 13(4):1043-55 (2004).
Lee, et al., "Overexpression of *Arabidopsis* homogentisate phytyltransferase or tocopherol cyclase elevates vitamin E content by increasing gamma-tocopherol level in lettuce (*Lactuca sativaL*.)", Molecules and Cells, vol. 24, Issue 2, Oct. 1, 2007, pp. 301-306.
McConnell et al., Role of Phabulosa and Phavoluta in determining radial patterning in shoots, Nature, 411 (6838):709-13 (2001).
Multari et al., Effects of aromatic herb flavoring on carotenoids and volatile compounds in edible oil from blue sweet lupin (*Lupinus angustifolius*), Eur. J. Lipid Sci. Tech, pp. 1-10 (2018).
Ngo et al., Computational complexity, protein structure prediction, and the Levinthal Paradox, pp. 492-495 In: Merz et al. (eds.), The Protein Folding Problem and Tertiary Structure Prediction, BirkHauser Boston (1994).
Nishimura et al.,Over-expression of tobacco knotted1-type class1 homeobox genes alters various leaf morphology, Plant Cell Physiol., 41(5):583-90 (2000).

(56) References Cited

OTHER PUBLICATIONS

Rossak et al., Expression of the FAE1 gene and FAE1 promoter activity in developing seeds of *Arabidopsis thaliana*, Plant Mol. Biol., 46(6):717-25 (2001).

Ruiz-Lopez et al., Modifying the lipid content and composition of plant seeds: engineering the production of LC-PUFA, Appl. Microbiol. Biotechnol., 99:143-54 (2015).

Ruiz-Lopez et al., Nutritional and bioactive compounds in Mexican lupin beans species: A mini-review, Nutrients, pp. 1-19 (2019).

Smith et al., The challenges of genome sequence annotation or "the devil is in the details", Nat. Biotechnol., 15(12):1222-3 (1997).

Thornton et al., From structure to function: approaches and limitations, Nat. Struct. Biol., 7 Suppl:991-4 (2000).

Truksa et al., Molecular analysis of flax 2S storage protein conlinin and seed specific activity of its promoter, Plant Physiol, and Biochem., 41:141-7 (2003).

Vrinten et al., Production of polyunsaturated fatty acids in transgenic plants, Biotechnology and Genetic Engineering Reviews, 24:263-80 (2007).

Wells, Additivity of mutational effects in proteins, Biochemistry, 29(37):8509-17 (1990).

Wishart et al., A single mutation converts a novel phosphotyrosine binding domain into a dual-specificity phosphatase, J. Biol. Chem., 270(45):26782-5 (1995).

Yan et al., Characterization of FAE1 in the zero erucic acid germplasm of *Brassica rapa* L, Breed Sci., 65(3):257-64 (2015).

Yang et al., Expression of the REB transcriptional activator in rice grains improves the yield of recombinant proteins whose genes are controlled by a Reb-responsive promoter, Proc. Natl. Acad. Sci. USA, 98(20):11438-43 (2001).

Zebarjadi et al., Transformation of rapeseed (*Brassica napus* L.) plants with sense and antisense constructs of the fatty acid elongase gene, Iranian J Biotechnol., 4(2):79-87 (2006).

\* cited by examiner

Fig. 2

Formula used for pathway step conversion efficiency Ceff $$C_{eff} = \frac{100}{S+P} \times P$$

| Pathway Step | Product Stream | pre-requisite of product stream | | | | | | |
|---|---|---|---|---|---|---|---|---|
| d12Des | d12Des Product Stream 1 | 18:1n-9 | 18:1n-9 | 18:2n-6 | | | | |
| | d12Des Product Stream 2 | 18:3n-3 from 18:2n-6 via d15Des | | 18:2n-6 / 18:3n-3 | 18:3n-6 / 18:4n-3 | | | |
| | d12Des Product Stream 3 | 20:2n-6 from 18:2n-6 via d6Elo | | 20:2n-6 / 20:3n-3 | | | | |
| | d12Des Product Stream 4 | 20:3n-3 from 18:3n-3 via d6Elo | | | | | | |
| d6Des | d12Des Product Stream 1 | 18:2n-6 | | 18:2n-6 / 18:3n-3 | 18:3n-6 / 18:4n-3 | 20:3n-6 / 20:4n-3 | 20:4n-6 / 20:5n-3 | 22:4n-6 / 22:5n-3 | 22:5n-6 / 22:6n-3 |
| | d12Des Product Stream 2 | 18:3n-3 produced by o3Des | | | | | | |
| d6Elo | d6Elo Product Stream 1 | 18:3n-6 produced by d6Des | | | 18:3n-6 / 18:4n-3 | 20:3n-6 / 20:4n-3 | 20:4n-6 / 20:5n-3 | 22:4n-6 / 22:5n-3 | 22:5n-6 / 22:6n-3 |
| | d6Elo Product Stream 2 | 18:4n-3 produced by d6Des or o3Des | | | | | | |
| d5Des | d5Des Product Stream 1 | 20:3n-6 produced by d6Elo | | | | 20:3n-6 / 20:4n-3 | 20:4n-6 / 20:5n-3 | 22:4n-6 / 22:5n-3 | 22:5n-6 / 22:6n-3 |
| | d5Des Product Stream 2 | 20:4n-3 produced by d6Elo or o3Des | | | | | | |
| d5Elo | d5Elo Product Stream 1 | 20:4n-6 produced by d5Des | | | | | 20:4n-6 / 20:5n-3 | 22:4n-6 / 22:5n-3 | 22:5n-6 / 22:6n-3 |
| | d5Elo Product Stream 2 | 20:4n-3 produced by d5Des or o3Des | | | | | | |
| d4Des | d4Des Product Stream 1 | 20:4n-6 produced by d5Des | | | | | | 22:4n-6 / 22:5n-3 | 22:5n-6 / 22:6n-3 |
| | d4Des Product Stream 2 | 20:4n-3 produced by d5Des or o3Des | | | | | | |
| o3Des | | List of all o6Des Fatty acid substrates | 18:2n-6 | 18:3n-6 | 20:3n-6 | 20:4n-6 | 22:4n-6 | 22:5n-6 |
| | | List of all o3Des Fatty acid products | 18:3n-3 | 18:4n-3 | 20:3n-3 | 20:5n-3 | 22:5n-3 | 22:6n-3 |

Fig. 24
A.
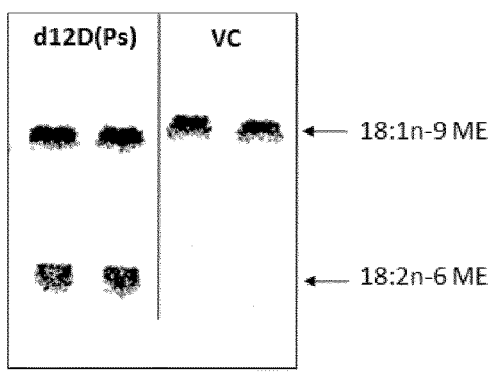
B.
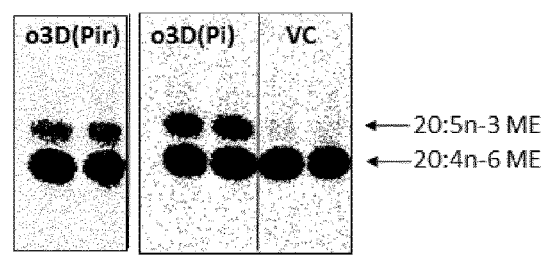
C.
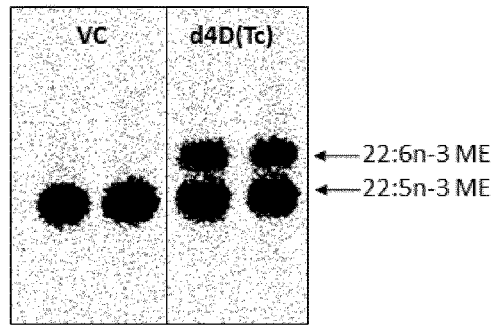
D.
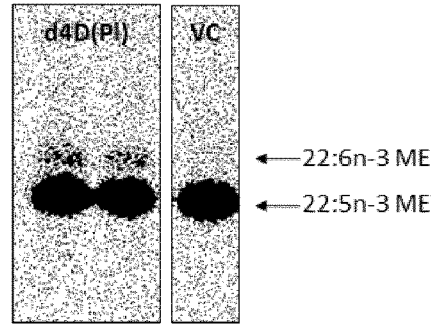

Fig. 25
A.
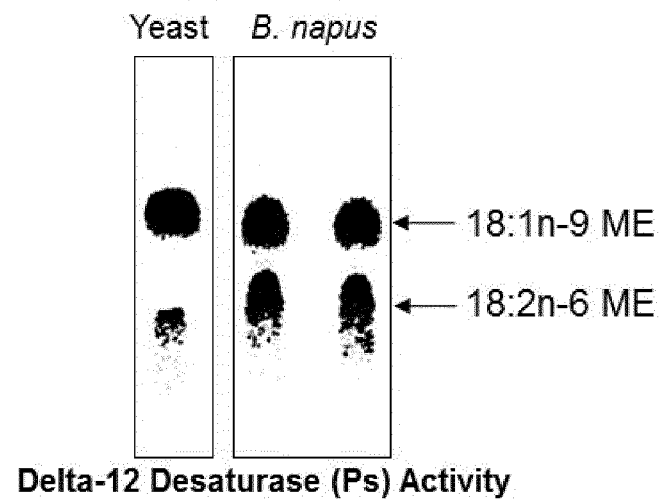
Delta-12 Desaturase (Ps) Activity
B.
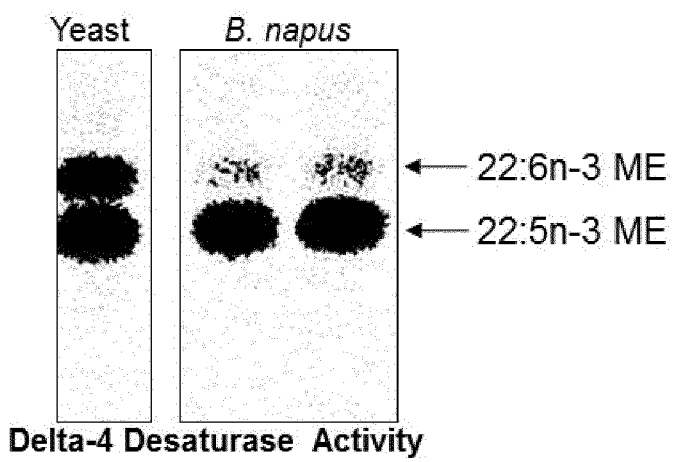
Delta-4 Desaturase Activity

Fig. 26
A.
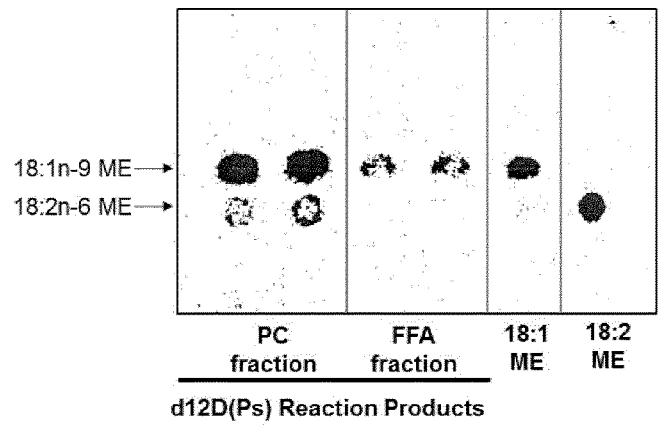
B.
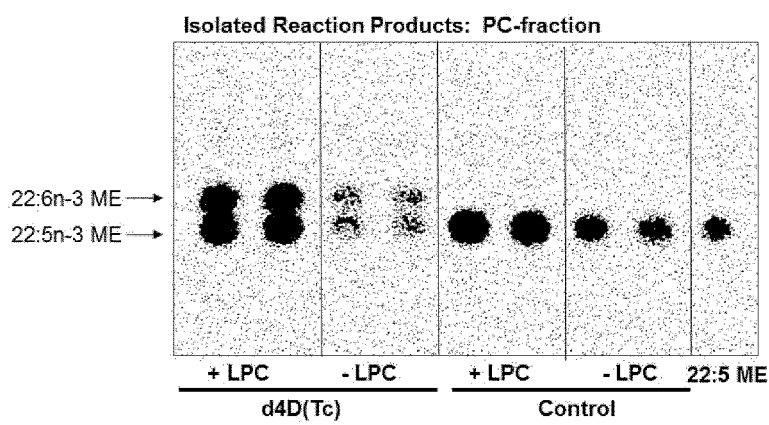
C.
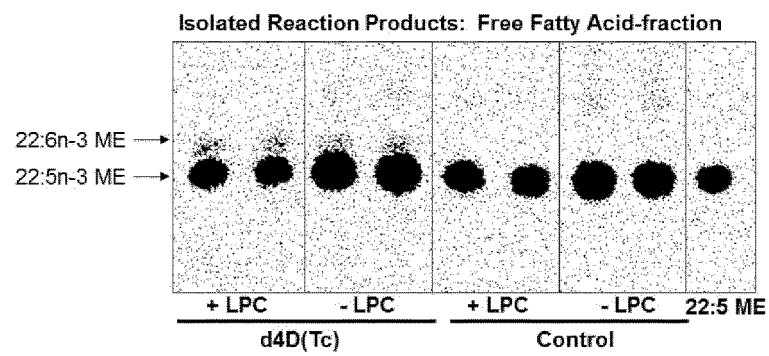
D.
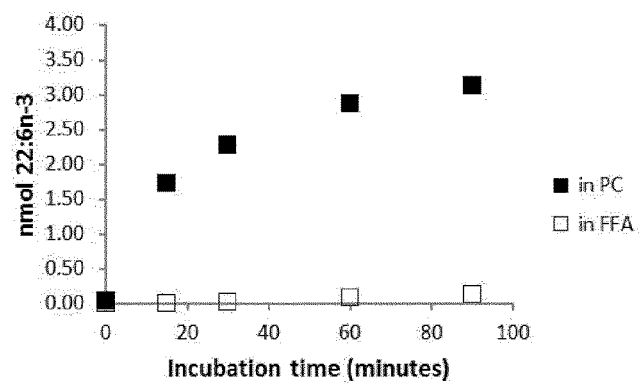

Fig. 27
A.
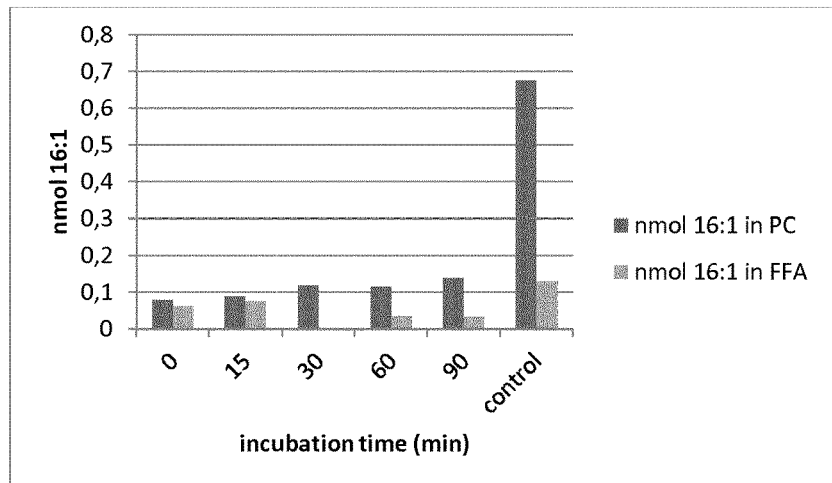
B.
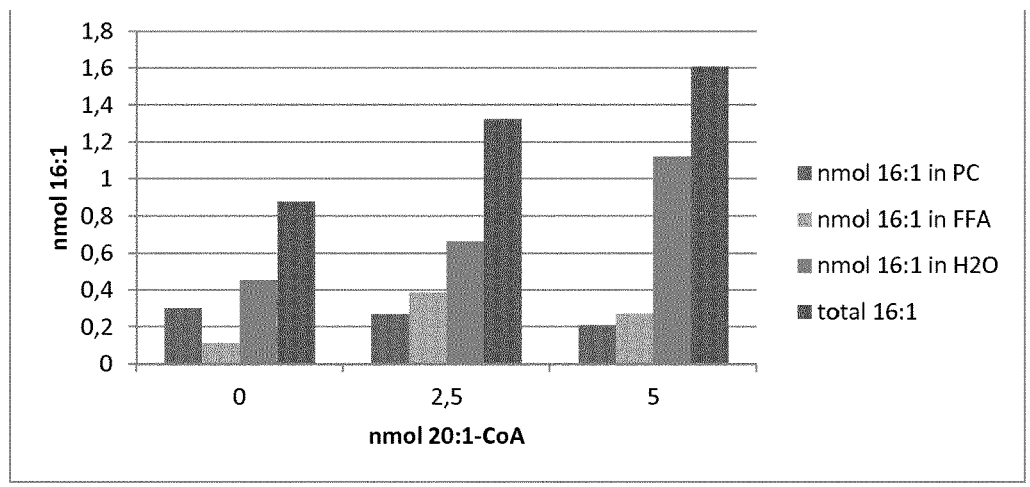
C.
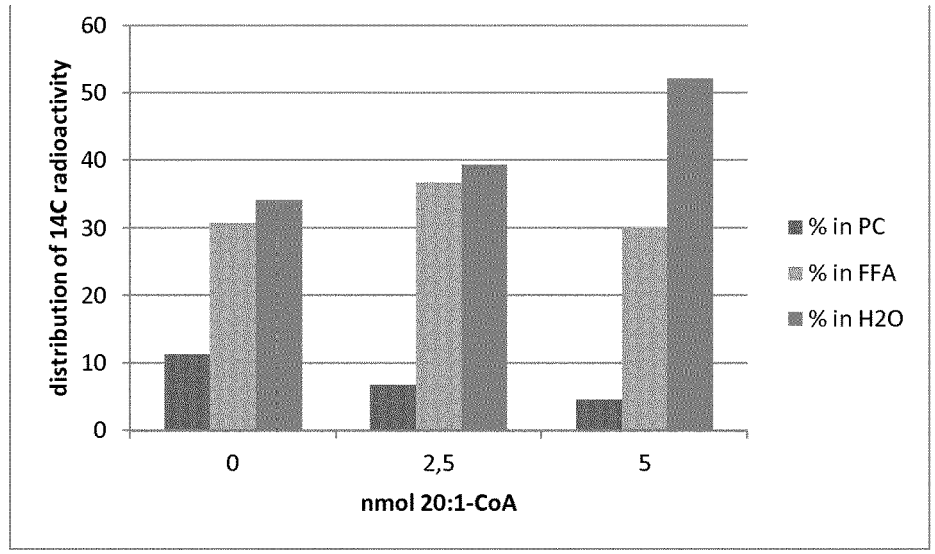

Fig. 28
A.
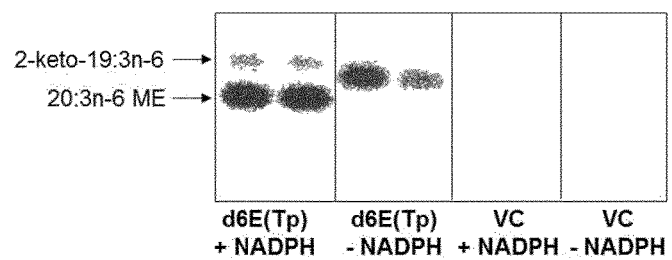
B.
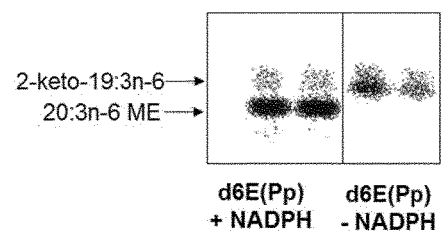
C.
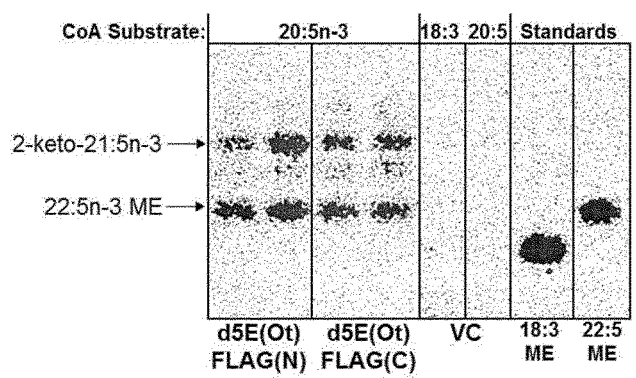

Fig. 29
A.
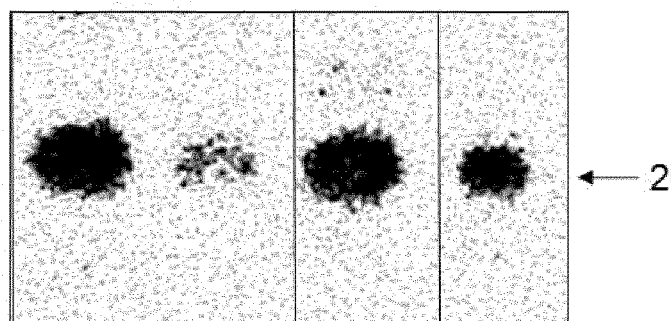
Delta-6 Elongase Activity
B.
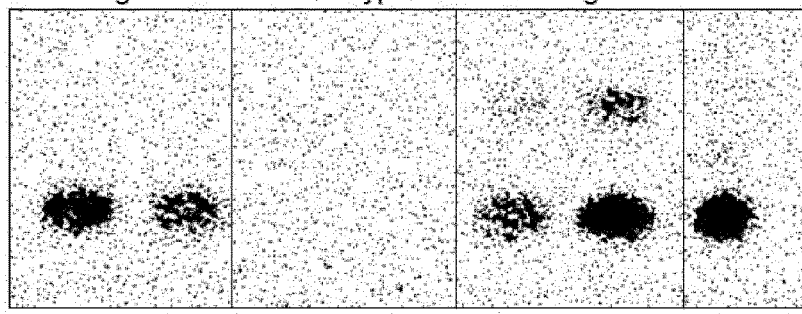
Delta-5 Elongase (Ot) Activity Fig. 85
A.
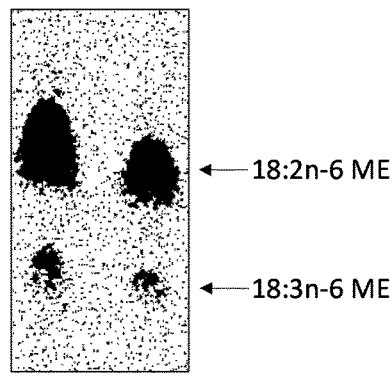
**Delta-6 Desaturase (*Ostreococcus tauri*)**
B.
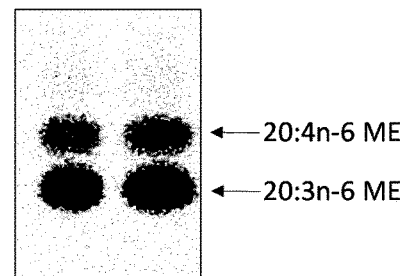
**Delta-5 Desaturase (*Thraustochytrium* ssp.)**
C.
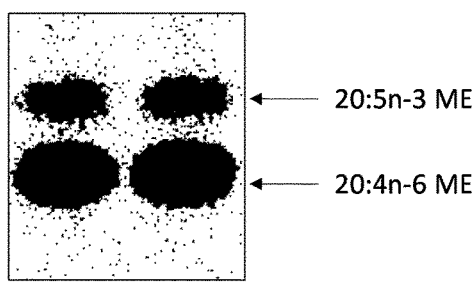
Omega-3 Desaturase

Fig. 86
A.
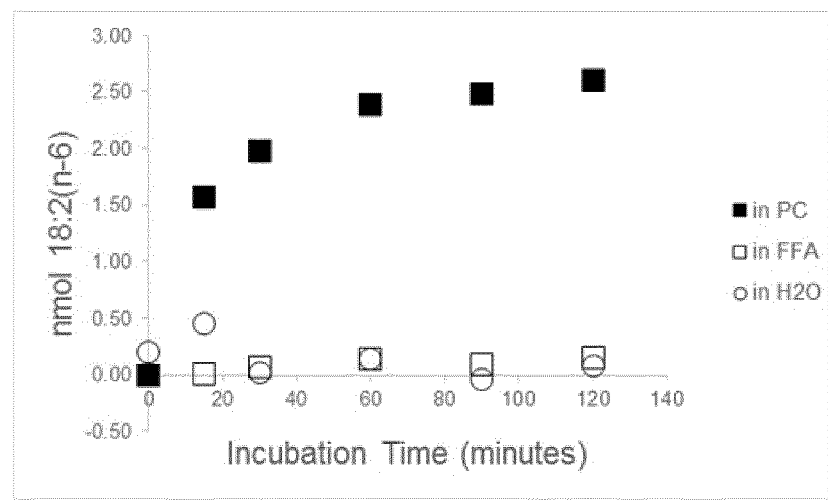
B.
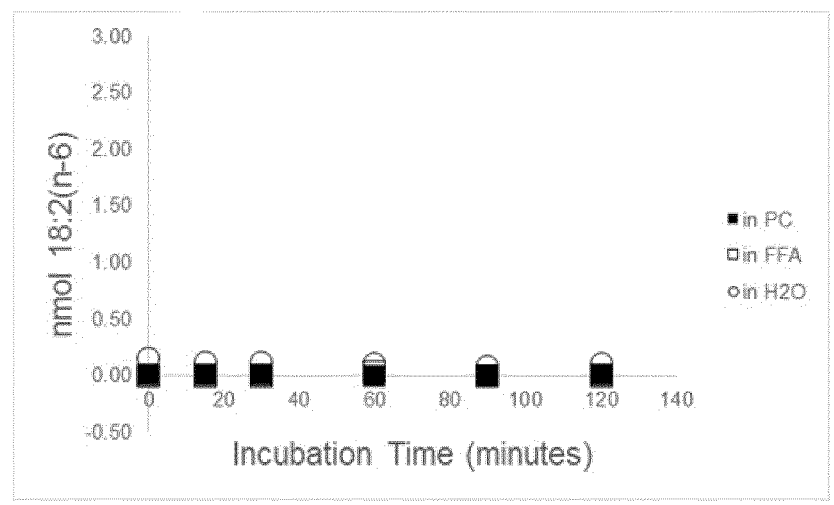

Fig. 87
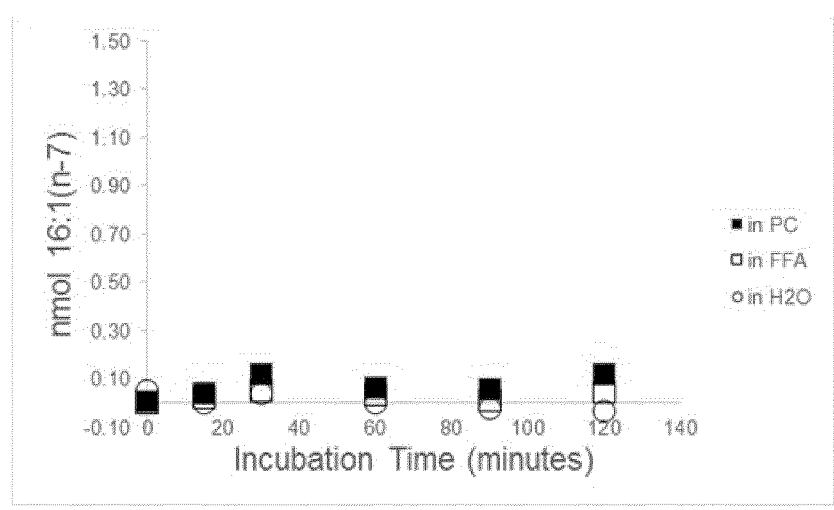
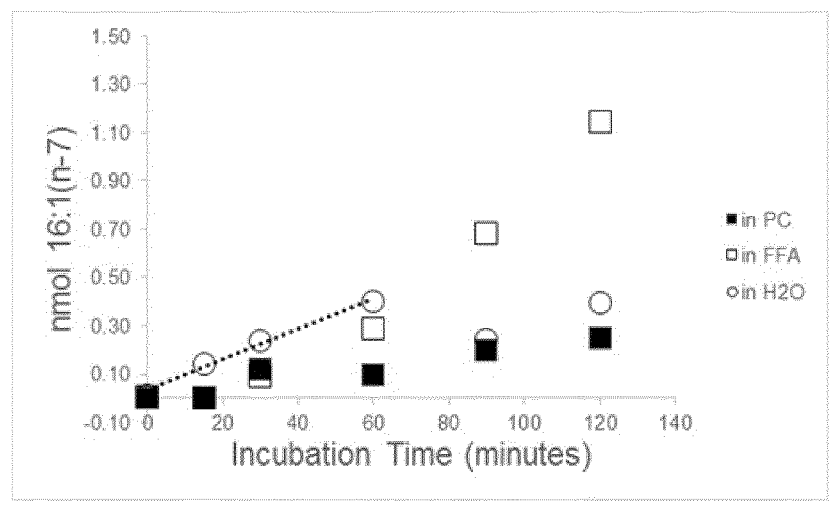

MATERIALS AND METHODS FOR PUFA PRODUCTION, AND PUFA-CONTAINING COMPOSITIONS

This application is a National Stage application of International Application No. PCT/EP2015/076631, filed Nov. 13, 2015, which claims the benefit of U.S. Provisional Patent Application No. 62/079,622, filed Nov. 14, 2014 and U.S. Provisional Patent Application No. 62/234,373, filed Sep. 29, 2015, which are incorporated herein by reference in their entirety.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "H77877 Seqlistinq.txt", which was created on May 12, 2017 and is 1,303,607 bytes in size. The subject matter of the Sequence Listing is incorporated herein in its entirety by reference.

FIELD OF THE INVENTION

The invention generally pertains to the field of manufacture of fatty acids, particularly for large-scale production of very long chain polyunsaturated fatty acids (VLC-PUFAs, also called polyunsaturated fatty acids or PUFAs), e.g. eicosapentaenoic acid (EPA), omega-3 docosapentaenoic acid (DPA) and docosahexaenoic acid (DHA). The invention particularly is concerned with the production of VLC-PUFAs in plants and thus inter alia provides nucleic acids for transformation of plants to enable such transformed plants to produce VLC-PUFAs. To this end, the invention also provides transgenic constructs and expression vectors containing desaturase and elongase genes and host cells into which the constructs and expression vectors have been introduced. The present invention also relates to methods for the manufacture of oil, fatty acid- or lipids-containing compositions, and to such oils and lipids as such. In addition, the invention is concerned with methods for further improving the production of VLC-PUFAs in plants.

BACKGROUND OF THE INVENTION

Fatty acids are carboxylic acids with long-chain hydrocarbon side groups that play a fundamental role in many biological processes. Fatty acids are rarely found free in nature but, rather, occur in esterified form as the major component of lipids. As such, lipids/fatty acids are sources of energy (e.g., beta-oxidation). In addition, lipids/fatty acids are an integral part of cell membranes and, therefore, are indispensable for processing biological or biochemical information.

Long chain polyunsaturated fatty acids (VLC-PUFAs) such as docosahexaenoic acid (DHA, 22:6(4,7,10,13,16,19)) are essential components of cell membranes of various tissues and organelles in mammals (nerve, retina, brain and immune cell). Clinical studies have shown that DHA is essential for the growth and development of the brain in infants, and for maintenance of normal brain function in adults (Martinetz, M. (1992) J. Pediatr. 120:S129 S138). DHA also has significant effects on photoreceptor function involved in the signal transduction process, rhodopsin activation, and rod and cone development (Giusto, N. M., et al. (2000) Prog. Lipid Res. 39:315-391). In addition, some positive effects of DHA were also found on diseases such as hypertension, arthritis, atherosclerosis, depression, thrombosis and cancers (Horrocks, L. A. and Yeo, Y. K. (1999) Pharmacol. Res. 40:211-215). Therefore, appropriate dietary supply of the fatty acid is important for human health. Because such fatty acids cannot be efficiently synthesized by infants, young children and senior citizens, it is particularly important for these individuals to adequately intake these fatty acids from the diet (Spector, A. A. (1999) Lipids 34:S1 S3). EPA (20:5n-3 5,8,11,14,17) and also ARA (arachidonic acid, 20:4n-6 (5,8,11,14)) are both delta 5 (d5) essential fatty acids. They form a unique class of food and feed constituents for humans and animals. EPA belongs to the n-3 series with five double bonds in the acyl chain. EPA is found in marine food and is abundant in oily fish from North Atlantic. ARA belongs to the n-6 series with four double bonds. The lack of a double bond in the omega-3 position confers on ARA different properties than those found in EPA. The eicosanoids produced from ARA (sometimes abbreviated "AA") have strong inflammatory and platelet aggregating properties, whereas those derived from EPA have anti-inflammatory and anti-platelet aggregating properties. ARA can be obtained from some foods such as meat, fish and eggs, but the concentration is low.

Gamma-linolenic acid (GLA, C18:3n-6 (6,9,12)) is another essential fatty acid found in mammals. GLA is the metabolic intermediate for very long chain n-6 fatty acids and for various active molecules. In mammals, formation of long chain polyunsaturated fatty acids is rate-limited by delta-6 desaturation. Many physiological and pathological conditions such as aging, stress, diabetes, eczema, and some infections have been shown to depress the delta-6 desaturation step. In addition, GLA is readily catabolized from the oxidation and rapid cell division associated with certain disorders, e.g., cancer or inflammation. Therefore, dietary supplementation with GLA can reduce the risks of these disorders. Clinical studies have shown that dietary supplementation with GLA is effective in treating some pathological conditions such as atopic eczema, premenstrual syndrome, diabetes, hypercholesterolemia, and inflammatory and cardiovascular disorders.

A large number of beneficial health effects have been shown for DHA or mixtures of EPA and DHA.

Although biotechnology offers an attractive route for the production of specialty fatty acids, current techniques fail to provide an efficient means for the large scale production of unsaturated fatty acids. Accordingly, there exists a need for an improved and efficient method of producing very long chain poly unsaturated fatty acids (VLC-PUFAs), such as EPA and DHA.

The current commercial source of EPA and DHA is fish oil. However, marine stocks are diminishing as a result of over-fishing, and alternative sustainable sources of EPA and DHA are needed to meet increasing demand. Numerous efforts have been made to develop transgenic oilseed plants that produce VLC-PUFAs, including EPA and DHA. See, e.g., WO 2004/071467, WO 2013/185184, WO 2015/089587, Ruiz-Lopez, et al. (2014) Plant J. 77, 198-208. However, no transgenic oilseed plant has been commercialized which produces EPA and DHA at commercially relevant levels.

To make possible the fortification of food and/or of feed with polyunsaturated omega-3-fatty acids, there is still a great need for a simple, inexpensive process for the production of each of the aforementioned long chain polyunsaturated fatty acids, especially in eukaryotic systems.

SUMMARY OF THE INVENTION

The invention is thus concerned with providing a reliable source for easy manufacture of VLC-PUFAs. To this end the invention is also concerned with providing plants reliably producing VLC-PUFAS, preferably EPA and/or DHA. The invention is also concerned with providing means and methods for obtaining, improving and farming such plants, and also with VLC-PUFA containing oil obtainable from such plants, particularly from the seeds thereof. Also, the invention provides uses for such plants and parts thereof.

According to the invention there is thus provided a T-DNA for expression of a target gene in a plant. The invention beneficially provides a system for transformation of plant tissue and for generation of recombinant plants, wherein the recombinant plant differs from the respective parental plant (for the purposes of the present invention the parental plant is termed a wild-type plant regardless of whether or not such parental plant is as such found in nature) by the introduction of T-DNA. The T-DNA introduced into the parental plant beneficially has a length of at least 30000 nucleotides.

The invention also provides plants with a genotype that confers a heritable phenotype of high seed oil VLC-PUFA content in one or more of their tissues or components, preferably a high content of EPA and/or DHA in seed oil. The invention further provides material comprising a high VLC-PUFA content relative to their total oil content, preferably a high content of EPA and/or DHA. Also, the invention provides exemplary events of Brassica plants. Most beneficially the invention provides oil comprising a high VLC-PUFA content, preferably a high content of EPA and/or DHA.

The invention also provides methods of producing an oil, wherein the oil has a high VLC-PUFA content, a high content of EPA and/or DHA. In particularly preferred aspects these methods are for producing a corresponding plant oil. Thus, invention also provides methods of producing an oil.

The invention also provides methods for creating a plant, such that the plant or progeny thereof can be used as a source of an oil, wherein the oil has a high VLC-PUFA content, a high content of EPA and/or DHA. Thus, the invention beneficially also provides methods for the production of plants having a heritable phenotype of high seed oil VLC-PUFA content in one or more of their tissues or components, preferably a high content of EPA and/or DHA in seed oil.

The present invention also provides a method for increasing the content of Mead acid (20:3n-9) in a plant relative to a control plant, comprising expressing in a plant, at least one polynucleotide encoding a delta-6-desaturase, at least one polynucleotide encoding a delta-6-elongase, and at least one polynucleotide encoding a delta-5-desaturase.

The invention also provides means for optimizing a method for creating plants according to the invention. In this respect, the invention provides a system of methods for analyzing enzyme specificities, particularly for analyzing desaturase reaction specificity and for analyzing elongase specificities, for optimization of a metabolic pathway and for determining CoA-dependence of a target desaturase.

BRIEF DESCRIPTION OF THE FIGURES

FIG. 2: Formulas to calculate pathway step conversion efficiencies. S: substrate of pathway step. P: product of pathway step. Product was always the sum of the immediate product of the conversion at this pathway step, and all downstream products that passed this pathway step in order to be formed. E.g. DHA (22:6n-3 does possess a double bond that was a result of the delta-12-desaturation of oleic acid (18:1n-9) to linoleic acid (18:2n-6).

FIG. 24: Examples of Desaturase Enzyme Activity Heterologously Expressed in Yeast. [14C]Fatty acid methyl esters (ME's) were isolated from the enzymatic reactions, resolved by TLC as described for each specific enzyme and detected by electronic autoradiography using Instant Imager. In panel A Delta-12 Desaturase (Ps), c-d12Des(Ps_GA), activity was demonstrated by comparison of enzyme activity present in yeast microsomes isolated from a strain expressing the c-d12Des(Ps_GA) protein relative to microsomes isolated from a control strain containing an empty vector (VC). In panel B Omega-3 Desaturase activities, c-o3Des (Pir_GA) and c-o3Des(Pi_GA2), activities were demonstrated by comparison of enzyme activity from yeast microsomes isolated from strains expressing c-o3Des (Pir_GA) protein, c-o3Des(Pi_GA2) protein or an empty vector (VC) control. In panel C Delta-4 Desaturase (Tc), c-d4Des(Tc_GA), activity was demonstrated by comparison of enzyme activity from yeast microsomes isolated from a strain expressing the c-d4Des(Tc_GA) protein relative to microsomes isolated from a control strain containing an empty vector (VC). In panel D Delta-4 Desaturase (PI), c-d4Des(PI_GA)2, activity was demonstrated by comparison of enzyme activity from yeast microsomes isolated from a strain expressing the c-d4Des(PI_GA)2 protein relative to microsomes isolated from a control strain containing an empty vector (VC).

FIG. 25: Examples of Desaturase Enzyme Activity in transgenic Brassica napus. [14C]Fatty acid methyl esters (ME's) were isolated from the enzymatic reactions, resolved by TLC as described for each specific enzyme and detected by electronic autoradiography using Instant Imager. In panel A Delta-12 Desaturase (Ps), c-d12Des(Ps_GA), activity was demonstrated by comparison of enzyme activity from yeast microsomes isolated from a strain expressing the c-d12Des (Ps_GA) protein relative to microsomes isolated from transgenic B. napus containing the d12Des(Ps_GA2) gene. In panel B Delta-4 Desaturase (Tc), c-d4Des(Tc_GA), and Delta-4 Desaturase (PI) activities were demonstrated by comparison of enzyme activity from yeast microsomes isolated from a strain expressing the c-d4Des(Tc_GA) protein relative to microsomes isolated from transgenic B. napus containing the d4Des(Tc_GA3) and d4Des(PI_GA)2 genes.

FIG. 26: Examples of Desaturase Enzyme Reactions Showing Specificity for Acyl-lipid substrates. [14C]Fatty acid methyl esters (ME's) were isolated from the enzymatic reactions containing microsomes obtained from a yeast strain expressing the protein of interest, resolved by TLC as described for each specific enzyme and detected by electronic autoradiography using Instant Imager. In panel A Delta-12 Desaturase (Ps), c-d12Des(Ps_GA), desaturated enzyme products were only detected in the phosphatidylcholine fraction indicating the enzyme was specific for an acyl-lipid substrate. In panel B and panel C Delta-4 Desaturase (Tc), c-d4Des(Tc_GA), desaturated enzyme products were detected in the phosphatidylcholine fraction indicating the enzyme was specific for an acyl-lipid substrate. In panel D a time-course demonstrates the activity of the Delta-4 Desaturase (Tc), c-d4Des(Tc_GA).

FIG. 27: Examples of Desaturase Enzyme Reactions Showing Specificity for Acyl-CoA substrates. [14C]Fatty acid methyl esters (ME's) were isolated from the enzymatic reactions containing microsomes obtained from a yeast strain expressing the protein of interest, resolved by TLC as described for each specific enzyme and detected by electronic autoradiography using Instant Imager. In panel A PC was in situ labeled with substrate according to the method for determining lipid linked desaturation. Delta-9 Desaturase (Sc), d9D(Sc), desaturated enzyme products were very low in the phosphatidylcholine fraction, except for in the control reaction (none in situ labeled PC), indicating the enzyme cannot desaturate an acyl-lipid substrate. In panel B and C the incubation was done according to the method for determining acyl-CoA linked desaturation. In panel B the amount of radioactivity in the acyl-CoA fraction (MeOH/ H2O-phase, called nmol 16:1 in H20) was increasing when 20:1-CoA was added to the assay. This indicates that the added 20:1-CoA was competing with the radioactive substrate in formation of PC and free fatty acids. In panel C the amount of desaturated enzyme products was increased in the acyl-CoA fraction when 20:1-CoA was added to the assay, indicating that the desaturation was acyl-CoA linked.

FIG. 28: Examples of Elongase Enzyme Activity Heterologously Expressed in Yeast. [14C]Fatty acid methyl esters (ME's) were isolated from the enzymatic reactions, resolved by TLC as described for each specific enzyme and detected by electronic autoradiography using Instant Imager. All FAME's shown had similar Rf's as authentic standards. In the absence of [14C]malonyl-CoA no radioactive fatty acids were observed in any of these elongase reactions. In panel A delta-6 elongase (Tp), c-d6Elo(Tp_GA2), activity was demonstrated by comparison of enzyme activity present in yeast microsomes isolated from a strain expressing the c-d6Elo(Tp_GA2) protein relative to microsomes isolated from a control strain containing an empty vector (VC). In panel B, delta-6 elongase (Pp), c-d6Elo(Pp_GA2), was demonstrated by comparison of enzyme acitivity from yeast microsomes isolated from a strains expressing c-d6Elo (Pp_GA2) protein to microsomes isolated from a control strain containing an empty vector (VC), as shown in panel A. In panel C, delta-5 elongase (Ot), c-d5Elo(Ot_GA3), activity was demonstrated by comparison of enzyme activity present in yeast microsomes isolated from a strain expressing the d5E(Ot) protein relative to microsomes isolated from a control strain containing an empty vector (VC).

FIG. 29: Examples of Elongase Activity in transgenic *Brassica napus*. [14C]Fatty acid methyl esters (ME's) were isolated from the enzymatic reactions, resolved by TLC as described for each specific enzyme and detected by electronic autoradiography using Instant Imager. In panel A Delta-6 Elongase activity was demonstrated by comparison of enzyme activity from yeast microsomes isolated from a strain expressing the d6E(Pp_GA2) protein relative to microsomes isolated from transgenic B. *Napus* containing the c-d6Elo(Pp_GA2) gene and the c-d6Elo(Tp_GA2) gene. In panel B the Delta-5 Elongase (Ot), d5Elo(Ot_GA3), activity was demonstrated by comparison of enzyme activity from yeast microsomes isolated from a strain expressing the c-d5Elo(Ot_GA3) protein relative to microsomes isolated from transgenic B. *Napus* containing the d5Elo(Ot_GA3) and a wild-type *B. napus* (control).

FIG. 85. Examples of Desaturase Enzyme Activity in Transgenic *Brassica napus*. [14C]Fatty acid methyl esters (ME's) were isolated from the enzymatic reactions, resolved by TLC as described for each specific enzyme and detected by electronic autoradiography using an Instant Imager. Duplicate reactions are shown for each enzyme activity in Panels A-C. In Panel A delta-6 desaturase (*Ostreococcus tauri*) activity was demonstrated by the presence of [14C] 18:3n-6 ME using membranes isolated from transgenic *Brassica napus*. This desaturase activity was not present in membranes derived from a wild-type (Kumily) *B. napus*. In Panel B delta-5 desaturase (*Thraustochytrium* ssp.) activity was demonstrated by the presence of [14C]20:4n-6 ME using membranes isolated from transgenic *Brassica napus*. This desaturase activity was not present in membranes derived from a wild-type (Kumily) *B. napus*. In Panel C omega-3 desaturase activity was demonstrated by the presence of [14C]20:5n-3 ME using membranes isolated from transgenic *Brassica napus*. This desaturase activity was not present in membranes derived from a wild-type (Kumily) *B. napus*.

FIG. 86. Delta-12 desaturase (*Phytophthora sojae*), c-d12Des(Ps_GA), substrate preference. During the course of the enzymatic reaction the following lipid pools were isolated: phosphatidylcholine (PC, ■), free fatty acid (FFA, •), and H2O (CoA, ○). In Panel A c-d12Des(Ps_GA) enzyme activity is shown using assay conditions to present the fatty acid substrate (18:1(n-9)) in the acyl-phosphatidylcholine form. Desaturated enzymatic product (18:2(n-6)) is found predominantly in the phosphatidylcholine (PC) pool, relative to the free fatty acid (FFA) or H2O (CoA) pools, indicating c-d12Des(Ps_GA) utilizes 18:1(n-9) attached to phosphatidylcholine as a substrate. In Panel B c-d12Des (Ps_GA) enzyme activity is shown using assay conditions to present the fatty acid substrate (18:1(n-9)) in the acyl-CoA form. Relative to Panel A, desaturated enzymatic product (18:2(n-6)) is not produced in the phosphatidylcholine (PC), free fatty acid (FFA) or H2O (CoA) pools indicating c-d12Des(Ps_GA) does not utilize 18:1(n-9) bound as an acyl-CoA ester.

FIG. 87. Delta-9 desaturase (*Saccharomyces cerevisiae*), d9Des(Sc) substrate preference. During the course of the enzymatic reaction the following lipid pools were isolated: phosphatidylcholine (PC, □), free fatty acid (FFA, •), and H2O (CoA, ○). In Panel A d9Des(Sc) enzyme activity is shown using assay conditions to present the fatty acid substrate (16:0) in the acyl-phosphatidylcholine form. Relative to Panel B, desaturated enzymatic product (16:1(n-7)) is not produced in the phosphatidylcholine (PC), free fatty acid (FFA), or H2O (CoA) pools indicating d9Des(Sc) does not utilize 18:0 attached to phosphatidylcholine as a substrate. In Panel B d9Des(Sc) enzyme activity is shown using assay conditions to present the fatty acid substrate (16:0) in the acyl-CoA form. Desaturated enzymatic product (16:1(n-7)) is isolated in both the free fatty acid (FFA) and H2O (CoA) pools, but not the phosphatidylcholine (PC) pool. Furthermore, production of the desaturated enzymatic product (16:1(n-7)) in the H2O (CoA) pool is linear for the first 60 minutes of the assay as shown by the hashed line (r2=0.99). The high levels of [14C]16:1(n-7) detected in the FFA pool likely result from hydrolysis of the desaturated enzymatic product, 16:1(n-7)-CoA, by endogenous thioesterases present in the membrane preparations.

DETAILED DESCRIPTION OF THE INVENTION

Figure 1:
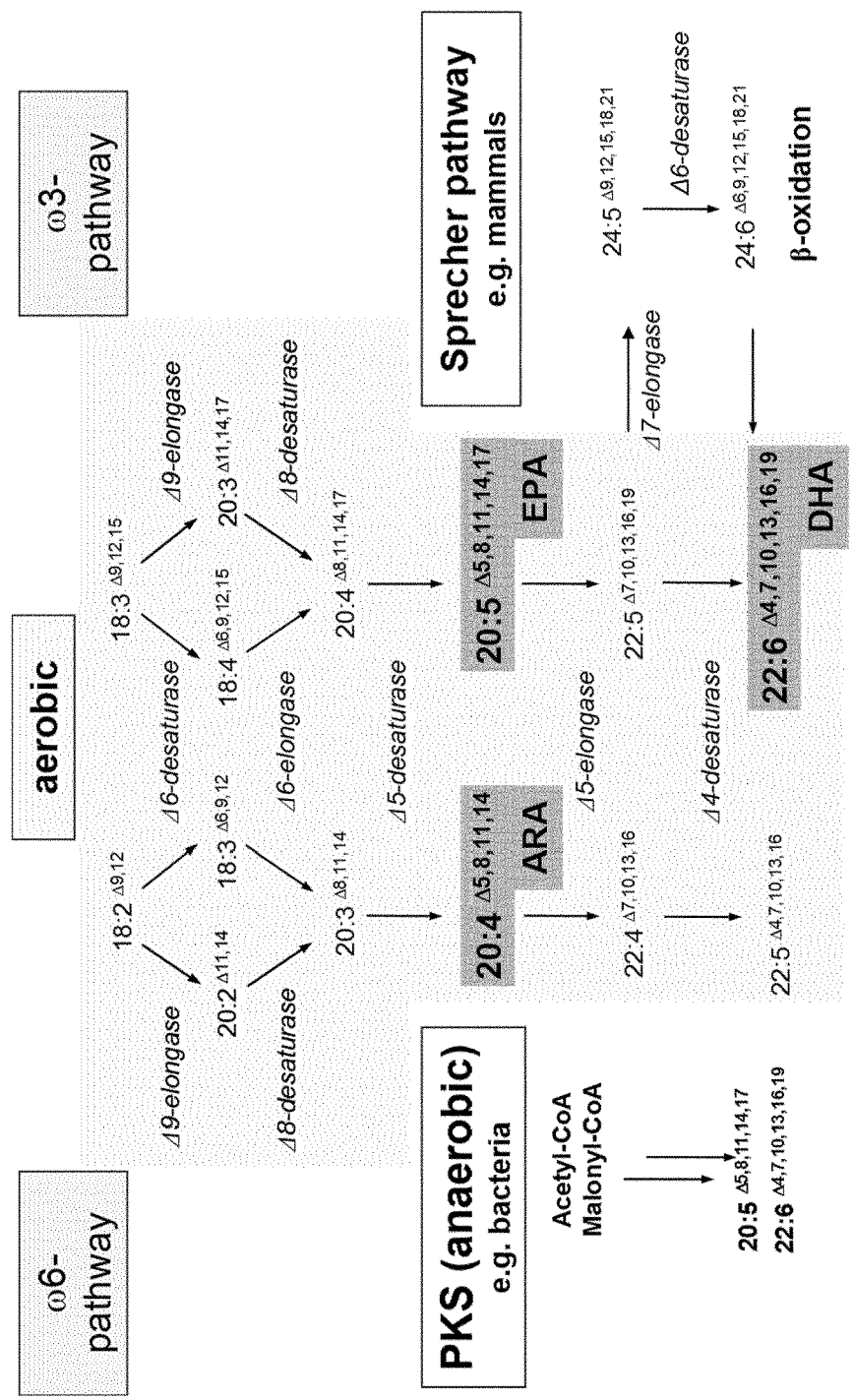
FIG. 1: Schematical figure of the different enzymatic activities leading to the production of ARA, EPA and DHA

Various aspects of the invention are hereinafter described in more detail. It is to be understood that the detailed description is not intended to limit the scope of the claims.

The term "polyunsaturated fatty acids (PUFA)" as used herein refers to fatty acids comprising at least two, preferably, three, four, five or six double bonds. Moreover, it is to be understood that such fatty acids comprise, preferably from 18 to 24 carbon atoms in the fatty acid chain. More preferably, the term relates to long chain PUFA (VLC-PUFA) having from 20 to 24 carbon atoms in the fatty acid chain. Particularly, polyunsaturated fatty acids in the sense of the present invention are DHGLA 20:3 (8,11,14), ARA 20:4 (5,8,11,14), ETA 20:4 (8,11,14,17), EPA 20:5 (5,8,11, 14,17), DPA 22:5 (4,7,10,13,16), DPA n-3 (7,10,13,16,19), DHA 22:6 (4,7,10,13,16,19), more preferably, eicosapentaenoic acid (EPA) 20:5 (5,8,11,14,17), and docosahexaenoic acid (DHA) 22:6 (4,7,10,13,16,19). Thus, it will be understood that most preferably, the methods provided by the present invention pertaining to the manufacture of EPA and/or DHA. Moreover, also encompassed are the intermediates of VLC-PUFA which occur during synthesis. Such intermediates are, preferably, formed from substrates by the desaturase, keto-acyl-CoA-synthase, keto-acyl-CoA-reductase, dehydratase and enoyl-CoA-reductase activity of the polypeptide of the present invention. Preferably, substrates encompass LA 18:2 (9,12), GLA 18:3 (6,9,12), DHGLA 20:3 (8,11,14), ARA 20:4 (5,8,11,14), eicosadienoic acid 20:2 (11,14), eicosatetraenoic acid 20:4 (8,11,14, 17), eicosapentaenoic acid 20:5 (5,8,11,14,17). Systematic names of fatty acids including polyunsaturated fatty acids, their corresponding trivial names and shorthand notations used according to the present invention are given in table Table 18 (and in table 181). The transgenic plants of this invention produce a number of VLC-PUFA and intermediates that are non-naturally occurring in wild type *Brassica* plants. While these VLC-PUFA and intermediates may occur in various organisms, they do not occur in wild type *Brassica* plants. These fatty acids include 18:2n-9, GLA, SDA, 20:2n-9, 20:3n-9, 20:3 n-6, 20:4n-6, 22:2n-6, 22:5n-6, 22:4n-3, 22:5n-3, and 22:6n-3.

The term "cultivating" as used herein refers to maintaining and growing the transgenic plant under culture conditions which allow the cells to produce the said polyunsaturated fatty acids, i.e. the PUFAs and/or VLC-PUFAs referred to above. This implies that the polynucleotide of the present invention is expressed in the transgenic plant so that the desaturase, elongase as also the keto-acyl-CoA-synthase, keto-acyl-CoA-reductase, dehydratase and enoyl-CoA-reductase activity is present. Suitable culture conditions for cultivating the host cell are described in more detail below.

The term "obtaining" as used herein encompasses the provision of the cell culture including the host cells and the culture medium or the plant or plant part, particularly the seed, of the current invention, as well as the provision of purified or partially purified preparations thereof comprising the polyunsaturated fatty acids, preferably, ARA, EPA, DHA, in free or in CoA bound form, as membrane phospholipids or as triacylglyceride esters. More preferably, the PUFA and VLC-PUFA are to be obtained as triglyceride esters, e.g., in form of an oil. More details on purification techniques can be found elsewhere herein below.

The term "polynucleotide" according to the present invention refers to a desoxyribonucleic acid or ribonucleic acid. Unless stated otherwise, "polynucleotide" herein refers to a single strand of a DNA polynucleotide or to a double stranded DNA polynucleotide. The length of a polynucleotide is designated according to the invention by the specification of a number of basebairs ("bp") or nucleotides ("nt"). According to the invention, both specifications are used interchangeably, regardless whether or not the respective nucleic acid is a single or double stranded nucleic acid. Also, as polynucleotides are defined by their respective nucleotide sequence, the terms nucleotide/polynucleotide and nucleotide sequence/polynucleotide sequence are used interchangeably, thus that a reference to a nucleic acid sequence also is meant to define a nucleic acid comprising or consisting of a nucleic acid stretch the sequence of which is identical to the nucleic acid sequence.

In particular, the term "polynucleotide" as used in accordance with the present invention as far as it relates to a desaturase or elongase gene relates to a polynucleotide comprising a nucleic acid sequence which encodes a polypeptide having desaturase or elongase activity. Preferably, the polypeptide encoded by the polynucleotide of the present invention having desaturase, or elongase activity upon expression in a plant shall be capable of increasing the amount of PUFA and, in particular, VLC-PUFA in, e.g., seed oils or an entire plant or parts thereof. Whether an increase is statistically significant can be determined by statistical tests well known in the art including, e.g., Student's t-test with a confidentiality level of at least 90%, preferably of at least 95% and even more preferably of at least 98%. More preferably, the increase is an increase of the amount of triglycerides containing VLC-PUFA of at least 5%, at least 10%, at least 15%, at least 20% or at least 30% compared to wildtype control (preferably by weight), in particular compared to seeds, seed oil, extracted seed oil, crude oil, or refined oil from a wild-type control. Preferably, the VLC-PUFA referred to before is a polyunsaturated fatty acid having a C20, C22 or C24 fatty acid body, more preferably EPA or DHA. Lipid analysis of oil samples are shown in the accompanying Examples.

Preferred polynucleotides encoding polypeptides having desaturase or elongase activity as shown in Table 130 in the Examples section (the SEQ ID Nos of the nucleic acid sequences and the polypeptide sequences are given in the last two columns).

In the plants of the present invention, in particular in the oil obtained or obtainable from the plant of the present invention, the content of certain fatty as shall be decreased or, in particular, increased as compared to the oil obtained or obtainable from a control plant. In particular decreased or increased as compared to seeds, seed oil, crude oil, or refined oil from a control plant. The choice of suitable control plants is a routine part of an experimental setup and may include corresponding wild type plants or corresponding plants without the polynucleotides as encoding desaturases and elongase as referred to herein. The control plant is typically of the same plant species or even of the same variety as the plant to be assessed. The control plant may also be a nullizygote of the plant to be assessed. Nullizygotes (or null control plants) are individuals missing the transgene by segregation. Further, control plants are grown under the same or essentially the same growing conditions to the growing conditions of the plants of the invention, i.e. in the vicinity of, and simultaneously with, the plants of the invention. A "control plant" as used herein preferably refers not only to whole plants, but also to plant parts, including seeds and seed parts. The control could also be the oil from a control plant.

Preferably, the control plant is an isogenic control plant. Thus, e.g. the control oil or seed shall be from an isogenic control plant.

The fatty acid esters with polyunsaturated C20- and/or C22-fatty acid molecules can be isolated in the form of an oil or lipid, for example, in the form of compounds such as sphingolipids, phosphoglycerides, lipids, glycolipids such as glycosphingolipids, phos-pholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetyl-coenzyme A esters which comprise the polyunsaturated fatty acids with at least two, three, four, five or six, preferably five or six, double bonds, from the organisms which were used for the preparation of the fatty acid esters. Preferably, they are isolated in the form of their diacylglycerides, triacylglycerides and/or in the form of phosphatidylcholine, especially preferably in the form of the triacylglycerides. In addition to these esters, the polyunsaturated fatty acids are also present in the non-human transgenic organisms or host cells, preferably in the plants, as free fatty acids or bound in other compounds. As a rule, the various abovementioned compounds (fatty acid esters and free fatty acids) are present in the organisms with an approximate distribution of 80 to 90% by weight of triglycerides, 2 to 5% by weight of diglycerides, 5 to 10% by weight of monoglycerides, 1 to 5% by weight of free fatty acids, 2 to 8% by weight of phospholipids, the total of the various compounds amounting to 100% by weight. In the process of the invention, the VLC-PUFAs which have been produced are produced in a content as for DHA of at least 5.5% by weight, at least 6% by weight, at least 7% by weight, advantageously at least 8% by weight, preferably at least 9% by weight, especially preferably at least 10.5% by weight, very especially preferably at least 20% by weight, as for EPA of at least 9.5% by weight, at least 10% by weight, at least 11% by weight, advantageously at least 12% by weight, preferably at least 13% by weight, especially preferably at least 14.5% by weight, very especially preferably at least 30% by weight based on the total fatty acids in the non-human transgenic organisms or the host cell referred to above. The fatty acids are, preferably, produced in bound form. It is possible, with the aid of the polynucleotides and polypeptides of the present invention, for these unsaturated fatty acids to be positioned at the sn1, sn2 and/or sn3 position of the triglycerides which are, preferably, to be produced.

In a method or manufacturing process of the present invention the polynucleotides and polypeptides of the present invention may be used with at least one further polynucleotide encoding an enzyme of the fatty acid or lipid biosynthesis. Preferred enzymes are in this context the desaturases and elongases as mentioned above, but also a polynucleotide encoding an enzyme having delta-8-desaturase and/or delta-9-elongase activity. All these enzymes reflect the individual steps according to which the end products of the method of the present invention, for example EPA or DHA are produced from the starting compounds oleic acid (C18:1), linoleic acid (C18:2) or linolenic acid (C18:3). As a rule, these compounds are not generated as essentially pure products. Rather, small traces of the precursors may be also present in the end product. If, for example, both linoleic acid and linolenic acid are present in the starting host cell, organism, or the starting plant, the end products, such as EPA or DHA, are present as mixtures. The precursors should advantageously not amount to more than 20% by weight, preferably not to more than 15% by weight, more preferably, not to more than 10% by weight, most preferably not to more than 5% by weight, based on the amount of the end product in question. Alternatively if, for example, appropriately all three oleic acid, linoleic acid and linolenic acid are present in the starting host cell, organism, or the starting plant, the end products, such as EPA or DHA, are present as mixtures. The precursors should advantageously not amount to more than 60% by weight, preferably not to more than 40% by weight, more preferably, not to more than 20% by weight, most preferably not to more than 10% by weight, based on the amount of the end product in question. Advantageously, only EPA or more preferably only DHA, bound or as free acids, is/are produced as end product(s) in the process of the invention in a host cell. If the compounds EPA and DHA are produced simultaneously, they are, preferably, produced in a ratio of at least 1:2 (DHA:EPA), more preferably, the ratios are at least 1:5 and, most preferably, 1:8. Fatty acid esters or fatty acid mixtures produced by the invention, preferably, comprise 6 to 15% of palmitic acid, 1 to 6% of stearic acid, 7-85% of oleic acid, 0.5 to 8% of vaccenic acid, 0.1 to 1% of arachidic acid, 7 to 25% of saturated fatty acids, 8 to 85% of monounsaturated fatty acids and 60 to 85% of polyunsaturated fatty acids, in each case based on 100% and on the total fatty acid content of the organisms. DHA as a preferred long chain polyunsaturated fatty acid is present in the fatty acid esters or fatty acid mixtures in a concentration of, preferably, at least 0.1; 0.2; 0.3; 0.4; 0.5; 0.6; 0.7; 0.8; 0.9 or 1%, based on the total fatty acid content.

Chemically pure VLC-PUFAs or fatty acid compositions can also be synthesized by the methods described herein. To this end, the fatty acids or the fatty acid compositions are isolated from a corresponding sample via extraction, distillation, crystallization, chromatography or a combination of these methods. These chemically pure fatty acids or fatty acid compositions are advantageous for applications in the food industry sector, the cosmetic sector and especially the pharmacological industry sector.

The term "desaturase" encompasses all enzymatic activities and enzymes catalyzing the desaturation of fatty acids with different lengths and numbers of unsaturated carbon atom double bonds. Specifically this includes delta 4 (d4)-desaturase, catalyzing the dehydrogenation of the 4th and 5th carbon atom; Delta 5 (d5)-desaturase catalyzing the dehydrogenation of the 5th and 6th carbon atom; Delta 6 (d6)-desaturase catalyzing the dehydrogenation of the 6th and 7th carbon atom; Delta 8 (d8)-desaturase catalyzing the dehydrogenation of the 8th and 9th carbon atom; Delta 9 (d9)-desaturase catalyzing the dehydrogenation of the 9th and 10th carbon atom; Delta 12 (d12)-desaturase catalyzing the dehydrogenation of the 12th and 13th carbon atom; Delta 15 (d15)-desaturase catalyzing the dehydrogenation of the 15th and 16th carbon atom. An omega 3 (o3)-desaturase preferably catalyzes the dehydrogenation of the n-3 and n-2 carbon atom.

The terms "elongase" encompasses all enzymatic activities and enzymes catalyzing the elongation of fatty acids with different lengths and numbers of unsaturated carbon atom double bonds. Especially, the term "elongase" as used herein refers to the activity of an elongase, introducing two carbon molecules into the carbon chain of a fatty acid, preferably in the positions 1, 5, 6, 9, 12 and/or 15 of fatty acids, in particular in the positions 5, 6, 9, 12 and/or 15 of fatty acids.

Moreover, the term "elongase" as used herein preferably refers to the activity of an elongase, introducing two carbon molecules to the carboxyl ends (i.e. position 1) of both saturated and unsaturated fatty acids.

In the studies underlying this invention, enzymes with superior desaturase and elongase catalytic activities for the production of VLC-PUFA has been provided.

Tables 11 and 130 in the Examples section list preferred polynucleotides encoding for preferred desaturases or elongases to be used in the present invention. Thus, polynucleotides for desaturases or elongases that can be used in the context of the present invention are shown in Table 11 and 130, respectively. The SEQ ID NOs of these desaturases and elongases are shown in the last two columns of Table 130 (nucleic acid sequence and amino acid sequence). As set forth elsewhere herein, also variants of the said polynucleotides can be used.

Polynucleotides encoding polypeptides which exhibit delta-6-elongase activity have been described in WO2001/059128, WO2004/087902 and WO2005/012316, said documents, describing this enzyme from *Physcomitrella patens*, are incorporated herein in their entirety.

Polynucleotides encoding polypeptides which exhibit delta-5-desaturase activity have been described in WO2002026946 and WO2003/093482, said documents, describing this enzyme from *Thraustochytrium* sp., are incorporated herein in their entirety.

Polynucleotides encoding polypeptides which exhibit delta-6-desaturase activity have been described in WO2005/012316, WO2005/083093, WO2006/008099 and WO2006/069710, said documents, describing this enzyme from *Ostreococcus tauri*, are incorporated herein in their entirety.

In a preferred embodiment of the present invention, the delta-6-desaturase is a CoA (Coenzyme A)-dependent delta-6-desaturase. Such enzymes are well known in the art. For example, the delta-6-desaturase from *Ostreococcus tauri* used in the the example section is a Coenzyme A-dependent delta-6-desaturase. The use of CoA (Coenzyme A)-dependent delta-6-desaturase in combination with a delta-12-desaturase may allow for reducing the content of 18:1n-9 in seeds, in particular in seed oil, as compared to a control. The use of CoA-dependent delta-6-desaturase in combination with a delta-6-elongase may allow for reducing the content of 18:3n-6 in seeds, in particular in seed oil, as compared to using a phospholipid-dependent delta-6-desaturase in combination with a delta-6-elongase.

Polynucleotides encoding polypeptides which exhibit delta-6-elongase activity have been described in WO2005/012316, WO2005/007845 and WO2006/069710, said documents, describing this enzyme from *Thalassiosira pseudonana*, are incorporated herein in their entirety.

Polynucleotides encoding polypeptides which exhibit delta-12-desaturase activity have been described for example in WO2006100241, said documents, describing this enzyme from *Phytophthora sojae*, are incorporated herein in their entirety.

Polynucleotides encoding polypeptides which exhibit delta-4-desaturase activity have been described for example in WO2004/090123, said documents, describing this enzyme from *Euglena gracilis*, are incorporated herein in their entirety.

Polynucleotides encoding polypeptides which exhibit delta-5-elongase activity have been described for example in WO2005/012316 and WO2007/096387, said documents, describing this enzyme from *Ostreococcus tauri*, are incorporated herein in their entirety.

Polynucleotides encoding polypeptides which exhibit omega 3-desaturase activity have been described for example in WO2008/022963, said documents, describing this enzyme from *Pythium irregulare*, are incorporated herein in their entirety.

Polynucleotides encoding polypeptides which exhibit omega 3-desaturase activity have been described for example in WO2005012316 and WO2005083053, said documents, describing this enzyme from *Phytophthora infestans*, are incorporated herein in their entirety.

Polynucleotides encoding polypeptides which exhibit delta-4-desaturase activity have been described for example in WO2002026946, said documents, describing this enzyme from *Thraustochytrium* sp., are incorporated herein in their entirety.

Polynucleotides coding for a delta-4 desaturase from *Pavlova lutheri* are described in WO2003078639 and WO2005007845. These documents are incorporated herein in their entirety, particularly in so far as the documents relate to the delta-4 desaturase "PIDES 1" and FIGS. 3a-3d of WO2003078639 and FIGS. 3a, 3b of WO2005007845, respectively.

The polynucleotides encoding the aforementioned polypeptides are herein also referred to as "target genes" or "nucleic acid of interest". The polynucleotides are well known in the art. The sequences of said polynucleotides can be found in the sequence of the T-DNAs disclosed in the Examples section (see e.g. the sequence of VC-LTM593-1qcz which has a sequence as shown in SEQ ID NO: 3). The SEQ ID Nos for the preferred polynucleotide and and polypeptide sequences are also given in Table 130 in the Examples section.

Sequences of preferred polynucleotides for the desaturases and elongases referred to herein in connection with the present invention are indicated below. As set forth elsewhere herein, also variants of the polynucleotides can be used. The polynucleotides encoding for desaturases and elogases to be used in accordance with the present invention can be derived from certain organisms. Preferably, a polynucleotide derived from an organism (e.g from *Physcomitrella patens*) is codon-optimized. In particular, the polynucleotide shall be codon-optimized for expression in a plant.

The term "codon-optimized" is well understood by the skilled person. Preferably, a codon optimized polynucleotide is a polynucleotide which is modified by comparison with the nucleic acid sequence in the organism from which the sequence originates in that it is adapted to the codon usage in one or more plant species. Typically, the polynucleotide, in particular the coding region, is adapted for expression in a given organism (in particular in a plant) by replacing at least one, or more than one of codons with one or more codons that are more frequently used in the genes of that organism (in particular of the plant). In accordance with the present invention, a codon optimized variant of a particular polynucleotide "from an organism" (or "derived from an organism") preferably shall be considered to be a polynucleotide derived from said organism.

Preferably, a codon-optimized polynucleotide shall encode for the same polypeptide having the same sequence as the polypeptide encoded by the non codon-optimized polynucleotide (i.e. the wild-type sequence). In the studies underlying the present invention, codon optimized polynucleotides were used (for the desaturases). The codon optimized polynucleotides are comprised by the T-DNA of the vector having a sequence as shown in SEQ ID NO: 3 (see table 130).

Preferably, a delta-6-elongase to be used in accordance with the present invention is derived from *Physcomitrella patens*. A preferred sequence of said delta-6-elongase is shown in SEQ ID NO:258. Preferably, said delta-6-elongase is encoded by a polynucleotide derived from *Physcomitrella patens*, in particular, said delta-6-elongase is encoded by a codon-optimized variant thereof (i.e. of said polynucleotide). Preferably, the polynucleotide encoding the delta-6-elongase derived from *Physcomitrella patens* is a polynucleotide having a sequence as shown in nucleotides 1267 to 2139 of SEQ ID NO: 3. The sequence of this polynucleotide is also shown in SEQ ID No: 257. (Thus, the polynucleotide encoding the delta-6-elongase derived from *Physcomitrella patens* preferably has a sequence as shown in SEQ ID NO: 257).

Preferably, a delta-5-desaturase to be used in accordance with the present invention is derived from *Thraustochytrium* sp. *Thraustochytrium* sp. in the context of the present invention preferably means *Thraustochytrium* sp. ATCC21685. A preferred sequence of said delta-5-desaturase is shown in SEQ ID NO:260. Preferably, said delta-5-desaturase is encoded by a polynucleotide derived from *Thraustochytrium* sp.; in particular, said delta-5-desaturase is encoded by a codon-optimized variant of said polynucleotide. Preferably, the polynucleotide encoding the delta-5-desaturase derived from *Thraustochytrium* sp. is a polynucleotide having a sequence as shown in nucleotides 3892 to 5211 of SEQ ID NO: 3. The sequence of this polynucleotide is also shown in SEQ ID No: 259. In accordance with the present invention, it is envisaged to express two or more polynucleotides (i.e. two or more copies of a polynucleotide) encoding a delta-5-desaturase derived from *Thraustochytrium* sp. (preferably two polynucleotides). Thus, the T-DNA, construct, plant, seed etc. of the present invention shall comprise two (or more) copies of a polynucleotide encoding a delta-5-desaturase derived from *Thraustochytrium* sp.

Preferably, a delta-6-desaturase to be used in accordance with the present invention is derived from *Ostreococcus tauri*. A preferred sequence of said delta-6-desaturase is shown in SEQ ID NO:262. Preferably, said delta-6-desaturase is encoded by a polynucleotide derived from *Ostreococcus tauri*; in particular, said delta-6-desaturase is encoded by a codon-optimized variant of said polynucleotide. Preferably, the polynucleotide encoding the delta-6-desaturase derived from *Ostreococcus tauri* is a polynucleotide having a sequence as shown in nucleotides 7802 to 9172 of SEQ ID NO: 3. The sequence of this polynucleotide is also shown in SEQ ID No: 261.

Preferably, a delta-6-elongase to be used in accordance with the present invention is derived from *Thalassiosira pseudonana*. A preferred sequence of said delta-6-elongase is shown in SEQ ID NO:264. Preferably, said delta-6-elongase is encoded by a polynucleotide derived from *Thalassiosira pseudonana*; in particular, said delta-6-elongase is encoded by a codon-optimized variant of said polynucleotide. Preferably, the polynucleotide encoding the delta-6-elongase derived from *Thalassiosira pseudonana* is a polynucleotide having a sequence as shown in nucleotides 12099 to 12917 of SEQ ID NO: 3. The sequence of this polynucleotide is also shown in SEQ ID No: 263.

Preferably, a delta-12-elongase to be used in accordance with the present invention is derived from *Phytophthora sojae*. A preferred sequence of said delta-12-elongase is shown in SEQ ID NO:266. Preferably, said delta-12-elongase is encoded by a polynucleotide derived from *Phytophthora sojae*; in particular, said delta-12-elongase is encoded by a codon-optimized variant of said polynucleotide. Preferably, the polynucleotide encoding the delta-12-elongase derived from *Phytophthora sojae* is a polynucleotide having a sequence as shown in nucleotides 14589 to 15785 of SEQ ID NO: 3. The sequence of this polynucleotide is also shown in SEQ ID No: 265.

Preferably, a delta-5-elongase to be used in accordance with the present invention is derived from *Ostreococcus tauri*. A preferred sequence of said delta-5-elongase is shown in SEQ ID NO:276. Preferably, said delta-5-elongase is encoded by a polynucleotide derived from *Ostreococcus tauri*; in particular, said delta-5-elongase is encoded by a codon-optimized variant of said polynucleotide. Preferably, the polynucleotide encoding the delta-5-elongase derived from *Ostreococcus tauri* is a polynucleotide having a sequence as shown in nucleotides 38388 to 39290 of SEQ ID NO: 3. The sequence of this polynucleotide is also shown in SEQ ID No: 275.

Preferably, an omega 3-desaturase to be used in accordance with the present invention is derived from *Pythium irregulare*. A preferred sequence of said omega 3-desaturase is shown in SEQ ID NO:268. Preferably, said omega 3-desaturase is encoded by a polynucleotide derived from *Pythium irregulare*; in particular, said omega 3-desaturase is encoded by a codon-optimized variant of said polynucleotide. Preferably, the polynucleotide encoding the omega 3-desaturase derived from *Pythium irregulare* is a polynucleotide having a sequence as shown in nucleotides 17690 to 18781 of SEQ ID NO: 3. The sequence of this polynucleotide is also shown in SEQ ID No: 267. In accordance with the present invention, it is envisaged to express two or more polynucleotides (i.e. two or more copies of a polynucleotide) encoding a omega 3-desaturase derived from *Pythium irregulare* (preferably two polynucleotides). Thus, the T-DNA, construct, plant, seed etc. of the present invention shall comprise two (or more) copies of a polynucleotide encoding a omega 3-desaturase derived from *Pythium irregulare*

Preferably, an omega 3-desaturase to be used in accordance with the present invention is derived from *Phytophthora infestans*. A preferred sequence of said omega 3-desaturase is shown in SEQ ID NO:270. Preferably, said omega 3-desaturase is encoded by a polynucleotide derived from *Phytophthora infestans*; in particular, said omega 3-desaturase is encoded by a codon-optimized variant of said polynucleotide. Preferably, the polynucleotide encoding the omega 3-desaturase derived from *Phytophthora infestans* is a polynucleotide having a sequence as shown in nucleotides 20441 to 21526 of SEQ ID NO: 3. The sequence of this polynucleotide is also shown in SEQ ID No: 269.

In accordance with the present invention, it is in particular envisaged to express two or more polynucleotides encoding for omega 3-desaturases in the plant. Preferably, at least one polynucleotide encoding an omega 3-desaturase from *Phytophthora infestans* and at least one polynucleotide (in particular two polynucleotides, i.e. two copies of a polynucleotide) encoding an omega 3-desaturase from *Pythium irregulare* are expressed.

Preferably, a delta-4-desaturase to be used in accordance with the present invention is derived from *Thraustochytrium* sp. A preferred sequence of said delta-4-desaturase is shown in SEQ ID NO:272. Preferably, said delta-4-desaturase is encoded by a polynucleotide derived from *Thraustochytrium* sp.; in particular, said delta-4-desaturase is encoded by a codon-optimized variant of said polynucleotide. Preferably, the polynucleotide encoding the delta-4-desaturase derived from *Thraustochytrium* sp. is a polynucleotide having a sequence as shown in nucleotides 26384 to 27943 of SEQ ID NO: 3. The sequence of this polynucleotide is also shown in SEQ ID No: 271.

Preferably, a delta-4-desaturase to be used in accordance with the present invention is derived from *Pavlova lutheri*. A preferred sequence of said delta-4-desaturase is shown in SEQ ID NO:274. Preferably, said delta-4-desaturase is encoded by a polynucleotide derived from *Pavlova lutheri*; in particular, said delta-4-desaturase is encoded by a codon-optimized variant of said polynucleotide. Preferably, the polynucleotide encoding the delta-4-desaturase derived from *Pavlova lutheri* is a polynucleotide having a sequence as shown in nucleotides 34360 to 35697 of SEQ ID NO: 3. The sequence of this polynucleotide is also shown in SEQ ID No: 273.

In accordance with the present invention, it is further envisaged to express two non-identical polynucleotides encoding, preferably non-identical delta-4-desaturases in the plant. Preferably, at least one polynucleotide encoding a delta-4-desaturase from *Thraustochytrium* sp. and at least one polynucleotide encoding a delta-4-desaturase from *Pavlova lutheri* are expressed.

Preferably, a delta-15-desaturase to be used in accordance with the present invention is derived from *Cochliobolus heterostrophus*. Preferably, said delta-15-desaturase is encoded by a polynucleotide derived from *Cochliobolus heterostrophus*; in particular, said delta-15-desaturase is encoded by a codon-optimized variant of said polynucleotide. Preferably, the polynucleotide encoding the delta-15-desaturase derived from *Cochliobolus heterostrophus* is a polynucleotide having a sequence as shown in nucleotides 2151 to 3654 of SEQ ID NO: 9.

As set forth above, the polynucleotide encoding a delta-6-elongase can be derived from *Physcomitrella patens*. Moreover, the polynucleotide encoding a delta-6-elongase can be derived from *Thalassiosira pseudonana*. In particular, it is envisaged in the context of the present invention to express at least one polynucleotide encoding a delta-6-elongase from *Physcomitrella patens* and at least one polynucleotide encoding a delta-6-elongase from *Thalassiosira pseudonana* in the plant. Thus, the T-DNA, plant, seed etc. shall comprise the said polynucleotides.

A polynucleotide encoding a polypeptide having a desaturase or elongase activity as specified above is obtainable or obtained in accordance with the present invention for example from an organism of genus *Ostreococcus, Thraustochytrium, Euglena, Thalassiosira, Phytophthora, Pythium, Cochliobolus, Physcomitrella*. However, orthologs, paralogs or other homologs may be identified from other species. Preferably, they are obtained from plants such as algae, for example *Isochrysis, Mantoniella, Crypthecodinium*, algae/diatoms such as *Phaeodactylum*, mosses such as *Ceratodon*, or higher plants such as the Primulaceae such as *Aleuritia, Calendula stellata, Osteospermum spinescens* or *Osteospermum hyoseroides*, microorganisms such as fungi, such as *Aspergillus, Entomophthora, Mucor* or *Mortierella*, bacteria such as *Shewanella*, yeasts or animals. Preferred animals are nematodes such as *Caenorhabditis*, insects or vertebrates. Among the vertebrates, the nucleic acid molecules may, preferably, be derived from Euteleostomi, Actinopterygii; Neopterygii; Teleostei; Euteleostei, Protacanthopterygii, Salmoniformes; Salmonidae or *Oncorhynchus*, more preferably, from the order of the Salmoniformes, most preferably, the family of the Salmonidae, such as the genus *Salmo*, for example from the genera and species *Oncorhynchus mykiss, Trutta trutta* or *Salmo trutta fario*. Moreover, the nucleic acid molecules may be obtained from the diatoms such as the genera *Thalassiosira* or *Phaeodactylum*.

Thus, the term "polynucleotide" as used in accordance with the present invention further encompasses variants or derivatives of the aforementioned specific polynucleotides representing orthologs, paralogs or other homologs of the polynucleotide of the present invention. Moreover, variants or derivatives of the polynucleotide of the present invention also include artificially generated muteins. Said muteins include, e.g., enzymes which are generated by mutagenesis techniques and which exhibit improved or altered substrate specificity, or codon optimized polynucleotides.

Nucleic acid variants or derivatives according to the invention are polynucleotides which differ from a given reference polynucleotide by at least one nucleotide substitution, addition and/or deletion. If the reference polynucleotide codes for a protein, the function of this protein is conserved in the variant or derivative polynucleotide, such that a variant nucleic acid sequence shall still encode a polypeptide having a desaturase or elongase activity as specified above. Variants or derivatives also encompass polynucleotides comprising a nucleic acid sequence which is capable of hybridizing to the aforementioned specific nucleic acid sequences, preferably, under stringent hybridization conditions. These stringent conditions are known to the skilled in the art and can be found in Current Protocols in Molecular Biology, John Wiley & Sons, N. Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature ranges depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA: DNA hybrids are, preferably, 0.1×SSC and 20° C. to 45° C., preferably between 30° C. and 45° C. The hybridization conditions for DNA:RNA hybrids are, preferably, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. In an embodiment, stringent hybridization conditions encompass hybridization at 65° C. in 1×SSC, or at 42° C. in 1×SSC and 50% formamide, followed by washing at 65° C. in 0.2×SSC. In another embodiment, stringent hybridization conditions encompass hybridization at 65° C. in 1×SSC, or at 42° C. in 1×SSC and 50% formamide, followed by washing at 65° C. in 0.1×SSC.

Alternatively, polynucleotide variants are obtainable by PCR-based techniques such as mixed oligonucleotide primer based amplification of DNA, i.e. using degenerate primers against conserved domains of the polypeptides of the present invention. Conserved domains of the polypeptide of the present invention may be identified by a sequence comparison of the nucleic acid sequences of the polynucleotides or the amino acid sequences of the polypeptides of the present invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 50%, at least 55%, at least 60%, at least 65%, at least 70%, at least 75%, at least 80%, at least 85%, at least 90%, at least 95%, at least 98% or at least 99% identical to the nucleic acid coding sequences shown in any one of the T-DNA sequences given in the corresponding tables of the examples. Of course, the variants must retain the function of the respective enzyme, e.g. a variant of a delta-4-desaturase shall have delta-4-desaturase activity.

The percent identity values are, preferably, calculated over the entire amino acid or nucleic acid sequence region. A series of programs based on a variety of algorithms is available to the skilled worker for comparing different sequences. In a preferred embodiment, the percent identity between two amino acid sequences is determined using the Needleman and Wunsch algorithm (Needleman 1970, J. Mol. Biol. (48):444-453) which has been incorporated into the needle program in the EMBOSS software package (EMBOSS: The European Molecular Biology Open Software Suite, Rice, P., Longden, I., and Bleasby, A., Trends in Genetics 16(6), 276-277, 2000), a BLOSUM62 scoring matrix, and a gap opening penalty of 10 and a gap extension penalty of 0.5. Guides for local installation of the EMBOSS package as well as links to WEB-Services can be found at http://emboss.sourceforge.net. A preferred, non-limiting example of parameters to be used for aligning two amino acid sequences using the needle program are the default parameters, including the EBLOSUM62 scoring matrix, a gap opening penalty of 10 and a gap extension penalty of 0.5. In yet another preferred embodiment, the percent identity between two nucleotide sequences is determined using the needle program in the EMBOSS software package (EMBOSS: The European Molecular Biology Open Software Suite, Rice, P., Longden, I., and Bleasby, A., Trends in Genetics 16(6), 276-277, 2000), using the EDNAFULL scoring matrix and a gap opening penalty of 10 and a gap extension penalty of 0.5. A preferred, non-limiting example of parameters to be used in conjunction for aligning two nucleic acid sequences using the needle program are the default parameters, including the EDNAFULL scoring matrix, a gap opening penalty of 10 and a gap extension penalty of 0.5. The nucleic acid and protein sequences of the present invention can further be used as a "query sequence" to perform a search against public databases to, for example, identify other family members or related sequences. Such searches can be performed using the BLAST series of programs (version 2.2) of Altschul et al. (Altschul 1990, J. Mol. Biol. 215:403-10). BLAST using desaturase and elongase nucleic acid sequences of the invention as query sequence can be performed with the BLASTn, BLASTx or the tBLASTx program using default parameters to obtain either nucleotide sequences (BLASTn, tBLASTx) or amino acid sequences (BLASTx) homologous to desaturase and elongase sequences of the invention. BLAST using desaturase and elongase protein sequences of the invention as query sequence can be performed with the BLASTp or the tBLASTn program using default parameters to obtain either amino acid sequences (BLASTp) or nucleic acid sequences (tBLASTn) homologous to desaturase and elongase sequences of the invention. To obtain gapped alignments for comparison purposes, Gapped BLAST using default parameters can be utilized as described in Altschul et al. (Altschul 1997, Nucleic Acids Res. 25(17):3389-3402).

In an embodiment, a variant of a polynucleotide encoding a desaturase or elongase as referred to herein is, preferably, a polynucleotide comprising a nucleic acid sequence selected from the group consisting of:
- a) a nucleic acid sequence being at least 70%, 80%, or 90% identical to the nucleic acid sequence having a nucleotide sequence as shown in SEQ ID NOs: 257, 259, 261, 263, 265, 267, 269, 271, 273, or 275,
- b) a nucleic acid sequence encoding a polypeptide which is at least 70%, 80, or 90% identical to a polypeptide having an amino acid sequence as shown in SEQ ID NOs: 258, 260, 262, 264, 266, 268, 270, 272, 274, or 276, and
- c) a nucleic acid sequence which is capable of hybridizing under stringent conditions to i) a nucleic acid sequence having a nucleotide sequence as shown in SEQ ID NOs: 257, 259, 261, 263, 265, 267, 269, 271, 273, or 275, or to ii) a nucleic acid sequence encoding a polypeptide having an amino acid sequence as shown in SEQ ID NOs: 258, 260, 262, 264, 266, 268, 270, 272, 274, or 276.

As set forth above, the polypeptide encoded by said nucleic acid must retain the function of the respective enzyme. For example, the polypeptide having a sequence as shown in SEQ ID NO: 270 has omega-3-desaturase activity. Accordingly, the variant of this polypeptide also shall have omega-3-desaturase activity. The function of desaturases and elongases of the present invention is analyzed in Example 22.

Thus, a polynucleotide encoding a desaturase or elongase as referred to herein is, preferably, a polynucleotide comprising a nucleic acid sequence selected from the group consisting of:
- a) a nucleic acid sequence having a nucleotide sequence as shown in SEQ ID NO: 257, 259, 261, 263, 265, 267, 269, 271, 273, or 275,
- b) a nucleic acid sequence encoding a polypeptide having an amino acid sequence as shown in SEQ ID NO: 258, 260, 262, 264, 266, 268, 270, 272, 274, or 276
- c) a nucleic acid sequence being at least 70%, 80%, or 90% identical to the nucleic acid sequence having a nucleotide sequence as shown in SEQ ID NOs: 257, 259, 261, 263, 265, 267, 269, 271, 273, or 275,
- d) a nucleic acid sequence encoding a polypeptide which is at least 70%, 80, or 90% identical to a polypeptide having an amino acid sequence as shown in SEQ ID NOs 258, 260, 262, 264, 266, 268, 270, 272, 274, or 276, and
- e) a nucleic acid sequence which is capable of hybridizing under stringent conditions to i) a nucleic acid sequence having a nucleotide sequence as shown in SEQ ID NOs: 257, 259, 261, 263, 265, 267, 269, 271, 273, or 275, or to ii) a nucleic acid sequence encoding a polypeptide having an amino acid sequence as shown in SEQ ID NOs: 258, 260, 262, 264, 266, 268, 270, 272, 274, or 276.

The event LBFLFK comprises two T-DNA insertions, the insertions being designated LBFLFK Locus 1 and LBFLFK Locus 2. Plants comprising this insertion were generated by transformation with the T-DNA vector having a sequence as shown in SEQ ID NO: 3. Sequencing of the insertions present in the plant revealed that each locus contained a point mutation in a coding sequence resulting in a single amino acid exchange. The mutations did not affect the function of the genes. Locus 1 has a point mutation in the coding sequence for the delta-12 desaturase from *Phythophthora sojae* (d12Des(Ps)). The resulting polynucleotide has a sequence as shown in SEQ ID NO: 324. Said polynucleotide encodes a polypeptide having a sequence as shown in SEQ ID NO: 325. Locus 2 has a point mutation in the coding sequence for the delta-4 desaturase from *Pavlova lutheri* (d4Des(PI)). The resulting polynucleotide has a sequence as shown in SEQ ID NO: 326. Said polynucleotide encodes a polypeptide having a sequence as shown in SEQ ID NO: 327. The aforementioned polynucleotides are considered as variants of the polynucleotide encoding the delta-12 desaturase from *Phythophthora sojae* and the polynucleotide encoding the delta-4 desaturase from *Pavlova lutheri*. The polynucleotides are considered as variants and can be used in the context of the present invention.

A polynucleotide comprising a fragment of any nucleic acid, particularly of any of the aforementioned nucleic acid sequences, is also encompassed as a polynucleotide of the present invention. The fragments shall encode polypeptides which still have desaturase or elongase activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The variant polynucleotides or fragments referred to above, preferably, encode polypeptides retaining desaturase or elongase activity to a significant extent, preferably, at least 10%, at least 20%, at least 30%, at least 40%, at least 50%, at least 60%, at least 70%, at least 80% or at least 90% of the desaturase or elongase activity exhibited by any of the polypeptide comprised in any of the T-DNAs given in the accompanying Examples (in particular of the desaturase or elongases listed in Table 11 and 130)

Further enzymes beneficial for the present invention as described in detail in the examples are aclytransferases and transacylases (cf. WO 2011161093 A1). One group of acyltransferases having three distinct enzymatic activities are enzymes of the "Kennedy pathway", which are located on the cytoplasmic side of the membrane system of the endoplasmic reticulum (ER). The ER-bound acyltransferases in the microsomal fraction use acyl-CoA as the activated form of fatty acids. Glycerol-3-phosphate acyltransferase (GPAT) catalyzes the incorporation of acyl groups at the sn-1 position of glycerol-3-phosphate. 1-Acylglycerol-3-phosphate acyltransferase, also known as lysophosphatidic acid acyltransferase (LPAAT), catalyze the incorporation of acyl groups at the sn-2 position of lysophosphatidic acid (LPA). After dephosphorylation of phosphatidic acid by phosphatidic acid phosphatase (PAP), diacylglycerol acyltransferase (DGAT) catalyzes the incorporation of acyl groups at the sn-3 position of diacylglycerols. Further enzymes directly involved in TAG biosynthesis—apart from the said Kennedy pathway enzymes—are the phospholipid diacylglycerol acyltransferase (PDAT), an enzyme that transfers acyl groups from the sn-2 position of membrane lipids to the sn-3 position of diacylglycerols, and diacylglyceroldiacylglycerol transacylase (DDAT), an enzyme that transfers acyl-groups from the sn-2 position of one diacylglycerol-molecule to the sn-3 position of another diacylglycerol-molecule. Lysophospholipid acyltransferase (LPLAT) represents a class of acyltransferases that are capable of incorporating activated acyl groups from acyl-CoA to membrane lipids, and possibly also catalyze the reverse reaction. More specifically, LPLATs can have activity as lysophosphophatidylethanolamine acyltransferase (LPEAT) and lysophosphatidylcholine acyltransferase (LPCAT). Further enzymes, such as lecithin cholesterol acyltransferase (LCAT) can be involved in the transfer of acyl groups from membrane lipids into triacylglycerides, as well.

The documents WO 98/54302 and WO 98/54303 disclose a human LPAAT and its potential use for the therapy of diseases, as a diagnostic, and a method for identifying modulators of the human LPAAT. Moreover, a variety of acyltransferases with a wide range of enzymatic functions have been described in the documents WO 98/55632, WO 98/55631, WO 94/13814, WO 96/24674, WO 95/27791, WO 00/18889, WO 00/18889, WO 93/10241, Akermoun 2000, Biochemical Society Transactions 28: 713-715, Tumaney 1999, Biochimica et Biophysica Acta 1439: 47-56, Fraser 2000, Biochemical Society Transactions 28: 715-7718, Stymne 1984, Biochem. J. 223: 305-314, Yamashita 2001, Journal of Biological Chemistry 276: 26745-26752, and WO 00/18889.

In order to express the polynucleotides encoding the desaturases or elongases as set forth in connection with the present invention, the polynucleotides shall be operably linked to expression control sequences. Preferably, the expression control sequences are heterologous with respect to the polynucleotides operably linked thereto. It is to be understood that each polynucleotide is operably linked to an expression control sequence.

The term "expression control sequence" as used herein refers to a nucleic acid sequence which is capable of governing, i.e. initiating and controlling, transcription of a nucleic acid sequence of interest, in the present case the nucleic sequences recited above. Such a sequence usually comprises or consists of a promoter or a combination of a promoter and enhancer sequences. Expression of a polynucleotide comprises transcription of the nucleic acid molecule, preferably, into a translatable mRNA. Additional regulatory elements may include transcriptional as well as translational enhancers. The following promoters and expression control sequences may be, preferably, used in an expression vector according to the present invention. The cos, tac, trp, tet, trp-tet, Ipp, lac, Ipp-lac, laclq, T7, T5, T3, gal, trc, ara, SP6, λ-PR or λ-PL promoters are, preferably, used in Gram-negative bacteria. For Gram-positive bacteria, promoters amy and SP02 may be used. From yeast or fungal promoters ADC1, AOX1r, GAL1, MFα, AC, P-60, CYC1, GAPDH, TEF, rp28, ADH are, preferably, used. For animal cell or organism expression, the promoters CMV-, SV40-, RSV-promoter (Rous sarcoma virus), CMV-enhancer, SV40-enhancer are preferably used. From plants the promoters CaMV/35S (Franck 1980, Cell 21: 285-294], PRP1 (Ward 1993, Plant. Mol. Biol. 22), SSU, OCS, lib4, usp, STLS1, B33, nos or the ubiquitin or phaseolin promoter. Also preferred in this context are inducible promoters, such as the promoters described in EP 0388186 A1 (i.e. a benzylsulfonamide-inducible promoter), Gatz 1992, Plant J. 2:397-404 (i.e. a tetracyclin-inducible promoter), EP 0335528 A1 (i.e. a abscisic-acid-inducible promoter) or WO 93/21334 (i.e. a ethanol- or cyclohexenol-inducible promoter). Further suitable plant promoters are the promoter of cytosolic FBPase or the ST-LSI promoter from potato (Stockhaus 1989, EMBO J. 8, 2445), the phosphoribosyl-pyrophosphate amidotransferase promoter from *Glycine max* (Genbank accession No. U87999) or the node-specific promoter described in EP 0249676 A1. Particularly preferred are promoters which enable the expression in tissues which are involved in the biosynthesis of fatty acids. Also particularly preferred are seed-specific promoters such as the USP promoter in accordance with the practice, but also other promoters such as the LeB4, DC3, phaseolin or napin promoters. Further especially preferred promoters are seed-specific promoters which can be used for monocotyledonous or dicotyledonous plants and which are described in U.S. Pat. No. 5,608,152 (napin promoter from oilseed rape), WO 98/45461 (oleosin promoter from Arobidopsis, U.S. Pat. No. 5,504,200 (phaseolin promoter from *Phaseolus vulgaris*), WO 91/13980 (Bce4 promoter from *Brassica*), by Baeumlein et al., Plant J., 2, 2, 1992:233-239 (LeB4 promoter from a legume), these promoters being suitable for dicots. The following promoters are suitable for monocots: Ipt-2 or Ipt-1 promoter from barley (WO 95/15389 and WO 95/23230), hordein promoter from barley and other promoters which are suitable and which are described in WO 99/16890. In principle, it is possible to use all natural promoters together with their regulatory sequences, such as those mentioned above, for the novel process. Likewise, it is possible and advantageous to use synthetic promoters, either additionally or alone, especially when they mediate a seed-specific expression, such as, for example, as described in WO 99/16890. Preferably, the polynucleotides encoding the desaturases and elongases as referred to herein are expressed in the seeds of the plants. In a particular embodiment, seed-specific promoters are utilized to enhance the production of the desired PUFA or VLC-PUFA. In a particular preferred embodiment the polynucleotides encoding the desaturates or elongases are operably linked to expression control sequences used for the the expression of the respective desaturases and elongases in the Examples section (see e.g. the promoters used for expressing the elongases and desaturases in VC-LTM593-1qcz rc, Table 11). The sequence of this vector is shown in SEQ ID NO: 3.

The term "operatively linked" as used herein means that the expression control sequence and the nucleic acid of interest are linked so that the expression of the said nucleic acid of interest can be governed by the said expression control sequence, i.e. the expression control sequence shall be functionally linked to the said nucleic acid sequence to be expressed. Accordingly, the expression control sequence and, the nucleic acid sequence to be expressed may be physically linked to each other, e.g., by inserting the expression control sequence at the 5'end of the nucleic acid sequence to be expressed. Alternatively, the expression control sequence and the nucleic acid to be expressed may be merely in physical proximity so that the expression control sequence is capable of governing the expression of at least one nucleic acid sequence of interest. The expression control sequence and the nucleic acid to be expressed are, preferably, separated by not more than 500 bp, 300 bp, 100 bp, 80 bp, 60 bp, 40 bp, 20 bp, 10 bp or 5 bp. Preferred polynucleotides of the present invention comprise, in addition to a promoter, a terminator sequence operatively linked to the nucleic acid sequence of interest.

The term "terminator" as used herein refers to a nucleic acid sequence which is capable of terminating transcription. These sequences will cause dissociation of the transcription machinery from the nucleic acid sequence to be transcribed. Preferably, the terminator shall be active in plants and, in particular, in plant seeds. Suitable terminators are known in the art and, preferably, include polyadenylation signals such as the SV40-poly-A site or the tk-poly-A site or one of the plant specific signals indicated in Loke et al. (Loke 2005, Plant Physiol 138, pp. 1457-1468), downstream of the nucleic acid sequence to be expressed.

The invention furthermore relates to recombinant nucleic acid molecules comprising at least one nucleic acid sequence which codes for a polypeptide having desaturase and/or elongase activity which is modified by comparison with the nucleic acid sequence in the organism from which the sequence originates in that it is adapted to the codon usage in one or more plant species.

For the purposes of the invention "recombinant" means with regard to, for example, a nucleic acid sequence, an expression cassette (=gene construct) or a vector comprising the nucleic acid sequences used in the process according to the invention or a host cell transformed with the nucleic acid sequences, expression cassette or vector used in the process according to the invention, all those constructions brought about by recombinant methods in which either the nucleic acid sequence, or a genetic control sequence which is operably linked with the nucleic acid sequence, for example a promoter, or are not located in their natural genetic environment or have been modified by recombinant methods.

Preferably, the plant cell (or plant) of the present invention is an oilseed crop plant cell (or oilseed crop plant). More preferably, said oilseed crop is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma* cacoa), peanut (*Arachis* sp.), hemp, camelina, crambe, oil palm, coconuts, groundnuts, sesame seed, castor bean, *lesquerella*, tallow tree, sheanuts, tungnuts, kapok fruit, poppy seed, jojoba seeds and *perilla*. Preferred plants to be used for introducing the polynucleotide or T-DNA of the invention are plants which are capable of synthesizing fatty acids, such as all dicotyledonous or monocotyledonous plants, algae or mosses. It is to be understood that host cells derived from a plant may also be used for producing a plant according to the present invention. Preferred plants are selected from the group of the plant families Adelotheciaceae, Anacardiaceae, Arecaceae, Asteraceae, Apiaceae, Betulaceae, Boraginaceae, Brassicaceae, Bromeliaceae, Caricaceae, Cannabaceae, Convolvulaceae, Chenopodiaceae, Compositae, Crypthecodiniaceae, Cruciferae, Cucurbitaceae, Ditrichaceae, Elaeagnaceae, Ericaceae, Euphorbiaceae, Fabaceae, Geraniaceae, Gramineae, Juglandaceae, Lauraceae, Leguminosae, Linaceae, Malvaceae, Moringaceae, Marchantiaceae, Onagraceae, Olacaceae, Oleaceae, Papaveraceae, Piperaceae, Pedaliaceae, Poaceae, Solanaceae, Prasinophyceae or vegetable plants or ornamentals such as *Tagetes*. Examples which may be mentioned are the following plants selected from the group consisting of: Adelotheciaceae such as the genera *Physcomitrella*, such as the genus and species *Physcomitrella patens*, Anacardiaceae such as the genera *Pistacia, Mangifera, Anacardium*, for example the genus and species *Pistacia vera* [pistachio], *Mangifer indica* [mango] or *Anacardium occidentale* [cashew], Asteraceae, such as the genera *Calendula, Carthamus, Centaurea, Cichorium, Cynara, Helianthus, Lactuca, Locusta, Tagetes, Valeriana*, for example the genus and species *Calendula officinalis* [common marigold], *Carthamus tinctorius* [safflower], *Centaurea cyanus* [cornflower], *Cichorium intybus* [chicory], *Cynara scolymus* [artichoke], *Helianthus annus* [sunflower], *Lactuca sativa, Lactuca crispa, Lactuca esculenta, Lactuca scariola* L. ssp. *sativa, Lactuca scariola* L. var. *integrata, Lactuca scariola* L. var. *integrifolia, Lactuca sativa* subsp. *romana, Locusta communis, Valeriana locusta* [salad vegetables], *Tagetes lucida, Tagetes erecta* or *Tagetes tenuifolia* [african or french marigold], Apiaceae, such as the genus *Daucus*, for example the genus and species *Daucus carota* [carrot], Betulaceae, such as the genus *Corylus*, for example the genera and species *Corylus avellana* or *Corylus colurna* [hazelnut], Boraginaceae, such as the genus *Borago*, for example the genus and species *Borago officinalis* [borage], Brassicaceae, such as the genera *Brassica, Melanosinapis, Sinapis, Arabadopsis*, for example the genera and species *Brassica napus, Brassica rapa* ssp. [oilseed rape], *Sinapis arvensis Brassica juncea, Brassica juncea* var. *juncea, Brassica juncea* var. *crispifolia, Brassica juncea* var. *foliosa, Brassica nigra, Brassica sinapioides, Melanosinapis communis* [mustard], *Brassica oleracea* [fodder beet] or *Arabidopsis thaliana*, Bromeliaceae, such as the genera *Anana, Bromelia* (pineapple), for example the genera and species *Anana comosus, Ananas ananas* or *Bromelia comosa* [pineapple], Caricaceae, such as the genus *Carica*, such as the genus and species *Carica papaya* [pawpaw], Cannabaceae, such as the genus *Cannabis*, such as the genus and species *Cannabis sativa* [hemp], Convolvulaceae, such as the genera *Ipomea, Convolvulus*, for example the genera and species *Ipomoea batatus, Ipomoea pandurata, Convolvulus batatas, Convolvulus tiliaceus, Ipomoea fastigiata, Ipomoea tiliacea, Ipomoea triloba* or *Convolvulus panduratus* [sweet potato, batate], Chenopodiaceae, such as the genus *Beta*, such as the genera and species *Beta vulgaris, Beta vulgaris* var. *altissima, Beta vulgaris* var. *Vulgaris, Beta maritima, Beta vulgaris* var. *perennis, Beta vulgaris* var. *conditiva* or *Beta vulgaris* var. *esculenta* [sugarbeet], Crypthecodiniaceae, such as the genus *Crypthecodinium*, for example the genus and species *Cryptecodinium cohnii*, Cucurbitaceae, such as the genus *Cucurbita*, for example the genera and species *Cucurbita maxima, Cucurbita mixta, Cucurbita pepo* or *Cucurbita moschata* [pumpkin/squash], Cymbellaceae such as the genera *Amphora, Cymbella, Okedenia, Phaeodactylum, Reimeria*, for example the genus and species *Phaeodactylum tricornutum*, Ditrichaceae such as the genera Ditrichaceae, *Astomiopsis, Ceratodon, Chrysoblastella, Ditrichum, Distichium, Eccremidium, Lophidion, Philibertiella, Pleuridium, Saelania, Trichodon, Skottsbergia*, for example the genera and species *Ceratodon antarcticus, Ceratodon* columbiae, *Ceratodon* heterophyllus, *Ceratodon* purpureus, *Ceratodon* purpureus, *Ceratodon purpureus* ssp. *convolutus, Ceratodon, purpureus* spp. *stenocarpus, Ceratodon purpureus* var. *rotundifolius, Ceratodon ratodon, Ceratodon stenocarpus, Chrysoblastella chilensis, Ditrichum ambiguum, Ditrichum brevisetum, Ditrichum crispatissimum, Ditrichum difficile, Ditrichum falcifolium, Ditrichum flexicaule, Ditrichum giganteum, Ditrichum heteromallum, Ditrichum lineare, Ditrichum lineare, Ditrichum montanum, Ditrichum montanum, Ditrichum pallidum, Ditrichum punctulatum, Ditrichum pusillum, Ditrichum pusillum* var. *tortile, Ditrichum rhynchostegium, Ditrichum schimperi, Ditrichum tortile, Distichium capillaceum, Distichium hagenii, Distichium inclinatum, Distichium macounii, Eccremidium floridanum, Eccremidium whiteleggei, Lophidion strictus, Pleuridium acuminatum, Pleuridium alternifolium, Pleuridium holdridgei, Pleuridium mexicanum, Pleuridium ravenelii, Pleuridium subulatum, Saelania glaucescens, Trichodon borealis, Trichodon cylindricus* or *Trichodon cylindricus* var. *oblongus*, Elaeagnaceae such as the genus *Elaeagnus*, for example the genus and species *Olea europaea* [olive], Ericaceae such as the genus *Kalmia*, for example the genera and species *Kalmia latifolia, Kalmia angustifolia, Kalmia microphylla, Kalmia polifolia, Kalmia occidentalis, Cistus chamaerhodendros* or *Kalmia lucida* [mountain laurel], Euphorbiaceae such as the genera *Manihot, Janipha, Jatropha, Ricinus*, for example the genera and species *Manihot utilissima, Janipha manihot, Jatropha manihot, Manihot aipil, Manihot dulcis, Manihot manihot, Manihot melanobasis, Manihot esculenta* [manihot] or *Ricinus communis* [castor-oil plant], Fabaceae such as the genera *Pisum, Albizia, Cathormion, Feuillea, Inga, Pithecolobium, Acacia, Mimosa, Medicajo, Glycine, Dolichos, Phaseolus, Soja*, for example the genera and species *Pisum sativum, Pisum arvense, Pisum humile* [pea], *Albizia berteriana, Albizia julibrissin, Albizia lebbeck, Acacia berteriana, Acacia littoralis, Albizia berteriana, Albizzia berteriana, Cathormion berteriana, Feuillea berteriana, Inga fragrans, Pithecellobium berterianum, Pithecellobium fragrans, Pithecolobium berterianum, Pseudalbizzia berteriana, Acacia julibrissin, Acacia nemu, Albizia nemu, Feuilleea julibrissin, Mimosa julibrissin, Mimosa speciosa, Sericanrda julibrissin, Acacia lebbeck, Acacia macrophylla, Albizia lebbek, Feuilleea lebbeck, Mimosa lebbeck, Mimosa speciosa* [silk tree], *Medicago sativa, Medicago falcata, Medicago varia* [alfalfa], *Glycine max Dolichos soja, Glycine gracilis, Glycine hispida, Phaseolus max, Soja hispida* or *Soja max* [soybean], Funariaceae such as the genera *Aphanorrhegma, Entosthodon, Funaria, Physcomitrella, Physcomitrium*, for example the genera and species *Aphanorrhegma serratum, Entosthodon attenuatus, Entosthodon bolanderi, Entosthodon bonplandii, Entosthodon californicus, Entosthodon drummondii, Entosthodon jamesonii, Entosthodon leibergii, Entosthodon neoscoticus, Entosthodon rubrisetus, Entosthodon spathulifolius, Entosthodon tucsoni, Funaria americana, Funaria bolanderi, Funaria calcarea, Funaria californica, Funaria calvescens, Funaria convoluta, Funaria flavicans, Funaria groutiana, Funaria hygrometrica, Funaria hygrometrica* var. *arctica, Funaria hygrometrica* var. *calvescens, Funaria hygrometrica* var. *convoluta, Funaria hygrometrica* var. *muralis, Funaria hygrometrica* var. *utahensis, Funaria microstoma, Funaria microstoma* var. *obtusifolia, Funaria muhlenbergii, Funaria orcuttii, Funaria plano-convexa, Funaria polaris, Funaria ravenelii, Funaria rubriseta, Funaria serrata, Funaria sonorae, Funaria sublimbatus, Funaria tucsoni, Physcomitrella californica, Physcomitrella patens, Physcomitrella readeri, Physco-mitrium australe, Physcomitrium californicum, Physcomitrium collenchymatum, Physcomitrium coloradense, Physcomitrium cupuliferum, Physcomitrium drummondii, Physcomitrium eurystomum, Physcomitrium flexifolium, Physcomitrium hookeri, Physcomitrium hookeri* var. *serratum, Physcomitrium immersum, Physcomitrium kellermanii, Physcomitrium megalocarpum, Physcomitrium pyriforme, Physcomitrium pyriforme* var. *serratum, Physcomitrium rufipes, Physcomitrium sandbergii, Physcomitrium subsphaericum, Physcomitrium washingtoniense*, Geraniaceae, such as the genera *Pelargonium, Cocos, Oleum*, for example the genera and species *Cocos nucifera, Pelargonium grossularioides* or *Oleum cocois* [coconut], Gramineae, such as the genus *Saccharum*, for example the genus and species *Saccharum officinarum*, Juglandaceae, such as the genera *Juglans, Wallia*, for example the genera and species *Juglans regia, Juglans ailanthifolia, Juglans sieboldiana, Juglans cinerea, Wallia cinerea, Juglans bixbyi, Juglans californica, Juglans hindsii, Juglans intermedia, Juglans jamaicensis, Juglans major, Juglans microcarpa, Juglans nigra* or *Wallia nigra* [walnut], Lauraceae, such as the genera *Persea, Laurus*, for example the genera and species *Laurus nobilis* [bay], *Persea americana, Persea gratissima* or *Persea persea* [avocado], Leguminosae, such as the genus *Arachis*, for example the genus and species *Arachis hypogaea* [peanut], Linaceae, such as the genera *Linum, Adenolinum*, for example the genera and species *Linum usitatissimum, Linum humile, Linum austriacum, Linum bienne, Linum angustifolium, Linum catharticum, Linum flavum, Linum grandiflorum, Adenolinum grandiflorum, Linum lewisii, Linum narbonense, Linum perenne, Linum perenne* var. *lewisii, Linum pratense* or *Linum trigynum* [linseed], Lythrarieae, such as the genus *Punica*, for example the genus and species *Punica granatum* [pomegranate], Malvaceae, such as the genus *Gossypium*, for example the genera and species *Gossypium hirsutum, Gossypium arboreum, Gossypium barbadense, Gossypium herbaceum* or *Gossypium thurberi* [cotton], Marchantiaceae, such as the genus *Marchantia*, for example the genera and species *Marchantia berteroana, Marchantia foliacea*,

*Marchantia macropora*, Musaceae, such as the genus *Musa*, for example the genera and species *Musa nana, Musa acuminata, Musa paradisiaca, Musa* spp. [banana], Onagraceae, such as the genera *Camissonia, Oenothera*, for example the genera and species *Oenothera biennis* or *Camissonia brevipes* [evening primrose], Palmae, such as the genus *Elaeis*, for example the genus and species *Elaeis guineensis* [oil palm], Papaveraceae, such as the genus *Papaver*, for example the genera and species *Papaver orientale, Papaver rhoeas, Papaver dubium* [poppy], Pedaliaceae, such as the genus *Sesamum*, for example the genus and species *Sesamum indicum* [sesame], Piperaceae, such as the genera *Piper, Artanthe, Peperomia, Steffensia*, for example the genera and species *Piper aduncum, Piper amalago, Piper angustifolium, Piper auritum, Piper betel, Piper cubeba, Piper longum, Piper nigrum, Piper retrofractum, Artanthe adunca, Artanthe elongata, Peperomia elongata, Piper elongatum, Steffensia elongata* [cayenne pepper], Poaceae, such as the genera *Hordeum, Secale, Avena, Sorghum, Andropogon, Holcus, Panicum, Oryza, Zea* (maize), *Triticum*, for example the genera and species *Hordeum vulgare, Hordeum jubatum, Hordeum murinum, Hordeum secalinum, Hordeum distichon, Hordeum aegiceras, Hordeum hexastichon, Hordeum hexastichum, Hordeum irregulare, Hordeum sativum, Hordeum secalinum* [barley], *Secale cereale* [rye], *Avena sativa, Avena fatua, Avena byzantina, Avena fatua* var. *sativa, Avena hybrida* [oats], *Sorghum bicolor, Sorghum halepense, Sorghum saccharatum, Sorghum vulgare, Andropogon drummondii, Holcus bicolor, Holcus sorghum, Sorghum aethiopicum, Sorghum arundinaceum, Sorghum caffrorum, Sorghum cernuum, Sorghum dochna, Sorghum drummondii, Sorghum durra, Sorghum guineense, Sorghum lanceolatum, Sorghum nervosum, Sorghum saccharatum, Sorghum subglabrescens, Sorghum verticilliflorum, Sorghum vulgare, Holcus halepensis, Sorghum miliaceum, Panicum militaceum* [millet], *Oryza sativa, Oryza latifolia* [rice], *Zea mays* [maize], *Triticum aestivum, Triticum durum, Triticum turgidum, Triticum hybernum, Triticum macha, Triticum sativum* or *Triticum vulgare* [wheat], Porphyridiaceae, such as the genera *Chroothece, Flintiella, Petrovanella, Porphyridium, Rhodella, Rhodosorus, Vanhoeffenia*, for example the genus and species *Porphyridium cruentum*, Proteaceae, such as the genus *Macadamia*, for example the genus and species *Macadamia intergrifolia* [macadamia], Prasinophyceae such as the genera *Nephroselmis, Prasinococcus, Scherffelia, Tetraselmis, Mantoniella, Ostreococcus*, for example the genera and species *Nephroselmis olivacea, Prasinococcus capsulatus, Scherffelia dubia, Tetraselmis chui, Tetraselmis suecica, Mantoniella squamata, Ostreococcus tauri*, Rubiaceae such as the genus *Cofea*, for example the genera and species *Cofea* spp., *Coffea arabica, Coffea canephora* or *Coffea liberica* [coffee], Scrophulariaceae such as the genus *Verbascum*, for example the genera and species *Verbascum blattaria, Verbascum chaixii, Verbascum densiflorum, Verbascum lagurus, Verbascum longifolium, Verbascum lychnitis, Verbascum nigrum, Verbascum olympicum, Verbascum phlomoides, Verbascum phoenicum, Verbascum pulverulentum* or *Verbascum thapsus* [mullein], Solanaceae such as the genera *Capsicum, Nicotiana, Solanum, Lycopersicon*, for example the genera and species *Capsicum annuum, Capsicum annuum* var. *glabriusculum, Capsicum frutescens* [pepper], *Capsicum annuum* [paprika], *Nicotiana tabacum, Nicotiana alata, Nicotiana attenuata, Nicotiana glauca, Nicotiana langsdorffii, Nicotiana obtusifolia, Nicotiana quadrivalvis, Nicotiana repanda, Nicotiana rustica, Nicotiana sylvestris* [tobacco], *Solanum tuberosum* [potato], *Solanum melongena* [eggplant], *Lycopersicon esculentum, Lycopersicon lycopersicum, Lycopersicon pyriforme, Solanum integrifolium* or *Solanum lycopersicum* [tomato], Sterculiaceae, such as the genus *Theobroma*, for example the genus and species *Theobroma cacao* [cacao] or Theaceae, such as the genus *Camellia*, for example the genus and species *Camellia sinensis* [tea]. In particular preferred plants to be used as transgenic plants in accordance with the present invention are oil fruit crops which comprise large amounts of lipid compounds, such as peanut, oilseed rape, canola, sunflower, safflower, poppy, mustard, hemp, castor-oil plant, olive, sesame, *Calendula, Punica*, evening primrose, mullein, thistle, wild roses, hazelnut, almond, *macadamia*, avocado, bay, pumpkin/squash, linseed, soybean, pistachios, borage, trees (oil palm, coconut, walnut) or crops such as maize, wheat, rye, oats, triticale, rice, barley, cotton, cassava, pepper, *Tagetes*, Solanaceae plants such as potato, tobacco, eggplant and tomato, *Vicia* species, pea, alfalfa or bushy plants (coffee, cacao, tea), *Salix* species, and perennial grasses and fodder crops. Preferred plants according to the invention are oil crop plants such as peanut, oilseed rape, canola, sunflower, safflower, poppy, mustard, hemp, castor-oil plant, olive, *Calendula, Punica*, evening primrose, pumpkin/squash, linseed, soybean, borage, trees (oil palm, coconut). Especially preferred are sunflower, safflower, tobacco, mullein, sesame, cotton, pumpkin/squash, poppy, evening primrose, walnut, linseed, hemp, thistle or safflower. Very especially preferred plants are plants such as safflower, sunflower, poppy, evening primrose, walnut, linseed, or hemp, or most preferred, plants of family Brassicaceae.

The invention is also concerned with providing constructs for establishing high content of VLC-PUFAs in plants or parts thereof, particularly in plant oils.

As such, the invention provides a T-DNA for expression of a target gene in a plant, wherein the T-DNA comprises a left and a right border element and at least one expression cassette comprising a promoter, operatively linked thereto a target gene, and downstream thereof a terminator, wherein the length of the T-DNA, preferably measured from left to right border element and comprising the target gene, has a length of at least 30000 bp. In an embodiment, the expression cassette is separated from the closest border of the T-DNA by a separator of at least 500 bp length. In another embodiment, the expression cassette is separated from the closest border of the T-DNA by a separator of at least 100 bp in length. In another embodiment, the expression cassette is separated from the closest border of the T-DNA by a separator of at least 200 bp in length.

Also, the invention relates to a construct comprising expression cassettes for various desaturase and elongase genes as described elsewhere herein in more detail.

As described elsewhere herein, the the T-DNA or construct of the present invention may comprise multiple expression cassettes encoding various, i.e. multiple proteins. In an embodiment, the T-DNA or construct of the present invention may comprise a separator between the expression cassettes encoding for the desaturases or elongases referred to above. In an embodiment, the expression cassettes are separated from each other by a separator of at least 100 base pairs, preferably they are separated by a separator of 100-200 base pairs. Thus, there is a separator between each expression cassette.

The invention thus provides nucleic acids, i.e. polynucleotides. A polynucleotide according to the present invention is or comprises a T-DNA according to the present invention. Thus, a T-DNA according to the present invention is a polynucleotide, preferably a DNA, and most preferably a double stranded DNA. A "T-DNA" according to the invention is a nucleic acid capable of eventual integration into the genetic material (genome) of a plant. The skilled person understands that for such integration a transformation of respective plant material is required, preferred transformation methods and plant generation methods are described herein.

According to the invention are also provided nucleic acids comprising a T-DNA or construct as defined according to the present invention. For example, a T-DNA or construct of the present invention may be comprised in a circular nucleic acid, e.g. a plasmid, such that an additional nucleic acid section is present between the left and right border elements, i.e. "opposite" of the expression cassette(s) according to the present invention. Such circular nucleic acid may be mapped into a linear form using an arbitrary starting point, e.g. such that the definition "left border element—expression cassette—right border element—additional nucleic acid section opposite of the expression cassette" defines the same circular nucleic acid as the definition "expression cassette—right border element—additional nucleic acid section opposite of the expression cassette—left border element". The additional nucleic acid section preferably comprises one or more genetic elements for replication of the total nucleic acid, i.e. the nucleic acid molecule comprising the T-DNA and the additional nucleic acid section, in one or more host microorganisms, preferably in a microorganism of genus *Escherichia*, preferably *E. coli*, and/or *Agrobacterium*. Preferable host microorganisms are described below in more detail. Such circular nucleic acids comprising a T-DNA of the present invention are particularly useful as transformation vectors; such vectors and are described below in more detail.

The polynucleotides as referred to herein preferably are expressed in a plant after introducing them into a plant. Thus, the method of the present invention may also comprise the step of introducing the polynucleotides into the plant. Preferably, the polynucleotides are introduced into the plant by transformation, in particular by *Agrobacterium*-mediated transformation. In an embodiment, the plants are transformed with a construct or T-DNA comprising the polynucleotides and/or expression cassette as set forth in connection with the present invention such as the expression cassettes encoding for desaturase and elongase as shown in Table 11. Thus, it is envisaged that the plant is (has been) transformed with a T-DNA or construct of the present invention. The construct or T-DNA used for the introduction, preferably comprises all polynucleotides to be expressed. Thus, a single construct or T-DNA shall be used for transformation, in other words, the polynucleotides encoding for desaturases and elongases shall be comprised by the same T-DNA. It is to be understood, however, that more than one copy of the T-DNA may be comprised by the plant.

The T-DNA length is preferably large, i.e. it has a minimum length of at least 30000 bp, preferably more than 30000 bp, more preferably at least 40000 bp, even more preferably at least 50000 bp and most preferably at least 60000 bp. Preferably, the length of the T-DNA is in a range of any of the aforementioned minimum lengths to 120000 bp, more preferably in a range of any of the aforementioned minimum lengths to 100000 bp, even more preferably in a range of any of the aforementioned minimum lengths to 90000 bp, even more preferably in a range of any of the aforementioned minimum lengths to 80000 bp. With such minimum lengths it is possible to introduce a number of genes in the form of expression cassettes such that each individual gene is operably liked to at least one promoter and at least one terminator. As is shown hereinafter in the examples section, the invention makes use of such minimum length T-DNA for introducing the genes required for the metabolic pathway of VLC-PUFA production in plants, e.g. oil seed plants, preferably plants of genus *Brassica*. Also, the length of the T-DNA is preferably limited as described before to allow for easy handling.

Moreover, the construct of the present invention may have a minimum length of at least 30000 bp, preferably more than 30000 bp, more preferably at least 40000 bp, even more preferably at least 50000 bp and most preferably at least 60000 bp.

In an embodiment, in 3' direction of the T-DNA left border element or in 5' direction of the T-DNA right border element, a separator is present setting the respective border element apart from the expression cassette comprising the target gene. The separator in 3' direction of the T-DNA left border element does not necessarily have the same length and/or sequence as the separator in 5' direction of the T-DNA right border element, as long as both separators suffice to the further requirements given below.

In another embodiment, the expression cassettes are separated from each other by a separator of at least 100 base pairs, preferably by a separator of 100 to 200 base pairs. Thus, there is a separator between the expression cassettes.

The separator or spacer is a section of DNA predominantly defined by its length. Its function is to separate a target gene from the T-DNA's left or right border, respectively. As will be shown in the examples, introducing a separator effectively separates the gene of interest from major influences exerted by the neighbouring genomic locations after insertion of the T-DNA into a genomic DNA. For example it is commonly believed that not all genomic loci are equally suitable for expression of a target gene, and that the same gene under the control of the same promoter and terminator may be expressed in different inensity in plants depending on the region of integration of the target gene (and its corresponding promoter and terminator) in the plant genome. It is generally believed that different regions of a plant genome are accessible with differing ease for transcription factors and/or polymerase enzymes, for example due to these regions being tightly wound around histones and/or attached to the chromosomal backbone (cf. for example Deal et al., Curr Opin Plant Biol. April 2011; 14(2): 116-122) or other scaffold material (cf. e.g. Fukuda Y., Plant Mol Biol. 1999 March; 39(5): 1051-62). The mechanism of achieving the above mentioned benefits by the T-DNA of the present invention is not easily understood, so it is convenient to think of the spacer as a means for physically providing a buffer to compensate for strain exerted by DNA winding by neighbouring histones or chromosomal backbone or other scaffold attached regions. As a model it can be thought that to transcribe a target gene, the DNA has to be partially unwound. If neighbouring regions of the target gene resist such unwinding, for example because they are tightly wound around histones or otherwise attached to a scaffold or backbone such that rotation of nucleic acid strands is limited, the spacer allows to distribute the strain created by the unwinding attempt over a longer stretch of nucleic acid, thereby reducing the force required for unwinding at the target gene.

In an embodiment, the separator has a length of at least 500 bp. The separator, thus, can be longer than 500 bp, and preferably is at least 800 bp in length, more preferably at least 1000 bp. Longer spacers allow for even more physical separation between the target gene and the nearest genomic flanking region.

In another embodiment, the spacer has a length of at least 100 bp. Preferably, the spacer has a length of 100 to 200 base pairs.

The separator preferably has a sequence devoid of matrix or scaffold attachment signals. Preferably, the separator or spacer is does not comprise more than once for a length of 500 bp, preferably not more than once for a length of 1000 bp, a 5-tuple which occurs in the spacers described below in the examples for 20 or more times, summarized over all spacers given in the examples. Those tuples are, in increasing frequency in the spacers given in the examples: AGCCT, CGTAA, CTAAC, CTAGG, GTGAC, TAGGC, TAGGT, AAAAA, AACGC, TTAGC, ACGCT, GCTGA, ACGTT, AGGCT, CGTAG, CTACG, GACGT, GCTTA, AGCTT, CGCTA, TGACG, ACGTG, AGCTG, CACGT, CGTGA, CGTTA, AGCGT, TCACG, CAGCT, CGTCA, CTAGC, GCGTC, TTACG, GTAGC, TAGCG, TCAGC, TAGCT, AGCTA, GCTAG, ACGTA, TACGT. By reducing the frequency of occurrence of one or more of the aforelisted tuples compared to the separators or spacers as given in the examples, a further increase in expression of a target gene in the T-DNA can be achieved.

The separator may contain a selectable marker. A selectable marker is a nucleic acid section whose presence preferably can be verified in seed without having to wait for the sprouting or full growth of the plant. Preferably the selectable marker conveys a phenotypical property to seed or to a growing plant, for example herbicide tolerance, coloration, seed surface properties (e.g. wrinkling), luminescence or fluorescence proteins, for example green fluorecent protein or luciferase. If for exhibiting the phenotypical feature an expression of a marker gene is required, then the separator correspondingly comprises the marker gene as selectable marker, preferably in the form of an expression cassette. Inclusion of a selectable marker in the separator is particularly advantageous since the marker allows to easily discard non-transformant plant material. Also, in such unexpected case where the T-DNA integrates in a location of the plant genome where the length and/or nucleobase composition of the spacer is insufficient to overcome gene silencing effects caused by the neighbouring genomic DNA, the selectable marker allows to easily discard such unfortunately badly performing exceptional transformants. Thus, preferably the separator comprises an expression cassette for expression of an herbicide tolerance gene. Such separator greatly reduces the chance of having to cultivate a transformant where silencing effects are so strong that even the expression of the selectable marker gene is greatly reduced or fully inhibited. According to the invention, the separator preferably does not comprise a desaturase or elongase gene, and also preferably does not comprise a promoter or operatively linked to a desaturase or elongase gene. Thus, the T-DNA of the present invention in preferred embodiments is useful for effective separation of the desaturase and elongase genes essential for the production of VLC-PUFAs from any influence of effects caused by neighbouring genomic plant DNA.

Another method of isolating T-DNAs from major influences exerted by the neighbouring genomic locations in is maximize the distance of the T-DNA insert from neighboring genes. In addition, disruption of neighboring genes could result in unexpected effects on the host plant. It is possible to determine the genomic insertion site of a T-DNA with various methods known to those skilled in the art, such as adapter ligation-mediated PCR as described in O'Malley et al. 2007 Nature Protocols 2(11):2910-2917. Such methods allow for the selection of transgenic plants where the T-DNA has been inserted at a desired distance away from endogenous genes. It is preferable to identify transgenic events where the T-DNA is more than 1000 bp away from a neighboring coding sequence. More preferable, the T-DNA is 2500 bp away, and most preferably the T-DNA is 5000 or more bp away from the nearest coding sequence.

In an embodiment, the T-DNA or T-DNAs comprised by the plant of the present invention, thus, does not (do not) disrupt an endogenous coding sequence. Preferably, the T-DNA is (the T-DNAs are) more than 1000 bp away from a neighboring coding sequence. More preferable, the T-DNA is (the T-DNAs are) 2500 bp away, and most preferably the T-DNA is (the T-DNAs are) 5000 or more bp away from the nearest coding sequence.

For the production of VLC-PUFAs in plants, the invention also provides a T-DNA or construct comprising the coding sequences of any single gene (in particular of the coding sequences for the desaturases and elongases) of the tables given in the examples, preferably comprising the coding sequences and and promoters of any single of the tables given in the examples, more preferably the coding sequences and promoters and terminators of any single of the tables given in the examples, and most preferably the expression cassettes of any single of the tables of the examples.

In an embodiment, the invention also provides a construct or a T-DNA comprising the coding sequences (in particular of the desaturases and elogases) as given in Table 11 and 130 in the examples, preferably comprising the coding sequences (in particular of the desaturases and elogases) and and promoters as given in Table 11 in the examples, more preferably the coding sequences (in particular of the desaturases and elogases) and promoters and terminators as given in Table 11 in the examples, and most preferably the expression cassettes for the desaturases and elongases as referred to in the context of the method of present invention as present in VC-LTM593-1qcz rc (see Examples section, SEQ ID NO: 3).

Also, the invention provides a T-DNA for production of VLC-PUFAs in a plant, wherein the T-DNA comprises a left and a right border element and in between one or more expression cassette(s), wherein the length of the T-DNA, measured from left to right border element and comprising the one or more expression cassettes, has a length of at least 30000 bp. In an embodiment, the expression cassette(s) closest to a left or right border element, respectively, is (are) separated from said closest border element of the T-DNA by a separator of at least 500 bp length. It is to be understood that the one or more expression cassette(s) each comprise a promoter, operatively linked to a target gene, and downstream thereof a terminator, wherein the target gene of a respective expression cassette is a desaturase or elongase gene as required for production of a VLC-PUFA. Preferably at least one and most preferably all of the target genes codes/code for a desaturase or elongase as given in any of the tables in the examples section, and further preferably at least one and most preferably all expression cassettes consist of a combination of promoter, desaturase/elongase gene and terminator as given in any of the examples below. In one embodiment a plant of the invention comprises one or more T-DNA of the present invention comprising one or more expression cassettes encoding for one or more d6Des (delta 6 desaturase), one or more d6Elo (delta 6 elongase), one or more d5Des (delta 5 desaturase), one or more o3Des (omega 3 desaturase), one or more d5Elo (delta 5 elongase) and one or more D4Des (delta 4 desaturase), preferably for at least one CoA-dependent D4Des and one Phospholipid-dependent d4Des. In one embodiment, the T-DNA encodes also for one or more d12Des (delta 12 desaturase). In an embodiment, the desaturases and elongases are derived from the organisms disclosed above. In one embodiment, a plant of the invention thus comprises one or more T-DNA of the present invention comprising at least one polynucleotide encoding a delta-6-desaturase (preferably a CoA-dependent delta-6-desaturase), at least two polynucleotides encoding a delta-6-elongase, at least two polynucleotides encoding a delta-5-desaturase, at least one polynucleotide encoding a delta-12-desaturase, at least three polynucleotides encoding an omega-3-desaturase, and at least one polynucleotide encoding a delta-5-elongase, and at least two polynucleotides encoding a delta-4-desaturase (preferably at least one for a CoA-dependent D4Des and at least one for Phospholipid-dependent d4Des).

Preferred polynucleotide sequences encoding for the desaturases and elongases referred to above are disclosed elsewherein herein (see also SEQ ID Nos in Table 130).

In a particular preferred embodiment, the desaturases and elongases are from the organisms disclosed above. In one embodiment, a plant of the invention thus comprises one or more T-DNA of the present invention comprising at least one polynucleotide encoding a delta-6-desaturase, at least two polynucleotides encoding a delta-6-elongase, at least two polynucleotides encoding a delta-5-desaturase, at least one polynucleotide encoding a delta-12-desaturase, at least three polynucleotides encoding an omega-3-desaturase, and at least one polynucleotide encoding a delta-5-elongase, and at least two polynucleotides encoding a delta-4-desaturase (preferably for at least one CoA-dependent D4Des and one Phospholipid-dependent d4Des).

In a further preferred embodiment of the present invention, a plant of the invention comprises one or more T-DNA of the present invention comprising one expression cassette for a delta-6 elongase from *Physcomitrella patens*, one expression cassette for a delta-6 elongase from *Thalassiosira pseudonana*, two expression cassettes for a delta-5 desaturase from *Thraustochytrium* sp. (in particular from *Thraustochytrium* sp. ATCC21685), two expression cassettes for an omega-3 desaturase from *Pythium irregulare*, one expression cassette for a omega-3-desaturase from *Phythophthora infestans*, one expression cassette for a delta-5 elongase from *Ostreococcus tauri*, one expression cassette for a delta-4 desaturase from *Thraustochytrium* sp., and one expression cassette for a delta-4 desaturase from *Pavlova lutheri*. The sequences of polynucleotides encoding the desaturases or elongases can be found in in the T-DNA vector VC-LTM593-1qcz (SEQ ID NO: 3). For more information, see also Table 11. In an even further preferred embodiment, a plant of the invention comprises one or more T-DNA, wherein the T-DNA comprises the expression cassettes for the desaturases and elongases of VC-LTM593-1qcz (see e.g. Table 11). Moreover, it is envisaged that the plant of the present invention comprises one or more T-DNA of the present invention, wherein the T-DNA has the sequence of the T-DNA of the vector VC-LTM593-1qcz. The position of the T-DNA in the vector is indicated in Table 11. The vector has a sequence shown in SEQ ID NO: 3.

In a preferred embodiment, the T-DNA, construct, or plant of the present invention comprises polynucleotides encoding for the following desaturases and elongases, in particular in the following order: Delta-6 ELONGASE from *Physcomitrella patens*; Delta-5 DESATURASE from *Thraustochytrium* (in particular from *Thraustochytrium* sp. ATCC21685); Delta-6 DESATURASE from *Ostreococcus tauri*; Delta-6 ELONGASE from *Thalassiosira pseudonana*; Delta-12 DESATURASE from *Phythophthora sojae*; Omega-3 DESATURASE from *Pythium irregulare*; Omega-3-DESATURASE from *Phythophthora infestans*; Delta-5 DESATURASE from *Thraustochytrium* (in particular from *Thraustochytrium* sp. ATCC21685); Delta-4 DESATURASE from *Thraustochytrium* sp.; Omega-3 DESATURASE from *Pythium* irregular; Delta-4 DESATURASE from *Pavlova lutheri*; Delta-5 ELONGASE from *Ostreococcus tauri*. Thus, T-DNA, construct, or plant of the present invention comprises two copies of a Delta-5 desaturase from *Thraustochytrium* and two copies of Delta-5 desaturase from *Thraustochytrium*. Also encompassed are variants thereof.

As set forth elsewhere herein, the T-DNA preferably shall have a length of at least 30000 bp.

In one embodiment, the plant of the invention or a part thereof as described herein comprises one or more T-DNAs of the invention which encode for at least two d6Des, at least two d6Elo and/or, at least two o3Des. In one embodiment, the present plant of the invention or a part thereof comprise a T-DNA comprising one or more expression cassettes encoding for at least one CoA-dependent d4Des and at least one phopho-lipid dependent d4Des. In one embodiment the activities of the enzymes expressed by the one or more T-DNAs in the plant of the invention or a part thereof are encoded and expressed polpeptides having the activities shown in column 1 of Table 19. In one embodiment the plant of the invention comprises at least one T-DNA as shown in columns 1 to 9 in Table 13. In one embodiment, one T-DNA of the present invention comprises one or more gene expression cassettes encoding for the activities or enzymes listed in Table 13.

In one embodiment, the at least one T-DNA further comprises an expression cassette which encodes for at least one d12Des. In one embodiemt, the T-DNA or T-DNAs comprise one or more expression cassettes encoding one or more d5Des(Tc_GA), o3Des(Pir_GA), d6Elo(Tp_GA) and/or d6Elo(Pp_GA). Such plants of the present invention have shown particularly high amounts and concentrations of VLC-PUFAs over three or more generations and under different growth conditions.

In one embodiment the T-DNA of the invention encodes for the activities of column 1 as disclosed in Table 19, preferably of gene combinations disclosed in Table 13, even more preferred for promoter-gene combinations as described in Table 13.

The contribution from each desaturase and elongase gene present in the T-DNA to the amount of VLC-PUFA is difficult to assess, but it is possible to calculate conversion efficiencies for each pathway step, for example by using the equations shown in FIG. 2. The calculations are based on fatty acid composition of the tissue or oil in question and indicate the amount of product fatty acid (and downstream products) formed from the substrate of a particular enzyme. The conversion efficiencies are sometimes referred to as "apparent" conversion efficiencies because for some of the calculations it is recognized that the calculations do not take into account all factors that could be influencing the reaction. Nevertheless, conversion efficiency values can be used to assess contribution of each desaturase or elongase reaction to the overall production of VLC-PUFA. By comparing conversion efficiencies, one can compare the relative effectiveness of a given enzymatic step between different individual seeds, plants, bulk seed batches, events, *Brassica* germplasm, or transgenic constructs.

In an embodiment of the present invention, the plant is a *Brassica napus* plant. Preferably, the plant comprises at least one T-DNA of the invention (and thus one or more T-DNAs).

The T-DNA shall have a length of at least at least 10.000 base pairs, in particular of at least 30.000 bp.

As set forth elsewhere herein, the T-DNA comprised by the invention shall comprise expression cassettes for desaturases and elongases. In an embodiment, the T-DNA comprises one or more expression cassettes for a delta-5 desaturase (preferably one), one or more expression cassettes for a omega-3 desaturase (preferably three), one or more expression cassettes for a delta 12 desaturase (preferably one), one or more expression cassettes for a delta 4 desaturase (preferably one CoA-dependent d4des and one phospholipid dependent d4des), one or more expression cassettes for a delta-5 elongase (preferably one), one or more expression cassettes for a delta-6 desaturase (preferably one), and one or more expression cassettes for a delta-6 elongase (preferably two). Preferably, the T-DNA comprises two expression cassettes for a delta-5 desaturase from *Thraustochytrium* sp., two expression cassettes for an omega-3-desaturase from *Phythophthora infestans*, one expression cassette for an omega-3-desaturase from *Pythium irregulare*, one expression cassette for a delta-12 desaturase from *Phythophthora sojae*, one expression cassette for a Delta-4 desaturase from *Pavlova lutheri*, one expression cassette for a Delta-4 desaturase from *Thraustochytrium* sp., one expression cassette for a Delta-6 desaturase from *Ostreococcus tauri*, one expression cassette for a Delta-6 elongase from *Physcomitrella patens*, and one expression cassette for a Delta-6 elongase from *Thalassiosira pseudonana*.

The SEQ ID Nos are given in Table 130. Further, it is envisaged that expression cassettes for variants of the aforementioned enzymes may be used.

The plant shall produce an oil as described elsewhere herein in more detail:

In connection with the present invention is envisaged, that the plant has one or more of the following features:
  (i) A delta 6 desaturase conversion efficiency in bulk seed of greater than about 28%, or greater than about 34%, or greater than about 40%,
  (ii) A delta 6 desaturase conversion efficiency in a single seed of greater than about 40%,
  (iii) A delta 6 elongase conversion efficiency in bulk seed of greater than about 75%, or greater than about 82%, or greater than about 89%,
  (iv) A delta 6 elongase conversion efficiency in single seed of greater than about 86%, (v) The T-DNA insert or inserts do not disrupt an endogenous coding sequence (as described elsewhere herein),
  (vi) The distance between any inserted T-DNA sequence and the nearest endogenous gene is about 1000, or about 2000, or about 5000 base pairs,
  (vii) The T-DNA insert or inserts do not cause rearrangements or any DNA surrounding the insertion location,
  (viii) No partial T-DNA inserts (Thus, the full length T-DNA shall be integrated in the genome),
  (ix) The T-DNA insert or inserts occur exclusively in the C genome of *Brassica*,
  (x) All inserted transgenes are fully functional (thus, the enzymes encoded by the genes shall retain their function).

How to calculate conversion efficiencies for a delta-6-desaturase of a delta 6-elongase is well known in the art. In an embodiment, the conversion efficiencies are calculated by using the equations shown in FIG. 2. Moreover, it is envisaged that conversion efficiencies are calculated as described in Examples 19 to 22.

As described in detail in the examples, with regards to the production of VLC-PUFAs three desaturase genes are particularly prone to gene dosage effects (also called "copy number effects"), such that increasing the number of expression cassettes comprising these respective genes leads to a stronger increase in VLC-PUFA levels in plant oils than increasing the number of expression cassettes of other genes. These genes are the genes coding for delta-12-desaturase activity, for delta-6-desaturase activity and omega-3-desaturase activity. Thus, according to the invention each expression cassette comprising a gene coding for a delta-12-desaturase, delta-6-desaturase or omega-3-desaturase is separated from the respective closest left or right border element by a separator and optionally one or more expression cassettes. It is to be understood that where the T-DNA of the present invention comprises more than one expression cassette comprising a gene of the same function, these genes do not need to be identical concerning their nucleic acid sequence or the polypeptide sequence encoded thereby, but should be functional homologs. Thus, for example, to make use of the gene dosage effect described herein a T-DNA according to the present invention may comprise, in addition to optionally a multiplicity of genes coding for delta-6-desaturases and/or omega-3-desaturases, two, three, four or more expression cassettes each comprising a gene coding for a delta-12-desaturase, wherein the delta-12-desaturase polypeptides coded by the respective genes differ in their amino acid sequence. Likewise, a T-DNA of the present invention may comprise, in addition to optionally a multiplicity of genes coding for delta-12-desaturases and/or omega-3-desaturases, two, three, four or more expression cassettes each comprising a gene coding for a delta-6-desaturase, wherein the delta-6-desaturase polypeptides coded by the respective genes differ in their amino acid sequence, or a T-DNA of the present invention may comprise, in addition to optionally a multiplicity of genes coding for delta-12-desaturases and/or delta-6-desaturases, two, three, four or more expression cassettes each comprising a gene coding for a omega-3-desaturase, wherein the omega-3-desaturase polypeptides coded by the respective genes differ in their amino acid sequence.

According to the invention, the T-DNA, construct or plant may also comprise, instead of one or more of the aforementioned coding sequences, a functional homolog thereof. A functional homolog of a coding sequence is a sequence coding for a polypeptide having the same metabolic function as the replaced coding sequence. For example, a functional homolog of a delta-5-desaturase would be another delta-5-desaturase, and a functional homolog of a delta-5-elongase would be another delta-5-elongase. The functional homolog of a coding sequence preferably codes for a polypeptide having at least 40% sequence identity to the polypeptide coded for by the corresponding coding sequence given in the corresponding table of the examples, more preferably at least 41%, more preferably at least 46%, more preferably at least 48%, more preferably at least 56%, more preferably at least 58%, more preferably at least 59%, more preferably at least 62%, more preferably at least 66%, more preferably at least 69%, more preferably at least 73%, more preferably at least 75%, more preferably at least 77%, more preferably at least 81%, more preferably at least 84%, more preferably at least 87%, more preferably at least 90%, more preferably at least 92%, more preferably at least 95%, more preferably at least 96%, more preferably at least 97%, more preferably at least 98% and even more preferably at least 99%. Likewise, a functional homolog of a promoter is a sequence for starting transcription of a coding sequence located within 500 bp for a proximal promoter or, for a distal promoter, within 3000 bp distant from the promoter TATA box closest to the coding sequence. Again, a functional homolog of a plant seed specific promoter is another plant seed specific promoter. The functional homolog of a terminator, correspondingly, is a sequence for ending transcription of a nucleic acid sequence.

The examples describe particularly preferred T-DNA sequences. As described above, the skilled person understands that the coding sequences, promoters and terminators described therein can be replaced by their functional homologs. However, the examples also describe that according to the invention, certain combinations of promoters and coding sequences, or certain combinations of promoters driving the expression of their corresponding coding sequences, or certain coding sequences or combinations thereof are particularly advantageous; such combinations or individual coding sequences should according to the invention not be replaced by functional homologs of the respective element (here: coding sequence or promoter).

A T-DNA or construct of the present invention preferably comprises two or more genes, preferably all genes, susceptible to a gene dosage effect. As described herein, it is advantageous for achieving high conversion efficiencies of certain enzymatic activities, e.g. delta-12-desaturase, delta-6-desaturase and/or omega-3-desaturase activity, to introduce more than one gene coding for an enzyme having the desired activity into a plant cell. When introducing T-DNA into plant cells, generally transformation methods involving exposition of plant cells to microorganisms are employed, e.g. as described herein. As each microorganism may comprise more than one nucleic acid comprising a T-DNA of the present invention, recombinant plant cells are frequently obtained comprising two or more T-DNAs of the present invention independently integrated into the cell's genetic material. Thus, by combining genes susceptible to a gene dosage effect on one construct for transformation allows to easily exploit the independence of transformations to achieve a higher frequency of multiple insertions of such T-DNAs. This could be e.g. useful for transformation methods relying on co-transformation to keep the size of each construct to be transformed low.

The invention accordingly also provides a construct comprising a T-DNA according to the present invention, wherein the construct preferably is a vector for transformation of a plant cell by microorganism-mediated transformation, preferably by *Agrobacterium*-mediated transformation. Correspondingly, the invention also provides a transforming microorganism comprising one T-DNA according to the present invention, preferably as a construct comprising said T-DNA. Preferably the microorganism is of genus *Agrobacterium*, preferably a disarmed strain thereof, and preferably of species *Agrobacterium tumefaciens* or, even more preferably, of species *Agrobacterium rhizogenes*. Corresponding strains are for example described in WO06024509A2, and methods for plant transformation using such microorganisms are for example described in WO13014585A1. These WO publications are incorporated herein in their entirety, because they contain valuable information about the creation, selection and use of such microorganisms.

The term "vector", preferably, encompasses phage, plasmid, viral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotide of the present invention, preferably, further comprises selectable markers for propagation and/or selection in a host. The vector may be incorporated into a host cell by various techniques well known in the art. If introduced into a host cell, the vector may reside in the cytoplasm or may be incorporated into the genome. In the latter case, it is to be understood that the vector may further comprise nucleic acid sequences which allow for homologous recombination or heterologous insertion. Vectors can be introduced into prokaryotic or eukaryotic cells via conventional transformation or transfection techniques. The terms "transformation" and "transfection", conjugation and transduction, as used in the present context, are intended to comprise a multiplicity of prior-art processes for introducing foreign nucleic acid (for example DNA) into a host cell, including calcium phosphate, rubidium chloride or calcium chloride co-precipitation, DEAE-dextran-mediated transfection, lipofection, natural competence, carbon-based clusters, chemically mediated transfer, electroporation or particle bombardment. Suitable methods for the transformation or transfection of host cells, including plant cells, can be found in Sambrook et al. (Molecular Cloning: A Laboratory Manual, 2nd ed., Cold Spring Harbor Laboratory, Cold Spring Harbor Laboratory Press, Cold Spring Harbor, N.Y., 1989) and other laboratory manuals, such as Methods in Molecular Biology, 1995, Vol. 44, *Agrobacterium* protocols, Ed.: Gartland and Davey, Humana Press, Totowa, N.J. Alternatively, a plasmid vector may be introduced by heat shock or electroporation techniques. Should the vector be a virus, it may be packaged in vitro using an appropriate packaging cell line prior to application to host cells.

Preferably, the vector referred to herein is suitable as a cloning vector, i.e. replicable in microbial systems. Such vectors ensure efficient cloning in bacteria and, preferably, yeasts or fungi and make possible the stable transformation of plants. Those which must be mentioned are, in particular, various binary and co-integrated vector systems which are suitable for the T DNA-mediated transformation. Such vector systems are, as a rule, characterized in that they contain at least the vir genes, which are required for the *Agrobacterium*-mediated transformation, and the sequences which delimit the T-DNA (T-DNA border). These vector systems, preferably, also comprise further cis-regulatory regions such as promoters and terminators and/or selection markers with which suitable transformed host cells or organisms can be identified. While co-integrated vector systems have vir genes and T-DNA sequences arranged on the same vector, binary systems are based on at least two vectors, one of which bears vir genes, but no T-DNA, while a second one bears T-DNA, but no vir gene. As a consequence, the last-mentioned vectors are relatively small, easy to manipulate and can be replicated both in *E. coli* and in *Agrobacterium*. These binary vectors include vectors from the pBIB-HYG, pPZP, pBecks, pGreen series. Preferably used in accordance with the invention are Bin19, pB1101, pBinAR, pGPTV and pCAMBIA. An overview of binary vectors and their use can be found in Hellens et al, Trends in Plant Science (2000) 5, 446-451. Furthermore, by using appropriate cloning vectors, the polynucleotides can be introduced into host cells or organisms such as plants or animals and, thus, be used in the transformation of plants, such as those which are published, and cited, in: Plant Molecular Biology and Biotechnology (CRC Press, Boca Raton, Fla.), chapter 6/7, pp. 71-119 (1993); F. F. White, Vectors for Gene Transfer in Higher Plants; in: Transgenic Plants, vol. 1, Engineering and Utilization, Ed.: Kung and R. Wu, Academic Press, 1993, 15-38; B. Jenes et al., Techniques for Gene Transfer, in: Transgenic Plants, vol. 1, Engineering and Utilization, Ed.: Kung and R. Wu, Academic Press (1993), 128-143; Potrykus 1991, Annu. Rev. Plant Physiol. Plant Molec. Biol. 42, 205-225.

More preferably, the vector of the present invention is an expression vector. In such an expression vector, i.e. a vector which comprises the polynucleotide of the invention having the nucleic acid sequence operatively linked to an expression control sequence (also called "expression cassette") allowing expression in prokaryotic plant cells or isolated fractions thereof.

Most important, the invention also provides a plant or seed thereof, comprising, integrated in its genome, a T-DNA or a construct of the present invention.

Thus, the construct or T-DNA shall be stably integrated into the genome of the plant or plant cell. In an embodiment, the plant is homozygous for the T-DNA. In another embodiment, the plant is hemizygous for the T-DNA. If the plant is homozygous for one T-DNA at one locus, this is nevertheless considered as a single copy herein, i.e. as one copy. Double copy, as used herein, refers to a plant in which two T-DNAs have been inserted, at one or two loci, and in the hemizygous or homozygous state.

Stability of the T-DNA can be assessed by determining the presence of the T-DNA in two or more subsequent generations of a transgenic event. Determining the presence of a T-DNA can be achieved by Southern blot analysis, PCR, DNA sequencing, or other methods that are suitable for the detection of specific DNA sequences. Stability of the T-DNA should also include copy number measurements for transgenic events that contain more than one copy of the T-DNA. In this case, instability of a single copy of the T-DNA may not be detectable by selecting for the trait, i.e. VLC-PUFA conent, because the presence of one stable T-DNA copy may mask the instability of the other. When working with large T-DNAs of at least 30000 bp in length, and with multiple copies of certain sequences (for example two copies of the same promoter) it is especially important to confirm presence and copy number at multiple locations within the T-DNA. The borders of a long T-DNA have an increased likelihood of being in linkage equilibrium, and duplicated sequences increase the possibility of homologous recombination. The effects of being in linkage equilibrium, and the potential for homologous recombination, mean that transgenes of a T-DNA could be disrupted or lost over generations. Therefore, it is preferred to test for the presence and copy number of a large T-DNA (at least 30000 bp) at more than three locations on the T-DNA, including a region at the right and left borders as well as a region internal to the T-DNA. It is more preferred to test for the presence and copy number of more than 5 regions, and most preferred to test presence and copy number of at least 7 regions on the T-DNA.

Such T-DNA or construct preferably allows for the expression of all genes required for production of VLC-PUFAs in plants and particularly in the seeds thereof, particularly in oilseed plants, and most beneficially in plants or seeds of family Brassicaceae, preferably of genus *Brassica* and most preferably of a species comprising a genome of one or two members of the species *Brassica oleracea, Brassica nigra* and *Brassica rapa*, thus preferably of the species *Brassica napus, Brassica carinata, Brassica juncea, Brassica oleracea, Brassica nigra* or *Brassica rapa*. *Particularly preferred according to the invention are plants and seeds of the species Brassica napus and Brassica carinata.*

The plants of the present invention are necessarily transgenic, i.e. they comprise genetic material not present in corresponding wild type plant or arranged differently in corresponding wild type plant, for example differing in the number of genetic elements. For example, the plants of the present invention comprise promoters also found in wild type plants, but the plants of the present invention comprise such promoter operatively linked to a coding sequence such that this combination of promoter and coding sequence is not found in the corresponding wild type plant. Accordingly, the polynucleotide encoding for the desaturases or elongases shall be recombinant polynucleotides.

The plants and seeds of the present invention differ from hitherto produced plants for production of VLC-PUFAs in a number of advantageous features, some of which are described in detail in the examples. In particular, T-DNAs of the present invention allow for the generation of transformant plants (also called "recombinant plants") and seeds thereof with a high transformation frequency, with a high stability of T-DNA insertions over multiple generations of self-fertilized plants, unchanged or unimpaired phenotypical and agronomic characteristics other than VLC-PUFA production, and with high amounts and concentration of VLC-PUFAs, particularly EPA and/or DHA, in the oil of populations of such transformed plants and their corresponding progeny.

Seed-to-seed variability and plant-to-plant variability in VLC-PUFA amounts per seed are high even for identical clones cultivated side by side under identical greenhouse conditions. Also, it has now been found and is reported below in the examples that the contentration of VLC-PUFAs is negatively correlated with seed oil content in *Brassica napus*. The mere statement of VLC-PUFA concentration in % (w/w) of all fatty acids of a plant oil is not indicative of the VLC-PUFA amount achievable by agricultural (i.e. large scale) growing of corresponding clones. VLC-PUFA amounts or concentrations depends on which genes, promoters, gene-promoter combinations, gene-gene combinations etc. are beneficial for VLC-PUFA synthesis in oilseed plants. Different classes of seed groupings based on the seeds used to generate that group are: (i) "individual seed" or "single seed" refers to one seed from one plant. (ii) seed derived from a "individual plant" refers to all seeds grown on a single plant without effort to select based on seed-to-seed variability. (iii) "batches of seed" or "seedbatches" refers to all of the seeds collected from a specific number of plants without selection based on plant-to-plant or seed-to-seed variability. The specific number of plants referred to in a batch can be any number, one or greater, where it is understood that a batch of one plant is equivalent to individual plant. (iv) "bulked seed" refers to all of the seed gathered from a large number of plants (equal to or greater than 100) without effort to select seeds based on plant-to-plant or seed-to-seed variability.

Also, it is important to note that VLC-PUFA amounts or concentrations can indeed be increased by increasing the number of expression cassettes of functionally identical genes. And it is also important to note that even though many prior art documents purport to comprise applicable technical teachings, e.g. to combine desaturases having a particular property, e.g. CoA-dependence, it is not known how to reduce such alleged technical teachings to practice, particularly as such documents only teach requirements (i.e. functional claim features) but not solutions for these requirements (i.e. structural features). For example, such prior art documents frequently comprise only one example of a single gene and leave the reader with the instruction to start a research program to find other enzymes satisfying the functional definition given therein, provided that any other enzyme exists that satisfies those functional requirements.

Unless stated otherwise, a plant of the present invention comprising a T-DNA or construct of the present invention can also be a plant comprising a part of a T-DNA or construct of the present invention, where such part is sufficient for the production of a desaturase and/or elongase coded for in the corresponding full T-DNA or construct of the present invention. Such plants most preferably comprise at least one full T-DNA or construct of the present invention in addition to the part of a T-DNA of the present invention as defined in the previous sentence. Such plants are hereinafter also termed "partial double copy" plants. Event LBFDAU is an example of a plant comprising a part of a T-DNA of the present invention, and still being a plant of the present invention. In one embodiment the T_DNA is a full T-DNA.

Preferred plants of the present invention comprise one or more T-DNA(s) or construct of the present invention comprising expression cassettes comprising, one or more genes encoding for one or more d5Des, one or more d6Elo, one or more d6Des, one or more o3Des, one or more d5Elo and one or more D4Des, preferably for at least one CoA-dependent D4Des and one Phospholipid-dependent d4Des. In one embodiment, at least one T-DNA further comprises an expression cassette which encodes for at least one d12Des. In one embodiemt, the T-DNA or T-DNAs further comprise one or more expression cassettes encoding one or more d5Des(Tc_GA), o3Des(Pir_GA), d6Elo(Tp_GA) and/or d6Elo(Pp_GA), an explanation for the abbreviation in the brackets is given e.g. in Table 130, e.g. d6Elo(Tp_GA) is a Delta-6 elongase from *Thalassiosira pseudonana*, d6Elo (Pp_GA) i a Delta-6 elongase from *Physcomitrella patens*. Such plants of the present invention have shown particularly high amounts and concentrations of VLC-PUFAs over three or more generations and under different growth conditions.

Preferred plants according to the invention are oilseed crop plants.

Most preferably, the plant of the present invention is a plant found in the "Triangle of U", i.e. a plant of genus *Brassica: Brassica napus* (AA CC genome; n=19) is an amphidiploid plant of the *Brassica* genus but is thought to have resulted from hybridization of *Brassica rapa* (AA genome; n=10) and *Brassica oleracea* (CC genome; n=9). *Brassica juncea* (AA BB genome; n=18) is an amphidiploid plant of the *Brassica* genus that is generally thought to have resulted from the hybridization of *Brassica rapa* and *Brassica nigra* (BB genome; n=8). Under some growing conditions, *B. juncea* may have certain superior traits to *B. napus*. These superior traits may include higher yield, better drought and heat tolerance and better disease resistance. *Brassica carinata* (BB CC genome; n=17) is an amphidiploid plant of the *Brassica* genus but is thought to have resulted from hybridization of *Brassica nigra* and *Brassica oleracea*. Under some growing conditions, *B. carinata* may have superior traits to *B. napus*. Particularly, *B. carinata* allows for an increase in VLC-PUFA concentrations by at least 20% compared to *B. napus* when transformed with the same T-DNA.

The plant of the present invention preferably is a "Canola" plant. Canola is a genetic variation of rapeseed developed by Canadian plant breeders specifically for its oil and meal attributes, particularly its low level of saturated fat. Canola herein generally refers to plants of *Brassica* species that have less than 2% erucic acid (Delta 13-22:1) by weight in seed oil and less than 30 micromoles of glucosinolates per gram of oil free meal. Typically, canola oil may include saturated fatty acids known as palmitic acid and stearic acid, a monounsaturated fatty acid known as oleic acid, and polyunsaturated fatty acids known as linoleic acid and linolenic acid. Canola oil may contain less than about 7% (w/w) total saturated fatty acids (mostly palmitic acid and stearic acid) and greater than 40% (w/w) oleic acid (as percentages of total fatty acids). Traditionally, canola crops include varieties of *Brassica napus* and *Brassica rapa*. Preferred plants of the present invention are spring canola (*Brassica napus* subsp. *oleifera* var. *annua*) and winter canola (*Brassica napus* subsp. *oleifera* var. *biennis*). Furthermore a canola quality *Brassica juncea* variety, which has oil and meal qualities similar to other canola types, has been added to the canola crop family (U.S. Pat. No. 6,303,849, to Potts et al., issued on Oct. 16, 2001; U.S. Pat. No. 7,423,198, to Yao et al.; Potts and Males, 1999; all of which are incorporated herein by reference). Likewise it is possible to establish canola quality *B. carinata* varieties by crossing canola quality variants of *Brassica napus* with *Brassica nigra* and appropriately selecting progeny thereof, optionally after further back-crossing with *B. carinata, B. napus* and/or *B. nigra*.

The invention also provides a plant or seed thereof of family Brassicaceae, preferably of genus *Brassica*, with a genotype that confers a heritable phenotype of seed oil VLC-PUFA content, obtainable or obtained from progeny lines prepared by a method comprising the steps of
  i) crossing a plant of family Brassicaceae, preferably of genus *Brassica*, most preferably of genus *Brassica napus, Brassica oleracea, Brassica nigra* or *Brassica carinata*, said plant comprising a T-DNA or construct of the present invention and/or part of such T-DNA, with a parent plant of family Brassicaceae, preferably of genus *Brassica*, most preferably of genus *Brassica napus, Brassica oleracea, Brassica nigra* or *Brassica carinata*, said plant not comprising said T-DNA and/or part thereof, to yield a F1 hybrid,
  ii) selfing the F1 hybrid for at least one generation, and
  iii) identifying the progeny of step (ii) comprising the T-DNA of the present invention capable of producing seed comprising VLC-PUFA.

Preferably, the progeny are capable of producing seed comprising an oil as described elsewhere herein (in particular, see the definition for the oil of the present invention). More preferably, the progeny shall be capable of producing seed comprising VLC-PUFA such that the content of all VLC-PUFA downstream of 18:1n-9 is at least 40% (w/w) of the total seed fatty acid content at an oil content of 40% (w/w), or preferably the content of EPA is at least 12% (w/w) and/or the content of DHA is at least 2% (w/w) of the total seed fatty acid content at an oil content of 40% (w/w). Also preferably, the content of all VLC-PUFA downstream of 18:1n-9 is at least 40% (w/w) of the total seed fatty acid content at an oil content of 40% (w/w), or preferably the content of EPA is at least 5%, in particular at least 8% (w/w) and/or the content of DHA is at least 1% (w/w), in particular 1.5% (w/w) of the total seed fatty acid content at an oil content of 40% (w/w).

This method allows to effectively incorporate genetic material of other members of family Brassicaceae, preferably of genus *Brassica*, into the genome of a plant comprising a T-DNA or construct of the present invention. The method is particularly useful for combining a T-DNA or construct of the present invention with genetic material responsible for beneficial traits exhibited in other members of family Brassicaceae. Beneficial traits of other members of family Brassicaceae are exemplarily described herein, other beneficial traits or genes and/or regulatory elements involved in the manifestation of a beneficial trait may be described elsewhere.

The parent plant not comprising the T-DNA or contruct of the present invention or part thereof preferably is an agronomically elite parent. In particular, the present invention teaches to transfer heterologous material from a plant or seed of the present invention to a different genomic background, for example a different variety or species.

In particular, the invention teaches to transfer the T-DNA or part thereof (the latter is particularly relevant for those plants of the present invention which comprise, in addition to a full T-DNA of the present invention, also a part of a T-DNA of the present invention, said part preferably comprising at least one expression cassette, the expression cassette preferably comprising a gene coding for a desaturase or elongase, preferably a delta-12-desaturase, delta-6-desaturase and/or omega-3-desaturase), or construct into a species of genus Brassica carinata, or to introduce genetic material from Brassica carinata or Brassica nigra into the plants of the present invention comprising the T-DNA of the present invention and/or a part or two or more parts thereof. According to the invention, genes of Brassica nigra replacing their homolog found in Brassica napus or added in addition to the homolog found in Brassica napus are particularly helpful in further increasing the amount of VLC-PUFAs in plant seeds and oils thereof.

Also, the invention teaches novel plant varieties comprising the T-DNA and/or part thereof of the present invention. Such varieties can, by selecting appropriate mating partners, be particularly adapted e.g. to selected climatic growth conditions, herbicide tolerance, stress resistance, fungal resistance, herbivore resistance, increased or reduced oil content or other beneficial features. As shown hereinafter in the examples it is particularly beneficial to provide plants of the present invention wherein the oil content thereof at harvest is lower than that of corresponding wild type plants of the same variety, such as to improve VLC-PUFA amounts in the oil of said plants of the present invention and/or VLC-PUFA concentrations in said oil.

Also, the invention provides a method for creating a plant with a genotype that confers a heritable phenotype of seed oil VLC-PUFA content, obtainable or obtained from progeny lines prepared by a method comprising the steps of
  i) crossing a transgenic plant of the invention with a parent plant not comprising a T-DNA of the present invention or part thereof, said parent plant being of family Brassicaceae, preferably of genus Brassica, most preferably of genus Brassica napus, Brassica oleracea, Brassica nigra or Brassica carinata, to yield a F1 hybrid,
  ii) selfing the F1 hybrid for at least one generation, and
  iii) identifying the progeny of step (ii) comprising the T-DNA of the present invention capable of producing seed comprising VLC-PUFA.

Preferably, the progeny are capable of producing seed comprising an oil as described elsewhere herein (in particular the oil of the present invention). More preferably, the progeny shall be capable of producing seed comprising VLC-PUFA such that the content of all VLC-PUFA downstream of 18:1 n-9 is at least 40% (w/w) of the total seed fatty acid content at an oil content of 40% (w/w), or preferably the content of EPA is at least 8% (w/w) and/or the content of DHA is at least 1% (w/w) of the total seed fatty acid content at an oil content of 30% (w/w), preferably at an oil content of 35% (w/w), and more preferably at an oil content of 40% (w/w).

The method allows the creation of novel variants and transgenic species of plants of the present invention, and the seeds thereof. Such plants and seeds exhibit the aforementioned benefits of the present invention. Preferably, the content of EPA is at least 5%, more preferably at least 8%, even more preferably at least 10% by weight, most preferably at least 13% (w/w), of the total lipid content of the oil. Also preferably, the content of DHA is at least 1.0% by weight, more preferably at least 1.5%, even more preferably at least 2% (w/w), of the total lipid content of the oil. The present invention for the first time allows to achieve such high levels of VLC-PUFA in seed reliably under agronomic conditions, i.e. representative for the real yield obtained from seeds of a commercial field of at least 1 ha planted with plants of the present invention, wherein the plants have a defined copy number of genes for implementing the pathway for production of EPA and/or DHA in said plants, and the copy number being low, i.e. single-copy or partial double copy.

A plant of the present invention also includes plants obtainable or obtained by backcrossing (cross into the non-transgenic, isogenic parent line), and by crossing with other germplasms of the Triangle of U. Accordingly, the invention provides a method for creating a plant with a genotype that confers a heritable phenotype of seed oil VLC-PUFA content, obtainable or obtained from a progeny line prepared by a method comprising the steps of
  i) crossing a transgenic plant of the invention (also called "non-recurring parent") with a parent plant not expressing a gene comprised in the T-DNA of the present invention, said parent plant being of family Brassicaceae, preferably of genus Brassica, most preferably of genus Brassica napus, Brassica oleracea, Brassica nigra or Brassica carinata, to yield a hybrid progeny,
  ii) crossing the hybrid progeny again with the parent to obtain another hybrid progeny,
  iii) optionally repeating step ii) and
  iv) selecting a hybrid progeny comprising the T-DNA of the present invention.

Backcrossing methods, e.g. as described above, can be used with the present invention to improve or introduce a characteristic into the plant line comprising the T-DNA of the present invention. Such hybrid progeny is selected in step iv) which suffices predetermined parameters. The backcrossing method of the present invention thereby beneficially facilitates a modification of the genetic material of the recurrent parent with the desired gene, or preferably the T-DNA of the present invention, from the non-recurrent parent, while retaining essentially all of the rest of the desired genetic material of the recurrent parent, and therefore the desired physiological and morphological, constitution of the parent line. The selected hybrid progeny is then preferably multiplied and constitutes a line as described herein. Selection of useful progeny for repetition of step ii) can be further facilitated by the use of genomic markers. For example, such progeny is selected for the repetition of step ii) which comprises, compared to other progeny obtained in the previous crossing step, most markers also found in the parent and/or least markers also found in the non-recurring parent except the desired T-DNA of the present invention or part thereof.

Preferably, a hybrid progeny is selected which comprises the T-DNA of the present invention, and even more preferably also comprises at least one further expression cassette from the non-recurring parent of the present invention, e.g. by incorporation of an additional part of the T-DNA of the present invention into the hybrid plant genetic material.

Further preferably a hybrid progeny is obtained wherein essentially all of the desired morphological and physiological characteristics of the parent are recovered in the converted plant, in addition to genetic material from the non-recurrent parent as determined at the 5% significance level when grown under the same environmental conditions.

Further preferably, a hybrid progeny is selected which produces seed comprising an oil as described elsewhere herein (i.e. an oil of the present invention). In particular, a hybrid progeny is selected which produces seed comprising VLC-PUFA such that the content of all VLC-PUFA downstream of 18:1n-9 is at least 40% (w/w) of the total seed fatty acid content at an oil content of 40% (w/w), or preferably the content of EPA is at least 8% (w/w) and/or the content of DHA is at least 1% (w/w) of the total seed fatty acid content at an oil content of 30% (w/w), preferably at an oil content of 35% (w/w), and more preferably at an oil content of 40% (w/w).

It is to be understood that such seed VLC-PUFA content is to be measured not from a single seed or from the seeds of an individual plant, but refer to the numeric average of seed VLC-PUFA content of at least 100 plants, even more preferably of at least 200 plants, even more preferably of at least 200 plants half of which have been grown in field trials in different years, in particular of bulked seed VLC-PUFA content of at least 100 plants, even more preferably of at least 200 plants, even more preferably of at least 200 plants half of which have been grown in field trials in different years.

The choice of the particular non-recurrent parent will depend on the purpose of the backcross. One of the major purposes is to add some commercially desirable, agronomically important trait to the line.

The term "line" refers to a group of plants that displays very little overall variation among individuals sharing that designation. A "line" generally refers to a group of plants that display little or no genetic variation between individuals for at least one trait. A "DH (doubled haploid) line," as used in this application refers to a group of plants generated by culturing a haploid tissue and then doubling the chromosome content without accompanying cell division, to yield a plant with the diploid number of chromosomes where each chromosome pair is comprised of two duplicated chromosomes. Therefore, a DH line normally displays little or no genetic variation between individuals for traits. Lines comprising one or more genes originally comprised in a T-DNA of the present invention in the non-recurring parent also constitute plants of the present invention.

The invention is also concerned with a method of plant oil production, comprising the steps of
  i) growing a plant of the present invention such as to obtain oil-containing seeds thereof,
  ii) harvesting said seeds, and
  iii) extracting oil from said seeds harvested in step ii).

Preferably, the oil is an oil as described herein below in more detail (i.e. an oil of the present invention). More preferably, the oil has a DHA content of at least 1% by weight based on the total lipid content and/or a EPA content of at least 8% by weight based on the total lipid content. Also preferably, the oil has a DHA content of at least 1% by weight based on the total fatty acid content and/or a EPA content of at least 8% by weight based on the total fatty acid content.

Again preferably, the content of EPA is at least 10% by weight, even more preferably at least 13% (w/w), of the total lipid content of the oil. Also preferably, the content of DHA is at least 1.5% by weight, even more preferably at least 2% (w/w), of the total lipid content of the oil. As described herein, the plant of the present invention comprises, for the purposes of such method of plant oil production, preferably comprises a T-DNA (or construct) of the present invention and optionally also one or more additional parts thereof, wherein the part or parts, respectively, comprise at least one expression cassette of the T-DNA of the present invention.

The invention is also concerned with parts of plants of the present invention. The term "parts of plants" includes anything derived from a plant of the invention, including plant parts such as cells, tissues, roots, stems, leaves, non-living harvest material, silage, seeds, seed meals and pollen. Preferably such plant part comprises a T-DNA of the present invention and/or comprises a content of EPA of at least 8% by weight, more preferably at least 10%, even more preferably at least 13% (w/w), of the total lipid content. Also preferably, the content of DHA is at least 1.0% by weight, more preferably at least 1.5%, even more preferably at least 2% (w/w), of the total lipid content of the plant part. Parts of plants of the present invention comprising, compared to wild-type plants, elevated content of EPA and/or DHA, or the oil or lipid of the present invention are particularly useful also for feed purposes, e.g. for aquaculture feed, e.g. as described in AU2011289381A and members of the patent family thereof.

The plants of the present invention do not necessarily have to comprise a complete T-DNA of the present invention. As described above, by crossing (or back-crossing) methods it is possible to transfer arbitrary genetic material of one line to another line. Thus, by applying such crossing or back-crossing it is possible to transfer one or more, even all, expression cassettes comprised in a plant of the present invention (such plant comprising a T-DNA of the present invention) to another plant line, thereby losing e.g. a left or right border element (or both) and/or a spacer.

Thus, the invention also provides plants comprising genetic material hybridizing to a primer as given in Example 24.

Also, the invention provides plants comprising a heterologous nucleic acid segment inserted in its genetic material. The insertion is according to the invention in one of the below listed flanking regions or between a pair of flanking regions. Due to plant-to-plant variability, each flanking region may differ from the below indicated flanking regions by at most 10% calculated over a consecutive stretch of at least 100 nt, preferably by at most 5% calculated over a consecutive stretch of at least—with increasing percentage identity more preferred—90. 91. 92, 93, 94, 95, 96, 97, 98 or 99, preferred 100% identity for 100 nt. Even more preferably, the flanking region(s) comprise at least—with increasing percentage identity more preferred—90. 91. 92, 93, 94, 95, 96, 97, 98 or 99, preferred 100% identity for 50 consecutive nucleotides identical to a fragment of a flanking region as given below, even more preferable the length of consecutive identical nucleotides is at least 100.

Example 24 provides an overview of all the flanking sequences of all loci obtained for each event listed in that table. In addition, event specific primers and probes are disclosed in Table 176 for event specific detection. The method for using those primers and probes is described in example 24.

As shown in the examples, insertions in these flanking regions have now been proven to lead to a surprisingly high production of VLC-PUFAs in seed, wherein such production is stable over many generations and under different growth conditions. Thus, insertion of other genetic material at these insertion locations also leads to a stable, high expression of inserted genes compared to insertions at other positions of the plant genome.

The invention is also concerned with establishing and optimizing efficient metabolic VLC-PUFA synthesis pathways. To this end, the invention provides a method for analysing desaturase reaction specificity, comprising the steps of
　i) providing, to a desaturase, a detectably labelled molecule comprising a fatty acid moiety and a headgroup,
　ii) allowing the desaturase to react on the labelled molecule, and
　iii) detecting desaturation products.

The labelled molecule preferably is a fatty acid-coenzyme A or a fatty acid-phospholipid, the latter preferably being a lysophosphatidylcholine bound fatty acid. The method advantageously allows to determining desaturase headgroup preference or even headgroup specificity by detecting whether coenzyme A bound fatty acids are desaturated and/or whether phospholipid-bound fatty acids are desaturated.

Preferably the desaturase is provided as a microsomal fraction of an organism, preferably of yeast. Transgenic yeasts expressing the desaturase in question are easy to prepare and handle, and microsomal fractions comprising functional desaturases can be reliably and reproducibly prepared thereof without major burden. Microsomal fractions, particularly of yeast, most preferably of *Saccharomyces cerevisiae*, also allow to convert fatty acid-coenzyme A molecules to fatty acids bound to other headgroups by using the yeast's native LPCAT. Likewise, microsomal fractions can be prepared from other cells and organisms.

Preferably the molecule is detectably labelled by including a radioactive isotope instead of a non-radioactive isotope. The isotope preferably is [14C]. Such label is easy to detect, does not intererefe in biochemical reactions and can be incorporated in virtually any carbon-containing molecule, thereby allowing sensitively detecting and characterizing any desaturation product.

The fatty acid moiety preferably is a PUFA moiety, more preferably a VLC-PUFA moiety and most preferably a VLC-PUFA moiety. This way, the headgroup preference or specificity for economically important desaturases can be determined without having to resort to error prone and laborious feeding of live organisms or living cells.

The desaturase is allowed to react on the labelled molecule. If the desaturase can accept the labelled molecule as a substrate, then the desaturation reaction is performed. Preferably, the method is repeated by including, as a positive control, a labelled molecule which had been confirmed to be a substrate for the desaturase.

Detection preferably is accomplished using chromatography, most preferably thin layer chromatography. This technique is well known to the skilled person, readily available, very sensitive and allows differentiating even between very similar molecules. Thus, even if the positive control molecule is similar to the molecule of interest, a clear detection of desaturation products (if desaturation of the molecule occurred) is still possible.

The above method allows preparing a collection of specificity data for each desaturase, type of microsomal fraction (e.g. from yeast, plant cells etc.), fatty acid moiety and headgroup. Thus, the method can be used to select a desaturase for a given need, e.g. to accept CoA-bound fatty acids in plant cells for further presentation to an elongase. The method also allows establishing substrate specificty of the desaturase in an organism or organ of interest, e.g. a yeast, a plant leaf cell or a plant seed cell.

The invention also provides a method for analysing elongase reaction specificity, comprising the steps of
　i) providing, to an elongase, a detectably labelled elongation substrate and a molecule to be elongated,
　ii) allowing the elongase to elongate the molecule to be elongated using the labelled elongation substrate, and
　iii) detecting elongation products.

Unless stated otherwise, the method for analysing elongase reaction specificity is performed corresponding to the method for analysing desaturase reaction specificity for corresponding reasons. The elongation substrate preferably is malonyl-CoA. The elongation substrate is preferably labelled radioactively, most preferably [14C] malonyl-CoA. Radioactive labelling allows for an easy and sensitive detection of elongation products. Also, labelling of the elongation substrate instead of the molecule to be elongated allows presenting a mixture of molecules to be elongated to the elongase, and only the elongation products will have incorporated significant amounts of label to render them easily detectable. Thus, in a single reaction vessel a multitude of potential molecules to be elongated can be assayed to determine which of these molecules are indeed elongated, and the relative affinity of the elongase to the respective molecule.

By combining both methods, it is possible to analyse even complex sequences of desaturation and elongation reactions. The invention thus also provides a method for pathway optimization, comprising the steps of
　i) providing enzymes of a metabolic pathway and one or more substrates to be used by the first enzyme or enzymes of the pathway,
　ii) reacting the enzymes and the substrates to produce products, which in turn are also exposed as potential substrates to the enzymes of the pathway, and
　iii) determining the accumulation of products.

The method particularly allows providing desaturases and elongases to form a pathway. This is useful to determine the yield of product(s) of the pathway and of any unwanted side products. Also, by providing two or more different enzymes which perform the same metabolic function, e.g. a particular desaturation step, e.g. a delta-5 desaturation, it is possible to analyse if the presence of more than one type of enzymes has an effect on product formation, particularly on product formation rate. For such analysis, one would compare the results with a method performed with only one of the at least two enzymes. Thus, if addition of enzymes performing the same metabolic function leads to an increased yield or product formation rate, then this metabolic step is subject to a gene dosage effect. To optimize the pathway in an organism one would correspondingly strive to implement the pathway step using the two or more enzymes as required.

Also, the method advantageously allows determining the mode of action of an enzyme in question. To this end, a helper enzyme is provided to produce a substrate for a target enzyme. The helper enzyme's mode of action is known. The helper enzyme is then provided with a substrate to turn into a product which could be used as a substrate of the target enzyme. Generation of product by the target enzyme is determined, preferably by measuring the amount of product per time or the final amount of product divided by the amount of substrate converted by the helper enzyme. Then the method is repeated using a helper enzyme of a different mode of action, and generation of product by the target enzyme is determined, too. By comparing the product generation by the target enzyme for each mode of action, the mode of action of the target enzyme is defined as being the mode of action of the helper enzyme giving rise to the most intense generation of product by the target enzyme.

For example, to determine the mode of action of a target desaturase, a helper elongase is provided for which it has been text book knowledge that it is utilizing acyl CoA substrate and produces acyl-CoA products. Then, product generation by the target desaturase is measured. In another step, a helper desaturase is provided for which it has been established that it produces phosphatidylcholine-bound fatty acids. Again, product generation by the target desaturase is measured. When comparing the product generation of the target desaturase, the target desaturase can be defined as being a CoA-dependent desaturase if the product generation of the target desaturase under conditions where CoA-bound fatty acids are provided by the helper enzyme is more intense (e.g. higher conversion efficiency) than under conditions where phosphatidylcholine-bound fatty acids are provided by the helper enzyme.

Thus, the invention also provides a method for determining CoA-dependence of a target desaturase, comprising the steps of
i) providing an elongase to produce a substrate for the target desaturase, and determining conversion efficiency of the target desaturase, and
ii) providing a non-CoA dependent desaturase to produce the substrate for the target desaturase, and determining conversion efficiency of the target desaturase, and
iii) comparing the target desaturase conversion efficiencies of step i) and ii).

If the conversion efficiency of the target desaturase is larger in step i) than in step ii), then the target desaturase is CoA-dependent. Of course, both steps must be performed under comparable conditions; particularly a substrate limitation of the target desaturase must be avoided.

The method can also be performed by providing an elongase which uses the substrate of the target desaturase. Thus, the invention provides a method for determining CoA-dependence of a target desaturase, comprising the steps of
i) providing an elongase to elongate the products of the target desaturase, and determining conversion efficiency of the elongase,
ii) providing the elongase to elongate the products of a comparison desaturase known to be non-CoA dependent, and determining conversion efficiency of the elongase,
iii) comparing the elongase conversion efficiencies of step i) and ii).

If the elongase conversion efficiency is higher in step i) than in step ii), the target desaturase is CoA-dependence. Without being bound by any particular theory it is presently expected that in such case the desaturation product does not have to be converted into an elongatable CoA-bound fatty acid, thus desaturated product can be immediately utilized by the elongase without accumulation. Of course, both steps must be performed under comparable conditions; particularly a substrate limitation of the elongase must be avoided.

The present invention also relates to oil comprising a polyunsaturated fatty acid obtainable by the aforementioned methods. In addition, the present invention also relates to a lipid or fatty acid composition comprising a polyunsaturated fatty acid obtainable by the aforementioned methods.

The term "oil" refers to a fatty acid mixture comprising unsaturated and/or saturated fatty acids which are esterified to triglycerides. Preferably, the triglycerides in the oil of the invention comprise PUFA or VLC-PUFA moieties as referred to above. The amount of esterified PUFA and/or VLC-PUFA is, preferably, approximately 30%, a content of 50% is more preferred, a content of 60%, 70%, 80% or more is even more preferred. The oil may further comprise free fatty acids, preferably, the PUFA and VLC-PUFA referred to above. For the analysis, the fatty acid content can be, e.g., determined by GC analysis after converting the fatty acids into the methyl esters by transesterification. The content of the various fatty acids in the oil or fat can vary, in particular depending on the source. The oil, however, shall have a non-naturally occurring composition with respect to the PUFA and/or VLC-PUFA composition and content. It is known that most of the fatty acids in plant oil are esterified in triacylglycerides. Accordingly, in the oil of the invention, the PUFAs and VLC-PUFAs are, preferably, also occur in esterified form in the triacylglcerides. It will be understood that such a unique oil composition and the unique esterification pattern of PUFA and VLC-PUFA in the triglycerides of the oil shall only be obtainable by applying the methods of the present invention specified above. Moreover, the oil of the invention may comprise other molecular species as well. Specifically, it may comprise minor impurities (and thus minor amounts) of the polynucleotide or vector of the invention. which however, can be detected only by highly sensitive techniques such as PCR.

As described above, these oils, lipids or fatty acids compositions, preferably, comprise 4 to 15% of palmitic acid (in an embodiment 6 to 15% of palmitic acid), 1 to 6% of stearic acid, 7-85% of oleic acid, 0.5 to 8% of vaccenic acid, 0.1 to 1% of arachidic acid, 7 to 25% of saturated fatty acids, 8 to 85% of monounsaturated fatty acids and 60 to 85% of polyunsaturated fatty acids, in each case based on 100% and on the total fatty acid content of the organisms (preferably by weight). Preferred VLC-PUFAs present in the fatty acid esters orfatty acid mixtures is, preferably, at least 5.5% to 20% of DHA and/or 9.5% to 30% EPA based on the total fatty acid content (preferably by weight).

The oils, lipids or fatty acids according to the invention, preferably, comprise at least 1%, 1.5%, 2%, 3%, 4%, 5.5%, 6%, 7% or 7.5%, more preferably, at least 8%, 9%, 10%, 11% or 12%, and most preferably at least 13%, 14%, 15%, 16%. 17%, 18%, 19% or 20% of DHA (preferably by weight), or at least 5%, 8%, 9.5%, 10%, 11% or 12%, more preferably, at least 13%, 14%, 14.5%, 15% or 16%, and most preferably at least 17%, 18%, 19%, 20%. 21%, 22%, 23%, 24%, 25%, 26%, 27%, 28%, 29% or 30% of EPA (preferably by weight) based on the total fatty acid content of the production host cell, organism, advantageously of a plant, especially of an oil crop such as soybean, oilseed rape, coconut, oil palm, safflower, flax, hemp, castor-oil plant, *Calendula*, peanut, cacao bean, sunflower or the abovementioned other monocotyledonous or dicotyledonous oil crops. In an embodiment, the oils, lipids or fatty acids according to the invention, preferably, comprise at least 1% of DHA, and/or at least 8% of EPA based on the total fatty acid content of the production host cell, organism, advantageously of a plant, especially of an oil crop such as soybean, oilseed rape, coconut, oil palm, safflower, flax, hemp, castor-oil plant, *Calendula*, peanut, cacao bean, sunflower or the abovementioned other monocotyledonous or dicotyledonous oil crops.

Preferably, the oil, lipid or fatty acid composition of the present invention is a plant oil, plant lipid, or plant fatty acid composition. Preferably, said oil or lipid is extracted, obtained, obtainable or produced from a plant, more preferably from seeds of a plant or plants (in particular a plant or plants of the present invention). The oil or lipid thus can be obtained by the methods of the present invention. In particular, the plant oil or plant lipid is an extracted plant oil or lipid. Also preferably, said oil or lipid is extracted, obtained, obtainable or produced from a plant, more preferably from batches of seeds or bulked seeds of a plant or plants (in particular a plant or plants of the present invention).

Preferably, the term "extracted" in connection with an oil or lipid refers to an oil or lipid that has been extracted from a plant, in particular from seeds of a plant or plants. More preferably, the term "extracted" in connection with an oil or lipid refers to an oil or lipid that has been extracted from a plant, in particular from batch of seeds or bulked seeds of a plant or plants. Such oil or lipid can be a crude composition. However, it may be also a purified oil or lipid in which e.g. the water has been removed. In an embodiment, the oil or lipid is not blended with fatty acids from other sources.

The oil or lipid of the present invention may be also an oil or lipid in a seed of plant. Preferably, said plant is a transgenic plant. More preferably, said plant is a plant of the present invention. In a particular preferred embodiment, the plant is a Brassica plant.

The oil or lipid of the present invention shall comprise fatty acids. In particular, the oil or lipid shall comprise fatty acids in esterified form. Thus, the fatty acids shall be esterified. Preferably, the oil or lipid of the present comprises one or more of following fatty acids (in esterified form): Oleic acid (OA), Linoleic acid (LA), gamma-Linolenic acid (GLA), alpha-Linolenic acid (ALA), Stearidonic acid (SDA), 20:2n-9 ((Z,Z)-8,11-Eicosadienoic acid), Mead acid (20:3n-9), Dihomo-gamma-linolenic acid (DHGLA), Eicosapentaenoic acid (Timnodonic acid, EPA, 20:5n-3), Clupanodonic acid (DPA n-3), and DHA ((Z,Z,Z,Z,Z,Z)-4,7,10,13,16,19-Docosahexaenoic acid). More preferably, the oil or lipid comprises EPA, DHA and Mead acid. Even more preferably, the oil or lipid comprises EPA, DHA, Mead acid, DPA n-3, and DHGLA. Most preferably, the oil or lipid comprises fatty acids mentioned in this paragraph.

It is in particular envisaged that the oil or lipid of the present invention comprises both EPA and DHA. Preferred contents of EPA and DHA are given elsewhere herein.

Further, it is envisaged that the oil or lipid comprises EPA, DHA, and DPA n-3. In an embodiment, the oil or lipid further comprises Mead Acid.

Also, it is envisaged that the oil or lipid comprises EPA, DHA, and DHGLA. In an embodiment, the oil or lipid further comprises Mead Acid.

In addition, the oil or lipid may comprise EPA, DHA, DPA n-3, and DHGLA. In an embodiment, the oil or lipid further comprises Mead Acid.

Thus, the expression cassettes, the construct or the T-DNA of the present invention can be used for modulating, in particular increasing, the content of one or more of the aforementioned fatty acids in plants, in seeds and/or in seed oil of a plant as compared to a control plant.

The preferred content of aforementioned fatty acids in the total fatty acid content of the lipid or oil of the present invention is further described in the following. In the following, ranges are given for the contents. The content (levels) of fatty acids are expressed as percentage (weight of a particular fatty acid) of the (total weight of all fatty acids), in particular of the (total weight of all fatty acids present in the oil or lipid). The contents are thus, preferably given as weight percentage (% (w/w)) of total fatty acids present in the oil or lipid. Accordingly, "%" preferably means "% (w/w)" for a fatty acid (or combination of fatty acids) compared to the total weight of fatty acids".

Preferably, the fatty acids are present in esterified form. Thus, the fatty acids shall be esterified fatty acids.

Preferably, the oil or lipid comprises Oleic acid (OA). Preferably, the content of Oleic acid (OA) is between 10% and 45%, more preferably between 20% and 38%, most preferably between 26% and 32% of the total fatty acid content.

Preferably, the oil or lipid comprises Linoleic acid (LA). Preferably, the content of Linoleic acid (LA) is between 5% and 40%, more preferably between 10% and 40%, most preferably between 20% and 35% of the total fatty acid content.

Preferably, the oil or lipid comprises gamma-Linolenic acid (GLA). Preferably, the content of gamma-Linolenic acid (GLA) is between 0.1% and 6%, more preferably between 0.1% and 3%, most preferably between 0.5% and 2% of the total fatty acid content.

Preferably, the oil or lipid comprises alpha-linolenic acid (ALA). Preferably, the content of alpha-Linolenic acid (ALA) is between 2% and 20%, more preferably between 4% and 10%, most preferably between 4% and 7% of the total fatty acid content.

Preferably, the oil or lipid comprises Stearidonic acid (SDA). Preferably, the content of Stearidonic acid (SDA) is between 0.1% and 10%, more preferably between 0.1% and 5%, most preferably between 0.1% and 1% of the total fatty acid content.

The content of SDA was surprisingly low. In an embodiment, the content of SDA is lower than 2%, in particular lower than 1%.

Preferably, the oil or lipid comprises 20:2n-9. Preferably, the content of 20:2n-9 ((Z,Z)-8,11-Eicosadienoic acid) is between 0.1% and 3%, more preferably between 0.1% and 2%, most preferably between 0.1% and 1% of the total fatty acid content.

Preferably, the oil or lipid comprises Mead acid (20:3n-9). Preferably, the content of Mead acid (20:3n-9) is between 0.1% and 2%, more preferably between 0.1% and 1%, most preferably between 0.1% and 0.5% of the total fatty acid content. In another embodiment, the content of Mead acid (20:3n-9) is between 0.1% and 0.3% of the total fatty acid content Preferably, the oil or lipid comprises Dihomo-gamma-linolenic acid (DHGLA). Preferably, the content of Dihomo-gamma-linolenic acid (DHGLA) is between 0.1% and 10%, more preferably between 1% and 6%, most preferably between 1% and 5%, in particular between 2 and 4% of the total fatty acid content. The accumulation of this internmediate was not necessarily expected.

Preferably, the oil or lipid comprises EPA (20:5n-3). Preferably, the content of Eicosapentaenoic acid (Timnodonic acid, EPA, 20:5n-3) is between 0.1% and 20%, more preferably between 2% and 15%, most preferably between 5% and 10% of the total fatty acid content.

Further, it is envisaged that the content of EPA is between 5% and 15% of the total fatty acid content Preferably, the oil or lipid comprises Clupanodonic acid (DPA n-3). Preferably, the content of Clupanodonic acid (DPA n-3) is between 0.1% and 10%, more preferably between 1% and 6%, most preferably between 2% and 4% of the total fatty acid content. In addition, the content of DPA n-3 may be at least 2% of the total fatty acids.

Preferably, the oil or lipid comprises DHA. Preferably, the content of DHA is between 1% and 10%, more preferably between 1% and 4%, most preferably between 1% and 2% of the total fatty acid content.

Further, it is envisaged that the content of DHA is between 1% and 3% of the total fatty acid content In a preferred embodiment, the oil or lipid of the invention has a content of DHA between 1% and 4% and a content of EPA between 2% and 15% of the total fatty acid content. In another preferred embodiment, the oil or lipid of the invention has a content of DHA between 1% and 3% and a content of EPA between 5% and 15% of the total fatty acid content.

In another preferred embodiment, the oil or lipid of the invention has a content of DHA between 1% and 2% and a content of EPA between 5% and 10% of the total fatty acid content.

The oil or lipid of the present invention may also comprise saturated fatty acids such as 16:0 (Palmitic acid) and/or 18:0 (Stearic acid). The contents of 16:0 and 18:0 are advantageously low as compared to wild-type plants. Low saturated fat is a desirable feature from the health perspective.

Thus, the oil or lipid may comprise 16:0. Preferably, the content of 16:0 is less than 6% of the total fatty acid content. More preferably, the content of 16:0 is between 3% and 6% of the total fatty acid content Thus, the oil or lipid may comprise 18:0. Preferably, the content of 18:0 is less than 4%, in particular less than 3% of the total fatty acid content. More preferably, the content of 18:0 is between 1.5% and 4%, in particular between 2% and 3% of the total fatty acid content.

In an embodiment of the oil or lipid of the present invention, the total content of EPA, DHA and DPA n-3 is preferably more than 6% and the content of SDA is lower than 2% of all fatty acids present in the oil or lipids. More preferably the content of EPA, DHA, and DPA n-3 is between 7% and 14% and the content of SDA is lower than 1% of all fatty acids present in the oil or lipids.

In another preferred embodiment of the oil or the lipid of the present invention, the content of DPA n-3 is preferably at least 2% of the total fatty acid content, and the total content of EPA and DHA is at least 3% of the total fatty acid content. More preferably the content of DPA n-3 is between 2% and 5%, and the total content of EPA and DHA is between 6% and 12% of all fatty acids present in the oil or lipids.

In an embodiment of the oil or the lipid of the present invention, the content of 16:0 is preferably lower than 6% of the total fatty acid content, and the total content of EPA and DHA is at least 3% of the total fatty acid content. More preferably the content of 16:0 is between 2% and 6%, and the total content of EPA and DHA is between 6% and 12% of all fatty acids present in the oil or lipids.

In an embodiment of the oil or the lipid of the present invention, the content of 16:0 is preferably lower than 5% of the total fatty acid content, and the total content of EPA, DHA, DPA n-3 is at least 6% of the total fatty acid content. More preferably content of 16:0 is between 2% and 5% and the total content of EPA, DHA, and DPA is between 8% and 14% of all fatty acids present in the oil or lipids.

Interestingly, the content of EPA of the total fatty acids in the seeds, in particular in the seed oil, was larger than the content of DHA. This is not always the case; see for examples US2015/0299676A1 and WO 2015/089587. Thus, it is in particular envisaged, that the oil and lipid of the present invention comprises more EPA than DHA. Thus, the content of EPA shall be larger than the content of DHA. Preferably, the content of EPA of the total fatty acid acid content is 3 to 7-fold the content of DHA of the total fatty acid content. More preferably, the content of EPA of the total fatty acid acid content is 4 to 5-fold the content of DHA of the total fatty acid content.

Preferably, the total content of all omega-3 polyunsaturated [n-3 (C18-C22)] fatty acids is between 1% and 40%, more preferably between 10% and 30%, most preferably between 15% and 22% of the total fatty acid content.

Also preferably, the total content of all omega-6 polyunsaturated [n-6 (C18-C22)] fatty acids is between 0.1% and 50%, more preferably between 20% and 50%, most preferably between 37% and 42% of the total fatty acid content.

The oil or lipid of the present invention may comprise fatty acids that are non-naturally occurring in wild type control *Brassica napus* lipid or oil, preferably greater than 10%, more preferably between 12% and 25.2%, and most preferably between 16% and 25.0% of the total fatty acid content. Preferably, non naturally occurding fatty acids are 18:2n-9, GLA, SDA, 20:2n-9, 20:3n-9, 20:3 n-6, 20:4n-6, 22:2n-6, 22:5n-6, 22:4n-3, 22:5n-3, and 22:6n-3. Thus, the total content of these fatty acids in the oil or lipid of the present invention is preferably greater than 10%, more preferably between 12% and 25.2%, and most preferably between 16% and 25.0% of the total fatty acid content In Example 32 it is shown that certain TAG (triacylglyceride) species were decreased and certain TAG species were increased in the seeds of the plants of the present invention (in particular in seed oil extracted from plants of the present invention).

The five most abundant TAG (triacylglyceride) species in wild-type Kumilly plants were TAG (18:1 18:1 18:3), TAG (18:1 18:2 18:3), TAG (18:1 18:1 18:2), TAG (18:1 18:1 18:1), and (TAG 18:1 18:2 18:2). Together, these account for 64.5% of all TAG species (in oil of wild-type plants). These species are specifically reduced in plants of the present invention (see Example 32, Table 192).

The two most abundant DHA containing TAG species in the transgenic canola samples were TAG (18:1 18:2 22:6) and TAG (18:2 18:2 22:6). Interestingly, the EPA and DHA are found most frequently esterified to TAG together with 18:1 and 18:2. This makeup is likely to be more oxidatively stable that TAG species containing multiple PUFAs (see Wijesundra 2008, Lipid Technology 20(9):199-202). For more details, see Example 32 and table 192.

The oil or lipid of the present invention thus may comprise certain TAG species. Preferably, the oil or lipid comprises one or more of the following TAG species: TAG (18:1 18:2 20:5), TAG (18:1 18:1 20:5), TAG (18:2 18:2 20:5), TAG (18:1 18:2 22:6) and TAG (18:2 18:2 22:6). More preferably, the oil of lipid of the present invention comprises all of the aforementioned TAG species. Alternatively or additionally, the oil or lipid of the present invention may comprise TAG (18:1 18:1 22:6).

The triacylglyceride nomenclature used herein is well known in the art and well understood by the skilled person. The triacylglyceride TAG ($x^1:y^1$ $x^2:y^2$ $x^3:y^3$) is preferably denoted to mean that the triacylglyceride comprises three fatty acid ester residues, wherein one fatty acid ester residue is $x^1:y^1$ which means that this residue comprises $x^1$ carbon atoms and $y^1$ double bonds, wherein one fatty acid ester residue is $x^2:y^2$ which means that this residue comprises $x^2$ carbon atoms and $y^2$ double bonds, and wherein one fatty acid ester residue is $x^3:y^3$ which means that this residue comprises $x^3$ carbon atoms and $y^3$ double bonds. Preferably, any of these fatty acid ester residues may be attached to any former hydroxyl groups of the glycerol.

The preferred content of aforementioned TAG species of the total TAG content of the lipid or oil of the present invention is further described in the following. In the following ranges are given for the contents. The content (levels) of TAGs are expressed as percentage (weight of a particular TAG, or a combinations of TAGs) of the total weight of total TAGs (i.e. all TAGs) present in the oil or lipid). The contents are thus, preferably, given as weight percentage (% (w/w)). Accordingly, "%" preferably means "% (w/w) for a TAG (or combination of TAGs) compared to the total weight of TAGs".

Preferably, the oil or lipid comprises TAG (18:1 18:2 20:5). Preferably, the content of TAG (18:1 18:2 20:5) is between 0.1% and 20%, more preferably between 5% and 15%, most preferably between 7% and 12% of the total TAG content.

As set forth above, the oil or lipid preferably comprises TAG (18:1 18:1 20:5). Preferably, the content of TAG (18:1 18:1 20:5) is between 1.5% and 15%, more preferably between 2% and 10%, most preferably between 4% and 7.6% of the total TAG content.

As set forth above, the oil or lipid preferably comprises TAG (18:2 18:2 20:5). Preferably, the content of TAG (18:2 18:2 20:5) is between 3% and 20%, more preferably between 3% and 15%, most preferably between 3.5% and 9% of the total TAG content.

Also preferably, the sum of the contents of TAG (18:1 18:2 20:5), TAG (18:1 18:1 20:5), and TAG (18:2 18:2 20:5), i.e. the combined contents of these three TAG species, is between 5% and 55%, more preferably between 10% and 45%, most preferably between 20% and 26% of the total TAG content.

Thus, the most abundant TAG species are those that contain esterified EPA. EPA is better than DHA for some health reasons.

As set forth above, the oil or lipid preferably comprises TAG (18:1 18:2 22:6). Preferably, the content of TAG (18:1 18:2 22:6) is between 0.1% and 15%, more preferably between 0.1% and 10%, most preferably between 0.5% and 3% of the total TAG content.

As set forth above, the oil or lipid preferably comprises TAG (18:2 18:2 22:6). Preferably, the content of TAG (18:2 18:2 22:6) is between 0.1% and 15%, more preferably between 0.1% and 10%, most preferably between 0.5% and 2% of the total TAG content.

As set forth above, the oil or lipid preferably comprises TAG (18:1 18:1 22:6). Preferably, the content of TAG (18:1 18:1 22:6) is between 0.1% and 15%, more preferably between 0.1% and 10%, most preferably between 0.3% and 1% of the total TAG content.

Also preferably, the sum of the contents of TAG (18:1 18:2 22:6), TAG (18:2 18:2 22:6) and TAG (18:1 18:1 22:6), i.e. the combined content of these three TAG species, is between 0.3% and 45%, more preferably between 1% and 30%, most preferably between 1% and 5% of the total TAG content.

The oil or lipid of the present invention may also comprise TAG (18:3 18:3 20:5) and/or TAG (18:3 18:3 22:6). As can be seen from the examples, a low abundance of these TAG species was observed (see table 192). The low abundance can have an oxidative stability benefit.

Preferably, the content of TAG (18:3 18:3 20:5) is between 0.1% and 2%, more preferably between 0.1% and 1%, most preferably between 0.1% and 0.5% of the total TAG content.

Preferably, the content of TAG (18:3 18:3 22:6) is between 0.03% and 2%, more preferably between 0.03% and 1%, most preferably between 0.03% and 0.5% of the total TAG content. Further, it is contemplated that the content of TAG (18:3 18:3 22:6) is between 0.03% and 0.2% of the total TAG content.

As set forth above, the most abundant TAG species in wild-type Kumily plants were TAG (18:1 18:1 18:3), TAG (18:1 18:2 18:3), TAG (18:1 18:1 18:2), TAG (18:1 18:1 18:1), and (TAG 18:1 18:2 18:2). As compared to wild-type oil, the content of these species in seed oil from transgenic Brassice plants was advantageously reduced. One of these species, TAG (18:1 18:1 18:3), was not detectable in the oil.

Thus, the oil or lipid of the present invention may further one or more of the following features: As set forth above, the oil or lipid preferably comprises TAG (18:1 18:1 18:3). Preferably, the content of TAG (18:1 18:1 18:3) is between 0% and 10%, more preferably between 0% and 5%, most preferably between 0% and 3% of the total TAG content.

Also preferably, the content of TAG (18:1 18:1 18:3) of the total TAG content may be lower than 3%, in particular lower than 1%.

As set forth above, the oil or lipid preferably comprises TAG (18:1 18:2 18:3). Preferably, the content of TAG (18:1 18:2 18:3) is between 3% and 19%, more preferably between 4% and 18%, most preferably between 4% and 7% of the total TAG content.

Also preferably, the content of TAG (18:1 18:2 18:3) of the total TAG content may be lower than 7%.

As set forth above, the oil or lipid preferably comprises TAG (18:1 18:1 18:2). Preferably, the content of TAG (18:1 18:1 18:2) is between 1% and 10%, more preferably between 2% and 10%, most preferably between 2% and 5% of the total TAG content.

Also preferably, the content of TAG (18:1 18:1 18:2) of the total TAG content may be lower than 5%.

As set forth above, the oil or lipid preferably comprises TAG (18:1 18:1 18:1). Preferably, the content of TAG (18:1 18:1 18:1) is between 0.1% and 8%, more preferably between 0.5% and 5%, most preferably between 1% and 3% of the total TAG content.

Also preferably, the content of TAG (18:1 18:1 18:1) of the total TAG content may be lower than 3%.

As set forth above, the oil or lipid preferably comprises TAG (18:1 18:2 18:2). Preferably, the content of TAG (18:1 18:2 18:2) is between 0.1% and 13%, more preferably between 3% and 11%, most preferably between 4% and 10% of the total TAG content.

Also preferably, the content of TAG (18:1 18:2 18:2) of the total TAG content may be lower than 10%.

Also preferably, the total content and thus sum of the contents of TAG (18:1 18:1 18:3), TAG (18:1 18:2 18:3), TAG (18:1 18:1 18:2), and TAG (18:1 18:1 18:1), TAG (18:1 18:2 18:2) is between 5% and 50%, more preferably between 10% and 30%, most preferably between 14% and 22% of the total TAG content. In an embodiment, the total content of the aforementioned TAG species of the total TAG content is lower that 21.2% of the total TAG content.

As can be derived from Example 32, EPA and DHA are found most frequently esterified to TAG together with 18:1 and/or 18:2. These combinations of fatty acids are advantageous because they are more oxidatively stable than TAG species with more than one PUFA. In a preferred embodiment of the oil or lipid of the present invention, less that 21% of the total TAG species comprised by the oil or lipid contain more than one EPA, DPA, and DHA n-3 residue.

The oil or lipid of the present invention comprises TAGs (triacylglycerides), DAGs (diacylglycerides), and DAGs (diacylglycerides). As set forth certain TAG (triacylglyceride) species were decreased and certain TAG species were increased in the seeds of the plants of the present invention (in particular in seed oil of plants of the present invention). In addition, certain MAG and DAG species were decreased and certain MAG and DAG species were increased in the seeds of the plants of the present invention (in particular in seed oil of plants of the present invention).

E.g., the examples show that there is more esterified EPA and DHA in DAG than in MAG. Thus, is is envisaged that the content of esterified EPA and DHA in DAG (with respect to the total esterfied fatty acid content in DAG) is larger than the content of esterified EPA and DHA in MAG (with respect to the total esterfied fatty acid content in MAG). Preferably, the ratio of the content of esterified EPA and DHA in DAG (with respect to the total esterfied fatty acid content in DAG) to the the content of esterified EPA and DHA in MAG (with respect to the total esterfied fatty acid content in MAG) is about 1.5.

Further, the Examples show that DHA is accumulated in the phosphatidylcholine (PC) fraction. This is thought to be achieved by expression of both a phospholipid and CoA dependent d4Des. It could be advantageous because DHA in phospholipids is thought to be more readily digestible.

Preferably, the content of DHA in in the phosphatidylcholine (PC) fraction in the oil or lipid of the present invention is between 2 and 12%, more preferably, between 2 and 10, most preferably between 5 and 9% of the total fatty acid content of the PC fraction (preferably % w/w).

Moreover, it is envisaged that the ratio of the content DHA in the PC fraction to the content in the TAG fraction of the oil or lipid of the present invention is larger than 1.

In addition, the studies underlying the present invention showed that the ratio of DHA to DPA n-3 is higher in the PC and PE (phosphatidylethanolamine) fraction than in the neutral lipid fraction (MAG, DAG, and TAG), see Example 30. This makes the PC and PE fractions potentially more valuable. In an embodiment of the oil or lipid of the present invention, the ratio of the content of DHA of all fatty acids in the PC and PE fraction to the content of DPA n-3 of all fatty acids in the PC and PE fraction is larger than the ratio of the content of DHA of all fatty acids in the MAG, DAG, and/or TAG fraction to the content of DPA n-3 of all fatty acids in the MAG, DAG, and/or TAG fraction.

Further, it is envisaged that the amount of DHA in the phospholipid fraction in the oil or lipid of the present is larger that the amount of EPA in the phospholipid fraction. In contrast, the amount of EPA in the TAG fraction in the oil or lipid of the present shall be larger that the amount of DHA in the TAG fraction. "Amount" is this paragraph preferably means absolute amount.

Example 31 shows that the abundant PC (phosphatidylcholine) species containing EPA or DHA are PC (18:2, 22:6) and PC (18:2 20:5). This majority of PUFA are combined with 18:2 which is more stable than if they are combined with 18:3 or another PUFA.

Thus, the oil or lipid of the present invention preferably comprises PC (18:2, 22:6), PC (18:2 20:5), or both. Preferred contents of the species in the oil or lipid of the present invention are given below. The content (levels) of the species are expressed as percentage (weight of a particular PC species) of the total weight of total PCs (i.e. all PCs) present in the oil or lipid). The contents are thus, preferably, given as weight percentage (% (w/w)). Accordingly, "%" preferably means "% (w/w) for a PC (or combination of PCs) compared to the total weight of PCs".

Preferably, the content of PC (18:2 20:5) is between 2.5% and 15%, more preferably between 2.5% and 12%, most preferably between 3% and 10% of the total phosphatidylcholine content. Also preferably the content of this species is at least 3%.

Preferably, the content of PC (18:2, 22:6) is between 0.5% and 10%, more preferably between 1% and 7%, most preferably between 1% and 6% of the total phosphatidylcholine content. Also preferably, the content of this species is at least 1.4%.

The present invention also relates to a plant comprising seeds comprising an oil of the present invention. Furthermore, the present invention relates to a seed comprising the oil of the present invention. Preferred plant species are described herein above. Preferably, the plant and the seed(s) comprises one ore more polynucleotides, expression cassettes, T-DNAs and/or construct as set forth in the context of the present invention.

The present invention also relates to a seed, in particular to bulked seeds, of the plant of the present invention. The seed/seeds shall contain the oil or lipid of the present invention.

In addition, as shown in the Examples, bulked seeds from event LBFGKN were determined to have 25.7 mg EPA+ DHA/g seed and bulked seeds from event LBFDAU was determined to have 47.4 mg EPA+DHA/g seed. Thus, the present invention relates to seeds, in particular Brassica seeds, wherein 1 g of the seeds comprises a combined content of EPA and DHA of at least 10 mg, in particular of at least 20 mg. Further, it is envisaged that 1 g of the seeds of the present invention comprise a combined content of EPA and DHA of preferably 15 to 75 mg, more preferably of 20 to 60 mg, and most preferably of 25 to 50 mg.

Preferably, the seeds of the present invention comprise at least one T-DNA of the present invention. Thus, it is envisaged that said seeds are transgenic.

The present invention also concerns seed meal and seed cake produced from the seeds of the present invention, in particular from bulked seeds of the present invention.

Interestingly, the seeds that were produced in the context of the studies underlying the present invention had higher yield and larger contents of seed oil than expected (see e.g. Example 18, EPA/DHA in tables 152 and 153, and oil in table 154). The degree of unsaturation and elongation was increased in transgenic seed oil relative to controls. To achieve these increases the introduced desaturases and elongases consume additional ATP and NADH compared to controls. Therefore, the desaturases and elongases that we introduced are in direct competition with de novo fatty acid and oil synthesis, which also require ATP and NADH (every elongation requires two NADH and one ATP, and every desaturation requires one NADH). Moreover, the provision of malonyl-CoA for elongating fatty acids results in the loss of carbon in form of $CO_2$ (see Schwender et al 2004 Nature 432: 779-782). Therefore, we expected lower yield or oil content due to increased consumption of NADH, ATP, and increased loss of $CO_2$. However, we produced seeds containing high amounts of EPA and DHA that did not have differences in yield or in oil content relative to controls (see Example 18 and Table 154). For example, seed were produced containing EPA/DHA and more than 38.2% oil. This was not expected because a negative correlation between oil and PUFA content was observed (see Examples). Thus, the seeds of the present invention and the seeds of the plant or plants of the present invention, preferably, have a seed oil content at least 38%, More preferably, the seeds have a seed oil content of 38 to 42%, in particular of 38% to 40%. Preferably, seed oil content is expressed as percentage of oil weight of the total weight of seeds. Also preferably, the seed oil is produced in plants that have a seed yield that is no different from control plants when cultivated in the field.

The plant of the present invention, is preferably a transgenic *B. napus* plant. As described elsewhere herein, the plant shall produce both EPA and DHA. It is envisaged that the oil from the bulked seed contains more than 12% non-naturally occurring PUFA. Thus, the content of the non-naturally occurring fatty acids shall be more than 12% of the total fatty acid content. In another embodiment, the oil from the bulked seed contains more than 16% non-naturally occurring PUFA. In another embodiment, the oil from the bulked seed contains more than 18% non-naturally occurring PUFA. The expression "non-naturally occurring" preferably refers to PUFAs which do not occur naturally in wild-type *Brassica* plant. Preferably, said non-naturally occurring PUFASs are 18:2n-9, GLA, SDA, 20:2n-9, 20:3n-9, 20:3 n-6, 20:4n-6, 22:2n-6, 22:5n-6, 22:4n-3, 22:5n-3, and 22:6n-3. Although these PUFAs do not naturally occur in *Brassica* plants, they may nevertheless occurring in other non-transgenic organisms.

In an embodiment of the plant of the present invention, each T-DNA copy of the transgenic plant is stable over multiple generations as determined by copy number analysis at three or more locations on the T-DNA. In an embodiment of the plant of the present invention, the transgenic construct inserted into the *B. napus* plant has a copy number of 1 or 2. Thus, one or two copies of the T-DNA of the invention shall be present in the plant. In a preferred embodiment of the plant of the present invention, the transgenic construct inserted into the *B. napus* plant has a copy number of 1. Preferably, all inserted transgenes are fully functional (thus, the enzymes encoded by the genes shall retain their function). Preferably, the genetic insertion is located >5000 base pairs away from any endogenous gene. In an embodiment, the distance is measured from the end of the left and right border.

Preferably, the plant of the present invention, in particular the plant described is used in a method using produce an oil containing EPA and DHA. The oil has been described in detail elsewhere herein. In an embodiment, the oil comprises non-naturally occurring PUFA as described above.

The method of producing the oil may comprise the steps of growing a plant of the present invention such as to obtain oil-containing seeds thereof, harvesting said seed, and extracting oil form said seeds.

The present invention further envisages an oil containing EPA and DHA produced by plants the plant described above.

A further embodiment according to the invention is the use of the oil, lipid, fatty acids and/or the fatty acid composition in feedstuffs, foodstuffs, dietary supplies, cosmetics or pharmaceutical compositions as set forth in detail below. The oils, lipids, fatty acids or fatty acid mixtures according to the invention can be used for mixing with other oils, lipids, fatty acids or fatty acid mixtures of animal origin such as, for example, fish oils.

The present invention thus envisages feedstuffs, foodstuffs and dietary supplies. In an embodiment, the feedstuffs, foodstuffs and dietary supplies comprise the plant of the present invention, a part of a plant of the present invention, in particular a seed or seed, and/or the oil or lipid of the present invention.

In an embodiment, the feedstuffs, foodstuffs and dietary supplies comprise seedcake or seedmeal produced from the plant of the present invention, in particular from seeds of the plant of the present invention. Thus, the present invention also concerns seedcake or seedmeal produced from the plant of the present invention, in particular from seeds of the plant of the present invention. In an embodiment, the seedmeal or seedcake comprises at least one T-DNA of the present invention.

The feedstuffs, foodstuffs and dietary supplies may comprise a fatty acid ester, or a fatty acid produced from a plant of the present invention (orfrom a part thereof, in particularfrom the seeds).

The feedstuff of the present invention can be used in aquaculture. Using the feedstuff will allow to increase the contents of VLC-PUFAs in fish. In an embodiment, the fish is salmon.

The term "composition" refers to any composition formulated in solid, liquid or gaseous form. Said composition comprises the compound of the invention optionally together with suitable auxiliary compounds such as diluents or carriers or further ingredients. In this context, it is distinguished for the present invention between auxiliary compounds, i.e. compounds which do not contribute to the effects elicited by the compounds of the present invention upon application of the composition for its desired purpose, and further ingredients, i.e. compounds which contribute a further effect or modulate the effect of the compounds of the present invention. Suitable diluents and/or carriers depend on the purpose for which the composition is to be used and the other ingredients. The person skilled in the art can determine such suitable diluents and/or carriers without further ado. Examples of suitable carriers and/or diluents are well known in the art and include saline solutions such as buffers, water, emulsions, such as oil/water emulsions, various types of wetting agents, etc.

In a more preferred embodiment of the oil-, fatty acid or lipid-containing composition, the said composition is further formulated as a pharmaceutical composition, a cosmetic composition, a foodstuff, a feedstuff, preferably, fish feed or a dietary supply.

The term "pharmaceutical composition" as used herein comprises the compounds of the present invention and optionally one or more pharmaceutically acceptable carrier. The compounds of the present invention can be formulated as pharmaceutically acceptable salts. Acceptable salts comprise acetate, methylester, Hel, sulfate, chloride and the like. The pharmaceutical compositions are, preferably, administered topically or systemically. Suitable routes of administration conventionally used for drug administration are oral, intravenous, or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be acceptable in the sense of being compatible with the other ingredients of the formulation and being not deleterious to the recipient thereof. The pharmaceutical carrier employed may be, for example, a solid, a gel or a liquid. Exemplary of solid carriers are lactose, terra alba, sucrose, talc, gelatin, agar, pectin, *acacia*, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa. The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The dosage regimen will be determined by the attending physician and other clinical factors; preferably in accordance with anyone of the above described methods. As is well known in the medical arts, dosages for anyone patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 pg; however, doses below or above this exemplary range are envisioned, especially considering the aforementioned factors. However, depending on the subject and the mode of administration, the quantity of substance administration may vary over a wide range. The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days. Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "cosmetic composition" relates to a composition which can be formulated as described for a pharmaceutical composition above. For a cosmetic composition, likewise, it is envisaged that the compounds of the present invention are also, preferably, used in substantially pure form. Impurities, however, may be less critical than for a pharmaceutical composition. Cosmetic compositions are, preferably, to be applied topically.

Preferred cosmetic compositions comprising the compounds of the present invention can be formulated as a hair tonic, a hair restorer composition, a shampoo, a powder, a jelly, a hair rinse, an ointment, a hair lotion, a paste, a hair cream, a hair spray and/or a hair aerosol.

Seeds of three events described in detail in the examples section below have been deposited at ATCC under the provisions of the Budapest treaty on the International Recognition of the Deposit of Microorganisms for the Purposes of Patent Procedure, i.e. seeds of event "LBFLFK"=ATCC Designation "PTA-121703", seeds of event "LBFDHG"=ATCC designation "PTA-121704", and seeds of event "LBFDAU"=ATCC Designation "PTA-122340". Applicants have no authority to waive any restrictions imposed by law on the transfer of biological material or its transportation in commerce. Applicants do not waive any infringement of their rights granted under this patent or rights applicable to the deposited events under the Plant Variety Protection Act (7 USC sec. 2321, et seq.), Unauthorized seed multiplication prohibited. This seed may be regulated according to national law. The deposition of seeds was made only for convenience of the person skilled in the art and does not constitute or imply any confession, admission, declaration or assertion that deposited seed are required to fully describe the invention, to fully enable the invention or for carrying out the invention or any part or aspect thereof. Also, the deposition of seeds does not constitute or imply any recommendation to limit the application of any method of the present invention to the application of such seed or any material comprised in such seed, e.g. nucleic acids, proteins or any fragment of such nucleic acid or protein.

The deposited seeds are derived from plants that were transformed with the T-DNA vector having a sequence as shown in SEQ ID NO: 3.

The events LBFLFK and LBFDAU are described herein in more detail. In an embodiment, the plant of the present invention comprises the T-DNAs comprised by LBFLFK and LBFDAU, preferably at the the position in the genome (as in the plants designated LBFLFK and LBFDAU.

In one embodiment, the present invention thus provides *Brassica* plants comprising transgenic *Brassica* event LBFLFK deposited as ATCC Designation "PTA-121703". *Brassica* event LBFLFK contains two insertions of T-DNA of the binary T-plasmid VC-LTM593-1qcz rc, the insertions being designated LBFLFK Locus 1 and LBFLFK Locus 2. The *Brassica* plants of this embodiment include progeny that are indistinguishable from *Brassica* event LBFLFK (to the extent that such progeny also contain at least one allele corresponding to LBKLFK Locus 1 and/or LBFLFK Locus 2). The *Brassica* plants of this embodiment comprise unique genomic DNA/transgene junction points, and consequently unique junction regions, for each LBFLFK insertion: the junction region for LBFLFK Locus 1 having at least the polynucleotide sequence of SEQ ID NO:282 or at least the polynucleotide sequence of SEQ ID NO:283, and the junction region for LBFLFK Locus 2 having at least the polynucleotide sequence of SEQ ID NO:291 or at least the polynucleotide sequence of SEQ ID NO:292. Also included in this embodiment are seeds, plant parts, plant cells, and plant products derived from *Brassica* event LBFLFK and progeny thereof. In another embodiment, the invention provides commodity products, including canola oil and meal, produced from *Brassica* event LBFLFK and/or its progeny.

In another embodiment, the invention provides *Brassica* plants comprising transgenic *Brassica* event LBFDAU deposited as ATCC Designation "PTA-122340". *Brassica* event LBFDAU contains two insertions of the T-DNA of the binary T-plasmid VC-LTM593-1qcz rc, the insertions being designated LBFDAU Locus 1 and/or LBFDAU Locus 2. The *Brassica* plants of this embodiment include and progeny thereof that are indistinguishable from *Brassica* event LBFDAU (to the extent that such progeny also contain at least one allele that corresponds to the inserted transgenic DNA). The *Brassica* plants of this embodiment comprise unique genomic DNA/transgene junction points, and consequently two unique junction regions, for each LBFDAU insertion: the junction region for LBFDAU Locus 1 having at least the polynucleotide sequence of SEQ ID NO:300 or at least the polynucleotide sequence of SEQ ID NO:301 and the junction region for LBFDAU Locus 2 having at least the polynucleotide sequence of SEQ ID NO:309 or at least the polynucleotide sequence of SEQ ID NO:310. Also included in this embodiment are seeds, plant parts, plant cells, and plant products derived from *Brassica* event LBFDAU and progeny thereof. In another embodiment, the invention provides commodity products, including canola oil and meal, produced from *Brassica* event LBFDAU and/or its progeny.

The aforementioned plant of the present invention can be used in method the context of the present invention. E.g, the oil, fatty acid, or lipid of the present invention is obtainable from the plant (and can be extracted).

The plants of the invention have been modified by the transformation binary T-plasmid VC-LTM593-1qcz rc (SEQ ID NO:3) described in the Examples section. The T-DNA of this vector (which is a T-DNA of the present invention) comprises (preferably in the following order), polynucleotides encoding the following enzymes of the VLC-PUFA biosynthetic pathway: Delta-6 ELONGASE from *Physcomitrella patens*; Delta-5 DESATURASE from *Thraustochytrium* sp. ATCC21685; Delta-6 DESATURASE from *Ostreococcus tauri*; Delta-6 ELONGASE from *Thalassiosira pseudonana*; Delta-12 DESATURASE from *Phytophthora sojae*; Omega-3 DESATURASE from *Pythium irregulare*; Omega-3-DESATURASE from *Phythophthora infestans*; Delta-5 DESATURASE from *Thraustochytrium* sp. ATCC21685; Delta-4 DESATURASE from *Thraustochytrium* sp.; Omega-3 DESATURASE from *Pythium irregulare*; Delta-4 DESATURASE from *Pavlova lutheri*; Delta-5 ELONGASE from *Ostreococcus tauri*. Thus, the aforementioned T-DNA of the present invention comprises two copies of a polynucleotide encoding a Delta-5 desaturase from *Thraustochytrium* sp. ATCC21685, and two copies of a polyncucleotide encoding Omega-3 desaturase from *Pythium irregulare*.

The T-DNA of VC-LTM593-1qcz (SEQ ID NO:3) further comprises a polynucleotide encoding the selectable marker acetohydroxy acid synthase, which confers tolerance to imidazolinone herbicides.

The invention further relates to the T-DNA insertions in each of *Brassica* events LBFLFK and LBFDAU, and to the genomic DNA/transgene insertions, i.e., the Locus 1 and Locus 2 junction regions found in *Brassica* plants or seeds comprising *Brassica* event LBFLFK, to the genomic DNA/ transgene insertions, i.e., Locus 1 and Locus 2 junction regions found in *Brassica* plants or seeds comprising *Brassica* event LBFDAU, and the detection of the respective genomic DNA/transgene insertions, i.e., the respective Locus 1 and Locus 2 junction regions in *Brassica* plants or seed comprising event LBFLFK or event LBFDAU and progeny thereof.

Progeny, variants and mutants of the regenerated plants are also included within the scope of the invention, provided that the progeny, variants and mutants comprise a LBFLFK or LBFDAU event. Preferably, the progeny, variants, and mutants contain two insertions of T-DNA of the binary T-plasmid VC-LTM593-1qcz rc, the insertions being designated LBFLFK Locus 1 and LBFLFK Locus 2, provided that the progeny, variants and mutants comprise two insertions of the T-DNA of the binary T-plasmid VC-LTM593-1qcz rc, the insertions being designated LBFDAU Locus 1 and LBFDAU Locus 2.

A transgenic "event" is preferably produced by transformation of plant cells with a heterologous DNA construct(s) including a nucleic acid expression cassette that comprises one or more transgene(s) of interest, the regeneration of a population of plants from cells which each comprise the inserted transgene(s) and selection of a particular plant characterized by insertion into a particular genome location. An event is characterized phenotypically by the expression of the transgene(s). At the genetic level, an event is part of the genetic makeup of a plant. The term "event" refers to the original transformant and progeny of the transformant that include the heterologous DNA. The term "event" also refers to progeny, produced by a sexual outcross between the transformant and another variety, that include the heterologous DNA. Even after repeated back-crossing to a recurrent parent, the inserted DNA and flanking DNA from the transformed parent are present in the progeny of the cross at the same chromosomal location. The term "event" also refers to DNA from the original transformant comprising the inserted DNA and flanking sequence immediately adjacent to the inserted DNA that would be expected to be transferred to a progeny as the result of a sexual cross of one parental line that includes the inserted DNA (e.g., the original transformant and progeny resulting from selfing) and a parental line that does not contain the inserted DNA. In accordance with the invention, progeny of the *Brassica* LBFLFK event preferably comprises either LBFLFK Locus 1 or LBFLFK Locus 2, or both LBFLFK Locus 1 and LBFLFK Locus 2. Similarly, progeny of the *Brassica* LBFDAU event preferably comprises either LBFDAU Locus 1 or LBFDAU Locus 2, or both LBFDAU Locus 1 and LBFDAU Locus 2.

A "flanking region" or "flanking sequence" as used herein preferably refers to a sequence of at least 20, 50, 100, 200, 300, 400, 1000, 1500, 2000, 2500 or 5000 base pairs or greater which is located either immediately upstream of and contiguous with, or immediately downstream of and contiguous with, the original foreign insert DNA molecule. Non-limiting examples of the flanking regions of the LBFLFK event comprise, for Locus 1, nucleotides 1 to 570 of SEQ ID NO: 284, nucleotides 229 to 811 of SEQ ID NO:285 and for Locus 2, nucleotides 1 to 2468 of SEQ ID NO:293, and/or nucleotides 242 to 1800 of SEQ ID NO:294 and variants and fragments thereof.

Non-limiting examples of the flanking regions of the LBFDAU event comprise, for Locus 1, nucleotides 1 to 1017 of SEQ ID NO: 302, nucleotides 637 to 1677 of SEQ ID NO:303, and for Locus 2, nucleotides 1 to 1099 of SEQ ID NO:311 and/or nucleotides 288 to 1321 of SEQ ID NO: 312 and variants and fragments thereof.

Non-limiting examples of junction DNA from the LBFLFK event comprise, for Locus 1, SEQ ID NO:282, SEQ ID NO:283, and for Locus 2, SEQ ID NO:291, and/or SEQ ID NO:292, complements thereof, or variants and fragments thereof. Non-limiting examples of junction DNA from the LBFDAU event comprise, for Locus 1, SEQ ID NO:300, SEQ ID NO:301, and for Locus 2, SEQ ID NO:309 and/or SEQ ID NO:310, complements thereof, or variants and fragments thereof.

The oil of the aforementioned plants of the present invention preferably is an oil as specified elsewhere herein.

In one embodiment, the transgenic Brassica plants of the invention comprise event LBFLFK (ATCC designation PTA-121703). Seed and progeny of event LBFLFK are also encompassed in this embodiment. In another embodiment, the transgenic Brassica plants of the invention comprise event LBFDAU (ATCC designation PTA-122340). Seed and progeny of event LBFDAU are also encompassed in this embodiment.

The Brassica plants LBFLFK and LBFDAU can be used to manufacture commodities typically acquired from Brassica. Seeds of LBFLFK and LBFDAU can be processed into meal or oil as well as be used as an oil source in animal feeds for both terrestrial and aquatic animals.

In accordance with the invention embodied in Brassica event LBFLFK, the LBFLFK Locus 1 genomic DNA/transgene junction region and/or the LBFLFK Locus 2 genomic DNA/transgene junction region is present in Brassica plant LBFLFK (ATCC Accession No. PTA-121703) and progeny thereof. The LBFLFK Locus 1 DNA/transgene right border junction region comprises SEQ ID NO:282 and the LBFLFK Locus 1 left border junction region comprises SEQ ID NO:283, and the LBFLFK Locus 2 right border junction region comprises SEQ ID NO:291 and the LBFLFK left border junction region comprises SEQ ID NO:292. DNA sequences are provided that comprise at least one junction region sequence of event LBFLFK selected from the group consisting of SEQ ID NO:282 corresponding to positions 561 through 580 of SEQ ID NO:280); SEQ ID NO:283 corresponding to positions 44318 through 44337 of SEQ ID NO:280); SEQ ID NO:291 corresponding to positions 2459 through 2478 of SEQ ID NO:289); and SEQ ID NO:292 corresponding to positions 46232 through 46251 of SEQ ID NO:289), and complements thereof; wherein detection of these sequences in a biological sample containing Brassica DNA is diagnostic for the presence of Brassica event LBFLFK DNA in said sample. A Brassica event LBFLFK and Brassica seed comprising these DNA molecules is an aspect of this invention.

For example, to determine whether the Brassica plant resulting from a sexual cross contains transgenic DNA from event LBFLFK, DNA extracted from a Brassica plant tissue sample may be subjected to nucleic acid amplification method using (i) a first primer pair that includes: (a) a first primer derived from an LBFLFK Locus 1 flanking sequence and (b) a second primer derived from the LBFLFK Locus 1 inserted heterologous DNA, wherein amplification of the first and second primers produces an amplicon that is diagnostic for the presence of event LBFLFK Locus 1 DNA; and (ii) a second primer pair that includes (a) a third primer derived from an LBFLFK Locus 2 flanking sequence and (b) a fourth primer derived from the LBFLFK Locus 2 inserted heterologous DNA, wherein amplification of the third and fourth primers produces an amplicon that is diagnostic for the presence of event LBFLFK Locus 2 DNA.

The primer DNA molecules specific for target sequences in Brassica event LBFLFK comprise at least 11 contiguous nucleotides of any portion of the insert DNAs, flanking regions, and/or junction regions of LBFLFK Locus 1 and Locus 2. For example, LBFLFK Locus 1 primer DNA molecules may be derived from any of SEQ ID NO:280, SEQ ID NO:281, SEQ ID NO:282, or SEQ ID NO:283; SEQ ID NO:284, or SEQ ID NO:285, or complements thereof, to detect LBFLFK Locus 1. Similarly, LBFLFK Locus 2 primer DNA molecules may be derived from any of SEQ ID NO:293, SEQ ID NO:294, SEQ ID NO:291, or SEQ ID NO:292; SEQ ID NO:290, or SEQ ID NO:289, or complements thereof, to detect LBFLFK Locus 2. Those of skill in the art may use these primers to design primer pairs to produce LBFLFK Locus 1 and Locus 2 amplicons using known DNA amplification methods. The LBFLFK Locus 1 and Locus 2 amplicons produced using these DNA primers in the DNA amplification method are diagnostic for Brassica event LBFLFK when the amplification product contains an amplicon comprising an LBFLFK Locus 1 junction region SEQ ID NO:282 or SEQ ID NO:283, or complements thereof, and an amplicon comprising an LBFLFK Locus 2 junction region SEQ ID NO:291, or SEQ ID NO:292, or complements thereof.

Figure 4:
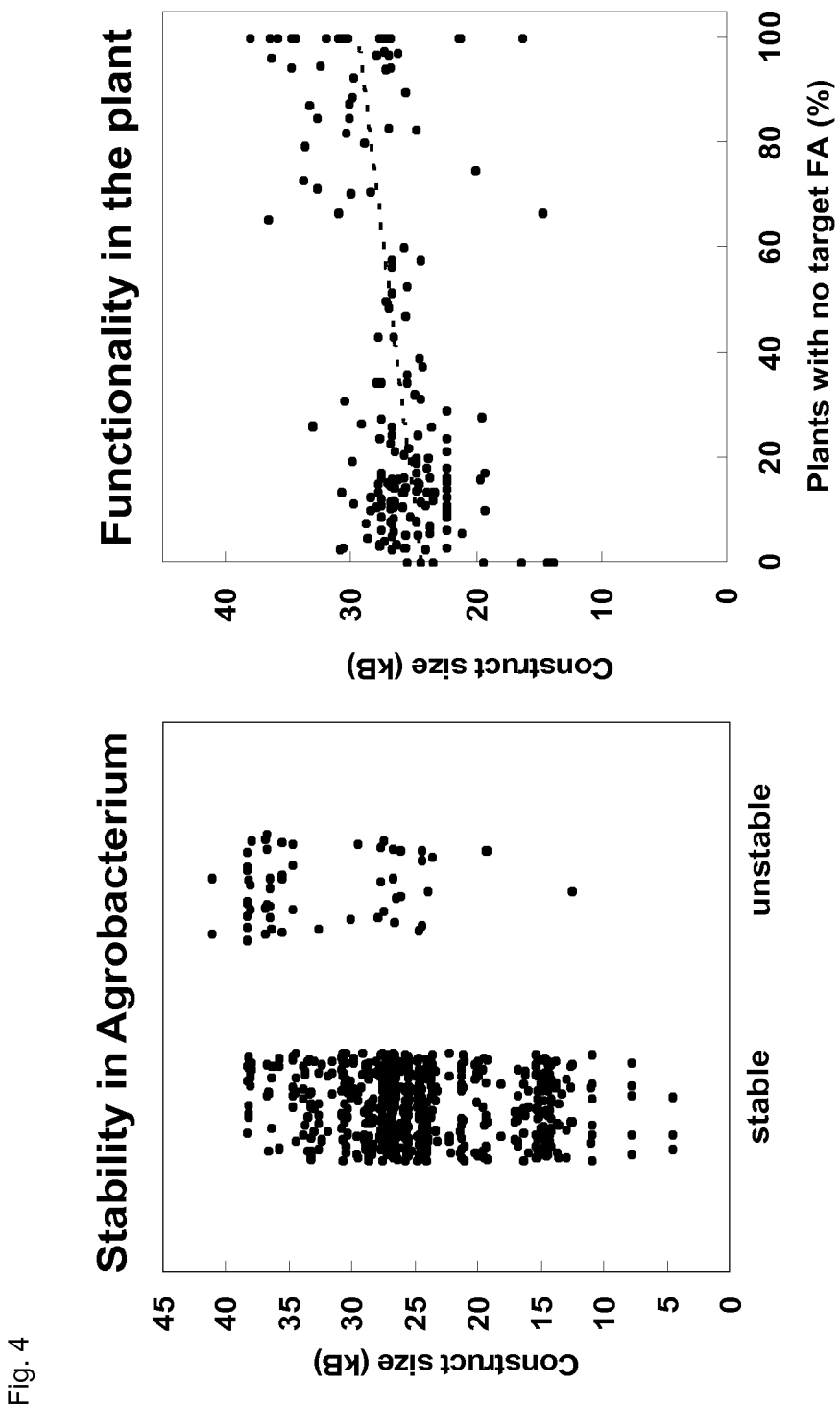
FIG. 4: Stability of binary plant expression plasmids containing the ColE1/pVS1 origin of replication for plasmid replication in *E. coli*/Agrobacteria. Left Panel: Stability in *Agrobacterium* cells by isolating plasmid DNA from *Agrobacterium* cultures prior to usage of this culture for plant transformation, and subjecting the plasmid DNA to a restriction digest. An unexpected restriction pattern indicates disintegration/instability of the plasmid either in *E. coli* or in *Agrobacterium*. Right panel: Under the assumption at least one intact T-DNA from LB to RB was integrated into the plant genome during the transformation process most plants obtained via transformation of a given plasmid are expected to reach the desired trait encoded by the plasmid (here: production of novel fatty acids (FA) in the seeds). The decrease in the percentage of such 'functional' plants indicates instability either in Agrobacteria or during the transfer process into the plant or during the integration process into the genome. As can be seen, the proportion of non functional plants goes sharply up for plasmids above 25,000 bp size when ColE1/pVS1 containing plasmids are used.
Figure 5:
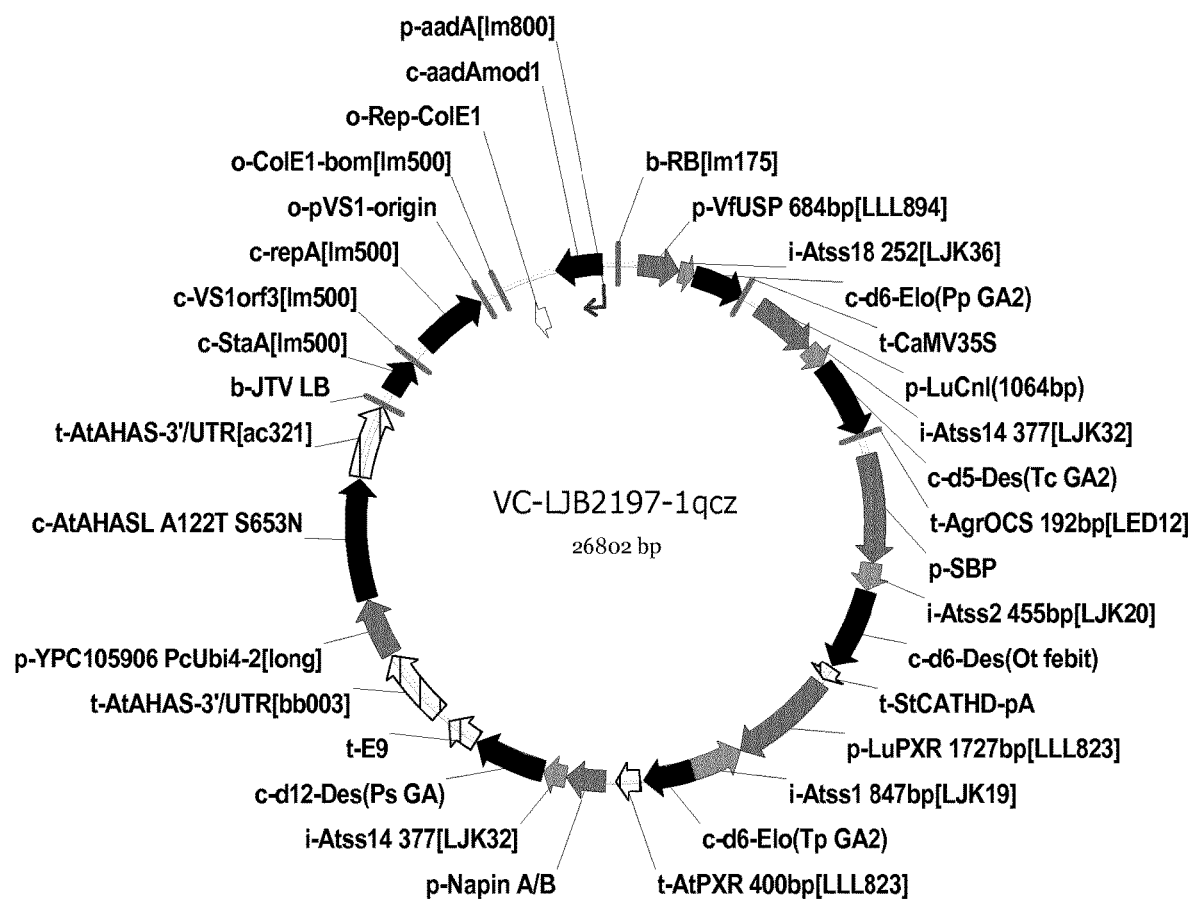
FIG. 5: Plasmid map of VC-LJB2197-1qcz indicating the position of genetic elements listed in table 1.
Figure 6:
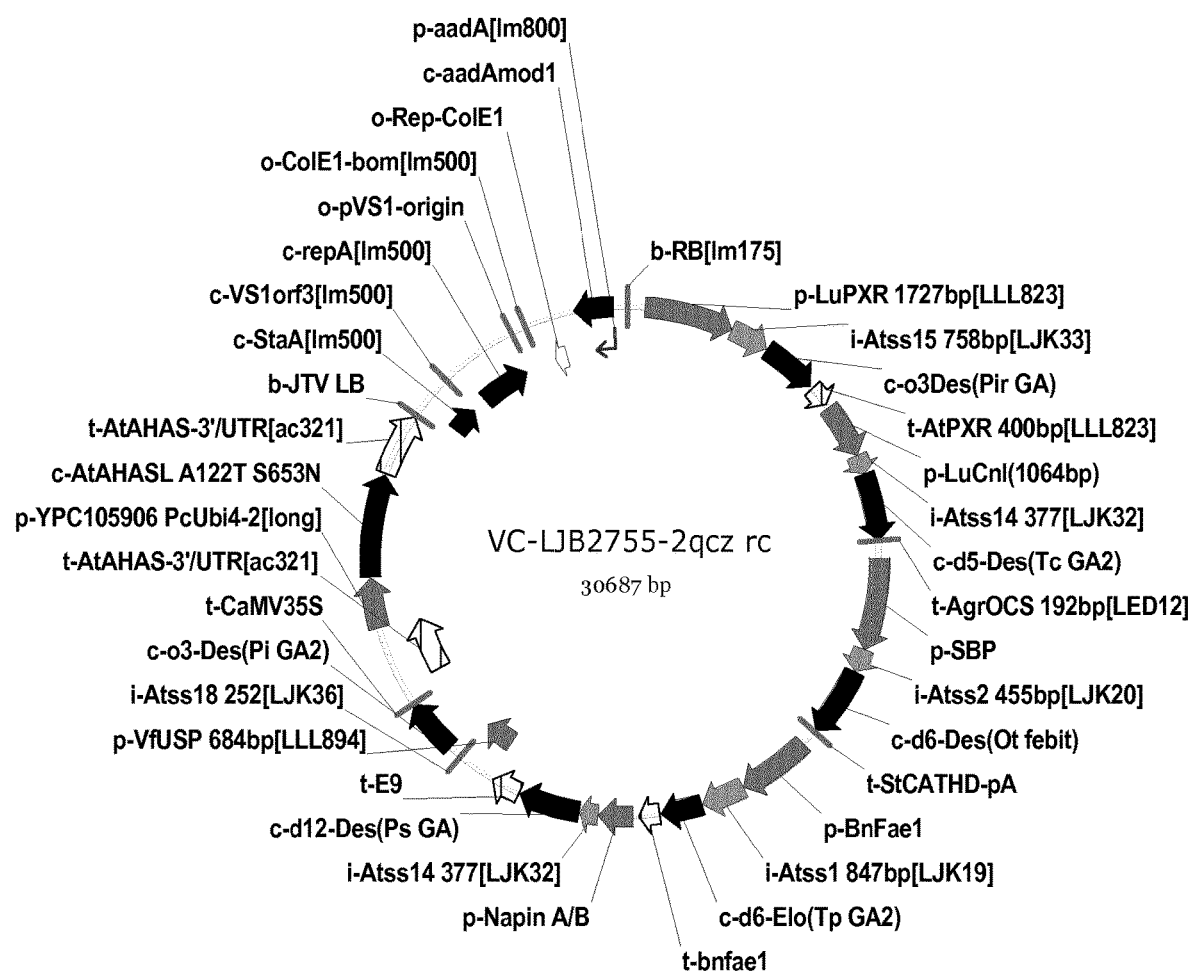
FIG. 6: Plasmid map of VC-LJB2755-2qcz rc indicating the position of genetic elements listed in table 2.
Figure 7:
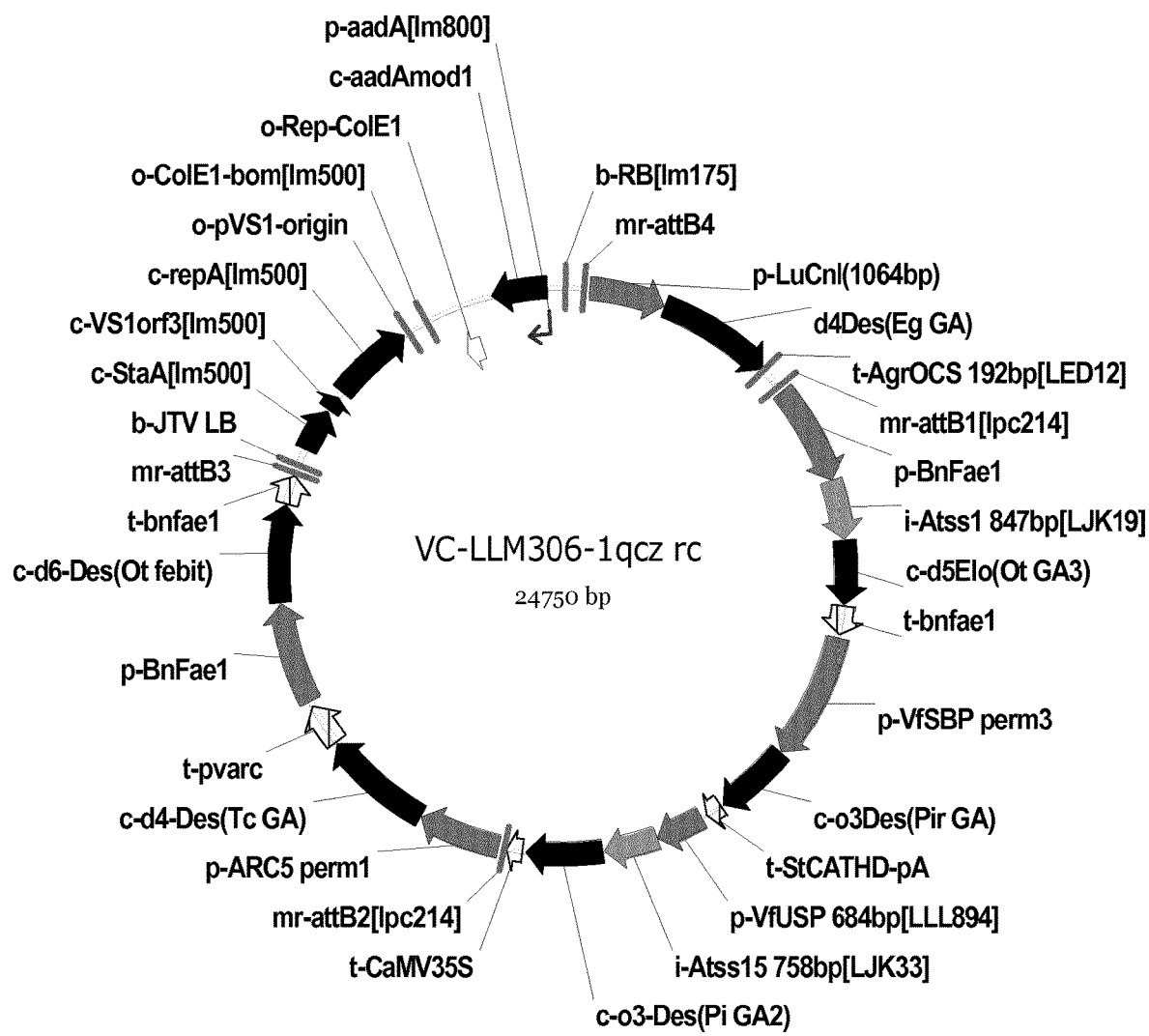
FIG. 7: Plasmid map of VC-LLM306-1qcz rc indicating the position of genetic elements listed in table 3.
Figure 8:
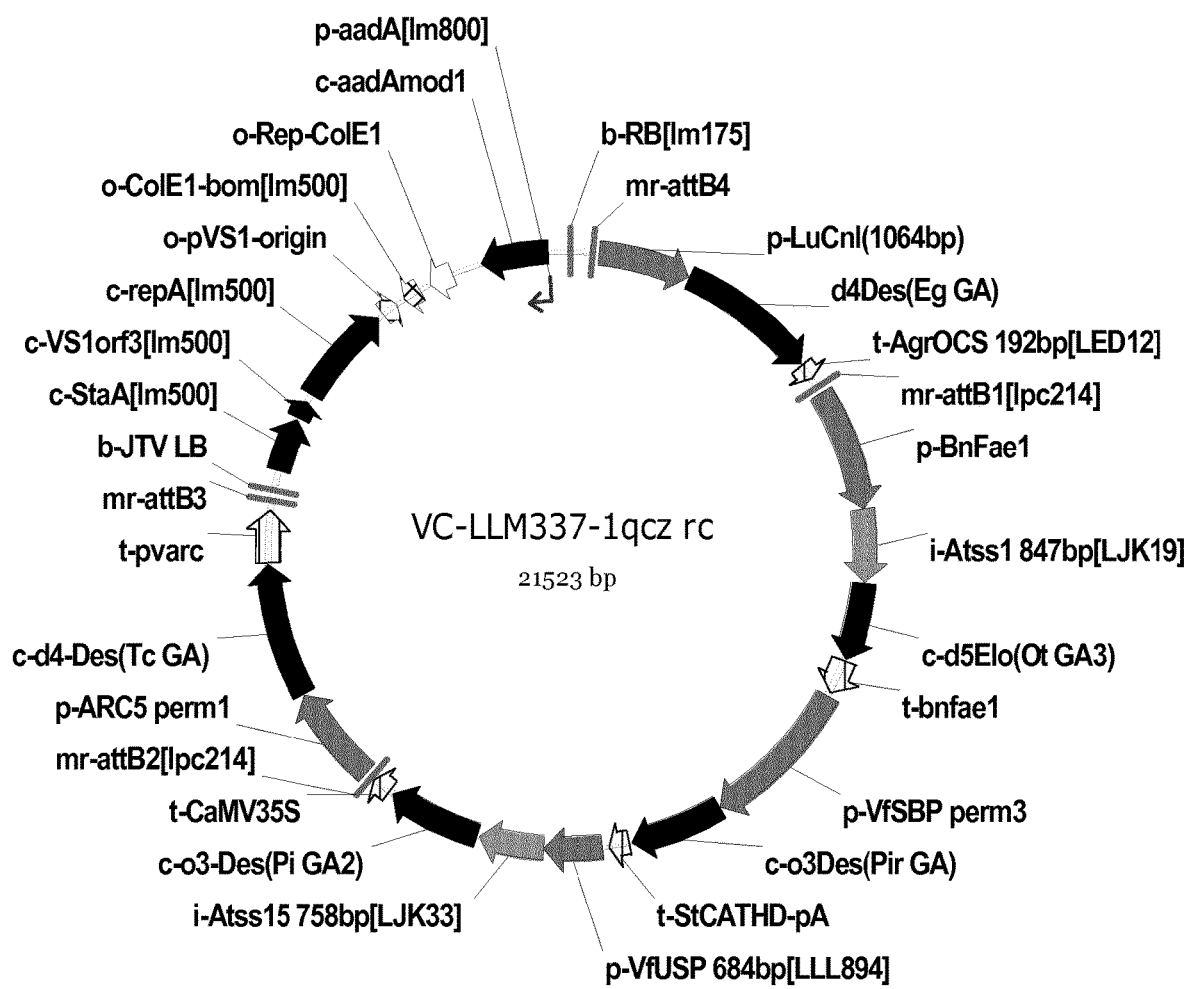
FIG. 8: Plasmid map of VC-LLM337-1qcz rc indicating the position of genetic elements listed in table 4.
Figure 9:
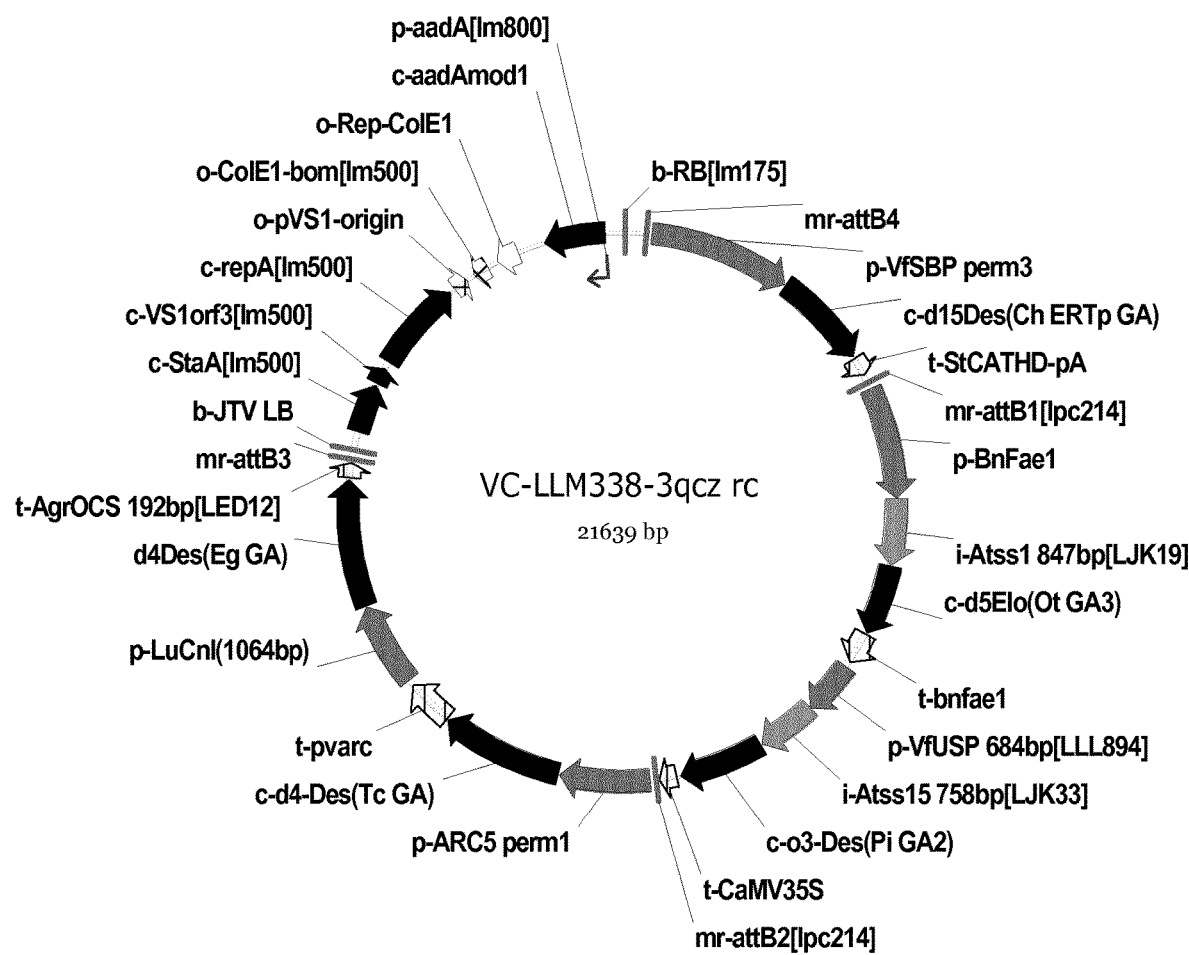
FIG. 9: Plasmid map of VC-LLM338-3qcz rc indicating the position of genetic elements listed in table 5.
Figure 10:
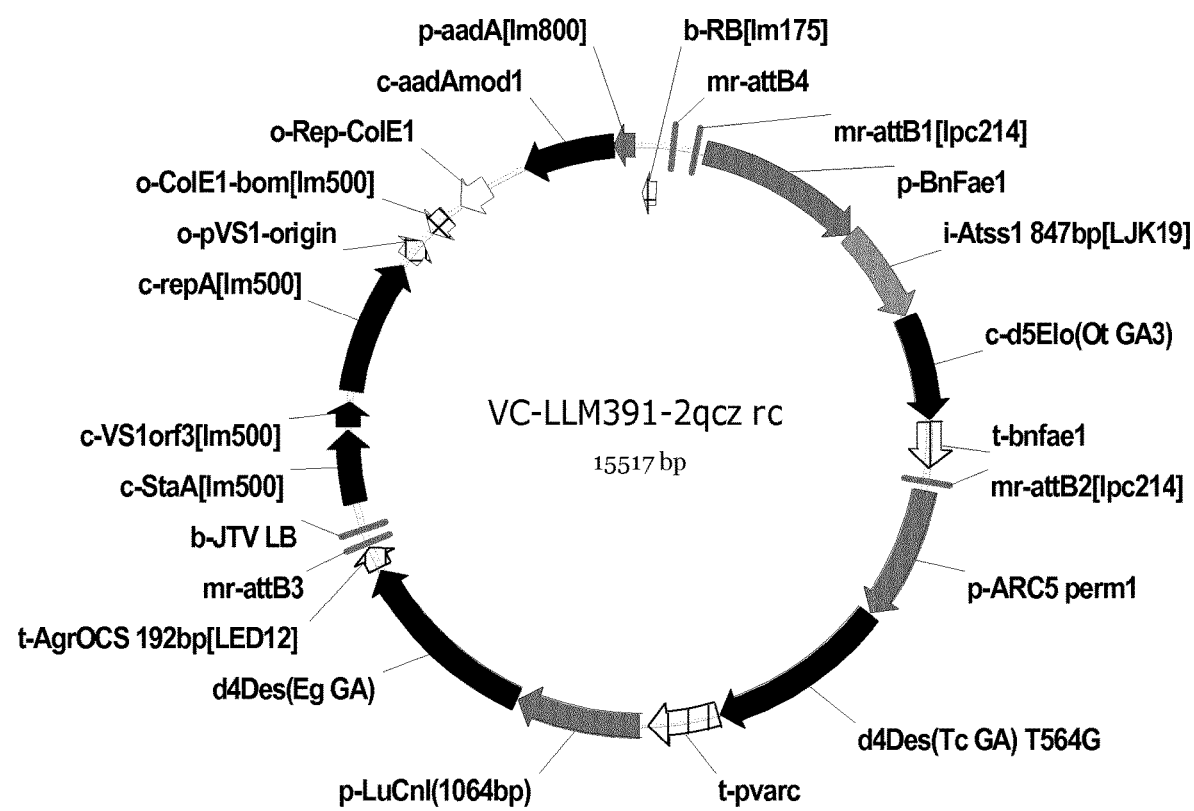
FIG. 10: Plasmid map of VC-LLM391-2qcz rc indicating the position of genetic elements listed in table 6.
Figure 11:
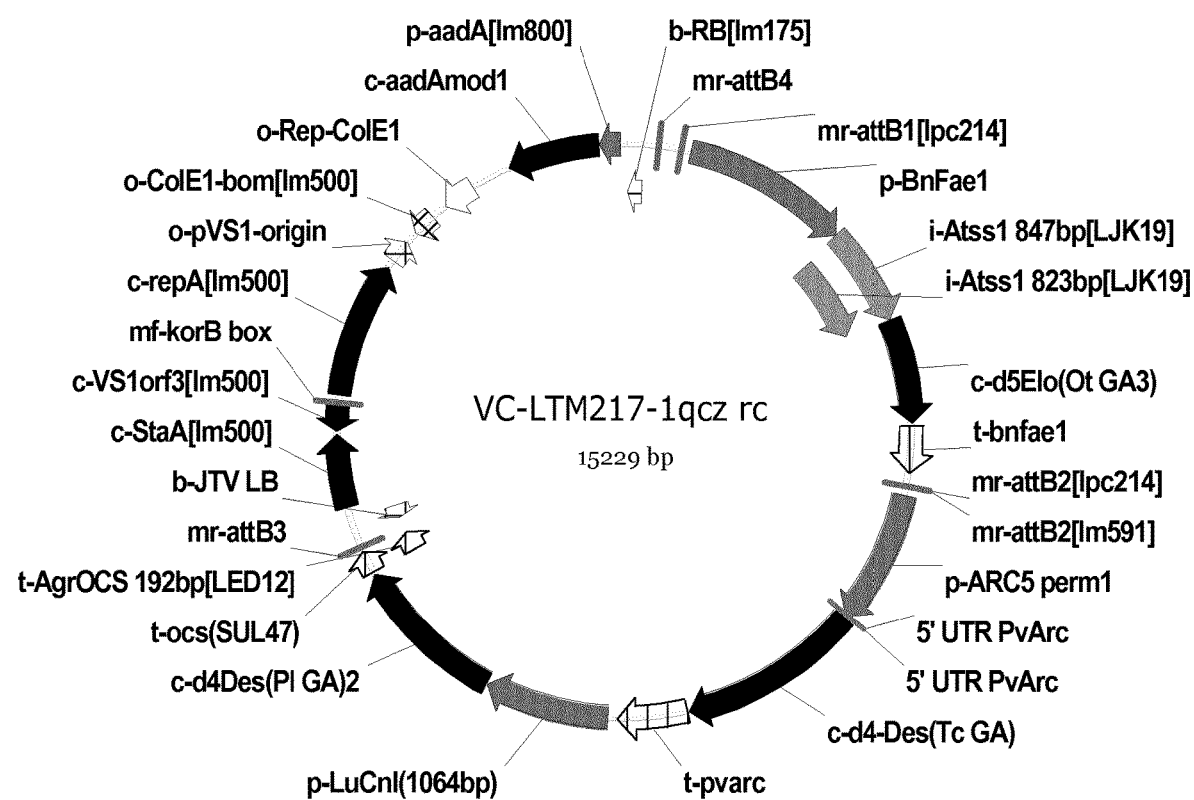
FIG. 11: Plasmid map of VC-LTM217-1qcz rc indicating the position of genetic elements listed in table 7.
Figure 12:
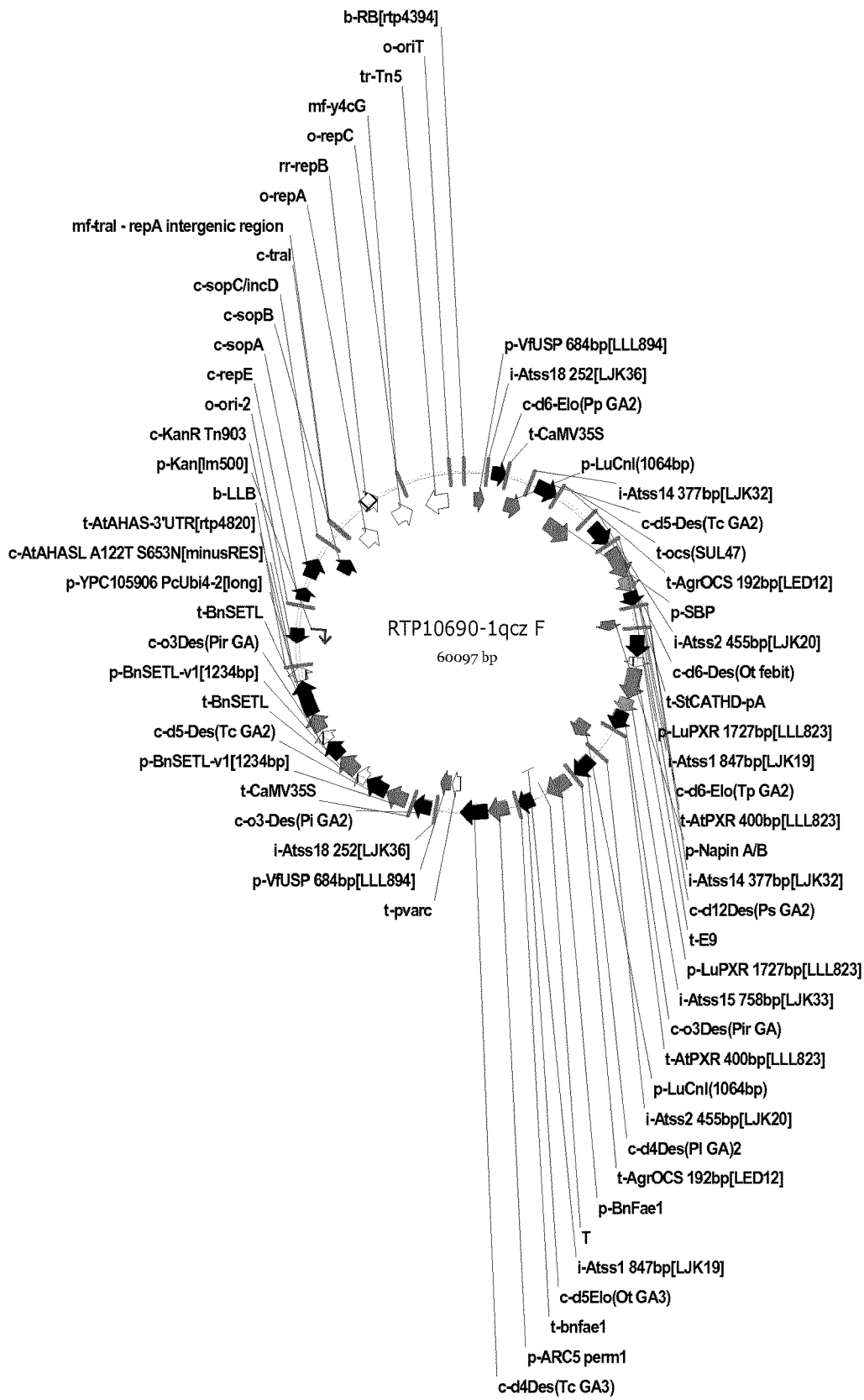
FIG. 12: Plasmid map of RTP10690-1qcz_F indicating the position of genetic elements listed in table 8.
Figure 13:
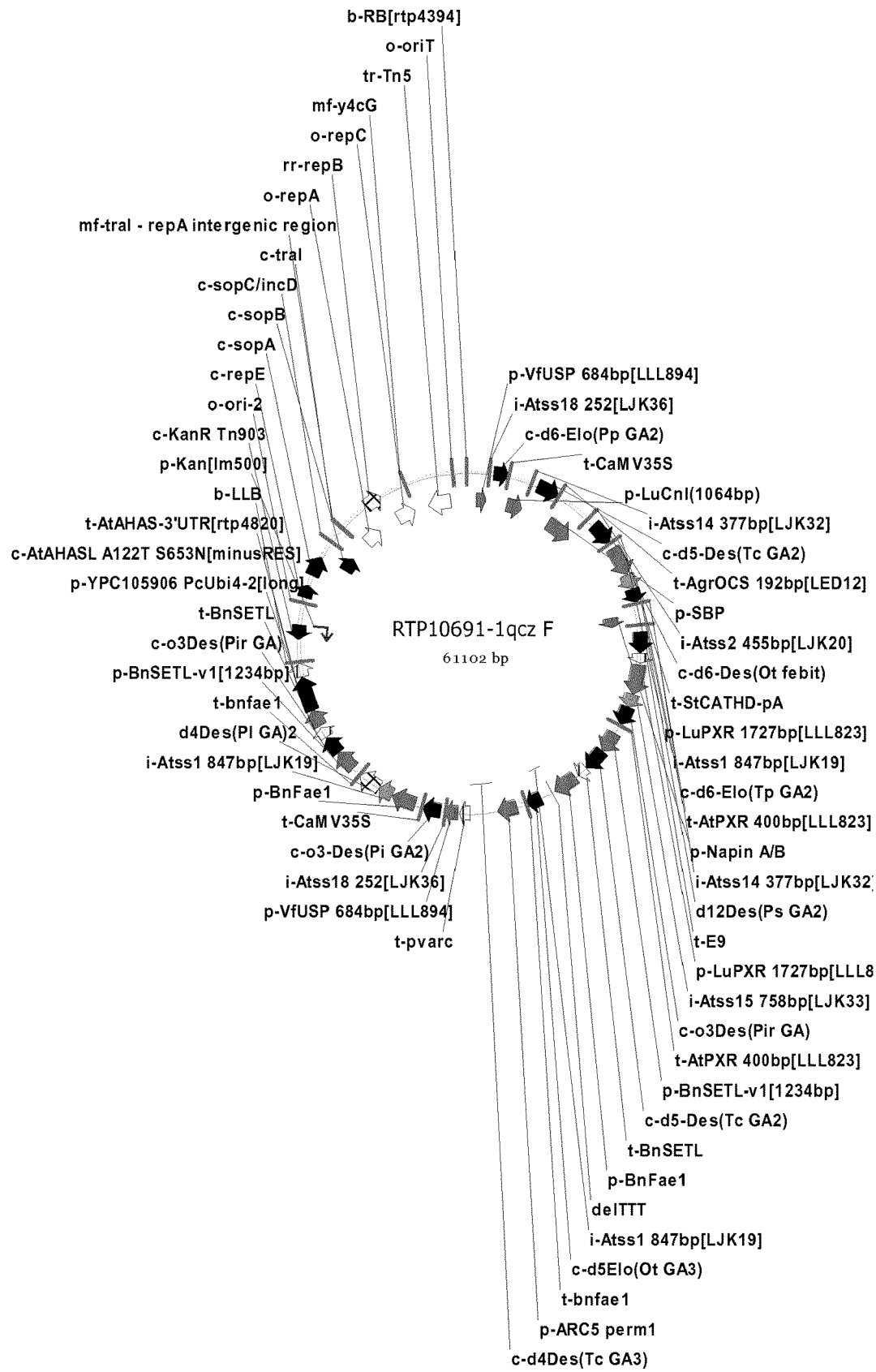
FIG. 13: Plasmid map of RTP10691-2qcz indicating the position of genetic elements listed in table 9.
Figure 14:
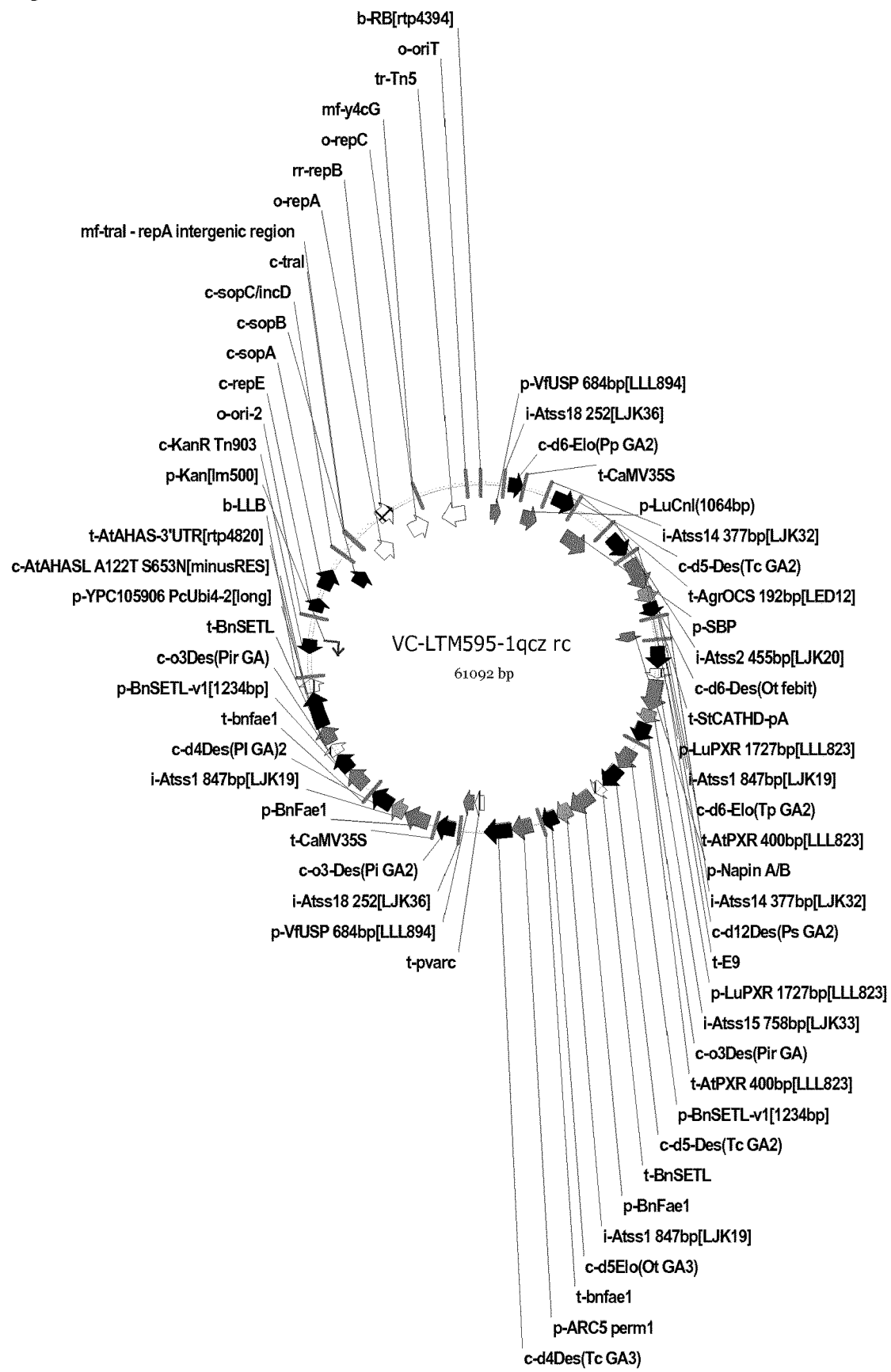
FIG. 14: Plasmid map of LTM595-1qcz rc indicating the position of genetic elements listed in table 10.
Figure 15:
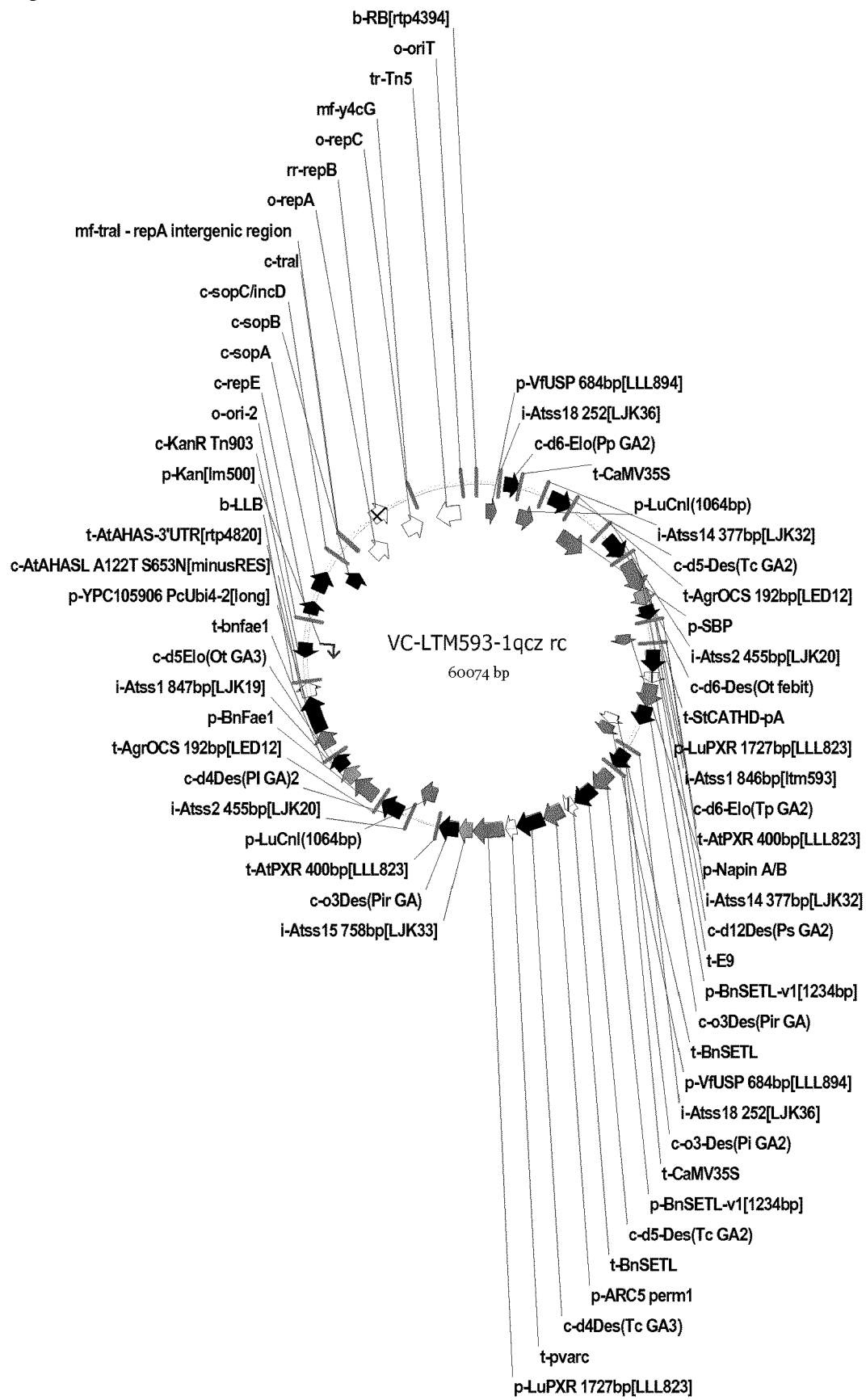
FIG. 15: Plasmid map of LTM593-1qcz rc indicating the position of genetic elements listed in table 11.
Figure 16:
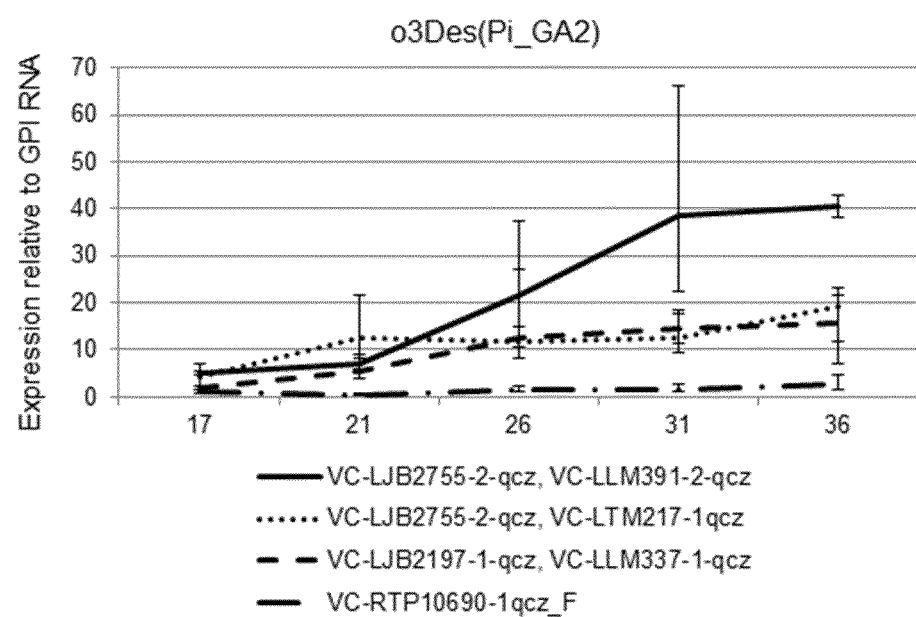
FIG. 16: Comparative transcript analysis o3Des(Pi_GA2) driven by the VfUSP promoter during seed development of single copy event of four different construct combinations.

In accordance with the invention embodied in Brassica event LBFDAU, the LBFDAU Locus 1 genomic DNA/transgene junction region and/or the LBFDAU Locus 2 genomic DNA/transgene junction region is present in Brassica event LBFDAU (ATCC Accession No. PTA-122340) and progeny thereof. The LBFDAU Locus 1 DNA/transgene right border junction region comprises SEQ ID NO:300 and the LBFDAU Locus 1 left border junction region comprises SEQ ID NO:301, and the LBFDAU Locus 2 right border junction region comprises SEQ ID NO:309 and the LBFDAU left border junction region comprises SEQ ID NO:310. DNA sequences are provided that comprise at least one junction region sequence of event LBFDAU selected from the group consisting of SEQ ID NO:300 (corresponding to positions 1008 through 1027 of SEQ ID NO:298, as shown in FIG. 4); SEQ ID NO:301 (corresponding to positions 44728 through 44747 of SEQ ID NO:298, as shown in FIG. 4); SEQ ID NO:309 (corresponding to positions 1090 through 1109 of SEQ ID NO:307, as shown in FIG. 5); and SEQ ID NO:310 (corresponding to positions 38577 through 38596 of SEQ ID NO:307, as shown in FIG. 5) and complements thereof; wherein detection of these sequences in a biological sample containing Brassica DNA is diagnostic for the presence of Brassica event LBFDAU DNA in said sample. A Brassica event LBFDAU and Brassica seed comprising these DNA molecules is an aspect of this invention.

For example, to determine whether the Brassica plant resulting from a sexual cross contains transgenic DNA from event LBFDAU, DNA extracted from a Brassica plant tissue sample may be subjected to nucleic acid amplification method using (i) a first primer pair that includes: (a) a first primer derived from an LBFDAU Locus 1 flanking sequence and (b) a second primer derived from the LBFDAU Locus 1 inserted heterologous DNA, wherein amplification of the first and second primers produces an amplicon that is diagnostic for the presence of event LBFDAU Locus 1 DNA; and/or (ii) a second primer pair that includes (a) a third primer derived from an LBFDAU Locus 2 flanking sequence and (b) a fourth primer derived from the LBFDAU Locus 2 inserted heterologous DNA, wherein amplification of the third and fourth primers produces an amplicon that is diagnostic for the presence of event LBFDAU Locus 2 DNA.

Seed derived from *Brassica* event LBFLFK or *Brassica* event LBFDAU for sale for planting or for making commodity products is an aspect of the invention. Such commodity products include canola oil or meal containing VLC-PUFAs including but not limited to EPA and DHA. Commodity products derived from *Brassica* event LBFLFK comprise a detectable amount a DNA molecule comprising SEQ ID NO:282, SEQ ID NO:283, SEQ ID NO:291, and/or SEQ ID NO:292. Commodity products derived from *Brassica* event LBFDAU comprise a detectable amount a DNA molecule comprising SEQ ID NO:300, SEQ ID NO:301, SEQ ID NO:309, and/or SEQ ID NO:310. Exemplary commodity products derived from events LBFLFK and LBFDAU include, but are not limited to, cooking oil, salad oil, shortening, nutritionally enhanced foods, animal feed, pharmaceutical compositions, cosmetic compositions, hair care products, and the like.

The invention also provides a commercially relevant source of plant material, preferably of seed. As such, the invention provides a heap of at least 5 kg, preferably of at least 10 kg, more preferably of at least 50 kg, even more preferably of at least 100 kg, even more preferably of at least 500 kg, even more preferably of at least 1t, even more preferably of at least 2t, even more preferably of at least 5t of plant material, wherein the plant material comprises VLC-PUFAs as described according to the invention. As described herein, it is a merit of the present invention to provide, for the first time, an agronomically reliable source of VLC-PUFA plant oil, and to this end such heap of plant material is provided. The plant material is preferably plant seed, even more preferably seed of VLC-PUFA producing seed, such that the content of all VLC-PUFA downstream of 18:1n-9 is at least 40% (w/w) of the total seed fatty acid content at an oil content of 40% (w/w), or preferably the content of EPA is at least 10% (w/w) and/or the content of DHA is at least 1% (w/w) of the total seed fatty acid content at an oil content of 30% (w/w), or meal of such plant seed. Also, the invention provides a container comprising such plant seed in an amount of at least 5 kg, preferably of at least 10 kg, more preferably of at least 50 kg, even more preferably of at least 100 kg, even more preferably of at least 500 kg, even more preferably of at least 1t, even more preferably of at least 2t, even more preferably of at least 5t. The invention thus demonstrates that the invention has well eclipsed anecdotal findings of lab scale VLC-PUFA containing plants, and instead has overcome the additional requirements for providing, on a large scale, a reliable source for VLC-PUFA and particularly for EPA and/or DHA in plant oil and plant material.

The present invention allows for the generation of plants comprising a modified fatty acid composition (as compared to control plants). Thus, the T-DNAs, the expression cassettes, vectors, polynucleotides (in particular the combination of polynucleotides), and polypeptides ((in particular the combination of polynucleotides) as disclosed herein can be used for modifying the fatty acid composition of a plant. In an embodiment, the content of at least one fatty acid disclosed in Table 18 or 181 is modified in seed oil (increased or decreased as compared to the content in seed oil of a control plant). In another embodiment, the content of at least one fatty acid disclosed in Table 18 or 181 is modified in in the monoacylgylcerol (MAG) fraction, the diacylgylcerol (DAG) fraction, the triacylgylcerol (TAG) fraction, phosphatidylcholine (PC) fraction and/or phosphatidylethanolamine (PE) fraction of seed oil (increased or decreased as compared to the content of seed oil of a control plant). In another embodiment, the content of at least one Lysophosphatidylcholine species shown in Table 189 is modified in seed oil (increased or decreased as compared to the content in seed oil of a control plant). In another embodiment, the content of at least one Phosphatidylethanolamine species shown in Table 190 is modified in seed oil (increased or decreased as compared to the content in seed oil of a control plant). In another embodiment, the content of at least one Lysophosphatidylethanolamine species shown in Table 191 is modified in seed oil (increased or decreased as compared to the content in seed oil of a control plant). In another embodiment, the content of at least one Triacylglycerol species shown in Table 192 is modified in seed oil (increased or decreased as compared to the content in seed oil of a control plant).

The definitions and explanations given herein above, preferably, apply mutatis mutandis to the following (e.g. with respect to the "plant", "the control plant" etc.).

It has been shown in the context of the studies underlying that the present invention that that the generated plants produce mead acid (20:3n-9, see Example 29). The mead acid may be made from the side activities of d6Des, d6Elo, and d5Des, using 18:1n-9 to make 18:2n-9 (by d6Des), then 20:2n-9 (by d6Elo), then 20:3n-9 (by d5Des). Interestingly, in mead acid in fungi is only made if the d12Des is mutated to be inactive (Takeno et al. 2005 App. Environ. Microbiol. 71(9): 5124-5128). However, the studies underlying the present invention surprisingly show that mead acid is produced in plants even when a d12Des is overexpressed.

Accordingly, the present invention relates to a method for increasing the content of Mead acid (20:3n-9) in a plant relative to a control plant, comprising expressing in a plant at least one polynucleotide encoding a delta-6-desaturase, at least one polynucleotide encoding a delta-6-elongase, and at least one polynucleotide encoding a delta-5-desaturase.

In addition, the present invention relates to a method for producing Mead acid (20:3n-9) in a plant relative to a control plant, comprising expressing in a plant, at least one polynucleotide encoding a delta-6-desaturase, at least one polynucleotide encoding a delta-6-elongase, and at least one polynucleotide encoding a delta-5-desaturase.

The aforementioned methods may further comprise the expression of further desatuarase or eleogase, in particular of one or more of a delta-12-desaturase, omega-3-desaturase, a delta-5-elongase, and delta-4-desaturase. Thus, at least one, two, three, or in particular four further enzymatic activities can be expressed in the plant.

In an embodiment, the methods further comprise expressing in the plant at least one polynucleotide encoding a delta-12-desaturase.

In an embodiment, the methods further comprise expressing in the plant at least one polynucleotide encoding an omega-3-desaturase.

In an embodiment, the methods further comprise expressing in the plant at least one polynucleotide encoding a delta-5-elongase.

In an embodiment, the methods further comprise expressing in the plant at least one polynucleotide encoding a delta-4-desaturase. In an embodiment, at least one CoA dependent delta-4-desaturase and at least one phospholipid dependent delta-4 desaturase is expressed.

In a particular preferred embodiment, the methods further comprise expressing in the plant at least one polynucleotide encoding a delta-12-desaturase, at least one polynucleotide encoding an omega-3-desaturase, at least one polynucleotide encoding a delta-5-elongase, and at least one polynucleotide encoding delta-4-desaturase.

Preferred polynucleotides encoding desaturases and elongases are described above.

The gene dosage effect described above may be also used for the the producing of mead acid or for increasing the content of mead acid in plants.

Thus, it is contemplated to express at least one polynucleotide encoding a delta-6-desaturase, at least two polynucleotides encoding a delta-6-elongase, and at least two polynucleotides encoding a delta-5-desaturase. Moreover, at least one polynucleotide encoding a delta-12-desaturase, at least three polynucleotides encoding an omega-3-desaturase, at least one polynucleotide encoding a delta-5-elongase, and/or at least two polynucleotides encoding a delta-4-desaturase can be further expressed (preferably at least one CoA dependent delta-4-desaturase and at least one phospholipid dependent delta-4 desaturase).

In an embodiment, at least one polynucleotide encoding a delta-6 elongase from *Physcomitrella patens*, at least one polynucleotide encoding a delta-6 elongase from *Thalassiosira pseudonana*, and at least two polynucleotides encoding a delta-5 desaturase from *Thraustochytrium* sp are expressed. Moreover, at least one polynucleotide encoding a omega-3-desaturase from *Phythophthora infestans*, at least two polynucleotides encoding a omega-3 desaturase from *Pythium irregulare*, at least one polynucleotide encoding a delta-5 elongase from *Ostreococcus tauri*, and at least one polynucleotide encoding a delta-4 desaturase from *Thraustochytrium* sp., and/or at least one polynucleotide encoding a delta-4 desaturase from *Pavlova lutheri* can be expressed.

Preferably, the polynucleotides to be expressed are recombinant polynucleotides. More preferably, the polynucleotides are present on one T-DNA which is comprised by the genome of the plant. Thus, the T-DNA is stably integrated into the genome. Preferably, the polynucleotides encoding for the desaturates and elongases as set forth herein are comprised by the same T-DNA.

Preferably, the polynucleotides encoding the desaturases or elongases (i.e. each of the polynucleotides) are operably linked to an expression control sequence (see elsewhere herein for a definition). Moreover, the polynucleotides may be linked to a terminator, thereby forming an expression cassette comprising an expression control sequence, the target gene, and the terminator.

In a particular preferred embodiment, the polynucleotides are expressed in the seeds of the plant.

Accordingly, the expression control sequences may be seed-specific promoters. Preferred seed-specific promoters are e.g. disclosed in Table 11 in the Examples section.

In an embodiment, the polynucleotides are expressed by introducing and expressing the polynucleotides in the plants. How to introduce polynucleotides into a plant is well known in the art. Preferred methods are described elsewhere herein. In an embodiment, the polynucleotides are introduced into a plant by *Agrobacterium*-mediated transformation.

In an embodiment, the mead acid content is increased in the seeds as compared to the mead acid in seeds of a control plant. Preferably, the mead acid content in seed oil is increased in the seeds is increased as compared to the mead acid in seed oil of a control plant.

Preferred plants are described above. In an embodiment, the plant is an oilseed plant. Preferably, the plant is selected from the group consisting of flax (*Linum* sp.), rapeseed (*Brassica* sp.), soybean (*Glycine* and *Soja* sp.), sunflower (*Helianthus* sp.), cotton (*Gossypium* sp.), corn (*Zea mays*), olive (*Olea* sp.), safflower (*Carthamus* sp.), cocoa (*Theobroma cacoa*), peanut (*Arachis* sp.), hemp, *camelina*, *crambe*, oil palm, coconuts, groundnuts, sesame seed, castor bean, *lesquerella*, tallow tree, sheanuts, tungnuts, kapok fruit, poppy seed, jojoba seeds and *perilla*. More preferably, the plant is a plant of the family Brassicaceae, preferably of genus *Brassica* and most preferably of a species comprising a genome of one or two members of the species *Brassica oleracea, Brassica nigra* and *Brassica rapa*, thus in particular of the species *Brassica napus, Brassica carinata, Brassica juncea, Brassica oleracea, Brassica nigra* or *Brassica rapa*.

In an embodiment, the method further comprises the step of a selecting for a plant having an increased mead acid content, in particular in seed oil. In embodiment, the selection is done based on the mead acid content. The step may thus comprise the step of determining the mead acid content in the seeds, or seed oil of the plant. How to determine the mead acid content is e.g. described in Example 29.

The Mead acid is preferably esterified mead acid.

Upon expression of the polynucleotides referred to above in the seeds of the plant, mead acid is produced. Thus, the plants expressing said polynucleotides, in particular the seeds of the plants shall comprise/produce mead acid. Preferably, the content of Mead acid (20:3n-9) in the seed oil of the plant is between about 0.1% and 2%, more preferably between about 0.1% and 1%, most preferably between about 0.1% and 0.5% of the total fatty acid content of seed oil (in particular the total content of esterified fatty acids). Further VLC-PUFAs may be present in the seed oil (as described elsewhere herein in connection with the oil of the present invention).

The present invention also relates to a construct or T-DNA comprising expression cassettes for the desaturases and elongases as referred to in the context of the method of increasing the content of mead acid. Thus, the present invention also relates to a construct comprising at least one expression cassette for for a delta-6-desaturase, at least one expression cassette for a delta-6-elongase, and at least one expression cassette for a delta-5-desaturase. The construct or T-DNA may further comprise at least one expression cassette for a delta-12-desaturase, at least one expression cassette for an omega-3-desaturase, at least one expression cassette for a delta-5-elongase, and/or at least one expression cassette for a delta-4-desaturase.

In an embodiment, the construct or T-DNA comprises at least one expression cassette for a delta-6 elongase from *Physcomitrella patens*, at least one expression cassette for a delta-6 elongase from *Thalassiosira pseudonana*, and at least two expression cassettes for a delta-5 desaturase from *Thraustochytrium* sp. (in particular *Thraustochytrium* sp. ATCC21685), and optionally at least two expression cassettes for an omega-3 desaturase from *Pythium irregulare*, at least one expression cassette for a omega-3-desaturase from *Phytophthora infestans*, at least one expression cassette for a delta-5 elongase from *Ostreococcus tauri*, and at least one expression cassette for a delta-4 desaturase from *Thraustochytrium* sp., and/or at least one expression cassette for a delta-4 desaturase from *Pavlova lutheri*.

The present invention further relates to the use of i) a construct or T-DNA of the present invention or of ii) at least one polynucleotide encoding a delta-6-desaturase, at least one polynucleotide encoding a delta-6-elongase, at least one polynucleotide encoding a delta-5-desaturase, for a) increasing the mead acid content of a plant (in particular in the seeds) relative to a control plants (in particular in the seeds of a control plant) or for producing mead acid in a plant, in particular in the seeds of a plant.

Preferably, also further polynucleotides encoding desaturases and/or elongases as referred to in the context of the method for increasing mead acid can be used (such as a polynucleotide encoding a delta-12-desaturase).

The present invention also relates to plant, or plant cells transformed with or comprising i) a construct or T-DNA of the present invention or ii) at least one polynucleotide encoding a delta-6-desaturase, at least one polynucleotide encoding a delta-6-elongase, at least one polynucleotide encoding a delta-5-desaturase. In an embodiment, the plant or plant cell further is transformed with or comprises the further polynucleotides encoding desaturases and/or elongases as referred to in the context of the method for increasing mead acid can be used (such as a polynucleotide encoding a delta-12-desaturase). Preferred polynucleotide sequences for the desaturases and elongases are disclosed above.

Further, the present invention relates to a method of mead acid production, comprising the steps of i) growing a plant of the present invention such as to obtain oil-containing seeds thereof, ii) harvesting said seeds, and iii) extracting oil comprising mead acid from said seeds harvested in step ii.

Preferably, the oil is an oil as described herein above. In particular, the oil shall have a mead acid content as described above.

As set forth above, the present invention pertains to plants that produce VLC-PUFAs (and to plants that produce Mead acid). Said plants shall comprise one or more T-DNAs comprising expression cassettes for certain desaturases and elongases as explained herein in detail. Preferably, said expression cassettes are comprised by the same T-DNA (or construct).

In an embodiment of the present invention, the T-DNA or construct of the present invention further comprises at least one expression cassette comprising a polynucleotide encoding for an acetohydroxy acid synthase (abbreviated AHAS enzyme, also known a acetolactate synthase), wherein said acetohydroxy acid synthase confers tolerance to an herbicide of the imidazolinone class. Thus, the AHAS enzyme is preferably a mutated AHAS enzyme.

Mutated AHAS enzymes that confer tolerance to an herbicide of the imidazolinone class are known in the art and e.g. disclosed in WO 2008/124495 which herewith is incorporated by reference in its entirety. In an embodiment, the matutated AHAS enzyme is a mutated *Arabidopsis thaliana* AHAS enzyme. As compared to the wild-type enzyme, the envisaged enzyme is mutated at two positions. The envisaged enzyme has at position 653 a serine replaced by an asparagine and at position 122 an alanine replaced by a threonine.

Also preferably, the polynucleotide encoding for an AHAS enzyme which confers tolerance to an herbicide of the imidazolinone class is selected from:

a) a nucleic acid sequence having a nucleotide sequence as shown in SEQ ID NO: 277, b) a nucleic acid sequence encoding a polypeptide having an amino acid sequence as shown in SEQ ID NO:278.

c) a nucleic acid sequence being at least 70%, 80%, or 90% identical to the nucleic acid sequence having a nucleotide sequence as shown in SEQ ID NO: 277, d) a nucleic acid sequence encoding a polypeptide which is at least 60%, 70%, 80, or 90% identical to a polypeptide having an amino acid sequence as shown in SEQ ID NO: 278, and e) a nucleic acid sequence which is capable of hybridizing under stringent conditions to i) a nucleic acid sequence having a nucleotide sequence as shown in SEQ ID NO: 277, or to ii) a nucleic acid sequence encoding a polypeptide having an amino acid sequence as shown in SEQ ID NO:278.

Is to be understood that the polypeptide encoded by the said polynucleotide shall confer tolerance to an herbicide of the imidazolinone class. In an embodiment, the polypeptide thus shall have a serine-to-asparagine substitution at the position corresponding to position 653 of SEQ ID NO:278, and/or an alanine-to-threonin substitution at the position corresponding to position 122 of SEQ ID NO:278.

The herbicide of the imidazolinone class is preferably selected from imazethapyr, imazapic, imazamox, imazaquin, imazethabenz, and imazapyr, in particular imazamox (IUPAC: (R/S)-2-(4-isopropyl-4-methyl-5-oxo-2-imidazolin-2-yl)-5-methoxymethylnicotinic acid). More specifically, the herbicide of the imidazolinone class can be selected from, but is not limited to, 2-(4-isopropyl-4-methyl-5-oxo-2-imidiazolin-2-yl)-nicotinic acid, [2-(4-isopropyl)-4-] [methyl-5-oxo-2-imidazolin-2-yl)-3-quinolinecarboxylic] acid, [5-ethyl-2-(4-isopropyl-] 4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-] imidazolin-2-yl)-5-methylnicotinic acid. The use of 5-ethyl-2-(4-isopropyl-4-methyl-5-oxo-2-imidazolin-2-yl)-nicotinic acid and [2-(4-isopropyl-4-methyl-5-oxo-2-imidazolin-2-] yl)-5-(methoxymethyl)-nicotinic acid is preferred. The use of [2-(4-isopropyl-4-] methyl-5-oxo-2-imidazolin-2-yl)-5-(methoxymethyl)-nicotinic acid is particularly preferred.

In addition, the present invention relates to a method of controlling weeds in the vicinity of a plant of the present invention, said method comprising applying at least one herbicide of the imidazolinone class to the weeds and to the plant of the present invention, thereby suppressing growth of the weeds in the vicinity of a plant of the present invention.

The plant of the present invention in the context with the aforementioned method shall comprise the expression cassettes for the desaturases and elongases as explained elsewhere herein (preferably, at least one T-DNA comprising the expression cassettes) and an expression cassette comprising a polynucleotide encoding for an acetohydroxy acid synthase, wherein said acetohydroxy acid synthase confers tolerance to an herbicide of the imidazolinone class. In an embodiment, the expression cassettes for the desaturases and elongases and the comprising a polynucleotide encoding for an acetohydroxy acid synthase are comprised by the same T-DNA. The present invention also relates to the aforementioned plant.

Preferably, the polynucleotide encoding for an acetohydroxy acid synthase as set forth above is overexpressed. In an embodiment, said polynucleotide is operably linked to a constitutive promoter. In an embodiment said constitutive promoter is a CaMV 35S promoter. In another embodiment, said constitutive promoter is a parsley ubiquitin promoter (such as the promoter used for the expression of the mutated AHAS genes in the examples, for the position in SEQ ID NO; 3, see table 11).

Thus, preferred plants of the current invention contain a gene for resistance to imidazolinone class of herbicides, which inhibit the aceto-hydroxy acid synthase (AHAS) gene of plants. The gene that confers resistance is a modified variant of AHAS. The expression cassettes for the polynucleotide encoding for an acetohydroxy acid synthase may be comprised by the same T-DNA as the expression cassettes for the elongases and desaturases as referred to herein, or by a different T-DNA. Preferably, the expression cassettes are comprised by the same T-DNA.

In an embodiment, the T-DNA or construct of the present invention comprises polynucleotides encoding the following enzymes (in particular in this order): Delta-6 ELONGASE from *Physcomitrella patens*; Delta-5 DESATURASE from *Thraustochytrium* sp. ATCC21685; Delta-6 DESATURASE from *Ostreococcus tauri*; Delta-6 ELONGASE from *Thalassiosira pseudonana*; Delta-12 DESATURASE from *Phythophthora sojae*; Omega-3 DESATURASE from *Pythium irregulare*; Omega-3-DESATURASE from *Phythophthora infestans*; Delta-5 DESATURASE from *Thraustochytrium* sp (in particular sp. ATCC21685); Delta-4 DESATURASE from *Thraustochytrium* sp.; Omega-3 DESATURASE from *Pythium irregulare*; Delta-4 DESATURASE from *Pavlova lutheri*; Delta-5 ELONGASE from *Ostreococcus tauri*, and an acetohydroxy acid synthase, which confers tolerance to imidazolinone herbicides (see definitions above). The sequences of the polynucleotides and polypeptides are given e.g. in Table 130.

Interestingly, the enzyme AHAS shares a common metabolic precursor with fatty acid biosynthesis (pyruvate). One result of the overexpression of AHAS could be increased consumption of pyruvate, leading to a reduction in oil content and potentially an increase in amino acid or protein content (see for example Blombach et al 2009, Applied and Environment Microbiology 75(2):419-427, where overexpression of AHAS results in increased lysine production in bacteria; see also Muhitch 1988 Plant Physiol 83:23-27, where the role of AHAS in amino acid supply is described). Therefore, it is surprising that overexpression of an AHAS variant, especially in combination with the AHAS inhibiting herbicide, did not result in changes to protein, oil, or VLC-PUFA content in seeds (see example 18). As such, the present invention provides for a method of production of VLC-PUFA in which field grown plants are sprayed with an AHAS-inhibiting herbicide. Preferably, said herbicide is of the imidazolinone class.

The invention is further described by means of accompanying examples and figures, which, however, are not intended to limit the scope of the invention described herein.

EXAMPLES

Example 1: General Cloning Methods

Cloning methods as e.g. use of restriction endonucleases to cut double stranded DNA at specific sites, agarose gel electrophoreses, purification of DNA fragments, transfer of nucleic acids onto nitrocellulose and nylon membranes, joining of DNA-fragments, transformation of E co/icells and culture of bacteria were performed as described in Sambrook et al. (1989) (Cold Spring Harbor Laboratory Press: ISBN 0-87965-309-6). Polymerase chain reaction was performed using Phusion™ High-Fidelity DNA Polymerase (NEB, Frankfurt, Germany) according to the manufactures instructions. In general, primers used in PCR were designed such, that at least 20 nucleotides of the 3' end of the primer anneal perfectly with the template to amplify. Restriction sites were added by attaching the corresponding nucleotides of the recognition sites to the 5' end of the primer. Fusion PCR, for example described by K. Heckman and L. R. Pease, Nature Protocols (2207) 2, 924-932 was used as an alternative method to join two fragments of interest, e.g. a promoter to a gene or a gene to a terminator. Gene Synthesis, as for example described by Czar et al. (Trends in Biotechnology, 2009, 27(2): 63-72), was performed by Life Technologies using their Geneart® service. The Geneart® technology, described in WO2013049227 allows production of genetic elements of a few basepair (bp) in length, and was used in this invention to produce entire plasmids of about 60,000 bp. Chemical synthesis of nucleotides to polynucleotides was employed for short DNA fragments, which were then combined in a sequential, modular fashion to fragments of increasing size using a combination of conventional cloning techniques as described in WO2013049227.

Example 2: Different Types of Plant Transformation Plasmids Suitable to Transfer of Multiple Expression Cassettes Encoding Multiple Proteins into the Plant Genome For agrobacteria based plant transformation, DNA constructs preferably meet a number of criteria: (1) The construct carries a number of genetic elements that are intended to be inserted into the plant genome on a so called Transfer DNA (T-DNA) between a 'T-DNA Left Border' (LB) and 'T-DNA Right Border' (2) The construct replicates in Ecoi, because most cloning steps require DNA multiplication steps in *E. coli*. (3) The construct replicates in *Agrobacterium* (e.g. *A. tumefaciens* or *A. rhizogenes*), because the plant transformation methods rely on using *Agrobacterium* to insert the genetic elements of interest into the plant genome of a cell that was infected by *Agrobacterium*. (4) The construct contains supporting genetic elements that encode proteins which are required for infection of the plant cell, and for transfer and integration of desired genetic elements into the plant genome of an plant cell infected by the *Agrobacterium*, or the construct was used in combination with a second construct containing such supporting genetic elements that was present in the same *Agrobacterium* cell. (5) The constructs can contain selection markers to facilitate selection or identification of bacterial cells that contain the entire construct, and of a plant cell(s) that contains the desired genetic elements. An overview of available plasmids was given in Komori et al (2007).

Agrobacteria mediated transformation results in an almost random integration (with some bias induced by a number of factors) of the desired genetic element into chromosomes of the plant cell. The goal of the transformation was to integrate the entire T-DNA from T-DNA Left border to T-DNA Right border into a random position of a random chromosome. It can also be desirable to integrate the entire T-DNA twice or three times into the genome, for example to increase the plant expression levels of genes encoded by the T-DNA. To avoid complex Mendelian segregation of multiple integrations, it was preferred to have all T-DNA insertions at one genomic location, ('locus'). Inserting more than 25,000 bp T-DNA into plant genomes has been found to be a particular challenge in the current invention. In particular, it has been found in this invention plasmids carrying a ColE1/pVS1 origin of replication for plasmid replication in *E. coli* and/or *Agrobacterium*, are not stable above ~25,000 bp. Such plasmids of the invention are described in Example 3. Because of this limitation, not more than ~4 to 5 gene expression cassettes can be transferred on one T-DNA containing plasmid into the plant genome. However, for the current invention up to 13 gene expression cassettes having a combined size of about 44,000 bp needed to be transferred into the plant genome. In contrast to plasmids containing the ColE1/pVS1 origin of replication for high copy plasmid replication in *E. coli* and/or *Agrobacterium*, BiBAC plasmids (Hammilton 1997) containing the F factor/pRi origin of replication for single copy plasmid replication in *E. coli* and/or *Agrobacterium* where found to be stable in this invention up to a size of ~60,000 bp. Such plasmids of the invention are described in Example 4. Both approaches described above were followed in the current invention.

Figure 3:
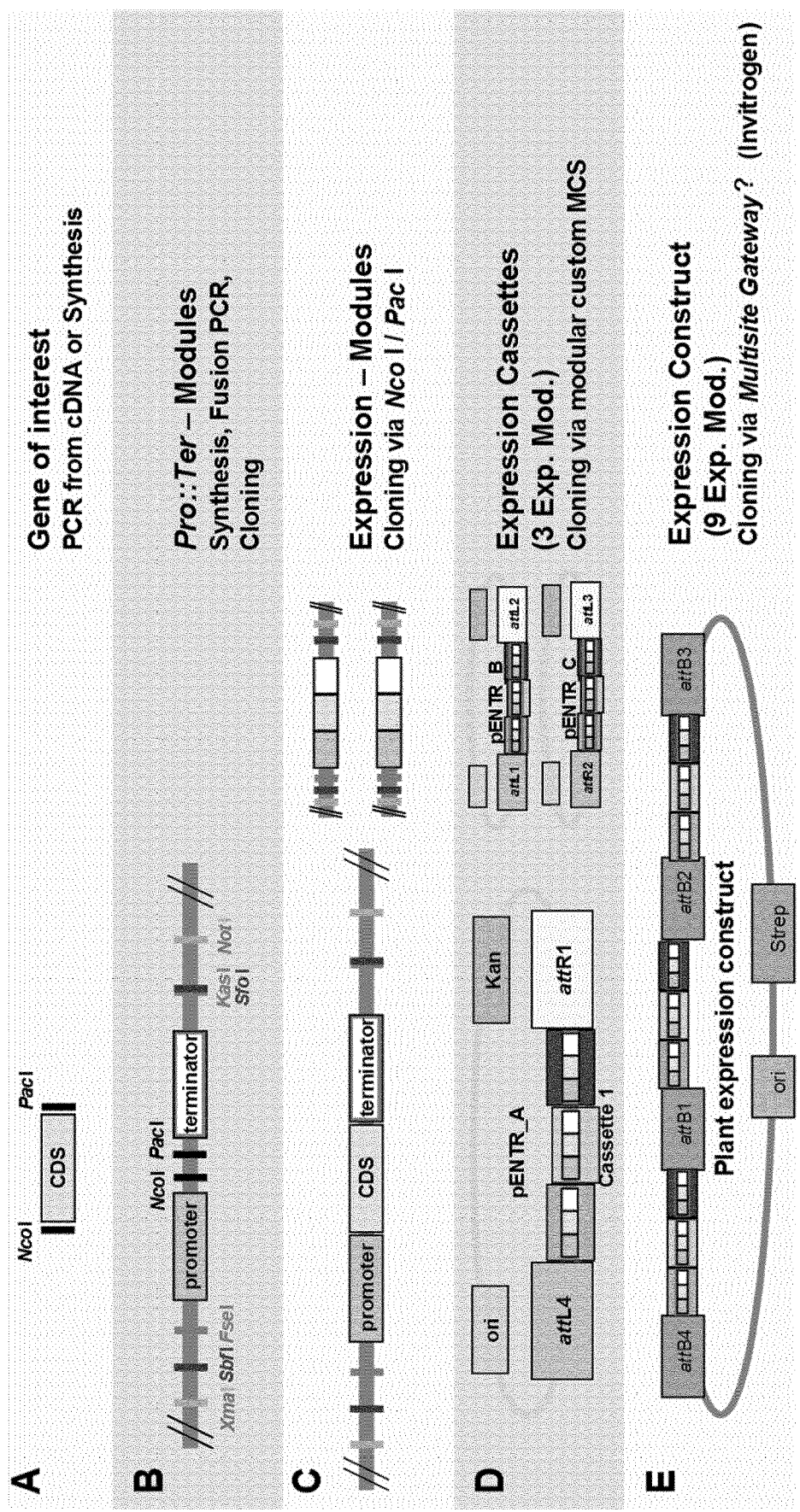
FIG. 3: Strategy employed for stepwise buildup of plant expression plasmids of the invention.

Example 3: Assembly of Genes Required for EPA and DHA Synthesis within T-Plasmids Containing the ColE1/pVS1 Origin of Replication For synthesis of VLC-PUFA in Brass/ca *napus* seeds, the set of genes encoding the proteins of the metabolic VLC-PUFA pathway were combined with expression elements (promoters, terminators, Introns) and transferred into binary t-plasmids that were used for agrobacteria mediated transformation of plants. Attributed to the large number of expression cassettes promoting expression of one protein each, two binary t-plasmids where used for cloning of the complete set of proteins required for EPA and DHA synthesis. To this end, the general cloning strategy depicted in FIG. 3 was employed. While FIG. 3 depicts the general strategy, cloning of the final plant expression vectors described in example 10 to 14 was not restricted to this strategy; specifically a combination of all methods known to one skilled in the art, such as cloning, the use of restriction endonucleases for generation of sticky and blunt ends, synthesis and fusion PCR has been used. Following the modular cloning scheme depicted in FIG. 3, genes were either synthesized by GeneArt (Regensburg) or PCR-amplified using Phusion™ High-Fidelity DNA Polymerase (NEB, Frankfurt, Germany) according to the manufacturer's instructions from cDNA. In both cases an Nco I and/or Asc I restriction site at the 5' terminus, and a PacI restriction site at the 3' terminus (FIG. 3A) were introduced to enable cloning of these genes between functional elements such as promoters and terminators using these restriction sites (see below in this example). Promoter-terminator modules or promoter-intron-terminator modules were created by complete synthesis by GeneArt (Regensburg) or by joining the corresponding expression elements using fusion PCR as described in example 1 and cloning the PCR-product into the TOPO-vector pCR2.1 (Invitrogen) according to the manufacturer's instructions (FIG. 3B). While joining terminator sequences to promoter sequences or promoter-intron sequences either via synthesis of whole cassettes or using fusion PCR, recognition sequences for the restriction endonucleases depicted in FIG. 3 were added to either side of the modules, and the recognition sites for the restriction endonucleases Nco I, Asc I and Pac I were introduced between promoter and terminator or between introns and terminator (see FIG. 3B). To obtain the final expression modules, PCR-amplified genes were cloned between promoter and terminator or intron and terminator via Nco I and/or Pac I restriction sites (FIG. 3C). Employing the custom multiple cloning site (MCS) up to three of those expression modules were combined as desired to expression cassettes harbored by either one of pENTR/A, pENTR/B or pENTR/C (FIG. 3D). Finally, the Multi-site Gateway™ System (Invitrogen) was used to combine three expression cassettes harbored by pENTR/A, pENTR/B and pENTR/C (FIG. 3E) to obtain the final binary pSUN T-plasmids for plant transformation: VC-LJB2197-1qcz, VC-LJB2755-2qcz rc, VC-LLM306-1qcz rc, VC-LLM337-1qcz rc, VC-LLM338-3qcz rc and VC-LLM391-2qcz rc. An overview of binary vectors and their usage was given by Hellens et al, Trends in Plant Science (2000) 5: 446-451.

The structure of the plamsids VC-LJB2197-1qcz, VC-LJB2755-2qcz rc, VC-LLM306-1qcz rc, VC-LLM337-1qcz rc, VC-LLM338-3qcz rc, VC-LLM391-2qcz rc, and VC-LTM217-1qcz rc was given in the Table 1, Table 2, Table 3, Table 4, Table 5, Table 6, and Table 7

Nomenclature of Genetic Elements:
j—indicates a junction between two genetic elements
c—coding sequence
t—terminator
p—promoter
i—intron
T-DNA Transferred DNA
RB Right Border of the T-DNA
LB Left Border of the T-DNA

TABLE 1

Genetic Elements of plasmid VC-LJB2197-1qcz.
Listed are the names of the elements, the position in VC-LJB2197-1qcz (note: start position was larger than stop position for elements encoded by the complementary strand of VC-LJB2197-1qcz), the function and source of the element. The T-DNA integrated into the plant genome during the transformation process was flanked by a right border (nucleotides 148 to 4 of VC-LJB2197-1qcz) and a left border (nucleotides 22232 to 22105 of VC-LJB2197-1qcz). Elements outside of that region (=vector backbone) are required for cloning and stable maintenance in *E.coli* and/or agrobacteria.

| Genetic Elements of plasmid VC-LJB2197-1qcz | From | To | Description, Function and Source of Element |
|---|---|---|---|
| b-RB[lm175] | 148 | 4 | Right border of T-DNA |
| p-VfUSP_684bp[LLL894] | 329 | 1012 | Promoter from UNKNOWN SEED PROTEIN gene USP (accession: X56240) from *Vicia faba* |
| i-Atss18_252[LJK36] | 1013 | 1264 | i-Atss18_252bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064bp) | 2448 | 3511 | Promoter from CONLININ gene from *Linum usitatissimum* |
| i-Atss14_377[LJK32] | 3512 | 3888 | i-Atss14_377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING PROTEIN-RELATED gene from *Vicia faba* |
| i-Atss2_455bp[LJK20] | 7338 | 7792 | i-Atss2_455bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from *Ostreococcus tauri* |
| t-StCATHD-pA | 9200 | 9434 | Terminator from CATHEPSIN D INHIBITORgene [CATHD] from *Solanum tuberosum* [Potato] |

TABLE 1-continued

Genetic Elements of plasmid VC-LJB2197-1qcz.
Listed are the names of the elements, the position in
VC-LJB2197-1qcz (note: start position was larger than
stop position for elements encoded by the
complementary strand of VC-LJB2197-1qcz),
the function and source of the element.
The T-DNA integrated into the plant genome
during the transformation process was flanked by a right border
(nucleotides 148 to 4 of VC-LJB2197-1qcz) and a left border
(nucleotides 22232 to 22105 of VC-LJB2197-1qcz).
Elements outside of that region (=vector backbone) are required for
cloning and stable maintenance in *E.coli* and/or agrobacteria.

| Genetic Elements of plasmid VC-LJB2197-1qcz | From | To | Description, Function and Source of Element |
|---|---|---|---|
| p-LuPXR 1727bp[LLL823] | 9513 | 11239 | Promoter from PEROXIREDOXIN LIKE PROTEIN gene PXR from *Linum usitatissimum* |
| i-Atss1_847bp[LJK19] | 11240 | 12086 | i-Atss1_847bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d6Elo(Tp_GA2) | 12100 | 12918 | Delta-6 ELONGASE from *Thalassiosira pseudonana* |
| t-AtPXR 400bp [LLL823] | 12974 | 13373 | Terminator from PEROXIREDOXIN LIKE PROTEIN gene PXR (At1g48130) from *Arabidopsis thaliana* |
| p-Napin A/B | 13543 | 14206 | Promoter from napA/Bgene (napin, seed storage protein) from *Brassica napus* |
| i-Atss14_377[LJK32] | 14207 | 14583 | i-Atss14_377bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d12Des(Ps_GA) | 14590 | 15786 | Delta-12 DESATURASE from *Phytophthora sojae* |
| t-E9 | 15805 | 16362 | Terminator from Small Subunit of RuBisCo rbcS gene (E9) from *Pisum sativum* |
| t-AtAHAS-3'/ UTR[bb003] | 16576 | 17790 | Terminator from AtAHASL [csr1-2] of acetohydroxyacid synthase gene from *Arabidopsis* |
| p-PcUbi4-2[long] | 17823 | 18804 | Promoter from UBIQUITIN gene UBI4-2 with internal intron from *Petroselinum crispum* |
| c-AtAHASL_A122T_S653N | 18812 | 20824 | ACETOHYDROXYACID SYNTHASE LARGE-SUBUNIT gene/CDS with S653N(csr1-2) mutation and A122T SDM mutation from *Arabidopsis* |
| t-AtAHAS-3'/ UTR[ac321] | 20849 | 22064 | Terminator from AtAHASL [csr1-2] of ACETOHYDROXYACID SYNTHASE gene from *Arabidopsis* |
| b-JTV_LB | 22232 | 22105 | Left border of T-DNA |
| c-StaA[lm500] | 22338 | 22967 | PVS1 partitioning protein |
| c-VS1orf3[lm500] | 23203 | 22988 | VS1orf3 |
| c-repA[lm500] | 23294 | 24469 | pVS1 replication protein [repA] gene/CDS |
| o-pVS1-origin | 24535 | 24729 | broad host-range replication origin of plasmid pVS1 (Genbank: AF133831, Itoh et al.1984) |
| o-ColE1-bom[lm500] | 25032 | 24830 | pBR322 bom site, partial, from AF234316 pCambia2301 |
| o-Rep-ColE1 | 25451 | 25171 | pBR322 origin of replication [*ecoli*] from AF234316 pCambia2301 |
| c-aadAmod1 | 26588 | 25797 | Codon Optimized *Adenyltransferase* [aadA] gene/CDS from SUN100 |
| p-aadA[lm800] | 26767 | 26589 | *Adenyltransferase* [aadA] Spectinomycin Prokaryotic promoter |

TABLE 2

Genetic Elements of plasmid VC-LJB2755-2qcz rc. Listed are the names of the elements, the position in VC-LJB2755-2qcz rc (note: start position was larger than stop position for elements encoded by the complementary strand of VC-LJB2755-2qcz rc), the function and source of the element. The T-DNA integrated into the plant genome during the transformation process was flanked by a right border (nucleotides 148 to 4 of VC-LJB2755-2qcz rc) and a left border (nucleotides 26117 to 25990 of VC-LJB2755-2qcz rc). Elements outside of that region (=vector backbone) are required for cloning and stable maintenance in *E. coli* and/or agrobacteria.

| Genetic Elements of plasmid VC-LJB2755-2qcz rc | From | To | Description, Function and Source of Element |
|---|---|---|---|
| b-RB[lm175] | 148 | 4 | Right border of T-DNA |
| p-LuPXR 1727 bp[LLL823] | 342 | 2068 | Promoter from PEROXIREDOXIN LIKE PROTEIN gene PXR from *Linum usitatissimum* |
| i-Atss15_758 bp[LJK33] | 2069 | 2826 | i-Atss15_758 bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir_GA) | 2842 | 3933 | Omega-3 DESATURASE from *Pythium irregulare* |
| t-AtPXR 400 bp[LLL823] | 3990 | 4389 | Terminator from PEROXIREDOXIN LIKE PROTEIN gene PXR (At1g48130) from *Arabidopsis thaliana* |
| p-LuCnl(1064 bp) | 4468 | 5531 | Promoter from CONLININ gene from *Linum usitatissimum* |
| i-Atss14_377[LJK32] | 5532 | 5908 | i-Atss14_377 bp functional intron region; intron with partial 5'UTR, *Arabidopsis thaliana*, Locus At5g63190, +166 to +542 bp (numbering relative to start of transcription) (+201 to +542 bp 5'UTR-Intron only) |

TABLE 2-continued

Genetic Elements of plasmid VC-LJB2755-2qcz rc. Listed are the names of the elements, the position in VC-LJB2755-2qcz rc (note: start position was larger than stop position for elements encoded by the complementary strand of VC-LJB2755-2qcz rc), the function and source of the element. The T-DNA integrated into the plant genome during the transformation process was flanked by a right border (nucleotides 148 to 4 of VC-LJB2755-2qcz rc) and a left border (nucleotides 26117 to 25990 of VC-LJB2755-2qcz rc). Elements outside of that region (=vector backbone) are required for cloning and stable maintenance in *E. coli* and/or agrobacteria.

| Genetic Elements of plasmid VC-LJB2755-2qcz rc | From | To | Description, Function and Source of Element |
|---|---|---|---|
| c-d5Des(Tc_GA2) | 5912 | 7231 | Delta-5 DESATURASE from *Thraustochytrium* sp. ATCC21685 |
| t-AgrOCS 192 bp[LED12] | 7232 | 7423 | Terminator from OCTOPINE SYNTHASE gene OCS from *Agrobacterium tumefaciens* |
| p-SBP | 7559 | 9357 | Promoter from a SUCROSE BINDING RELATED-PROTEIN gene from *Vicia faba* |
| i-Atss2_455 bp[LJK20] | 9358 | 9812 | i-Atss2_455 bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 9822 | 11192 | Delta-6 DESATURASE from *Ostreococcus tauri* |
| t-StCATHD-pA | 11220 | 11454 | Terminator from CATHEPSIN D INHIBITOR gene [CATHD] from *Solanum tuberosum* [Potato] |
| p-BnFae1 | 11533 | 12962 | Promoter from Beta-KETOACYL-CoA SYNTHASE (FAE1.1) gene from *Brassica napus* |
| i-Atss1_847 bp[LJK19] | 12963 | 13809 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d6Elo(Tp_GA2) | 13812 | 14630 | Delta-6 ELONGASE from *Thalassiosira pseudonana* |
| t-bnFae1 | 14646 | 15045 | Terminator from FATTY ACID ELONGASE (FAE1, At4g34520) gene of *Arabidopsis thaliana* |
| p-Napin A/B | 15166 | 15829 | Promoter from napA/B gene (napin, seed storage protein) from *Brassica napus* |
| i-Atss14_377[LJK32] | 15830 | 16206 | i-Atss14_377 bp functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d12Des(Ps_GA) | 16213 | 17409 | Delta-12 DESATURASE from *Phytophthora sojae* |
| t-E9 | 17428 | 17985 | Terminator from Small Subunit of RuBisCo rbcS gene (E9) from *Pisum sativum* |
| p-VfUSP_684 bp[LLL894] | 18064 | 18747 | Promoter from UNKNOWN SEED PROTEIN gene USP (accession: X56240) from *Vicia faba* |
| i-Atss18_252[LJK36] | 18748 | 18999 | i-Atss18_252 bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-o3Des(Pi_GA2) | 19010 | 20095 | Omega-3-DESATURASE from *Phytophthora infestans* |
| t-CaMV35S | 20104 | 20319 | Terminator CaMV35S from 35S gene from Cauliflower mosaic virus |
| t-AtAHAS-3'/UTR[ac321] | 20460 | 21675 | Terminator from AtAHASL [csr1-2] of ACETYOHYDROXYACID SYNTHASE gene from *Arabidopsis* |
| p-PcUbi4-2[long] | 21708 | 22689 | Promoter from UBIQUITIN gene UBI4-2 with internal intron from *Petroselinum crispum* |
| c-AtAHASL_A122T_S653N | 22697 | 24709 | ACETOHYDROXYACID SYNTHASE LARGE-SUBUNIT gene/CDS with S653N(csr1-2) mutation and A122T SDM mutation from *Arabidopsis* |
| t-AtAHAS-3'/UTR[ac321] | 24734 | 25949 | Terminator from AtAHASL [csr1-2] of ACETOHYDROXYACID SYNTHASE gene from *Arabidopsis* |
| b-JTV_LB | 26117 | 25990 | Left border of T-DNA |
| c-StaA[lm500] | 26223 | 26852 | PVS1 partitioning protein |
| c-VSforf3[lm500] | 27088 | 26873 | VSforf3 |
| c-repA[lm500] | 27179 | 28354 | pVS1 replication protein [repA] gene/CDS |
| o-pVS1-origin | 28420 | 28614 | broad host-range replication origin of plasmid pVS1 (Genbank: AF133831, Itoh et al. 1984) |
| o-ColE1-bom[lm500] | 28917 | 28715 | pBR322 bom site, partial, from AF234316 pCambia2301 |
| o-Rep-ColE1 | 29336 | 29056 | pBR322 origin of replication [*E. coli*] from AF234316 pCambia2301 |
| c-aadAmod1 | 30473 | 29682 | Codon Optimized Adenyltransferase [aadA] gene/CDS from SUN100 |
| p-aadA[lm800] | 30652 | 30474 | Adenyltransferase [aadA] Spectinomycin Prokaryotic promoter |

TABLE 3

Genetic Elements of plasmid VC-LLM306-1qcz rc. Listed are the names of the elements, the position in VC-LLM306-1qcz rc (note: start position was larger than stop position for elements encoded by the complementary strand of VC-LLM306-1qcz rc), the function and source of the element. The T-DNA integrated into the plant genome during the transformation process was flanked by a right border (nucleotides 148 to 4 of VC-LLM306-1qcz rc) and a left border (nucleotides 20180 to 20053 of VC-LLM306-1qcz rc). Elements outside of that region (=vector backbone) are required for cloning and stable maintenance in *E. coli* and/or agrobacteria.

| Genetic Elements of plasmid VC-LLM306-1qcz rc | From | To | Description, Function and Source of Element |
|---|---|---|---|
| b-RB[lm175] | 148 | 4 | Right border of T-DNA |
| p-LuCnl(1064 bp) | 342 | 1405 | Promoter from CONLININ gene from *Linum usitatissimum* |
| c-d4Des(Eg_GA) | 1416 | 3041 | Delta 4 DESATURASE from *Euglena gracilis* |

TABLE 3-continued

Genetic Elements of plasmid VC-LLM306-1qcz rc. Listed are the names of the elements, the position in VC-LLM306-1qcz rc (note: start position was larger than stop position for elements encoded by the complementary strand of VC-LLM306-1qcz rc), the function and source of the element. The T-DNA integrated into the plant genome during the transformation process was flanked by a right border (nucleotides 148 to 4 of VC-LLM306-1qcz rc) and a left border (nucleotides 20180 to 20053 of VC-LLM306-1qcz rc). Elements outside of that region (=vector backbone) are required for cloning and stable maintenance in *E. coli* and/or agrobacteria.

| Genetic Elements of plasmid VC-LLM306-1qcz rc | From | To | Description, Function and Source of Element |
|---|---|---|---|
| t-AgrOCS 192 bp[LED12] | 3063 | 3254 | Terminator from OCTOPINE SYNTHASE gene OCS from *Agrobacterium tumefaciens* |
| p-BnFAE1 | 3448 | 4877 | Promoter from Beta-KETOACYL-CoA SYNTHASE (FAE1.1) gene from *Brassica napus* |
| i-Atss1_847 bp[LJK19] | 4878 | 5724 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 5732 | 6634 | Delta-5 ELONGASE from *Ostreococcus tauri* |
| t-bnFAE1 | 6651 | 7050 | Terminator from FATTY ACID ELONGASE (FAE1, At4g34520) gene of *Arabidopsis thaliana* |
| p-VfSBP_perm3 | 7099 | 8897 | Promoter derived from a promoter from a SUCROSE-BINDING PROTEIN-RELATED gene from *Vicia faba* |
| c-o3Des(Pir_GA) | 8901 | 9992 | Omega-3 DESATURASE from *Pythium Irregulare* |
| t-StCATHD-pA | 10023 | 10257 | Terminator from CATHEPSIN D INHIBITOR gene [CATHD] from *Solanum tuberosum* [Potato] |
| p-VfUSP_684 bp[LLL894] | 10331 | 11014 | Promoter from UNKNOWN SEED PROTEIN gene USP (accession: X56240) from *Vicia faba* |
| i-Atss15_758 bp[LJK33] | 11015 | 11772 | i-Atss15_758 bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pi_GA2) | 11789 | 12874 | Omega-3-DESATURASE from *Phythophthora infestans* |
| t-CaMV35S | 12924 | 13139 | Terminator CaMV35S from 35S gene from Cauliflower mosaic virus |
| p-ARC5_perm1 | 13259 | 14409 | Promoter derived from a promoter from ARCLINE 5 gene from *Phaseolus vulgaris* |
| c-d4Des(Tc_GA) | 14420 | 15979 | Delta-4 DESATURASE from *Thraustochytrium* sp. |
| t-pvarc | 15993 | 16592 | Terminator of ARC5 gene from *Phaseolus vulgaris* |
| p-BnFae1 | 16671 | 18100 | Promoter from Beta-KETOACYL-CoA SYNTHASE (FAE1.1) gene from *Brassica napus* |
| c-d6Des(Ot_febit) | 18109 | 19479 | Delta-6 DESATURASE from *Ostreococcus tauri* |
| t-bnFae1 | 19493 | 19892 | Terminator from FATTY ACID ELONGASE (FAE1, At4g34520) gene of *Arabidopsis thaliana* |
| b-JTV_LB | 20180 | 20053 | Left border of T-DNA |
| c-StaA[lm500] | 20286 | 20915 | PVS1 partitioning protein |
| c-VS1orf3[lm500] | 21151 | 20936 | VSforf3 |
| c-repA[lm500] | 21242 | 22417 | pVS1 replication protein [repA] gene/CDS |
| o-pVS1-origin | 22483 | 22677 | broad host-range replication origin of plasmid pVS1 (Genbank: AF133831, Itoh et al. 1984) |
| o-ColE1-bom[lm500] | 22980 | 22778 | pBR322 bom site, partial, from AF234316 pCambia2301 |
| o-Rep-ColE1 | 23399 | 23119 | pBR322 origin of replication [*E. coli*] from AF234316 pCambia2301 |
| c-aadAmod1 | 24536 | 23745 | Codon Optimized Adenyltransferase [aadA] gene/CDS from SUN100 |
| p-aadA[lm800] | 24715 | 24537 | Adenyltransferase [aadA] Spectinomycin Prokaryotic promoter |

TABLE 4

Genetic Elements of plasmid VC-LLM337-1qcz rc. Listed are the names of the elements, the position in VC-LLM337-1qcz rc (nucleotide number, note: start position was larger than stop position for elements encoded by the complementary strand of VC-LLM337-1qcz rc), the function and source of the element. The T-DNA integrated into the plant genome during the transformation process was flanked by a right border (nucleotides 148 to 4 of VC-LLM337-1qcz rc) and a left border (nucleotides 16953 to 16826 of VC-LLM337-1qcz rc). Elements outside of that region (=vector backbone) are required for cloning and stable maintenance in *E. coli* and/or agrobacteria.

| Genetic Elements of plasmid VC-LLM337-1qcz rc | From | To | Description, Function and Source of Element |
|---|---|---|---|
| b-RB[lm175] | 148 | 4 | Right border of T-DNA |
| p-LuCnl(1064 bp) | 342 | 1405 | Promoter from CONLININ gene from *Linum usitatissimum* |
| c-d4Des(Eg_GA) | 1416 | 3041 | Delta-4 DESATURASE from *Euglena gracilis* |
| t-AgrOCS 192 bp[LED12] | 3063 | 3254 | Terminator from OCTOPINE SYNTHASE gene OCS from *Agrobacterium tumefaciens* |
| p-BnFae1 | 3448 | 4877 | Promoter from Beta-KETOACYL-CoA SYNTHASE (FAE1.1) gene from *Brassica napus* |
| i-Atss1_847 bp[LJK19] | 4878 | 5724 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |

TABLE 4-continued

Genetic Elements of plasmid VC-LLM337-1qcz rc. Listed are the names of the elements, the position in VC-LLM337-1qcz rc (nucleotide number, note: start position was larger than stop position for elements encoded by the complementary strand of VC-LLM337-1qcz rc), the function and source of the element. The T-DNA integrated into the plant genome during the transformation process was flanked by a right border (nucleotides 148 to 4 of VC-LLM337-1qcz rc) and a left border (nucleotides 16953 to 16826 of VC-LLM337-1qcz rc. Elements outside of that region (=vector backbone) are required for cloning and stable maintenance in *E. coli* and/or agrobacteria.

| Genetic Elements of plasmid VC-LLM337-1qcz rc | From | To | Description, Function and Source of Element |
|---|---|---|---|
| c-d5Elo(Ot_GA3) | 5732 | 6634 | Delta-5 ELONGASE from *Ostreococcus tauri* |
| t-bnFae1 | 6651 | 7050 | Terminator from FATTY ACID ELONGASE (FAE1, At4g34520) gene of *Arabidopsis thaliana* |
| p-VfSBP_perm3 | 7099 | 8897 | Promoter derived from a promoter from a SUCROSE-BINDING PROTEIN-RELATED gene from *Vicia faba* |
| c-o3Des(Pir_GA) | 8901 | 9992 | Omega-3 DESATURASE from *Pythium irregulare* |
| t-StCATHD-pA | 10023 | 10257 | Terminator from CATHEPSIN D INHIBITOR gene [CATHD] from *Solanum tuberosum* [Potato] |
| p-VfUSP_684 bp[LLL894] | 10331 | 11014 | Promoter from UNKNOWN SEED PROTEIN gene USP (accession: X56240) from *Vicia faba* |
| i-Atss15_758 bp[LJK33] | 11015 | 11772 | i-Atss15_758 bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pi_GA2) | 11789 | 12874 | Omega-3-DESATURASE from *Phythophthora infestans* |
| t-CaMV35S | 12924 | 13139 | Terminator CaMV35S from 35S gene from Cauliflower mosaic virus |
| p-ARC5_perm1 | 13259 | 14409 | Promoter derived from a promoter from ARCLINE 5 gene from *Phaseolus vulgaris* |
| c-d4Des(Tc_GA) | 14420 | 15979 | Delta-4 DESATURASE from *Thraustochytrium* sp. |
| t-pvarc | 15993 | 16592 | Terminator of ARC5 gene from *Phaseolus vulgaris* |
| b-JTV_LB | 16953 | 16826 | Left border of T-DNA |
| c-StaA[lm500] | 17059 | 17688 | PVS1 partitioning protein |
| c-VS1orf3[lm500] | 17924 | 17709 | VSforf3 |
| c-repA[lm500] | 18015 | 19190 | pVS1 replication protein [repA] gene/CDS |
| o-pVS1-origin | 19256 | 19450 | broad host-range replication origin of plasmid pVS1 (Genbank: AF133831, Itoh et al. 1984) |
| o-ColE1-bom[lm500] | 19753 | 19551 | pBR322 bom site, partial, from AF234316 pCambia2301 |
| o-Rep-ColE1 | 20172 | 19892 | pBR322 origin of replication [*E. coli*] from AF234316 pCambia2301 |
| c-aadAmod1 | 21309 | 20518 | Codon Optimized Adenyltransferase [aadA] gene/CDS from SUN100 |
| p-aadA[lm800] | 21488 | 21310 | Adenyltransferase [aadA] Spectinomycin Prokaryotic promoter |

TABLE 5

Genetic Elements of plasmid VC-LLM338-3qcz rc. Listed are the name of the element, the position in VC-LLM338-3qcz rc (nucleotide number, note: start position was larger than stop position for elements encoded by the complementary strand VC-LLM338-3qcz rc), the function and source of the element. The T-DNA integrated into the plant genome during the transformation process was flanked by a right border (nucleotides 148 to 4 of VC-LLM338-3qcz rc) and a left border (nucleotides 17069 to 16942 of VC-LLM338-3qcz rc). Elements outside of that region (=vector backbone) are required for cloning and stable maintenance in *E. coli* and/or agrobacteria.

| Genetic Elements of plasmid VC-LLM338-3qcz rc | From | To | Description, Function and Source of Element |
|---|---|---|---|
| b-RB[lm175] | 148 | 4 | Right border of T-DNA |
| p-VfSBP_perm3 | 341 | 2139 | Promoter derived from a promoter from a SUCROSE-BINDING RELATED-PROTEIN gene from *Vicia faba* |
| c-d15Des(Ch_ERTp_GA) | 2151 | 3389 | Delta-15 DESATURASE from *Cochliobolus heterostrophus* C5 |
| t-StCATHD-pA | 3420 | 3654 | Terminator from CATHEPSIN D INHIBITOR gene [CATHD] from *Solanum tuberosum* [Potato] |
| p-BnFae1 | 3848 | 5277 | Promoter from Beta-KETOACYL-CoA SYNTHASE (FAE1.1) gene from *Brassica napus* |
| i-Atss1_847 bp[LJK19] | 5278 | 6124 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 6132 | 7034 | Delta-5 ELONGASE from *Ostreococcus tauri* |
| t-bnFae1 | 7051 | 7450 | Terminator from FATTY ACID ELONGASE (FAE1, At4g34520) gene of *Arabidopsis thaliana* |
| p-VfUSP_684 bp[LLL894] | 7529 | 8212 | Promoter from UNKNOWN SEED PROTEIN gene USP (accession: X56240) from *Vicia faba* |
| i-Atss15_758 bp[LJK33] | 8213 | 8970 | i-Atss15_758 bp functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pi_GA2) | 8987 | 10072 | Omega-3-DESATURASE from *Phythophthora infestans* |
| t-CaMV35S | 10122 | 10337 | Terminator CaMV35S from 35S gene from Cauliflower mosaic virus |
| p-ARC5_perm1 | 10457 | 11607 | Promoter derived from a promoter from ARCLINE 5 gene from *Phaseolus vulgaris* |
| c-d4Des(Tc_GA) | 11618 | 13177 | Delta-4 DESATURASE from *Thraustochytrium* sp. |
| t-pvarc | 13191 | 13790 | Terminator of ARC5gene from *Phaseolus vulgaris* |

TABLE 5-continued

Genetic Elements of plasmid VC-LLM338-3qcz rc. Listed are the name of the element, the position in VC-LLM338-3qcz rc (nucleotide number, note: start position was larger than stop position for elements encoded by the complementary strand VC-LLM338-3qcz rc), the function and source of the element. The T-DNA integrated into the plant genome during the transformation process was flanked by a right border (nucleotides 148 to 4 of VC-LLM338-3qcz rc) and a left border (nucleotides 17069 to 16942 of VC-LLM338-3qcz rc). Elements outside of that region (=vector backbone) are required for cloning and stable maintenance in *E. coli* and/or agrobacteria.

| Genetic Elements of plasmid VC-LLM338-3qcz rc | From | To | Description, Function and Source of Element |
|---|---|---|---|
| p-LuCnl(1064 bp) | 13869 | 14932 | Promoter from CONLININ gene from *Linum usitatissimum* |
| c-d4Des(Eg_GA) | 14943 | 16568 | Delta-4 DESATURASE from *Euglena gracilis* |
| t-AgrOCS 192 bp[LED12] | 16590 | 16781 | Terminator from OCTOPINE SYNTHASE gene OCS from *Agrobacterium tumefaciens* |
| b-JTV_LB | 17069 | 16942 | Left border of T-DNA |
| c-StaA[lm500] | 17175 | 17804 | PVS1 partitioning protein |
| c-VS1orf3[lm500] | 18040 | 17825 | VSforf3 |
| c-repA[lm500] | 18131 | 19306 | pVS1 replication protein [repA] gene/CDS |
| o-pVS1-origin | 19372 | 19566 | broad host-range replication origin of plasmid pVS1 (Genbank: AF133831, Itoh et al. 1984) |
| o-ColE1-bom[lm500] | 19869 | 19667 | pBR322 bom site, partial, from AF234316 pCambia2301 |
| o-Rep-ColE1 | 20288 | 20008 | pBR322 origin of replication [*E. Coli*] from AF234316 pCambia2301 |
| c-aadAmod1 | 21425 | 20634 | Codon Optimized Adenyltransferase [aadA] gene/CDS from SUN100 |
| p-aadA[lm800] | 21604 | 21426 | Adenyltransferase [aadA] Spectinomycin Prokaryotic promoter |

TABLE 6

Genetic Elements of plasmid VC-LLM391-2qcz rc rc. Listed are the names of the elements, the position in VC-LLM391-2qcz rc rc (nucleotide number, note: start position was larger than stop position for elements encoded by the complementary strand of VC-LLM391-2qcz rc rc), the function and source of the element. The T-DNA integrated into the plant genome during the transformation process was flanked by a right border (nucleotides 148 to 4 of VC-LLM391-2qcz rc rc) and a left border (nucleotides 10947 to 10820 of VC-LLM391-2qcz rc rc). Elements outside of that region (=vector backbone) are required for cloning and stable maintenance in *E. coli* and/or agrobacteria.

| Genetic Elements of plasmid VC-LLM391-2qcz rc | From | To | Description, Function and Source of Element |
|---|---|---|---|
| b-RB[lm175] | 148 | 4 | Right border of T-DNA |
| p-BnFae1 | 540 | 1969 | Promoter from Beta-KETOACYL-CoA SYNTHASE(FAE1.1) gene from *Brassica napus* |
| i-Atss1_847 bp[LJK19] | 1970 | 2816 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 2824 | 3726 | Delta-5 ELONGASE from *Ostreococcus tauri* |
| t-bnFae1 | 3743 | 4142 | Terminator from FATTY ACID ELONGASE (FAE1, At4g34520) gene of *Arabidopsis thaliana* |
| p-ARC5perm1 | 4335 | 5485 | Promoter derived from a promoter from ARCLINE 5 gene from *Phaseolus vulgaris* |
| c-d4Des(Tc_GA)_T564G | 5496 | 7055 | Delta-4 DESATURASE from *Thraustochytrium* spp. |
| t-pvarc | 7069 | 7668 | Terminator of Arc5 gene from *Phaseolus vulgaris* |
| p-LuCnl(1064 bp) | 7747 | 8810 | Promoter from CONLININ gene from *Linum usitatissimum* |
| c-d4Des(Eg_GA) | 8821 | 10446 | Delta-4 DESATURASE from *Euglena gracilis* |
| t-AgrOCS 192 bp[LED12] | 10468 | 10659 | Terminator from OCTOPINE SYNTHASE gene OCS from *Agrobacterium tumefaciens* |
| b-JTV_LB | 10947 | 10820 | Left border of T-DNA |
| c-StaA[lm500] | 11053 | 11682 | PVS1 partitioning protein |
| c-VS1orf3[lm500] | 11918 | 11703 | VSforf3 |
| c-repA[lm500] | 12009 | 13184 | pVS1 replication protein [repA] gene/CDS |
| o-pVS1-origin | 13250 | 13444 | broad host-range replication origin of plasmid pVS1 (Genbank: AF133831, Itoh et al. 1984) |
| o-ColE1-bom[lm500] | 13747 | 13545 | pBR322 bom site, partial, from AF234316 pCambia2301 |
| o-Rep-ColE1 | 14166 | 13886 | pBR322 origin of replication [*E. coli*] from AF234316 pCambia2301 |
| c-aadAmod1 | 15303 | 14512 | Codon Optimized Adenyltransferase [aadA] gene/CDS from SUN100 |
| p-aadA[lm800] | 15482 | 15304 | Adenyltransferase [aadA] Spectinomycin Prokaryotic promoter |

TABLE 7

Genetic Elements of plasmid VC-LLTM217-1qcz rc. Listed are the names of the elements, the position in VC-LLTM217-1qcz rc (nucleotide number, note: start position was larger than stop position for elements encoded by the complementary strand of VC-LLTM217-1qcz rc), the function and source of the element. The T-DNA integrated into the plant genome during the transformation process was flanked by a right border (nucleotides 148 to 4 of VC-LLTM217-1qcz rc) and a left border (nucleotides 10659 to 10532 of VC-LLTM217-1qcz rc). Elements outside of that region (=vector backbone) are required for cloning and stable maintenance in *E. coli* and/or agrobacteria.

| Genetic Elements of plasmid VC-LLTM217-1qcz rc | From | To | Description, Function and Source of Element |
|---|---|---|---|
| b-RB[lm175] | 148 | 4 | Right border of T-DNA |
| p-BnFae1 | 540 | 1969 | Promoter from Beta-KETOACYL-CoA SYNTHASE(FAE1.1) gene from *Brassica napus* |
| i-Atss1_847 bp[LJK19] | 1970 | 2816 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 2824 | 3726 | Delta-5 ELONGASE from *Ostreococcus tauri* |
| t-bnFae1 | 3743 | 4142 | Terminator from FATTY ACID ELONGASE (FAE1, At4g34520) gene of *Arabidopsis thaliana* |
| p-ARC5_perm1 | 4335 | 5485 | Promoter derived from a promoter from ARCILINE 5 gene from *Phaseolus vulgaris* |
| c-d4Des(Tc_GA) | 5496 | 7055 | Delta-4 DESATURASE from *Thraustochytrium* spp. |
| t-pvarc | 7069 | 7668 | Terminator of Arc5 gene from *Phaseolus vulgaris* |
| p-LuCnl(1064 bp) | 7747 | 8810 | Promoter from CONLININ gene from *Linum usitatissimum* |
| c-d4Des(Pl_GA)2 | 8821 | 10158 | Delta-4 DESATURASE from *Pavlova lutheri* |
| t-AgrOCS 192 bp[LED12] | 10180 | 10371 | Terminator from OCTOPINE SYNTHASE gene OCS from *Agrobacterium tumefaciens* |
| b-JTV_LB | 10659 | 10532 | Left border of T-DNA |
| c-StaA[lm500] | 10765 | 11394 | PVS1 partitioning protein |
| c-VS1orf3[lm500] | 11630 | 11415 | VSforf3 |
| c-repA[lm500] | 11721 | 12896 | pVS1 replication protein [repA] gene/CDS |
| o-pVS1-origin | 12962 | 13156 | broad host-range replication origin of plasmid pVS1 (Genbank: AF133831, Itoh et al. 1984) |
| o-ColE1-bom[lm500] | 13459 | 13257 | pBR322 bom site, partial, from AF234316 pCambia2301 |
| o-Rep-ColE1 | 13878 | 13598 | pBR322 origin of replication [*E. coli*] from AF234316 pCambia2301 |
| c-aadAmod1 | 15015 | 14224 | Codon Optimized Adenyltransferase [aadA] gene/CDS from SUN100 |
| p-aadA[lm800] | 15194 | 15016 | Adenyltransferase [aadA] Spectinomycin Prokaryotic promoter |

Example 4: Assembly of Genes Required for EPA and DHA Synthesis within BiBAC T-Plasmids Containing the F Factor/pRI Origin of Replication For synthesis of VLC-PUFA in *Brassica napus* seeds, the set of genes encoding the proteins of the metabolic VLC-PUFA pathway were combined with expression elements (promoters, terminators and introns) and transferred into binary t-plasmids that were used for agrobacteria mediated transformation of plants. While the large number of expression cassettes promoting expression of one protein each, were distributed in example 3 onto two binary t-plasmids T-DNA, in this example all expression cassettes have been combined onto a single binary T-plasmid. The advance of DNA synthesis allows numerous companies to offer services to use a combination of chemical synthesis and molecular biological techniques to synthesize de novo, without an initial template, polynucleotides up to the size of microbial genomes. Synthesis used in the construction of the plasmids described in this example was performed by Life Technologies using their Geneart® service. The Geneart® technology, described in WO2013049227 allows production of genetic elements of a few basepair (bp) length, and was used in this invention to produce the binary T-plasmids for plant transformation VC-RTP169-1qczF, VC-RTP1691-2cz, V-LTM595-1qcz rc and VC-LTM593-1qcz rc having a total size of ~61C.5 bp for each construct. The structure of the plasmids VC-RTP10690-1qcz_F, VC-RTP10691-2qcz, VC-LTM595-1qcz rc and VC-LTM593-12qcz rc is given in: Table 8, Table 9, Table 10 and Table 11.

TABLE 8

Genetic Elements of plasmid RTP10690-1qcz_F. Listed are the names of the elements, the position in RTP10690-1qcz_F (nucleotide number, note: start position was larger than stop position for elements encoded by the complementary strand of SEQ ID NO. 6), the function and source of the element. The T-DNA integrated into the plant genome during the transformation process was flanked by a right border (nucleotides 59918 to 148 of RTP10690-1qcz_F) and a left border (nucleotides 43853 to 43718 of RTP10690-1qcz_F). Elements outside of that region (=vector backbone) are required for cloning and stable maintenance in *E. coli* and/or agrobacteria.

| Genetic Elements of plasmid RTP10690-1qcz_F | From | To | Description, Function and Source of Element |
|---|---|---|---|
| p-VfUSP_684 bp[LLL894] | 329 | 1012 | Promoter from UNKNOWN SEED PROTEIN gene USP (accession: X56240) from *Vicia faba* |

TABLE 8-continued

Genetic Elements of plasmid RTP10690-1qcz_F. Listed are the names of the elements, the position in RTP10690-1qcz_F (nucleotide number, note: start position was larger than stop position for elements encoded by the complementary strand of SEQ ID NO. 6), the function and source of the element. The T-DNA integrated into the plant genome during the transformation process was flanked by a right border (nucleotides 59918 to 148 of RTP10690-1qcz_F) and a left border (nucleotides 43853 to 43718 of RTP10690-1qcz_F). Elements outside of that region (=vector backbone) are required for cloning and stable maintenance in *E. coli* and/or agrobacteria.

| Genetic Elements of plasmid RTP10690-1qcz_F | From | To | Description, Function and Source of Element |
|---|---|---|---|
| i-Atss18_252[LJK36] | 1013 | 1264 | i-Atss18_252 bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064 bp) | 2448 | 3511 | Promoter from CONLININ gene from *Linum usitatissimum* |
| i-Atss14_377 bp[LJK32] | 3512 | 3888 | i-Atss14_377 bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192 bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING PROTEIN-RELATED gene from *Vicia faba* |
| i-Atss2_455 bp[LJK20] | 7338 | 7792 | i-Atss2_455 bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from *Ostreococcus tauri* |
| t-StCATHD-pA | 9200 | 9434 | Terminator from CATHEPSIN D INHIBITOR gene [CATHD] from *Solanum tuberosum* [Potato] |
| p-LuPXR 1727 bp[LLL823] | 9513 | 11239 | Promoter from PEROXIREDOXIN LIKE protein gene PXR from *Linum usitatissimum* |
| i-Atss1_847 bp[LJK19] | 11240 | 12086 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d6Elo(Tp_GA2) | 12100 | 12918 | Delta-6 ELONGASE from *Thalassiosira pseudonana* |
| t-AtPXR 400 bp[LLL823] | 12974 | 13373 | Terminator from PEROXIREDOXIN LIKE protein gene PXR (At1g48130) from *Arabidopsis thaliana* |
| p-Napin A/B | 13543 | 14206 | Promoter from napA/Bgene (napin, seed storage protein) from *Brassica napus* |
| i-Atss14_377 bp[LJK32] | 14207 | 14583 | i-Atss14_377 bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |

TABLE 8-continued

Genetic Elements of plasmid RTP10690-1qcz_F. Listed are the names of the elements, the position in RTP10690-1qcz_F (nucleotide number, note: start position was larger than stop position for elements encoded by the complementary strand of SEQ ID NO. 6), the function and source of the element. The T-DNA integrated into the plant genome during the transformation process was flanked by a right border (nucleotides 59918 to 148 of RTP10690-1qcz_F) and a left border (nucleotides 43853 to 43718 of RTP10690-1qcz_F). Elements outside of that region (=vector backbone) are required for cloning and stable maintenance in *E. coli* and/or agrobacteria.

| Genetic Elements of plasmid RTP10690-1qcz_F | From | To | Description, Function and Source of Element |
|---|---|---|---|
| c-d12Des(Ps_GA2) | 14590 | 15786 | Delta-12 DESATURASE from *Phythophthora sojae* |
| t-E9 | 15805 | 16362 | Terminator from Small Subunit of RuBisCo rbcS gene (E9) from *Pisum sativum* |
| p-LuPXR 1727 bp[LLL823] | 16462 | 18188 | Promoter from PEROXIREDOXIN LIKE protein gene PXR from *Linum usitatissimum* |
| i-Atss15_758 bp[LJK33] | 18189 | 18946 | i-Atss15_758 bp[LJK33] functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir_GA) | 18962 | 20053 | Omega-3 DESATURASE from *Pythium irregulare* |
| t-AtPXR 400 bp[LLL823] | 20110 | 20509 | Terminator from PEROXIREDOXIN LIKE protein gene PXR (At1g48130) from *Arabidopsis thaliana* |
| p-LuCnl(1064 bp) | 20645 | 21708 | Promoter from CONLININ gene from *Linum usitatissimum* |
| i-Atss2_455 bp[LJK20] | 21709 | 22163 | i-Atss2_455 bp functional intron region; intron with partial 5'UTR, *Arabidopsis thaliana*, Locus At1g65090, +77 to +531 bp (numbering relative to start of transcription)(+113 to +508 bp 5'UTR-Intron only) |
| c-d4Des(Pl_GA)2 | 22181 | 23518 | Delta-4 DESATURASE from *Pavlova lutheri* |
| t-AgrOCS 192 bp[LED12] | 23540 | 23731 | Terminator from OCTOPINE SYNTHASE gene OCS from *Agrobacterium tumefaciens* |
| p-BnFae1 | 23925 | 25354 | Promoter from Beta-KETOACYL-CoA SYNTHASE (FAE1.1) gene from *Brassica napus* |
| i-Atss1_847 bp[LJK19] | 25355 | 26202 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| T | 25513 | 25513 | T inserted [14-T string found verses 13-T string in original i-Atss1_847 bp[LJK19] |
| c-d5Elo(Ot_GA3) | 26210 | 27112 | Delta-5 ELONGASE from *Ostreococcus tauri* |
| t-bnFae1 | 27129 | 27528 | Terminator from FATTY ACID ELONGASE (FAE1, At4g34520) gene of *Arabidopsis thaliana* |
| p-ARC5_perm1 | 27681 | 28831 | Promoter derived from a promoter from ARCILINE 5 gene from *Phaseolus vulgaris* |
| c-d4Des(Tc_GA3) | 28842 | 30401 | Delta-4 DESATURASE from *Thraustochytrium* sp. |
| t-pvarc | 30415 | 31014 | Terminator of ARC5 gene from *Phaseolus vulgaris* |
| p-VfUSP_684 bp[LLL894] | 31093 | 31776 | Promoter from unknown seed protein gene USP (accession: X56240) from *Vicia faba* |
| i-Atss18_252[LJK36] | 31777 | 32028 | i-Atss18_252 bp functional intron region; intron with partial 5'UTR, *Arabidopsis thaliana*, Locus At1g01170, +37 to +288 bp |

TABLE 8-continued

Genetic Elements of plasmid RTP10690-1qcz_F. Listed are the names of the elements, the position in RTP10690-1qcz_F (nucleotide number, note: start position was larger than stop position for elements encoded by the complementary strand of SEQ ID NO. 6), the function and source of the element. The T-DNA integrated into the plant genome during the transformation process was flanked by a right border (nucleotides 59918 to 148 of RTP10690-1qcz_F) and a left border (nucleotides 43853 to 43718 of RTP10690-1qcz_F). Elements outside of that region (=vector backbone) are required for cloning and stable maintenance in *E. coli* and/or agrobacteria.

| Genetic Elements of plasmid RTP10690-1qcz_F | From | To | Description, Function and Source of Element |
|---|---|---|---|
| | | | (numbering relative to start of transcription) (+72 to +282 bp 5'UTR-Intron only) |
| c-o3Des(Pi_GA2) | 32039 | 33124 | Omega-3-DESATURASE from *Phytophthora infestans* |
| t-CaMV35S | 33133 | 33348 | Terminator CaMV35S from 35S gene from Cauliflower mosaic virus |
| p-BnSETL-v1[1234 bp] | 33484 | 34717 | SETL-v1 *Brassica napus* promoter |
| c-d5Des(Tc_GA2) | 34720 | 36039 | Delta-5 DESATURASE from *Thraustochytrium* sp. ATCC21685 |
| t-BnSETL | 36061 | 36674 | SETL-v1 *Brassica napus* terminator |
| p-BnSETL-v1[1234 bp] | 36767 | 38000 | SETL-v1 *Brassica napus* promoter |
| c-o3Des(Pir_GA) | 38003 | 39094 | Omega-3 DESATURASE from *Pythium irregulare* |
| t-BnSETL | 39116 | 39729 | SETL-v1 *Brassica napus* terminator |
| P-YPC105906_PcUbi4-2[long] | 39853 | 40829 | MTX Parsley UBI4-2 promoter with internal intron |
| c-AtAHASL_A122T_S653N[minusRES] | 40837 | 42849 | ACETOHYDROXYACID SYNTHASE LARGE SUBUNIT gene/CDS from *Arabidopsis* with S653N (csr1-2) mutation and A122T SDM mutation minus restriction sites |
| t-AtAHAS-3'UTR[rtp4820] | 42850 | 43629 | *Arabidopsis* (dicot) AtAHASL 3' Un-translated Region [trimmed] terminator for ACETOHYDROXYACID SYNTHASE gene |
| b-LLB | 43853 | 43718 | Left T-DNA Left border from pTi15955 [Genbank #AF242881] |
| c-KanR_Tn903 | 45800 | 44985 | Kanamycin Resistance selection gene/CDS |
| p-Kan[lm500] | 45921 | 45801 | Promoter for Kanamycin resistance gene |
| o-ori-2 | 47074 | 47290 | ori-2 origin of replication |
| c-repE | 47384 | 48139 | repE gene/CDS |
| c-sopA | 48718 | 49893 | sapA gene/CDS |
| c-sopB | 49893 | 50864 | sopB gene/CDS |
| c-sopC/incD | 50937 | 51410 | incD/sopC partial gene/CDS |
| c-traI | 51913 | 51972 | traI gene/CDS |
| mf-traI - repA intergenic region | 51961 | 52323 | regulatory region of traR dependent quorum sensing regulon - containing 2 tra-boxes (see LI AND FARRAND JOURNAL OF BACTERIOLOGY, January 2000, p. 179-188) |
| o-repA | 52324 | 53541 | Rep-A gene from pTiC58 replicon (LI AND FARRAND JOURNAL OF BACTERIOLOGY, January 2000, p. 179 . . . 188) |
| rr-repB | 53771 | 54781 | rep-B gene from pTiC58 replicon (LI AND FARRAND JOURNAL OF BACTERIOLOGY, January 2000, p. 179 . . . 188) |
| o-repC | 54996 | 56315 | rep-C gene from pTiC58 replicon (LI AND FARRAND JOURNAL OF BACTERIOLOGY, January 2000, p. 179 . . . 188) |
| mf-y4cG | 56794 | 56324 | fragment of DNA invertase homolog; similar to *Rhizobium* sp. NGR234 pNGR234a Y4CG |
| tr-Tn5 | 58834 | 57273 | Transposon Tn5 sequence |
| o-oriT | 59130 | 59298 | oriT from pRK310 genbank file |
| b-RB[rtp4394] | 148 | 59918 | Right T-DNA Right border |

TABLE 9

Genetic Elements of plasmid RTP10691-2qcz. Listed are the names of the elements, the position in RTP10691-2qcz (nucleotide number, note: start position was larger than stop position for elements encoded by the complementary strand of RTP10691-2qcz), the function and source of the element. The T-DNA integrated into the plant genome during the transformation process was flanked by a right border (nucleotides 60923 to 148 of RTP10691-2qcz and a left border (nucleotides 44858 to 44723 of RTP10691-2qcz). Elements outside of that region (=vector backbone) are required for cloning and stable maintenance in *E. coli* and/or agrobacteria.

| Genetic Elements of plasmid RTP10691-2qcz | From | To | Description, Function and Source of Element |
|---|---|---|---|
| p-VfUSP_684 bp[LLL894] | 329 | 1012 | Promoter from UNKNOWN SEED PROTEIN gene USP (accession: X56240) from *Vicia faba* |
| i-Atss18_252[LJK36] | 1013 | 1264 | i-Atss18_252 bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064 bp) | 2448 | 3511 | Promoter from CONLININ gene from *Linum usitatissimum* |
| i-Atss14_377 bp[LJK32] | 3512 | 3888 | i-Atss14_377 bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192 bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING RELATED-PROTEIN gene from *Vicia faba* |
| i-Atss2_455 bp[LJK20] | 7338 | 7792 | i-Atss2_455 bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from *Ostreococcus tauri* |
| t-StCATHD-pA | 9200 | 9434 | Terminator from CATHEPSIS D INHIBITOR gene [CATHD] from *Solanum tuberosum* [Potato] |
| p-LuPXR 1727 bp[LLL823] | 9513 | 11239 | Promoter from PEROXIREDOXIN LIKE protein gene PXR from *Linum usitatissimum* |
| i-Atss1_847 bp[LJK19] | 11240 | 12086 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d6Elo(Tp_GA2) | 12100 | 12918 | Delta-6 ELONGASE from *Thalassiosira pseudonana* |
| t-AtPXR 400 bp[LLL823] | 12974 | 13373 | Terminator from PEROXIREDOXIN LIKE protein gene PXR (At1g48130) from *Arabidopsis thaliana* |
| p-Napin A/B | 13543 | 14206 | Promoter from napA/B gene (napin, seed storage protein) from *Brassica napus* |
| i-Atss14_377 bp[LJK32] | 14207 | 14583 | i-Atss14_377 bp[LJK32] functional intron region; intron with partial 5'UTR, *Arabidopsis thaliana*, Locus At5g63190, +166 to +542 bp (numbering relative to start of |

TABLE 9-continued

Genetic Elements of plasmid RTP10691-2qcz. Listed are the names of the elements, the position in RTP10691-2qcz (nucleotide number, note: start position was larger than stop position for elements encoded by the complementary strand of RTP10691-2qcz), the function and source of the element. The T-DNA integrated into the plant genome during the transformation process was flanked by a right border (nucleotides 60923 to 148 of RTP10691-2qcz and a left border (nucleotides 44858 to 44723 of RTP10691-2qcz). Elements outside of that region (=vector backbone) are required for cloning and stable maintenance in *E. coli* and/or agrobacteria.

| Genetic Elements of plasmid RTP10691-2qcz | From | To | Description, Function and Source of Element |
|---|---|---|---|
| | | | transcription) (+201 to +542 bp 5'UTR-Intron only) |
| c-d12Des(Ps_GA2) | 14590 | 15786 | Delta-12 DESATURASE from *Phythophthora sojae* |
| t-E9 | 15805 | 16362 | Terminator from Small Subunit of RuBisCo rbcS gene (E9) from *Pisum sativum* |
| p-LuPXR 1727 bp[LLL823] | 16462 | 18188 | Promoter from PEROXIREDOXIN LIKE protein gene PXR from *Linum usitatissimum* |
| i-Atss15_758 bp[LJK33] | 18189 | 18946 | i-Atss15_758 bp[LJK33] functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir_GA) | 18962 | 20053 | Omega-3 DESATURASE from *Pythium irregulare* |
| t-AtPXR 400 bp[LLL823] | 20110 | 20509 | Terminator from PEROXIREDOXIN LIKE protein gene PXR (At1g48130) from *Arabidopsis thaliana* |
| p-BnSETL-v1[1234 bp] | 20645 | 21878 | SETL-v1 *Brassica napus* promoter |
| c-d5Des(Tc_GA2) | 21881 | 23200 | Delta-5 DESATURASE from *Thraustochytrium* sp. ATCC21685 |
| t-BnSETL | 23222 | 23835 | SETL-v1 *Brassica napus* terminator |
| p-BnFae1 | 24029 | 25458 | Promoter from Beta-KETOACYL-CoA SYNTHASE (FAE1.1) gene from *Brassica napus* |
| i-Atss1_847 bp[LJK19] | 25459 | 26302 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| delTTT | 25612 | 25612 | Three T deleted compared to original i-Atss1_847 bp[LJK19] |
| c-d5Elo(Ot_GA3) | 26310 | 27212 | Delta-5 ELONGASE from *Ostreococcus tauri* |
| t-bnFae1 | 27229 | 27628 | Terminator from FATTY ACID ELONGASE (FAE1, At4g34520) gene of *Arabidopsis thaliana* |
| p-ARC5_perm1 | 27781 | 28931 | Promoter derived from a promoter from ARCILINE 5 gene from *Phaseolus vulgaris* |
| c-d4Des(Tc_GA3) | 28942 | 30501 | Delta-4 DESATURASE from *Thraustochytrium* sp. |
| t-pvarc | 30515 | 31114 | Terminator of ARC5 gene from *Phaseolus vulgaris* |
| p-VfUSP_684 bp[LLL894] | 31193 | 31876 | Promoter from UNKNOWN SEED PROTEIN gene USP (accession: X56240) from *Vicia faba* |
| i-Atss18_252[LJK36] | 31877 | 32128 | i-Atss18_252 bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-o3Des(Pi_GA2) | 32139 | 33224 | Omega-3-DESATURASE from *Phythophthora infestans* |
| t-CaMV35S | 33233 | 33448 | Terminator CaMV35S from 35S gene from Cauliflower mosaic virus |

TABLE 9-continued

Genetic Elements of plasmid RTP10691-2qcz. Listed are the names of the elements, the position in RTP10691-2qcz (nucleotide number, note: start position was larger than stop position for elements encoded by the complementary strand of RTP10691-2qcz), the function and source of the element. The T-DNA integrated into the plant genome during the transformation process was flanked by a right border (nucleotides 60923 to 148 of RTP10691-2qcz and a left border (nucleotides 44858 to 44723 of RTP10691-2qcz). Elements outside of that region (=vector backbone) are required for cloning and stable maintenance in *E. coli* and/or agrobacteria.

| Genetic Elements of plasmid RTP10691-2qcz | From | To | Description, Function and Source of Element |
|---|---|---|---|
| p-BnFae1 | 33642 | 35071 | Promoter from Beta-KETOACYL-CoA SYNTHASE (FAE1.1) gene from *Brassica napus* |
| i-Atss1_847 bp[LJK19] | 35072 | 35918 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d4Des(Pl_GA)2 | 35926 | 37263 | Delta-4 DESATURASE from *Pavlova lutheri* |
| t-bnFae1 | 37280 | 37679 | Terminator from FATTY ACID ELONGASE (FAE1, At4g34520) gene of *Arabidopsis thaliana* |
| p-BnSETL-v1[1234 bp] | 37772 | 39005 | SETL-v1 *Brassica napus* promoter |
| c-o3Des(Pir_GA) | 39008 | 40099 | Omega-3 DESATURASE from *Pythium irregulare* |
| t-BnSETL | 40121 | 40734 | SETL-v1 *Brassica napus* terminator |
| P-YPC105906_PcUbi4-2[long] | 40858 | 41834 | MTX Parsley UBI4-2 promoter with internal intron |
| c-AtAHASL_A122T_S653N[minusRES] | 41842 | 43854 | ACETOHYDROXYACID SYNTHASE LARGE SUBUNIT gene/CDS from *Arabidopsis* with S653N (csr1-2) mutation and A122T SDM mutation minus restriction sites |
| t-AtAHAS-3'UTR[rtp4820] | 43855 | 44634 | *Arabidopsis* (dicot) AtAHASL 3' Un-translated Region [trimmed] terminator for ACETOHYDROXYACID SYNTHASE gene |
| b-LLB | 44858 | 44723 | Left T-DNA Left border from pTi15955 [Genbank #AF242881] |
| c-KanR_Tn903 | 46805 | 45990 | Kanamycin Resistance selection gene/CDS |
| p-Kan[lm500] | 46926 | 46806 | Promoter for Kanamycin resistance gene |
| o-ori-2 | 48079 | 48295 | ori-2 origin of replication |
| c-repE | 48389 | 49144 | repE gene/CDS |
| c-sopA | 49723 | 50898 | sapA gene/CDS |
| c-sopB | 50898 | 51869 | sopB gene/CDS |
| c-sopC/incD | 51942 | 52415 | incD/sopC partial gene/CDS |
| c-traI | 52918 | 52977 | traI gene/CDS |
| mf-traI - repA intergenic region | 52966 | 53328 | regulatory region of traR dependent quorum sensing regulon - containing 2 tra-boxes (see LI AND FARRAND JOURNAL OF BACTERIOLOGY, January 2000, p. 179-188) |
| o-repA | 53329 | 54546 | Rep-A gene from pTiC58 replicon (LI AND FARRAND JOURNAL OF BACTERIOLOGY, January 2000, p. 179 . . . 188) |
| rr-repB | 54776 | 55786 | rep-B gene from pTiC58 replicon (LI AND FARRAND JOURNAL OF BACTERIOLOGY, January 2000, p. 179 . . . 188) |
| o-repC | 56001 | 57320 | rep-C gene from pTiC58 replicon (LI AND FARRAND JOURNAL OF BACTERIOLOGY, January 2000, p. 179 . . . 188) |
| mf-y4cG | 57799 | 57329 | fragment of DNA invertase homolog; similar to *Rhizobium* sp. NGR234 pNGR234a Y4CG |

TABLE 9-continued

Genetic Elements of plasmid RTP10691-2qcz. Listed are the names of the elements, the position in RTP10691-2qcz (nucleotide number, note: start position was larger than stop position for elements encoded by the complementary strand of RTP10691-2qcz), the function and source of the element. The T-DNA integrated into the plant genome during the transformation process was flanked by a right border (nucleotides 60923 to 148 of RTP10691-2qcz and a left border (nucleotides 44858 to 44723 of RTP10691-2qcz). Elements outside of that region (=vector backbone) are required for cloning and stable maintenance in *E. coli* and/or agrobacteria.

| Genetic Elements of plasmid RTP10691-2qcz | From | To | Description, Function and Source of Element |
| --- | --- | --- | --- |
| tr-Tn5 | 59839 | 58278 | Transposon Tn5 sequence |
| o-oriT | 60135 | 60303 | oriT from pRK310 genbank file |
| b-RB[rtp4394] | 60923 | 148 | Right T-DNA Right border |

TABLE 10

Genetic Elements of plasmid VC-LTM595-1qcz rc. Listed are the names of the elements, the position in VC-LTM595-1qcz rc (nucleotide number, note: start position was larger than stop position for elements encoded by the complementary strand of VC-LTM595-1qcz rc), the function and source of the element. The T-DNA integrated into the plant genome during the transformation process was flanked by a right border (nucleotides 60913 to 148 of VC-LTM595-1qcz rc) and a left border (nucleotides 44848 to 44713 of VC-LTM595-1qcz rc). Elements outside of that region (=vector backbone) are required for cloning and stable maintenance in *E. coli* and/or agrobacteria.

| Genetic Elements of plasmid VC-LTM595-1qcz rc | From | To | Description, Function and Source of Element |
| --- | --- | --- | --- |
| p-VfUSP_684 bp[LLL894] | 329 | 1012 | Promoter from UNKNOWN SEED PROTEIN gene USP (accession: X56240) from *Vicia faba* |
| i-Atss18_252[LJK36] | 1013 | 1264 | i-Atss18_252 bp functional intron region; intron with partial 5'UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064 bp) | 2448 | 3511 | Promoter from CONLININ gene from *Linum usitatissimum* |
| i-Atss14_377 bp[LJK32] | 3512 | 3888 | i-Atss14_377 bp[LJK32] functional intron region; intron with partial 5' UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192 bp[LED12] | 5212 | 5403 | Terminator from OCTOPINE SYNTHASE gene OCS from *Agrobacterium tumefaciens* |
| p-SBP | 5539 | 7337 | Promoter from a SUCROSE-BINDING RELATED-PROTEIN gene from *Vicia faba* |
| i-Atss2_455 bp[LJK20] | 7338 | 7792 | i-Atss2_455 bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from *Ostreococcus tauri* |
| t-StCATHD-pA | 9200 | 9434 | Terminator from CATHEPSIS D INHIBITOR gene [CATHD] from *Solanum tuberosum* [Potato] |
| p-LuPXR 1727 bp[LLL823] | 9513 | 11239 | Promoter from PEROXIREDOXIN LIKE protein gene PXR from *Linum usitatissimum* |
| i-Atss1_847 bp[LJK19] | 11240 | 12086 | i-Atss1_847 bp functional intron region; intron with partial 5' UTR, |

TABLE 10-continued

Genetic Elements of plasmid VC-LTM595-1qcz rc. Listed are the names of the elements, the position in VC-LTM595-1qcz rc (nucleotide number, note: start position was larger than stop position for elements encoded by the complementary strand of VC-LTM595-1qcz rc), the function and source of the element. The T-DNA integrated into the plant genome during the transformation process was flanked by a right border (nucleotides 60913 to 148 of VC-LTM595-1qcz rc) and a left border (nucleotides 44848 to 44713 of VC-LTM595-1qcz rc). Elements outside of that region (=vector backbone) are required for cloning and stable maintenance in *E. coli* and/or agrobacteria.

| Genetic Elements of plasmid VC-LTM595-1qcz rc | From | To | Description, Function and Source of Element |
|---|---|---|---|
| | | | *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d6Elo(Tp_GA2) | 12100 | 12918 | Delta-6 ELONGASE from *Thalassiosira pseudonana* |
| t-AtPXR 400 bp[LLL823] | 12974 | 13373 | Terminator from PEROXIREDOXIN LIKE protein gene PXR (At1g48130) from *Arabidopsis thaliana* |
| p-Napin A/B | 13543 | 14206 | Promoter from napA/B gene (napin, seed storage protein) from *Brassica napus* |
| i-Atss14_377 bp[LJK32] | 14207 | 14583 | i-Atss14_377 bp[LJK32] functional intron region; intron with partial 5' UTR, *Arabidopsis thaliana*, Locus At5g63190, +166 to +542 bp (numbering relative to start of transcription) (+201 to +542 bp 5'UTR-Intron only) |
| c-d12Des(Ps_GA2) | 14590 | 15786 | Delta-12 DESATURASE from *Phythophthora sojae* |
| t-E9 | 15805 | 16362 | Terminator from Small Subunit of RuBisCo rbcS gene (E9) from *Pisum sativum* |
| p-LuPXR 1727 bp[LLL823] | 16455 | 18181 | Promoter from PEROXIREDOXIN LIKE protein gene PXR from *Linum usitatissimum* |
| i-Atss15_758 bp[LJK33] | 18182 | 18939 | i-Atss15_758 bp[LJK33] functional intron region; intron with partial 5' UTR, *Arabidopsis thaliana*, Locus At2g27040, +93 bp to +850 bp (numbering relative to start of transcription) (+128 to +847 bp 5'UTR-Intron only) |
| c-o3Des(Pir_GA) | 18955 | 20046 | Omega-3 DESATURASE from *Pythium irregulare* |
| t-AtPXR 400 bp[LLL823] | 20103 | 20502 | Terminator from PEROXIREDOXIN LIKE protein gene PXR (At1g48130) from *Arabidopsis thaliana* |
| p-BnSETL-v1[1234 bp] | 20638 | 21871 | SETL-v1 *Brassica napus* promoter |
| c-d5Des(Tc_GA2) | 21874 | 23193 | Delta-5 DESATURASE from *Thraustochytrium* sp. ATCC21685 |
| t-BnSETL | 23215 | 23828 | SETL-v1 *Brassica napus* terminator |
| p-BnFae1 | 24022 | 25451 | Promoter from Beta-KETOACYL-CoA SYNTHASE (FAE1.1) gene from *Brassica napus* |
| i-Atss1_847 bp[LJK19] | 25452 | 26298 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 26306 | 27208 | Delta-5 ELONGASE from *Ostreococcus tauri* |
| t-bnFae1 | 27225 | 27624 | Terminator from FATTY ACID ELONGASE (FAE1, At4g34520) gene of *Arabidopsis thaliana* |
| p-ARC5_perm1 | 27771 | 28921 | Promoter derived from a promoter from ARCILINE 5 gene from *Phaseolus vulgaris* |

TABLE 10-continued

Genetic Elements of plasmid VC-LTM595-1qcz rc. Listed are the names of the elements, the position in VC-LTM595-1qcz rc (nucleotide number, note: start position was larger than stop position for elements encoded by the complementary strand of VC-LTM595-1qcz rc), the function and source of the element. The T-DNA integrated into the plant genome during the transformation process was flanked by a right border (nucleotides 60913 to 148 of VC-LTM595-1qcz rc) and a left border (nucleotides 44848 to 44713 of VC-LTM595-1qcz rc). Elements outside of that region (=vector backbone) are required for cloning and stable maintenance in *E. coli* and/or agrobacteria.

| Genetic Elements of plasmid VC-LTM595-1qcz rc | From | To | Description, Function and Source of Element |
|---|---|---|---|
| c-d4Des(Tc_GA3) | 28932 | 30491 | Delta-4 DESATURASE from *Thraustochytrium* sp. |
| t-pvarc | 30505 | 31104 | Terminator of ARC5 gene from *Phaseolus vulgaris* |
| p-VfUSP_684 bp[LLL894] | 31183 | 31866 | Promoter from UNKNOWN SEED PROTEIN gene USP (accession: X56240) from *Vicia faba* |
| i-Atss18_252[LJK36] | 31867 | 32118 | i-Atss18_252 bp functional intron region; intron with partial 5' UTR, *Arabidopsis thaliana*, Locus At1g01170, +37 to +288 bp (numbering relative to start of transcription) (+72 to +282 bp 5'UTR-Intron only) |
| c-o3Des(Pi_GA2) | 32129 | 33214 | Omega-3-DESATURASE from *Phythophthora infestans* |
| t-CaMV35S | 33223 | 33438 | Terminator CaMV35S from 35S gene from Cauliflower mosaic virus |
| p-BnFae1 | 33632 | 35061 | Promoter from Beta-KETOACYL-CoA SYNTHASE (FAE1.1) gene from *Brassica napus* |
| i-Atss1_847 bp[LJK19] | 35062 | 35908 | i-Atss1_847 bp functional intron region; intron with partial 5'UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d4Des(PI_GA)2 | 35916 | 37253 | Delta-4 DESATURASE from *Pavlova lutheri* |
| t-bnFae1 | 37270 | 37669 | Terminator from FATTY ACID ELONGASE (FAE1, At4g34520) gene of *Arabidopsis thaliana* |
| p-BnSETL-v1[1234 bp] | 37762 | 38995 | SETL-v1 *Brassica napus* promoter |
| c-o3Des(Pir_GA) | 38998 | 40089 | Omega-3 DESATURASE from *Pythium irregulare* |
| t-BnSETL | 40111 | 40724 | SETL-v1 *Brassica napus* terminator |
| p-YPC105906_PcUbi4-2[long] | 40848 | 41824 | MTX Parsley (*Petroselinum crispum*) UBI4-2 promoter with internal intron |
| c-AtAHASL_A122T_S653N[minusRES] | 41832 | 43844 | ACETOHYDROXYACID SYNTHASE LARGE-SUBUNIT gene/CDS from *Arabidopsis* with S653N (csr1-2) mutation and A122T SDM mutation minus restriction sites |
| t-AtAHAS-3'UTR[rtp4820] | 43845 | 44624 | *Arabidopsis* (dicot) AtAHASL 3' Un-uranslated Region [trimmed] terminator for ACETOHYDROXYACID SYNTHASE gene |
| b-LLB | 44848 | 44713 | Left T-DNA Left border from pTi15955 [Genbank #AF242881] |
| c-KanR_Tn903 | 46795 | 45980 | Kanamycin Resistance selection gene/CDS |
| p-Kan[lm500] | 46916 | 46796 | Promoter for Kanamycin resistance gene |
| o-ori-2 | 48069 | 48285 | ori-2 origin of replication |
| c-repE | 48379 | 49134 | repE gene/CDS |
| c-sopA | 49713 | 50888 | sapA gene/CDS |
| c-sopB | 50888 | 51859 | sopB gene/CDS |
| c-sopC/incD | 51932 | 52405 | incD/sopC partial gene/CDS |
| c-tral | 52908 | 52967 | tral gene/CDS |
| mf-tral - repA intergenic region | 52956 | 53318 | regulatory region of traR dependent quorum sensing regulon - containing 2 tra-boxes (see LI AND |

TABLE 10-continued

Genetic Elements of plasmid VC-LTM595-1qcz rc. Listed are the names of the elements, the position in VC-LTM595-1qcz rc (nucleotide number, note: start position was larger than stop position for elements encoded by the complementary strand of VC-LTM595-1qcz rc), the function and source of the element. The T-DNA integrated into the plant genome during the transformation process was flanked by a right border (nucleotides 60913 to 148 of VC-LTM595-1qcz rc) and a left border (nucleotides 44848 to 44713 of VC-LTM595-1qcz rc). Elements outside of that region (=vector backbone) are required for cloning and stable maintenance in *E. coli* and/or agrobacteria.

| Genetic Elements of plasmid VC-LTM595-1qcz rc | From | To | Description, Function and Source of Element |
|---|---|---|---|
| o-repA | 53319 | 54536 | FARRAND JOURNAL OF BACTERIOLOGY, January 2000, p. 179-188) Rep-A gene from pTiC58 replicon (LI AND FARRAND JOURNAL OF BACTERIOLOGY, January 2000, p. 179 . . . 188) |
| rr-repB | 54766 | 55776 | rep-B gene from pTiC58 replicon (LI AND FARRAND JOURNAL OF BACTERIOLOGY, January 2000, p. 179 . . . 188) |
| o-repC | 55991 | 57310 | rep-C gene from pTiC58 replicon (LI AND FARRAND JOURNAL OF BACTERIOLOGY, January 2000, p. 179 . . . 188) |
| mf-y4cG | 57789 | 57319 | fragment of DNA invertase homolog; similar to *Rhizobium* sp. NGR234 pNGR234a Y4CG |
| tr-Tn5 | 59829 | 58268 | Transposon Tn5 sequence |
| o-oriT | 60125 | 60293 | oriT from pRK310 genbank file |
| b-RB[rtp4394] | 148 | 60913 | Right T-DNA Right border |

TABLE 11

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to 43695 of VC-LTM593-1qcz rc). Elements outside of that region (=vector backbone) are required for cloning and stable maintenance in *E. coli* and/or agrobacteria.

| Genetic Elements of plasmid VC-LTM593-1qcz rc | From | To | Description, Function and Source of Element |
|---|---|---|---|
| p-VfUSP_684 bp[LLL894] | 329 | 1012 | Promoter from UNKNOWN SEED PROTEIN gene USP (accession: X56240) from *Vicia faba* |
| i-Atss18_252[LJK36] | 1013 | 1264 | i-Atss18_252 bp functional intron region; intron with partial 5' UTR, *Arabidopsis thaliana*, Locus At1g01170, +37 to +288 bp (numbering relative to start of transcription) (+72 to +282 bp 5'UTR-Intron only) |
| c-d6Elo(Pp_GA2) | 1267 | 2139 | Delta-6 ELONGASE from *Physcomitrella patens* |
| t-CaMV35S | 2140 | 2355 | Terminator CaMV35S from 35S gene from Cauliflower mosaic virus |
| p-LuCnl(1064 bp) | 2448 | 3511 | Promoter from CONLININ gene from *Linum usitatissimum* |
| i-Atss14_377 bp[LJK32] | 3512 | 3888 | i-Atss14_377 bp[LJK32] functional intron region; intron with partial 5'UTR, *Arabidopsis thaliana*, Locus At5g63190, +166 to +542 bp (numbering relative to start of transcription) (+201 to +542 bp 5'UTR-Intron only) |
| c-d5Des(Tc_GA2) | 3892 | 5211 | Delta-5 DESATURASE from *Thraustochytrium* sp. ATCC21685 |
| t-AgrOCS 192 bp[LED12] | 5212 | 5403 | Terminator from OCTOPINE SYNTHASE gene OCS from *Agrobacterium tumefaciens* |

TABLE 11-continued

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to 43695 of VC-LTM593-1qcz rc). Elements outside of that region (=vector backbone) are required for cloning and stable maintenance in E. coli and/or agrobacteria.

| Genetic Elements of plasmid VC-LTM593-1qcz rc | From | To | Description, Function and Source of Element |
|---|---|---|---|
| p-SBP | 5539 | 7337 | Promoter from a SUCROSE-BINDING PROTEIN-RELATED gene from Vicia faba |
| i-Atss2_455 bp[LJK20] | 7338 | 7792 | i-Atss2_455 bp functional intron region; intron with partial 5'UTR, Arabidopsis thaliana, Locus At1g65090, +77 to +531 bp (numbering relative to start of transcription) (+113 to +508 bp 5'UTR-Intron only) |
| c-d6Des(Ot_febit) | 7802 | 9172 | Delta-6 DESATURASE from Ostreococcus tauri |
| t-StCATHD-pA | 9200 | 9434 | Terminator from CATHEPSIN D INHIBITOR gene [CATHD] from Solanum tuberosum [Potato] |
| p-LuPXR 1727 bp[LLL823] | 9513 | 11239 | Promoter from PEROXIREDOXIN LIKE protein gene PXR from Linum usitatissimum |
| i-Atss1_846 bp[ltm593] | 11240 | 12085 | i-Atss1_847 bp functional intron region; intron with partial 5' UTR, Arabidopsis thaliana, Locus At1g62290 (aspartyl protease family protein), +1 to +847 bp (numbering relative to start of transcription) (+19 to +841 bp 5'UTR-Intron only); 1 bp at poly T stretch shorter compared to original i-Atss1_847 bp |
| c-d6Elo(Tp_GA2) | 12099 | 12917 | Delta-6 ELONGASE from Thalassiosira pseudonana |
| t-AtPXR 400 bp[LLL823] | 12973 | 13372 | Terminator from peroxiredoxin like protein gene PXR (At1 g48130) from Arabidopsis thaliana |
| p-Napin A/B | 13542 | 14205 | Promoter from napA/B gene (napin, seed storage protein) from Brassica napus |
| i-Atss14_377 bp[LJK32] | 14206 | 14582 | i-Atss14_377 bp[LJK32] functional intron region; intron with partial 5' UTR, Arabidopsis thaliana, Locus At5g63190, +166 to +542 bp (numbering relative to start of transcription) (+201 to +542 bp 5'UTR-Intron only) |
| c-d12Des(Ps_GA2) | 14589 | 15785 | Delta-12 DESATURASE from Phythophthora sojae |
| t-E9 | 15804 | 16361 | Terminator from Small Subunit of RuBisCo rbcS gene (E9) from Pisum sativum |
| p-BnSETL-v1[1234 bp] | 16454 | 17687 | SETL-v1 Brassica napus promoter |
| c-o3Des(Pir_GA) | 17690 | 18781 | Omega-3 DESATURASE from Pythium irregulare |
| t-BnSETL | 18803 | 19416 | SETL-v1 Brassica napus terminator |
| p-VfUSP_684 bp[LLL894] | 19495 | 20178 | Promoter from UNKNOWN SEED PROTEIN gene USP (accession: X56240) from Vicia faba |
| i-Atss18_252[LJK36] | 20179 | 20430 | i-Atss18_252 bp functional intron region; intron with partial 5' UTR, Arabidopsis thaliana, Locus At1g01170, +37 to +288 bp (numbering relative to start of transcription) (+72 to +282 bp 5'UTR-Intron only) |
| c-o3Des(Pi_GA2) | 20441 | 21526 | Omega-3-DESATURASE from Phythophthora infestans |
| t-CaMV35S | 21535 | 21750 | Terminator CaMV35S from 35S gene from Cauliflower mosaic virus |

TABLE 11-continued

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to 43695 of VC-LTM593-1qcz rc). Elements outside of that region (=vector backbone) are required for cloning and stable maintenance in *E. coli* and/or agrobacteria.

| Genetic Elements of plasmid VC-LTM593-1qcz rc | From | To | Description, Function and Source of Element |
|---|---|---|---|
| p-BnSETL-v1[1234 bp] | 21886 | 23119 | SETL-v1 *Brassica napus* promoter |
| c-d5Des(Tc_GA2) | 23122 | 24441 | Delta-5 DESATURASE from *Thraustochytrium* sp. ATCC21685 |
| t-BnSETL | 24463 | 25076 | SETL-v1 *Brassica napus* terminator |
| p-ARC5_perm1 | 25223 | 26373 | Promoter derived from a promoter from ARCILINE 5 gene from *Phaseolus vulgaris* |
| c-d4Des(Tc_GA3) | 26384 | 27943 | Delta-4 DESATURASE from *Thraustochytrium* sp. |
| t-pvarc | 27957 | 28556 | Terminator of ARC5 gene from *Phaseolus vulgaris* |
| p-LuPXR 1727 bp[LLL823] | 28649 | 30375 | Promoter from PEROXIREDOXIN LIKE protein gene PXR from *Linum usitatissimum* |
| i-Atss15_758 bp[LJK33] | 30376 | 31133 | i-Atss15_758 bp[LJK33] functional intron region; intron with partial 5'UTR, *Arabidopsis thaliana*, Locus At2g27040, +93 bp to +850 bp (numbering relative to start of transcription) (+128 to +847 bp 5'UTR-Intron only) |
| c-o3Des(Pir_GA) | 31149 | 32240 | Omega-3 DESATURASE from *Pythium irregulare* |
| t-AtPXR 400 bp[LLL823] | 32297 | 32696 | Terminator from PEROXIREDOXIN LIKE protein gene PXR (At1g48130) from *Arabidopsis thaliana* |
| p-LuCnl(1064 bp) | 32832 | 33895 | Promoter from CONLININ gene from *Linum usitatissimum* |
| i-Atss2_455 bp[LJK20] | 33896 | 34350 | i-Atss2_455 bp functional intron region; intron with partial 5'UTR, *Arabidopsis thaliana*, Locus At1g65090, +77 to +531 bp (numbering relative to start of transcription) (+113 to +508 bp 5'UTR-Intron only) |
| c-d4Des(Pl_GA)2 | 34360 | 35697 | Delta-4 DESATURASE from *Pavlova lutheri* |
| t-AgrOCS 192 bp[LED12] | 35719 | 35910 | Terminator from OCTOPINE SYNTHASE gene OCS from *Agrobacterium tumefaciens* |
| p-BnFae1 | 36104 | 37533 | Promoter from Beta-KETOACYL-CoA SYNTHASE (FAE1.1) gene from *Brassica napus* |
| i-Atss1_847 bp[LJK19] | 37534 | 38380 | i-Atss1_847 bp functional intron region; intron with partial 5' UTR, *Arabidopsis thaliana*, Locus At1g62290 (aspartyl protease family protein), +1 to +847 bp (numbering relative to start of transcription) (+19 to +841 bp 5'UTR-Intron only); from QC1153-1/RTP6393. |
| c-d5Elo(Ot_GA3) | 38388 | 39290 | Delta-5 ELONGASE from *Ostreococcus tauri* |
| t-bnFae1 | 39307 | 39706 | Terminator from FATTY ACID ELONGASE (FAE1, At4g34520) gene of *Arabidopsis thaliana* |
| P-YPC105906_PcUbi4-2[long] | 39830 | 40806 | MTX Parsley UBI4-2 promoter with internal intron |
| c-AtAHASL_A122T_S653N[minusRES] | 40814 | 42826 | ACETOHYDROXYACID SYNTHASE LARGE-SUBUNIT gene/CDS from *Arabidopsis* with S653N (csr1-2) mutation and A122T SDM mutation minus restriction sites |
| t-AtAHAS-3'UTR[rtp4820] | 42827 | 43606 | *Arabidopsis* (dicot) AtAHASL 3' Un-translated Region [trimmed] |

TABLE 11-continued

Genetic Elements of plasmid VC-LTM593-1qcz rc. Listed are the names of the elements, the position in VC-LTM593-1qcz rc (nucleotide number, note: start position was larger than stop position for elements encoded by the complementary strand of VC-LTM593-1qcz rc), the function and source of the element. The T-DNA integrated into the plant genome during the transformation process was flanked by a right border (nucleotides 59895 to 148 of VC-LTM593-1qcz rc) and a left border (nucleotides 43830 to 43695 of VC-LTM593-1qcz rc). Elements outside of that region (=vector backbone) are required for cloning and stable maintenance in E. coli and/or agrobacteria.

| Genetic Elements of plasmid VC-LTM593-1qcz rc | From | To | Description, Function and Source of Element |
|---|---|---|---|
| | | | terminator for ACETOHYDROXYACID SYNTHASE gene |
| b-LLB | 43830 | 43695 | Left T-DNA Left border from pTi15955 [Genbank #AF242881] |
| c-KanR_Tn903 | 45777 | 44962 | Kanamycin Resistance selection gene/CDS |
| p-Kan[lm500] | 45898 | 45778 | Promoter for Kanamycin resistance gene |
| o-ori-2 | 47051 | 47267 | ori-2 origin of replication |
| c-repE | 47361 | 48116 | repE gene/CDS |
| c-sopA | 48695 | 49870 | sapA gene/CDS |
| c-sopB | 49870 | 50841 | sopB gene/CDS |
| c-sopC/incD | 50914 | 51387 | incD/sopC partial gene/CDS |
| c-tral | 51890 | 51949 | tral gene/CDS |
| mf-tral - repA intergenic region | 51938 | 52300 | regulatory region of traR dependent quorum sensing regulon - containing 2 tra-boxes (see LI AND FARRAN DJOURNAL OF BACTERIOLOGY, January 2000, p. 179-188) |
| o-repA | 52301 | 53518 | Rep-A gene from pTiC58 replicon (LI AND FARRAND JOURNAL OF BACTERIOLOGY, January 2000, p. 179 . . . 188) |
| rr-repB | 53748 | 54758 | rep-B gene from pTiC58 replicon (LI AND FARRAND JOURNAL OF BACTERIOLOGY, January 2000, p. 179 . . . 188) |
| o-repC | 54973 | 56292 | rep-Cgene from pTiC58 replicon (LI AND FARRAND JOURNAL OF BACTERIOLOGY, January 2000, p. 179 . . . 188) |
| mf-y4cG | 56771 | 56301 | fragment of DNA invertase homolog; similar to Rhizobium sp. NGR234 pNGR234a Y4CG |
| tr-Tn5 | 58811 | 57250 | Transposon Tn5 sequence |
| o-oriT | 59107 | 59275 | oriT from pRK310 genbank file |
| b-RB[rtp4394] | 148 | 59895 | Right T-DNA Right border |

Figure 39:
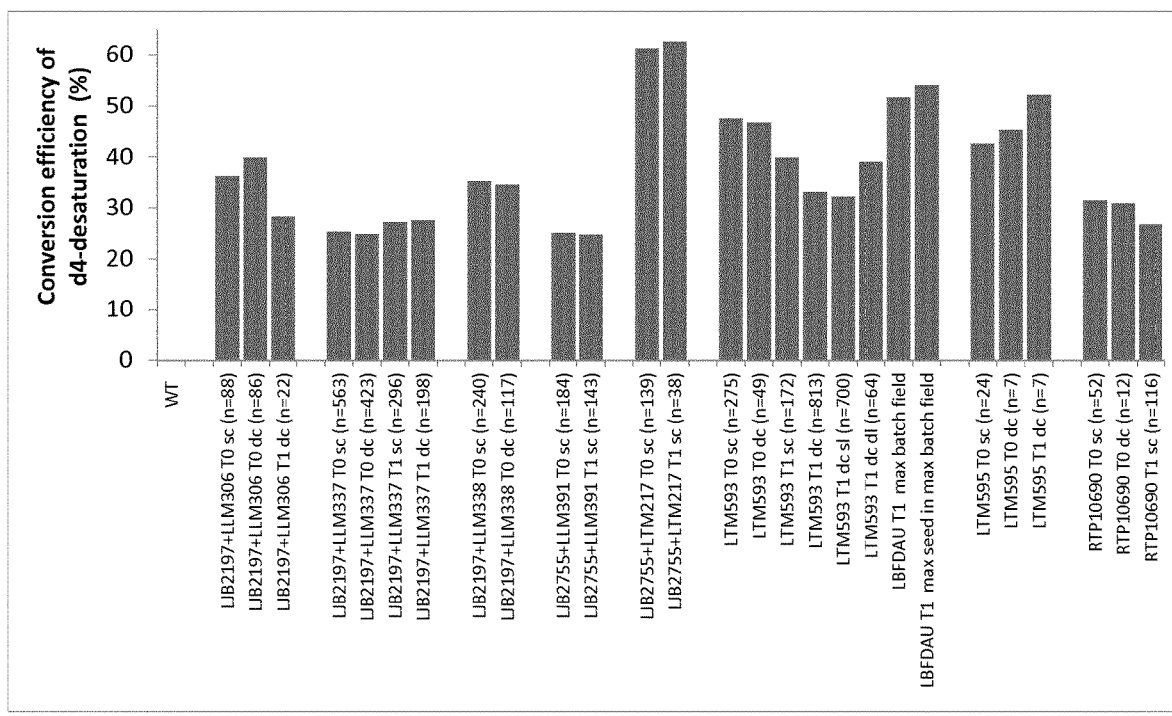
FIG. 39: Conversion efficiencies of delta-4-desaturation in seed of transgenic *Brassica napus* and in *Brassica napus* wildtype seeds. See caption in FIG. 32 for further details.

Table 13 compares the order of the gene expression cassettes among all the different constructs and the construct combinations, using short terms for these expression cassettes, see Table 12 for definitions. The data in Examples 10 to 19 demonstrate significant differences among the different construct or construct combinations in terms of the PUFA profile measured in transgenic seed. The differences between constructs and the construct combinations were evident even when eliminating all other sources that affect PUFA levels (e.g. different environments, plant-to-plant variability, seed oil content, T-DNA copy number). For example VC-RTP10690-1qcz_F and VC-LMT593-1qcz rc are isogenic, i.e. the two constructs contained exactly the same gene expression cassettes. Because of the similarity between RTP10690-1qcz_F and VC-LMT593-1qcz one would expect exactly the same pathway step conversion efficiencies e.g. when comparing the average conversion efficiencies of all single copy events. However, FIG. 39 shows that VC-RTP10690-1qcz_F had a Delta-4 DESATURASE conversion efficiency of 32%, (average of T1 seeds of 52 single copy T0 events), whereas VC-LMT593-1qcz rc had a Delta-4 DESATURASE conversion efficiency of 47% (average of T1 seeds of 241 single copy T0 events). This was not expected, and can be explained by transcript levels, which in turn determine protein levels. The transcript levels are affected by the genetic elements that flank the Delta-4 DESATURASE cassettes in VC-LMT593-1qcz rc. The observations between the two constructs is an unexpected finding and indicates that not only the genome but also the T-DNA itself impacts the Delta-4 DESATURASE conversion efficiency, that was dependent on "gene dosage" as described in Example 19. Furthermore, the data in Example 10 to 19 demonstrate that it was possible to insulate expression cassettes from such effects. As can be seen in those Examples 10-19 all single copy events were capable of producing almost exactly the same VLC-PUFA levels when eliminating all other sources that affect PUFA levels (e.g. different environments, plant-to-plant variability, seed oil content). This was particularly striking when comparing all the single copy events in Example 18. Comparing the total C20+C22 VLC-PUFA content, which was largely controlled by how much was converted by the delta-12 desaturase and by the delta-6 desaturase, it was striking to observe there was virtually no difference between e.g. the single copy event LANPMZ obtained from the contruct combination VC-LJB2197-1qcz+VC-LLM337-1qcz rc, and all single copy events listed in Example 18. To this end, it is important to note that one side of the T-DNA that encodes either the entire pathway (Example 15 to 18) or at least the first steps of the pathway up to ARA and EPA production (Example 10 to 14) always contains the AHAS gene which confers herbicide tolerance but was not involved in the VLC-PUFA pathway. The other side of the T-DNA encodes either the entire pathway (Example 15 to 18) or at least the first steps of the pathway up to ARA and EPA production (Example 10 to 14) in most cases the Delta-6 ELONGASEfrom Physcomitrallapatens (except in Example 13 and 14). As described in Example 19, the Delta-6 ELONGASE protein encoded by the *Physcomitrella patens* gene works close to maximum conversion efficiency (>90%), thus any increase in delta-6 elongase enzyme levels due to any effect that increases transcript levels will have virtually no effect on the C20 and C22 VLC-PUFA levels. Effectively, the T-DNA determining the total level of VLC-PUFA accumulation are flanked on both sides by genes where expression level differences will have no impact on the VLC-PUFA accumulation. As these two genes were encoded by expression cassettes that were several thousand bp in size, it appears the genes inside the T-DNA were shielded/insulated from any effects the genomic environment could have on the expression level of those genes (e.g. the delta-12-desaturase, compare with Example 19). This effect was consistent with the observation that double copy events differ considerably more in total C20 and C22 VLC-PUFA levels: As in many cases the additional T-DNA insertions are not complete (see Example 10 to 18), resulting in exposure of T-DNA internal genes to the genome. When these genes are susceptible to gene-dosage effects (the conversion efficiency of those genes depends on the amount of transcript and the derived amount of enzyme, compare with Example 19), then in some genomic locations the genomic environment boosted the transcript level.

TABLE 12

Definition of shorthands used for plant expression cassettes of this invention

| Cassette shorthand | Promoter | Intron | Coding sequence | Terminator |
|---|---|---|---|---|
| USP/c-d6Elo(Pp_GA2) | p-VfUSP_684 bp[LLL894] | i-Atss18_252[LJK36] | c-d6Elo(Pp_GA2) | t-CaMV35S |
| PXR/c-o3Des(Pir_GA) | p-LuPXR 1727 bp[LLL823] | i-Atss15_758 bp[LJK33] | c-o3Des(Pir_GA) | t-AtPXR 400 bp[LLL823] |
| Conlinin/c-d5Des(Tc_GA2) | p-LuCnl(1064 bp) | i-Atss14_377[LJK32] | c-d5Des(Tc_GA2) | t-AgrOCS 192 bp[LED12] |
| SBP/c-d6Des(Ot_febit) | p-SBP | i-Atss2_455 bp[LJK20] | c-d6Des(Ot_febit) | t-StCATHD-pA |
| PXR/c-d6Elo(Tp_GA2) | p-LuPXR 1727 bp[LLL823] | i-Atss1_847 bp[LJK19] | c-d6Elo(Tp_GA2) | t-AtPXR 400 bp[LLL823] |
| Fae/c-d6Elo(Tp_GA2) | p-BnFae1 | i-Atss1_847 bp[LJK19] | c-d6Elo(Tp_GA2) | t-bnFae1 |
| Napin/c-d12Des(Ps_GA) | p-Napin A/B | i-Atss14_377[LJK32] | c-d12Des(Ps_GA) | t-E9 |
| USP/c-o3Des(Pi_GA) | p-VfUSP_684 bp[LLL894] | i-Atss18_252[LJK36] | c-o3Des(Pi_GA2) | t-CaMV35S |
| UBI/AHAS | p-PcUbi4-2[long] | part of PcUBI promoter | c-AtAHASL_A122T_S653N | t-AtAHAS-3'/UTR[ac321] |
| Conlinin/d4Des(Eg) | p-LuCnl(1064 bp) | N/A | c-d4Des(Eg_GA) | t-AgrOCS 192 bp[LED12] |
| SBP/d15Des(Ch) | p-VfSBP_perm3 | N/A | c-d15Des(Ch_ERTp_GA) | t-StCATHD-pA |
| Conlinin/c-d4Des(PI_GA)2_var1 | p-LuCnl(1064 bp) | i-Atss2_455 bp[LJK20] | c-d4Des(PI_GA)2 | t-AgrOCS 192 bp[LED12] |
| SETL/c-d5Des(Tc_GA2) | p-BnSETL-v1[1234 bp] | N/A | c-d5Des(Tc_GA2) | t-BnSETL |
| SETL/c-o3Des(Pir_GA) | p-BnSETL-v1[1234 bp] | N/A | c-o3Des(Pir_GA) | t-BnSETL |
| FAE/c-d5Elo(Ot_GA3) | p-BnFAE1 | i-Atss1_847 bp[LJK19] | c-d5Elo(Ot_GA3) | t-bnFAE1 |
| SETL/c-o3Des(Pir_GA) | p-VfSBP_perm3 | N/A | c-o3Des(Pir_GA) | t-StCATHD-pA |
| ARC/c-d4Des(Tc_GA)_var1 | p-ARC5_perm1 | N/A | c-d4Des(Tc_GA) | t-pvarc |
| ARC/c-d4Des(Tc_GA)_var2 | p-ARC5_perm1 | N/A | c-d4Des(Tc_GA3) | t-pvarc |
| Conlinin/c-d4Des(PI_GA)2_var2 | p-LuCnl(1064 bp) | N/A | c-d4Des(PI_GA)2 | t-AgrOCS 192 bp[LED12] |
| FAE/c-d4Des(PI_GA)2 | p-BnFAE1 | i-Atss1_847 bp[LJK19] | c-d4Des(PI_GA)2 | t-bnFAE1 |

TABLE 13

Order and orientation of plant expression cassettes on T-DNAs.
Per column, expression cassettes are abbreviated according to Table 12
and listed from top to bottom in the following way: The top row indicated
the right border of the first T-DNA introduced into the plant genome; the
following proteins are all listed according to sense orientation of transcription,
pointing away from the right border. The end of the first T-DNA was
indicated by 'LB'. In case a second T-DNA was used to transfer all
pathway genes into the plant genome according to example 7 to 11, the right
border of this T-DNA was indicated as 'RB2'. The expression cassettes
of the second T-DNA are listed in the following rows. Empty cells have been
introduced to facilitate comparison of the different constructs.

| VC-LJB2197-1qcz + VC-LLM306-1qcz rc | VC-LJB2197-1qcz + VC-LLM337-1qcz rc | VC-LJB2197-1qcz + VC-LLM338-3qcz rc | VC-LJB2755-2qcz + VC-LLM391-2qcz rc | VC-LJB2755-2qcz + VC-LLM217-1qcz rc | RTP10690-1qcz_F | RTP10691-2qcz | VC-LMT595-1qcz rc | VC-LMT593-1qcz rc |
|---|---|---|---|---|---|---|---|---|
| RB | RB | RB | RB | RB | RB | RB | RB | RB |
| USP/c-d6Elo(Pp_GA2) | USP/c-d6Elo(Pp_GA2) | USP/c-d6Elo(Pp_GA2) | PXR/c-o3Des(Pir_GA) | PXR/c-o3Des(Pir_GA) | USP/c-d6Elo(Pp_GA2) | USP/c-d6Elo(Pp_GA2) | USP/c-d6Elo(Pp_GA2) | USP/c-d6Elo(Pp_GA2) |
| Conlinin/c-d5Des(Tc_GA2) | Conlinin/c-d5Des(Tc_GA2) | Conlinin/c-d5Des(Tc_GA2) | Conlinin/c-d5Des(Tc_GA2) | Conlinin/c-d5Des(Tc_GA2) | Conlinin/c-d5Des(Tc_GA2) | Conlinin/c-d5Des(Tc_GA2) | Conlinin/c-d5Des(Tc_GA2) | Conlinin/c-d5Des(Tc_GA2) |

TABLE 13-continued

Order and orientation of plant expression cassettes on T-DNAs.
Per column, expression cassettes are abbreviated according to Table 12
and listed from top to bottom in the following way: The top row indicated
the right border of the first T-DNA introduced into the plant genome; the
following proteins are all listed according to sense orientation of transcription,
pointing away from the right border. The end of the first T-DNA was
indicated by 'LB'. In case a second T-DNA was used to transfer all
pathway genes into the plant genome according to example 7 to 11, the right
border of this T-DNA was indicated as 'RB2'. The expression cassettes
of the second T-DNA are listed in the following rows. Empty cells have been
introduced to facilitate comparison of the different constructs.

| VC-LJB2197-1qcz + VC-LLM306-1qcz rc | VC-LJB2197-1qcz + VC-LLM337-1qcz rc | VC-LJB2197-1qcz + VC-LLM338-3qcz rc | VC-LJB2755-2qcz + VC-LLM391-2qcz rc | VC-LJB2755-2qcz + VC-LLM217-1qcz rc | RTP10690-1qcz_F | RTP10691-2qcz | VC-LMT595-1qcz rc | VC-LMT593-1qcz rc |
|---|---|---|---|---|---|---|---|---|
| SBP/c-d6Des(Ot_febit) | SBP/c-d6Des(Ot_febit) | SBP/c-d6Des(Ot_febit) | SBP/c-d6Des(Ot_febit) | SBP/c-d6Des(Ot_febit) | SBP/c-d6Des(Ot_febit) | SBP/c-d6Des(Ot_febit) | SBP/c-d6Des(Ot_febit) | SBP/c-d6Des(Ot_febit) |
| PXR/c-d6Elo(Tp_GA2) | PXR/c-d6Elo(Tp_GA2) | PXR/c-d6Elo(Tp_GA2) | FAE/c-d6Elo(Tp_GA2) | FAE/c-d6Elo(Tp_GA2) | PXR/c-d6Elo(Tp_GA2) | PXR/c-d6Elo(Tp_GA2) | PXR/c-d6Elo(Tp_GA2) | PXR/c-d6Elo(Tp_GA2) |
| Napin/c-d12Des(Ps_GA) | Napin/c-d12Des(Ps_GA) | Napin/c-d12Des(Ps_GA) | Napin/c-d12Des(Ps_GA) | Napin/c-d12Des(Ps_GA) | Napin/c-d12Des(Ps_GA) | Napin/c-d12Des(Ps_GA) | Napin/c-d12Des(Ps_GA) | Napin/c-d12Des(Ps_GA) |
|  |  |  | USP/c-o3Des(Pi_GA2) | USP/c-o3Des(Pi_GA2) | PXR/c-o3Des(Pir_GA) | PXR/c-o3Des(Pir_GA) | PXR/c-o3Des(Pir_GA) |  |
| UBI/AHAS | UBI/AHAS | UBI/AHAS | UBI/AHAS | UBI/AHAS |  |  |  |  |
| LB | LB | LB | LB | LB |  |  |  |  |
| RB2 | RB2 | RB2 | RB2 | RB2 |  |  |  |  |
| Conlinin/d4Des(Eg) | Conlinin/d4Des(Eg) |  |  |  | Conlinin/c-d4Des(Pl_GA)2_var1 | SETL/c-d5Des(Tc_GA2) | SETL/c-d5Des(Tc_GA2) | SETL/c-o3Des(Pir_GA) |
| FAE/c-d5Elo(Ot_GA3) | FAE/c-d5Elo(Ot_GA3) | FAE/c-d5Elo(Ot_GA3) | FAE/c-d5Elo(Ot_GA3) | FAE/c-d5Elo(Ot_GA3) | FAE/c-d5Elo(Ot_GA3) | FAE/c-d5Elo(Ot_GA3) | FAE/c-d5Elo(Ot_GA3) | USP/c-o3Des(Pi_GA2) |
| SETL/c-o3Des(Pir_GA) | SETL/c-o3Des(Pir_GA) |  |  |  |  |  |  | SETL/c-d5Des(Tc_GA2) |
|  |  |  |  |  | ARC/C-d4Des(Tc_GA) var2 | ARC/C-d4Des(Tc_GA) var2 | ARC/C-d4Des(Tc_GA) var2 | ARC/c-d4Des(Tc_GA) var2 |
| USP/c-o3Des(Pi_GA2) | USP/c-o3Des(Pi_GA2) | USP/c-o3Des(Pi_GA2) |  |  | USP/c-o3Des(Pi_GA2) | USP/c-o3Des(Pi_GA2) | USP/c-o3Des(Pi_GA2) | PXR/c-o3Des(Pir_GA) |
| ARC/c-d4Des(Tc_GA) var1 | ARC/c-d4Des(Tc_GA) var1 | ARC/c-d4Des(Tc_GA) var1 | ARC/C-d4Des(Tc_GA) var1 | ARC/C-d4Des(Tc_GA) var1 | SETL/c-d5Des(Tc_GA2) |  |  | Conlinin/c-d4Des(Pl_GA)2_var1 |
|  |  |  | Conlinin/d4Des(Eg) | Conlinin/d4Des(Eg) | Conlinin/c-d4Des(Pl_GA)2_var2 |  | FAE/c-d4Des(Pl_GA)2 | FAE/c-d4Des(Pl_GA)2 | FAE/c-d5Elo(Ot_GA3) |
|  |  |  |  |  | SETL/c-o3Des(Pir_GA) | SETL/c-o3Des(Pir_GA) | SETL/c-o3Des(Pir_GA) |  |
|  |  |  |  |  | UBI/AHAS | UBI/AHAS | UBI/AHAS | UBI/AHAS |
| LB2 | LB2 | LB2 | LB2 | LB2 | LB | LB | LB | LB |

Example 5: Procedure for Production of Transgenic Plants Using a Co-Transformation Approach In general, the transgenic rapeseed plants were generated by a modified protocol according to DeBlock et al. 1989, Plant Physiology, 91:694-701). For the generation of rapeseed plants transgenic for two different T-DNAs, the binary vectors described in example 3 were transformed into *Agrobacterium rhizogenes* SHAO1 (see WO2006024509 A2 for full description of the *Agrobacterium* used). For the transformation of rapeseed plants (cv. Kumily), a co-transformation strategy was used. Transformation was performed with two different agrobacteria strains harbouring one of the two different plasmids listed in Table 14 and described in detail in Example 3, Example 4, Example 6 and/or Example 7

TABLE 14

Overview of combinations used in Co-transformation Strategy described in Example 3 for generation of plants harboring two different T-DNAs

| ID of Combination | Plasmid containing T-DNA 1 harbored by *Agrobacterium tumefaciens* clone 1 | | Plasmid containing T-DNA 2 harbored by *Agrobacterium tumefaciens* clone 2 | |
|---|---|---|---|---|
| | Plasmid name | Selectable marker for transgenic plants | Plasmid name | Selectable marker for transgenic plants |
| A | VC-LJB2197-1qcz | AHAS | VC-LLM306-1qcz rc | None |
| B | VC-LJB2197-1qcz | AHAS | VC-LLM337-1qcz rc | None |
| C | VC-LJB2197-1qcz | AHAS | VC-LLM338-3qcz rc | None |
| D | VC-LJB2755-2qcz rc | AHAS | VC-LLM391-2qcz rc | None |
| E | VC-LJB2755-2qcz rc | AHAS | VC-LTM217-1qcz rc | None |

Overnight cultures of the two strains intended to be co-transformed were prepared in YEB medium with antibiotics (20 mg/L chloramphenicol, 5 mg/L tetracycline, 25 mg/L Spectinomycin) and grown at 28° C. On the next day the optical density of the culture was checked at 600 nm wave length. It reached about 1 0.0. Cultures of lower optical density were extended in cultivation period. Cultures with an optical density of above 1.3 were diluted with YEB medium to an 00 of approximately 0.2 and cultured until they reached an 00 of 1 0.0.

Cultures were pelleted at about 4000 g and re-suspended in liquid MS medium (Murashige and Skoog 1962), pH 5.8, 3% sucrose with 100 mg/L Acetosyringone to reach an $OD_{600\ nm}$ of 0.1. The *Agrobacterium* suspensions corresponding to each of the two constructs to be co-transformed were mixed in equal parts and used for inoculation of hypocotyl segments prepared from 5 days old etiolated seedlings.

Seeds were germinated under low light conditions (<50 µMol/m2 s) using MSB5 medium from Duchefa (Duchefa Biochemie, PO Box 809 2003 R V Haarlem, Netherlands), pH 5.8, 3% sucrose and 0.8% Oxoid agar. Germination under light conditions produces explants, which are more stable and easier to handle compared to etiolated hypocotyls. Hypocotyl segments of 4 to 7 mm length were inoculated in a bath of *Agrobacterium* cells under gentle shaking up to 4 min, followed by sieving the explants. Infected explants were transferred to petri dishes with co-cultivation medium (MS medium, pH 5.6, 3% sucrose, 0.6 g/L MES (2-(N-Morpholino)ethanesulfonic acid), 18 g/L mannitol, 0.7% phytoagar (Duchefa Biochemie, PO Box 809 2003 R V Haarlem, Netherlands, part number SKU:P1003), 100 mg/L Acetosyringone, 200 mg/L L-Cysteine, 1 mg/L 2,4D (2,4-Dichlorophenoxyacetic acid)) carrying one layer of Whatman filter paper on its surface. Petri dishes were sealed with tape and incubated at 23 C under long day conditions (16 h light/8 h darkness) for three days. After the three days co-cultivation period explants were transferred to MS medium, pH 5.6, 3% sucrose, 0.6 g/L MES, 18 g/L mannitol, 07% Phytoagar, 1 mg/L 2,4D and 500 mg/L Carbenicillin to prevent *Agrobacterium* growth and incubated for a recovery period under the same physical conditions as for the co-cultivation for 7 days.

For selective regeneration explants were transferred after the recovery period to MS medium, pH 5.8, 3% sucrose, 0.7% Phytoagar, 2.5 mg/L $AgNO_3$, 3 mg/L BAP (6-Benzylaminopurine), 0.1 mg/L GA (Gibberellic acid), 0.1 mg/L NAA (1-Naphthaleneacetic acid), 500 mg/L Carbenicillin, 100 nM Imazethapyr (Pursuit) and cultured for two weeks under long day conditions as described above. Sub-cultivation takes place every two weeks. Hormones were stepwise reduced as follows: BAP 3 to 0.5 to 0.05 mg/L; GA (Gibberellic acid) 0.1 to 0.25 to 0.25 mg/L; NAA 0.1 to 0 to 0 mg/L.

Developing shootlets could be harvested after the second cycle of selective regeneration. Shootlets were cut and transferred to either Elongation/rooting medium (MS medium, pH 5.8, 2% sucrose, 100 mg/L myo-inositol, 40 mg/L Adenine sulphate, 500 mg/L MES, 0.4% Sigma Agar, 150 mg/L Timentin, 0.1 mg/L IBA (Indole-3-butyric acid)) or to rock wool/stone wool or foam mats (Grodan, GRODAN Group P.O. Box 1160, 6040 KD Roermond The Netherlands, or Oasis, 919 Marvin Street, Kent, Ohio 44240 USA) watered with ⅒ Vol. of MS medium, pH 5.8 without sucrose under ex vitro long day conditions in covered boxes.

Shoots were elongated and rooted in in vitro medium and were transferred directly to soil.

Either in vitro shoots or GH adapted shoots were sampled for molecular analysis.

Medium were used either autoclaved (except antibiotics, hormones, additives such as L-cysteine, Acetosyringon, imidazolinone components) or filter sterilized prepared (Agar component autoclaved, allowed to cool to 42 C and then used).

Example 6: Procedure for Production of Transgenic Plants Using BiBACs

For BiBAC transformation the same protocol as described for the co-transformation approach was used except that only one construct was used. According to the prokaryotic kanamycin resistance gene of binary plasmid 50 mg/L kanamycin was used instead of Spectinomycin for *Agrobacterium* growth. It was observed during the course of this work that *Agrobacterium* carrying BiBACs grow very slowly, often taking 18 hours to reach a liquid culture $OD_{600\ nm}$ considered optimal for use in plant transformation.

The table below gives an example for some key data documented during the transformation of the construct LTM593

| | VC-LTM593-1qcz rc |
|---|---|
| Explants inoculated | 37 600 |
| Shoots harvested | 2 630 |
| Shoots sampled and analyzed for gene AHAS | 1 543 |
| Transgenic events with gene AHAS | 1 050 |
| Transformation efficiency (%) | 2.8 |
| Percentage of events that grown on herbicide seelction plates but where confirmed using qPCR to lack the herbiced resitstance marker (%) | 32.0 |

The amount of single copy events produced by the plant transformation protocol described above was 45% and 38% of vector backbone-free events selected after transformation of the constructs LTM593 and LTM595, respectively, were single copy events (see Table 15).

TABLE 15

Statistics of single and double copy events with and without vector backbone in transformation experiments performed with the two BiBAC strains VC-LTM593-1qcz rc and VC-LTM595-1qcz rc

| | VC-LTM593-1qcz rc | | VC-LTM595-1qcz rc | |
|---|---|---|---|---|
| | # | % | # | % |
| Number of transgenic events confirmed to contain at least 1 copy of gene c-AtAHAS | 1050 | | 217 | |
| Single copy | 535 | 50 | 92 | 42 |
| Single copy, vector backbone-free | 478 | 45 | 83 | 38 |
| Double copy | 320 | 30 | 49 | 23 |
| Double copy vector backbone-free | 227 | 22 | 41 | 18 |

One important key finding for successful transformation was the choice of *Agrobacterium* strain. While the original method (see De Block et al. (1989) Plant Physiology 91:694-701) used the *Agrobacterium tumefaciens* strain 05801 pMP90, the described method was based on the *Agrobacterium rhizogenes* strain SHAO01 (see WO2006024509 A2 for SHAO01 and SHA017). Even within *Agrobacterium rhizogenes* strains we have realized a clear response of transformation success to the strain and construct used (seeTable 16).

TABLE 16

Impact of *Agrobacterium rhizogenes* strains on transformation success of BiBACs

| | VC-RTP10690-1qcz_f | VC-LTM593-1qcz rc |
|---|---|---|
| Strain used | SHA017 | SHA001 |
| Number of inoculated explants | 60700 | 37600 |
| Regeneration efficiency (%) | 1.8 | 4.1 |
| Shoots sampled and analysed for gene AHAS | 1084 | 1543 |
| Number of transgenic plants based on the presence of gene c-AHAS | 333 | 1050 |
| Transformation efficiency (TE) (%) | 0.6 | 2.8 |
| Percentage of events that grown on herbicide seelction plates but where confirmed using qPCR to lack the herbiced resitstance marker (%) | 69.3 | 32.0 |

TABLE 17

Transformation Efficiencies of the various plasmids and *Agrobacterium* strains used.
With respect to the integration of the T-DNA, it was possible that multiple copies or single copies of intact or truncated or duplicated T-DNA's could be inserted into the genome. The terms copy or copies refer to the number of copies of a particular T-DNA or fragment of a T-DNA that were inserted into the plant genome. The term locus refers to how many different locations within the plant genome the copy or copies of the T-DNA were inserted into and is defined as a region of disequilibrium within the genome and which can vary between plant species and even within cultivars of a given species. For the purpose of this definition this is within one genetic map unit or CentiMorgan.

| Outcome | VC-LJB2197-1qcz + VC-LLM337-1qcz rc | VC-LJB2755-2qcz rc + VC-LLM391-2qcz rc | VC-RTP10690-1qcz_f | VC-LTM593-1qcz rc |
|---|---|---|---|---|
| *Agrobacterium* strain | SHA001 | SHA001 | SHA017 | SHA001 |
| Transformation efficiency (TE) (%) based on the presence of gene AHAS | 17 | 19.7 | 0.6 | 2.8 |
| Percentage of events that grown on herbicide seelction plates but where confirmed using qPCR to lack the herbiced resitstance marker (%) | 1.1 | 0.6 | 69.3 | 32.0 |

TABLE 17-continued

Transformation Efficiencies of the various plasmids and *Agrobacterium* strains used.
With respect to the integration of the T-DNA, it was possible that multiple copies or single copies
of intact or truncated or duplicated T-DNA's could be inserted into the genome. The terms copy
or copies refer to the number of copies of a particular T-DNA or fragment of a T-DNA that were
inserted into the plant genome. The term locus refers to how many different locations within the
plant genome the copy or copies of the T-DNA were inserted into and is defined as a region of
disequilibrium within the genome and which can vary between plant species and even within
cultivars of a given species. For the purpose of this definition this is within one genetic map unit
or CentiMorgan.

| Outcome | VC-LJB2197-1qcz + VC-LLM337-1qcz rc | VC-LJB2755-2qcz rc + VC-LLM391-2qcz rc | VC-RTP10690-1qcz_f | VC-LTM593-1qcz rc |
|---|---|---|---|---|
| Genes of both T-DNAs present (% co-transformed) | 11.2 | 15.1 | n. a. | n. a. |
| % of single copy events one locus integration | 0 | 0 | 100 | 100 |
| Portion of selected "more copy events" (2 to 3 copies) with one locus integration | 0 | 0 | n.d. | 25 from 33 |

Example 7: Seed Germination and Plant Growth in the Greenhouse and Field

Transformed plants were cultivated for seed production and phenotypic assessment in both the greenhouse and in the field. Greenhouse growth conditions were a sixteen hour light period followed by an eight hour dark period. The temperature was 20 degrees Celsius during the light period (also called the day period) with a level of light corresponding to 200-300 micromoles of photons m-2 s-1 (this is the incident of light at the top of the plant and lights were adjusted in terms of distance from the plant to achieve this rate). During the day period the range of light in the greenhouse varied between 130 and 500 micromoles of photons m-2 s-1. Getting out of the day range just cited triggered either the use of artificial light to bring the level up to 200-300 micromoles of photons m-2 s-1 or shading and/or shut off of lights to bring the level back to 200-300 micromoles of photons m-2 s-1. The dark period (also referred to as the night period) temperature was 18 C. Four hours before the light period began the temperature was lowered to 15 C for the remainder of the dark period. Plants were irrigated and treated for insects as necessary. The soil type was 50% Floradur B Seed+50% Floradur B Cutting (including sand and perlite) provided by Floragard (Oldenburg, Germany). Plant growth was enhanced by nutrient supplementation. Nutrients were combined with the daily watering. A 0.1% (w/v) fertilizer solution (Hakaphos Blue 15(N)-10 (P)-15 (K), Compo GmbH & Co KG, MOnster, Germany) was used to water the plants. Water was supplied on demand (e.g. depending on plant growth stage, water consumption etc.). To avoid cross-pollination, plants were bagged at the time when the first flowers opened. Plants were checked daily in order to ensure that all open flowers were covered by the bags. Open flowers that were not covered properly were removed.

For field grown plants, the plants were grown in six locations which correspond climatically to USDA growth zones 3a-4b and 5a, and five locations corresponding climatically to USDA growth zones 8a-9b and 11. The plants grown in the regions corresponding to USDA growth zones 3a-4b and 5a were grown in the summer and the plants grown in the regions corresponding to USDA growth zones 8a-9b and 11 were grown in the winter. Standard horticultural practices for canola were followed. Netting and other measures to protect from birds and insects were used as deemed necessary by the growers, as were herbicides and fertilizer applications. The planting density for all locations was eighty seeds per square meter with germination rate of 95 or better percent.

In the case where it was necessary to determine germination rates for the purpose of seed quality assurance or control, or where it was advantageous to germinate seeds to obtain cotyledons or seedling tissues, the following protocol was used: 150 mm by 15 mm petri-plates and Whatman (no. 2) filter paper cut into 120 mm disks were used. The filter paper was pre-moistened with sterile deionized water. One hundred seeds of the appropriate line were obtained and spread evenly across the pre-moistened filter paper.

Clean and sterile tweezers were used to spread the seeds to obtain the uniform pattern as shown above. Additional sterile water was added to ensure the seeds and paper were wetted, but not floating. The total amount of water used per petri-plate was approximately 20 mL. Three plates were done for each genotype tested. The plates were sealed with surgical tape, VWR (1050 Satellite Blvd. Suwanee, Ga. 30024 USA) catalog number 56222-110. After the plates were sealed, they were then incubated in a germination chamber set to 90% humidity, set to a sixteen hour photoperiod with 20 degrees Celsius day temperature and 15 degrees Celsius night temperature. The light intensity was 90-120 micro-moles per square meter per second. Germination was scored twice, once at four days after placing the plates into the growth chamber and again at eight days after incubation.

Example 8: Lipid Extraction and Lipid Analysis of Plant Oils

The results of genetic modifications in plants or on the production of a desired molecule, e.g. a certain fatty acid, were determined by growing the plant under suitable conditions, e.g. as described above and analyzing the growth media and/or the cellular components for enhanced production of the desired molecule, e.g. lipids or a certain fatty acid. Lipids were extracted as described in the standard literature including Ullman, Encyclopedia of Industrial Chemistry, Bd. A2, S. 89-90 und S. 443-613, VCH: Weinheim (1985); Fallon, A., et al., (1987) "Applications of HPLC in Biochemistry" in: Laboratory Techniques in Biochemistry and Molecular Biology, Bd. 17; Rehm et al. (1993) Biotechnology, Bd. 3, Kapitel III: "Product recovery and purification", S. 469-714, VCH: Weinheim; Belter, P. A., et al. (1988) Bioseparations: downstream processing for Biotechnology, John Wiley and Sons; Kennedy, J. F., und Cabral, J. M. S. (1992) Recovery processes for biological Materials, John Wiley and Sons; Shaeiwitz, J. A., und Henry, J. D. (1988) Biochemical Separations, in: Ullmann's Encyclopedia of Industrial Chemistry, Bd. B3; Kapitel 11, S. 1-27, VCH: Weinheim; and Dechow, F. J. (1989) Separation and purification techniques in biotechnology, Noyes Publications.

It is acknowledged that extraction of lipids and fatty acids can be carried out using other protocols than those cited above, such as described in Cahoon et al. (1999) Proc. Natl. Acad. Sci. USA 96 (22):12935-12940, and Browse et al. (1986) Analytic Biochemistry 152:141-145. The protocols used for quantitative and qualitative analysis of lipids or fatty acids are described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) u.d.T.: Progress in the Chemistry of Fats and Other Lipids CODEN.

To generate transgenic plants containing the genetic elements described in examples 3 and 4 for production of EPA and DHA in seeds, rapeseed (*Brassica napus*) was transformed as described in examples 5 and 6. Selected plants containing the genetic elements described in examples 3 and 4 were grown until development of mature seeds under the conditions cited in Example 7. Fatty acids from harvested seeds were extracted as described above and analyzed using gas chromatography as described above. The content (levels) of fatty acids is expressed throughout the present invention as percentage (weight of a particular fatty acid) of the (total weight of all fatty acids). Similiarly, the contents of other component of the oil are given in "% w/w". E.g., the content (levels) of TAGs or PCs is expressed throughout the present invention as percentage (weight of a particular TAGs or PCs) of the (total weight of all TAGs or PCs), in particular ot the total weight off all TAGs or PCs present in the oil or lipid of the present invention. In an embodiment, the contents of the compounds are determined as described in the Examples. For example, the contents can be determined as in Examples 29, 31 or 32. Seed oil content is expressed throughout the present invention as percentage of (oil weight) of the (total weight of seeds).

TABLE 18

Fatty acids analyzed using gas chromatography

| Systematic name | Trivial Name | Short hand 1 | Short hand 2 |
|---|---|---|---|
| Hexadecanoic acid | Palmitic acid | 16:0 | |
| (Z)-7-Hexadecenoic acid | | 16:1n-9 | |
| (Z,Z,Z)-7,10,13-Hexadecatrienoic acid | | 16:3n-3 | |
| Octadecanoic acid | Stearic acid | 18:0 | |
| (Z)-9-Octadecenoic acid | Oleic acid | 18:1n-9 | OA |
| (Z,Z)-9,12-Octadecadienoic acid | Linoleic acid | 18:2n-6 | LA |
| (Z,Z)-6,9-Octadecadienoic acid | | 18:2n-9 | |
| (Z,Z,Z)-9,12,15-Octadecatrienoic acid | alpha-Linolenic acid | 18:3n-3 | ALA |
| (Z,Z,Z)-6,9,12-Octadecatrienoic acid | gamma-Linolenic acid | 18:3n-6 | GLA |
| (Z,Z,Z,Z)-6,9,12,15-Octadecatetraenoic acid | Stearidonic acid | 18:4n-3 | SDA |
| Eicosanoic acid | Arachidic acid | 20:0 | |
| (Z)-11-Eicosenoic acid | Gondoic acid | 20:1n-9 | |
| (Z,Z)-11,14-Eicosadienoic acid | | 20:2n-6 | |
| (Z,Z,Z)-11,14,17-Eicosatrienoic acid | | 20:3n-3 | |
| (Z,Z,Z)-8,11,14-Eicosatrienoic acid | Dihomo-gamma-linolenic acid | 20:3n-6 | DHGLA |
| (Z,Z,Z)-5,8,11-Eicosatrienoic acid | Mead acid | 20:3n-9 | |
| (Z,Z,Z,Z)-8,11,14,17-Eicosatetraenoic acid | | 20:4n-3 | ETA |
| (Z,Z,Z,Z)-5,8,11,14-Eicosatetraenoic acid | Arachidonic acid | 20:4n-6 | ARA |
| (Z,Z,Z,Z,Z)-5,8,11,14,17-Eicosapentaenoic acid | Timnodonic acid | 20:5n-3 | EPA |
| Docosanoic acid | Behenic acid | 22:0 | |
| (Z)-13-Docosenoic acid | Erucic acid | 22:1n-9 | |
| (Z,Z,Z,Z)-7,10,13,16-Docosatetraenoic acid | Adrenic acid | 22:4n-6 | DTA |
| (Z,Z,Z,Z,Z)-7,10,13,16,19-Docosapentaenoic acid | Clupanodonic acid | 22:5n-3 | DPAn-3 |
| (Z,Z,Z,Z,Z)-4,7,10,13,16-Docosapentaenoic acid | Osbond acid | 22:5n-6 | DPAn-6 |
| (Z,Z,Z,Z,Z,Z)-4,7,10,13,16,19-Docosahexaenoic acid | | 22:6n-3 | DHA |

Example 9: Non-Destructive Analysis of Lipids in Single Cotyledons of Seedlings

Transformation of plants according to the methods described in Example 5 and Example 6 results in a random integration of the T-DNA into the genome. It was known that such integrations can also occur in a partial manner, furthermore multiple integrations of complete and partial T-DNAs can occur. Self pollination of the T0 plant will result in production of T1 seeds which will be segregating for the T-DNA insertion(s) according to the ratios observed by Gregor Mendel (Mendel, 1866) and which are now part of the basic general knowledge in the life sciences. Due to the Mendelian segregation; for each integration of the T-DNA, one quarter (~25%) of the T1 seed have lost the integration, and can be called "null segregants". 50% of the T1 seed will carry the T-DNA integration either on the maternal chromosome (25%), or paternal chromosome (25%); these seeds are 'heterozygous' or 'hemizygous' related to the T-DNA integration. The remaining quarter (~25%) of the T1 seed will carry the T-DNA on the maternal and paternal chromosome; these seeds are 'homozygous' related to the T-DNA integration. For plants that follow such a sexual propagation, it is essential to genetically fix the T-DNA integration(s), by selecting progenies that are homozygous for the T-DNA integration(s).

Figure 22:
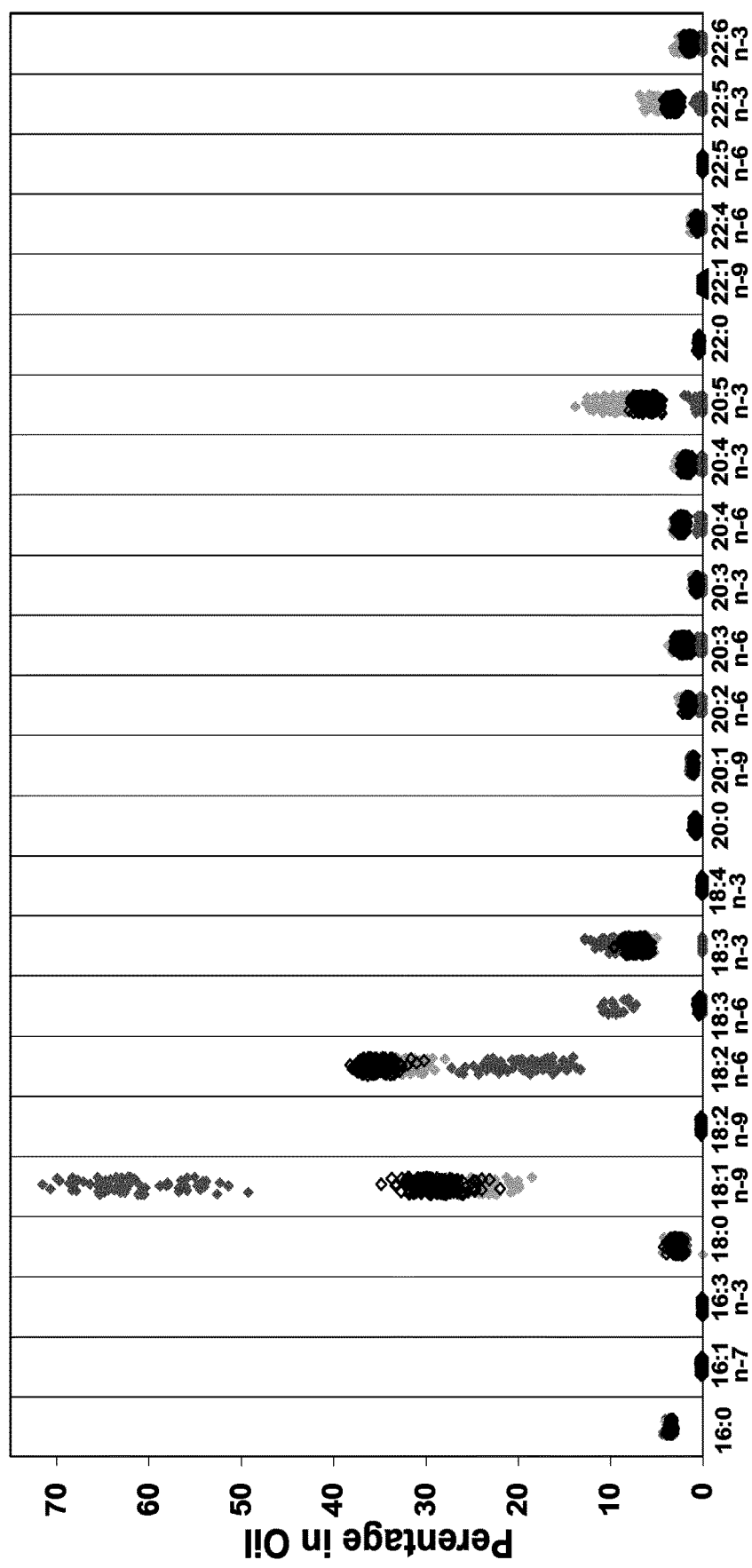
FIG. 22: Half Kernel Analysis of segregating T1 seeds of Event LANPMZ. A total of 288 seedlings where analysed. 71 of those seedlings were found to produce no significant amount of VLC-PUFA (dark grey diamonds) while containing >49% Oleic acid and <28% Linoleic acid. 71 seed of 288 seed correspond to 24.65% of the total analysed seed. All remaining seed were capable of producing DHA, indicating the presence of both T-DNA from construct VC-LJB2197-1qcz and VC-LLM337-1qcz rc. Among those seeds producing DHA, one can discriminate a group of 146 seeds showing medium VLC-PUFA levels (open diamonds), and a group of 71 seed showing high VLC-PUFA levels (light grey diamonds). The ratios of these three groups is 71:146:71, which corresponds to the Medelain 1:2:1 ratio (NULL: HETEROZYGOUS:HOMOZYGOUS) expected for a phenotype when all genes conveying this phenotype (in this case the two T-DNAs of plasmid VC-LJB2197-1qcz and VC-LLM337-1qcz rc) integrated into one locus in the genome.
Figure 23:
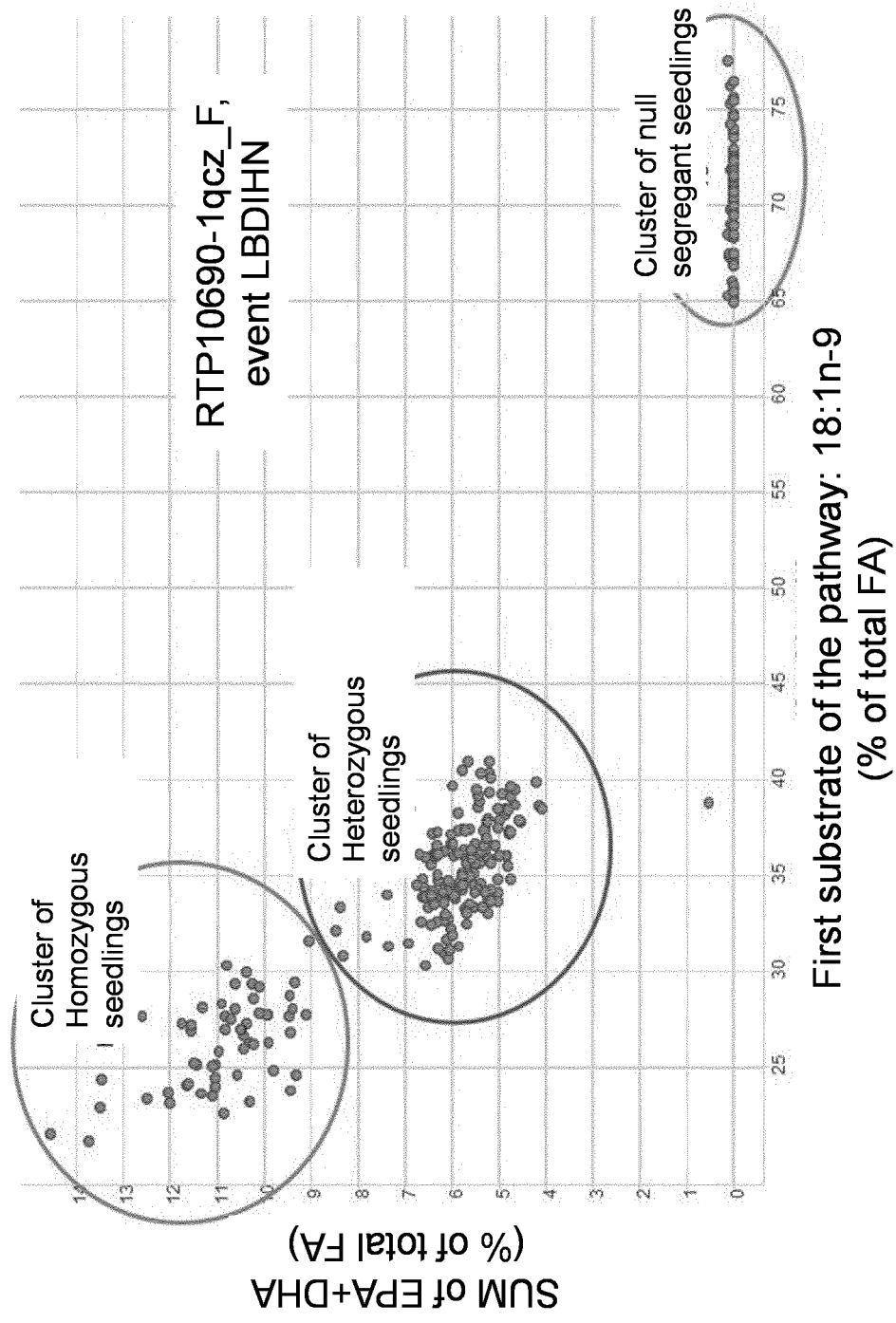
FIG. 23: Half Kernel Analysis of segregating T1 seeds of Event LBDIHN. A total of 288 seedlings where analysed. The levels of first substrate fatty acid of the pathway was plotted on the x-axis, the levels of the sum of two products of the pathways (EPA+DHA) was plotted on the y-axis. One can clearly see three clusters, where the ratio of the number of seeds in the these three clusters was 1:2:1 (Homozygous: Heterozygous:Null segregant). This segregation of the phenotype according to the first Mendelian law demonstrates a single locus insertion of the T-DNA of construct RTP10690-1qcz_F into the genome of B. napus cv Kumily.

In order to identify T1 seedlings where each T-DNA integration that was essential for the trait was present, ideally homozygous, one can perform quantitative PCR to measure the copy number of the T-DNA integration(s) directly. Alternatively one can analyse the trait conferred by the presence of the T-DNAs, which at least enables the identification of all seeds that do not contain all T-DNA of interest (null-segregants). For all constructs described in Example 10 to Example 14, and where indicated, a non-destructive analysis of VLC-PUFA production was performed. To this end, T1 seeds were germinated in the dark for three days on wet filter paper. After three days, one of the two cotyledons was cut off to subject it to lipid analysis as described in Example 8. The other cotyledon, including the hypocotyl and root, was planted in soil. As an example, the result from the lipid content analysis of these cotyledons from segregating T1 seedlings of event LANPMZ obtained from the construct combination described in Example 11 are shown in FIG. 22; the results of event LBDIHN obtained from the construct combination described in Example 15 are shown in FIG. 23. In both of these figures, it is observed that one quarter of the seed do not produce a significant amount of VLC-PUFA, while producing wildtype levels of Oleic acid (null segregant seedlings). One can furthermore see in both FIGS. two additional clusters of seedlings that produce different amounts of VLC-PUFA, see FIG. 23. Counting the number of seed in these respective clusters, a 1:2:1 segregation ratio was observed for the clusters that produce (~0 VLC-PUFA):(intermediate level of VLC-PUFAs):(higher level of VLC-PUFAs). The observations demonstrate a relationship between 'gene dosage', that was the number of T-DNA copies present in the genome, and VLC-PUFA levels. For all constructs described in Example 10 to Example 13, and where indicated, this relationship was exploited to identify T1 plants where at least one T-DNA locus has become homozygous, or where multiple T-DNA integration loci are at least present, or some are homozygous while others still segregate. The applicability of this method can be demonstrated for event LANPMZ, see FIG. 22, all heterozygous (hemizygous) and homozygous T1 seeds of event LANPMZ that produce VLC_PUFA are capable of producing both EPA and DHA. As DHA production requires the presence of both T-DNAs, it can be concluded that at least one copy of the T-DNA of VC-LJB2197-1qcz and one copy of the T-DNA of VC-LLM337-1qcz rc have inserted into the genome, likely at the same locus. 13 T1 seedlings of those 288 seedlings of event LANPMZ having the highest VLC-PUFA levels have been selected and have been grown to mature plants. Copy number analysis on those 13 selected plants shown in Table 40 indicates that both T-DNAs are present in a single copy, and comparison of the T0 plant copy number results against the average result of the 13 T1 plants demonstrates that these single T-DNA insertions are homozygous (duplicated copy number). All results combined provide the information that the event LANPMZ contains the T-DNAs of construct VC-LJB2197-1qcz and the T-DNA of construct VC-LLM337-1qcz rc in one copy each, whereby both T-DNAs co-segregate in a single locus.

For a single T-DNA integration into the genome, 1 out of 4 T1 seed are expected to be homozygous for that T-DNA integration. For each additional T-DNA integration, just one quarter of all seed homozygous for all other T-DNA integrations are homozygous for the additional T-DNA integration, consequently for two T-DNA integration events into the genome 1 out of 16 T1 seed are expected to be homozygous for both T-DNA integration; for three T-DNA integration into the genome 1 out of 64 T1 seed are expected to be homozygous for all three T-DNA integration; for four T-DNA integration into the genome 1 out of 256 T1 seed are expected to be homozygous for all four T-DNA integration; and so forth. All plants in Example 10 to Example 14 contain a minimum of two T-DNA insertion events (one from each plasmid) in order for the plant to contain all the necessary genes to generate all the required enzymes to reconstitute the PUFA pathway sufficiently to generate the VLC-PUFAs: DHA and EPA as well as ARA.

Example 10: Plants Containing the T-DNAs of Plasmid VC-LJB2197-1Qcz and VC-LLM306-1Qcz Rc (Combination a in Example 5) for Production of EPA and DHA in Seeds In this example, the genetic elements required for EPA and DHA synthesis were transferred into the plant genome on two different T-DNAs. To this end, the two different plasmids VC-LJB2197-1qcz and VC-LLM306-1qcz rc containing two different T-DNAs where cloned into agrobacteria, and plant tissue was incubated according Example 5 at the same time with these two agrobacterial cultures that are identical apart from containing either VC-LJB2197-1qcz or VC-LLM306-1qcz rc. Due to the selectable herbicide resistance marker, regenerated plants contained at least the T-DNA of VC-LJB2197-1qcz. Only those plants were kept, that also contained the T-DNA of plasmid VC-LLM306-1qcz rc as confirmed by PCR, conducted as described in Example 24, which contains a description of PCR used for gene expression and gene copy number determination. Only plants containing both the T-DNA of plasmid VC-LJB2197-1qcz as well as the T-DNA of plasmid VC-LLM306-1qcz rc contain all the genetic elements required for EPA and DHA synthesis in seeds. The genetic elements of VC-LJB2197-1qcz, and the function of each of the elements, are listed in Table 1. The genetic elements of VC-LLM306-1qcz rc, and the function of each of the elements, are listed in Table 3. For convenience, all enzymes expressed in seeds of plants carrying both T-DNA of VC-LJB2197-1qcz and VC-LLM306-1qcz rc that are required for EPA and DHA synthesis are additionally listed in Table 19.

TABLE 19

Combined list of useful genes of EPA and DHA synthesis carried by the T-DNAs of plasmids VC-LJB2197-1qcz and VC-LLM306-1qcz rc.

| Genes encoding enzymes for EPA and DHA synthesis | Plasmid containing T-DNA with the gene | Length (bp) | Enzymatic function and source of encoded protein |
|---|---|---|---|
| c-d12Des(Ps_GA) | VC-LJB2197-1qcz | 1196 | Delta-12 desaturase from *Phythophthora sojae* |
| c-d6Des(Ot_febit) | VC-LJB2197-1qcz | 1370 | Delta-6 desaturase from *Ostreococcus tauri* |
| c-d6Des(Ot_febit) | VC-LLM306-1qcz rc | 1370 | Delta-6 desaturase from *Ostreococcus tauri* |
| c-d6Elo(Pp_GA2) | VC-LJB2197-1qcz | 872 | Delta-6 elongase from *Physcomitrella patens* |
| c-d6Elo(Tp_GA2) | VC-LJB2197-1qcz | 818 | Delta-6 elongase from *Thalassiosira pseudonana* |
| c-d5Des(Tc_GA2) | VC-LJB2197-1qcz | 1319 | Delta-5 desaturase from *Thraustochytrium* sp. ATCC21685 |
| c-o3Des(Pi_GA2) | VC-LLM306-1qcz rc | 1085 | Omega-3-desaturase from *Phythophthora infestans* |
| c-o3Des(Pir_GA) | VC-LLM306-1qcz rc | 1091 | Omega-3 desaturase from *Pythium irregulare* |
| c-d5Elo(Ot_GA3) | VC-LLM306-1qcz rc | 902 | Delta-5 elongase from *Ostreococcus tauri* |
| c-d4Des(Eg_GA) | VC-LLM338-3qcz rc | 1625 | Delta-4 desaturase from *Euglena gracilis* |
| c-d4Des(Tc_GA) | VC-LLM306-1qcz rc | 1559 | Delta-4 desaturase from *Thraustochytrium* sp. |

Fatty Acid Profiles, Copy Number Measurements, and Phenotypic Observations of T0 Plants Carrying T-DNAs of Plasmids VC-LJB2197-1Qcz and VC-LLM306-1Qcz Rc Cultivated in Greenhouses During the Summer.

The data in Table 20, Table 21 and Table 22 show that there was an increase in DHA and EPA content when comparing one versus two copies of each of the T-DNAs (VC-LJB2197-1qcz and VC-LLM306-1qcz rc) in the plant. The copy number of the construct VC-LJB2197-1qcz has been determined by measuring the left border of the T-DNA in the T0 generation and not other genetic elements along the T-DNA (see Table 20). It was possible that the 88 plants representing the single copy category do in fact contain additional partial T-DNA insertions, and that the 86 plant representing the double copy category might in fact lack parts of one of the T-DNAs. Therefore, due to insufficient data to correctly classify T0 plants into "single copy" and "double copy" groups, both populations overlap. Comparisons between two and three copies of the T-DNA's revealed that there was a minimal increase in DHA and EPA, suggesting that two copies of each gene was sufficient to reach maximum performance of the VLC-PUFA biosynthesis pathway (C20 and C22 PUFAs, including, but not limited to, EPA, DHA and ARA) when considering copy numbers up to three. Of note was that the majority of insertions in this example are one or two copy events. Table 23 indicates that with respect to the PUFA pathway or the copy number of the T-DNA encoding genes of the PUFA pathway, there was no significant effect on plant morphology or development when the plant carries one, two or three copies of the T-DNA's of interest.

TABLE 20

Copy number measurement of T0 plants cultivated in the greenhouse of canola events containing the T-DNAs of plasmids VC-LJB2197-1qcz and VC-LLM306-1qcz rc. Considering each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49, tc: all T0 plants where the average of all copy number assays listed in this table was 2.51-3.49.

| | Copy number assays targeting the T-DNA of VC-LJB2197-1qcz. Assays are listed according to the position of the assay target along the T-DNA, with target c-AHAS located near the left T-DNA border and target c-d6Des(Ot_febit) near the right T-DNA border. | | | | | | | | Copy number assays targeting the T-DNA of VC-LLM306-1qcz rc. Assays are listed according to the position of the assay target along the T-DNA, with target j-p-BnFAE_ t-PvARC located near the left T-DNA border and target c-d4Des(Eg_GA) near the right T-DNA border. | | | | |
|---|---|---|---|---|---|---|---|---|---|---|---|---|---|
| Event | c-AHAS | j-t-E9-p3-2 | c-d6Elo (Tp_GA) | j-t-StCAT_p2_p-LuPXR | c-d6Des(Ot_febit) | j-t-CaMV_p-LuCnl-2 | j-i-Atssl8_c-d6Elo (Pp_GA2) | c-d6Des (Ot_febit) | j-p-BnFAE_t-PvARC | c-d4Des (Tc_GA) | c-o3Des (Pi_GA2_SNP) | c-d5Elo (Ot_GA 3) | j-i-Atssl_c-d5Elo (Ot_GA3) | c-d4Des (Eg_GA) |
| sc (n = 88) | 1.2 | | | | | | | | | 1.1 | 1.2 | | 1.1 |
| dc (n = 86) | 1.6 | | | | | | | | | 1.8 | 2.4 | | 1.7 |
| tc (n = 5) | 1.9 | | | | | | | | | 3.4 | 4.2 | | 3.2 |

TABLE 21

Fatty acid profiles of T1 seeds harvested from T0 plants cultivated in the greenhouse of canola events containing the T-DNAs of plasmids VC-LJB2197-1qcz and VC-LLM306-1qcz rc. Considering each event in this generation was represented by only 1 plant, all events have been grouped into the categories indicated in the first column as described in Table 20. The number of T1 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 88) | 4.9 ± 0.9 | 0.3 ± 0.1 | 0.1 ± 0 | 2.9 ± 0.6 | 39.3 ± 8.2 | 28.4 ± 5.8 | 0.7 ± 4.4 | 5.8 ± 1.3 | 0.4 ± 0.6 | 0.1 ± 0.2 | 0.8 ± 0.1 | 0.9 ± 0.2 | 0.9 ± 0.6 |
| dc (n = 86) | 4.8 ± 1 | 0.3 ± 0.1 | 0.1 ± 0 | 3 ± 0.7 | 37.9 ± 9.2 | 27.9 ± 6.4 | 1.1 ± 5.7 | 5.8 ± 1.4 | 0.7 ± 0.7 | 0.1 ± 0.1 | 0.8 ± 0.2 | 0.9 ± 0.2 | 0.8 ± 0.6 |
| tc (n = 5) | 5 ± 0.9 | 0.3 ± 0.1 | 0.1 ± 0 | 3.1 ± 0.7 | 39.1 ± 8.1 | 28.4 ± 4.5 | 0.5 ± 0.3 | 6.1 ± 1.5 | 0.9 ± 0.6 | 0.2 ± 0.1 | 0.8 ± 0.2 | 0.9 ± 0.2 | 0.7 ± 0.6 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 88) | 0.3 ± 0.3 | 1.6 ± 0.8 | 0.9 ± 0.6 | 2.2 ± 1.7 | 3.3 ± 1.4 | 0.3 ± 0.1 | 0 ± 0 | 0.3 ± 0.3 | 1.3 ± 0.7 | 0 ± 0 | 0.5 ± 0.3 | 0.2 ± 0.3 | |
| dc (n = 86) | 0.3 ± 0.3 | 1.6 ± 1 | 1 ± 0.5 | 2 ± 1.6 | 4 ± 2.1 | 0.3 ± 0.1 | 0 ± 0 | 0.6 ± 0.4 | 1.8 ± 0.9 | 0 ± 0 | 0.8 ± 0.5 | 0.4 ± 0.3 | |
| tc (n = 5) | 0.3 ± 0.2 | 2.1 ± 2.1 | 1.2 ± 1 | 1.9 ± 2.4 | 4 ± 2.9 | 0.3 ± 0.1 | 0 ± 0 | 0.7 ± 0.4 | 1.9 ± 1.1 | 0 ± 0 | 0.8 ± 0.5 | 0.8 ± 0.9 | |

TABLE 22

Fatty acid profiles of T1 seeds harvested from T0 plants cultivated
in the greenhouse of canola events containing the T-DNAs of plasmids
VC-LJB2197-1qcz and VC-LLM306-1qcz rc. Considering each event
in this generation was represented by only 1 plant, all events have been
grouped into the categories indicated in the first column as described in
Table 20. For each category, the fatty acid profile of the plant/event having
the highest EPA+DHA levels was shown. Per seed batch
a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 4.9 | 0.2 | 0.0 | 3.5 | 23.1 | 34.2 | 0.2 | 5.4 | 0.4 | 0.2 | 0.8 | 0.9 | 2.5 |
| dc (n = 1) | 7.1 | 0.0 | 0.0 | 4.5 | 3.2 | 44.5 | 1.5 | 0.3 | 0.0 | 0.0 | 1.0 | 1.1 | 2.3 |
| tc (n = 1) | 3.4 | 0.1 | 0.0 | 2.8 | 29.4 | 27.4 | 0.6 | 6.6 | 1.0 | 0.3 | 0.7 | 0.9 | 1.1 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 1.1 | 3.0 | 2.4 | 3.5 | 13.5 | 0.3 | 0.0 | 0.0 | 0.0 | 0.0 | 0.0 | 0.0 | |
| dc (n = 1) | 0.5 | 9.8 | 1.8 | 0.0 | 12.6 | 0.4 | 0.0 | 1.3 | 4.9 | 0.0 | 2.8 | 0.6 | |
| tc (n = 1) | 0.5 | 1.5 | 1.6 | 2.6 | 10.4 | 0.3 | 0.0 | 1.1 | 5.1 | 0.0 | 1.9 | 0.5 | |

TABLE 23

Phenotypic rating of T0 plants cultivated in the greenhouse of canola
events containing the T-DNAs of plasmids VC-LJB2197-1qcz and
VC-LLM306-1qcz rc. Considering each event in this generation was
represented by only 1 plant, all events were grouped into the categories indicated
in the first column as described in Table 20. The number of T1
plants/events fullfilling these criteria are displayed in parentheses. DFF: days to first
flower (days), DF: deformed flower (9 = deformed, 1 = normal), DL:
deformed leaf (9 = deformed, 1 = normal), DP: deformed plant (9 = deformed,
1 = normal), DS: deformed silique (9 = deformed, 1 = normal), FC: flower color
(1 = white, 3 = optimal, 4 = orange/yellow), LD: leaf dentation (3 = no
dentation, 7 = strong dentation), LGC: leaf color (3 = yellow, 5 = optimal, 7 = blueish),
LF: fertility (1 = low, 9 = very high), NoL: number of lobes (#), PH: plant
height (cm), TKW: thousand kernel weight (g), SC: seed quality (1 = good, 9 = bad)

| Category of T0 plants | DFF | DF | DL | DP | DS | FC | LD | LGC | LF | NoL | PH | TKW | SC |
|---|---|---|---|---|---|---|---|---|---|---|---|---|---|
| sc (n = 88) | 68.6 ± 9.2 | 1 ± 0 | 1.5 ± 1.4 | 2.2 ± 1.7 | 3.1 ± 3.1 | 3 ± 0 | 3 ± 0 | 5 ± 0 | 3.3 ± 2.5 | 3.8 ± 0.6 | 115.9 ± 12.6 | 3.6 ± 0.4 | 4.1 ± 1.9 |
| dc (n = 86) | 69.4 ± 8.8 | 1 ± 0 | 1.5 ± 1.1 | 2.2 ± 1.5 | 2.9 ± 2.7 | 3 ± 0 | 3 ± 0.2 | 5 ± 0 | 2.9 ± 2.3 | 3.8 ± 0.6 | 115.8 ± 10.2 | 3.7 ± 0.4 | 4.5 ± 1.8 |
| tc (n = 5) | 72.2 ± 8.2 | 1 ± 0 | 1 ± 0 | 1.6 + 1.3 | 2.4 ± 0.9 | 3 ± 0 | 3 ± 0 | 5 ± 0 | 2.4 ± 1.5 | 4 ± 0 | 117 ± 9.7 | 4 ± 0.5 | 4 ± 0.8 |

Fatty Acid Profiles, Copy Number Measurements, and Phenotypic Observations of T1 Plants Carrying T-DNAs of Plasmids VC-LJB2197-1Qcz and VC-LLM306-1Qcz Rc Cultivated in Greenhouses During Winter The copy number analysis indicates that LALTHK was homozygous for two copies of the VC-LJB2197-1qcz T-DNA and homozygous for one copy of the VC-LLM306-1qcz rc while LALJCX was homozygous for two copies of both T-DNAs (VC-LJB2197-1qcz and VC-LLM306-1qcz rc). The other events were still partially segregating for the T-DNAs but contained at least one copy of each T-DNA in all plants. Event LALTHK had no accumulation of DHA, which illustrates the effects of truncations which can occur during insertion of the T-DNA. The events, with the exception of LALTHK, are, within error, similar to one another in terms of EPA+DHA accumulation. The similarity in copy numbers of the events, see Table 23, indicates that insertion site effects that could enhance or repress gene expression are impacting all events equally. The lack of significant variation in EPA and DHA accumulation suggests that there may be a buffering effect in the construct design, such that the T-DNA's integrate into the genome in a manner that minimizes positional effects in gene expression in the T-DNA. The event with the highest VLC-PUFA accumulation, in particular EPA and DHA, was LALFWA which had a maximum accumulation of 4.2 percent DHA and 16 percent EPA with respect to total fatty acid content in the mature seed, but on the average was similar to the other events.

TABLE 24

Copy number measurement of T1 plants cultivated in the greenhouse of canola events containing the T-DNAs of plasmids VC-LJB2197-1qcz and VC-LLM306-1qcz rc. The events are indicated in the first column, along with the number of T1 plants that where measured per event. The T1 plants underwent a selection from 250 segregating T1 seedlings using half-kernel analysis, where the correlation of VLC-PUFA levels with copy number was employed to select for homozygous plants, or on case of multilocus events to seleecct for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-UB2197-1qcz. Assays are listed according to the position of the assay target along the T-DNA, with target c-AHAS located near the left T-DNA border and target c-d6Des(Ot_febit) near the right T-DNA border. Copy number results obtained on the T0 plants are indicated in parentheses. Homozygosity was indicated if the average result of the selected T1 plants was about two fold higher than the T0 generation.

Copy number assays targeting the T-DNA of VC-LLM306-1qcz rc. Assays are listed according to the position of the assay target along the T-DNA, with target j-p-BnFAE_ t-PvARC located near the left T-DNA border and target c-d4Des. (Eg_GA) near the right T-DNA border Copy number results obtained on the T0 plants are indicated in parentheses. Homozygosity was indicated if the average result of the selected TI plants was about two fold higher than the T0 generation.

| Event | c-AHAS | j-t-E9-p3-2 | c-d6EIo(Tp_GA) | j-t-StCAT_p2_p-LuPXR | c-d6Des(Ot_febit) | j-t-CaMV_p-LuCnl-2 | j-i-Atssl8_c-d6Elo(Pp_GA2) | c-d6Des(Ot_febit) | j-p-BnFAE_t-PvARC | c-d4Des(Tc_GA) | c-o3Des(Pi_GA2_SNP) | c-d5Elo(Ot_GA3) | j-i-Atss1_c-d5Elo(Ot_GA3) | c-d4Des(Eg_GA) |
|---|---|---|---|---|---|---|---|---|---|---|---|---|---|---|
| LAUAU (n = 18) | 3.1 (T0: 2) | | | | | | | | | 1.3 | (T0: 1.1) | | | |
| LALFWA (n = 16) | 3.1 (T0: 1.8) | | | | | | | | | 2.6 | (T0: 1.9) | | | (T0: 1.9) |
| LAUDF (n = 17) | 3.2 (T0: 2) | | | | | | | | | 3.3 | (T0: 2) | | | |
| LALTHK (n = 15) | 3.8 (T0: 2.1) | | | | | | | | | 2.1 | (T0: 1.1) | | | |
| LALTLE (n = 18) | 3.4 (T0: 2.8) | | | | | | | | | 2.4 | (T0: 2.4) | | | |
| LALIVY (n = 16) | 3 (T0: 1.9) | | | | | | | | | 3.1 | (T0: 2.1) | | | |
| LAUCX (n = 16) | 3.4 (T0: 1.9) | | | | | | | | | 3.4 | (T0: 1.8) | | | |

TABLE 25

Fatty acid profiles of T2 seeds harvested from T1 plants cultivated in the greenhouse of canola events containing the T-DNAs of plasmids VC-LJB2197-1qcz and VC-LLM306-1qcz rc. The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAUAU (n = 18) | 4.5 ± 0.1 | 0.1 ± 0 | 0 ± 0 | 3.6 ± 0.4 | 21.5 ± 1.8 | 31.6 ± 0.9 | 0.8 ± 0.2 | 3.3 ± 0.3 | 1.9 ± 0.7 | 0.2 ± 0.1 | 0.9 ± 0.1 | 0.7 ± 0.1 | 0.8 ± 0.4 |
| LALFWA (n = 16) | 4.5 ± 0.5 | 0.1 ± 0 | 0 ± 0 | 3.5 ± 0.5 | 20 ± 2 | 30 ± 2.1 | 1 ± 0.1 | 3.8 ± 0.4 | 2.6 ± 0.3 | 0.4 ± 0.1 | 0.8 ± 0.1 | 0.6 ± 0 | 0.2 ± 0.1 |
| LAUDF (n = 17) | 4.3 ± 0.7 | 0.2 ± 0.1 | 0 ± 0.1 | 3.3 ± 0.5 | 20.7 ± 4.1 | 29.3 ± 4 | 2.5 ± 5.9 | 4.1 ± 0.4 | 2.4 ± 0.5 | 0.7 ± 1.1 | 0.8 ± 0.1 | 0.7 ± 0.1 | 0.3 ± 0.1 |
| LALTHK (n = 15) | 4.7 ± 0.6 | 0.1 ± 0.1 | 0 ± 0 | 3.7 ± 0.4 | 21.4 ± 1.8 | 32.9 ± 1.9 | 0 ± 0.1 | 4.9 ± 0.6 | 0.6 ± 0.1 | 0 ± 0 | 1 ± 0.1 | 0.9 ± 0.1 | 1.7 ± 0.3 |
| LALTLE (n = 18) | 4.6 ± 0.6 | 0.1 ± 0 | 0 ± 0 | 3.6 ± 0.4 | 24.1 ± 4.5 | 29.8 ± 2.2 | 1 ± 0.3 | 4.2 ± 0.5 | 2 ± 0.6 | 0.3 ± 0.1 | 0.9 ± 0.1 | 0.7 ± 0.1 | 0.3 ± 0.3 |
| LALIVY (n = 16) | 5.4 ± 1 | 0.2 ± 0.1 | 0 ± 0 | 3.6 ± 0.4 | 21.6 ± 2.9 | 30.9 ± 2 | 0.9 ± 0.2 | 4.4 ± 0.5 | 2.1 ± 0.5 | 0.3 ± 0.1 | 0.8 ± 0.1 | 0.6 ± 0.2 | 0.3 ± 0.2 |
| LAUCX (n = 16) | 5 ± 0.1 | 0.2 ± 0 | 0 ± 0 | 3.4 ± 0.2 | 23.9 ± 1.6 | 32.4 ± 1.1 | 1.1 ± 0.1 | 4.1 ± 0.4 | 2.5 ± 0.3 | 0.4 ± 0 | 0.8 ± 0 | 0.7 ± 0 | 0.2 ± 0 |

TABLE 25-continued

Fatty acid profiles of T2 seeds harvested from T1 plants cultivated in the greenhouse of canola events containing the T-DNAs of plasmids VC-LJB2197-1qcz and VC-LLM306-1qcz rc. The events are indicated in the first column, along with the number of T2 seed batches that were measured per event. Per seed batch a random selection of ~30 seed was measured in two technical repeats.

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAUAU (n = 18) | 0.1 ± 0.2 | 3.7 ± 0.6 | 1.6 ± 0.4 | 8.6 ± 2.7 | 9.6 ± 1.4 | 0.3 ± 0 | 0 ± 0 | 0.8 ± 0.2 | 3.3 ± 0.6 | 0 ± 0 | 1.7 ± 0.5 | 0.1 ± 0.2 | |
| LALFWA (n = 16) | 0 ± 0 | 3.7 ± 0.4 | 1.9 ± 0.4 | 5.6 ± 2.3 | 11.6 ± 2.2 | 0.2 ± 0.1 | 0 ± 0 | 1.4 ± 0.3 | 4.7 ± 1.1 | 0 ± 0 | 2.6 ± 0.8 | 0.5 ± 0.4 | 0.4 ± 0 |
| LAUDF (n = 17) | 0 ± 0 | 2.7 ± 0.4 | 1.7 ± 0.3 | 4.6 ± 0.6 | 13.1 ± 3 | 0.3 ± 0 | 0 ± 0 | 0.9 ± 0.3 | 4.7 ± 1.2 | 0.1 ± 0.3 | 2.2 ± 0.6 | 0.2 ± 0.2 | 0.2 ± 0 |
| LALTHK (n = 15) | 0.7 ± 0.2 | 2.2 ± 0.3 | 1.6 ± 0.2 | 4.3 ± 0.8 | 18.9 ± 2.5 | 0.4 ± 0.1 | 0 ± 0 | 0 ± 0 | 0 ± 0 | 0 ± 0 | 0 ± 0 | 0 ± 0 | |
| LALTLE (n = 18) | 0 ± 0.1 | 3 ± 0.2 | 2 ± 0.3 | 3.8 ± 0.9 | 10.9 ± 3 | 0.1 ± 0.1 | 0 ± 0 | 1.4 ± 0.6 | 4.7 ± 1.1 | 0 ± 0 | 2.3 ± 0.8 | 0.2 ± 0.3 | 0.6 ± 0.1 |
| LALIVY (n = 16) | 0.1 ± 0.1 | 2.8 ± 0.2 | 1.9 ± 0.3 | 4.2 ± 1.2 | 10.4 ± 1.8 | 0.3 ± 0.1 | 0 ± 0 | 1.3 ± 0.3 | 4.4 ± 0.9 | 0 ± 0 | 2.4 ± 0.6 | 0.6 ± 0.2 | 0.5 ± 0.3 |
| LAUCX (n = 16) | 0 ± 0 | 2.5 ± 0.7 | 1.3 ± 0.3 | 4.2 ± 0.3 | 9.9 ± 0.7 | 0.3 ± 0 | 0 ± 0 | 1.1 ± 0.2 | 3.8 ± 0.3 | 0 ± 0 | 1.7 ± 0.2 | 0.4 ± 0.2 | |

TABLE 26

Fatty acid profiles of one T2 seed batch per event harvested from T1 plants cultivated in the greenhouse of canola events containing the T-DNAs of plasmids VC-LJB2197-1qcz and VC-LLM306-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LALJAU (n = 1) | 4.9 | 0.2 | 0.0 | 4.7 | 18.8 | 30.6 | 1.1 | 3.1 | 3.6 | 0.4 | 1.0 | 0.6 | 0.1 |
| LALFWA (n = 1) | 3.8 | 0.1 | 0.0 | 3.2 | 16.1 | 26.2 | 1.2 | 4.4 | 3.0 | 0.5 | 0.7 | 0.7 | 0.3 |
| LALJDF (n = 1) | 3.5 | 0.1 | 0.1 | 2.8 | 15.8 | 27.7 | 1.2 | 3.7 | 3.6 | 0.5 | 0.7 | 0.7 | 0.3 |
| LALTHK (n = 1) | 4.7 | 0.0 | 0.0 | 4.2 | 18.6 | 30.7 | 0.0 | 4.6 | 0.6 | 0.0 | 1.1 | 0.9 | 2.0 |
| LALTLE (n = 1) | 3.3 | 0.2 | 0.1 | 2.8 | 15.0 | 24.9 | 1.5 | 3.3 | 3.3 | 0.5 | 0.7 | 0.6 | 0.5 |
| LALIVY (n = 1) | 5.9 | 0.3 | 0.0 | 3.9 | 16.5 | 26.5 | 0.9 | 4.2 | 2.3 | 0.5 | 0.9 | 0.7 | 0.5 |
| LALJCX (n = 1) | 6.1 | 0.7 | 0.2 | 2.3 | 22.0 | 15.1 | 15.3 | 6.6 | 2.5 | 0.5 | 0.6 | 0.6 | 0.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LALJAU (n = 1) | 0.0 | 2.4 | 1.1 | 5.7 | 12.6 | 0.4 | 0.0 | 1.3 | 4.4 | 0.0 | 2.8 | 0.0 | 0.0 |
| LALFWA (n = 1) | 0.1 | 2.9 | 2.4 | 3.6 | 16.0 | 0.1 | 0.0 | 1.9 | 7.4 | 0.0 | 4.2 | 0.7 | 0.4 |
| LALJDF (n = 1) | 0.0 | 2.6 | 1.9 | 5.5 | 18.0 | 0.3 | 0.0 | 1.4 | 6.2 | 0.0 | 3.2 | 0.1 | 0.2 |
| LALTHK (n = 1) | 1.0 | 2.2 | 1.7 | 4.6 | 22.7 | 0.4 | 0.0 | 0.0 | 0.0 | 0.0 | 0.0 | 0.0 | |
| LALTLE (n = 1) | 0.0 | 3.1 | 2.2 | 5.7 | 17.6 | 0.3 | 0.0 | 2.4 | 6.9 | 0.0 | 4.1 | 0.5 | 0.5 |
| LALIVY (n = 1) | 0.3 | 2.6 | 2.2 | 3.9 | 14.2 | 0.4 | 0.0 | 1.7 | 6.7 | 0.0 | 4.2 | 0.6 | 0.0 |
| LALJCX (n = 1) | 0.0 | 1.2 | 0.9 | 4.6 | 10.0 | 0.4 | 0.0 | 0.8 | 5.5 | 0.0 | 3.5 | 0.0 | 0.0 |

TABLE 27

Phenotypic rating of T1 plants cultivated in the greenhouse of canola events containing the T-DNAs of plasmids VC-LJB2197-1qcz and VC-LLM306-1qcz rc.
The events are indicated in the first column, along with the number of T1 plants that where rated per event. DFF: days to first flower (days), DF: deformed flower (9 = deformed, 1 = normal), DL: deformed leaf (9 = deformed, 1 = normal), DP: deformed plant (9 = deformed, 1 = normal), DS: deformed silique (9 = deformed, 1 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoI: number of lobes(#), PH: plant height (cm), TKW: thousand kernel weight (g), SC: seed quality (1 = good, 9 = bad),

| Event | DFF | DF | DL | DP | DS | FC | LD |
|---|---|---|---|---|---|---|---|
| LAUAU (n = 18) | 62.2 ± 2.3 | 1 ± 0 | 1 ± 0 | 1 ± 0 | 1.9 ± 1 | 3 ± 0 | 3 ± 0 |
| LALFWA (n = 16) | 61.6 ± 3.3 | 1 ± 0 | 1.2 ± 0.8 | 1 ± 0 | 3.5 ± 2.4 | 3 ± 0 | 3 ± 0 |

TABLE 27-continued

Phenotypic rating of T1 plants cultivated in the greenhouse of canola events containing the
T-DNAs of plasmids VC-LJB2197-1qcz and VC-LLM306-1qcz rc.
The events are indicated in the first column, along with the number of T1 plants that where rated
per event. DFF: days to first flower (days), DF: deformed flower (9 = deformed, 1 = normal),
DL: deformed leaf (9 = deformed, 1 = normal), DP: deformed plant (9 = deformed,
1 = normal), DS: deformed silique (9 = deformed, 1 = normal), FC: flower color
(1 = white, 3 = optimal, 4 = orange/yellow), LD: leaf dentation (3 = no dentation,
7 = strong dentation), LGC: leaf color (3 = yellow, 5 = optimal, 7 = blueish),
LF: fertility (1 = low, 9 = very high), NoI: number of lobes(#), PH: plant
height (cm), TKW: thousand kernel weight (g), SC: seed quality (1 = good, 9 = bad),

| Event | | | | | | | |
|---|---|---|---|---|---|---|---|
| LAUDF (n = 17) | 58.7 ± 2.6 | 1 ± 0 | 1 ± 0 | 1 ± 0 | 1.6 ± 0.8 | 3 ± 0 | 3 ± 0 |
| LALTHK (n = 15) | 62.1 ± 5.5 | 1 ± 0 | 1 ± 0 | 1 ± 0 | 1.7 ± 1.1 | 3 ± 0 | 3 ± 0 |
| LALTLE (n = 18) | 67.8 ± 6.7 | 1 ± 0 | 1 ± 0 | 1 ± 0 | 1.7 ± 0.8 | 3 ± 0 | 3 ± 0 |
| LALIVY (n = 16) | 69.5 ± 6.2 | 1 ± 0 | 2.7 ± 1.4 | 1.3 ± 0.6 | 2.4 ± 1.4 | 3 ± 0 | 3 ± 0 |
| LALICX (n = 16) | 64.2 + 2.7 | 1 ± 0 | 2.7 ± 0.7 | 1 ± 0 | 1.4 ± 0.6 | 3 ± 0 | 3 ± 0 |

| Event | LGC | LF | NoL | PH | TKW | SC |
|---|---|---|---|---|---|---|
| LAUAU (n = 18) | 5 ± 0 | 1.3 ± 0.7 | 4 ± 0 | 129.7 ± 5.5 | 4.7 ± 0.2 | 2.1 ± 1 |
| LALFWA (n = 16) | 5 ± 0 | 3.1 ± 2.6 | 3.9 ± 0.5 | 127.7 ± 6.2 | 4.9 ± 0.4 | 3.5 ± 1.8 |
| LAUDF (n = 17) | 5 ± 0 | 1.2 ± 0.6 | 4 ± 0 | 128 ± 6.2 | 5 ± 0.2 | 2.4 ± 0.6 |
| LALTHK (n = 15) | 5 ± 0 | 1.1 ± 0.5 | 4 ± 0 | 124.3 ± 5 | 4.8 ± 0.3 | 3.1 ± 1.2 |
| LALTLE (n = 18) | 5 ± 0 | 1 ± 0 | 4 ± 0 | 126.7 ± 5.2 | 4.4 ± 0.3 | 4.2 ± 1.7 |
| LALIVY (n = 16) | 5 ± 0 | 1.6 ± 0.9 | 3.3 ± 1 | 127.1 ± 5.8 | 4.4 ± 0.4 | 4.9 ± 3.2 |
| LALICX (n = 16) | 5 ± 0 | 1 ± 0 | 4 ± 0 | 131.4 ± 5.7 | 4.5 ± 0.3 | 2.2 ± 0.9 |

Fatty Acid Profiles, Copy Number Measurements, and Phenotypic Observations of T2 Plants Carrying T-DNAs of Plasmids VC-LJB2197-1Qcz and VC-LLM306-1Qcz Rc Cultivated in Greenhouses During Summer Copy number analysis, see Table 28, indicates that the chosen events are largely homozygous for the genes encoded on the T-DNAs of VC-LJB2197-1qcz and VC-LLM306-1qcz rc. All events but LALTLE had two copies of the T-DNAs inserted into the genome. LALTLE appeared to have more than two copies with some segregation still ongoing. Based on the copy number analysis, LALJDF had integrated one copy of the d4Des(Eg_GA) gene and LALTLE was segregating for one or two copies of that gene. The EPA and DHA data in Table 29 and Table 30 indicated the events perform equally well with perhaps LALJDF accumulating less DHA, based on Table 30. Plant morphology was the same for all the events examined. As discussed above for T1 plants grown in the greenhouse, the event to event variation was minimal, suggesting that the impacts of insertion site position effects (both negative and positive) were similar for all events. The lack of insertion site effects indicates that the plasmid design/T-DNA topology was exerting a normalizing effect/mitigates insertion site effects.

TABLE 28

Copy number measurement of T2 plants cultivated in the greenhouse of canola events containing
the T-DNAs of plasmids VC-LJB2197-1qcz and VC-LLM306-1qcz re. The events are indicated
in the first column, along with the number of T2 plants that where measured per event. The
T2 plants underwent a selection from 250 segregating T2 seedlings using half-kernel analysis,
where the correlation of VCL-PUFA levels with copy number was employed to select
for homozygous plants, or in case of multilocus events to selecect for plants where one
or more loci are homozygous. A copy number of ~2 therefore was indicative for
one homozygous locus, a copy number of ~4 indicative for two homozygous loci or indicative
for one homozygous locus containing two copies of the target gene measured by the assay,
and so forth. Odd results of 3 and 5 indicate that at least some of the selected T2
plants carry a heterozygous locus.

Copy number assays targeting the T-DNA of VC-UB2197-lqcz.
Assays are listed according to the position of the assay target along
the T-DNA, with target c-AHAS located near the left T-DNA border
and target c-d6Des(Ot_febit) near the right T-DNA border.

| Event | c-AHAS | j-t-E9-p3-2 | c-d6Elo (Tp_GA) | j-t-StCAT_p2_p-LuPXR | c-d6Des (Ot_febit) | j-t-CaMV_p-LuCnl-2 | j-i-Atss18_c-d6Elo (Pp_GA2) |
|---|---|---|---|---|---|---|---|
| LALFWA (n = 30) | 4.0 | 3.6 | 3.7 | 3.9 | 7.7 | 4.6 | 3.7 |
| LALJDF (n = 30) | 4.2 | 3.9 | 3.9 | 3.8 | 8.5 | 3.3 | 3.5 |
| LALTLE (n = 30) | 5.2 | 4.6 | 4.7 | 5.0 | 8.9 | 4.4 | 1.8 |
| LALIVY (n = 30) | 4.1 | 3.6 | 3.7 | 3.8 | 8.1 | 4.4 | 5.4 |

TABLE 28-continued

Copy number measurement of T2 plants cultivated in the greenhouse of canola events containing the T-DNAs of plasmids VC-LJB2197-1qcz and VC-LLM306-1qcz re. The events are indicated in the first column, along with the number of T2 plants that where measured per event. The T2 plants underwent a selection from 250 segregating T2 seedlings using half-kernel analysis, where the correlation of VCL-PUFA levels with copy number was employed to select for homozygous plants, or in case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T2 plants carry a heterozygous locus.

Copy number assays targeting the T-DNA of VC-LLM306-1qcz rc. Assays are listed according to the position of the assay target along the T-DNA, with target j-p-BnFAE_ t-PvARC located near the left T-DNA border and target c-d4Des(Eg_GA) near the right T-DNA border.

| Event | c-d6Des (Ot_feb it) | j-p-BnFAE t-PvARC | c-d4Des (Tc_GA) | c-o3Des(Pi_GA2_SNP) | c-d5Elo (Ot_GA3) | j-i-Atss1_c-d5Elo (Ot_GA3) | c-d4Des (Eg_GA) |
|---|---|---|---|---|---|---|---|
| LALFWA (n = 30) | 7.7 | 3.5 | 3.7 | | | 3.5 | 3.5 |
| LALJDF (n = 30) | 8.5 | 5.1 | 4.1 | | | 4.0 | 2.2 |
| LALTLE (n = 30) | 8.9 | 2.6 | 3.6 | | | 4.6 | 3.2 |
| LALIVY (n = 30) | 8.1 | 3.7 | 4.0 | | | 3.8 | 3.5 |

TABLE 29

Fatty acid profiles of T3 seeds harvested from T2 plants cultivated in the greenhouse of canola events containing the T-DNAs of plasmids VC-LJB2197-1qcz and VC-LLM306-1qcz rc. The events are indicated in the first column, along with the number of T3 seed batches that where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LALFWA (n = 30) | 4.9 ± 0.2 | 0.3 ± 0.1 | 0.2 ± 0 | 4.4 ± 0.2 | 19.9 ± 0.8 | 29.5 ± 0.8 | 1.3 ± 0.1 | 3.2 ± 0.2 | 3 ± 0.2 | 0.4 ± 0 | 0.9 ± 0.1 | 0.6 ± 0 | 0.3 ± 0 |
| LALJDF (n = 30) | 5.4 ± 0.3 | 0.3 ± 0 | 0.2 ± 0 | 4.4 ± 0.2 | 21.4 ± 0.7 | 30.1 ± 1.1 | 1.2 ± 0.1 | 3.8 ± 0.3 | 2.7 ± 0.2 | 0.4 ± 0 | 0.9 ± 0 | 0.6 ± 0 | 0.1 ± 0.1 |
| LALTLE (n = 30) | 5.2 ± 0.4 | 0.3 ± 0 | 0.2 ± 0.1 | 4.6 ± 0.3 | 20.3 ± 0.8 | 28.7 ± 0.8 | 1.3 ± 0.2 | 3.4 + 0.3 | 2.8 + 0.2 | 0.4 + 0.1 | 0.8 + 0.1 | 0.5 + 0.1 | 0.3 + 0.1 |
| LALIVY (n = 30) | 5.3 ± 0.6 | 0.3 ± 0.1 | 0.2 ± 0 | 4.8 ± 0.5 | 20.4 ± 1.4 | 29.6 ± 1 | 1.2 ± 0.2 | 3.6 ± 0.2 | 2.7 ± 0.3 | 0.4 ± 0 | 0.9 ± 0.1 | 0.6 ± 0 | 0.4 ± 0.1 |
| WT Kumily (n = 46) | 5 ± 0.1 | 0.4 ± 0 | 0.2 ± 0 | 2.6 ± 0.1 | 66.3 + 1.7 | 16.8 + 1.3 | 0 ± 0 | 6.1 + 0.4 | 0 ± 0 | 0 ± 0 | 0.9 + 0 | 1.2 + 0 | 0 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LALFWA (n = 30) | 0 ± 0 | 3.8 ± 0.6 | 2.1 ± 0.3 | 4 ± 0.4 | 11.3 ± 0.6 | 0.3 ± 0 | 0 ± 0 | 1.7 ± 0.2 | 4.3 ± 0.3 | 0 ± 0 | 2.5 ± 0.2 | 0.7 ± 0.2 | 0.3 ± 0 |
| LALJDF (n = 30) | 0 ± 0 | 2.2 ± 0.2 | 1.4 ± 0.1 | 4.3 ± 0.2 | 12.4 ± 0.7 | 0.2 ± 0.1 | 0 ± 0 | 1 ± 0.1 | 4.4 ± 0.4 | 0 ± 0 | 2.2 ± 0.2 | 0.1 ± 0.1 | 0.2 ± 0.1 |
| LALTLE (n = 30) | 0.1 + 0.1 | 2.3 + 0.2 | 1.6 + 0.2 | 3.9 + 0.2 | 12.1 ± 0.7 | 0.2 + 0.1 | 0 ± 0 | 1.9 + 0.2 | 4.9 + 0.3 | 0 ± 0 | 2.9 + 0.4 | 0.5 + 0.1 | 0.3 + 0.1 |
| LALIVY (n = 30) | 0.1 ± 0.1 | 2.5 ± 0.3 | 1.7 ± 0.3 | 4 ± 0.7 | 11.4 ± 0.7 | 0.3 ± 0 | 0 ± 0 | 1.5 ± 0.1 | 4.5 ± 0.4 | 0 ± 0 | 2.7 ± 0.4 | 0.5 ± 0.2 | 0.3 ± 0.1 |
| WT Kumily (n = 46) | 0 ± 0 | 0 ± 0 | 0 ± 0 | 0 ± 0 | 0 ± 0 | 0.5 + 0 | 0 ± 0 | 0 ± 0 | 0 ± 0 | 0 ± 0 | 0 ± 0 | 0 ± 0 | 0 ± 0 |

TABLE 30

Fatty acid profiles of one T3 seed batch per event harvested from T2 plants cultivated in the greenhouse of canola events containing the T-DNAs of plasmids VC-LJB2197-1qcz and VC-LLM306-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LALFWA (n = 1) | 5.4 | 0.4 | 0.2 | 4.6 | 17.5 | 27.9 | 1.1 | 2.9 | 3.3 | 0.4 | 0.9 | 0.5 | 0.3 |
| LALJDF (n = 1) | 5.1 | 0.3 | 0.2 | 4.5 | 19.7 | 28.9 | 1.1 | 3.8 | 2.8 | 0.5 | 0.9 | 0.6 | 0.1 |

TABLE 30-continued

Fatty acid profiles of one T3 seed batch per event harvested from T2 plants cultivated in the greenhouse of canola events containing theT-DNAs of plasmids VC-LJB2197-1qcz and VC-LLM306-1qcz rc. The events are indicated in the first column. Fatty acid profiles of T3 seed batches having the highest EPA + DHA levels per event are shown. Per seed batch, a random selection of ~30 seed was measured in two technical repeats.

| | | | | | | | | | | | | | |
|---|---|---|---|---|---|---|---|---|---|---|---|---|---|
| LALTLE (n = 1) | 5.8 | 0.1 | 0.1 | 5.5 | 20.1 | 27.3 | 1.9 | 3.1 | 3.5 | 0.2 | 0.4 | 0.3 | 0.2 |
| LALIVY (n = 1) | 5.5 | 0.4 | 0.2 | 4.4 | 18.4 | 28.6 | 1.1 | 3.4 | 3.3 | 0.4 | 0.9 | 0.5 | 0.3 |
| LALHCY (n = 1) | 7.6 | 1.1 | 0.7 | 2.3 | 19.7 | 25.6 | 0.9 | 6.3 | 3.6 | 0.7 | 0.8 | 0.6 | 0.0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:6 n-6 | 22:6 n-3 | 22:4 n-3 | 20:2 n-9 |
|---|---|---|---|---|---|---|---|---|---|---|---|---|---|
| LALFWA (n = 1) | 0.0 | 3.7 | 2.0 | 4.5 | 12.7 | 0.3 | 0.0 | 2.2 | 5.0 | 0.0 | 3.2 | 0.6 | 0.3 |
| LALJDF (n = 1) | 0.0 | 2.4 | 1.6 | 4.4 | 13.7 | 0.3 | 0.0 | 1.1 | 5.1 | 0.0 | 2.5 | 0.2 | 0.2 |
| LALTLE (n = 1) | 0.0 | 1.9 | 0.7 | 4.0 | 13.4 | 0.1 | 0.0 | 1.1 | 5.5 | 0.0 | 4.2 | 0.2 | 0.1 |
| LALIVY (n = 1) | 0.0 | 2.2 | 1.4 | 5.3 | 12.8 | 0.3 | 0.0 | 1.8 | 5.0 | 0.0 | 3.4 | 0.2 | 0.2 |
| LALHCY (n = 1) | 0.0 | 1.2 | 1.1 | 3.9 | 10.4 | 0.0 | 0.0 | 1.0 | 7.0 | 0.0 | 3.4 | 0.0 | 0.0 |

TABLE 31

Phenotypic rating of T2 plants cultivated in the greenhouse o f canola events containing the T-DNAs of plasmids VC-LJB2197-1qcz and VC-LLM306-1qcz rc. The events are indicated in the first column, along with the number of T2 plants that where rated per event. DFF: days to first flower (days), DF: deformed flower (9 = deformed, 1 = normal), DL: deformed leaf (9 = deformed, 1 = normal), DP: deformed plant (9 = deformed, 1 = normal), DS: deformed silique (9 = deformed, 1 = normal), FC: flowe r color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes(#), PH: plant height (cm), Oil: oil content (% of seed weight), Protein: Protein content % of seed cake without oil)

| Event | DFF | DF | DL | DP | DS | FC | LD | LGC | LF | NoL | PH | Oil | Protein |
|---|---|---|---|---|---|---|---|---|---|---|---|---|---|
| LALFWA (n = 30) | 57.3 ± 2.2 | 9 ± 0 | 8.9 ± 0.4 | 8.9 ± 0.4 | 7.2 ± 1 | 3 ± 0 | 3 ± 0 | 5 ± 0 | 8 ± 1.2 | 3.9 ± 0.4 | 126.8 ± 4.3 | | |
| LAUDF (n = 30) | 58.1 ± 2.5 | 9 ± 0 | 9 ± 0 | 9 ± 0 | 7.7 ± 0.5 | 3 ± 0 | 3 ± 0 | 5 ± 0 | 8.2 ± 0.9 | 4 ± 0 | 130.2 ± 0.9 | | |
| LALTLE (n = 30) | 59.9 ± 2.8 | 9 ± 0 | 8.1 ± 1.3 | 8.8 ± 0.5 | 7.2 ± 0.9 | 3 ± 0 | 3 ± 0 | 5 ± 0 | 7.7 ± 1.3 | 3.9 ± 0.5 | 128 ± 2.8 | | |
| LALIVY (n = 30) | 59.6 ± 2.9 | 9 ± 0 | 8.8 ± 0.9 | 8.6 ± 1 | 6.8 ± 1.3 | 3 ± 0 | 3 ± 0 | 5 ± 0 | 7.3 ± 1.7 | 3.8 ± 0.6 | 126.8 ± 3.3 | | |
| WT Kumily (n = 46) | | | | | | | | | | | | 34.9 ± 1.1 | 32.2 ± 1 |

Fatty Acid Profiles, Copy Number Measurements, and Phenotypic Observations of T2 Plants Carrying T-DNAs of Plasmids VC-LJB2197-1Qcz and VC-LLM306-1Qcz Rc Cultivated in Field Trials in USDA Growth Zones 3a-4b and 5a During Summer.

The field data on Table 32 and Table 33 indicate a consistent performance across generations for T2 and T3. The data show that the PUFA (EPA and DHA) accumulation was higher for greenhouse grown plants. Besides levels in VLC-PUFA, there was also a difference in seed oil content observed compared to the greenhouse (e.g. comparing Table 34 and Table 31). Results of this analysis are described in Example 20. The field data also demonstrate that the greenhouse data accurately indicated the consistency between events with respect to EPA and DHA accumulation, though not overall levels. As remarked upon above for T1 and T2 plants grown in the greenhouse, the event to event variation was low for this construct, indicating that the T-DNAs/T-DNA design seem to be exerting a buffering/mitigating effect on gene silencing and other positional effects.

TABLE 32

Fatty acid profiles of T3 seeds harvested from T2 plants cultivated in the field corresponding to USDA growth zones 3a-4b and 5a. Field trials of canola events containing the T-DNAs of plasmids VC-LJB2197-1qcz and VC-LLM306-1qcz rc are given below. The events are indicated in the first column, along with the number of T3 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LALFWA (n = 30) | 5.1 ± 0.2 | 0.3 ± 0.1 | 0.1 ± 0 | 2.6 ± 0.2 | 25.1 ± 1.8 | 30.8 ± 1.4 | 1.1 ± 0.1 | 5.9 ± 0.9 | 1.8 ± 0.2 | 0.3 ± 0.1 | 0.7 ± 0 | 0.7 ± 0 | 0.4 ± 0.1 |
| LALJDF (n = 30) | 5.1 ± 0.3 | 0.3 ± 0 | 0.1 ± 0 | 2.7 ± 0.2 | 24.4 ± 1.7 | 29.4 ± 1.5 | 1.2 ± 0.1 | 5.6 ± 0.4 | 1.8 ± 0.2 | 0.3 ± 0 | 0.7 ± 0 | 0.7 ± 0 | 0.4 ± 0.1 |
| LALTLE (n = 30) | 5.4 ± 0.2 | 0.3 ± 0.1 | 0.1 ± 0 | 2.7 ± 0.2 | 26.4 ± 3.2 | 28.1 ± 1 | 1.2 + 0.2 | 5.6 + 0.6 | 1.7 + 0.3 | 0.3 + 0.1 | 0.7 + 0 | 0.7 + 0 | 0.5 + 0.2 |

TABLE 32-continued

Fatty acid profiles of T3 seeds harvested from T2 plants cultivated in the field corresponding to USDA growth zones 3a-4b and 5a. Field trials of canola events containing the T-DNAs of plasmids VC-LJB2197-1qcz and VC-LLM306-1qcz rc are given below. The events are indicated in the first column, along with the number of T3 seed aliquots representing a plot were measured per event. Per seed batch a random selection of ~30 seed was measured in two technical repeats.

| | | | | | | | | | | | | |
|---|---|---|---|---|---|---|---|---|---|---|---|---|
| LALIVY (n = 29) | 5.2 ± 0.4 | 0.3 ± 0.1 | 0.1 ± 0 | 2.9 ± 0.3 | 26.7 ± 3.1 | 28.3 ± 2.2 | 1 ± 0.2 | 6.3 ± 0.6 | 1.4 ± 0.3 | 0.3 ± 0 | 0.7 ± 0.1 | 0.8 ± 0.1 | 0.6 ± 0.2 |
| WT Kumily (n = 60) | 5 ± 0.3 | 0.4 ± 0 | 0.1 ± 0.1 | 2 ± 0.1 | 56.2 ± 4.2 | 23.3 ± 1.7 | 0 ± 0.1 | 9.5 ± 0.7 | 0.1 ± 0.2 | 0 ± 0 | 0.7 ± 0 | 1.1 ± 0.1 | 0.1 ± 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LALFWA (n = 30) | 0.1 ± 0.1 | 2.6 ± 0.3 | 1.4 ± 0.2 | 4.4 ± 1.2 | 8.5 ± 1.2 | 0.3 ± 0 | 0 ± 0 | 1.2 ± 0.2 | 4.4 ± 0.5 | 0 ± 0 | 1.4 ± 0.2 | 0.5 ± 0.2 | 0.3 ± 0.1 |
| LALJDF (n = 30) | 0.1 ± 0 | 2.2 ± 0.1 | 1.3 ± 0.1 | 4.5 ± 0.4 | 11.1 ± 0.9 | 0.2 ± 0.1 | 0 ± 0 | 0.9 ± 0.1 | 5.1 ± 0.4 | 0 ± 0 | 1.4 ± 0.2 | 0.1 ± 0.1 | 0.4 ± 0.1 |
| LALTLE (n = 30) | 0 ± 0.1 | 2.1 ± 0.2 | 1.2 ± 0.1 | 3.9 ± 0.5 | 9.6 ± 1.2 | 0.2 ± 0.1 | 0 ± 0 | 1.5 ± 0.2 | 5.3 ± 0.6 | 0 ± 0 | 1.5 ± 0.2 | 0.4 ± 0.2 | 0.5 ± 0.1 |
| LALIVY (n = 29) | 0.2 ± 0.1 | 2.1 ± 0.2 | 1.4 ± 0.1 | 3.3 ± 0.5 | 9.2 ± 1.1 | 0.3 ± 0.1 | 0 ± 0 | 1.3 ± 0.1 | 5 ± 0.5 | 0 ± 0 | 1.5 ± 0.2 | 0.5 ± 0.1 | 0.5 ± 0.1 |
| WT Kumily (n = 60) | 0 ± 0 | 0.2 ± 0.3 | 0.1 ± 0.3 | 0.2 ± 0.5 | 0.4 ± 1.1 | 0.3 ± 0.1 | 0 ± 0 | 0 ± 0.2 | 0.2 ± 0.6 | 0 ± 0 | 0 ± 0.2 | | |

TABLE 33

Fatty acid profiles of one T3 seed batch per event harvested from T2 plants cultivated in USDA growth zones 3a-4b and 5a field trials of canola events containing the T-DNAs of plasmids VC-LJB2197-1qcz and VC-LLM306-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LALFWA (n = 1) | 5.2 | 0.3 | 0.1 | 2.6 | 25.0 | 28.2 | 1.1 | 5.0 | 2.1 | 0.4 | 0.6 | 0.6 | 0.3 |
| LALJDF (n = 1) | 5.7 | 0.3 | 0.1 | 2.7 | 23.1 | 23.6 | 1.3 | 6.0 | 2.3 | 0.4 | 0.8 | 0.8 | 0.4 |
| LALTLE (n = 1) | 5.5 | 0.3 | 0.1 | 2.6 | 24.9 | 26.7 | 1.3 | 4.7 | 2.1 | 0.4 | 0.7 | 0.6 | 0.4 |
| LALIVY (n = 1) | 5.9 | 0.2 | 0.1 | 3.5 | 24.5 | 23.7 | 1.3 | 5.6 | 2.1 | 0.4 | 0.9 | 0.8 | 0.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LALFWA (n = 1) | 0.0 | 2.7 | 1.4 | 4.5 | 10.5 | 0.3 | 0.0 | 1.4 | 5.2 | 0.0 | 1.8 | 0.4 | 0.3 |
| LALJDF (n = 1) | 0.0 | 2.3 | 1.3 | 5.4 | 13.5 | 0.3 | 0.0 | 1.0 | 6.3 | 0.0 | 1.8 | 0.0 | 0.3 |
| LALTLE (n = 1) | 0.1 | 2.1 | 1.2 | 5.0 | 10.9 | 0.3 | 0.0 | 1.8 | 5.8 | 0.0 | 1.9 | 0.2 | 0.5 |
| LALIVY (n = 1) | 0.0 | 2.5 | 1.4 | 4.8 | 11.3 | 0.3 | 0.0 | 1.7 | 5.9 | 0.0 | 1.9 | 0.4 | 0.4 |

TABLE 34

Phenotypic rating of T2 plants cultivated in the field of canola events containing the T-DNAs of plasmids VC-LJB2197-1qcz and VC-LLM306-1qcz rc. The events are indicated in the first column, along with the number of field plots that where rated per event. Oil: oil content (% of seed weight), protein: Protein content (% of seed cake without oil)

| Event | Oil | protein |
|---|---|---|
| LALFWA (n = 30) | 38.2 ± 1 | 27.9 ± 0.6 |
| LALJDF (n = 30) | 37.6 ± 1.2 | 27.9 ± 0.8 |
| LALTLE (n = 30) | 38.2 ± 0.9 | 27.5 ± 0.7 |
| LALIVY (n = 29) | 37.6 ± 0.6 | 27.8 ± 0.5 |
| WT Kumily (n = 60) | 38.7 ± 1.1 | |

Example 11: Plants Containing the T-DNAs of Plasmid VC-LJB2197-1Qcz and VC-LLM337-1Qcz rc (Combination B in Example 5) for Production of EPA and DHA in Seeds In this example, the genetic elements required for EPA and DHA synthesis were transferred into the plant genome on two different T-DNAs. To this end, the two different plasmids VC-LJB2197-Tqcz and VC-LLM337-Dqcz rc containing two different T-DNAs were cloned into agrobacteria, and plant tissue was incubated according to Example 5 at the same time with these two agrobacterial cultures that were identical apart from containing either VC-LJB2197-11qcz or VC-LLM337-1qcz rc. Due to the selectable herbicide resistance marker, regenerated plants contained the T-DNA of VC-LJB2197-1qcz. Only those plants were kept, that also contained the T-DNA of plasmid VC-LLM337-11qcz rc as confirmed by PCR, conducted as described in Example 24, which contains PCR protocols for both gene expression and copy number analysis. Only plants containing the T-DNA of plasmid VC-LJB2197-1qcz as well as the T-DNA of plasmid VC-LLM337-1qcz rc combined all the genetic elements required for EPA and DHA synthesis in seeds. The genetic elements of VC-LJB2197-1qcz and the function of each element were listed in Table 1. The genetic elements of VC-LLM337-1qcz rc and the function of each element were listed in Table 4. For convenience, all enzymes expressed in seeds of plants carrying both T-DNA of VC-LJB2197-1qcz and VC-LLM337-1qcz rc that were required for EPA and DHA synthesis are additionally listed on Table 35.

TABLE 35

Combined list of genes essential of EPA and DHA synthesis carried by the T-DNAs of plasmids VC-LJB2197-1qcz and VC-LLM337-1qcz rc.

| Genes encoding enzmyes for EPA and DHA synthesis | Plasmid containing T-DNA with the gene | Length | Enzymatic function and source of encoded protein |
|---|---|---|---|
| c-d12Des(Ps_GA) | VC-LJB2197-1qcz | 1196 | Delta-12 desaturase from *Phythophthora sojae* |
| c-d6Des(Ot_febit) | VC-LJB2197-1qcz | 1370 | Delta-6 desaturase from *Ostreococcus tauri* |
| c-d6Elo(Pp_GA2) | VC-LJB2197-1qcz | 872 | Delta-6 elongase from *Physcomitrella patens* |
| c-d6Elo(Tp_GA2) | VC-LJB2197-1qcz | 818 | Delta-6 elongase from *Thalassiosira pseudonana* |
| c-d5Des(Tc_GA2) | VC-LJB2197-1qcz | 1319 | Delta-5 desaturase from *Thraustochytrium* sp. ATCC21685 |

TABLE 35-continued

Combined list of genes essential of EPA and DHA synthesis carried by the T-DNAs of plasmids VC-LJB2197-1qcz and VC-LLM337-1qcz rc.

| Genes encoding enzmyes for EPA and DHA synthesis | Plasmid containing T-DNA with the gene | Length | Enzymatic function and source of encoded protein |
|---|---|---|---|
| c-o3Des(Pi_GA2) | VC-LLM337-1qcz rc | 1085 | Omega-3-desaturase from *Phythophthora infestans* |
| c-o3Des(Pir_GA) | VC-LLM337-1qcz rc | 1091 | Omega-3 desaturase from *Pythium irregulare* |
| c-d5Elo(Ot_GA3) | VC-LLM337-1qcz rc | 902 | Delta-5 elongase from *Ostreococcus tauri* |
| c-d4Des(Eg_GA) | VC-LLM337-1qcz rc | 1625 | Delta-4 desaturase from *Euglena gracilis* |
| c-d4Des(Tc_GA) | VC-LLM337-1qcz rc | 1559 | Delta-4 desaturase from *Thraustochytrium* sp. |

Fatty Acid Profiles, Copy Number Measurements, and Phenotypic Observations of T0 Plants Carrying T-DNAs of Plasmids VC-LJB2197-1Qcz and VC-LLM337-1Qcz Rc Cultivated in Greenhouses During Summer Table 34 indicates that the T-DNA integrated as predominantly single and double copies. As observed in Example 10 there was an increase in EPA and DHA between one copy and two copies of the T-DNA from the two constructs, see Table 36, but less of a difference between two and three copies. The T1 data in Table 37 reflects this as well. As noted in Example 10, there was no observed alteration of the phenotype of the plants bearing the T-DNA from both constructs, regardless of copy number (up to three).

TABLE 36

Copy number measurement of T2 plants cultivated in the greenhouse of canola events containing the T-DNAs of plasmids VC-LJB2197-1qcz and VC-LLM306-1qcz rc.
Considering each event in this generation was represented by only 1 plant, all events have been grouped into the categories indicated in the first column; sc; all T0 plants where the average of all copy number assays listed in this table was 0.51-1.49, dc: all T0 plants where the average of all copy number assays listed in this table was 1.51-2.49, tc: all T0 plants where the average of all copy number assays listed in this table was 2.51-3.49.

Copy number assays targeting the T-DNA of VC-LJB2197-1qcz.
Assays are listed according to the position of the assay target along the T-DNA, with target c-AHAS located near the left T-DNA border and target j-i-Atss18_c-d6Elo(Pp_GA2) near the right T-DNA border.

| Event | c-AHAS | j-t-E9-p3-2 | c-d6Elo (Tp_GA) | j-t-StCAT_p2_p-LuPXR | j-t-CaMV_p-LuCnl-2 | c-d6Elo (Pp_GA) | j-i-Atss18_c-d6Elo (Pp_GA2) |
|---|---|---|---|---|---|---|---|
| sc (n = 563) | 1.1 | | | | | 1.1 | |
| dc (n = 423) | 1.4 | | | | | 1.6 | |
| tc (n = 17) | 2.0 | | | | | 2.6 | |

Copy number assays targeting the T-DNA of VC-LLM337-1qcz rc.
Assays are listed according to the position of the assay target along the T-DNA, with target j-t-PvARC-p3 located near the left T-DNA border and target c-d4Des(Eg_GA) near the right T-DNA border.

| Event | j-t-PvARC-p3 | c-d4Des (Tc_GA) | c-o3Des (Pi_GA2_SNP) | j-i-Atss15_c-o3Des (Pi_GA2) | c-o3Des (Pir_GA) | j-p-VfSBPperm3_c-o3Des(Pir_GA) | j-i-Atss1_c-d5Elo (Ot_GA3) | c-d4Des (Eg_GA) |
|---|---|---|---|---|---|---|---|---|
| sc (n = 563) | | 1.2 | 1.2 | 1.2 | 1.2 | | | 1.2 |
| dc (n = 423) | | 2.0 | 2.0 | 2.0 | 1.8 | | | 2.2 |
| tc (n = 17) | | 2.8 | 1.8 | 3.2 | 2.4 | | | 3.8 |

TABLE 37

Fatty acid profiles of T1 seeds harvested from T0 plants cultivated in the greenhouse of canola events containing the T-DNAs of plasmids VC-LJB2197-1qcz and VC-LLM337-1qcz rc. Considering each event in this generation was represented by only 1 plant, all events have been grouped into the categories indicated in the first column as described in Table 36. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 563) | 5.1 ± 0.6 | 0.3 ± 0.1 | 0.1 ± 0 | 3 ± 0.5 | 40.6 ± 6.2 | 29.4 ± 4.2 | 0.7 ± 4.7 | 6 ± 1.1 | 0.5 ± 0.6 | 0.1 ± 0.2 | 0.8 ± 0.1 | 0.9 ± 0.2 | 0.9 ± 0.6 |
| dc (n = 423) | 5 ± 0.8 | 0.3 ± 0.1 | 0.1 ± 0 | 3.1 ± 0.6 | 38.6 ± 8.2 | 28.8 ± 5.3 | 1.1 ± 5.9 | 5.9 ± 1.2 | 0.7 ± 0.6 | 0.1 ± 0.1 | 0.8 ± 0.1 | 0.9 ± 0.2 | 0.8 ± 0.6 |
| tc (n = 17) | 5 ± 0.9 | 0.3 ± 0.1 | 0.1 ± 0 | 3.1 ± 0.7 | 39.1 ± 8.1 | 28.4 ± 4.5 | 0.5 ± 0.3 | 6.1 ± 1.5 | 0.9 ± 0.6 | 0.2 ± 0.1 | 0.8 ± 0.2 | 0.9 ± 0.2 | 0.7 ± 0.6 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 563) | 0.3 ± 0.3 | 1.6 ± 0.8 | 0.9 ± 0.5 | 2.1 ± 1.3 | 3.4 ± 1.2 | 0.3 ± 0.1 | 0 ± 0 | 0.4 ± 0.3 | 1.5 ± 0.5 | 0 ± 0 | 0.6 ± 0.3 | 0.3 ± 0.3 | |
| dc (n = 423) | 0.3 ± 0.3 | 1.7 ± 0.9 | 1 ± 0.5 | 2.1 ± 1.5 | 4.3 ± 2 | 0.3 ± 0.1 | 0 ± 0 | 0.6 ± 0.4 | 1.9 ± 0.9 | 0 ± 0 | 0.8 ± 0.5 | 0.4 ± 0.3 | |
| tc (n = 17) | 0.3 ± 0.2 | 2.1 ± 2.1 | 1.2 ± 1 | 1.9 ± 2.4 | 4 ± 2.9 | 0.3 ± 0.1 | 0 ± 0 | 0.7 ± 0.4 | 1.9 ± 1.1 | 0 ± 0 | 0.8 ± 0.5 | 0.8 ± 0.9 | |

TABLE 38

Fatty acid profiles of T1 seeds harvested from T0 plants cultivated in the greenhouse of canola events containing the T-DNAs of plasmids VC-LJB2197-1qcz and VC-LLM337-1qcz rc. Considering each event in this generation was represented by only 1 plant, all events have been grouped into the categories indicated in the first column as described in Table 36. For each category, the fatty acid profile of the plant/event having the highest EPA+DHA levels was shown. Per seed batch a random selection of -30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 3.6 | 0.1 | 0.1 | 2.8 | 37.6 | 22.1 | 0.8 | 6.4 | 0.5 | 0.3 | 0.8 | 1.2 | 1.1 |
| dc (n = 1) | 7.1 | 0.0 | 0.0 | 4.5 | 3.2 | 1.5 | 44.5 | 0.3 | 0.0 | 0.0 | 1.0 | 1.1 | 2.3 |
| tc (n = 1) | 3.4 | 0.1 | 0.0 | 2.8 | 29.4 | 27.4 | 0.6 | 6.6 | 1.0 | 0.3 | 0.7 | 0.9 | 1.1 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.6 | 1.8 | 2.1 | 2.9 | 9.0 | 0.4 | 0.0 | 0.5 | 3.5 | 0.0 | 1.6 | 0.3 | |
| dc (n = 1) | 0.5 | 9.8 | 1.8 | 0.0 | 12.6 | 0.4 | 0.0 | 1.3 | 4.9 | 0.0 | 2.8 | 0.6 | |
| tc (n = 1) | 0.5 | 1.5 | 1.6 | 2.6 | 10.4 | 0.3 | 0.0 | 1.1 | 5.1 | 0.0 | 1.9 | 0.5 | |

TABLE 39

Phenotypic rating of T0 plants cultivated in the greenhouse of canola events containing the T-DNAs of plasmids VC-LJB2197-1qcz and VC-LLM337-1qcz rc. Considering each event in this generation was represented by only 1 plant, all events have been grouped into the categories indicated in the first column as described in Table 36. The number of T0 plants/events fullfilling these criteria are displayed in parentheses. DFF: days to first flower (days), DF: deformed flower (9 = deformed, 1 = normal), DL: deformed leaf (9 = deformed, 1 = normal), DP: deformed plant (9 = deformed, 1 = normal), S: deformed silique (9 = deformed, 1 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm), TKW: thousand kernel weight (g), SC: seed quality (1 = good, 9 = bad)

| Category of T0 plants | DFF | DF | DL | DP | DS | FC | LD |
|---|---|---|---|---|---|---|---|
| sc (n = 563) | 66.1 ± 8.3 | 1 ± 0 | 1.4 ± 1.1 | 1.7 ± 1.6 | 3 ± 2.8 | 3 ± 0 | 3 ± 0.1 |
| dc (n = 423) | 66 ± 7.5 | 1 ± 0 | 1.4 ± 1.2 | 1.7 ± 1.4 | 3 ± 2.9 | 3 ± 0 | 3 ± 0.1 |
| tc (n = 17) | 64.6 + 7.4 | 1 ± 0 | 1.5 + 1.5 | 2.8 + 2.5 | 4.4 ± 3.7 | 3 ± 0 | 3 ± 0 |

| Category of T0 plants | LGC | LF | NoL | PH | TKW | SC |
|---|---|---|---|---|---|---|
| sc (n = 563) | 5 ± 0 | 3.2 ± 2.6 | 3.8 ± 0.6 | 119.5 ± 9.8 | 4.7 ± 0.6 | 4.8 ± 2.5 |
| dc (n = 423) | 5 ± 0.1 | 3.1 ± 2.6 | 3.7 ± 0.7 | 119.2 ± 9.5 | 4.6 ± 0.6 | 5 ± 2.3 |
| tc (n = 17) | 5 ± 0 | 4.5 ± 3.5 | 3.9 ± 0.5 | 117.1 ± 10.5 | 4.6 ± 0.4 | 6.5 + 2.2 |

Fatty Acid Profiles, Copy Number Measurements, and Phenotypic Observations of T1 Plants Carrying T-DNAs of Plasmids VC-LJB2197-1Qcz and VC-LLM337-1Qcz Rc Cultivated in Greenhouses During Winter The data on Table 39 indicate that the integration of these two T-DNA's (VC-LJB2197-1qcz and VC-LLM337-1qcz rc), has occurred in such a way as to introduce copy number variation of individual genes on a given T-DNA (indicating truncations and deletions along with multiple copies being inserted). For example the event LAMABL on Table 39 was segregating for a single copy of AHAS (homozygous), two copies of j-t-StCAT_p2_p-LuPXR (homozygous), possibly three copies of c-d6Elo(Pp_GA) likely homozygous, though it could be three copies which are not homozygous for all three, and three copies of j-i-Atss18_c-d6Elo(Pp_GA2) (homozygous for all three). Data on Table 42 to Table 45 for fatty acid profile indicates some variation among the events, though not large differences. The highest event average for both DHA and EPA for the events listed on Table 41 was LAMRHL which has DHA of 1.9 and EPA of 10.5 with respect to percent of the total fatty acid content of the seed and contains what was likely a single copy of the T-DNA of of VC-LJB2197-1qcz still segregating, while VC-LLM337-1qcz rc seems to be a single copy homozygous insertion. The event, LANMGC, with the lowest levels of EPA and DHA combined, contained EPA of 3.7 and 0.8 for DHA with respect to percent of the total fatty acid content of the seed. LANMGC appeared to be homozygous single copy for VC-LJB2197 and carried at least two separate integrations of VC-LLM337. For the highest single plant level of EPA and DHA, event LAPWLP had 3.2 percent of DHA and 15.9 percent of EPA with respect to percentage of total fatty acids in the seed, Table 43. The data indicate that the location of the insertion site is important for EPA and DHA accumulation in this combination of constructs. As seen in previous examples, comparison of single copy insertions versus double copy insertions revealed that between single copy and double copy containing plants there was an increase in VLC-PUFA levels, but between double and triple copy containing plants there was less distinction. Table 46 displays phenotypic scoring/assessment and shows some small differences in aerial phenotype among events and between the transformed plants and untransformed reference.

TABLE 40

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-LJB2197-1qcz. Assays are listed according to the position of the assay target along the T-DNA, with target c-AHAS located near the left T-DNA border and target j-i-Atss18_c-d6Elo(Pp_GA2) near the right T-DNA border. Copy number results obtained on the T0 plants are indicated in parentheses. Homozygosity was indicated if the average result of the selected T1 plants was about two fold higher than the T0 generation.

| Event | c-AHAS | j-t-E9-p3-2 | c-d6Elo(Tp_GA) | j-t-StCAT_p2_p- | j-t-CaMV_p-LuCnl-2 | c-d6Elo(Pp_GA) | j-i-Atss18_c-o3Des(Pir_GA3) |
|---|---|---|---|---|---|---|---|
| LALHCY (n = 15) | 2.9 (T0: 1.8) | 4.4 | | 4.6 | 3.5 | 1.9 (T0: 1.1) | 2.0 |
| LALIAO (n = 15) | 3 (T0: 1.8) | 2.7 | | 3.3 | 3.6 | 2.8 (T0: 1.9) | 3.1 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LALJKA (n = 15) | 2 (T0: 1.1) | 2.0 | 2.0 | 4.1 | 3.6 (T0: 1.9) | 3.8 |
| LALLTL (n = 11) | 1.7 (T0: 1.8) | 3.5 | 3.5 | 3.1 | 3.2 (T0: 3) | 3.2 |
| LALQAM (n = 15) | 3.4 (T0: 1.9) | 3.3 | 3.3 | 3.1 | 3.3 (T0: 1.9) | 3.3 |
| LALQDS (n = 14) | 2.7 (T0: 2) | 2.8 | 3.6 | 2.3 | 2.3 (T0: 2.2) | 2.3 |
| LALRCQ (n = 14) | 3.2 (T0: 2) | 3.2 | 3.3 | 3.0 | 3.2 (T0: 2.1) | 3.3 |
| LALWKF (n = 14) | 1.9 (T0: 1.2) | 1.9 | 4.8 | 4.8 | 4.7 (T0: 3.2) | 4.8 |
| LAMABL (n = 8) | 1.8 (T0: 1) | 1.9 | 3.6 | 5.8 | 5.2 (T0: 3.7) | 5.6 |
| LAMCKI (n = 10) | 2 (T0: 1) | 3.9 | 3.6 | 2.7 | 2.3 (T0: 1) | 2.0 |
| LAMCLE (n = 14) | 3 (T0: 2) | 3.0 | 4.3 | 4.2 | 4.2 (T0: 2.9) | 4.4 |
| LAMCLF (n = 9) | 1.6 (T0: 1) | 3.3 | 4.1 | 4.7 | 4.4 (T0: 2.8) | 3.8 |
| LAMEUB (n = 15) | 1.9 (T0: 1) | 2.1 | 3.6 | 3.9 | 3.7 (T0: 2.2) | 3.8 |
| LAMEUU (n = 13) | 1.9 (T0: 0.9) | 3.8 | 3.3 | 5.6 | 5.4 (T0: 2.8) | 5.2 |
| LAMFJO (n = 15) | 2 (T0: 1.1) | 2.1 | 2.0 | 2.1 | 2 (T0: 0.9) | 2.0 |
| LAMIRY (n = 10) | 1.9 (T0: 1) | 1.9 | 2.6 | 2.7 | 2.7 (T0: 2) | 2.8 |
| LAMJIC (n = 9) | 1.9 (T0: 1.1) | 1.7 | 1.6 | 2.5 | 1.8 (T0: 1) | 1.8 |
| LAMPJB (n = 13) | 2.8 (T0: 2) | 2.9 | 3.6 | 4.4 | 4.1 (T0: 3) | 4.1 |
| LAMQDL (n = 14) | 2 (T0: 1) | 2.1 | 2.3 | 2.6 | 2.3 (T0: 1) | 2.0 |
| LAMQNE (n = 14) | 2.6 (T0: 1.1) | 2.6 | 2.7 | 2.8 | 2.8 (T0: 1.3) | 2.5 |
| LAMQSF (n = 14) | 3.5 (T0:: 2.1) | 4.5 | 3.8 | 4.7 | 4.2 (T0: 3.2) | 4.0 |
| LAMRCO (n = 14) | 2.8 (T0: 1.9) | 3.7 | 6.6 | 6.5 | 6 (T0: 4.1) | 5.5 |
| LAMRDS (n = 15) | 3.2 (T0: 1.9) | 3.2 | 3.0 | 3.6 | 3 (T0: 1.8) | 3.0 |
| LAMRHL (n = 14) | 2 (T0: 1.3) | 2.2 | 3.2 | 2.8 | 2.1 (T0: 1.5) | 1.9 |
| LAMRJK (n = 15) | 3 (T0: 2) | 3.0 | 2.9 | 1.3 | 1.2 (T0: 0.9) | 1.0 |
| LAMRNQ (n = 9) | 2.2 (T0: 1.9) | 2.1 | 2.2 | 2.3 | 2.3 (T0: 2.1) | 2.1 |
| LAMVUB (n = 15) | 2.1 (T0: 1.1) | 2.1 | 2.1 | 2.7 | 2.1 (T0: 1) | 2.1 |
| LAMYDP (n = 14) | 3.9 (T0: 2) | 4.0 | 3.7 | 4.2 | 3.8 (T0: 1.9) | 3.9 |
| LANBCH (n = 14) | 3.5 (T0: 1.9) | 3.2 | 3.3 | 4.0 | 3.5 (T0: 2) | 3.4 |
| LANCEG (n = 4) | 4 (T0: 2.1) | 4.0 | 3.5 | 5.9 | 5.4 (T0: 2.9) | 3.6 |
| LANCOX (n = 10) | 2.2 (T0: 1) | 2.5 | 2.2 | 5.4 | 5.1 (T0: 4.3) | 4.5 |
| LANFEF (n = 15) | 2.1 (T0: 1.1) | 2.0 | 2.3 | 2.6 | 2.1 (T0: 1) | 2.1 |
| LANMGC (n = 15) | 4.2 (T0: 1.9) | 4.0 | 4.1 | 4.7 | 4.2 (T0: 2) | 4.2 |
| LANMOM (n = 10) | 1.4 (T0: 1.2) | 1.4 | 3.0 | 2.7 | 2 (T0: 1.1) | 1.5 |
| LANPMZ (n = 13) | 2.1 (T0: 1.1) | 2.1 | 2.0 | 2.3 | 2.2 (T0: 1) | 2.2 |
| LANTLE (n = 15) | 2.7 (T0: 2) | 2.8 | 2.7 | 3.3 | 2.8 (T0: 2) | 3.0 |
| LANTSP (n = 12) | 1.4 (T0: 1) | 1.3 | 2.9 | 3.7 | 3 (T0: 1.9) | 3.0 |
| LANUCB (n = 14) | 2 (T0: 1.1) | 2.1 | 4.6 | 4.5 | 3.5 (T0: 2.1) | 3.1 |
| LAOBGQ (n = 15) | 1.4 (T0: 1) | 1.4 | 6.1 | 5.2 | 4 (T0: 2.8) | 4.2 |
| LAOHLR (n = 14) | 1.9 (T0: 1.2) | 4.9 | 4.0 | 4.3 | 3.7 (T0: 2) | 3.1 |
| LAOJAT (n = 15) | 2.2 (T0: 1.9) | 3.4 | 3.2 | 3.8 | 3.4 (T0: 3) | 3.3 |
| LAOKLP (n = 15) | 2.1 (T0: 0.8) | 2.1 | 2.1 | 2.5 | 2.2 (T0: 1) | 2.1 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LAOKTE (n = 15) | 3 (T0: 2) | 2.8 | 3.5 | 3.5 | 3.3 (T0: 2.1) | 3.2 |
| LAPKLS (n = 12) | 3.4 (T0: 2.1) | 3.1 | 3.6 | 4.2 | 3.1 (T0: 2.1) | 3.2 |
| LAPKXM (n = 15) | 3.2 (T0: 1.8) | 3.2 | 3.8 | 4.2 | 3.3 (T0: 2) | 3.4 |
| LAPKZJ (n = 15) | 3.3 (T0: 1.4) | 3.2 | 3.6 | 4.3 | 3.2 (T0: 1.9) | 3.3 |
| LAPWJD (n = 14) | 2.1 (T0: 1.1) | 2.0 | 2.3 | 2.8 | 2.1 (T0: 1) | 2.1 |
| LAPWLP (n = 14) | 1.3 (T0: 1.1) | 1.2 | 3.1 | 3.4 | 2.8 (T0: 1.9) | 2.9 |
| LAQYTA (n = 15) | 4.5 (T0: 2.8) | 5.1 | 5.0 | 3.2 | 2.6 (T0: 2.1) | 2.8 |
| LAQYUT (n = 15) | 4.3 (T0: 1.9) | 3.9 | 4.6 | 4.3 | 3 (T0: 2) | 2.8 |
| LAQYWQ (n = 15) | 2.6 (T0: 1.2) | 2.8 | 5.6 | 5.9 | 4.5 (T0: 3) | 4.6 |
| LAQZME (n = 12) | 1.4 (T0: 1.2) | 1.3 | 3.7 | 4.4 | 3.8 (T0: 2.3) | 4.0 |

Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border. Copy number results obtained on the T0 plants are indicated in parentheses. Homozygosity was indicated if the average result of the selected T1 plants was about two fold higher than the T0 generation.

| Event | j-t-PvARC-p3 | c-d4Des(Tc_GA) | j-i-Atss15_c-o3Des(Pi_GA2) | c-o3Des(Pir_GA) | j-p-VfSBPperm3-c-o3Des(Pir_GA) | j-i-Atss1_c-d5Elo(Ot_GA3) | c-d4Des-(Eg_GA) |
|---|---|---|---|---|---|---|---|
| LALHCY (n = 15) | 2.9 | 2.9 (T0: 2.1) | (T0: 2.6) | (T0: 2.1) | | 4.5 | 3.0 |
| LALIAO (n = 15) | 3.2 | 2.8 (T0: 2) | (T0: 2.2) | (T0: 1.9) | | 2.9 | 1.5 |
| LALJKA (n = 15) | 3.5 | 3.8 (T0: 2) | (T0: 1.9) | | | 4.0 | 5.5 |
| LALLTL (n = 11) | 2.3 | 2.4 (T0: 2) | (T0: 1.9) | | | 2.3 | 2.8 |
| LALQAM (n = 15) | 2.9 | 3.1 (T0: 2) | (T0: 2.1) | | | 1.6 | 1.6 |
| LALQDS (n = 14) | 2.8 | 2.9 (T0: 2) | (T0: 1.9) | | | 4.0 | 2.8 |
| LALRCQ (n = 14) | 3.0 | 3.2 (T0: 2.1) | (T0: 2.2) | | | 4.4 | 4.3 |
| LALWKF (n = 14) | 1.4 | 1.3 (T0: 1) | (T0: 1) | | | 1.3 | 1.3 |
| LAMABL (n = 8) | 1.9 | 1.8 (T0: 1) | (T0: 1) | (T0: 1.2) | | 1.8 | 3.5 |
| LAMCKI (n = 10) | 3.8 | 4 (T0: 1.9) | (T0: 2.1) | (T0: 1.8) | | 3.9 | 3.9 |
| LAMCLE (n = 14) | 2.5 | 2.4 (T0: 2) | (T0: 2) | (T0: 2.1) | | 3.4 | 1.3 |
| LAMCLF (n = 9) | 2.2 | 1.8 (T0: 2.1) | (T0: 1.9) | (T0: 1.4) | | 1.8 | 1.8 |
| LAMEUB (n = 15) | 1.3 | 1.2 (T0: 1) | (T0: 1) | | | 1.2 | 1.1 |
| LAMEUU (n = 13) | 3.1 | 3.8 (T0: 1.9) | (T0: 1.9) | | | 3.7 | 3.7 |
| LAMFJO (n = 15) | 1.1 | 1.1 (T0: 0.5) | (T0: 0.8) | | | 1.2 | 1.1 |
| LAMIRY (n = 10) | 1.7 | 2 (T0: 2.3) | (T0: 2) | | | 3.1 | 2.1 |
| LAMJIC (n = 9) | 2.3 | 1.8 (T0: 1) | (T0: 1) | | | 1.8 | 1.8 |
| LAMPJB (n = 13) | 2.6 | 2.8 (T0: 2.1) | (T0: 1) | (T0: 1.8) | | 2.8 | 2.6 |
| LAMQDL (n = 14) | 0.0 | 2.6 (T0: 2) | (T0: 1) | (T0: 1) | | 1.3 | 1.3 |
| LAMQNE (n = 14) | 2.0 | 1.5 (T0: 1.1) | (T0: 0.9) | (T0: 1.9) | | 4.0 | 4.2 |
| LAMQSF (n = 14) | 2.9 | 3.7 (T0: 3.9) | (T0: 4.2) | (T0: 2.2) | | 3.6 | 3.6 |
| LAMRCO (n = 14) | 1.8 | 1.3 (T0: 1.1) | (T0: 1) | (T0: 2.1) | | 3.9 | 2.5 |
| LAMRDS (n = 15) | 3.0 | 3 (T0: 2) | (T0: 1.9) | (T0: 1.7) | | 3.1 | 2.6 |
| LAMRHL (n = 14) | 4.1 | 3.8 (T0: 2.7) | (T0: 1.3) | (T0: 1.3) | | 1.9 | 2.0 |
| LAMRJK (n = 15) | 3.0 | 4.5 (T0: 2.9) | (T0: 1.9) | (T0: 1.7) | | 2.9 | 2.7 |
| LAMRNQ (n = 9) | 2.5 | 2 (T0: 1.9) | (T0: 2) | (T0: 1.9) | | 2.0 | 2.7 |
| LAMVUB (n = 15) | 0.6 | 0.8 (T0: 0.8) | (T0: 0.9) | | | 1.1 | 0.8 |
| LAMYDP (n = 14) | 3.2 | 3.4 (T0: 2.1) | (T0: 1.9) | (T0: 1.7) | | 3.3 | 3.2 |
| LANBCH (n = 14) | 3.5 | 3 (T0: 1.8) | (T0: 2) | | | 3.3 | 3.3 |
| LANCEG (n = 4) | 3.6 | 4.1 (T0: 2) | (T0: 2) | | | 4.1 | 1.9 |

TABLE 40-continued

Copy number measurement of T1 plants cultivated in the greenhouse of canola events containing the T-DNAs of plasmids VC-LJB2197-1qcz and VC-LLM337-1qcz rc. The events are indicated in the first column, along with the number of T1 plants that where measured per event. The T1 plants underwent a selection from 250 segregating T1 seedlings using half-kernel analysis, where the correlation of VCL-PUFA levels with copy number was employed to select for homozygous plants, or in the case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

| | | | | | | |
|---|---|---|---|---|---|---|
| LANCOX (n = 10) | 1.7 | 1.7 (T0: 1) | (T0: 1.1) | | 1.8 | 2.6 |
| LANFEF (n = 15) | 1.0 | 0.7 (T0: 1.1) | (T0: 1) | (T0: 1.8) | 2.9 | 2.9 |
| LANMGC (n = 15) | 2.2 | 3.8 (T0: 1.9) | (T0: 2) | | 4.0 | 6.0 |
| LANMOM (n = 10) | 3.5 | 2.9 (T0: 1.9) | (T0: 1.9) | | 2.9 | 4.8 |
| LANPMZ (n = 13) | 2.0 | 2.1 (T0: 1.1) | (T0: 1.1) | | 2.1 | 1.9 |
| LANTLE (n = 15) | 2.5 | 2.2 (T0: 2) | (T0: 1.9) | | 2.3 | 2.3 |
| LANTSP (n = 12) | 0.6 | 1.5 (T0: 0.9) | (T0: 1.6) | | 2.5 | 3.3 |
| LANUCB (n = 14) | 1.1 | 0.9 (T0: 2.1) | (T0: 2.8) | | 2.3 | 2.3 |
| LAOBGQ (n = 15) | 1.6 | 2.7 (T0: 1.8) | (T0: 2.1) | (T0: 1.8) | 2.8 | 4.0 |
| LAOHLR (n = 14) | 2.1 | 1.7 (T0: 1.1) | (T0: 1) | | 1.7 | 1.7 |
| LAOJAT (n = 15) | 2.3 | 2.2 (T0: 1.9) | (T0: 1.9) | (T0: 1.9) | 2.3 | 1.2 |
| LAOKLP (n = 15) | 1.4 | 1.2 (T0: 0.7) | (T0: 1) | (T0: 0.6) | 1.2 | 1.2 |
| LAOKTE (n = 15) | 3.0 | 2.4 (T0: 2) | (T0: 1.9) | (T0: 2.1) | 2.5 | 2.4 |
| LAPKLS (n = 12) | 2.5 | 1.9 (T0: 2) | (T0: 2.1) | | 2.0 | 2.1 |
| LAPKXM (n = 15) | 3.7 | 2.9 (T0: 1.9) | (T0: 1.9) | | 3.6 | 0.0 |
| LAPKZJ (n = 15) | 2.0 | 1.6 (T0: 2) | (T0: 1.9) | | 1.7 | 1.6 |
| LAPWJD (n = 14) | 2.4 | 2 (T0: 1) | (T0: 1) | | 2.2 | 2.1 |
| LAPWLP (n = 14) | 0.0 | 1.3 (T0: 1) | (T0: 1.1) | | 2.3 | 2.3 |
| LAQYTA (n = 15) | 2.4 | 2.2 (T0: 1.9) | (T0: 2) | (T0: 2.4) | 3.2 | 3.3 |
| LAQYUT (n = 15) | 3.6 | 2.8 (T0: 1.6) | (T0: 1.9) | (T0: 0.6) | 3.0 | 4.3 |
| LAQYWQ (n = 15) | 3.2 | 2.7 (T0: 2) | (T0: 1.9) | (T0: 2.2) | 2.6 | 1.4 |
| LAQZME (n = 12) | 1.8 | 1.4 (T0: 1.1) | (T0: 1.2) | (T0: 1.2) | 1.4 | 1.3 |

TABLE 41

Copy number measurement of T1 plants cultivated in the greenhouse of canola events containing the T-DNAs of plasmids VC-LJB2197-1qcz and VC-LLM337-1qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fullfilling these criteria are displayed in parentheses.

Copy number assays targeting the T-DNA of VC-LJB2197-1qcz. Assays are listed according to the position of the assay target along the T-DNA, with assay A1 located near the left T-DNA border and assay A13 near the right T-DNA border. Copy number results obtained on the T0 plants are indicated in parentheses. Homozygosity was indicated if the average result of the selected T1 plants was about two fold higher than the T0 generation.

| Event | c-AHAS | j-t-E9-p3-2 | c-d6Elo (Tp_GA) | j-t-StCAT_p2_p- | j-t-CaMV_p-LuCnl- | c-d6Elo (Pp_GA) | j-i-Atss18_c-d6Elo(Pp_GA2) |
|---|---|---|---|---|---|---|---|
| sc (n = 296) | 1.9 | 2.1 | | 2.6 | 2.7 | 2.4 | 2.3 |
| dc (n = 198) | 3.4 | 3.7 | | 4.2 | 4.8 | 4.2 | 4.2 |
| tc (n = 2) | 4.0 | 5.6 | | 7.6 | 7.5 | 7.1 | 6.3 |

TABLE 41-continued

Copy number measurement of T1 plants cultivated in the greenhouse of canola events containing the T-DNAs of plasmids VC-LJB2197-1qcz and VC-LLM337-1qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fullfilling these criteria are displayed in parentheses.

Copy number assays targeting the T-DNA of VC-LJB2197-1qcz. Assays are listed according to the position of the assay target along the T-DNA, with assay A1 located near the left T-DNA border and assay A13 near the right T-DNA border. Copy number results obtained on the T0 plants are indicated in parentheses. Homozygosity was indicated if the average result of the selected T1 plants was about two fold higher than the T0 generation.

| Event | j-t-PvARC-p3 | c-d4Des (Tc_GA) | c- | j-i-Atss15_c-o3Des(Pi_GA2) | c-o3Des (Pir_GA) | j-p-VfSBPperm3_c-o3Des(Pir_GA) | j-i-Atss1_c-d5Elo(Ot_GA3) | c-d4Des (Eg_GA) |
|---|---|---|---|---|---|---|---|---|
| sc (n = 296) | 1.5 | 1.6 | | | | 1.8 | | 1.7 |
| dc (n = 198) | 3.2 | 3.4 | | | | 3.8 | | 3.6 |
| tc (n = 2) | 4.6 | 4.4 | | | | 5.9 | | 4.7 |

TABLE 42

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 |
|---|---|---|---|---|---|---|---|---|---|
| LALHCY (n = 15) | 4.9 ± 0.1 | 0.3 ± 0 | 0 ± 0 | 4 ± 0.2 | .7 ± 1 | 32 ± 0.9 | 1.2 ± 0.1 | 4.2 ± 0.4 | 2.2 ± 0.2 |
| LALIAO (n = 15) | 5 ± 0.2 | 0.2 ± 0 | 0 ± 0 | 2.9 ± 0.4 | 26.8 ± 3.4 | 30.8 ± 1.6 | 0.6 ± 0.2 | 5.5 ± 0.9 | 0.9 ± 0.4 |
| LALJKA (n = 15) | 5.4 ± 0.2 | 0.3 ± 0 | 0 ± 0 | 2.7 ± 0.5 | 25.3 ± 2.2 | 36.4 ± 1.1 | 0.6 ± 0.1 | 5.7 ± 0.5 | 2.2 ± 0.3 |
| LALLTL (n = 11) | 5 ± 0.2 | 0.3 ± 0 | 0 ± 0 | 3.6 ± 0.3 | 28.5 ± 4.4 | 31.5 ± 1.1 | 0.8 ± 0.2 | 4.6 ± 0.5 | 1.3 ± 0.4 |
| LALQAM (n = 15) | 5.4 ± 0.8 | 0.3 ± 0.1 | 0 ± 0 | 3.8 ± 0.2 | 23.3 ± 1.4 | 32.7 ± 1 | 0.5 ± 0.2 | 3.8 ± 0.3 | 1 ± 0.4 |
| LALQDS (n = 14) | 5 ± 0.1 | 0.3 ± 0 | 0 ± 0 | 3.2 ± 0.4 | 29.1 ± 2.4 | 35.7 ± 1.1 | 0.6 ± 0.1 | 6.2 ± 0.6 | 1 ± 0.2 |
| LALRCQ (n = 14) | 5.1 ± 0.1 | 0.3 ± 0 | 0 ± 0 | 4 ± 0.5 | 23 ± 1.1 | 33.2 ± 1.2 | 1 ± 0.2 | 3.5 ± 0.5 | 2.3 ± 0.2 |
| LALWKF (n = 14) | 5.3 ± 0.1 | 0.3 ± 0.1 | 0 ± 0 | 3.7 ± 0.3 | 26.7 ± 6.7 | 27.6 ± 3.6 | 1.3 ± 0.4 | 3.3 ± 0.3 | 2.2 ± 0.7 |
| LAMABL (n = 8) | 4.8 ± 0.2 | 0.3 ± 0 | 0 ± 0 | 3.3 ± 0.5 | 27.8 ± 6.3 | 30 ± 3.8 | 1.4 ± 0.2 | 3.7 ± 0.5 | 2.7 ± 0.7 |
| LAMCKI (n = 10) | 5.1 ± 0.1 | 0.2 ± 0 | 0 ± 0 | 3.5 ± 0.2 | 26.4 ± 0.7 | 33.8 ± 0.5 | 1.1 ± 0 | 4.2 ± 0.2 | 1.8 ± 0.2 |
| LAMCLE (n = 14) | 4.9 ± 0.2 | 0.2 ± 0.1 | 0 ± 0 | 3.4 ± 0.2 | 25.1 ± 2.4 | 32.2 ± 1.6 | 1.1 ± 0.3 | 3.5 ± 0.3 | 2.4 ± 0.6 |
| LAMCLF (n = 9) | 5.1 ± 0.1 | 0.3 ± 0 | 0 ± 0 | 3.6 ± 0.1 | 24.7 ± 3.5 | 28.5 ± 2 | 1.1 ± 0.6 | 2.8 ± 0.5 | 2 ± 0.6 |
| LAMEUB (n = 15) | 5 ± 0.2 | 0.3 ± 0.1 | 0 ± 0 | 3.8 ± 0.5 | 28.4 ± 5.6 | 29.7 ± 2.1 | 0.9 ± 0.3 | 3.4 ± 0.6 | 1.3 ± 0.4 |
| LAMEUU (n = 13) | 5 ± 0.1 | 0.1 ± 0.1 | 0 ± 0 | 3.3 ± 0.4 | 25.8 ± 4.8 | 34.3 ± 1.8 | 1.4 ± 0.3 | 4.2 ± 0.7 | 2.1 ± 0.4 |
| LAMFJO (n = 15) | 5.1 ± 0.7 | 0.2 ± 0.1 | 0 ± 0 | 3.5 ± 0.7 | 26.5 ± 1.9 | 32.9 ± 0.8 | 0.2 ± 0.1 | 4.5 ± 0.4 | 0.4 ± 0.1 |
| LAMIRY (n = 10) | 5 ± 0.2 | 0.3 ± 0 | 0 ± 0 | 3.5 ± 0.3 | 26.9 ± 6.8 | 30.9 ± 2.8 | 0.6 ± 0.1 | 4.6 ± 0.5 | 1.2 ± 0.3 |
| LAMJIC (n = 9) | 5.8 ± 0.4 | 0.2 ± 0.1 | 0 ± 0 | 3.1 ± 0.5 | 28.5 ± 6.6 | 33.1 ± 3.9 | 0.6 ± 0.2 | 5.3 ± 1.2 | 1.3 ± 0.6 |
| LAMPJB (n = 13) | 4.8 ± 0.1 | 0.1 ± 0 | 0 ± 0 | 3.1 ± 0.3 | 24.1 ± 1.7 | 33.6 ± 0.9 | 0.9 ± 0.2 | 3.7 ± 0.5 | 2.2 ± 0.5 |
| LAMQDL (n = 14) | 5 ± 0.5 | 0.2 ± 0 | 0 ± 0 | 2.7 ± 0.4 | 26.4 ± 2.2 | 31.2 ± 1 | 0.2 ± 0 | 5.2 ± 0.6 | 0.4 ± 0.1 |
| LAMQNE (n = 14) | 6.9 ± 1.3 | 0.3 ± 0.1 | 0 ± 0 | 2.7 ± 0.3 | 27.8 ± 2.6 | 31.8 ± 0.7 | 0.8 ± 0.1 | 4.9 ± 0.6 | 1.3 ± 0.1 |
| LAMQSF (n = 14) | 5.2 ± 0.1 | 0.3 ± 0 | 0 ± 0 | 3.4 ± 0.3 | 24.3 ± 2.7 | 31.5 ± 1.2 | 0.8 ± 0.4 | 4.5 ± 0.7 | 2 ± 0.8 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | | | | | | | | | |
|---|---|---|---|---|---|---|---|---|---|
| LAMRCO (n = 14) | 5.5 ± 0.6 | 0.3 ± 0.1 | 0 ± 0 | 4.4 ± 0.6 | 23.9 ± 6.8 | 28.4 ± 3.1 | 1.3 ± 0.4 | 2.7 ± 0.4 | 3.4 ± 0.8 |
| LAMRDS (n = 15) | 4.8 ± 0.1 | 0 ± 0 | 0 ± 0 | 3.6 ± 0.4 | 23.4 ± 1.7 | 32.7 ± 1.3 | 1.1 ± 0.2 | 3.4 ± 0.5 | 2.3 ± 0.3 |
| LAMRHL (n = 14) | 6 ± 1 | 0.3 ± 0.1 | 0 ± 0 | 3.5 ± 0.5 | 26.5 ± 6 | 26.2 ± 3.9 | 0.6 ± 0.1 | 3.7 ± 0.8 | 1 ± 0.3 |
| LAMRJK (n = 15) | 4.9 ± 0.2 | 0.1 ± 0 | 0 ± 0 | 3.6 ± 0.4 | 26.4 ± 2.9 | 33 ± 1 | 1 ± 0.2 | 4.1 ± 0.6 | 2 ± 0.4 |
| LAMRNQ (n = 9) | 4.8 ± 0.1 | 0.2 ± 0 | 0 ± 0 | 2.7 ± 0.4 | 29.6 ± 3.8 | 32.2 ± 0.9 | 0.5 ± 0.1 | 5.1 ± 0.8 | 0.9 ± 0.2 |
| LAMVUB (n = 15) | 4.9 ± 0.3 | 0.2 ± 0 | 0 ± 0 | 3.6 ± 0.4 | 24.6 ± 1.9 | 33.4 ± 0.5 | 0.2 ± 0.1 | 4.8 ± 0.4 | 0.4 ± 0.1 |
| LAMYDP (n = 14) | 5.1 ± 0.5 | 0.2 ± 0.1 | 0 ± 0 | 4 ± 0.8 | 23.1 ± 2.3 | 31.7 ± 1.1 | 1.2 ± 0.1 | 4.1 ± 0.5 | 2.4 ± 0.3 |
| LANBCH (n = 14) | 4.7 ± 0.8 | 0.2 ± 0.1 | 0 ± 0 | 3.4 ± 0.4 | 25 ± 3.9 | 32.7 ± 1.5 | 0.8 ± 0.2 | 4.7 ± 0.5 | 1.5 ± 0.5 |
| LANCEG (n = 4) | 4.9 ± 0.1 | 0.1 ± 0.1 | 0 ± 0 | 3.3 ± 0.2 | 23.8 ± 1.2 | 33.2 ± 0.5 | 0.9 ± 0.1 | 3.7 ± 0.4 | 2 ± 0.3 |
| LANCOX (n = 10) | 5.1 ± 0.7 | 0.2 ± 0.1 | 0 ± 0 | 3.1 ± 0.2 | 25 ± 2.5 | 35.5 ± 1.3 | 0.7 ± 0.1 | 4.1 ± 0.3 | 2.1 ± 0.3 |
| LANFEF (n = 15) | 5.1 ± 0.3 | 0.1 ± 0.1 | 0 ± 0 | 3.5 ± 0.4 | 27.2 ± 1 | 34.3 ± 1.1 | 0.2 ± 0.1 | 4.5 ± 0.9 | 0.3 ± 0 |
| LANMGC (n = 15) | 5.6 ± 0.9 | 0.2 ± 0.1 | 0 ± 0 | 4 ± 0.5 | 25.1 ± 1.9 | 33.1 ± 1.8 | 1 ± 0.2 | 4.3 ± 0.3 | 2.1 ± 0.2 |
| LANMOM (n = 10) | 5.4 ± 0.4 | 0.2 ± 0 | 0 ± 0 | 2.8 ± 0.2 | 26.9 ± 3.1 | 31.8 ± 1.3 | 0.8 ± 0.2 | 4.9 ± 0.5 | 1.4 ± 0.4 |
| LANPMZ (n = 13) | 4.8 ± 0.6 | 0.2 ± 0.1 | 0 ± 0 | 3.7 ± 0.3 | 26.2 ± 1.4 | 34.4 ± 1 | 0.3 ± 0.1 | 5 ± 0.4 | 0.5 ± 0.1 |
| LANTLE (n = 15) | 5 ± 0.4 | 0.2 ± 0.1 | 0 ± 0 | 2.4 ± 0.4 | 26.7 ± 4 | 32.7 ± 1.2 | 0.4 ± 0.3 | 6.1 ± 0.8 | 1 ± 0.5 |
| LANTSP (n = 12) | 4.9 ± 0.2 | 0.2 ± 0 | 0.1 ± 0 | 3.3 ± 0.3 | 35.9 ± 6.9 | 26.8 ± 4 | 0.8 ± 0.2 | 4.6 ± 0.9 | 1.1 ± 0.4 |
| LANUCB (n = 14) | 5 ± 0.5 | 0.3 ± 0 | 0 ± 0 | 2.9 ± 0.4 | 28.2 ± 4.5 | 28.8 ± 2.2 | 1.5 ± 0.6 | 3.8 ± 0.8 | 2.7 ± 1.5 |
| LAOBGQ (n = 15) | 5.2 ± 0.4 | 0.2 ± 0.1 | 0 ± 0 | 3.5 ± 0.3 | 31.8 ± 7.9 | 29.2 ± 4.2 | 1.2 ± 0.4 | 3.9 ± 0.6 | 2.5 ± 0.7 |
| LAOHLR (n = 14) | 5.1 ± 0.2 | 0.2 ± 0 | 0 ± 0 | 3.5 ± 0.3 | 26.5 ± 6.1 | 33 ± 2.7 | 1.1 ± 0.2 | 3.7 ± 0.7 | 2.1 ± 0.4 |
| LAOJAT (n = 15) | 5.1 ± 0.5 | 0.1 ± 0.1 | 0 ± 0 | 2.8 ± 0.7 | 28.7 ± 4 | 34 ± 1.8 | 0.6 ± 0.1 | 5 ± 0.8 | 1.3 ± 0.4 |
| LAOKLP (n = 15) | 4.7 ± 0.4 | 0.2 ± 0 | 0 ± 0 | 3.1 ± 0.2 | 26 ± 2.2 | 32.5 ± 1.3 | 0.2 ± 0 | 5.2 ± 0.5 | 0.3 ± 0 |
| LAOKTE (n = 15) | 4.7 ± 0.3 | 0.2 ± 0.1 | 0.1 ± 0 | 2.8 ± 0.4 | 27.1 ± 7.8 | 31.4 ± 2.3 | 0.5 ± 0.3 | 5.5 ± 1.7 | 0.9 ± 0.6 |
| LAPKLS (n = 12) | 5.2 ± 0.3 | 0.2 ± 0.1 | 0 ± 0 | 3.7 ± 0.5 | 23.8 ± 1.9 | 33.6 ± 0.7 | 0.9 ± 0.1 | 4.1 ± 0.5 | 1.9 ± 0.4 |
| LAPKXM (n = 15) | 4.6 ± 0.3 | 0.2 ± 0 | 0 ± 0 | 3.2 ± 0.3 | 26.1 ± 2 | 32 ± 0.9 | 0.7 ± 0.2 | 5.2 ± 0.5 | 1.2 ± 0.4 |
| LAPKZJ (n = 15) | 5.1 ± 0.5 | 0.1 ± 0.1 | 0 ± 0 | 3.6 ± 0.4 | 24.6 ± 1.9 | 31.8 ± 1.6 | 0.4 ± 0.2 | 4.7 ± 0.7 | 0.6 ± 0.3 |
| LAPWJD (n = 14) | 5.1 ± 0.4 | 0.1 ± 0.1 | 0 ± 0 | 3.6 ± 0.1 | 7 ± 0.9 | 34 ± 0.7 | 0.3 ± 0.1 | 4.9 ± 0.2 | 0.5 ± 0.1 |
| LAPWLP (n = 14) | 4.5 ± 0.4 | 0.2 ± 0 | 0 ± 0 | 3 ± 0.3 | 32.5 ± 6.3 | 23.1 ± 3.7 | 0.5 ± 0.3 | 5.1 ± 0.8 | 0.5 ± 0.3 |
| LAQYTA (n = 15) | 5.6 ± 0.2 | 0 ± 0 | 0 ± 0 | 3.3 ± 0.3 | 24.7 ± 1.3 | 31.5 ± 1.3 | 1.3 ± 0.2 | 4.1 ± 0.5 | 2.1 ± 0.3 |
| LAQYUT (n = 15) | 5.5 ± 0.3 | 0.2 ± 0 | 0 ± 0 | 3.3 ± 0.3 | 26.6 ± 4 | 33.4 ± 1.5 | 1 ± 0.2 | 4 ± 0.6 | 2.2 ± 0.5 |
| LAQYWQ (n = 15) | 5.6 ± 0.2 | 0.2 ± 0.1 | 0 ± 0 | 3.9 ± 0.5 | 26.9 ± 6 | 30.3 ± 2.1 | 1.3 ± 0.4 | 4.1 ± 0.6 | 2.5 ± 0.8 |
| LAQZME (n = 12) | 5.3 ± 0.7 | 0.2 ± 0.1 | 0 ± 0 | 2.5 ± 0.2 | 33.3 ± 6.9 | 24.1 ± 4.6 | 0.5 ± 0.1 | 4.1 ± 0.5 | 0.9 ± 1 |

| Event | 18:4 n-3 | 20:0 | 20:1 n-9 | 20:2 n-6 | 20:3 n-3 | 20:3 n-6 | 20:4 n-3 | 20:4 n-6 | 20:5 n-3 |
|---|---|---|---|---|---|---|---|---|---|
| LALHCY (n = 15) | 0.3 ± 0 | 0.8 ± 0 | 0.3 ± 0.3 | 0.2 ± 0 | 0.1 ± 0 | 4.4 ± 1.4 | 2.5 ± 0.7 | 2.9 ± 0.4 | 8.1 ± 0.8 |
| LALIAO (n = 15) | 0.2 ± 0.1 | 0.7 ± 0.1 | 0.8 ± 0.1 | 1.2 ± 0.7 | 0.4 ± 0.3 | 2.5 ± 0.4 | 1.6 ± 0.1 | 3.7 ± 1.3 | 9.9 ± 2.5 |
| LALJKA (n = 15) | 0.5 ± 0.1 | 0.7 ± 0.1 | 0.6 ± 0 | 0.1 ± 0.1 | 0.1 ± 0 | 1.7 ± 1 | 1 ± 0.5 | 2.2 ± 0.5 | 6.9 ± 1.5 |
| LALLTL (n = 11) | 0.2 ± 0 | 0.8 ± 0 | 0.6 ± 0.3 | 0.6 ± 0.2 | 0.2 ± 0.1 | 2.6 ± 1 | 1.3 ± 0.6 | 6 ± 2.4 | 6.2 ± 1.5 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | | | | | | | | | |
|---|---|---|---|---|---|---|---|---|---|
| LALQAM (n = 15) | 0.1 ± 0 | 0.8 ± 0 | 0.7 ± 0.1 | 1.5 ± 0.9 | 0.4 ± 0.2 | 3.5 ± 0.8 | 1.5 ± 0.2 | 6.4 ± 1.4 | 8 ± 1.3 |
| LALQDS (n = 14) | 0.2 ± 0 | 0.8 ± 0.1 | 0.5 ± 0.2 | 0.4 ± 0.2 | 0.2 ± 0.1 | 1.5 ± 0.5 | 1 ± 0.2 | 2.4 ± 0.6 | 6.7 ± 0.7 |
| LALRCQ (n = 14) | 0.2 ± 0 | 0.8 ± 0.1 | 0.6 ± 0 | 0.2 ± 0.1 | 0 ± 0 | 5.1 ± 1.6 | 1.7 ± 0.4 | 4.1 ± 0.7 | 6.6 ± 0.9 |
| LALWKF (n = 14) | 0.3 ± 0.1 | 0.8 ± 0 | 0.7 ± 0.1 | 0.6 ± 0.5 | 0.2 ± 0.2 | 2.1 ± 0.5 | 0.9 ± 0.3 | 9.3 ± 2.7 | 8.8 ± 1.5 |
| LAMABL (n = 8) | 0.4 ± 0.1 | 0.8 ± 0.1 | 0.7 ± 0.1 | 0.3 ± 0.1 | 0 ± 0 | 1.3 ± 0.4 | 0.6 ± 0.1 | 7 ± 0.8 | 8.6 ± 1.7 |
| LAMCKI (n = 10) | 0.2 ± 0 | 0.8 ± 0 | 0.6 ± 0 | 0.1 ± 0 | 0 ± 0 | 3.9 ± 0.6 | 1.7 ± 0.2 | 2.9 ± 0.2 | 6.8 ± 0.6 |
| LAMCLE (n = 14) | 0.3 ± 0.1 | 0.8 ± 0 | 0.7 ± 0.1 | 0.4 ± 0.2 | 0 ± 0.1 | 2.3 ± 0.5 | 1 ± 0.2 | 5.8 ± 1.3 | 8.4 ± 1.3 |
| LAMCLF (n = 9) | 0.2 ± 0.1 | 0.8 ± 0 | 0.6 ± 0.1 | 1.4 ± 0.7 | 0.1 ± 0.1 | 2.8 ± 0.7 | 1 ± 0.2 | 9.7 ± 2.2 | 9.4 ± 1 |
| LAMEUB (n = 15) | 0.1 ± 0.1 | 0.9 ± 0.1 | 0.8 ± 0.1 | 1 ± 0.4 | 0.2 ± 0.1 | 2.7 ± 0.3 | 1.1 ± 0.3 | 8.4 ± 2.9 | 7.6 ± 1.9 |
| LAMEUU (n = 13) | 0.2 ± 0.1 | 0.9 ± 0.1 | 0.7 ± 0.1 | 0.2 ± 0.2 | 1.8 ± 1.8 | 1.4 ± 1.5 | 1.2 ± 0.3 | 3.1 ± 0.8 | 7.8 ± 1.1 |
| LAMFJO (n = 15) | 0 ± 0 | 0.9 ± 0.1 | 1 ± 0.1 | 2.2 ± 0.7 | 1.7 ± 1.9 | 3.7 ± 0.6 | 3 ± 0.3 | 4.7 ± 1.8 | 6.2 ± 0.7 |
| LAMIRY (n = 10) | 0.2 ± 0 | 0.8 ± 0 | 0.7 ± 0.2 | 1.1 ± 0.2 | 0.4 ± 0.1 | 2.4 ± 0.4 | 1.4 ± 0.3 | 4.5 ± 0.9 | 9.1 ± 2.1 |
| LAMJIC (n = 9) | 0.2 ± 0.1 | 0.8 ± 0.1 | 0.7 ± 0.1 | 0.5 ± 0.3 | 0.1 ± 0.1 | 2.6 ± 0.4 | 1.3 ± 0.3 | 3.9 ± 1.3 | 6.2 ± 1.8 |
| LAMPJB (n = 13) | 0.3 ± 0.1 | 0.8 ± 0.1 | 0.7 ± 0 | 0.4 ± 0.3 | 0 ± 0 | 2.8 ± 0.4 | 1.2 ± 0.2 | 5.5 ± 2.2 | 8.7 ± 1 |
| LAMQDL (n = 14) | 0.1 ± 0 | 0.7 ± 0.1 | 1 ± 0.1 | 2.8 ± 0.5 | 1 ± 0.2 | 3.7 ± 0.4 | 2.1 ± 0.4 | 4.7 ± 2 | 6.7 ± 1.2 |
| LAMQNE (n = 14) | 0.2 ± 0 | 0.7 ± 0.1 | 0.7 ± 0.1 | 0.4 ± 0.1 | 0.2 ± 0.1 | 4 ± 1.7 | 1.9 ± 0.8 | 2.7 ± 1 | 5.9 ± 1.1 |
| LAMQSF (n = 14) | 0.3 ± 0.1 | 0.8 ± 0.1 | 0.6 ± 0.1 | 0.6 ± 0.2 | 0.2 ± 0.2 | 1.9 ± 0.6 | 1.3 ± 0.5 | 4.1 ± 1.5 | 10.6 ± 1.7 |
| LAMRCO (n = 14) | 0.3 ± 0.1 | 1 ± 0.2 | 0.6 ± 0.1 | 0.4 ± 0.2 | 0.1 ± 0.1 | 3.7 ± 0.8 | 1.3 ± 0.3 | 5.7 ± 1.3 | 8.7 ± 1.7 |
| LAMRDS (n = 15) | 0.2 ± 0 | 0.9 ± 0.1 | 0.7 ± 0 | 0.2 ± 0.1 | 5.4 ± 0.9 | 0 ± 0.1 | 1.2 ± 0.1 | 3.4 ± 0.8 | 8.2 ± 0.7 |
| LAMRHL (n = 14) | 0.2 ± 0.1 | 0.9 ± 0.1 | 0.8 ± 0.2 | 1.6 ± 0.6 | 0.4 ± 0.1 | 3 ± 0.6 | 1.9 ± 0.4 | 4.6 ± 0.8 | 10.5 ± 1.9 |
| LAMRJK (n = 15) | 0.2 ± 0.1 | 0.9 ± 0.1 | 0.7 ± 0.1 | 0 ± 0.1 | 0.5 ± 1.4 | 2.6 ± 1.4 | 1.3 ± 0.3 | 4.4 ± 1.3 | 7.7 ± 1.2 |
| LAMRNQ (n = 9) | 0.1 ± 0 | 0.8 ± 0.1 | 0.9 ± 0 | 1.2 ± 0.2 | 0.3 ± 0.1 | 2.8 ± 0.7 | 1.3 ± 0.3 | 4.6 ± 1.3 | 6 ± 1.2 |
| LAMVUB (n = 15) | 0 ± 0 | 0.9 ± 0.1 | 1 ± 0.1 | 2.8 ± 0.5 | 1 ± 0.2 | 4 ± 0.4 | 2.4 ± 0.3 | 4 ± 1.4 | 6.7 ± 1 |
| LAMYDP (n = 14) | 0.3 ± 0 | 0.9 ± 0.1 | 0.6 ± 0 | 0.3 ± 0.1 | 0 ± 0 | 2.5 ± 0.4 | 1.3 ± 0.3 | 4.1 ± 0.8 | 10.3 ± 1.6 |
| LANBCH (n = 14) | 0.2 ± 0.1 | 0.8 ± 0.1 | 0.7 ± 0.1 | 0.5 ± 0.2 | 0.2 ± 0.1 | 2.3 ± 0.4 | 1.5 ± 0.2 | 3.5 ± 0.5 | 9.2 ± 1.8 |
| LANCEG (n = 4) | 0.3 ± 0 | 0.8 ± 0 | 0.7 ± 0 | 0.2 ± 0.1 | 5.5 ± 0.2 | 0.2 ± 0.1 | 0.7 ± 0.1 | 1.5 ± 0.4 | 10.8 ± 0.4 |
| LANCOX (n = 10) | 0.3 ± 0 | 0.8 ± 0.1 | 0.7 ± 0 | 0 ± 0 | 7.2 ± 2.4 | 0.2 ± 0.1 | 0.6 ± 0.1 | 1.6 ± 0.3 | 7.3 ± 1.5 |
| LANFEF (n = 15) | 0 ± 0 | 0.8 ± 0.1 | 1 ± 0 | 2.5 ± 0.3 | 0.8 ± 0.2 | 3.5 ± 0.5 | 1.6 ± 0.4 | 3.3 ± 1.4 | 5.5 ± 0.5 |
| LANMGC (n = 15) | 0.2 ± 0 | 0.9 ± 0.1 | 0.7 ± 0 | 0.2 ± 0 | 0 ± 0 | 7.9 ± 1.3 | 3.6 ± 0.7 | 1.4 ± 0.5 | 3.7 ± 1.3 |
| LANMOM (n = 10) | 0.2 ± 0.1 | 0.8 ± 0.1 | 0.7 ± 0.1 | 0.6 ± 0.3 | 0.2 ± 0.1 | 3 ± 0.3 | 1.2 ± 0.2 | 3.9 ± 0.5 | 8.6 ± 1.5 |
| LANPMZ (n = 13) | 0.1 ± 0 | 0.9 ± 0 | 0.9 ± 0.1 | 1.5 ± 0.3 | 0.5 ± 0.2 | 3 ± 0.2 | 3 ± 0.3 | 2.7 ± 0.3 | 6.9 ± 0.8 |
| LANTLE (n = 15) | 0.1 ± 0.1 | 0.6 ± 0.1 | 0.8 ± 0.2 | 1.4 ± 1 | 0.5 ± 0.5 | 2.5 ± 0.5 | 1.7 ± 0.4 | 3.9 ± 1.4 | 7.9 ± 1.9 |
| LANTSP (n = 12) | 0.2 ± 0.1 | 0.9 ± 0.1 | 0.9 ± 0.2 | 0.8 ± 0.3 | 0.2 ± 0.1 | 2.1 ± 0.4 | 1.2 ± 0.2 | 3.4 ± 0.9 | 6.6 ± 1.8 |
| LANUCB (n = 14) | 0.4 ± 0.3 | 0.7 ± 0.1 | 0.7 ± 0.1 | 0.5 ± 0.5 | 0.1 ± 0.1 | 2.2 ± 0.7 | 1.1 ± 0.3 | 5.7 ± 1.9 | 9.2 ± 1.4 |
| LAOBGQ (n = 15) | 0.4 ± 0.2 | 0.8 ± 0.1 | 0.7 ± 0.1 | 0.2 ± 0.2 | 0 ± 0 | 2.1 ± 0.9 | 1.1 ± 0.5 | 3.9 ± 0.6 | 7.3 ± 1.5 |
| LAOHLR (n = 14) | 0.2 ± 0 | 0.9 ± 0.1 | 0.7 ± 0.1 | 0.1 ± 0.1 | 0 ± 0 | 4.1 ± 1.6 | 1.4 ± 0.5 | 5.3 ± 0.8 | 6.8 ± 1.2 |
| LAOJAT (n = 15) | 0.1 ± 0.1 | 0.6 ± 0.1 | 0.8 ± 0.1 | 0.7 ± 0.4 | 0.1 ± 0.2 | 1.5 ± 0.5 | 0.9 ± 0.2 | 4.3 ± 0.7 | 7.9 ± 1.3 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | | | | | | | | | |
|---|---|---|---|---|---|---|---|---|---|
| LAOKLP (n = 15) | 0 ± 0 | 0.8 ± 0 | 1 ± 0 | 2.5 ± 0.7 | 1 ± 0.2 | 3.5 ± 0.4 | 2.1 ± 0.3 | 4.4 ± 1.6 | 6.5 ± 0.9 |
| LAOKTE (n = 15) | 0.1 ± 0.1 | 0.8 ± 0.1 | 0.8 ± 0.1 | 1.2 ± 0.7 | 0.4 ± 0.2 | 2.5 ± 0.8 | 1.6 ± 0.4 | 4.1 ± 2.2 | 8.2 ± 2.9 |
| LAPKLS (n = 12) | 0.2 ± 0.1 | 0.8 ± 0.1 | 0.7 ± 0 | 0.4 ± 0.3 | 0.1 ± 0.1 | 3.1 ± 0.5 | 1.5 ± 0.4 | 6 ± 2.3 | 7.9 ± 1.5 |
| LAPKXM (n = 15) | 0.2 ± 0.1 | 0.8 ± 0.1 | 0.8 ± 0.1 | 0.9 ± 0.7 | 0.3 ± 0.3 | 2.3 ± 0.4 | 1.7 ± 0.2 | 3.1 ± 0.7 | 9.8 ± 2 |
| LAPKZJ (n = 15) | 0 ± 0 | 0.8 ± 0.1 | 0.9 ± 0.2 | 2.1 ± 0.8 | 0.8 ± 0.4 | 3.4 ± 0.5 | 2.1 ± 0.5 | 4.9 ± 2.1 | 7.7 ± 1.1 |
| LAPWJD (n = 14) | 0 ± 0 | 0.8 ± 0.1 | 0.9 ± 0.1 | 1.6 ± 0.4 | 0.6 ± 0.2 | 3.4 ± 0.2 | 2.2 ± 0.2 | 2.5 ± 0.3 | 6.2 ± 0.3 |
| LAPWLP (n = 14) | 0.1 ± 0.1 | 0.8 ± 0.1 | 1.2 ± 0.2 | 2.5 ± 0.9 | 0.9 ± 0.4 | 2.2 ± 0.4 | 1.8 ± 0.4 | 3.5 ± 0.7 | 10 ± 2.3 |
| LAQYTA (n = 15) | 0.1 ± 0.1 | 0.7 ± 0.1 | 0.6 ± 0 | 0.2 ± 0.2 | 0 ± 0 | 3.6 ± 1.6 | 1.6 ± 0.8 | 5.8 ± 2.6 | 8.2 ± 1.4 |
| LAQYUT (n = 15) | 0.2 ± 0.1 | 0.7 ± 0.1 | 0.6 ± 0.1 | 0.1 ± 0.1 | 0 ± 0 | 3.7 ± 2.1 | 1.5 ± 0.8 | 4.1 ± 1.4 | 7.1 ± 1.5 |
| LAQYWQ (n = 15) | 0.3 ± 0.1 | 0.8 ± 0.1 | 0.6 ± 0.1 | 0.2 ± 0.2 | 0 ± 0 | 2.3 ± 1.1 | 1.1 ± 0.6 | 6.5 ± 3 | 7.9 ± 2 |
| LAQZME (n = 12) | 0.2 ± 0.1 | 0.7 ± 0.1 | 1.1 ± 0.4 | 1.3 ± 1.1 | 0.6 ± 0.3 | 2.7 ± 0.2 | 1.8 ± 0.3 | 5.6 ± 0.5 | 8.2 ± 1.2 |

| Event | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|
| LALHCY (n = 15) | 0.3 ± 0 | 0 ± 0 | 1.3 ± 0.1 | 3.1 ± 0.3 | 0 ± 0 | 1.9 ± 0.2 | 1.2 ± 0.5 | |
| LALIAO (n = 15) | 0.3 ± 0.1 | 0 ± 0 | 0.7 ± 0.3 | 3.3 ± 1 | 0 ± 0 | 1.2 ± 0.4 | 0.2 ± 0.3 | 0.6 ± 0.2 |
| LALJKA (n = 15) | 0.3 ± 0 | 0 ± 0 | 1.3 ± 0.2 | 3.4 ± 0.9 | 0 ± 0 | 1.8 ± 0.4 | 0.6 ± 0.5 | |
| LALLTL (n = 11) | 0.3 ± 0 | 0 ± 0 | 1.1 ± 0.4 | 2.4 ± 0.6 | 0 ± 0.1 | 1.3 ± 0.4 | 0.6 ± 0.5 | |
| LALQAM (n = 15) | 0.3 ± 0 | 0 ± 0 | 0.9 ± 0.3 | 2.9 ± 0.7 | 0 ± 0 | 1.6 ± 0.4 | 0.3 ± 0.1 | |
| LALQDS (n = 14) | 0.3 ± 0 | 0 ± 0 | 0.7 ± 0.1 | 2.7 ± 0.3 | 0 ± 0 | 1 ± 0.2 | 0.3 ± 0.1 | |
| LALRCQ (n = 14) | 0.3 ± 0 | 0 ± 0 | 1.9 ± 0.3 | 2.8 ± 0.4 | 0 ± 0 | 1.8 ± 0.3 | 1.1 ± 0.4 | |
| LALWKF (n = 14) | 0.3 ± 0.1 | 0 ± 0 | 0.7 ± 0.3 | 2.9 ± 0.6 | 0 ± 0 | 1.6 ± 0.5 | 0.1 ± 0.1 | |
| LAMABL (n = 8) | 0.3 ± 0 | 0 ± 0 | 1.3 ± 0.3 | 3.2 ± 0.4 | 0 ± 0 | 1.4 ± 0.3 | 0.1 ± 0.1 | |
| LAMCKI (n = 10) | 0.3 ± 0 | 0 ± 0 | 1.2 ± 0.1 | 2.7 ± 0.3 | 0 ± 0 | 1.3 ± 0.1 | 0.9 ± 0.1 | |
| LAMCLE (n = 14) | 0.1 ± 0.1 | 0 ± 0 | 1.8 ± 0.4 | 3.4 ± 0.6 | 0 ± 0 | 1.8 ± 0.5 | 0.1 ± 0.2 | |
| LAMCLF (n = 9) | 0.3 ± 0 | 0 ± 0 | 1 ± 0.3 | 2.8 ± 0.5 | 0 ± 0 | 1.5 ± 0.3 | 0 ± 0.1 | |
| LAMEUB (n = 15) | 0.3 ± 0 | 0 ± 0 | 0.5 ± 0.2 | 2.2 ± 0.7 | 0 ± 0 | 1.2 ± 0.5 | 0.1 ± 0.1 | |
| LAMEUU (n = 13) | 0.2 ± 0.2 | 0 ± 0 | 1.4 ± 0.2 | 3 ± 0.4 | 0 ± 0 | 1.5 ± 0.3 | 0.3 ± 0.3 | |
| LAMFJO (n = 15) | 0.3 ± 0.1 | 0 ± 0 | 0.3 ± 0.2 | 2.2 ± 0.3 | 0 ± 0.1 | 1 ± 0.2 | 0.4 ± 0.3 | |
| LAMIRY (n = 10) | 0.3 ± 0 | 0 ± 0 | 1 ± 0.2 | 3 ± 0.6 | 0 ± 0 | 1.6 ± 0.4 | 0.5 ± 0.1 | |
| LAMJIC (n = 9) | 0.3 ± 0.1 | 0 ± 0 | 0.9 ± 0.3 | 2.6 ± 1 | 0 ± 0 | 1.4 ± 0.4 | 0.4 ± 0.1 | |
| LAMPJB (n = 13) | 0 ± 0.1 | 0 ± 0 | 1.5 ± 0.3 | 3.2 ± 0.4 | 0 ± 0 | 2 ± 0.3 | 0.1 ± 0.3 | |
| LAMQDL (n = 14) | 0.3 ± 0 | 0 ± 0 | 0.4 ± 0.1 | 2.7 ± 0.7 | 0 ± 0 | 0.8 ± 0.2 | 0.4 ± 0.2 | 1.1 ± 0.1 |
| LAMQNE (n = 14) | 0.3 ± 0 | 0 ± 0 | 1.2 ± 0.2 | 2.8 ± 0.6 | 0 ± 0 | 1.2 ± 0.3 | 0.8 ± 0.6 | 0.4 ± 0.1 |
| LAMQSF (n = 14) | 0.3 ± 0 | 0 ± 0 | 1.1 ± 0.2 | 3.6 ± 0.5 | 0 ± 0 | 1.8 ± 0.5 | 0.3 ± 0.3 | |
| LAMRCO (n = 14) | 0.4 ± 0.1 | 0 ± 0 | 1.8 ± 0.4 | 3.3 ± 0.8 | 0 ± 0 | 2.1 ± 0.6 | 0.4 ± 0.2 | 0.4 ± 0.1 |
| LAMRDS (n = 15) | 0.4 ± 0.1 | 0 ± 0 | 2 ± 0.4 | 3.5 ± 0.3 | 0 ± 0 | 1.8 ± 0.3 | 0.5 ± 0.3 | |
| LAMRHL (n = 14) | 0.4 ± 0 | 0 ± 0 | 1 ± 0.3 | 3.9 ± 1 | 0 ± 0 | 1.9 ± 0.5 | 0.3 ± 0.2 | 1.4 ± 0.4 |

TABLE 42-continued

Fatty acid profiles of T2 seeds harvested from T1 cultivated in the greenhouse of canola events containing the T-DNAs of plasmids VC-LJB2197-1qcz and VC-LLM337-1qcz rc The events are indicated in the first column, along with the number of T2 seed batches that were measured per event. Per seed batch a random selection of ~30 seed was measured in two technical repeats.

| Event | | | | | | | | |
|---|---|---|---|---|---|---|---|---|
| LAMRJK (n = 15) | 0.1 ± 0.2 | 0 ± 0 | 1.3 ± 0.4 | 3.2 ± 0.6 | 0 ± 0 | 1.5 ± 0.2 | 0.2 ± 0.4 | |
| LAMRNQ (n = 9) | 0.3 ± 0 | 0 ± 0 | 0.9 ± 0.1 | 2.4 ± 0.3 | 0 ± 0 | 1.2 ± 0.3 | 0.4 ± 0.2 | 0.6 ± 0.2 |
| LAMVUB (n = 15) | 0.4 ± 0 | 0 ± 0 | 0.5 ± 0.1 | 2.3 ± 0.4 | 0 ± 0 | 1.3 ± 0.3 | 0.6 ± 0.2 | |
| LAMYDP (n = 14) | 0.3 ± 0.1 | 0 ± 0 | 1.3 ± 0.3 | 3.6 ± 0.7 | 0 ± 0 | 2.1 ± 0.5 | 0.4 ± 0.2 | |
| LANBCH (n = 14) | 0.3 ± 0 | 0 ± 0 | 1.3 ± 0.4 | 3.7 ± 0.9 | 0 ± 0 | 2 ± 0.6 | 0.5 ± 0.1 | 0.3 ± 0 |
| LANCEG (n = 4) | 0.3 ± 0.1 | 0 ± 0 | 1.2 ± 0.1 | 3.8 ± 0.2 | 0 ± 0 | 1.7 ± 0.2 | 0 ± 0 | |
| LANCOX (n = 10) | 0.3 ± 0.1 | 0 ± 0 | 0.9 ± 0.4 | 2.7 ± 0.7 | 0 ± 0.1 | 1.4 ± 0.5 | 0 ± 0 | |
| LANFEF (n = 15) | 0.2 ± 0.1 | 0 ± 0 | 1 ± 0.1 | 2.2 ± 0.3 | 0 ± 0 | 1.1 ± 0.1 | 0.8 ± 0.2 | 0.9 ± 0 |
| LANMGC (n = 15) | 0.3 ± 0 | 0 ± 0 | 0.7 ± 0.2 | 1.5 ± 0.6 | 0 ± 0 | 0.8 ± 0.4 | 2.4 ± 0.6 | |
| LANMOM (n = 10) | 0.3 ± 0 | 0 ± 0 | 1.2 ± 0.2 | 3.7 ± 0.7 | 0 ± 0 | 1.5 ± 0.4 | 0.4 ± 0.1 | 0.3 ± 0.1 |
| LANPMZ (n = 13) | 0.4 ± 0 | 0 ± 0 | 0.8 ± 0.2 | 2.8 ± 0.6 | 0 ± 0 | 1.5 ± 0.3 | 0.7 ± 0.1 | 1 ± 0.1 |
| LANTLE (n = 15) | 0 ± 0.1 | 0 ± 0 | 0.7 ± 0.4 | 3.3 ± 0.8 | 0 ± 0 | 1.5 ± 0.4 | 0.1 ± 0.2 | 0.4 ± 0.2 |
| LANTSP (n = 12) | 0.4 ± 0 | 0 ± 0 | 1 ± 0.4 | 2.5 ± 0.7 | 0 ± 0 | 1.3 ± 0.4 | 0.4 ± 0.2 | 0.4 ± 0.3 |
| LANUCB (n = 14) | 0.2 ± 0.1 | 0 ± 0 | 0.9 ± 0.3 | 3.3 ± 0.5 | 0 ± 0 | 1.3 ± 0.4 | 0 ± 0.1 | 0.6 ± 0.5 |
| LAOBGQ (n = 15) | 0.2 ± 0.2 | 0 ± 0 | 1.1 ± 0.3 | 2.9 ± 0.6 | 0 ± 0 | 1.4 ± 0.4 | 0.1 ± 0.3 | 0.1 ± 0.1 |
| LAOHLR (n = 14) | 0.3 ± 0.1 | 0 ± 0 | 0.8 ± 0.2 | 2.3 ± 0.4 | 0 ± 0 | 1.2 ± 0.3 | 0.3 ± 0.3 | |
| LAOJAT (n = 15) | 0 ± 0 | 0 ± 0 | 0.8 ± 0.3 | 2.9 ± 0.4 | 0 ± 0 | 1.4 ± 0.3 | 0 ± 0 | 0.3 ± 0.1 |
| LAOKLP (n = 15) | 0.3 ± 0 | 0 ± 0 | 0.5 ± 0.1 | 2.5 ± 0.6 | 0 ± 0 | 1.2 ± 0.3 | 0.5 ± 0.2 | 1.1 ± 0.6 |
| LAOKTE (n = 15) | 0.3 ± 0.1 | 0 ± 0 | 0.9 ± 0.4 | 3 3 ± 1 | 0 ± 0 | 1.6 ± 0.6 | 0.4 ± 0.2 | 0.5 ± 0.2 |
| LAPKLS (n = 12) | 0.2 ± 0.1 | 0 ± 0 | 0.8 ± 0.3 | 2.6 ± 0.7 | 0 ± 0 | 1.4 ± 0.5 | 0.3 ± 0.3 | 0.4 ± 0.2 |
| LAPKXM (n = 15) | 0.3 ± 0 | 0 ± 0 | 0.9 ± 0.3 | 3.4 ± 0.7 | 0 ± 0 | 1.4 ± 0.4 | 0.4 ± 0.3 | 0.5 ± 0.2 |
| LAPKZJ (n = 15) | 0.2 ± 0.2 | 0 ± 0 | 0.6 ± 0.3 | 2.8 ± 0.5 | 0 ± 0 | 1.4 ± 0.3 | 0.4 ± 0.5 | 1 ± 0.2 |
| LAPWJD (n = 14) | 0.2 ± 0.2 | 0 ± 0 | 0.7 ± 0.1 | 2.5 ± 0.2 | 0 ± 0 | 1.3 ± 0.1 | 0.7 ± 0.1 | 0.8 ± 0.1 |
| LAPWLP (n = 14) | 0.3 ± 0 | 0 ± 0 | 0.7 ± 0.2 | 3.6 ± 1 | 0 ± 0 | 1.7 ± 0.6 | 0.2 ± 0.2 | 1.3 ± 0.4 |
| LAQYTA (n = 15) | 0 ± 0 | 0 ± 0 | 1 ± 0.2 | 2.9 ± 0.5 | 0 ± 0 | 1.4 ± 0.3 | 0.5 ± 0.7 | 0.5 ± 0.2 |
| LAQYUT (n = 15) | 0.1 ± 0.1 | 0 ± 0 | 1.1 ± 0.2 | 2.4 ± 0.5 | 0 ± 0 | 1.3 ± 0.3 | 0.5 ± 0.6 | 0.2 ± 0.2 |
| LAQYWQ (n = 15) | 0.1 ± 0.1 | 0 ± 0 | 0.8 ± 0.4 | 2.5 ± 0.7 | 0 ± 0 | 1.4 ± 0.6 | 0.2 ± 0.4 | 0.2 ± 0.2 |
| LAQZME (n = 12) | 0.3 ± 0 | 0 ± 0 | 0.7 ± 0.3 | 3 ± 0.5 | 0 ± 0 | 1.6 ± 0.6 | 0.1 ± 0.1 | 1.4 ± 1.1 |

TABLE 43

Fatty acid profiles of one T2 seed batch per event harvested from T1 plants cultivated in the greenhouse of canola events containing the T-DNAs of plasmids VC-LJB2197-1qcz and VC-LLM337-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LALHCY (n = 1) | 7.6 | 1.1 | 0.7 | 2.3 | 19.7 | 25.6 | 0.9 | 6.3 | 3.6 | 0.7 | 0.8 | 0.6 | 0.0 | 0.0 |
| LALIAO (n = 1) | 5.1 | 0.2 | 0.0 | 3.1 | 23.3 | 31.4 | 0.8 | 4.2 | 1.4 | 0.2 | 0.8 | 0.7 | 0.7 | 0.1 |
| LAUKA (n = 1) | 5.6 | 0.3 | 0.0 | 2.1 | 22.4 | 34.6 | 0.5 | 6.2 | 2.6 | 0.6 | 0.6 | 0.6 | 0.2 | 0.1 |
| LALLTL (n = 1) | 5.4 | 0.3 | 0.0 | 3.6 | 24.5 | 31.8 | 0.9 | 5.0 | 1.7 | 0.3 | 0.8 | 0.0 | 0.3 | 0.2 |

TABLE 43-continued

Fatty acid profiles of one T2 seed batch per event harvested from T1 plants cultivated in the greenhouse of canola events containing the T-DNAs of plasmids VC-LJB2197-1qcz and VC-LLM337-1qcz rc. The events are indicated in the first column. Fatty acid profiles of T2 seed batches having the highest EPA + DHA levels per event are shown. Per seed batch, a random selection of ~30 seed was measured in two technical repeats.

| Event | | | | | | | | | | | | | | |
|---|---|---|---|---|---|---|---|---|---|---|---|---|---|---|
| LALQAM (n = 1) | 7.1 | 0.5 | 0.0 | 3.9 | 21.1 | 30.2 | 0.8 | 4.0 | 1.7 | 0.2 | 0.8 | 0.5 | 0.5 | 0.2 |
| LALQDS (n = 1) | 5.3 | 0.3 | 0.0 | 3.4 | 25.3 | 35.7 | 0.7 | 6.1 | 1.4 | 0.3 | 0.8 | 0.0 | 0.3 | 0.2 |
| LALRCQ (n = 1) | 5.0 | 0.3 | 0.0 | 3.6 | 23.0 | 32.7 | 1.0 | 4.0 | 2.3 | 0.3 | 0.8 | 0.6 | 0.3 | 0.1 |
| LALWKF (n = 1) | 5.5 | 0.3 | 0.0 | 3.7 | 23.0 | 29.0 | 1.4 | 3.4 | 2.9 | 0.4 | 0.8 | 0.6 | 0.3 | 0.1 |
| LAMABL (n = 1) | 4.6 | 0.3 | 0.0 | 3.7 | 24.3 | 31.5 | 1.4 | 3.4 | 2.8 | 0.3 | 0.9 | 0.6 | 0.2 | 0.0 |
| LAMCKI (n = 1) | 5.1 | 0.2 | 0.0 | 3.4 | 25.6 | 33.0 | 1.1 | 4.2 | 2.0 | 0.3 | 0.8 | 0.6 | 0.1 | 0.0 |
| LAMCLE (n = 1) | 4.8 | 0.2 | 0.0 | 3.9 | 22.2 | 31.9 | 1.3 | 3.3 | 3.1 | 0.4 | 0.9 | 0.6 | 0.0 | 0.0 |
| LAMCLF (n = 1) | 5.2 | 0.3 | 0.0 | 3.8 | 24.0 | 27.7 | 1.7 | 3.1 | 3.1 | 0.3 | 0.8 | 0.5 | 0.7 | 0.0 |
| LAMEUB (n = 1) | 5.4 | 0.4 | 0.0 | 4.7 | 26.2 | 27.5 | 1.0 | 3.4 | 1.5 | 0.2 | 1.0 | 0.7 | 1.2 | 0.3 |
| LAMEUU (n = 1) | 10.9 | 1.2 | 1.0 | 2.9 | 16.4 | 27.3 | 0.0 | 8.4 | 2.3 | 0.7 | 1.0 | 0.7 | 0.0 | 0.0 |
| LAMFJO (n = 1) | 5.5 | 0.4 | 0.0 | 2.4 | 26.8 | 30.6 | 0.2 | 7.3 | 0.4 | 0.1 | 0.6 | 0.8 | 2.1 | 1.0 |
| LAMIRY (n = 1) | 5.1 | 0.3 | 0.0 | 3.7 | 23.0 | 30.3 | 0.7 | 4.5 | 1.4 | 0.2 | 0.8 | 0.7 | 1.1 | 0.3 |
| LAMJIC (n = 1) | 6.3 | 0.3 | 0.0 | 2.9 | 24.5 | 28.3 | 0.7 | 6.4 | 1.3 | 0.3 | 0.7 | 0.7 | 0.7 | 0.2 |
| LAMPJB (n = 1) | 4.9 | 0.2 | 0.0 | 3.2 | 24.2 | 32.0 | 1.1 | 4.0 | 2.7 | 0.4 | 0.8 | 0.7 | 0.0 | 0.0 |
| LAMQDL (n = 1) | 4.3 | 0.2 | 0.0 | 2.4 | 24.7 | 28.5 | 0.2 | 6.1 | 0.5 | 0.1 | 0.8 | 1.1 | 2.6 | 1.4 |
| LAMQNE (n = 1) | 7.6 | 0.4 | 0.0 | 2.7 | 25.4 | 30.7 | 0.7 | 4.7 | 1.4 | 0.2 | 0.7 | 0.6 | 0.5 | 0.2 |
| LAMQSF (n = 1) | 5.4 | 0.3 | 0.0 | 3.8 | 20.3 | 30.2 | 0.5 | 3.9 | 3.6 | 0.5 | 0.8 | 0.6 | 0.4 | 0.1 |
| LAMRCO (n = 1) | 6.7 | 0.4 | 0.0 | 4.2 | 14.8 | 26.6 | 1.0 | 2.4 | 4.7 | 0.5 | 1.0 | 0.4 | 0.3 | 0.0 |
| LAMRDS (n = 1) | 4.9 | 0.0 | 0.0 | 3.4 | 20.9 | 31.3 | 1.4 | 2.7 | 2.7 | 0.2 | 0.9 | 0.6 | 0.3 | 6.6 |
| LAMRHL (n = 1) | 6.4 | 0.3 | 0.0 | 4.0 | 19.7 | 23.4 | 0.8 | 2.6 | 1.1 | 0.2 | 1.0 | 0.7 | 1.9 | 0.5 |
| LAMRJK (n = 1) | 5.0 | 0.2 | 0.0 | 3.6 | 25.5 | 31.1 | 1.5 | 4.3 | 2.6 | 0.4 | 0.9 | 0.7 | 0.0 | 0.0 |
| LAMRNQ (n = 1) | 5.0 | 0.2 | 0.1 | 3.1 | 23.5 | 31.7 | 0.6 | 4.2 | 1.2 | 0.2 | 0.8 | 0.8 | 1.4 | 0.4 |
| LAMVUB (n = 1) | 4.3 | 0.2 | 0.0 | 3.2 | 21.9 | 33.5 | 0.2 | 4.8 | 0.4 | 0.1 | 0.8 | 1.0 | 3.0 | 1.2 |
| LAMYDP (n = 1) | 3.4 | 0.1 | 0.0 | 2.9 | 19.2 | 29.9 | 1.1 | 4.6 | 2.8 | 0.4 | 0.7 | 0.7 | 0.4 | 0.1 |
| LANBCH (n = 1) | 3.7 | 0.1 | 0.0 | 3.2 | 19.5 | 31.2 | 1.0 | 4.7 | 2.2 | 0.4 | 0.8 | 0.7 | 0.3 | 0.0 |
| LANCEG (n=1) | 5.0 | 0.0 | 0.0 | 3.7 | 22.4 | 33.6 | 0.8 | 4.1 | 2.0 | 0.3 | 0.9 | 0.6 | 0.1 | 5.5 |
| LANCOX (n = 1) | 4.9 | 0.2 | 0.0 | 3.2 | 22.1 | 33.9 | 0.6 | 4.4 | 2.3 | 0.4 | 0.8 | 0.6 | 0.0 | 4.9 |
| LANFEF (n = 1) | 5.3 | 0.0 | 0.0 | 2.5 | 28.8 | 32.0 | 0.0 | 6.0 | 0.3 | 0.0 | 0.6 | 1.0 | 2.7 | 1.1 |
| LANMGC (n = 1) | 5.2 | 0.2 | 0.0 | 3.4 | 25.2 | 33.1 | 1.0 | 4.1 | 2.2 | 0.2 | 0.8 | 0.6 | 0.2 | 0.0 |
| LANPMZ (n = 1) | 3.6 | 0.1 | 0.0 | 3.1 | 22.5 | 32.7 | 0.3 | 5.8 | 0.4 | 0.1 | 0.8 | 1.0 | 2.0 | 0.8 |
| LANMOM (n = 1) | 5.3 | 0.2 | 0.0 | 2.8 | 19.6 | 32.5 | 0.8 | 4.5 | 2.2 | 0.4 | 0.7 | 0.6 | 0.4 | 0.2 |
| LANTLE (n = 1) | 4.4 | 0.3 | 0.0 | 2.3 | 19.0 | 31.5 | 0.5 | 5.3 | 1.6 | 0.3 | 0.6 | 0.7 | 1.4 | 0.7 |
| LANTSP (n = 1) | 5.3 | 0.2 | 0.0 | 2.9 | 23.5 | 32.1 | 0.8 | 4.6 | 1.9 | 0.3 | 0.7 | 0.7 | 0.4 | 0.1 |
| LANUCB (n = 1) | 4.8 | 0.3 | 0.0 | 3.4 | 25.7 | 27.9 | 2.1 | 3.6 | 4.2 | 0.6 | 0.8 | 0.7 | 0.1 | 0.0 |
| LAOBGQ (n = 1) | 4.8 | 0.2 | 0.0 | 3.4 | 23.0 | 34.0 | 0.9 | 3.9 | 2.0 | 0.2 | 0.9 | 0.7 | 0.4 | 0.0 |
| LAOHLR (n = 1) | 5.5 | 0.2 | 0.0 | 3.2 | 21.7 | 34.5 | 1.1 | 3.2 | 2.3 | 0.2 | 0.8 | 0.6 | 0.0 | 0.0 |
| LAOJAT (n = 1) | 5.3 | 0.2 | 0.0 | 2.9 | 22.5 | 34.1 | 0.8 | 5.0 | 2.3 | 0.4 | 0.6 | 0.6 | 0.4 | 0.0 |
| LAOKLP (n = 1) | 5.0 | 0.2 | 0.0 | 3.1 | 22.9 | 32.5 | 0.2 | 5.5 | 0.4 | 0.1 | 0.8 | 1.0 | 3.0 | 1.3 |
| LAOKTE (n = 1) | 4.9 | 0.2 | 0.0 | 2.6 | 21.3 | 29.8 | 0.9 | 4.6 | 1.9 | 0.3 | 0.7 | 0.6 | 0.3 | 0.2 |
| LAPKLS (n = 1) | 5.7 | 0.3 | 0.0 | 3.8 | 20.0 | 32.5 | 1.1 | 3.9 | 3.0 | 0.4 | 0.8 | 0.6 | 0.0 | 0.0 |
| LAPKXM (n = 1) | 4.4 | 0.2 | 0.0 | 3.6 | 23.0 | 33.1 | 0.8 | 4.3 | 1.7 | 0.2 | 0.9 | 0.7 | 0.5 | 0.0 |
| LAPKZJ (n = 1) | 4.8 | 0.1 | 0.0 | 3.7 | 23.2 | 30.4 | 0.4 | 4.7 | 0.6 | 0.1 | 0.9 | 1.0 | 2.2 | 0.9 |
| LAPWJD (n = 1) | 5.5 | 0.1 | 0.0 | 3.5 | 25.6 | 35.2 | 0.4 | 4.6 | 0.7 | 0.0 | 0.8 | 0.8 | 1.5 | 0.6 |
| LAPWLP (n = 1) | 4.5 | 0.1 | 0.0 | 2.9 | 28.2 | 18.2 | 0.5 | 4.7 | 0.5 | 0.2 | 0.8 | 1.2 | 2.9 | 1.1 |
| LAQYTA (n = 1) | 5.3 | 0.0 | 0.0 | 3.0 | 24.8 | 30.1 | 1.2 | 4.3 | 2.1 | 0.1 | 0.7 | 0.6 | 0.4 | 0.0 |
| LAQYUT (n = 1) | 5.6 | 0.2 | 0.0 | 3.5 | 21.5 | 32.5 | 1.4 | 3.0 | 3.1 | 0.3 | 0.7 | 0.6 | 0.0 | 0.0 |
| LAQYWQ (n = 1) | 5.8 | 0.3 | 0.0 | 4.3 | 22.3 | 30.0 | 2.1 | 3.6 | 4.1 | 0.6 | 0.8 | 0.5 | 0.3 | 0.0 |
| LAQZME (n = 1) | 6.3 | 0.3 | 0.0 | 2.5 | 21.7 | 30.7 | 0.7 | 3.3 | 2.7 | 0.4 | 0.6 | 0.6 | 0.7 | 0.2 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LALHCY (n = 1) | 1.2 | 1.1 | 3.9 | 10.4 | 0.0 | 0.0 | 1.0 | 7.0 | 0.0 | 3.4 | 0.0 | 0.0 |
| LALIAO (n = 1) | 2.4 | 1.5 | 5.7 | 13.2 | 0.4 | 0.0 | 0.6 | 2.7 | 0.0 | 1.1 | 0.0 | 0.4 |
| LAUKA (n = 1) | 1.0 | 0.7 | 2.9 | 9.4 | 0.3 | 0.0 | 1.6 | 4.9 | 0.0 | 2.3 | 0.4 | |
| LALLTL (n = 1) | 2.8 | 1.9 | 2.8 | 8.6 | 0.3 | 0.0 | 1.7 | 3.7 | 0.0 | 2.2 | 1.1 | |
| LALQAM (n = 1) | 2.3 | 1.2 | 6.2 | 10.4 | 0.0 | 0.0 | 1.3 | 4.3 | 0.0 | 2.2 | 0.3 | 0.0 |
| LALQDS (n = 1) | 1.6 | 1.2 | 2.4 | 8.3 | 0.4 | 0.0 | 0.9 | 3.4 | 0.0 | 1.5 | 0.4 | 0.0 |
| LALRCQ (n = 1) | 3.5 | 1.5 | 3.8 | 8.4 | 0.3 | 0.0 | 2.0 | 3.5 | 0.0 | 2.1 | 0.9 | 0.0 |
| LALWKF (n = 1) | 1.9 | 1.2 | 5.9 | 11.3 | 0.3 | 0.0 | 1.2 | 3.9 | 0.0 | 2.4 | 0.2 | 0.0 |
| LAMABL (n = 1) | 1.1 | 0.6 | 7.3 | 10.1 | 0.3 | 0.0 | 1.2 | 3.6 | 0.0 | 1.5 | 0.0 | 0.0 |
| LAMCKI (n = 1) | 3.9 | 1.8 | 3.1 | 7.7 | 0.3 | 0.0 | 1.3 | 3.0 | 0.0 | 1.5 | 0.9 | |
| LAMCLE (n = 1) | 2.0 | 1.1 | 3.8 | 10.5 | 0.0 | 0.0 | 2.8 | 4.3 | 0.0 | 2.8 | 0.0 | 0.0 |
| LAMCLF (n = 1) | 1.9 | 0.9 | 7.5 | 11.2 | 0.3 | 0.0 | 1.3 | 3.6 | 0.0 | 1.9 | 0.2 | 0.0 |
| LAMEUB (n = 1) | 2.6 | 1.8 | 3.8 | 11.1 | 0.3 | 0.0 | 0.8 | 3.6 | 0.0 | 2.2 | 0.3 | 0.0 |
| LAMEUU (n = 1) | 1.1 | 0.7 | 4.5 | 6.6 | 0.3 | 0.0 | 1.4 | 6.3 | 0.0 | 4.5 | 0.0 | 0.0 |
| LAMFJO (n = 1) | 1.7 | 1.4 | 2.8 | 7.4 | 0.2 | 0.0 | 0.9 | 4.5 | 0.0 | 1.8 | 0.5 | 0.5 |
| LAMIRY (n = 1) | 2.4 | 1.6 | 4.4 | 11.6 | 0.3 | 0.0 | 1.1 | 3.7 | 0.0 | 2.0 | 0.5 | 0.0 |
| LAMJIC (n = 1) | 2.7 | 1.7 | 4.9 | 9.4 | 0.3 | 0.0 | 1.1 | 4.3 | 0.0 | 1.8 | 0.5 | 0.0 |
| LAMPJB (n = 1) | 2.2 | 1.1 | 4.0 | 10.3 | 0.0 | 0.0 | 1.8 | 4.0 | 0.0 | 2.4 | 0.0 | 0.0 |
| LAMQDL (n = 1) | 3.6 | 2.9 | 2.5 | 9.4 | 0.4 | 0.0 | 0.7 | 4.7 | 0.0 | 1.3 | 0.8 | 1.1 |
| LAMQNE (n = 1) | 3.0 | 1.5 | 3.6 | 7.8 | 0.3 | 0.0 | 1.4 | 3.7 | 0.0 | 1.7 | 0.8 | 0.3 |
| LAMQSF (n = 1) | 1.3 | 0.9 | 6.1 | 13.3 | 0.3 | 0.0 | 1.0 | 4.0 | 0.0 | 2.4 | 0.0 | 0.0 |
| LAMRCO (n = 1) | 3.9 | 1.5 | 6.7 | 12.3 | 0.4 | 0.0 | 2.6 | 5.3 | 0.0 | 3.5 | 0.5 | 0.0 |

TABLE 43-continued

Fatty acid profiles of one T2 seed batch per event harvested from T1 plants cultivated in the greenhouse of canola events containing the T-DNAs of plasmids VC-LJB2197-1qcz and VC-LLM337-1qcz rc. The events are indicated in the first column. Fatty acid profiles of T2 seed batches having the highest EPA + DHA levels per event are shown. Per seed batch, a random selection of ~30 seed was measured in two technical repeats.

| Event | | | | | | | | | | | | |
|---|---|---|---|---|---|---|---|---|---|---|---|---|
| LAMRDS (n = 1) | 0.0 | 1.2 | 4.0 | 9.1 | 0.3 | 0.0 | 2.7 | 3.8 | 0.0 | 2.1 | 0.7 | 0.0 |
| LAMRHL (n = 1) | 4.4 | 2.7 | 4.7 | 13.7 | 0.3 | 0.0 | 1.3 | 5.0 | 0.0 | 2.8 | 0.6 | 1.8 |
| LAMRJK (n = 1) | 2.8 | 1.4 | 4.0 | 9.5 | 0.0 | 0.0 | 1.3 | 3.8 | 0.0 | 1.7 | 0.0 | |
| LAMRNQ (n = 1) | 3.4 | 1.8 | 5.5 | 8.5 | 0.3 | 0.0 | 1.1 | 3.0 | 0.0 | 1.8 | 0.5 | 0.9 |
| LAMVUB (n = 1) | 3.7 | 2.4 | 4.7 | 8.4 | 0.3 | 0.0 | 0.6 | 3.0 | 0.0 | 1.7 | 0.6 | |
| LAMYDP (n = 1) | 2.0 | 1.5 | 4.2 | 14.1 | 0.3 | 0.0 | 1.9 | 5.7 | 0.0 | 3.3 | 0.5 | 0.2 |
| LANBCH (n = 1) | 1.9 | 1.6 | 4.5 | 12.5 | 0.3 | 0.0 | 2.1 | 5.7 | 0.0 | 3.2 | 0.0 | 0.3 |
| LANCEG (n=1) | 0.4 | 0.7 | 1.3 | 11.2 | 0.2 | 0.0 | 1.2 | 4.0 | 0.0 | 2.0 | 0.0 | 0.3 |
| LANCOX (n = 1) | 0.3 | 0.8 | 1.6 | 10.5 | 0.3 | 0.0 | 1.4 | 4.1 | 0.0 | 2.6 | 0.0 | 0.0 |
| LANFEF (n = 1) | 2.7 | 1.6 | 2.4 | 6.3 | 0.0 | 0.0 | 1.0 | 2.9 | 0.0 | 1.1 | 0.9 | 0.8 |
| LANMGC (n = 1) | 5.1 | 2.3 | 2.7 | 6.5 | 0.3 | 0.0 | 1.1 | 2.6 | 0.0 | 1.4 | 1.3 | 0.0 |
| LANPMZ (n = 1) | 3.0 | 2.6 | 2.7 | 8.8 | 0.4 | 0.0 | 1.2 | 4.1 | 0.0 | 2.2 | 0.9 | 1.0 |
| LANMOM (n = 1) | 2.3 | 1.6 | 4.3 | 11.9 | 0.3 | 0.0 | 1.5 | 4.6 | 0.0 | 2.5 | 0.4 | 0.3 |
| LANTLE (n = 1) | 3.2 | 2.5 | 5.1 | 11.6 | 0.2 | 0.0 | 1.0 | 4.7 | 0.0 | 2.6 | 0.2 | 0.4 |
| LANTSP (n = 1) | 2.3 | 1.5 | 3.6 | 9.9 | 0.3 | 0.0 | 1.8 | 3.9 | 0.0 | 2.3 | 0.6 | 0.1 |
| LANUCB (n = 1) | 1.9 | 1.1 | 4.2 | 10.7 | 0.3 | 0.0 | 1.3 | 4.0 | 0.0 | 1.9 | 0.0 | 0.3 |
| LAOBGQ (n = 1) | 2.4 | 1.2 | 4.8 | 9.2 | 0.4 | 0.0 | 1.6 | 3.8 | 0.0 | 1.9 | 0.0 | 0.2 |
| LAOHLR (n = 1) | 4.6 | 1.6 | 6.0 | 8.4 | 0.3 | 0.0 | 1.1 | 2.6 | 0.0 | 1.6 | 0.3 | 0.0 |
| LAOJAT (n = 1) | 2.1 | 1.3 | 4.3 | 10.3 | 0.0 | 0.0 | 1.0 | 3.6 | 0.0 | 2.0 | 0.0 | 0.2 |
| LAOKLP (n = 1) | 3.2 | 2.5 | 3.4 | 8.4 | 0.3 | 0.0 | 0.7 | 3.3 | 0.0 | 1.8 | 0.6 | 0.0 |
| LAOKTE (n = 1) | 2.3 | 1.6 | 5.4 | 12.6 | 0.3 | 0.0 | 1.4 | 4.8 | 0.0 | 2.4 | 0.4 | 0.3 |
| LAPKLS (n = 1) | 3.1 | 2.0 | 4.0 | 10.6 | 0.2 | 0.0 | 1.4 | 3.5 | 0.0 | 2.3 | 0.6 | 0.1 |
| LAPKXM (n = 1) | 2.3 | 1.6 | 4.3 | 13.3 | 0.4 | 0.0 | 0.6 | 2.5 | 0.0 | 1.2 | 0.0 | 0.3 |
| LAPKZJ (n = 1) | 3.4 | 2.7 | 2.9 | 9.2 | 0.4 | 0.0 | 0.9 | 3.7 | 0.0 | 1.9 | 0.8 | 1.1 |
| LAPWJD (n = 1) | 3.4 | 2.1 | 2.7 | 6.6 | 0.2 | 0.0 | 0.8 | 2.4 | 0.0 | 1.4 | 0.6 | 0.7 |
| LAPWLP (n = 1) | 1.9 | 2.1 | 3.6 | 15.9 | 0.4 | 0.0 | 0.7 | 4.8 | 0.0 | 3.2 | 0.0 | 1.7 |
| LAQYTA (n = 1) | 2.1 | 1.1 | 7.5 | 10.2 | 0.0 | 0.0 | 0.9 | 3.7 | 0.0 | 1.5 | 0.0 | 0.5 |
| LAQYUT (n = 1) | 4.6 | 1.6 | 6.8 | 8.9 | 0.0 | 0.0 | 1.0 | 2.6 | 0.0 | 1.6 | 0.0 | 0.3 |
| LAQYWQ (n = 1) | 1.7 | 1.1 | 3.8 | 11.5 | 0.0 | 0.0 | 1.5 | 3.5 | 0.0 | 1.9 | 0.0 | 0.1 |
| LAQZME (n = 1) | 2.7 | 1.6 | 6.4 | 10.3 | 0.3 | 0.0 | 1.2 | 3.8 | 0.0 | 2.6 | 0.1 | 0.2 |

TABLE 44

Fatty acid profiles of T2 seeds harvested from T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. The number of T1 plants fullfilling these criteria are displayed in parentheses. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| sc (n = 296) | 4.9 ± 0.5 | 0.2 ± 0.1 | 0 ± 0 | 3.2 ± 0.6 | 28.5 ± 5.4 | 31 ± 4 | 0.5 ± 0.3 | 4.7 ± 1 | 0.8 ± 0.5 | 0.1 ± 0.1 | 0.8 ± 0.1 | 0.9 ± 0.2 | 1.6 ± 0.9 | 0.7 ± 1.2 |
| dc (n = 198) | 5.1 ± 0.6 | 0.2 ± 0.1 | 0 ± 0 | 3.5 ± 0.6 | 23.7 ± 3.1 | 32.2 ± 2.5 | 1.1 ± 0.3 | 4.1 ± 0.7 | 2.3 ± 0.6 | 0.3 ± 0.1 | 0.8 ± 0.1 | 0.6 ± 0.1 | 0.3 ± 0.2 | 0.4 ± 1.4 |
| tc (n = 2) | 5.6 ± 0.4 | 0.3 ± 0 | 0 ± 0 | 4.4 ± 0.7 | 22 ± 1.5 | 30.2 ± 0.1 | 1.6 ± 0.7 | 3.6 ± 1.2 | 3.1 ± 0.7 | 0.4 ± 0.1 | 0.9 ± 0 | 0.6 ± 0 | 0.3 ± 0.1 | 0.1 ± 0.1 |

| Category of T1 plants | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| sc (n = 296) | 2.7 ± 0.9 | 1.6 ± 0.6 | 4.6 ± 2.3 | 7.2 ± 1.9 | 0.3 ± 0.1 | 0 ± 0 | 0.7 ± 0.3 | 2.7 ± 0.7 | 0 ± 0 | 1.3 ± 0.4 | 0.3 ± 0.3 | 0.9 ± 0.5 |
| dc (n = 198) | 3 ± 2 | 1.6 ± 0.8 | 4 ± 1.8 | 9.1 ± 2.8 | 0.3 ± 0.1 | 0 ± 0 | 1.4 ± 0.5 | 3.4 ± 1.2 | 0 ± 0 | 1.8 ± 0.6 | 0.6 ± 0.7 | 0.3 ± 0.2 |
| tc (n=2) | 3.5 ± 1.5 | 1.7 ± 0.4 | 3.4 ± 1.1 | 9.7 ± 3 | 0.3 ± 0 | 0 ± 0 | 1.6 ± 0.2 | 3.6 ± 1.4 | 0 ± 0 | 2.2 ± 0.7 | 0.7 ± 0 | |

TABLE 45

Fatty acid profiles of T2 seeds harvested from T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. For each category, the fatty acid profile of the plant having the highest EPA+DHA levels was shown. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| sc (n = 1) | 5.3 | 0.3 | 0.0 | 3.2 | 26.0 | 32.3 | 0.6 | 4.5 | 1.0 | 0.2 | 0.8 | 0.8 | 1.1 | 0.4 |
| dc (n = 1) | 4.5 | 0.1 | 0.0 | 2.9 | 28.2 | 18.2 | 0.5 | 4.7 | 0.5 | 0.2 | 0.8 | 1.2 | 2.9 | 1.1 |
| tc (n = 1) | 3.5 | 0.1 | 0.0 | 2.7 | 18.2 | 26.4 | 0.4 | 4.6 | 0.9 | 0.2 | 0.7 | 0.9 | 2.0 | 0.7 |

| Category of T1 plants | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| sc (n = 1) | 1.8 | 1.1 | 5.7 | 9.3 | 0.4 | 0.0 | 0.7 | 3.2 | 0.0 | 1.4 | 0.0 | 0.0 |
| dc (n = 1) | 1.9 | 2.1 | 3.6 | 15.9 | 0.4 | 0.0 | 0.7 | 4.8 | 0.0 | 3.2 | 0.0 | 1.7 |
| tc (n = 1) | 2.2 | 1.9 | 5.5 | 16.7 | 0.3 | 0.0 | 1.2 | 6.6 | 0.0 | 3.3 | 0.2 | 1.0 |

TABLE 46

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | DFF | DF | DL | DP | DS | FC | LD | LGC | LF | NoL | PH | TKW | SC |
|---|---|---|---|---|---|---|---|---|---|---|---|---|---|
| LALHCY (n = 15) | 59.3 ± 2.6 | 1 ± 0 | 1 ± 0 | 1 ± 0 | 1.3 ± 0.5 | 3 ± 0 | 3 ± 0 | 5 ± 0 | 1.7 ± 1.1 | 4 ± 0 | 136 ± 3.9 | 4.7 ± 0.2 | 3.3 ± 1.1 |
| LALIAO (n = 15) | 65.9 ± 3.2 | 1 ± 0 | 1.2 ± 0.8 | 1.3 ± 0.5 | 1.8 ± 0.7 | 3 ± 0 | 3 ± 0 | 5 ± 0 | 1.3 ± 1.3 | 3.5 ± 0.9 | 124.3 ± 3.7 | 4 ± 0.5 | 3 ± 0.7 |
| LAUKA (n = 15) | 62.1 ± 5.5 | 1 ± 0 | 1 ± 0 | 1.1 ± 0.3 | 2.5 ± 2.2 | 3 ± 0 | 3 ± 0 | 5 ± 0 | 1.6 ± 1.8 | 3.6 ± 0.7 | 126 ± 5.1 | 4.6 ± 0.2 | 3.4 ± 2 |
| LALLTL (n = 11) | 55.3 ± 2.2 | 1 ± 0 | 1 ± 0 | 1 ± 0 | 1.5 ± 0.7 | 3 ± 0 | 3 ± 0 | 5 ± 0 | 1.2 ± 0.6 | 4 ± 0 | 128.6 ± 5.5 | 4.5 ± 0.2 | 2.2 ± 1.2 |
| LALQAM (n = 15) | 58.3 ± 2.8 | 1 ± 0 | 1 ± 0 | 1 ± 0 | 2.7 ± 2.1 | 3 ± 0 | 3 ± 0 | 5 ± 0 | 2.1 ± 2.3 | 4 ± 0 | 133.7 ± 4 | 4.8 ± 0.2 | 4.7 ± 1.8 |
| LALQDS (n = 14) | 54.5 ± 3.1 | 1 ± 0 | 1 ± 0 | 1.6 ± 0.9 | 2.6 ± 1.8 | 3 ± 0 | 3 ± 0 | 5 ± 0 | 1.9 ± 1.6 | 4 ± 0 | 127.1 ± 5.4 | 4.6 ± 0.2 | 3.4 ± 1.4 |
| LALRCQ (n = 14) | 61.7 ± 1.7 | 1 ± 0 | 1 ± 0 | 1 ± 0 | 2.1 ± 1.1 | 3 ± 0 | 3 ± 0 | 5 ± 0 | 1.9 ± 1.5 | 3.7 ± 0.7 | 127.1 ± 3.8 | 4.8 ± 0.3 | 3.3 ± 1.2 |
| LALWKF (n = 14) | 62.1 ± 3.2 | 1 ± 0 | 1.4 ± 1.1 | 1 ± 0 | 1.4 ± 0.8 | 3 ± 0 | 3 ± 0 | 5 ± 0 | 1.2 ± 0.6 | 4 ± 0 | 132.9 ± 5.8 | 4.5 ± 0.2 | 3.1 ± 0.8 |
| LAMABL (n = 8) | 56.1 ± 1.6 | 1 ± 0 | 2.9 ± 1.6 | 2.1 ± 0.6 | 6.5 ± 2 | 3 ± 0 | 3 ± 0 | 5 ± 0 | 5 ± 2.3 | 4 ± 0 | 123.1 ± 4.6 | 4.1 ± 0.4 | 5.3 ± 1.6 |
| LAMCKI (n = 10) | 61.5 ± 2.4 | 1 ± 0 | 1 ± 0 | 1 ± 0 | 1.6 ± 0.7 | 3 ± 0 | 3 ± 0 | 5 ± 0 | 1 ± 0 | 4 ± 0 | 131 ± 3.9 | 4.1 ± 0.2 | 2.8 ± 0.6 |
| LAMCLE (n = 14) | 65.4 ± 1.9 | 1 ± 0 | 1.4 ± 1.1 | 1.5 ± 0.8 | 2 ± 0.7 | 3 ± 0 | 3 ± 0 | 5 ± 0 | 1.3 ± 0.6 | 3.7 ± 0.7 | 124.3 ± 4.3 | 4.3 ± 0.3 | 3 ± 1 |
| LAMCLF (n = 9) | 66.4 ± 4.3 | 1 ± 0 | 1.3 ± 1 | 1 ± 0 | 1.1 ± 0.3 | 3 ± 0 | 3 ± 0 | 5 ± 0 | 1 ± 0 | 3.1 ± 1.1 | 121.1 ± 3.3 | 4 ± 0.5 | 2.1 ± 0.3 |
| LAMEUB (n = 15) | 57.7 ± 2.4 | 1 ± 0 | 1 ± 0 | 1.5 ± 0.7 | 4.5 ± 2.3 | 3 ± 0 | 3 ± 0 | 5 ± 0 | 3.9 ± 2.3 | 4 ± 0 | 128.3 ± 3.6 | 4.2 ± 0.4 | 3.1 ± 1 |
| LAMEUU (n = 13) | 65.8 ± 3.6 | 1 ± 0 | 1.5 ± 1.1 | 1.5 ± 0.9 | 2.2 ± 1.9 | 3 ± 0 | 3 ± 0 | 5 ± 0 | 2.1 ± 1.7 | 3.7 ± 0.8 | 126.2 ± 4.2 | 4.2 ± 0.4 | 3.2 ± 0.7 |
| LAMFJO (n = 15) | 64.7 ± 2.9 | 1 ± 0 | 1.6 ± 1.2 | 1.1 ± 0.3 | 3.7 ± 2.4 | 3 ± 0 | 3 ± 0 | 5 ± 0 | 2.3 ± 1.7 | 4 ± 0 | 123.7 ± 3.5 | 4.1 ± 0.5 | 4.1 ± 2.4 |
| LAMIRY (n = 10) | 54.7 ± 2.3 | 1 ± 0 | 1 ± 0 | 1 ± 0 | 2.2 ± 2.1 | 3 ± 0 | 3 ± 0 | 5 ± 0 | 1.6 ± 1.9 | 4 ± 0 | 123 ± 4.2 | 4.9 ± 0.2 | 3.3 ± 1.7 |
| LAMJIC (n = 9) | 60.1 ± 2.9 | 1 ± 0 | 2 ± 1.5 | 2.7 ± 2.5 | 5.3 ± 3.1 | 3 ± 0 | 3 ± 0 | 5 ± 0 | 3.6 ± 2 | 3.3 ± 1 | 111.1 ± 26.8 | 3.9 ± 0.7 | 4.4 ± 1.1 |
| LAMPJB (n = 13) | 64.8 ± 2.5 | 1 ± 0 | 1.1 ± 0.3 | 1 ± 0 | 2.1 ± 0.8 | 3 ± 0 | 3 ± 0 | 5 ± 0 | 1.5 ± 0.9 | 4 ± 0 | 123.5 ± 2.4 | 4.6 ± 0.3 | 3.8 ± 1.5 |
| LAMQDL (n = 14) | 67.9 ± 4.5 | 1 ± 0 | 1.2 ± 0.8 | 1.6 ± 0.8 | 2.6 ± 2.3 | 3 ± 0 | 3 ± 0 | 5 ± 0 | 1.6 ± 0.9 | 4 ± 0 | 117.1 ± 6.4 | 3.5 ± 0.4 | 3.8 ± 1.6 |
| LAMQNE (n = 14) | 71.9 ± 6.2 | 1 ± 0 | 1.2 ± 0.8 | 1 ± 0 | 1.5 ± 1.3 | 3 ± 0 | 3 ± 0 | 5 ± 0 | 1.1 ± 0.5 | 4 ± 0 | 119.3 ± 3.3 | 4.2 ± 0.3 | 3.6 ± 1.3 |
| LAMQSF (n = 14) | 61.1 ± 1.8 | 1 ± 0 | 1 ± 0 | 1 ± 0 | 1.6 ± 0.7 | 3 ± 0 | 3 ± 0 | 5 ± 0 | 1.1 ± 0.5 | 4 ± 0 | 123.9 ± 4 | 3.9 ± 0.5 | 2.6 ± 0.7 |
| LAMRCO (n = 14) | 62.1 ± 2.9 | 1 ± 0 | 1 ± 0 | 1.6 ± 1 | 2.9 ± 1.7 | 3 ± 0 | 3 ± 0 | 5 ± 0 | 2.1 ± 1.3 | 4 ± 0 | 119.3 ± 4.3 | 3.9 ± 0.4 | 3.9 ± 2.1 |
| LAMRDS (n = 15) | 63.7 ± 2.3 | 1 ± 0 | 1.4 ± 1.1 | 1.1 ± 0.3 | 1.9 ± 1.4 | 3 ± 0 | 3 ± 0 | 5 ± 0 | 1.4 ± 1.1 | 4 ± 0 | 125.7 ± 3.7 | 4.4 ± 0.4 | 2.7 ± 1.3 |

TABLE 46-continued

Phenotypic rating of T1 plants cultivated in the greenhouse of canola events containing the T-DNAs of plasmids VC-LJB2197-1qcz and VC-LLM337-1qcz rc. The events are indicated in the first column, along with the number of T1 plants that where rated per event.

| Event | DFF | DF | DL | DP | DS | FC | LD | LGC | LF | NoL | PH | TKW | SC |
|---|---|---|---|---|---|---|---|---|---|---|---|---|---|
| LAMRHL (n = 14) | 67.7 ± 4 | 1 ± 0 | 1 ± 0 | 1 ± 0 | 2.9 ± 2 | 3 ± 0 | 3 ± 0 | 5 ± 0 | 2.7 ± 2.4 | 4 ± 0 | 122.1 ± 2.6 | 4.1 ± 0.5 | 4.1 ± 1.1 |
| LAMRJK (n = 15) | 63.4 ± 2.6 | 1 ± 0 | 1.3 ± 1 | 1 ± 0 | 3.5 ± 2 | 3 ± 0 | 3 ± 0 | 5 ± 0 | 2.5 ± 1.6 | 4 ± 0 | 124.7 ± 4.4 | 4.5 ± 0.4 | 3.8 ± 1.1 |
| LAMRNQ (n = 9) | 63.1 ± 3 | 1 ± 0 | 1 ± 0 | 1 ± 0 | 1.1 ± 0.4 | 3 ± 0 | 3 ± 0 | 5 ± 0 | 1 ± 0 | 4 ± 0 | 121.9 ± 2.6 | 3.8 ± 0.5 | 2.6 ± 1.3 |
| LAMVUB (n = 15) | 65.5 ± 3.3 | 1 ± 0 | 1 ± 0 | 1 ± 0 | 3.3 ± 2.6 | 3 ± 0 | 3 ± 0 | 5 ± 0 | 2.3 ± 1.9 | 4 ± 0 | 124.3 ± 4.2 | 4.6 ± 0.3 | 4.2 ± 2.2 |
| LAMYDP (n = 14) | 64.1 ± 4.6 | 1 ± 0 | 1 ± 0 | 1 ± 0 | 1.9 ± 0.7 | 3 ± 0 | 3 ± 0 | 5 ± 0 | 1.4 ± 0.9 | 4 ± 0 | 123.2 ± 3.7 | 4.5 ± 0.3 | 3.9 ± 1.4 |
| LANBCH (n = 14) | 64.4 ± 2.8 | 1 ± 0 | 1 ± 0 | 1 ± 0 | 1.1 ± 0.4 | 3 ± 0 | 3 ± 0 | 5 ± 0 | 1 ± 0 | 4 ± 0 | 123.9 ± 3.5 | 4.2 ± 0.2 | 3.1 ± 0.7 |
| LANCEG (n = 4) | 67.3 ± 3.3 | 1 ± 0 | 1 ± 0 | 1.3 ± 0.5 | 1.3 ± 0.5 | 3 ± 0 | 3 ± 0 | 5 ± 0 | 1 ± 0 | 4 ± 0 | 123.8 ± 2.5 | 4.1 ± 0.4 | 2.5 ± 0.6 |
| LANCOX (n = 10) | 66.3 ± 3.2 | 1 ± 0 | 1 ± 0 | 1.6 ± 0.8 | 4.2 ± 2.3 | 3 ± 0 | 3 ± 0 | 5 ± 0 | 2.9 ± 1.4 | 3.6 ± 0.8 | 127.5 ± 2.6 | 4.6 ± 0.3 | 4 ± 1.5 |
| LANFEF (n = 15) | 67.4 ± 2.4 | 1 ± 0 | 1.2 ± 0.8 | 1.1 ± 0.4 | 1.5 ± 0.6 | 3 ± 0 | 3 ± 0 | 5 ± 0 | 1.1 ± 0.5 | 4 ± 0 | 127 ± 3.2 | 4.7 ± 0.3 | 2.9 ± 0.5 |
| LANMGC (n = 15) | 64.2 ± 2 | 1 ± 0 | 1 ± 0 | 1 ± 0 | 2.3 ± 2.2 | 3 ± 0 | 3 ± 0 | 5 ± 0 | 1.7 ± 1.6 | 4 ± 0 | 123.7 ± 4 | 4.4 ± 0.3 | 3 ± 0.8 |
| LANMOM (n = 10) | 65.9 ± 3.1 | 1 ± 0 | 1 ± 0 | 1 ± 0 | 1.4 ± 1 | 3 ± 0 | 3 ± 0 | 5 ± 0 | 1.1 ± 0.3 | 4 ± 0 | 119.5 ± 3.7 | 3.4 ± 0.7 | 3.3 ± 1.2 |
| LANPMZ (n = 13) | 65.3 ± 3.1 | 1 ± 0 | 1 ± 0 | 1 ± 0 | 1.2 ± 0.4 | 3 ± 0 | 3 ± 0 | 5 ± 0 | 1 ± 0 | 4 ± 0 | 124.2 ± 3.4 | 4.4 ± 0.2 | 2.4 ± 0.5 |
| LANTLE (n = 15) | 55.6 ± 2 | 1 ± 0 | 2.5 ± 1.7 | 3.1 ± 0.9 | 1.9 ± 1.8 | 3 ± 0 | 3 ± 0 | 5 ± 0 | 1.3 ± 0.6 | 3.9 ± 0.5 | 106 ± 9.3 | 3.2 ± 0.3 | 2.6 ± 0.8 |
| LANTSP (n = 12) | 65.3 ± 3.4 | 1 ± 0 | 1 ± 0 | 1.2 ± 0.4 | 1.3 ± 0.5 | 3 ± 0 | 3 ± 0 | 5 ± 0 | 1.2 ± 0.6 | 4 ± 0 | 124.6 ± 4 | 4.1 ± 0.4 | 3.8 ± 1.3 |
| LANUCB (n = 14) | 58.3 ± 2.2 | 1 ± 0 | 1.2 ± 0.8 | 2.6 ± 0.6 | 1.9 ± 0.8 | 3 ± 0 | 3 ± 0 | 5 ± 0 | 1.4 ± 0.7 | 4 ± 0 | 117.9 ± 5.4 | 3.6 ± 0.3 | 3.1 ± 1 |
| LAOBGQ (n = 15) | 67.8 ± 3.4 | 1 ± 0 | 1 ± 0 | 1.1 ± 0.4 | 1.2 ± 0.4 | 3 ± 0 | 3 ± 0 | 5 ± 0 | 1 ± 0 | 4 ± 0 | 127 ± 3.2 | 4.2 ± 0.3 | 3.1 ± 0.6 |
| LAOHLR (n = 14) | 61.7 ± 2.7 | 1 ± 0 | 1 ± 0 | 1 ± 0 | 1.1 ± 0.4 | 3 ± 0 | 3 ± 0 | 5 ± 0 | 1 ± 0 | 3.9 ± 0.5 | 123.2 ± 4.2 | 4.2 ± 0.5 | 2.8 ± 0.7 |
| LAOJAT (n = 15) | 60.3 ± 2.8 | 1 ± 0 | 1 ± 0 | 1.4 ± 0.6 | 1.4 ± 0.5 | 3 ± 0 | 3 ± 0 | 5 ± 0 | 1 ± 0 | 4 ± 0 | 124.3 ± 5 | 4 ± 0.4 | 4.8 ± 1.6 |
| LAOKLP (n = 15) | 62 ± 2.9 | 1 ± 0 | 1 ± 0 | 1.1 ± 0.4 | 1.9 ± 1.5 | 3 ± 0 | 3 ± 0 | 5 ± 0 | 1 ± 0 | 4 ± 0 | 125.7 ± 3.2 | 4.1 ± 0.3 | 3.8 ± 1.9 |
| LAOKTE (n = 15) | 62.9 ± 3.7 | 1 ± 0 | 1.4 ± 1.1 | 1.7 ± 0.6 | 2.1 ± 1.1 | 3 ± 0 | 3 ± 0 | 5 ± 0 | 1.3 ± 1 | 4 ± 0 | 122.3 ± 4.2 | 3.7 ± 0.5 | 5.6 ± 2.7 |
| LAPKLS (n = 12) | 66.3 ± 2.7 | 1 ± 0 | 1 ± 0 | 1.7 ± 0.9 | 1.9 ± 0.7 | 3 ± 0 | 3 ± 0 | 5 ± 0 | 1.2 ± 0.6 | 2.8 ± 1 | 118.3 ± 6.2 | 4.2 ± 0.3 | 4.5 ± 1.4 |
| LAPKXM (n = 15) | 68.2 ± 3.2 | 1 ± 0 | 1.2 ± 0.8 | 1.9 ± 0.7 | 1.3 ± 0.5 | 3 ± 0 | 3 ± 0 | 5 ± 0 | 1 ± 0 | 3.2 ± 1 | 127.3 ± 2.6 | 4 ± 0.4 | 3.5 ± 0.5 |
| LAPKZJ (n = 15) | 67.9 ± 2.7 | 1 ± 0 | 1.2 ± 0.8 | 1.1 ± 0.3 | 1.5 ± 0.5 | 3 ± 0 | 3 ± 0 | 5 ± 0 | 1 ± 0 | 3.9 ± 0.5 | 127 ± 3.2 | 4.2 ± 0.3 | 3.3 ± 0.8 |
| LAPWJD (n = 14) | 68.3 ± 2.9 | 1 ± 0 | 1 ± 0 | 1.1 ± 0.4 | 1.7 ± 0.9 | 3 ± 0 | 3 ± 0 | 5 ± 0 | 1 ± 0 | 4 ± 0 | 126.1 ± 4 | 4.6 ± 0.3 | 3.1 ± 0.3 |
| LAPWLP (n = 14) | 64.9 ± 4 | 1 ± 0 | 1.5 ± 1.3 | 2 ± 1.4 | 3.6 ± 3 | 3 ± 0 | 3 ± 0 | 5 ± 0 | 2.6 ± 2.8 | 3.6 ± 0.9 | 119.3 ± 8.7 | 3.5 ± 0.4 | 4.1 ± 0.9 |
| LAQYTA (n = 15) | 59.2 ± 3.9 | 1 ± 0 | 1.2 ± 0.8 | 2.6 ± 0.8 | 2.1 ± 1.5 | 3 ± 0 | 3 ± 0 | 5 ± 0 | 1.7 ± 1 | 3.7 ± 0.7 | 111.3 ± 6.1 | 3.6 ± 0.3 | 4.2 ± 1.3 |
| LAQYUT (n = 15) | 66.3 ± 3 | 1 ± 0 | 1 ± 0 | 1.1 ± 0.3 | 1.6 ± 0.5 | 3 ± 0 | 3 ± 0 | 5 ± 0 | 1 ± 0 | 3.7 ± 0.7 | 126.3 ± 3 | 4.3 ± 0.2 | 3.7 ± 0.6 |
| LAQYWQ (n = 15) | 66.7 ± 4.6 | 1 ± 0 | 1 ± 0 | 1.6 ± 0.7 | 2.5 ± 1.8 | 3 ± 0 | 3 ± 0 | 5 ± 0 | 1.2 ± 0.6 | 4 ± 0 | 124 ± 3.9 | 4.1 ± 0.4 | 3.8 ± 0.7 |
| LAQZME (n = 12) | 64.3 ± 4.7 | 3 ± 3.6 | 1.8 ± 1.5 | 1.5 ± 0.5 | 4.1 ± 3.4 | 3 ± 0 | 3 ± 0 | 5 ± 0 | 2.8 ± 3.3 | 4 ± 0 | 124.2 ± 5.1 | 4.2 ± 0.4 | 4.8 ± 2.8 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoI: number of lobes(#),
PH: plant height (cm),
TKW: thousand kernel weight (g),
SC: seed quality (1 = good, 9 = bad)

TABLE 47

Phenotypic rating of T1 plants cultivated in the greenhouse of canola events containing the T-DNAs of plasmids VC-LJB2197-1qcz and VC-LLM337-1qcz rc. Plants of all events combined have been grouped into the categories indicated in the first column; as defined in Table 41. The number of T1 plants fullfilling these criteria are displayed in parentheses.

| Category of T1 plants | DFF | DF | DL | DP | DS | FC | LD | LGC | LF | NoL | PH | TKW | SC |
|---|---|---|---|---|---|---|---|---|---|---|---|---|---|
| sc (n = 296) | 62.9 ± 4.8 | 1 ± 0 | 1.2 ± 0.7 | 1.4 ± 0.9 | 2.5 ± 2 | 3 ± 0 | 3 ± 0 | 5 ± 0 | 1.7 ± 1.6 | 3.9 ± 0.4 | 123.9 ± 8 | 4.2 ± 0.6 | 3.6 ± 1.6 |
| dc (n = 198) | 63.4 ± 4.5 | 1 ± 0.6 | 1.2 ± 0.7 | 1.2 ± 0.5 | 2 ± 1.6 | 3 ± 0 | 3 ± 0 | 5 ± 0 | 1.6 ± 1.4 | 3.8 ± 0.5 | 123.9 ± 10.4 | 4.2 ± 0.4 | 3.6 ± 1.6 |
| tc (n = 2) | 59.5 ± 0.7 | 1 ± 0 | 1 ± 0 | 1 ± 0 | 1 ± 0 | 3 ± 0 | 3 ± 0 | 5 ± 0 | 1 ± 0 | 4 ± 0 | 125 ± 0 | 3.7 ± 0.1 | 3.5 ± 0.7 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality 1 = good, 9 = bad)

Fatty Acid Profiles, Copy Number Measurements, and Phenotypic Observations of T2 Plants Carrying T-DNAs of Plasmids VC-LJB2197-1Qcz and VC-LLM337-1Qcz Rc Cultivated in Greenhouses During Summer Table 48 shows the copy number analysis of select events. The events comprised one to two homozygous insertions and some had additional insertions still segregating. For example LANBCH segregated as homozygous for one T-DNA insertions for each construct, while LANPMZ segregated as homozygous for two T-DNA insertions for each construct. LALXOL seems to segregate for one insertion of VC-LLM337-1qcz rc, not homozygous, and for one homozygous insertion of LJB2197-1qcz_F with another copy which was not homozygous with the exception of the region around j-t-StCAT_p2_p-LuPXR, which seems to be a double copy event homozygous for each copy. For the T2 events selected, combined DHA and EPA levels were from nine to thirteen percent of the total fatty acids present in the seed. Whereas the selected T3 events had combined DHA and EPA levels varying from eleven to twenty three percent, with LALWPA having a DHA level of five percent and an EPA level of eighteen percent with respect to total fatty acid content in the seed, see Table 50. The selected events exhibited no morphological or anatomical defects relative to one another or to wild type.

TABLE 48

Copy number measurement of T2 plants cultivated in the greenhouse of canola events containing the T-DNAs of plasmids VC-LJB2197-1qcz and VC-LLM337-1qcz re. The events are indicated in the first column, along with the number of T2 plants that where measured per event. As the T2 plants underwent two cylces of selecting homozygous plants, all plants of all events are homozygous for all T-DNA insertions. A copy number of ~2 therefore was indicative of one homozygous locus, a copy number of ~4 indicative for two homozygous loci or indicative for one homozygous locus containing two copies of the target gene measured by the assay, and so forth. Odd results of 3 and 5 indicate that at least some of the selected T2 plants carry a heterozygous locus.

Copy number assays targeting the T-DNA of VC-LIB2197-1qcz. Assays are listed according to the position of the assay target along the T-DNA, with target c-AHAS located near the left T-DNA border and target j-i-Atss18_c-d6Elo(Pp_GA2) near the right T-DNA border.

| Event | c-AHAS | j-t-E9-p3-2 | c-d6Elo (Tp_GA) | j-t-StCAT_p2_p-LuPXR | j-t-CaMV_p-LuCnl2 | c-d6Elo (Pp_GA) | j-i-Atss19_c-d6Elo (Pp_GA2) |
|---|---|---|---|---|---|---|---|
| LANBCH (n = 30) | 4.0 | 3.7 | 4.1 | 4.0 | 4.4 | 4.0 | 3.8 |
| LANPMZ (n = 74) | 2.0 | 2.0 | 2.0 | 2.0 | 1.6 | 2.0 | 2.0 |
| LAOIKC (n = 29) | 2.1 | 4.0 | 3.9 | 4.2 | 4.3 | 4.1 | 4.3 |
| LALHBO (n = 29) | 4.1 | 3.9 | 4.1 | 4.0 | 3.9 | 3.9 | 3.8 |
| LALRCH (n = 30) | 4.1 | 3.8 | 4.0 | 3.9 | 3.4 | 4.1 | 4.0 |
| LALWPA (n = 29) | 4.0 | 3.9 | 4.1 | 6.0 | 5.7 | 4.1 | 3.9 |
| LALXOL (n = 15) | 2.1 | 2.1 | 2.1 | 4.1 | 2.7 | 2.0 | 2.1 |
| LALXVM (n = 30) | 3.8 | 3.6 | 3.9 | 3.5 | 1.8 | 2.0 | 1.9 |
| LALZGS (n = 24) | 1.9 | 4.0 | 3.8 | 4.0 | 1.8 | 2.0 | 2.0 |
| LAMADR (n = 44) | 4.0 | 3.9 | 3.8 | 4.0 | 4.6 | 4.0 | 3.9 |
| LAMQJH (n = 30) | 4.0 | 4.0 | 4.0 | 3.9 | 2.9 | 4.1 | 4.1 |

TABLE 48-continued

Copy number measurement of T2 plants cultivated in the greenhouse of canola events containing the T-DNAs of plasmids VC-LJB2197-1qcz and VC-LLM337-1qcz re. The events are indicated in the first column, along with the number of T2 plants that where measured per event. As the T2 plants underwent two cylces of selecting homozygous plants, all plants of all events are homozygous for all T-DNA insertions. A copy number of ~2 therefore was indicative of one homozygous locus, a copy number of ~4 indicative for two homozygous loci or indicative for one homozygous locus containing two copies of the target gene measured by the assay, and so forth. Odd results of 3 and 5 indicate that at least some of the selected T2 plants carry a heterozygous locus.

| | | | | | | | |
|---|---|---|---|---|---|---|---|
| LAMQUI (n = 36) | 2.2 | 2.1 | 4.0 | 3.7 | 3.5 | 3.6 | 3.8 |
| LAMRUR (n = 30) | 3.6 | 3.7 | 3.4 | 3.7 | 4.1 | 3.6 | 3.8 |
| LANPSF (n = 30) | 4.0 | 4.0 | 3.8 | 3.9 | 4.1 | 3.9 | 4.1 |

Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border.

| Event | j-t-PvARC-p3 | c-d4Des (Tc_GA) | c-o3Des (Pi_GA2_SNP) | j-i-Atss15_c-o3Des (Pi_GA2) | c-o3Des (Pir_GA) | j-p-VfSBPperm3_c-o3Des(Pir_GA) | j-i-Atss1_c-d5Elo (Ot_GA3) | c-d4Des (Eg_GA) |
|---|---|---|---|---|---|---|---|---|
| LANBCH (n = 30) | 2.9 | 3.9 | | | | 3.8 | 3.8 | 3.8 |
| LANPMZ (n = 74) | 1.8 | 2.1 | | | | 2.0 | 2.0 | 2.1 |
| LAOIKC (n = 29) | 2.3 | 2.0 | | | | 2.1 | 2.3 | 2.2 |
| LALHBO (n = 29) | 3.9 | 3.5 | | | | 3.8 | 2.1 | 2.0 |
| LALRCH (n = 30) | 3.9 | 4.1 | | | | 3.6 | 3.8 | 4.0 |
| LALWPA (n = 29) | 2.3 | 3.6 | | | | 3.5 | 3.4 | 3.6 |
| LALXOL (n = 15) | 0.9 | 1.2 | | | | 1.2 | 1.1 | 1.2 |
| LALXVM (n = 30) | 2.5 | 2.5 | | | | 2.4 | 2.2 | 2.3 |
| LALZGS (n = 24) | 2.1 | 2.0 | | | | 2.0 | 2.1 | 2.2 |
| LAMADR (n = 44) | 2.5 | 3.4 | | | | 3.1 | 3.0 | 3.1 |
| LAMQJH (n = 30) | 4.5 | 4.1 | | | | 4.0 | 3.9 | 4.2 |
| LAMQUI (n = 36) | 1.5 | 1.3 | | | | 2.9 | 5.2 | 5.5 |
| LAMRUR (n = 30) | 3.7 | 3.6 | | | | 3.8 | 4.3 | 3.9 |
| LANPSF (n = 30) | 1.5 | 3.5 | | | | 3.4 | 4.3 | 3.9 |

TABLE 49

Fatty acid profiles of T3 seeds harvested from T2 plants cultivated in the greenhouse of canola events containing the T-DNAs of plasmids VC-LJB2197-1qcz and VC-LLM337-1qcz rc The events are indicated in the first column, along with the number of T3 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LANBCH (n = 30) | 4.5 ± 0.6 | 0.2 ± 0 | 0.1 ± 0 | 4 ± 0.2 | 22.2 ± 1.1 | 31.1 ± 0.7 | 1 ± 0.1 | 4 ± 0.2 | 1.8 ± 0.2 | 0.2 ± 0 | 0.8 ± 0.1 | 0.6 ± 0 | 0.5 ± 0.1 | 0.1 ± 0 |
| LANPMZ (n = 74) | 5 ± 0.4 | 0.2 ± 0 | 0 ± 0 | 3.6 ± 0.4 | 26.3 ± 2.1 | 35.2 ± 1.6 | 0.4 ± 0.1 | 4.6 ± 0.6 | 0.7 ± 0.2 | 0.1 ± 0.1 | 0.8 ± 0.1 | 0.8 ± 0.1 | 1.1 ± 0.4 | 0.3 ± 0.2 |
| LAOIKC (n = 29) | 5.1 ± 0.6 | 0.2 ± 0 | 0.1 ± 0 | 3.6 ± 0.3 | 22.1 ± 1.7 | 30.8 ± 1 | 0.9 ± 0.1 | 4 ± 0.3 | 1.8 ± 0.2 | 0.2 ± 0 | 0.8 ± 0.1 | 0.6 ± 0 | 0.5 ± 0.1 | 0.1 ± 0 |
| LALHBO (n = 29) | 4.4 ± 0.3 | 0.2 ± 0.1 | 0 ± 0 | 3.9 ± 0.4 | 19.6 ± 2.3 | 28.8 ± 1.5 | 0.6 ± 0.1 | 4.9 ± 0.3 | 1.3 ± 0.3 | 0.2 ± 0.1 | 0.9 ± 0.1 | 0.7 ± 0 | 0.9 ± 0.3 | 0.3 ± 0.1 |
| LALRCH (n = 30) | 4.6 ± 0.2 | 0.2 ± 0 | 0.1 ± 0 | 3.7 ± 0.3 | 22.3 ± 1.2 | 30.1 ± 1 | 0.9 ± 0.1 | 4.2 ± 0.2 | 1.6 ± 0.2 | 0.2 ± 0 | 0.8 ± 0 | 0.7 ± 0 | 0.7 ± 0.2 | 0.2 ± 0.1 |
| LALWPA (n = 29) | 4.4 ± 0.2 | 0.2 ± 0.1 | 0 ± 0 | 3.3 ± 0.2 | 17.3 ± 1.6 | 25.6 ± 1.4 | 1 ± 0.1 | 4.4 ± 0.4 | 2.3 ± 0.3 | 0.4 ± 0.1 | 0.8 ± 0 | 0.7 ± 0 | 0.5 ± 0.2 | 0.2 ± 0 |
| LALXOL (n = 15) | 4.4 ± 0.3 | 0.2 ± 0 | 0 ± 0 | 4.4 ± 0.6 | 21.4 ± 1.1 | 28.4 ± 1.2 | 0.4 ± 0.1 | 3.5 ± 0.3 | 0.8 ± 0.2 | 0.1 ± 0 | 0.9 ± 0.1 | 0.9 ± 0.1 | 2.5 ± 0.5 | 0.5 ± 0.2 |
| LALXVM (n = 30) | 4.5 ± 1 | 0.2 ± 0 | 0 ± 0 | 3.8 ± 0.4 | 21.3 ± 1.6 | 28.8 ± 1.7 | 0.7 ± 0.2 | 4.5 ± 0.6 | 1.2 ± 0.6 | 0.2 ± 0.1 | 0.8 ± 0.1 | 0.8 ± 0.1 | 1.5 ± 0.8 | 0.5 ± 0.3 |
| LALZGS (n = 24) | 4.5 ± 0.7 | 0.3 ± 0 | 0 ± 0 | 3.4 ± 0.5 | 21.8 ± 1.8 | 29.4 ± 1.4 | 0.6 ± 0.1 | 4.2 ± 0.5 | 1.2 ± 0.3 | 0.2 ± 0 | 0.8 ± 0.1 | 0.7 ± 0.1 | 1.3 ± 0.3 | 0.3 ± 0.1 |
| LAMADR (n = 44) | 3.7 ± 1.6 | 0.2 ± 0 | 0.1 ± 0 | 4 ± 0.5 | 22.3 ± 2.8 | 32.5 ± 1.5 | 0.8 ± 0.2 | 4.3 ± 0.6 | 1.9 ± 0.4 | 0.3 ± 0.1 | 0.9 ± 0.1 | 0.7 ± 0 | 0.5 ± 0.2 | 0.1 ± 0 |
| LAMQJH (n = 30) | 4.9 ± 0.3 | 0.3 ± 0 | 0.1 ± 0.1 | 3.8 ± 0.3 | 21.9 ± 1.7 | 30.9 ± 1.1 | 1 ± 0.2 | 4.3 ± 0.3 | 2.2 ± 0.2 | 0.3 ± 0.1 | 0.8 ± 0 | 0.6 ± 0 | 0.2 ± 0.1 | 0 ± 0 |
| LAM QU I (n = 36) | 3.2 ± 2 | 0.2 ± 0.1 | 0.1 ± 0 | 3.1 ± 0.8 | 25.1 ± 1.4 | 26 ± 0.3 | 1.1 ± 0.9 | 4.5 ± 0.4 | 1.5 ± 0.1 | 0.2 ± 0.1 | 0.7 ± 0.1 | 0.8 ± 0 | 1.1 ± 0.7 | 0.3 ± 0.2 |
| LAMRUR (n = 30) | 4.9 ± 0.3 | 0.2 ± 0 | 0.2 ± 0.1 | 3.9 ± 0.3 | 23.4 ± 1.7 | 32 ± 1.1 | 1.1 ± 0.2 | 4 ± 0.5 | 2.3 ± 0 | 0.3 ± 0.1 | 0.8 ± 0 | 0.7 ± 0.1 | 0.2 ± 0 | 0 ± 0 |
| LAN PS F (n = 30) | 4.7 ± 0.2 | 0.3 ± 0 | 0.1 ± 0 | 3.9 ± 0.2 | 23.2 ± 1.3 | 30.9 ± 0.9 | 0.8 ± 0.1 | 4.5 ± 0.5 | 1.7 ± 0.3 | 0.3 ± 0 | 0.8 ± 0.1 | 0.7 ± 0 | 0.5 ± 0.1 | 0.1 ± 0 |

TABLE 49-continued

Fatty acid profiles of T3 seeds harvested from T2 plants cultivated in the greenhouse of canola events containing the T-DNAs of plasmids VC-LJB2197-1qcz and VC-LLM337-1qcz rc The events are indicated in the first column, along with the number of T3 seed batches that were measured per event. Per seed batch a random selection of ~30 seed was measured in two technical repeats.

| WT Kumily (n = 46) | 5 ± 0.1 | 0.4 ± 0 | 0.2 ± 0 | 2.6 ± 0.1 | 66.3 ± 1.7 | 16.8 ± 1.3 | 0 ± 0 | 6.1 ± 0.4 | 0 ± 0 | 0 ± 0 | 0.9 ± 0 | 1.2 ± 0 | 0 ± 0 | 0 ± 0 |
|---|---|---|---|---|---|---|---|---|---|---|---|---|---|---|

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANBCH (n = 30) | 2.6 ± 0.3 | 1.8 ± 0.1 | 3.3 ± 0.1 | 11.4 ± 0.5 | 0.3 ± 0 | 0 ± 0 | 1.7 ± 0.1 | 4.4 ± 0.2 | 0 ± 0 | 2.3 ± 0.2 | 0.6 ± 0.1 | 0.4 ± 0.1 |
| LANPMZ (n = 74) | 2.4 ± 0.3 | 1.5 ± 0.2 | 3.1 ± 0.4 | 7.2 ± 0.8 | 0.3 ± 0.1 | 0 ± 0 | 1 ± 0.1 | 2.9 ± 0.5 | 0 ± 0 | 1.5 ± 0.3 | 0.4 ± 0.1 | 0.5 ± 0.1 |
| LAOIKC (n = 29) | 3.1 ± 0.8 | 1.6 ± 0.3 | 5.9 ± 0.5 | 10.3 ± 0.8 | 0.3 ± 0 | 0 ± 0 | 1.3 ± 0.1 | 4 ± 0.3 | 0 ± 0 | 1.8 ± 0.2 | 0.4 ± 0.1 | 0.3 ± 0 |
| LALHBO (n = 29) | 2.4 ± 0.3 | 2 ± 0.2 | 4.3 ± 0.3 | 13.4 ± 1.9 | 0.3 ± 0 | 0 ± 0 | 1.3 ± 0.2 | 5.7 ± 0.8 | 0 ± 0 | 2.7 ± 0.4 | 0.4 ± 0.1 | 0.6 ± 0.1 |
| LALRCH (n = 30) | 2.7 ± 0.3 | 1.8 ± 0.2 | 4 ± 0.4 | 11.2 ± 0.8 | 0.3 ± 0 | 0 ± 0 | 1.8 ± 0.1 | 4.5 ± 0.4 | 0 ± 0 | 2.3 ± 0.4 | 0.6 ± 0.1 | 0.6 ± 0.2 |
| LALWPA (n = 29) | 2 ± 0.2 | 1.6 ± 0.1 | 5.7 ± 0.7 | 14.8 ± 1.5 | 0.4 ± 0 | 0 ± 0 | 2.1 ± 0.2 | 7.3 ± 0.8 | 0 ± 0 | 4 ± 0.7 | 0.5 ± 0.1 | 0.3 ± 0.1 |
| LALXOL (n = 15) | 2.2 ± 0.3 | 1.3 ± 0.3 | 8.7 ± 2.1 | 11.6 ± 1.3 | 0.3 ± 0 | 0 ± 0 | 0.8 ± 0.2 | 3.5 ± 0.8 | 0 ± 0 | 1.8 ± 0.4 | 0.1 ± 0.1 | 1 ± 0.2 |
| LALXVM (n = 30) | 2.7 ± 0.3 | 1.9 ± 0.3 | 4.7 ± 0.9 | 11.7 ± 1.3 | 0.3 ± 0 | 0 ± 0 | 1.4 ± 0.4 | 5.1 ± 0.8 | 0 ± 0 | 2.3 ± 0.3 | 0.4 ± 0.2 | 0.8 ± 0.4 |
| LALZGS (n = 24) | 2.6 ± 0.3 | 1.8 ± 0.3 | 5.6 ± 0.6 | 12.1 ± 1.2 | 0.3 ± 0 | 0 ± 0 | 1.2 ± 0.1 | 4.7 ± 0.6 | 0 ± 0 | 2.1 ± 0.4 | 0.2 ± 0.2 | 0.8 ± 0.2 |
| LAMADR (n = 44) | 2.2 ± 0.4 | 1.4 ± 0.2 | 4.4 ± 2 | 10.8 ± 1.6 | 0.3 ± 0 | 0 ± 0 | 1.6 ± 0.2 | 4.1 ± 0.5 | 0 ± 0 | 2.1 ± 0.3 | 0.5 ± 0.2 | 0.3 ± 0.1 |
| LAMQJH (n = 30) | 3 ± 0.5 | 1.7 ± 0.2 | 3.4 ± 0.4 | 10.7 ± 1 | 0.3 ± 0.1 | 0 ± 0 | 1.8 ± 0.2 | 4.4 ± 0.6 | 0 ± 0 | 2.3 ± 0.5 | 0.7 ± 0.1 | 0.2 ± 0 |
| LAM QU I (n = 36) | 2.2 ± 0.4 | 1.3 ± 0.3 | 4.7 ± 1.7 | 11.6 ± 2.2 | 0.2 ± 0 | 0 ± 0 | 2.4 ± 0.4 | 6.1 ± 0.9 | 0 ± 0 | 2.3 ± 0.6 | 0.6 ± 0.1 | 0.7 ± 0.3 |
| LAMRUR (n = 30) | 2.9 ± 0.6 | 1.5 ± 0.2 | 4 ± 0.4 | 9.4 ± 0.9 | 0.2 ± 0.1 | 0 ± 0 | 1.6 ± 0.2 | 3.7 ± 0.3 | 0 ± 0 | 1.9 ± 0.3 | 0.6 ± 0.1 | 0.2 ± 0.1 |
| LAN PS F (n = 30) | 2.2 ± 0.2 | 1.5 ± 0.1 | 3.7 ± 0.7 | 9.9 ± 0.8 | 0.3 ± 0 | 0 ± 0 | 2.1 ± 0.2 | 4.4 ± 0.4 | 0 ± 0 | 2.3 ± 0.2 | 0.7 ± 0.2 | 0.3 ± 0.1 |
| WT Kumily (n = 46) | 0 ± 0 | 0 ± 0 | 0 ± 0 | 0 ± 0 | 0.5 ± 0 | 0 ± 0 | 0 ± 0 | 0 ± 0 | 0 ± 0 | 0 ± 0 | 0 ± 0 | 0 ± 0 |

TABLE 50

Fatty acid profiles of one T3 seed batch per event harvested from T2 plants cultivated in the greenhouse of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LANBCH (n = 1) | 4.6 | 0.2 | 0.1 | 3.9 | 21.3 | 30.3 | 1.1 | 4.0 | 2.0 | 0.3 | 0.8 | 0.6 | 0.4 | 0.1 |
| LANPMZ (n = 1) | 4.6 | 0.3 | 0.1 | 4.0 | 22.6 | 32.2 | 0.3 | 5.2 | 0.7 | 0.1 | 0.9 | 0.8 | 1.4 | 0.5 |
| LAOIKC (n = 1) | 7.9 | 0.5 | 0.1 | 3.2 | 19.0 | 28.4 | 0.8 | 3.4 | 1.9 | 0.2 | 0.7 | 0.5 | 0.5 | 0.1 |
| LALHBO (n = 1) | 4.1 | 0.1 | 0.0 | 3.6 | 16.4 | 26.5 | 0.6 | 4.8 | 1.5 | 0.3 | 0.9 | 0.7 | 1.1 | 0.4 |
| LALRCH (n = 1) | 4.1 | 0.2 | 0.1 | 3.6 | 20.5 | 28.5 | 0.8 | 4.3 | 1.3 | 0.2 | 0.7 | 0.7 | 1.2 | 0.3 |
| LALWPA (n = 1) | 4.7 | 0.2 | 0.0 | 3.0 | 14.6 | 20.2 | 1.1 | 4.7 | 2.8 | 0.7 | 0.8 | 0.7 | 0.7 | 0.2 |
| LALXOL (n = 1) | 4.6 | 0.2 | 0.0 | 4.9 | 21.0 | 26.0 | 0.5 | 4.2 | 0.7 | 0.2 | 1.0 | 0.9 | 2.3 | 0.9 |
| LALXVM (n = 1) | 4.7 | 0.3 | 0.0 | 3.7 | 18.3 | 26.9 | 0.5 | 4.5 | 0.8 | 0.2 | 0.8 | 0.9 | 2.4 | 0.8 |
| LALZGS (n = 1) | 4.6 | 0.3 | 0.0 | 2.5 | 19.0 | 28.4 | 0.6 | 3.7 | 1.5 | 0.2 | 0.6 | 0.7 | 1.2 | 0.3 |
| LAMADR (n = 1) | 4.2 | 0.2 | 0.1 | 3.6 | 17.2 | 29.3 | 0.9 | 3.4 | 3.1 | 0.4 | 0.7 | 0.7 | 0.5 | 0.1 |
| LAMQJH (n = 1) | 4.8 | 0.3 | 0.1 | 3.0 | 17.7 | 28.1 | 0.7 | 4.6 | 2.3 | 0.4 | 0.7 | 0.6 | 0.4 | 0.1 |
| LAMQUI (n = 1) | 0.2 | 0.1 | 0.1 | 3.8 | 24.4 | 25.8 | 1.2 | 2.4 | 1.9 | 0.4 | 0.7 | 0.8 | 1.1 | 0.3 |
| LAMRUR (n = 1) | 4.9 | 0.2 | 0.3 | 4.2 | 20.3 | 32.0 | 1.1 | 3.2 | 2.7 | 0.3 | 0.8 | 0.6 | 0.0 | 0.0 |
| LANPSF (n = 1) | 4.7 | 0.3 | 0.0 | 3.9 | 20.8 | 30.7 | 0.8 | 4.1 | 2.0 | 0.3 | 0.8 | 0.6 | 0.5 | 0.1 |
| LANBCH (n = 1) | 4.6 | 0.2 | 0.1 | 3.9 | 21.3 | 30.3 | 1.1 | 4.0 | 2.0 | 0.3 | 0.8 | 0.6 | 0.4 | 0.1 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANBCH (n = 1) | 2.5 | 1.8 | 3.3 | 12.4 | 0.3 | 0.0 | 1.8 | 4.8 | 0.0 | 2.5 | 0.7 | 0.3 |
| LANPMZ (n = 1) | 2.6 | 2.1 | 3.1 | 9.7 | 0.3 | 0.0 | 1.1 | 4.2 | 0.0 | 2.3 | 0.5 | 0.5 |
| LAOIKC (n = 1) | 3.0 | 1.6 | 6.5 | 12.2 | 0.3 | 0.0 | 1.5 | 4.6 | 0.0 | 2.2 | 0.3 | 0.4 |
| LALHBO (n = 1) | 2.7 | 2.3 | 4.3 | 16.6 | 0.4 | 0.0 | 1.4 | 7.0 | 0.0 | 3.5 | 0.5 | 0.6 |

TABLE 50-continued

Fatty acid profiles of one T3 seed batch per event harvested from T2 plants cultivated in the greenhouse of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| | | | | | | | | | | | |
|---|---|---|---|---|---|---|---|---|---|---|---|
| LALRCH (n = 1) | 2.7 | 2.0 | 4.6 | 12.3 | 0.3 | 0.0 | 1.8 | 5.0 | 0.0 | 3.3 | 0.6 | 1.0 |
| LALWPA (n = 1) | 1.6 | 1.6 | 5.4 | 18.1 | 0.4 | 0.0 | 2.0 | 10.0 | 0.0 | 5.7 | 0.5 | 0.4 |
| LALXOL (n = 1) | 2.1 | 1.9 | 3.4 | 14.0 | 0.4 | 0.0 | 1.1 | 5.4 | 0.0 | 2.7 | 0.4 | 1.1 |
| LALXVM (n = 1) | 2.7 | 2.2 | 4.7 | 14.3 | 0.3 | 0.0 | 1.1 | 5.6 | 0.0 | 2.8 | 0.4 | 1.1 |
| LALZGS (n = 1) | 2.7 | 1.9 | 7.0 | 14.1 | 0.2 | 0.0 | 1.4 | 5.5 | 0.0 | 2.9 | 0.0 | 0.7 |
| LAMADR (n = 1) | 2.6 | 1.5 | 5.8 | 14.7 | 0.3 | 0.0 | 2.1 | 5.1 | 0.0 | 2.7 | 0.5 | 0.3 |
| LAMQJH (n = 1) | 2.2 | 1.5 | 4.7 | 14.4 | 0.4 | 0.0 | 2.2 | 6.8 | 0.0 | 3.5 | 0.5 | 0.2 |
| LAMQUI (n = 1) | 2.2 | 1.6 | 4.0 | 14.9 | 0.2 | 0.0 | 2.2 | 7.3 | 0.0 | 3.1 | 0.6 | 0.8 |
| LAMRUR (n = 1) | 3.0 | 1.7 | 4.0 | 11.3 | 0.3 | 0.0 | 1.8 | 3.8 | 0.0 | 2.7 | 0.6 | 0.3 |
| LANPSF (n = 1) | 2.4 | 1.4 | 4.5 | 11.4 | 0.3 | 0.0 | 2.1 | 4.7 | 0.0 | 2.6 | 0.6 | 0.4 |
| LANBCH (n = 1) | 2.5 | 1.8 | 3.3 | 12.4 | 0.3 | 0.0 | 1.8 | 4.8 | 0.0 | 2.5 | 0.7 | 0.3 |

TABLE 51

Phenotypic rating of T2 plants cultivated in the greenhouse of canola events containing the T-DNAs of plasmids VC-LJB2197-1qcz and VC-LLM337-1qcz rc. The events are indicated in the first column, along with the number of T2 plants that where rated per event.

| Event | DFF | DF | DL | DP | DS | FC | LD | LGC |
|---|---|---|---|---|---|---|---|---|
| LALHCY (n = 1) | 59.1 ± 3.3 | 9 ± 0 | 8.9 ± 0.4 | 9 ± 0 | 7 ± 0.9 | 3 ± 0 | 3 ± 0 | 5 ± 0 |
| LANBCH (n = 30) | 51.9 ± 3.1 | 9 ± 0.2 | 8.5 ± 0.7 | 9 ± 0.2 | 8.1 ± 0.7 | 3 ± 0 | 3 ± 0 | 5 ± 0 |
| LANPMZ (n = 74) | 57.3 ± 1.6 | 9 ± 0 | 8.9 ± 0.4 | 9 ± 0 | 7.3 ± 0.7 | 3 ± 0 | 3 ± 0 | 5 ± 0 |
| LAOIKC (n = 29) | 65.2 ± 2.1 | 9 ± 0 | 7.1 ± 1.7 | 7.4 ± 1.1 | 6.2 ± 2.9 | 3 ± 0 | 3 ± 0 | 5 ± 0 |
| LALHBO (n = 29) | 61.3 ± 1.9 | 9 ± 0 | 7.9 ± 1.3 | 8.8 ± 0.4 | 7.3 ± 0.5 | 3 ± 0 | 3 ± 0 | 5.1 ± 0.4 |
| LALRCH (n = 30) | 61.3 ± 1.8 | 9 ± 0 | 8.2 ± 1.4 | 7.8 ± 1 | 7.7 ± 1.9 | 3 ± 0 | 3 ± 0 | 5 ± 0 |
| LALWPA (n = 29) | 60.4 ± 3.9 | 9 ± 0 | 9 ± 0 | 9 ± 0 | 7.6 ± 1.1 | 3 ± 0 | 3 ± 0 | 5 ± 0 |
| LALXOL (n = 15) | 60.7 ± 4.6 | 9 ± 0 | 8.9 ± 0.7 | 8.2 ± 0.8 | 7.6 ± 0.9 | 3 ± 0 | 3 ± 0 | 5 ± 0 |
| LALXVM (n = 30) | 56.7 ± 4 | 8.7 ± 1.3 | 9 ± 0 | 8.9 ± 0.4 | 7.3 ± 1.3 | 3 ± 0 | 3 ± 0 | 5 ± 0 |
| LALZGS (n = 24) | 56.9 ± 6 | 9 ± 0 | 8.4 ± 1.3 | 9 ± 0 | 7.8 ± 1 | 3 ± 0 | 3 ± 0 | 5 ± 0 |
| LAMADR (n = 44) | 59.9 ± 2.6 | 9 ± 0 | 8.7 ± 0.9 | 8.8 ± 0.5 | 7.5 ± 1.1 | 3 ± 0 | 3 ± 0 | 5 ± 0 |
| LAMQJH (n = 30) | 60.3 ± 3.1 | 9 ± 0 | 8.5 ± 1.1 | 8.3 ± 0.6 | 8.1 ± 0.9 | 3 ± 0 | 3 ± 0 | 5 ± 0 |
| LAMQUI (n = 36) | 59.6 ± 1.9 | 9 ± 0 | 9 ± 0 | 9 ± 0 | 8.3 ± 0.7 | 3 ± 0 | 3 ± 0 | 5 ± 0 |
| LAMRUR (n = 30) | 55.1 ± 2.9 | 9 ± 0 | 9 ± 0 | 9 ± 0 | 7.3 ± 0.8 | 3 ± 0 | 3 ± 0 | 5 ± 0 |
| LANPSF (n = 30) WT Kumily (n = 46) | 59.1 ± 3.3 | 9 ± 0 | 8.9 ± 0.4 | 9 ± 0 | 7 ± 0.9 | 3 ± 0 | 3 ± 0 | 5 ± 0 |

| Event | LF | NoL | PH | TKW | SC | Oil | Protein |
|---|---|---|---|---|---|---|---|
| LALHCY (n = 1) | 7.5 ± 1.4 | 4 ± 0.2 | 129.2 ± 3.5 | | | | |
| LANBCH (n = 30) | 8 ± 0.7 | 5 ± 0.8 | 127.7 ± 6.6 | | | 35.2 ± 2.8 | 30 ± 2 |
| LANPMZ (n = 74) | 7.9 ± 1.1 | 4 ± 0 | 125.3 ± 5 | | | | |
| LAOIKC (n = 29) | 7.7 ± 2 | 4.1 ± 0.4 | 118.8 ± 5.8 | 4.9 ± 0.5 | 5.3 ± 2.3 | | |
| LALHBO (n = 29) | 8 ± 0.9 | 3.9 ± 0.4 | 128.3 ± 3.3 | | | | |
| LALRCH (n = 30) | 8.2 ± 1.3 | 3.8 ± 0.6 | 125 ± 3 | 5.2 ± 0.4 | 3.7 ± 1 | | |
| LALWPA (n = 29) | 7.6 ± 1.1 | 4.9 ± 0.8 | 127.3 ± 3.7 | | | | |
| LALXOL (n = 15) | 8.4 ± 0.9 | 4 ± 0.6 | 126 ± 4.6 | 5.4 ± 0.4 | 3.3 ± 1.3 | | |
| LALXVM (n = 30) | 7.3 ± 1.4 | 5.6 ± 1.3 | 121 ± 24.4 | | | | |
| LALZGS (n = 24) | 7.9 ± 0.9 | 5.1 ± 0.7 | 128.4 ± 5.5 | | | | |
| LAMADR (n = 44) | 8.2 ± 1.2 | 4 ± 0.2 | 126.5 ± 5.3 | | | | |
| LAMQJH (n = 30) | 8.6 ± 0.9 | 3.9 ± 0.3 | 124 ± 4.6 | 5.3 ± 0.4 | 4.7 ± 1.3 | | |
| LAMQUI (n = 36) | 8.3 ± 0.7 | 4.9 ± 0.5 | 129.3 ± 4.5 | | | | |

TABLE 51-continued

Phenotypic rating of T2 plants cultivated in the greenhouse of canola events containing the T-DNAs of plasmids VC-LJB2197-1qcz and VC-LLM337-1qcz rc. The events are indicated in the first column, along with the number of T2 plants that where rated per event.

| | | | | | |
|---|---|---|---|---|---|
| LAMRUR (n = 30) | 7.4 ± 0.9 | 5.7 ± 0.8 | 126.8 ± 4.4 | | |
| LANPSF (n = 30) | 7.5 ± 1.4 | 4 ± 0.2 | 129.2 ± 3.5 | | |
| WT Kumily (n = 46) | | | | 34.9 ± 1.1 | 32.2 ± 1 |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoI: number of lobes(#),
PH: plant height (cm),
TKW: thousand kernel weight (g),
SC: seed quality (1 = good, 9 = bad),
Oil: oil content (% of seed weight),
Protein: Protein content (% of seed cake without oil)

Fatty Acid Profiles of T2 Plants Carrying T-DNAs of Plasmids VC-LJB2197-1Qcz and VC-LLM337-1Qcz Rc Cultivated in Field Trials in USDA Growth Zones 3a-4b and 5a During Summer.

Field data from the T3 seed indicate that field values are lower for EPA and DHA than what was observed in the greenhouse, with values ranging from six to thirteen percent of the total fatty acid content of the seed for EPA and DHA combined. These data show a difference in seed oil content observed in field studies compared to the greenhouse (e.g. comparing Table 54 with Table 51), see also Example 10. Results of this analysis are described in Example 20.

TABLE 52

Fatty acid profiles of T3 seeds harvested from T2 plants cultivated in the field in field trials, corresponding to USDA zones 3a-4b and zone 5a , of canola events containing the T-DNAs of plasmids VC-LJB2197-1qcz and VC-LLM337-1qcz rc The events are indicated in the first column, along with the number of T3 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LANBCH (n = 30) | 5.1 ± 0.2 | 0.4 ± 0 | 0 ± 0 | 2.6 ± 0.1 | 26 ± 1.9 | 31.3 ± 1 | 0.7 ± 0.1 | 6.2 ± 0.4 | 1.2 ± 0.2 | 0.2 ± 0 | 0.7 ± 0 | 0.7 ± 0 | 0.7 ± 0.1 | 0.2 ± 0 |
| LANPMZ (n = 30) | 4.9 ± 0.1 | 0.3 ± 0 | 0 ± 0 | 2.4 ± 0.1 | 30.7 ± 1.5 | 32.1 ± 0.8 | 0.3 ± 0 | 6.9 ± 0.3 | 0.5 ± 0.1 | 0.1 ± 0 | 0.7 ± 0 | 0.9 ± 0 | 1.4 ± 0.3 | 0.5 ± 0.1 |
| LAOIKC (n = 31) | 5.2 ± 0.2 | 0.3 ± 0 | 0 ± 0 | 2.5 ± 0.1 | 26 ± 2.2 | 31.4 ± 1.1 | 0.8 ± 0.1 | 5.5 ± 0.3 | 1.4 ± 0.2 | 0.2 ± 0 | 0.7 ± 0 | 0.7 ± 0 | 0.6 ± 0.1 | 0.1 ± 0 |
| LALHBO (n = 29) | 5.1 ± 0.2 | 0.2 ± 0.1 | 0 ± 0 | 2.5 ± 0.2 | 28 ± 6.4 | 30.3 ± 2 | 0.6 ± 0.2 | 6.7 ± 1.1 | 1.1 ± 0.4 | 0.2 ± 0.1 | 0.7 ± 0 | 0.8 ± 0.1 | 0.9 ± 0.2 | 0.3 ± 0.1 |
| LALWPA (n = 30) | 5 ± 0.4 | 0.3 ± 0 | 0 ± 0 | 2.2 ± 0.2 | 21.3 ± 2.7 | 28.8 ± 1.8 | 0.8 ± 0.1 | 5.5 ± 0.5 | 1.6 ± 0.3 | 0.3 ± 0.1 | 0.7 ± 0 | 0.8 ± 0 | 1 ± 0.2 | 0.3 ± 0 |
| LALXOL (n = 29) | 5.1 ± 0.2 | 0.3 ± 0.1 | 0 ± 0 | 2.6 ± 0.2 | 26.8 ± 1.9 | 29.7 ± 1.8 | 0.4 ± 0.1 | 6 ± 0.8 | 0.8 ± 0.2 | 0.2 ± 0.1 | 0.7 ± 0 | 1 ± 0.1 | 2.1 ± 0.7 | 0.5 ± 0.2 |
| LALXVM (n = 30) | 5 ± 0.3 | 0.3 ± 0 | 0 ± 0 | 2.4 ± 0.1 | 29 ± 4 | 29.9 ± 1.3 | 0.5 ± 0.1 | 6.3 ± 0.9 | 0.8 ± 0.2 | 0.2 ± 0 | 0.7 ± 0 | 0.9 ± 0.1 | 1.3 ± 0.4 | 0.4 ± 0.1 |
| LALZGS (n = 29) | 5.1 ± 0.2 | 0.2 ± 0.1 | 0 ± 0 | 2.6 ± 0.2 | 25.1 ± 1.4 | 30.6 ± 1.2 | 0.6 ± 0.1 | 5.9 ± 0.4 | 1 ± 0.1 | 0.2 ± 0 | 0.7 ± 0 | 0.8 ± 0 | 1 ± 0.2 | 0.3 ± 0.1 |
| LAMADR (n = 30) | 5.1 ± 0.1 | 0.2 ± 0.1 | 0 ± 0 | 2.7 ± 0.2 | 25.9 ± 1 | 32 ± 1.2 | 0.7 ± 0.1 | 5.9 ± 0.4 | 1.3 ± 0.2 | 0.2 ± 0 | 0.7 ± 0 | 0.8 ± 0 | 0.7 ± 0.1 | 0.2 ± 0 |
| LAMQUI (n = 30) | 4.7 ± 0.2 | 0.3 ± 0.1 | 0 ± 0 | 2.5 ± 0.2 | 28.8 ± 1.9 | 29 ± 1.6 | 0.8 ± 0.2 | 5.7 ± 0.5 | 1.2 ± 0.2 | 0.2 ± 0 | 0.6 ± 0 | 0.9 ± 0.1 | 1 ± 0.3 | 0.2 ± 0.1 |
| LAMRUR (n = 29) | 5.1 ± 0.3 | 0.3 ± 0 | 0 ± 0 | 2.6 ± 0.1 | 28.5 ± 2.3 | 32 ± 1.9 | 0.8 ± 0.2 | 5.8 ± 0.8 | 1.3 ± 0.2 | 0.2 ± 0 | 0.7 ± 0.1 | 0.7 ± 0.1 | 0.4 ± 0.1 | 0 ± 0.1 |
| LANPSF (n = 28) | 5.1 ± 0.2 | 0.3 ± 0.1 | 0 ± 0 | 2.6 ± 0.1 | 26.9 ± 1.8 | 31.4 ± 1.4 | 0.7 ± 0.2 | 6.1 ± 0.7 | 1.2 ± 0.3 | 0.2 ± 0 | 0.7 ± 0 | 0.8 ± 0 | 0.7 ± 0.2 | 0.2 ± 0.1 |
| WT Kumily (n = 60) | 5 ± 0.3 | 0.4 ± 0 | 0.1 ± 0.1 | 2 ± 0.1 | 56.2 ± 4.2 | 23.3 ± 1.7 | 0 ± 0.1 | 9.5 ± 0.7 | 0.1 ± 0.2 | 0 ± 0 | 0.7 ± 0 | 1.1 ± 0.1 | 0.1 ± 0.1 | 0 ± 0 |

TABLE 52-continued

Fatty acid profiles of T3 seeds harvested from T2 plants cultivated in the field in field trials, corresponding to USDA zones 3a-4b and zone 5a, of canola events containing the T-DNAs of plasmids VC-LJB2197-1qcz and VC-LLM337-1qcz rc The events are indicated in the first column, along with the number of T3 seed aliquots representing a plot were measured per event. Per seed batch a random selection of ~30 seed was measured in two technical repeats.

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANBCH (n = 30) | 1.9 ± 0.1 | 1.1 ± 0.1 | 3.4 ± 0.3 | 8.9 ± 0.8 | 0.3 ± 0 | 0 ± 0 | 1.4 ± 0.2 | 4.7 ± 0.4 | 0 ± 0 | 1.5 ± 0.2 | 0.4 ± 0.1 | 0.3 ± 0.1 |
| LANPMZ (n = 30) | 2 ± 0.1 | 1.2 ± 0.1 | 2.9 ± 0.2 | 5.8 ± 0.5 | 0.3 ± 0 | 0 ± 0 | 0.8 ± 0.1 | 3.3 ± 0.2 | 0 ± 0 | 1 ± 0.1 | 0.4 ± 0.1 | 0.5 ± 0.1 |
| LAOIKC (n = 31) | 2.4 ± 0.2 | 1.1 ± 0.1 | 5.7 ± 0.5 | 8 ± 0.6 | 0.2 ± 0 | 0 ± 0 | 1.1 ± 0.1 | 4.1 ± 0.3 | 0 ± 0 | 1.2 ± 0.2 | 0.1 ± 0.1 | 0.4 ± 0.1 |
| LALHBO (n = 29) | 1.9 ± 0.4 | 1.1 ± 0.2 | 3.8 ± 1 | 8.5 ± 2.1 | 0.3 ± 0 | 0 ± 0 | 0.9 ± 0.3 | 4.2 ± 1 | 0 ± 0 | 1.2 ± 0.3 | 0.1 ± 0.1 | 0.4 ± 0.1 |
| LALWPA (n = 30) | 2.3 ± 0.3 | 1.3 ± 0.1 | 6 ± 1.4 | 11.1 ± 1.3 | 0.3 ± 0 | 0 ± 0 | 1.5 ± 0.1 | 5.9 ± 0.7 | 0 ± 0 | 2 ± 0.3 | 0.3 ± 0.2 | 0.5 ± 0.1 |
| LALXOL (n = 29) | 1.9 ± 0.2 | 1 ± 0.1 | 5.5 ± 1.6 | 8.5 ± 1 | 0.3 ± 0 | 0 ± 0 | 0.8 ± 0.1 | 3.8 ± 0.6 | 0 ± 0 | 1.1 ± 0.2 | 0 ± 0 | 0.8 ± 0.2 |
| LALXVM (n = 30) | 2 ± 0.3 | 1.1 ± 0.1 | 4.4 ± 1.3 | 7.7 ± 1.8 | 0.3 ± 0 | 0 ± 0 | 0.8 ± 0.2 | 3.9 ± 0.9 | 0 ± 0 | 1.1 ± 0.3 | 0.2 ± 0.1 | 0.6 ± 0.2 |
| LALZGS (n = 29) | 2.3 ± 0.1 | 1.2 ± 0.1 | 5.7 ± 0.5 | 8.8 ± 0.5 | 0.2 ± 0.1 | 0 ± 0 | 0.9 ± 0.1 | 4.5 ± 0.2 | 0 ± 0 | 1.2 ± 0.1 | 0 ± 0.1 | 0.7 ± 0.1 |
| LAMADR (n = 30) | 2.1 ± 0.1 | 1 ± 0.1 | 4.7 ± 0.6 | 8 ± 0.7 | 0.3 ± 0 | 0 ± 0 | 1.3 ± 0.1 | 4.1 ± 0.3 | 0 ± 0 | 1.2 ± 0.1 | 0.2 ± 0.1 | 0.4 ± 0.1 |
| LAMQUI (n = 30) | 1.7 ± 0.3 | 0.8 ± 0.1 | 4.6 ± 0.9 | 7.6 ± 1 | 0.2 ± 0 | 0 ± 0 | 2.1 ± 0.3 | 4.6 ± 0.7 | 0 ± 0 | 1.4 ± 0.2 | 0.5 ± 0.1 | 0.5 ± 0.1 |
| LAMRUR (n = 29) | 2.1 ± 0.2 | 1 ± 0.1 | 3.8 ± 0.6 | 7.2 ± 0.7 | 0.2 ± 0.1 | 0 ± 0 | 1.3 ± 0.2 | 3.9 ± 0.4 | 0 ± 0 | 1.2 ± 0.2 | 0.3 ± 0.1 | 0.3 ± 0.1 |
| LANPSF (n = 28) | 1.9 ± 0.2 | 1 ± 0.1 | 3.9 ± 0.9 | 7.6 ± 1.1 | 0.3 ± 0 | 0 ± 0 | 1.7 ± 0.2 | 4.2 ± 0.4 | 0 ± 0 | 1.4 ± 0.2 | 0.6 ± 0.2 | 0.4 ± 0.1 |
| WT Kumily (n = 60) | 0.2 ± 0.3 | 0.1 ± 0.3 | 0.2 ± 0.5 | 0.4 ± 1.1 | 0.3 ± 0.1 | 0 ± 0 | 0 ± 0.2 | 0.2 ± 0.6 | 0 ± 0 | 0 ± 0.2 | | |

TABLE 53

Fatty acid profiles of one T3 seed batch per event harvested from T2 plants cultivated in field trials, corresponding to USDA zones 3a-4b and zone 5a, of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LANBCH (n = 30) | 5.3 | 0.4 | 0.1 | 2.5 | 25.5 | 29.5 | 0.7 | 6.1 | 1.3 | 0.3 | 0.6 | 0.7 | 0.8 | 0.2 |
| LANPMZ (n = 30) | 5.1 | 0.3 | 0.0 | 2.3 | 27.1 | 31.5 | 0.2 | 6.9 | 0.4 | 0.1 | 0.7 | 0.9 | 2.1 | 0.8 |
| LAOIKC (n = 31) | 5.3 | 0.3 | 0.0 | 2.6 | 23.3 | 32.0 | 0.8 | 5.3 | 1.5 | 0.2 | 0.7 | 0.7 | 0.5 | 0.1 |
| LALHBO (n = 29) | 5.2 | 0.4 | 0.1 | 2.5 | 25.8 | 29.0 | 0.8 | 5.5 | 1.5 | 0.3 | 0.7 | 0.7 | 0.7 | 0.2 |
| LALWPA (n = 30) | 5.9 | 0.4 | 0.0 | 2.0 | 15.4 | 27.9 | 0.8 | 5.2 | 2.5 | 0.5 | 0.7 | 0.7 | 0.9 | 0.2 |
| LALXOL (n = 29) | 5.2 | 0.2 | 0.0 | 2.7 | 24.3 | 28.8 | 0.5 | 5.9 | 0.9 | 0.2 | 0.7 | 1.0 | 2.3 | 0.6 |
| LALXVM (n = 30) | 4.9 | 0.3 | 0.1 | 2.4 | 26.7 | 28.2 | 0.5 | 5.3 | 0.8 | 0.2 | 0.7 | 0.9 | 1.6 | 0.5 |
| LALZGS (n = 29) | 5.4 | 0.3 | 0.0 | 2.4 | 24.5 | 29.1 | 0.6 | 5.6 | 1.1 | 0.2 | 0.6 | 0.8 | 1.1 | 0.3 |
| LAMADR (n = 30) | 5.2 | 0.3 | 0.0 | 2.6 | 25.6 | 30.1 | 0.7 | 5.5 | 1.4 | 0.3 | 0.7 | 0.8 | 0.8 | 0.1 |
| LAMQUI (n = 30) | 4.4 | 0.4 | 0.0 | 2.3 | 26.7 | 26.2 | 0.9 | 5.3 | 1.2 | 0.2 | 0.6 | 0.9 | 1.3 | 0.3 |
| LAMRUR (n = 29) | 6.3 | 0.3 | 0.0 | 2.8 | 34.5 | 23.3 | 0.5 | 4.5 | 1.1 | 0.2 | 0.5 | 0.5 | 0.4 | 0.1 |
| LANPSF (n = 28) | 5.0 | 0.3 | 0.1 | 2.5 | 26.6 | 29.7 | 0.8 | 4.9 | 1.6 | 0.3 | 0.7 | 0.7 | 0.5 | 0.1 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANBCH (n = 30) | 1.9 | 1.1 | 3.7 | 10.1 | 0.2 | 0.0 | 1.4 | 5.2 | 0.0 | 1.6 | 0.2 | 0.4 |
| LANPMZ (n = 30) | 2.4 | 1.5 | 3.0 | 6.8 | 0.3 | 0.0 | 0.9 | 4.1 | 0.0 | 1.4 | 0.5 | 0.6 |
| LAOIKC (n = 31) | 2.5 | 1.2 | 6.1 | 8.9 | 0.2 | 0.0 | 1.2 | 4.5 | 0.0 | 1.4 | 0.1 | 0.4 |
| LALHBO (n = 29) | 2.1 | 1.2 | 4.5 | 10.6 | 0.3 | 0.0 | 1.1 | 4.9 | 0.0 | 1.6 | 0.0 | 0.4 |
| LALWPA (n = 30) | 2.7 | 1.4 | 7.1 | 13.2 | 0.4 | 0.0 | 1.8 | 6.9 | 0.0 | 2.7 | 0.3 | 0.4 |
| LALXOL (n = 29) | 1.9 | 1.1 | 5.3 | 10.1 | 0.3 | 0.0 | 0.9 | 4.8 | 0.0 | 1.4 | 0.0 | 1.0 |
| LALXVM (n = 30) | 2.1 | 1.2 | 5.3 | 10.2 | 0.3 | 0.0 | 0.8 | 4.5 | 0.0 | 1.4 | 0.1 | 0.9 |
| LALZGS (n = 29) | 2.5 | 1.3 | 6.3 | 9.6 | 0.2 | 0.0 | 1.0 | 4.9 | 0.0 | 1.5 | 0.0 | 0.7 |
| LAMADR (n = 30) | 2.1 | 1.0 | 5.4 | 9.1 | 0.3 | 0.0 | 1.3 | 4.5 | 0.0 | 1.5 | 0.0 | 0.4 |
| LAMQUI (n = 30) | 2.0 | 1.0 | 5.0 | 9.8 | 0.2 | 0.0 | 2.4 | 6.0 | 0.0 | 1.7 | 0.6 | 0.7 |

TABLE 53-continued

Fatty acid profiles of one T3 seed batch per event harvested from T2 plants cultivated in field trials, corresponding to USDA zones 3a-4b and zone 5a, of canola events containing the T-DNAs of plasmids VC-LJB2197-1qcz and VC-LLM337-1qcz rc. The events are indicated in the first column. Fatty acid profiles of T3 seed batches having the highest EPA + DHA levels per event are shown. Per seed batch, a random selection of ~30 seed was measured in two technical repeats.

| | | | | | | | | | | | | |
|---|---|---|---|---|---|---|---|---|---|---|---|---|
| LAMRUR (n = 29) | 2.3 | 1.2 | 3.5 | 9.6 | 0.2 | 0.0 | 1.1 | 5.1 | 0.0 | 1.7 | 0.0 | 0.3 |
| LANPSF (n = 28) | 1.9 | 1.0 | 5.4 | 9.2 | 0.3 | 0.0 | 1.7 | 4.6 | 0.0 | 1.5 | 0.4 | 0.3 |

TABLE 54

Phenotypic rating of T2 plants cultivated in the field of canola events containing the T-DNAs of plasmids VC-LJB2197-1qcz and VC-LLM337-1qcz rc. The events are indicated in the first column, along with the number of field plots that where rated per event. Oil: oil content (% of seed weight), protein: Protein content (% of seed cake without oil)

| Event | Oil | protein |
|---|---|---|
| LANBCH (n = 30) | 37.9 ± 1.2 | 27.9 ± 0.9 |
| LANPMZ (n = 30) | 38.7 ± 1 | 27.8 ± 0.9 |
| LAOIKC (n = 31) | 38.8 ± 1.1 | 28.1 ± 2.7 |
| LALHBO (n = 29) | 37.9 ± 1.4 | 28.2 ± 0.7 |
| LALWPA (n = 30) | 36.5 ± 1.4 | 28 ± 0.7 |
| LALXOL (n = 29) | 38.4 ± 1.1 | 27.7 ± 0.6 |
| LALXVM (n = 30) | 38.3 ± 1.1 | 27.7 ± 1 |
| LALZGS (n = 29) | 39.5 ± 0.7 | 27.2 ± 0.6 |
| LAMADR (n = 30) | 38.7 ± 0.9 | 27.6 ± 0.5 |
| LAMQUI (n = 30) | 38.3 ± 0.9 | 28.7 ± 0.8 |
| LAMRUR (n = 29) | 38.3 ± 1.1 | 27.8 ± 0.8 |
| LANPSF (n = 28) | 38.4 ± 1.1 | 27.6 ± 0.8 |
| WT Kumily (n = 60) | 38.7 ± 1.1 | |

Fatty Acid Profiles Copy Number Measurements, and Phenotypic Observations of T3 Plants Carrying T-DNAs of Plasmids VC-LJB2197-1Qcz and VC-LLM337-1Qcz Rc Cultivated in Greenhouses During Winter The data indicate that EPA and DHA are still being synthesized by the plant in the T4 seed/generation.

TABLE 55

Copy number measurement of T3 plants cultivated in the greenhouse of canola events containing the T-DNAs of plasmids VC-LJB2197-1qcz and VC-LLM337-1qcz rc. The events are indicated in the first column, along with the number of T3 plants that were measured per event. As the T3 plants underwent two cylces of selecting homozygous plants, all plants of all events are homozygous for all T-DNA insertions. A copy number of ~2 therefore was indicative for one homozygous locus, a copy number of ~4 indicative for two homozygous loci or indicative for one homozygous locus containing two copies of the target gene measured by the assay, and so forth.

Copy number assays targeting the T-DNA of VC-LJB2197-1qcz. Assays are listed according to the position of the assay target along the T-DNA, with target c-AHAS located near the left T-DNA border and target j-i-Atss18_c-d6Elo(Pp_GA2) near the right T-DNA border.

| Event | c-AHAS | j-t-E9-p3-2 | c-d6Elo (Tp_GA) | StCAT_p2_p-LuPXR | j-t-CaMV_p-LuCnl2 | c-d6Elo (Pp_GA) | j-i-Atss19_c-d6Elo (Pp_GA2) |
|---|---|---|---|---|---|---|---|
| LANPMZ (n = 74) | 1.9 | | | | | 2 | 2.02 |

Copy number assays targeting the T-DNA of VC-LLM337-1qcz rc. Assays are listed according to the position of the assay target along the T-DNA, with target j-t-PvARC-p3 located near the left T-DNA border and target c-d4Des(Eg_GA) near the right T-DNA border.

| Event | j-t-PvARC-p3 | c-d4Des (Tc_GA) | c-o3Des (Pi_GA2_SNP) | j-i-Atss15_c-o3Des (Pi_GA2) | c-o3Des (Pir_GA) | j-p-VfSBPperm3_c-o3Des(Pir_GA) | j-i-Atss1_c-d5Elo (Ot_GA3) | c-d4Des (Eg_GA) |
|---|---|---|---|---|---|---|---|---|
| LANPMZ (n = 74) | | 1.94 | | | | 2.04 | | 1.88 |

TABLE 56

Fatty acid profiles of T4 seeds harvested from T3 plants cultivated in greenhouses of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|

TABLE 56-continued

Fatty acid profiles of T4 seeds harvested from T3 plants cultivated in greenhouses of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| LANPMZ (n = 30) | 5.3 ± 0.3 | 0.2 ± 0 | 0 ± 0 | 3.6 ± 0.8 | 25.2 ± 5.3 | 38.1 ± 2.8 | 0.5 ± 0.1 | 4.1 ± 0.6 | 1.1 ± 0.3 | 0.1 ± 0.1 | 0.8 ± 0.2 | 0.7 ± 0 | 0.5 ± 0.1 | 0.1 ± 0.1 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANPMZ (n = 30) | 1.9 ± 0.2 | 0.9 ± 0.1 | 3.8 ± 0.6 | 6.9 ± 1.3 | 0.3 ± 0.1 | 0 ± 0 | 1.2 ± 0.4 | 2.6 ± 0.5 | 0 ± 0 | 1.5 ± 0.6 | 0.2 ± 0.1 | 0.3 ± 0.1 |

TABLE 57

Fatty acid profiles of one T4 seed batch per event harvested from T3 plants cultivated in greenhouses of canola events containing the T-DNAs of plasmids VC-LJB2197-1qcz and VC-LLM337-1qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 | 20:3 n-3 |
|---|---|---|---|---|---|---|---|---|---|---|---|---|---|---|
| LANPMZ (n = 1) | 4.9 | 0.2 | 0.0 | 4.0 | 19.5 | 38.5 | 0.5 | 3.6 | 1.6 | 0.2 | 1.0 | 0.7 | 0.4 | 0.0 |

| Event | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|
| LANPMZ (n = 1) | 1.6 | 0.8 | 4.8 | 9.2 | 0.4 | 0.0 | 1.7 | 3.8 | 0.0 | 2.5 | 0.0 | 0.2 |

TABLE 58

Phenotypic rating of T3 plants cultivated in the greenhouse of canola events containing the T-DNAs of plasmids VC-LJB2197-1qcz and VC-LLM337-1qcz rc. The events are indicated in the first column, along with the number of T3 plants that where rated per event.

| Event | DFF | DF | DL | DP | DS | FC | LD | LGC | LF | NoL | PH | TKW | SC | Oil | Protein |
|---|---|---|---|---|---|---|---|---|---|---|---|---|---|---|---|
| LANPMZ (n = 30) | 42.4 ± 2 | 8.2 ± 0.8 | 8.7 ± 0.7 | 9 ± 0 | 8 ± 0.7 | 3 ± 0 | 5 ± 0 | 5 ± 0 | | | 5.2 ± 0.8 | 128.5 ± 8.5 | | | |

DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes(#),
PH: plant height (cm),
TKW: thousand kernel weight (g),
SC: seed quality (1 = good, 9 = bad),
Oil: oil content (% of seed weight),
Protein: Protein content (% of seed cake without oil)

Fatty Acid Profiles and Phenotypes of T3 Plants Carrying T-DNAs of Plasmids VC-LJB2197-1Qcz and VC-LLM337-1Qcz Rc Cultivated in Field Trials in USDA Growth Zones 8a-9a During Winter The data indicate that in the field the T4 seed are making EPA and DHA, but at lower levels than seen in the summerfield trial (above, T2 plants cultivated in the field in summer)). The greenhouse data show higher oil content compared to the summer field trials (Comparison of Table 61 with Table 54). This data was analyzed in detail in Example 20.

TABLE 59

Fatty acid profiles of T4 seeds harvested from T3 plants cultivated in the field in USDA growth zones 8a-9a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 56) | 5.2 ± 0.5 | 0.3 ± 0.1 | 0.1 ± 0.2 | 2.6 ± 0.5 | 35.6 ± 2.7 | 30.4 ± 1.8 | 0.3 ± 0.1 | 7.1 ± 0.5 | 0.5 ± 0.3 | 0.1 ± 0.1 | 0.6 ± 0 | 0.9 ± 0.1 | 1.3 ± 0.3 |
| LAOIKC (n = 16) | 5.3 ± 0.2 | 0.3 ± 0 | 0 ± 0 | 2.5 ± 0.2 | 32.6 ± 2.2 | 29.9 ± 0.9 | 0.7 ± 0.1 | 5.9 ± 0.4 | 1 ± 0.2 | 0.2 ± 0 | 0.6 ± 0 | 0.7 ± 0 | 0.6 ± 0.1 |
| WT Kumily (n = 83) | 5.1 ± 0.5 | 0.4 ± 0.1 | 0.1 ± 0.1 | 2.1 ± 0.5 | 59.1 + 1.8 | 21.3 + 1.5 | 0 ± 0.1 | 9.5 ± 0.7 | 0 ± 0.1 | 0 ± 0 | 0.6 ± 0.1 | 1 ± 0.1 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 56) | 0.4 ± 0.1 | 1.6 ± 0.2 | 1 ± 0.1 | 2.5 ± 0.3 | 4.5 ± 0.6 | 0.2 ± 0.1 | 0 ± 0 | 0.5 ± 0.3 | 2.6 ± 0.3 | 0 ± 0 | 0.7 ± 0.2 | 0.3 ± 0.1 | 0.5 ± 0.1 |
| LAOIKC (n = 16) | 0 ± 0 | 2.1 ± 0.1 | 1 ± 0.1 | 4.6 ± 0.4 | 6.2 ± 0.5 | 0.2 ± 0 | 0 ± 0 | 0.8 ± 0.1 | 3.3 ± 0.2 | 0 ± 0 | 0.9 ± 0.2 | 0 ± 0.1 | 0.4 ± 0.1 |
| WT Kumily (n = 83) | 0 ± 0 | 0 ± 0 | 0 ± 0 | 0 ± 0.1 | 0.1 ± 0.1 | 0.3 ± 0 | 0 ± 0 | 0 ± 0.1 | 0 ± 0.1 | 0 ± 0 | 0 ± 0 | 0 ± 0 | 0 ± 0 |

TABLE 60

Fatty acid profiles of one T4 seed batch per event harvested from T3 plants cultivated in the field in USDA growth zones 8a-9a of canola events containing the T-DNAs of plasmids VC-LJB2197-1qcz and VC-LLM337-1qcz re. The events are indicated in the first column. Fatty acid profiles of T4 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n= 1) | 4.9 | 0.3 | 0.0 | 2.3 | 31.2 | 32.0 | 0.2 | 7.6 | 0.4 | 0.1 | 0.6 | 0.9 | 1.6 |
| LAOIKC (n = 1) | 5.4 | 0.3 | 0.0 | 2.4 | 29.6 | 30.3 | 0.7 | 5.5 | 1.4 | 0.2 | 0.5 | 0.7 | 0.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n= 1) | 0.6 | 1.6 | 1.1 | 2.8 | 5.7 | 0.2 | 0.0 | 0.8 | 3.3 | 0.0 | 1.1 | 0.4 | 0.5 |
| LAOIKC (n = 1) | 0.0 | 2.2 | 1.1 | 5.4 | 7.3 | 0.2 | 0.0 | 1.0 | 3.6 | 0.0 | 1.3 | 0.0 | 0.3 |

TABLE 61

Phenotypic rating of T3 plants cultivated in the field in USDA growth zones 8a-9b of canola events containing the T-DNAs of plasmids VC-LJB2197-1qcz and VC-LLM337-1qcz rc. The events are indicated in the first column, along with the number of field plots that where rated per event. Oil: oil content in T4 seeds harvested from T3 plants (% of seed weight), Protein: Protein content in T4 seeds harvested from T3 plants (% of seed cake without oil)

| Event | Oil | Protein |
|---|---|---|
| LANPMZ (n = 56) | 43.9 ± 7.8 | 23.2 ± 3.2 |
| LAOIKC (n = 16) | 42.6 ± 4 | 23.1 ± 3 |
| WT Kumily (n = 83) | 45.3 ± 3.9 | |

Fatty Acid Profiles and Phenotypes of T4 Plants Carrying T-DNAs of Plasmids VC-LJB2197-1Qcz and VC-LLM337-1Qcz Rc Cultivated in Field Trials in USDA Growth Zones 3a-4b and 5a During Summer.

The data indicate that through the T5 generation the transformants are still producing EPA and DHA at a level consistent with the field trial of T2 plants in summer. An additional observation is that the oil levels are comparable between these two field trials.

TABLE 62

Fatty acid profiles of T5 seeds harvested from T4 plants cultivated in the fied in USDA growth zones 3a-4b and 5a of canola events containing the T-DNAs of plasmids VC-LJB2197-1qcz and VC-LLM337-1qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 124) | 4.5 ± 0.4 | 0.2 ± 0.1 | 0 ± 0 | 2.8 ± 0.4 | 34.7 ± 3.9 | 33 ± 4.8 | 0.1 ± 0.2 | 6.5 ± 0.8 | 0.6 ± 0.2 | 0.1 ± 0.1 | 0.7 ± 0.1 | 0.9 ± 0.1 | 0.7 ± 0.3 |
| WT Kumily (n = 56) | 4.5 ± 0.5 | 0.1 ± 0.1 | 0 ± 0 | 1.8 ± 1 | 60 ± 3.8 | 22.5 ± 3.6 | 0.6 ± 1.5 | 7.9 ± 2.2 | 0.1 ± 0.1 | 0 ± 0 | 0.8 ± 0.2 | 1 ± 0.4 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 124) | 0.2 ± 0.1 | 1.7 ± 0.3 | 1.2 ± 1.3 | 2.8 ± 0.6 | 4.3 ± 1.9 | 0.3 ± 0.1 | 0 ± 0 | 0.7 ± 0.4 | 2.8 ± 0.6 | 0 ± 0.2 | 0.8 ± 0.3 | 0.1 ± 0.2 | 0.4 ± 0.2 |
| WT Kumily (n = 56) | 0 ± 0 | 0.2 + 0.8 | 0 ± 0 | 0 ± 0 | 0 ± 0.1 | 0.2 ± 0.2 | 0 ± 0 | 0 ± 0.1 | 0 ± 0 | 0 ± 0 | 0 ± 0 | 0 ± 0 | 0 ± 0 |

TABLE 63

Fatty acid profiles of one T5 seed batch per event harvested from T4 plants cultivated in the field in USDA growth zones 3a-4b and 5a of canola events containing the T-DNAs of plasmids VC-LJB2197-1qcz and VC-LLM337-1qcz rc. The events are indicated in the first column. Fatty acid profiles of T5 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LANPMZ (n = 1) | 5.6 | 0.3 | 0.0 | 2.7 | 21.8 | 32.3 | 0.0 | 6.3 | 0.9 | 0.0 | 0.8 | 0.8 | 1.5 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LANPMZ (n = 1) | 0.5 | 2.2 | 1.5 | 4.7 | 8.0 | 0.4 | 0.0 | 1.6 | 5.1 | 0.0 | 2.7 | 0.0 | 0.4 |

TABLE 64

Phenotypic rating of T4 plants cultivated in the field in USDA growth zones 3a-4b and 5a of canola events containing the T-DNAs of plasmids VC-LJB2197-1qcz and VC-LLM337-1qcz rc. The events are indicated in the first column, along with the number of field plots that were rated per event. Oil: oil content in T5 seeds harvested from T4 plants (% of seed weight), Protein: Protein content in T5 seeds harvested from T4 plants (% of seed cake without oil)

| Event | Oil | Protein |
|---|---|---|
| LANPMZ (n = 124) | 39.7 ± 2.7 | 25.8 ± 1.4 |
| WT Kumily (n = 56) | 40.6 ± 2.3 | 26.4 ± 1.3 |

Example 12: Plants Containing the T-DNAs of Plasmid VC-LJB2197-Lhcz and VC-LLM338-3Qcz Rc (Combination C in Example 5) for Production of EPA and DHA in Seeds In this example, the genetic elements required for EPA and DHA synthesis were transferred into the plant genome on two different T-DNA. To this end, the two different plasmids VC-LJB2197-1qcz and VC-LLM338-3qcz rc containing two different T-DNAs where cloned into Agrobacteria, and plant tissue was incubated according to example 5 at the same time with these two agrobacterial cultures that are identical apart from containing either VC-LJB2197-qzcz or V-LLM338-3qcz rc. Due to the selectable herbicide resistance marker, regenerated plants contained the T-DNA of VC-LJB2197-1qcz. Only those plants where kept, that also contained the T-DNA of plasmid VC-LLM338-3qcz rc as confirmed by PCR, conducted as described in example 5. Only plants containing the T-DNA of plasmid VC-LJB2197-qzcz as well as the T-DNA of plasmid Vo-LLM338-3qcz rc combine all the genetic elements required for EPA and DHA synthesis in seeds. The genetic elements of VC-LJB2197-1qcz and the function of each element are listed in Table 1. The genetic elements of VC-LLM338-3qcz rc and the function of each element was listed in Table 5. For convenience, all enzymes expressed in seeds of plants carrying both T-DNA of VC-LJB2197-(Gcz and VC-LLM338-3Lcz rc that are required for EPA and DHA synthesis are additionally listed in Table 65.

TABLE 65

Combined list of genes essential of EPA and DHA synthesis carried by the T-DNAs of plasmids VC-LJB2197-1qcz and VC-LLM338-3qcz rc.

| Genes encoding enzmyes for EPA and DHA synthesis | Plasmid containing T-DNA with the gene | Length (bp) | Enzymatic function and source of encoded protein |
|---|---|---|---|
| c-d12Des (Ps_GA) | VC-LJB2197-1qcz | 1196 | Delta-12 desaturase from *Phythophthora sojae* |
| c-d15Des (Ch_ERTp_GA) | VC-LLM338-3qcz rc | 1238 | Delta-15 desaturase from *Cochliobolus heterostrophus* C5 |
| c-d6Des (Ot_febit) | VC-LJB2197-1qcz | 1370 | Delta-6 desaturase from *Ostreococcus tauri* |
| c-d6Elo (Pp_GA2) | VC-LJB2197-1qcz | 872 | Delta-6 elongase from *Physcomitrella patens* |
| c-d6Elo (Tp_GA2) | VC-LJB2197-1qcz | 818 | Delta-6 elongase from *Thalassiosira pseudonana* |
| c-d5Des (Tc_GA2) | VC-LJB2197-1qcz | 1319 | Delta-5 desaturase from *Thraustochytrium* sp. ATCC21685 |
| c-o3Des (Pi_GA2) | VC-LLM338-3qcz rc | 1085 | Omega-3-desaturase from *Phythophthora infestans* |
| c-d5Elo (Ot_GA3) | VC-LLM338-3qcz rc | 902 | Delta-5 elongase from *Ostreococcus tauri* |
| c-d4Des (Eg_GA) | VC-LLM338-3qcz rc | 1625 | Delta-4 desaturase from *Euglena gracilis* |
| c-d4Des (Tc_GA) | VC-LLM338-3qcz rc | 1559 | Delta-4 desaturase from *Thraustochytrium* sp. |

Fatty Acid Profiles, Copy Number Measurements, and Phenotypic Observations of T0 Plants Carrying T-DNAs of Plasmids VC-LJB2197-1Qcz and VC-LLM338-3Qcz Rc Cultivated in Greenhouses During Summer The data in Table 67 and Table 68 indicate that for this construct the increase in EPA and DHA, when comparing single copy to double copy events, was more subtle, but double copy events still had an increase in EPA and DHA over single copy events. As observed in the other examples, there was no significant observed alteration of the phenotype of the plants bearing the T-DNA from both constructs.

TABLE 66

Copy number measurement of T0 plants cultivated in the greenhouse of canola events containing the T-DNAs of plasmids VC-LJB2197-1qcz and VC-LLM338-3qcz rc. Considering each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49.

| | Copy number assays targeting the T-DNA of VC-UB2197-1qcz. Assays are listed according to the position of the assay target along the T-DNA, with assay of target c-AHAS was located near the left T-DNA border and assay of target c-d6Elo (Pp_GA) near the right T-DNA border. | | Copy number assays targeting the T-DNA of VC-LLM338-3qcz rc. Assays are listed according to the position of the assay target along the T-DNA, with assay of target c-d4Des(Eg_GA) was located near the left T-DNA border and assay of target c-d15Des(Ch_ERTp_GA) near the right T-DNA border. | |
|---|---|---|---|---|
| Category of T0 plants | c-AHAS | c-d6Elo (Pp_GA) | c-d4Des (Eg_GA) | c-d15Des (Ch_ERTp_GA) |
| sc (n = 240) | 1.0 | 1.0 | 1.2 | 1.2 |
| dc (n = 117) | 1.6 | 1.7 | 1.8 | 2.0 |

TABLE 67

Fatty acid profiles of T1 seeds harvested from T0 plants cultivated in the greenhouse of canola events containing the T-DNAs of plasmids VC-LJB2197-1qcz and VC-LLM338-3qcz re. Considering each event in this generation was represented by only 1 plant, all events have been grouped into the categories indicated in the first column as described in Table 66. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 240) | 5.8 ± 0.9 | 0.4 ± 0.3 | 0 ± 0 | 2.8 ± 0.9 | 34.2 ± 5.7 | 30.5 ± 3.3 | 0.2 ± 1.2 | 7.9 ± 1.6 | 0.7 ± 0.5 | 0.2 ± 0.2 | 0.9 ± 0.1 | 0.9 ± 0.1 | 1 ± 0.6 |
| dc (n = 117) | 5.8 ± 0.9 | 0.4 ± 0.2 | 0 ± 0 | 2.9 ± 0.4 | 31.7 ± 6.5 | 30.3 ± 3.3 | 0.2 ± 0.2 | 7.9 ± 1.9 | 1.3 ± 1.1 | 0.4 ± 0.5 | 0.9 ± 0.1 | 0.8 ± 0.1 | 0.7 ± 0.5 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 240) | 0.3 ± 0.3 | 1.6 ± 0.6 | 1 ± 0.5 | 3.5 ± 1.7 | 3 ± 1.1 | 0.4 ± 0.2 | 0 ± 0 | 0.5 ± 0.3 | 2.1 ± 0.8 | 0 ± 0 | 1.4 ± 0.6 | 0.4 ± 0.4 | |
| dc (n = 117) | 0.2 ± 0.2 | 1.8 ± 1 | 1.1 ± 0.6 | 4 ± 2.1 | 3.2 ± 1.3 | 0.4 ± 0.2 | 0 ± 0 | 0.8 ± 0.4 | 2.6 ± 0.9 | 0 ± 0.1 | 1.8 ± 0.6 | 0.6 ± 0.6 | |

TABLE 68

Fatty acid profiles of T1 seeds harvested from T0 plants cultivated in the greenhouse of canola events containing the T-DNAs of plasmids VC-LJB2197-1qcz and VC-LLM338-3qcz re. Considering each event in this generation was represented by only 1 plant, all events have been grouped into the categories indicated in the first column as described in Table 66. For each category, the fatty acid profile of the plant/event having the highest EPA+DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 6.0 | 0.3 | 0.1 | 3.8 | 19.5 | 34.3 | 0.2 | 4.4 | 1.0 | 0.2 | 0.8 | 0.7 | 1.9 |
| dc (n = 1) | 5.8 | 0.4 | 0.0 | 3.2 | 19.5 | 29.5 | 0.1 | 8.5 | 1.6 | 0.7 | 0.9 | 0.7 | 1.7 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.6 | 2.0 | 1.3 | 8.0 | 8.9 | 0.3 | 0.0 | 0.7 | 3.1 | 0.0 | 1.9 | 0.0 | |
| dc (n = 1) | 0.7 | 1.6 | 1.2 | 6.5 | 7.2 | 0.4 | 0.0 | 0.9 | 4.9 | 0.0 | 3.9 | 0.3 | |

TABLE 69

Phenotypic rating of T0 plants cultivated in the greenhouse of canola events containing the T-DNAs of plasmids VC-LJB2197-1qcz and VC-LLM338-3qcz re. Considering each event in this generation was represented by only 1 plant, all events have been grouped into the categories indicated in the first column as described in Table 66.

| Category of T0 plants | DFF | DF | DL | DP | DS | FC | LD |
|---|---|---|---|---|---|---|---|
| sc (n = 240) | 81.4 ± 12.3 | 1.3 ± 0.6 | 1.9 ± 1.1 | 2.2 ± 1.3 | 2.1 ± 1.3 | 3 ± 0.1 | 4.6 ± 0.7 |
| dc (n = 117) | 78.6 ± 10.1 | 1.3 ± 0.5 | 1.9 ± 1 | 2.3 ± 1.4 | 2.4 ± 1.2 | 3 ± 0.1 | 4.6 ± 0.7 |

TABLE 69-continued

Phenotypic rating of T0 plants cultivated in the greenhouse of canola events containing the T-DNAs of plasmids VC-LJB2197-1qcz and VC-LLM338-3qcz rc. Considering each event in this generation was represented by only 1 plant, all events have been grouped into the categories indicated in the first column as described in Table 66.

| Category of T0 plants | LGC | LF | NoL | PH | TKW | SC |
|---|---|---|---|---|---|---|
| sc(n = 240) | 5 ± 0.3 | 3.1 ± 1.4 | 3.6 ± 0.9 | 93.7 ± 15.3 | 2.3 ± 0.7 | 7.4 ± 1.7 |
| dc (n = 117) | 5 ± 0 | 3.1 ± 1.4 | 3.9 ± 4.6 | 93.1 ± 17.4 | 2.2 ± 0.6 | 7.5 ± 1.5 |

The number of T0 plants/events fullfilling these criteria are displayed in parentheses.
DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoI: number of lobes (#),
PH: plant height (cm),
TKW: thousand kernel weight (g),
SC: seed quality (1 = good, 9 = bad)

Example 13: Plants Containing the T-DNAs of Plasmid VC-LJB2755-2Qcz Rc and VC-LLM39-2Qcz Rc (Combination D in Example 5) for Production of EPA and DHA in Seeds In this example, the genetic elements required for EPA and DHA synthesis were transferred into the plant genome on two different T-DNAs. To this end, the two different plasmids VC-LJB2755-2qcz rc and VC-LLM391-2Lcz rc containing two different T-DNAs where cloned into agrobacteria, and plant tissue was incubated according to example 5 at the same time with these two agrobacterial cultures that are identical apart from containing either VC-LJB2755-2qcz rc or V-LLM391-2qcz rc. Due to the selectable herbicide resistance marker, regenerated plants contained the T-DNA ofVC-LJB2755-2qcz rc. Only those plants where kept, that also contained the T-DNA of plasmid VC-LLM391-2cz rc as confirmed by PCR, conducted as described in example f. Only plants containing the T-DNA of plasmid VC-LJB2755-2qcz rc as well as the T-DNA of plasmid VC-LLM391-2-cz rc combine all the genetic elements required for EPA and DHA synthesis in seeds. The genetic elements of VC-LJB2755-2qcz rc and the function of each element are listed in Table 2. The genetic elements of VC-LLM391-29cz rc and the function of each element was listed in Table 6. For convenience, all enzymes expressed in seeds of plants carrying both T-DNA of VC-LJB2755-2gcz rc and VC-LLM391-2qcz rc that are required for EPA and DHA synthesis are additionally listed Table 70.

TABLE 70

Combined list of genes essential of EPA and DHA synthesis carried by the T-DNAs of plasmids VC-LJB2755-2qcz rc and VC-LLM391-2qcz rc.

| Genes encoding enzmyes for EPA and DHA synthesis | Plasmid containing T-DNA with the gene | Length (bp) | Enzymatic function and source of encoded protein |
|---|---|---|---|
| c-d12Des(Ps_GA) | VC-LJB2755-2qcz rc | 1196 | Delta-12 desaturase from *Phythophthora sojae* |
| c-d5Des(Tc_GA2) | VC-LJB2755-2qcz rc | 1319 | Delta-5 desaturase from *Thraustochytrium* sp. ATCC21685 |
| c-d6Des(Ot_febit) | VC-LJB2755-2qcz rc | 1370 | Delta-6 desaturase from *Ostreococcus tauri* |
| c-d6Elo(Tp_GA2) | VC-LJB2755-2qcz rc | 818 | Delta-6 elongase from *Thalassiosira pseudonana* |
| c-o3Des(Pi_GA2) | VC-LJB2755-2qcz rc | 1085 | Omega-3-desaturase from *Phytophthora infestans* |
| c-o3Des(Pir_GA) | VC-LJB2755-2qcz rc | 1091 | Omega-3 desaturase from *Pythium irregulare* |
| c-d5Elo(Ot_GA3) | VC-LLM391-2qcz rc | 902 | Delta-5 elongase from *Ostreococcus tauri* |
| c-d4Des(Eg_GA) | VC-LLM391-2qcz rc | 1625 | Delta-4 desaturase from *Euglena gracilis* |
| c-d4Des (Tc_GA)_T564G | VC-LLM391-2qcz rc | 1559 | Delta-4desaturasefrom *Thraustochytrium* spp. |

Fatty Acid Profiles, Copy Number Measurements, and Phenotypic Observations of T0 Plants Carrying T-DNAs of Plasmids VC-LJB2755-2Qcz Rc and VC-LLM391-2Qcz Rc Cultivated in Greenhouses During Summer The data in Table 72, Table 73 and Table 74 show that this combination of constructs was able to insert the T-DNA into the genome, but EPA and DHA accumulation was again at a more subtle level than observed in previous examples. None the less the constructs successfully recapitulated the pathway to generate EPA and DHA and ARA with no impact on the aerial portion of the plant.

TABLE 71

Copy number measurement of T0 plants cultivated in the greenhouse of canola events containing the T-DNAs of plasmids VC-LJB2755-2qcz rc and VC-LLM391-2qcz rc. Considering that each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49

Copy number assays targeting the T-DNA of VC-UB2755-2qcz rc. Assays are listed according to the position of the assay target along the T-DNA, with target c-AHAS located near the left T-DNA border and target j-p-LuPXR_i-Atss15 near the right T-DNA border.

| Event | c-AHAS | c-o3Des(Pi_GA) | j-i-Atss18_c-o3Des(Pi_GA2) | j-i-Atss14_c-d12Des(Ps_GA) | c-d6Elo(Tp_GA) | j-i-Atss1_c-d6Elo(Tp_Ga2) | c-o3Des(Pir_GA) | j-p-LuPXR_i-Atss15 |
|---|---|---|---|---|---|---|---|---|
| sc (n = 184) | 1.0 | | | | | | | 1.1 |
| dc (n = 6) | 1.0 | | | | | | | 2.1 |

Copy number assays targeting the T-DNA of VC-LLM391-2qcz rc. Assays are listed according to the position of the assay target along the T-DNA, with target c-d4Des(Eg_GA) located near the left T-DNA border and target j-i-Atss1_c-d5Elo(Ot_GA3) near the right T-DNA border.

| Event | c-d4Des(Eg_GA) | j-t-PvARC-p-LuCnl | j-i-Atss2_c-d4Des(Tc_GA) | c-d4Des(Tc_GA) | j-p-PvARC5_t-BnFAE | c-d5Elo(Ot_GA3) | j-i-Atss1_c-d5Elo(Ot_GA3) |
|---|---|---|---|---|---|---|---|
| sc (n = 184) | 1.0 | 1.0 | | 1.0 | | 1.1 | |
| dc (n = 6) | 1.1 | 1.5 | | | | 2.2 | |

TABLE 72

Fatty acid profiles of T1 seeds harvested from T0 plants cultivated in the greenhouse of canola events containing the T-DNAs of plasmids VC-LJB2755-2qcz rc and VC-LLM391-2qcz re. Considering that each event in this generation was represented by only 1 plant, all events have been grouped into the categories indicated in the first column as described in Table 71. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 184) | 5.4 ± 0.5 | 0.3 ± 0.1 | 0.2 ± 0.1 | 3 ± 0.4 | 39.5 ± 5.1 | 31.2 ± 2.9 | 0.4 ± 0.1 | 6.1 ± 0.9 | 1.3 ± 0.5 | 0.3 ± 0.1 | 0.7 ± 0.1 | 0.8 ± 0.1 | 0.1 ± 0.1 |
| dc (n = 6) | 4.7 ± 0.8 | 0.3 ± 0.1 | 0.1 ± 0.1 | 2.9 ± 0.4 | 34.2 ± 5.2 | 30.6 ± 3.9 | 0.8 ± 0.6 | 5.8 ± 0.9 | 3.8 ± 3.4 | 0.9 ± 0.8 | 0.7 ± 0.1 | 0.8 ± 0 | 0.1 ± 0.1 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 184) | 0 ± 0 | 1.3 ± 0.4 | 0.8 ± 0.2 | 1.3 ± 0.6 | 4.2 ± 1.4 | 0.3 ± 0 | 0 ± 0 | 0.4 ± 0.2 | 1.5 ± 0.5 | 0 ± 0 | 0.6 ± 0.3 | 0.2 ± 0.1 | |
| dc (n = 6) | 0 ± 0 | 1.9 ± 1.3 | 1.2 ± 0.8 | 1.2 ± 1 | 5.9 ± 5.8 | 0.3 ± 0 | 0 ± 0 | 0.5 ± 0.2 | 1.9 ± 1.3 | 0 ± 0 | 0.6 ± 0.4 | 0.6 ± 0.6 | |

TABLE 73

Fatty acid profiles of T1 seeds harvested from T0 plants cultivated in the greenhouse of canola events containing the T-DNAs of plasmids VC-LJB2755-2qcz rc and VC-LLM391-2qcz re. Considering each event in this generation was represented by only 1 plant, all events have been grouped into the categories indicated in the first column as described in Table 71. For each category, the fatty acid profile of the plant/event having the highest EPA+DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 3.8 | 0.1 | 0.1 | 2.8 | 41.9 | 22.2 | 1.0 | 5.5 | 1.9 | 0.4 | 0.8 | 1.0 | 0.1 |
| dc (n = 1) | 3.6 | 0.1 | 0.0 | 2.6 | 25.9 | 28.4 | 1.3 | 4.7 | 3.9 | 1.0 | 0.7 | 0.8 | 0.1 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.0 | 2.1 | 1.6 | 1.4 | 8.4 | 0.4 | 0.0 | 0.5 | 2.6 | 0.0 | 1.0 | 0.3 | |
| dc (n = 1) | 0.1 | 2.3 | 1.6 | 2.7 | 14.0 | 0.4 | 0.0 | 0.6 | 3.6 | 0.0 | 1.4 | 0.2 | |

TABLE 74

Phenotypic rating of T0 plants cultivated in the greenhouse of canola events containing the T-DNAs of plasmids VC-LJB2755-2qcz rc and VC-LLM391-2qcz rc. Considering each event in this generation was represented by only 1 plant, all events have been grouped into the categories indicated in the first column as described in Table 71.

| Category of T0 plants | DFF | DF | DL | DP | DS | FC | LD |
|---|---|---|---|---|---|---|---|
| sc (n = 184) | 61.7 ± 7.8 | 1 ± 0 | 1.4 ± 1.2 | 1.6 ± 1.4 | 2.9 ± 2.5 | 3 ± 0 | 3 ± 0.1 |
| dc (n = 6) | 63.7 ± 8 | 1 ± 0 | 1 ± 0 | 1.8 ± 1.3 | 2.8 ± 0.4 | 3 ± 0 | 3 ± 0 |

TABLE 74-continued

Phenotypic rating of T0 plants cultivated in the greenhouse of canola events
containing the T-DNAs of plasmids VC-LJB2755-2qcz rc and VC-LLM391-2qcz rc.
Considering each event in this generation was represented by only 1 plant, all events
have been grouped into the categories indicated in the first column as described in Table 71.

| Category of T0 plants | LGC | LF | NoL | PH | TKW | SC |
|---|---|---|---|---|---|---|
| sc (n = 184) | 5 ± 0 | 3.2 ± 2.5 | 3.7 ± 0.7 | 121.7 ± 9.4 | 4.9 ± 0.6 | 5.5 ± 2.1 |
| dc (n = 6) | 5 ± 0 | 2.8 ± 1 | 3.3 ± 1 | 123.3 ± 5.2 | 4.9 ± 1.2 | 5.5 ± 1.8 |

The number of T0 plants/events fullfilling these criteria are displayed in parentheses.
DFF: days to first flower (days),
DF: deformed flower (9 = deformed, 1 = normal),
DL: deformed leaf (9 = deformed, 1 = normal),
DP: deformed plant (9 = deformed, 1 = normal),
DS: deformed silique (9 = deformed, 1 = normal),
FC: flower color (1 = white, 3 = optimal, 4 = orange/yellow),
LD: leaf dentation (3 = no dentation, 7 = strong dentation),
LGC: leaf c olor (3 = yellow, 5 = optimal, 7 = blueish),
LF: fertility (1 = low, 9 =v ery high),
Nol: number of lobes (#),
PH: plant height (cm),
TKW: thousand kernel weig ht (g),
SC: seed quality (1 = good, 9 = bad)

qFatty Acid Profiles, Copy Number Measurements, and Phenotypic Observations of T1 Plants Carrying T-DNAs of Plasmids VC-LJB2755-2Qcz Rc and VC-LLM391-2Qcz Rc Cultivated in Greenhouses During Winter.

The data on Table 75, Table 76, Table 77, Table 78, Table 79, Table 80, Table 81 and Table 82 demonstrate that this pair of constructs was successful in recapitulating the pathway to generate VLC-PUFA (C20 and C22, including EPA, DHA and ARA). The copy numberfor each gene varied from homozygous single insertion of the T-DNA to insertions of parts of the T-DNA's and/or deletions of the T-DNA after insertion into the genome. The fatty acid profile indicated that some events (see Table 78, event LAPCSC) were able to accumulate up to 18 percent EPA and DHA combined). Table 75 indicates that LAPCSC was largely homozygous for a single insertion of each T-DNA with the exception of region of j-p-LuPXR_i-Atss15 on construct VC-LJB2755-2qcz, which contained at least four copies of the regions around that marker. The data presented on Table 81 indicate there was no obvious alteration of the phenotype of the plants bearing T-DNA corresponding to the constructs VC-LJB2755-2acz and VC-LLM391-2acz rc.

TABLE 75

Copy number measurement of T1 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. The T1 plants underwent a selection from 250 segregating T1 seedlings using half-kernel analysis, where the correlation of VCL-PUFA levels with copy number was employed to select for homozygous plants, or on case of multilocus events to selecect for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-UB2755-2qcz rc. Assays are listed according to the position of the assay target along the T-DNA, with target c-AHAS located near the left T-DNA border and target j-p-LuPXR_j-Atss15 near the right T-DNA border. Copy number results obtained on the T0 plants are indicated in parentheses. Homozygosity of all plants per event was indicated if the average result of the selected T1 plants was about two fold higher than the T0 generation.

| Event | c-AHAS | c-o3Des(Pi_GA) | j-i-Atss18_c-o3Des(Pi_GA2) | j-i-Atss14_c-d12Des(Ps_GA) | c-d6Elo(Tp_GA) | j-i-Atss1_c-d6Elo(Tp_Ga2) | c-o3Des(Pir_GA) | j-p-LuPXR_j-Atss15 |
|---|---|---|---|---|---|---|---|---|
| LAPCTC (n = 11) | 1.3 (TO: 1.1) | | | 2.3 | | 2.1 | | 4.6 (TO: 3.6) |
| LAPCSC (n = 11) | 1.4 (TO: 1) | | | 2.7 | | 2.6 | | 5.1 (TO: 4) |
| LAPYTI (n = 15) | 1.7 (TO: 0.9) | | | 3.2 | | 3.3 | | 3.2 (TO: 2.1) |
| LAQKQS (n = 15) | 1.5 (TO: 1.1) | | | 1.7 | | 1.4 | | 2 (TO: 1.3) |
| LAPARV (n = 15) | 2 (TO: 1.1) | | | 1.9 | | 2.0 | | 2 (TO: 1.1) |
| LAPCMY (n = 15) | 2 (TO: 1) | | | 2.0 | | 2.1 | | 2.2 (TO: 1.1) |
| LAPBOW (n = 15) | 2 (TO: 1) | | | 1.9 | | 2.1 | | 2 (TO: 1) |
| LAPAWA (n = 15) | 1.9 (TO: 1.1) | | | 2.0 | | 2.0 | | 2.1 (TO: 1.1) |
| LAPBYW (n = 13) | 2 (TO: 1) | | | 2.0 | | 2.2 | | 2.3 (TO: 1) |
| LAPQEP (n = 15) | 1.4 (TO: 0.9) | | | 2.8 | | 2.6 | | 4 (TO: 3.1) |
| LAODDN (n = 15) | 2.1 (TO: 1.1) | | | 2.0 | | 2.1 | | 2.1 (TO: 1.1) |
| LAPAUX (n = 10) | 1.5 (TO: 1) | | | 1.6 | | 1.7 | | 1.7 (TO: 1) |
| LAPZOJ (n = 10) | 1.8 (TO: 1) | | | 2.1 | | 1.9 | | 2 (TO: 1.1) |

TABLE 75-continued

Copy number measurement of T1 plants cultivated in the greenhouse of canola events containing the T-DNAs of plasmids VC-LJB2755-2qcz rc and VC-LLM391-2qcz rc. The events are indicated in the first column, along with the number of T1 plants that were measured per event. The T1 plants underwent a selection from 250 segregating T1 seedlings using half-kernel analysis, where the correlation of VCL-PUFA levels with copy number was employed to select for homozygous plants, or on case of multilocus events to seleccet for plants where one or more loci are homozygous. A copy number of ~2 therefore was indicative for one homozygous locus, a copy number of ~4 indicative for two homozygous loci or indicative for one homozygous locus containing two copies of the target gene measured by the assay, and so forth. Odd results of 3 and 5 indicate that at least some of the selected T1 plants carry a heterozygous locus.

Copy number assays targeting the T-DNA of VC-LLM391-2qcz rc. Assays are listed according to the position of the assay target along the T-DNA, with target c-d4Des(Eg_GA) located near the left T-DNA border and target j-i-Atss1_c-d5Elo(Ot_GA3) near the right T-DNA border. Copy number results obtained on the T0 plants are indicated in parentheses. Homozygosity was indicated if the average result of the selected T1 plants was about two fold higher than the T0 generation.

| Event | c-d4Des(Eg_GA) | j-t-PvARC-p-LuCnl | j-i-Atss2_c d4Des(Tc_GA) | c-d4Des(Tc_GA) | j-p-PvARC5_t-BnFAE | c-d5Elo(Ot_GA3) | j-i-Atss1_c-d5Elo(Ot_GA3) |
|---|---|---|---|---|---|---|---|
| LAPCTC (n = 11) | 1.7 (T0: 1) | N/A (T0: 1.2) | | 1.7 | | 1.7 (T0: 1.1) | |
| LAPCSC (n = 11) | 1.6 (T0: 1) | N/A (T0: 1) | | 1.7 | | 1.6 (T0: 1.1) | |
| LAPYTI (n = 15) | 1.7 (T0: 1.1) | N/A (T0: 1.1) | | 1.8 | | 1.7 (T0: 1.1) | |
| LAQKQS (n = 15) | 1.4 (T0: 1) | N/A (T0: 1) | | 1.5 | | 1.4 (T0: 1) | |
| LAPARV (n = 15) | 1.2 (T0: 1.1) | N/A (T0: 0.9) | | 1.2 | | 1.2 (T0: 1.1) | |
| LAPCMY (n = 15) | 1.7 (T0: 1) | N/A (T0: 1.1) | | 1.7 | | 1.9 (T0: 1.2) | |
| LAPBOW (n = 15) | 2 (T0: 1) | N/A (T0: 1.2) | | 1.9 | | 2.1 (T0: 1.1) | |
| LAPAWA (n = 15) | 1.5 (T0: 1) | N/A (T0: 1) | | 1.5 | | 1.5 (T0: 1.2) | |
| LAPBYW (n = 13) | 1.3 (T0: 1) | N/A (T0: 0.8) | | 1.3 | | 1.5 (T0: 1.1) | |
| LAPQEP (n = 15) | 1.3 (T0: 0.9) | N/A (T0: 1.2) | | 1.4 | | 1.4 (T0: 1.1) | |
| LAODDN (n = 15) | 2 (T0: 1) | N/A (T0: 1.1) | | 2.0 | | 2.1 (T0: 1.1) | |
| LAPAUX (n = 10) | 1 (T0: 0.9) | N/A (T0: 0.8) | | 1.0 | | 1.1 (T0: 0.6) | |
| LAPZOJ (n = 10) | 1.8 (T0: 1) | N/A (T0: 1.2) | | 1.9 | | 1.9 (T0: 1) | |

TABLE 76

Copy number measurement of T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; sc: all T1 plants where the average of all copy number assays listed in this table was 1.51-2.49, dc: all T1 plants where the average of all copy number assays listed in this table was 3.51-4.49, tc: all T1 plants where the average of all copy number assays listed in this table was 5.51-6.49. The number of T1 plants fullfilling these criteria are displayed in parentheses.

Copy number assays targeting the T-DNA of VC-UB2755-2qcz rc. Assays are listed according to the position of the assay target along the T-DNA, with target c-AHAS located near the left T-DNA border and target j-p-LuPXR_j-Atss15 near the right T-DNA border. Copy number results obtained on the T0 plants are indicated in parentheses. Homozygosity of all plants per event was indicated if the average result of the selected T1 plants was about two fold higher than the T0 generation.

| Category of T1 plants | c-AHAS | c-o3Des(Pir_GA) | j-p-LuPXR_j-Atss15 | c-o3Des(Pi_GA) | j-i-Atss18_c-o3Des(Pi_GA2) | j-i-Atss14_c-d12Des(Ps_GA) | c-d6Elo(Tp_GA) | j-i-Atss1_c-d6Elo(Tp_Ga2) |
|---|---|---|---|---|---|---|---|---|
| sc (n = 140) | 1.8 | | 2.6 | | | 2.1 | | 2.1 |

Copy number assays targeting the T-DNA of VC-LLM391-2qcz rc. Assays are listed according to the position of the assay target along the T-DNA, with target c-d4Des(Eg_GA) located near the left T-DNA border and target j-i-Atssl_c-d5Elo(Ot_GA3) near the right T-DNA border. Copy number results obtained on the T0 plants are indicated in parentheses. Homozygosity was indicated if the average result of the selected T1 plants was about two fold higher than the T0 generation.

| Category of T1 plants | c-d4Des(Eg_GA) | j-t-PvARC-p-LuCnl | j-i-Atss2_c-d4Des(Tc_GA) | c-d4Des(Tc_GA) | j-p-PvARC5_t-BnFAE | c-d5Elo(Ot_GA3) |
|---|---|---|---|---|---|---|
| sc (n = 140) | 1.6 | | | 1.6 | | 1.6 |

TABLE 77

Fatty acid profiles of T2 seeds harvested from T1 plants cultivated in the greenhouse of canola events containing the T-DNAs of plasmids VC-LJB2755-2qcz rc and VC-LLM391-2qcz rc The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPCTC (n = 11) | 5.1 ± 0.2 | 0.3 ± 0 | 0 ± 0 | 3 ± 0.3 | 28.2 ± 5.5 | 28.9 ± 1.6 | 1.3 ± 0.2 | 5 ± 0.2 | 3 ± 0.5 | 0.8 ± 0.2 | 0.9 ± 0.1 | 0.7 ± 0.1 | 0.2 ± 0 |
| LAPCSC (n = 11) | 5.1 ± 0.1 | 0.3 ± 0 | 0 ± 0 | 3.2 ± 0.4 | 27.9 ± 4.2 | 28.8 ± 2.3 | 1.3 ± 0.2 | 4.9 ± 0.2 | 3.2 ± 0.4 | 0.8 ± 0.1 | 0.9 ± 0.1 | 0.7 ± 0.1 | 0.2 ± 0.1 |
| LAPYTJ (n = 15) | 5.9 ± 0.3 | 0.3 ± 0.1 | 0 ± 0 | 3.3 ± 0.6 | 26.5 ± 1.9 | 34 ± 1.6 | 0.9 ± 0.2 | 4.9 ± 0.7 | 2.1 ± 0.3 | 0.4 ± 0.1 | 0.8 ± 0.1 | 0.6 ± 0 | 0±0 |
| LAQKQS (n = 15) | 5.3 ± 0.3 | 0.3 ± 0.1 | 0 ± 0 | 3.2 ± 0.6 | 32.7 ± 8 | 29.7 ± 2.7 | 1.1 ± 0.3 | 5.3 ± 0.5 | 2.6 ± 0.6 | 0.6 ± 0.1 | 0.9 ± 0.2 | 0.7 ± 0.1 | 0.1 ± 0.1 |
| LAPARV (n = 15) | 5.3 ± 0.2 | 0.3 ± 0 | 0 ± 0 | 3.5 ± 0.3 | 26.5 ± 1.9 | 36 ± 1.2 | 0.7 ± 0.1 | 5.4 ± 0.3 | 1.9 ± 0.2 | 0.4 ± 0.1 | 0.9 ± 0.1 | 0.7 ± 0 | 0±0 |
| LAPCMY (n = 15) | 6.2 ± 1.3 | 0.3 ± 0.1 | 0 ± 0 | 2.4 ± 1.4 | 34 ± 8.6 | 26.7 ± 14.5 | 0.5 ± 0.3 | 6.5 ± 1.4 | 1.9 ± 0.4 | 0.4 ± 0.1 | 1 ± 0.2 | 0.7 ± 0.1 | 0.1 ± 0.1 |
| LAPBOW (n = 15) | 5.1 ± 0.6 | 0.2 ± 0.1 | 0 ± 0 | 2.9 ± 0.2 | 27.3 ± 2.6 | 34.9 ± 0.9 | 0.7 ± 0 | 5.6 ± 0.2 | 1.9 ± 0 | 0.4 ± 0.1 | 0.8 ± 0 | 0.7 ± 0 | 0.1 ± 0 |
| LAPAWA (n = 15) | 5.2 ± 0.1 | 0.3 ± 0 | 0 ± 0 | 3.1 ± 0.2 | 28.3 ± 1.3 | 35.9 ± 1.1 | 0.7 ± 0.1 | 5.3 ± 0.3 | 1.7 ± 0.2 | 0.3 ± 0 | 0.8 ± 0.1 | 0.7 ± 0 | 0.1 ± 0.1 |
| LAPBYW (n = 13) | 5.6 ± 0.3 | 0.3 ± 0.1 | 0 ± 0 | 2.6 ± 1.2 | 28.4 ± 1.2 | 36 ± 1.2 | 0.7 ± 0.1 | 5.4 ± 0.3 | 1.7 ± 0.2 | 0.4 ± 0 | 0.8 ± 0.1 | 0.7 ± 0 | 0.1 ± 0.1 |
| LAPQEP (n = 15) | 5 ± 0.3 | 0.3 ± 0 | 0 ± 0 | 2.7 ± 0.3 | 38.1 ± 5.8 | 26.7 ± 4 | 1.1 ± 0.3 | 6.1 ± 0.9 | 1.2 ± 0.2 | 0.3 ± 0 | 0.8 ± 0.1 | 0.8 ± 0.1 | 0.2 ± 0.1 |
| LAODDN (n = 15) | 5.2 ± 0.6 | 0.2 ± 0.1 | 0 ± 0 | 3.1 ± 0.3 | 28 ± 2 | 35.8 ± 1.1 | 0.7 ± 0.1 | 5.9 ± 0.4 | 1.6 ± 0.2 | 0.4 ± 0 | 0.8 ± 0.1 | 0.7 ± 0 | 0 ± 0 |
| LAPAUX (n = 10) | 5.5 ± 0.5 | 0.3 ± 0 | 0 ± 0 | 2.8 ± 0.3 | 31.3 ± 7.3 | 34.9 ± 2.5 | 0.5 ± 0.1 | 6.1 ± 0.6 | 1.5 ± 0.5 | 0.4 ± 0.1 | 0.8 ± 0.1 | 0.7 ± 0.1 | 0.1 ± 0 |
| LAPZOJ (n = 10) | 5.6 ± 0.6 | 0.3 ± 0 | 0 ± 0 | 3 ± 0.3 | 34.1 ± 6.8 | 33.5 ± 2.8 | 0.6 ± 0.2 | 6.5 ± 0.6 | 1.3 ± 0.3 | 0.3 ± 0.1 | 0.8 ± 0.1 | 0.7 ± 0.1 | 0 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPCTC (n = 11) | 0.1 ± 0 | 2.2 ± 0.4 | 1.8 ± 0.5 | 1.2 ± 0.4 | 10.9 ± 2.1 | 0.4 ± 0 | 0 ± 0 | 0.6 ± 0.2 | 3.5 ± 1.1 | 0 ± 0 | 1.3 ± 0.4 | 0.4 ± 0.2 | 0.2 ± 0.1 |
| LAPCSC (n = 11) | 0.1 ± 0 | 2.1 ± 0.4 | 1.7 ± 0.5 | 1.3 ± 0.3 | 11.4 ± 2.4 | 0.4 ± 0.1 | 0 ± 0 | 0.6 ± 0.1 | 3.4 ± 1 | 0 ± 0 | 1.2 ± 0.3 | 0.3 ± 0.1 | 0.2 ± 0.1 |
| LAPYTJ (n = 15) | 0 ± 0 | 2.2 ± 0.3 | 1.3 ± 0.3 | 2.9 ± 0.5 | 8.4 ± 1.7 | 0.1 ± 0.1 | 0 ± 0 | 0.9 ± 0.3 | 2.8 ± 0.5 | 0 ± 0 | 1.2 ± 0.3 | 0.2 ± 0.2 | 0.1 ± 0.1 |
| LAQKQS (n = 15) | 0 ± 0 | 1.7 ± 0.6 | 1.3 ± 0.5 | 1.1 ± 0.2 | 8.8 ± 3.2 | 0.2 ± 0.2 | 0 ± 0 | 0.5 ± 0.3 | 2.4 ± 0.6 | 0 ± 0 | 1 ± 0.4 | 0.2 ± 0.2 | 0.1 ± 0.1 |
| LAPARV (n = 15) | 0 ± 0 | 1.9 ± 0.3 | 1.4 ± 0.2 | 1.7 ± 0.3 | 8.4 ± 1.6 | 0.4 ± 0 | 0 ± 0 | 0.6 ± 0.2 | 2.4 ± 0.5 | 0 ± 0 | 1.2 ± 0.3 | 0.3 ± 0.2 | |
| LAPCMY (n = 15) | 0 ± 0 | 2.5 ± 0.5 | 1.8 ± 0.4 | 1.6 ± 0.4 | 7.9 ± 2 | 0.4 ± 0.1 | 0 ± 0 | 0.6 ± 0.3 | 2.6 ± 0.8 | 0 ± 0 | 1.2 ± 0.4 | 0.3 ± 0.2 | |
| LAPBOW (n = 15) | 0 ± 0 | 2 ± 0.3 | 1.4 ± 0.2 | 1.6 ± 0.1 | 7.8 ± 1.1 | 0.3 ± 0 | 0 ± 0 | 0.9 ± 0.2 | 3.1 ± 0.7 | 0 ± 0 | 1.3 ± 0.4 | 0.6 ± 0.1 | 0.1 ± 0 |
| LAPAWA (n = 15) | 0 ± 0 | 2.1 ± 0.2 | 1.4 ± 0.2 | 1.6 ± 0.1 | 7.4 ± 0.7 | 0.3 ± 0 | 0 ± 0 | 0.7 ± 0.2 | 2.2 ± 0.5 | 0 ± 0 | 1 ± 0.3 | 0.5 ± 0.2 | |
| LAPBYW (n = 13) | 0.1 ± 0.1 | 1.9 ± 0.2 | 1.4 ± 0.2 | 1.6 ± 0.1 | 7.9 ± 0.8 | 0.4 ± 0.1 | 0 ± 0 | 0.5 ± 0.2 | 2 ± 0.4 | 0 ± 0 | 1 ± 0.2 | 0.3 ± 0.2 | |
| LAPQEP (n = 15) | 0.1 ± 0 | 1.6 ± 0.4 | 1.5 ± 0.4 | 0.7 ± 0.2 | 7.7 ± 1.6 | 0.4 ± 0 | 0 ± 0 | 0.4 ± 0.1 | 2.8 ± 0.7 | 0 ± 0 | 0.7 ± 0.2 | 0.3 ± 0.1 | 0.2 ± 0.1 |
| LAODDN (n = 15) | 0 ± 0 | 2 ± 0.2 | 1.4 ± 0.2 | 1.2 ± 0.1 | 7.1 ± 0.9 | 0.4 ± 0 | 0 ± 0 | 0.8 ± 0.1 | 2.8 ± 0.4 | 0 ± 0 | 1.1 ± 0.3 | 0.6 ± 0.1 | 0.1 ± 0 |
| LAPAUX (n = 10) | 0 ± 0 | 1.7 ± 0.5 | 1.2 ± 0.4 | 1.7 ± 0.5 | 8.3 ± 3.4 | 0.4 ± 0 | 0 ± 0 | 0.2 ± 0.1 | 1.1 ± 0.4 | 0 ± 0 | 0.4 ± 0.2 | 0 ± 0.1 | |
| LAPZOJ (n = 10) | 0 ± 0 | 1.6 ± 0.4 | 1.1 ± 0.3 | 1 ± 0.2 | 5.5 ± 1.5 | 0.2 ± 0.1 | 0 ± 0 | 0.4 ± 0.2 | 2.2 ± 0.6 | 0 ± 0 | 0.8 ± 0.3 | 0.3 ± 0.2 | 0 ± 0 |

TABLE 78

Fatty acid profiles of one T2 seed batch per event harvested from T1 plants cultivated in the greenhouse of canola events containing the T-DNAs of plasmids VC-LJB2755-2qcz rc and VC-LLM391-2qcz re. The events are indicated in the first column. Fatty acid profiles of T2 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPCTC (n = 1) | 5.1 | 0.3 | 0.0 | 2.7 | 25.2 | 29.7 | 1.3 | 4.8 | 2.6 | 0.5 | 0.8 | 0.6 | 0.3 |
| LAPCSC (n = 1) | 5.0 | 0.3 | 0.0 | 3.4 | 20.8 | 25.8 | 1.7 | 5.2 | 3.5 | 1.0 | 0.8 | 0.6 | 0.3 |
| LAPYTJ (n =1) | 5.5 | 0.3 | 0.0 | 3.0 | 24.0 | 31.1 | 1.1 | 4.9 | 2.4 | 0.5 | 0.8 | 0.6 | 0.0 |
| LAQKQS (n = 1) | 5.8 | 0.3 | 0.0 | 3.6 | 24.4 | 31.3 | 1.4 | 4.7 | 3.9 | 0.9 | 0.8 | 0.6 | 0.0 |
| LAPARV (n = 1) | 5.3 | 0.2 | 0.0 | 3.2 | 24.3 | 34.2 | 0.6 | 5.6 | 2.0 | 0.5 | 0.8 | 0.6 | 0.1 |
| LAPCMY (n = 1) | 8.1 | 0.5 | 0.0 | 0.0 | 51.4 | 1.0 | 0.0 | 9.5 | 2.3 | 0.6 | 1.2 | 1.0 | 0.1 |
| LAPBOW (n = 1) | 3.8 | 0.1 | 0.0 | 2.3 | 21.5 | 33.7 | 0.7 | 6.7 | 2.3 | 0.6 | 0.7 | 0.7 | 0.1 |
| LAPAWA (n = 1) | 5.3 | 0.3 | 0.0 | 3.4 | 26.2 | 36.5 | 0.7 | 4.8 | 1.8 | 0.4 | 0.9 | 0.7 | 0.1 |
| LAPBYW (n = 1) | 5.5 | 0.3 | 0.0 | 0.0 | 29.4 | 36.1 | 0.6 | 5.8 | 1.8 | 0.4 | 0.8 | 0.8 | 0.1 |
| LAPQEP (n = 1) | 4.9 | 0.4 | 0.0 | 2.3 | 36.6 | 23.9 | 1.5 | 5.7 | 1.3 | 0.4 | 0.7 | 0.8 | 0.3 |
| LAODDN (n = 1) | 3.8 | 0.1 | 0.0 | 2.6 | 24.1 | 36.0 | 0.8 | 5.7 | 2.0 | 0.4 | 0.8 | 0.7 | 0.0 |
| LAPAUX (n =1) | 5.5 | 0.3 | 0.0 | 3.1 | 25.6 | 33.6 | 0.7 | 5.4 | 1.9 | 0.4 | 0.8 | 0.6 | 0.1 |
| LAPZOJ (n = 1) | 5.7 | 0.3 | 0.0 | 2.1 | 25.8 | 31.3 | 0.4 | 7.9 | 2.2 | 0.7 | 0.6 | 0.6 | 0.0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPCTC (n = 1) | 0.1 | 2.4 | 1.9 | 1.9 | 14.1 | 0.3 | 0.0 | 0.4 | 3.3 | 0.0 | 1.0 | 0.2 | 0.3 |
| LAPCSC (n = 1) | 0.1 | 2.5 | 2.7 | 1.0 | 16.1 | 0.3 | 0.0 | 0.6 | 5.3 | 0.0 | 1.9 | 0.4 | 0.3 |
| LAPYTJ (n =1) | 0.0 | 2.4 | 1.7 | 2.8 | 10.8 | 0.3 | 0.0 | 1.1 | 4.1 | 0.0 | 1.7 | 0.5 | 0.3 |
| LAQKQS (n = 1) | 0.0 | 2.2 | 1.8 | 1.5 | 13.8 | 0.0 | 0.0 | 0.0 | 1.8 | 0.0 | 1.0 | 0.0 | 0.0 |
| LAPARV (n = 1) | 0.0 | 2.0 | 1.5 | 2.3 | 11.9 | 0.3 | 0.0 | 0.6 | 2.4 | 0.0 | 1.1 | 0.3 |  |
| LAPCMY (n = 1) | 0.0 | 2.9 | 2.1 | 2.4 | 12.5 | 0.5 | 0.0 | 0.3 | 2.6 | 0.0 | 0.8 | 0.0 |  |
| LAPBOW (n = 1) | 0.1 | 2.2 | 1.8 | 2.0 | 10.8 | 0.4 | 0.0 | 1.5 | 5.2 | 0.0 | 2.1 | 0.7 | 0.1 |
| LAPAWA (n = 1) | 0.0 | 2.7 | 1.9 | 1.7 | 8.7 | 0.4 | 0.0 | 0.5 | 1.7 | 0.0 | 0.9 | 0.3 |  |
| LAPBYW (n = 1) | 0.0 | 1.9 | 1.5 | 1.7 | 9.5 | 0.4 | 0.0 | 0.4 | 1.7 | 0.0 | 0.8 | 0.3 |  |
| LAPQEP (n = 1) | 0.1 | 1.9 | 1.6 | 1.0 | 10.9 | 0.4 | 0.0 | 0.3 | 3.7 | 0.0 | 0.7 | 0.3 | 0.3 |
| LAODDN (n = 1) | 0.0 | 2.3 | 1.8 | 1.6 | 9.4 | 0.4 | 0.0 | 1.1 | 3.8 | 0.0 | 1.6 | 0.6 | 0.1 |
| LAPAUX (n =1) | 0.0 | 2.4 | 1.7 | 2.3 | 12.8 | 0.3 | 0.0 | 0.2 | 1.5 | 0.0 | 0.5 | 0.0 |  |
| LAPZOJ (n = 1) | 0.0 | 1.3 | 1.0 | 2.1 | 9.3 | 0.0 | 0.0 | 1.0 | 5.6 | 0.0 | 2.2 | 0.0 | 0.0 |

TABLE 79

Fatty acid profiles of T2 seeds harvested from T1 plants cultivated in the greenhouse of canola events containing the T-DNAs of plasmids VC-LJB2755-2qcz rc and VC-LLM391-2qcz re. Plants of all events combined have been grouped into the categories indicated in the first column; as defined in Table 76. The number of T1 plants fullfilling these criteria are displayed in parentheses. Per seed batch a random selection of ~30 seed was measured in two technical repeats.

| Category of TI plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 143) | 5.4 ± 0.7 | 0.3 ± 0.1 | 0 ± 0 | 2.9 ± 0.7 | 29.6 ± 5.5 | 32.8 ± 6.2 | 0.8 ± 0.3 | 5.6 ± 0.8 | 1.9 ± 0.6 | 0.4 ± 0.2 | 0.8 ± 0.1 | 0.7 ± 0.1 | 0.1 ± 0.1 |

| Category of TI plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 143) | 0 ± 0 | 2 ± 0.4 | 1.5 ± 0.3 | 1.5 ± 0.5 | 8.3 ± 2 | 0.3 ± 0.1 | 0 ± 0 | 0.6 ± 0.3 | 2.6 ± 0.7 | 0 ± 0 | 1.1 ± 0.4 | 0.4 ± 0.2 | 0.1 ± 0.1 |

TABLE 80

Fatty acid profiles of T2 seeds harvested from T1 plants cultivated in the greenhouse of canola events containing the T-DNAs of plasmids VC-LJB2755-2qcz rc and VC-LLM391-2qcz re. Plants of all events combined have been grouped into the categories indicated in the first column; as defined in Table 76. For each category, the fatty acid profile of the plant having the highest EPA + DHA levels was shown. Per seed batch a random selection of ~30 seed was measured in two technical repeats.

| Category of TI plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 5.1 | 0.3 | 0.0 | 2.7 | 25.2 | 29.7 | 1.3 | 4.8 | 2.6 | 0.5 | 0.8 | 0.6 | 0.3 |

| Category of TI plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.1 | 2.4 | 1.9 | 1.9 | 14.1 | 0.3 | 0.0 | 0.4 | 3.3 | 0.0 | 1.0 | 0.2 | 0.3 |

TABLE 81

Phenotypic rating of T1 plants cultivated in the greenhouse of canola events containing the T-DNAs of plasmids VC-LJB2755-2qcz rc and VC-LLM391-2qcz rc. The events are indicated in the first column, along with the number of T1 plants that where rated per event.

| Event | DFF | DF | DL | DP | DS | FC | LD | LGC |
|---|---|---|---|---|---|---|---|---|
| LAPCTC (n = 11) | 67.5 ± 1.5 | 1 ± 0 | 1 ± 0 | 1 ± 0 | 1.8 ± 0.6 | 3 ± 0 | 3 ± 0 | 5 ± 0 |
| LAPCSC (n = 11) | 68.6 ± 3.3 | 1 ± 0 | 1 ± 0 | 1 ± 0 | 1.7 ± 0.6 | 3 ± 0 | 3 ± 0 | 5 ± 0 |
| LAPYTJ (n = 15) | 72.3 ± 7.1 | 1 ± 0 | 1.4 ± 1.1 | 1.1 ± 0.5 | 1.6 ± 0.8 | 3 ± 0 | 3 ± 0 | 5 ± 0 |
| LAQKQS (n = 15) | 67.4 ± 4.4 | 1 ± 0 | 1.4 ± 0.8 | 1.1 ± 0.3 | 3.1 ± 1.6 | 3 ± 0 | 3 ± 0 | 5 ± 0 |
| LAPARV (n = 15) | 68.1 ± 2.6 | 1 ± 0 | 1.2 ± 0.8 | 1 ± 0 | 2.3 ± 2.1 | 3 ± 0 | 3 ± 0 | 5 ± 0 |
| LAPCMY (n = 15) | 68.7 ± 2.4 | 1 ± 0 | 1 ± 0 | 1 ± 0 | 1.7 ± 0.6 | 3 ± 0 | 3 ± 0 | 5 ± 0 |
| LAPBOW (n = 15) | 68.1 ± 0.9 | 1 ± 0 | 1 ± 0 | 1 ± 0 | 1.2 ± 0.6 | 3 ± 0 | 3 ± 0 | 5 ± 0 |
| LAPAWA (n = 15) | 66.5 ± 1.4 | 1 ± 0 | 1 ± 0 | 1 ± 0 | 1.2 ± 0.4 | 3 ± 0 | 3 ± 0 | 5 ± 0 |
| LAPBYW (n = 13) | 65.7 ± 2.6 | 1 ± 0 | 1.2 ± 0.8 | 1.2 ± 0.6 | 1.7 ± 0.6 | 3 ± 0 | 3 ± 0 | 5 ± 0 |
| LAPQEP (n = 15) | 66.9 ± 2.6 | 1 ± 0 | 1.2 ± 0.8 | 1 ± 0 | 1.7 ± 0.7 | 3 ± 0 | 3 ± 0 | 5 ± 0 |
| LAODDN (n = 15) | 69.3 ± 2 | 1 ± 0 | 1 ± 0 | 1 ± 0 | 1.2 ± 0.4 | 3 ± 0 | 3 ± 0 | 5 ± 0 |
| LAPAUX (n = 10) | 70 ± 4.5 | 1 ± 0 | 1.3 ± 0.9 | 1 ± 0 | 3.1 ± 2.3 | 3 ± 0 | 3 ± 0 | 5 ± 0 |
| LAPZOJ (n = 10) | 68 + 6.7 | 1 ± 0 | 1.2 ± 0.6 | 1 ± 0 | 1.1 ± 0.3 | 3 ± 0 | 3 ± 0 | 5 ± 0 |

| Event | LF | NoL | PH | TKW | SC | Oil | Protein |
|---|---|---|---|---|---|---|---|
| LAPCTC (n = 11) | 1 ± 0 | 4 ± 0 | 129.5 ± 3.5 | 3.6 ±0.6 | 3.6 ± 0.9 | | |
| LAPCSC (n = 11) | 1 ± 0 | 3.6 ± 0.8 | 126.4 ± 3.2 | 3.2 ± 0.3 | 3.9 ± 0.5 | | |
| LAPYTJ (n = 15) | 1.3 ± 0.7 | 4 ± 0 | 123 ± 4.9 | 3.6 ± 0.3 | 3.5 ± 0.8 | | |
| LAQKQS (n = 15) | 1.8 ± 1.5 | 4 ± 0 | 130.3 ± 4.8 | 3.8 ± 0.5 | 3.7 ± 1 | | |
| LAPARV (n = 15) | 1.3 ± 0.9 | 4 ± 0 | 128 ± 3.2 | 4 ± 0.6 | 3.9 ± 1.3 | | |
| LAPCMY (n = 15) | 1 ± 0 | 3.9 ± 0.5 | 130.7 ± 1.8 | 3.6 ± 0.4 | 3.3 ± 0.7 | | |
| LAPBOW (n = 15) | 1 ± 0 | 4 ± 0 | 127.3 ± 3.2 | 4 ± 0.4 | 3.7 ± 1 | 35.3 ± 1.3 | 29.2 ± 0.3 |
| LAPAWA (n = 15) | 1 ± 0 | 4 ± 0 | 128.7 ± 3.5 | 3.7 ± 0.4 | 2.6 ± 0.5 | | |
| LAPBYW (n = 13) | 1.2 ± 0.6 | 3.8 ± 0.6 | 128.1 ± 5.2 | 4 ± 0.5 | 3.9 ± 1.7 | | |
| LAPQEP (n = 15) | 1 ± 0 | 4 ± 0 | 128 ± 4.6 | 3.2 ± 0.3 | 3.3 ± 0.6 | | |
| LAODDN (n = 15) | 1 ± 0 | 4 ± 0 | 125.7 ± 3.2 | 3.9 ± 0.5 | 3.8 ± 1.2 | 36.6 ± 1.2 | 27.9 ± 0.4 |
| LAPAUX (n = 10) | 2.4 ± 2.1 | 3.8 ± 0.6 | 130 ± 2.4 | 4.3 ± 0.5 | 4.5 ± 1.4 | | |
| LAPZOJ (n = 10) | 1 ± 0 | 4 ± 0 | 126.5 ± 3.4 | 3.8 ± 0.6 | 3.3 ± 0.9 | | |

DFF: days to first flower (days), DF: deformed flower (9 = deformed, 1 = normal), DL: deformed leaf (9 = deformed, 1 = normal), DP: deformed plant (9 = deformed, 1 = normal), DS: deformed silique (9 = deformed, 1 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoI: number of lobes(#), PH: plant height (cm), TKW: thousand kernel weight (g), SC: seed quality (1 = good, 9 = bad), Oil: oil content (% of seed weight), Protein: Protein content (% of seed cake without oil)

TABLE 82

Phenotypic rating of T1 plants cultivated in the greenhouse of canola events containing the T-DNAs of plasmids VC-LJB2755-2qcz rc and VC-LLM391-2qcz rc. Plants of all events combined have been grouped into the categories indicated in the first column; as defined in Table 76. The number of T1 plants fullfilling these criteria are displayed in parentheses.

| Category of TI plants | DFF | DF | DL | DP | DS | FC | LD | LGC |
|---|---|---|---|---|---|---|---|---|
| sc (n = 143; n = 30 for oil and protein) | 67.9 ± 3 | 1 ± 0 | 1.1 ± 0.5 | 1 ± 0.2 | 1.7 ± 1.1 | 3 ± 0 | 3 ± 0 | 5 ± 0 |

| Category of TI plants | LF | NoL | PH | TKW | SC | Oil | Protein |
|---|---|---|---|---|---|---|---|
| sc (n = 143; n = 30 for oil and protein) | 1.1 ± 0.7 | 3.9 ± 0.3 | 127.9 ± 4 | 3.6 ± 0.4 | 3.5 ± 1.1 | 36 ± 1.4 | 28.5 ± 0.8 |

DFF: days to first flower (days), DF: deformed flower (9 = deformed, 1 = normal), DL: deformed leaf (9 = deformed, 1 = normal), DP: deformed plant (9 = deformed, 1 = normal), DS: deformed silique (9 = deformed, 1 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoI: number of lobes (#), PH: plant height (cm), TKW: thousand kernel weight (g), SC: seed quality 1 = good, 9 = bad), Oil: oil content (% of seed weight), Protein: Protein content (% of seed cake without oil)

Fatty Acid Profiles, Copy Number Measurements, and Phenotypic Observations of T2 Plants Carrying T-DNAs of Plasmids VC-LJB2755-2Qcz Rc and VC-LLM391-2Qcz Rc Cultivated in Greenhouses During Summer.

The data in Table 83 indicate the copy number of the selected events was a single insertion which was homozygous in the T3 seed. Fatty acid profile measurements, see Table 84 and Table 85, indicated the combination of T-DNAs from VC-LJB2755-2qcz and VC-LLM391-2qcz rc are capable of bringing in the VLC-PUFA pathway to successfully accumulate ARA, EPA and DHA. The data on Table 86 show that there was no significant impact on the aerial portion of the plant caused by VC-LJB2755-2acz and VC-LLM391-2acz rc.

TABLE 83

Copy number measurement of T2 plants cultivated in the greenhouse of canola events containing the T-DNAs of plasmids VC-LJB2755-2qcz rc and VC-LLM391-2qcz rc.
The events are indicated in the first column, along with the number of T2 plants that were measured per event. As the T2 plants underwent two cylces of selecting homozygous plants, all plants of all events are homozygous for all T-DNA insertions. A copy number homozygous locus, a copy number of ~4 indicative for two homozygous loci or indicative for one homozygous locus containing two copies of the target gene measured by the assay, and so forth.

Copy number assays targeting the T-DNA of VC-UB2755-2qcz rc. Assays are listed according to the position of the assay target along the T-DNA, with target c-AHAS located near the left T-DNA border and target j-p-LuPXR_i-Atss15 near the right T-DNA border.

| Event | c-AHAS | c-o3Des (Pi_GA) | j-i-Atss18_ c-o3Des(Pi_GA2) | j-i-Atss14_ c-d12Des(Ps_GA) | c-d6Elo (Tp_GA) | j-i-Atss1_ c-d6Elo (Tp_GA2) | c-o3Des (Pir_GA) | j-p-LuPRX_ i-Atss15 |
|---|---|---|---|---|---|---|---|---|
| LAPBOW (n = 54) | 1.9 | 2.0 | | | | | 2.0 | 2.4 |
| LAODDN (n = 63) | 1.9 | 2.0 | | | | | 2.0 | 2.1 |

Copy number assays targeting the T-DNA of VC-LLM391-2qcz rc. Assays are listed according to the position of the assay target along the T-DNA, with target c-d4Des(Eg_GA) located near the left T-DNA border and target j-i-Atssl_c-d5Elo(Ot_GA3) near the right T-DNA border.

| Event | c-d4Des (Eg_GA) | j-t-PvARC-p-LuCnl | j-i-Atss2_ c-d4Des (Tc_GA3) | c-d4Des (Tc_GA) | j-p-PvARC5_ t-BnFAE | c-d5Elo (Ot_GA3) | j-i-Atss1_ c-d5Elo (Ot_GA3) |
|---|---|---|---|---|---|---|---|
| LAPBOW (n = 54) | 2.0 | | | | | 2.0 | 2.0 |
| LAODDN (n = 63) | 2.0 | | | | | 2.0 | 1.9 |

TABLE 84

Fatty acid profiles of T3 seeds harvested from T2 plants cultivated in the greenhouse of canola events containing the T-DNAs of plasmids VC-LJB2755-2qcz rc and VC-LLM391-2qcz rc. The events are indicated in the first column, along with the number of T3 seed batches that where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 54) | 5.3 ± 0.3 | 0.3 ± 0.1 | 0.2 ± 0.1 | 3.4 ± 0.2 | 26.8 ± 1.9 | 35.6 ± 2.1 | 0.6 ± 0.1 | 6.1 ± 0.8 | 1.6 ± 0.2 | 0.4 ± 0.1 | 0.8 ± 0.1 | 0.7 ± 0 | 0.1 ± 0.1 |
| LAODDN (n = 63) | 5.4 ± 0.4 | 0.3 ± 0.1 | 0.2 ± 0.1 | 3.5 ± 0.4 | 27.7 ± 2.4 | 35.4 ± 1.8 | 0.6 ± 0.1 | 6.5 ± 0.8 | 1.4 ± 0.2 | 0.4 ± 0 | 0.8 ± 0.1 | 0.7 ± 0 | 0.1 ± 0.1 |
| WT Kumily (n = 46) | 5 ± 0.1 | 0.4 ± 0 | 0.2 ± 0 | 2.6 ± 0.1 | 66.3 ± 1.7 | 16.8 ± 1.3 | 0 ± 0 | 6.1 ± 0.4 | 0 ± 0 | 0 ± 0 | 0.9 ± 0 | 1.2 ± 0 | 0 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 54) | 0 ± 0 | 1.8 ± 0.3 | 1.4 ± 0.3 | 1.4 ± 0.2 | 7.1 ± 0.8 | 0.3 ± 0.1 | 0 ± 0 | 1 ± 0.1 | 3.2 ± 0.5 | 0 ± 0 | 1.3 ± 0.3 | 0.6 ± 0.2 | 0.1 ± 0.1 |
| LAODDN (n = 63) | 0 ± 0 | 1.8 ± 0.2 | 1.4 ± 0.2 | 1 ± 0.2 | 6.8 ± 0.6 | 0.3 ± 0.1 | 0 ± 0 | 0.8 ± 0.1 | 3 ± 0.3 | 0 ± 0 | 1.1 ± 0.3 | 0.6 ± 0.1 | 0.1 ± 0.1 |
| WT Kumily (n = 46) | 0 ± 0 | 0 ± 0 | 0 ± 0 | 0 ± 0 | 0 ± 0 | 0.5 ± 0 | 0 ± 0 | 0 ± 0 | 0 ± 0 | 0 ± 0 | 0 ± 0 | 0 ± 0 | 0 ± 0 |

TABLE 85

Fatty acid profiles of one T3 seed batch per event harvested from T2 plants cultivated in the greenhouse of canola events containing the T-DNAs of plasmids VC-LJB2755-2qcz rc and VC-LLM391-2qcz re. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.7 | 0.3 | 0.2 | 3.3 | 24.1 | 34.3 | 0.6 | 6.1 | 2.0 | 0.5 | 0.7 | 0.6 | 0.0 |
| LAODDN (n = 1) | 5.3 | 0.3 | 0.2 | 3.1 | 25.1 | 34.7 | 0.7 | 6.0 | 1.8 | 0.5 | 0.7 | 0.7 | 0.0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 2.1 | 1.7 | 1.6 | 8.7 | 0.1 | 0.0 | 1.1 | 3.8 | 0.0 | 1.7 | 0.7 | 0.0 |
| LAODDN (n = 1) | 0.0 | 2.2 | 2.0 | 1.1 | 8.7 | 0.3 | 0.0 | 0.8 | 3.6 | 0.0 | 1.5 | 0.7 | 0.1 |

TABLE 86

Phenotypic rating of T2 plants cultivated in the greenhouse of canola events containing the T-DNAs of plasmids VC-LJB2755-2qcz rc and VC-LLM391-2qcz rc. The events are indicated in the first column, along with the number of T2 plants that where rated per event. Oil: oil content (% of seed weight), protein: Protein content (% of seed cake without oil)

| Event | Oil | protein |
|---|---|---|
| LAPBOW (n = 54) | 34.8 ± 2.9 | 30.8 ± 2.3 |
| LAODDN (n = 63) | 36.6 ± 3 | 28.6 ± 2.4 |
| WT Kumily (n = 46) | 34.9 ± 1.1 | 32.2 ± 1 |

Fatty Acid Profiles, Copy Number Measurements, and Phenotypic Observations of T2 Plants Carrying T-DNAs of Plasmids VC-LJB2755-2Qcz Rc and VC-LLM391-2Qcz Rc Cultivated in Field Trials in USDA Growth Zones 3a-4b and 5a During the Summer Field data for the T3 seed from the events carrying the T-DNA from VC-LJB2755-2qcz and VC-LLM391-2qcz rc, shown in Table 87 and Table 88, indicate that the plants are capable of making VLC-PUFAs in the field (ARA, EPA and DHA), though not at the level observed in the greenhouse. However, there was also a difference in seed oil content observed compared to the greenhouse (e.g. comparing Table 89 with Table 86). These observations are in agreement with previous examples where it was observed that increased oil contents in the field grown plants concomitant with a decrease in VLC-PUFAs, in particular EPA, DHA and ARA. A more detailed description of the observations regarding oil content and VLC-PUFAs is given in Example 20.

TABLE 87

Fatty acid profiles of T3 seeds harvested from T2 plants cultivated in the field, corresponding to USDA growth zones 3a-4b and 5a, for field trials of canola events containing the T-DNAs of plasmids VC-LJB2755-2qcz rc and VC-LLM391-2qcz rc The events are indicated in the first column, along with the number of T3 seed aliquots representing a plot where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 31) | 5.3 ± 0.2 | 0.4 ± 0.1 | 0 ± 0 | 2.4 ± 0.1 | 31.9 ± 1.6 | 33.3 ± 1 | 0.6 ± 0.1 | 7.7 ± 0.5 | 1.4 ± 0.2 | 0.4 ± 0.1 | 0.6 ± 0 | 0.7 ± 0 | 0.1 ± 0.1 |
| LAODDN (n = 31) | 5.1 ± 0.2 | 0.4 ± 0 | 0.1 ± 0 | 2.5 ± 0.2 | 32.1 ± 2.3 | 33.4 ± 1.4 | 0.6 ± 0.1 | 7.9 ± 0.5 | 1.3 ± 0.2 | 0.4 ± 0.1 | 0.6 ± 0 | 0.7 ± 0 | 0.2 ± 0.1 |
| WT Kumily (n = 60) | 5 ± 0.3 | 0.4 ± 0 | 0.1 ± 0.1 | 2 ± 0.1 | 56.2 ± 4.2 | 23.3 ± 1.7 | 0 ± 0.1 | 9.5 ± 0.7 | 0.1 ± 0.2 | 0 ± 0 | 0.7 ± 0 | 1.1 ± 0.1 | 0.1 ± 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 31) | 0 ± 0 | 1.5 ± 0.1 | 0.9 ± 0.1 | 1.6 ± 0.2 | 5.5 ± 0.5 | 0.2 ± 0.1 | 0 ± 0 | 0.9 ± 0.1 | 3.1 ± 0.3 | 0 ± 0 | 0.8 ± 0.1 | 0.4 ± 0.1 | 0.1 ± 0.1 |
| LAODDN (n = 31) | 0.1 ± 0.1 | 1.3 ± 0.1 | 0.8 ± 0.1 | 1.4 ± 0.2 | 5.7 ± 0.7 | 0.3 ± 0 | 0 ± 0 | 0.8 ± 0.1 | 3.1 ± 0.4 | 0 ± 0 | 0.8 ± 0.1 | 0.4 ± 0.1 | 0.1 ± 0 |
| WT Kumily (n = 60) | 0 ± 0 | 0.2 ± 0.3 | 0.1 ± 0.3 | 0.2 ± 0.5 | 0.4 ± 1.1 | 0.3 ± 0.1 | 0 ± 0 | 0 ± 0.2 | 0.2 ± 0.6 | 0 ± 0 | 0 ± 0.2 | | |

TABLE 88

Fatty acid profiles of one T3 seed batch per event harvested from T2 plants cultivated in USDA growth zones 3a-4b and 5a for field trials of canola events containing the T-DNAs of plasmids VC-LJB2755-2qcz rc and VC-LLM391-2qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.5 | 0.4 | 0.1 | 2.3 | 30.3 | 32.9 | 0.6 | 7.6 | 1.8 | 0.5 | 0.6 | 0.7 | 0.1 |
| LAODDN (n = 1) | 5.4 | 0.4 | 0.0 | 2.6 | 30.1 | 33.3 | 0.7 | 6.9 | 1.5 | 0.4 | 0.6 | 0.6 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 1.6 | 1.0 | 1.7 | 6.5 | 0.1 | 0.0 | 1.0 | 3.5 | 0.0 | 1.1 | 0.2 | 0.1 |
| LAODDN (n = 1) | 0.0 | 1.5 | 0.9 | 1.8 | 6.8 | 0.2 | 0.0 | 1.0 | 3.5 | 0.0 | 0.9 | 0.4 | 0.1 |

TABLE 89

Phenotypic rating of T2 plants cultivated in USDA growth zones 3a-4b and 5a for field trials of canola events containing the T-DNAs of plasmids VC-LJB2755-2qcz rc and VC-LLM391-2qcz rc. The events are indicated in the first column, along with the number of field plots that where rated per event. Oil: oil content (% of seed weight), protein: Protein content (% of seed cake without oil)

| Event | Oil | protein |
|---|---|---|
| LAPBOW (n = 31) | 38.7 ± 1.2 | 28 ± 1.1 |
| LAODDN (n = 31) | 38.3 ± 1.4 | 27.9 ± 1.2 |
| WT Kumily (n = 60) | 38.7 ± 1.1 | |

Fatty Acid Profiles, Copy Number Measurements, and Phenotypic Observations of T3 Plants Carrying T-DNAs of Plasmids VC-LJB2755-2Qcz Rc and VC-LLM391-2Qcz Rc Cultivated in Greenhouses During Winter.

T4 seed from T3 plants from the event LAODDN, which was homozygous for T-DNA from both VC-LJB2755-2qcz and VC-LLM391-2qcz rc (see Table 90) accumulated VLC-PUFAs (in particular ARA, EPA and DHA, see Table 91 and Table 92). The combination of EPA and DHA was up to approximately ten percent of the total fatty acid content in the seed for this event.

TABLE 90

Copy number measurement of T3 plants cultivated in the greenhouse of canola events containing the T-DNAs of plasmids VC-LJB2755-2qcz rc and VC-LLM391-2qcz rc.
The events are indicated in the first column, along with the number of T3 plants that where measured per event. As the T3 plants underwent two cylces of selecting homozygous plants, all plants of all events are homozygous for all T-DNA insertions. A copy number of ~2 therefore was indicative for one homozygous locus, a copy number of ~4 indicative for two homozygous loci or indicative for one homozygous locus containing two copies of the target gene measured by the assay, and so forth.

Copy number assays targeting the T-DNA of VC-UB2755-2qcz rc.
Assays are listed according to the position of the assay target along the T-DNA, with target c-AHAS located near the left T-DNA border and target j-p-LuPXR_i-Ats15 near the right T-DNA border.

| Event | c-AHAS | j-i-Atss18_ c-o3Des (Pi_GA) | j-i-Atss14_ c-o3Des(Pi_GA2) | c-d12Des(Ps_GA) | c-d6Elo (Tp_GA) | j-i-Atss1_ c-d6Elo (Tp_GA2) | c-o3Des (Pir_GA) | j-p-LuPRX_i-Atss15 |
|---|---|---|---|---|---|---|---|---|
| LAODDN (n = 30) | 1.92 | | 2.0 | | | | | 1.9 |

Copy number assays targeting the T-DNA of VC-LLM391-2qcz rc. Assays are listed according to the position of the assay target along the T-DNA, with target c-d4Des(Eg_GA) located near the left T-DNA border and target j-i-Atssl_c-d5Elo(Ot_GA3) near the right T-DNA border.

| Event | c-d4Des (Eg_GA) | j-t-PvARC-p-LuCnl | j-i-Atss2_ c-d4Des (Tc_GA3) | c-d4Des (Tc_GA) | j-p-PvARC5_ t-BnFAE | c-d5Elo (Ot_GA3) | j-i-Atss1_ c-d5Elo (Ot_GA3) |
|---|---|---|---|---|---|---|---|
| LAODDN (n = 30) | 1.8 | | | 1.9 | 2.1 | | 1.9 |

TABLE 91

Fatty acid profiles of T4 seeds harvested from T3 plants cultivated in the greenhouse of canola events containing the T-DNAs of plasmids VC-LJB2755-2qcz rc and VC-LLM391-2qcz rc The events are indicated in the first column, along with the number of T4 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAODDN (n = 30) | 5.3 ± 0.5 | 0.3 ± 0 | 0 ± 0 | 3.3 ± 0.7 | 27.2 ± 2.5 | 37.7 ± 4.1 | 2.3 ± 5.1 | 5.1 ± 0.7 | 1.7 ± 0.3 | 0.4 ± 0.1 | 0.8 ± 0.1 | 0.6 ± 0.1 | 0.1 ± 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAODDN (n = 30) | 0 ± 0 | 1.2 ± 0.2 | 0.3 ± 0.5 | 1.3 ± 0.2 | 6.5 ± 0.8 | 0.2 ± 0.2 | 0 ± 0 | 1 ± 0.3 | 2.7 ± 0.4 | 0 ± 0 | 1.3 ± 0.4 | 0.4 ± 0.1 | 0 ± 0 |

TABLE 92

Fatty acid profiles of one T4 seed batch per event harvested from T3 plants cultivated in the greenhouse of canola events containing the T-DNAs of plasmids VC-LJB2755-2qcz rc and VC-LLM391-2qcz rc. The events are indicated in the first column. Fatty acid profiles of T4 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAODDN (n = 1) | 5.2 | 0.2 | 0.0 | 3.7 | 24.2 | 39.5 | 0.4 | 4.8 | 2.0 | 0.5 | 0.9 | 0.6 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAODDN (n = 1) | 0.1 | 1.0 | 0.0 | 1.5 | 7.7 | 0.4 | 0.0 | 1.3 | 3.3 | 0.0 | 1.9 | 0.3 | 0.1 |

TABLE 93

Phenotypic rating of T3 plants cultivated in the greenhouse of canola events containing the T-DNAs of plasmids VC-LJB2755-2qcz rc and VC-LLM391-2qcz re. The events are indicated in the first column, along with the number of T3 plants that where rated per event.

| Event | DFF | DF | DL | DP | DS | FC |
|---|---|---|---|---|---|---|
| LAODDN (n = 30) | 43.5 ± 4.1 | 8.5 ± 0.5 | 7.8 ± 0.8 | 9 ± 0 | 7.9 ± 1 | 3 ± 0 |

| Event | LD | LGC | LF | NoL | PH |
|---|---|---|---|---|---|
| LAODDN (n = 30) | 4.6 ± 0.7 | 4.5 ± 0.7 | 8.8 ± 0.4 | 5 ± 0.8 | 115 ± 12.5 |

DFF: days to first flower (days), DF: deformed flower (9 = deformed, 1 = normal), DL: deformed leaf (9 = deformed, 1 = normal), DP: deformed plant (9 =deformed, 1= normal), DS: deformed silique (9 = deformed, 1 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm)

Fatty Acid Profiles, Copy Number Measurements, and Phenotypic Observations of T3 Plants Carrying T-DNAs of Plasmids VC-LJB2755-2Qcz Rc and VC-LLM391-2Qcz Rc Cultivated in Field Trials in USDA Growth Zones 8a-9a in the Winter.

Field data for T4 seed of two events carrying homozygous T-DNA insertions from VC-LJB2755-2qcz and VC-LLM391-2qcz rc (see Table 83 and Table 90 and Table 84, Table 87, Table 91) indicate these events do accumulate EPA, DHA and ARA when grown in the greenhouse and field, though as consistently observed, the field grown material did not accumulate the VLC-PUFAs (ARA, EPA, DHA) to the extent observed in the greenhouse (see Table 94 and Table 95 in comparison with Table 91, Table 92, Table 87 and Table 88). As observed in in Example 11 part F, higher oil content was observed compared to the summer field trials (Comparison Table 96 with Table 89). This phenomenon is analyzed in detail in Example 20.

TABLE 94

Fatty acid profiles of T4 seeds harvested from T3 plants cultivated in the field corresponding to USDA growth zones 8a-9a for field trials of canola events containing the T-DNAs of plasmids VC-LJB2755-2qcz rc and VC-LLM391-2qcz rc The events are indicated in the first column, along with the number of T4 seed aliquots representing a plot were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 16) | 5.3 ± 0.2 | 0.4 ± 0 | 0 ± 0 | 2.4 ± 0.2 | 36.1 ± 3.1 | 31.3 ± 2 | 0.5 ± 0.1 | 7.9 ± 0.5 | 1.3 ± 0.3 | 0.4 ± 0.1 | 0.6 ± 0 | 0.7 ± 0 | 0.1 ± 0.1 |
| LAODDN (n = 47) | 5.5 ± 0.6 | 0.5 ± 0.2 | 0.2 ± 0.3 | 2.7 ± 0.5 | 36.8 ± 3.2 | 30.3 ± 2.2 | 0.6 ± 0.2 | 7.9 ± 0.5 | 1.3 ± 0.3 | 0.4 ± 0.1 | 0.6 ± 0.1 | 0.7 ± 0 | 0.1 ± 0.1 |
| WT Kumily (n = 83) | 5.1 ± 0.5 | 0.4 ± 0.1 | 0.1 ± 0.1 | 2.1 ± 0.5 | 59.1 + 1.8 | 21.3 + 1.5 | 0 ± 0.1 | 9.5 ± 0.7 | 0 ± 0.1 | 0 ± 0 | 0.6 ± 0.1 | 1 ± 0.1 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 16) | 0 ± 0 | 1.2 ± 0.1 | 0.8 ± 0.1 | 1.4 ± 0.2 | 4.5 ± 0.5 | 0.2 ± 0 | 0 ± 0 | 0.7 ± 0.2 | 2.7 ± 0.2 | 0 ± 0 | 0.7 ± 0.2 | 0.3 ± 0.2 | 0.1 ± 0.1 |
| LAODDN (n = 47) | 0 ± 0 | 1 ± 0.1 | 0.8 ± 0.1 | 1.2 ± 0.2 | 4.7 ± 0.7 | 0.2 ± 0 | 0 ± 0 | 0.4 ± 0.3 | 2.6 ± 0.3 | 0 ± 0 | 0.6 ± 0.2 | 0.2 ± 0.1 | 0.1 ± 0.1 |
| WT Kumily (n = 83) | 0 ± 0 | 0 ± 0 | 0 ± 0 | 0 ± 0.1 | 0.1 ± 0.1 | 0.3 ± 0 | 0 ± 0 | 0 ± 0.1 | 0 ± 0.1 | 0 ± 0 | 0 ± 0 | 5.1 ± 0.5 | 0.4 ± 0.1 |

TABLE 95

Fatty acid profiles of one T4 seed batch per event harvested from T3 plants cultivated in the field corresponding to USDA growth zones 8a-9a for field trials of canola events containing the T-DNAs of plasmids VC-LJB2755-2qcz rc and VC-LLM391-2qcz rc. The events are indicated in the first column. Fatty acid profiles of T4 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAPBOW (n = 1) | 5.3 | 0.4 | 0.0 | 2.3 | 31.5 | 34.0 | 0.5 | 7.3 | 1.8 | 0.6 | 0.6 | 0.7 | 0.1 |
| LAODDN (n = 1) | 5.6 | 0.4 | 0.0 | 2.1 | 33.8 | 31.1 | 0.7 | 8.0 | 1.5 | 0.5 | 0.5 | 0.7 | 0.1 |

TABLE 95-continued

Fatty acid profiles of one T4 seed batch per event harvested from T3 plants cultivated in the field corresponding to USDA growth zones 8a-9a for field trials of canola events containing the T-DNAs of plasmids VC-LJB2755-2qcz rc and VC-LLM391-2qcz rc. The events are indicated in the first column. Fatty acid profiles of T4 seed batches having the highest EPA+DHA levels per event are shown. Per seed batch, a random selection of ~30 seed was measured in two technical repeats.

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAPBOW (n = 1) | 0.0 | 1.2 | 0.8 | 1.8 | 5.5 | 0.2 | 0.0 | 1.0 | 3.1 | 0.0 | 1.1 | 0.2 | 0.0 |
| LAODDN (n = 1) | 0.0 | 1.2 | 0.8 | 1.6 | 6.2 | 0.1 | 0.0 | 0.7 | 3.3 | 0.0 | 1.0 | 0.2 | 0.1 |

TABLE 96

Phenotypic rating of T3 plants cultivated in the field corresponding to USDA growth zones 8a-9a for trials of canola events containing the T-DNAs of plasmids VC-LJB2755-2qcz rc and VC-LLM391-2qcz rc. The events are indicated in the first column, along with the number of field plots that were rated per event. Oil: oil content (% of seed weight), protein: Protein content (% of seed cake without oil)

| Event | Oil | protein |
|---|---|---|
| LAPBOW (n = 16) | 42.9 ± 4.2 | 23.3 ± 3.1 |
| LAODDN (n = 47) | 43.5 ± 3.8 | 22.7 ± 2.7 |
| WT Kumily (n = 83) | 45.3 ± 3.9 | |

Fatty Acid Profiles, Copy Number Measurements, and Phenotypic Observations of T4 Plants Carrying T-DNAs of Plasmids VC-LJB2755-2Qcz Rc and VC-LLM391-2Qcz Rc Cultivated in Field Trials in USDA Zones 3a-4b and 5a During the Summer.

The data indicate that through the T5 generation the event LAODDN was still producing EPA and DHA at a level consistent with the field trial (described in part D). Also oil content was comparable between these two field trials.

TABLE 97

Fatty acid profiles of T5 seeds harvested from T4 plants cultivated in the field corresponding to USDA growth zones 3a-3b and 5a for field trials of canola events containing the T-DNAs of plasmids VC-LJB2755-2qcz rc and VC-LLM391-2qcz rc The events are indicated in the first column, along with the number of T5 seed aliquots representing a plot where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAODDN (n = 142) | 4.7 ± 0.4 | 0.2 ± 0.1 | 0 ± 0 | 2.8 ± 0.4 | 34.8 ± 3.5 | 33.8 ±4.8 | 0.3 ± 0.3 | 7.7 ± 1 | 1.1 ± 0.4 | 0.2 ± 0.2 | 0.7 ± 0.1 | 0.8 ± 0.1 | 0.1 ± 0.1 |
| WT Kumily (n = 56) | 4.5 ± 0.5 | 0.1 ± 0.1 | 0 ± 0 | 1.8 ± 1 | 60 ± 3.8 | 22.5 ±3.6 | 0.6 ± 1.5 | 7.9 ± 2.2 | 0.1 ± 0.1 | 0 ± 0 | 0.8 ± 0.2 | 1 ± 0.4 | 0.1 + 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAODDN (n = 142) | 0.1 ± 0.1 | 1.2 ± 0.3 | 1.1 ± 1.2 | 1.4 ± 0.4 | 4.5 ± 1.9 | 0.3 ± 0.1 | 0 ± 0 | 0.5 ± 0.4 | 2.9 ± 0.5 | 0.1 ± 0.2 | 0.7 ± 0.2 | 0.1 ± 0.2 | 0.1 ± 0.1 |
| WT Kumily (n = 56) | 0 ± 0 | 0.2 + 0.8 | 0 ± 0 | 0 ± 0 | 0 + 0.1 | 0.2 ± 0.2 | 0 ± 0 | 0 ± 0.1 | 0 ± 0 | 0 ± 0 | 0 ± 0 | 0 ± 0 | 0 ± 0 |

TABLE 98

Fatty acid profiles of one T5 seed batch per event harvested from T4 plants cultivated in the field corresponding to USDA growth zones 3a-3b and 5a for field trials of canola events containing the T-DNAs of plasmids VC-LJB2755-2qcz rc and VC-LLM391-2qcz rc. The events are indicated in the first column. Fatty acid profiles of T5 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LAODDN (n = 1) | 4.5 | 0.2 | 0.0 | 2.6 | 30.3 | 30.8 | 0.4 | 5.8 | 0.6 | 0.1 | 0.6 | 0.9 | 0.3 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LAODDN (n = 1) | 0.4 | 2.4 | 1.3 | 3.7 | 8.1 | 0.3 | 0.0 | 0.0 | 4.2 | 1.2 | 1.2 | 0.0 | 0.0 |

TABLE 99

Phenotypic rating of T4 plants cultivated in the greenhouse of canola events containing the T-DNAs of plasmids VC-LJB2755-2qcz rc and VC-LLM391-2qcz rc. The events are indicated in the first column, along with the number of field plots that were rated per event. Oil: oil content (% of seed weight), protein: Protein content (% of seed cake without oil)

| Event | Oil | protein |
|---|---|---|
| LAODDN (n = 47) | 39.9 ± 4.4 | 25.4 ± 1.8 |
| WT Kumily (n = 56) | 40.6 ± 2.3 | 26.4 ± 1.3 |

Example 14: Plants Containing the T-DNAs of Plasmid VC-LJB2755-2Qcz Rc and VC-LTM27-1Lcz Rc (Combination E in Example 5) for Production of EPA and DHA in Seeds In this example, the genetic elements required for EPA and DHA synthesis were transferred into the plant genome on two different T-DNAs. To this end, the two different plasmids VC-LJB2755-2qcz rc and VC-LTM217-1qcz rc containing two different T-DNAs were cloned into Agrobacteria, and plant tissue was incubated according to example 5 at the same time with these two agrobacterial cultures that are identical apart from containing either VC-LJB2755-2qcz rc or VC-LTM217-qcz rc rc. Due to the selectable herbicide resistance marker, regenerated plants contained the T-DNA of VC-LJB2755-2qcz rc. Only those plants were kept, that also contained the T-DNA of plasmid VC-LTM217-1 qcz rc rc as confirmed by PCR, conducted as described in example 5. Only plants containing the T-DNA of plasmid VC-LJB2755-2qcz rc as well as the T-DNA of plasmid VC-LTM217-qcz rc combined all the genetic elements required for EPA and DHA synthesis in seeds. The genetic elements of VC-LJB2755-2qcz rc and the function of each element are listed in Table 2. The genetic elements of VC-LTM217-1 qcz rc and the function of each element were listed in Table 7. For convenience, all enzymes expressed in seeds of plants carrying both T-DNA of VC-LJB2755-2qcz rc and VC-LTM217-1qcz rc that were required for EPA and DHA synthesis are additionally listed Table 100.

TABLE 100

Combined list of genes essential of EPA and DHA synthesis carried by the T-DNAs of plasmids VC-LJB2755-2qcz rc and VC-LTM217-1qcz rc.

| Genes encoding enzmyes for EPA and DHA synthesis | Plasmid containing T-DNA with the gene | Length (bp) | Enzymatic function and source of encoded protein |
|---|---|---|---|
| c-d12Des (Ps_GA) | VC-LJB2755-2qcz rc | 1196 | Delta-12 desaturase from *Phytophthora sojae* |
| c-d6Des (Ot_febit) | VC-LJB2755-2qcz rc | 1370 | Delta-6 desaturase from *Ostreococcus tauri* |
| c-d6Elo (Tp_GA2) | VC-LJB2755-2qcz rc | 818 | Delta-6 elongase from *Thalassiosira pseudonana* |
| c-d5Des (Tc_GA2) | VC-LJB2755-2qcz rc | 1319 | Delta-5 desaturase from *Thraustochytrium* sp. ATCC21685 |
| c-o3Des (Pi_GA2) | VC-LJB2755-2qcz rc | 1085 | Omega-3-desaturase from *Phytophthora infestans* |
| c-o3Des (Pir_GA) | VC-LJB2755-2qcz rc | 1091 | Omega-3 desaturase from *Pythium irregulare* |
| c-d5Elo (Ot_GA3) | VC-LTM217-1qcz rc | 902 | Delta-5 elongase from *Ostreococcus tauri* |
| c-d4Des (Pl_GA)2 | VC-LTM217-1qcz rc | 1338 | Delta-4 desaturase from *Pavlova lutheri* |
| c-d4Des (Tc_GA) | VC-LTM217-1qcz rc | 1560 | Delta-4 desaturase from *Thraustochytrium* spp. |

Fatty Acid Profiles, Copy Number Measurements, and Phenotypic Observations of T0 Plants Carrying T-DNAs of Plasmids VC-LJB2755-2Qcz Rc and VC-LTM217-1Qcz Rc Cultivated in Greenhouses During Winter.

Table 102 and Table 103 indicate the single copy events for insertions of VC-LJB2755-2qcz and VC-LTM217-1qcz rc did not accumulate as much EPA and DHA as the double copy events. Table 103 indicates that the combined EPA and DHA content, for the highest producers in T1 seed, was in the range of 15 percent of the total fatty acid content of the seed (5% of the total seed fatty acid content being DHA and 10% being EPA).

TABLE 101

Copy number measurement of T0 plants cultivated in the greenhouse of canola events containing the T-DNAs of plasmids VC-LJB2755-2qcz rc and VC-LTM217-1qcz rc. Considering each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49, Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border.

| Event | c-AHAS | c-o3Des (Pi_GA) | j-i-Atss18_ c-o3De s(Pi_GA2) | j-i-Atss14_ c-d12De s(Ps_GA) | c-d6Elo (Tp_GA) | j-i-Atss1_ cc-d6Elo (Tp_GA2) | c-o3Des (Pir_GA) | j-p-LuPRX_ i-Atss15 |
|---|---|---|---|---|---|---|---|---|
| sc (n = 139) | 1.2 | 1.2 | | | | | 1.2 | 1.2 |
| dc (n = 77) | 1.6 | 1.8 | | | 2.0 | | 1.8 | 1.8 |

TABLE 101-continued

Copy number measurement of T0 plants cultivated in the greenhouse of canola events containing the T-DNAs of plasmids VC-LJB2755-2qcz rc and VC-LTM217-1qcz rc. Considering each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49, Copy number assays targeting the T-DNA of VC-LTM217-1qcz rc. Assays are listed according to the position of the assay target along the T-DNA, with target c-d4Des(Eg_GA) located near the left T-DNA border and target j-i-Atssl_c-d5Elo(Ot_GA3) near the right T-DNA border.

| Event | c-d4Des (Pl_GA)2 | j-t-PvARc-p-LuCnl | j-i-Atss2_c-d4Des (Tc_GA3) | c-d4Des (Tc_GA) | j-p-PvARC5_t-BnFAE | c-d5Elo (Ot_GA3) | j-i-Atss1_c-d5Elo (Ot_GA3) |
|---|---|---|---|---|---|---|---|
| sc (n = 139) | 1.2 |  | 1.1 | 1.2 |  |  | 1.1 |
| dc (n = 77) | 1.9 |  | 1.9 | 1.9 |  |  | 1.9 |

TABLE 102

Fatty acid profiles of T1 seeds harvested from T0 plants cultivated in the greenhouse of canola events containing the T-DNAs of plasmids VC-LJB2755-2qcz rc and VC-LTM217-1qcz rc. Considering each event in this generation was represented by only 1 plant, all events have been grouped into the categories indicated in the first column as described in Table 101. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 139) | 5.1 ± 0.5 | 0.3 ± 0.1 | 0 ± 0.1 | 3.7 ± 0.8 | 37.8 ± 7.2 | 32 ± 4.4 | 0.4 ± 0.3 | 4.6 ± 0.6 | 1.7 ± 1.2 | 0.3 ± 0.3 | 0.9 ± 0.1 | 0.8 ± 0.1 | 0 ± 0.1 |
| dc (n = 77) | 5 ± 0.4 | 0.3 ± 0.1 | 0 ± 0.1 | 3.7 ± 0.6 | 35.5 ± 7.4 | 32.8 ± 4.4 | 0.5 ± 0.2 | 4.7 ± 0.8 | 1.8 ± 0.7 | 0.3 ± 0.1 | 0.9 ± 0.1 | 0.8 ± 0.1 | 0 ± 0.1 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 139) | 0 ± 0 | 1.4 ± 0.6 | 0.8 ± 0.4 | 1.8 ± 0.7 | 4.8 ± 1.8 | 0.4 ± 0.1 | 0 ± 0.3 | 0.2 ± 0.2 | 0.8 ± 0.5 | 0.3 ± 0.4 | 1.4 ± 0.6 | 0.1 ± 0.2 | 0 ± 0.1 |
| dc (n = 77) | 0 ± 0 | 1.5 ± 0.8 | 0.9 ± 0.5 | 1.7 ± 0.6 | 5.5 ± 2.6 | 0.3 ± 0.1 | 0 ± 0 | 0.3 ± 0.2 | 1 ± 0.5 | 0.4 ± 0.4 | 1.7 ± 0.6 | 0.2 ± 0.3 | 0 ± 0.1 |

TABLE 103

Fatty acid profiles of T1 seeds harvested from T0 plants cultivated in the greenhouse of canola events containing the T-DNAs of plasmids VC-LJB2755-2qcz rc and VC-LTM217-1qcz rc. Considering each event in this generation was represented by only 1 plant, all events have been grouped into the categories indicated in the first column as described in Table 101. For each category, the fatty acid profile of the plant/event having the highest EPA + DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 5.0 | 0.4 | 0.0 | 2.9 | 32.0 | 26.7 | 1.3 | 3.3 | 3.4 | 0.6 | 0.9 | 0.8 | 0.1 |
| dc (n = 1) | 5.1 | 0.2 | 0.1 | 5.1 | 23.3 | 31.7 | 0.7 | 3.8 | 2.9 | 0.6 | 1.0 | 0.8 | 0.2 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.0 | 1.6 | 1.0 | 2.7 | 10.3 | 0.4 | 0.0 | 1.2 | 0.0 | 0.0 | 5.2 | 0.2 | 0.1 |
| dc (n = 1) | 0.1 | 1.7 | 1.3 | 2.2 | 12.5 | 0.4 | 0.0 | 0.5 | 1.9 | 0.7 | 3.0 | 0.2 | 0.1 |

TABLE 104

Phenotypic rating of T0 plants cultivated in the greenhouse of canola events containing the T-DNAs of plasmids VC-LJB2755-2qcz rc and VC-LTM217-1qcz rc. Plants of all events combined have been grouped into the categories indicated in the first column; as defined in Table 101. The number of T0 plants fullfilling these criteria are displayed in parentheses. TKW: thousand kernel weight (g), SC: seed quality (1 = good, 9 = bad), Oil: oil content (% of seed weight), Protein: Protein content (% of seed cake without oil)

| Category of T0 plants | TKW | SC | Oil | Protein |
|---|---|---|---|---|
| sc (n = 139) | 4.3 ± 0.5 | 5 ± 1.8 | 33.3 ± 1.6 | 30.5 ± 0.6 |
| dc (n = 77) | 4.1 ± 0.5 | 5.3 ± 2 | 33.5 ± 3 | 29.7 ± 1.1 |

Fatty Acid Profiles, Copy Number Measurements, and Phenotypic Observations of T1 Plants Carrying T-DNAs of Plasmids VC-LJB2755-2Qcz Rc and VC-LTM217-1Qcz Rc Cultivated in Greenhouses During Summer.

Measurements carried out on plants from selected T1 events indicated single copy homozygous insertions of the T-DNA corresponding to VC-LJB2755-2qcz and VC-LTM217-1qcz rc (see table 104, in particular the table legend) and the T2 accumulates EPA and DHA in similar levels as the T1. Measurements on T2 seed (see Table 106 and Table 107) showed that EPA and DHA accumulated up to 13% of the total fatty acid content of the seed (with ca. 3% of the seed total fatty acid content being DHA).

TABLE 105

Copy number measurement of T1 plants cultivated in the greenhouse of canola events containing the T-DNAs of plasmids VC-LJB2755-2qcz rc and VC-LTM217-1qcz rc. Homozygous plants of the T1 generation of these two events have been selected using Half Kernel Analysis (Example 9). Based on the proven ability to discriminate homozygous and heterozygous seeds using half kernel analysis, it can be assumed all T1 plants in Table 106, Table 107, and Table 108 are homozygous, but no copy number analysis has been performed to confirm this.

Copy number assays targeting the T-DNA of VC-LJB2755-2qcz rc. Assays are listed according to the position of the assay target along the T-DNA, with target c-AHAS located near the left T-DNA border and target j-p-LuPXR_i-Atss15 near the right T-DNA border.

| Event | c-AHAS | c-o3Des (Pi_GA) | j-i-Atss18_c-o3Des(Pi_GA2) | j-i-Atss14_c-d12Des(Ps_GA) | c-d6Elo (Tp_GA) | j-i-Atss1_cc-d6Elo (Tp_GA2) | c-o3Des (Pir_GA) | j-p-LuPRX_i-Atss15 |
|---|---|---|---|---|---|---|---|---|
| LBAIID (n = 1) | 1.1 | 1.0 | | | | | 1.0 | 1.0 |
| LBAPPG (n = 1) | 1.0 | 1.0 | | | | | 1.0 | 1.0 |

Copy number assays targeting the T-DNA of VC-LTM217-1qcz rc. Assays are listed according to the position of the assay target along the T-DNA, with target c-d4Des(Eg_GA) located near the left T-DNA border and target j-i-Atss1_c-d5Elo(Ot_GA3) near the right T-DNA border.

| Event | c-d4Des (PI_GA)2 | j-t-PvARc-p-LuCnl | j-i-Atss2_c-d4Des (Tc_GA3) | c-d4Des (Tc_GA) | j-p-PvARC5_t-BnFAE | j-i-Atss1_c-d5Elo (Ot_GA3) |
|---|---|---|---|---|---|---|
| LBAIID (n = 1) | 1.2 | | 1.0 | | | 1.1 |
| LBAPPG (n = 1) | 1.2 | | 1.1 | | | 0.9 |

TABLE 106

Fatty acid profiles of T2 seeds harvested from homozygous T1 plants cultivated in the greenhouse of canola events containing the T-DNAs of plasmids VC-LJB2755-2qcz rc and VC-LTM217-1qcz rc The events are indicated in the first column, along with the number of T2 seed batches that where measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBAIID (n = 20) | 5.1 ± 0.2 | 0.2 ± 0 | 0 ± 0 | 3.6 ± 0.3 | 23.6 ± 1.8 | 38.4 ± 0.9 | 0.5 ± 0.1 | 4.9 ± 0.3 | 2.1 ± 0.2 | 0.5 ± 0.1 | 0.9 ± 0.1 | 0.6 ± 0 | 0.1 ± 0 |
| LBAPPG (n = 18) | 5.6 ± 0.5 | 0.3 ± 0.1 | 0 ± 0 | 4.3 ± 0.3 | 24.2 ± 2.7 | 39.9 ± 1.2 | 0.3 ± 0.1 | 4.7 ± 0.3 | 2 ± 0.3 | 0.4 ± 0.1 | 1 ± 0.1 | 0.6 ± 0 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBAIID (n = 20) | 0.1 ± 0 | 1.2 ± 0.1 | 0.9 ± 0.1 | 1.8 ± 0.2 | 8.1 ± 0.8 | 0.4 ± 0 | 0 ± 0 | 0.7 ± 0.1 | 1.8 ± 0.2 | 0.8 ± 0.1 | 3.4 ± 0.4 | 0.3 ± 0.1 | 0 ± 0 |
| LBAPPG (n = 18) | 0 ± 0 | 1 ± 0.1 | 0.7 ± 0.2 | 1.8 ± 0.2 | 6.9 ± 1.2 | 0.4 ± 0 | 0 ± 0 | 0.6 ± 0.1 | 1.6 ± 0.2 | 0.6 ± 0.2 | 2.9 ± 0.5 | 0 ± 0.1 | 0 ± 0 |

TABLE 107

Fatty acid profiles of one T2 seed batch per event harvested from homozygous T1 plants cultivated in the greenhouse of canola events containing the T-DNAs of plasmids VC-LJB2755-2qcz rc and VC-LTM217-1qcz re. The events are indicated in the first column. Fatty acid profiles of T2 seed batches having the highest EPA+DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBAIID (n = 1) | 5.2 | 0.3 | 0.0 | 3.7 | 20.9 | 37.3 | 0.4 | 5.3 | 2.4 | 0.6 | 0.9 | 0.6 | 0.1 |
| LBAPPG (n = 1) | 4.9 | 0.2 | 0.0 | 4.6 | 22.3 | 38.8 | 0.3 | 4.7 | 2.1 | 0.5 | 1.2 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBAIID (n = 1) | 0.1 | 1.0 | 0.8 | 2.0 | 9.2 | 0.4 | 0.0 | 0.8 | 2.2 | 1.0 | 4.5 | 0.3 | 0.0 |
| LBAPPG (n = 1) | 0.0 | 1.2 | 0.9 | 2.0 | 8.2 | 0.5 | 0.0 | 0.6 | 1.8 | 0.7 | 3.7 | 0.0 | 0.0 |

TABLE 108

Fatty acid profiles of T2 seeds harvested from homozygous T1 plants cultivated in the greenhouse of canola events containing the T-DNAs of plasmids VC-LJB2755-2qcz rc and VC-LTM217-1qcz rc. Plants of all events combined have been grouped into the category "sc". The number of T1 plants fullfilling these criteria are displayed in parentheses. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 38) | 2.6 ± 0.2 | 0.1 ± 0 | 0±0 | 2 ± 0.2 | 12 ± 1.1 | 19.5 ± 0.6 | 0.2 ± 0 | 2.4 ± 0.1 | 1 ± 0.1 | 0.2 ± 0 | 0.5 ± 0 | 0.3 ± 0 | 0 ± 0 |

| Category of T1 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 38) | 0 ± 0 | 0.5 ± 0.1 | 0.4 ± 0.1 | 0.9 ± 0.1 | 3.7 ± 0.6 | 0.2 ± 0 | 0 ± 0 | 0.3 ± 0 | 0.8 ± 0.1 | 0.3 ± 0.1 | 1.6 ± 0.3 | 0.1 ± 0.1 | 0 ± 0 |

Example 15: Plants Containing the T-DNA of Plasmid RTP0690-1qczF for Production of EPA and DHA in Seeds All genetic elements required for EPA and DHA synthesis described in this example, were transferred on a single T-DNA using a BiBAC plasmid into the plant genome. To this end, the plasmid RTP10690-1qcz_F was cloned into agrobacteria, and plant tissue was incubated according to example 6 with this agrobacterial culture. Due to the selectable herbicide resistance marker, regenerated plants contained the T-DNA of RTP10690-1qcz_F. The genetic elements of RTP10690-1qcz_F and the function of each element are listed in Table 8. For convenience, all enzymes expressed in seeds of plants carrying both T-DNA of RTP10690-1qcz_F that required for EPA and DHA synthesis are additionally listed Table 109.

TABLE 109

List of genes essential of EPA and DHA synthesis carried by the T-DNA of plasmid RTP10690-1qcz_F.

| Genes encoding enzmyes for EPA and DHA synthesis | Length (bp) | Enzymatic function and source of encoded protein |
|---|---|---|
| c-d12Des(Ps_GA2) | 1197 | Delta-12 desaturase from Phythophthora sojae |
| c-d6Des(Ot_febit) | 1371 | Delta-6 desaturase from Ostreococcus tauri |
| c-d6Elo(Pp_GA2) | 873 | Delta-6 elongase from Physcomitrella patens |
| c-d6Elo(Tp_GA2) | 819 | Delta-6 elongase from Thalassiosira pseudonana |
| c-d5Des(Tc_GA2) | 1320 | Delta-5 desaturase from Thraustochytrium sp. ATCC21685 |
| 2 copies of c-d5Des(Tc_GA2) | 1320 | Delta-5 desaturase from Thraustochytrium sp. ATCC21685 |
| c-o3Des(Pi_GA2) | 1086 | Omega-3-desaturase from Phythophthora infestans |
| 2 copies of c-o3Des(Pir_GA) | 1092 | Omega-3-desaturase from Pythium irregulare |
| c-d5Elo(Ot_GA3) | 903 | Delta-5 elongase from Ostreococcus tauri |
| c-d4Des(Pl_GA)2 | 1338 | Delta-4 desaturase from Pavlova lutheri |
| c-d4Des(Tc_GA3) | 1560 | Delta-4 desaturase from Thraustochytrium sp. |

Fatty Acid Profiles, Copy Number Measurements, and Phenotypic Observations of T0 Plants Carrying T-DNA of Plasmids RTP10690-1Qcz_F Cultivated in Greenhouses During Winter As Table 110 indicates there were fewer insertion events of this construct observed than for other constructs, with more single copy events than double copy, by approximately four fold. Fatty acid profile data on Table 111 and Table 112 indicated that DHA and EPA can accumulate up to 4% of the total seed fatty acid content in the T1 with similar performance between single and double copy events, within error. Table 113 demonstrates that there was no significant aerial phenotype associated with this construct in the T0.

TABLE 110

Copy number measurement of T0 plants cultivated in the greenhouse of canola events containing the T-DNAs of plasmid RTP10690-1qcz rc. Considering each event in this generation was represented by only 1 plant, all events have been grouped into the categories indicated in the first column; sc: all T0 plants where the average of all copy number assays listed in this table was 0.51-1.49, dc: all T0 plants where the average of all copy number assays listed in this table was 1.51-2.49.

Copy number assays targeting the T-DNA of RTP10690-1qcz_F. Assays are listed according to the position of the assay target along the T-DNA, with target c-AHAS located near the left T-DNA border and target c-d6Elo(Pp_GA) near the right T-DNA border.

| Category of T0 plants | c-AHAS | c-d5Des (Tc_GA) | j-i-Atss18_c-o3Des (Pi_GA2) | j-i-Atss2_c-d4Des (Tc_GA3) | j-i-Atss1_c-d5Elo (Ot_GA3) | c-d4Des (Pl_GA)2 | j-i-Atss2_c-d4Des (Pl_GA)-195R |
|---|---|---|---|---|---|---|---|
| sc (n = 52) | 1.1 | 2.0 | 1.2 | 1.0 | 1.1 | 1.0 | |
| dc (n = 12) | 1.6 | 3.5 | 2.0 | 1.8 | 1.9 | 2.0 | |

Copy number assays targeting the T-D NA of RTP10690-1qcz_F. Assays are listed according to the position of the assay target along the T-DNA, with target c-AHAS located near the le T-DNA border and target c-d6Elo(Pp_GA) near the right T-DNA border.

| Category of T0 plants | j-p-LuPXR_i-Atss15 | j-i-Atss14_c-d12Des (Ps_GA) | c-d6Elo (Tp_GA) | j-t-StCAT_p2_p-LuPXR | j-i-Atss2_c-d6Des(Ot febit_GA) | cd5Des (Tc_GA) | c-d6Elo (Pp_GA) |
|---|---|---|---|---|---|---|---|
| sc (n = 52) | 1.0 | 1.2 | 1.0 | 1.1 | 1.0 | 2.0 | 1.1 |
| dc (n = 12) | 1.9 | 2.2 | 1.8 | 2.1 | 1.8 | 3.5 | 1.8 |

TABLE 111

Fatty acid profiles of T1 seeds harvested from T0 plants cultivated in the greenhouse of canola events containing the T-DNAs of plasmid RTP10690-1 qcz rc. Considering each event in this generation was represented by only 1 plant, all events have been grouped into the categories indicated in the first column as described in Table 110. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 52) | 5.1 ± 0.7 | 0.3 ± 0.1 | 0±0 | 3.1 ± 0.4 | 43.8 ± 7.3 | 28.3 ± 4.5 | 0.3 ± 0.2 | 5.1 ± 0.8 | 0.8 ± 0.4 | 0.1 ± 0.1 | 0.9 ± 0.1 | 1 ± 0.1 | 0.5 ± 0.6 |
| dc (n = 12) | 5.2 ± 0.4 | 0.3 ± 0.1 | 0 ± 0.1 | 3.5 ± 0.5 | 39 ± 6.7 | 30.1 ±3 | 0.5 ± 0.2 | 4.5 ± 0.6 | 1.6 ± 0.6 | 0.2 ± 0.1 | 0.9 ± 0.1 | 0.9 ± 0.1 | 0.3 ± 0.4 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 52) | 0.2 ± 0.3 | 2.2 ± 0.7 | 1.1 ± 0.4 | 1.6 ± 0.5 | 3.2 ± 1 | 0.4 ± 0.1 | 0 ± 0 | 0.1 ± 0.1 | 1.1 ± 0.4 | 0 ± 0 | 0.5 ± 0.3 | 0.1 ± 0.1 | 0.2 ± 0.2 |
| dc (n = 12) | 0.1 ± 0.1 | 3.1 ± 1 | 1.2 ± 0.4 | 2 ± 1.4 | 3.7 ± 1.3 | 0.4 ± 0 | 0 ± 0 | 0.3 ± 0.2 | 1.2 ± 0.4 | 0 ± 0 | 0.7 ± 0.3 | 0.2 ± 0.2 | 0.1 ± 0.2 |

TABLE 112

Fatty acid profiles of T1 seeds harvested from T0 plants cultivated in the greenhouse of canola events containing the T-DNAs of plasmid RTP10690-1qcz rc. Considering each event in this generation was represented by only 1 plant, all events have been grouped into the categories indicated in the first column as described in Table 110. For each category, the fatty acid profile of the plant/event having the highest EPA + DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 5.5 | 0.3 | 0.0 | 4.1 | 27.2 | 33.6 | 0.7 | 4.1 | 1.9 | 0.3 | 0.9 | 0.7 | 0.3 |
| dc (n = 1) | 5.3 | 0.3 | 0.0 | 3.8 | 31.9 | 32.9 | 0.6 | 3.8 | 1.6 | 0.2 | 0.9 | 0.8 | 0.4 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.2 | 4.5 | 2.1 | 2.7 | 5.8 | 0.4 | 0.0 | 0.3 | 2.2 | 0.1 | 1.4 | 0.4 | 0.2 |
| dc (n = 1) | 0.2 | 3.6 | 1.5 | 2.7 | 5.7 | 0.4 | 0.0 | 0.3 | 1.7 | 0.0 | 1.1 | 0.2 | 0.3 |

TABLE 113

Phenotypic rating of T0 plants cultivated in the greenhouse of canola events containing the T-DNAs of plasmid RTP10690-1qcz rc. Considering each event was in this generation represented by only 1 plant, all events have been grouped into the categories indicated in the first column as described in Table 110. The number of T0 plants/events fullfilling these criteria are displayed in parentheses. DFF: days to first flower (days), DF: deformed flower (1 = deformed, 9 = normal), DL: deformed leaf (1 = deformed, 9 = normal), DP: deformed plant (1 = deformed, 9 = normal), DS: deformed silique (1 = deformed, 9 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm), TKW: thousand kernel weight (g), SC: seed quality (1 = good, 9 = bad), Oil: oil content (% of seed weight), Protein: Protein content (% of seed cake without oil)

| Category of T0 plants | DFF | DF | DL | DP | DS | FC | LD | LGC |
|---|---|---|---|---|---|---|---|---|
| sc (n = 52) | 61.4 ± 15.5 | 8.7 ± 1.2 | 8.7 ± 1.2 | 8.8 ± 0.9 | 7.6 ± 2.5 | 3 ± 0 | 5.4 ± 7.9 | 5.9 ± 6.9 |
| dc (n = 12) | 56.3 ± 9.6 | 9 ± 0 | 9 ± 0 | 9 ± 0 | 8.1 ± 2.1 | 3 ± 0 | 4.3 ± 1 | 5 ± 0 |

| Category of T0 plants | LF | NoL | PH | TKW | SC | Oil | Protein |
|---|---|---|---|---|---|---|---|
| sc (n = 52) | 7.3 ± 2.6 | 4.9 ± 1.3 | 123.8 ± 7.5 | | | 35.4 ± 2.4 | 30.1 ± 1.1 |
| dc (n = 12) | 8.1 ± 2.1 | 5 ± 0.9 | 125.4 ± 5.4 | | | 34.8 ± 1.1 | 29.9 ± 1 |

Fatty Acid Profiles, Copy Number Measurements, and Phenotypic Observations of T1 Plants Carrying T-DNA of Plasmids RTP10690-1Qcz_F Cultivated in Greenhouses During Summer Data in Table 115 and Table 116 indicate a similar performance of the T2 seed as that of the T1 seed with respect to EPA and DHA, see also Table 111 and Table 112 for comparison. The selected events all performed at a similar level and segregated for one to two copies of each gene.

TABLE 114

Copy number measurement of T1 plants cultivated in the greenhouse of canola events containing the T-DNAs of plasmid RTP10690-1qcz rc. The events are indicated in the first column, along with the number of T1 plants that were measured per event.

Copy number assays targeting the T-DNA of RTP10690-1qcz_F. Assays are listed according to the position of the assay target along the T-DNA, with target c-AHAS located near the left T-DNA border and target c-d6Elo(Pp_GA) near the right T-DNA border. Copy number results obtained on the T0 plants are indicated in parentheses. Homozygosity of all plants per event was indicated if the average result of the selected T1 plants was about two fold higher than the T0 generation.

| Event | c-AHAS | c-d5Des (Tc_GA) | j-i-Atss18_c-o3Des (Pi_GA2) | j-i-Atss2_c-d4Des (Tc_GA3) | j-i-Atss1_c-d5Elo (Ot_GA3) | c-d4Des (PI_GA)2 | j-i-Atss2_c-d4Des (PI_GA)-195R |
|---|---|---|---|---|---|---|---|
| LBDGCA (n = 94) | 1.5 (T0: 1) | 3.2 (T0: 2) | 1.6 (T0: 1.4) | (T0: 1) | (T0: 1.2) | 1.7 (T0: 0.9) | 1.6 |
| LBDGBP (n = 20) | (T0: 1.1) | (T0: 2.1) | (T0: 1.4) | (T0: 1.2) | (T0: 1.3) | (T0: 1.1) | |
| LBDIHN (n = 114) | 1.6 (T0: 1.2) | 3.3 (T0: 2.2) | 1.6 (T0 :1.7) | (T0: 1.1) | (T0 :1.2) | 1.7 (T0: 1) | 1.6 |

Copy number assays targeting the T-DNA of RTP10690-1qcz_F. Assays are listed according to the position of the assay target along the T-DNA, with target c-AHAS located near the left T-DNA border and target c-d6Elo(Pp_GA) near the right T-DNA border. Copy number results obtained on the T0 plants are indicated in parentheses. Homozygosity of all plants per event was indicated if the average result of the selected T1 plants was about two fold higher than the T0 generation.

| Event | j-p-LuPXR_i-Atss15 | j-i-Atss14_c-d12Des (Ps_GA) | c-d6Elo (Tp_GA) | j-t-StCAT_p2_p-LuPXR | j-i-Atss2_c-d6Des(Ot febit_GA) | cd5Des (Tc_GA) | c-d6Elo (Pp_GA) |
|---|---|---|---|---|---|---|---|
| LBDGCA (n = 94) | 1.6 (T0: 1) | (T0: 1.2) | 1.7 (T0: 1) | (T0: 1.1) | (T0: 1.1) | 3.2 (T0: 2) | 1.6 (T0: 1) |
| LBDGBP (n = 20) | (T0: 1.1) | (T0: 1.3) | (T0: 1) | (T0: 1) | (T0: 1.2) | (T0: 2.1) | (T0: 1) |
| LBDIHN (n = 114) | 1.6 (T0: 1.1) | | 1.7 (T0: 1) | (T0: 0.9) | (T0: 1.2) | 3.3 (T0: 2.2) | 1.6 (T0: 1.1) |

TABLE 115

Fatty acid profiles of T2 seeds harvested from T1 plants cultivated in the greenhouse of canola events containing the T-DNAs of plasmid RTP10690-1qcz re. The events are indicated in the first column, along with the number of T1 plants that were measured per event.

| event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBDGCA (n = 90) | 5.7 ± 0.5 | 0.2 ± 0.1 | 0 ± 0.1 | 4.1 ± 0.7 | 36.4 ± 7.3 | 32.5 ± 3.9 | 0.5 ± 0.2 | 4.5 ± 0.9 | 1.7 ± 0.7 | 0.2 ± 0.1 | 1.1 ± 0.2 | 0.8 ± 0.1 | 0.2 ± 0.1 |
| LBDGBP (n = 20) | 5.4 ± 0.5 | 0.3 ± 0 | 0 ± 0 | 3.9 ± 0.4 | 25.4 ± 2.3 | 37.1 ± 1.6 | 0.5 ± 0 | 3.4 ± 0.2 | 2.4 ± 0.3 | 0.2 ± 0 | 1 ± 0.1 | 0.6 ± 0 | 0.1 ± 0 |
| LBDIHN (n = 110) | 4.9 ± 0.4 | 0.2 ± 0.1 | 0 ± 0 | 3.6 ± 0.5 | 32.5 ± 7.6 | 34.5 ± 4.1 | 0.6 ± 0.2 | 4.4 ± 1 | 1.7 ± 0.7 | 0.2 ± 0.1 | 0.9 ± 0.1 | 0.8 ± 0.1 | 0.3 ± 0.2 |

| event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBDGCA (n = 90) | 0 ± 0 | 2.6 ± 0.6 | 1 ± 0.2 | 1.9 ± 0.7 | 3.3 ± 1.2 | 0.4 ± 0.1 | 0 ± 0 | 0.4 ± 0.2 | 1.4 ± 0.5 | 0 ± 0 | 0.6 ± 0.3 | 0.3 ± 0.1 | 0.1 ± 0.1 |
| LBDGBP (n = 20) | 0 ± 0 | 2.3 ± 0.2 | 0.9 ± 0.2 | 3.8 ± 0.5 | 7.5 ± 1.6 | 0.4 ± 0 | 0 ± 0 | 0.6 ± 0.1 | 2.4 ± 0.4 | 0 ± 0.2 | 1.7 ± 0.7 | 0 ± 0 | 0 ± 0 |
| LBDIHN (n = 110) | 0.1 ± 0.1 | 2.3 ± 0.4 | 1.1 ± 0.4 | 2.7 ± 0.9 | 5.2 ± 1.6 | 0.4 ± 0.1 | 0 ± 0 | 0.4 ± 0.2 | 1.9 ± 0.6 | 0 ± 0 | 0.9 ± 0.4 | 0.2 ± 0.1 | 0.1 ± 0.1 |

TABLE 116

Fatty acid profiles of T2 seeds harvested from T1 plants cultivated in the greenhouse of canola events containing the T-DNAs of plasmid RTP10690-1qcz rc. The events are indicated in the first column.
Fatty acid profiles of T2 seed batches having the highest EPA + DHA levels per event are shown.
Per seed batch, a random selection of ~30 seed was measured in two technical repeats.

| Events | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBDGCA (n = 1) | 5.5 | 0.2 | 0.0 | 3.3 | 29.2 | 31.8 | 0.9 | 5.3 | 2.8 | 0.4 | 0.7 | 0.7 | 0.1 |
| LBDGBP (n = 1) | 5.2 | 0.3 | 0.0 | 3.9 | 20.3 | 35.1 | 0.5 | 3.6 | 2.7 | 0.3 | 1.0 | 0.6 | 0.1 |
| LBDIHN (n = 1) | 5.0 | 0.3 | 0.0 | 3.5 | 23.8 | 36.3 | 0.6 | 2.6 | 2.6 | 0.2 | 0.9 | 0.6 | 0.1 |

| Events | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBDGCA (n = 1) | 0.1 | 2.9 | 1.2 | 3.6 | 5.9 | 0.3 | 0.0 | 0.6 | 2.6 | 0.0 | 1.3 | 0.4 | 0.1 |
| LBDGBP (n = 1) | 0.0 | 2.6 | 1.3 | 4.4 | 10.8 | 0.4 | 0.0 | 0.7 | 3.3 | 0.0 | 3.0 | 0.0 | 0.0 |
| LBDIHN (n = 1) | 0.0 | 2.8 | 1.1 | 4.1 | 9.1 | 0.4 | 0.0 | 1.0 | 2.8 | 0.0 | 2.1 | 0.0 | 0.1 |

TABLE 117

Phenotypic rating of T1 plants cultivated in the greenhouse of canola events containing the T-DNAs of plasmid RTP10690-1qcz rc. The events are indicated in the first column, along with the number of T1 plants that were measured per event. Oil: oil content (% of seed weight), Protein: Protein content (% of seed cake without oil)

| Events | Oil | Protein |
|---|---|---|
| LBDGCA (n = 90) | 34.1 ± 3.1 | 30.1 ± 1.9 |
| LBDIHN (n = 110) | 35.3 ± 2.7 | 29.9 ± 1.8 |

Example 16: Plants Containing the T-DNA of Plasmid RTP10691-2Qcz for Production of EPA and DHA in Seeds All genetic elements required for EPA and DHA synthesis described in this example, were transferred on a single T-DNA using a BiBAC plasmid into the plant genome. To this end, the plasmid RTP10691-2qcz was cloned into agrobacteria, and plant tissue was incubated according to example 6 with this agrobacterial culture. Due to the selectable herbicide resistance marker, regenerated plants contained the T-DNA of RTP10691-2qcz. The genetic elements of RTP10691-2qcz and the function of each element are listed in Table 9. For convenience, all enzymes expressed in seeds of plants carrying both T-DNA of RTP10691-2qcz that required for EPA and DHA synthesis are additionally listed in Table 118.

TABLE 118

List of genes essential of EPA and DHA synthesis carried by the T-DNA of plasmid RTP10691-2qcz.

| Genes encoding enzmyes for EPA and DHA synthesis | Length (bp) | Enzymatic function and source of encoded protein |
|---|---|---|
| c-d12Des(Ps_GA2) | 1196 | Delta-12 desaturase from *Phythophthora sojae* |
| c-d6Des(Ot_febit) | 1371 | Delta-6 desaturase from *Ostreococcus tauri* |
| c-d6Elo(Pp_GA2) | 873 | Delta-6 elongase from *Physcomitrella patens* |
| c-d6Elo(Tp_GA2) | 819 | Delta-6 elongase from *Thalassiosira pseudonana* |
| 2 copies of c-d5Des(Tc_GA2) | 1320 | Delta-5 desaturase from *Thraustochytrium* sp. ATCC21685 |
| c-o3Des(Pi_GA2) | 1086 | Omega-3-desaturase from *Phythophthora infestans* |
| 2 copies of c-o3Des(Pir_GA) | 1092 | Omega-3 desaturase from *Pythium irregulare* |
| c-d5Elo(Ot_GA3) | 903 | Delta-5 elongase from *Ostreococcus tauri* |
| c-d4Des(Pl_GA)2 | 1337 | Delta-4 desaturase from *Pavlova lutheri* |
| c-d4Des(Tc_GA3) | 1560 | Delta-4 desaturase from *Thraustochytrium* sp. |

TABLE 119

List of genes essential of EPA and DHA synthesis carried by the T-DNA of plasmid VC-LTM595-1qcz rc.

| Genes encoding enzmyes for EPA and DHA synthesis | Length (bp) | Enzymatic function and source of encoded protein |
|---|---|---|
| c-d12Des(Ps_GA2) | 1197 | Delta-12 desaturase from *Phythophthora sojae* |
| c-d6Des(Ot_febit) | 1371 | Delta-6 desaturase from *Ostreococcus tauri* |
| c-d6Elo(Pp_GA2) | 873 | Delta-6 elongase from *Physcomitrella patens* |
| c-d6Elo(Tp_GA2) | 819 | Delta-6 elongase from *Thalassiosira pseudonana* |
| c-d5Des(Tc_GA2) | 1320 | Delta-5 desaturase from *Thraustochytrium* sp. ATCC21685 |
| c-d5Des(Tc_GA2) | 1320 | Delta-5 desaturase from *Thraustochytrium* sp. ATCC21685 |
| c-o3Des(Pi_GA2) | 1086 | Omega-3-desaturase from *Phythophthora infestans* |
| 2 copies of c-o3Des(Pir_GA) | 1092 | Omega-3 desaturase from *Pythium irregulare* |
| c-d5Elo(Ot_GA3) | 903 | Delta-5 elongase from *Ostreococcus tauri* |
| c-d4Des(Pl_GA)2 | 1338 | Delta-4 desaturase from *Pavlova lutheri* |
| c-d4Des(Tc_GA3) | 1560 | Delta-4 desaturase from *Thraustochytrium* sp. |

Example 17: Plants Containing the T-DNA of Plasmid VC-LTM595-1Qcz Rc for Production of EPA and DHA in Seeds All genetic elements required for EPA and DHA synthesis described in this example, were transferred on a single T-DNA using a BiBAC plasmid into the plant genome. To this end, the plasmid VC-LTM595-1 qcz rc was cloned into agrobacteria, and plant tissue was incubated according to example 6 with this agrobacterial culture. Due to the selectable herbicide resistance marker, regenerated plants contained the T-DNA of VC-LTM595-qcz rc. The genetic elements of VC-LTM595-1qcz rc and the function of each element are listed in Table 10. For convenience, all enzymes expressed in seeds of plants carrying both T-DNA of VC-LTM595-1qcz rc that required for EPA and DHA synthesis are additionally listed Table 119.

Fatty acid profiles, copy number measurements, and phenotypic observations of T0 plants carrying T-DNA of plasmids VC-LTM595-1qcz rc cultivated in greenhouses during summer Similar to VC-RTP10690-1qcz_F, the number of insertions of the entire T-DNA was not as high as obtained for the multi-construct transformations, see Table 120. Table 121 and Table 122 show the fatty acid profile measurements for single, double and triple copy T-DNA, and indicate that the double copy constructs perform marginally better than the single copy constructs and perhaps marginally better than the triple copy constructs in terms of EPA and DHA accumulation. The fatty acid profile data further indicate that the accumulation of EPA and DHA in the T1 seed was up to 10% of the total fatty acids with up to 2% of the total fatty acids in the seed being DHA. Phenotypic measurements, shown on Table 123, indicated some variability in flowering time (as represented by DFF).

TABLE 120

Copy number measurement of T0 plants cultivated in the greenhouse of canola events containing the T-DNAs of plasmid VC-LTM595-1qcz rc.
Considering each event in this generation was represented by only 1 plant, all events have been grouped into the categories indicated in the first column;

Copy number assays targeting the T-DNA of VC-LTM595-1qcz rc.
Assays are listed according to the position of the assay target along the T-DNA, with target c-AHAS located near the left T-DNA border and target c-d6Elo(Pp_GA) near the right T-DNA border.

| Category of T0 plants | c-AHAS | j-p-BnSETL-v1_c-o3Des (Pir_GA) | c-d4Des (Pl_GA)2 | j-i-Atss18_c-o3Des (Pi_GA2) | j-p-PvARC5_t-BnFAE | j-i-Atss1_c-d5Elo (Ot_GA3) | c-d5Des (Tc_GA) |
|---|---|---|---|---|---|---|---|
| sc (n = 24) | 1.1 | | 1.0 | 1.0 | 0.9 | 0.9 | 1.9 |
| de (n = 7) | 2.2 | | 2.3 | 2.1 | 2.0 | 1.9 | 3.8 |
| tc (n = 3) | 2.4 | | 2.4 | 1.9 | 2.5 | 2.0 | 4.6 |

TABLE 120-continued

Copy number measurement of T0 plants cultivated in the greenhouse of canola events containing the T-DNAs of plasmid VC-LTM595-1qcz rc.
Considering each event in this generation was represented by only 1 plant, all events have been grouped into the categories indicated in the first column;

Copy number assays targeting the T-DNA of VC-LTM595-1qcz rc.
Assays are listed according to the position of the assay target along the T-DNA, with target c-AHAS located near the left T-DNA border and target c-d6Elo(Pp_GA) near the right T-DNA border.

| Category of T0 plants | j-p-LuPXR_i-Atss15 | j-i-Atss14_c-d12Des (Ps_GA) | c-d6Elo (Tp_GA) | j-t-StCAT_p2_p-LuPXR | j-i-Atss2_c-d6Des(Otfebit_GA) | c-d5Des (Tc_GA) | c-d6Elo (Pp_GA) |
|---|---|---|---|---|---|---|---|
| sc (n = 24) | 1.1 | 1.0 | 0.9 | 1.1 | 1.9 | 1.0 | |
| de (n = 7) | 2.3 | 2.2 | 2.3 | 2.1 | 3.8 | 1.9 | |
| tc (n = 3) | 3.3 | 2.4 | 2.9 | 2.4 | 4.6 | 2.4 | | sc: all T0 plants where the average of all copy number assays listed in this table except the assay c-d5Des(Tc_GA) was 0.51-1.49,
de: all T0 plants where the average of all copy number assays listed in this table was 1.51-2.49,
tc: all T0 plants where the average of all copy number assays listed in this table was 2.51-3.49.

TABLE 121

Fatty acid profiles of T1 seeds harvested from T0 plants cultivated in the greenhouse of canola events containing the T-DNAs of plasmid VC-LTM595-1qcz rc.
Considering each event in this generation was represented by only 1 plant, all events have been grouped into the categories indicated in the first column as described in Table 120. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 24) | 5.2 ± 0.6 | 0.3 ± 0.1 | 0 ± 0 | 3 ± 0.4 | 41.2 ± 4.8 | 28.6 ± 2.3 | 0.3 ± 0.1 | 5.9 ± 0.6 | 0.6 ± 0.3 | 0.1 ± 0.1 | 0.8 ± 0.1 | 0.9 ± 0.1 | 0.6 ± 0.3 |
| de (n = 7) | 5.6 ± 1.4 | 0.3 ± 0.2 | 0 ± 0 | 3.7 ± 0.7 | 34.4 ± 7.3 | 31.2 ± 3.4 | 0.4 ± 0.2 | 5.7 ± 1.4 | 1.5 ± 0.5 | 0.2 ± 0.2 | 0.9 ± 0.2 | 0.8 ± 0.2 | 0.3 ± 0.2 |
| tc (n = 3) | 4.1 ± 1.3 | 0.2 ± 0.1 | 0 ± 0 | 3 ± 0.1 | 45.4 ± 8.4 | 26.2 ± 2.2 | 0.4 ± 0.3 | 6 ± 0.9 | 1.7 + 2 | 0.2 ± 0.3 | 0.8 ± 0 | 1 ± 0.1 | 0.3 ± 0.2 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 24) | 0.3 ± 0.1 | 1.9 ± 0.7 | 1.2 ± 0.5 | 1.5 ± 0.3 | 3.5 ± 0.8 | 0.4 ± 0.1 | 0 ± 0 | 0.3 ± 0.1 | 1.2 ± 0.3 | 0 ± 0.1 | 1.1 ± 0.3 | 0.4 ± 0.2 | 0.3 ± 0.2 |
| de (n = 7) | 0.1 ± 0.1 | 2.7 ± 0.8 | 1.5 ± 1 | 1.6 ± 0.8 | 3.8 ± 2.2 | 0.4 ± 0 | 0 ± 0 | 0.6 ± 0.4 | 1.5 ± 0.8 | 0.2 ± 0.1 | 1.6 ± 0.6 | 0.7 ± 0.1 | 0.2 ± 0.1 |
| tc (n = 3) | 0.1 ± 0.1 | 1.5 ± 0.4 | 0.7 ± 0.1 | 1.5 ± 0.7 | 3.3 ± 1.6 | 0.4 ± 0 | 0 ± 0 | 0.5 ± 0.3 | 1 ± 0.4 | 0.2 ± 0.1 | 1.1 ± 0.5 | 0.3 ± 0.1 | 0.2 ± 0.1 |

TABLE 122

Fatty acid profiles of T1 seeds harvested from T0 plants cultivated in the greenhouse of canola events containing the T-DNAs of plasmid VC-LTM595-1qcz rc.
Considering each event in this generation was represented by only 1 plant, all events have been grouped into the categories indicated in the first column as described in Table 120. For each category, the fatty acid profile of the plant/event having the highest EPA + DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 6.3 | 0.4 | 0.0 | 3.4 | 34.6 | 29.8 | 0.4 | 5.3 | 1.0 | 0.1 | 0.8 | 0.8 | 0.6 |
| de (n = 1) | 4.9 | 0.2 | 0.0 | 2.8 | 25.8 | 33.9 | 0.3 | 4.8 | 1.7 | 0.3 | 0.7 | 0.7 | 0.5 |
| te (n = 1) | 4.5 | 0.2 | 0.0 | 3.1 | 37.8 | 28.0 | 0.7 | 5.7 | 3.9 | 0.5 | 0.8 | 0.9 | 0.1 |

TABLE 122-continued

Fatty acid profiles of T1 seeds harvested from T0 plants cultivated in the greenhouse of canola events containing the T-DNAs of plasmid VC-LTM595-1qcz rc. Considering each event in this generation was represented by only 1 plant, all events have been grouped into the categories indicated in the first column as described in Table 120. For each category, the fatty acid profile of the plant/event having the highest EPA + DHA levels was shown. Per seed batch a random selection of ~30 seed was measured in two technical repeats.

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.3 | 2.9 | 1.6 | 1.8 | 4.6 | 0.3 | 0.0 | 0.5 | 1.6 | 0.2 | 1.6 | 0.7 | 0.3 |
| de (n = 1) | 0.2 | 3.2 | 1.7 | 2.8 | 7.4 | 0.4 | 0.0 | 1.2 | 2.9 | 0.2 | 2.3 | 0.8 | 0.3 |
| te (n = 1) | 0.0 | 1.6 | 0.6 | 1.8 | 4.8 | 0.4 | 0.0 | 0.8 | 1.3 | 0.3 | 1.5 | 0.4 | 0.1 |

TABLE 123

Phenotypic rating of T0 plants cultivated in the greenhouse of canola events containing the T-DNAs of plasmid VC-LTM595-1qcz rc. Considering each event in this generation was represented by only 1 plant, all events have been grouped into the categories indicated in the first column as described in Table 120. The number of T0 plants/events fullfilling these criteria are displayed in parentheses.

| Category of T0 plants | DFF | DF | DL | DP | DS | FC | LD |
|---|---|---|---|---|---|---|---|
| sc (n = 24) | 44.8 ± 17.3 | 9 ± 0 | 8.7 ± 1.1 | 9 ± 0 | 6.7 ± 2.4 | 3 ± 0 | 4.7 ± 0.8 |
| de (n = 7) | 47.1 ± 10.3 | 9 ± 0 | 8.7 ± 0.8 | 9 ± 0 | 4.7 ± 2.6 | 3 ± 0 | 5 ± 0 |
| tc (n = 3) | 42.3 ± 2.5 | 9 ± 0 | 9 ± 0 | 9 ± 0 | 6 ± 4.4 | 3 ± 0 | 5 ± 0 |

| Category of T0 plants | LGC | LF | NoL | PH | TKW | SC |
|---|---|---|---|---|---|---|
| sc (n = 24) | 5 ± 0 | 6.7 ± 2.4 | 4.7 ± 1 | 123.5 ± 7.7 | 4.4 ± 0.5 | 1.6 ± 0.9 |
| de (n = 7) | 5 ± 0 | 4.7 ± 2.6 | 4.7 ± 1.1 | 122.9 ± 5.7 | 4.3 ± 0.9 | 2.1 ± 1.5 |
| tc (n = 3) | 5 ± 0 | 6 ± 4.4 | 5 ± 1.7 | 125 ± 10 | 4.2 ± 0.2 | 4.3 ± 3.2 |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoI: number of lobes (#),
PH: plant height (cm),
TKW: thousand kernel weight (g),
SC: seed quality (1 = good, 9 = bad)

Fatty Acid Profiles, Copy Number Measurements, and Phenotypic Observations of T1 Plants Carrying T-DNA of Plasmids VC-LTM595-1Qcz Rc Cultivated in Greenhouses During Winter The data Table 124, Table 125 and Table 126 indicate that a variety of copy numbers for the genes contained on the T-DNA were obtained, with copy number values ranging from 1 to 3. The performance of the events selected for measurements of fatty acid profiles (see Table 127 and Table 128) was similar to that observed in the previous example with the EPA and DHA combined value being approximately ten percent of the total fatty acid content of the seed, for the upper end of values. The data in Table 129 indicate, as observed in prior generations for this construct (see example 17 part A), that there was some variation in flowering time among the various events.

TABLE 124

Copy number measurement of T1 plants cultivated in the greenhouse of canola events containing the T-DNAs of plasmids VC-LTM595-1qcz rc. The events are indicated in the first column, along with the number of T1 plants that where measured per event. The T1 plants underwent a selection from 250 segregating T1 seedlings, using zygosity analysis as illustrated in Table 125, keeping only plants that are homozygous for the desired number of loci (which are indicated in the last column of Table 125). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygosity was indicated if the average result of the selected T1 plants was about two fold higher than the the result oberved in the T0 generation (indicated in parentheses). For some events this was not the case because during selection of T1 plants, undesired loci have been segregated out while retaining only desired loci in a homozygous state.

Copy number assays targeting the T-DNA of VC-LTM595-1qcz rc. Assays are listed according to the position of the assay target along the T-DNA, with target c-AHAS located near the left T-DNA border and target c-d6Elo(Pp_GA) near the right T-DNA border.

| Event | c-AHAS | c-d5Des (Tc_GA) | j-i-Atss18_c-o3Des (Pi_GA2) | j-i-Atss2_c-d4Des (Tc_GA3) | j-i-Atss1_c-d5Elo (Ot_GA3) | c-d4Des (Pl_GA)2 | j-i-Atss2_c-d4Des (Pl_GA)-195R | j-p-LuPXR_i-Atss15 |
|---|---|---|---|---|---|---|---|---|
| LBEDTZ | 4.1 (T0: 2.2) | 4 | 4 (T0: 2) | 4 (T0: 1.8) | (T0: 1.8) | 4.3 (T0: 1.8) | 8.1 (T0: 3.8) | 3.8 (T0: 2.5) |
| LBEDUA | 4.3 (T0: 2.7) | 4.2 | 4 (T0: 2.3) | 3 (T0: 2.2) | (T0: 2) | 4.5 (T0: 2.3) | 8 (T0: 4) | 4 (T0: 2.4) |
| LBEDWU | 4.2 (T0 :1.8) | 3.4 | 3.3 (T0: 1.9) | 2.7 (T0: 1.6) | (T0: 1.7) | 3.6 (T0: 1.7) | 6.7 (T0: 3.5) | 3.2 (T0: 1.9) |
| LBEFME | (T0: 2.6) | | (T0: 2.5) | (T0: 2.6) | (T0: 2.4) | | (T0: 3.7) | (T0: 3) |
| LBEEIL | (T0: 2.4) | | (T0: 2.7) | (T0: 2.5) | (T0: 2.5) | | (T0: 3.7) | (T0: 2) |
| LBEEBO | (T0: 2.1) | | (T0: 2.7) | (T0: 1.8) | (T0: 1.6) | (T0: 1.9) | (T0: 3.6) | (T0: 1.9) |
| LBERLW | (T0: 2.1) | | (T0: 1.4) | (T0: 1.7) | (T0: 1.6) | | (T0: 2.6) | (T0: 2) |

Copy number assays targeting the T-DNA of VC-LTM595-1qcz rc. Assays are listed according to the position of the assay target along the T-DNA, with target c-AHAS located near the left T-DNA border and target c-d6Elo(Pp_GA) near the right T-DNA border.

| Event | j-i-Atss14_c-d12Des (Ps_GA) | c-d6Elo (Tp_GA) | j-t-StCAT_p2_p-LuPXR | j-i-Atss2_c-d6Des(Ot febit_GA) | c-d5Des (Tc_GA) | c-d6Elo (Pp_GA) | Conclusion from individual assays: number of T-DNA copies inserted into the genome |
|---|---|---|---|---|---|---|---|
| LBEDTZ | 5.7 | | 5 (T0: 4.7) (T0: 2.8) 2.8 | 5.5 (T0: 3.1) | 8.1 (T0: 3.8) | 4.1 (T0: 2) | partial double copy |
| LBEDUA | 4.3 | | 3.7 (T0:3.6) (T0: 2.2) 2.4 | 4 (T0: 2.1) | 8 (T0: 4) | 3.8 (T0: 2.4) | partial double copy |
| LBEDWU | 3.2 | | 3.3 (T0:3) (T0: 1.7) 1.7 | 3.3 (T0: 1.8) | 6.7 (T0: 3.5) | 3.9 (T0: 2-1) | partial double copy |
| LBEFME | | | (T0: 2.4) (T0: 2.7) | (T0: 2) | (T0: 3.7) | (T0: 1.1) | partial double copy |
| LBEEIL | | | (T0: 1.9) (T0: 2) | (T0: 1.8) | (T0: 3.7) | (T0: 2.1) | partial double copy |
| LBEEBO | | | (T0: 2) (T0: 2.1) | (T0: 1.8) | (T0: 3.6) | (T0: 2.1) | partial double copy |
| LBERLW | | | (T0: 1.2) (T0: 0.9) | (T0: 1.6) | (T0: 2.6) | (T0: 1.6) | partial double copy |

TABLE 125

Observed Medelian segregation of the genotype of T1 seeds of events from construct VC-LTM595-1qcz rc. The segregation has been analysed at three positions of the T-DNA. For each position, the number of seedlings have been counted that have a copy number (arithmetically rounded) of 0, 1, 2, 3, 4, 5, 6, 7, 8, 9, 10, 11 and 12. The of seedlings counted for each copy number category are separated by colon, displaying the categories in the following order: 0:1:2:3:4:5:6:7:8:9:10:11:12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate single copy insertion at e.g. the left border (e.g. event LBEDTZ), while other position on the T-DNA clearly indicate a double copy insertion that are either inserted in one locus (e.g. event LBEDTZ), or in two loci (e.g. event LBEDWU)

| Event | Copy number ratios measured near the left border of the T-DNA using an assay targeting c-AHAS | Copy number ratios measured using T-DNA internal assays targeting reagions that had copy number results indicating truncated T-DNA insertions using assay A04(target:j-i-Atss18_c-o3Des(Pi_GA2)), or A10 (target:c-d6Elo(Tp_GA)), or A11 (target j-t-StCAT_p2_p-LuPXR) | Copy number ratios measured near the right border of the T-DNA using an assay targeting c-d6Elo(Pp_GA) | Most likely number of loci containing one or more T-DNA copies, tested using Chi-Square test |
|---|---|---|---|---|
| LBEDTZ | 084:001:111:002:050:000:000:000:000:000:000:000:000 | A10: 085:000:001:111:002:048:002:000:000:000:000:000:000 | 084:000:111:000:052:001:000:000:000:000:000:000:000 | single locus |
| LBEDUA | | | | double locus |
| LBEDWU | 023:071:098:043:014:000:000:000:000:000:000:000:000 | A10: 023:075:098:048:004:000:000:000:000:000:000:000:000 | 023:071:099:045:011:000:000:000:000:000:000:000:000 | double locus |
| LBEFME | 011:025:039:062:040:041:023:005:001:000:000:001:000 | A11: 010:024:043:063:073:027:004:001:001:000:000:000:000 | 059:137:052:000:000:000:000:000:000:000:000:000:000 | triple locus |
| LBEEIL | 075:020:044:051:039:018:001:000:000:000:000:000:000 | A04: 073:020:046:050:046:010:001:000:000:000:000:000:000 | 075:020:043:052:039:017:002:000:000:000:000:000:000 | triple locus |
| LBEEBO | 019:072:090:055:012:000:000:000:000:000:000:000:000 | A10: 019:073:090:052:015:000:000:000:000:000:000:000:000 | 065:118:059:007:000:000:000:000:000:000:000:000:000 | double locus |
| LBERLW | 012:039:057:058:050:023:010:000:000:000:000:000:000 | A10: 010:046:065:034:009:000:000:000:000:000:000:000:000 | 011:072:096:054:014:000:000:000:000:000:000:000:000 | double locus |

TABLE 126

Copy number measurement of T1 plants cultivated in the greenhouse of canola events containing the T-DNAs of plasmid VC-LTM595-1qcz rc. The events are indicated in the first column, along with the number of T1 plants that were measured per event.

Copy number assays targeting the T-DNA of VC-LTM595-1qcz rc.

Assays are listed according to the position of the assay target along the T-DNA, with target c-AHAS located near the left T-DNA border and target c-d6Elo(Pp_GA)near the right T-DNA border. Copy number results obtained on the T0 plants are indicated in parentheses. Homozygosity of all plants per event was indicated if the average result of the selected T1 plants was about two fold higher than the T0 generation.

| Event | c-AHAS | c-d5Des (Tc_GA) | j-i-Atss18_c-o3Des (Pi_GA2) | j-i-Atss2_c-d4Des (Tc_GA3) | j-i-Atss1_c-d5Elo (Ot_GA3) | c-d4Des (Pl_GA)2 | j-i-Atss2_c-d4Des (Pl_GA)-195R |
|---|---|---|---|---|---|---|---|
| LBDGCA (n = 94) | 1.5 (T0: 1) | 3.2 (T0: 2) | 1.6 (T0: 1.4) | (T0: 1) | (T0: 1.2) | 1.7 (T0: 0.9) | 1.6 |
| LBDGBP (n = 20) | (T0: 1.1) | (T0: 2.1) | (T0: 1.4) | (T0: 1.2) | (T0: 1.3) | (T0: 1.1) | |
| LBDIHN (n = 114) | 1.6 (T0: 1.2) | 3.3 (T0: 2.2) | 1.6 (T0: 1.7) | (T0: 1.1) | (T0: 1.2) | 1.7 (T0 :1) | 1.6 |

TABLE 126-continued

Copy number measurement of T1 plants cultivated in the greenhouse of canola events containing the T-DNAs of plasmid VC-LTM595-1qcz rc. The events are indicated in the first column, along with the number of T1 plants that were measured per event.

Copy number assays targeting the T-DNA of VC-LTM595-1qcz rc.
Assays are listed according to the position of the assay target along the T-DNA,
with target c-AHAS located near the left T-DNA border and
target c-d6Elo(Pp_GA) near the right T-DNA border. Copy number results
obtained on the T0 plants are indicated in parentheses. Homozygosity of all plants per event
was indicated if the average result of the selected T1 plants was about two fold higher than the T0 generation.

| Event | j-p-LuPXR_i-Atss15 | j-i-Atss14_c-d12Des (Ps_GA) | c-d6Elo (Tp_GA) | j-t-StCAT_p2_p-LuPXR | j-i-Atss2_c-d6Des(Otfebit_GA) | c-d5Des (Tc_GA) | c-d6Elo (Pp_GA) |
|---|---|---|---|---|---|---|---|
| LBDGCA (n = 94) | 1.6 (T0: 1) | (T0: 1.2) | 1.7 (T0: 1) | (T0: 1.1) | (T0: 1.1) | 3.2 (T0: 2) | 1.6 (T0: 1) |
| LBDGBP (n = 20) | (T0: 1.1) | (T0: 1.3) | (T0: 1) | (T0: 1) | (T0: 1.2) | (T0: 2.1) | (T0: 1) |
| LBDIHN (n = 114) | 1.6 (T0: 1.1) | | 1.7 (T0: 1) | (T0: 0.9) | (T0: 1.2) | 3.3 (T0: 2.2) | 1.6 (T0: 1.1) |

TABLE 127

Fatty acid profiles of T2 seeds harvested from T1 plants cultivated in the greenhouse of canola events containing the T-DNAs of plasmid VC-LTM595-1qcz rc. The events are indicated in the first column, along with the number of T1 plants that were measured per event.

| event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBEDTZ (n = 34) | 4.9 ± 0.2 | 0.2 ± 0 | 0 ± 0 | 2.4 ± 0.2 | 28 ± 1.7 | 31.1 ± 2.2 | 1.3 ± 0.2 | 4.9 ± 0.5 | 4.9 ± 2 | 0.8 ± 0.3 | 0.8 ± 0.1 | 0.7 ± 0.1 | 0.1 ± 0.1 |
| LBEDUA (n = 4) | 7.7 ± 0.2 | 0.4 ± 0.1 | 0 ± 0 | 3.6 ± 0.5 | 24.3 ± 0.7 | 32.6 ± 1 | 0.9 ± 0.1 | 4.1 ± 0.4 | 2.4 ± 0.2 | 0.3 ± 0 | 1.1 ± 0.1 | 0.7 ± 0 | 0.1 ± 0 |
| LBEDWU (n = 6) | 6.4 ± 0.4 | 0.3 ± 0.1 | 0 ± 0 | 5.1 ± 0.9 | 26.4 ± 3.4 | 31.5 ± 1.2 | 0.8 ± 0.2 | 4.4 ± 0.2 | 2.1 ± 0.5 | 0.3 ± 0.1 | 1.4 ± 0.2 | 0.7 ± 0.1 | 0.1 ± 0 |

| event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBEDTZ (n = 34) | 0.1 ± 0 | 3.9 ± 0.8 | 1.5 ± 0.5 | 2.4 ± 0.4 | 4.7 ± 1.6 | 0.4 ± 0 | 0 ± 0 | 0.9 ± 0.1 | 1.8 ± 0.6 | 0.8 ± 0.1 | 1.7 ± 0.6 | 1.2 ± 0.3 | 0.2 ± 0.1 |
| LBEDUA (n = 4) | 0.1 ± 0 | 3.9 ± 0.6 | 1.4 ± 0.1 | 2.2 ± 0.2 | 6.5 ± 0.3 | 0.5 ± 0 | 0 ± 0 | 1.1 ± 0 | 1.8 ± 0.2 | 0.7 ± 0.1 | 2.5 ± 0.1 | 0.8 ± 0.1 | 0.1 ± 0 |
| LBEDWU (n = 6) | 0.2 ± 0.1 | 3.3 ± 0.3 | 1.4 ± 0.2 | 1.7 ± 0.2 | 6.1 ± 1.4 | 0.6 ± 0.1 | 0 ± 0 | 1 ± 0.2 | 1.8 ± 0.4 | 0.6 ± 0.2 | 2.6 ± 0.5 | 0.9 ± 0.2 | 0.1 ± 0 |

TABLE 128

Fatty acid profiles of T2 seeds harvested from T1 plants cultivated in the greenhouse of canola events containing the T-DNAs of plasmid VC-LTM595-1qcz rc. The events are indicated in the first column, along with the number of T1 plants that where measured per event. For each event, the fatty acid profile of the plant having the highest EPA + DHA levels was shown. Per seed batch a random selection of ~30 seed was measured in two technical repeats.

| Events | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBEDTZ (n = 1) | 4.9 | 0.2 | 0.0 | 2.5 | 26.4 | 27.0 | 1.3 | 5.6 | 2.2 | 0.3 | 0.8 | 0.7 | 0.1 |
| LBEDUA (n = 1) | 8.0 | 0.4 | 0.0 | 3.9 | 23.6 | 32.3 | 0.9 | 4.2 | 2.1 | 0.2 | 1.2 | 0.7 | 0.1 |
| LBEDWU (n = 1) | 6.1 | 0.3 | 0.0 | 4.9 | 22.2 | 32.8 | 0.8 | 4.8 | 1.9 | 0.3 | 1.2 | 0.6 | 0.1 |

TABLE 128-continued

Fatty acid profiles of T2 seeds harvested from T1 plants cultivated in the greenhouse of canola events containing the T-DNAs of plasmid VC-LTM595-1qcz rc. The events are indicated in the first column, along with the number of T1 plants that where measured per event. For each event, the fatty acid profile of the plant having the highest EPA + DHA levels was shown. Per seed batch a random selection of ~30 seed was measured in two technical repeats.

| Events | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBEDTZ (n = 1) | 0.1 | 4.3 | 2.4 | 2.0 | 8.5 | 0.3 | 0.0 | 0.9 | 3.2 | 0.9 | 3.3 | 1.7 | 0.3 |
| LBEDUA (n = 1) | 0.1 | 3.9 | 1.5 | 2.2 | 6.7 | 0.5 | 0.0 | 1.1 | 2.0 | 0.7 | 2.7 | 0.9 | 0.1 |
| LBEDWU (n = 1) | 0.1 | 3.0 | 1.4 | 1.7 | 7.7 | 0.5 | 0.0 | 1.3 | 2.5 | 0.9 | 3.4 | 1.2 | 0.1 |

TABLE 129

Phenotypic rating of T1 plants cultivated in the greenhouse of canola events containing the T-DNAs of plasmid VC-LTM595-1qcz rc. The events are indicated in the first column, along with the number of T1 plants that where measured per event.

| Events | DFF | DF | DL | DP | DS | FC | LD | LGC |
|---|---|---|---|---|---|---|---|---|
| LBEDTZ (n = 34) | 46.7 ± 3.7 | 8.9 ± 0.5 | 7.8 ± 0.6 | 7.9 ± 0.4 | 8.8 ± 0.7 | 3 ± 0 | 4 ± 0 | 5 ± 0 |
| LBEDUA (n = 4) | 60.8 ± 2.6 | 5.3 ± 1.5 | 8 ± 0 | 3.8 ± 0.5 | 5.5 ± 0.6 | 3 ± 0 | 5 ± 0 | 5 ± 0 |
| LBEDWU (n = 6) | 47.2 ± 2.7 | 6 ± 0 | 8 ± 0 | 3.5 ± 0.8 | 5.8 ± 0.4 | 3 ± 0 | 4 ±0 | 4.8 ± 0.4 |

| Events | LF | NoL | PH | TKW | SC | Oil | Protein |
|---|---|---|---|---|---|---|---|
| LBEDTZ (n = 34) | 9 ± 0 | 5.2 ± 0.6 | 102.6 ±7.1 | 3.4 ± 1.2 | 3.7 ± 1.1 | 36.3 | 30.5 |
| LBEDUA (n = 4) | 6.3 ± 0.5 | 4.5 ± 0.6 | 83.8 ± 2.5 | 3.7 ± 0 | 8 ± 0.8 | 32.4 | 30.9 |
| LBEDWU (n = 6) | 6.7 ± 1.8 | 4.3 ± 0.5 | 71.7 ± 12.1 | 2.5 ± 0.3 | 6.7 + 2.1 | 33.8 | 30.0 |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
Nol: number of lobes (#),
PH: plant height (cm),
TKW: thousand kernel weight (g),
SC: seed quality (1 = good, 9 = bad),
Oil: oil content (% of seed weight),
Protein: Protein content (% of seed cake without oil)

Example 18: Plants Containing the T-DNA of Plasmid VC-LTM593-Pcz Rc for Production of EPA and DHA in Seeds All genetic elements required for EPA and DHA synthesis described in this example, were transferred on a single T-DNA using a BiBAC plasmid into the plant genome. To this end, the plasmid VC-LTM593-11qcz rc where cloned into agrobacteria, and plant tissue was incubated according to example 6 with this agrobacterial culture. Due to the selectable herbicide resistance marker, regenerated plants contained the T-DNA of VC-LTM593-11qcz rc. The genetic elements of VC-LTM593-1 qcz rc and the function of each element are listed in Table 11. For convenience, all enzymes expressed in seeds of plants carrying both T-DNA of VC-LTM593-11qcz rc that are required for EPA and DHA synthesis are additionally listed Table 130.

TABLE 130

List of genes essential of EPA and DHA synthesis carried by the T-DNA of plasmid VC-LTM593-1qcz rc. Preferred polynucleotide and protein seqences are shown in column 4 and 5.

| Genes encoding enzmyes for EPA and DHA synthesis | Length (bp) | Enzymatic function and source of encoded protein | Poly-nucleotide SEQ ID NO: | Protein sequence SEQ ID NO |
|---|---|---|---|---|
| c-d12Des(Ps_GA2) | 1197 | Delta-12 desaturase from *Phythophthora sojae* | 265 | 266 |
| c-d6Des(Ot_febit) | 1371 | Delta-6 desaturase from *Ostreococcus tauri* | 261 | 262 |
| c-d6Elo(Pp_GA2) | 873 | Delta-6 elongase from *Physcomitrella patens* | 257 | 258 |
| c-d6Elo(Tp_GA2) | 819 | Delta-6 elongase from *Thalassiosira pseudonana* | 263 | 264 |
| 2 copies of c-d5Des(Tc_GA2) | 1320 | Delta-5 desaturase from *Thraustochytrium* sp. ATCC21685 | 259 | 260 |
| c-o3Des(Pi_GA2) | 1086 | Omega-3-desaturase from *Phythophthora infestans* | 269 | 270 |
| 2 copies of c-o3Des(Pir_GA) | 1092 | Omega-3 desaturase from *Pythium irregulare* | 267 | 268 |
| c-d5Elo(Ot_GA3) | 903 | Delta-5 elongase from *Ostreococcus tauri* | 275 | 276 |
| c-d4Des(Pl_GA)2 | 1338 | Delta-4 desaturase from *Pavlova lutheri* | 273 | 274 |
| c-d4Des(Tc_GA3) | 1560 | Delta-4 desaturase from *Thraustochytrium* sp. | 271 | 272 |

Fatty Acid Profiles, Copy Number Measurements, and Phenotypic Observations of T0 Plants Carrying T-DNAs of Plasmid VC-LTM593-1Qcz Rc Cultivated in Greenhouses During Summer One observation from the data on Table 131 was that there was a higher number of insertion events obtained from VC-LTP593-1qcz than obtained from the BiBAC constructs in examples 16 or 17. The data on Table 132 and Table 133 indicate that with respect to VLC-PUFA accumulation, in particular EPA and DHA, double copy events accumulated more than single copy events and that triple copy events accumulated more than double copy events, with accumulation for the triple copy events being approximately eight percent of total fatty acids (EPA and DHA combined, with 1.6% accumulation of total fatty acids being DHA). The highest amount accumulated was approximately fifteen percent of the total fatty acid content in the seed being EPA and DHA combined, with 3 percent of the total seed fatty acid content being DHA, see Table 133. The aerial phenotype of this construct in the T0 plant and T1 seed showed less variation than that seen in examples 16 or 17.

TABLE 131

Copy number measurement of T0 plants cultivated in the greenhouse of canola events containing the T-DNAs of plasmids VC-LTM593-1qcz rc. Considering each event was in this generation represented by only 1 plant, all events have been grouped into the categories indicated in the first column;

Copy number assays targeting the T-E )NA of VC-LTM593-1qcz rc. Assays are listed according to the position of the assay tar get along the T-DNA, with target c-AHAS located near the left T-DNA border and target c-c 6Elo(Pp_GA) near the right T-DNA border.

| Event | c-AHAS | j-i-Atss1_c-d5Elo (Ot_GA3) | c-d4Des (Pl_GA)2 | j-p-LuPXR_i-Atss15 | j-p-PvARC5_t-BnSETL | c-d5Des (Tc_GA) | j-i-Atss18_c-o3Des (Pi_GA2) |
|---|---|---|---|---|---|---|---|
| sc (n = 275) | 1.1 | 1.2 | 1.1 | 1.1 | 1.0 | 2.1 | 1.1 |
| dc (n = 49) | 1.7 | 1.6 | 1.8 | 1.7 | 1.6 | 3.5 | 1.9 |
| tc (n = 11) | 2.6 | | 3.0 | 3.2 | 2.5 | 5.3 | 3.0 |

TABLE 131-continued

Copy number measurement of T0 plants cultivated in the greenhouse of canola events containing the T-DNAs of plasmids VC-LTM593-1qcz rc. Considering each event was in this generation represented by only 1 plant, all events have been grouped into the categories indicated in the first column;

Copy number assays targeting the T-E )NA of VC-LTM593-1qcz rc. Assays are listed according to the position of the assay tar get along the T-DNA, with target c-AHAS located near the left T-DNA border and target c-c 6Elo(Pp_GA) near the right T-DNA border.

| Event | j-p-BnSETL-v1_c-o3Des(Pir_GA) | j-i-Atss14_c-d12Des (Ps_GA) | c-d6Elo (Tp_GA) | j-t-StCAT_p2_p-LuPXR | j-i-Atss2_c-d6Des(Ot febit_GA) | c-d5Des (Tc_GA) | c-d6Elo (Pp_GA) |
|---|---|---|---|---|---|---|---|
| sc (n = 275) | | | 1.1 | 1.1 | 1.0 | 2.1 | 1.1 |
| dc (n = 49) | | | 1.9 | 2.3 | 1.8 | 3.5 | 1.7 |
| tc (n = 11) | | | 2.9 | 3.8 | 2.6 | 5.3 | 2.8 | sc: all T0 plants where the average of all copy number assays listed in this table except the assay c-d5Des(Tc_GA) was 0.51-1.49,
de: all T0 plants where the average of all copy number assays listed in this table was 1.51-2.49,
tc: all T0 plants where the average of all copy number assays listed in this table was 2.51-3.49.

TABLE 132

Fatty acid profiles of T1 seeds harvested from T0 plants cultivated in the greenhouse of canola events containing the T-DNAs of plasmid VC-LTM593-1qcz rc. Considering each event was in this generation represented by only 1 plant, all events have been grouped into the categories indicated in the first column as described in Table 131. The number of T0 plants/events fullfilling these criteria are displayed in parentheses. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 275) | 5.1 ± 0.5 | 0.3 ± 0.1 | 0.1 ± 0.1 | 3.2 ± 0.5 | 41.3 ± 5.3 | 29.6 ± 2.9 | 0.4 ± 0.2 | 6 ± 0.9 | 0.8 ± 0.4 | 0.1 ± 0.1 | 0.8 ± 0.1 | 0.9 ± 0.1 | 0.4 ± 0.2 |
| dc (n = 49) | 5.3 ± 0.6 | 0.3 ± 0.1 | 0 ± 0 | 3.5 ± 0.5 | 34.4 ± 5.9 | 31 ± 2.6 | 0.5 ± 0.2 | 5.5 ± 1.1 | 1.5 ± 0.5 | 0.2 ± 0.1 | 0.8 ± 0.1 | 0.7 ± 0.1 | 0.3 ± 0.3 |
| tc (n = 11) | 5.6 ± 0.6 | 0.3 ± 0.1 | 0 ± 0.1 | 3.7 ± 0.6 | 28 ± 5.6 | 31.6 ± 2.1 | 0.9 ± 0.4 | 5.1 ± 0.5 | 2.2 ± 0.8 | 0.3 ± 0.1 | 0.8 ± 0.1 | 0.7 ± 0.1 | 0.3 ± 0.2 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 275) | 0.1 ± 0.1 | 2 ± 0.5 | 1.2 ± 0.3 | 1.4 ± 0.5 | 3.8 ± 1.2 | 0.3 ± 0.1 | 0 ± 0 | 0 ± 0.1 | 0.9 ± 0.3 | 0 ± 0 | 0.9 ± 0.3 | 0.1 ± 0.1 | 0.2 ± 0.1 |
| dc (n = 49) | 0.1 ± 0.1 | 2.7 ± 0.8 | 1.5 ± 0.5 | 2.2 ± 1.4 | 5.9 ± 2.4 | 0.3 ± 0 | 0 ± 0 | 0.1 ± 0.1 | 1.3 ± 0.4 | 0 ± 0 | 1.2 ± 0.5 | 0.2 ± 0.2 | 0.2 ± 0.1 |
| tc (n = 11) | 0.1 ± 0.1 | 4.7 ± 1.7 | 2.8 ± 1.3 | 1.7 ± 1.2 | 6.6 ± 3.7 | 0.3 ± 0.1 | 0 ± 0 | 0.2 ± 0.2 | 1.5 ± 0.7 | 0 ± 0 | 1.6 ± 0.9 | 0.6 ± 0.9 | 0.3 ± 0.1 |

TABLE 133

Fatty acid profiles of T1 seeds harvested from T0 plants cultivated in the greenhouse of canola events containing the T-DNAs of plasmids VC-LTM593-1qcz rc. Considering each event was in this generation represented by only 1 plant, all events have been grouped into the categories indicated in the first column as described in Table 131. For each category, the fatty acid profile of the plant/event having the highest EPA + DHA levels was shown. Per seed batch a random selection of ~30 seed was measured in two technical repeats.

| Category of T0 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|

TABLE 133-continued

Fatty acid profiles of T1 seeds harvested from T0 plants cultivated in the greenhouse of canola events containing the T-DNAs of plasmids VC-LTM593-1qcz rc. Considering each event was in this generation represented by only 1 plant, all events have been grouped into the categories indicated in the first column as described in Table 131. For each category, the fatty acid profile of the plant/event having the highest EPA + DHA levels was shown. Per seed batch a random selection of ~30 seed was measured in two technical repeats.

| | | | | | | | | | | | | | |
|---|---|---|---|---|---|---|---|---|---|---|---|---|---|
| sc (n = 1) | 4.7 | 0.2 | 0.2 | 3.2 | 25.1 | 36.0 | 0.6 | 5.0 | 2.2 | 0.3 | 0.7 | 0.6 | 0.4 |
| dc (n = 1) | 5.4 | 0.2 | 0.0 | 3.1 | 23.8 | 29.4 | 0.5 | 4.9 | 1.8 | 0.2 | 0.7 | 0.7 | 0.8 |
| tc (n = 1) | 5.7 | 0.2 | 0.1 | 3.7 | 21.5 | 32.7 | 0.6 | 4.8 | 1.9 | 0.3 | 0.9 | 0.6 | 0.9 |

| Category of T0 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.1 | 2.6 | 1.3 | 4.1 | 8.6 | 0.2 | 0.0 | 0.2 | 1.8 | 0.0 | 1.6 | 0.0 | 0.2 |
| dc (n = 1) | 0.1 | 3.5 | 2.2 | 4.1 | 12.3 | 0.3 | 0.0 | 0.2 | 2.7 | 0.0 | 2.4 | 0.1 | 0.5 |
| tc (n = 1) | 0.4 | 1.8 | 1.3 | 3.0 | 12.4 | 0.4 | 0.0 | 0.5 | 2.6 | 0.1 | 3.2 | 0.0 | 0.4 |

TABLE 134

Phenotypic rating of T0 plants cultivated in the greenhouse of canola events containing the T-DNAs of plasmid VC-LTM593-1qcz rc. Considering each event was in this generation represented by only 1 plant, all events have been grouped into the categories indicated in the first column as described in Table 131. The number of T0 plants/events fullfilling these criteria are displayed in parentheses.

| Category of T0 plants | DFF | DF | DL | DP | DS | FC | LD | LGC |
|---|---|---|---|---|---|---|---|---|
| sc (n = 275) | 56.5 ± 6.1 | 9 ± 0 | 8.6 ± 1.1 | 9 ± 0 | 5 ± 4.1 | 3 ± 0 | 4.9 ± 0.5 | 5 ± 0 |
| dc (n = 49) | 57.4 ± 6 | 8.9 ± 1 | 8.4 ± 1.4 | 8.9 ± 0.5 | 4.3 ± 2.7 | 3 ± 0 | 4.8 ± 0.8 | 5 ± 0 |
| tc (n = 11) | 60.3 ± 5.5 | 9 ± 0 | 8.5 ± 1 | 9 ± 0 | 3.5 ± 2.2 | 3 ± 0 | 5 ± 0 | 5 ± 0 |

| Category of T0 plants | LF | NoL | PH | TKW | SC | Oil | Protein |
|---|---|---|---|---|---|---|---|
| sc (n = 275) | 4.8 ± 2.9 | 5 ± 1.1 | 123.9 ± 8.9 | 4.6 ± 0.6 | 1.8 ± 1.7 | 36.5 ± 1.1 | 29.1 ± 0.8 |
| dc (n = 49) | 4.3 ± 2.7 | 5 ± 1.2 | 119.1 ± 15.7 | 4.5 ± 0.6 | 1.6 ± 1.2 | 36.2 ± 1.5 | 28.7 ± 1.2 |
| tc (n = 11) | 3.5 ± 2.2 | 4.8 ± 1.5 | 125.9 ± 7 | 4.4 ± 0.6 | 3.5 ± 2.9 | | |

DFF: days to first flower (days),
DF: deformed flower (1 = deformed, 9 = normal),
DL: deformed leaf (1 = deformed, 9 = normal),
DP: deformed plant (1 = deformed, 9 = normal),
DS: deformed silique (1 = deformed, 9 = normal),
FC: flower color (1 = white, 3 = optimal, 4 = orange/yellow),
LD: leaf dentation (3 = no dentation, 7 = strong dentation),
LGC: leaf color (3 = yellow, 5 = optimal, 7 = blueish),
LF: fertility (1 = low, 9 = very high),
NoL: number of lobes (#),
PH: plant height (cm),
TKW: thousand kernel weight (g),
SC: seed quality (1 = good, 9 = bad),
Oil: oil content (% of seed weight),
Protein: Protein content (% of seed cake without oil)

Fatty Acid Profiles, Copy Number Measurements, and Phenotypic Observations of T1 Plants Carrying T-DNAs of Plasmids VC-LTM593-1Qcz Rc Cultivated in Greenhouses During Winter Specific events were examined further for copy number and displayed a variation in insertion number for the T-DNA from single insertion to partial double insertions along with double insertions. Additionally there were some variations in gene copy number (corresponding to the partial insertions and possible deletions), see Table 135, Table 136 and Table 137. The fatty acid profile data shown on Table 138 and Table 139 indicate an upper range of accumulation of combined EPA and DHA of eighteen percent of the total seed fatty acid content (event LBFDAU). In the event LBFDAU the percent of total seed fatty acid content being EPA is 15% and total seed fatty acid content being DHA is 3% in the T1. LBFDAU was analysed with a copy number indicative of a partial double copy. Another example of specific events having higher levels of EPA and DHA was LBFGKN with approximately 12 percent of the total seed fatty acid content being EPA and DHA, with 10 percent of the total seed fatty acid content being EPA and 2% being DHA. The T1 generation LBFGKN had only a single copy insertion event for VC-LTM593-1qcz rc, though data on Table 140, Table 141 and Table 142 indicate that double copy double locus events tended to accumulate more EPA and DHA combined than other copy and locus numbers with respect to the T2 seed fatty acid profile. This observation likely reflects the nature of insertion site effects and the various factors that affect the generation of elite events. Table 142 indicates that with respect to the aerial phenotype of the plants there was a range of flowering times, as indicated by DFF (days to the first flower) from 36-48. Event LBFDAU did not vary significantly from the majority of other events with a DFF value of 43, thus showing no significant effect on the aerial phenotype or significant impact on total oil or protein accumulation in the seed in the T1 plant and T2 seed.

TABLE 135

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo (Ot_GA3) | c-d4Des (Pl_GA)2 | j-p-LuPXR_i-Atss15 | j-p-PvARC5_t-BnSETL | c-d5Des (Tc_GA) | j-i-Atss18_c-o3Des (Pi_GA2) | j-p-BnSETL-v1_c-o3Des (Pir_GA) |
|---|---|---|---|---|---|---|---|---|
| LBFDGG (n = 50) | 2.1 (T0: 1.1) | 2 | 2 (T0: 1.3) | 1.8 (T0: 1.1) | (T0: 1) | 4.2 (T0: 2.2) | 2 (T0: 1.1) | 1.9 |
| LBFGKN (n = 50) | 2.1 (T0: 1) | 2.2 | 2.1 (T0: 1.3) | 2.2 (T0: 1.1) | (T0: 0.8) | 4.2 (T0: 2) | 2.2 (T0: 1.2) | 2.1 |
| LBFIHE (n = 34) | 2 (T0: 1) | 2.2 | 2.1 (T0: 1.1) | 2.1 (T0: 1.2) | (T0: 1) | 4.1 (T0: 1.9) | 2.2 (T0: 1.1) | 2.3 |
| LBFLDI (n = 60) | 2.5 (T0: 1) | 2.3 | 2.4 (T0: 1.1) | 2.4 (T0: 1) | (T0: 1) | 4.4 (T0: 1.9) | 2.2 (T0: 1.2) | 2.3 |
| LBFPNF (n = 52) | 1.9 (T0: 1.1) | 2.1 | 2.1 (T0: 1.1) | 2.1 (T0: 1.3) | (T0: 1) | 5.6 (T0: 2.8) | 1.9 (T0: 1) | 2.1 |
| LBFNSQ (n = 51) | 2 (T0: 1.1) | 2 | 1.9 (T0: 1.2) | 1.9 (T0: 1.1) | (T0: 1.6) | 7.1 (T0: 3.1) | 3.8 (T0: 1.9) | 4 |
| LBFDGL (n = 57) | 2.1 (T0: 1) | 2.2 | 3.9 (T0: 2) | 3.9 (T0: 1.7) | (T0: 1.9) | 6.7 (T0: 2.9) | 3.8 (T0: 2) | 3.8 |
| LBFIEF (n = 6) | 4.2 (T0: 2.5) | 3.7 | 3.6 (T0: 2.7) | 3.7 (T0: 2.7) | (T0: 2) | 6.4 (T0: 3.5) | 3.8 (T0: 2.3) | 4.2 |
| LBFBAV (n = 50) | 2 (T0: 1.1) | 2.2 (T0: 1.3) | 3.7 (T0: 1.5) | 4 (T0: 1.7) | (T0: 1.4) | 8.2 (T0: 3.7) | 3.8 (T0: 1.8) | 3.9 |
| LBFPNC (n = 32) | 2.1 (T0: 1.1) | 2 | 2.3 (T0: 1.2) | 2 (T0: 1) | (T0: 1.4) | 7.5 (T0: 3.4) | 4.2 (T0: 1.7) | 4 |
| LBFGHQ (n = 46) | 3.6 (T0: 1.8) | 3.8 | 4.1 (T0: 1.8) | 4 (T0: 2.2) | (T0: 1.7) | 6.1 (T0: 3.1) | 3.8 (T0: 1.7) | 3.8 |
| LBFAZB (n = 49) | 3.9 (T0: 1.8) | 4 (T0: 1.7) | 3.9 (T0: 1.8) | 3.9 (T0: 1.7) | (T0: 1.3) | 6.6 (T0: 3.1) | 3.7 (T0: 1.8) | 4.1 |
| LBFGKW (n = 72) | 3.8 (T0: 1.8) | 3.8 | 4.2 (T0: 2.1) | 4.1 (T0: 1.9) | (T0: 1.6) | 7 (T0: 3.2) | 3.9 (T0: 2) | 4 |
| LBFNRU (n = 58) | 3.8 (T0: 1.9) | 4 | 3.8 (T0: 1.9) | 3.7 (T0: 2) | (T0: 1.7) | 7 (T0: 3.2) | 4 (T0: 1.7) | 3.7 |
| LBFGIZ (n = 43) | 3.8 (T0: 1.9) | 4.1 | 3.9 (T0: 1.9) | 3.8 (T0: 2-1) | (T0: 1.6) | 7 (T0: 2.8) | 4.2 (T0: 1.8) | 3.8 |
| LBFIGM (n = 56) | 4.1 (T0: 2) | 3.9 | 3.8 (T0: 2) | 3.8 (T0: 1.7) | 4 (T0: 1.5) | 7.6 (T0: 2.8) | 3.9 (T0: 1.7) | 3.9 |
| LBFNRR (n = 61) | 3.7 (T0: 1.9) | 4.2 | 4 (T0: 2.2) | 3.8 (T0: 2) | (T0: 1.7) | 7.1 (T0: 2.8) | 4.3 (T0: 2) | 3.8 |
| LBFNTK (n = 69) | 4.1 (T0: 1.9) | 4.1 | 3.9 (T0: 2-1) | 3.9 (T0: 2) | 4 (T0: 1.7) | 7.6 (T0: 2.9) | 4 (T0: 1.8) | 3.9 |
| LBFGJA (n = 42) | 3.7 (T0: 1.6) | 3.7 | 3.9 (T0: 2-1) | 3.6 (T0: 2-1) | (T0: 1.7) | 7.6 (T0: 3.6) | 3.4 (T0: 1.7) | 3.8 |
| LBFIFV (n = 58) | 3.9 (T0: 1.7) | 4 | 3.9 (T0: 2.4) | 1.9 (T0: 1) | (T0: 1.8) | 7.7 (T0: 3.9) | 3.9 (T0: 1.8) | 3.9 |
| LBFLER (n = 52) | 3.8 (T0: 1.9) | 3.9 | 3.9 (T0: 2.3) | 3.8 (T0: 1.9) | (T0: 1.7) | 7.7 (T0: 3.3) | 3.9 (T0: 2.2) | 4 |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| Event | | | | | | | | |
|---|---|---|---|---|---|---|---|---|
| LBFLDL (n = 44) | 3.8 (T0: 1.7) | 3.9 | 3.8 (T0: 2) | 3.8 (T0: 1.8) | (T0: 1.8) | 7.8 (T0: 3.5) | 3.9 (T0: 2-1) | 3.8 |
| LBFNQW (n = 51) | 3.8 (T0: 1.8) | 3.9 | 3.9 (T0: 1.9) | 3.9 (T0: 1.9) | (T0: 1.6) | 7.9 (T0: 3.4) | 3.9 (T0: 1.8) | 3.9 |
| LBFBAP (n = 19) | 2 (T0: 1.1) | 2 (T0: 1.2) | 2 (T0: 1) | 1.8 (T0: 1.3) | (T0: 1.1) | 7.5 (T0: 2.8) | 3.8 (T0: 1.8) | 3.9 |
| LBFDAU (n = 10) | 2 (T0: 1.1) | 2 | 3.8 (T0: 1.9) | 3.8 (T0: 1.8) | (T0: 1.5) | 7.3 (T0: 3.7) | 3.8 (T0: 2) | 3.9 |
| LBFPRA (n = 16) | 2.1 (T0: 2) | 2 | 6 (T0: 3) | 1.8 (T0: 1.8) | (T0: 2) | 7.4 (T0: 4.7) | 3.8 (T0: 2.8) | 4.1 |
| LBFIFU (n = 11) | 2.2 (T0: 2) | 2.5 | 2.4 (T0: 2.2) | 2.4 (T0: 2.1) | (T0: 1.7) | 6.5 (T0: 4.2) | 2.6 (T0: 1.9) | 3.2 |
| LBFDKD (n = 2) | 3.6 (T0: 1.6) | 3.7 | 3.6 (T0: 2.1) | 3.9 (T0: 2.2) | (T0: 1.8) | 7.6 (T0: 3.4) | 2.9 (T0: 2-1) | 3.5 |
| LBFDJG (n = 12) | 3.6 (T0: 1.6) | 3.7 | 4 (T0: 1.8) | 3.7 (T0: 1.6) | (T0: 1.9) | 8 (T0: 3.6) | 3.6 (T0: 2) | 4 |
| LBFLFK (n = 15) | 3.7 (T0: 2) | 3.9 | 3.7 (T0: 2.4) | 3.6 (T0: 2.3) | (T0: 2) | 7.5 (T0: 5.2) | 4.1 (T0: 2.2) | 3.7 |
| LBFLCG (n = 15) | 3.8 (T0: 1.9) | 3.9 | 3.7 (T0: 2.3) | 3.7 (T0: 1.9) | (T0: 1.7) | 9 (T0: 5.1) | 3.8 (T0: 1.9) | 3.9 |
| LBFPQM (n = 12) | 4 (T0: 2) | 3.8 | 4.1 (T0: 1.8) | 4.1 (T0: 2) | (T0: 1.5) | 7.6 (T0: 3.7) | 3.9 (T0: 2) | 4 |
| LBFDHG (n = 5) | 4.2 (T0: 1.9) | 4 | 3.8 (T0: 2.3) | 3.8 (T0: 1.8) | (T0: 1.6) | 7.7 (T0: 3.3) | 3.9 (T0: 1.9) | 3.7 |
| LBFCYO (n = 0) | (T0: 3) | | (T0: 2.2) | (T0: 2) | (T0: 2) | (T0: 3) | (T0: 3.4) | |
| LBFBAJ (n = 0) | (T0: 1) | (T0: 1.1) | (T0: 1.1) | (T0: 1) | (T0: 1.7) | (T0: 4.8) | (T0: 2) | |
| LBFDJI (n = 0) | (T0: 1.1) | | (T0: 1.2) | (T0: 1) | (T0: 1) | (T0: 3) | (T0: 2) | |
| LBFGGO (n = 0) | (T0: 1) | | (T0: 1) | (T0: 1.1) | (T0: 1) | (T0: 2.6) | (T0: 1) | |
| LBFLFP (n = 0) | (T0: 0.9) | | (T0: 1.2) | (T0: 1.2) | (T0: 1.8) | (T0: 3.5) | (T0: 2) | |
| LBFNQV (n = 0) | (T0: 1.1) | | (T0: 1.2) | (T0: 1) | (T0: 1) | (T0: 2.7) | (T0: 1.8) | |
| LBFNLT (n = 0) | (T0: 1.1) | | (T0: 1.2) | (T0: 1) | (T0: 1.8) | (T0: 3.3) | (T0: 1.8) | |
| LBFLGC (n = 0) | (T0: 1) | | (T0: 1.1) | (T0: 1.1) | (T0: 1) | (T0: 2.5) | (T0: 1.1) | |
| LBFLCW (n = 0) | (T0: 0.9) | | (T0: 1.2) | (T0: 1) | (T0: 0.8) | (T0: 3.6) | (T0: 1.7) | |
| LBFZPJ (n = 0) | (T0: 2) | | (T0: 1.8) | (T0: 1.9) | (T0: 1) | (T0: 3.5) | (T0: 1) | |
| LBFNSS (n = 0) | (T0: 1.1) | | (T0: 1) | (T0: 1.2) | (T0: 1.1) | (T0: 2.5) | (T0: 1.8) | |
| LBGAOR (n = 0) | (T0: 1.1) | | (T0: 1.8) | (T0: 2) | (T0: 1.7) | (T0: 2.9) | (T0: 1.8) | |
| LBFZOE (n = 0) | (T0: 1) | | (T0: 1) | (T0: 1.1) | (T0: 1.1) | (T0: 2.8) | (T0: 1) | |
| LBFDJS (n = 0) | (T0: 1) | | (T0: 1.2) | (T0: 1) | (T0: 1) | (T0: 2.9) | (T0: 1.2) | |
| LBFDKC (n = 0) | (T0: 1) | | (T0: 1) | (T0: 1.2) | (T0: 1.8) | (T0: 2.5) | (T0: 2.2) | |
| LBFDKA (n = 5) | 4.2 (T0: 1.6) | 3.8 | 5.4 (T0: 2.6) | 5.2 (T0: 3.1) | (T0: 2.4) | 10.1 (T0: 5.6) | 4.8 (T0: 3.1) | 6 |
| LBFLGH (n = 0) | (T0: 0.9) | | (T0: 1) | (T0: 1.1) | (T0: 1.1) | (T0: 2.9) | (T0: 2.3) | |
| LBFNUS (n = 0) | (T0: 1.1) | | (T0: 1) | (T0: 0.9) | (T0: 1.4) | (T0: 3.9) | (T0: 2.2) | |
| LBFLCH (n = 0) | (T0: 1.8) | | (T0: 2.1) | (T0: 2.1) | (T0: 2.3) | (T0: 5) | (T0: 3.1) | |
| LBFZMI (n = 0) | (T0: 3.3) | | (T0: 2.1) | (T0: 2) | (T0: 1.5) | (T0: 4.6) | (T0: 2.2) | |
| LBFIDT (n = 7) | 3.8 (T0: 1.5) | 4 | 4.3 (T0: 2.2) | 4.2 (T0: 1.9) | (T0: 1.5) | 8.5 (T0: 4.5) | 4 (T0: 2.5) | 4.3 |
| LBFAZW (n = 0) | (T0: 1.8) | (T0: 2) | (T0: 2.1) | (T0: 1.8) | (T0: 1.4) | (T0: 4.5) | (T0: 1.7) | |
| LBFBBI (n = 0) | (T0: 2) | (T0: 2) | (T0: 1.9) | (T0: 1.5) | (T0: 1.6) | (T0: 4.2) | (T0: 1.9) | |
| LBFAZW (n = 0) | (T0: 1.8) | (T0: 2) | (T0: 2.1) | (T0: 1.8) | (T0: 1.4) | (T0: 4.5) | (T0: 1.7) | |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | j-i-Atss14_c-d12Des (Ps_GA) | c-d6Elo (Tp_GA) | j-t-StCAT_p2_p-LuPXR | j-i-Atss2_c-d6Des(Otfebit_GA) | c-d5Des (Tc_GA) | c-d6Elo (Pp_GA) | Conclusion from individual assays: number of T-DNA copies inserted into the genome |
|---|---|---|---|---|---|---|---|
| LBFDGG (n = 50) | 2 | 2.1 (T0: 1.1) | 2.2 (T0: 1) | 2.1 (T0: 1) | 4.2 (T0: 2.2) | 1.9 (T0: 1) | single copy |
| LBFGKN (n = 50) | 2.1 | 2.1 (T0: 1) | 2.2 (T0: 1) | 2.1 (T0: 1.1) | 4.2 (T0: 2) | 1.9 (T0: 1.1) | single copy |
| LBFIHE (n = 34) | 2.3 | 2.1 (T0: 1) | 2.1 (T0: 1.2) | 2.3 (T0: 1) | 4.1 (T0: 1.9) | 2.1 (T0: 1.1) | single copy |
| LBFLDI (n = 60) | 2.4 | 2.3 (T0: 0.8) | 2.3 (T0: 1) | 2.3 (T0: 0.9) | 4.4 (T0: 1.9) | 2.5 (T0: 1) | single copy |
| LBFPNF (n = 52) | 2 | 2 (T0: 1.2) | 4 (T0: 1.9) | 4.1 (T0: 1.7) | 5.6 (T0: 2.8) | 4.2 (T0: 1.9) | partial double copy |
| LBFNSQ (n = 51) | 3.9 | 3.7 (T0: 1.9) | 4.1 (T0: 1.9) | 3.8 (T0: 1.9) | 7.1 (T0: 3.1) | 2 (T0: 0.7) | partial double copy |
| LBFDGL (n = 57) | 4.1 | 3.8 (T0: 1.7) | 4 (T0: 1.9) | 3.8 (T0: 1.4) | 6.7 (T0: 2.9) | 1.8 (T0: 0.7) | partial double copy |
| LBFIEF (n = 6) | 4.1 | 3.6 (T0: 2.3) | 3.8 (T0: 2.6) | 3.7 (T0: 1.6) | 6.4 (T0: 3.5) | 2.1 (T0: 0.8) | partial double copy |
| LBFBAV (n = 50) | 3.9 | 4 (T0: 1.9) | 3.7 (T0: 2) | 4.1 (T0: 1.7) | 8.2 (T0: 3.7) | 6.3 (T0: 2.9) | partial double copy |
| LBFPNC (n = 32) | 3.8 | 3.8 (T0: 1.8) | 4.1 (T0: 1.8) | 4.2 (T0: 1.4) | 7.5 (T0: 3.4) | 4 (T0: 1.9) | partial double copy |
| LBFGHQ (n = 46) | 3.7 | 2.1 (T0: 1.1) | 2 (T0: 1.1) | 2 (T0: 1.1) | 6.1 (T0: 3.1) | 2 (T0: 1) | partial double copy |
| LBFAZB (n = 49) | 4 | 3.8 (T0: 1.7) | 4 (T0: 1.8) | 3.7 (T0: 1.3) | 6.6 (T0: 3.1) | 1.9 (T0: 0.6) | partial double copy |
| LBFGKW (n = 72) | 4 | 4 (T0: 1.7) | 3.6 (T0: 1.8) | 3.7 (T0: 1.5) | 7 (T0: 3.2) | 1.7 (T0: 0.6) | partial double copy |
| LBFNRU (n = 58) | 3.9 | 3.8 (T0: 1.7) | 4.2 (T0: 1.9) | 3.8 (T0: 1.6) | 7 (T0: 3.2) | 1.9 (T0: 0.8) | partial double copy |
| LBFGIZ (n = 43) | 3.9 | 3.8 (T0: 1.7) | 4.3 (T0: 1.5) | 3.8 (T0: 1.5) | 7 (T0: 2.8) | 1.9 (T0: 0.8) | partial double copy |
| LBFIGM (n = 56) | 3.8 | 3.8 (T0: 1.8) | 4.2 (T0: 2.2) | 4.1 (T0: 1.6) | 7.6 (T0: 2.8) | 1.9 (T0: 0.6) | partial double copy |
| LBFNRR (n = 61) | 4.1 | 3.9 (T0: 1.7) | 4.3 (T0: 1.6) | 3.9 (T0: 1.6) | 7.1 (T0: 2.8) | 1.9 (T0: 0.7) | partial double copy |
| LBFNTK (n = 69) | 4.1 | 3.8 (T0: 1.7) | 4.3 (T0: 1.9) | 4.1 (T0: 1.5) | 7.6 (T0: 2.9) | 1.9 (T0: 0.7) | partial double copy |
| LBFGJA (n = 42) | 3.7 | 4.1 (T0: 1.9) | 3.9 (T0: 1.9) | 3.6 (T0: 1.9) | 7.6 (T0: 3.6) | 3.9 (T0: 2-1) | double copy |
| LBFIFV (n = 58) | 4 | 3.9 (T0: 2) | 4 (T0: 2.6) | 4.2 (T0: 1.8) | 7.7 (T0: 3.9) | 3.9 (T0: 2) | double copy |
| LBFLER (n = 52) | 4 | 4.1 (T0: 1.8) | 4.2 (T0: 2.3) | 4 (T0: 1.6) | 7.7 (T0: 3.3) | 3.8 (T0: 1.9) | double copy |
| LBFLDL (n = 44) | 4.1 | 4.1 (T0: 1.8) | 4.1 (T0: 2-1) | 3.9 (T0: 1.6) | 7.8 (T0: 3.5) | 3.8 (T0: 1.9) | double copy |
| LBFNQW (n = 51) | 4 | 4.2 (T0: 1.6) | 4.2 (T0: 2) | 3.9 (T0: 1.9) | 7.9 (T0: 3.4) | 3.9 (T0: 1.8) | double copy |
| LBFBAP (n = 19) | 3.8 | 5.7 (T0: 2.3) | 5.5 (T0: 2.3) | 5.7 (T0: 1.8) | 7.5 (T0: 2.8) | 4 (T0: 2.4) | partial triple copy |
| LBFDAU (n = 10) | 3.9 | 3.7 (T0: 1.8) | 3.9 (T0: 2.4) | 4.1 (T0: 1.7) | 7.3 (T0: 3.7) | 3.7 (T0: 1.9) | partial double copy |
| LBFPRA (n = 16) | 3.7 | 3.7 (T0: 2.4) | 3.9 (T0: 3.1) | 3.7 (T0: 2.3) | 7.4 (T0: 4.7) | 3.8 (T0: 2.8) | partial double copy |

TABLE 135-continued

Copy number measurement of T1 plants cultivated in the greenhouse of canola events containing the T-DNAs of plasmids VC-LTM593-1qcz rc. The events are indicated in the first column, along with the number of T1 plants that where measured per event. The T1 plants underwent a selection from 250 segregating T1 seedlings, using zygocity analysis as illustrated in Table 137, keeping only plants that are homozygous for the desired number of loci (which are indicated in the last column of Table 137). A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result observed in the T0 generation (indicated in parentheses). For some events this was not the case because during selection of T1 plants, undesired loci have been segregated out while retaining only desired loci in a homozygous state.

| Event | | | | | | | |
|---|---|---|---|---|---|---|---|
| LBFIFU (n = 11) | 4.9 | 4.3 (T0: 2.3) | 4.2 | 4 (T0: 2.6) | 6.5 (T0: 4.2) | 3.8 (T0: 3) | partial double copy |
| LBFDKD (n = 2) | 3.6 | 3.8 (T0: 1.9) | 4.3 (T0: 2) | 4.3 (T0: 1.8) | 7.6 (T0: 3.4) | 4 (T0: 1.6) | double copy |
| LBFDJG (n = 12) | 3.9 | 4.1 (T0: 1.9) | 4.1 (T0: 2.2) | 3.7 (T0: 1.9) | 8 (T0: 3.6) | 4.5 (T0: 1.9) | double copy |
| LBFLFK (n = 15) | 3.8 | 3.8 (T0: 1.3) | 4.1 (T0: 2.4) | 3.9 (T0: 1.8) | 7.5 (T0: 5.2) | 4 (T0: 2) | double copy |
| LBFLCG (n = 15) | 3.9 | 3.7 (T0: 2) | 3.9 (T0: 2.5) | 5.6 (T0: 2.2) | 9 (T0: 5.1) | 3.9 (T0: 2) | double copy |
| LBFPQM (n = 12) | 3.8 | 3.8 (T0: 1.8) | 4 (T0: 2) | 4.2 (T0: 1.5) | 7.6 (T0: 3.7) | 4.1 (T0: 1.8) | double copy |
| LBFDHG (n = 5) | 3.6 | 3.8 (T0: 2) | 3.9 (T0: 2.3) | 3.9 (T0: 1.7) | 7.7 (T0: 3.3) | 3.9 (T0: 1.9) | double copy |
| LBFCYO (n = 0) | | (T0: 2) | (T0: 2-1) | (T0: 1.8) | (T0: 3) | (T0: 0.6) | partial double copy |
| LBFBAJ (n = 0) | | (T0: 2) | (T0: 2.5) | (T0: 1.8) | (T0: 4.8) | (T0: 2) | partial double copy |
| LBFDJI (n = 0) | | (T0: 1.5) | (T0: 2.5) | (T0: 2-1) | (T0: 3) | (T0: 1.7) | partial double copy |
| LBFGGO (n = 0) | | (T0: 2.1) | (T0: 2-1) | (T0: 2) | (T0: 2.6) | (T0: 1.9) | partial double copy |
| LBFLFP (n = 0) | | (T0: 1.8) | (T0: 2-1) | (T0: 1.7) | (T0: 3.5) | (T0: 1.7) | partial double copy |
| LBFNQV (n = 0) | | (T0: 1.7) | (T0: 2.3) | (T0: 1.7) | (T0: 2.7) | (T0: 2) | partial double copy |
| LBFNLT (n = 0) | | (T0: 1.8) | (T0: 2.2) | (T0: 1.8) | (T0: 3.3) | (T0: 1.9) | partial double copy |
| LBFLGC (n = 0) | | (T0: 3) | (T0: 2.6) | (T0: 2.2) | (T0: 2.5) | (T0: 1.8) | partial double copy |
| LBFLCW (n = 0) | | (T0: 1.5) | (T0: 2) | (T0: 1.6) | (T0: 3.6) | (T0: 1.5) | partial double copy |
| LBFZPJ (n = 0) | | (T0: 2.3) | (T0: 3) | (T0: 2.4) | (T0: 3.5) | (T0: 2.4) | partial double copy |
| LBFNSS (n = 0) | | (T0: 2.3) | (T0: 2.5) | (T0: 2) | (T0: 2.5) | (T0: 2) | partial double copy |
| LBGAOR (n = 0) | | (T0: 1.8) | (T0: 1.1) | (T0: 1) | (T0: 2.9) | (T0: 1.1) | partial double copy |
| LBFZOE (n = 0) | | (T0: 1.1) | (T0: 2-1) | (T0: 1.7) | (T0: 2.8) | (T0: 1.8) | partial double copy |
| LBFDJS (n = 0) | | (T0: 0.9) | (T0: 2.2) | (T0: 1.9) | (T0: 2.9) | (T0: 1.9) | partial copy |
| LBFDKC (n = 0) | | (T0: 1.7) | (T0: 1.6) | (T0: 1.4) | (T0: 2.5) | (T0: 0.6) | partial double copy |
| LBFDKA (n = 5) | 5.7 | 5.7 (T0: 3.3) | 5.7 (T0: 3.9) | 5.9 (T0: 2.9) | 10.1 (T0: 5.6) | 5.7 (T0: 3.5) | partial triple copy |
| LBFLGH (n = 0) | | (T0: 2.5) | (T0: 3) | (T0: 2.1) | (T0: 2.9) | (T0: 2.5) | partial triple copy |
| LBFNUS (n = 0) | | (T0: 2.3) | (T0: 3.1) | (T0: 2.3) | (T0: 3.9) | (T0: 3.3) | partial triple copy |
| LBFLCH (n = 0) | | (T0: 2.3) | (T0: 5.3) | (T0: 3.3) | (T0: 5) | (T0: 3.4) | partial triple copy |
| LBFZMI (n = 0) | | (T0: 1.7) | (T0: 1.9) | (T0: 2.9) | (T0: 4.6) | (T0: 2.6) | partial triple copy |
| LBFIDT (n = 7) | 4.3 | 4.3 (T0: 2.5) | 3.8 (T0: 3.8) | 4.2 (T0: 2.4) | 8.5 (T0: 4.5) | 3.9 (T0: 2.4) | partial triple copy |
| LBFAZW (n = 0) | | (T0: 2.5) | (T0: 3.3) | (T0: 2.4) | (T0: 4.5) | (T0: 2.5) | partial triple copy |
| LBFBBI (n = 0) | | (T0: 1.9) | (T0: 2.7) | (T0: 1.9) | (T0: 4.2) | (T0: 1.7) | partial triple copy |
| LBFAZW (n = 0) | | (T0: 2.5) | (T0: 3.3) | (T0: 2.4) | (T0: 4.5) | (T0: 2.5) | partial triple copy |

TABLE 136

Expected Mendelian segregation of the genotype in T1 seeds for some possible T-DNA insertion scenarios. Listed are the expected copy number segregation ratios for T1 seeds segregating for one or more unlinked genomic loci, which contain one or more linked copies of T-DNA insertions, sc: single copy, dc: double copy

| Locus configuration | Ratio of copy numbers (cn) expected T1 seed segregating for given locus configuration | | | | | | | | | | | | |
|---|---|---|---|---|---|---|---|---|---|---|---|---|---|
| | cn = 0 | cn = 1 | cn = 2 | cn = 3 | cn = 4 | cn = 5 | cn = 6 | cn = 7 | cn = 8 | cn = 9 | cn = 10 | cn = 11 | cn = 12 |
| 1 sc locus | 1 | 2 | 1 | | | | | | | | | | |
| 1 dc locus | 1 | | 2 | | 1 | | | | | | | | |
| 2 sc loci | 1 | 4 | 6 | 4 | 1 | | | | | | | | |
| 2 sc loci, 1 dc locus | 1 | 2 | 3 | 4 | 3 | 2 | 1 | | | | | | |
| 3 sc loci, 1 dc locus | 1 | 4 | 8 | 12 | 14 | 12 | 8 | 4 | 1 | | | | |

TABLE 137

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order:0:1:2:3:4:5:6:7:8:9:10:11:12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFDGG | 073:122:053:000:000:000:000:000:000:000:000:000:000 | A07:076:119:053:000:000:000:000:000:000:000:000:000 | 073:123:052:001:000:000:000:000:000:000:000:000:000 | one locus |
| LBFGKN | 057:131:059:001:000:000:000:000:000:000:000:000:000 | A07:057:130:059:001:000:000:000:000:000:000:000:000 | 057:130:060:000:000:000:000:000:000:000:000:000:000 | one locus |
| LBFIHE | 076:125:042:001:000:000:000:000:000:000:000:000:000 | A12:075:123:035:009:000:000:000:000:000:000:000:000 | 076:122:036:010:000:000:000:000:000:000:000:000:000 | one locus |
| LBFLDI | 068:101:059:018:003:000:000:000:000:000:000:000:000 | A12:075:094:062:015:002:000:000:000:000:000:000:000 | 068:106:053:018:002:001:000:000:000:000:000:000:000 | one locus |
| LBFPNF | 065:128:055:001:000:000:000:000:000:000:000:000:000 | A12:066:000:127:001:053:002:000:000:000:000:000:000 | 064:001:127:001:051:002:002:000:000:000:000:000:000 | one locus |
| LBFNSQ | 063:109:066:005:000:000:000:000:000:000:000:000:000 | A12:063:000:110:011:049:010:000:000:000:000:000:000 | 063:114:061:005:000:000:000:000:000:000:000:000:000 | one locus |
| LBFDGL | 072:113:062:001:000:000:000:000:000:000:000:000:000 | A12:072:000:108:007:061:000:001:000:000:000:000:000 | 073:113:061:002:000:000:000:000:000:000:000:000:000 | one locus |
| LBFIEF | 042:000:018:020:013:002:004:000:001:000:000:000:000 | A12:042:000:025:015:012:005:000:001:000:000:000:000 | 041:032:020:005:001:000:000:000:000:000:000:000:000 | one locus |
| LBFBAV | 068:128:053:000:000:000:000:000:000:000:000:000:000 | A04:068:000:128:000:053:000:000:000:000:000:000:000 | 068:000:000:122:006:000:044:009:000:000:000:000:000 | one locus |
| LBFPNC | 043:074:035:001:000:000:000:000:000:000:000:000:000 | A12:043:002:072:001:034:001:001:000:000:000:000:000 | 043:000:074:001:034:000:001:000:000:000:000:000:000 | one locus |
| LBFGHQ | 067:000:113:007:051:001:000:000:001:000:000:000:000 | A12:065:110:057:001:000:000:000:000:000:000:000:000 | 066:104:059:003:003:001:000:000:000:000:000:000:000 | one locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order:0:1:2:3:4:5:6:7:8:9:10:11:12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFAZB | 078:001:158:002:055:001:000:000:001:000:000:000:000 | A12:078:001:151:008:055:002:001:000:000:000:000:000:000 | 078:161:054:003:000:000:000:000:000:000:000:000:000 | one locus |
| LBFGKW | 047:000:124:007:070:000:001:000:000:000:000:000 | A13:047:000:124:012:065:000:000:000:000:000:000:000 | 047:129:073:000:000:000:000:000:000:000:000:000 | one locus |
| LBFNRU | 070:000:120:003:056:000:000:000:000:000:000:000:000 | A11:069:000:121:001:056:001:000:000:000:000:000:000 | 070:121:058:000:000:000:000:000:000:000:000:000 | one locus |
| LBFGIZ | 073:000:108:001:045:004:000:000:000:000:000:000:000 | A11:073:000:108:002:044:004:000:000:000:000:000:000 | 072:109:048:001:000:000:000:000:000:000:000:000 | one locus |
| LBFIGM | 055:000:133:004:056:000:001:000:000:000:000:000:000 | A04:054:000:133:004:056:001:000:000:000:000:000:000 | 055:137:057:000:000:000:000:000:000:000:000:000 | one locus |
| LBFNRR | 070:000:116:004:057:000:000:000:001:000:000:000:000 | A11:070:000:115:001:062:000:000:000:000:000:000:000 | 070:117:061:000:000:000:000:000:000:000:000:000 | one locus |
| LBFNTK | 054:003:119:005:063:004:000:000:000:000:000:000:000 | A04:053:003:115:003:070:002:000:000:000:000:000:000 | 053:122:072:000:000:000:000:000:000:000:000:000 | one locus |
| LBFGJA | 088:000:111:006:041:000:000:000:000:000:000:000:000 | A12:088:002:111:003:041:000:000:000:000:000:000:000 | 089:001:113:003:039:001:000:000:000:000:000:000 | one locus |
| LBFIFV | 070:000:119:000:056:002:000:000:000:000:000:000:000 | A04:070:119:057:001:000:000:000:000:000:000:000:000 | 070:000:119:000:056:001:001:000:000:000:000:000 | one locus |
| LBFLER | 073:000:123:002:051:000:000:000:000:000:000:000:000 | A13:074:000:121:002:050:001:000:000:000:000:000:000 | 073:000:123:002:051:000:000:000:000:000:000:000 | one locus |
| LBFLDL | 069:000:129:008:043:000:000:000:000:000:000:000:000 | A13:069:000:130:002:045:001:000:000:000:000:000:000 | 068:000:130:006:041:001:001:0 00:000:000:000:000 | one locus |
| LBFNQW | 070:001:123:007:045:002:000:000:000:000:000:000:000 | A13:070:000:123:001:053:001:000:000:000:000:000:000 | 070:001:122:005:047:003:000:000:000:000:000:000 | one locus |
| LBFBAP | 059:123:064:001:001:000:000:000:000:000:000:000:000 | A07:059:001:123:015:049:001:000:000:000:000:000:000 | 009:037:068:057:051:022:002:000:000:000:000:000 | double locus, isolation of one locus |
| LBFDAU | 059:123:062:000:000:000:000:000:000:000:000:000:000 | A12:013:069:090:062:010:000:000:000:000:000:000:000 | 013:072:087:062:010:000:000:000:000:000:000:000 | double locus |
| LBFPRA | 024:075:087:057:005:000:000:000:000:000:000:000:000 | A12:024:041:060:058:052:012:001:000:000:000:000:000 | 024:041:060:051:049:022:001:000:000:000:000:000 | double locus, isolation of one locus |
| LBFIFU | 019:075:105:034:013:000:000:000:000:000:000:000:000 | A13:019:040:060:067:044:013:003:000:000:000:000:000 | 019:040:060:072:039:013:003:000:000:000:000:000 | double locus, isolation of one locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order:0:1:2:3:4:5:6:7:8:9:10:11:12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFDKD | 007:031:045:018:002:000:000:000:000:000:000:000:000 | A07:007:031:046:017:002:000:000:000:000:000:000:000 | 007:031:044:017:003:000:000:000:000:000:000:000:000 | double locus |
| LBFDJG | 026:078:088:036:014:000:000:000:000:000:000:000:000 | A12:029:072:085:035:017:001:000:000:000:000:000:000 | 026:076:077:037:022:004:001:000:000:000:000:000:000 | double locus |
| LBFLFK | 018:062:096:058:015:000:000:000:000:000:000:000:000 | A11:018:061:096:059:015:000:000:000:000:000:000:000 | 018:061:098:057:015:000:000:000:000:000:000:000:000 | double locus |
| LBFLCG | 015:059:087:068:015:000:000:000:000:000:000:000:000 | A12:016:058:087:067:016:000:000:000:000:000:000:000 | 016:056:090:065:015:000:000:000:000:000:000:000:000 | double locus |
| LBFPQM | 008:058:094:060:014:000:000:000:000:000:000:000:000 | A12:008:058:094:062:012:000:000:000:000:000:000:000 | 008:058:095:061:012:000:000:000:000:000:000:000:000 | double locus |
| LBFDHG | 022:064:084:037:004:001:000:000:000:000:000:000:000 | A07:023:062:090:033:005:000:000:000:000:000:000:000 | 023:063:089:037:005:000:000:000:000:000:000:000:000 | double locus |
| LBFCYO | 091:001:002:013:090:001:006:031:001:000:000:000:000 | A14:059:126:051:000:000:000:000:000:000:000:000:000 | 059:126:051:000:000:000:000:000:000:000:000:000:000 | double locus |
| LBFBAJ | 056:140:048:000:000:000:000:000:000:000:000:000:000 | A12:017:056:093:064:014:000:000:000:000:000:000:000 | 016:056:091:032:043:005:000:000:000:000:000:000:000 | double locus |
| LBFDJI | 151:285:171:003:000:000:000:000:000:000:000:000:000 | A12:051:073:118:157:149:036:023:002:001:000:000:000 | 049:152:228:129:041:003:000:000:000:000:000:000:000 | double locus |
| LBFGGO | 017:034:030:000:000:000:000:000:000:000:000:000:000 | A12:009:011:030:023:008:000:000:000:000:000:000:000 | 009:011:031:023:007:000:000:000:000:000:000:000:000 | double locus |
| LBFLFP | 047:094:053:001:000:000:000:000:000:000:000:000:000 | A04:046:092:056:001:000:000:000:000:000:000:000:000 | 010:038:069:049:027:001:001:000:000:000:000:000:000 | double locus |
| LBFNQV | 174:289:138:000:000:000:000:000:000:000:000:000:000 | A04:174:286:138:002:000:000:000:000:000:000:000:000 | 049:163:210:126:048:003:000:000:000:000:000:000:000 | double locus |
| LBFNLT | 149:279:145:010:000:000:000:000:000:000:000:000:000 | A07:015:067:130:063:033:001:000:000:000:000:000:000 | 029:146:214:136:055:007:000:000:000:000:000:000:000 | double locus |
| LBFLGC | 064:121:057:005:002:000:000:000:000:000:000:000:000 | A12:013:034:059:060:049:026:006:000:002:000:000:000 | 013:068:112:048:008:000:000:000:000:000:000:000:000 | double locus |
| LBFLCW | 207:283:098:003:000:000:000:000:000:000:000:000:000 | A12:065:152:224:131:018:001:000:000:000:000:000:000 | 064:156:232:110:022:001:000:000:000:000:000:000:000 | double locus |
| LBFZPJ | 060:000:129:000:059:000:001:000:000:000:000:000:000 | A12:013:032:042:066:059:029:008:000:000:000:000:000 | 013:032:044:065:049:036:010:000:000:000:000:000:000 | double locus |
| LBFNSS | 155:359:142:000:000:000:000:000:000:000:000:000:000 | A12:044:094:127:183:113:058:033:003:002:000:000:000 | 042:163:268:141:039:003:001:000:000:000:000:000:000 | double locus |
| LBGAOR | 149:302:144:000:000:000:000:000:000:000:000:000:000 | A04:040:158:274:103:019:000:000:000:000:000:000:000 | 161:310:120:003:000:000:000:000:000:000:000:000:000 | double locus |

TABLE 137-continued

Observed Medelian segregation of the genotype of T1 seeds of events from construct VC-LTM593-1qcz rc. The segregation has been analysed at three positions of the T-DNA. For each position, the number of seedlings have been counted that have a copy number (aritmetically rounded) of 0, 1, 2, 3, 4, 5, 6, 7, 8, 9, 10, 11, 12. The of seedlings counted for each copy number category are separated by colon, displaying the categories in the following order:0:1:2:3:4:5:6:7:8:9:10:11:12. Listed are the observed copy number segregation ratios for T1 seeds segregating for one or more unlinked genomic loci, which contain one or more linked copies of T-DNA insertions. The observed frequencies for each assay have been compared against expected frequencies for various locus configurations listed in Table 136 using Chi-Square analysis. The last column displays the total number of loci that are segregating in the genome of a given event. Many events contain truncated insertions, as was evident when some assays indicate singl ecopy insertion at e.g. the left border (e.g. event LBFDAU, LPFPNC), while other positions on the T-DNA clearly indicate a double copy insertion that was either inserted in one locus (e.g. event LBFPNC), or in two loci (e.g. event LBFDAU)

| Event | Copy number ratios measured near the left border of the T-DNA using assay A1 | Copy number ratios measured using T-DNA internal assays targeting reagions that had copy number results indicating truncated T-DNA insertions using assay A06, or A08, or A09, or A10 | Copy number ratios measured near the right border of the T-DNA using assay A12 | Most likely number of loci containing one or more T-DNA copies, tested using Chi-Square test |
|---|---|---|---|---|
| LBFZOE | 026:060:035:000:000:000:000:000:000:000:000:000:000 | A12:010:025:051:026:008:002:000:000:000:000:000:000 | 010:025:049:031:006:000:000:000:000:000:000:000:000 | double locus |
| LBFDJS | 048:131:060:001:000:000:000:000:000:000:000:000:000 | A12:008:043:090:074:026:000:000:000:000:000:000:000 | 008:043:089:075:025:000:000:000:000:000:000:000:000 | double locus |
| LBFDKC | 001:109:133:001:000:000:000:000:000:000:000:000:000 | A07:001:000:109:008:126:001:000:000:000:000:000:000 | 001:108:132:004:000:000:000:000:000:000:000:000:000 | no wildtypes |
| LBFDKA | 015:072:101:052:008:000:000:000:000:000:000:000:000 | A12:001:012:041:054:076:045:018:001:000:000:000:000 | 001:012:041:053:069:050:019:003:000:000:000:000:000 | triple locus |
| LBFLGH | 061:137:051:000:000:000:000:000:000:000:000:000:000 | A12:015:034:052:068:039:026:012:002:001:000:000:000 | 014:033:053:060:045:030:012:001:000:000:000:000:000 | triple locus |
| LBFNUS | 054:137:058:000:000:000:000:000:000:000:000:000:000 | A12:003:016:048:054:034:008:003:000:000:000:000:000 | 004:020:071:081:060:010:003:000:000:000:000:000:000 | triple locus |
| LBFLCH | 019:077:090:052:011:000:000:000:000:000:000:000:000 | A12:019:039:013:006:050:050:021:008:019:013:009:002:000 | 019:039:013:041:063:027:026:013:007:000:000:000:000 | triple locus |
| LBFZMI | 017:016:036:038:023:027:005:000:000:000:000:000:000 | A12:017:043:061:033:008:000:000:000:000:000:000:000 | 007:015:039:051:034:014:002:000:000:000:000:000:000 | triple locus |
| LBFIDT | 069:000:131:000:045:001:000:000:000:000:000:000:000 | A12:015:033:058:064:048:015:012:002:000:000:000:000 | 003:018:050:056:061:031:019:008:000:000:000:000:000 | triple locus, isolation of one locus |
| LBFAZW | 013:065:109:041:006:000:000:000:000:000:000:000:000 | A12:004:021:073:086:040:010:001:000:000:000:000:000 | 003:018:069:079:048:013:002:000:001:000:000:000:000 | trippel locus |
| LBFBBI | 005:057:139:040:004:000:000:000:000:000:000:000:000 | A12:009:030:074:066:051:014:001:000:000:000:000:000 | 005:065:127:044:004:000:000:000:000:000:000:000:000 | trippel locus |
| LBFAZW | 013:065:109:041:006:000:000:000:000:000:000:000:000 | A12:004:021:073:086:040:010:001:000:000:000:000:000 | 003:018:069:079:048:013:002:000:001:000:000:000:000 | trippel locus |

TABLE 138

Fatty acid profiles of T2 seeds harvested from T1 plants cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDGG (n = 50) | 4.8 ± 0.2 | 0.2 ± 0 | 0 ± 0 | 2.9 ± 0.3 | 28.3 ± 1.5 | 35.6 ± 1 | 0.8 ± 0.1 | 4.5 ± 0.3 | 1.9 ± 0.2 | 0.4 ± 0.1 | 0.8 ± 0.1 | 0.7 ± 0 | 0.1 ± 0 |
| LBFGKN (n = 50) | 4.6 ± 0.3 | 0.1 ± 0 | 0 ± 0 | 3 ± 0.2 | 28.3 ± 1.6 | 35.2 ± 0.7 | 1 ± 0.1 | 4.6 ± 0.3 | 2 ± 0.3 | 0.5 ± 0.2 | 0.8 ± 0 | 0.7 ± 0 | 0.2 ± 0 |

TABLE 138-continued

Fatty acid profiles of T2 seeds harvested from T1 plants cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | | | | | | | | | | | | | |
|---|---|---|---|---|---|---|---|---|---|---|---|---|---|
| LBFIHE (n = 34) | 5.4 ± 0.9 | 0.2 ± 0.1 | 0 ± 0 | 3.1 ± 0.4 | 26.6 ± 2.1 | 34.7 ± 1.4 | 0.9 ± 0.2 | 3.9 ± 0.4 | 2.6 ± 0.9 | 0.3 ± 0.1 | 1 ± 0.1 | 0.9 ± 0.1 | 0.2 ± 0.1 |
| LBFLDI (n = 60) | 6.6 ± 1.2 | 0.3 ± 0.1 | 0 ± 0 | 2.2 ± 0.2 | 31.1 ± 3.3 | 30 ± 1.9 | 0.7 ± 0.2 | 6 ± 0.6 | 1.1 ± 0.3 | 0.2 ± 0.1 | 0.8 ± 0.1 | 0.8 ± 0.1 | 0.4 ± 0.3 |
| LBFPNF (n = 52) | 5 ± 0.2 | 0.2 ± 0 | 0 ± 0 | 2.5 ± 0.2 | 30.5 ± 1.3 | 27.8 ± 1.1 | 1.8 ± 0.2 | 4.5 ± 0.4 | 2.9 ± 0.3 | 0.4 ± 0.1 | 0.8 ± 0.1 | 0.7 ± 0.1 | 0.1 ± 0 |
| LBFNSQ (n = 51) | 5 ± 0.4 | 0.1 ± 0 | 0 ± 0 | 2.7 ± 0.5 | 26.9 ± 1.6 | 35.7 ± 1.9 | 0.8 ± 0.2 | 5.4 ± 0.6 | 1.5 ± 0.2 | 0.3 ± 0.1 | 0.8 ± 0.1 | 0.4 ± 0.4 | 0.2 ± 0.1 |
| LBFDGL (n = 57) | 4.9 ± 0.1 | 0.1 ± 0 | 0 ± 0 | 3 ± 0.4 | 26.9 ± 2.2 | 36.3 ± 1.9 | 0.6 ± 0.2 | 5.8 ± 0.7 | 1.5 ± 0.8 | 0.3 ± 0.1 | 0.8 ± 0.1 | 0.7 ± 0 | 0.2 ± 0 |
| LBFIEF (n = 6) | 5 ± 0.2 | 0.1 ± 0 | 0 ± 0 | 3.4 ± 0.4 | 27.6 ± 2.9 | 36.2 ± 2.1 | 0.6 ± 0.1 | 5.7 ± 0.5 | 1.5 ± 0.2 | 0.4 ± 0.2 | 1 ± 0.1 | 0.7 ± 0 | 0.2 ± 0 |
| LBFBAV (n = 50) | 5.1 ± 0.2 | 0.2 ± 0 | 0 ± 0 | 2.6 ± 0.3 | 29.5 ± 1.3 | 27.2 ± 1.4 | 1.6 ± 0.2 | 5.3 ± 0.3 | 1.6 ± 0.1 | 0.3 ± 0 | 0.8 ± 0.2 | 0.7 ± 0 | 0.1 ± 0 |
| LBFPNC (n = 32) | 4.8 ± 0.3 | 0.1 ± 0 | 0 ± 0 | 3.9 ± 0.7 | 26.7 ± 1.7 | 35.6 ± 1 | 0.8 ± 0.1 | 3.3 ± 0.5 | 1.7 ± 0.3 | 0.2 ± 0.1 | 1.1 ± 0.2 | 0.7 ± 0 | 0.2 ± 0 |
| LBFGHQ (n = 46) | 5.1 ± 0.2 | 0.1 ± 0.1 | 0 ± 0 | 2.4 ± 0.1 | 30.7 ± 1.3 | 35 ± 1.7 | 0.5 ± 0.1 | 7.7 ± 0.6 | 1.3 ± 0.2 | 0.4 ± 0.1 | 0.9 ± 0.3 | 0.8 ± 0.1 | 0.1 ± 0 |
| LBFAZB (n = 49) | 4.9 ± 0.1 | 0.1 ± 0 | 0 ± 0 | 3.1 ± 0.2 | 28.4 ± 1.6 | 34.1 ± 1.1 | 1 ± 0.1 | 4.7 ± 0.4 | 1.9 ± 0.3 | 0.3 ± 0.1 | 0.8 ± 0.1 | 0.6 ± 0.1 | 0.1 ± 0.1 |
| LBFGKW (n = 72) | 5.1 ± 0.2 | 0.2 ± 0 | 0 ± 0 | 2.5 ± 0.2 | 30.1 ± 1.3 | 32.1 ± 1.6 | 1.1 ± 0.1 | 6.1 ± 0.4 | 1.7 ± 0.3 | 0.2 ± 0.1 | 0.8 ± 0.1 | 0.7 ± 0 | 0.1 ± 0 |
| LBFNRU (n = 58) | 5 ± 0.2 | 0.2 ± 0 | 0 ± 0 | 2.6 ± 0.2 | 31.8 ± 2.5 | 29.2 ± 1.9 | 1 ± 0.1 | 7.1 ± 0.5 | 1.2 ± 0.2 | 0.2 ± 0 | 0.8 ± 0.1 | 0.8 ± 0 | 0.1 ± 0 |
| LBFGIZ (n = 43) | 4.9 ± 0.6 | 0.2 ± 0.1 | 0 ± 0 | 2.6 ± 0.4 | 30.5 ± 3 | 30 ± 2.6 | 1 ± 0.2 | 6.2 ± 0.8 | 1.3 ± 0.2 | 0.2 ± 0 | 0.8 ± 0.1 | 0.7 ± 0.1 | 0.2 ± 0 |
| LBFIGM (n = 56) | 4.8 ± 0.4 | 0.2 ± 0 | 0 ± 0 | 2.3 ± 0.2 | 31.9 ± 2.7 | 30.6 ± 2.7 | 1 ± 0.1 | 6.3 ± 0.7 | 1.3 ± 0.2 | 0.2 ± 0 | 0.7 ± 0.1 | 0.8 ± 0.1 | 0.1 ± 0 |
| LBFNRR (n = 61) | 5 ± 0.2 | 0.2 ± 0 | 0 ± 0 | 2.8 ± 0.4 | 31.4 ± 1.5 | 30 ± 2.1 | 1.1 ± 0.1 | 7 ± 0.6 | 1.3 ± 0.2 | 0.3 ± 0 | 0.9 ± 0.1 | 0.8 ± 0.1 | 0.1 ± 0 |
| LBFNTK (n = 69) | 5.1 ± 0.4 | 0.2 ± 0 | 0 ± 0 | 2.5 ± 0.2 | 29.6 ± 1.4 | 29 ± 1.8 | 1.3 ± 0.2 | 6.4 ± 0.6 | 1.5 ± 0.3 | 0.1 ± 0.1 | 0.8 ± 0.1 | 0.8 ± 0 | 0.1 ± 0 |
| LBFGJA (n = 42) | 5.2 ± 0.2 | 0.2 ± 0 | 0 ± 0 | 3.1 ± 0.2 | 27.7 ± 0.8 | 34.5 ± 0.8 | 1.9 ± 0.2 | 3.3 ± 0.2 | 5.8 ± 0.9 | 0.5 ± 0.2 | 0.8 ± 0 | 0.7 ± 0.1 | 0.1 ± 0 |
| LBFIFV (n = 58) | 4.8 ± 0.4 | 0.1 ± 0 | 0 ± 0 | 3.2 ± 0.3 | 27.6 ± 1.5 | 37.3 ± 0.9 | 0.8 ± 0.1 | 3.7 ± 0.2 | 1.8 ± 0.3 | 0.2 ± 0 | 0.9 ± 0.1 | 0.7 ± 0.2 | 0.1 ± 0 |
| LBFLER (n = 52) | 4.7 ± 0.1 | 0.1 ± 0 | 0 ± 0 | 3.1 ± 0.2 | 28.7 ± 2 | 33.9 ± 1.1 | 1 ± 0.1 | 4.4 ± 0.3 | 1.9 ± 0.5 | 0.3 ± 0 | 0.9 ± 0 | 0.7 ± 0 | 0.1 ± 0 |
| LBFLDL (n = 44) | 4.8 ± 0.1 | 0.1 ± 0 | 0 ± 0 | 3.4 ± 0.3 | 28 ± 1 | 34.6 ± 1 | 1 ± 0.1 | 4.2 ± 0.2 | 2.2 ± 0.5 | 0.3 ± 0 | 0.9 ± 0.1 | 0.7 ± 0 | 0.1 ± 0 |
| LBFNQW (n = 51) | 4.8 ± 0.2 | 0.1 ± 0 | 0 ± 0 | 3.2 ± 0.3 | 27.6 ± 1.5 | 33.5 ± 1.1 | 1 ± 0.1 | 4.2 ± 0.3 | 2 ± 0.3 | 0.3 ± 0 | 1.3 ± 0.3 | 0.9 ± 0.1 | 0.2 ± 0.1 |
| LBFBAP (n = 19) | 4.8 ± 0.1 | 0.1 ± 0 | 0 ± 0 | 3 ± 0.2 | 26 ± 0.9 | 33.8 ± 1 | 1.2 ± 0.1 | 3.4 ± 0.2 | 2.4 ± 0.3 | 0.3 ± 0 | 0.8 ± 0 | 0.7 ± 0 | 0.2 ± 0 |
| LBFDAU (n = 10) | 5.2 ± 1 | 0.2 ± 0 | 0 ± 0 | 3.3 ± 0.3 | 20.5 ± 0.9 | 31.8 ± 0.5 | 0.9 ± 0.1 | 4.1 ± 0.2 | 2.5 ± 0.2 | 0.3 ± 0 | 0.9 ± 0.1 | 0.6 ± 0.1 | 0.2 ± 0 |
| LBFPRA (n = 16) | 4.9 ± 0.2 | 0.2 ± 0 | 0 ± 0 | 2.6 ± 0.6 | 25.4 ± 2.2 | 31 ± 1.3 | 1.3 ± 0.2 | 5.4 ± 0.8 | 2 ± 0.4 | 0.2 ± 0.1 | 0.8 ± 0.1 | 0.8 ± 0 | 0.1 ± 0 |
| LBFIFU (n = 11) | 4.7 ± 0.2 | 0.1 ± 0 | 0 ± 0 | 3.8 ± 0.9 | 25.9 ± 2.6 | 34.7 ± 1.3 | 1.1 ± 0.3 | 3.6 ± 0.6 | 2.7 ± 0.9 | 0.3 ± 0.1 | 0.9 ± 0.1 | 0.7 ± 0 | 0.1 ± 0 |
| LBFDKD (n = 2) | 5.1 ± 0.2 | 0.2 ± 0 | 0 ± 0 | 3 ± 0.9 | 26.1 ± 3.9 | 35.6 ± 0.6 | 0.6 ± 0 | 4.8 ± 0.7 | 1.3 ± 0.4 | 0.2 ± 0.1 | 0.9 ± 0.2 | 0.8 ± 0 | 0.3 ± 0 |
| LBFDJG (n = 12) | 4.4 ± 0.1 | 0.1 ± 0 | 0 ± 0 | 3.4 ± 0.3 | 27.3 ± 1.4 | 33.1 ± 1.9 | 1.1 ± 0.2 | 3.6 ± 0.1 | 2.1 ± 0.4 | 0.4 ± 0.1 | 0.9 ± 0.1 | 0.6 ± 0.2 | 0.1 ± 0 |
| LBFLFK (n = 15) | 5.1 ± 0.3 | 0.2 ± 0 | 0 ± 0 | 2.5 ± 0.1 | 28.7 ± 1.6 | 29 ± 1.7 | 1.2 ± 0.2 | 5.6 ± 0.4 | 1.5 ± 0.2 | 0.2 ± 0 | 0.8 ± 0 | 0.7 ± 0 | 0.1 ± 0 |
| LBFLCG (n = 15) | 4.9 ± 0.3 | 0.1 ± 0 | 0 ± 0 | 3.6 ± 0.3 | 25.8 ± 1.4 | 34.1 ± 0.8 | 0.9 ± 0.1 | 4.4 ± 0.2 | 1.9 ± 0.2 | 0.3 ± 0 | 0.9 ± 0 | 0.6 ± 0 | 0.1 ± 0 |
| LBFPQM (n = 12) | 5.2 ± 0.3 | 0.1 ± 0 | 0 ± 0 | 3.8 ± 0.4 | 26.3 ± 1.2 | 31.6 ± 1 | 1.2 ± 0.1 | 4.3 ± 0.4 | 1.8 ± 0.2 | 0.2 ± 0 | 1.1 ± 0.1 | 0.9 ± 0.1 | 0.2 ± 0.1 |
| LBFDHG (n = 5) | 5.4 ± 0.1 | 0.2 ± 0 | 0 ± 0 | 2.3 ± 0.2 | 24 ± 0.6 | 34 ± 0.7 | 1 ± 0.1 | 4.1 ± 0.2 | 2.7 ± 0.1 | 0.3 ± 0 | 0.7 ± 0 | 0.7 ± 0 | 0.1 ± 0 |
| LBFDKA (n = 5) | 5.1 ± 0.3 | 0.1 ± 0 | 0 ± 0 | 3.7 ± 0.4 | 24.2 ± 2.8 | 29.7 ± 1.1 | 1.5 ± 0.3 | 4.4 ± 0.3 | 1.8 ± 0.1 | 0.2 ± 0 | 1.1 ± 0.1 | 0.9 ± 0.1 | 0.2 ± 0.1 |
| LBFIDT (n = 7) | 5 ± 0.1 | 0.2 ± 0 | 0 ± 0 | 2.6 ± 0.1 | 27 ± 1.7 | 30.8 ± 1.2 | 1.1 ± 0.2 | 6.2 ± 0.4 | 1.8 ± 0.2 | 0.4 ± 0.1 | 0.8 ± 0 | 0.7 ± 0 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDGG (n = 50) | 0.1 ± 0 | 2.7 ± 0.2 | 1.5 ± 0.1 | 2.2 ± 0.3 | 7.7 ± 0.8 | 0.4 ± 0 | 0 ± 0 | 0.3 ± 0.1 | 1.9 ± 0.2 | 0.2 ± 0 | 1.4 ± 0.3 | 0.3 ± 0.1 | 0.2 ± 0.1 |
| LBFGKN (n = 50) | 0.1 ± 0 | 2.8 ± 0.2 | 1.4 ± 0.1 | 2.3 ± 0.2 | 8.1 ± 0.9 | 0.4 ± 0 | 0 ± 0 | 0.3 ± 0 | 1.9 ± 0.2 | 0 ± 0 | 1.4 ± 0.3 | 0.2 ± 0 | 0.2 ± 0 |
| LBFIHE (n = 34) | 0.1 ± 0 | 3.1 ± 0.3 | 1.5 ± 0.2 | 2.5 ± 0.4 | 8.4 ± 1 | 0.4 ± 0 | 0 ± 0 | 0.3 ± 0.1 | 1.6 ± 0.2 | 0.1 ± 0 | 1.5 ± 0.3 | 0.2 ± 0.1 | 0.3 ± 0.1 |

TABLE 138-continued

Fatty acid profiles of T2 seeds harvested from T1 plants cultivated in the greenhouse of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | | | | | | | | | | | | | | |
|---|---|---|---|---|---|---|---|---|---|---|---|---|---|---|
| LBFLDI (n = 60) | 0.2 ± 0.1 | 2.6 ± 0.2 | 1.6 ± 0.2 | 1.7 ± 0.2 | 8.2 ± 1.7 | 0.4 ± 0 | 0 ± 0 | 0.3 ± 0.1 | 2.4 ± 0.5 | 0.1 ± 0 | 1.4 ± 0.3 | 0.3 ± 0 | 0.4 ± 0.1 |
| LBFPNF (n = 52) | 0 ± 0 | 3.5 ± 0.3 | 1.5 ± 0.4 | 2.5 ± 0.2 | 9.8 ± 0.8 | 0.4 ± 0 | 0 ± 0 | 0.3 ± 0 | 2.7 ± 0.3 | 0.1 ± 0 | 1.2 ± 0.1 | 0.3 ± 0 | 0.2 ± 0.1 |
| LBFNSQ (n = 51) | 0.1 ± 0 | 4.3 ± 0.6 | 2.2 ± 0.3 | 1.6 ± 0.4 | 6.8 ± 1.4 | 0.4 ± 0 | 0 ± 0 | 0.4 ± 0 | 1.7 ± 0.3 | 0.1 ± 0 | 1.3 ± 0.3 | 0.6 ± 0.2 | 0.5 ± 0.3 |
| LBFDGL (n = 57) | 0.1 ± 0 | 4.7 ± 0.7 | 3 ± 0.5 | 0.8 ± 0.3 | 5.5 ± 1.8 | 0.4 ± 0 | 0 ± 0 | 0.3 ± 0.1 | 1.4 ± 0.3 | 0.1 ± 0 | 1 ± 0.4 | 0.9 ± 0.3 | 0.2 ± 0.1 |
| LBFIEF (n = 6) | 0.1 ± 0.1 | 4.2 ± 0.3 | 2.5 ± 0.3 | 0.7 ± 0.3 | 5.2 ± 0.8 | 0.4 ± 0 | 0 ± 0 | 0.4 ± 0.1 | 1.6 ± 0.3 | 0.1 ± 0 | 1 ± 0.3 | 0.9 ± 0.2 | 0.2 ± 0 |
| LBFBAV (n = 50) | 0.1 ± 0.1 | 10.9 ± 0.7 | 6.5 ± 0.5 | 0.1 ± 0.1 | 1.8 ± 0.7 | 0.4 ± 0 | 0 ± 0 | 0.1 ± 0.1 | 0.8 ± 0.3 | 0.1 ± 0.1 | 0.3 ± 0.1 | 3 ± 0.5 | 0.7 ± 0.1 |
| LBFPNC (n = 32) | 0 ± 0 | 4.9 ± 0.9 | 2 ± 0.4 | 2.4 ± 0.7 | 6.9 ± 1.6 | 0.4 ± 0.1 | 0 ± 0 | 0.3 ± 0.1 | 1.9 ± 0.5 | 0.1 ± 0 | 0.9 ± 0.2 | 0.4 ± 0.2 | 0.4 ± 0.1 |
| LBFGHQ (n = 46) | 0.1 ± 0 | 2.5 ± 0.3 | 1.7 ± 0.2 | 0.6 ± 0.1 | 4.9 ± 0.7 | 0.4 ± 0 | 0 ± 0 | 0.3 ± 0 | 1.9 ± 0.3 | 0.2 ± 0 | 1 ± 0.2 | 0.8 ± 0.1 | 0.3 ± 0.1 |
| LBFAZB (n = 49) | 0.1 ± 0 | 6.3 ± 0.7 | 3.3 ± 0.3 | 0.8 ± 0.2 | 4.5 ± 0.9 | 0.3 ± 0 | 0 ± 0 | 0.4 ± 0 | 1.4 ± 0.2 | 0.1 ± 0 | 0.9 ± 0.2 | 1.5 ± 0.3 | 0.2 ± 0 |
| LBFGKW (n = 72) | 0.1 ± 0 | 6 ± 0.7 | 3.3 ± 0.4 | 0.5 ± 0.1 | 4.1 ± 0.8 | 0.4 ± 0 | 0 ± 0 | 0.4 ± 0.1 | 1.5 ± 0.3 | 0.1 ± 0 | 0.8 ± 0.2 | 1.7 ± 0.3 | 0.3 ± 0.1 |
| LBFNRU (n = 58) | 0.1 ± 0 | 5.9 ± 0.7 | 3.6 ± 0.5 | 0.4 ± 0.1 | 4.2 ± 0.9 | 0.4 ± 0 | 0 ± 0 | 0.4 ± 0 | 1.7 ± 0.4 | 0.1 ± 0 | 0.9 ± 0.3 | 1.9 ± 0.4 | 0.3 ± 0.1 |
| LBFGIZ (n = 43) | 0.2 ± 0 | 5.7 ± 0.8 | 3.5 ± 0.5 | 0.6 ± 0.1 | 5.3 ± 1.1 | 0.4 ± 0 | 0 ± 0 | 0.4 ± 0.1 | 2.1 ± 0.4 | 0.1 ± 0 | 1 ± 0.2 | 1.7 ± 0.4 | 0.4 ± 0.1 |
| LBFIGM (n = 56) | 0.1 ± 0 | 5 ± 0.7 | 2.5 ± 0.3 | 1 ± 0.2 | 5.4 ± 1 | 0.4 ± 0 | 0 ± 0 | 0.4 ± 0.1 | 2 ± 0.5 | 0.4 ± 2.2 | 1 ± 0.2 | 1.2 ± 0.2 | 0.3 ± 0.1 |
| LBFNRR (n = 61) | 0.1 ± 0 | 5.3 ± 1.2 | 3.5 ± 0.3 | 0.4 ± 0.1 | 4.4 ± 1.1 | 0.4 ± 0 | 0 ± 0 | 0.3 ± 0 | 1.7 ± 0.4 | 0 ± 0 | 0.8 ± 0.2 | 1.7 ± 0.3 | 0.3 ± 0.1 |
| LBFNTK (n = 69) | 0.1 ± 0 | 6.7 ± 0.8 | 3.8 ± 0.5 | 0.6 ± 0.2 | 5 ± 0.9 | 0.4 ± 0 | 0 ± 0 | 0.5 ± 0.1 | 2 ± 0.4 | 0.1 ± 0 | 0.9 ± 0.2 | 1.8 ± 0.3 | 0.5 ± 0.1 |
| LBFGJA (n = 42) | 0.1 ± 0 | 4.7 ± 0.6 | 1.5 ± 0.2 | 1.3 ± 0.2 | 3.8 ± 0.6 | 0.3 ± 0 | 0 ± 0 | 0.7 ± 0.1 | 1.4 ± 0.2 | 0.1 ± 0 | 0.8 ± 0.2 | 1.2 ± 0.2 | 0.1 ± 0 |
| LBFIFV (n = 58) | 0.1 ± 0 | 6.3 ± 0.6 | 2.5 ± 0.2 | 1.3 ± 0.2 | 4.2 ± 0.7 | 0.4 ± 0 | 0 ± 0 | 0.4 ± 0.1 | 1.1 ± 0.2 | 0.1 ± 0 | 1.1 ± 0.3 | 1 ± 0.2 | 0.2 ± 0 |
| LBFLER (n = 52) | 0.1 ± 0 | 5.9 ± 0.6 | 2.9 ± 0.3 | 1.1 ± 0.2 | 5.3 ± 0.7 | 0.4 ± 0 | 0 ± 0 | 0.5 ± 0.1 | 1.7 ± 0.2 | 0 ± 0 | 1 ± 0.2 | 1.1 ± 0.2 | 0.2 ± 0.1 |
| LBFLDL (n = 44) | 0.1 ± 0 | 5.2 ± 0.6 | 2.5 ± 0.4 | 1.2 ± 0.3 | 5.5 ± 0.7 | 0.4 ± 0 | 0 ± 0 | 0.6 ± 0.1 | 1.9 ± 0.2 | 0.1 ± 0 | 0.8 ± 0.2 | 1 ± 0.2 | 0.2 ± 0 |
| LBFNQW (n = 51) | 0.1 ± 0.1 | 5.3 ± 0.5 | 2.7 ± 0.4 | 1.1 ± 0.2 | 6.2 ± 1 | 0.4 ± 0 | 0 ± 0 | 0.5 ± 0.1 | 2 ± 0.3 | 0.1 ± 0 | 0.9 ± 0.2 | 0.8 ± 0.4 | 0.5 ± 0.1 |
| LBFBAP (n = 19) | 0.1 ± 0 | 7.4 ± 0.7 | 2.9 ± 0.3 | 2.1 ± 0.3 | 6.2 ± 0.8 | 0.3 ± 0 | 0 ± 0 | 0.3 ± 0 | 1.7 ± 0.2 | 0.1 ± 0 | 1.1 ± 0.1 | 0.6 ± 0.1 | 0.4 ± 0.1 |
| LBFDAU (n = 10) | 0.1 ± 0 | 4.2 ± 0.2 | 3.1 ± 0.3 | 1.6 ± 0.3 | 13.9 ± 1 | 0.4 ± 0 | 0 ± 0 | 0.2 ± 0 | 2.3 ± 0.2 | 0.1 ± 0 | 2.6 ± 0.4 | 0.4 ± 0.1 | 0.3 ± 0 |
| LBFPRA (n = 16) | 0.1 ± 0 | 2.9 ± 0.6 | 1.6 ± 0.3 | 3 ± 0.3 | 12.3 ± 1.4 | 0.4 ± 0 | 0 ± 0 | 0.2 ± 0 | 2.7 ± 0.2 | 0 ± 0 | 1.4 ± 0.2 | 0.1 ± 0 | 0.4 ± 0.1 |
| LBFIFU (n = 11) | 0.1 ± 0 | 4.2 ± 0.6 | 1.7 ± 0.3 | 2.7 ± 0.5 | 8 ± 1.8 | 0.3 ± 0 | 0 ± 0 | 0.4 ± 0.1 | 2 ± 0.3 | 0.1 ± 0.1 | 1.3 ± 0.4 | 0.3 ± 0.2 | 0.2 ± 0 |
| LBFDKD (n = 2) | 0.2 ± 0 | 5.1 ± 1.6 | 3 ± 1.3 | 0.9 ± 0.4 | 5.7 ± 0.7 | 0.4 ± 0 | 0 ± 0 | 0.5 ± 0.1 | 2.2 ± 0.5 | 0.1 ± 0 | 1.1 ± 0.2 | 1.4 ± 0.7 | 0.3 ± 0 |
| LBFDJG (n = 12) | 0 ± 0 | 6.1 ± 1.1 | 2.6 ± 0.4 | 1.6 ± 0.4 | 6.8 ± 1.4 | 0.4 ± 0 | 0 ± 0 | 0.4 ± 0.1 | 1.7 ± 0.2 | 0.1 ± 0 | 1.3 ± 0.4 | 1 ± 0.4 | 0.4 ± 0.1 |
| LBFLFK (n = 15) | 0.1 ± 0 | 3.8 ± 0.3 | 2.4 ± 0.1 | 1.3 ± 0.1 | 9.9 ± 0.8 | 0.4 ± 0.1 | 0 ± 0 | 0.5 ± 0 | 3 ± 0.3 | 0.1 ± 0 | 1.8 ± 0.2 | 0.6 ± 0.1 | 0.3 ± 0.1 |
| LBFLCG (n = 15) | 0.1 ± 0 | 3.7 ± 0.5 | 2.2 ± 0.3 | 1.4 ± 0.2 | 9 ± 0.7 | 0.3 ± 0 | 0 ± 0 | 0.4 ± 0.1 | 2.5 ± 0.2 | 0.1 ± 0 | 1.6 ± 0.3 | 0.6 ± 0.2 | 0.2 ± 0 |
| LBFPQM (n = 12) | 0.2 ± 0 | 4.8 ± 0.6 | 3 ± 0.4 | 1.1 ± 0.2 | 8.2 ± 1.1 | 0.4 ± 0 | 0 ± 0 | 0.4 ± 0.1 | 2.2 ± 0.2 | 0.1 ± 0 | 1.5 ± 0.2 | 0.8 ± 0.1 | 0.5 ± 0.2 |
| LBFDHG (n = 5) | 0.1 ± 0 | 3 ± 0.1 | 1.7 ± 0.1 | 1.7 ± 0.1 | 10.4 ± 0.8 | 0.4 ± 0 | 0 ± 0 | 0.6 ± 0.1 | 2.4 ± 0.1 | 0.3 ± 0 | 2.7 ± 0.2 | 0.5 ± 0 | 0.2 ± 0 |
| LBFDKA (n = 5) | 0.2 ± 0 | 7.6 ± 0.6 | 5.1 ± 0.8 | 0.6 ± 0.1 | 6.6 ± 1 | 0.4 ± 0 | 0 ± 0 | 0.3 ± 0.1 | 2 ± 0.3 | 0.1 ± 0 | 1.3 ± 0.5 | 1.8 ± 0.2 | 0.9 ± 0 |
| LBFIDT (n = 7) | 0.1 ± 0 | 4.5 ± 1.3 | 3 ± 0.9 | 1 ± 0.2 | 8.2 ± 0.6 | 0.4 ± 0 | 0 ± 0 | 0.5 ± 0.1 | 2.6 ± 0.2 | 0.1 ± 0 | 1.7 ± 0.2 | 1 ± 0.3 | 0.3 ± 0.1 |

TABLE 139

Fatty acid profiles of one T2 seed batch per event harvested from T1 plants cultivated in the greenhouse of canola events containing theT-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDGG (n = 1) | 4.6 | 0.2 | 0.0 | 2.6 | 26.6 | 34.2 | 0.8 | 4.6 | 2.0 | 0.3 | 0.8 | 0.7 | 0.1 |
| LBFGKN (n = 1) | 4.7 | 0.2 | 0.0 | 3.0 | 25.0 | 34.6 | 0.8 | 4.3 | 2.2 | 0.3 | 0.8 | 0.7 | 0.2 |
| LBFIHE (n = 1) | 4.8 | 0.1 | 0.0 | 3.0 | 23.7 | 34.1 | 0.9 | 3.6 | 4.0 | 0.4 | 1.0 | 0.9 | 0.2 |
| LBFLDI (n = 1) | 6.4 | 0.1 | 0.0 | 2.1 | 28.5 | 28.4 | 0.9 | 5.9 | 1.2 | 0.2 | 0.7 | 0.7 | 0.3 |
| LBFPNF (n = 1) | 5.4 | 0.2 | 0.0 | 2.3 | 26.9 | 28.9 | 1.3 | 5.1 | 3.0 | 0.4 | 0.8 | 0.7 | 0.1 |
| LBFNSQ (n = 1) | 4.7 | 0.1 | 0.0 | 2.4 | 23.6 | 34.2 | 1.0 | 4.7 | 2.2 | 0.4 | 0.7 | 0.0 | 0.3 |
| LBFDGL (n = 1) | 4.9 | 0.1 | 0.0 | 2.5 | 23.9 | 32.2 | 1.0 | 6.0 | 1.7 | 0.3 | 0.7 | 0.7 | 0.1 |
| LBFIEF (n = 1) | 4.7 | 0.1 | 0.0 | 3.0 | 27.0 | 37.2 | 0.6 | 5.1 | 1.4 | 0.2 | 1.0 | 0.7 | 0.2 |
| LBFBAV (n = 1) | 5.9 | 0.2 | 0.0 | 2.5 | 23.9 | 27.6 | 1.0 | 5.7 | 1.8 | 0.3 | 0.9 | 0.7 | 0.1 |
| LBFPNC (n = 1) | 4.7 | 0.1 | 0.0 | 2.3 | 19.8 | 35.1 | 0.6 | 3.9 | 2.7 | 0.3 | 0.6 | 0.7 | 0.2 |
| LBFGHQ (n = 1) | 5.4 | 0.2 | 0.0 | 2.3 | 28.7 | 31.5 | 0.5 | 9.0 | 1.4 | 0.6 | 0.9 | 0.8 | 0.1 |
| LBFAZB (n = 1) | 5.1 | 0.1 | 0.0 | 3.1 | 26.6 | 30.1 | 1.6 | 4.7 | 2.5 | 0.4 | 0.8 | 0.6 | 0.0 |
| LBFGKW (n = 1) | 4.4 | 0.2 | 0.0 | 2.0 | 26.5 | 31.5 | 1.2 | 6.8 | 1.9 | 0.3 | 0.6 | 0.7 | 0.1 |
| LBFNRU (n = 1) | 5.0 | 0.2 | 0.0 | 2.5 | 27.2 | 26.6 | 0.9 | 8.0 | 1.4 | 0.3 | 0.8 | 0.7 | 0.1 |
| LBFGIZ (n = 1) | 5.2 | 0.2 | 0.0 | 2.3 | 27.3 | 31.2 | 0.7 | 6.1 | 1.5 | 0.2 | 0.7 | 0.4 | 0.2 |
| LBFIGM (n = 1) | 4.9 | 0.1 | 0.0 | 2.5 | 28.9 | 29.6 | 1.6 | 5.8 | 1.8 | 0.3 | 0.8 | 0.8 | 0.1 |
| LBFNRR (n = 1) | 4.8 | 0.1 | 0.0 | 2.8 | 27.3 | 26.9 | 1.9 | 6.5 | 1.9 | 0.3 | 0.9 | 0.8 | 0.1 |
| LBFNTK (n = 1) | 4.9 | 0.2 | 0.0 | 2.4 | 29.0 | 27.5 | 1.1 | 6.8 | 1.4 | 0.2 | 0.7 | 0.7 | 0.2 |
| LBFGJA (n = 1) | 5.2 | 0.2 | 0.0 | 3.0 | 27.1 | 33.5 | 2.1 | 3.4 | 5.2 | 0.6 | 0.8 | 0.7 | 0.1 |
| LBFIFV (n = 1) | 4.8 | 0.1 | 0.0 | 3.4 | 21.6 | 34.4 | 0.8 | 3.5 | 2.8 | 0.3 | 0.9 | 0.7 | 0.2 |
| LBFLER (n = 1) | 5.1 | 0.2 | 0.0 | 2.8 | 22.8 | 32.5 | 1.1 | 3.7 | 4.1 | 0.5 | 0.8 | 0.7 | 0.1 |
| LBFLDL (n = 1) | 4.7 | 0.1 | 0.0 | 3.4 | 26.9 | 33.7 | 1.0 | 4.4 | 1.8 | 0.2 | 0.9 | 0.7 | 0.1 |
| LBFNQW (n = 1) | 4.8 | 0.1 | 0.0 | 2.7 | 24.8 | 33.0 | 1.1 | 4.3 | 2.0 | 0.3 | 1.6 | 0.9 | 0.2 |
| LBFBAP (n = 1) | 4.9 | 0.1 | 0.0 | 3.2 | 24.5 | 31.9 | 1.4 | 3.2 | 2.7 | 0.3 | 0.8 | 0.7 | 0.2 |
| LBFDAU (n = 1) | 4.6 | 0.2 | 0.0 | 3.4 | 18.7 | 31.8 | 0.9 | 4.1 | 2.9 | 0.4 | 0.8 | 0.7 | 0.2 |
| LBFPRA (n = 1) | 4.8 | 0.1 | 0.0 | 3.2 | 21.9 | 28.7 | 1.8 | 4.4 | 2.7 | 0.3 | 0.9 | 0.8 | 0.1 |
| LBFIFU (n = 1) | 4.8 | 0.1 | 0.0 | 3.2 | 22.4 | 34.7 | 0.9 | 4.5 | 2.5 | 0.3 | 0.7 | 0.6 | 0.2 |
| LBFDKD (n = 1) | 5.0 | 0.2 | 0.0 | 2.4 | 28.9 | 35.2 | 0.6 | 5.3 | 1.0 | 0.1 | 0.7 | 0.8 | 0.3 |
| LBFDJG (n = 1) | 4.4 | 0.1 | 0.0 | 3.3 | 25.4 | 32.3 | 1.2 | 3.5 | 2.3 | 0.5 | 0.9 | 0.7 | 0.1 |
| LBFLFK (n = 1) | 5.2 | 0.2 | 0.0 | 2.5 | 26.2 | 29.0 | 1.2 | 5.9 | 1.7 | 0.3 | 0.8 | 0.7 | 0.1 |
| LBFLCG (n = 1) | 5.0 | 0.2 | 0.0 | 4.4 | 22.6 | 34.7 | 0.7 | 4.1 | 2.1 | 0.3 | 1.1 | 0.6 | 0.1 |
| LBFPQM (n = 1) | 5.1 | 0.2 | 0.0 | 3.3 | 25.7 | 30.4 | 1.4 | 4.4 | 1.9 | 0.3 | 1.0 | 0.9 | 0.2 |
| LBFDHG (n = 1) | 5.4 | 0.2 | 0.0 | 2.1 | 23.9 | 33.5 | 1.1 | 4.0 | 2.6 | 0.3 | 0.7 | 0.7 | 0.1 |
| LBFDKA (n = 1) | 5.6 | 0.2 | 0.0 | 3.2 | 20.9 | 30.0 | 1.3 | 3.9 | 1.9 | 0.2 | 1.0 | 1.0 | 0.3 |
| LBFIDT (n = 1) | 5.1 | 0.2 | 0.0 | 2.6 | 26.4 | 32.0 | 1.0 | 5.7 | 2.0 | 0.4 | 0.8 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDGG (n = 1) | 0.1 | 2.7 | 1.6 | 2.8 | 9.7 | 0.4 | 0.0 | 0.3 | 2.2 | 0.2 | 1.9 | 0.2 | 0.3 |
| LBFGKN (n = 1) | 0.1 | 3.1 | 1.7 | 2.5 | 10.4 | 0.3 | 0.0 | 0.4 | 2.4 | 0.1 | 2.0 | 0.2 | 0.2 |
| LBFIHE (n = 1) | 0.1 | 3.1 | 1.3 | 3.3 | 10.3 | 0.4 | 0.0 | 0.3 | 1.9 | 0.1 | 1.8 | 0.2 | 0.3 |
| LBFLDI (n = 1) | 0.2 | 3.0 | 1.9 | 1.7 | 10.8 | 0.3 | 0.0 | 0.4 | 3.3 | 0.2 | 1.7 | 0.4 | 0.4 |
| LBFPNF (n = 1) | 0.0 | 3.3 | 1.6 | 2.8 | 11.0 | 0.4 | 0.0 | 0.2 | 3.2 | 0.1 | 1.7 | 0.3 | 0.2 |
| LBFNSQ (n = 1) | 0.1 | 4.3 | 2.3 | 2.3 | 10.2 | 0.4 | 0.0 | 0.5 | 2.2 | 0.1 | 2.0 | 0.4 | 0.7 |
| LBFDGL (n = 1) | 0.1 | 4.6 | 2.9 | 1.4 | 10.1 | 0.4 | 0.0 | 0.3 | 2.0 | 0.2 | 2.2 | 1.0 | 0.3 |
| LBFIEF (n = 1) | 0.3 | 4.3 | 2.6 | 0.9 | 5.9 | 0.4 | 0.0 | 0.5 | 1.4 | 0.1 | 1.2 | 0.7 | 0.2 |
| LBFBAV (n = 1) | 0.3 | 10.2 | 7.6 | 0.3 | 4.2 | 0.5 | 0.0 | 0.0 | 2.0 | 0.0 | 1.1 | 2.6 | 0.4 |
| LBFPNC (n = 1) | 0.1 | 4.3 | 1.8 | 4.6 | 11.4 | 0.3 | 0.0 | 0.6 | 3.9 | 0.1 | 1.1 | 0.4 | 0.3 |
| LBFGHQ (n = 1) | 0.1 | 2.6 | 2.1 | 0.6 | 6.5 | 0.4 | 0.0 | 0.3 | 2.8 | 0.2 | 1.6 | 0.9 | 0.4 |
| LBFAZB (n = 1) | 0.1 | 5.4 | 2.9 | 1.6 | 8.7 | 0.4 | 0.0 | 0.4 | 2.2 | 0.1 | 1.5 | 0.9 | 0.3 |
| LBFGKW (n = 1) | 0.1 | 6.7 | 4.1 | 0.5 | 5.9 | 0.3 | 0.0 | 0.4 | 2.0 | 0.2 | 1.2 | 2.0 | 0.3 |
| LBFNRU (n = 1) | 0.2 | 6.0 | 4.6 | 0.4 | 7.0 | 0.4 | 0.0 | 0.4 | 3.0 | 0.1 | 1.8 | 1.9 | 0.3 |
| LBFGIZ (n = 1) | 0.2 | 5.3 | 3.1 | 1.0 | 7.4 | 0.4 | 0.0 | 0.5 | 2.8 | 0.1 | 1.4 | 1.4 | 0.5 |
| LBFIGM (n = 1) | 0.1 | 5.0 | 2.5 | 1.5 | 7.9 | 0.4 | 0.0 | 0.4 | 2.2 | 0.1 | 1.5 | 0.9 | 0.4 |
| LBFNRR (n = 1) | 0.1 | 5.4 | 3.7 | 0.8 | 8.9 | 0.4 | 0.0 | 0.3 | 2.5 | 0.1 | 1.6 | 1.1 | 0.5 |
| LBFNTK (n = 1) | 0.1 | 5.9 | 3.6 | 1.0 | 7.3 | 0.4 | 0.0 | 0.6 | 3.0 | 0.1 | 1.1 | 1.5 | 0.4 |
| LBFGJA (n = 1) | 0.1 | 4.2 | 1.6 | 1.5 | 5.4 | 0.3 | 0.0 | 0.7 | 1.6 | 0.2 | 1.2 | 1.0 | 0.2 |
| LBFIFV (n = 1) | 0.1 | 6.8 | 2.9 | 2.2 | 7.6 | 0.4 | 0.0 | 0.6 | 1.8 | 0.3 | 2.6 | 1.0 | 0.2 |
| LBFLER (n = 1) | 0.1 | 6.4 | 3.2 | 1.7 | 7.9 | 0.3 | 0.0 | 0.7 | 2.1 | 0.1 | 1.9 | 1.1 | 0.2 |
| LBFLDL (n = 1) | 0.1 | 4.6 | 2.6 | 1.2 | 7.8 | 0.4 | 0.0 | 0.6 | 2.4 | 0.1 | 1.3 | 0.8 | 0.3 |
| LBFNQW (n = 1) | 0.1 | 5.1 | 3.0 | 1.3 | 8.6 | 0.3 | 0.0 | 0.5 | 2.5 | 0.1 | 1.4 | 0.9 | 0.4 |
| LBFBAP (n = 1) | 0.1 | 7.6 | 3.1 | 2.5 | 7.6 | 0.3 | 0.0 | 0.3 | 1.9 | 0.0 | 1.3 | 0.7 | 0.4 |
| LBFDAU (n = 1) | 0.1 | 4.2 | 3.4 | 1.5 | 15.1 | 0.3 | 0.0 | 0.2 | 2.5 | 0.1 | 3.0 | 0.4 | 0.3 |
| LBFPRA (n = 1) | 0.1 | 3.6 | 2.0 | 3.4 | 15.6 | 0.4 | 0.0 | 0.2 | 2.5 | 0.0 | 1.8 | 0.1 | 0.5 |
| LBFIFU (n = 1) | 0.1 | 4.2 | 2.3 | 2.1 | 9.6 | 0.2 | 0.0 | 0.5 | 2.5 | 0.2 | 2.3 | 0.6 | 0.2 |
| LBFDKD (n = 1) | 0.2 | 4.0 | 2.1 | 1.2 | 6.2 | 0.4 | 0.0 | 0.6 | 2.5 | 0.1 | 1.0 | 0.9 | 0.3 |
| LBFDJG (n = 1) | 0.1 | 5.5 | 2.6 | 2.1 | 9.0 | 0.4 | 0.0 | 0.4 | 1.8 | 0.1 | 1.9 | 0.6 | 0.4 |
| LBFLFK (n = 1) | 0.1 | 3.4 | 2.4 | 1.3 | 11.4 | 0.4 | 0.0 | 0.5 | 3.4 | 0.1 | 2.3 | 0.6 | 0.3 |
| LBFLCG (n = 1) | 0.1 | 3.4 | 2.1 | 1.6 | 10.1 | 0.4 | 0.0 | 0.5 | 2.6 | 0.1 | 2.3 | 0.6 | 0.2 |
| LBFPQM (n = 1) | 0.2 | 4.3 | 2.5 | 1.8 | 10.2 | 0.4 | 0.0 | 0.4 | 2.6 | 0.1 | 1.8 | 0.6 | 0.5 |
| LBFDHG (n = 1) | 0.1 | 3.0 | 1.8 | 1.7 | 11.4 | 0.4 | 0.0 | 0.6 | 2.4 | 0.3 | 2.8 | 0.5 | 0.2 |

TABLE 139-continued

Fatty acid profiles of one T2 seed batch per event harvested from T1 plants cultivated in the greenhouse of canola events containing the T-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| | | | | | | | | | | | | | |
|---|---|---|---|---|---|---|---|---|---|---|---|---|---|
| LBFDKA (n = 1) | 0.2 | 8.3 | 5.8 | 0.7 | 7.6 | 0.3 | 0.0 | 0.4 | 2.2 | 0.1 | 1.8 | 2.0 | 0.9 |
| LBFIDT (n = 1) | 0.1 | 3.5 | 2.2 | 1.3 | 9.1 | 0.4 | 0.0 | 0.6 | 2.8 | 0.1 | 2.0 | 0.7 | 0.2 |

TABLE 140

Fatty acid profiles of T2 seeds harvested from T1 plants cultivated in the greenhouse of canola events containing the T-DNAs of plasmids VC-LTM593-1qcz rc. Plants of all events combined have been grouped into the categories indicated in the first column; as defined in Table 131. In addition to those categories, the catergory "dc" was sub-divided into the category dc sl: all T1 plants where the average of all copy number assays listed in Table 135 was 3.51-4.49, and the zygocity analysis listed in Table 137 revelead a single locus insertion of both copies, and into the category dc dl: all T1 plants where the average of all copy number assays listed in Table 135 was 3.51-4.49, and the zygocity analysis listed in Table 137 revelead a double locus insertion of both copies. The number of T1 plants fullfilling these criteria are displayed in parentheses. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 172) | 5.1 ± 0.9 | 0.2 ± 0.1 | 0 ± 0 | 2.8 ± 0.5 | 29.1 ± 3 | 33.8 ± 2.8 | 0.8 ± 0.2 | 4.8 ± 0.9 | 1.9 ± 0.7 | 0.3 ± 0.2 | 0.8 ± 0.1 | 0.8 ± 0.1 | 0.2 ± 0.2 |
| dc (n = 813) | 4.9 ± 0.4 | 0.2 ± 0 | 0 ± 0 | 2.9 ± 0.5 | 29.1 ± 2.6 | 32 ± 3.1 | 1.1 ± 0.3 | 5.3 ± 1.3 | 1.9 ± 1 | 0.3 ± 0.1 | 0.9 ± 0.2 | 0.7 ± 0.1 | 0.1 ± 0 |
| dc sl (n = 700) | 4.9 ± 0.4 | 0.2 ± 0 | 0 ± 0 | 2.8 ± 0.4 | 29.4 ± 2.5 | 31.9 ± 3.2 | 1.1 ± 0.3 | 5.4 ± 1.4 | 1.9 ± 1.1 | 0.3 ± 0.1 | 0.8 ± 0.2 | 0.7 ± 0.1 | 0.1 ± 0 |
| dc dl (n = 64) | 5 ± 0.5 | 0.2 ± 0 | 0 ± 0 | 3.2 ± 0.6 | 26.3 ± 2.5 | 32.2 ± 2.4 | 1.1 ± 0.2 | 4.5 ± 0.7 | 1.9 ± 0.4 | 0.3 ± 0.1 | 0.9 ± 0.1 | 0.7 ± 0.1 | 0.1 ± 0 |

| Category of T1 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 172) | 0.1 ± 0.1 | 2.8 ± 0.3 | 1.5 ± 0.2 | 2.1 ± 0.4 | 7.9 ± 1.3 | 0.4 ± 0 | 0 ± 0 | 0.3 ± 0.1 | 1.9 ± 0.4 | 0.1 ± 0.1 | 1.4 ± 0.3 | 0.3 ± 0.1 | 0.3 ± 0.1 |
| dc (n = 813) | 0.1 ± 0 | 5.9 ± 1.7 | 3.1 ± 1.1 | 0.9 ± 0.5 | 5.1 ± 2.1 | 0.4 ± 0 | 0 ± 0 | 0.4 ± 0.1 | 1.7 ± 0.5 | 0.1 ± 0.6 | 1 ± 0.4 | 1.4 ± 0.7 | 0.3 ± 0.1 |
| dc sl (n = 700) | 0.1 ± 0 | 6 ± 1.7 | 3.2 ± 1.2 | 0.9 ± 0.6 | 4.8 ± 1.7 | 0.4 ± 0 | 0 ± 0 | 0.4 ± 0.2 | 1.7 ± 0.5 | 0.1 ± 0.6 | 0.9 ± 0.3 | 1.4 ± 0.7 | 0.3 ± 0.2 |
| dc dl (n = 64) | 0.1 ± 0 | 4.3 ± 1.1 | 2.5 ± 0.5 | 1.4 ± 0.3 | 9 ± 2 | 0.4 ± 0 | 0 ± 0 | 0.4 ± 0.1 | 2.4 ± 0.5 | 0.1 ± 0.1 | 1.7 ± 0.5 | 0.7 ± 0.3 | 0.3 ± 0.1 |

TABLE 141

Fatty acid profiles of T2 seeds harvested from T1 plants cultivated in the greenhouse of canola events containing the T-DNAs of plasmids VC-LTM593-1qcz rc. Plants of all events combined have been grouped into the categories indicated in the first column as defined in the description of Table 140. For each category, the fatty acid profile of the plant having the highest EPA + DHA levels was shown. Per seed batch a random selection of ~30 seed was measured in two technical repeats.

| Category of T1 plants | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| sc (n = 1) | 6.4 | 0.1 | 0.0 | 3.0 | 23.7 | 34.1 | 0.9 | 3.6 | 4.0 | 0.4 | 1.0 | 0.9 | 0.2 |
| dc (n = 1) | 4.6 | 0.1 | 0.0 | 2.3 | 19.8 | 35.1 | 0.6 | 3.9 | 2.7 | 0.3 | 0.6 | 0.7 | 0.2 |

TABLE 141-continued

Fatty acid profiles of T2 seeds harvested from T1 plants cultivated in the greenhouse of canola events containing the T-DNAs of plasmids VC-LTM593-1qcz rc. Plants of all events combined have been grouped into the categories indicated in the first column as defined in the description of Table 140. For each category, the fatty acid profile of the plant having the highest EPA + DHA levels was shown. Per seed batch a random selection of ~30 seed was measured in two technical repeats.

| | | | | | | | | | | | | | |
|---|---|---|---|---|---|---|---|---|---|---|---|---|---|
| dc sl (n = 1) | 4.8 | 0.1 | 0.0 | 2.3 | 19.8 | 35.1 | 0.6 | 3.9 | 2.7 | 0.3 | 0.6 | 0.7 | 0.2 |
| dc dl (n = 1) | 4.6 | 0.3 | 0.0 | 2.7 | 20.4 | 31.3 | 0.8 | 3.9 | 2.3 | 0.3 | 0.7 | 0.5 | 0.2 |

| Category of T1 plants | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| sc (n = 1) | 0.1 | 3.1 | 1.3 | 3.3 | 10.3 | 0.4 | 0.0 | 0.3 | 1.9 | 0.1 | 1.8 | 0.2 | 0.3 |
| dc (n = 1) | 0.1 | 4.3 | 1.8 | 4.6 | 11.4 | 0.3 | 0.0 | 0.6 | 3.9 | 0.1 | 1.1 | 0.4 | 0.3 |
| dc sl (n = 1) | 0.1 | 4.3 | 1.8 | 4.6 | 11.4 | 0.3 | 0.0 | 0.6 | 3.9 | 0.1 | 1.1 | 0.4 | 0.3 |
| dc dl (n = 1) | 0.1 | 3.9 | 2.5 | 2.4 | 13.7 | 0.3 | 0.0 | 0.3 | 2.6 | 0.2 | 2.9 | 0.4 | 0.2 |

TABLE 142

Phenotypic rating of T1 plants cultivated in the greenhouse of canola events containing the T-DNAs of plasmids VC-LTM593-1qcz rc. The events are indicated in the first column, along with the number of T1 plants that where rated per event. DFF: days to first flower (days), DF: deformed flower (1 = deformed, 9 = normal), DL: deformed leaf (1 = deformed, 9 = normal), DP: deformed plant (1 = deformed, 9 = normal), DS: deformed silique (1 = deformed, 9 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), Nol: number of lobes (#), PH: plant height (cm), TKW: thousand kernel weight (g), SC: seed quality (1 = good, 9 = bad), Oil: oil content (% of seed weight), protein: Protein content (% of seed cake without oil)

| Event | DFF | DF | DL | DP | DS | FC | LD |
|---|---|---|---|---|---|---|---|
| LBFDGG (n = 50) | 43.6 ± 2.7 | 9 ± 0 | 9 ± 0 | 9 ± 0 | 8.1 ± 1.6 | 3 ± 0 | 5 ± 0 |
| LBFGKN (n = 50) | 43.3 ± 1.7 | 9 ± 0 | 9 ± 0 | 9 ± 0 | 8.1 ± 0.7 | 3 ± 0 | 5 ± 0 |
| LBFIHE (n = 34) | 47.4 ± 5.1 | 9 ± 0 | 9 ± 0 | 9 ± 0 | 6.6 ± 1.6 | 3 ± 0 | 5 ± 0 |
| LBFLDI (n = 60) | 35.8 ± 2.9 | 9 ± 0 | 7.5 ± 0.6 | 8.9 ± 0.7 | 8.2 ± 1.1 | 3 ± 0 | 4 ± 0.5 |
| LBFPNF (n = 52) | 35.3 ± 2.2 | 9 ± 0 | 7.6 ± 0.6 | 8.8 ± 0.5 | 8.4 ± 0.6 | 3 ± 0 | 3.9 ± 0.3 |
| LBFNSQ (n = 51) | 45.2 ± 7 | 9 ± 0 | 7.7 ± 0.9 | 6.8 ± 1.3 | 6.8 ± 1.2 | 3 ± 0 | 5 ± 0.2 |
| LBFDGL (n = 57) | 43.9 ± 2.4 | 9 ± 0 | 9 ± 0 | 9 ± 0 | 7.7 ± 0.8 | 3 ± 0 | 5 ± 0 |
| LBFIEF (n = 6) | 47.2 ± 5 | 9 ± 0 | 9 ± 0 | 9 ± 0 | 4 ± 2 | 3 ± 0 | 5 ± 0 |
| LBFBAV (n = 50) | 46.6 ± 1.6 | 9 ± 0 | 7.4 ± 0.8 | 9 ± 0 | 8.9 ± 0.3 | 3 ± 0 | 5 ± 0 |
| LBFPNC (n = 32) | 44.6 ± 4.2 | 9 ± 0 | 9 ± 0 | 9 ± 0 | 8.3 ± 0.7 | 3 ± 0 | 5 ± 0 |
| LBFGHQ (n = 46) | 44.4 ± 4 | 9 ± 0 | 7.3 ± 1.9 | 9 ± 0 | 8.9 ± 0.3 | 3 ± 0 | 5 ± 0 |
| LBFAZB (n = 49) | 47.6 ± 3.2 | 9 ± 0 | 9 ± 0 | 9 ± 0 | 7.9 ± 0.8 | 3 ± 0 | 5 ± 0 |
| LBFGKW (n = 72) | 46.7 ± 1.9 | 9 ± 0 | 7.3 ± 0.5 | 9 ± 0 | 8.9 ± 0.3 | 3 ± 0 | 5 ± 0 |
| LBFNRU (n = 58) | 41.4 ± 1.7 | 9 ± 0 | 7.6 ± 0.6 | 8.9 ± 0.7 | 8.2 ± 0.7 | 3 ± 0 | 5 ± 0 |
| LBFGIZ (n = 43) | 41.5 ± 2.8 | 9 ± 0 | 7.6 ± 0.6 | 9 ± 0 | 8.3 ± 0.5 | 3 ± 0 | 5 ± 0 |
| LBFIGM (n = 56) | 36.1 ± 1.3 | 9 ± 0 | 6.7 ± 0.8 | 9 ± 0.3 | 8.8 ± 0.4 | 3 ± 0 | 2.7 ± 0.7 |
| LBFNRR (n = 61) | 41.3 ± 2.2 | 9 ± 0 | 7.8 ± 0.6 | 9 ± 0 | 8 ± 0.6 | 3 ± 0 | 5 ± 0 |
| LBFNTK (n = 69) | 34.5 ± 2.8 | 8 ± 0 | 6.6 ± 1.1 | 9 ± 0 | 8.7 ± 0.5 | 3 ± 0 | 2.4 ± 0.6 |
| LBFGJA (n = 42) | 45.1 ± 1 | 9 ± 0 | 9 ± 0 | 9 ± 0 | 7.6 ± 0.5 | 3 ± 0 | 5 ± 0 |
| LBFIFV (n = 58) | 42.4 ± 0.6 | 9 ± 0 | 9 ± 0 | 9 ± 0 | 8.8 ± 0.6 | 3 ± 0 | 5 ± 0 |
| LBFLER (n = 52) | 45.1 ± 3.5 | 9 ± 0 | 9 ± 0 | 9 ± 0 | 8.5 ± 0.7 | 3 ± 0 | 5 ± 0 |
| LBFLDL (n = 44) | 44.7 ± 3.7 | 9 ± 0 | 9 ± 0 | 9 ± 0 | 8.5 ± 0.6 | 3 ± 0 | 5 ± 0 |
| LBFNQW (n = 51) | 42.8 ± 1.9 | 9 ± 0 | 9 ± 0 | 9 ± 0 | 8.7 ± 0.5 | 3 ± 0 | 5 ± 0 |
| LBFBAP (n = 19) | 43.3 ± 1.8 | 9 ± 0 | 9 ± 0 | 9 ± 0 | 8.9 ± 0.2 | 3 ± 0 | 5 ± 0 |
| LBFDAU (n = 10) | 43.6 ± 1.7 | 9 ± 0 | 9 ± 0 | 9 ± 0 | 9 ± 0 | 3 ± 0 | 5 ± 0 |
| LBFPRA (n = 16) | 47.8 ± 2.5 | 9 ± 0 | 7.9 ± 0.8 | 7.8 ± 0.4 | 7.4 ± 0.8 | 3 ± 0 | 5.2 ± 0.4 |
| LBFIFU (n = 11) | 46.8 ± 6.4 | 9 ± 0 | 8.7 ± 0.9 | 8.7 ± 0.9 | 7.3 ± 1.1 | 3 ± 0 | 5 ± 0 |
| LBFDKD (n = 2) | 43 ± 4.2 | 9 ± 0 | 9 ± 0 | 9 ± 0 | 7.5 ± 0.7 | 3 ± 0 | 5 ± 0 |
| LBFDJG (n = 12) | 45.1 ± 1 | 9 ± 0 | 9 ± 0 | 9 ± 0 | 8.8 ± 0.6 | 3 ± 0 | 5 ± 0 |
| LBFLFK (n = 15) | 42.5 ± 5.5 | 9 ± 0 | 7.9 ± 1.2 | 8.7 ± 1.3 | 8.1 ± 1.3 | 3 ± 0 | 4.9 ± 0.5 |
| LBFLCG (n = 15) | 42.5 ± 0.6 | 9 ± 0 | 9 ± 0 | 9 ± 0 | 9 ± 0 | 3 ± 0 | 5 ± 0 |
| LBFPQM (n = 12) | 42.7 ± 2.5 | 9 ± 0 | 9 ± 0 | 9 ± 0 | 8.7 ± 0.5 | 3 ± 0 | 5 ± 0 |
| LBFDHG (n = 5) | 44.8 ± 3 | 9 ± 0 | 9 ± 0 | 9 ± 0 | 6.4 ± 0.9 | 3 ± 0 | 5 ± 0 |
| LBFDKA (n = 5) | 48.6 ± 1.7 | 9 ± 0 | 9 ± 0 | 9 ± 0 | 9 ± 0 | 3 ± 0 | 5 ± 0 |
| LBFIDT (n = 7) | 46.3 ± 1.3 | 9 ± 0 | 7.7 ± 0.5 | 9 ± 0 | 8 ± 0 | 3 ± 0 | 5 ± 0 |

| Event | LGC | LF | NoL | PH | TKW | SC | Oil | Protein |
|---|---|---|---|---|---|---|---|---|
| LBFDGG (n = 50) | 5 ± 0 | 8.1 ± 1.6 | 4.5 ± 0.8 | 118.8 ± 6.1 | 4.4 ± 0.3 | 3.5 ± 0.9 | 36.1 | 30.2 |
| LBFGKN (n = 50) | 5 ± 0 | 8.1 ± 0.7 | 5.1 ± 0.8 | 112.4 ± 4.1 | 4.4 ± 0.3 | 3 ± 0.8 | 36.9 | 30.1 |
| LBFIHE (n = 34) | 5 ± 0 | 6.6 ± 1.6 | 5.6 ± 0.9 | 105.7 ± 6.3 | 4.2 ± 0.5 | 3.8 ± 0.6 | 36.0 | 29.4 |
| LBFLDI (n = 60) | 4 ± 0 | 8.4 ± 1.2 | 5.4 ± 0.9 | 94 ± 5.1 | 3.6 ± 0.8 | 4.8 ± 1.8 | 36.9 | 30.1 |
| LBFPNF (n = 52) | 4 ± 0 | 8.3 ± 1.2 | 5.3 ± 0.9 | 88.4 ± 7.9 | 3.6 ± 0.9 | 3.5 ± 0.7 | 39.1 | 28.3 |
| LBFNSQ (n = 51) | 4.1 ± 0.5 | 8.7 ± 0.6 | 5 ± 1 | 109.6 ± 10.9 | 3.4 ± 0.3 | 4.4 ± 1.8 | 37.5 | 28.7 |

TABLE 142-continued

Phenotypic rating of T1 plants cultivated in the greenhouse of canola events containing the T-DNAs of plasmids VC-LTM593-1qcz rc.
The events are indicated in the first column, along with the number of T1 plants that where rated per event. DFF: days to first flower (days), DF: deformed flower (1 = deformed, 9 = normal), DL: deformed leaf (1 = deformed, 9 = normal), DP: deformed plant (1 = deformed, 9 = normal), DS: deformed silique (1 = deformed, 9 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm), TKW: thousand kernel weight (g), SC: seed quality (1 = good, 9 = bad), Oil: oil content (% of seed weight), protein: Protein content (% of seed cake without oil),

| | | | | | | | | |
|---|---|---|---|---|---|---|---|---|
| LBFDGL (n = 57) | 5 ± 0 | 7.7 ± 0.8 | 5.1 ± 0.8 | 109.4 ± 6.6 | 4.1 ± 0.4 | 2.8 ± 0.7 | 36.9 | 29.9 |
| LBFIEF (n = 6) | 5 ± 0 | 4 ± 2 | 6.2 ± 0.8 | 98.3 ± 4.1 | 3.4 ± 0.3 | 3.8 ± 1 | 38.9 | 29.9 |
| LBFBAV (n = 50) | 4 ± 0 | 9 ± 0 | 3.5 ± 0.5 | 125.1 ± 5.6 | 2.7 ± 0.3 | 3.9 ± 1 | 39.0 | 28.0 |
| LBFPNC (n = 32) | 5 ± 0 | 8.3 ± 0.7 | 5.5 ± 0.9 | 105.6 ± 5.6 | 4.1 ± 0.3 | 2.8 ± 0.5 | 39.4 | 28.3 |
| LBFGHQ (n = 46) | 4 ± 0 | 9 ± 0.1 | 3.9 ± 0.7 | 124.5 ± 6.2 | 2.6 ± 0.3 | 3.7 ± 0.9 | 38.3 | 27.8 |
| LBFAZB (n = 49) | 5 ± 0 | 7.9 ± 0.8 | 5.1 ± 0.8 | 112.3 ± 4.9 | 3.9 ± 0.4 | 2.6 ± 0.6 | 38.2 | 29.4 |
| LBFGKW (n = 72) | 4 ± 0 | 8.9 ± 0.3 | 4.1 ± 0.6 | 125.2 ± 6.2 | 2.6 ± 0.3 | 3.7 ± 0.8 | 38.8 | 27.9 |
| LBFNRU (n = 58) | 4 ± 0 | 8.9 ± 0.8 | 5.6 ± 0.8 | 117 ± 5 | 2.6 ± 0.3 | 3.6 ± 1.3 | 39.5 | 27.6 |
| LBFGIZ (n = 43) | 4 ± 0 | 8.9 ± 0.3 | 5.3 ± 0.9 | 113.5 ± 5.9 | 2.4 ± 0.2 | 3.9 ± 0.7 | 38.4 | 28.6 |
| LBFIGM (n = 56) | 4 ± 0 | 8.8 ± 0.5 | 3.9 ± 0.7 | 107.6 ± 9 | 2.7 ± 0.3 | 3.4 ± 0.8 | 39.1 | 28.6 |
| LBFNRR (n = 61) | 4 ± 0 | 9 ± 0 | 5.3 ± 0.6 | 116.5 ± 6.3 | 2.9 ± 0.3 | 3.2 ± 0.9 | 40.6 | 27.1 |
| LBFNTK (n = 69) | 4 ± 0 | 8.8 ± 0.7 | 3.7 ± 0.6 | 93.4 ± 8.2 | 2.8 ± 0.3 | 3.8 ± 0.8 | 39.8 | 28.3 |
| LBFGJA (n = 42) | 5 ± 0 | 7.6 ± 0.5 | 4.3 ± 1.1 | 113.3 ± 2.4 | 4.9 ± 0.2 | 2.4 ± 0.8 | 32.9 | 25.6 |
| LBFIFV (n = 58) | 5 ± 0 | 8.8 ± 0.6 | 4.5 ± 0.8 | 113.1 ± 2.4 | 4.2 ± 0.2 | 2.6 ± 0.6 | 37.3 | 29.4 |
| LBFLER (n = 52) | 5 ± 0 | 8.5 ± 0.7 | 5.6 ± 1 | 108.3 ± 6.8 | 3.9 ± 0.3 | 2.6 ± 0.7 | 40.8 | 27.7 |
| LBFLDL (n = 44) | 5 ± 0 | 8.5 ± 0.6 | 5.1 ± 0.8 | 109.3 ± 5.3 | 4 ± 0.2 | 2.6 ± 0.8 | 38.6 | 29.2 |
| LBFNQW (n = 51) | 5 ± 0 | 8.7 ± 0.5 | 5.7 ± 0.9 | 105.5 ± 6.3 | 4.1 ± 0.3 | 3.1 ± 0.5 | 38.4 | 28.9 |
| LBFBAP (n = 19) | 5 ± 0 | 8.9 ± 0.2 | 4.6 ± 0.8 | 117.4 ± 6.1 | 4 ± 0.5 | 2.4 ± 0.5 | 38.7 | 28.8 |
| LBFDAU (n = 10) | 5 ± 0 | 8.5 ± 1.6 | 4.4 ± 0.8 | 110 ± 5.8 | 4.5 ± 0.5 | 2.6 ± 0.5 | 34.5 | 30.2 |
| LBFPRA (n = 16) | 4 ± 0 | 9 ± 0 | 5.6 ± 0.8 | 123.4 ± 4 | 4.2 ± 0.6 | 2.3 ± 0.8 | 38.1 | 28.2 |
| LBFIFU (n = 11) | 5 ± 0 | 7.3 ± 1.1 | 5.6 ± 1.1 | 103.6 ± 8.1 | 3.8 ± 0.5 | 3.5 ± 0.9 | 37.4 | 28.7 |
| LBFDKD (n = 2) | 5 ± 0 | 7.5 ± 0.7 | 5 ± 1.4 | 107.5 ± 10.6 | 4.3 ± 0.8 | 4 ± 1.4 | 36.6 | 31.2 |
| LBFDJG (n = 12) | 5 ± 0 | 8.8 ± 0.6 | 4.3 ± 1 | 104.2 ± 29.8 | 3.8 ± 0.2 | 2.8 ± 0.5 | 37.7 | 29.8 |
| LBFLFK (n = 15) | 4 ± 0 | 8.9 ± 0.4 | 5.1 ± 1.2 | 113.7 ± 9 | 4.1 ± 1 | 3.7 ± 0.6 | 39.3 | 27.2 |
| LBFLCG (n = 15) | 5 ± 0 | 8.7 ± 1 | 4.5 ± 0.8 | 113.7 ± 2.3 | 4.3 ± 0.5 | 2.7 ± 0.8 | 37.7 | 29.1 |
| LBFPQM (n = 12) | 5 ± 0 | 8.7 ± 0.5 | 5.5 ± 1 | 110 ± 6 | 4.2 ± 0.5 | 2.8 ± 0.4 | 39.2 | 27.7 |
| LBFDHG (n = 5) | 5 ± 0 | 6.4 ± 0.9 | 4.2 ± 0.8 | 115 ± 0 | 4.2 ± 0.2 | 5 ± 0 | 33.5 | 28.0 |
| LBFDKA (n = 5) | 5 ± 0 | 9 ± 0 | 5.6 ± 0.9 | 108 ± 4.5 | 3.8 ± 0.2 | 2.4 ± 0.5 | 40.0 | 26.6 |
| LBFIDT (n = 7) | 4 ± 0 | 9 ± 0 | 4.1 ± 0.7 | 125.7 ± 6.7 | 2.5 ± 0.2 | 3.7 ± 0.5 | 38.1 | 28.0 |

TABLE 143

Phenotypic rating of T1 plants cultivated in the greenhouse of canola events containing the T-DNAs of plasmids VC-LTM593-1qcz rc.
Plants of all events combined have been grouped into the categories indicated in the first column as defined in the description of Table 140. The number of T1 plants fullfilling these criteria are displayed in parentheses. DFF: days to first flower (days), DF: deformed flower (1 = deformed, 9 = normal), DL: deformed leaf (1 = deformed, 9 = normal), DP: deformed plant (1 = deformed, 9 = normal), DS: deformed silique (1 = deformed, 9 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm), TKW: thousand kernel weight (g), SC: seed quality (1 = good, 9 = bad), Oil: oil content (% of seed weight), protein: Protein content (% of seed cake without oil)

| Category of T1 plants | DFF | DF | DL | DP | DS | FC | LD | LGC |
|---|---|---|---|---|---|---|---|---|
| sc (n = 177) | 41.5 ± 5.2 | 9 ± 0 | 8.6 ± 0.7 | 9 ± 0.4 | 7.9 ± 1.5 | 3 ± 0 | 4.8 ± 0.5 | 4.8 ± 0.4 |
| dc (n = 781) | 43.4 ± 4.4 | 8.9 ± 0.3 | 8.1 ± 1.1 | 9 ± 0.3 | 8.4 ± 0.8 | 3 ± 0 | 4.6 ± 0.9 | 4.5 ± 0.5 |
| dc sl (n = 677) | 43.1 ± 4.4 | 8.9 ± 0.3 | 8 ± 1.1 | 9 ± 0.2 | 8.5 ± 0.8 | 3 ± 0 | 4.6 ± 1 | 4.4 ± 0.5 |
| dc dl (n = 55) | 43.3 ± 3.3 | 9 ± 0 | 8.7 ± 0.8 | 8.9 ± 0.6 | 8.4 ± 1 | 3 ± 0 | 5 ± 0.3 | 4.8 ± 0.4 |

| Category of T1 plants | LF | NoL | PH | TKW | SC | oil | protein |
|---|---|---|---|---|---|---|---|
| sc (n = 177) | 8 ± 1.5 | 5.1 ± 1 | 109.1 ± 10.6 | 3.9 ± 0.6 | 3.8 ± 1.4 | 37 ± 1.4 | 29.5 ± 0.9 |
| dc (n = 781) | 8.6 ± 0.8 | 4.7 ± 1.1 | 112.2 ± 11 | 3.3 ± 0.8 | 3.2 ± 1 | 38 ± 2.1 | 28.5 ± 1.2 |
| dc sl (n = 677) | 8.7 ± 0.8 | 4.7 ± 1.1 | 112.3 ± 11 | 3.3 ± 0.8 | 3.2 ± 1 | 38.4 ± 1.8 | 28.3 ± 1.1 |
| dc dl (n = 55) | 8.5 + 1.1 | 4.8 ± 1.1 | 110.8 ± 14.3 | 3.5 ± 0.7 | 3.2 ± 0.9 | 36.6 ± 2.7 | 28.9 ± 1.7 |

Fatty Acid Profiles, Copy Number Measurements, and Phenotypic Observations of T1 Plants Carrying T-DNAs of Plasmids VC-LTM593-1Qcz Rc Cultivated in Field Trials in USDA Growth Zone 11 During Winter.

Certain events that had higher levels of EPA and DHA were tested in the field and examined for fatty acid profile, aerial phenotype (if any) and copy number in the T1 generation. A variety of constructs were examined including those with partial double copy insertions, single copy insertions and double copy insertions being represented (see Table 144). Table 145 indicates that LBFDAU had an EPA content of ca. 13% and a DHA content of ca. 3% of the total seed fatty acid content, and a maximum content for DHA of 3.6% and EPA of 17% of total seed fatty acids (Table 146). Measurements of single seeds from LBFDAU had as much as 26% EPA and 4.6% DHA, see Table 147. Overall the field performance of LBFDAU matched or exceeded that of the greenhouse.

TABLE 144

Copy number measurement of T1 plants cultivated in field, corresponding to USDA growth zone 11, during the winter for field trials of canola events containing the T-DNAs of plasmids VC-LTM593-1qcz rc. The events are indicated in the first column, along with the number of T1 plants that where measured per event. The T1 plants underwent a selection from ~80 segregating T1 seedlings, using zygocity analysis similar to the selection performed in the greenhouse (which was illustrated in Table 137), keeping only plants that are homozygous for the desired number of loci. A copy number of ~2 therefore was indicative for one homozygous copy, a copy number of ~4 indicative for two homozygous copies (located either at on or at two different loci) and so forth. Odd results of 3, 5, 7, 9 etc indicate that at least some of the selected T1 plants carry at least one heterozygous locus. Homozygocity was indicated if the average result of the selected T1 plants was about two fold higher than the the result oberved in the T0 generation (indicated in parentheses). For some events this was not the case because during selection of T1 plants, undesired loci have been segregated out while retaining only desired loci in a homozygous state.

Copy number assays targeting the T-DNA of VC-LTM593-lqcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo (Ot_GA3) | c-d4Des (Pl_GA)2 | j-p-LuPXR_i-Atss15 | j-p-PvARC5_t-BnSETL | c-d5Des (Tc_GA) | j-i-Atss18_c-o3Des (Pir_GA2) | j-p-BnSETL-v1-c-o3Des(Pir_GA) |
|---|---|---|---|---|---|---|---|---|
| LBFDGG (n = 5) | 2 (T0: 1.1) | | | | | | | |
| LBFGKN (n = 12) | 2.1 (T0: 1) | | | | | | | |
| LBFIHE (n = 8) | 2.1 (T0: 1) | | | | | | | |
| LBFLDI (n = 13) | 2 (T0: 1) | | | | | | | |
| LBFPNF (n = 9) | 2 (T0: 1.1) | | | | | | | |
| LBFDAU (n = 4) | 2 (T0: 1.1) | | | | | | | |
| LBFPRA (n = 5) | 3.2 (T0: 2) | | | | | | | |
| LBFLFK (n = 4) | 3.9 (T0: 2) | | | | | | | |
| LBFLCG (n = 3) | 4.3 (T0: 1.9) | | | | | | | |
| LBFPQM (n = 1) | 3.7 (T0: 2) | | | | | | | |

| | Copy number assays targeting the T-DNA of VC-LTM593-lqcz rc. Assays are listed according to the position of the assay target along the T-DNA, with target c-AHAS located near the left T-DNA border and target c-d6Elo(Pp_GA) near the right T-DNA border. | | | | | | Conclusion from individual assays: |
|---|---|---|---|---|---|---|---|
| Event | j-i-Atss14_c-d12Des (Ps_GA) | c-d6Elo (Tp_GA) | j-t-StCAT_p2_p-LuPXR | j-iAtss2_c-d6Des (Otfebit_GA) | c-d5Des (Tc_GA) | c-d6Elo (Pp_GA) | number of T-DNA copies inserted into the genome |
| LBFDGG (n = 5) | | | 1.9 (T0: 1) | | | 1.9 (T0: 1) | single copy |
| LBFGKN (n = 12) | | | 2 (T0: 1) | | | 1.9 (T0: 1.1) | single copy |
| LBFIHE (n = 8) | | | 1.9 (T0: 1.2) | | | 1.9 (T0: 1.1) | single copy |
| LBFLDI (n = 13) | | | 1.9 (T0: 1) | | | 1.8 (T0: 1) | single copy |
| LBFPNF (n = 9) | | | 3.7 (T0: 1.9) | | | 3.3 (T0: 1.9) | partial double copy |
| LBFDAU (n = 4) | | | 3.8 (T0: 2.4) | | | 3.6 (T0: 1.9) | partial double copy |
| LBFPRA (n = 5) | | | 4.9 (T0: 3.1) | | | 4 (T0: 2.8) | partial double copy |
| LBFLFK (n = 4) | | | 3.4 (T0: 2.4) | | | 3.4 (T0: 2) | partial double copy |
| LBFLCG (n = 3) | | | 2.9 (T0: 2.5) | | | 3.4 (T0: 2) | partial double copy |
| LBFPQM (n = 1) | | | (T0: 2) | | | 3.9 (T0: 1.8) | partial double copy |

TABLE 145

Fatty acid profiles of T2 seeds harvested from T1 plants cultivated in the field, corresponding to USDA growth zone 11, during winter of canola events containing the T-DNAs of plasmids VC-LTM593-1qcz rc. The events are indicated in the first column, along with the number of T2 seed batches that were measured per event. Per seed batch a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDGG (n = 5) | 4.4 ± 0.2 | 0.2 ± 0 | 0.1 ± 0 | 2.4 ± 0.1 | 32.3 ± 1.9 | 34.4 ± 1.6 | 0.7 ± 0 | 5.3 ± 0.6 | 1.5 ± 0.1 | 0.4 ± 0.1 | 0.6 ± 0 | 0.7 ± 0 | 0.1 ± 0 |
| LBFGKN (n = 12) | 4.8 ± 0.3 | 0.2 ± 0 | 0.1 ± 0 | 2.6 ± 0.3 | 27.8 ± 1.9 | 36 ± 1.3 | 0.5 ± 0.1 | 4.8 ± 0.7 | 1.5 ± 0.2 | 0.4 ± 0.1 | 0.7 ± 0.1 | 0.7 ± 0 | 0.2 ± 0.1 |

TABLE 145-continued

Fatty acid profiles of T2 seeds harvested from T1 plants cultivated in the field,
corresponding to USDA growth zone 11, during winter of canola events containing the T-DNAs of plasmids
VC-LTM593-1qcz rc. The events are indicated in the first column, along with the number of T2 seed batches that
were measured per event. Per seed batch a random selection of ~30 seed was measured in two technical repeats.

| | | | | | | | | | | | | | |
|---|---|---|---|---|---|---|---|---|---|---|---|---|---|
| LBFIHE (n = 8) | 4.9 ± 0.8 | 0.3 ± 0.1 | 0.1 ± 0 | 2.4 ± 0.4 | 30.8 ± 3.1 | 36.1 ± 1.2 | 0.5 ± 0.1 | 5.4 ± 1.3 | 1.5 ± 0.5 | 0.3 ± 0.1 | 0.7 ± 0.1 | 0.7 ± 0.1 | 0.2 ± 0 |
| LBFLDI (n = 13) | 4.5 ± 1.1 | 0.2 ± 0.1 | 0.1 ± 0 | 2.3 ± 0.6 | 30 ± 5.9 | 35.4 ± 6.1 | 0.5 ± 0.1 | 4.1 ± 0.8 | 1.3 ± 0.3 | 0.3 ± 0.1 | 0.6 ± 0.1 | 0.7 ± 0.1 | 0.2 ± 0 |
| LBFPNF (n = 9) | 4.7 ± 0.2 | 0.2 ± 0 | 0.1 ± 0 | 2.4 ± 0.3 | 29.2 ± 1.8 | 31.7 ± 1 | 1.1 ± 0.1 | 4 ± 0.6 | 2.6 ± 1.4 | 0.6 ± 0.1 | 0.7 ± 0 | 0.7 ± 0 | 0.1 ± 0 |
| LBFDAU (n = 4) | 4.6 ± 0.2 | 0.2 ± 0 | 0.1 ± 0 | 2.3 ± 0.3 | 24.3 ± 3.7 | 31.2 ± 2.5 | 0.8 ± 0.1 | 5.2 ± 0.6 | 2.2 ± 0.5 | 0.4 ± 0.1 | 0.6 ± 0 | 0.7 ± 0.1 | 0.1 ± 0 |
| LBFPRA (n = 5) | 4.8 ± 0.2 | 0.2 ± 0 | 0.1 ± 0 | 2.5 ± 0.4 | 25.1 ± 0.9 | 34.5 ± 2.4 | 0.9 ± 0.2 | 4.4 ± 0.7 | 2.2 ± 0.2 | 0.4 ± 0.1 | 0.6 ± 0.1 | 0.7 ± 0 | 0.1 ± 0 |
| LBFLFK (n = 4) | 5.1 ± 0.8 | 0.2 ± 0.1 | 0.1 ± 0 | 2.1 ± 0.4 | 27 ± 4.3 | 32.3 ± 0.5 | 0.8 ± 0.1 | 5.4 ± 0.8 | 1.9 ± 0.5 | 0.4 ± 0 | 0.6 ± 0.1 | 0.7 ± 0.1 | 0.2 ± 0 |
| LBFLCG (n = 3) | 4.8 ± 0.2 | 0.2 ± 0 | 0.1 ± 0 | 3 ± 0.3 | 26.4 ± 1.3 | 33.3 ± 1 | 0.8 ± 0 | 4.7 ± 0.7 | 2 ± 0.2 | 0.5 ± 0.1 | 0.7 ± 0 | 0.7 ± 0 | 0.1 ± 0 |
| LBFPQM (n = 1) | 5.0 | 0.2 | 0.1 | 2.7 | 26.1 | 30.8 | 1.0 | 4.3 | 2.3 | 0.5 | 0.7 | 0.6 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDGG (n = 5) | 0 ± 0 | 2 ± 0.2 | 1.1 ± 0.2 | 2.7 ± 0.3 | 6.9 ± 0.7 | 0.3 ± 0 | 0 ± 0 | 0.3 ± 0 | 1.9 ± 0.2 | 0.1 ± 0 | 1.4 ± 0.3 | 0 ± 0 | 0.1 ± 0 |
| LBFGKN (n = 12) | 0.1 ± 0 | 2.3 ± 0.2 | 1.1 ± 0.2 | 3.3 ± 0.4 | 8 ± 0.8 | 0.3 ± 0.1 | 0 ± 0 | 0.4 ± 0.1 | 1.9 ± 0.3 | 0.1 ± 0 | 1.8 ± 0.4 | 0.1 ± 0 | 0.2 ± 0 |
| LBFIHE (n = 8) | 0.1 ± 0 | 1.9 ± 0.5 | 0.9 ± 0.1 | 2.8 ± 0.7 | 6.4 ± 1.1 | 0.3 ± 0 | 0 ± 0 | 0.5 ± 0.1 | 1.7 ± 0.3 | 0.1 ± 0 | 1.3 ± 0.2 | 0 ± 0.1 | 0.1 ± 0 |
| LBFLDI (n = 13) | 0.1 ± 0 | 1.9 ± 0.5 | 0.8 ± 0.2 | 2.9 ± 0.8 | 6.4 ± 1.6 | 0.3 ± 0.1 | 0 ± 0 | 0.4 ± 0.1 | 1.6 ± 0.3 | 0.1 ± 0.1 | 1.3 ± 0.4 | 0.1 ± 0 | 0.1 ± 0 |
| LBFPNF (n = 9) | 0 ± 0 | 3.3 ± 0.4 | 1.2 ± 0.1 | 4.2 ± 0.5 | 8.4 ± 1.1 | 0.3 ± 0 | 0 ± 0 | 0.5 ± 0.1 | 2.3 ± 0.4 | 0.1 ± 0 | 1.5 ± 0.3 | 0.1 ± 0.1 | 0.1 ± 0 |
| LBFDAU (n = 4) | 0.1 ± 0 | 2.5 ± 0.4 | 1.7 ± 0.5 | 2.9 ± 0.4 | 13.4 ± 3.4 | 0.3 ± 0 | 0 ± 0 | 0.3 ± 0 | 2.7 ± 0.7 | 0.1 ± 0 | 2.7 ± 0.7 | 0.1 ± 0.1 | 0.2 ± 0 |
| LBFPRA (n = 5) | 0.1 ± 0 | 2.6 ± 0.6 | 1.3 ± 0.3 | 3.6 ± 0.6 | 10.7 ± 1.9 | 0.3 ± 0 | 0 ± 0 | 0.5 ± 0.1 | 2.3 ± 0.3 | 0.1 ± 0 | 1.7 ± 0.2 | 0.1 ± 0.1 | 0.2 ± 0.1 |
| LBFLFK (n = 4) | 0.1 ± 0 | 3.1 ± 0.6 | 1.7 ± 0.3 | 2.7 ± 0.5 | 9.5 ± 1.8 | 0.3 ± 0 | 0 ± 0 | 0.5 ± 0.2 | 2.9 ± 0.4 | 0.2 ± 0.1 | 2.1 ± 0.5 | 0.3 ± 0.1 | 0.2 ± 0 |
| LBFLCG (n = 3) | 0.1 ± 0 | 2.3 ± 0.1 | 1.2 ± 0.1 | 2.9 ± 0.2 | 9.9 ± 0.9 | 0.3 ± 0 | 0 ± 0 | 0.7 ± 0.1 | 2.6 ± 0.3 | 0.2 ± 0 | 2.3 ± 0.5 | 0.2 ± 0 | 0.2 ± 0 |
| LBFPQM (n = 1) | 0.1 | 3.4 | 1.8 | 2.8 | 10.8 | 0.3 | 0.0 | 0.5 | 2.5 | 0.3 | 2.5 | 0.4 | 0.2 |

TABLE 146

Fatty acid profiles of one T2 seed batch per event harvested from T1 plants cultivated in the field, corresponding to USDA growth zone
11, during winter of canola events containing the T-DNAs of plasmids VC-LTM593-1qcz rc. The events are indicated in the first column. Fatty acid
profiles of T2 seed batches having the highest EPA + DHA levels per event are shown. Per seed batch, a random selection of ~30 seed was measured
in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDGG (n = 1) | 4.5 | 0.21 | 0.1 | 2.4 | 29.86 | 33.45 | 0.71 | 5.74 | 1.69 | 0.45 | 0.62 | 0.74 | 0.12 |
| LBFGKN (n = 1) | 4.5 | 0.21 | 0.09 | 2.28 | 26.68 | 34.29 | 0.65 | 4.99 | 1.73 | 0.42 | 0.61 | 0.69 | 0.23 |
| LBFIHE (n = 1) | 4.8 | 0.22 | 0.09 | 2.95 | 26.2 | 38.09 | 0.52 | 3.19 | 2.12 | 0.22 | 0.78 | 0.69 | 0.15 |
| LBFLDI (n = 1) | 4.8 | 0.24 | 0.09 | 2.51 | 27.6 | 35.76 | 0.54 | 4.15 | 1.66 | 0.26 | 0.7 | 0.69 | 0.29 |
| LBFPNF (n = 1) | 4.9 | 0.27 | 0.13 | 2.11 | 26.29 | 31.14 | 0.91 | 5.04 | 1.72 | 0.68 | 0.67 | 0.7 | 0.11 |
| LBFDAU (n = 1) | 4.8 | 0.23 | 0.14 | 1.94 | 20.37 | 28.27 | 0.98 | 5.23 | 2.78 | 0.5 | 0.63 | 0.62 | 0.13 |
| LBFPRA (n = 1) | 4.7 | 0.16 | 0.14 | 1.92 | 25.56 | 32.27 | 1.21 | 4.87 | 2.09 | 0.44 | 0.51 | 0.66 | 0.13 |
| LBFLFK (n = 1) | 4.9 | 0.21 | 0.12 | 2.34 | 22.43 | 32.9 | 0.9 | 4.55 | 2.5 | 0.42 | 0.66 | 0.62 | 0.13 |
| LBFLCG (n = 1) | 5.0 | 0.27 | 0.12 | 2.65 | 24.88 | 32.2 | 0.74 | 5.16 | 2.3 | 0.46 | 0.69 | 0.65 | 0.14 |
| LBFPQM (n = 1) | 5.0 | 0.22 | 0.11 | 2.67 | 26.07 | 30.83 | 1.02 | 4.34 | 2.31 | 0.45 | 0.69 | 0.63 | 0.12 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDGG (n = 1) | 0.05 | 2.25 | 1.38 | 2.83 | 8.02 | 0.29 | 0 | 0.35 | 2.21 | 0.1 | 1.79 | 0 | 0.13 |
| LBFGKN (n = 1) | 0.1 | 2.43 | 1.22 | 3.34 | 9.74 | 0.31 | 0 | 0.48 | 2.27 | 0.17 | 2.31 | 0 | 0.23 |
| LBFIHE (n = 1) | 0 | 2.73 | 1.03 | 3.67 | 8.16 | 0.35 | 0 | 0.59 | 1.72 | 0.12 | 1.55 | 0 | 0.09 |
| LBFLDI (n = 1) | 0.1 | 2.63 | 1.16 | 3.5 | 8.32 | 0.31 | 0 | 0.47 | 1.89 | 0.19 | 1.85 | 0.15 | 0.21 |
| LBFPNF (n = 1) | 0.04 | 2.8 | 1.34 | 4.26 | 10.24 | 0.36 | 0 | 0.54 | 3.24 | 0.14 | 2.09 | 0.15 | 0.12 |
| LBFDAU (n = 1) | 0.13 | 3.08 | 2.3 | 2.51 | 17.57 | 0.36 | 0 | 0.29 | 3.16 | 0.09 | 3.62 | 0 | 0.25 |

TABLE 146-continued

Fatty acid profiles of one T2 seed batch per event harvested from T1 plants cultivated in the field, corresponding to USDA growth zone 11, during winter of canola events containing the T-DNAs of plasmids VC-LTM593-1qcz rc. The events are indicated in the first column. Fatty acid profiles of T2 seed batches having the highest EPA + DHA levels per event are shown. Per seed batch, a random selection of ~30 seed was measured in two technical repeats.

| | | | | | | | | | | | | |
|---|---|---|---|---|---|---|---|---|---|---|---|---|
| LBFPRA (n = 1) | 0.07 | 2.34 | 1.29 | 3.67 | 12.46 | 0.28 | 0 | 0.44 | 2.58 | 0.08 | 1.8 | 0.08 | 0.26 |
| LBFLFK (n = 1) | 0.07 | 3.86 | 2.18 | 2.37 | 11.06 | 0.3 | 0 | 0.76 | 3.2 | 0.24 | 2.66 | 0.46 | 0.21 |
| LBFLCG (n = 1) | 0.09 | 2.24 | 1.36 | 2.85 | 10.87 | 0.31 | 0 | 0.69 | 2.92 | 0.22 | 2.82 | 0.21 | 0.15 |
| LBFPQM (n = 1) | 0.07 | 3.4 | 1.75 | 2.78 | 10.78 | 0.3 | 0 | 0.54 | 2.53 | 0.27 | 2.5 | 0.4 | 0.23 |

TABLE 147

Fatty acid profiles of 95 single seeds of the one seedbatch of event LBFDAU shown in Table 146 having highest EPA + DHA levels.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU seed 1 | 4.2 | 0.2 | 0.2 | 2.1 | 11.3 | 26.5 | 1.2 | 3.8 | 4.3 | 0.6 | 0.7 | 0.5 | 0.1 |
| LBFDAU seed 2 | 5.5 | 0.3 | 0.1 | 2.5 | 14.3 | 25.0 | 0.8 | 4.5 | 2.5 | 0.5 | 0.7 | 0.5 | 0.2 |
| LBFDAU seed 3 | 5.1 | 0.3 | 0.1 | 2.0 | 16.0 | 25.5 | 1.2 | 4.4 | 3.4 | 0.6 | 0.7 | 0.5 | 0.1 |
| LBFDAU seed 4 | 6.7 | 0.4 | 0.2 | 3.8 | 15.8 | 23.5 | 1.5 | 4.9 | 3.3 | 0.9 | 1.2 | 0.5 | 0.0 |
| LBFDAU seed 5 | 5.4 | 0.4 | 0.2 | 1.5 | 16.1 | 24.4 | 1.0 | 5.4 | 3.4 | 0.8 | 0.6 | 0.5 | 0.1 |
| LBFDAU seed 6 | 5.5 | 0.3 | 0.1 | 1.9 | 16.6 | 25.6 | 0.9 | 5.3 | 3.3 | 0.7 | 0.7 | 0.6 | 0.1 |
| LBFDAU seed 7 | 5.0 | 0.4 | 0.2 | 2.4 | 16.3 | 25.3 | 1.1 | 4.6 | 3.5 | 0.6 | 0.7 | 0.5 | 0.1 |
| LBFDAU seed 8 | 5.3 | 0.3 | 0.1 | 2.3 | 17.4 | 26.0 | 1.2 | 4.1 | 3.7 | 0.7 | 0.7 | 0.5 | 0.1 |
| LBFDAU seed 9 | 5.3 | 0.2 | 0.2 | 2.4 | 14.3 | 27.8 | 1.0 | 4.0 | 4.2 | 0.6 | 0.7 | 0.5 | 0.1 |
| LBFDAU seed 10 | 6.7 | 0.5 | 0.2 | 2.8 | 15.8 | 23.3 | 0.8 | 5.7 | 2.9 | 0.8 | 0.9 | 0.5 | 0.0 |
| LBFDAU seed 11 | 5.9 | 0.6 | 0.2 | 3.4 | 19.3 | 22.2 | 1.5 | 4.0 | 3.1 | 0.7 | 0.9 | 0.6 | 0.0 |
| LBFDAU seed 12 | 5.2 | 0.4 | 0.2 | 2.2 | 16.1 | 25.2 | 0.8 | 5.5 | 3.3 | 0.7 | 0.8 | 0.5 | 0.1 |
| LBFDAU seed 13 | 4.3 | 0.2 | 0.1 | 2.0 | 17.5 | 27.7 | 1.2 | 4.9 | 2.9 | 0.5 | 0.6 | 0.6 | 0.1 |
| LBFDAU seed 14 | 4.2 | 0.3 | 0.1 | 2.0 | 16.4 | 27.9 | 0.9 | 5.1 | 2.9 | 0.5 | 0.6 | 0.5 | 0.1 |
| LBFDAU seed 15 | 4.5 | 0.4 | 0.1 | 1.5 | 17.0 | 25.7 | 1.1 | 5.3 | 2.9 | 0.6 | 0.5 | 0.6 | 0.1 |
| LBFDAU seed 16 | 4.7 | 0.6 | 0.2 | 2.0 | 17.2 | 25.9 | 1.1 | 5.9 | 3.0 | 0.7 | 0.7 | 0.5 | 0.1 |
| LBFDAU seed 17 | 4.5 | 0.3 | 0.1 | 2.3 | 18.4 | 27.0 | 1.5 | 4.6 | 3.4 | 0.7 | 0.7 | 0.6 | 0.1 |
| LBFDAU seed 18 | 5.1 | 0.2 | 0.2 | 2.9 | 16.1 | 27.1 | 1.5 | 4.7 | 4.2 | 0.7 | 0.9 | 0.7 | 0.0 |
| LBFDAU seed 19 | 4.5 | 0.3 | 0.1 | 1.7 | 18.7 | 27.0 | 1.4 | 4.5 | 2.9 | 0.4 | 0.5 | 0.6 | 0.1 |
| LBFDAU seed 20 | 5.3 | 0.2 | 0.1 | 2.6 | 17.9 | 26.4 | 1.1 | 4.4 | 2.9 | 0.5 | 0.7 | 0.6 | 0.1 |
| LBFDAU seed 21 | 5.2 | 0.3 | 0.2 | 2.1 | 16.3 | 27.8 | 0.7 | 5.1 | 3.5 | 0.7 | 0.7 | 0.6 | 0.2 |
| LBFDAU seed 22 | 4.8 | 0.2 | 0.1 | 2.4 | 17.7 | 28.9 | 0.9 | 4.9 | 3.1 | 0.5 | 0.7 | 0.6 | 0.1 |
| LBFDAU seed 23 | 4.5 | 0.2 | 0.1 | 1.6 | 19.4 | 26.9 | 1.3 | 5.6 | 2.8 | 0.5 | 0.5 | 0.6 | 0.1 |
| LBFDAU seed 24 | 6.6 | 0.6 | 0.2 | 3.4 | 18.4 | 23.0 | 1.0 | 3.9 | 4.6 | 1.1 | 1.1 | 0.7 | 0.0 |
| LBFDAU seed 25 | 5.2 | 0.3 | 0.2 | 2.1 | 16.0 | 26.6 | 0.9 | 4.9 | 3.7 | 0.8 | 0.7 | 0.6 | 0.0 |
| LBFDAU seed 26 | 5.5 | 0.6 | 0.2 | 2.6 | 19.9 | 23.4 | 2.1 | 3.8 | 3.0 | 0.6 | 0.8 | 0.6 | 0.0 |
| LBFDAU seed 27 | 4.5 | 0.3 | 0.1 | 1.7 | 19.5 | 26.6 | 1.5 | 5.2 | 2.3 | 0.5 | 0.5 | 0.6 | 0.1 |
| LBFDAU seed 28 | 5.1 | 0.3 | 0.2 | 2.5 | 17.2 | 27.3 | 0.8 | 4.6 | 2.9 | 0.5 | 0.9 | 0.5 | 0.1 |
| LBFDAU seed 29 | 5.0 | 0.3 | 0.2 | 3.2 | 20.0 | 28.0 | 1.3 | 4.7 | 2.9 | 0.5 | 0.9 | 0.6 | 0.1 |

TABLE 147-continued

Fatty acid profiles of 95 single
seeds of the one seedbatch of event LBFDAU shown in Table 146 having highest EPA + DHA levels.

| | | | | | | | | | | | | | |
|---|---|---|---|---|---|---|---|---|---|---|---|---|---|
| LBFDAU seed 30 | 4.7 | 0.2 | 0.1 | 2.4 | 18.6 | 29.3 | 1.6 | 4.4 | 3.2 | 0.5 | 0.7 | 0.6 | 0.1 |
| LBFDAU seed 31 | 4.9 | 0.3 | 0.1 | 2.5 | 18.8 | 28.0 | 1.5 | 4.1 | 3.0 | 0.4 | 0.8 | 0.6 | 0.1 |
| LBFDAU seed 32 | 4.8 | 0.3 | 0.1 | 2.2 | 19.6 | 28.3 | 1.0 | 5.5 | 2.6 | 0.5 | 0.6 | 0.6 | 0.1 |
| LBFDAU seed 33 | 4.6 | 0.3 | 0.1 | 2.3 | 19.6 | 28.4 | 1.3 | 5.2 | 3.1 | 0.6 | 0.8 | 0.6 | 0.1 |
| LBFDAU seed 34 | 4.9 | 0.3 | 0.1 | 3.4 | 19.2 | 25.9 | 1.8 | 4.0 | 3.1 | 0.5 | 1.0 | 0.7 | 0.1 |
| LBFDAU seed 35 | 4.6 | 0.3 | 0.2 | 2.0 | 19.1 | 28.5 | 1.1 | 5.7 | 3.0 | 0.6 | 0.6 | 0.6 | 0.1 |
| LBFDAU seed 36 | 4.2 | 0.2 | 0.1 | 2.1 | 18.1 | 30.5 | 1.0 | 4.9 | 2.9 | 0.4 | 0.6 | 0.6 | 0.1 |
| LBFDAU seed 37 | 4.9 | 0.2 | 0.1 | 2.0 | 19.0 | 29.0 | 1.1 | 5.0 | 3.0 | 0.5 | 0.6 | 0.6 | 0.1 |
| LBFDAU seed 38 | 4.4 | 0.3 | 0.1 | 1.9 | 19.7 | 29.9 | 1.2 | 4.5 | 2.6 | 0.4 | 0.6 | 0.5 | 0.1 |
| LBFDAU seed 39 | 4.8 | 0.2 | 0.1 | 2.2 | 19.2 | 28.6 | 1.0 | 5.0 | 2.4 | 0.4 | 0.6 | 0.6 | 0.1 |
| LBFDAU seed 40 | 4.3 | 0.3 | 0.1 | 1.8 | 20.2 | 28.8 | 1.4 | 4.8 | 2.6 | 0.4 | 0.6 | 0.6 | 0.1 |
| LBFDAU seed 41 | 5.8 | 0.4 | 0.2 | 3.0 | 19.3 | 26.9 | 0.9 | 4.6 | 3.6 | 0.7 | 1.0 | 0.6 | 0.0 |
| LBFDAU seed 42 | 4.6 | 0.3 | 0.1 | 2.3 | 21.3 | 27.8 | 1.2 | 5.2 | 2.8 | 0.6 | 0.6 | 0.6 | 0.1 |
| LBFDAU seed 43 | 5.3 | 0.3 | 0.2 | 2.0 | 18.1 | 29.2 | 1.0 | 4.2 | 3.1 | 0.5 | 0.7 | 0.6 | 0.1 |
| LBFDAU seed 44 | 4.7 | 0.3 | 0.2 | 1.9 | 19.3 | 29.3 | 1.0 | 5.7 | 2.7 | 0.5 | 0.7 | 0.7 | 0.1 |
| LBFDAU seed 45 | 4.3 | 0.2 | 0.1 | 2.2 | 19.4 | 29.8 | 1.1 | 5.0 | 2.5 | 0.4 | 0.7 | 0.6 | 0.1 |
| LBFDAU seed 46 | 4.5 | 0.2 | 0.2 | 2.4 | 18.8 | 29.0 | 1.1 | 5.0 | 3.7 | 0.6 | 0.7 | 0.6 | 0.1 |
| LBFDAU seed 47 | 4.0 | 0.2 | 0.1 | 1.8 | 19.2 | 30.1 | 1.3 | 4.9 | 2.9 | 0.4 | 0.6 | 0.6 | 0.1 |
| LBFDAU seed 48 | 4.3 | 0.2 | 0.1 | 2.0 | 20.0 | 30.1 | 1.3 | 4.5 | 2.7 | 0.4 | 0.6 | 0.5 | 0.1 |
| LBFDAU seed 49 | 4.4 | 0.2 | 0.1 | 2.5 | 18.3 | 30.1 | 1.6 | 3.7 | 3.2 | 0.5 | 0.8 | 0.6 | 0.1 |
| LBFDAU seed 50 | 4.3 | 0.3 | 0.1 | 1.9 | 21.5 | 29.2 | 1.3 | 5.2 | 2.5 | 0.5 | 0.6 | 0.6 | 0.1 |
| LBFDAU seed 70 | 5.3 | 0.3 | 0.2 | 3.1 | 20.0 | 28.7 | 1.4 | 4.1 | 3.0 | 0.4 | 1.0 | 0.6 | 0.1 |
| LBFDAU seed 71 | 4.2 | 0.2 | 0.1 | 2.0 | 22.1 | 29.1 | 1.7 | 4.9 | 2.3 | 0.3 | 0.6 | 0.6 | 0.1 |
| LBFDAU seed 75 | 4.7 | 0.2 | 0.1 | 2.4 | 21.4 | 28.0 | 2.2 | 4.8 | 2.5 | 0.4 | 0.7 | 0.6 | 0.1 |
| LBFDAU seed 76 | 4.7 | 0.3 | 0.1 | 2.1 | 20.9 | 28.1 | 1.0 | 5.4 | 3.1 | 0.6 | 0.6 | 0.6 | 0.1 |
| LBFDAU seed 77 | 5.0 | 0.2 | 0.1 | 2.1 | 18.5 | 29.7 | 1.6 | 4.8 | 2.9 | 0.5 | 0.7 | 0.6 | 0.1 |
| LBFDAU seed 78 | 4.8 | 0.2 | 0.1 | 1.9 | 20.1 | 29.2 | 1.1 | 5.1 | 2.6 | 0.4 | 0.6 | 0.7 | 0.1 |
| LBFDAU seed 79 | 4.3 | 0.2 | 0.1 | 1.9 | 21.6 | 28.7 | 1.5 | 5.1 | 2.6 | 0.4 | 0.5 | 0.6 | 0.1 |
| LBFDAU seed 80 | 4.7 | 0.3 | 0.2 | 1.9 | 19.0 | 31.0 | 0.7 | 4.6 | 2.7 | 0.5 | 0.6 | 0.6 | 0.1 |
| LBFDAU seed 81 | 4.3 | 0.2 | 0.1 | 2.1 | 21.0 | 29.5 | 1.4 | 5.1 | 2.6 | 0.4 | 0.6 | 0.6 | 0.1 |
| LBFDAU seed 82 | 4.5 | 0.3 | 0.1 | 2.0 | 21.0 | 29.6 | 1.4 | 5.5 | 2.5 | 0.5 | 0.6 | 0.6 | 0.1 |
| LBFDAU seed 83 | 5.0 | 0.3 | 0.1 | 2.3 | 20.6 | 28.3 | 0.9 | 5.8 | 2.8 | 0.6 | 0.6 | 0.6 | 0.1 |
| LBFDAU seed 84 | 6.2 | 0.5 | 0.2 | 2.9 | 20.3 | 27.1 | 0.8 | 5.6 | 3.0 | 0.9 | 0.9 | 0.6 | 0.0 |
| LBFDAU seed 85 | 4.1 | 0.2 | 0.1 | 2.2 | 21.5 | 30.4 | 1.4 | 4.8 | 2.6 | 0.4 | 0.6 | 0.6 | 0.1 |
| LBFDAU seed 86 | 4.7 | 0.3 | 0.2 | 2.2 | 20.6 | 30.6 | 1.0 | 5.5 | 2.8 | 0.5 | 0.7 | 0.6 | 0.1 |
| LBFDAU seed 87 | 4.3 | 0.3 | 0.1 | 2.2 | 20.9 | 31.0 | 1.6 | 4.5 | 2.7 | 0.3 | 0.6 | 0.6 | 0.1 |
| LBFDAU seed 88 | 4.1 | 0.2 | 0.1 | 1.9 | 22.2 | 30.6 | 1.3 | 4.6 | 2.5 | 0.5 | 0.5 | 0.6 | 0.1 |
| LBFDAU seed 89 | 4.4 | 0.3 | 0.1 | 2.0 | 21.6 | 30.5 | 1.2 | 5.4 | 2.3 | 0.4 | 0.6 | 0.6 | 0.1 |

TABLE 147-continued

Fatty acid profiles of 95 single
seeds of the one seedbatch of event LBFDAU shown in Table 146 having highest EPA + DHA levels.

| | | | | | | | | | | | | | |
|---|---|---|---|---|---|---|---|---|---|---|---|---|---|
| LBFDAU seed 90 | 4.8 | 0.2 | 0.1 | 2.4 | 22.3 | 29.6 | 1.1 | 5.2 | 2.3 | 0.4 | 0.7 | 0.6 | 0.1 |
| LBFDAU seed 91 | 4.8 | 0.2 | 0.1 | 2.2 | 22.0 | 30.2 | 1.3 | 4.9 | 2.7 | 0.6 | 0.7 | 0.7 | 0.1 |
| LBFDAU seed 92 | 5.2 | 0.3 | 0.2 | 2.0 | 20.3 | 29.7 | 1.1 | 5.1 | 3.2 | 0.6 | 0.6 | 0.6 | 0.1 |
| LBFDAU seed 93 | 4.7 | 0.2 | 0.1 | 2.4 | 23.0 | 30.3 | 1.1 | 5.3 | 2.1 | 0.5 | 0.7 | 0.7 | 0.1 |
| LBFDAU seed 94 | 5.0 | 0.3 | 0.2 | 2.3 | 21.9 | 30.6 | 1.3 | 5.2 | 2.4 | 0.7 | 0.8 | 0.6 | 0.1 |
| LBFDAU seed 95 | 4.8 | 0.2 | 0.1 | 2.5 | 24.6 | 29.6 | 1.3 | 5.2 | 2.1 | 0.5 | 0.7 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU seed 1 | 0.1 | 3.3 | 3.0 | 1.9 | 26.2 | 0.4 | 0.0 | 0.6 | 3.7 | 0.2 | 4.9 | 0.0 | 0.2 |
| LBFDAU seed 2 | 0.1 | 3.0 | 2.5 | 2.5 | 23.6 | 0.5 | 0.0 | 0.5 | 3.8 | 0.3 | 5.8 | 0.0 | 0.2 |
| LBFDAU seed 3 | 0.1 | 3.4 | 2.5 | 2.5 | 23.1 | 0.3 | 0.0 | 0.6 | 3.3 | 0.1 | 4.2 | 0.0 | 0.2 |
| LBFDAU seed 4 | 0.0 | 1.7 | 1.3 | 1.9 | 21.2 | 0.7 | 0.0 | 0.8 | 3.5 | 0.4 | 5.8 | 0.0 | 0.0 |
| LBFDAU seed 5 | 0.1 | 2.9 | 2.1 | 3.5 | 22.0 | 0.3 | 0.0 | 0.5 | 3.7 | 0.2 | 4.8 | 0.0 | 0.2 |
| LBFDAU seed 6 | 0.1 | 2.9 | 2.3 | 2.4 | 21.8 | 0.3 | 0.0 | 0.4 | 3.4 | 0.2 | 4.4 | 0.0 | 0.2 |
| LBFDAU seed 7 | 0.0 | 3.6 | 3.1 | 2.0 | 21.9 | 0.5 | 0.0 | 0.5 | 3.5 | 0.0 | 4.3 | 0.0 | 0.1 |
| LBFDAU seed 8 | 0.1 | 2.6 | 2.0 | 2.7 | 21.7 | 0.4 | 0.0 | 0.4 | 3.1 | 0.2 | 4.0 | 0.0 | 0.2 |
| LBFDAU seed 9 | 0.1 | 3.6 | 2.9 | 2.3 | 21.1 | 0.4 | 0.0 | 0.5 | 2.8 | 0.3 | 4.4 | 0.0 | 0.1 |
| LBFDAU seed 10 | 0.0 | 3.1 | 2.4 | 2.2 | 19.8 | 0.8 | 0.0 | 0.6 | 4.7 | 0.1 | 5.4 | 0.0 | 0.0 |
| LBFDAU seed 11 | 0.0 | 3.0 | 2.1 | 2.0 | 20.8 | 0.8 | 0.0 | 0.2 | 4.6 | 0.0 | 4.2 | 0.0 | 0.0 |
| LBFDAU seed 12 | 0.1 | 3.7 | 2.9 | 2.4 | 20.1 | 0.4 | 0.0 | 0.4 | 4.2 | 0.2 | 4.7 | 0.0 | 0.2 |
| LBFDAU seed 13 | 0.1 | 2.9 | 2.3 | 2.6 | 20.7 | 0.3 | 0.0 | 0.4 | 3.6 | 0.2 | 4.1 | 0.0 | 0.2 |
| LBFDAU seed 14 | 0.1 | 3.5 | 3.2 | 2.0 | 20.5 | 0.3 | 0.0 | 0.4 | 3.7 | 0.1 | 4.3 | 0.0 | 0.2 |
| LBFDAU seed 15 | 0.1 | 3.4 | 2.4 | 2.9 | 19.7 | 0.3 | 0.0 | 0.5 | 4.8 | 0.3 | 5.1 | 0.0 | 0.3 |
| LBFDAU seed 16 | 0.0 | 3.2 | 2.6 | 2.3 | 20.1 | 0.6 | 0.0 | 0.7 | 3.4 | 0.1 | 4.3 | 0.0 | 0.2 |
| LBFDAU seed 17 | 0.0 | 2.7 | 1.9 | 2.8 | 20.8 | 0.5 | 0.0 | 0.6 | 2.8 | 0.1 | 3.5 | 0.0 | 0.2 |
| LBFDAU seed 18 | 0.0 | 2.3 | 2.3 | 2.1 | 19.5 | 0.7 | 0.0 | 0.4 | 3.4 | 0.0 | 4.8 | 0.0 | 0.2 |
| LBFDAU seed 19 | 0.1 | 3.1 | 2.1 | 2.9 | 19.8 | 0.2 | 0.0 | 0.5 | 3.7 | 0.2 | 4.3 | 0.0 | 0.4 |
| LBFDAU seed 20 | 0.1 | 3.4 | 2.7 | 2.8 | 20.8 | 0.3 | 0.0 | 0.4 | 3.0 | 0.1 | 3.3 | 0.0 | 0.2 |
| LBFDAU seed 21 | 0.1 | 3.1 | 2.4 | 2.7 | 19.7 | 0.4 | 0.0 | 0.5 | 3.6 | 0.2 | 4.0 | 0.0 | 0.1 |
| LBFDAU seed 22 | 0.1 | 2.4 | 2.1 | 2.7 | 19.9 | 0.3 | 0.0 | 0.4 | 3.0 | 0.1 | 3.8 | 0.0 | 0.2 |
| LBFDAU seed 23 | 0.1 | 3.0 | 2.3 | 3.1 | 19.1 | 0.2 | 0.0 | 0.4 | 3.7 | 0.1 | 3.7 | 0.0 | 0.2 |
| LBFDAU seed 24 | 0.0 | 3.6 | 2.0 | 1.6 | 17.9 | 0.7 | 0.0 | 0.9 | 3.7 | 0.0 | 4.8 | 0.0 | 0.0 |
| LBFDAU seed 25 | 0.0 | 3.9 | 2.6 | 2.8 | 18.0 | 0.6 | 0.0 | 0.7 | 4.6 | 0.3 | 4.4 | 0.0 | 0.1 |
| LBFDAU seed 26 | 0.0 | 4.0 | 2.0 | 2.8 | 18.5 | 0.6 | 0.0 | 1.0 | 3.8 | 0.2 | 3.9 | 0.0 | 0.2 |
| LBFDAU seed 27 | 0.1 | 3.6 | 2.5 | 2.6 | 18.6 | 0.3 | 0.0 | 0.5 | 4.1 | 0.2 | 3.8 | 0.0 | 0.4 |
| LBFDAU seed 28 | 0.0 | 3.7 | 2.3 | 3.6 | 18.6 | 0.5 | 0.0 | 0.5 | 3.7 | 0.2 | 3.8 | 0.0 | 0.2 |
| LBFDAU seed 29 | 0.0 | 2.2 | 1.5 | 2.3 | 18.5 | 0.4 | 0.0 | 0.5 | 2.8 | 0.2 | 3.6 | 0.0 | 0.2 |
| LBFDAU seed 30 | 0.1 | 2.9 | 2.1 | 2.5 | 18.6 | 0.3 | 0.0 | 0.7 | 2.7 | 0.2 | 3.2 | 0.0 | 0.2 |

TABLE 147-continued

Fatty acid profiles of 95 single
seeds of the one seedbatch of event LBFDAU shown in Table 146 having highest EPA + DHA levels.

| | | | | | | | | | | | | | |
|---|---|---|---|---|---|---|---|---|---|---|---|---|---|
| LBFDAU seed 31 | 0.1 | 3.9 | 2.8 | 1.8 | 18.2 | 0.4 | 0.0 | 0.6 | 3.1 | 0.2 | 3.6 | 0.0 | 0.3 |
| LBFDAU seed 32 | 0.1 | 3.1 | 2.5 | 2.4 | 18.3 | 0.3 | 0.0 | 0.4 | 3.1 | 0.1 | 3.4 | 0.0 | 0.2 |
| LBFDAU seed 33 | 0.0 | 2.7 | 2.0 | 2.4 | 18.2 | 0.4 | 0.0 | 0.5 | 3.1 | 0.1 | 3.5 | 0.0 | 0.2 |
| LBFDAU seed 34 | 0.0 | 3.9 | 2.7 | 2.1 | 17.9 | 0.5 | 0.0 | 0.6 | 3.0 | 0.2 | 3.7 | 0.0 | 0.3 |
| LBFDAU seed 35 | 0.1 | 3.0 | 2.3 | 2.6 | 17.9 | 0.3 | 0.0 | 0.4 | 3.3 | 0.1 | 3.6 | 0.0 | 0.2 |
| LBFDAU seed 36 | 0.1 | 3.5 | 3.0 | 2.1 | 17.6 | 0.3 | 0.0 | 0.4 | 3.2 | 0.1 | 3.8 | 0.0 | 0.2 |
| LBFDAU seed 37 | 0.1 | 3.1 | 2.2 | 2.9 | 17.8 | 0.3 | 0.0 | 0.4 | 3.0 | 0.2 | 3.5 | 0.0 | 0.2 |
| LBFDAU seed 38 | 0.1 | 3.0 | 2.0 | 2.6 | 17.8 | 0.3 | 0.0 | 0.5 | 3.4 | 0.2 | 3.5 | 0.0 | 0.2 |
| LBFDAU seed 39 | 0.1 | 4.0 | 3.2 | 1.9 | 17.8 | 0.3 | 0.0 | 0.5 | 3.1 | 0.1 | 3.4 | 0.0 | 0.3 |
| LBFDAU seed 40 | 0.1 | 3.2 | 2.2 | 2.5 | 17.7 | 0.3 | 0.0 | 0.5 | 3.6 | 0.2 | 3.5 | 0.0 | 0.3 |
| LBFDAU seed 41 | 0.0 | 3.1 | 1.8 | 2.1 | 17.7 | 0.7 | 0.0 | 1.0 | 3.1 | 0.1 | 3.5 | 0.0 | 0.0 |
| LBFDAU seed 42 | 0.1 | 2.7 | 2.1 | 2.3 | 18.0 | 0.3 | 0.0 | 0.7 | 2.9 | 0.1 | 3.2 | 0.0 | 0.2 |
| LBFDAU seed 43 | 0.1 | 3.4 | 2.1 | 3.7 | 17.6 | 0.3 | 0.0 | 0.5 | 3.5 | 0.2 | 3.4 | 0.0 | 0.2 |
| LBFDAU seed 44 | 0.1 | 2.7 | 2.1 | 2.6 | 17.3 | 0.3 | 0.0 | 0.5 | 3.6 | 0.2 | 3.6 | 0.0 | 0.2 |
| LBFDAU seed 45 | 0.1 | 3.3 | 2.6 | 2.4 | 17.7 | 0.3 | 0.0 | 0.5 | 3.2 | 0.2 | 3.2 | 0.0 | 0.2 |
| LBFDAU seed 46 | 0.1 | 3.1 | 2.2 | 2.8 | 17.1 | 0.3 | 0.0 | 0.5 | 3.1 | 0.2 | 3.5 | 0.0 | 0.2 |
| LBFDAU seed 47 | 0.1 | 3.5 | 2.5 | 2.6 | 17.0 | 0.3 | 0.0 | 0.5 | 3.5 | 0.2 | 3.5 | 0.0 | 0.3 |
| LBFDAU seed 48 | 0.1 | 3.5 | 2.3 | 2.7 | 16.9 | 0.3 | 0.0 | 0.4 | 3.1 | 0.2 | 3.5 | 0.0 | 0.3 |
| LBFDAU seed 49 | 0.1 | 4.3 | 3.3 | 2.0 | 17.2 | 0.4 | 0.0 | 0.4 | 2.5 | 0.2 | 3.2 | 0.0 | 0.3 |
| LBFDAU seed 50 | 0.1 | 2.8 | 2.1 | 2.3 | 17.0 | 0.3 | 0.0 | 0.4 | 3.2 | 0.2 | 3.3 | 0.0 | 0.2 |
| LBFDAU seed 70 | 0.1 | 3.5 | 2.3 | 2.3 | 16.8 | 0.5 | 0.0 | 0.5 | 2.4 | 0.2 | 3.2 | 0.0 | 0.3 |
| LBFDAU seed 71 | 0.1 | 2.9 | 2.3 | 2.2 | 16.7 | 0.3 | 0.0 | 0.7 | 2.7 | 0.2 | 3.3 | 0.0 | 0.3 |
| LBFDAU seed 75 | 0.1 | 3.1 | 2.2 | 2.4 | 17.2 | 0.4 | 0.0 | 0.5 | 2.7 | 0.2 | 2.8 | 0.0 | 0.3 |
| LBFDAU seed 76 | 0.1 | 2.9 | 2.1 | 2.6 | 16.3 | 0.3 | 0.0 | 0.6 | 3.4 | 0.2 | 3.7 | 0.0 | 0.2 |
| LBFDAU seed 77 | 0.1 | 3.9 | 2.9 | 2.4 | 16.7 | 0.3 | 0.0 | 0.5 | 2.8 | 0.2 | 3.3 | 0.0 | 0.2 |
| LBFDAU seed 78 | 0.1 | 3.4 | 2.4 | 2.7 | 16.7 | 0.3 | 0.0 | 0.7 | 3.2 | 0.2 | 3.2 | 0.0 | 0.2 |
| LBFDAU seed 79 | 0.1 | 3.3 | 2.3 | 2.6 | 16.6 | 0.3 | 0.0 | 0.6 | 2.9 | 0.2 | 3.3 | 0.0 | 0.4 |
| LBFDAU seed 80 | 0.0 | 3.3 | 2.2 | 2.5 | 16.1 | 0.4 | 0.0 | 0.6 | 3.8 | 0.3 | 3.7 | 0.0 | 0.1 |
| LBFDAU seed 81 | 0.1 | 3.4 | 2.5 | 2.3 | 16.7 | 0.3 | 0.0 | 0.4 | 3.1 | 0.1 | 2.9 | 0.0 | 0.2 |
| LBFDAU seed 82 | 0.1 | 2.7 | 1.9 | 2.7 | 16.2 | 0.3 | 0.0 | 0.5 | 3.2 | 0.2 | 3.5 | 0.0 | 0.3 |
| LBFDAU seed 83 | 0.1 | 3.0 | 2.4 | 2.5 | 16.2 | 0.4 | 0.0 | 0.5 | 3.3 | 0.1 | 3.3 | 0.0 | 0.2 |
| LBFDAU seed 84 | 0.0 | 3.0 | 2.1 | 2.1 | 15.4 | 0.7 | 0.0 | 0.5 | 3.5 | 0.0 | 3.9 | 0.0 | 0.0 |
| LBFDAU seed 85 | 0.1 | 3.1 | 2.4 | 2.3 | 16.1 | 0.4 | 0.0 | 0.5 | 2.6 | 0.2 | 3.1 | 0.0 | 0.4 |
| LBFDAU seed 86 | 0.1 | 2.7 | 2.0 | 2.7 | 15.5 | 0.4 | 0.0 | 0.5 | 2.7 | 0.2 | 3.2 | 0.0 | 0.2 |
| LBFDAU seed 87 | 0.1 | 3.3 | 2.2 | 2.1 | 15.6 | 0.3 | 0.0 | 0.9 | 2.8 | 0.2 | 3.0 | 0.0 | 0.3 |
| LBFDAU seed 88 | 0.1 | 2.9 | 1.7 | 3.1 | 15.6 | 0.3 | 0.0 | 0.7 | 3.0 | 0.2 | 2.9 | 0.0 | 0.3 |
| LBFDAU seed 89 | 0.1 | 2.9 | 2.1 | 2.2 | 15.3 | 0.4 | 0.0 | 0.7 | 3.3 | 0.1 | 3.1 | 0.0 | 0.2 |

TABLE 147-continued

Fatty acid profiles of 95 single seeds of the one seedbatch of event LBFDAU shown in Table 146 having highest EPA + DHA levels.

| | | | | | | | | | | | | | |
|---|---|---|---|---|---|---|---|---|---|---|---|---|---|
| LBFDAU seed 90 | 0.1 | 3.2 | 2.6 | 2.2 | 15.6 | 0.3 | 0.0 | 0.5 | 2.7 | 0.1 | 2.7 | 0.0 | 0.3 |
| LBFDAU seed 91 | 0.0 | 3.2 | 2.2 | 2.5 | 15.1 | 0.3 | 0.0 | 0.4 | 2.5 | 0.2 | 3.0 | 0.0 | 0.3 |
| LBFDAU seed 92 | 0.0 | 3.1 | 1.9 | 3.4 | 14.8 | 0.4 | 0.0 | 0.6 | 3.3 | 0.2 | 3.2 | 0.0 | 0.2 |
| LBFDAU seed 93 | 0.1 | 3.0 | 2.2 | 2.2 | 15.1 | 0.3 | 0.0 | 0.4 | 2.7 | 0.1 | 2.5 | 0.0 | 0.3 |
| LBFDAU seed 94 | 0.1 | 2.9 | 2.1 | 2.4 | 14.7 | 0.4 | 0.0 | 0.4 | 2.7 | 0.2 | 2.8 | 0.0 | 0.3 |
| LBFDAU seed 95 | 0.1 | 3.2 | 2.2 | 2.4 | 13.5 | 0.3 | 0.0 | 0.5 | 2.2 | 0.1 | 2.5 | 0.0 | 0.3 |

Fatty Acid Profiles, Copy Number Measurements, and Phenotypic Observations of T2 Plants Carrying T-DNAs of Plasmids VC-LTM593-1Qcz Rc Cultivated in Greenhouses During the Summer The data in Table 148 indicate the copy number of the selected events was a single insertion which was homozygous in the T3 seed. Fatty acid profile measurements, see Table 149 and Table 150, indicated the combination of T-DNA from VC-LTM593-1qcz rc are capable of bringing in the VLC-PUFA pathway to successfully accumulate ARA, EPA and DHA. The data on Table 151 show that there was no significant impact on the aerial portion of the plant caused by VC-LTM593-1qcz rc.

TABLE 148

Copy number measurement of T2 plants cultivated in the greenhouse of canola events containing the T-DNAs of plasmids VC-LTM593-1qcz rc. The events are indicated in the first column, along with the number of T2 plants that where measured per event. For each event, T2 seedbatches of two homozygous T1 plants where selected for seeding. Comparison of the results with Table 135 confirmes homozygosity of all T2 plants.

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | c-AHAS | j-i-Atss1_c-d5Elo (Ot_GA3) | c-d4Des (Pl_GA)2 | j-p-LuPXR_i-Atss15 | j-p-PvARC5_t-BnSETL | c-d5Des (Tc_GA) | j-i-Atss18_c-o3Des (Pi_GA2) | c-o3Des (Pi_GA) |
|---|---|---|---|---|---|---|---|---|
| LBFDAU (n = 218) | 2.0 | 2.1 | 4.1 | | 3.8 | 8.1 | 4.0 | 4.0 |
| LBFDGG (n = 200) | 2.0 | 2.0 | 2.0 | | 2.0 | 4.0 | 2.0 | 2.0 |
| LBFGKN (n = 182) | 2.0 | 2.0 | 2.0 | | 2.0 | 4.2 | 2.1 | 1.9 |
| LBFIHE (n = 157) | 2.1 | 2.0 | 2.0 | | 2.1 | 4.3 | 2.0 | 2.0 |
| LBFLDI (n = 229) | 2.3 | 2.2 | 2.3 | | 2.3 | 4.7 | 2.3 | 2.3 |
| LBFPRA (n = 196) | 2.0 | 1.9 | 5.8 | | 3.9 | 7.9 | 4.0 | 4.1 |
| LBFDHG (n = 177) | 4.1 | 4.2 | 4.2 | | 4.0 | 8.3 | 4.1 | 4.1 |
| LBFLFK (n = 195) | 4.0 | 4.1 | 4.0 | | 4.0 | 8.2 | 4.0 | 4.0 |

Copy number assays targeting the T-DNA of VC-LTM593-1qcz rc. Assays are listed according to the position of the assay target along the T-DNA, with target c-AHAS located near the left T-DNA border and target c-d6Elo(Pp_GA) near the right T-DNA border.

| Event | j-p-BnSETL-v1_c-(Pir_GA) | j-i-Atss144_c-d12Des (Ps_GA) | c-d6Elo (Tp_GA) | j-t-StCAT_p2_p-LuPXR | j-i-Atss2_c-d6Des (Otfebit_GA) | c-d5Des (Tc_GA) | c-D6Elo (Pp_GA) | j-i-Atss18_c-d6Elo (Pp_GA2) |
|---|---|---|---|---|---|---|---|---|
| LBFDAU (n = 218) | | | 4.1 | 4.2 | 4.0 | 8.1 | 4.1 | 4.0 |
| LBFDGG (n = 200) | | | 2.1 | 2.1 | 2.0 | 4.0 | 2.2 | 2.1 |
| LBFGKN (n = 182) | | | 2.0 | 2.2 | 2.0 | 4.2 | 2.1 | 2.1 |
| LBFIHE (n = 157) | | | 2.2 | 2.1 | 2.0 | 4.3 | 2.1 | 2.0 |
| LBFLDI (n = 229) | | | 2.4 | 2.4 | 2.3 | 4.7 | 2.4 | 2.2 |
| LBFPRA (n = 196) | | | 3.9 | 4.0 | 3.9 | 7.9 | 4.0 | 1.9 |

TABLE 148-continued

Copy number measurement of T2 plants cultivated in the greenhouse of canola events containing the T-DNAs of plasmids VC-LTM593-1qcz rc. The events are indicated in the first column, along with the number of T2 plants that where measured per event. For each event, T2 seedbatches of two homozygous T1 plants where selected for seeding. Comparison of the results with Table 135 confirms homozygozity of all T2 plants.

| | | | | | | |
|---|---|---|---|---|---|---|
| LBFDHG (n = 177) | 4.2 | 4.1 | 4.0 | 8.3 | 4.1 | 4.0 |
| LBFLFK (n = 195) | 4.0 | 4.0 | 4.0 | 8.2 | 4.0 | 4.0 |

TABLE 149

Fatty acid profiles of T3 seeds harvested from T2 plants cultivated in the greenhouse of canola events containing the T-DNAs of plasmid VC-LTM593-1qcz re. The events are indicated in the first column, along with the number of T3 seed batches representing a plant measured per event. Per seed batch a random selection of ~15 seed was measured in five technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 218) | 4.8 ± 0.2 | 0.2 ± 0 | 0 ± 0 | 4.2 ± 0.3 | 23 ± 1.6 | 31.5 ± 1.2 | 1.1 ± 0.2 | 4.6 ± 0.4 | 2.2 ± 0.4 | 0.4 ± 0.1 | 1 ± 0.1 | 0.7 ± 0 | 0.1 ± 0 |
| LBFDGG (n = 200) | 5 ± 0.2 | 0.2 ± 0 | 0 ± 0 | 3.2 ± 0.3 | 30.4 ± 2.2 | 34.1 ± 1.6 | 0.8 ± 0.1 | 5 ± 0.5 | 1.6 ± 0.2 | 0.3 ± 0 | 0.9 ± 0.1 | 0.7 ± 0 | 0.1 ± 0 |
| LBFGKN (n = 182) | 4.8 ± 0.2 | 0.2 ± 0 | 0 ± 0 | 3.6 ± 0.4 | 28.3 ± 1.9 | 34.6 ± 1.6 | 0.7 ± 0.2 | 4.7 ± 0.5 | 1.8 ± 0.4 | 0.3 ± 0.2 | 0.9 ± 0.1 | 0.7 ± 0 | 0.2 ± 0.1 |
| LBFIHE (n = 157) | 4.9 ± 0.3 | 0.2 ± 0 | 0 ± 0 | 3.7 ± 0.6 | 25.9 ± 1.9 | 32.9 ± 1.8 | 0.8 ± 0.1 | 4.7 ± 0.6 | 2.4 ± 0.7 | 0.3 ± 0.1 | 0.8 ± 0.1 | 0.7 ± 0 | 0.2 ± 0.1 |
| LBFLDI (n = 229) | 5.9 ± 1 | 0.3 ± 0.1 | 0 ± 0.1 | 2.9 ± 0.3 | 27.8 ± 2.5 | 32.5 ± 1.8 | 0.7 ± 0.1 | 4.7 ± 0.5 | 1.7 ± 0.3 | 0.4 ± 0.1 | 0.8 ± 0.1 | 0.6 ± 0.1 | 0.1 ± 0 |
| LBFPRA (n = 196) | 5 ± 0.2 | 0.2 ± 0 | 0 ± 0 | 3.9 ± 0.7 | 23.2 ± 2 | 30.9 ± 1.9 | 1.1 ± 0.2 | 3.8 ± 0.6 | 2.6 ± 0.5 | 0.3 ± 0.1 | 0.9 ± 0.1 | 0.6 ± 0 | 0.1 ± 0 |
| LBFDHG (n = 177) | 5.7 ± 0.2 | 0.3 ± 0 | 0 ± 0 | 3.2 ± 0.5 | 24.1 ± 0.8 | 34.5 ± 1.4 | 0.8 ± 0.1 | 4.4 ± 0.3 | 2.5 ± 0.5 | 0.3 ± 0.1 | 0.9 ± 0.1 | 0.7 ± 0 | 0.1 ± 0 |
| LBFLFK (n = 195) | 5 ± 0.1 | 0.2 ± 0 | 0.1 ± 0.1 | 4 ± 0.4 | 25.9 ± 1.8 | 31.9 ± 1.3 | 1 ± 0.2 | 4.7 ± 0.4 | 1.8 ± 0.3 | 0.4 ± 0.1 | 1 ± 0.1 | 0.7 ± 0 | 0.1 ± 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU (n = 218) | 0.1 ± 0 | 4.5 ± 0.8 | 3.2 ± 0.6 | 1.4 ± 0.3 | 10.5 ± 1.4 | 0.4 ± 0 | 0 ± 0 | 0.4 ± 0.1 | 2.3 ± 0.3 | 0.2 ± 0.1 | 2.1 ± 0.4 | 0.6 ± 0.2 | 0.4 ± 0.1 |
| LBFDGG (n = 200) | 0.1 ± 0 | 2.4 ± 0.2 | 1.4 ± 0.2 | 2 ± 0.3 | 7 ± 0.8 | 0.4 ± 0 | 0 ± 0 | 0.4 ± 0.1 | 2 ± 0.2 | 0.1 ± 0 | 1.3 ± 0.3 | 0.3 ± 0 | 0.1 ± 0 |
| LBFGKN (n = 182) | 0.1 ± 0 | 2.4 ± 0.3 | 1.3 ± 0.2 | 2.4 ± 0.3 | 7.9 ± 0.9 | 0.4 ± 0 | 0 ± 0 | 0.4 ± 0.1 | 2 ± 0.2 | 0.1 ± 0.1 | 1.6 ± 0.3 | 0.3 ± 0.1 | 0.2 ± 0.1 |
| LBFIHE (n = 157) | 0.1 ± 0.1 | 2.7 ± 0.3 | 1.7 ± 0.3 | 2.5 ± 0.4 | 9.6 ± 1.3 | 0.4 ± 0 | 0 ± 0 | 0.4 ± 0.1 | 2.2 ± 0.3 | 0.2 ± 0.1 | 2 ± 0.5 | 0.3 ± 0.1 | 0.3 ± 0.1 |
| LBFLDI (n = 229) | 0.1 ± 0 | 2.4 ± 0.3 | 1.4 ± 0.2 | 2.4 ± 0.4 | 9.2 ± 1.5 | 0.3 ± 0 | 0 ± 0 | 0.5 ± 0.1 | 2.6 ± 0.4 | 0.1 ± 0 | 1.7 ± 0.4 | 0.3 ± 0.1 | 0.2 ± 0 |
| LBFPRA (n = 196) | 0.1 ± 0 | 3 ± 0.4 | 1.7 ± 0.2 | 3.5 ± 0.4 | 13.5 ± 2 | 0.4 ± 0 | 0 ± 0 | 0.3 ± 0.1 | 2.6 ± 0.3 | 0.1 ± 0.1 | 1.7 ± 0.3 | 0.1 ± 0 | 0.3 ± 0.1 |
| LBFDHG (n = 177) | 0.1 ± 0 | 3.1 ± 0.6 | 1.9 ± 0.4 | 1.5 ± 0.3 | 8.5 ± 1.2 | 0.4 ± 0 | 0 ± 0 | 0.8 ± 0.1 | 2.5 ± 0.3 | 0.2 ± 0.1 | 2.4 ± 0.3 | 0.8 ± 0.2 | 0.2 ± 0.1 |
| LBFLFK (n = 195) | 0.1 ± 0 | 4 ± 0.9 | 2.4 ± 0.5 | 1.4 ± 0.3 | 8.3 ± 1 | 0.4 ± 0 | 0 ± 0 | 0.6 ± 0.1 | 2.7 ± 0.5 | 0.2 ± 0 | 1.5 ± 0.4 | 0.8 ± 0.3 | 0.3 ± 0.1 |

TABLE 150

Fatty acid profiles of one T3 seed batch per event harvested from T2 plants cultivated in the greenhouse of canola events containing the T-DNAs of plasmid VC-LTM593-1qcz rc. The events are indicated in the first column. Fatty acid profiles of T3 seed batches having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 1) | 5.1 | 0.3 | 0.0 | 4.7 | 20.6 | 27.6 | 1.1 | 4.3 | 2.5 | 0.5 | 1.3 | 0.6 | 0.2 |
| LBFDGG (n = 1) | 5.2 | 0.3 | 0.0 | 2.9 | 25.6 | 33.8 | 0.7 | 5.2 | 2.0 | 0.4 | 0.8 | 0.7 | 0.2 |
| LBFGKN (n = 1) | 4.8 | 0.2 | 0.0 | 3.7 | 26.5 | 30.2 | 1.2 | 4.9 | 2.3 | 0.3 | 0.8 | 0.6 | 0.2 |
| LBFIHE (n = 1) | 4.4 | 0.1 | 0.0 | 3.0 | 20.2 | 29.0 | 0.8 | 4.7 | 2.8 | 0.5 | 0.7 | 0.7 | 0.4 |
| LBFLDI (n = 1) | 6.7 | 0.3 | 0.0 | 3.0 | 22.2 | 28.3 | 1.1 | 4.0 | 2.7 | 0.7 | 0.8 | 0.5 | 0.1 |
| LBFPRA (n = 1) | 5.0 | 0.2 | 0.0 | 3.5 | 20.0 | 27.6 | 1.4 | 3.1 | 3.4 | 0.4 | 0.8 | 0.6 | 0.1 |

TABLE 150-continued

Fatty acid profiles of one T3 seed batch per event harvested from T2 plants cultivated in the greenhouse of canola events containing the T-DNAs of plasmid VC-LTM593-1qcz rc. The events are indicated in the first column. Fatty acid profiles of T3 seed batches having the highest EPA + DHA levels per event are shown. Per seed batch, a random selection of ~30 seed was measured in two technical repeats.

| | | | | | | | | | | | | |
|---|---|---|---|---|---|---|---|---|---|---|---|---|
| LBFDHG (n = 1) | 6.0 | 0.3 | 0.0 | 2.6 | 23.3 | 29.4 | 1.1 | 5.0 | 2.3 | 0.4 | 0.8 | 0.7 | 0.1 |
| LBFLFK (n = 1) | 4.9 | 0.2 | 0.2 | 3.8 | 23.0 | 31.9 | 1.0 | 4.4 | 2.3 | 0.5 | 0.9 | 0.7 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU (n = 1) | 0.1 | 4.0 | 2.8 | 1.6 | 14.1 | 0.5 | 0.0 | 0.4 | 2.8 | 0.3 | 3.5 | 0.5 | 0.3 |
| LBFDGG (n = 1) | 0.1 | 2.5 | 1.6 | 2.9 | 9.1 | 0.4 | 0.0 | 0.5 | 2.4 | 0.2 | 2.2 | 0.3 | 0.1 |
| LBFGKN (n = 1) | 0.1 | 2.5 | 1.4 | 3.2 | 10.9 | 0.3 | 0.0 | 0.4 | 2.4 | 0.1 | 2.5 | 0.2 | 0.3 |
| LBFIHE (n = 1) | 0.3 | 2.9 | 2.1 | 3.3 | 15.3 | 0.3 | 0.0 | 0.5 | 2.9 | 0.4 | 3.9 | 0.2 | 0.5 |
| LBFLDI (n = 1) | 0.1 | 3.2 | 2.1 | 2.5 | 13.8 | 0.4 | 0.0 | 0.5 | 3.4 | 0.3 | 2.7 | 0.5 | 0.2 |
| LBFPRA (n = 1) | 0.1 | 2.9 | 1.9 | 3.8 | 19.0 | 0.3 | 0.0 | 0.3 | 2.7 | 0.1 | 2.4 | 0.1 | 0.4 |
| LBFDHG (n = 1) | 0.1 | 2.8 | 1.9 | 1.6 | 12.8 | 0.4 | 0.0 | 0.7 | 3.3 | 0.4 | 3.3 | 0.6 | 0.3 |
| LBFLFK (n = 1) | 0.1 | 3.2 | 2.1 | 2.0 | 11.6 | 0.3 | 0.0 | 0.7 | 3.0 | 0.2 | 2.3 | 0.5 | 0.3 |

TABLE 151

Phenotypic rating of T2 plants cultivated in the greenhouse of canola events containing the T-DNAs of plasmids VC-LTM593-1qcz rc. The events are indicated in the first column, along with the number of T2 plants that where rated per event. DFF: days to first flower (days), DF: deformed flower (1 = deformed, 9 = normal), DL: deformed leaf (1 = deformed, 9 = normal), DP: deformed plant (1 = deformed, 9 = normal), DS: deformed silique (1 = deformed, 9 = normal), FC: flower color (1 = white, 3 = optimal, 4 = orange/yellow), LD: leaf dentation (3 = no dentation, 7 = strong dentation), LGC: leaf color (3 = yellow, 5 = optimal, 7 = blueish), LF: fertility (1 = low, 9 = very high), NoL: number of lobes (#), PH: plant height (cm), TKW: thousand kernel weight (g), SC: seed quality (1 = good, 9 = bad), Oil: oil content (% of seed weight), protein: Protein content (% of seed cake without oil)

| Event | DFF | DF | DL | DP | DS | FC | LD |
|---|---|---|---|---|---|---|---|
| LBFDAU (n = 218) | 43.2 ± 2.9 | 9 ± 0 | 9 ± 0 | 8 ± 0 | 9 ± 0 | 3 ± 0 | 4 ± 0.1 |
| LBFDGG (n = 200) | 43 ± 3.7 | 8.6 ± 1.5 | 8.5 ± 0.5 | 8 ± 0 | 8.6 ± 1.3 | 3 ± 0 | 4 ± 0 |
| LBFGKN (n = 182) | 42.5 ± 4.3 | 8 ± 2.7 | 8.5 ± 1 | 7.6 ± 1.6 | 8.1 ± 1.9 | 2.9 ± 0.3 | 4.1 ± 0.8 |
| LBFIHE (n = 157) | 51.1 ± 5.2 | 8.9 ± 0.4 | 8.9 ± 0.5 | 8.9 ± 0.5 | 5.2 ± 2.6 | 3 ± 0 | 5.1 ± 0.4 |
| LBFLDI (n = 229) | 48.6 ± 4.5 | 9 ± 0 | 9 ± 0 | 9 ± 0 | 7.6 ± 2.5 | 3 ± 0 | 5 ± 0.1 |
| LBFPRA (n = 196) | 51.2 ± 2.4 | 9 ± 0 | 9 ± 0 | 9 ± 0 | 5.8 ± 3.2 | 3 ± 0 | 5 ± 0 |
| LBFDHG (n = 177) | 46 ± 3.5 | 9 ± 0 | 9 ± 0 | 8 ± 0 | 4.7 ± 1.6 | 3 ± 0 | 4 ± 0 |
| LBFLFK (n = 195) | 42.3 ± 2.8 | 9 ± 0 | 9 ± 0 | 9 ± 0.3 | 8.9 ± 0.7 | 3 ± 0 | 4 ± 0.1 |

| Event | LGC | LF | NoL | PH | TKW | SC | Oil | Protein |
|---|---|---|---|---|---|---|---|---|
| LBFDAU (n = 218) | 5 ± 0 | 8.6 ± 0.8 | 5.1 ± 0.6 | 107.5 ± 7.6 | 3 ± 0.3 | 3.7 ± 1.2 | 35.6 | |
| LBFDGG (n = 200) | 5 ± 0 | 8.7 ± 0.7 | 4.5 ± 0.5 | 112.1 ± 5.5 | 3 ± 0.3 | 3.7 ± 0.7 | N/A | |
| LBFGKN (n = 182) | 5 ± 0.3 | 8.5 ± 1 | 5 ± 0 | 111.6 ± 15.2 | 3.3 ± 0.4 | 3.3 ± 0.6 | 36.1 | |
| LBFIHE (n = 157) | 4.9 ± 0.4 | 5.2 ± 2.6 | 6.6 ± 1.1 | 139.4 ± 14.7 | 4 ± 0.5 | 3.8 ± 1.9 | 34.1 | |
| LBFLDI (n = 229) | 5 ± 0.1 | 7.6 ± 2.5 | 6.2 ± 1.1 | 145.5 ± 15.9 | 4.2 ± 0.4 | 3.1 ± 1.3 | N/A | |
| LBFPRA (n = 196) | 5 ± 0 | 5.8 ± 3.2 | 7.3 ± 1 | 138.7 ± 16.6 | 4.2 ± 0.4 | 2.4 ± 1.5 | 34.7 | |
| LBFDHG (n = 177) | 5 ± 0 | 8.5 ± 0.8 | 5.2 ± 0.8 | 112.5 ± 5.4 | 3.4 ± 0.4 | 5.3 ± 1 | 32.3 | |
| LBFLFK (n = 195) | 5 ± 0 | 8.7 ± 0.9 | 5.3 ± 0.5 | 113.4 ± 8 | 3.3 ± 0.3 | 3.9 ± 1.5 | 37.1 | |

Fatty Acid Profiles, Copy Number Measurements, and Phenotypic Observations of T2 Plants Carrying T-DNAs of Plasmids VC-LTM593-1Qcz Rc Cultivated in Field Trials in USDA Growth Zones 3a-4b and 5a During the Summer Field data for the T3 seed from the events carrying the T-DNA from VC-LTM593-1qcz rc, shown in Table 152 and Table 153, indicate that the plants are capable of making VLC-PUFAs in the field (ARA, EPA and DHA), though not at the level observed in the greenhouse. ANOVA was conducted with using the software JMP 11.0. Analysis was conducted at the 95% confidence level using Tukey test. To compensate for unbalance in the data obtained from the field trial (e.g. due to e.g. weather), Least Square menas instead of means where used in the statistical analysis. Common letters in the Table 154, Table 155 and Table 156 inidcate no significant difference of the least square means. Table 154 shows the statistical analysis of agronomical parameters.

There was a difference in seed oil content observed compared to the greenhouse (e.g. comparing Table 154 with Table 151), indicating oil content and the fatty acid profile could be linked. These observations are in agreement with previous examples (Examples 10, 11, and 13) where it was observed that increased oil contents in the field grown plants concomitant with a decrease in VLC-PUFAs, in particular EPA, DHA and ARA. A more detailed description of the observations regarding oil content and VLC-PUFAs is given in Example 20.

The % of EPA and DHA (% (w/w) for each fatty acid compared to the total weight of fatty acids) in Table 152 can be combined with the oil amount in Table 154 to calculate the mg EPA+DHA/g seed produced in the transgenic events. Using this calculation, bulked seeds from event LBFGKN were determined to have 25.7 mg EPA+DHA/g seed and bulked seeds from event LBFDAU was determined to have 47.4 mg EPA+DHA/g seed.

Figure 88:
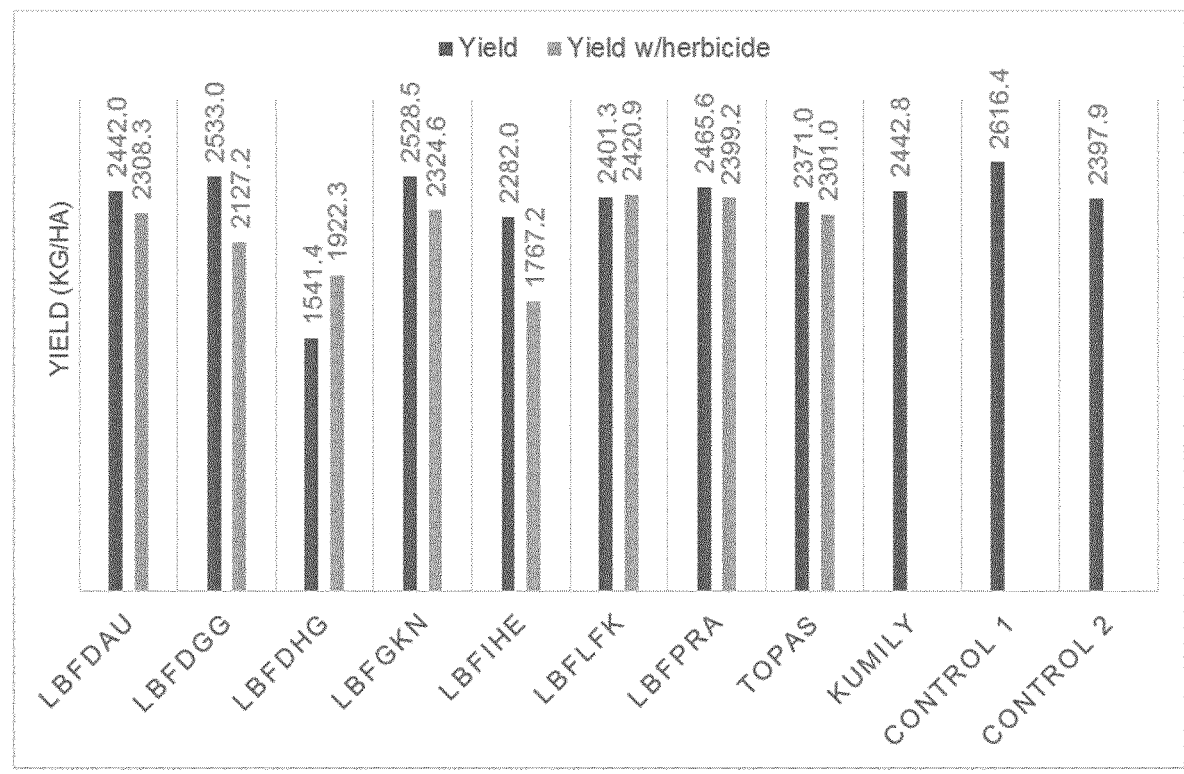
FIG. 88. Yield (kg seeds/ha) of canola plants grown in the field in 2014. Plants were either not treated (Yield) or were treated with 2× rate of imidazolinone herbicide (Yield w/herbicide).

For seed yield (kg per ha, FIG. 88), no statistically relevant difference was found comparing the events against wildtype Kumily when grown in the field with or without treatment with imidazolinone herbicide (tested using Tukey, 0.05% level). Thus, in one embodiment, the present invention relates to one or more transgenic plants, preferably *B. napus* plant(s), producing EPA and DHA, according to the present invention whereby the seed yield of the plant is 80%, 85%, 90%, 95%, 96%, 97%, 98%, 99% or more identical to a control plant. Preferably, the seed yield of the plant is 80%, 85%, 90%, 95%, 96%, 97%, 98%, 99% or more identical to a control grown without treatment with imidazolinone herbicide whereas the plant of the invention is grown with an imidazoline herbicide treatment.

In one embodiment, the harvesting bulk seed from the plants of the invention, preferably from the plants grown in a field, has a measured yield (kg seed/ha) that is 15%, 8%, 4%, or preferably 1% or less lower than the yield of a control plant. Preferably, the harvested bulk seed yield of the plant is 80%, 85%, 90%, 95%, 96%, 97%, 98%, 99% or more identical to a control grown without treatment with imidazolinone herbicide whereas the plant of the invention is grown with an imidazoline herbicide treatment.

Thus, a transgenic *B. napus* plant of the invention is able to produce more than 1% EPH+DHA in the oil in the bulk seed, preferably, it produces more than 2%, e.g. more than 3%, 4%, 5%, 6%, 7%, 8%, 9% or more than 10% oil in the bulk seed. Preferably, the oil in the bulk seed of the plant of the invention is 80%, 85%, 90%, 95%, 96%, 97%, 98%, 99% or more identical to a control plant grown without treatment with imidazolinone herbicide whereas the plant of the invention is grown with an imidazoline herbicide treatment. The contents are expressed as percentage (weight of EPA+DHA) of the total weight of all fatty acids (present in the oil or lipid). The contents are thus, preferably given as weight percentage (% (w/w)).

A control plant is preferably a plant that is at least genetically 90%, 95%, 96%, 97%, 98%, or preferably 99% or 99.5% or more identical to the plant of the invention, e.g. to the plants described in the examples, but does not produce any VLC-PUFA grown under the same conditions, e.g. a wild type grown under the same conditions.

Figure 89:
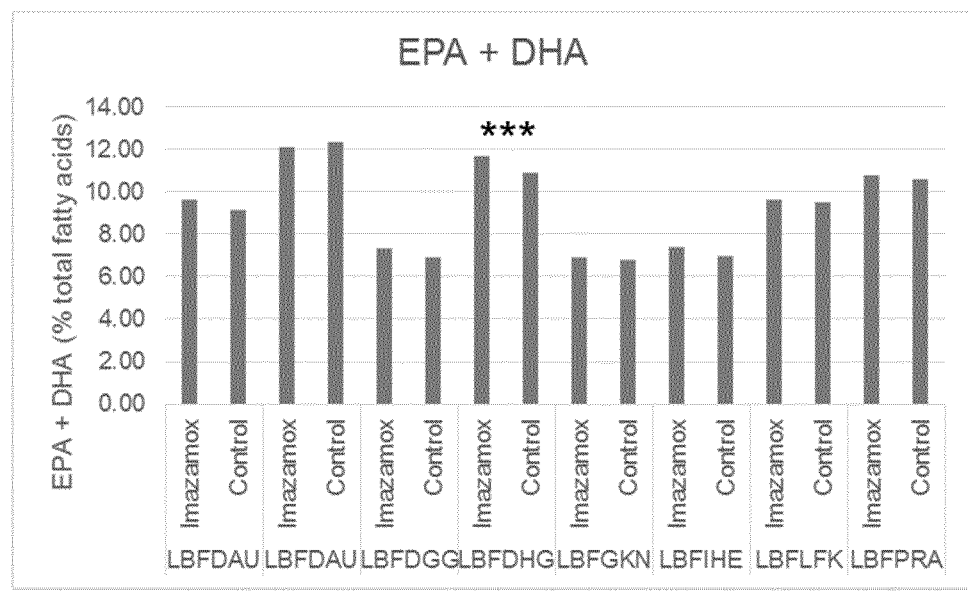
FIG. 89. EPA plus DHA content in seeds of plants grown in the field with (Imazamox) or without (control) herbicide treatment. *** denotes a significant difference between herbicide treatment and control as calculated by ANOVA, p<0.05.
Figure 90:
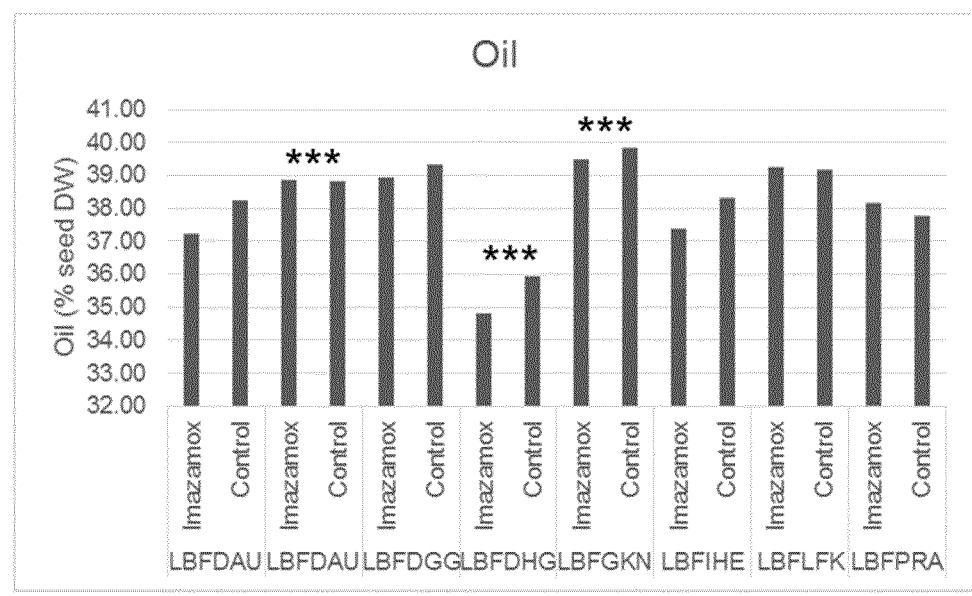
FIG. 90. Oil content in seeds of plants grown in the field with (Imazamox) or without (control) herbicide treatment. *** denotes a significant difference between herbicide treatment and control as calculated by ANOVA, p<0.05.
Figure 91:
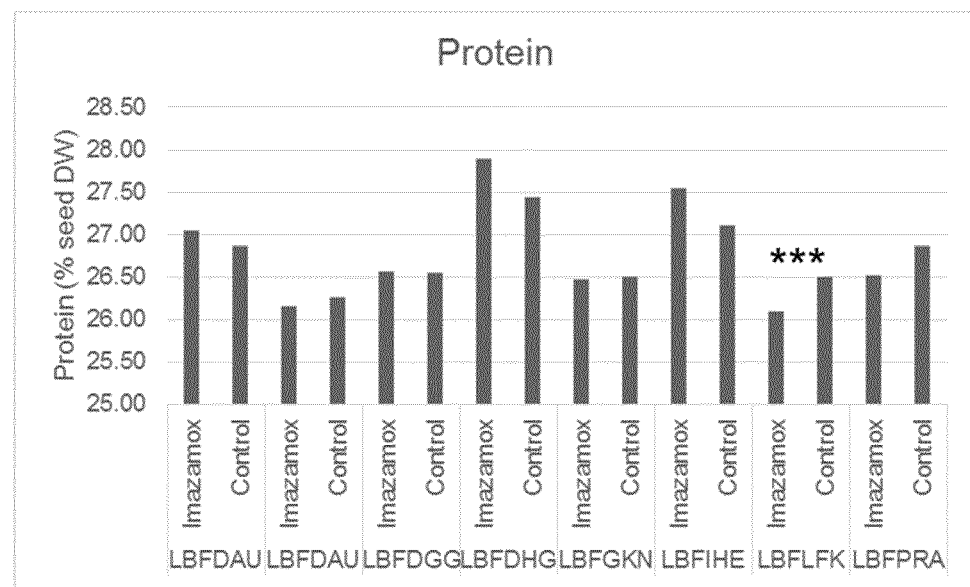
FIG. 91. Protein content in seeds of plants grown in the field with (Imazamox) or without (control) herbicide treatment. *** denotes a significant difference between herbicide treatment and control as calculated by ANOVA, p<0.05.

Herbicide treatment also did not have a consistent effect on EPA and DHA (FIG. 89), oil (FIG. 90), or protein (FIG. 91) content in seeds compared to plants that were not sprayed with imidazolinone. Thus, in one embodiment, the present invention relates to one or more transgenic plants, preferably *B. napus* plant(s), producing EPA and DHA, according to the present invention whereby the oil (FIG. 90), or protein (FIG. 91) content of the plant is 80%, 85%, 90%, 95%, 96%, 97%, 98%, 99% or more identical to a control plant.

A control plant is preferably a plant that is at least genetically 90%, 95%, 96%, 97%, 98%, or preferably 99% or 99.5% or more identical to the plant of the invention, e.g. to the plants described in the examples, but does not produce any VLC-PUFA, in particular a control plant grown without treatment with imidazolinone herbicide whereas the plant of the invention is grown with a imidazoline herbicide treatment.

Thus, in one embodiment, the bulk seed of the transgenic plant of the invention comprises a seed oil that contains EPA and DHA, wherein the the content of EPA and DHA in the seed oil is more than 2%, 3, %, 4%, 5%, 5.9%, 6%, 7%, 8%, 9%, 10%, 12%, 15% of the total fatty acid content in seed oil, even after treatment with imidazolinone herbicide Fertility of plants in the field was assessed by rating the percent of sterile pods on mulitple plants from each plot. Fertility was assessed for WT Kumily, and for events LBFDGG, LBFGKN, LBFIDT, LBFIHE, LBFLDI, and LBFPRA. On a scale of 0 to 10, a score of 0 means that 0% of pods were sterile, 1 means that 10% of pods were sterile, 2 means that 20% of pods were sterile, and so on up to 10, which means that 100% of pods were sterile. The mean fertility score for wild type Kumily control plants across all plots was 0.17, meaning that 1.7% of pods were sterile. The mean score for the transgenic events ranged from 0.33 to 0.63, meaning that 3.3 to 5.3% of pods were sterile.

Interestingly, expression of the polynucleotides encoding the desaturases or elongases as referred to herein did not significantly affect the fertility of the generated plants. As compared to control plants (wild-type plants), the fertility was only slighty decreased.

Thus, the present invention relates in one embodiment to a a transgenic plant, preferably to a transgenic *B. napus* plant seed containing more than 2%, 2.5%, 3%, 4%, 5%, 6%, 7%, 8%; 9%, 10%, 12% or more EPA and DHA in the seed oil when grown in field conditions. The average plant fertility as measured by selecting at random a number of plants then observing percent plants with one or more sterile pods/bud is 30% or less, or is 20% or less, or is about 10% or less or is 5% or less or is 4% or less or is 3.3% or less, preferably is between 1% and 10%, more preferred between 3% and 7%, e.g. between 3.3% and 5.3% of the same measure observed in a control plant, e.g. in a wild type plant grown under the same conditions.

Preferably, a control plant is preferably a plant that at least genetically 90%, 95%, 96%, 97%, 98%, or preferably 99% or 99.5% or more identical to the plant of the invention, e.g. to the plants described in the examples, but does not produce any VLC-PUFA.

In one embodiment, the plant of the invention was transformed with a medium (>10,000 base pairs) or large (>30,000 base pairs) T-DNA insert, e.g. a T-DNA described in the Examples. In one embodiment, the T-DNA is consists of 1000 bps to 10,000 bps, e.g. between 3000 bps and 9000 bps, preferably between 4000 bps and 8500 bps.

TABLE 152

Fatty acid profiles of T3 seeds harvested from T2 plants cultivated in the field, corresponding to USDA growth zones 3a-4b and 5a, for field trials of canola events containing the T-DNAs of plasmid VC-LTM593-1qcz rc. The events are indicated in the first column, along with the number of T3 seed aliquots representing a plot where measured per event. For event LBFGKN, 36 plots and 60 single plants from those plots where measured. Per seed batch a random selection of ~15 seed was measured in five technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 16) | 4.7 ± 0.1 | 0.2 ± 0 | 0 ± 0 | 2.7 ± 0.1 | 28.6 ± 1.5 | 29.2 ± 0.7 | 1 ± 0.1 | 6.1 ± 0.3 | 1.6 ± 0.1 | 0.3 ± 0 | 0.7 ± 0 | 0.7 ± 0 | 0.1 ± 0 |
| LBFDGG (n = 36) | 4.7 ± 0.1 | 0.2 ± 0 | 0 ± 0 | 2.5 ± 0.2 | 34.2 ± 1.9 | 32.3 ± 1.2 | 0.6 ± 0.1 | 7 ± 0.5 | 1.2 ± 0.1 | 0.2 ± 0 | 0.6 ± 0 | 0.8 ± 0 | 0.1 ± 0 |

TABLE 152-continued

Fatty acid profiles of T3 seeds harvested from T2 plants cultivated in the field, corresponding to USDA growth zones 3a-4b and 5a, for field trials of canola events containing the T-DNAs of plasmid VC-LTM593-1qcz rc. The events are indicated in the first column, along with the number of T3 seed aliquots representing a plot where measured per event. For event LBFGKN, 36 plots and 60 single plants from those plots where measured. Per seed batch a random selection of ~15 seed was measured in five technical repeats.

| | | | | | | | | | | | | | |
|---|---|---|---|---|---|---|---|---|---|---|---|---|---|
| LBFGKN | 4.6 ± | 0.2 ± | 0 ± 0 | 2.6 ± | 33.7 ± | 32.8 ± | 0.6 ± | 7.5 ± | 0.9 ± | 0.2 ± | 0.7 ± | 0.8 ± | 0.2 ± |
| (n = 36 + 60) | 0.2 | 0 | | 0.2 | 1.7 | 1.4 | 0.1 | 0.6 | 0.1 | 0 | 0 | 0.1 | 0 |
| LBFIHE | 4.8 ± | 0.2 ± | 0 ± 0 | 2.6 ± | 31.2 ± | 33.9 ± | 0.6 ± | 6.7 ± | 1.3 ± | 0.3 ± | 0.7 ± | 0.8 ± | 0.2 ± |
| (n = 36) | 0.2 | 0 | | 0.2 | 1.7 | 1.2 | 0.1 | 0.7 | 0.2 | 0 | 0.1 | 0 | 0 |
| LBFLDI | 4.9 ± | 0.3 ± | 0 ± 0 | 2.5 ± | 33.4 ± | 32.7 ± | 0.6 ± | 6.8 ± | 1 ± | 0.2 ± | 0.7 ± | 0.8 ± | 0.2 ± |
| (n = 36) | 0.2 | 0 | | 0.2 | 1.7 | 1.2 | 0.1 | 0.6 | 0.1 | 0 | 0.1 | 0 | 0 |
| LBFIDT | 4.6 ± | 0.2 ± | 0 ± 0 | 2.7 ± | 30 ± | 29.9 ± | 0.9 ± | 6.5 ± | 1.6 ± | 0.3 ± | 0.7 ± | 0.7 ± | 0.1 ± |
| (n = 32) | 0.1 | 0 | | 0.2 | 1.4 | 1 | 0.1 | 0.5 | 0.1 | 0 | 0.1 | 0 | 0 |
| LBFPRA | 4.8 ± | 0.2 ± | 0 ± 0 | 2.6 ± | 28.4 ± | 32.7 ± | 0.8 ± | 5.7 ± | 1.6 ± | 0.3 ± | 0.7 ± | 0.8 ± | 0.2 ± |
| (n = 36) | 0.2 | 0 | | 0.2 | 2.1 | 1.4 | 0.1 | 0.4 | 0.2 | 0.1 | 0 | 0 | 0 |
| LBFDHG | 5.2 ± | 0.2 ± | 0 ± 0 | 2.4 ± | 28.2 ± | 29.5 ± | 0.9 ± | 6.5 ± | 1.6 ± | 0.3 ± | 0.6 ± | 0.7 ± | 0.2 ± |
| (n = 4) | 0.1 | 0 | | 0.1 | 1.4 | 1 | 0.2 | 0 | 0.1 | 0 | 0 | 0 | 0 |
| LBFLFK | 4.7 ± | 0.2 ± | 0 ± 0 | 2.6 ± | 30.1 ± | 30.2 ± | 0.9 ± | 6.2 ± | 1.5 ± | 0.3 ± | 0.6 ± | 0.8 ± | 0.1 ± |
| (n = 36) | 0.2 | 0 | | 0.2 | 1.9 | 1.1 | 0.1 | 0.4 | 0.2 | 0.1 | 0 | 0 | 0 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU | 0.1 ± | 3.3 ± | 2.2 ± | 2 ± | 10.7 ± | 0.3 ± | 0 ± 0 | 0.3 ± | 2.9 ± | 0.1 ± | 1.6 ± | 0.3 ± | 0.3 ± |
| (n = 16) | 0 | 0.3 | 0.2 | 0.2 | 0.7 | 0 | | 0 | 0.2 | 0 | 0.2 | 0.1 | 0 |
| LBFDGG | 0.1 ± | 2 ± | 1.3 ± | 1.9 ± | 6.1 ± | 0.3 ± | 0 ± 0 | 0.3 ± | 2.1 ± | 0.1 ± | 1.1 ± | 0.2 ± | 0.1 ± |
| (n = 36) | 0 | 0.3 | 0.2 | 0.2 | 0.7 | 0 | | 0 | 0.2 | 0 | 0.2 | 0.1 | 0 |
| LBFGKN | 0.1 ± | 2.1 ± | 1.2 ± | 1.8 ± | 6 ± | 0.3 ± | 0 ± 0 | 0.3 ± | 2.1 ± | 0.1 ± | 1 ± | 0.2 ± | 0.2 ± |
| (n = 36 + 60) | 0 | 0.3 | 0.1 | 0.2 | 0.6 | 0 | | 0.1 | 0.2 | 0 | 0.1 | 0 | 0 |
| LBFIHE | 0.1 ± | 2.1 ± | 1.2 ± | 2.4 ± | 6.7 ± | 0.3 ± | 0 ± 0 | 0.3 ± | 1.9 ± | 0.1 ± | 1.2 ± | 0.2 ± | 0.2 ± |
| (n = 36) | 0 | 0.2 | 0.1 | 0.3 | 0.6 | 0 | | 0.1 | 0.2 | 0 | 0.2 | 0.1 | 0 |
| LBFLDI | 0.1 ± | 2 ± | 1.2 ± | 2 ± | 6.2 ± | 0.3 ± | 0 ± 0 | 0.3 ± | 2.1 ± | 0.1 ± | 1.1 ± | 0.2 ± | 0.2 ± |
| (n = 36) | 0 | 0.3 | 0.2 | 0.2 | 0.7 | 0 | | 0 | 0.2 | 0 | 0.2 | 0 | 0 |
| LBFIDT | 0.1 ± | 4.4 ± | 2.6 ± | 1.5 ± | 6.8 ± | 0.3 ± | 0 ± 0 | 0.6 ± | 2.9 ± | 0.1 ± | 1.2 ± | 1 ± | 0.3 ± |
| (n = 32) | 0 | 0.4 | 0.2 | 0.2 | 0.7 | 0 | | 0.1 | 0.3 | 0 | 0.2 | 0.1 | 0 |
| LBFPRA | 0.1 ± | 2.3 ± | 1.2 ± | 3.8 ± | 9.6 ± | 0.3 ± | 0 ± 0 | 0.3 ± | 2.4 ± | 0.1 ± | 1.1 ± | 0.1 ± | 0.2 ± |
| (n = 36) | 0 | 0.3 | 0.2 | 0.5 | 1 | 0 | | 0 | 0.3 | 0 | 0.2 | 0 | 0.1 |
| LBFDHG | 0.1 ± | 2.9 ± | 1.7 ± | 2 ± | 9.6 ± | 0.3 ± | 0 ± 0 | 0.6 ± | 3.5 ± | 0.2 ± | 1.9 ± | 0.5 ± | 0.3 ± |
| (n = 4) | 0 | 0 | 0 | 0.1 | 0.4 | 0 | | 0 | 0.1 | 0 | 0.2 | 0.1 | 0 |
| LBFLFK | 0.1 ± | 3.3 ± | 1.9 ± | 1.9 ± | 8.2 ± | 0.3 ± | 0 ± 0 | 0.5 ± | 3.2 ± | 0.1 ± | 1.4 ± | 0.5 ± | 0.3 ± |
| (n = 36) | 0 | 0.3 | 0.2 | 0.2 | 1 | 0 | | 0 | 0.4 | 0 | 0.3 | 0.1 | 0.1 |

TABLE 153

Fatty acid profiles of one T3 seed batch per event harvested from T2 plants cultivated in USDA growth zones 3a-4b and 5a for field trials of canola events containing the T-DNAs of plasmid VC-LTM593-1qcz rc. The events are indicated in the first column. Fatty acid profiles of T3 seed batches representing a field plot having the highest EPA + DHA levels per event are shown. Per seed batch, a random selection of ~30 seed was measured in two technical repeats.

| Event | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 | 20:0 | 20:1 n-9 | 20:2 n-6 |
|---|---|---|---|---|---|---|---|---|---|---|---|---|---|
| LBFDAU (n = 1) | 4.9 | 0.2 | 0.0 | 2.6 | 26.0 | 28.9 | 0.8 | 6.2 | 1.7 | 0.3 | 0.7 | 0.8 | 0.2 |
| LBFDGG (n = 1) | 5.0 | 0.3 | 0.0 | 2.7 | 30.1 | 33.1 | 0.5 | 6.5 | 1.5 | 0.3 | 0.7 | 0.8 | 0.2 |
| LBFGKN (n = 1) | 4.4 | 0.2 | 0.0 | 2.6 | 32.6 | 31.1 | 0.7 | 7.3 | 1.1 | 0.3 | 0.6 | 0.8 | 0.2 |
| LBFIHE (n = 1) | 4.8 | 0.2 | 0.0 | 2.5 | 28.0 | 33.9 | 0.6 | 6.3 | 1.6 | 0.3 | 0.8 | 0.8 | 0.2 |
| LBFLDI(n = 1) | 5.2 | 0.3 | 0.0 | 2.5 | 29.8 | 33.3 | 0.4 | 6.8 | 1.3 | 0.4 | 1.1 | 0.8 | 0.2 |
| LBFIDT (n = 1) | 4.7 | 0.2 | 0.0 | 2.6 | 28.6 | 28.8 | 1.0 | 7.1 | 1.6 | 0.3 | 0.7 | 0.7 | 0.1 |
| LBFPRA (n = 1) | 5.1 | 0.2 | 0.0 | 2.6 | 26.0 | 31.5 | 0.7 | 5.3 | 1.8 | 0.3 | 0.7 | 0.7 | 0.2 |
| LBFDHG (n = 1) | 5.1 | 0.2 | 0.0 | 2.4 | 29.0 | 28.4 | 1.0 | 6.6 | 1.6 | 0.3 | 0.6 | 0.8 | 0.1 |
| LBFLFK(n = 1) | 5.1 | 0.2 | 0.0 | 2.6 | 26.9 | 29.3 | 0.8 | 5.9 | 1.9 | 0.4 | 0.7 | 0.8 | 0.1 |

| Event | 20:3 n-3 | 20:3 n-6 | 20:4 n-3 | 20:4 n-6 | 20:5 n-3 | 22:0 | 22:1 n-9 | 22:4 n-6 | 22:5 n-3 | 22:5 n-6 | 22:6 n-3 | 22:4 n-3 | 20:2 n-9 |
|---|---|---|---|---|---|---|---|---|---|---|---|---|---|
| LBFDAU (n = 1) | 0.1 | 3.6 | 2.4 | 2.0 | 12.0 | 0.3 | 0.0 | 0.3 | 3.2 | 0.1 | 2.1 | 0.4 | 0.3 |
| LBFDGG (n = 1) | 0.1 | 2.1 | 1.4 | 2.4 | 7.5 | 0.3 | 0.0 | 0.4 | 2.4 | 0.1 | 1.6 | 0.2 | 0.1 |
| LBFGKN (n = 1) | 0.1 | 2.1 | 1.3 | 2.1 | 7.7 | 0.3 | 0.0 | 0.3 | 2.5 | 0.1 | 1.3 | 0.2 | 0.2 |
| LBFIHE (n = 1) | 0.1 | 2.4 | 1.5 | 2.7 | 8.2 | 0.3 | 0.0 | 0.4 | 2.3 | 0.1 | 1.6 | 0.2 | 0.2 |
| LBFLDI(n = 1) | 0.1 | 1.8 | 1.2 | 2.4 | 7.2 | 0.4 | 0.0 | 0.4 | 2.4 | 0.1 | 1.6 | 0.2 | 0.2 |
| LBFIDT (n = 1) | 0.1 | 4.3 | 2.6 | 1.5 | 8.1 | 0.3 | 0.0 | 0.6 | 3.4 | 0.1 | 1.4 | 1.0 | 0.4 |

TABLE 153-continued

Fatty acid profiles of one T3 seed batch per event harvested from T2 plants cultivated in USDA growth zones 3a-4b and 5a for field trials of canola events containing the T-DNAs of plasmid VC-LTM593-1qcz rc. The events are indicated in the first column. Fatty acid profiles of T3 seed batches representing a field plot having the highest EPA + DHA levels per event are shown. Per seed batch, a random selection of ~30 seed was measured in two technical repeats.

| | | | | | | | | | | | | | |
|---|---|---|---|---|---|---|---|---|---|---|---|---|---|
| LBFPRA (n = 1) | 0.1 | 2.4 | 1.3 | 4.3 | 11.7 | 0.3 | 0.0 | 0.3 | 2.8 | 0.0 | 1.3 | 0.1 | 0.2 |
| LBFDHG (n = 1) | 0.1 | 2.9 | 1.7 | 1.9 | 10.2 | 0.3 | 0.0 | 0.5 | 3.5 | 0.2 | 1.9 | 0.5 | 0.3 |
| LBFLFK (n = 1) | 0.1 | 3.1 | 2.0 | 2.3 | 10.3 | 0.3 | 0.0 | 0.6 | 3.9 | 0.1 | 2.0 | 0.5 | 0.2 |

TABLE 154

Phenotypic rating of T2 plants cultivated in USDA growth zones 3a-4b and 5a for field trials of canola events containing the T-DNAs of plasmid VC-LTM593-1qcz rc. The events are indicated in the first column, along with the number of field plots that where rated per event. Stand: the number of plants that emerged within a 1 meter section of row at GS 14 (4 leaves unfolded), rating of a seedlings ability to grow and develop at GS 14

| Event | Stand | | Vigor | | Plant Height | | Lodging | | Shatter | |
|---|---|---|---|---|---|---|---|---|---|---|
| LBFDAU (n= 16) | 23.7 | a | 5.7 | bcd | 115.5 | b | 2.3 | ab | 1.5 | a |
| LBFDGG (n = 36) | 23.0 | a | 5.9 | bcd | 116.2 | b | 2.3 | b | 1.6 | a |
| LBFDHG (n = 4) | 23.4 | | 5.8 | | 115.9 | | 2.3 | | 1.5 | |
| LBFGKN (n = 36) | 22.8 | a | 6.3 | bcd | 118.8 | b | 2.8 | ab | 1.8 | a |
| LBFIHE (n = 36) | 21.7 | a | 5.6 | cd | 115.2 | b | 2.3 | b | 1.6 | a |
| LBFLFK(n = 36) | 22.5 | a | 5.1 | d | 118.4 | b | 2.6 | ab | 1.5 | a |
| LBFPRA(n = 36) | 22.5 | a | 6.3 | bcd | 121.2 | b | 2.9 | ab | 1.9 | a |
| Topas | 24.8 | a | 5.2 | d | 139.7 | a | 3.2 | ab | 2.6 | a |
| Kumily | 28.2 | a | 6.9 | ab | 119.9 | b | 2.8 | ab | 1.8 | a |
| Control 1 | 28.1 | a | 7.7 | a | 121.1 | b | 3.9 | a | 2.7 | a |
| Control 2 | 25.3 | a | 6.6 | abc | 119.1 | b | 3.8 | a | 2.7 | a |

| Agron Score | | Moisture | | TWK | | Oil | | Protein | |
|---|---|---|---|---|---|---|---|---|---|
| 4.7 | ab | 9.0 | a | 3.5 | abcd | 38.5 | bc | 26.6 | c |
| 4.2 | ab | 8.9 | a | 3.8 | a | 38.8 | abc | 26.3 | c |
| 4.4 | | 9.0 | | 3.7 | | 39.3 | abc | 26.5 | c |
| 4.1 | ab | 8.5 | a | 3.7 | ab | 36.7 | c | 26.5 | c |
| 4.1 | ab | 8.7 | a | 3.4 | bcd | 39.8 | ab | 26.5 | c |
| 4.1 | ab | 8.6 | a | 3.7 | a | 38.3 | bc | 27.1 | c |
| 4.2 | ab | 8.5 | a | 3.5 | abc | 39.2 | abc | 26.5 | c |
| 4.4 | a | 7.3 | b | 3.3 | cd | 37.8 | c | 26.9 | c |
| 4.5 | a | 7.4 | b | 3.7 | ab | 39.8 | ab | 28.5 | a |
| 3.4 | b | 7.0 | b | 3.2 | d | 39.9 | ab | 27.1 | c |
| 3.4 | b | 7.0 | b | 3.1 | d | 40.7 | a | 27.4 | bc |

(4 leaves unfolded, 1 = All plants at different growth stages and all plants appear unhealthy, 9 = All plants at same growth stage and all plants appear healthy), Plant Height: the average height (cm) of five plants in a plot measured from soil level to the top of the plant at GS 69 (cm), Lodging: rating of the average standability of plants in a plot at GS 83 (30% of pods ripe, 1 = 0-10% average lean of plants in plot from horizontal (standing erect), 9 = 81%+ average lean of plants in plot from horizontal (nearly prostrate)), Shatter: rating of the ability of plants to retain seed in the pod at GS 89 (all pods fully ripe, 1 =0 –10% perished pods, 9 = 81%+ perished pods), Agron Score: scale of 1-5 with 1 being the best, 5 the worst ranking of plant phenotype (measurements occurred post flower during pods formation and seed development),Moisture (% of seed weight), TKW: thousand kernel weight (g), Oil: oil content (% of seed weight), protein: Protein content (% of seed cake without oil).

TABLE 155

Compositional analysis of T3 seeds of T2 plants cultivated in USDA growth zones 3a-4b and 5a for field trials of canola events containing the T-DNAs of plasmid VC-LTM593-1qcz rc. The events are indicated in the first column. The analysis has been done on 4 BULK, whereby each BULK is a representative sample of all seeds harvedted from 4 different geographic reagions.

| Event | Alpha-Tocopherol | | Beta-Tocopherol | | Delta-Tocopherol | | Gamma-Tocopherol | | Tocopherols (VitE) | | Sinapine | |
|---|---|---|---|---|---|---|---|---|---|---|---|---|
| LBFDAU | 13.3 | ab | 0.2 | a | 0.58 | a | 29.5 | a | 43.7 | a | 0.64 | cd |
| LBFDGG | 14.1 | ab | 0.2 | a | 0.45 | bcd | 25.6 | b | 40.4 | abc | 0.69 | bcd |
| LBFGKN | 12.9 | b | 0.23 | a | 0.52 | abc | 26.9 | ab | 40.6 | abc | 0.70 | bc |
| LBFIHE | 13.2 | ab | 0.23 | a | 0.45 | bcd | 22.0 | cd | 35.9 | cde | 0.65 | cd |
| LBFLFK | 12.5 | b | 0.23 | a | 0.52 | abc | 25.7 | b | 38.9 | abc | 0.68 | bcd |
| LBFPRA | 13.6 | ab | 0.22 | a | 0.47 | bcd | 24.9 | bc | 39.2 | abc | 0.62 | d |
| Topas | 14.7 | ab | 0.25 | a | 0.36 | d | 16.6 | e | 31.9 | e | 0.69 | bcd |
| Kumily | 12.3 | b | 0.23 | a | 0.54 | ab | 24.4 | bc | 37.5 | bcd | 0.78 | a |

TABLE 155-continued

Compositional analysis of T3 seeds of T2 plants cultivated in USDA growth zones 3a-4b and 5a for field trials of canola events containing the T-DNAs of plasmid VC-LTM593-1qcz rc. The events are indicated in the first column. The analysis has been done on 4 BULK, whereby each BULK is a representative sample of all seeds harvedted from 4 different geographic reagions.

| | | | | | | | | | | | | |
|---|---|---|---|---|---|---|---|---|---|---|---|---|
| Control 1 | 16.6 | a | 0.25 | a | 0.43 | cd | 24.1 | bc | 41.4 | ab | 0.73 | ab |
| Control 2 | 12.0 | b | 0.20 | a | 0.45 | bcd | 20.8 | d | 33.5 | dc | 0.72 | ab |

| Event | Glucosinolate | | Phytate | | Ash | | Crude Fiber | | ADF | | NDF | |
|---|---|---|---|---|---|---|---|---|---|---|---|---|
| LBFDAU | 11.0 | bcd | 2.3 | B | 4.5 | ab | 9.4 | a | 11.8 | ab | 14.5 | a |
| LBFDGG | 13.1 | ab | 2.3 | B | 4.3 | ab | 9.2 | a | 10.9 | cdef | 13.6 | ab |
| LBFGKN | 11.3 | bc | 2.3 | b | 4.4 | ab | 9.3 | a | 11.0 | bcdef | 13.5 | ab |
| LBFIHE | 15.7 | a | 2.2 | b | 4.7 | ab | 9.1 | a | 10.8 | cdef | 13.4 | ab |
| LBFLFK | 12.6 | abc | 2.3 | b | 4.3 | b | 9.6 | a | 11.3 | abcde | 13.7 | ab |
| LBFPRA | 10.9 | bcd | 2.2 | b | 4.3 | ab | 9.6 | a | 12.0 | a | 14.6 | a |
| Topas | 7.6 | d | 2.7 | a | 4.8 | a | 9.0 | a | 10.5 | ef | 12.9 | b |
| Kumily | 11.0 | bcd | 2.2 | b | 4.3 | b | 9.1 | a | 11.5 | abc | 14.3 | a |
| Control 1 | 9.5 | cd | 2.3 | b | 4.6 | ab | 8.6 | a | 10.2 | f | 12.8 | b |
| Control 2 | 11.9 | bc | 2.3 | b | 4.4 | ab | 9.2 | a | 10.6 | def | 13.8 | ab |

Alpha-Tocopherol (mg/100 g seed), Beta-Tocopherol (mg/100 g seed), Delta-Tocopherol (mg/100 g seed), Gamma-Tocopherol (mg/100 g seed), Tocopherol (mg/100 g seed), Sinapine (pu/g (ppm)), Phytate (% of seed weight (w/w)), Ash (% of seed weight (w/w)), Crude Fiber (% of seed weight (w/w)), ADF: acid detergent fiber (% of seed weight w/w)), NDF: neutral detergent fiber (% of seed weight (w/w)). All results have been normalized to the seed weight of seeds having 0% moisture.

TABLE 156

Herbicide tolerance of T2 plants cultivated in USDA growth zones 3a-4b and 5a for field trials of canola events containing the T-DNAs of plasmid VC-VC-LTM593-1qcz rc. The events are indicated in the first column. IMI Injury:injury according to the scale detailed in Table 157 (DAT = days after treatment). Herbicide imazamox was aplied at a 2× rate of 70 g imazamox/ha. Brassica napus cv Kumily, which is the non-transgeneic comparator line that is otherwise isogenic to the events, was rated at 6 to 7, and was removed from the statistical analysis to make the Tukey test more sensitive to detect significant differences between events that are very similar in their tolerance.

| Event | IMI Injury 7 DAT | | IMI Injury 14 DAT | | IMI Injury 21 DAT | |
|---|---|---|---|---|---|---|
| LBFDAU | 2 | a | 1 | ab | 1 | a |
| LBFDGG | 2 | a | 1 | ab | 1 | a |
| LBFDHG | 2 | | 1 | | 1 | |
| LBFGKN | 2 | a | 1 | ab | 1 | a |
| LBFIHE | 2 | a | 2 | a | 1 | a |
| LBFLFK | 2 | a | 1 | b | 1 | a |
| LBFPRA | 2 | a | 1 | ab | 1 | a |
| Topas | 1 | a | 1 | b | 1 | a |
| Kumily | 6 | | 6 | | 7 | |

TABLE 157

Canola rating scale for herbicide

| % Injury | 1-7 Scale | Category | Injury Symptoms | Growth Rates and Recovery Effects |
|---|---|---|---|---|
| 0 | 1 | Excellent | None | None |
| 1-6 | 2 | Very Good | Leaf and petiole epinasty, chlorosis. | Minor or temporary growth effects. Injury and effects should be minor enough to not cause commercialization concerns. |
| 7-14 | 3 | Good | Leaf, petiole and stem epinasty, chlorosis, stem swelling. Leaf cupping be observed. | This would be the maximum allowable injury for commercial evaluations. Fairly temporary in nature without any effect on final yield and minimal delay in maturity, |
| 15-20 | 4 | Fair | Above symptoms plus stunting in height, smaller leaf size or impact on LAI, in this class: Basal swelling may be observed. Expect recovery and seed production with this set of symptoms but delayed, reduced growth and reduced seed set. Plant stand may be non-uniform upon recovery. | Appearance of unaffected new growth impeded for <7 days. Slight delay in bolting and flower production. Yield impact minimal or small at harvest. |
| 21-40 | 5 | Poor | Injury in this class would be as above and more than evaluator's estimate of the level of commercial acceptance. | Significant delay in plant development significant malformations in growth and development vs. control. Malformations persist Serious reduction in maturity, height and harvest yield. |

TABLE 157-continued

Canola rating scale for herbicide

| % Injury | 1-7 Scale | Category | Injury Symptoms | Growth Rates and Recovery Effects |
|---|---|---|---|---|
| 41-79 | 6 | Non Tolerant | | Equivalent to suppression as a volunteer crop in a weed control assessment. Minimal regrowth following application. Plants survive but fail to flower and mature as normal. |
| 80-100 | 7 | Susceptible | Severe injury or death. | Severe injury or death. |

Example 19: Gene Copy Number Effects on Observed Conversion Efficiencies at Each Pathway Step When analysing the VLC-PUFA levels of the various constructs listed in this invention, distinct differences were observed in conversion efficiency at the pathway steps when the T-DNA copy number increased. This was observed when comparing the VLC-PUFA levels of (1) events having a single copy T-DNA insertion vs a double copy T-DNA insertion, (2) heterozygous plants vs homozygous plants, and (3) when analysing segregating single seeds as described in Example 9 and shown in FIG. 22 and FIG. 23. This demonstrates a relationship between 'gene dosage', that is the number of T-DNA copies present in the genome, and VLC-PUFA levels. Upon further investigation it is clear that certain genes/steps of the VLC-PUFA pathway benefit more in terms of impact on the pathway when the gene number and/or expression level of the gene or activity at that step is increased. While the contribution from each gene present, when multiple genes which encode enzymes with identical activities are present, are difficult to assess (e.g. two different omega-3-desaturases are technically difficult to assess), it was possible to calculate conversion efficiencies for each pathway step, by using the equations shown in FIG. 2. These conversion efficiencies for each pathway step were calculated for various populations of plants that represent a certain gene dosage, in order to investigate if the observed increase in conversion efficiency can be assigned to one or more individual pathway steps (e.g. increasing conversion efficiency due to increased gene dosage at one early step in the pathway may increase conversion efficiency at a later step simply be providing more of a limiting substrate).

Figure 33:
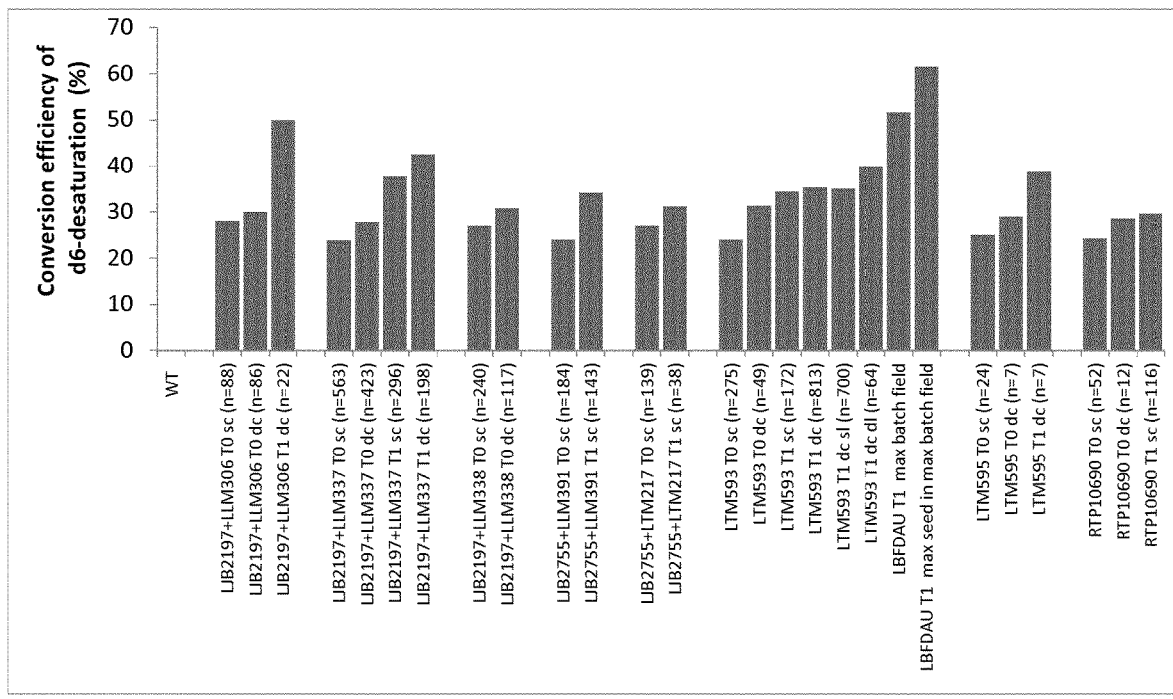
FIG. 33: Conversion efficiencies of delta-6-desaturation in seed of transgenic *Brassica napus* and in *Brassica napus* wildtype seeds. See caption in FIG. 32 for further details.

The conversion efficiencies are sometimes referred to as "apparent" conversion efficiencies because for some of the calculations it is recognized that the calculations do not take into account all factors that could be influencing the reaction. As an example of factors that may be influencing a reaction but are not taken into account during the conversion efficiency calculation; the substrates of the delta-6-desaturase are produced while bound at the sn-2 positions of phospholipids, whereas the product of the delta-6-desaturase is formed while the fatty acid is bound to CoA. It is therefore not immediately clear if the lower delta-6-desaturase conversion efficiencies shown in FIG. 33 are due to inefficient provision of substrate to the delta-6-desaturase via trans-esterification from PC (phosphatidylcholine) bound LA/ALA to CoA bound LA/ALA, or whether the delta-6-desature had low activity/low conversion efficiency.

For the interpretation of the conversion efficiencies it was also important to note that any catalyzed conversion of substrate to product was dependent on the substrate concentration, catalyst (enzyme) concentration, and product concentration.

Analysing the data pathway step by pathway step, the following observations can be made in FIG. 32 to FIG. 39:

Conversion Efficiency of Delta-12-Desaturation

The delta-12-desaturase conversion efficiency encompasses all steps that influence substrate concentration, product concentration, and enzyme concentrations. From the data in example 21 it is evident that the delta-12-desaturase, c-d12Des(Ps_GA), enzymatically produces phosphatidylcholine bound 18:2n-6 (FIG. 26, Panel A), which implies the substrate was phosphatidylcholine bound 18:1n-9. The primary flux of newly formed 18:1n-9 was derived from plastid produced 18:1n-9, which was exported into the cytosol, where it was bound to CoA. Therefore, a prerequisite of delta-12-desaturation was the incorporation of CoA-bound 18:1n-9 into the sn2 position of phosphatidylcholine via LPCAT (Lysophosphatidylcholine acetyltransferase EC 2.3.1.23), or via LPAAT (Lysophosphatidic acid acyltransferase E.C. 2.3.1.51), with subsequent conversion of the formed (sn2)18:1n-9-phosphatidic acid into (sn2)18:1n-9-DAG (DAG is an abbreviation for diacylglycerol), whereby (sn2)18:1n-9-DAG was either directly converted into (sn2) 18:1n-9-PC (PC is an abbreviation for phosphatidylcholine) substrate for the delta-12-desaturases via PDCT (phosphatidylcholine diacylglycerol cholinephosphotransferase EC 2.7.8.2), or obtains a phosphocholine headgroup via CPT (CPT is an abbreviation for sn-1,2-diacylglycerol:cholinephosphotransferase EC 2.7.8.2) to be converted into (sn2) 18:1n-9-PC. The efficiency of this incorporation of plastid synthesized 18:1n-9 directly affects delta-12-desaturase substrate concentration. As mentioned already, PC is converted by PDCT into DAG, which was subsequently converted into TAG. The amount of PC bound delta-12-desaturase substrate and product that was part of the delta-12-desaturase reaction was therefore also directly linked to the substrate specificity of PDCT.

Figure 32:
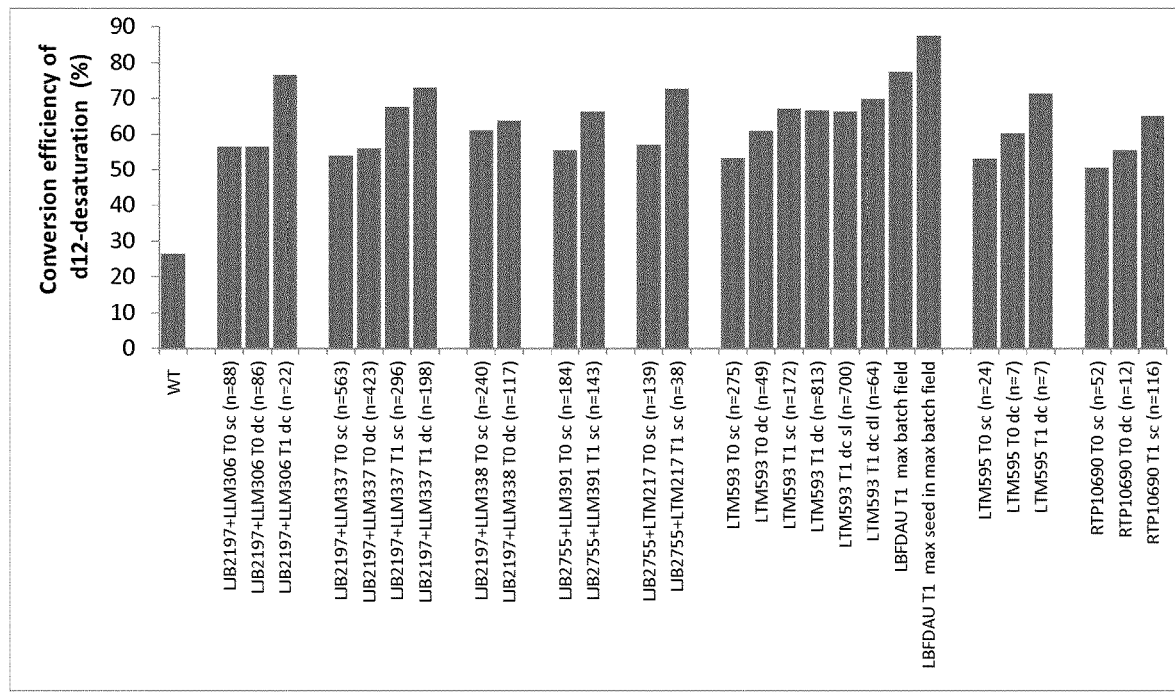
FIG. 32: Conversion efficiencies of delta-12-desaturation in seed of transgenic *Brassica napus* and in *Brassica napus* wildtype seeds. Shown are average conversion efficiencies of various plant populations, as well as the conversion efficiencies observed in a seedbacth of event LBFDAU having highest EPA+DHA levels, and those observed in a single seed of that seedbatch, where this single seed had highest EPA+DHA levels among all 95 measured single seeds. Data were taken from Example 10 to Example 18. T0 and T1 designates the plant generation producing the seeds (all grown in the greenhouse except for the two LBFDAU datapoints)

There was a strong correlation of the delta-12-desaturation conversion efficiency with the copy number of the delta-12-desaturase (FIG. 32). This was evident when comparing the average conversion efficiency of T0 single copy plants (across all events per construct), with the average conversion efficiency of T0 double copy plants (across all events per construct). The same correlation can be seen in the T1 generation. The strong correlation of the delta-12-desaturation conversion efficiency with the copy number of the delta-12-desaturase was also seen when comparing copy number differences due to heterozygous vs homozygous T-DNA integrations: The T0 generation always consist of heterozygous plants, whereas the T1 generation largely consists of homozygous plants due to the selection applied in Example 10 through Example 18.

The delta-12-desaturation conversion efficiency increases when comparing the average conversion efficiency of T0 single copy plants (across all events per construct), with the average conversion efficiency of T1 single copy plants (across all events per construct). Similarly, the delta-12-desaturation conversion efficiency increases when comparing the average conversion efficiency of T0 double copy plants (across all events per construct), with the average conversion efficiency of T1 double copy plants (across all events per construct). The only exceptions are:

1) T0 single copy events vs T0 double copy events containing the T-DNAs of VC-LJB2197-1qcz and VC-LLM337-1qcz rc: while not as pronounced as for VC-LJB2197-1qcz and VC-LLM306-1qcz rc, there are also subtle differences here in delta-12-desaturase conversion efficiencies. The slight differences are due to insufficient data in the T0 generation to accurately assign the events to the two copy number categories for events containing the T-DNAs of construct VC-LJB2197-1qcz and VC-LLM337-1qcz rc, and 2) T0 single copy events vs T0 double copy events containing the T-DNAs of VC-LJB2197-1qcz and VC-LLM338-3qcz rc: while not as pronounced as for VC-LJB2197-1qcz and VC-LLM306-1qcz rc, also here the subtle differences in delta-12-desaturase conversion efficiencies are due to insufficient data in the T0 generation to accurately assign the events to the two copy number categories for events containing the T-DNAs of construct VC-LJB2197-1qcz and VC-LLM338-3qcz rc, and 3) T1 single copy events vs T1 single copy (single locus) events containing the construct VC-LTM593-1qcz rc: there was no effect on the conversion efficiency due to the 2-fold copy number difference between these groups. The group of single copy (single locus) events is affected by an additional phenomenon whereby the average VLC-PUFA level in T2 seeds of T1 plants of this homozygous group decreases instead of increasing compared to segregating T1 seeds of heterozygous T0 plants. A further indication that this group was an outlier group can be seen in FIG. 35, where it was evident that the delta-5-desaturase conversion efficiency was significantly lower in homozygous plants compared to heterozygous plants.

Considering the high conversion efficiency of the delta-12-desaturase, it is likely that the provision of substrate via LPCAT is not a bottleneck. Also, the data suggest that efficient removal of delta-12-desaturase products contributes to the high conversion efficiency. However; taking into account the high levels of 18:2n-6 accumulated in the oil and the low delta-6-conversion efficiency, it was evident that not all delta-12-desaturated 18:2n-6 was removed from PC via trans-esterification to CoA (the site of action for the next pathway step). With respect to the fate of 18:2n-6; our observations indicate that the delta-12-desaturated 18:2n-6 was likely removed by the direct conversion of unsaturated PC into DAG via PDCT as discussed by Bates et al. (2012) Plant Physiology 160: 1530-1539. This activity of PDCT strongly supports a high delta-12-desaturase conversion efficiency by providing fresh 18:1n-9-PC substrate to the delta-12-desaturase, while simultaneously removing 18:2n-6-PC product (by conversion into DAG). However, the latter activity poses a strong bottleneck for the continuation of the pathway, which is evident by the low delta-6-desaturase conversion efficiencies.

This effect of increased conversion efficiency of the delta-12-desaturase has been observed when analyzing the PUFA profile of more than 6.000 plants that have been obtained by transforming more than 300 multi-gene constructs into Canloa and *Arabidopsis*, whereby all of these constructs carried genes having the essential activities required for Arachidonic acid synthesis. Across these more then 300 constructs, more than 10 different delta-12-desaturase enzymes have been investigated.

Conversion Efficiency of Delta-6-Desaturation

For the delta-6-desaturation, it was of particular importance to highlight that conversion efficiencies observed for this step are dependent on the substrate concentration (which was CoA bound linoleic acid), catalyst concentration (which was the delta-6-desaturase), and product concentration. It was, that PC bound 18:2n-6 produced by the delta-12-desaturase needs to be trans-esterified to CoA before delta-6-desaturation can take place. The absence of accumulation of 18:3n-6 and 18:4n-3 in the examples 10-18 strongly indicates that CoA-bound 18:3n-6 and CoA-bound 18:4n-3 was efficiently converted by the delta-6-elongase, effectively preventing any significant accumulation of 18:3n-6 and 18:4n-3. In general, delta-6-desaturase conversion efficiencies are low for all constructs. Considering efficient removal of product was not a bottleneck, the low conversion efficiencies can be either due to low activity of the delta-6-desaturase enzyme, or because of inefficient conversion of PC-bound substrate into CoA-bound substrate. Regardless of this, there was a clear correlation of the delta-6-desaturation conversion efficiency with the copy number of the delta-6-desaturase. In a manner similar to that of the delta-12-desaturase, this was seen regardless of the reason for the copy number increases (heterozygous vs homozygous, single copy genomic integrations vs double copy genomic integrations). In fact, plants of the construct combination VC-LJB2197-1qcz and VC-LLM306-1qcz rc contain an additional copy of the delta-6-desaturase on the T-DNA. It was therefore consistent that the group of 22 double copy T1 plants would have in the T2 seeds the highest delta-6-desaturase conversion efficiencies of all similar double copy groups of different constructs.

For the delta-6-desaturase, the same exceptions to this copy number effect as for the delta-12-desaturase are seen. The same for the interpretation mentioned for the delta-12-desaturase of why these exceptions are observed are assumed to be the reasons for the delta-6-desaturase also applies in this case. The exceptions are:

1) T0 single copy events vs T0 double copy events containing the T-DNAs of VC-LJB2197-1qcz and VC-LLM306-1qcz rc, and 2) T0 single copy events vs T0 double copy events containing the T-DNAs of VC-LJB2197-1qcz and VC-LLM337-1qcz rc, and 3) T0 single copy events vs T0 double copy events containing the T-DNAs of VC-LJB2197-1qcz and VC-LLM338-3qcz rc, and 4) T1 single copy events vs T1 single copy(single locus) events containing the construct VC-LTM593-1qcz rc.

As demonstrated for the delta-12-desaturase, the amount of delta-12-desaturase product increases with increasing copy number of the delta-12-desaturases, which implies an increased amount of substrate for the delta-6-desaturase. As both the delta-12-desaturases and the delta-6-desaturase are contained on the same T-DNA in all examples 10 to 18, the copy number of the delta-6-desatuases will also increase when copy number of the delta-12-desaturase increases, with the exceptions of events where truncated insertion of the T-DNA contain either the delta-12-desaturase and not the delta-6-desaturases, or vice versa.

In summary, not only was the effect of the gene copy duplication of the delta-12-desaturase surprising, but it was also unexpected that the increased copy number of delta-6-desaturase led to an increased amount of delta-6-desaturase protein, and this increased amount of protein can convert the additional amount of delta-12-desaturated fatty acids with an increased conversion rate. To illustrate the effect, here as an example of the comparison of two groups shown in examples 10 to 18 that have a gene copy number difference of "four":

Group A: All 275 heterozygous T0 plants containing a single copy of the T-DNA of construct VC-LTM593-1qcz rc Group B: All 64 homozygous T1 plants containing two copies the T-DNA of of construct VC-LTM593-1qcz rc at two different chromosomal loci.

In group A, the total sum of fatty acid that contain a double bond due to the activity of the delta-12-desaturase was 47.3% and total sum of fatty acids that contain a double bond due to the activity of the delta-6-desaturase was 11.2%. Consequently, 23.7% of all fatty acids that underwent delta-12-desaturation also underwent delta-6-desaturation.

In group B, the total sum of fatty acid that contain a double bond due to the activity of the delta-12-desaturase was 61% and total sum of fatty acid that contain a double bond due to the activity of the delta-6-desaturase was 23.7%. Consequently, 38.8% of all fatty acids that underwent delta-12-desaturation also underwent delta-6-desaturation.

As a result of that, the sum of all fatty acids downstream of the delta-6-desaturase in the pathway more than doubled in group B versus group A.

This effect of increased conversion efficiency of the delta-6-desaturase has been observed when analyzing the PUFA profile of more than 6.000 plants, that have been obtained by transforming more than 300 multi-gene constructs into Canloa and *Arabidopsis*, whereby all of these constructs carried genes having the essential activities required for Arachidonic acid synthesis. Across these more then 300 constructs, more than 5 different delta-6-desaturase enzymes have been investigated.

Conversion Efficiency of Delta-6-Elongation

Figure 34:
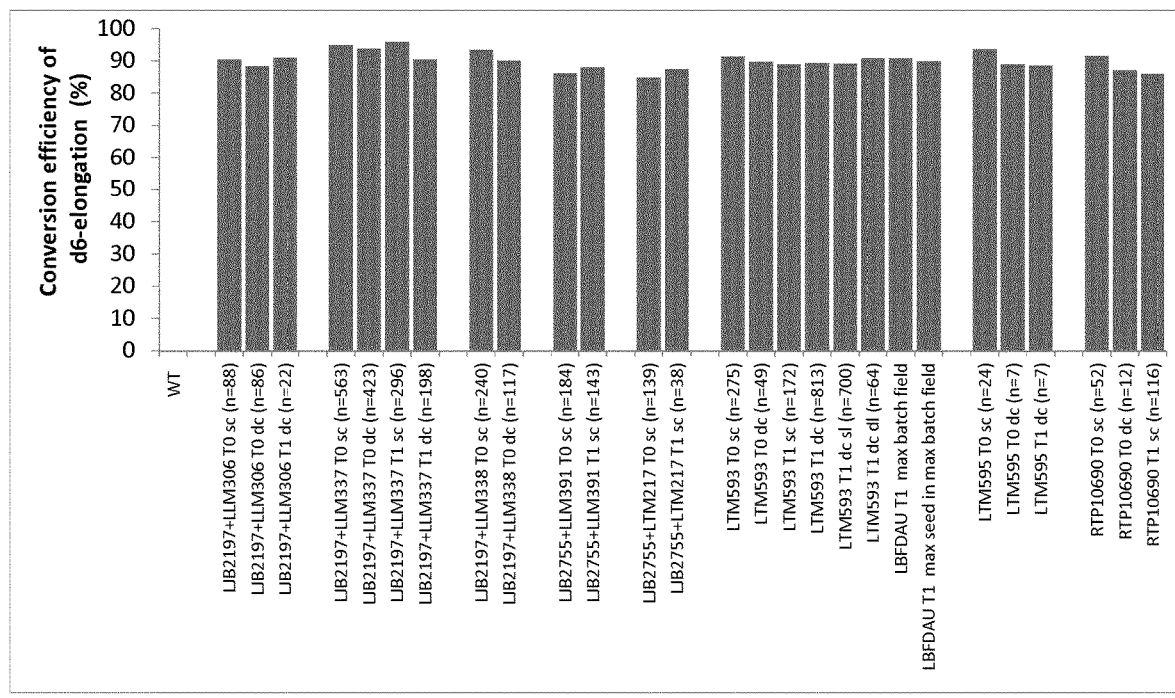
FIG. 34: Conversion efficiencies of delta-6-elongation in seed of transgenic *Brassica napus* and in *Brassica napus* wildtype seeds. See caption in FIG. 32 for further details.

As was evident in FIG. 34, the conversion efficiency of the delta-6-elongation was very high regardless of the copy number. Because of that, copy number mediated effects on the conversion efficiency are sometimes insignificant, but are sometimes clearly observed. E.g. the events obtained for the construct combinations VC-LJB2755-2qcz rc+VC-LLM391-2qcz rc and for the combination LJB2755-2qcz rc and VC-LTM217-1qcz rc contain the lowest delta-6-elongation conversion efficiencies of all constructs, which can be attributed to the fact that these construct combinations encode just one delta-6-elongation enzyme [c-d6Elo (Tp_GA2)], instead of two [(c-d6Elo(Tp_GA2), c-d6Elo (Pp_GA2)].

Conversion Efficiency of Delta-5-Desaturation

Figure 35:
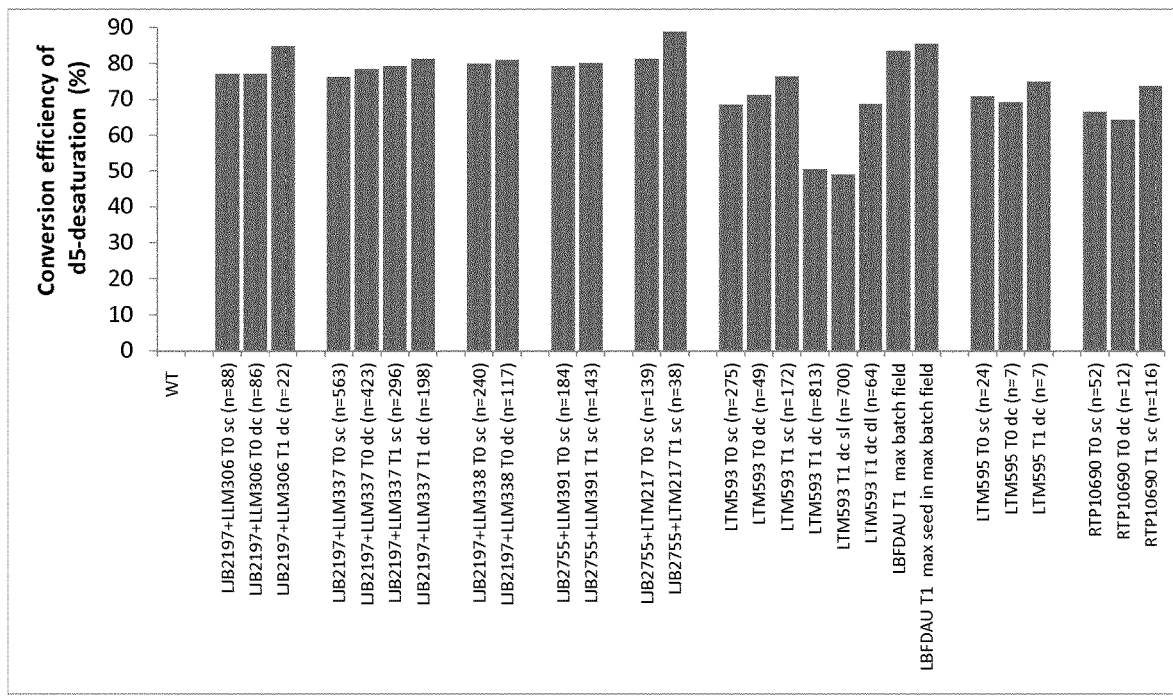
FIG. 35: Conversion efficiencies of delta-5-desaturation in seed of transgenic *Brassica napus* and in *Brassica napus* wildtype seeds. See caption in FIG. 32 for further details.

The data in FIG. 35 do not indicate a consistent construct independent copy number dependence of the delta-5-desaturase.

Conversion Efficiency of Omega-3-Desaturation

Figure 36:
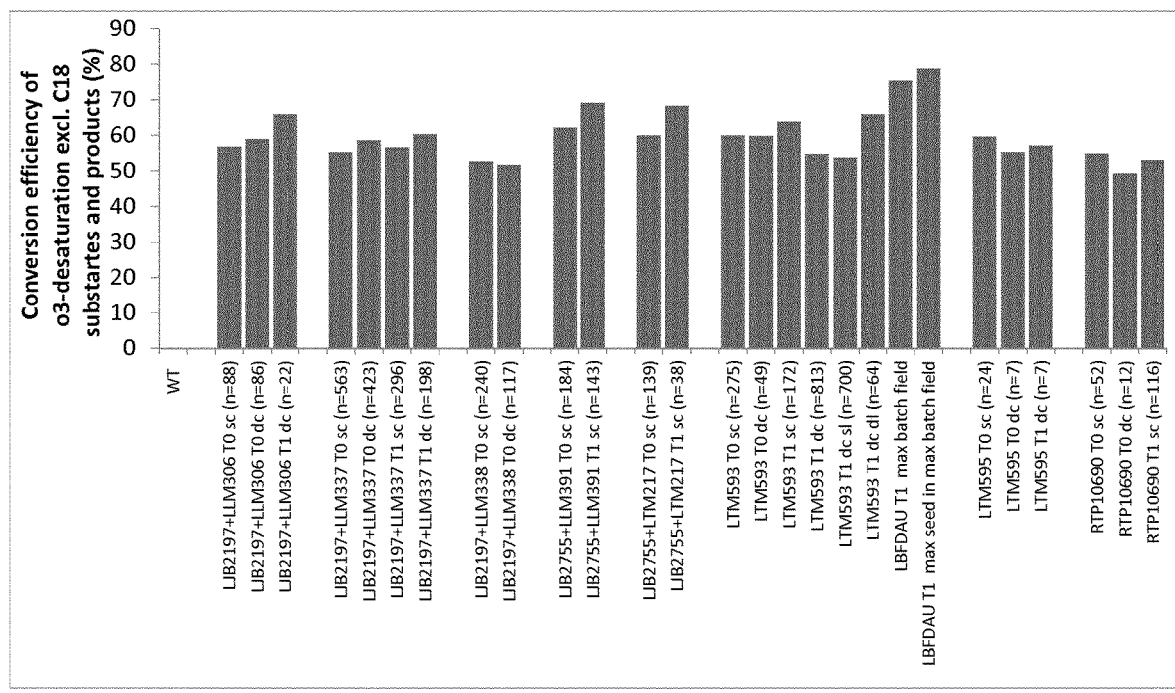
FIG. 36: Conversion efficiencies of omega-3 desaturation (excluding C18 fatty acids) in seed of transgenic *Brassica napus* and in *Brassica napus* wildtype seeds. See caption in FIG. 32 for further details.
Figure 37:
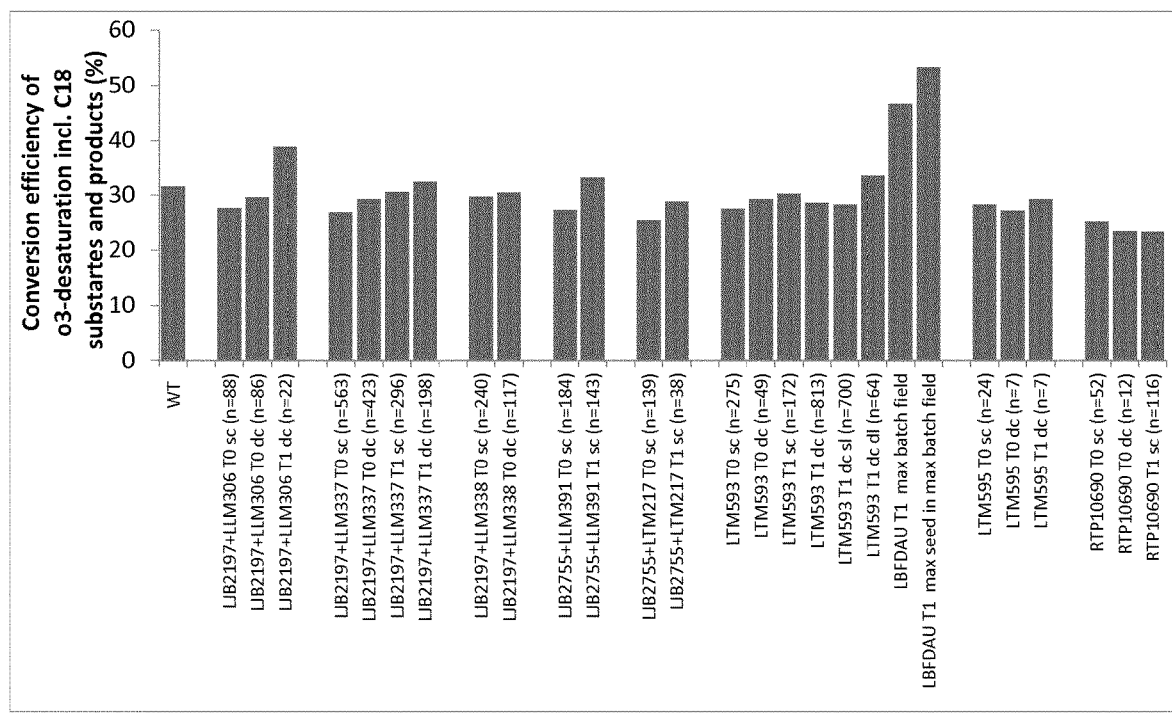
FIG. 37: Conversion efficiencies of omega-3 desaturation (including C18 fatty acids) in seed of transgenic *Brassica napus* and in *Brassica napus* wildtype seeds. See caption in FIG. 32 for further details.
Figure 38:
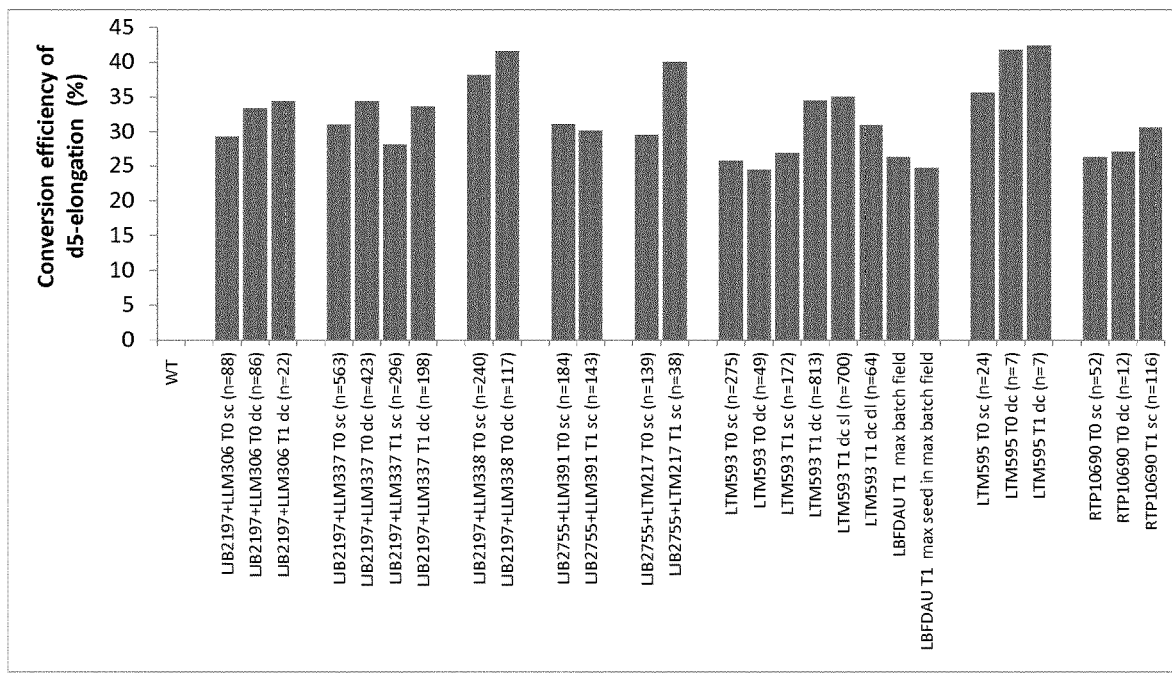
FIG. 38: Conversion efficiencies of delta-5-elongation in seed of transgenic *Brassica napus* and in *Brassica napus* wildtype seeds. See caption in FIG. 32 for further details.

FIG. 36 shows the omega-3-desaturase conversion efficiencies that have been calculated by excluding the C18 substrates and products shown in FIG. 2, thereby excluding the delta-15-desaturase specific activity of omega-3-desaturases. FIG. 37 shows the omega-3-desaturase conversion efficiencies that have been calculated by including the C18 substrates and products, thereby including the delta-15-desaturase specific activity of omega-3-desaturases. As both omega-3-desaturases used in the invention have virtually no delta-15-desaturase activity, conclusions on the effect of copy number on the omega-3-desaturase are best drawn from FIG. 36. While not as pronounced as observed for the delta-12-desaturase or delta-6-desaturase, there is, in many cases, a clear link between omega-3-desaturase copy number and the omega-3-desaturase conversion efficiency. This was particularly evident as plants of the construct combination as VC-LJB2197-1qcz+VC-LLM338-3qcz rc display the lowest omega-3-desaturase conversion efficiency of all other constructs, which can be attributed to the fact that this construct combination encodes just one omega-3-desaturase enzyme [c-o3Des(Pi_GA2)], instead of two [(c-o3Des (Pi_GA2), c-o3Des(Pir_GA)]. Exceptions to the copy number dependence of the omega-3-desaturase conversion efficiency are:

1) Plants containing the T-DNAs of construct RTP10690-1qcz_f, and
2) Plants containing the T-DNAs of construct VC-LTM595-1qcz rc, and
3) Plants containing the T-DNAs of VC-LJB2197-1qcz and VC-LLM338-3qcz rc, and Conversion Efficiency of Delta-5-Elongation The complex interdependency of all the pathway step conversion efficiencies between each other can be seen by comparing FIG. 38 with FIG. 35: the high delta-5-elongation conversion efficiency for two groups of plants containing the T-DNAs of construct VC-LTM593-1qcz rc (813 T1 plants of the double copy group, 700 plants of the double copy/single locus group) was in fact not due to a high delta-5-elongation conversion efficiency, but rather due to an inefficient supply of substrate to the delta-5-elogase at the delta-5-desaturase pathway step. Similar to the omega-3-desaturase, while not as pronounced as for the delta-12-desaturase or delta-6-desaturase, there was a link between delta-5-elongase copy number and the delta-5-elongase conversion efficiency.

Conversion Efficiency of Delta-4-Desaturation

As can be seen in FIG. 39, there was no direct evidence for a dependence of delta-4-desaturase conversion efficiency on delta-4-desaturase copy number. The highest delta-4-desaturase conversion efficiency has been observed for plants containing the T-DNAs of construct LJB2755-2qcz rc and VC-LTM217-1qcz rc. This construct combination differs only from the combination VC-LJB2755-2qcz rc+VC-LLM391-2qcz rc in replacing the d4Des(Eg) by the c-d4Des (PI_GA)2. As a conclusion of the plant data shown in Example 10 to 18 and the yeast data shown in Example 22, it can be clearly seen that the delta-4-desaturation conversion efficiency reaches an upper limit using the genes c-d4Des(Tc_GA) and d4Des(Eg), that cannot be overcome by increased gene copy numbers. All constructs that encode the c-d4Des(PI_GA)2 instead of d4Des(Eg) have a higher delta-4-desaturation conversion efficiency, and the only exception to that are plants containing the construct RTP10690-1qcz_F. As shown in Example 25, this was due to very low expression of both delta-4-desaturases. This in turn highlights that the conversion efficiency does depend on the gene expression, but cannot overcome an upper limit.

Example 20: Environmental Effects on VLC-PUFA Levels. Correlation Between Oil Content, VLC-PUFA Levels, and Observed Conversion Efficiencies at Each Pathway Step Analysing the VLC-PUFA levels presented in the Examples 10 to 18, we have oberserved that there is, in most cases, a level of variability, within a genetically identical population of plants (e.g. a genetically stable event where all plants are genetically identical), even when these plants are grown in a controlled greenhouse environment. To illustrate the effect more clearly, VLC-PUFA profiles of seed batches having highest EPA+DHA levels among several type of plant populations are shown in the examples 10 to 18. Such plant populations are (1) either genetically identical due to the T-DNA integrations (i.e. all plants of the same event, where either all or at least most are homozygous for all T-DNA integrations in those events), or (2) identical related to the T-DNA copy number, and these populations have been grown in the same environment. For example, out of 249 segregating T1 seedlings, 10 T1 plants for event LBFDAU (see Example 18) have been identified in the greenhouse to be identical in having one complete T-DNA integration, and one truncated T-DNA integration, whereby both T-DNA insertions where found to be homozygous (Table 135). In a field trial conducted in parallel, out of about segregating T1 seedlings, 4 plants have been identified as being homozygous for both T-DNA insertions (Table 144). The average EPA+DHA content measured in randomly selected seed from seed batches of these 10 greenhouse grown plants was found to be 13.9% EPA+2.6% DHA. Similarly, the EPA+DHA content of the 4 field grown plants was found to be 13.4% EPA+2.7% DHA. Among the 10 greenhouse grown plants was a plant that produced up to 15.1% EPA+3.0% DHA (Table 139). Similarly, among the 4 field grown plants was a plant that produced up to 17.6% EPA+3.6% DHA (Table 146). Analysing single seed of this field grown plant, single seeds having up to 26.2% EPA+4.9% DHA, or 23.6% EPA+5.8% DHA where found (Table 147). The lowest EPA+DHA content found among these 95 seed contained 13.5% EPA and 2.5% DHA, and the average content among these seed was 18.2% EPA and 3.7% DHA, which matched the content measured in the random selection of twice 15 seed as shown in Table 146 (17.6% EPA+3.6% DHA). This event LBFDAU is just a representative example to illustrate that for every event, and for all constructs, there is plant-to-plant variability, and seed-to-seed variability. The extent of the plant to plant variability is shown in the examples 10 to 18, where it is shown that the average PUFA profile of a certain population (e.g. all plants belonging to the same event and are genetically identical, or all plants are single copy, heterozygous) is always different than the profile observed in individual plants. To illustrate the magnitude of this variability, examples 10 to 18 show the average PUFA profile of such populations and also the profile of the single plant having the highest EPA+DHA levels.

Figure 42:
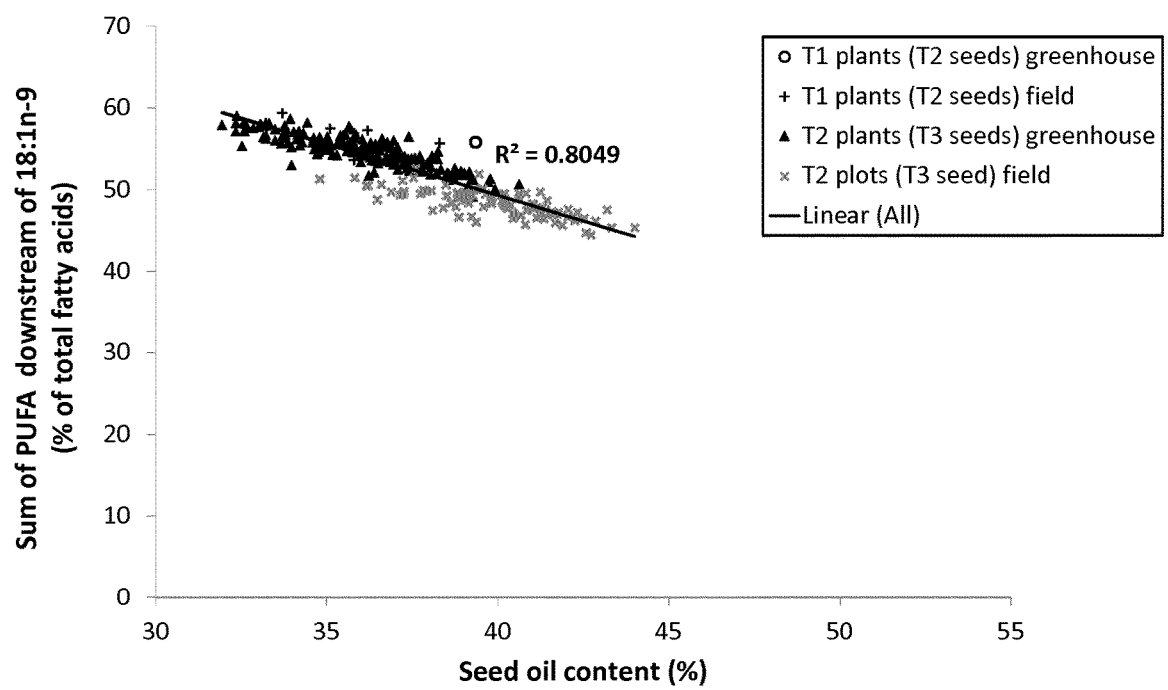
FIG. 42: The sum of all pathway fatty acids was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 43:
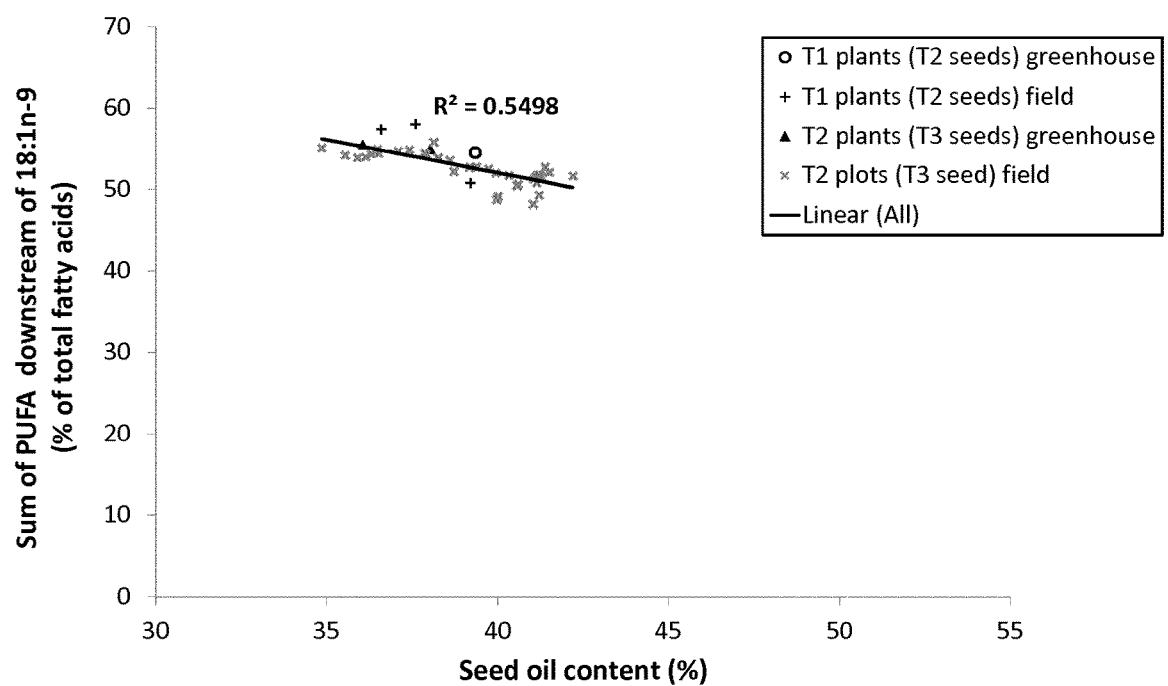
FIG. 43: The sum of all pathway fatty acids was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 44:
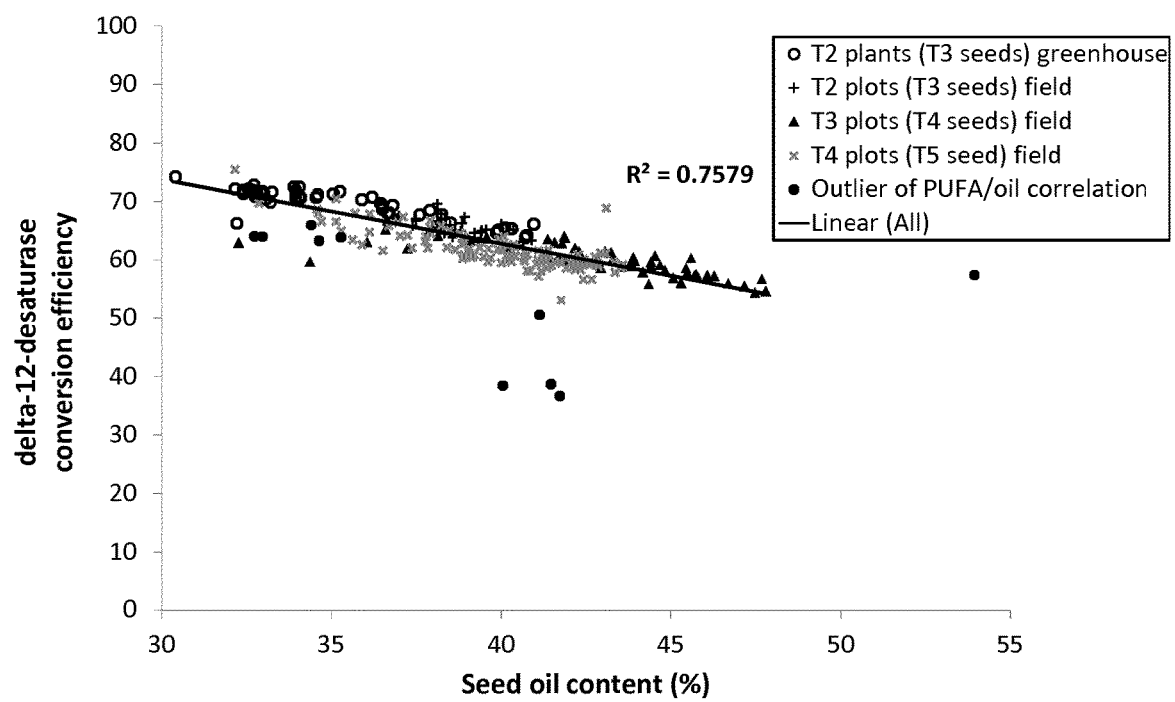
FIG. 44: The conversion efficiency of the delta-12-desaturase was negatively correlated with seed oil content. Shown are data of 3 generations of event LANPMZ. For the greenhouse data, one marker corresponds to one seed batch of one plant, for the field data, one marker corresponds to an analysis on a random selection of seeds representing one plot.
Figure 45:
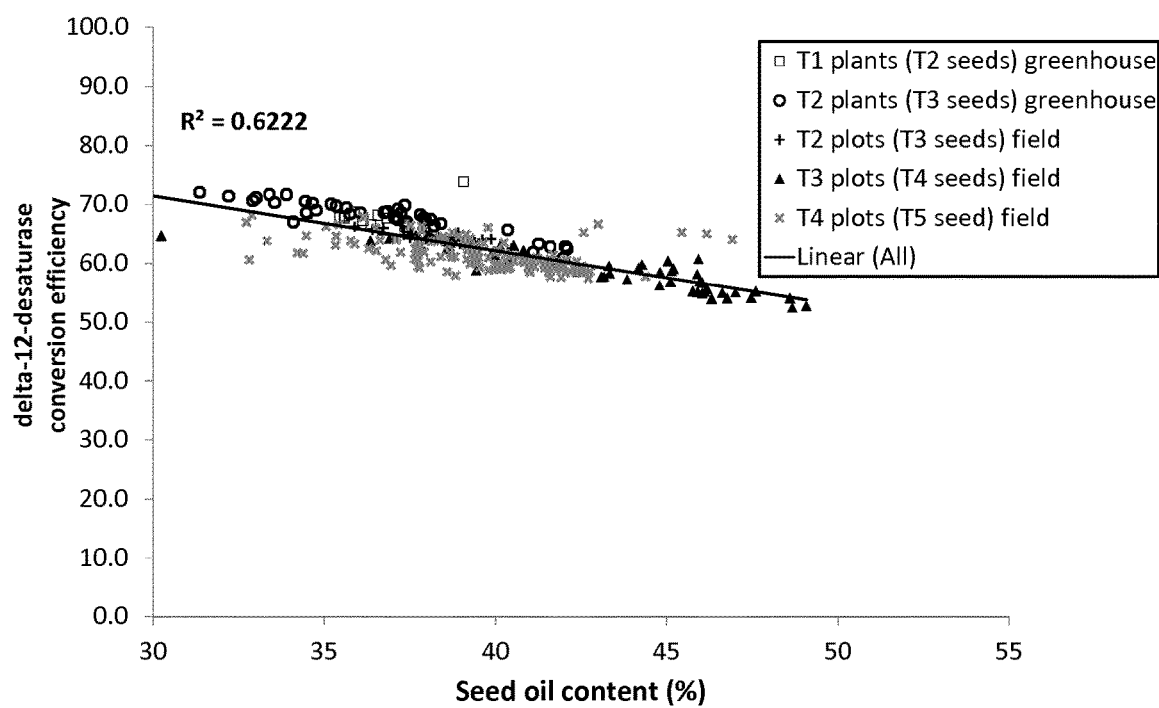
FIG. 45: The conversion efficiency of the delta-12-desaturase was negatively correlated with seed oil content. Shown are data of 4 generations of event LAODDN. For the greenhouse data, one marker corresponds to one seed batch
Figure 46:
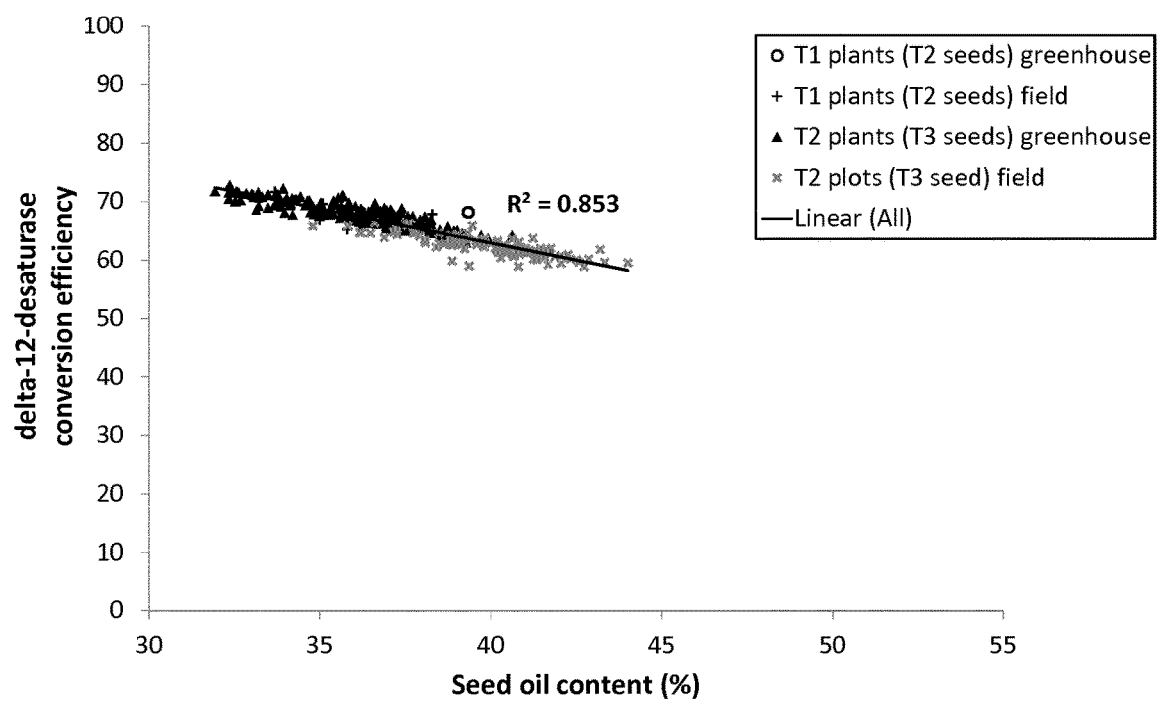
FIG. 46: The conversion efficiency of the delta-12-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 47:
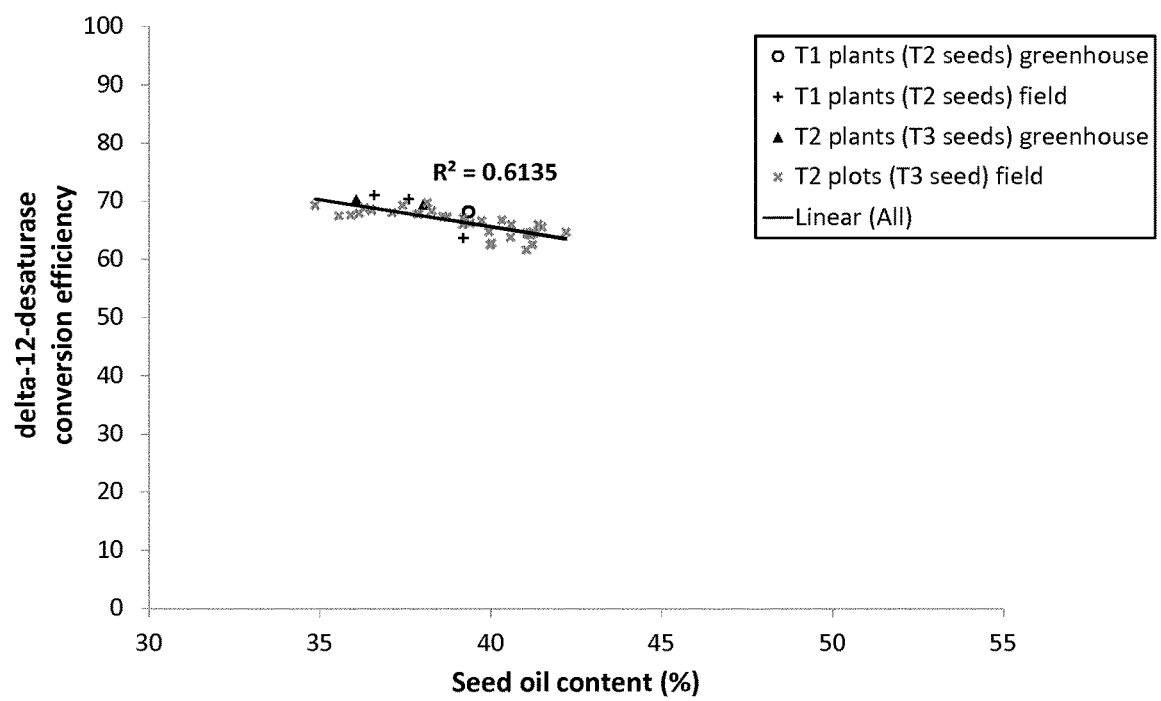
FIG. 47: The conversion efficiency of the delta-12-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 48:
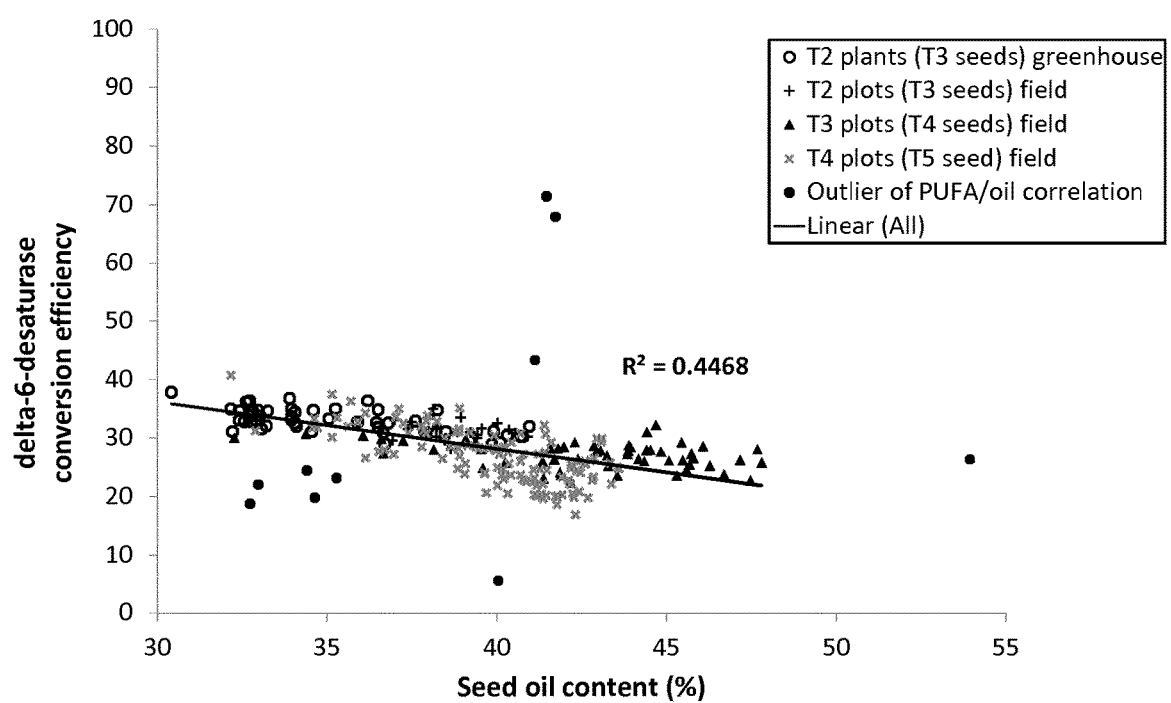
FIG. 48: The conversion efficiency of the delta-6-desaturase was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 49:
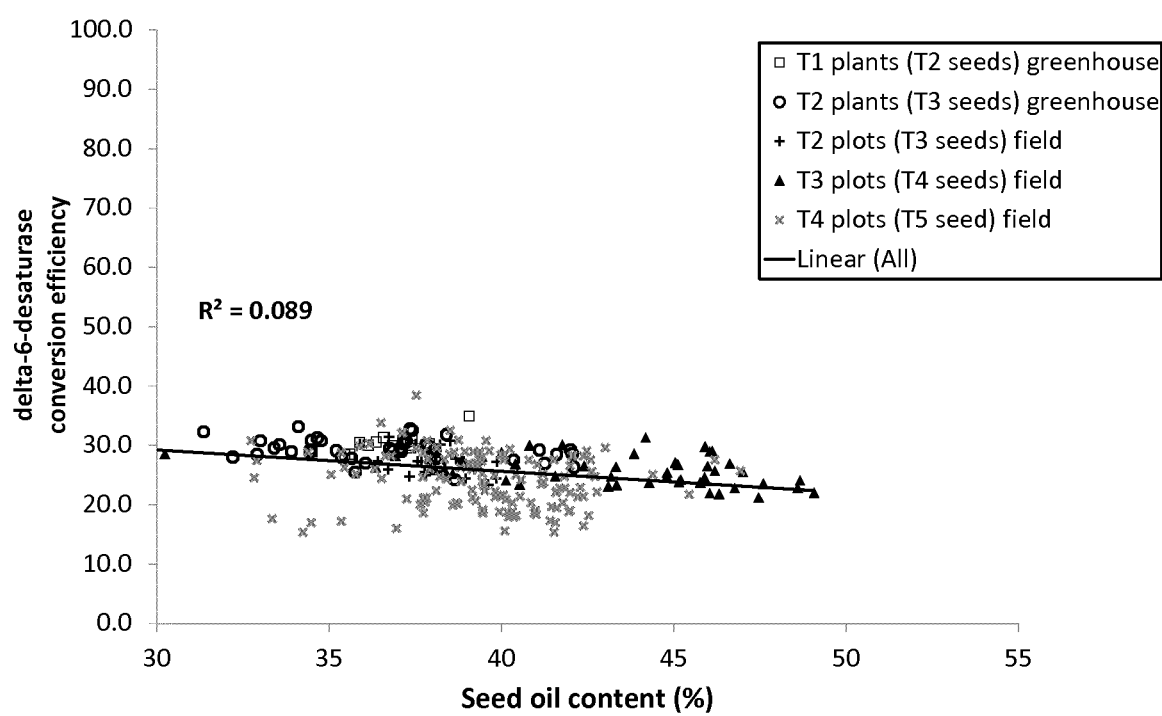
FIG. 49: The conversion efficiency of the delta-6-desaturase was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 50:
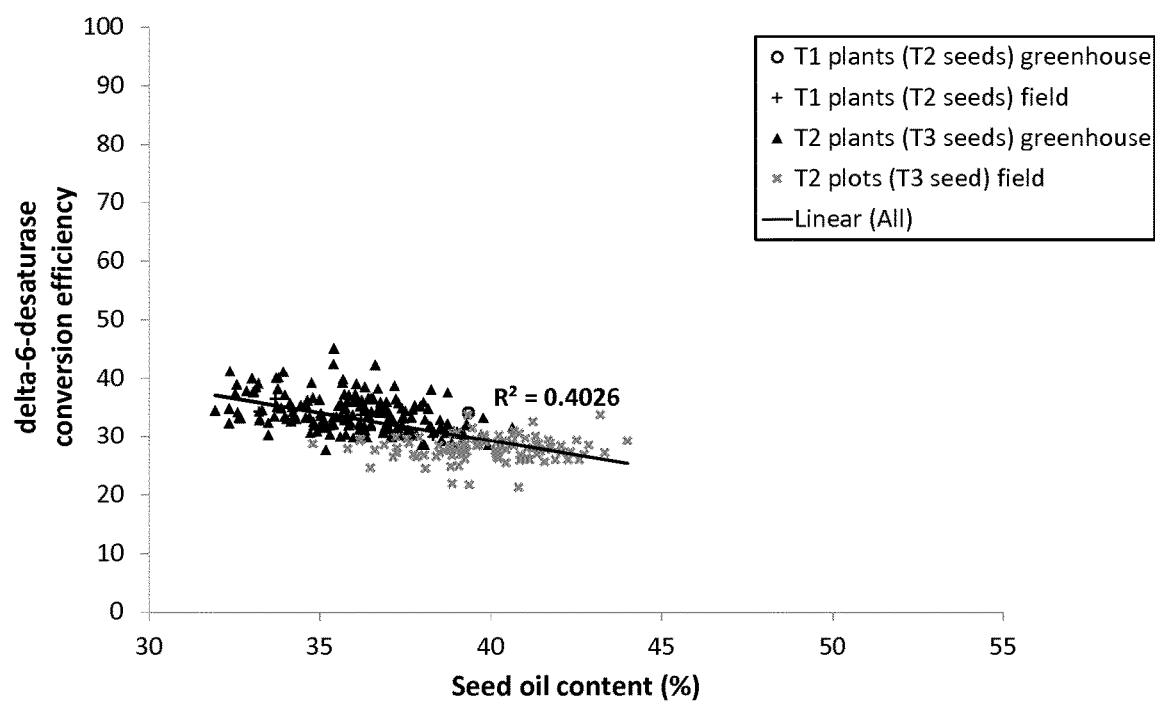
FIG. 50: The conversion efficiency of the delta-6-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 51:
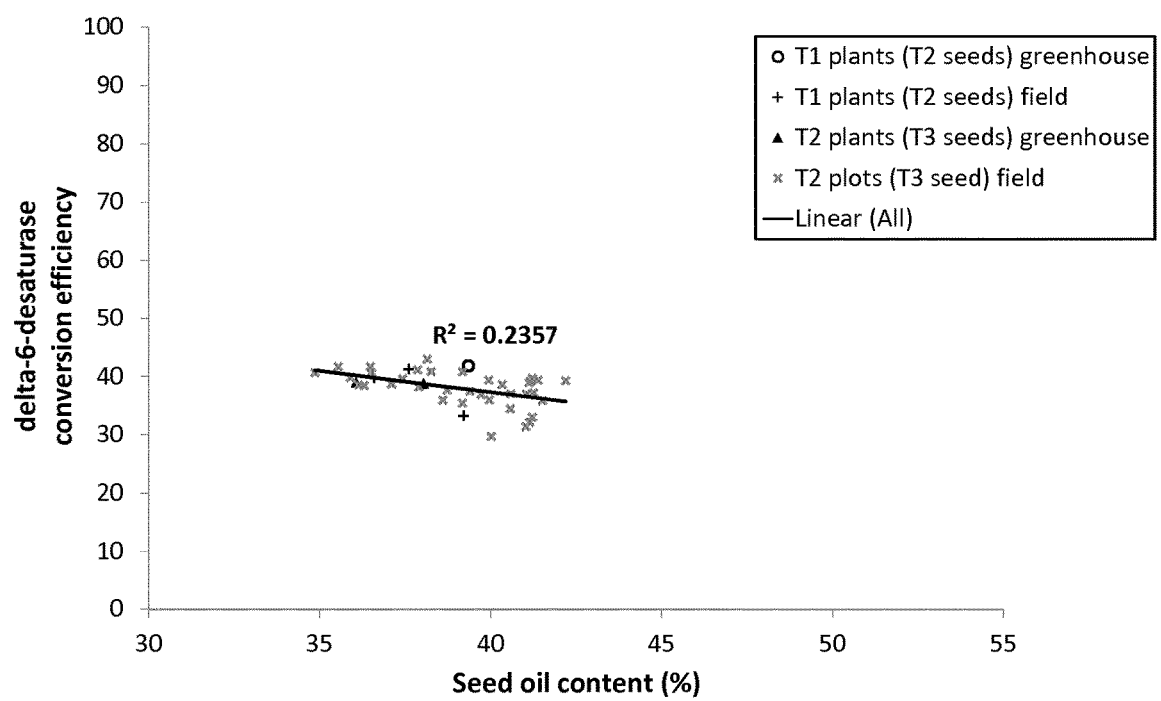
FIG. 51: The conversion efficiency of the delta-6-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of one T2 seedbtach of one T1 plant, or a the analysis of a random selection of T3 seeds representing one plot.
Figure 52:
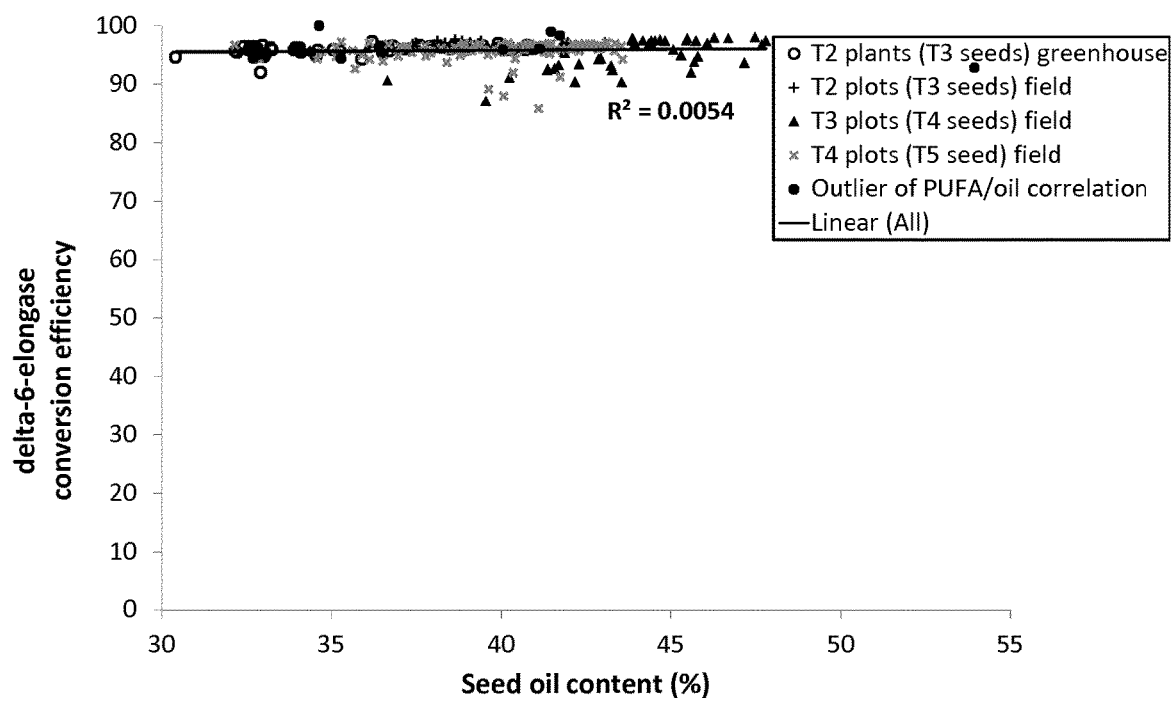
FIG. 52: The conversion efficiency of the delta-6 elongase was not negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 53:
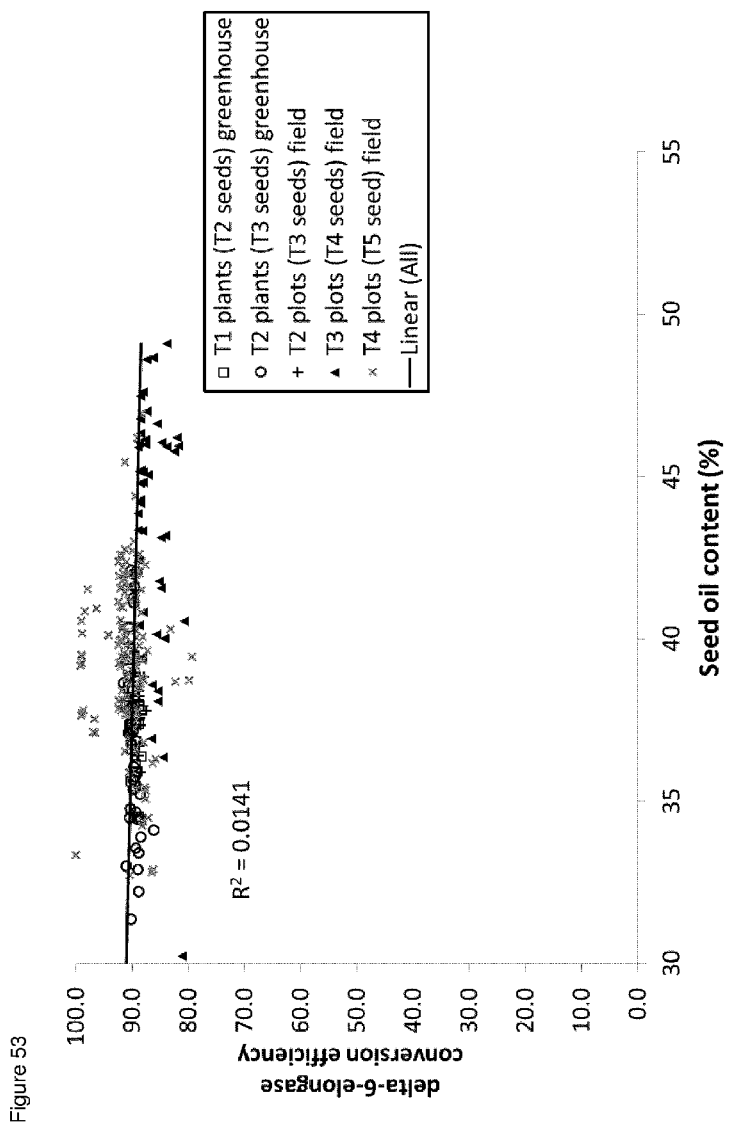
FIG. 53: The conversion efficiency of the delta-6 elongase was not negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 54:
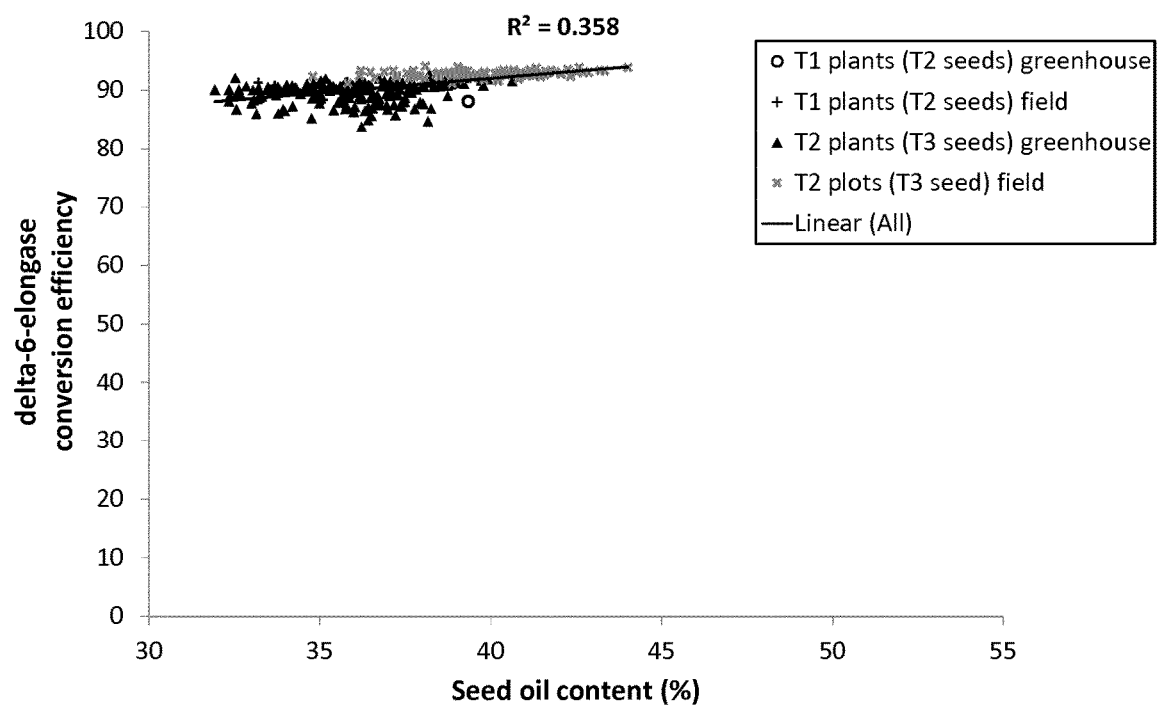
FIG. 54: The conversion efficiency of the delta-6 elongase was not negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 55:
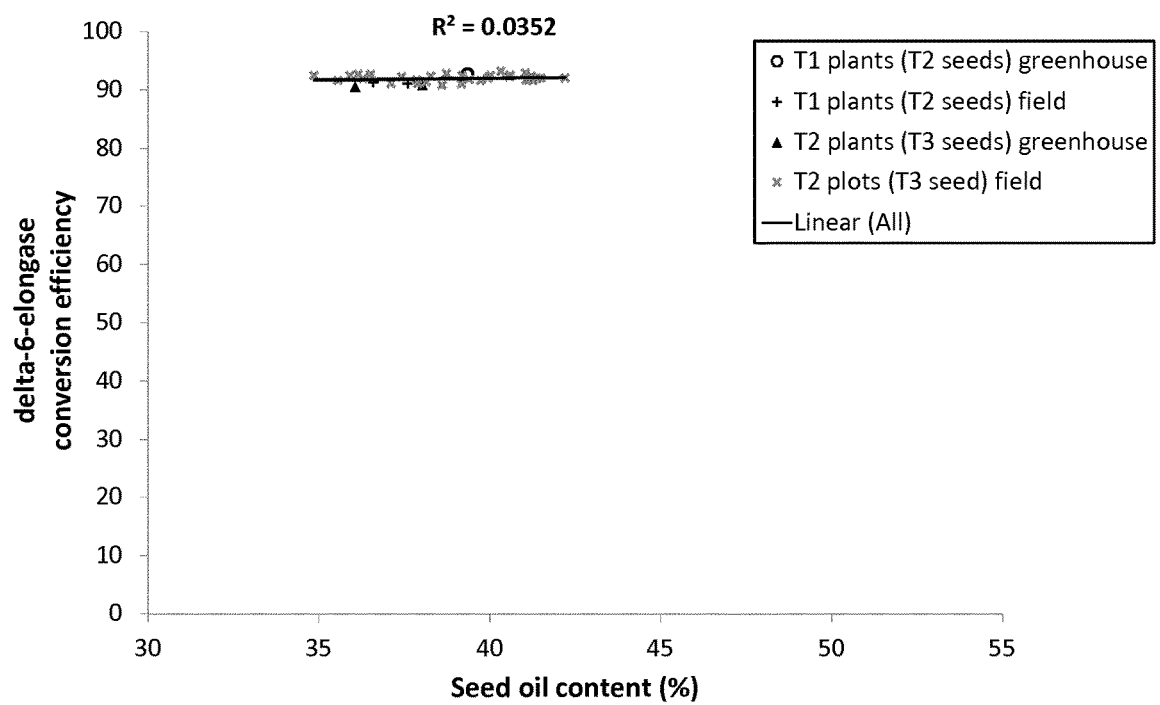
FIG. 55: The conversion efficiency of the delta-6 elongase was not negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 56:
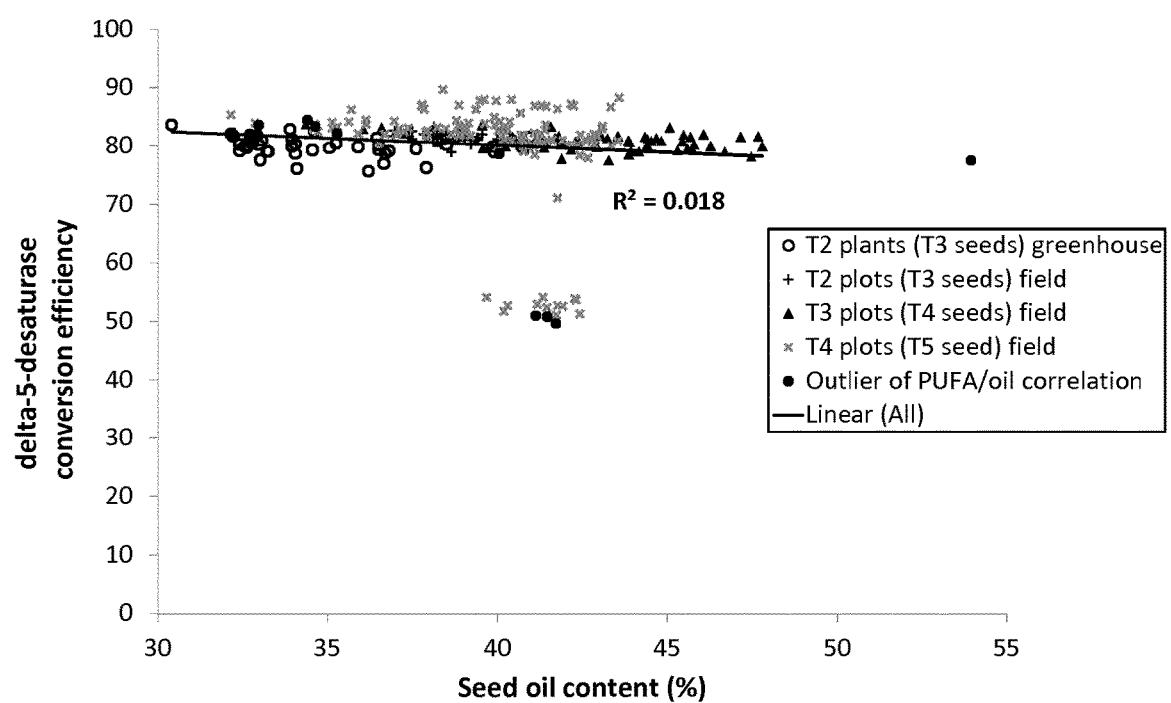
FIG. 56: The conversion efficiency of the delta-5-desaturase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 57:
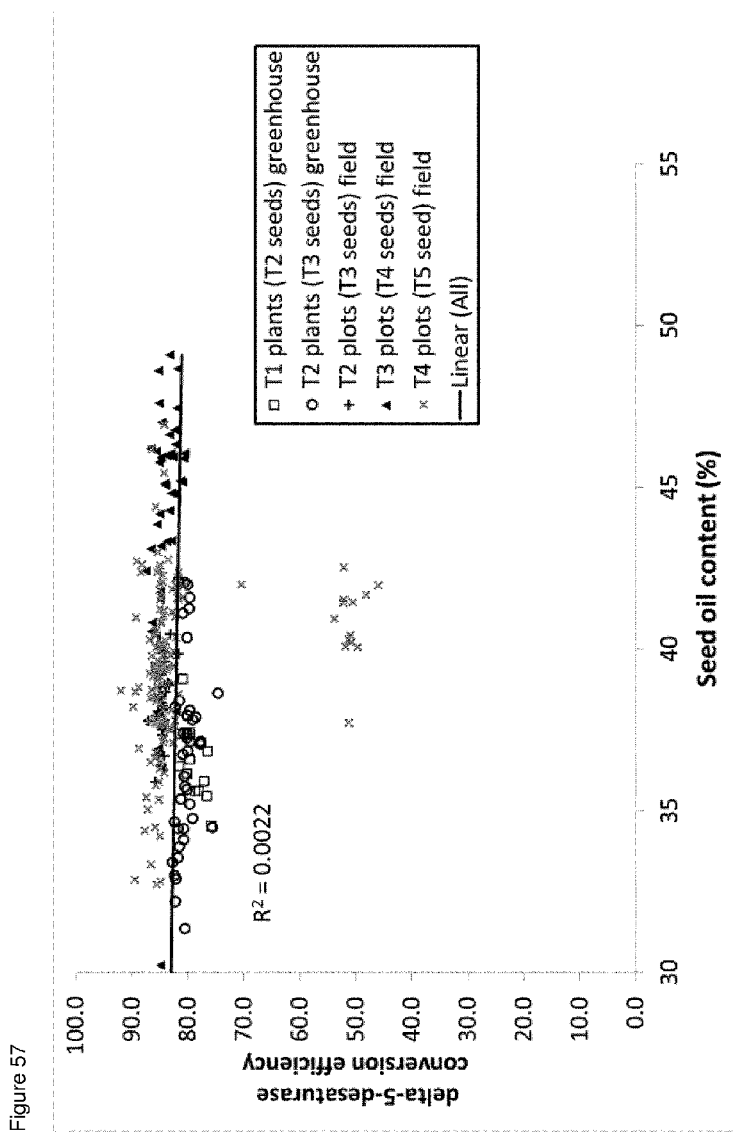
FIG. 57: The conversion efficiency of the delta-5-desaturase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 58:
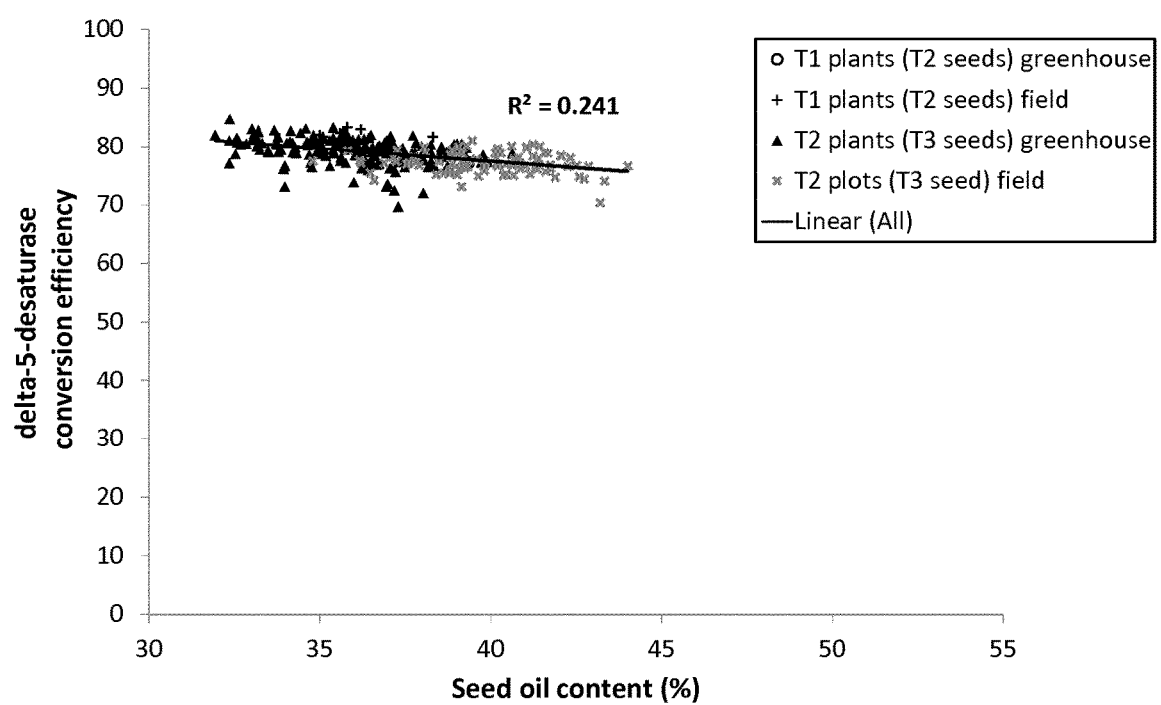
FIG. 58: The conversion efficiency of the delta-5-desaturase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 59:
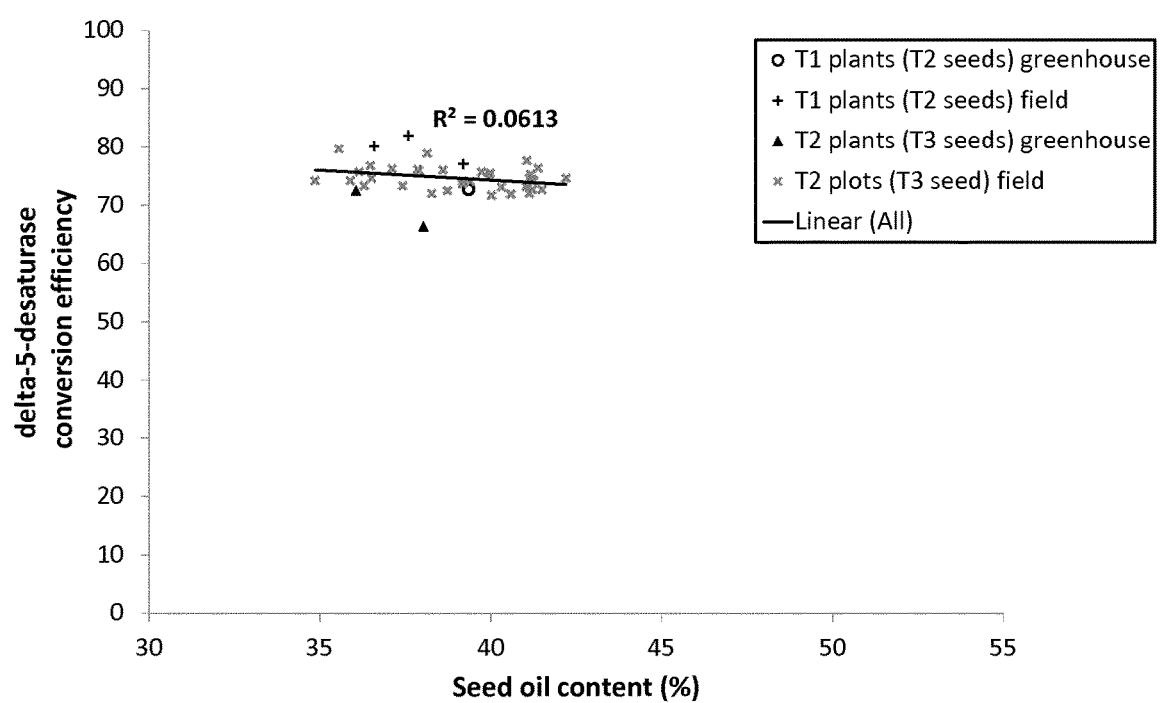
FIG. 59: The conversion efficiency of the delta-5-desaturase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 60:
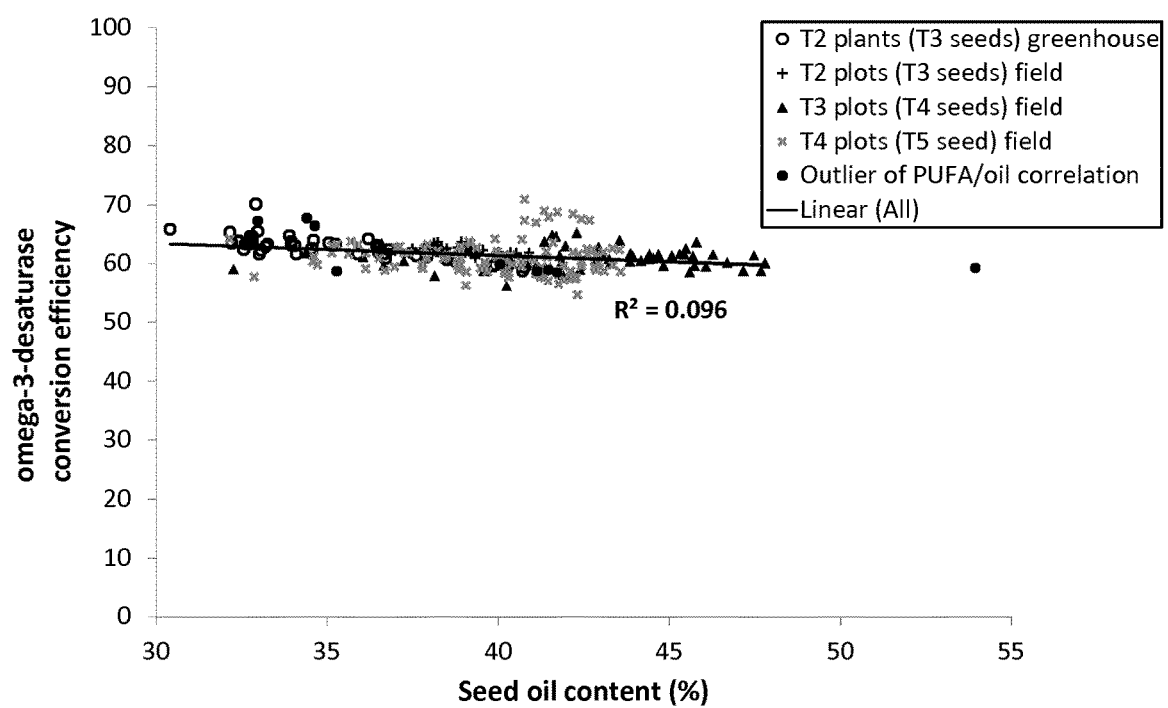
FIG. 60: The conversion efficiency of the omega-3-desaturase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 61:
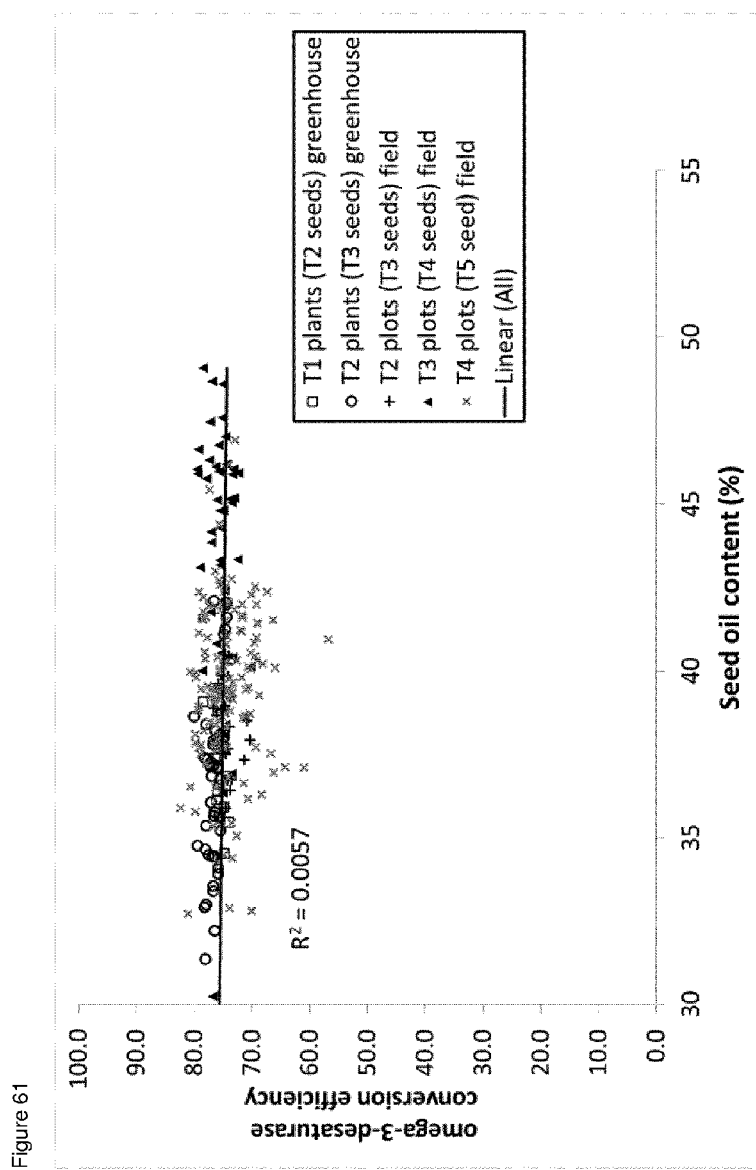
FIG. 61: The conversion efficiency of the omega-3-desaturase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 62:
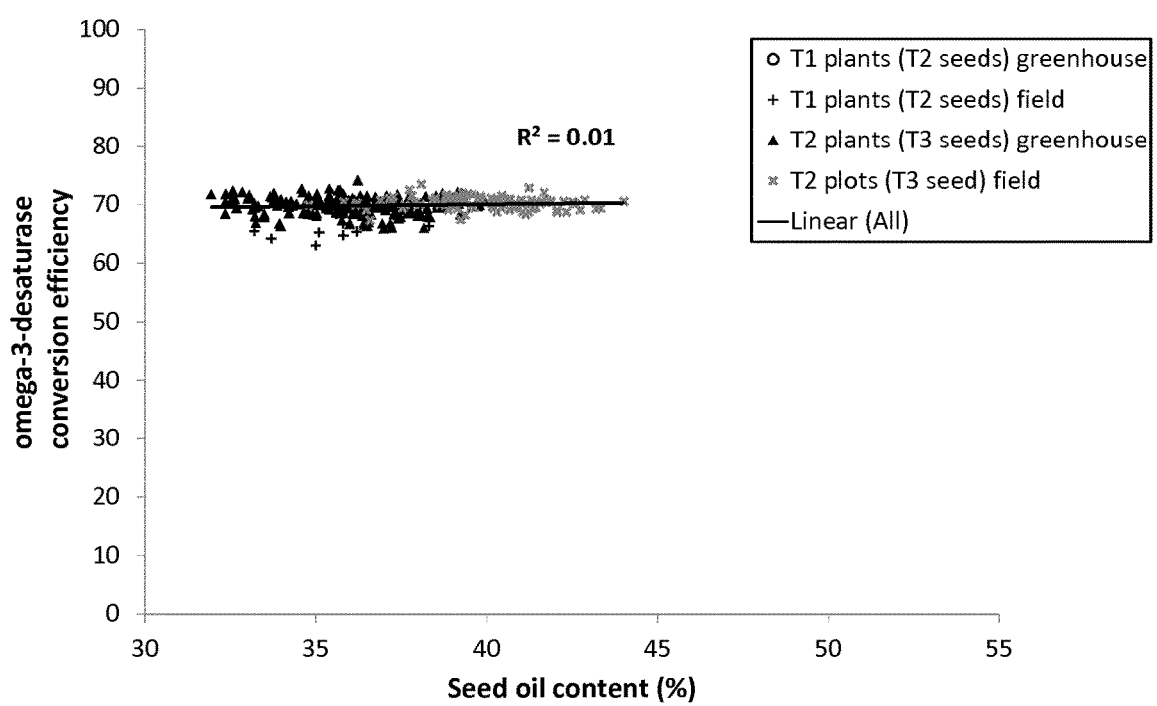
FIG. 62: The conversion efficiency of the omega-3-desaturase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 63:
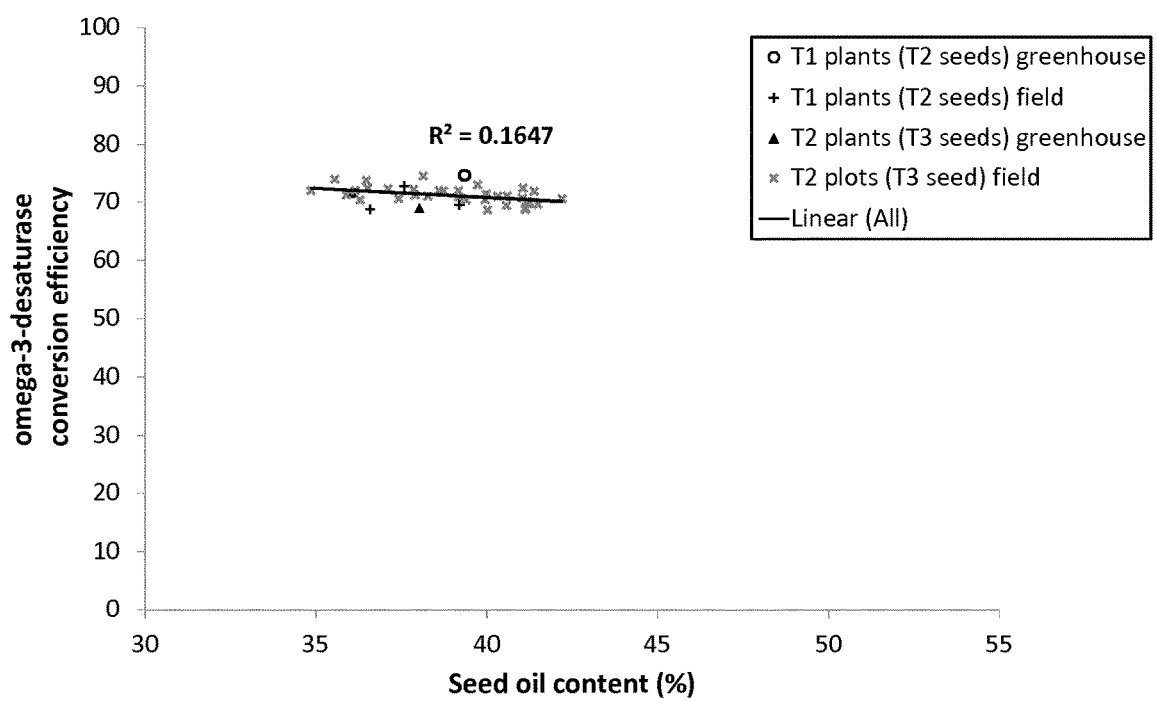
FIG. 63: The conversion efficiency of the omega-3-desaturase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 64:
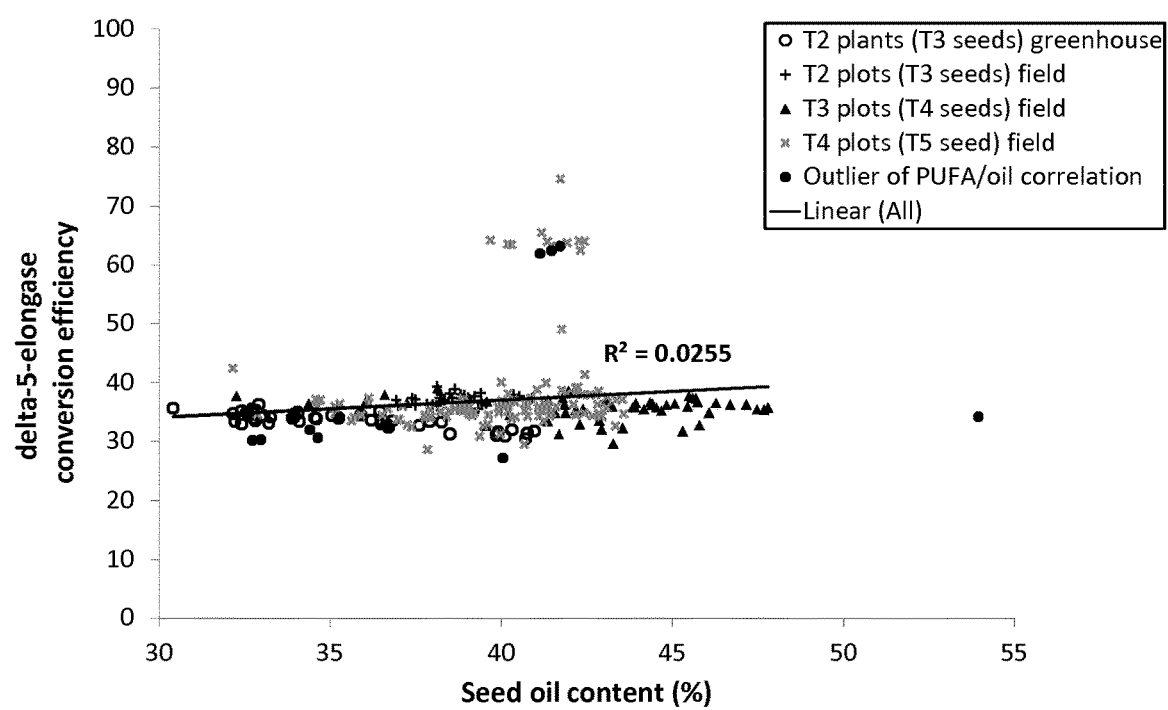
FIG. 64: The conversion efficiency of the delta-5-elongase was not correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 65:
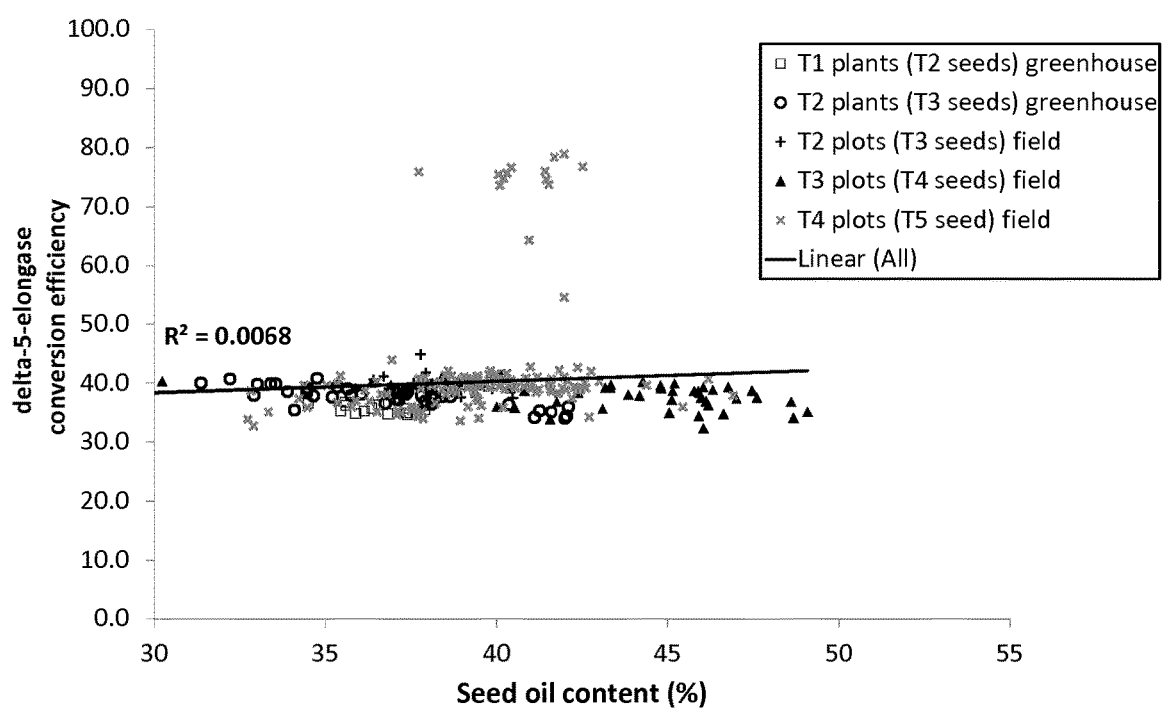
FIG. 65: The conversion efficiency of the delta-5-elongase was not correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 66:
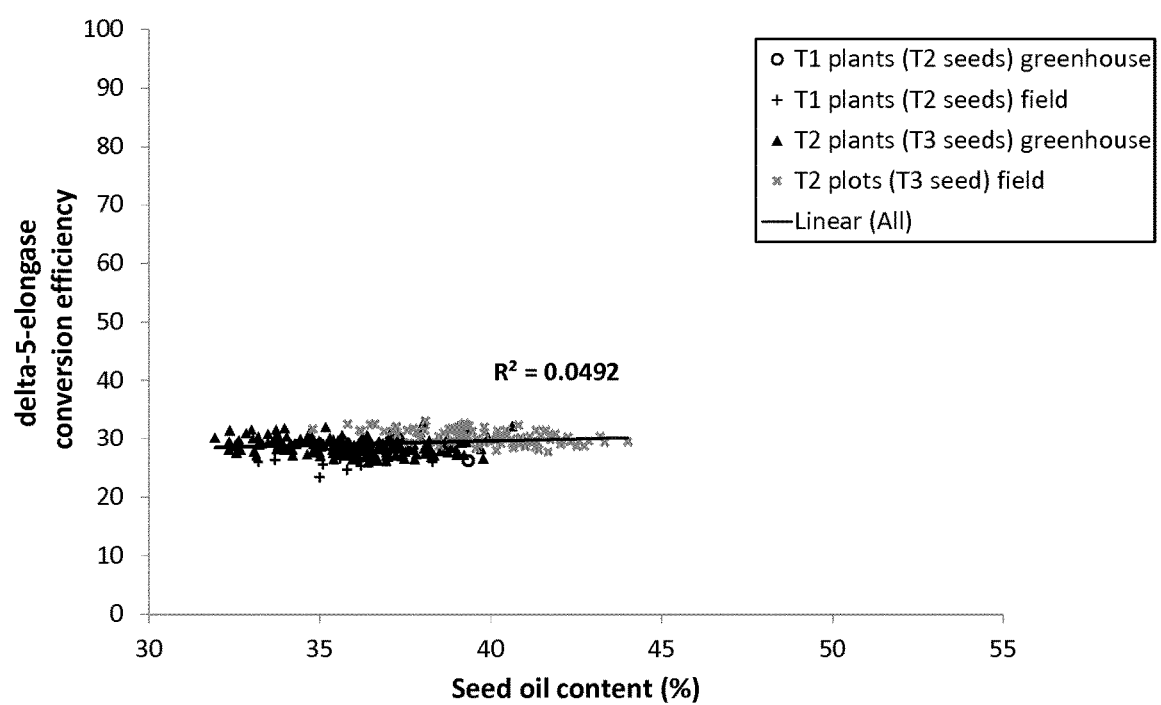
FIG. 66: The conversion efficiency of the delta-5-elongase was not correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 67:
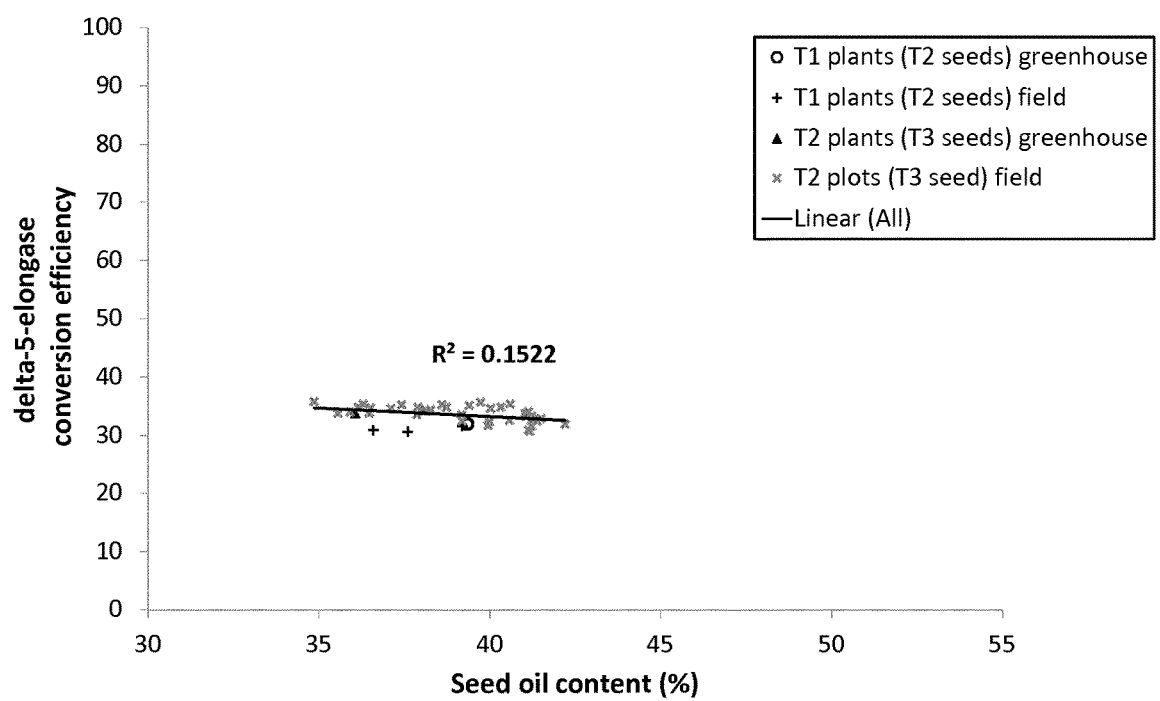
FIG. 67: The conversion efficiency of the delta-5-elongase was not correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of one T2 seedbtach of one T1 plant, or the analysis of a random selection of T3 seeds representing one plot.
Figure 68:
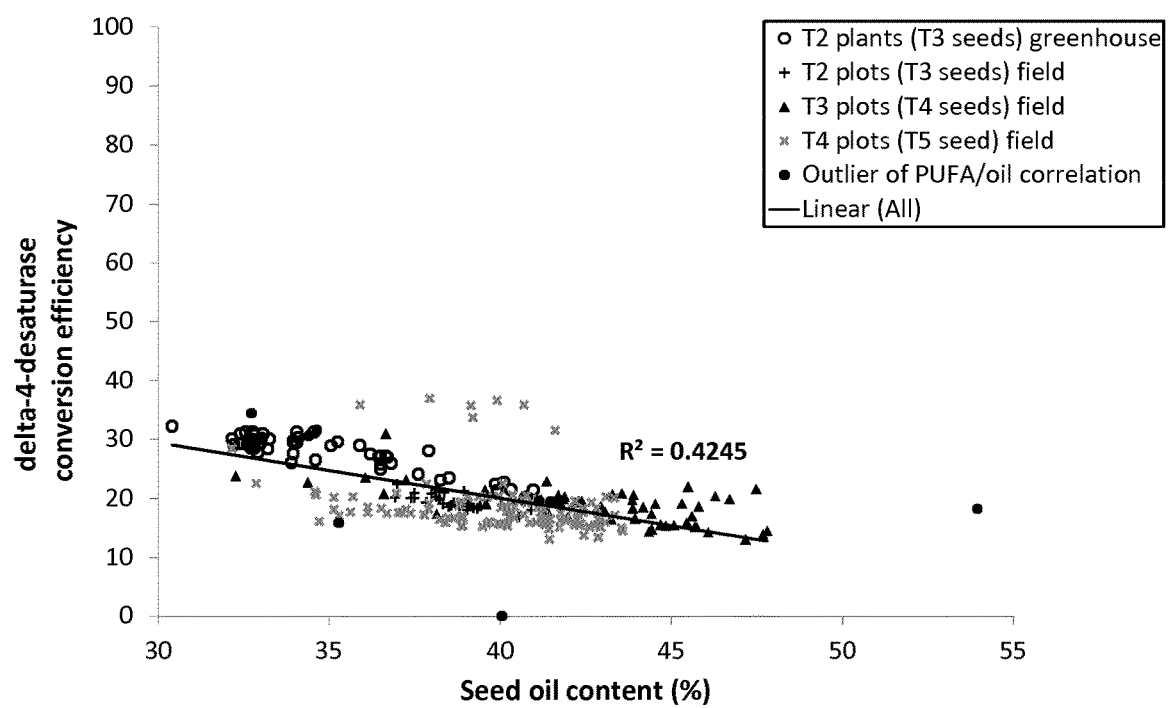
FIG. 68: The conversion efficiency of the delta-4-desaturase was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 69:
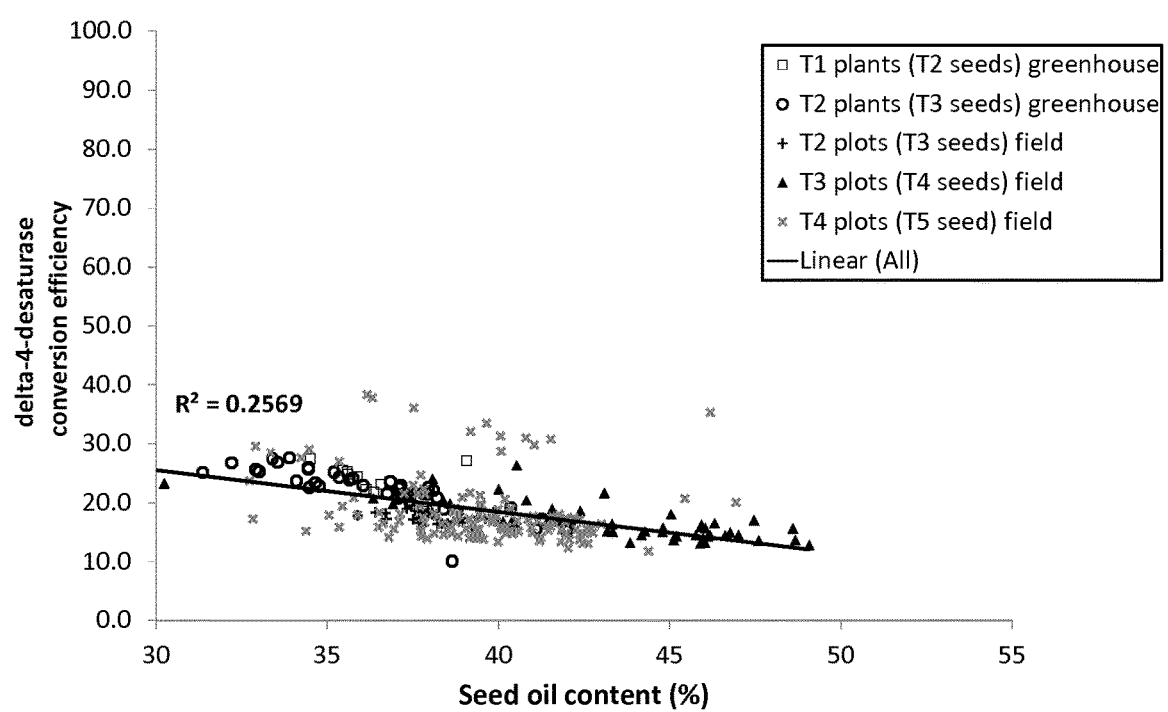
FIG. 69: The conversion efficiency of the delta-4-desaturase was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 70:
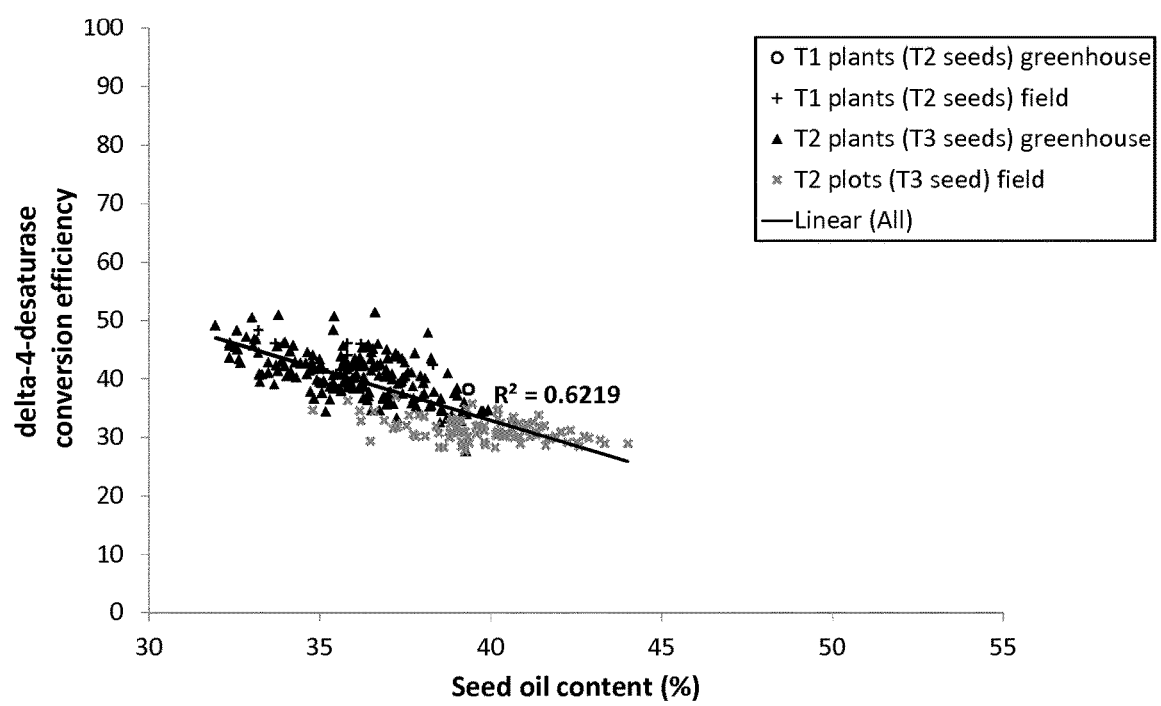
FIG. 70: The conversion efficiency of the delta-4-desaturase was negatively correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 71:
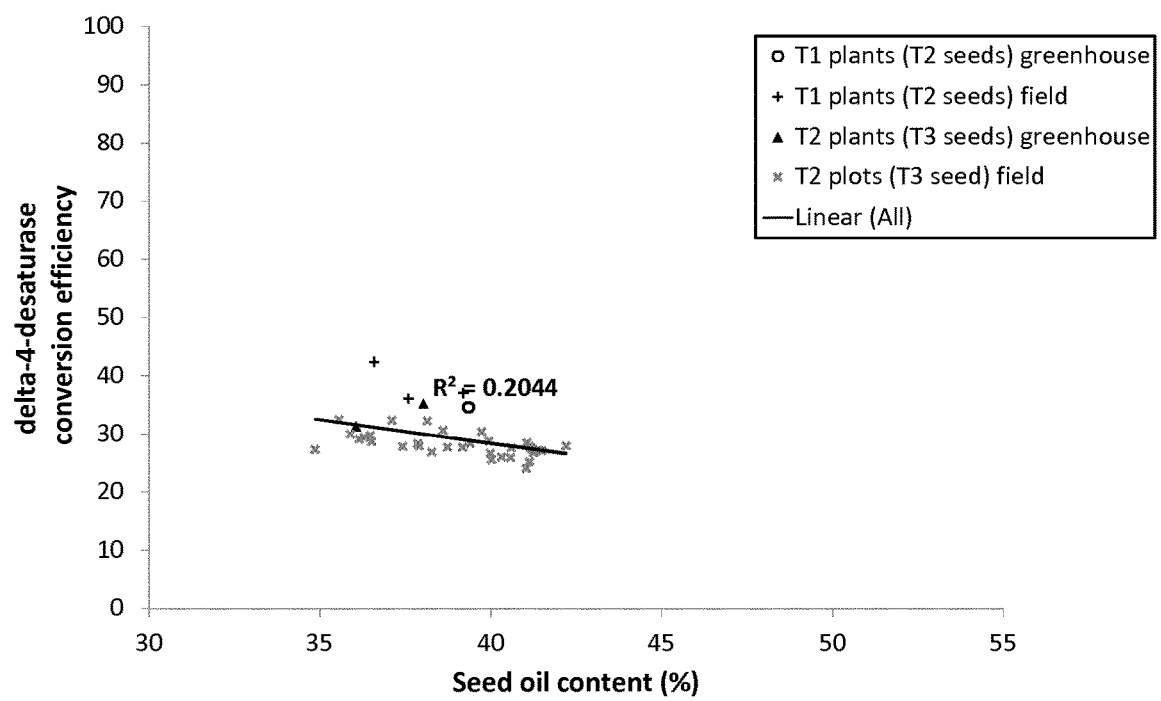
FIG. 71: The conversion efficiency of the delta-4-desaturase was negatively correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.

While the event LBFDAU was capable of producing in a genetically identical plant population ~13.5% EPA+2.6% DHA in a given environment, there are individual plants within this population that produce up to ~18% EPA+3.7% DHA as an average of all seeds produced by this plant, and single seed of this plant can reach up to ~26% EPA and ~5% DHA. These differences in EPA+DHA levels are due to the interaction of the genetic constituents of the event with the environment. However, it was consistently observed that comparable populations yield higher VLC-PUFA levels in the greenhouse compared to the field. This trend usually correlates with lower oil content in the greenhouse, compared to the field. To investigate this observation in more detail, oil content measured in all homozygous seed batches of the single copy event LANPMZ (event described in example 11) was plotted in FIG. 40 against the sum of all VLC-PUFA that are downstream of the delta-12-desaturase (see FIG. 2) measured in the same seed batches. The same has been done for event LAODDN (event described in example 13), and is plotted FIG. 41. This analysis was also done for two events described in example 18, namely for event LBFGKN (FIG. 42), and for event LBFLFK (FIG. 43). What was observed is a strong correlation between these two parameters. The same analysis for wildtypes (FIG. 72) reveals no such correlation, instead, FIG. 72 shows a difference between greehouse grown and field grown wild-type plants, in that field grown wildtype plants have higher levels of 18:2n-6 and 18:3n-3 and lower 18:1n-9 compared to greenhouse grown wildype plants.

Figure 40:
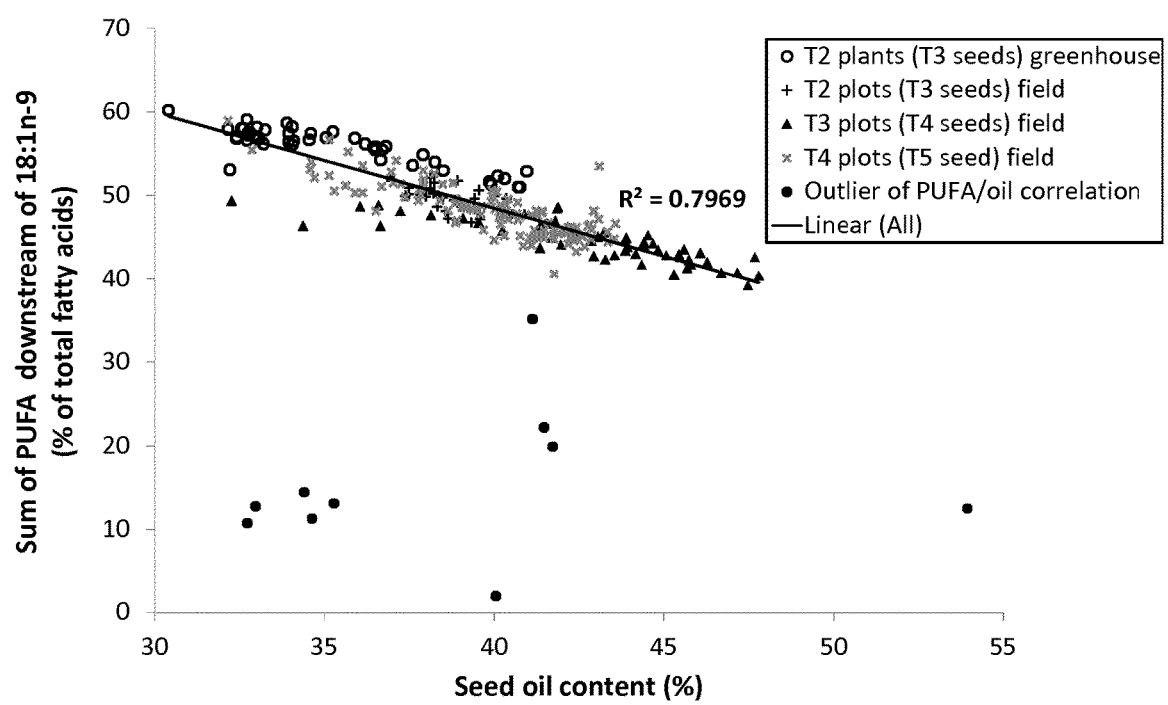
FIG. 40: The sum of all pathway fatty acids was negatively correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 41:
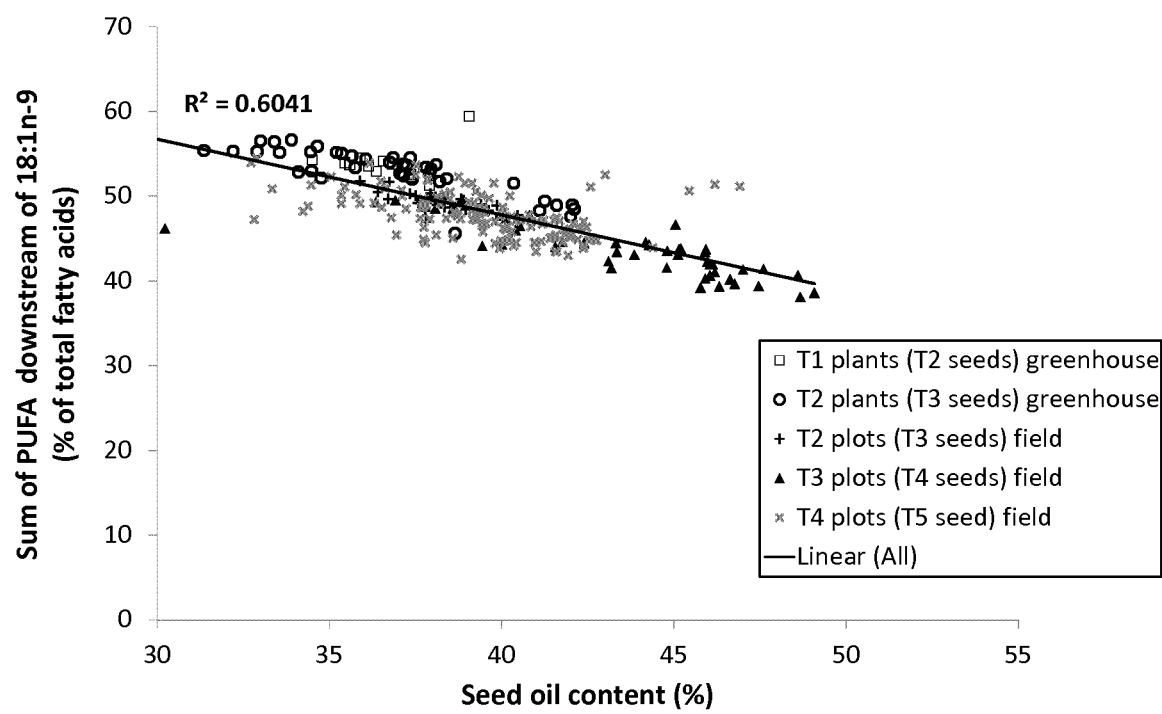
FIG. 41: The sum of all pathway fatty acids was negatively correlated with seed oil content. Shown are data of 4 generations of event LAODDN. For the greenhouse data, one marker corresponds to one seedbatch of one plant, for the field data, one marker corresponds to an analysis on a random selection of seeds representing one plot.

To analyse in detail if this correlation depicted for event LANPMZ in FIG. 40 can be attributed to certain pathway steps, conversion efficiencies for each pathway step and for each seedbatch analysed in FIG. 40 have been calculated, and plotted in FIG. 44, FIG. 48, FIG. 52, FIG. 56, FIG. 60, FIG. 64, and FIG. 68. The same analysis has been done for event LAODDN, and is plotted in FIG. 45, FIG. 49, FIG. 53, FIG. 57, FIG. 61, FIG. 65 and FIG. 69. The same analysis was also been done for event LBFGKN, (plotted in FIG. 46, FIG. 50, FIG. 54, FIG. 58, FIG. 62, FIG. 66 and FIG. 70), and for event LBFLFK (FIG. 47, FIG. 51, FIG. 55, FIG. 59, FIG. 63, FIG. 67 and FIG. 71). Comparing all these figures, one can see that the correlation observed in FIG. 40 and FIG. 41 is largely attributed to the delta-12-desaturase pathway step (FIG. 44 to FIG. 47), the delta-6-desaturase pathway step (FIG. 48 to FIG. 51), and the delta-4-desaturase pathway step (FIG. 68 to FIG. 71): in these figures, there is a construct and event independent negative correlation between the pathway steps and the seed oil content visible, which cannot be observed for the other pathway steps.

Figure 72:
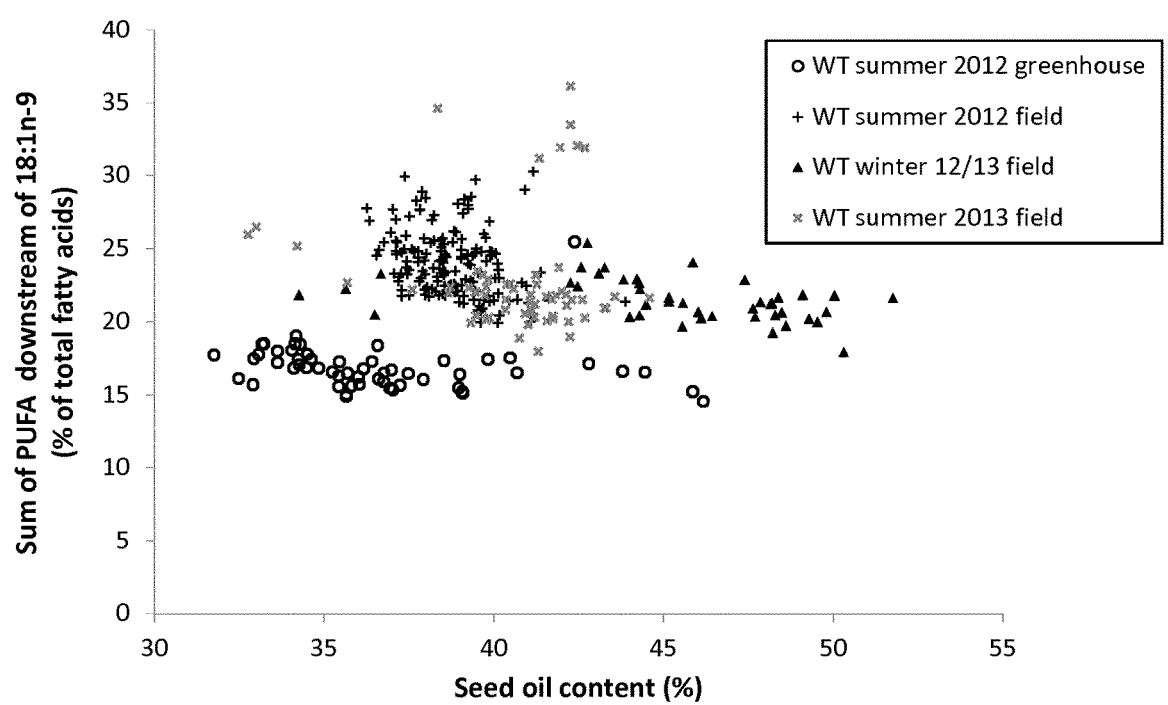
FIG. 72: The sum of all pathway fatty acids was not correlated with seed oil content in wildtype canola, but differs between greenhouse and field. Shown are data of three seasons. For the greenhouse data, one marker corresponds to one seedbatch of one plant, for the field data, one marker corresponds to an analysis on a random selection of seeds representing one plot.
Figure 73:
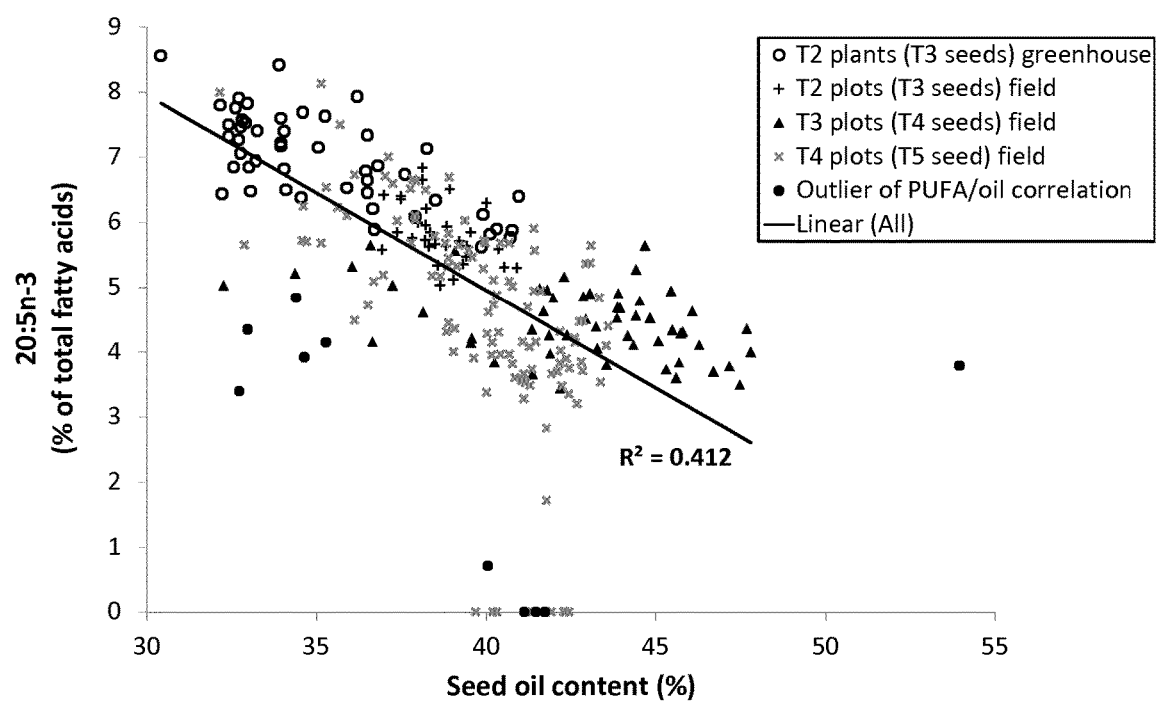
FIG. 73: The total fatty acid percentage of 20:5n-3 (EPA) correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 74:
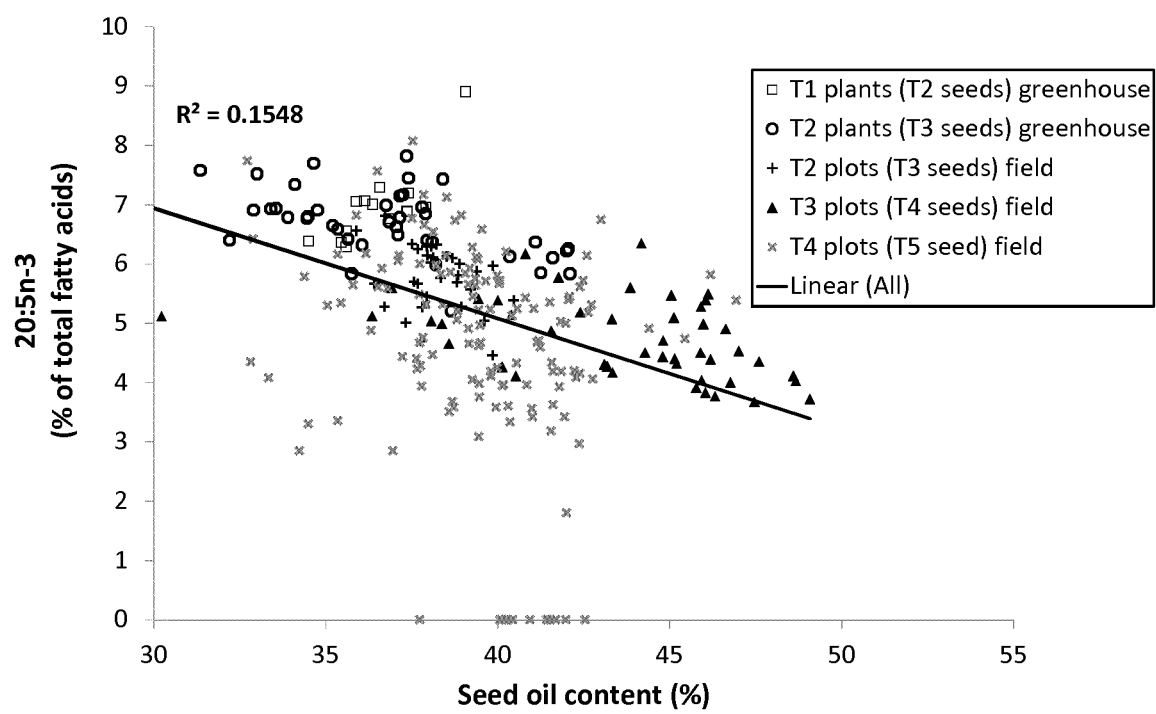
FIG. 74: The total fatty acid percentage of 20:5n-3 (EPA) correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 75:
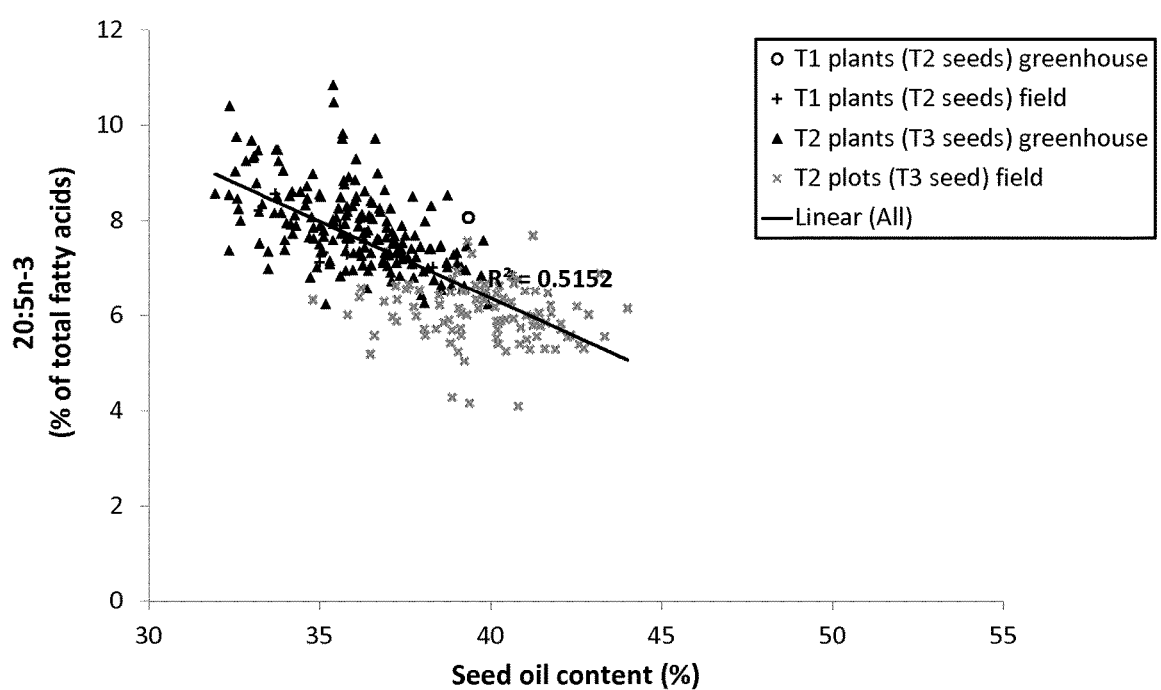
FIG. 75: The total fatty acid percentage of 20:5n-3 (EPA) correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 76:
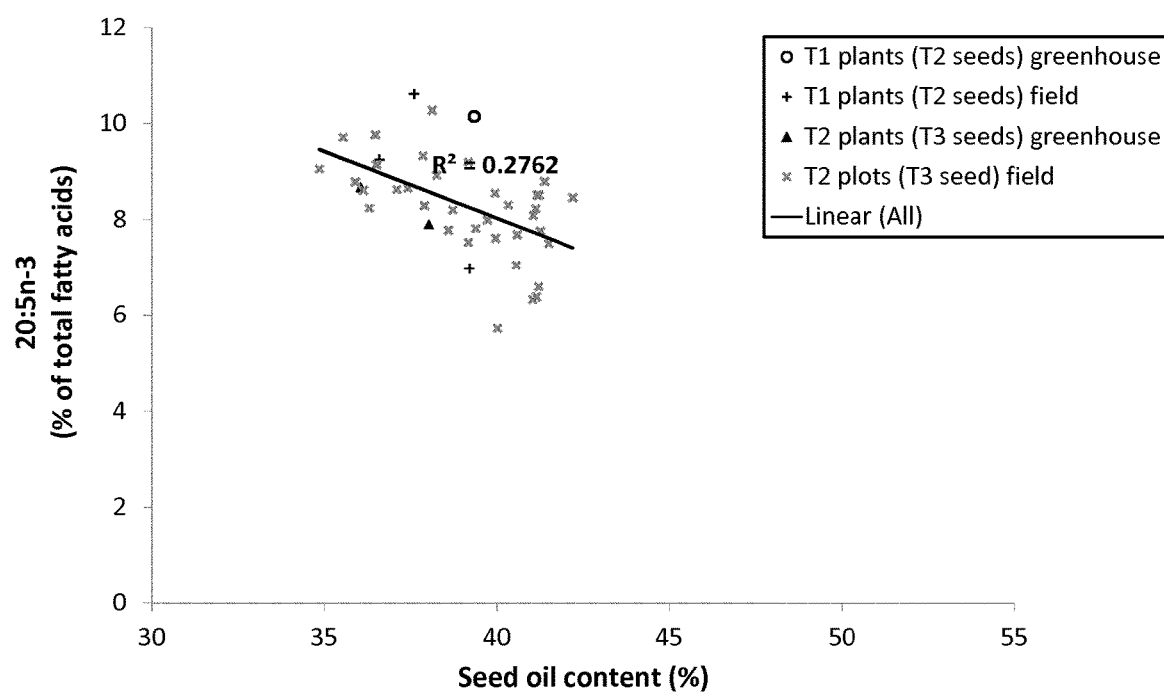
FIG. 76: The total fatty acid percentage of 20:5n-3 (EPA) correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 77:
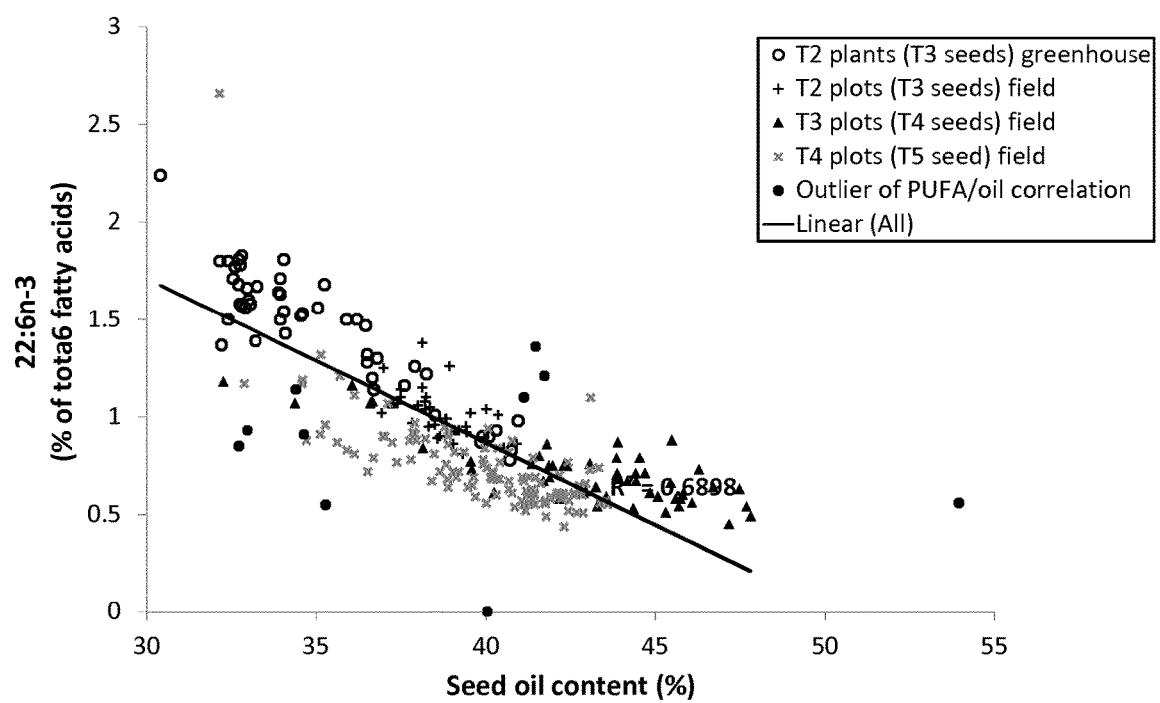
FIG. 77: The total fatty acid percentage of 22:6n-3 (DHA) correlated with seed oil content. Shown are data of 3 generations of event LANPMZ. For the greenhouse data, one marker corresponds to one seedbatch of one plant, for the field data, one marker corresponds to an analysis on a random selection of seeds representing one plot.
Figure 78:
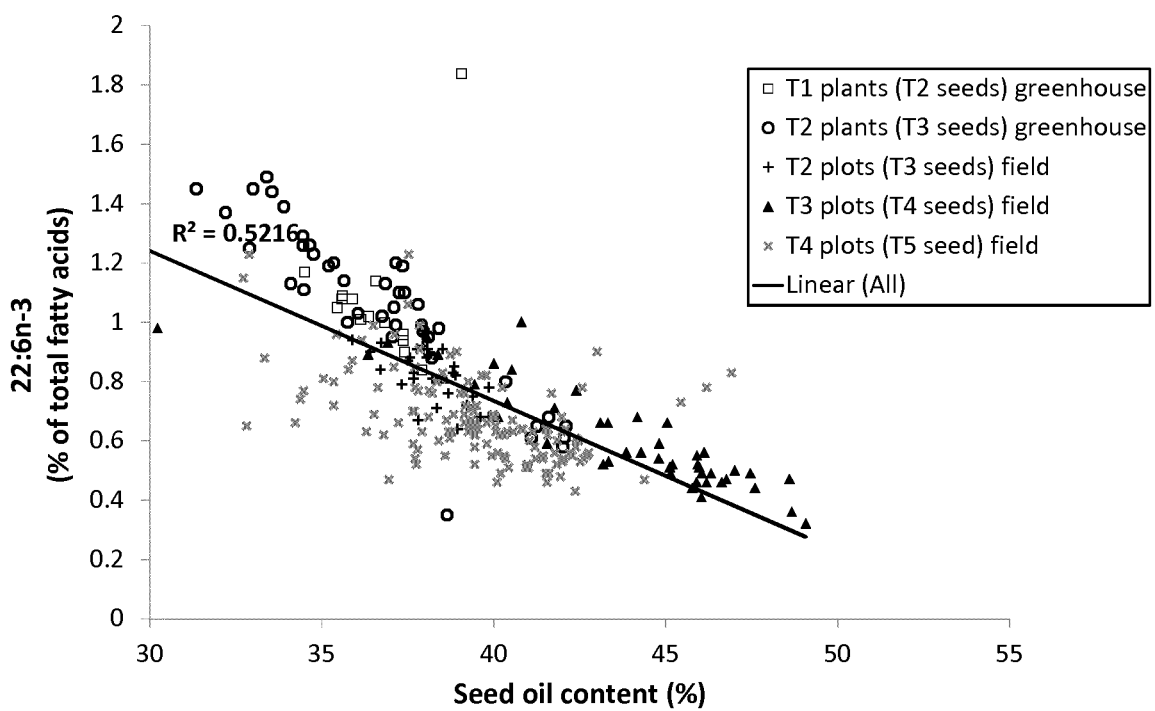
FIG. 78: The total fatty acid percentage of 22:6n-3 (DHA) correlated with seed oil content. Shown are data of 4 generations of event LAODDN. For the greenhouse data, one marker corresponds to one seedbatch of one plant, for the field data, one marker corresponds to an analysis on a random selection of seeds representing one plot.
Figure 79:
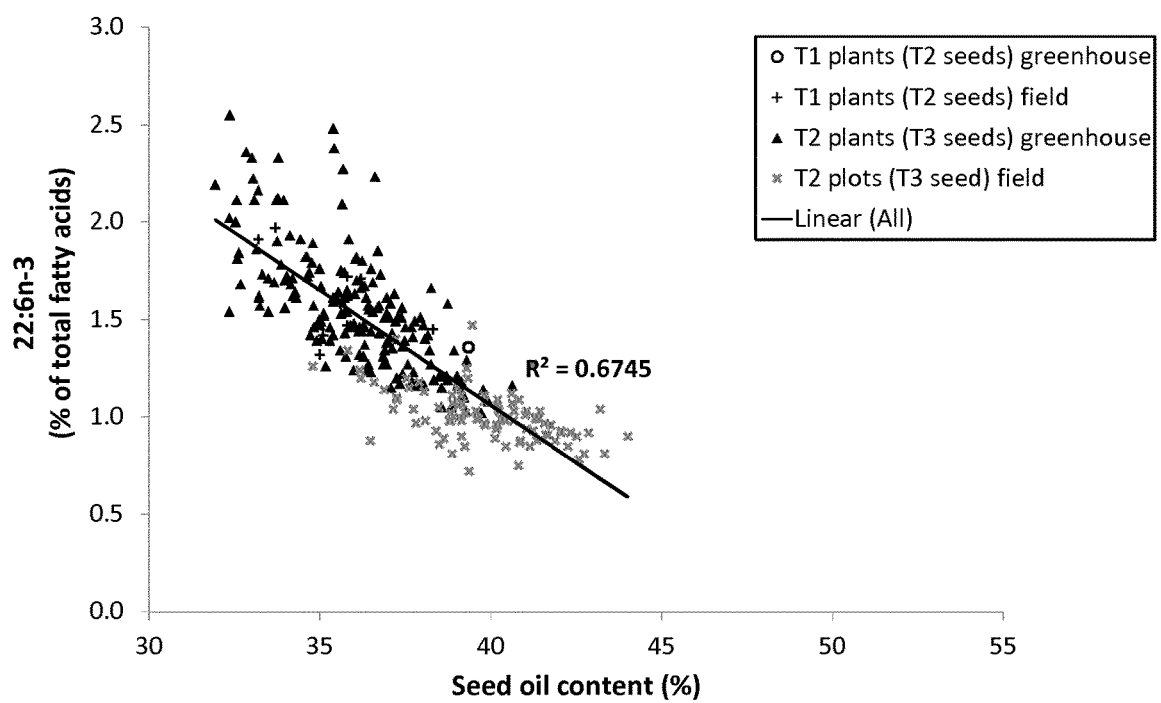
FIG. 79: The total fatty acid percentage of 22:6n-3 (DHA) correlated with seed oil content. Shown are data of 2 generations of event LBFGKN. For the greenhouse data, one marker corresponds to the analysis of a random selection of seeds representing a bulk of 50 T2 seedbatches, or 182 T3 seedbatches, for the field data, one marker corresponds to an analysis of one T2 seedbtach of one T1 plant, or the analysis of a random selection of T3 seeds representing plots (36 plots) or single plants (60 plants).
Figure 80:
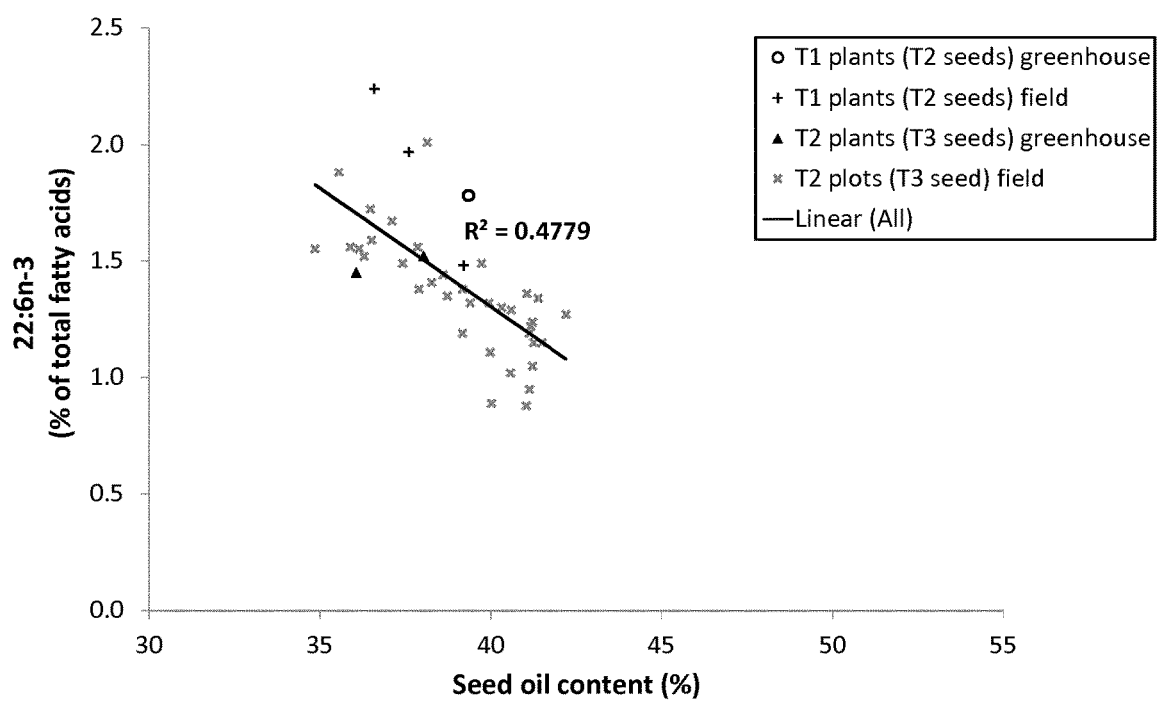
FIG. 80: The total fatty acid percentage of 22:6n-3 (DHA) correlated with seed oil content. Shown are data of 2 generations of event LBFLFK. For the greenhouse data, one marker corresponds to the analysis of a random selection of seeds representing a bulk of 10 T2 seedbatches, or 195 T3 seedbatches, for the field data, one marker corresponds to an analysis of 1 T2 seedbtach of one T1 plant, or a the analysis of a random selection of T3 seeds representing one plot.
Figure 81:
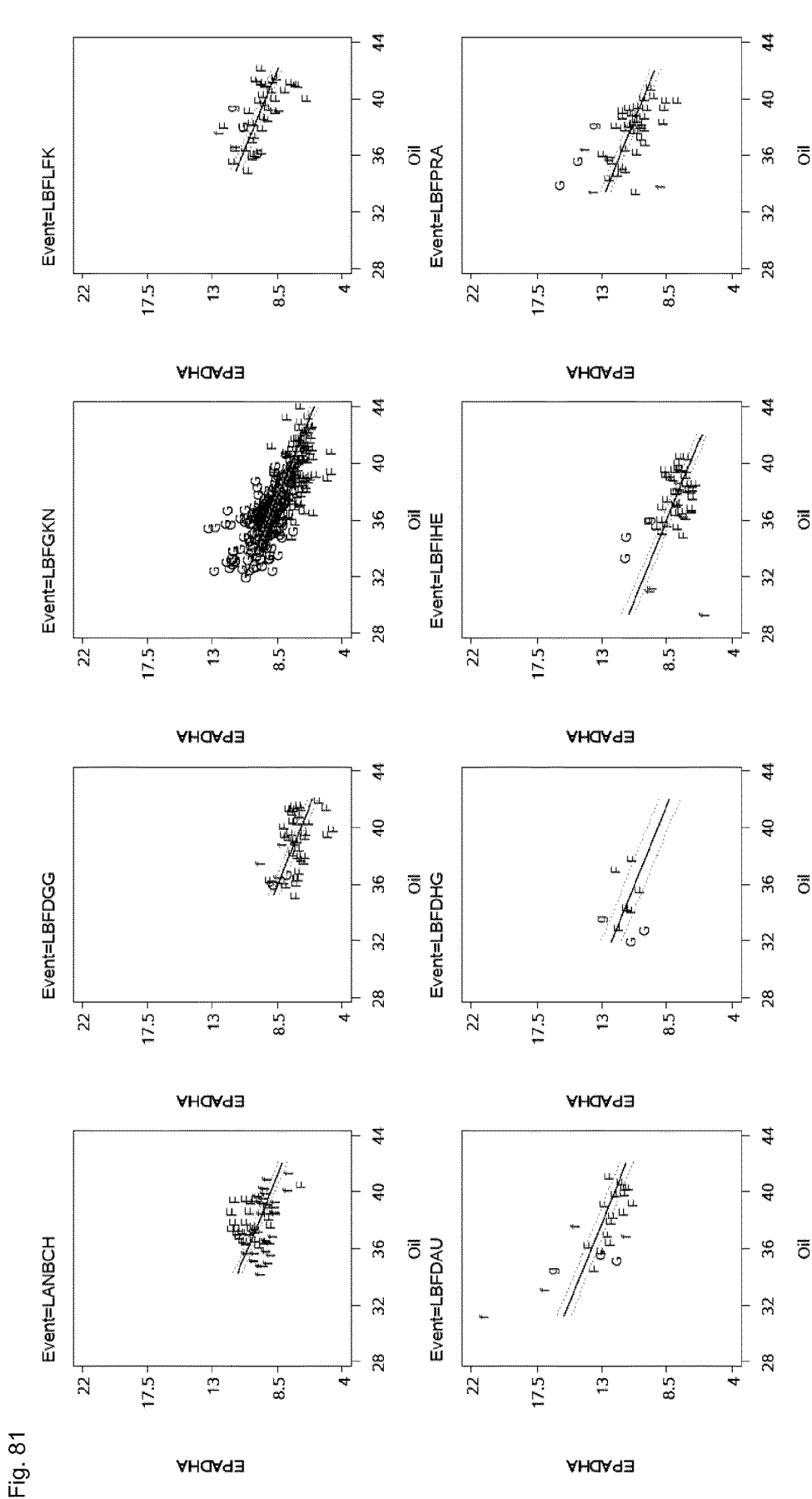
FIG. 81: The levels of EPA+DHA (20:5n-3 and 22:6n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 82:
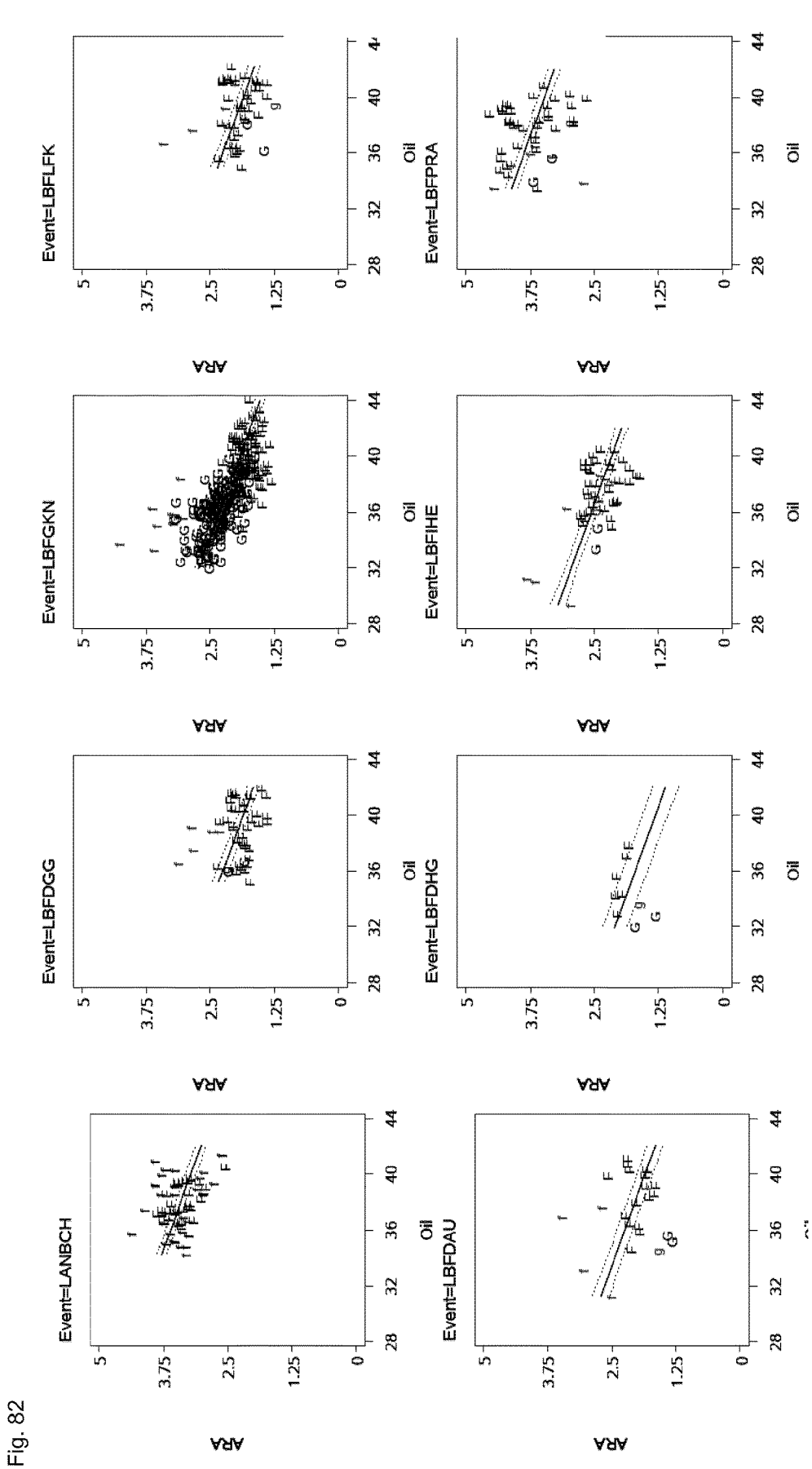
FIG. 82: The levels of ARA (20:4n-6) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 83:
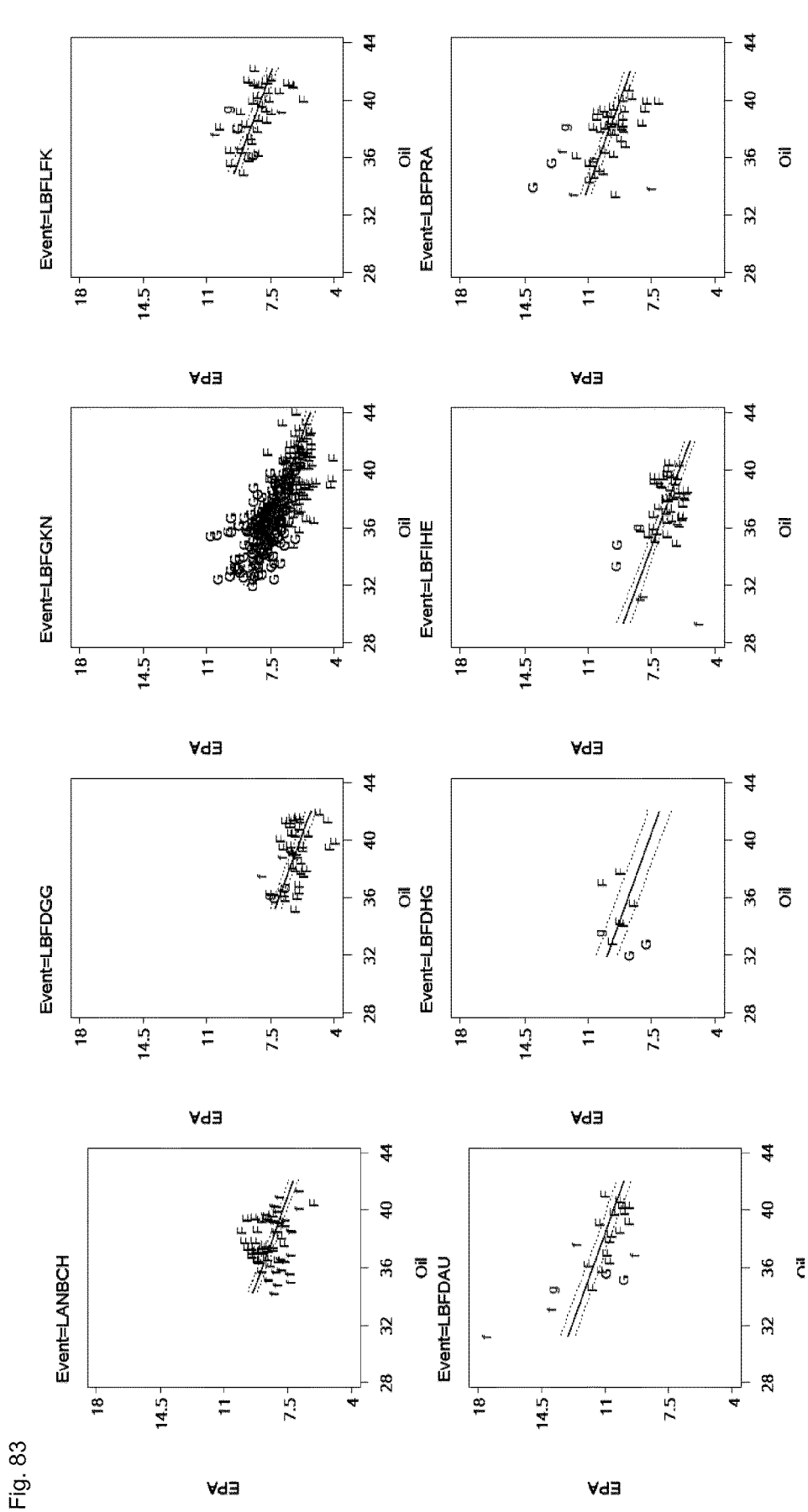
FIG. 83: The levels of EPA (20:5n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and Example 14 (all other events).
Figure 84:
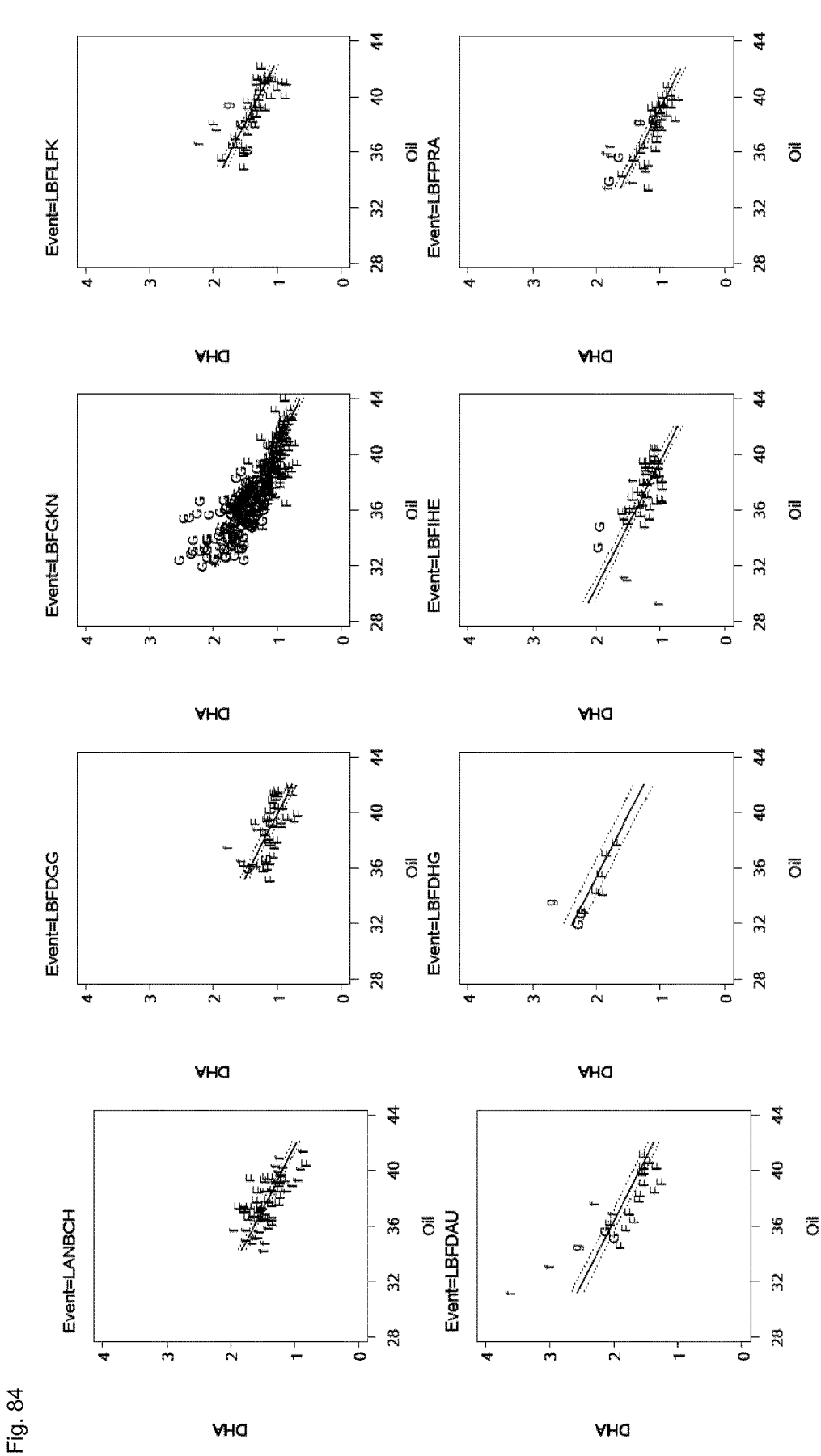
FIG. 84: The levels of DHA (22:6n-3) correlated with seed oil content. Shown are data of homozygous plants (single plant: capital G or F, plots: lower case f, grown in greenhouses: G, grown in field trials: f and F). The data are described in more detail in Example 12 (event LANBCH), and example 14 (all other events).

The negative correlation of the delta-12-desaturase pathway with seed oil content in event LANPMZ was observed in wild type plants, as shown in FIG. 72. Moreover, FIG. 72 shows that field grown wildtype plants have higher levels of 18:2n-6 and 18:3n-3 and lower 18:1n-9 compared to greenhouse grown wildtype plants. This can most likely be explained with previous observations (Xiao et al. 2014), in that the native Canola endogenous delta-12-desaturase was regulated by temperature and that temperature regulation of delta-12-desaturase at the transcript level and protein level is a recurring theme in plants (Kargiotidou et al. 2008, Tang et al. 2005, Sanchez-Garcia et al. 2004), whereby under field conditions the delta-12-desaturase would be up-regulated compared to greenhouse conditions. However, it can be concluded that there was no regulation of the delta-12-desaturase in dependence of the oil content observed in wildtype canola plant. Consequently comparing FIG. 72 with FIG. 40 to FIG. 43), it can furthermore be concluded that only the introduced transgenic delta-12-desaturase was subject to a regulation that was seed oil content dependent.

A further observation is that field grown transgenic plants do not have a higher delta-12-desaturase conversion efficiency compared to greenhouse grown plants, even though this was clearly observed for wildtype plants in FIG. 72. It can be concluded that the endogenous native delta-12-desaturase does not significantly contribute to the overall observed delta-12-desaturase conversion efficiency in the transgenic plants of the invention.

In addition to plotting pathway step conversion efficiencies vs seed oil content, levels of some key fatty acids have been plotted agains seed oil content (FIG. 81, FIG. 82, FIG. 83, FIG. 84). The data have been fitted in those FIGS. by using all datapoints of all depicted events to determine the slope of the regression, and by subsequently using all datapoints for single events to determine the intercept of the regression line with the x-axis (0% oil content) of the regressions shown in (FIG. 81, FIG. 82, FIG. 83, FIG. 84). The results of this analysis are shown in Table 158.

TABLE 158

Regression equations of fitting the data in FIG. 81, FIG. 82, FIG. 83, FIG. 84 as described in example 20.

| Event | N | EPA + DHA vs oil | | ARA vs oil | | EPA vs oil | | DHA vs oil | |
|---|---|---|---|---|---|---|---|---|---|
| | | Intercept | Slope | Intercept | Slope | Intercept | Slope | Intercept | Slope |
| LBFDAU | 23 | 28.054 | −0.398 | 5.774 | −0.098 | 22.053 | −0.288 | 6.003 | −0.110 |
| LBFPRA | 44 | 26.075 | −0.398 | 7.399 | −0.098 | 20.762 | −0.288 | 5.315 | −0.110 |
| LBFLFK | 42 | 25.280 | −0.398 | 5.788 | −0.098 | 19.578 | −0.288 | 5.703 | −0.110 |
| LBFDHG | 9 | 25.058 | −0.398 | 5.235 | −0.098 | 19.167 | −0.288 | 5.892 | −0.110 |
| LANBCH | 60 | 24.910 | −0.398 | 7.142 | −0.098 | 19.305 | −0.288 | 5.606 | −0.110 |
| LBFGKN | 291 | 23.481 | −0.398 | 5.856 | −0.098 | 17.994 | −0.288 | 5.488 | −0.110 |
| LBFIHE | 47 | 22.841 | −0.398 | 6.086 | −0.098 | 17.489 | −0.288 | 5.353 | −0.110 |
| LBFDGG | 44 | 22.800 | −0.398 | 5.789 | −0.098 | 17.403 | −0.288 | 5.398 | −0.110 |

Listed are the parameters for the equation (Fatty acid) = (seed oil content) * Slope + Intercept.

Example 21: In Vitro Demonstration of Enzyme Activity

Desaturase Enzyme Activity in Microsomes Isolated from Transgenic Yeast Expression of desaturases and elongases was accomplished in *Saccharomyces cerevisiae*. Briefly, yeast strains containing the appropriate plasmid were grown overnight at 30° C. (in SD-medium-uracil+raffinose) and then used to inoculate a larger culture at a starting $OD_{600}$=0.2 (in SD-medium-uracil+raffinose+galactose). After 24 hours at 30° C. the culture (typically $OD_{600}$=0.6-0.8) was harvested by centrifugation and washed once in 25 mM Tris Buffer (pH 7.6). Preparation of crude extracts and microsomes from yeast expressing genes encoding desaturases and elongases was accomplished using standard procedures. Briefly, cells expressing desaturases were resuspended in 2 ml Desaturase Disruption Buffer (0.1 M potassium phosphate pH 7.2, 0.33 M sucrose, 4 mM NADH, 1 mg/ml BSA (fatty acid free), 4000 U/ml catalase and protease inhibitors (Complete EDTA-free (Roche)) and disrupted using silica/zirconium beads in a BeadBeater. The crude extract was clarified by centrifugation twice at 8,000× g, 4° C.). After an additional centrifugation at 100,000×g (30 minutes at 4° C.) the microsomes were pelleted and ultimately resuspended in Desaturase Disruption Buffer (300 microliters). Protein concentrations in both the crude extract and microsomes were measured using the bicinchoninic acid (BCA) procedure (Smith, P. K., et al (1985) *Anal. Biochem.* (150): 76-85).

General Desaturase Activity Assays:

In the desaturase assay a [$^{14}$C]-labeled acyl-CoA was provided as a substrate and after the reaction the acyl-CoAs (and phospholipids) were hydrolyzed and methylated to fatty acid methyl esters (FAMEs), which were analyzed using argentation-TLC. The general assay conditions were modified from Banas et al. (Banas et al. (1997) *Physiology, Biochemistry and Molecular Biology of Plant Lipids* (Williams, J. P., Khan, M. U. and Lem, N. W. eds.) pp. 57-59).

The assay contained: 1 mg enzyme (crude extract) or 150 μg (microsomal fraction), 10 nmol [$^{14}$C]-acyl-CoA (3000 dpm/nmol), 7.2 mM NADH (total), 0.36 mg BSA (total) in a buffer comprised of 0.1 M K-phosphate pH 7.2, 0.33 M sucrose, 4 mM NADH, 1 mg/ml BSA and protease inhibitors in a total volume of 200 μl. After incubation at 30° C. for the desired time, 200 μl of 2 M KOH in MeOH:H$_2$O (1:4) was added and incubated for 20 minutes at 90° C. Fatty acids were extracted by addition of 3 M HCl (200 μl), 1.5 ml of MeOH:CHCl$_3$ (2:1) and CHCl$_3$ (500 μl). The chloroform phase was recovered, dried under N$_2$(g) and fatty acids were methylated by addition of 2 ml MeOH containing 2% H$_2$SO$_4$ and incubation of 30 minutes at 90° C. FAMEs were extracted by addition of 2 ml H$_2$O and 2 ml hexane and separated by AgNO$_3$-TLC and Heptane:Diethyl ether:Acetic Acid (70:30:1) as a solvent. The radioactive lipids were visualized and quantified by electronic autoradiography using Instant Imager.

Delta-12 desaturase (*Phytophthora sojae*), c-d12Des (Ps_GA) Enzyme Activity: Enzyme assays were performed using re-suspended microsomes isolated from a yeast strain expressing the c-d12Des(Ps_GA) protein and compared to microsomes isolated from a control yeast strain containing an empty vector (LJB2126). In the presence of [$^{14}$C]18:1n-9-CoA, 16:0-lysphosphatidylcholine (LPC), and NADH membranes containing c-d12Des(Ps_GA) form an [$^{14}$C]18:2-fatty acid that can be isolated as a methyl ester and resolves on AgNO$_3$-TLC [heptane:diethyl ether (90:10)] similar to known synthetic standards. This enzyme activity requires NADH and was not observed in membranes isolated from the empty vector control strain. Control assays without 16:0-LPC contain a small-amount of activity, presumably due to endogenous 16:0-LPC found in yeast microsomes. Furthermore, separation of the phospholipids from the free-fatty acids after the enzymatic reaction and characterization of the isolabled fatty acid methyl esters demonstrated that all of the c-d12Des(Ps_GA) enzymatically produced 18:2n-6-fatty acid methyl ester (FAME) was found in the phosphatidylcholine fraction. c-d12Des (Ps_GA) enzyme activity may also be demonstrated using other [$^{14}$C]acyl-CoA's which may include, but are not limited to: [$^{14}$C]18:2n-6-CoA, [$^{14}$C]20:3n-6-CoA, [$^{14}$C]20:4n-6-CoA, [$^{14}$C]22:5n-3-CoA.

Delta-6 desaturase (*Ostreococcus tauri*), c-d6Des(Ot-_febit) Enzyme Activity: c-d6Des(Ot_febit) enzyme activity and substrate specificity can be demonstrated in microsomes isolated from a yeast strain expressing the c-d6Des(Ot_febit) protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using AgNO$_3$-TLC and Heptane:Diethyl ether:Acetic Acid (70:30:1) as a solvent. Furthermore, the c-d6Des(Ot_febit) enzyme can be shown to directly desaturate an acyl-CoA substrate, as described in "Desaturase Headgroup (CoA vs PC) Preference", as suggested in previous reports (Domergue et al. (2005) Biochem. J. 389: 483-490).

Delta-5 desaturase (*Thraustochytrium* ssp.), c-d5Des (Tc_GA2) Enzyme Activity: c-d5Des(Tc_GA2) enzyme activity and substrate specificity can be demonstrated in microsomes isolated from a yeast strain expressing the c-d5Des(Tc_GA2) protein using an [$^{14}$C]acyl-CoA general assay as described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Omega-3 desaturase (*Phytophthora infestans*), c-o3Des (Pi_GA2) Enzyme Activity: c-o3Des(Pi_GA2) enzyme activity and substrate specificity can be demonstrated in microsomes isolated from a yeast strain expressing the c-o3Des(Pi_GA2) protein using [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Omega-3 desaturase (*Pythium irregulare*), c-o3Des (Pir_GA) Enzyme Activity: c-o3Des(Pir_GA) enzyme activity and substrate specificity can be demonstrated in microsomes isolated from a yeast strain expressing the c-o3Des(Pir_GA) protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Delta-4 desaturase (*Thraustochytrium* ssp.), c-d4Des (Tc_GA) Enzyme Activity: c-d4Des(Tc_GA) enzyme activity and substrate specificity can be demonstrated in microsomes isolated from a yeast strain expressing the c-d4Des(Tc_GA) protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Delta-4 desaturase (*Pavlova lutheri*), c-d4Des(PI_GA)2 Enzyme Activity: c-d4Des(PI_GA)2 enzyme activity and substrate specificity can be demonstrated in microsomes isolated from a yeast strain expressing the c-d4Des(PI_GA)2 protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-.18) and acetonitrile (100%) as a solvent.

Delta-4 desaturase (*Euglena gracilis*), c-d4Des(Eg) Enzyme Activity: c-d4Des(Eg) enzyme activity and substrate specificity can be demonstrated in microsomes isolated from a yeast strain expressing the c-d4Des(Eg) protein using an [$^{14}$C]acyl-CoA in the general assay described above. [$^{14}$C]Acyl-CoA's may include, but are not limited to: [$^{14}$C]18:1n-9-CoA, [$^{14}$C]18:2n-6-CoA, [$^{14}$C]20:3n-6-CoA, [$^{14}$C]20:4n-6-CoA, [$^{14}$C]22:5n-3-CoA. Isolated fatty acid methyl esters derived from enzymatic substrates and products can be resolved using Reverse Phase-TLC (Silica gel 60 RP-18) and acetonitrile (100%) as a solvent.

Desaturase Activity in Microsomes Isolated from Transgenic *Brassica napus*.

Microsomes containing recombinant desaturases and elongases capable of synthesizing docosahexaenoic acid (22:6n-3) were isolated from immature seeds from transgenic *B. napus* using a procedure adopted from Bafor, M. et al. Biochem J. (1991) 280, 507-514. Briefly, immature seeds were first seperated from canola pods and then the developing embryos were isolated from the seed coat and transferred to ice-cold 0.1 M Phosphate buffer (pH 7.2). The developing embryos were then washed with fresh Phosphate buffer, transferred to an ice-cold mortar, and ground to a homogenous solution in Extraction Buffer (0.1 M Phosphate, pH 7.2, 0.33 M sucrose, 1 mg/ml BSA (essentially fatty acid free), 4000 U/ml catalase, 4 mM NADH and protease inhibitor-Complete EDTA-free (Roche)). The lysed developing embryo's were diluted 20-fold with additional Extraction Buffer and passed through 2 layers of Miracloth into a centrifuge tube. Following centrifugation at 18,000×g for 10 minutes at 4° C., the clarified supernatant was passed through Miracloth into an ultracentrifuge tube. Following centrifugation at 105,000 xg for 60 minutes at 4° C., the supernatant was removed from the microsomal pellet, which was then washed once with Extraction Buffer, and then using a Dounce homogenizer resuspended as a homogenous solution in Extraction Buffer (about 1 ml per 500 embryo's).

Enzyme activity can be demonstrated for the desaturases using the assays described above in "Desaturase Enzyme Activity in Microsomes Isolated from Transgenic Yeast" for microsomes isolated from yeast expression strains.

In summary in "Desaturase Enzyme Activity in Microsomes Isolated from Transgenic Yeast" we have provided a method that allows unambiguous demonstration of fatty acyl desaturase enzyme activity. We provide data demonstrating that: (1) gene c-d12Des(Ps_GA) encodes a delta-12 desaturase protein from *Phytophthora sojae* (c-d12Des(Ps_GA) that desaturates oleic acid (18:1n-9) to form linoleic acid (18:2n-6) in both microsomes isolated from a transgenic yeast (FIG. 24, panel A) and from a transgenic *B. napus* event (FIG. 25, panel A) expressing this protein, (2) gene c-o3Des(Pi_GA2) encodes a protein from *Phytophthora infestans* (c-o3Des(Pi_GA2)) that desaturates arachidonic acid (20:4n-6) to form eicosapentaenoic acid (20:5n-3) in microsomes isolated from a transgenic yeast (FIG. 24, panel B) expressing this protein, (3) gene c-o3Des (Pir_GA) encodes an omega-3 desaturase protein from *Pythium irregulare* (c-o3Des(Pir_GA)) that desaturates arachidonic acid (20:4n-6) to form eicosapentaenoic acid (20:5n-3) in microsomes isolated from a transgenic yeast (FIG. 24, panel B) expressing this protein, (4) a transgenic *B. napus* event containing genes encoding omega-3 desaturase proteins from both Phytophthorainfestans (c-o3Des (Pi_GA2)) and *Pythium irregulare* (c-o3Des(Pir_GA)) that contains at least one enzyme, localized to the microsomes, capable of desaturating arachidonic acid (20:4n-6) to form eicosapentaenoic acid (20:5n-3) (FIG. 85, Panel C), (5) gene c-d4Des(Tc_GA) encodes a delta-4 desaturase protein from *Thraustochytrium* sp. (c-d4Des(Tc_GA)) that desaturates docosapentaenoic acid (22:5n-3) to form docosahexaenoic acid (22:6n-3) in microsomes isolated from a transgenic yeast (FIG. 24, panel C) expressing this protein, (6) gene c-d4Des(PI_GA)2 encodes a delta-4 desaturase protein from Pav/ovalutheri (c-d4Des(PI_GA)2 that desaturates docosapentaenoic acid (22:5n-3) to form docosahexaenoic acid (22:6n-3) in microsomes isolated from a transgenic yeast (FIG. 24, panel D), (7) a transgenic *B. napus* event containing both the gene encoding the delta-4 desaturase protein from *Thraustochytrium* sp, gene c-d4Des(Tc_GA), and the gene c-d4-Des(Pl_GA) from *Pavlova lutheti* contains at least one enzyme, localized to the microsomes, capable of desaturating docosapentaenoic acid (22:5n-3) to form docosahexaenoic acid (22:6n-3) (FIG. 25, panel C), (8) a transgenic *B. napus* event containing the gene encoding a delta-6 desaturase protein from *Ostreococcus tauri* (c-d6Des (Ot_febit), capable of desaturating linoleic acid (18:2n-6) to form gamma-linolenic acid (18:3n-6) (FIG. 85, Panel A), and (9) a transgenic *B. napus* event containing the gene encoding a delta-5 desaturase protein from *Thraustachytrium* ssp. (c-d5Des(Tc_GA2), capable of desaturating dihomo-gamma-linolenic acid (20:3n-6) to form arachidonic acid (20:4n-6) (FIG. 85, Panel B). Except for the c-d12Des (Ps_GA), which has a known endogenous enzyme in *Brassica*, all other examples presented contain no detectable endogenous desaturase activity in microsomes isolated from either control yeast strains (FIG. 24) or control *Brassica* lines (FIG. 25 and FIG. 85).

Using the methods described in "Desaturase Enzyme Activity in Microsomes Isolated from Transgenic Yeast" for desaturase proteins the level of expression or detected enzyme activity may be influenced by the presence or absence of fusion tags to the native protein. Fusion tags or proteins to the desaturases may be attached the amino-terminus (N-terminal fusions) or the carboxy-terminus (C-terminal fusions) of the protein and may include but are not limited to: FLAG, hexa-Histidine, Maltose Binding Protein, and Chitin Binding Protein.

We have provided methods to establish enzyme catalyzed desaturation reactions required in an engineered pathway to biosynthesize docosohexaenoic acid (DHA, 22:6n-3) from oleic acid (18:1n-9) in canola. The methods presented in Example 21, "Desaturase Enzyme Activity in Microsomes Isolated from Transgenic Yeast" were developed to demonstrate desaturase activity in yeast strains expressing individual desaturases and can be further used to confirm the respective desaturase enzyme activities in transgenic canola, as described and demonstrated in Example 21, "Desaturase Activity in Microsomes Isolated from Transgenic *Brassica napus*". Furthermore these methods can be incorporated, by one skilled in the art, to measure desaturase enzyme activities in other organisms including, but not limited to: *Saccharomyces cerevisiae, Arabidopsis thaliana, Brassica* spp., *Camelina sativa, Carthamus tinctorius*, and *Salvia hispanica*.

Desaturase Headgroup (CoA vs PC) Preference

Fatty acid desaturases catalyze the abstraction of two hydrogen atoms from the hydrocarbon chain of a fatty acid to form a double bond in an unsaturated fatty acid and can be classified according to the backbone that their substrate was connected to: an acyl-CoA, an acyl-ACP (ACP, acyl carrier protein) or an acyl-lipid. To date a few examples exist where the acyl-CoA substrate has been confirmed. These involve purified enzymes and examples include a Linoleoyl-CoA Desaturase (Okayasu et al. (1981) Arch. Biochem. Biophys. 206: 21-28), a stearoyl-CoA desaturase from rat liver (Strittmatter et al (1974) Proc. Nat. Acad. Sci. USA 71: 4565-4569), and a Stearoyl-ACP desaturase from avocado (Shanklin J and Somerville C (1991) Proc Natl Acad Sci USA 88:2510-2514).

Alternatively, Heinz and coworkers have reported a strategy employing in vivo feeding of substrates to yeast strains expressing desaturases to examine substrate specificity of desaturases (Domergue et al. (2003) J. Biol. Chem. 278: 35115-35126, Domergue et al. (2005) Biochem. J. 389: 483-490). In these studies predictions of a desaturases's preference for acyl-lipid substrates were based on data obtained from a thorough analysis of the desaturated products in the CoA, phospholipid and neutral lipid pools over a growth time course. However, highly active endogenous acyltransferases which transfer acyl-groups between various pools (e.g. CoA, ACP, and lipid) may influence or convolute these data (Domergue et al. (2005) Biochem. J. 389: 483-490, Meesapyodsuk, D., Qui, X. (2012) Lipids 47: 227-237). Therefore this approach was still limited by the absence of direct evidence, such as obtained from in vitroassays, needed for conclusive determination of the substrate backbone utilized by the desaturase of interest.

Herein, we provide a previously unreported method to distinguish between enzymes that desaturate acyl-CoA fatty acids from enzymes that desaturate phospholipid linked fatty acids using microsomal preparations of proteins. We have improved upon initial reports of strategies to generate [$^{14}$C]-phosphatidylcholine analogs in situ (Stymne, S., and Stobart, A. K. (1986) Biochem. J. 240: 385-393, Griffiths, G., Stobart, A. K., and Stymne, S. (1988) Biochem. J. 252: 641-647) by: (1) monitoring the initial acyl-transfer reaction catalyzed by lysophosphatidyl choline acyl transferase (LPCAT) to establish that all of the [$^{14}$C]-acyl-CoA has been consumed, and (2) including exogenous lysophosphatidyl choline (LPC). Our improvements therefore establish that only [$^{14}$C]-phosphatidylcholine analogs are present upon initiation of the desaturase assay and allow for testing of other phospholipids by adding their corresponding lysolipid. Furthermore, the assays testing for desaturation of acyl-phospholipid substrates, described in Demonstration of Phosphatidylcholine Specificity, can be complemented by testing in an assay developed to monitor desaturation of the substrate in the acyl-CoA form. Specifically, we have devised a strategy, described in Demonstration of acyl-CoA Specificity, in which the substrate to be tested remains in its acyl-CoA form and is not incorporated into phospholipids (e.g. phosphatidylcholine) by lysophosphatidyl choline acyl transferase (LPCAT). By comparing the relative desaturase activity, observed in assays where the substrate is in the acyl-phospholipid form compared to the acyl-CoA form, the actual backbone (e.g. phosphatidylcholine or CoA) covalently bound to the desaturated fatty acid product can be determined.

Demonstration of Phosphatidylcholine Specificity:

To test if a desaturase accepts an acyl-lipid (e.g. a phospholipid) substrate the enzyme reaction was performed as described above ""Desaturase Enzyme Activity in Microsomes Isolated from Transgenic Yeast", but after a pre-incubation in the presence of exogenous lysophosphatidyl choline (LPC). The microsomal fraction of the yeast strain expressing the enzyme of interest was pre-incubated with a [$^{14}$C]-labelled acyl-CoA substrate in the presence of 16:0-lysophosphatidyl choline, which was typically 50 µM but may vary from 0-500 µM. During the pre-incubation endogenous lysophosphatidyl choline acyl transferase (LPCAT), present in the microsomes, transfers the [$^{14}$C]fatty acid from CoA to 16:0-LPC generating, in situ, a [$^{14}$C]fatty acid-phosphatidylcholine (PC) (Jain et al. (2007) *J. Biol. Chem.* 282:30562-30569, Riekhof et al. (2007) *J. Biol. Chem.* 282:36853-36861, Tamaki et al. (2007) *J. Biol. Chem.* 282:34288-34298)). After a pre-incubation (typically 15 minutes, but may vary from 1-300 minutes) essentially all of the [$^{14}$C]-labelled acyl-CoA substrate was consumed, as measured by scintillation counting and TLC analysis of the aqueous phase.

The reaction was stopped and lipids were extracted using the method of Bligh and Dyer (Bligh, E. G., and Dyer, J. J.

(1959) *Can J. Biochem. Physiol* 37: 911-918), by addition of 200 μl 0.15 M acetic acid and 1 ml MeOH:CHCl$_3$ (1:1). Part (about 10%) of the CHCl$_3$ phase (containing phosphatidyl choline (PC) and free fatty acids (FFA's)) was analyzed by scintillation counting and the rest was applied to a silica thin layer chromatography (TLC) plate. The plate was first developed in a polar solvent [CHCl$_3$:MeOH:acetic acid (90:15:10:3) and then in Heptane:diethylether:acetic acid (70:30:1) to measure incorporation into PC and the amount of FFA's (likely generated by thioesterases). PC and FFA's were scraped off the plate and methylated by addition of MeOH containing 2% H$_2$SO$_4$ at 90° C. for 30 minutes. The methyl esters were extracted in hexane and analyzed as described above for the respective enzymes (Example 21, "Desaturase Enzyme Activity in Microsomes Isolated from Transgenic Yeast"). The upper (aqueous) phase of the reaction mixture extraction contains acyl-CoA's and was hydrolyzed by addition of an equal volume of 2 M KOH in MeOH:H$_2$O (1:4) and incubated for 20 minutes at 90° C. Part of the aqueous phase was then analyzed by scintillation counting before fatty acids were extracted by addition of 3 M HCl (0.7 ml), 1.4 ml of MeOH) and CHCl$_3$ (1.9 ml). The chloroform phase was recovered, dried under N$_2$(g) and fatty acids were methylated by addition of 2 ml MeOH containing 2% H$_2$SO$_4$ and incubation of 30 minutes at 90° C. FAMEs were extracted by addition of 2 ml H$_2$O and 2 ml hexane and separated by AgNO$_3$-TLC and Heptane:Diethyl ether:acetic acid (70:30:1) as a solvent or Reverse Phase-TLC (Silica gel 60 RP-18 using acetonitrile (100%)). The radioactive lipids were visualized and quantified by electronic autoradiography using Instant Imager.

Delta-12 desaturase (*Phytophthora sojae*), c-d12Des (Ps_GA) Substrate Preference: The c-d12Des(Ps_GA) enzyme activity demonstrated in "Desaturase Enzyme Activity in Microsomes Isolated from Transgenic Yeast" can be further characterized to establish the backbone of the oleic acid substrate. In the desaturase assay described in "Desaturase Headgroup (CoA vs PC) Preference" containing 16:0-lysphosphatidylcholine (LPC) substantial desaturation was observed. A significantly reduced, but detectable, desaturase activity was observed in control reactions lacking 16:0-LPC which likely results from acylation of endogenous LPC present in the yeast microsomes containing the d12Des (Ps_GA) protein. However, a preincubation with 20:1n-9-CoA results in PC saturated with 20:1n-9, thus precluding incorporation of [$^{14}$C]-18:1n-9 into PC (described in "Demonstration of Acyl-CoA Specificity"). Additionally, separation of the phospholipids from the free-fatty acids after the enzymatic reaction and characterization of the isolable fatty acid methyl esters demonstrated that all of the d12Des (Ps_GA) enzymatically produced 18:2n-6-fatty acid methyl ester (FAME) was found in the phosphatidylcholine fraction (FIG. 26, Panel A and FIG. 86, Panel A). Furthermore, the d12Des(Ps_GA) activity was negligible in the assay for demonstration of acyl-CoA specificity (FIG. 86, Panel B), showing that 18:1n-9-acyl-CoA is not a preferred substrate for the delta-12 desaturase (*Phytophthora sojae*). In conclusion, delta-12 desaturase (*Phytophthora sojae*) clearly desaturates 18:1n-9 covalently bound to PC, but not an 18:1n-9-acyl CoA substrate.

Delta-4 desaturase (*Thraustochytrium* ssp.), c-d4Des (Tc_GA) Substrate Preference: The c-d4Des(Tc_GA) enzyme activity demonstrated in "Desaturase Enzyme Activity in Microsomes Isolated from Transgenic Yeast" can be further characterized to establish the backbone of the docosopentaenoic acid substrate. In the desaturase assay described in "Desaturase Headgroup (CoA vs PC) Preference" without additional 16:0-lysphosphatidylcholine (LPC), desaturation was observed (FIG. 26, Panel B), and likely results from the presence of endogenous 16:0-LPC present in the membranes containing the c-d4Des(Tc_GA) protein. The c-d4Des(Tc_GA) desaturase activity was dramatically stimulated by including additional 16:0-LPC in the assay (FIG. 26, Panel B), consistent with the observation endogenous lysophosphatidyl choline acyl transferase (LPCAT), present in the microsomes, transfers the [$^{14}$C]22:5n-3 from CoA to 16:0-LPC generating a [$^{14}$C]22:5n-3-phosphatidylcholine (PC) that was desaturated. Additionally, separation of the phospholipids from the free-fatty acids after the enzymatic reaction and characterization of the isolable fatty acid methyl esters demonstrated that essentially all of the c-d4Des(Tc_GA) enzymatically produced 22:6n-3-fatty acid methyl ester (FAME) was found in the phosphatidylcholine fraction (FIG. 26, Panel B and Panel C).

Demonstration of Acyl-CoA Specificity:

The assay conditions were as described above in "Desaturase Enzyme Activity in Microsomes Isolated from Transgenic Yeast". The microsomal fraction of the yeast strain expressing the enzyme of interest was pre-incubated with 10 nmol 20:1n-9-CoA (50 μM) and 0.5 mM DTNB (5,5'-dithiobis-(2-nitrobenzoic acid) for 10 min before addition of NADH and [$^{14}$C]labelled acyl-CoA substrate. The preincubation with 20:1n-9-CoA minimizes the incorporation of [$^{14}$C]labelled substrate into PC. DTNB prevents the reverse reaction of LPCAT and thereby the entering of acyl-CoA into PC via acyl exchange. This assay may also include alternative acyl-CoA's such as: 18:1n-9-CoA, 18:2n-6-CoA, 20:3n-6-CoA, 20:4n-6-CoA, 22:5n-3-CoA. The reaction was stopped and lipids were extracted using the method of Bligh and Dyer (Bligh, E. G., and Dyer, J. J. (1959) *Can J. Biochem. Physiol.* 37, 911-918), by addition of 200 μl 0.15 M acetic acid and 1 ml MeOH:CHCl$_3$ (1:1). Part (about 10%) of the CHCl$_3$ phase (containing phosphatidyl choline (PC) and free fatty acids (FFA's)) was analyzed by scintillation counting and the rest was applied to a silica thin layer chromatography (TLC) plate. The plate was first developed in a polar solvent [CHCl$_3$:MeOH:acetic acid (90:15:10:3) and then in Heptane:diethylether:acetic acid (70:30:1) to measure incorporation into PC and the amount of FFA's (likely generated by thioesterases). PC and FFA's were scraped off the plate and methylated by addition of MeOH containing 2% H$_2$SO$_4$ at 90° C. for 30 minutes. The methyl esters were extracted in hexane and analyzed as described above for the respective enzymes "Desaturase Enzyme Activity in Microsomes Isolated from Transgenic Yeast". The upper (aqueous) phase of the reaction mixture extraction contains acyl-CoA's and was hydrolyzed by addition of an equal volume of 2 M KOH in MeOH:H$_2$O (1:4) and incubated for 20 minutes at 90° C. Fatty acids were extracted by addition of 3 M HCl (0.7 ml), 1.4 ml of MeOH and CHCl$_3$ (1.9 ml). The chloroform phase was recovered, dried under N$_2$(g) and fatty acids were methylated by addition of 2 ml MeOH containing 2% H$_2$SO$_4$ and incubation of 30 minutes at 90° C. FAMEs were extracted by addition of 2 ml H$_2$O and 2 ml hexane and separated by AgNO$_3$-TLC and Heptane:Diethyl ether:acetic acid (70:30:1) as a solvent or Reverse Phase-TLC (Silica gel 60 RP-18 using acetonitrile (100%)). The radioactive lipids were visualized and quantified by electronic autoradiography using Instant Imager.

To demonstrate acyl-CoA dependency both methods are tested. If desaturation does not occur in the method for determining PC-specificity (LPC addition and preincubation before adding NADH) and the method for determining acyl-CoA specificity (20:1-CoA and DTNB addition) leads to the desaturated product in the H₂O-phase (or product in any of the lipid pools PC/FFA/H₂O since PC-dependent enzymes cannot be active if the substrate is not incorporated into PC (see FIG. 86, Panel B), it can be concluded that the enzyme was acyl-CoA dependent (see FIG. 27 and FIG. 87, Panels A and B). Similarly if a desaturase demonstrates activity in the PC-specific assay, but not in the assay where the substrate is presented as an acyl-CoA, then it can be concluded the enzyme utilizes a fatty acid covalently attached to phosphatidylcholine as a substrate.

Delta-9 Desaturase (*Saccharomyces cerevisiae*), d9Des (Sc) Substrate Preference:

Analysis of the [$^{14}$C]-distribution during of the d9Des(Sc) reaction, in the assay for demonstration of acyl-CoA dependency, shows that greater than 95% of the radioactivity (substrate and product) is present in the H₂O (CoA) and FFA-pools (data not shown), indicating incorporation into PC was insignificant. During the reaction, product (16:1n-9) in the acyl-CoA pool increases linearly up to 60 minutes, showing that the enzyme preferentially converts 16:0 covalently bound to CoA (FIG. 87, Panel B). The amount of 16:1n-9 in the H₂O fraction then levels out or slightly decreases, while the 16:1n-9 in the FFA pool increases, due to degradation of acyl-CoA by thioesterases present in the isolated membranes.

In the assay for demonstrating PC specificity, the d9Des (Sc) showed no activity (FIG. 87, Panel A), which indicates that when 16:0 fatty acid is attached to PC (or a FFA) it is not a preferred substrate.

The clear presence of desaturase activity in the "Acyl-CoA Specific" assay compared to the absence of activity in the "Phosphatidylcholine Specific" assay demonstrates that the delta-9 desaturase (*Saccharomyces cerevisiae*) utilizes 16:0 covalently attached to Coenzyme A. Interestingly, recent crystal structures of both the human and mouse stearoyl-coenzyme A desaturases have been reported with bound stearoyl-CoA confirming that this desaturase utilizes a coenzyme A substrate (Wang et al (2015) Nat Struct Mol Bio 22: 581-585 and Bai et al (2015) Nature 524: 252-257).

In summary, we presented a previously unreported method to distinguish between enzymes that desaturate acyl-CoA fatty acids from enzymes that desaturate phospholipid linked fatty acids. This embodiment of the invention t uses microsomal preparations of enzymes and does not, as in previous examples, require purification of the enzyme of interest. Furthermore, this embodiment allows isolation of the intact desaturated enzymatic product, allowing characterization of the backbone to which it was linked (e.g. lipid-, CoA-, or free fatty acid). An important consideration was that the endogenous lysophosphatidyl choline acyl transferase (LPCAT) present in yeast-derived microsomes can utilize a broad range of acyl-CoA's (Jain et al. (2007) *J. Biol. Chem.* 282:30562-30569, Riekhof et al. (2007) *J. Biol. Chem.* 282:36853-36861, Tamaki et al. (2007) *J. Biol. Chem.* 282:34288-34298)) making it suitable for generating an extensive variety of different phosphatidylcholine derivatives for assaying desaturase enzymes. LPCAT is able to accept 18:1 n-9-CoA and 20:4n-6-CoA and this enzyme can acylate LPC with 22:5n-3-CoA. Microsomes isolated from any cells or tissue can be used in this embodiment of the invention, including but not limited to bacterial cells (e.g. *Escherichia coli, Psuedomonas aeruginosa, Bacillus thuringiensis*), mammalian tissue (e.g. liver) and plant tissue (e.g. leafs, roots, seeds, and pods) and could use exogenously supplied lysophosphatidyl choline acyl transferase from *Saccharomyces cerevisiae*, if necessary. Slight modifications to the general method presented here may include a pre-incubation with alternate acyl-CoA's, not the potential desaturase substrate, which could reduce the observed background due to endogenous LPC present in the membranes and also minimize thioesterase degradation of enzyme substrate or product acyl-CoA's.

Elongase Activity.

Expression of elongase enzymes in yeast was performed as described above for the desaturase enzymes in "Desaturase Enzyme Activity in Microsomes Isolated from Transgenic Yeast". Isolation of microsomes containing expressed elongases was generally as described above in "Desaturase Enzyme Activity in Microsomes Isolated from Transgenic Yeast" and by Denic (Denic, V. and Weissman (2007) Cell 130, 663-677). Briefly, cells from a yeast expression culture (50 ml) were resuspended in 1 ml of Elongase Disruption Buffer (20 mM Tris-HCl, pH 7.9, 10 mM MgCl₂, 1 mM EDTA, 5% glycerol, 0.3 M ammonium sulfate, protease inhibitor), mixed with 1 ml silica/zirconium beads (0.5 mm) and disrupted in a BeadBeater. After centrifugation (two times for 5 minutes at 8000×g, 4° C.) the crude extract was recovered and after a second centrifugation (100,000×g, 2 hours at 4° C.), the microsomal fraction was resuspended in 500 µl of assay buffer (50 mM HEPES-KOH pH 6.8, 150 mM KOAc, 2 mM MgOAc, 1 mM CaCl₂, protease inhibitor). The protein concentrations in the microsomes were measured according to the BCA method. Resuspended microsomes were aliquoted and frozen in N₂(l) and stored at −80° C.

In the elongase assay [$^{14}$C]-labeled malonyl-CoA and non-labeled acyl-CoA were provided as substrates. After the reaction has proceeded an appropriate time, which may vary between 0-300 minutes depending on the purpose of the experiment, the reaction mixture was subjected to hydrolysis and methylation and the FAMEs were analyzed by RP-TLC combined with by electronic autoradiography using Instant Imager.

The assay contains about 170 µg microsomal protein, 7.5 nmol [$^{14}$C]malonyl-CoA (3000 dpm/nmol), 5 nmol acyl-CoA in a total volume of 100 µl. After incubation for the desired time at 30° C., the reaction was stopped with the addition of 100 µl of 2 M KOH in MeOH (1:4) followed by a 20 minute incubation at 90° C. Fatty acids were extracted by addition of 3 M HCl (100 µl), 0.75 ml of MeOH:CHCl₃ (2:1) and CHCl₃ (250 µl). The chloroform phase was recovered, dried under N₂(g), and fatty acids were methylated by addition of 2 ml MeOH containing 2% H₂SO₄ and incubation of 30 minutes at 90° C. FAMEs were extracted by addition of 2 ml H₂O and 2 ml hexane and separated by Reverse Phase-TLC (Silica gel 60 RP-18) using a solvent of acetonitrile:tetrahydrofuran (85:15). The radioactive lipids were visualized and quantified by electronic autoradiography using Instant Imager.

Furthermore, assays may include additional components (e.g. 1 mM NADPH, 2 mM MgCl₂, and 100 µM cerulenin) to complete the fatty acid reduction cycle by endogenous yeast enzymes, but limit further elongation of the acyl-CoA.

Delta-6 Elongase (*Thalassiosira pseudonana*), c-d6Elo (Tp_GA2) Enzyme Activity: c-d6Elo(Tp_GA2) enzyme activity and substrate specificity can be demonstrated in microsomes isolated from a yeast strain expressing the c-d6Elo(Tp_GA2) protein using [$^{14}$C]malonyl-CoA and an acyl-CoA in the general elongase assay described above. Acyl-CoA's may include, but are not limited to: 18:1n-9-CoA, 18:2n-6-CoA, 18:3n-6-CoA, 20:3n-6-CoA, 20:4n-6-CoA, 20:5n-3-CoA, 22:5n-3-CoA.

Delta-6 Elongase (*Physcomitrellapatens*), c-d6Elo (Pp_GA2) Enzyme Activity: c-d6Elo(Pp_GA2) enzyme activity and substrate specificity can be demonstrated in microsomes isolated from a yeast strain expressing the c-d6Elo(Tp_GA2) protein using [$^{14}$C]malonyl-CoA and an acyl-CoA in the general elongase assay described above. Acyl-CoA's may include, but are not limited to: 18:1 n-9-CoA, 18:2n-6-CoA, 18:3n-6-CoA, 20:3n-6-CoA, 20:4n-6-CoA, 20:5n-3-CoA, 22:5n-3-CoA.

Delta-5 Elongase (*Ostreococcus tauri*), c-d5Elo(Ot_GA3) Enzyme Activity: c-d5Elo(Ot_GA3) enzyme activity and substrate specificity can be demonstrated in microsomes isolated from a yeast strain expressing the c-d5Elo(Ot_GA3) protein using [$^{14}$C]malonyl-CoA and an acyl-CoA in the general elongase assay described above. Acyl-CoA's may include, but are not limited to: 18:1 n-9-CoA, 18:2n-6-CoA, 18:3n-6-CoA, 20:3n-6-CoA, 20:4n-6-CoA, 20:5n-3-CoA, 22:5n-3-CoA.

In the presence of NADPH and [$^{14}$C]malonyl-CoA, 18:3n-6-CoA was elongated to 20:3 n-6-CoA by the delta-6 Elongases isolated from Thalassiosirapseudonana(Tp) and Physcomitrellapatens (Pp) as shown if FIG. 28, panels A and B. In both delta-6 elongase reactions the observed FAME-product co-migrates with 20:3n-6-methyl ester standards and was radioactive, consistent with transfer of two-carbons from [$^{14}$C]-malonyl-CoA to 18:3n-6-CoA. In the presence of NADPH the fatty acid reduction cycle was completed resulting in a saturated enzymatic product. However in the absence of NADPH a derivative of the direct enzymatic product, 3-keto-20:3n-6-CoA, was isolated as a FAME. The isolated enzymatic product was decarboxylated and converted to the 2-keto-19:3n-6-FAME as described previously (Bernert, J. T and Sprecher, H. (1977) J. Biol. Chem. 252:6736-6744 and Paul et al (2006) J. Biol. Chem. 281: 9018-9029). Appropriate controls demonstrate that this elongation reaction was dependent upon either the Delta-6 Elo (Tp) or the Delta-6 Elo (Pp) and not catalyzed by endogenous yeast enzymes.

In the presence of NADPH and [$^{14}$C]malonyl-CoA, 20:5n-3-CoA was elongated to 22:5 n-3-CoA by the c-d5Elo (Ot_GA3), and containing either an N-terminal FLAG tag or a C-terminal FLAG tag, as shown in FIG. 28, panel C. In the Delta-5 elongase reaction the observed FAME-product co-migrates with a 22:5n-3-methyl ester standard and was radioactive, consistent with transfer of two-carbons from [$^{14}$C]-malonyl CoA to 20:5n-3-CoA. In the presence of NADPH the fatty acid reduction cycle was completed resulting in a saturated enzymatic product. However in the absence of NADPH a derivative of the direct 3-keto-22:5n-3-CoA product was isolated as a FAME. The isolated enzymatic product was decarboxylated and a 2-keto-21:5n-3-FAME as described previously (Bernert, J. T and Sprecher, H. (1977) J. Biol. Chem. 252:6736-6744 and Paul et al (2006) J. Biol. Chem. 281: 9018-9029). Appropriate controls demonstrate that this elongation reaction was dependent upon the Delta-5 Elo (Ot) and not catalyzed by endogenous yeast enzymes.

Herein, using a highly sensitive elongase assay, we have demonstrated the enzyme activities of the Delta-6 Elongases used (FIG. 28, panel A and B) and a Delta-5 Elongase (FIG. 28, panel C), enzymes that are central to engineering canola to biosynthesize docosahexaenoic acid. For each of these elongases we have shown that in the presence of [$^{14}$C] malonyl-CoA and the appropriate fatty-acyl CoA ester substrate these enzymes can transfer two-carbons (containing [$^{14}$C]) from malonyl-CoA to the appropriate fatty-acyl-CoA ester to synthesize a new fatty acid which has been elongated by two carbons. In some cases a derivative (decarboxylated 2-keto compound) of the direct enzymatic product (3-Keto-acylCoA ester) of the elongase was observed, however in the absence of NADPH only this decarboxylated 2-keto compound was observed, consistent with previous observations by Napier (Bernert, J. T and Sprecher, H. (1977) J. Biol. Chem. 252:6736-6744 and Paul et al (2006) J. Biol. Chem. 281: 9018-9029).

In summary we have provided a method that allows unequivocal demonstration of fatty acyl elongation enzyme activity. We provide data demonstrating that: (1) gene c-d6Elo(Tp_GA2) encodes a delta-6 elongase protein from *Thalassiosira pseudonana* (c-d6Elo(Tp_GA2)) that converts 18:3n-6-CoA to 20:3n-6-CoA in microsomes isolated from a transgenic yeast (FIG. 28, panel A), (2) gene c-d6Elo (Pp_GA2) encodes a delta-6 elongase protein from *Physcomitrella patens* (c-d6Elo(Pp_GA2)) that converts 18:3n-6-CoA to 20:3n-6-CoA in microsomes isolated from a transgenic yeast (FIG. 28, panel B), (3) a transgenic *B. napus* event containing both the gene encoding for the delta-6 elongase protein from *Thalassiosira pseudonana*, gene c-d6Elo(Tp_GA2), and the gene encoding for the gene the delta-6 elongase protein from *Physcomitrella patens*, gene c-d6Elo(Pp_GA2), contains at least one enzyme, localized to the microsomes, capable of elongating 18:3n-6-CoA to 20:3n-6-CoA (FIG. 28, panel A) (4) gene c-d5-Elo(Ot_GA3) encodes a delta-5 elongase protein from *Ostreococcus tauri* (c-d5Elo(Ot_GA3)) that converts 20:5n-3-CoA to 22:5n-3-CoA in microsomes isolated from both a transgenic yeast (FIG. 28, Panel C) and transgenic *B. napus* event (FIG. 29, Panel B). In all examples presented no endogenous elongase activity was detected in microsomes isolated from either control yeast strains (FIG. 28) or control *Brassica* lines (FIG. 29).

Using the methods described in "Elongase Activity" for elongase proteins the level of expression or detected enzyme activity may be influenced by the presence or absence of fusion tags to the native protein. Fusion tags or proteins to the desaturases may be attached the amino-terminus (N-terminal fusions) or the carboxy-terminus (C-terminal fusions) of the protein and may include but are not limited to: FLAG, hexa-Histidine, Maltose Binding Protein, and Chitin Binding Protein.

We have provided methods to establish enzyme catalyzed elongase reactions required in an engineered pathway to biosynthesize docosohexaenoic acid (DHA, 22:6n-3) from oleic acid (18:1n-9) in canola. The methods presented in Example 21 were developed to demonstrate elongase activity in yeast strains expressing individual elongases and can be further used to confirm the respective elongase enzyme activities in transgenic canola. Furthermore these methods can be incorporated, by one skilled in the art, to establish elongase enzyme activities in other organisms including, but not limited to: *Saccharomyces cerevisiae, Arabidopsis thaliana, Brassica* spp., *Camelina sativa, Carthamus tinctorius,* and *Salvia hispanica*.

Example 22: In Vivo Demonstration of Mode of Action: Substrate Specificity, Substrate Selectivity Cloning of Genes into Yeast Expression Vectors:

For single gene expression, the yeast expression vector pYES2.1/V5-His-TOPO (Invitrogen) was used. Flanking primers were designed according to the manufacturer's instructions, and genes were amplified from plant expression vectors using the proof-reading polymerase Phusion high-fidelity polymerase (New England Biolabs). After agarose gel electrophoresis PCR fragments were cut out and purified using an EZ-10 spin column gel extraction kit (Bio Basic Inc.), cloned into the yeast expression vector pYES2.1/V5-His-TOPO (Invitrogen), transformed into *E. coli*, and gene orientation was checked by PCR. For co-expression of multiple genes, genes were cloned into pESC yeast expression vectors (Stratagene) under the control of the GAL1 promoter. To do this, appropriate restriction sites were introduced upstream and downstream of coding regions via PCR, followed by fragment isolation, TA-cloning into the pGEM-T vector, release of the gene fragment by enzyme digestion, and ligation into the pESC vector. For all constructs plasmids were isolated using an EZ-10 spin column plasmid DNA miniprep kit (Bio Basic Inc.). All constructs were sequenced prior to yeast transformation. After sequencing, plasmids were transformed into *Saccharomyces cerevisiae* (yeast) strain INVSc1 (Invitrogen), using the Sc EasyComp Transformation Kit (Invitrogen) according to the manufacturer's protocol, and selected on plates lacking the appropriate amino acids.

Expression of Heterologous Genes in Yeast:

Yeast cultures were grown overnight at 30° C. in drop out base (DOB-URA: 1.7 g/L yeast nitrogen base, 5 g ammonium sulfate, and complete supplement mixture minus appropriate amino acids for selection) containing 2% glucose. The OD600 of the overnight yeast cultures were obtained and culture concentrations were standardized between samples. The samples were washed with DOB-URA containing 2% galactose and expression was carried out for 3 days at 20° C. in the same media supplemented with exogenous fatty acids and 0.01% tergitol. For exogenous fatty acid feeding, cells were fed with 0.25 mM of the appropriate fatty acids, except where indicated otherwise. Fatty acid substrates and FAME standards were purchased from Nu-Chek Prep Inc (Elysian, Minn.).

Fatty Acid Analysis by Gas Chromatography:

5 mL cultures were precipitated by centrifugation and washed once with induction buffer and once with water. The supernatant was removed, and 2 mL of 3N methanolic-HCl (Supelco) was added to the cell pellet. After gentle mixing, the mixture was incubated at 80° C. for 40 min, cooled to room temperature, and 1 mL 0.9% NaCl plus 2 mL hexane was added. The sample was vortexed and centrifuged, and the hexane phase was removed and dried under nitrogen gas. Fatty acid methyl esters (FAMEs) were resuspended in 100 µl hexane and analyzed by gas chromatography using an Agilent 6890N gas chromatograph equipped with a DB-23 column. The thermal program used was 160° C. for 1 min, then temperature was increased to 240° C. at a rate of 4° C./min. FAMEs were identified based on known standards and the conversion percent was calculated as: [(Product)× 100%]/(Substrate+Product).

Time Course Studies:

Samples were grown overnight at 30° C., sample concentrations were standardized prior to feeding, and cultures were induced at 20° C. For some time course studies, samples were pre-induced overnight prior to feeding as indicated in results. Samples (1 ml of culture) were collected at the indicated time intervals, washed once with 0.5% tergitol and once with double distilled water, and pellets were stored at −80° C. until the completion of the time course. Fatty acid extraction and GC analysis basically followed methods described for "Fatty Acid Analysis by Gas Chromatography", however 1 mL methanolic HCl and 0.5 mL 0.9% NaCl and 1 mL hexane were used for fatty acid extraction, and the final resuspension was performed in 100 µL hexane.

Feeding Studies with Individual Fatty Acids:

Samples were grown overnight at 30° C., sample concentrations were standardized prior to feeding, and cultures were induced at 20° C. for 3 days. Measurements from at least 3 clones were used to calculate averages.

Feeding Studies with Multiple Fatty Acids:

Fatty acids for co-feeding were selected based on results from experiments described above where cells expressing each construct were fed with all possible substrates. The positive substrates for a given enzyme were fed together, however, if one substrate formed a product that also was a known substrate (for example, with certain elongases), separate mixtures were used. For omega-3-desaturases, two mixtures, each containing SDA as a standard, were used for feeding. Initially, cultures were fed mixtures containing 0.25 mM total fatty acid substrate. However, due to differences in uptake, it was necessary to optimize fatty acid mixtures so that the levels of Substrate A+Product A was equal to Substrate B+Product B within ±5%. The final fatty acid mixtures used were also subjected to GC to obtain an estimation of relative uptake. After appropriate fatty acid mixtures were obtained, induction and feeding was performed as described above (Expression of Heterologous Genes in Yeast). After induction, yeast cells were induced for 3 days at 20° C. before harvesting of cells and GC analysis as described above (Expression of Heterologous Genes in Yeast and Fatty Acid Analysis by Gas Chromatography). All experiments were replicated three times.

Co-Expression Heterologous Genes in Yeast:

Protocols for co-expression of genes basically followed those provided for single gene expression experiments. Cultures were grow overnight at 30° C., sample concentrations were standardized prior to feeding, and cultures were induced at 20° C. for 3 days. The following sets of genes were co-expressed (pY=pYES2.1/V5-His-TOPO; pT=pESC-Typ, pL=pESC-Leu):

1) pY-c-d12Des(Ps_GA)/pT-c-d6Des(Pir_GA)
2) pY-c-d12Des(Ps_GA)/pT-c-d6Des(Ot_febit)
3) pY-c-d6Elo(Tp_GA2)/pT-c-d6Des(Ot_febit)
4) pY-c-d6Elo(Tp_GA2)/pT-c-d6Des(Pir_GA)
5) pL-c-d6Elo(Tp_GA2)/pY-c-d5Des(Tc_GA2)
6) pL-c-d8Des(Eg)/pY-c-d5Des(Tc_GA2)
7) pL-c-d6Elo(Tp_GA2)/pY-c-d5Des(Sa)
8) pL-c-d8Des(Eg)/pY-c-d5Des(Sa)

Isolation and Analysis of Lipids:

For expression of desaturases or elongases, yeast cultures were grown overnight at 30° C. in drop out base (DOB-ura) containing 2% glucose. The samples were washed with induction media (DOB-ura) containing 2% galactose and expression was induced for 3 days at 20° C. in the same media supplemented with the appropriate fatty acids and 0.01% tergitol (NP-40). After 3 days of incubation, yeast cells were collected by centrifugation and washed twice with distilled water. Fifteen mL of chloroform:methanol (1:1) was added to the collected yeast pellet and the sample was incubated at room temperature with shaking for 3 hr. After the 3 hr incubation, the sample was centrifuged and the aqueous phase was collected and stored at −20° C. Chloroform:methanol (2:1) was added to the pellet, and it was incubated overnight at 4° C., then subjected to centrifugation. The aqueous phase was collected and pooled with the aqueous phase collected previously. Nine mL of 0.45% NaCl was added to the pooled aqueous phase, the sample was vortexed and the organic phase was collected after separated by centrifugation at 1500×g for 3 min. The organic phase was dried under nitrogen gas and resuspended in 100 uL of chloroform to give the total fatty acid fraction. 5 uL of the total fatty acid fraction was analyzed by GC, and the remainder was separated by TLC as described below.

TLC plates were heat activated for at least 3 hrs at 120° C. before use. The mobile phase used to separate the fatty acids consisted of chloroform:methanol:acetic acid (65:35:8) and primuline (5 mg in 100 mL acetone:water, 80:20) was used to visualize the separated lipid fractions under UV light. The individual lipid fractions (PC, PE, PI+PS, and neutral lipids) were identified using standards and removed separately from the TLC plate. To extract the lipids from the silica, 400 uL water, 2 mL chloroform and 2 mL methanol were added, the sample was vortexed vigorously, and 2 mL of 0.2 M $H_3PO_4$/1 M KCl was added. The lower organic phase was collected and the remaining aqueous phase was re-extracted by adding 2 mL of chloroform. The pooled organic phase was dry under nitrogen gas, and the fatty acid profile of individual lipid fractions was analyzed by gas chromatography. GC was performed by adding 2 mL of 3N methanolic HCl, followed by incubation at 80° C. for 40 min, then adding 1 ml of 0.9% NaCl and 2 mL of hexane and vortexing. The hexane phase was collected, dried under nitrogen gas, and resuspended in 100 µL of hexane for GC analysis. Gas chromatography was performed using an Agilent 6890N gas chromatograph equipped with a DB-23 column and a thermal program consisting of: 160° C. for 1 min, then temperature was increased to 240° C. at a rate of 4° C./min. After the initial GC analysis, samples with low concentrations were re-suspended in 40 µL of hexane and re-analyzed.

Figure 30:
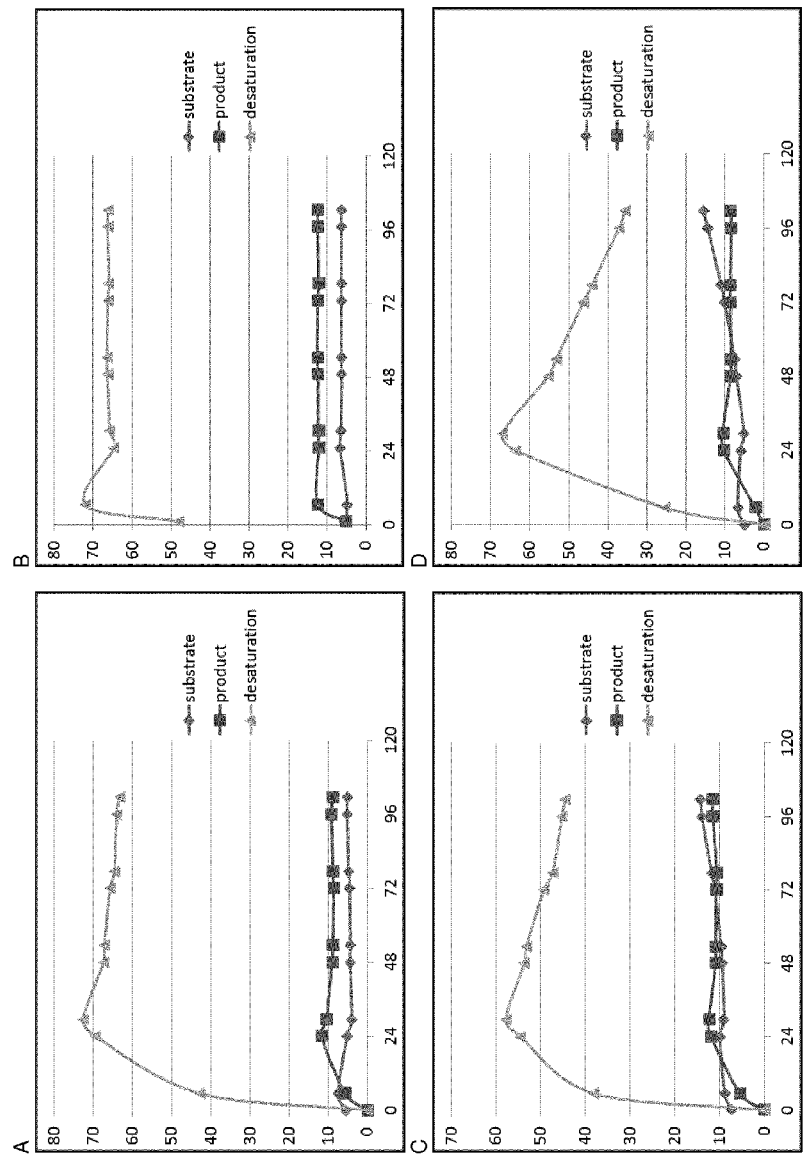
FIG. 30: Time course optimization. Yeast cells expressing the c-d5Des(Tc_GA2) were fed with 0.25 mM DHGLA and the production of ARA was determined by GC. Samples were collected starting immediately after feeding. In Panels A-D, Desaturation was represented as % Conversion vs Growth Time (hours) and Product and Substrate levels are represented as % Total Fatty acid vs Growth time (hours). Panel A pertains to samples supplied with DHGLA immediately after induction. Panel B is overnight induction (22 hrs) before feeding. Panel C is for cultures supplied with 3× normal DHGLA level. Panel D is for cultures supplied with normal rate of DHGLA (0.25 mM) daily.

Time Course Studies:

Initially, a range of conditions were tested with the c-d5Des(Tc_GA2) (FIG. 30). When cultures were fed with 0.25 mM exogenous substrate at the beginning of induction the amounts of product and substrate and the desaturation percentage remained steady from approximately 48-92 hours (FIG. 30, Panel A). Therefore, these conditions were used for further time course experiments.

To determine if these conditions were acceptable for all gene constructs, time courses were conducted with yeast cultures expressing all 10 genes individually. The preferred substrate for each enzyme was supplied exogenously (FIG. 31).

Figure 31:
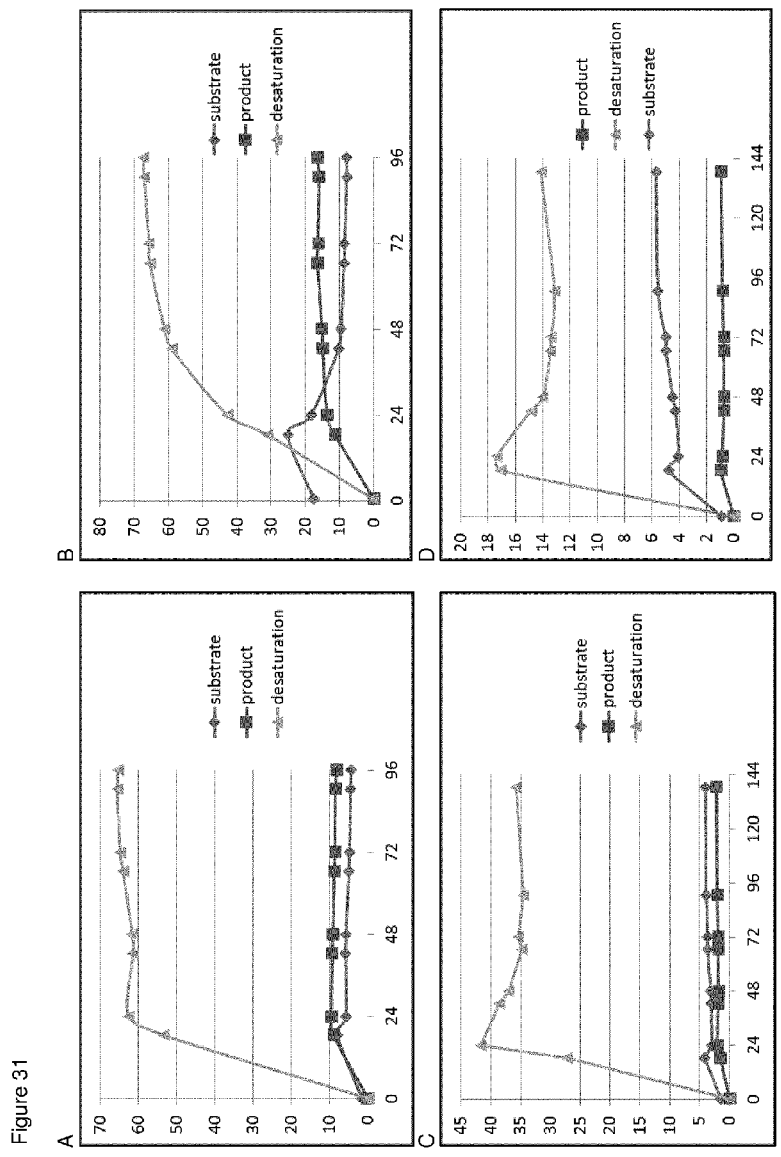
FIG. 31: Representative time course graphs for all desaturases and elongases. Yeast cells expressing each enzyme were supplied with 0.25 mM of preferred fatty acid substrate, and fatty acid profiles were obtained by GC at the indicated time points. In Panels A-J, Desaturation and Elongation were represented as % Conversion vs Growth Time (hours), and Product and Substrate levels were represented as % Total Fatty acid vs Growth time (hours). A. c-d5Des (Tc_GA2)+DHGLA B. c-d6Des(Ot_febit)+ALA C. c-d4Des (PI_GA)2+DTA D. c-d4Des(Tc_GA)+DTA E. c-o3Des (Pir_GA)+ARA F. c-o3Des(Pi_GA2)+ARA G. c-d12Des (Ps_GA)+OA H. c-d5Elo(Ot_GA3)+EPA I. c-d6Elo (Tp_GA2)+GLA J. c-d6Elo(Pp_GA2)+SDA.
Figure 31:
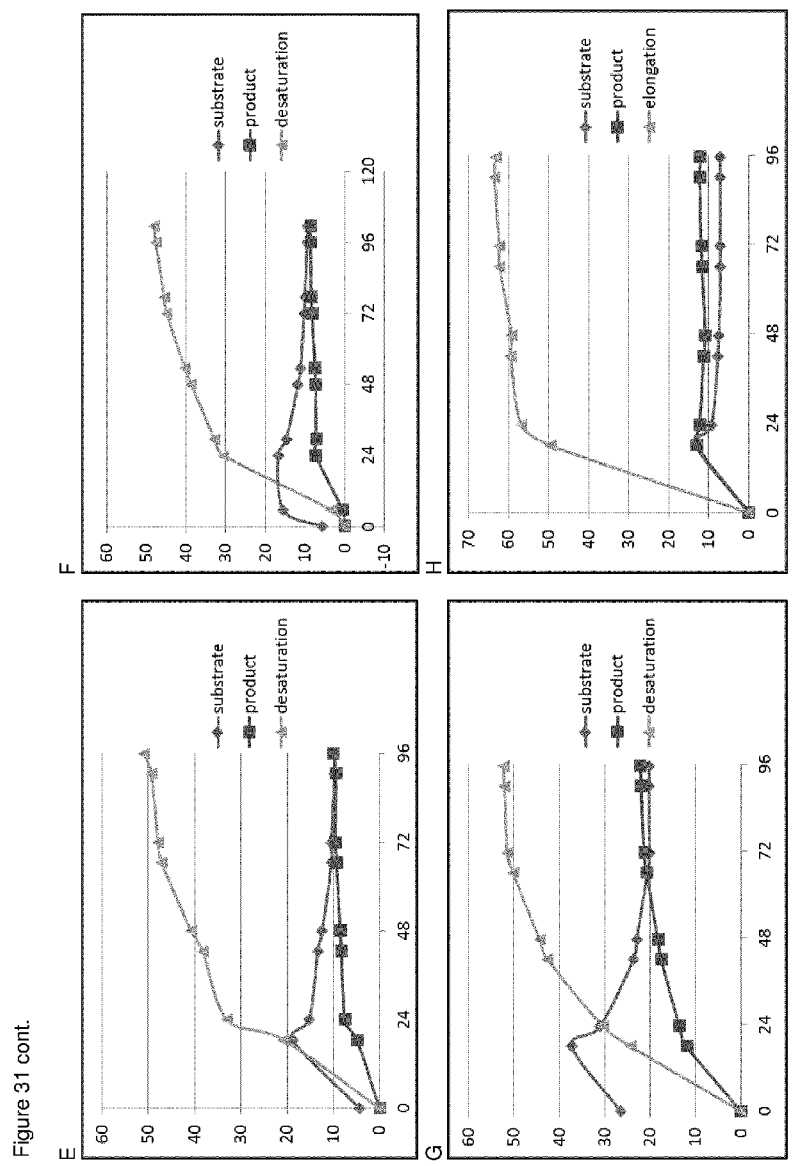
Figure 31:
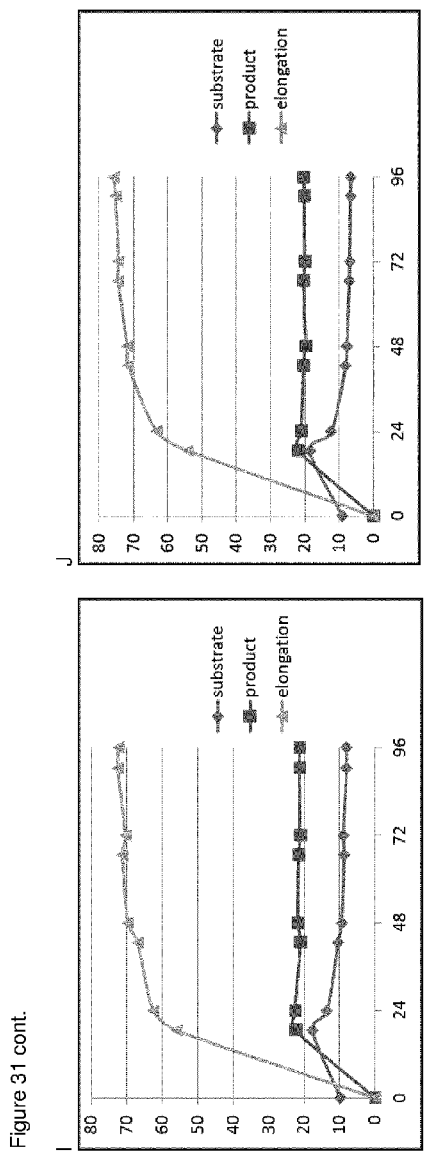

Although the rate of uptake of fatty acids and the activity of enzymes varied, the levels of product, substrate and percent elongation or desaturation was relatively stable at the 72 hour time point (FIG. 31). Therefore data collection at 72 hours was used in all further experiments, except where noted otherwise.

Analysis of all Enzymes with all Fatty Acids:

The major activity of each desaturase and elongase used in the plant construct was determined upon gene isolation. However, many desaturases and elongases have secondary activities.

When all enzymes are present together, such secondary activities affect the overall production rates of desired fatty acids, or lead to the production of side-products. In this experiment, we tested all enzymes with all fatty acids that might be expected to be present in a plant expressing all 10 genes. The enzymes and fatty acids used in this experiment are listed below:

| Enzyme | Fatty acid |
|---|---|
| c-d12Des(Ps_GA) | 18:1n-9 |
| c-d6Des(Ot_febit) | LA (18:2n-6) |
| c-d6Elo(Pp_GA2) | ALA (18:3n-3) |

-continued

| Enzyme | Fatty acid |
|---|---|
| c-d6Elo(Tp_GA2) | GLA (18:3n-6) |
| c-d5Des(Tc_GA2) | SDA (18:4n-3) |
| c-o3Des(Pi_GA2) | DHGLA (20:3n-6) |
| c-o3Des(Pir_GA) | ETA (20:4n-3) |
| c-d5Elo(Ot_GA3) | ARA (20:4n-6) |
| c-d4Des(Pl_GA)2 | DTA (22:4n-6) |
| c-d4Des(Tc_GA) | DPAn-3 (22:5n-3) |
| DHAn-3(22:6n-3) | DPAn-6 (22:5n-6) |

Although each individual substrate fatty acid was tested with each individual enzyme, results are only given for fatty acid/enzyme combinations where a detectable level of activity was obtained (see Table 159, Table 160, and Table 161).

Although we saw some side activities with the desaturases, such as the conversion of GLA to SDA by the c-d5Des(Tc_GA2) and conversion of DHGLA to ARA by the c-d4Des(Tc_GA), these activity levels were low and produce fatty acids that would be expected in the DHA synthesis pathway (Table 159).

We also analyzed the substrate profile of single point mutants of c-d12Des(Ps_GA) and c-d4Des(PI_GA)2. The single nucleotide change leading to the F83L mutation in c-d12Des(Ps_GA) did not lead to any significant change in either the substrate preference or efficiency of desaturation relative to the wild-type version of c-d12Des(Ps_GA) (data shown in Table 159). Similarly, a single nucleotide change leading to the A102S mutation in d4Des(PI_GA)2) did not lead to any significant change in either the substrate preference or efficiency of desaturation relative to the wild-type version of d4Des(PI_GA)2 (data shown in Table 159).

TABLE 159

Conversion percentages of exogenous fatty acids by desaturases

| Enzyme | Substrate | Product | % desaturation |
|---|---|---|---|
| c-o3Des(Pir_GA) | GLA | SDA | 2.7 ± 0.05 |
| | DPAn-6 | DHAn-6 | 6.93 ± 0.85 |
| | ARA | EPA | 45.44 ± 2.40 |
| | LA | ALA | 6.29 ± 0.28 |
| | DTA | DPAn-3 | 25.57 ± 1.16 |
| | DHGLA | ETA | 31.64 ± 3.38 |
| c-o3Des(Pi_GA2) | GLA | SDA | 7.84 ± 0.53 |
| | DPAn-6 | DHAn-3 | 4.77 ± 0.78 |
| | ARA | EPA | 40.0 ± 3.38 |
| | LA | ALA | 5.47 ± 0.76 |
| | DTA | DPAn-3 | 17.86 ± 0.43 |
| | DHGLA | ETA | 39.71 ± 2.37 |
| c-d5Des(Tc_GA2) | DHGLA | ARA | 58.03 ± 2.01 |
| | GLA | SDA | 0.23 + 0.06 |
| c-d4Des(Tc_GA) | DPAn-3 | DHAn-3 | 20.74 ± 1.43 |
| | DTA | DPAn-6 | 17.33 ± 0.24 |
| | DHGLA | ARA | 1.15 ± 0.12 |
| c-d4Des(Pl_GA)2 | DPAn-3 | DHAn-3 | 43.78 ± 3.85 |
| | DTA | DPAn-6 | 44.26 + 4.83 |
| c-d12Des(Ps_GA) | 18:1 | LA | 57.04 ± 0.49 |
| | 16:1* | 16:2 | 32.42 + 0.64 |
| c-d6Des(Ot_febit) | LA | GLA | 68.82 ± 1.89 |
| | ALA | SDA | 71.0 + 0.68 |

The elongases generally showed a higher level of side activities (Table 160, Table 161). While the two delta-6 elongases showed similar conversion percentages for the main substrates GLA and SDA, the *P. patens* enzyme showed higher levels of activity on LA and ALA, and only the *P. patens* delta-6 elongases showed detectable activity of ARA and EPA. Nonetheless, activity levels were substantially higher with GLA and SDA, suggesting that if these fatty acids, which were expected to be available in the pathway, would be the preferred substrate of the enzyme.

TABLE 160

Conversion percentages of exogenous fatty acids by Delta-6 Elongases

| Enzyme | Substrate | Product | % Elongation |
|---|---|---|---|
| c-d6Elo(Pp_GA2) | GLA | DHGLA | 80.23 ± 0.81 |
|  | SDA | 20:4n-3 | 85.67 ± 1.18 |
|  | LA | 20:2n-6 | 20.86 ± 1.23 |
|  | ALA | 20:3n-3 | 31.19 ± 0.23 |
|  | ARA | DTA | 2.42 ± 0.08 |
|  | EPA | DPAn-3 | 5.16 ± 0.29 |
| c-d6Elo(Tp_GA2) | GLA | DHGLA | 70.11 ± 1.37 |
|  | SDA | 20:4n-3 | 85.55 ± 0.32 |
|  | LA | 20:2n-6 | 2.22 ± 0.15 |
|  | ALA | 20:3n-3 | 4.63 ± 0.35 |

The c-dElo(Ot_GA3) was capable of consecutive elongations of most fatty acids (Table 161). However, the highest conversion by a large margin was for the desired EPA to DPAn-3 conversion. In the engineered plant system, the two delta-4 desaturases are available to desaturate DPAn-3, preventing further elongation. The levels of fatty acids containing 24 carbons produced by this elongase are small given that high levels of substrate are present in the yeast system and no competing enzymes are present.

TABLE 161

Conversion percentages of exogenous fatty acids by c-d5Elo(Ot_GA3) elongase. Substrate and Product values represent % of total fatty acids.

| Substrate | Product 1 | Product 2 | Product 3 | % Elongation |
|---|---|---|---|---|
| LA | 20:2n-6 |  |  |  |
| 24.34 ± 1.28 | 0.41 ± 0.07 |  |  | 1.64 ± 0.18 |
| DHGLA | 22:3n-6 |  |  |  |
| 12.92 ± 0.93 | 1.24 ± 0.22 |  |  | 8.73 ± 1.10 |
| DHAn-3 | 24:6n-3 |  |  |  |
| 9.41 ± 0.86 | 1.37 ± 0.12 |  |  | 12.84 ± 1.84 |
| DPAn-3 | 24:5n-3 |  |  |  |
| 10.85 ± 0.46 | 2.15 ± 0.28 |  |  | 16.59 ± 2.37 |
| GLA | DHGLA | 22:3n-6 |  |  |
| 23.95 ± 3.22 | 1.0 ± 0.13 | 0.24 ± 0.03 |  | 4.91 ± 0.24 |
| ARA | 22:4n-6 | 24:4n-6 |  |  |
| 7.12 ± 1.33 | 11.23 ± 0.28 | 0.26 ± 0.05 |  | 61.92 ± 5.22 |
| EPA | DPAn-3 | 24:5n-3 |  |  |
| 0.85 ± 0.01 | 6.76 ± 0.85 | 1.74 ± 0.21 |  | 90.8 ± 0.98 |
| SDA | 20:4n-3 | 22:4n-3 | 24:4n-3 |  |
| 14.42 ± 1.18 | 0.47 ± 0.04 | 4.17 ± 0.12 | 0.26 ± 0.03 | 25.48 ± 1.72 |
| ALA | 20:3n-3 | 22:3n-3 | 24:3n-3 |  |
| 20.09 ± 3.23 | 1.79 ± 0.28 | 1.70 ± 0.35 | 0.15 ± 0.03 | 15.38 ± 2.06 |

Since 20:4n-3 was not commercially available it was generated in vivo by co-expression of c-d6Elo(Tp_GA2) with each of the other desaturases or elongases. Therefore upon supplying exogenous SDA, 20:4n-3 was produced by the c-d6Elo(Tp_GA2) and the efficiency of conversion of this fatty acid by the second enzyme was measured.

TABLE 162

Enzyme activity with 20:4n-3.

| Helper Enzyme (delta-6 elongase) pL vector | $2^{nd}$ enzyme in pY vector | delta-6 elongase conversion efficiency (%) | Conversion efficiency of $2^{nd}$ enzyme (%) | Gene dosage effect |
|---|---|---|---|---|
| c-d6Elo(Tp_GA2) | c-d4Des(Pl_GA2)2 | 70.0 ± 1.2 | N/A | N/A |
| c-d6Elo(Tp_GA2) | c-d4Des(Tc_GA) | 69.1 ± 0.7 | 3.3 ± 0.2 | N/A |
| c-d6Elo(Tp_GA2) | c-d5Des(Tc_GA2) | 64.3 ± 1.4 | 86.2 ± 1.0 | N/A |
| c-d6Elo(Tp_GA2) | c-d6Des(Ot_febit) | 72.9 ± 2.1 | 2.9 ± 0.2 | N/A |
| c-d6Elo(Tp_GA2) | c-d12Des(Ps_GA) | 70.3 ± 1.3 | N/A | N/A |
| c-d6Elo(Tp_GA2) | c-o3Des(Pi_GA2) | 67.4 ± 3.6 | N/A | N/A |
| c-d6Elo(Tp_GA2) | c-o3Des(Pir_GA) | 70.0 ± 1.1 | N/A | N/A |
| c-d6Elo(Tp_GA2) | c-d5Elo(Ot_GA3) | 68.8 ± 1.4 | 80.2 ± 2.5 | N/A |
| c-d6Elo(Tp_GA2) | c-d6Elo(Pp_GA2) | 89.8 ± 0.7 | N/A | YES (A6 ELO) |
| c-d6Elo(Tp_GA2) | c-d6Elo(Tp_GA2) | 90.3 ± 0.8 | N/A | YES (A6 ELO) |

*Cultures were fed with SDA and 20:4n-3 (delta-6 elongation) was produced as a substrate for either desaturases or elongases. Three repeats were measured. pY:pYES2.W5-His-TOPO expression vector; pL:pESC-Leu expression vector. All genes were placed under the control of the Gal1 promoter. N/A:not applicable; DES:desaturase; ELO:elongase The c-d4Des(Tc_GA), the c-d5Des(Tc_GA2), the c-d6Des(Ot_febit), and the c-d5Elo(Ot_GA3) were able to use 20:4n-3 as a substrate (Table 162). The c-d5Des (Tc_GA2) showed the highest conversion percentage, which would be expected as 20:4n-3 was a known substrate for delta-5 desaturases. The c-d5Elo(Ot_GA3) was also able to efficiently produce 22:4n-3. When using two delta-6 elongases in one construct, a gene dosage effect was observed; the delta-6 elongase activity increased in the presence of two c-d6Elo(Tp_GA2), or a gene pair consisting of a c-d6Elo (Tp_GA2) and a c-d6Elo(Pp_GA2).

Fatty Acid Specificity of Desaturases and Elongases of this Invention

Enzymes were provided with mixtures of fatty acids to allow comparisons of relative activity when two substrates were present concurrently; an enzyme may be more active on substrate A than substrate B when they are supplied individually, but when they are supplied at the same time the relative activity of the enzyme on each substrate could change. Fatty acids of the same length were preferably provided at the same time, since they would be most likely to be present in the plant concurrently. Mixtures of fatty acids were adjusted so that the level of (substrate 1+product 1)=(substrate 2+product 2) within ±5%.

TABLE 163

Fatty acid preferences of elongases and desaturases

| Gene (Fatty Acid Mix) | Substrate | % conversion |
|---|---|---|
| c-d5Elo(Ot_GA3) (EPA/ARA/DHGLA) | EPA | 90.36 ± 2.17 |
|  | ARA | 40.96 ± 4.50 |
|  | DHGLA | 3.14 ± 0.47 |
| c-d5Elo(Ot_GA3) (DPAn-3/DHA) | DPAn-3 | 4.75 ± 0.57 |
|  | DHA | 5.69 ± 0.56 |
| c-d5Elo(Ot_GA3) (LA/ALA) | LA | 0.57 ± 0.06 |
|  | ALA | 13.43 ± 1.65 |
| c-d5Elo(Ot_GA3) (GLA/SDA) | GLA | 2.89 ± 0.06 |
|  | SDA | 29.24 ± 0.73 |
| c-d4-Des(Tc_GA) (DTA/DPAn-3) | DTA | 21.01 ± 2.28 |
|  | DP An-3 | 25.18 ± 2.08 |
| c-d4-Des(Pl_GA2)2 (DTA/DPAn-3) | DTA | 34.41 ± 1.63 |
|  | DP An-3 | 41.27 ± 2.07 |
| c-d6-Des(Ot_febit) (LA/ALA) | LA | 56.62 ± 2.06 |
|  | ALA | 77.66 ± 0.80 |

TABLE 163-continued

Fatty acid preferences of elongases and desaturases

| Gene (Fatty Acid Mix) | Substrate | % conversion |
|---|---|---|
| c-d6-Elo(Pp_GA2) (LA/ALA) | LA | 11.38 ± 0.94 |
| | ALA | 24.41 ± 1.84 |
| c-d6-Elo(Pp_GA2) (GLA/SDA) | GLA | 81.59 ± 1.66 |
| | SDA | 85.23 ± 1.28 |
| c-d6-Elo(Tp_GA2) (LA/ALA) | LA | 1.93 ± 0.15 |
| | ALA | 6.41 ± 0.68 |
| c-d6-Elo(Tp_GA2) (GLA/SDA) | GLA | 81.61 ± 1.03 |
| | SDA | 87.70 ± 0.87 |
| c-d5-Des(Tc_GA2) (DHGLA/ETA) | DHGLA | 85.0 ± 2.38 |
| | ETA (20:4n-3) | 90.75 ± 1.15 |
| c-o3-Des(Pi_GA2) (DHGLA/ARA/DTA) | DHGLA | 28.82 ± 1.26 |
| | ARA | 39.15 ± 1.19 |
| | DTA | 7.32 ± 0.63 |
| c-o3Des(Pir_GA) (DHGLA/ARA/DTA) | DHGLA | 25.22 ± 1.70 |
| | ARA | 53.19 ± 2.52 |
| | DTA | 12.66 ± 1.17 |

As described in Table 163 the relative activities of the omega-3 desaturases follow the same order as described earlier (Table 159), but that the activity of both omega-3 desaturases was lower on DTA when DHGLA and ARA were available. Both delta-4 desaturases showed a preference for the omega-3 substrate when the omega-3 and omega-6 substrates were present in equal amounts. The preference of the c-d6Des(Ot_febit) for the omega-3 substrate was also increased when both substrates are available (Table 163). For the delta-5 elongase, the relative elongation of secondary substrates generally dropped when the primary, or preferred substrate was available (Table 163).

Additive Enzyme Activity Supporting MoA (CoA Vs PC)

The delta-5 desaturase genes from S. arctica and Thraustochytrium sp. were cloned into the pYES2.1/V5-His-TOPO expression vector, and both the c-d6Elo(Tp_GA2) and the c-d8Des(Eg) were cloned into the pESC-Leu expression vector. Yeast was transformed with the appropriate vector pairs and selection on DOB-uracil-leucine. Positive cultures were grown and induced and GC analysis was conducted as described above in Example 23. All cultures were grown concurrently.

TABLE 164

Deduced mode of action of the Delta-5 desaturases.

| Helper Enyzme known to work in PC (delta-8 DES) | delta-5 DES | delta-% DES Conversion efficiency | Deduced MoA of delta-5 DES |
|---|---|---|---|
| c-d8Des(Eg) | c-d5Des(Sa) | 38% | |
| c-d8Des(Eg) | c-d5Des(Tc_GA2) | 36% | |
| Helper Enyzme known to work in CoA (delta-6 ELO) | delta-5 DES | delta-% DES Conversion efficiency | |
| c-d6Elo(Tp_GA2) | c-d5Des(Sa) | 32% | PC |
| c-d6Elo(Tp_GA2) | c-d5Des(Tc_GA2) | 80% | CoA |

As described in Table 164, the delta-5 desaturase activity of the c-d5Des(Sa) on DHGLA was similar regardless if the DHGLA was derived from elongation in the coenzyme A (CoA) pool or desaturation in the phosphatidylcholine (PC) pool. Conversely, Table 164 also shows that the delta-5 desaturase activity of the c-d5Des(Tc_GA2) was much higher if the DHGLA substrate was derived from elongation in the CoA pool. In combination with data from lipid analysis by TLC, this suggests that the c-d5Des(Tc_GA2) was capable of desaturating substrates in the CoA pool, although it does not indicate that desaturation was limited to this pool.

The level of delta-6-elongation following desaturation by a desaturase active in the PC pool (c-d6Des(Pir_GA)) and a desaturase thought to be active in the CoA pool (c-d6Des (Ot_febit)) was determined. Since elongation takes place in the acyl-CoA pool, more efficient elongation can occur following desaturation by an acyl-CoA dependent desaturase. The two desaturases were also expressed in the presence of a delta-12 desaturase that was active on PC substrates, to allow the efficiency of subsequent delta-6 desaturation to be compared. Finally, the effects of individual desaturase genes and pairs of desaturase genes on elongase and desaturase activity were compared to determine dosage effects.

TABLE 165

Effects of various delta-6 desaturases on subsequent delta-6 elongation*.

| Construct | delta-6 Des % | delta-6 ELO % |
|---|---|---|
| pT-c-d6Des(Ot_febit) & pY-c-d6Elo(Tp_GA2) | 44.9 ± 1.0 | 89.3 ± 1.4 |
| pT-c-d6Des(Pir_GA) & pY-c-d6Elo(Tp_GA2) | 19.7 ± 0.5 | 63.7 ± 4.8 |

*Cultures were fed with LA and production of GLA (delta-6 desaturation) and DHGLA (delta-6 elongation) were measured. pY:pYES2. W5-His-T0P0 expression vector pT:pESC-trp expression vector. All genes were under the control of the Gal1 promoter.

TABLE 166

Effects of delta-12 desaturation on subsequent delta-6 elongation*.

| Construct | delta-12 DES % | delta-6 DES % |
|---|---|---|
| pT-c-d6Des(Ot_febit) & pY-c-d12Des(Ps_GA) | 60.2 ± 2.9 | 23.2 ± 0.1 |
| pT-c-d6Des(Pir_GA) & pY-c-d12Des(Ps_GA) | 62.8 ± 1.4 | 17.1 ± 1.7 |

*Cultures were supplied with exogenous 18:1n-9. The production of LA (delta-12 desaturation) and GLA (delta-6 desaturation) were measured. pY:pYES2. W5-His-T0P0 expression vector pT:pESC-trp expression vector. All genes were under the control of the Gal1 promoter.

GLA conversion by the c-d6Elo(Tp_GA2) was higher with GLA derived from desaturation by the c-d6Des (Ot_febit) compared to GLA derived by desaturation with the c-d6Des(Pir_GA) (Table 165). This shows that c-d6Des (Ot_febit) acts in the acyl-CoA pool, making the resulting substrate more readily available for the delta-6 elongase, and therefore resulting in a higher elongase activity. Correspondingly, the delta-6 desaturase activity of the c-d6Des (Ot_febit) was reduced by almost half if the substrate was derived from delta-12 desaturation in the PC pool (Table 165 and Table 166), whereas the the delta-6 desaturase activity of the c-d6Des(Pir_GA) was similar whether the substrate (LA) was derived from delta-12-desaturation of OA in the PC pool, or was supplied exogenously (Table 165 and Table 166). Exogenously supplied substrate was believed to enter the yeast cell in the form of acyl-CoA. In combination with data from lipid analysis by TLC, this data suggests that the c-d6Des(Ot_febit) was acyl-CoA-dependent enzyme, consistent with a previous prediction (Domergue et al. (2005) Biochem. J. 389: 483-490).

TABLE 167

Effect of substrate pool and gene dosage on delta-6-desaturation and subsequent delta-6-elongation of ALA.

| Helper Enzyme (delta-6 elongase) pL vector | First delta-6 desaturase pY vector | Second delta-6 desaturase pT vector | delta-6 desaturase conversion efficiency | delta-6 elongase conversion efficiency | Gene dosage effect | Deduced MoA of 1st delta-6 desaturase | Deduced MoA of 2nd delta-6 desaturase |
|---|---|---|---|---|---|---|---|
| c-d6Elo(Tp_GA2) | c-d6Des(Ot_febit) | pT vector | 64.3 ± 1.5 | 73.3 ± 0.2 | N/A | CoA | N/A |
| c-d6Elo(Tp_GA2) | c-d6Des(Pir_GA) | pT vector | 26.8 ± 11.0 | 53.0 ± 8.8 | N/A | PC | N/A |
| c-d6Elo(Tp_GA2) | pY vector | c-d6Des(Ot_febit) | 60.8 ± 2.3 | 80.8 ± 0.6 | N/A | N/A | CoA |
| c-d6Elo(Tp_GA2) | pY vector | c-d6Des(Pir_GA) | 27.9 ± 0.9 | 52.0 ± 0.9 | N/A | N/A | PC |
| c-d6Elo(Tp_GA2) | c-d6Des(Ot_febit) | c-d6Des(Pir_GA) | 72.5 ± 2.2 | 71.1 ± 2.1 | Yes (DES) | CoA | PC |
| c-d6Elo(Tp_GA2) | c-d6Des(Pir_GA) | c-d6Des(Pir_GA) | 40.5 ± 1.3 | 47.5 ± 2.0 | Yes (DES) | PC | PC |
| c-d6Elo(Tp_GA2) | c-d6Des(Ot_febit) | c-d6Des(Ot_febit) | 72.4 ± 0.9 | 78.1 ± 0.7 | Yes (DES) | CoA | CoA |

*Cultures were fed with ALA and production of SDA (delta-6 desaturation) and 20:4n-3 (delta-6 elongation) was measured. pY: pYES2.1/V5-His-TOPO expression vector; pL: pESC-Leu expression vector; pT: PESC-trp. All regulated by Gal1 promoter. N/A: not applicable; DES: desaturation conversion percent. Data from at least 3 clones were used for each measurement.

TABLE 168

Effect of substrate pool and gene dosage on delta-6-desaturation and subsequent delta-6-elongation of LA.

| Helper Enzyme (delta-6 elongase) pL vector | First delta-6 desaturase pY vector | Second delta-6 desaturase pT vector | delta-6 desaturase conversion efficiency | delta-6 elongase conversion efficiency | Gene dosage effect | Deduced MoA of 1st delta-6 desaturase | Deduced MoA of 2nd delta-6 desaturase |
|---|---|---|---|---|---|---|---|
| c-d6Elo(Tp_GA2) | c-d6Des(Ot_febit) | pT vector | 60.3 ± 7.0 | 65.6 ± 1.8 | N/A | CoA | N/A |
| c-d6Elo(Tp_GA2) | c-d6Des(Pir_GA) | pT vector | 23.4 ± 15.5 | 43.2 ± 8.6 | N/A | PC | N/A |
| c-d6Elo(Tp_GA2) | pY vector | c-d6Des(Ot_febit) | 48.5 ± 0.2 | 75.6 ± 1.5 | N/A | N/A | CoA |
| c-d6Elo(Tp_GA2) | pY vector | c-d6Des(Pir_GA) | 23.0 ± 0.8 | 36.9 ± 2.2 | N/A | N/A | PC |
| c-d6Elo(Tp_GA2) | c-d6Des(Ot_febit) | c-d6Des(Pir_GA) | 3.0 ± 1.4 | 60.1 ± 1.9 | Yes (DES) | CoA | PC |
| c-d6Elo(Tp_GA2) | c-d6Des(Pir_GA) | c-d6Des(Pir_GA) | 35.1 ± 2.2 | 35.4 ± 4.8 | Yes (DES) | PC | PC |
| c-d6Elo(Tp_GA2) | c-d6Des(Ot_febit) | c-d6Des(Ot_febit) | 62.5 ± 1.4 | 66.8 ± 2.5 | Yes (DES) | CoA | CoA |

*Cultures were fed with LA and production of GLA (delta-6 desaturation) and DHGLA (delta-6 elongation), three repeats were measured. pY: pYES2.1/V5-His-TOPO expression vector; pL: pESC-Leu expression vector; pT: PESC-trp. All genes were placed under the control of the Gal1 promoter. N/A: not applicable; DES: desaturation conversion percent.

When co-expressing the c-d6Elo(Tp_GA2) and the c-d6Des(Ot_febit) (CoA), a higher elongase conversion efficiency was achieved compared to co-expressing the c-d6Elo(Tp_GA2) and the c-d6Des(Pir_GA) (PC), regardless of whether n-3 or omega-6 substrate was supplied exogenously (Table 167, Table 168). This was observed whether the relevant desaturase gene was cloned into the pYes vector or the pESC-trp vector. A slight increase in desaturation efficiency was observed in the presence of two desaturase genes, particularly in cultures supplied with the omega-3 substrate ALA. Compared to cultures carrying a single c-d6Des(Ot_febit), the proportion of substrate elongated was only slightly enhanced in the presence of two acyl-CoA dependent c-d6Des(Ot_febit), or in the presence of both desaturases. Co-expression of the c-d6Elo(Tp_GA2) with two copies of Sc-d6Des(PirGA) (PC) resulted in the lowest elongation conversion level among the cultures carrying two desaturases. The presence of the with acyl-CoA dependent delta-6 desaturase contributed to a higher delta-6 elongation activity whether it was expressed alone or along with a second desaturase, further indicating the usefulness of this gene for VLC-PUFA synthesis.

The effect of substrate pool for various delta-4 desaturases was determined in the presence of a helper enzyme, the c-d5Elo(Ot_GA3), which was known to work in the CoA pool. The gene dosage effect of delta-4 desaturase genes was also determined.

TABLE 169

Effect of substrate pool and gene dosage effect for delta-4 desaturases (exogenous EPA supplied).

| Helper Enzyme (delta-5 elongase) pL vector | First delta-4 desaturase pY vector | Second delta-4 desaturase pT vector | delta-4 desaturase conversion efficiency | Gene dosage effect | Deduced MoA of 1st delta-4 desaturase | Deduced MoA of 2nd delta-4 desaturase |
|---|---|---|---|---|---|---|
| c-d5Elo(Ot_GA3) | c-d4Des(Pl_GA)2 | pT vector | 29.9 ± 4.0 | N/A | CoA | NA |
| c-d5Elo(Ot_GA3) | c-d4Des(Tc_GA) | pT vector | 31.2 ± 2.8 | N/A | PC | NA |
| c-d5Elo(Ot_GA3) | c-d4Des(Pl_GA)2 | c-d4Des(Tc_GA) | 53.6 ± 1.0 | ++ (0.88) | CoA | PC |
| c-d5Elo(Ot_GA3) | c-d4Des(Eg) | c-d4Des(Tc_GA) | 36.9 ± 3.5 | Yes | PC | PC |
| c-d5Elo(Ot_GA3) | c-d4Des(Tc_GA) | c-d4Des(Tc_GA) | 40.2 ± 0.2 | + (0.64) | PC | PC |

* Cultures were fed with EPA and production of DPA (delta-5 elongation) and DHA (delta-4 desaturation) was measured for at least three samples. pY: pYES2.1/V5-His-TOPO expression vector; pL: pESC-Leu expression vector; pT: PESC-trp. All genes were placed under the control of the Gal1 promoter. N/A: not applicable. Dosage effect: number in brackets = conversion efficiency of two-desaturase construct/ (conversion efficiency of single gene A construct + conversion efficiency of single gene B construct).

TABLE 170

Effect of substrate pool and gene dosage effect for delta-4 desaturases (exogenous ARA supplied).

| Helper Enzyme (delta-5 elongase) pL vector | First delta-4 desaturase pY vector | Second delta-4 desaturase pT vector | delta-4 desaturase conversion efficiency | Gene dosage effect | Deduced MoA of 1st delta-4 desaturase | Deduced MoA of 2nd delta-4 desaturase |
|---|---|---|---|---|---|---|
| c-d5Elo(Ot_GA3) | c-d4Des(Pl_GA)2 | pT vector | 28.8 ± 1.0 | N/A | CoA | N/A |
| c-d5Elo(Ot_GA3) | c-d4Des(Tc_GA) | pT vector | 27.0 ± 2.5 | N/A | PC | N/A |
| c-d5Elo(Ot_GA3) | c-d4Des(Pl_GA)2 | c-d4Des(Tc_GA) | 44.0 ± 0.9 | (0.79) | CoA | PC |
| c-d5Elo(Ot_GA3) | c-d4Des(Eg) | c-d4Des(Tc_GA) | 29.4 ± 0.6 | – | PC | PC |
| c-d5Elo(Ot_GA3) | c-d4Des(Tc_GA) | c-d4Des(Tc_GA) | 32.2 ± 0.8 | – | PC | PC |

*Cultures were fed with ARA and production of DTA (delta-5 elongation) and DPAn-6 (delta-4 desaturation) were measured. pY: pYES2.1/V5-His-TOPO expression vector; pL: pESC-Leu expression vector; pT: PESC-Trp expression vector. All genes were placed under control of the Gal1 promoter. N/A: not applicable. Dosage effect: number in brackets = conversion efficiency of two-desaturase construct/ (conversion efficiency of single gene A construct + conversion efficiency of single gene B construct).

The desaturation levels achieved by the *P. lutheri* and c-d4Des(Tc_GA)s were similar. When two delta-4 desaturases were used, a significant gene dosage effects only observed with the *P. lutheri/Thraustochyrium* sp. pair, and the lowest with two copies of the *Thraustocytrium* sp desaturase. These trends were observed in the presence of elongated ARA (Table 170) and EPA (Table 169). However, with the n-6 elongation substrate (ARA), the desaturation conversion percentage was generally slightly lower compared to the omega-3 substrate (EPA).

Example 23: Spacer Regions Containing Transcription Factor Binding Motifs

As indicated in examples 3 and 4, between each expression cassette in the constructs used in the invention there is a spacer region of 100-200 base pairs. For the BiBAC T-DNAs, the short stretches of sequence in between the gene cassettes, which had been multi-cloning sites and Gateway site sequences in the co-transformation vectors, were subjected to randomization to maintain the GC content and to remove multiple repeats of identical sequence. The skilled worker would recognize that the presence of multiple repeats within a construct, in particular large multi-gene constructs, could result in internal deletions and rearrangements as the plasmid was cloned into *Escherichia coli* and passaged through the *Agrobacterium* strain/species used. After removal of repeats and adjustment of GC content, the sequences of the spacer regions were then examined for any possible binding sites for transcription factors and other DNA interacting proteins. The spacer region sequences used are RTP10690_1 through RTP10690_12, including the AtAHAS promoter and terminator, RTP10690_5', LJB2197_5' and LJB2197_1 through LJB2197_4. The underscore numbers also represent the order in which that spacer region appears in the cassette reading from the right border towards the left border, in the sense orientation of the GOI in the proceeding cassette. For example, RTP10690_1 was the sequence after the terminator of the first cassette and before the promoter of the second cassette in the construct VC-RTP10690-1qcz_F. The terminator of the AHAS selection cassette and the 5' region of the first cassette were also examined.

>RTP10690_1
TTAATTCAGCTAGCTAGCCTCAGCTGACGTTACGTAACGCTAGGTAGCGT
CACGTGACGTTAGCTAACGCTAGGTAGCGTCAGCTGAGCTTACGTAAGCG
CTTAGCAGATATTT

>RTP10690_2
TTACTGATTGTCTACGTAGGCTCAGCTGAGCTTACCTAAGGCTACGTAGG
CTCACGTGACGTTACGTAAGGCTACGTAGCGTCACGTGAGCTTACCTAAC
TCTAGCTAGCCTCACGTGACCTTAGCTAACACTAGGTAGCGTCAGCTCGA
CGGCCCG

>RTP10690_3
GGCGGAGTGGGGCTACGTAGCGTCACGTGACGTTACCTAAGCCTAGGTAG
CCTCAGCTGACGTTACGTAACGCTAGGTAGGCTCAGCTGACACGGGCAGG
ACATAG

>RTP10690_4
GAATGAAACCGATCTACGTAGGCTCAGCTGAGCTTAGCTAAGCCTACCTA
GCCTCACGTGAGATTATGTAAGGCTAGGTAGCGTCACGTGACGTTACCTA
ACACTAGCTAGCGTCAGCTGAGCTTAGCTAACCCTACGTAGCCTCACGTG
AGCTTACCTAACGCTACGTAGCCTCACGTGACTAAGGATGACCTACCCAT
TCTT

>RTP10690_5
GCGGCCGCTAGCTAGCCTCAGCTGACGTTACGTAACGCTAGGTAGCGTCA
CGTGACGTTAGCTAACGCTAGGTAGCGTCAGCTGAGCTTACGTAAGCGCC
ACGGGCAGGACATAGGGACTACTACAA

>RTP10690_6
CGAATGAAACCGATCTACGTAGGCTCAGCTGAGCTTACCTAAGGCTACGT
AGGCTCACGTGACGTTACGTAAGGCTACGTAGCGTCACGTGAGCTTACCT
AACTCTAGCTAGCCTCACGTGACCTTAGCTAACACTAGGTAGCGTCAGCT
TAGCAGATAT

>RTP10690_7
CCGTTCAATTTACTGATTGTCTACGTAGCGTCACCTGACGTTACGTAAGG
CTACCTAGGCTCACGTGACGTTACGTAACGCTACGTAGCGTCAGGTGAGG
TTAGCTAACGCTAGCTAGCCTCACCTGACGTTAGGTAAGGCTACGTAGCG
TCACCTGAGATTAGCTAAGCCTACCTAGACTCACGTGACCTTAGGTAACG
CTACGTAGCGTCAAAGCTTTACAACGCTACACAAA

>RTP10690_8
TTACCTAACTTAGAACTAAAATCAACTCTTTGTGACGCGTCTACCTAGAG
TCAGCTGAGCTTAGCTAACGCTAGCTAGTGTCAGCTGACGTTACGTAAGG
CTAACTAGCGTCACGTGACCTTACGTAACGCTACGTAGGCTCAGCTGAGC
TTAGCTAACCCTAGCTAGTGTCACGTGAGCTTACGCTACTATAGAAAATG
TGTTATAT

>RTP10690_9
TTCAGTCTAAAACAACTACGTAGCGTCACGTGACGTTACCTAAGCCTAGG
TAGCCTCAGCTGACGTTACGTAACGCTAGGTAGGCTCAGCTGACTGCAGC
AAATTTACACATTGCCA

>RTP10690_10
TAATTCGGCGTTAATTCAGCTACGTAGGCTCAGCTGAGCTTACCTAAGGC
TACGTAGGCTCACGTGACGTTACGTAAGGCTACGTAGCGTCACGTGAGCT
TACCTAACTCTAGCTAGCCTCACGTGACCTTAGCTAACACTAGGTAGCGT
CAGCACAGATGAATACTAGCTGTTGTTCA

>RTP10690_11
ATCATGATGCTTCTCTGAGCCGTGTTTGCTAGCTAGCCTCAGCTGACGTT
ACGTAACGCTAGGTAGCGTCACGTGACGTTAGCTAACGCTAGGTAGCGTC
AGCTGAGCTTACGTAAGCGCACAGATGAATACTAGCTGTTGTTCACA

>RTP10690_12
CTTCTCTGAGCCGTGTTTGCTAGCTAGCCTCAGCTGACGTTACGTAACGC
TAGGTAGCGTCACGTGACGTTAGCTAACGCTAGGTAGCGTCAGCTGAGCT
TACGTAAGCGCTTAATTAAAGTACTGATATCGGTACCAAATCGAATCCAA
AAATTACGGATATGAATAT

>RTP10690_5'
ATTACAACGGTATATATCCTGCCAGTCAGCATCATCACACCAAAAGTTAG
GCCCGAATAGTTTGAAATTAGAAAGCTCGCAATTGAGGTCTACAGGCCAA
ATTCGCTCTTAGCCGTACAATATTACTCACCGGTGCGATGCCCCCATCG
TAGGTGAAGGTGGAAATTAATGGCGCGCCTGATCACTGATTAGTAACTAT
TACGTAAGCCTACGTAGCGTCACGTGACGTTAGCTAACGCTACGTAGCCT
CAGCTGACGTTACGTAAGCCTACGTAGCGTCACGTGAGCTTAGCTAACGC
TACCTAGGCTCAGCTGACGTTACGTAACGCTAGCTAGCGTCACTCCTGCA
GCAAATTTACACA

>t-AtAHASL
GAGATGAAACCGGTGATTATCAGAACCTTTTATGGTCTTTGTATGCATAT
GGTAAAAAAACTTAGTTTGCAATTTCCTGTTTGTTTTGGTAATTTGAGTT
TCTTTTAGTTGTTGATCTGCCTGCTTTTTGGTTTACGTCAGACTACTACT
GCTGTTGTTGTTTGGTTTCCTTCTTTCATTTTATAAATAAATAATCCGGT
TCGGTTTACTCCTTGTGACTGGCTCAGTTTGGTTATTGCGAAATGCGAAT
GGTAAATTGAGTAATTGAAATTCGTTATTAGGGTTCTAAGCTGTTTTAAC
AGTCACTGGGTTAATATCTCTCGAATCTTGCATGGAAAATGCTCTTACCA
TTGGTTTTTAATTGAAATGTGCTCATATGGGCCGTGGTTTCCAAATTAAA
TAAAACTACGATGTCATCGAGAAGTAAAATCAACTGTGTCCACATTATCA
GTTTTGTGTATACGATGAAATAGGGTAATTCAAAATCTAGCTTGATATGC
CTTTTGGTTCATTTTAACCTTCTGTAAACATTTTTTCAGATTTTGAACAA
GTAAATCCAAAAAAAAAAAAAAAATCTCAACTCAACACTAAATTATTTT
AATGTATAAAAGATGCTTAAAACATTTGGCTTAAAAGAAAGAAGCTAAAA
ACATAGAGAACTCTTGTAAATTGAAGTATGAAAATATACTGAATTGGGTA
TTATATGAATTTTTCTGATTTAGGATTCACATGATCCAAAAAGGAAATCC
AGAAGCACTAATCAGACATTGGAAGTAGG

>LJB2197_5'
ACATACAAATGGACGAACGGATAAACCTTTTCACGCCCTTTTAAATATCC
GATTATTCTAATAAACGCTCTTTTCTCTTAGGTTTACCCGCCAATATATC
CTGTCAAACACTGATAGTTTAAACTGAAGGCGGGAAACGACAATCTGATC
ACTGATTAGTAACTAAGGCCTTTAATTAATCTAGAGGCGCGCCGGGCCC
CTGCAGGGAGCTCGGCCGGCCAATTTAAATTGATATCGGTACATCGATTA
CGCCAAGCTATCAACTTTGTATAGAAAAGTTGCCATGATTACGCCAAGCT
TGGCCACTAAGGCCAATTTCGCGCCCTGCAGCAAATTTACACA

>LJB2197_1
CAATTTACTGATTGTGTCGACGCGATCGCGTGCAAACACTGTACGGACCG
TGGCCTAATAGGCCGGTACCCAAGTTTGTACAAAAAAGCAGGCTCCATGA
TTACGCCAAGCTTGGCCACTAAGGCCAATTTAAATCTACTAGGCCGGCCA
TCGACGGCCCGGACTGTA

>LJB2197_2
GGCGGAGTGGGGGCGCCTACTACCGGTAATTCCCGGGATTAGCGGCCGC
TAGTCTGTGCGCACTTGTATCCTGCAGGTTAGGCCGGCCACACGGGCAGG
ACATAGGG

>LJB2197_3
AAACCGAATGAAACCGATGGCGCCTACCGGTATCGGTCCGATTGCGGCCG
CTTAAAGGGCGAATTCGTTTAAACACTGTACGGACCGTGGCCTAATAGGC
CGGTACCACCCAGCTTTCTTGTACAAAGTGGCCATGATTACGCCAAGCTT
GGCCACTAAGGCCAATTTAAATCTACTAGGCCGGCCATAAGGATGACCTA
CCCATTCTT

>LJB2197_4
TTAATTCAGGGCCGGCCAAAGTAGGCGCCTACTACCGGTAATTCCCGGGA
TTAGCGGCCGCTAGTCTGTGCGCACTTGTATCCTGCAGGTTAGGCCGGCC
ATTAGCAGATATTT

TABLE 171

Cassettes contained in the constructs
VC-RTP10960-1qcz_F and VC-LJB2197-1qcz
and the spacer regions in front of them, which was 5' of
the promoter region.

VC-RTP10960-1 qcz_F
p-VfUSP_684bp::i-Atss18_252bp::c-d6-Elo[Pp_GA2]::t-CaMV35S
RTP10690_1
p-LuCnl[1064bp]::i-Atss14_377bp::c-d5Des[Tc_GA2]::t-AgrOCS_192bp
RTP10690_2
p-SB P::i-Atss2_455bp::c-d6-Des[Ot_febit]::t-StCATH D-pA
RTP10690_3
p-LuPXR_1727bp::i-Atss1_847bp::c-d6-Elo[Tp_GA2]::t-AtPXR_400bp
RTP10690_4
p-Napin_A/B::i-Atss14_377bp::c-d12Des[Ps_GA2]::t-E9
RTP10690_5
p-LuPXR_1727bp::i-Atss15_758bp::c-w3Des[pPir_GA]::AtPXR_400bp
RTP10690_6
p-LuCnl[1064bp]::i-Atss2_455bp::c-d4Des[Pl_GA]2::t-AgrOCS_192bp TABLE 171-continued Cassettes contained in the constructs
VC-RTP10960-1qcz_F and VC-LJB2197-1qcz
and the spacer regions in front of them, which was 5' of
the promoter region.

RTP10690_7
p-Bn FAE1::i-Atss1 _847bp: :c-d5 Elo[Ot_GA3]::t-bn FAE1
RTP10690_8
p-ARC5_perm 1::c-d4Des[T c_GA3]: :t-pvarc
RTP10690_9
p-VfUSP_684bp::i-Atss18_252::c-w3-Des[Pi_GA2]::t-CaMV35S
RTP10690_10
p-BnSETL-v1[1234bp]::c-d5-Des[Tc_GA2]::t-BnSETL
RTP10690_11
p-BnSETL-v1[1234bp]::c-w3Des[Pir_GA]::t-BnSETL
RTP10690_12
RTP10690_5'
t-AtAHASL
VC-LJB2197-1qcz
LJB2197_5'
p-VfUSP_684bp::i-Atss18_252bp::c-d6-Elo[PpGA2]::t-CaMV35S
LJB2197_1
p-LuCnl[1064bp]::i-Atss14_377bp::c-d5Des[Tc_GA2]::t-AgrOCS_192bp
LJB2197_2
p-SB P::i-Atss2_455bp: :c-d6-Des[Ot_febit]::StCATH D-pA
LJB2197_3
p-LuPXR_1727bp::i-Atss1_847bp::c-d6-Elo[Tp_GA2]::t-AtPXR_400bp
LJB2197_4
p-Napin_A/B::i-Atss14_377bp::c-d12-Des[Ps_GA]::t-E9

The bold lettering indicates the spacer, which corresponds to the Seq ID's listed above.

Transcription factors are known to bind certain sequences of DNA and from this point of interaction with the chromosome they regulate transcription of a certain gene or subset of genes. The specific sequences which are bound by the transcription factor are referred to as DNA binding motifs and can be in the range of tens of base pairs to as few as four base pairs. The majority of DNA binding motifs consist of less than ten base pairs but those motifs have been documented to be necessary and sufficient for up (or down) regulation of transcription by the transcription factor binding to them. For examples of transcription factor motifs and the enabling data that are used to support the motifs see; Hattori et al., 2002, Keller et al., 1995, Kim et al., 2014, Lopez et al., 2013, Machens et al., 2014, Muino, 2013, Sarkar, 2013, Dubos et al., 2014). Identified motifs have been curated and archived in various data bases, such as PLACE (Higo et al., 1999), which can be accessed and queried by the public. While certain characterized promoters are used as the primary means to regulate expression of a given transgene in the invention, it was possible that alternative regulation of a transgene was occurring in the plants described in the invention due to the presence of one or more active transcription factor binding motifs in the spacer region. Examples of artificial/synthetic promoters in the public literature support this line of reasoning; see Kong et al. (2014), Nishikata et al. (2013), and Brown et al. (2014) for examples of promoters made by random assembly of nucleotides and iterative testing as well as specific fragments of known transcriptional activity assembled to make an artificial promoter. Thus the regulatory region of a given transgene in the invention also includes, in addition to the intron, terminator and the promoter used, the spacer region in front of the cassette containing the transgene.

TABLE 172 lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_1 | Plant G-box/C-box bZIP proteins | gttacgtaACGTcagctgagg |
| RTP10690_1 | Plant G-box/C-box bZIP proteins | ctcagcTGACgttacgtaacg |
| RTP10690_1 | Plant specific NAC [NAM (no apical meristem), ATAF172, CUC2 (cup-shaped cotyledons 2)] transcription factors | agcctcagctgacgtTACGtaacgcta |
| RTP10690_1 | Opaque-2 like transcriptional activators | cagctgACGTtacgtaa |
| RTP10690_1 | GT-box elements | gctgacGTTAcgtaacg |
| RTP10690_1 | Cell-death specification 2 | gttacGTAAcg |
| RTP10690_1 | Plant G-box/C-box bZIP proteins | ctagcgttACGTaacgtcagc |
| RTP10690_1 | Opaque-2 like transcriptional activators | agcgttACGTaacgtca |
| RTP10690_1 | Cell-death specification 2 | gttacGTAAcg |
| RTP10690_1 | Opaque-2 like transcriptional activators | gacgttACGTaacgcta |
| RTP10690_1 | GT-box elements | cctagcGTTAcgtaacg |
| RTP10690_1 | Plant specific NAC [NAM (no apical meristem), ATAF172, CUC2 (cup-shaped cotyledons 2)] transcription factors | gacgctacctagcgtTACGtaacgtca |
| RTP10690_1 | Plant G-box/C-box bZIP proteins | gtcacgTGACgctacctagcg |
| RTP10690_1 | Plant G-box/C-box bZIP proteins | gctaggtaGCGTcacgtgacg |
| RTP10690_1 | ABA response elements | tagcgtcaCGTGacgtt |
| RTP10690_1 | Plant G-box/C-box bZIP proteins | ctaacgtcACGTgacgctacc |
| RTP10690_1 | Myc-like basic helix-loop-helix binding factors | taacgtCACGtgacgctac |
| RTP10690_1 | Opaque-2 like transcriptional activators | aacgtcACGTgacgcta |
| RTP10690_1 | ABA response elements | taacgtcaCGTGacgct |
| RTP10690_1 | Plant G-box/C-box bZIP proteins | gtagcgtcACGTgacgttagc |
| RTP10690_1 | Myc-like basic helix-loop-helix binding factors | tagcgtCACGtgacgttag |
| RTP10690_1 | Opaque-2 like transcriptional activators | agcgtcACGTgacgtta |
| RTP10690_1 | Plant G-box/C-box bZIP proteins | gttagctaACGTcacgtgacg |
| RTP10690_1 | Plant specific NAC [NAM (no apical meristem), ATAF172, CUC2 (cup-shaped cotyledons 2)] transcription factors | agcgttagctaacgtCACGtgacgcta |
| RTP10690_1 | Opaque-2 like transcriptional activators | tagctaACGTcacgtga |
| RTP10690_1 | Plant G-box/C-box bZIP proteins | gtcacgTGACgttagctaacg |
| RTP10690_1 | MYB-like proteins | cacgtgacGTTAgctaa |
| RTP10690_1 | Plant G-box/C-box bZIP proteins | ctcagcTGACgctacctagcg |

TABLE 172-continued lists the spacer region and the transcription factor binding motif present in the region
and the nucleotide sequence. Upper case letters denote the motif while surrounding bases
indicate examples of sequences that might neighbor the predicted motif but are not necessary for
the motif to function in the regulation of transcription

| Spacer ID | Detailed Family Information | Sequence |
| --- | --- | --- |
| RTP10690_1 | Plant G-box/C-box bZIP proteins | gctaggtaGCGTcagctgagc |
| RTP10690_1 | Plant specific NAC [NAM (no apical meristem), ATAF172, CUC2 (cup-shaped cotyledons 2)] transcription factors | agcgtcagctgagctTACGtaagcgct |
| RTP10690_1 | Vertebrate TATA binding protein factor | gcttacgTAAGctcagc |
| RTP10690_1 | Cell-death specification 2 | cttacGTAAgc |
| RTP10690_1 | Plant G-box/C-box bZIP proteins | aagcgcttACGTaagctcagc |
| RTP10690_1 | Opaque-2 like transcriptional activators | gcgcttACGTaagctca |
| RTP10690_1 | Cell-death specification 2 | cttacGTAAgc |
| RTP10690_1 | Plant G-box/C-box bZIP proteins | ctgagcttACGTaagcgctta |
| RTP10690_1 | Opaque-2 like transcriptional activators | gagcttACGTaagcgct |
| RTP10690_1 | Vertebrate TATA binding protein factor | gcttacgTAAGcgctta |
| RTP10690_1 | Plant specific NAC [NAM (no apical meristem), ATAF172, CUC2 (cup-shaped cotyledons 2)] transcription factors | tatctgctaagcgcttTACGtaagctca |
| RTP10690_1 | Enhancer element first identified in the promoter of the octopine synthase gene (OCS) of the Agrobacterium | tctgctaagcgcttACGTaag |
| RTP10690_1 | Arabidopsis CDC5 homolog | tgctaAGCGct |
| RTP10690_2 | Cell-death specification 2 | cttagGTAAgc |
| RTP10690_2 | Opaque-2 like transcriptional activators | gagcctACGTagcctta |
| RTP10690_2 | ABA response elements | taggctcaCGTGacgtt |
| RTP10690_2 | Plant G-box/C-box bZIP proteins | gtaacgtcACGTgagcctacg |
| RTP10690_2 | Myc-like basic helix-loop-helix binding factors | taacgtCACGtgagcctac |
| RTP10690_2 | Opaque-2 like transcriptional activators | aacgtcACGTgagccta |
| RTP10690_2 | Plant G-box/C-box bZIP proteins | gtaggctcACGTgacgttacg |
| RTP10690_2 | Myc-like basic helix-loop-helix binding factors | taggctCACGtgacgttac |
| RTP10690_2 | Opaque-2 like transcriptional activators | aggctcACGTgacgtta |
| RTP10690_2 | Cell-death specification 2 | gtaacGTCAcg |
| RTP10690_2 | Plant G-box/C-box bZIP proteins | cttacgtaACGTcacgtgagc |
| RTP10690_2 | Opaque-2 like transcriptional activators | tacgtaACGTcacgtga |
| RTP10690_2 | Plant G-box/C-box bZIP proteins | ctcacgTGACgttacgtaagg |
| RTP10690_2 | Plant specific NAC [NAM (no apical meristem), ATAF172, CUC2 (cup-shaped cotyledons 2)] transcription factors | aggctcacgtgacgtTACGtaaggcta |
| RTP10690_2 | Opaque-2 like transcriptional activators | cacgtgACGTtacgtaa |
| RTP10690_2 | GT-box elements | cgtgacGTTAcgtaagg |
| RTP10690_2 | Cell-death specification 2 | cttacGTAAcg |
| RTP10690_2 | Plant G-box/C-box bZIP proteins | gtagccttACGTaacgtcacg |
| RTP10690_2 | Opaque-2 like transcriptional activators | agccttACGTaacgtca |
| RTP10690_2 | Cell-death specification 2 | gttacGTAAgg |
| RTP10690_2 | Opaque-2 like transcriptional activators | gacgttACGTaaggcta |
| RTP10690_2 | Plant specific NAC [NAM (no apical meristem), ATAF172, CUC2 (cup-shaped cotyledons 2)] transcription factors | gacgctacgtagcctTACGtaacgtca |
| RTP10690_2 | Opaque-2 like transcriptional activators | gacgctACGTagcctta |
| RTP10690_2 | Plant G-box/C-box bZIP proteins | gtaaggctACGTagcgtcacg |
| RTP10690_2 | Opaque-2 like transcriptional activators | aaggctACGTagcgtca |
| RTP10690_2 | Plant G-box/C-box bZIP proteins | ctcacgTGACgctacgtagcc |
| RTP10690_2 | Plant G-box/C-box bZIP proteins | gctacgtaGCGTcacgtgagc |
| RTP10690_2 | Plant G-box/C-box bZIP proteins | gtaagctcACGTgacgctacg |
| RTP10690_2 | Myc-like basic helix-loop-helix binding factors | taagctCACGtgacgctac |
| RTP10690_2 | Opaque-2 like transcriptional activators | aagctcACGTgacgcta |
| RTP10690_2 | ABA response elements | taagctcaCGTGacgct |
| RTP10690_2 | Plant G-box/C-box bZIP proteins | gtagcgtcACGTgagcttacc |
| RTP10690_2 | Myc-like basic helix-loop-helix binding factors | tagcgtCACGtgagcttac |
| RTP10690_2 | Opaque-2 like transcriptional activators | agcgtcACGTgagctta |
| RTP10690_2 | GT-box elements | cgtcacGTGAgcttacc |
| RTP10690_2 | Plant specific NAC [NAM (no apical meristem), ATAF172, CUC2 (cup-shaped cotyledons 2)] transcription factors | agagttaggtaagctCACGtgacgcta |
| RTP10690_2 | Cell-death specification 2 | gttagGTAAgc |
| RTP10690_2 | MYB IIG-type binding sites | tagagttaGGTAagc |
| RTP10690_2 | MYB-like proteins | tagctagAGTTaggtaa |
| RTP10690_2 | ABA response elements | tagcctcaCGTGaccttt |
| RTP10690_2 | Plant G-box/C-box bZIP proteins | ctaaggtcACGTgaggctagc |
| RTP10690_2 | Myc-like basic helix-loop-helix binding factors | taaggtCACGtgaggctag |
| RTP10690_2 | Opaque-2 like transcriptional activators | aaggtcACGTgaggcta |
| RTP10690_2 | Dc3 promoter binding factors | cTCACgtgacc |
| RTP10690_2 | Plant G-box/C-box bZIP proteins | ctagcctcACGTgaccttagc |
| RTP10690_2 | Myc-like basic helix-loop-helix binding factors | tagcctCACGtgaccttag |
| RTP10690_2 | Opaque-2 like transcriptional activators | agcctcACGTgaccttа |
| RTP10690_2 | GT-box elements | cctcacGTGAccttagc |
| RTP10690_2 | Plant specific NAC [NAM (no apical meristem), ATAF172, CUC2 (cup-shaped cotyledons 2)] transcription factors | agtgttagctaaggtCACGtgaggcta |
| RTP10690_2 | Plant G-box/C-box bZIP proteins | tcgagcTGACgctacctagtg |
| RTP10690_2 | Plant G-box/C-box bZIP proteins | actaggtaGCGTcagctcgac |
| RTP10690_3 | Opaque-2 like transcriptional activators | gacgctACGTagcccca |
| RTP10690_3 | Plant G-box/C-box bZIP proteins | gtggggctACGTagcgtcacg |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_3 | Opaque-2 like transcriptional activators | ggggctACGTagcgtca |
| RTP10690_3 | Plant G-box/C-box bZIP proteins | gtcacgTGACgctacgtagcc |
| RTP10690_3 | Plant G-box/C-box bZIP proteins | gctacgtaGCGTcacgtgacg |
| RTP10690_3 | ABA response elements | tagcgtcaCGTGacgtt |
| RTP10690_3 | Plant G-box/C-box bZIP proteins | gtaacgtcACGTgacgctacg |
| RTP10690_3 | Myc-like basic helix-loop-helix binding factors | taacgtCACGtgacgctac |
| RTP10690_3 | Opaque-2 like transcriptional activators | aacgtcACGTgacgcta |
| RTP10690_3 | ABA response elements | taacgtcaCGTGacgct |
| RTP10690_3 | Plant G-box/C-box bZIP proteins | gtagcgtcACGTgacgttacc |
| RTP10690_3 | Myc-like basic helix-loop-helix binding factors | tagcgtCACGtgacgttac |
| RTP10690_3 | Opaque-2 like transcriptional activators | agcgtcACGTgacgtta |
| RTP10690_3 | Cell-death specification 2 | gtaacGTCAcg |
| RTP10690_3 | Plant G-box/C-box bZIP proteins | cttaggtaACGTcacgtgacg |
| RTP10690_3 | Plant specific NAC [NAM (no apical meristem), ATAF172, CUC2 (cup-shaped cotyledons 2)] transcription factors | aggcttaggtaacgtCACGtgacgcta |
| RTP10690_3 | Opaque-2 like transcriptional activators | taggtaACGTcacgtga |
| RTP10690_3 | Plant G-box/C-box bZIP proteins | gtcacgTGACgttacctaagc |
| RTP10690_3 | Opaque-2 like transcriptional activators | cacgtgACGTtacctaa |
| RTP10690_3 | GT-box elements | cgtgacGTTAcctaagc |
| RTP10690_3 | Cell-death specification 2 | cttagGTAAcg |
| RTP10690_3 | Vertebrate TATA binding protein factor | cgttaccTAAGcctagg |
| RTP10690_3 | Plant G-box/C-box bZIP proteins | gttacgtaACGTcagctgagg |
| RTP10690_3 | Plant G-box/C-box bZIP proteins | ctcagcTGACgttacgtaacg |
| RTP10690_3 | Plant specific NAC [NAM (no apical meristem), ATAF172, CUC2 (cup-shaped cotyledons 2)] transcription factors | agcctcagctgacgtTACGtaacgcta |
| RTP10690_3 | Opaque-2 like transcriptional activators | cagctgACGTtacgtaa |
| RTP10690_3 | GT-box elements | gctgacGTTAcgtaacg |
| RTP10690_3 | Cell-death specification 2 | gttacGTAAcg |
| RTP10690_3 | Plant G-box/C-box bZIP proteins | ctagcgttACGTaacgtcagc |
| RTP10690_3 | Opaque-2 like transcriptional activators | agcgttACGTaacgtca |
| RTP10690_3 | Cell-death specification 2 | gttacGTAAcg |
| RTP10690_3 | Opaque-2 like transcriptional activators | gacgttACGTaacgcta |
| RTP10690_3 | GT-box elements | cctagcGTTAcgtaacg |
| RTP10690_3 | Plant specific NAC [NAM (no apical meristem), ATAF172, CUC2 (cup-shaped cotyledons 2)] transcription factors | gagcctacctagcgtTACGtaacgtca |
| RTP10690_3 | Calmodulin binding/CGCG box binding proteins | gccCGTGtcagctgagc |
| RTP10690_3 | Bel-1 similar region | tgtcctgcccgtgTCAGctgagc |
| RTP10690_4 | Dehydration responsive element binding factors | gaatgaaaCCGAtctacgtag |
| RTP10690_4 | Light responsive element motif, not modulated by different light qualities | cgATCTacgta |
| RTP10690_4 | Plant G-box/C-box bZIP proteins | ataatctcACGTgaggctagg |
| RTP10690_4 | Myc-like basic helix-loop-helix binding factors | taatctCACGtgaggctag |
| RTP10690_4 | Opaque-2 like transcriptional activators | aatctcACGTgaggcta |
| RTP10690_4 | ABA response elements | taatctcACGTgaggct |
| RTP10690_4 | Plant G-box/C-box bZIP proteins | ctagcctcACGTgagattatg |
| RTP10690_4 | Myc-like basic helix-loop-helix binding factors | tagcctCACGtgagattat |
| RTP10690_4 | Opaque-2 like transcriptional activators | agcctcACGTgagatta |
| RTP10690_4 | Brassinosteroid (BR) response element | cctcaCGTGagattatg |
| RTP10690_4 | Cell-death specification 2 | attatGTAAgg |
| RTP10690_4 | Vertebrate TATA binding protein factor | gattatgTAAGgctagg |
| RTP10690_4 | Plant G-box/C-box bZIP proteins | gtcacgTGACgctacctagcc |
| RTP10690_4 | Plant G-box/C-box bZIP proteins | gctaggtaGCGTcacgtgacg |
| RTP10690_4 | ABA response elements | tagcgtcaCGTGacgtt |
| RTP10690_4 | Plant G-box/C-box bZIP proteins | gtaacgtcACGTgacgctacc |
| RTP10690_4 | Myc-like basic helix-loop-helix binding factors | taacgtCACGtgacgctac |
| RTP10690_4 | Opaque-2 like transcriptional activators | aacgtcACGTgacgcta |
| RTP10690_4 | ABA response elements | taacgtcaCGTGacgct |
| RTP10690_4 | Plant G-box/C-box bZIP proteins | gtagcgtcACGTgacgttacc |
| RTP10690_4 | Myc-like basic helix-loop-helix binding factors | tagcgtCACGtgacgttac |
| RTP10690_4 | Opaque-2 like transcriptional activators | agcgtcACGTgacgtta |
| RTP10690_4 | Cell-death specification 2 | gtaacGTCAcg |
| RTP10690_4 | Plant G-box/C-box bZIP proteins | gttaggtaACGTcacgtgacg |
| RTP10690_4 | Plant specific NAC [NAM (no apical meristem), ATAF172, CUC2 (cup-shaped cotyledons 2)] transcription factors | agtgttaggtaacgtCACGtgacgcta |
| RTP10690_4 | Opaque-2 like transcriptional activators | taggtaACGTcacgtga |
| RTP10690_4 | Plant G-box/C-box bZIP proteins | gtcacgTGACgttacctaaca |
| RTP10690_4 | Opaque-2 like transcriptional activators | cacgtgACGTtacctaa |
| RTP10690_4 | GT-box elements | cgtgacGTTAcctaaca |
| RTP10690_4 | Cell-death specification 2 | gttagGTAAcg |
| RTP10690_4 | Plant G-box/C-box bZIP proteins | ctcagcTGACgctagctagtg |
| RTP10690_4 | Plant G-box/C-box bZIP proteins | actagctaGCGTcagctgagc |
| RTP10690_4 | Telo box (plant interstitial telomere motifs) | gctaaCCCTacgtag |
| RTP10690_4 | Opaque-2 like transcriptional activators | aaccctACGTagcctca |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_4 | Brassinosteroid (BR) response element | gctcaCGTGaggctacg |
| RTP10690_4 | Plant G-box/C-box bZIP proteins | gtaagctcACGTgaggctacg |
| RTP10690_4 | Myc-like basic helix-loop-helix binding factors | taagctCACGtgaggctac |
| RTP10690_4 | Opaque-2 like transcriptional activators | aagctcACGTgaggcta |
| RTP10690_4 | Plant G-box/C-box bZIP proteins | gtagcctcACGTgagcttacc |
| RTP10690_4 | Myc-like basic helix-loop-helix binding factors | tagcctCACGtgagcttac |
| RTP10690_4 | Opaque-2 like transcriptional activators | agcctcACGTgagctta |
| RTP10690_4 | Brassinosteroid (BR) response element | cctcaCGTGagcttacc |
| RTP10690_4 | GT-box elements | cctcacGTGAgcttacc |
| RTP10690_4 | Cell-death specification 2 | gttagGTAAgc |
| RTP10690_4 | MYB IIG-type binding sites | tagcgttaGGTAAgc |
| RTP10690_4 | Core promoter motif ten elements | cttacctAACGctacgtagcc |
| RTP10690_4 | Plant G-box/C-box bZIP proteins | gtgaggctACGTagcgttagg |
| RTP10690_4 | Opaque-2 like transcriptional activators | gaggctACGTagcgtta |
| RTP10690_4 | Opaque-2 like transcriptional activators | aacgctACGTagcctca |
| RTP10690_4 | Root hair-specific cis-elements in angiosperms | aacgctacgtagcctCACGtgacta |
| RTP10690_4 | Plant specific NAC [NAM (no apical meristem), ATAF172, CUC2 (cup-shaped cotyledons 2)] transcription factors | aacgctacgtagcctCACGtgactaag |
| RTP10690_4 | ABA response elements | tagcctcaCGTGactaa |
| RTP10690_4 | Plant G-box/C-box bZIP proteins | ccttagtcACGTgaggctacg |
| RTP10690_4 | Myc-like basic helix-loop-helix binding factors | cttagtCACGtgaggctac |
| RTP10690_4 | Opaque-2 like transcriptional activators | ttagtcACGTgaggcta |
| RTP10690_4 | Plant G-box/C-box bZIP proteins | gtagcctcACGTgactaagga |
| RTP10690_4 | Myc-like basic helix-loop-helix binding factors | tagcctCACGtgactaagg |
| RTP10690_4 | Opaque-2 like transcriptional activators | agcctcACGTgactaag |
| RTP10690_4 | GT-box elements | cctcacGTGActaagga |
| RTP10690_4 | MYB IIG-type binding sites | aatgGGTAggtcatc |
| RTP10690_5 | Plant G-box/C-box bZIP proteins | gttacgtaACGTcagctgagg |
| RTP10690_5 | Plant G-box/C-box bZIP proteins | ctcagcTGACgttacgtaacg |
| RTP10690_5 | Plant specific NAC [NAM (no apical meristem), ATAF172, CUC2 (cup-shaped cotyledons 2)] transcription factors | agcctcagctgacgtTACGtaacgcta |
| RTP10690_5 | Opaque-2 like transcriptional activators | cagctgACGTtacgtaa |
| RTP10690_5 | GT-box elements | gctgacGTTAcgtaacg |
| RTP10690_5 | Cell-death specification 2 | gttacGTAAcg |
| RTP10690_5 | Plant G-box/C-box bZIP proteins | ctagcgttACGTaacgtcagc |
| RTP10690_5 | Opaque-2 like transcriptional activators | agcgttACGTaacgtca |
| RTP10690_5 | Cell-death specification 2 | gttacGTAAcg |
| RTP10690_5 | Opaque-2 like transcriptional activators | gacgttACGTaacgcta |
| RTP10690_5 | GT-box elements | cctagcGTTAcgtaacg |
| RTP10690_5 | Plant specific NAC [NAM (no apical meristem), ATAF172, CUC2 (cup-shaped cotyledons 2)] transcription factors | gacgctacctagcgtTACGtaacgtca |
| RTP10690_5 | Plant G-box/C-box bZIP proteins | gtcacgTGACgctacctagcg |
| RTP10690_5 | Plant G-box/C-box bZIP proteins | gctaggtaGCGTcacgtgacg |
| RTP10690_5 | ABA response elements | tagcgtcaCGTGacgtt |
| RTP10690_5 | Plant G-box/C-box bZIP proteins | ctaacgtcACGTgacgctacc |
| RTP10690_5 | Myc-like basic helix-loop-helix binding factors | taacgtCACGtgacgctac |
| RTP10690_5 | Opaque-2 like transcriptional activators | aacgtcACGTgacgcta |
| RTP10690_5 | ABA response elements | taacgtcaCGTGacgct |
| RTP10690_5 | Plant G-box/C-box bZIP proteins | gtagcgtcACGTgacgttagc |
| RTP10690_5 | Myc-like basic helix-loop-helix binding factors | tagcgtCACGtgacgttag |
| RTP10690_5 | Opaque-2 like transcriptional activators | agcgtcACGTgacgtta |
| RTP10690_5 | Plant G-box/C-box bZIP proteins | gttagctaACGTcacgtgacg |
| RTP10690_5 | Plant specific NAC [NAM (no apical meristem), ATAF172, CUC2 (cup-shaped cotyledons 2)] transcription factors | agcgttagctaacgtCACGtgacgcta |
| RTP10690_5 | Opaque-2 like transcriptional activators | tagctaACGTcacgtga |
| RTP10690_5 | Plant G-box/C-box bZIP proteins | gtcacgTGACgttagctaacg |
| RTP10690_5 | MYB-like proteins | cacgtgacGTTAgctaa |
| RTP10690_5 | Plant G-box/C-box bZIP proteins | ctcagcTGACgctacctagcg |
| RTP10690_5 | Plant G-box/C-box bZIP proteins | gctaggtaGCGTcagctgagc |
| RTP10690_5 | Plant specific NAC [NAM (no apical meristem), ATAF172, CUC2 (cup-shaped cotyledons 2)] transcription factors | agcgtcagctgagctTACGtaagcgcc |
| RTP10690_5 | Vertebrate TATA binding protein factor | gcttacgTAAGctcagc |
| RTP10690_5 | Cell-death specification 2 | cttacGTAAgc |
| RTP10690_5 | Plant G-box/C-box bZIP proteins | tggcgcttACGTaagctcagc |
| RTP10690_5 | Opaque-2 like transcriptional activators | gcgcttACGTaagctca |
| RTP10690_5 | Cell-death specification 2 | cttacGTAAgc |
| RTP10690_5 | Plant G-box/C-box bZIP proteins | ctgagcttACGTaagcgccac |
| RTP10690_5 | Opaque-2 like transcriptional activators | gagcttACGTaagcgcc |
| RTP10690_5 | Vertebrate TATA binding protein factor | gcttacgTAAGcgccac |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
|---|---|---|
| RTP10690_5 | Plant specific NAC [NAM (no apical meristem), ATAF172, CUC2 (cup-shaped cotyledons 2)] transcription factors | cctgcccgtggcgctTACGtaagctca |
| RTP10690_5 | Enhancer element first identified in the promoter of the octopine synthase gene (OCS) of the Agrobacterium tumefaciens T-DNA | tgcccgtggcgctTACGtaag |
| RTP10690_5 | Calmodulin binding/CGCG box binding proteins | gccCGTGgcgcttacgt |
| RTP10690_5 | Plant specific NAC [NAM (no apical meristem), ATAF172, CUC2 (cup-shaped cotyledons 2)] transcription factors | agcttacgtaagcgccACGGgcaggac |
| RTP10690_5 | Plant G-box/C-box bZIP proteins | tgtcctgcCCGTggcgcttac |
| RTP10690_6 | Dehydration responsive element binding factors | gaatgaaaCCGAtctacgtag |
| RTP10690_6 | Light responsive element motif, not modulated by different light qualities | cgATCTacgta |
| RTP10690_6 | Cell-death specification 2 | cttagGTAAgc |
| RTP10690_6 | Opaque-2 like transcriptional activators | gagcctACGTagcctta |
| RTP10690_6 | ABA response elements | taggctcaCGTGacgtt |
| RTP10690_6 | Plant G-box/C-box bZIP proteins | gtaacgtcACGTgagcctacg |
| RTP10690_6 | Myc-like basic helix-loop-helix binding factors | taacgtCACGtgagcctac |
| RTP10690_6 | Opaque-2 like transcriptional activators | aacgtcACGTgagcta |
| RTP10690_6 | Plant G-box/C-box bZIP proteins | gtaggctcACGTgacgttacg |
| RTP10690_6 | Myc-like basic helix-loop-helix binding factors | taggctCACGtgacgttac |
| RTP10690_6 | Opaque-2 like transcriptional activators | aggctcACGTgacgtta |
| RTP10690_6 | Cell-death specification 2 | gtaacGTCAcg |
| RTP10690_6 | Plant G-box/C-box bZIP proteins | cttacgtaACGTcacgtgagc |
| RTP10690_6 | Opaque-2 like transcriptional activators | tacgtaACGTcacgtga |
| RTP10690_6 | Plant G-box/C-box bZIP proteins | ctcacgTGACgttacgtaagg |
| RTP10690_6 | Plant specific NAC [NAM (no apical meristem), ATAF172, CUC2 (cup-shaped cotyledons 2)] transcription factors | aggctcacgtgacgtTACGtaaggcta |
| RTP10690_6 | Opaque-2 like transcriptional activators | cacgtgACGTtacgtaa |
| RTP10690_6 | GT-box elements | cgtgacGTTAcgtaagg |
| RTP10690_6 | Cell-death specification 2 | cttacGTAAcg |
| RTP10690_6 | Plant G-box/C-box bZIP proteins | gtagccttACGTaacgtcacg |
| RTP10690_6 | Opaque-2 like transcriptional activators | agccttACGTaacgtca |
| RTP10690_6 | Cell-death specification 2 | gttacGTAAgg |
| RTP10690_6 | Opaque-2 like transcriptional activators | gacgttACGTaaggcta |
| RTP10690_6 | Plant specific NAC [NAM (no apical meristem), ATAF172, CUC2 (cup-shaped cotyledons 2)] transcription factors | gacgctacgtagcctTACGtaacgtca |
| RTP10690_6 | Opaque-2 like transcriptional activators | gacgctACGTagcctta |
| RTP10690_6 | Plant G-box/C-box bZIP proteins | gtaaggctACGTagcgtcacg |
| RTP10690_6 | Opaque-2 like transcriptional activators | aaggctACGTagcgtca |
| RTP10690_6 | Plant G-box/C-box bZIP proteins | ctcacgTGACgctacgtagcc |
| RTP10690_6 | Plant G-box/C-box bZIP proteins | gctacgtaGCGTcacgtgagc |
| RTP10690_6 | Plant G-box/C-box bZIP proteins | gtaagctcACGTgacgctacg |
| RTP10690_6 | Myc-like basic helix-loop-helix binding factors | taagctCACGtgacgctac |
| RTP10690_6 | Opaque-2 like transcriptional activators | aagctcACGTgacgcta |
| RTP10690_6 | ABA response elements | taagctcaCGTGacgct |
| RTP10690_6 | Plant G-box/C-box bZIP proteins | gtagcgtcACGTgagcttacc |
| RTP10690_6 | Myc-like basic helix-loop-helix binding factors | tagcgtCACGtgagcttac |
| RTP10690_6 | Opaque-2 like transcriptional activators | agcgtcACGTgagctta |
| RTP10690_6 | GT-box elements | cgtcacGTGAgcttacc |
| RTP10690_6 | Plant specific NAC [NAM (no apical meristem), ATAF172, CUC2 (cup-shaped cotyledons 2)] transcription factors | agagttaggtaagctCACGtgacgcta |
| RTP10690_6 | Cell-death specification 2 | gttagGTAAgc |
| RTP10690_6 | MYB IIG-type binding sites | tagagttaGGTAagc |
| RTP10690_6 | MYB-like proteins | tagctagAGTTaggtaa |
| RTP10690_6 | ABA response elements | tagcctcaCGTGacctt |
| RTP10690_6 | Plant G-box/C-box bZIP proteins | ctaaggtcACGTgaggctagc |
| RTP10690_6 | Myc-like basic helix-loop-helix binding factors | taaggtCACGtgaggctag |
| RTP10690_6 | Opaque-2 like transcriptional activators | aaggtcACGTgaggcta |
| RTP10690_6 | Dc3 promoter binding factors | cTCACgtgacc |
| RTP10690_6 | Plant G-box/C-box bZIP proteins | ctagcctcACGTgaccttagc |
| RTP10690_6 | Myc-like basic helix-loop-helix binding factors | tagcctCACGtgaccttag |
| RTP10690_6 | Opaque-2 like transcriptional activators | agcctcACGTgaccttа |
| RTP10690_6 | GT-box elements | cctcacGTGAccttagc |
| RTP10690_6 | Plant specific NAC [NAM (no apical meristem), ATAF172, CUC2 (cup-shaped cotyledons 2)] transcription factors | agtgttagctaaggtCACGtgaggcta |
| RTP10690_6 | Plant G-box/C-box bZIP proteins | ctaagcTGACgctacctagtg |
| RTP10690_7 | L1 box, motif for L1 layer-specific expression | aatCAGTaaattgaacg |
| RTP10690_7 | Arabidopsis homeobox protein | caaTTTActga |
| RTP10690_7 | Sucrose box | gaCAATcagtaaattgaac |
| RTP10690_7 | Enhancer element first identified in the promoter of the octopine synthase gene (OCS) of the Agrobacterium tumefaciens T-DNA | tttactgattgtctACGTagc |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
|---|---|---|
| RTP10690_7 | Plant specific NAC [NAM (no apical meristem), ATAF172, CUC2 (cup-shaped cotyledons 2)] transcription factors | aatttactgattgtcTACGtagcgtca |
| RTP10690_7 | Plant G-box/C-box bZIP proteins | gattgtctACGTagcgtcacc |
| RTP10690_7 | Plant G-box/C-box bZIP proteins | gtcaggTGACgctacgtagac |
| RTP10690_7 | Plant G-box/C-box bZIP proteins | tctacgtaGCGTcacctgacg |
| RTP10690_7 | Plant G-box/C-box bZIP proteins | cgtagcgtcaccTGACgttac |
| RTP10690_7 | Plant G-box/C-box bZIP proteins | cttacgtaACGTcaggtgacg |
| RTP10690_7 | Plant G-box/C-box bZIP proteins | gtcaccTGACgttacgtaagg |
| RTP10690_7 | Plant specific NAC [NAM (no apical meristem), ATAF172, CUC2 (cup-shaped cotyledons 2)] transcription factors | agcgtcacctgacgtTACGtaaggcta |
| RTP10690_7 | Opaque-2 like transcriptional activators | cacctgACGTtacgtaa |
| RTP10690_7 | GT-box elements | cctgacGTTAcgtaagg |
| RTP10690_7 | Cell-death specification 2 | cttacGTAAcg |
| RTP10690_7 | Plant G-box/C-box bZIP proteins | gtagccttACGTaacgtcagg |
| RTP10690_7 | Opaque-2 like transcriptional activators | agccttACGTaacgtca |
| RTP10690_7 | Cell-death specification 2 | gttacGTAAgg |
| RTP10690_7 | Opaque-2 like transcriptional activators | gacgttACGTaaggcta |
| RTP10690_7 | Plant specific NAC [NAM (no apical meristem), ATAF172, CUC2 (cup-shaped cotyledons 2)] transcription factors | gagcctaggtagcctTACGtaacgtca |
| RTP10690_7 | ABA response elements | taggctcaCGTGacgtt |
| RTP10690_7 | Plant G-box/C-box bZIP proteins | gtaacgtcACGTgagcctagg |
| RTP10690_7 | Myc-like basic helix-loop-helix binding factors | taacgtCACGtgagcctag |
| RTP10690_7 | Opaque-2 like transcriptional activators | aacgtcACGTgagccta |
| RTP10690_7 | Plant G-box/C-box bZIP proteins | ctaggctcACGTgacgttacg |
| RTP10690_7 | Myc-like basic helix-loop-helix binding factors | taggctCACGtgacgttac |
| RTP10690_7 | Opaque-2 like transcriptional activators | aggctcACGTgacgtta |
| RTP10690_7 | Cell-death specification 2 | gtaacGTCAcg |
| RTP10690_7 | Plant G-box/C-box bZIP proteins | gttacgtaACGTcacgtgagc |
| RTP10690_7 | Opaque-2 like transcriptional activators | tacgtaACGTcacgtga |
| RTP10690_7 | Plant G-box/C-box bZIP proteins | ctcacgTGACgttacgtaacg |
| RTP10690_7 | Plant specific NAC [NAM (no apical meristem), ATAF172, CUC2 (cup-shaped cotyledons 2)] transcription factors | aggctcacgtgacgtTACGtaacgcta |
| RTP10690_7 | Opaque-2 like transcriptional activators | cacgtgACGTtacgtaa |
| RTP10690_7 | GT-box elements | cgtgacGTTAcgtaacg |
| RTP10690_7 | Cell-death specification 2 | gttacGTAAcg |
| RTP10690_7 | Plant G-box/C-box bZIP proteins | gtagcgttACGTaacgtcacg |
| RTP10690_7 | Opaque-2 like transcriptional activators | agcgttACGTaacgtca |
| RTP10690_7 | Cell-death specification 2 | gttacGTAAcg |
| RTP10690_7 | Opaque-2 like transcriptional activators | gacgttACGTaacgcta |
| RTP10690_7 | GT-box elements | cgtagcGTTAcgtaacg |
| RTP10690_7 | Plant specific NAC [NAM (no apical meristem), ATAF172, CUC2 (cup-shaped cotyledons 2)] transcription factors | gacgctacgtagcgtTACGtaacgtca |
| RTP10690_7 | Plant G-box/C-box bZIP proteins | ctgacgctACGTagcgttacg |
| RTP10690_7 | Opaque-2 like transcriptional activators | gacgctACGTagcgtta |
| RTP10690_7 | Plant G-box/C-box bZIP proteins | gtaacgctACGTagcgtcagg |
| RTP10690_7 | Opaque-2 like transcriptional activators | aacgctACGTagcgtca |
| RTP10690_7 | Plant G-box/C-box bZIP proteins | ctcaccTGACgctacgtagcg |
| RTP10690_7 | Plant G-box/C-box bZIP proteins | gctacgtaGCGTcaggtgagg |
| RTP10690_7 | MYB-like proteins | caggtgagGTTAgctaa |
| RTP10690_7 | Plant G-box/C-box bZIP proteins | cttacctaACGTcaggtgagg |
| RTP10690_7 | Plant G-box/C-box bZIP proteins | ctcaccTGACgttaggtaagg |
| RTP10690_7 | MYB IIG-type binding sites | tgacgttaGGTAagg |
| RTP10690_7 | Cell-death specification 2 | gttagGTAAgg |
| RTP10690_7 | GT-box elements | cgttagGTAAggctacg |
| RTP10690_7 | Opaque-2 like transcriptional activators | gacgctACGTagcctta |
| RTP10690_7 | Plant G-box/C-box bZIP proteins | gtaaggctACGTagcgtcacc |
| RTP10690_7 | Opaque-2 like transcriptional activators | aaggctACGTagcgtca |
| RTP10690_7 | Plant G-box/C-box bZIP proteins | ctcaggTGACgctacgtagcc |
| RTP10690_7 | Plant G-box/C-box bZIP proteins | gctacgtaGCGTcacctgaga |
| RTP10690_7 | Myc-like basic helix-loop-helix binding factors | tagcgtCACCtgagattag |
| RTP10690_7 | ABA response elements | tagactcaCGTGaccttt |
| RTP10690_7 | Plant G-box/C-box bZIP proteins | ctaaggtcACGTgagtctagg |
| RTP10690_7 | Myc-like basic helix-loop-helix binding factors | taaggtCACGtgagtctag |
| RTP10690_7 | Opaque-2 like transcriptional activators | aaggtcACGTgagtcta |
| RTP10690_7 | TEF-box | ctAAGGtcacgtgagtctagg |
| RTP10690_7 | Dc3 promoter binding factors | cTCACgtgacc |
| RTP10690_7 | Plant G-box/C-box bZIP proteins | ctagactcACGTgaccttagg |
| RTP10690_7 | Myc-like basic helix-loop-helix binding factors | tagactCACGtgaccttag |
| RTP10690_7 | Opaque-2 like transcriptional activators | agactcACGTgacctta |
| RTP10690_7 | GT-box elements | actcacGTGAccttagg |
| RTP10690_7 | Cell-death specification 2 | cttagGTAAcg |
| RTP10690_7 | GT-box elements | ccttagGTAAcgctacg |
| RTP10690_7 | GT-box elements | cgtagcGTTAcctaagg |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_7 | Plant G-box/C-box bZIP proteins | ttgacgctACGTagcgttacc |
| RTP10690_7 | Opaque-2 like transcriptional activators | gacgctACGTagcgtta |
| RTP10690_7 | Plant G-box/C-box bZIP proteins | gtaacgctACGTagcgtcaaa |
| RTP10690_7 | Opaque-2 like transcriptional activators | aacgctACGTagcgtca |
| RTP10690_7 | Plant specific NAC [NAM (no apical meristem), ATAF172, CUC2 (cup-shaped cotyledons 2)] transcription factors | gtaaagctttgacgctACGTagcgtta |
| RTP10690_7 | Plant G-box/C-box bZIP proteins | gctacgtaGCGTcaaagcttt |
| RTP10690_7 | Calcium regulated NAC-factors | taaaGCTTtgacgctacgtag |
| RTP10690_7 | W Box family | aagctTTGAcgctacgt |
| RTP10690_7 | Tracheary-element-regulating cis-elements, conferring TE-specific expression | cgtcAAAGctt |
| RTP10690_7 | Vertebrate TATA binding protein factor | cgttgTAAAgctttgac |
| RTP10690_7 | DNA binding with one finger (DOF) | agcgttgtAAAGctttg |
| RTP10690_7 | Mitochondral HMG-box transcription factor | tgtagcgTTGTaa |
| RTP10690_8 | Secondary wall NACS | gattttagttcTAAGttag |
| RTP10690_8 | AS1/AS2 repressor complex | gagTTGAtt |
| RTP10690_8 | Calmodulin binding/CGCG box binding proteins | agaCGCGtcacaaagag |
| RTP10690_8 | Coupling element 3 sequence | ggtagaCGCGtcacaaaga |
| RTP10690_8 | Plant G-box/C-box bZIP proteins | aggtagacGCGTcacaaagag |
| RTP10690_8 | Plant G-box/C-box bZIP proteins | tctttgTGACgcgtctaccta |
| RTP10690_8 | Calmodulin binding/CGCG box binding proteins | tgaCGCGtctacctaga |
| RTP10690_8 | Plant G-box/C-box bZIP proteins | gctagtgtcagcTGACgttac |
| RTP10690_8 | Plant G-box/C-box bZIP proteins | cttacgtaACGTcagctgaca |
| RTP10690_8 | Plant G-box/C-box bZIP proteins | gtcagcTGACgttacgtaagg |
| RTP10690_8 | Plant specific NAC [NAM (no apical meristem), ATAF172, CUC2 (cup-shaped cotyledons 2)] transcription factors | agtgtcagctgacgtTACGtaaggcta |
| RTP10690_8 | Opaque-2 like transcriptional activators | cagctgACGTtacgtaa |
| RTP10690_8 | GT-box elements | gctgacGTTAcgtaagg |
| RTP10690_8 | Cell-death specification 2 | cttacGTAAcg |
| RTP10690_8 | Plant G-box/C-box bZIP proteins | ttagccttACGTaacgtcagc |
| RTP10690_8 | Opaque-2 like transcriptional activators | agccttACGTaacgtca |
| RTP10690_8 | Cell-death specification 2 | gttacGTAAgg |
| RTP10690_8 | Opaque-2 like transcriptional activators | gacgttACGTaaggcta |
| RTP10690_8 | Plant specific NAC [NAM (no apical meristem), ATAF172, CUC2 (cup-shaped cotyledons 2)] transcription factors | gacgctagttagcctTACGtaacgtca |
| RTP10690_8 | MYB-like proteins | tgacgctAGTTagccctt |
| RTP10690_8 | Plant G-box/C-box bZIP proteins | gtcacgTGACgctagttagcc |
| RTP10690_8 | ABA response elements | tagcgtcaCGTGacctt |
| RTP10690_8 | Plant G-box/C-box bZIP proteins | gtaaggtcACGTgacgctagt |
| RTP10690_8 | Myc-like basic helix-loop-helix binding factors | taaggtCACGtgacgctag |
| RTP10690_8 | Opaque-2 like transcriptional activators | aaggtcACGtgacgcta |
| RTP10690_8 | ABA response elements | taaggtcaCGTGacgct |
| RTP10690_8 | Dc3 promoter binding factors | gTCACgtgacc |
| RTP10690_8 | Plant G-box/C-box bZIP proteins | ctagcgtcACGTgaccttacg |
| RTP10690_8 | Myc-like basic helix-loop-helix binding factors | tagcgtCACGtgaccttac |
| RTP10690_8 | Opaque-2 like transcriptional activators | agcgtcACGTgacctta |
| RTP10690_8 | GT-box elements | cgtcacGTGAccttacg |
| RTP10690_8 | Plant specific NAC [NAM (no apical meristem), ATAF172, CUC2 (cup-shaped cotyledons 2)] transcription factors | agcgttacgtaaggtCACGtgacgcta |
| RTP10690_8 | Plant specific NAC [NAM (no apical meristem), ATAF172, CUC2 (cup-shaped cotyledons 2)] transcription factors | agcgtcacgtgacctTACGtaacgcta |
| RTP10690_8 | Cell-death specification 2 | gttacGTAAgg |
| RTP10690_8 | Plant G-box/C-box bZIP proteins | gtagcgttACGTaaggtcacg |
| RTP10690_8 | Opaque-2 like transcriptional activators | agcgttACGTaaggtca |
| RTP10690_8 | Cell-death specification 2 | cttacGTAAcg |
| RTP10690_8 | Opaque-2 like transcriptional activators | gaccttACGTaacgcta |
| RTP10690_8 | GT-box elements | cgtagcGTTAcgtaagg |
| RTP10690_8 | Plant specific NAC [NAM (no apical meristem), ATAF172, CUC2 (cup-shaped cotyledons 2)] transcription factors | gagcctacgtagcgtTACGtaaggtca |
| RTP10690_8 | Plant G-box/C-box bZIP proteins | ctgagcctACGTagcgttacg |
| RTP10690_8 | Opaque-2 like transcriptional activators | gagcctACGTagcgtta |
| RTP10690_8 | Telo box (plant interstitial telomere motifs) | gctaACCCtagctag |
| RTP10690_8 | ABA response elements | tagtgtcACGTgagctt |
| RTP10690_8 | Plant G-box/C-box bZIP proteins | gtaagctcACGTgacactagc |
| RTP10690_8 | Myc-like basic helix-loop-helix binding factors | taagctCACGtgacactag |
| RTP10690_8 | Opaque-2 like transcriptional activators | aagctcACGTgacacta |
| RTP10690_8 | ABA response elements | taagctcaCGTGacact |
| RTP10690_8 | Plant G-box/C-box bZIP proteins | ctagtgtcACGTgagcttacg |
| RTP10690_8 | Myc-like basic helix-loop-helix binding factors | tagtgtCACGtgagcttac |
| RTP10690_8 | Opaque-2 like transcriptional activators | agtgtcACGTgagctta |
| RTP10690_8 | GT-box elements | tgtcacGTGAgcttacg |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_8 | Enhancer element first identified in the promoter of the octopine synthase gene (OCS) of the Agrobacterium tumefaciens T-DNA | tgtcacgtgagctTACGctac |
| RTP10690_8 | Plant specific NAC [NAM (no apical meristem), ATAF172, CUC2 (cup-shaped cotyledons 2)] transcription factors | agtgtcacgtgagctTACGctactata |
| RTP10690_8 | Cell-death specification 2 | gtagcGTAAgc |
| RTP10690_8 | Pollen-specific regulatory elements | ctataGAAAatgtgtta |
| RTP10690_9 | CA-rich motif | agtctaaAACAactacgta |
| RTP10690_9 | General transcription factor HD, GTF2D | tcagtctaaaacaactacgtagcgtca cgtGACGttacc |
| RTP10690_9 | Plant G-box/C-box bZIP proteins | gtcacgTGACgctacgtagtt |
| RTP10690_9 | Plant G-box/C-box bZIP proteins | actacgtaGCGTcacgtgacg |
| RTP10690_9 | ABA response elements | tagcgtcaCGTGacgtt |
| RTP10690_9 | Plant G-box/C-box bZIP proteins | gtaacgtcACGTgacgctacg |
| RTP10690_9 | Myc-like basic helix-loop-helix binding factors | taacgtCACGtgacgctac |
| RTP10690_9 | Opaque-2 like transcriptional activators | aacgtcACGTgacgcta |
| RTP10690_9 | ABA response elements | taacgtcaCGTGacgct |
| RTP10690_9 | Plant G-box/C-box bZIP proteins | gtagcgtcACGTgacgttacc |
| RTP10690_9 | Myc-like basic helix-loop-helix binding factors | tagcgtCACGtgacgttac |
| RTP10690_9 | Opaque-2 like transcriptional activators | agcgtcACGTgacgtta |
| RTP10690_9 | Cell-death specification 2 | gtaacGTCAcg |
| RTP10690_9 | Plant G-box/C-box bZIP proteins | cttaggtaACGTcacgtgacg |
| RTP10690_9 | Plant specific NAC [NAM (no apical meristem), ATAF172, CUC2 (cup-shaped cotyledons 2)] transcription factors | aggcttaggtaacgtCACGtgacgcta |
| RTP10690_9 | Opaque-2 like transcriptional activators | taggtaACGTcacgtga |
| RTP10690_9 | Plant G-box/C-box bZIP proteins | gtcacgTGACgttacctaagc |
| RTP10690_9 | Opaque-2 like transcriptional activators | cacgtgACGTtacctaa |
| RTP10690_9 | GT-box elements | cgtgacGTTAcctaagc |
| RTP10690_9 | Cell-death specification 2 | cttagGTAAcg |
| RTP10690_9 | Vertebrate TATA binding protein factor | cgttaccTAAGcctagg |
| RTP10690_9 | Plant G-box/C-box bZIP proteins | gttacgtaACGTcagctgagg |
| RTP10690_9 | Plant G-box/C-box bZIP proteins | ctcagcTGACgttacgtaacg |
| RTP10690_9 | Plant specific NAC [NAM (no apical meristem), ATAF172, CUC2 (cup-shaped cotyledons 2)] transcription factors | agcctcagctgacgtTACGtaacgcta |
| RTP10690_9 | Opaque-2 like transcriptional activators | cagctgACGTtacgtaa |
| RTP10690_9 | GT-box elements | gctgacGTTAcgtaacg |
| RTP10690_9 | Cell-death specification 2 | gttacGTAAcg |
| RTP10690_9 | Plant G-box/C-box bZIP proteins | ctagcgttACGTaacgtcagc |
| RTP10690_9 | Opaque-2 like transcriptional activators | agcgttACGTaacgtca |
| RTP10690_9 | Cell-death specification 2 | gttacGTAAcg |
| RTP10690_9 | Opaque-2 like transcriptional activators | gacgttACGTaacgcta |
| RTP10690_9 | GT-box elements | cctagcGTTAcgtaacg |
| RTP10690_9 | Plant specific NAC [NAM (no apical meristem), ATAF172, CUC2 (cup-shaped cotyledons 2)] transcription factors | gagcctacctagcgtTACGtaacgtca |
| RTP10690_9 | Upstream sequence element of U-snRNA genes | aaatttACACattgcca |
| RTP10690_10 | Opaque-2 like transcriptional activators | gagcctACGTagctgaa |
| RTP10690_10 | Cell-death specification 2 | cttagGTAAgc |
| RTP10690_10 | Opaque-2 like transcriptional activators | gagcctACGTagcctta |
| RTP10690_10 | ABA response elements | taggctcaCGTGacgtt |
| RTP10690_10 | Plant G-box/C-box bZIP proteins | gtaacgtcACGTgagcctacg |
| RTP10690_10 | Myc-like basic helix-loop-helix binding factors | taacgtCACGtgagcctac |
| RTP10690_10 | Opaque-2 like transcriptional activators | aacgtcACGTgagccta |
| RTP10690_10 | Plant G-box/C-box bZIP proteins | gtaggctcACGTgacgttacg |
| RTP10690_10 | Myc-like basic helix-loop-helix binding factors | taggctCACGtgacgttac |
| RTP10690_10 | Opaque-2 like transcriptional activators | aggctcACGTgacgtta |
| RTP10690_10 | Cell-death specification 2 | gtaacGTCAcg |
| RTP10690_10 | Plant G-box/C-box bZIP proteins | cttacgtaACGTcacgtgagc |
| RTP10690_10 | Opaque-2 like transcriptional activators | tacgtaACGTcacgtga |
| RTP10690_10 | Plant G-box/C-box bZIP proteins | ctcacgTGACgttacgtaagg |
| RTP10690_10 | Plant specific NAC [NAM (no apical meristem), ATAF172, CUC2 (cup-shaped cotyledons 2)] transcription factors | aggctcacgtgacgtTACGtaaggcta |
| RTP10690_10 | Opaque-2 like transcriptional activators | cacgtgACGTtacgtaa |
| RTP10690_10 | GT-box elements | cgtgacGTTAcgtaagg |
| RTP10690_10 | Cell-death specification 2 | cttacGTAAcg |
| RTP10690_10 | Plant G-box/C-box bZIP proteins | gtagccttACGTaacgtcacg |
| RTP10690_10 | Opaque-2 like transcriptional activators | agccttACGTaacgtca |
| RTP10690_10 | Cell-death specification 2 | gttacGTAAgg |
| RTP10690_10 | Opaque-2 like transcriptional activators | gacgttACGTaaggcta |
| RTP10690_10 | Plant specific NAC [NAM (no apical meristem), ATAF172, CUC2 (cup-shaped cotyledons 2)] transcription factors | gacgctacgtagcctTACGtaacgtca |
| RTP10690_10 | Opaque-2 like transcriptional activators | gacgctACGTagcctta |
| RTP10690_10 | Plant G-box/C-box bZIP proteins | gtaaggctACGTagcgtcacg |
| RTP10690_10 | Opaque-2 like transcriptional activators | aaggctACGTagcgtca |

TABLE 172-continued lists the spacer region and the transcription factor binding motif present in the region
and the nucleotide sequence. Upper case letters denote the motif while surrounding bases
indicate examples of sequences that might neighbor the predicted motif but are not necessary for
the motif to function in the regulation of transcription

| Spacer ID | Detailed Family Information | Sequence |
| --- | --- | --- |
| RTP10690_10 | Plant G-box/C-box bZIP proteins | ctcacgTGACgctacgtagcc |
| RTP10690_10 | Plant G-box/C-box bZIP proteins | gctacgtaGCGTcacgtgagc |
| RTP10690_10 | Plant G-box/C-box bZIP proteins | gtaagctcACGTgacgctacg |
| RTP10690_10 | Myc-like basic helix-loop-helix binding factors | taagctCACGtgacgctac |
| RTP10690_10 | Opaque-2 like transcriptional activators | aagctcACGTgacgcta |
| RTP10690_10 | ABA response elements | taagctcaCGTGacgct |
| RTP10690_10 | Plant G-box/C-box bZIP proteins | gtagcgtcACGTgagcttacc |
| RTP10690_10 | Myc-like basic helix-loop-helix binding factors | tagcgtCACGtgagcttac |
| RTP10690_10 | Opaque-2 like transcriptional activators | agcgtcACGTgagctta |
| RTP10690_10 | GT-box elements | cgtcacGTGAgcttacc |
| RTP10690_10 | Plant specific NAC [NAM (no apical meristem), ATAF172, CUC2 (cup-shaped cotyledons 2)] transcription factors | agagttaggtaagctCACGtgacgcta |
| RTP10690_10 | Cell-death specification 2 | gttagGTAAgc |
| RTP10690_10 | MYB IIG-type binding sites | tagagttaGGTAagc |
| RTP10690_10 | MYB-like proteins | tagctagAGTTaggtaa |
| RTP10690_10 | ABA response elements | tagcctcaCGTGacctt |
| RTP10690_10 | Plant G-box/C-box bZIP proteins | ctaaggtcACGTgaggctagc |
| RTP10690_10 | Myc-like basic helix-loop-helix binding factors | taaggtCACGtgaggctag |
| RTP10690_10 | Opaque-2 like transcriptional activators | aaggtcACGTgaggcta |
| RTP10690_10 | Dc3 promoter binding factors | cTCACgtgacc |
| RTP10690_10 | Plant G-box/C-box bZIP proteins | ctagcctcACGTgaccttagc |
| RTP10690_10 | Myc-like basic helix-loop-helix binding factors | tagcctCACGtgaccttag |
| RTP10690_10 | Opaque-2 like transcriptional activators | agcctcACGTgacctta |
| RTP10690_10 | GT-box elements | cctcacGTGAccttagc |
| RTP10690_10 | Plant specific NAC [NAM (no apical meristem), ATAF172, CUC2 (cup-shaped cotyledons 2)] transcription factors | agtgttagctaaggtCACGtgaggcta |
| RTP10690_10 | Plant G-box/C-box bZIP proteins | ctgtgcTGACgctacctagtg |
| RTP10690_10 | Plant G-box/C-box bZIP proteins | actaggtaGCGTcagcacaga |
| RTP10690_10 | Myc-like basic helix-loop-helix binding factors | agtattCATCtgtgctgac |
| RTP10690_10 | GAP-Box (light response elements) | acagATGAatactag |
| RTP10690_11 | VIP1 responsive elements | acacgGCTCag |
| RTP10690_11 | Plant G-box/C-box bZIP proteins | gttacgtaACGTcagctgagg |
| RTP10690_11 | Plant G-box/C-box bZIP proteins | ctcagcTGACgttacgtaacg |
| RTP10690_11 | Plant specific NAC [NAM (no apical meristem), ATAF172, CUC2 (cup-shaped cotyledons 2)] transcription factors | agcctcagctgacgtTACGtaacgcta |
| RTP10690_11 | Opaque-2 like transcriptional activators | cagctgACGTtacgtaa |
| RTP10690_11 | GT-box elements | gctgacGTTAcgtaacg |
| RTP10690_11 | Cell-death specification 2 | gttacGTAAcg |
| RTP10690_11 | Plant G-box/C-box bZIP proteins | ctagcgttACGTaacgtcagc |
| RTP10690_11 | Opaque-2 like transcriptional activators | agcgttACGTaacgtca |
| RTP10690_11 | Cell-death specification 2 | gttacGTAAcg |
| RTP10690_11 | Opaque-2 like transcriptional activators | gacgttACGTaacgcta |
| RTP10690_11 | GT-box elements | cctagcGTTAcgtaacg |
| RTP10690_11 | Plant specific NAC [NAM (no apical meristem), ATAF172, CUC2 (cup-shaped cotyledons 2)] transcription factors | gacgctacctagcgtTACGtaacgtca |
| RTP10690_11 | Plant G-box/C-box bZIP proteins | gtcacgTGACgctacctagcg |
| RTP10690_11 | Plant G-box/C-box bZIP proteins | gctaggtaGCGTcacgtgacg |
| RTP10690_11 | ABA response elements | tagcgtcaCGTGacgtt |
| RTP10690_11 | Plant G-box/C-box bZIP proteins | ctaacgtcACGTgacgctacc |
| RTP10690_11 | Myc-like basic helix-loop-helix binding factors | taacgtCACGtgacgctac |
| RTP10690_11 | Opaque-2 like transcriptional activators | aacgtcACGTgacgcta |
| RTP10690_11 | ABA response elements | taacgtcaCGTGacgct |
| RTP10690_11 | Plant G-box/C-box bZIP proteins | gtagcgtcACGTgacgttagc |
| RTP10690_11 | Myc-like basic helix-loop-helix binding factors | tagcgtCACGtgacgttag |
| RTP10690_11 | Opaque-2 like transcriptional activators | agcgtcACGTgacgtta |
| RTP10690_11 | Plant G-box/C-box bZIP proteins | gttagctaACGTcacgtgacg |
| RTP10690_11 | Plant specific NAC [NAM (no apical meristem), ATAF172, CUC2 (cup-shaped cotyledons 2)] transcription factors | agcgttagctaacgtCACGtgacgcta |
| RTP10690_11 | Opaque-2 like transcriptional activators | tagctaACGTcacgtga |
| RTP10690_11 | Plant G-box/C-box bZIP proteins | gtcacgTGACgttagctaacg |
| RTP10690_11 | MYB-like proteins | cacgtgacGTTAgctaa |
| RTP10690_11 | Plant G-box/C-box bZIP proteins | ctcagcTGACgctacctagcg |
| RTP10690_11 | Plant G-box/C-box bZIP proteins | gctaggtaGCGTcagctgagc |
| RTP10690_11 | Plant specific NAC [NAM (no apical meristem), ATAF172, CUC2 (cup-shaped cotyledons 2)] transcription factors | agcgtcagctgagctTACGtaagcgca |
| RTP10690_11 | Vertebrate TATA binding protein factor | gcttacgTAAGctcagc |
| RTP10690_11 | Cell-death specification 2 | cttacGTAAgc |
| RTP10690_11 | Plant G-box/C-box bZIP proteins | gtgcgcttACGTaagctcagc |
| RTP10690_11 | Opaque-2 like transcriptional activators | gcgcttACGTaagctca |
| RTP10690_11 | Cell-death specification 2 | cttacGTAAgc |
| RTP10690_11 | Plant G-box/C-box bZIP proteins | ctgagcttACGTaagcgcaca |
| RTP10690_11 | Opaque-2 like transcriptional activators | gagcttACGTaagcgca |
| RTP10690_11 | Vertebrate TATA binding protein factor | gcttacgTAAGcgcaca |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_11 | Plant specific NAC [NAM (no apical meristem), ATAF172, CUC2 (cup-shaped cotyledons 2)] transcription factors | attcatctgtgcgctTACGtaagctca |
| RTP10690_11 | Plant G-box/C-box bZIP proteins | tcatctgtgcgcTTACgtaag |
| RTP10690_11 | Enhancer element first identified in the promoter of the octopine synthase gene (OCS) of the Agrobacterium tumefaciens T-DNA | tcatctgtgcgctTACGtaag |
| RTP10690_11 | Myc-like basic helix-loop-helix binding factors | agtattCATCtgtgcgctt |
| RTP10690_11 | GAP-Box (light response elements) | acagATGAatactag |
| RTP10690_11 | MYB-like proteins | tactagctGTTGttcac |
| RTP10690_12 | VIP1 responsive elements | acacgGCTCag |
| RTP10690_12 | Plant G-box/C-box bZIP proteins | gttacgtaACGTcagctgagg |
| RTP10690_12 | Plant G-box/C-box bZIP proteins | ctcagcTGACgttacgtaacg |
| RTP10690_12 | Plant specific NAC [NAM (no apical meristem), ATAF172, CUC2 (cup-shaped cotyledons 2)] transcription factors | agcctcagctgacgtTACGtaacgcta |
| RTP10690_12 | Opaque-2 like transcriptional activators | cagctgACGTtacgtaa |
| RTP10690_12 | GT-box elements | gctgacGTTAcgtaacg |
| RTP10690_12 | Cell-death specification 2 | gttacGTAAcg |
| RTP10690_12 | Plant G-box/C-box bZIP proteins | ctagcgttACGTaacgtcagc |
| RTP10690_12 | Opaque-2 like transcriptional activators | agcgttACGTaacgtca |
| RTP10690_12 | Cell-death specification 2 | gttacGTAAcg |
| RTP10690_12 | Opaque-2 like transcriptional activators | gacgttACGTaacgcta |
| RTP10690_12 | GT-box elements | cctagcGTTAcgtaacg |
| RTP10690_12 | Plant specific NAC [NAM (no apical meristem), ATAF172, CUC2 (cup-shaped cotyledons 2)] transcription factors | gacgctacctagcgtTACGtaacgtca |
| RTP10690_12 | Plant G-box/C-box bZIP proteins | gtcacgTGACgctacctagcg |
| RTP10690_12 | Plant G-box/C-box bZIP proteins | gctaggtaGCGTcacgtgacg |
| RTP10690_12 | ABA response elements | tagcgtcaCGTGacgtt |
| RTP10690_12 | Plant G-box/C-box bZIP proteins | ctaacgtcACGTgacgctacc |
| RTP10690_12 | Myc-like basic helix-loop-helix binding factors | taacgtCACGtgacgctac |
| RTP10690_12 | Opaque-2 like transcriptional activators | aacgtcACGTgacgcta |
| RTP10690_12 | ABA response elements | taacgtcaCGTGacgct |
| RTP10690_12 | Plant G-box/C-box bZIP proteins | gtagcgtcACGTgacgttagc |
| RTP10690_12 | Myc-like basic helix-loop-helix binding factors | tagcgtCACGtgacgttag |
| RTP10690_12 | Opaque-2 like transcriptional activators | agcgtcACGTgacgtta |
| RTP10690_12 | Plant G-box/C-box bZIP proteins | gttagctaACGTcacgtgacg |
| RTP10690_12 | Plant specific NAC [NAM (no apical meristem), ATAF172, CUC2 (cup-shaped cotyledons 2)] transcription factors | agcgttagctaacgtCACGtgacgcta |
| RTP10690_12 | Opaque-2 like transcriptional activators | tagctaACGTcacgtga |
| RTP10690_12 | Plant G-box/C-box bZIP proteins | gtcacgTGACgttagctaacg |
| RTP10690_12 | MYB-like proteins | cacgtgacGTTAgctaa |
| RTP10690_12 | Plant G-box/C-box bZIP proteins | ctcagcTGACgctacctagcg |
| RTP10690_12 | Plant G-box/C-box bZIP proteins | gctaggtaGCGTcagctgagc |
| RTP10690_12 | Plant specific NAC [NAM (no apical meristem), ATAF172, CUC2 (cup-shaped cotyledons 2)] transcription factors | agcgtcagctgagctTACGtaagcgct |
| RTP10690_12 | Vertebrate TATA binding protein factor | gcttacgTAAGctcagc |
| RTP10690_12 | Cell-death specification 2 | cttacGTAAgc |
| RTP10690_12 | Plant G-box/C-box bZIP proteins | aagcgcttACGTaagctcagc |
| RTP10690_12 | Opaque-2 like transcriptional activators | gcgcttACGTaagctca |
| RTP10690_12 | Cell-death specification 2 | cttacGTAAgc |
| RTP10690_12 | Plant G-box/C-box bZIP proteins | ctgagcttACGTaagcgctta |
| RTP10690_12 | Opaque-2 like transcriptional activators | gagcttACGTaagcgct |
| RTP10690_12 | Vertebrate TATA binding protein factor | gcttacgTAAGcgtta |
| RTP10690_12 | Plant specific NAC [NAM (no apical meristem), ATAF172, CUC2 (cup-shaped cotyledons 2)] transcription factors | ctttaattaagcgcttTACGtaagctca |
| RTP10690_12 | Enhancer element first identified in the promoter of the octopine synthase gene (OCS) of the Agrobacterium tumefaciens T-DNA | ttaattaagcgcttACGTaag |
| RTP10690_12 | Vertebrate TATA binding protein factor | ctttaatTAAGcgctta |
| RTP10690_12 | DNA binding with one finger (DOF) | gcttaattAAAGtactg |
| RTP10690_12 | Arabidopsis homeobox protein | gtaCTGAtatc |
| RTP10690_12 | Dehydration responsive element binding factors | atttggtaCCGAtatcagtac |
| RTP10690_12 | SBP-domain proteins | tatcgGTACcaaatcga |
| RTP10690_12 | Sucrose box | aaAAATtacggatatgaat |
| RTP10690_12 | MYB proteins with single DNA binding repeat | attcatATCCgtaattt |
| RTP10690_5 | M-phase-specific activator elements | attacAACGgtatat |
| RTP10690_5 | Yeast TATA binding protein factor | aacggtaTATAtcctgc |
| RTP10690_5 | Yeast TATA binding protein factor | ggcaggaTATAtaccgt |
| RTP10690_5 | Vertebrate TATA binding protein factor | cggtaTATAtcctgcca |
| RTP10690_5 | MYB proteins with single DNA binding repeat | gtatatATCCtgccagt |
| RTP10690_5 | Caenorhabditis maternal gene product SKN-1 | cagcATCAtcaca |
| RTP10690_5 | Fungal and oomycete pathogen response cluster - promoter motif | ctattcGGGCctaactt |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_5 | Retroviral upstream element | ggcccgaatagTTTGaaatta |
| RTP10690_5 | SBP-domain proteins | tagcCGTAcaatattac |
| RTP10690_5 | Enhancer element first identified in the promoter of the octopine synthase gene (OCS) of the Agrobacterium tumefaciens T-DNA | gtgagtaatattgtACGGcta |
| RTP10690_5 | Arabidopsis homeobox protein | aatATTActca |
| RTP10690_5 | Opaque-2 like transcriptional activators | accggTGAGtaatattg |
| RTP10690_5 | Epstein-Barr virus transcription factor R | atgcccccatcgtaGGTGaa |
| RTP10690_5 | Retroviral PolyA signal | gCCATtaatttccaccttcac |
| RTP10690_5 | Retroviral upstream element | cgcgccattaaTTTCcacctt |
| RTP10690_5 | L1 box, motif for L1 layer-specific expression | cgcCATTaatttccacc |
| RTP10690_5 | Arabidopsis homeobox protein | gaaATTAatgg |
| RTP10690_5 | GT-box elements | gtaataGTTActaatca |
| RTP10690_5 | MYB-like proteins | acgtaatAGTTactaat |
| RTP10690_5 | Plant specific NAC [NAM (no apical meristem), ATAF172, CUC2 (cup-shaped cotyledons 2)] transcription factors | cactgattagtaactatTACGtaagcc |
| RTP10690_5 | Plant specific NAC [NAM (no apical meristem), ATAF172, CUC2 (cup-shaped cotyledons 2)] transcription factors | ctgattagtaactatTACGtaagccta |
| RTP10690_5 | Cell-death specification 2 | cttacGTAAta |
| RTP10690_5 | Plant G-box/C-box bZIP proteins | gtaggcttACGTaatagttac |
| RTP10690_5 | Cell-death specification 2 | attacGTAAgc |
| RTP10690_5 | Vertebrate TATA binding protein factor | tattacgTAAGcctacg |
| RTP10690_5 | Plant specific NAC [NAM (no apical meristem), ATAF172, CUC2 (cup-shaped cotyledons 2)] transcription factors | gacgctacgtaggctTACGtaatagtt |
| RTP10690_5 | Plant specific NAC [NAM (no apical meristem), ATAF172, CUC2 (cup-shaped cotyledons 2)] transcription factors | actattacgtaagccTACGtagcgtca |
| RTP10690_5 | Plant G-box/C-box bZIP proteins | gtaagcctACGTagcgtcacg |
| RTP10690_5 | Opaque-2 like transcriptional activators | aagcctACGTagcgtca |
| RTP10690_5 | Plant G-box/C-box bZIP proteins | gtcacgTGACgctacgtaggc |
| RTP10690_5 | Plant G-box/C-box bZIP proteins | cctacgtaGCGTcacgtgacg |
| RTP10690_5 | ABA response elements | tagcgtcaCGTGacgtt |
| RTP10690_5 | Plant G-box/C-box bZIP proteins | ctaacgtcACGTgacgctacg |
| RTP10690_5 | Myc-like basic helix-loop-helix binding factors | taacgtCACGtgacgctac |
| RTP10690_5 | Opaque-2 like transcriptional activators | aacgtcACGTgacgcta |
| RTP10690_5 | ABA response elements | taacgtcaCGTGacgct |
| RTP10690_5 | Plant G-box/C-box bZIP proteins | gtagcgtcACGTgacgttagc |
| RTP10690_5 | Myc-like basic helix-loop-helix binding factors | tagcgtCACGtgacgttag |
| RTP10690_5 | Opaque-2 like transcriptional activators | agcgtcACGTgacgtta |
| RTP10690_5 | Plant G-box/C-box bZIP proteins | gttagctaACGTcacgtgacg |
| RTP10690_5 | Plant specific NAC [NAM (no apical meristem), ATAF172, CUC2 (cup-shaped cotyledons 2)] transcription factors | agcgttagctaacgtCACGtgacgcta |
| RTP10690_5 | Opaque-2 like transcriptional activators | tagctaACGTcacgtga |
| RTP10690_5 | Plant G-box/C-box bZIP proteins | gtcacgTGACgttagctaacg |
| RTP10690_5 | MYB-like proteins | cacgtgacGTTAgctaa |
| RTP10690_5 | Plant G-box/C-box bZIP proteins | ctgaggctACGTagcgttagc |
| RTP10690_5 | Opaque-2 like transcriptional activators | gaggctACGTagcgtta |
| RTP10690_5 | Opaque-2 like transcriptional activators | aacgctACGTagcctca |
| RTP10690_5 | Plant G-box/C-box bZIP proteins | cttacgtaACGTcagctgagg |
| RTP10690_5 | Plant G-box/C-box bZIP proteins | ctcagcTGACgttacgtaagc |
| RTP10690_5 | Plant specific NAC [NAM (no apical meristem), ATAF172, CUC2 (cup-shaped cotyledons 2)] transcription factors | agcctcagctgacgtTACGtaagccta |
| RTP10690_5 | Opaque-2 like transcriptional activators | cagctgACGTtacgtaa |
| RTP10690_5 | GT-box elements | gctgacGTTAcgtaagc |
| RTP10690_5 | Cell-death specification 2 | cttacGTAAcg |
| RTP10690_5 | Plant G-box/C-box bZIP proteins | gtaggcttACGTaacgtcagc |
| RTP10690_5 | Opaque-2 like transcriptional activators | aggcttACGTaacgtca |
| RTP10690_5 | Cell-death specification 2 | gttacGTAAgc |
| RTP10690_5 | Plant G-box/C-box bZIP proteins | ctgacgttACGTaagcctacg |
| RTP10690_5 | Opaque-2 like transcriptional activators | gacgttACGTaagccta |
| RTP10690_5 | Vertebrate TATA binding protein factor | cgttacgTAAGcctacg |
| RTP10690_5 | Plant specific NAC [NAM (no apical meristem), ATAF172, CUC2 (cup-shaped cotyledons 2)] transcription factors | gacgctacgtaggctTACGtaacgtca |
| RTP10690_5 | Plant G-box/C-box bZIP proteins | gtaagcctACGTagcgtcacg |
| RTP10690_5 | Opaque-2 like transcriptional activators | aagcctACGTagcgtca |
| RTP10690_5 | Plant G-box/C-box bZIP proteins | ctcacgTGACgctacgtaggc |
| RTP10690_5 | Plant G-box/C-box bZIP proteins | cctacgtaGCGTcacgtgagc |
| RTP10690_5 | Plant G-box/C-box bZIP proteins | ctaagctcACGTgacgctacg |
| RTP10690_5 | Myc-like basic helix-loop-helix binding factors | taagctCACGtgacgctac |
| RTP10690_5 | Opaque-2 like transcriptional activators | aagctcACGTgacgcta |
| RTP10690_5 | ABA response elements | taagctcaCGTGacgct |
| RTP10690_5 | Plant G-box/C-box bZIP proteins | gtagcgtcACGTgagcttagc |
| RTP10690_5 | Myc-like basic helix-loop-helix binding factors | tagcgtCACGtgagcttag |
| RTP10690_5 | Opaque-2 like transcriptional activators | agcgtcACGTgagctta |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| RTP10690_5 | GT-box elements | cgtcacGTGAgcttagc |
| RTP10690_5 | Plant specific NAC [NAM (no apical meristem), ATAF172, CUC2 (cup-shaped cotyledons 2)] transcription factors | agcgttagctaagctCACGtgacgcta |
| RTP10690_5 | Plant G-box/C-box bZIP proteins | gttacgtaACGTcagctgagc |
| RTP10690_5 | Plant G-box/C-box bZIP proteins | ctcagcTGACgttacgtaacg |
| RTP10690_5 | Plant specific NAC [NAM (no apical meristem), ATAF172, CUC2 (cup-shaped cotyledons 2)] transcription factors | aggctcagctgacgtTACGtaacgcta |
| RTP10690_5 | Opaque-2 like transcriptional activators | cagctgACGTtacgtaa |
| RTP10690_5 | GT-box elements | gctgacGTTAcgtaacg |
| RTP10690_5 | Cell-death specification 2 | gttacGTAAcg |
| RTP10690_5 | Plant G-box/C-box bZIP proteins | ctagcgttACGTaacgtcagc |
| RTP10690_5 | Opaque-2 like transcriptional activators | agcgttACGTaacgtca |
| RTP10690_5 | Cell-death specification 2 | gttacGTAAcg |
| RTP10690_5 | Opaque-2 like transcriptional activators | gacgttACGTaacgcta |
| RTP10690_5 | GT-box elements | gctagcGTTAcgtaacg |
| RTP10690_5 | Plant specific NAC [NAM (no apical meristem), ATAF172, CUC2 (cup-shaped cotyledons 2)] transcription factors | gacgctagctagcgtTACGtaacgtca |
| RTP10690_5 | Plant G-box/C-box bZIP proteins | caggagTGACgctagctagcg |
| RTP10690_5 | Plant G-box/C-box bZIP proteins | gctagctaGCGTcactcctgc |
| RTP10690_5 | Enhancer element first identified in the promoter of the octopine synthase gene (OCS) of the Agrobacterium tumefaciens T-DNA | ttgctgcaggagtGACGctag |
| t-AtAHASL | Retroviral PolyA signal | aCCATaaaaggttctgataat |
| t-AtAHASL | Vertebrate TATA binding protein factor | gaccaTAAAaggttctg |
| t-AtAHASL | Papillioma virus E2 transcriptional activator | agaccataaaAGGTtct |
| t-AtAHASL | MADS box proteins | aaagaccatAAAAggttctga |
| t-AtAHASL | Papillioma virus E2 transcriptional activator | gaacctttaTGGTctt |
| t-AtAHASL | GT-box elements | ttttATGGtcttttgtat |
| t-AtAHASL | MYB proteins with single DNA binding repeat | taccaTATGcatacaaa |
| t-AtAHASL | Arabidopsis homeobox protein | aaaCTTAgttt |
| t-AtAHASL | MYB-like proteins | aaaactTAGTttgcaat |
| t-AtAHASL | GT-box elements | gttttgGTAAtttgagt |
| t-AtAHASL | MYB-like proteins | ttcttttAGTTgttgat |
| t-AtAHASL | Retroviral CCAAT binding factors | aCCAAaaagcaggcagatcaacaac |
| t-AtAHASL | Sucrose box | aaAAAGcaggcagatcaac |
| t-AtAHASL | Legumin Box family | ttgatctGCCTgcttttggtttacgt |
| t-AtAHASL | DNA binding with one finger (DOF) | taaaccaaAAAGcaggc |
| t-AtAHASL | Plant specific NAC [NAM (no apical meristem), ATAF172, CUC2 (cup-shaped cotyledons 2)] transcription factors | gcctgcttttggttTACGtcagacta |
| t-AtAHASL | Cell-death specification 2 | ctgacGTAAac |
| t-AtAHASL | Plant G-box/C-box bZIP proteins | gtagtcTGACgtaaaccaaaa |
| t-AtAHASL | Cell-death specification 2 | tttacGTCAga |
| t-AtAHASL | Plant G-box/C-box bZIP proteins | tttggtttACGTcagactact |
| t-AtAHASL | Plant G-box/C-box bZIP proteins | gcagtagtagtcTGACgtaaa |
| t-AtAHASL | Secondary wall NACS | tttataaaatgAAAGaaag |
| t-AtAHASL | Core promoter initiator elements | ttTCATttat |
| t-AtAHASL | Vertebrate TATA binding protein factor | atttaTAAAatgaaaga |
| t-AtAHASL | Plant TATA binding protein factor | atttTATAaataaat |
| t-AtAHASL | Vertebrate TATA binding protein factor | ttttaTAAAtaaataat |
| t-AtAHASL | L1 box, motif for L1 layer-specific expression | tataaaTAAAtaatccg |
| t-AtAHASL | Retroviral PolyA signal | ataaaTAAAtaatccggttcg |
| t-AtAHASL | Dehydration responsive element binding factors | ggagtaaaCCGAaccggatta |
| t-AtAHASL | MYB-like proteins | tcagtttgGTTAttgcg |
| t-AtAHASL | GT-box elements | agtttgGTTAttgcgaa |
| t-AtAHASL | Cell-death specification 2 | atttcGCAAta |
| t-AtAHASL | Cell-death specification 2 | attgcGAAAtg |
| t-AtAHASL | Plant nitrate-responsive cis-elements | tcaatttaccattcgcatttcgcAATAaccaaa |
| t-AtAHASL | TEF-box | gaATGGtaaattgagtaattg |
| t-AtAHASL | Cell-death specification 2 | attgaGTAAtt |
| t-AtAHASL | MYB-like proteins | tgaaatTCGTtattagg |
| t-AtAHASL | Telo box (plant interstitial telomere motifs) | tagaaCCCTaataac |
| t-AtAHASL | Mitochondral HMG-box transcription factor | attagggTTCTaa |
| t-AtAHASL | VIP1 responsive elements | aaacaGCTTag |
| t-AtAHASL | CA-rich motif | ctgttaaAACAgcttagaa |
| t-AtAHASL | MYB-like proteins | cagtgaCTGTtaaaaca |
| t-AtAHASL | GT-box elements | cactggGTTAatatctc |
| t-AtAHASL | Circadian control factors | tggggttAATAtctct |
| t-AtAHASL | Myb-related DNA binding proteins (Golden2, ARR, Psr) | AGATcgag |
| t-AtAHASL | Legumin Box family | gcattttcCATGcaagattcgagagat |
| t-AtAHASL | GT-box elements | ttgcATGGaaaatgctc |
| t-AtAHASL | Retroviral upstream element | ggtaagagcatTTTCcatgca |
| t-AtAHASL | Mitochondral HMG-box transcription factor | aagagcaTTTTcc |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
|---|---|---|
| t-AtAHASL | MYB proteins with single DNA binding repeat | tggaAAATgctcttacc |
| t-AtAHASL | LFY binding site | aACCAatggtaag |
| t-AtAHASL | CCAAT binding factors | aaCCAatgg |
| t-AtAHASL | LFY binding site | tACCAttggtttt |
| t-AtAHASL | Retroviral PolyA signal | ttcaaTTAAaaaccaatggta |
| t-AtAHASL | Soybean embryo factor 4 | ggTTTTtaatt |
| t-AtAHASL | DNA-binding proteins with the plant specific TCP-domain | cacgGCCCatatg |
| t-AtAHASL | Root hair-specific cis-elements in angiosperms | atttaatttggaaacCACGgcccat |
| t-AtAHASL | MADS box proteins | ggtTTCCaaattaaataaaac |
| t-AtAHASL | Vertebrate TATA binding protein factor | ttttattTAATttggaa |
| t-AtAHASL | Sulphur limitation, elements found in genes inducible during sulphur deprivation | agtttTATTtaatttggaaac |
| t-AtAHASL | High mobility group factors | gtttTATTtaatttg |
| t-AtAHASL | L1 box, motif for L1 layer-specific expression | ccaaatTAAAtaaaact |
| t-AtAHASL | Retroviral PolyA signal | ttaaaTAAAactacgatgtca |
| t-AtAHASL | Opaque-2 like transcriptional activators | actacgatgTCATcgag |
| t-AtAHASL | Caenorhabditis maternal gene product SKN-1 | cgatGTCAtcgag |
| t-AtAHASL | Sucrose box | taAAATcaactgtgtccac |
| t-AtAHASL | Lentiviral Poly A downstream element | aaCTGTgtccacatt |
| t-AtAHASL | MYB-like proteins | acaaaactGATAatgtg |
| t-AtAHASL | Retroviral upstream element | cacattatcagTTTTgtgtat |
| t-AtAHASL | Core promoter initiator elements | taTCAGttttg |
| t-AtAHASL | GT-box elements | aataggGTAAttcaaaa |
| t-AtAHASL | Circadian control factors | taattcaaAATCtag |
| t-AtAHASL | Lentiviral Tata upstream element | aaggttaaaatgAACCaaaaggc |
| t-AtAHASL | GT-box elements | cagaaggTTAAaatgaa |
| t-AtAHASL | Heat shock factors | ttttaacCTTCtgtaaac |
| t-AtAHASL | Nodulin consensus sequence 1 | aAAATgtttac |
| t-AtAHASL | Circadian control factors | ttgttcaaAATCtga |
| t-AtAHASL | L1 box, motif for L1 layer-specific expression | aacaagTAAAtccaaaa |
| t-AtAHASL | Circadian control factors | aaaaaaaaAATCtca |
| t-AtAHASL | Mitochondral HMG-box transcription factor | ttgagatTTTTtt |
| t-AtAHASL | Arabidopsis homeobox protein | taaTTTAgtgt |
| t-AtAHASL | L1 box, motif for L1 layer-specific expression | caaCACTaaattatttt |
| t-AtAHASL | Storekeeper motif | cacTAAAttatttta |
| t-AtAHASL | Arabidopsis homeobox protein | aaaATAAttta |
| t-AtAHASL | Arabidopsis homeobox protein | taaATTAtttt |
| t-AtAHASL | Arabidopsis homeobox protein | tatttTAATgt |
| t-AtAHASL | Vertebrate TATA binding protein factor | atgtaTAAAagatgctt |
| t-AtAHASL | Nodulin consensus sequence 1 | tAAAAgatgct |
| t-AtAHASL | Storekeeper motif | gctTAAAacatttgg |
| t-AtAHASL | Myc-like basic helix-loop-helix binding factors | ttaaaACATtggcttaaa |
| t-AtAHASL | Sucrose box | ttAAAAcatttggcttaaa |
| t-AtAHASL | Secondary wall NACS | catttggcttaAAAGaaag |
| t-AtAHASL | Tracheary-element-regulating cis-elements, conferring TE-specific expression | cttaAAAGaaa |
| t-AtAHASL | Heat shock factors | taaaaacatagAGAAct |
| t-AtAHASL | DNA binding with one finger (DOF) | actcttgtAAATgaag |
| t-AtAHASL | MYB proteins with single DNA binding repeat | cagtATATtttcatact |
| t-AtAHASL | MADS box proteins | taataCCCAattcagtatatt |
| t-AtAHASL | MADS box proteins | ataTACTgaattgggtattat |
| t-AtAHASL | CCAAT binding factors | acCCAattc |
| t-AtAHASL | Sucrose box | ctAAATcagaaaaattcat |
| t-AtAHASL | MADS box proteins | tgaatcctaaatcaGAAAaat |
| UB2197_5 | M-phase-specific activator elements | ggacgAACGgataaa |
| UB2197_5 | MYB proteins with single DNA binding repeat | aggtttATCCgttcgtc |
| UB2197_5 | Nodulin consensus sequence 1 | gAAAAggttta |
| UB2197_5 | DNA binding with one finger (DOF) | gggcgtgaAAAGgttta |
| UB2197_5 | Plant specific NAC [NAM (no apical meristem), ATAF172, CUC2 (cup-shaped cotyledons 2)] transcription factors | acggataaaccttttCACGcccttta |
| UB2197_5 | E2F-homolog cell cycle regulators | ccttTTCAcgccctt |
| UB2197_5 | Transposase-derived transcription factors | ttttCACGcccttttaa |
| UB2197_5 | Vertebrate TATA binding protein factor | atattTAAAagggcgtg |
| UB2197_5 | DNA binding with one finger (DOF) | gatatttaAAAGggcgt |
| UB2197_5 | Vertebrate TATA binding protein factor | cctttTAAAatatccgat |
| UB2197_5 | Arabidopsis homeobox protein | ccgATTAttct |
| UB2197_5 | Retroviral PolyA signal | tctaaTAAAcgctcttttctc |
| UB2197_5 | Retroviral CCAAT binding factors | tCTAAtaaacgctcttttctcttag |
| UB2197_5 | DNA binding with one finger (DOF) | ctaagagaAAAGagcgt |
| UB2197_5 | Nodulin consensus sequence 2 | tcttttCTCTtaggt |
| UB2197_5 | Ethylen response element factors | gGCGGgtaaacctaagaga |
| UB2197_5 | DNA binding with one finger (DOF) | tggcgggtAAACctaag |
| UB2197_5 | MYB proteins with single DNA binding repeat | caggATATattggcggg |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
| --- | --- | --- |
| UB2197_5 | MYB proteins with single DNA binding repeat | caatatATCCtgtcaaa |
| UB2197_5 | TALE (3-aa acid loop extension) class homeodomain proteins | tttGACAggatat |
| UB2197_5 | W Box family | agtgtTTGAcaggatat |
| UB2197_5 | E2F-homolog cell cycle regulators | tcgtTTCCcgccttc |
| UB2197_5 | Circadian control factors | gaaacgacAATCtga |
| UB2197_5 | MYB-like proteins | aggcctTAGTtactaat |
| UB2197_5 | Vertebrate TATA binding protein factor | tagtaacTAAGgccttt |
| UB2197_5 | Retroviral PolyA signal | attaaTTAAaggccttagtta |
| UB2197_5 | DNA binding with one finger (DOF) | gattaattAAAGgcctt |
| UB2197_5 | Arabidopsis homeobox protein | ttaatTAATct |
| UB2197_5 | Arabidopsis homeobox protein | tagATTAatta |
| UB2197_5 | Light responsive element motif, not modulated by different light qualities | taATCTagagg |
| UB2197_5 | Vertebrate TATA binding protein factor | caattTAAAttggccgg |
| UB2197_5 | L1 box, motif for L1 layer-specific expression | tcaattTAAAttggccg |
| UB2197_5 | Retroviral upstream element | accgatatcaaTTTAaattgg |
| UB2197_5 | MYB proteins with single DNA binding repeat | accgaTATCaatttaaa |
| UB2197_5 | Dehydration responsive element binding factors | tcgtgtaCCGAtatcaattt |
| UB2197_5 | Plant specific NAC [NAM (no apical meristem), ATAF172, CUC2 (cup-shaped cotyledons 2)] transcription factors | tatcggtacatcgatTACGccaagcta |
| UB2197_5 | Cell-death specification 2 | ttggcGTAAtc |
| UB2197_5 | MADS box proteins | cttTTCTatacaaagttgata |
| UB2197_5 | Plant TATA binding protein factor | tttcTATAcaaagtt |
| UB2197_5 | Pollen-specific regulatory elements | gtataGAAAagttgcca |
| UB2197_5 | GT-box elements | aatcATGGcaactttc |
| UB2197_5 | Arabidopsis homeobox protein | gtaATCAtggc |
| UB2197_5 | Arabidopsis homeobox protein | gccatgATTAc |
| UB2197_5 | Plant specific NAC [NAM (no apical meristem), ATAF172, CUC2 (cup-shaped cotyledons 2)] transcription factors | aaaagttgccatgatTACGccaagctt |
| UB2197_5 | Cell-death specification 2 | ttggcGTAAtc |
| UB2197_5 | Calcium regulated NAC-factors | ccaaGCTTggccactaaggcc |
| UB2197_5 | E2F-homolog cell cycle regulators | caatTTCGcgccctg |
| UB2197_1 | Arabidopsis homeobox protein | caaTTTActga |
| UB2197_1 | Motifs of plastid response elements | cacgCGATcgcgtcgacacaatcagtaaatt |
| UB2197_1 | Calmodulin binding/CGCG box binding proteins | gatCGCGtcgacacaat |
| UB2197_1 | Core promoter motif ten elements | gcacgcgATCGcgtcgacaca |
| UB2197_1 | Calmodulin binding/CGCG box binding proteins | gatCGCGtgcaaacact |
| UB2197_1 | Root hair-specific cis-elements in angiosperms | tccgtacagtgtttgCACGcgatcg |
| UB2197_1 | Plant specific NAC [NAM (no apical meristem), ATAF172, CUC2 (cup-shaped cotyledons 2)] transcription factors | ggtccgtacagtgtttgCACGcgatcg |
| UB2197_1 | SBP-domain proteins | ggtcCGTAcagtgtttg |
| UB2197_1 | SBP-domain proteins | ggccgGTACccaagttt |
| UB2197_1 | SBP-domain proteins | agtttGTACaaaaaagc |
| UB2197_1 | DNA binding with one finger (DOF) | tgtacaaaAAAGcaggc |
| UB2197_1 | Legumin Box family | caaaaaaGCAGgctccatgattacgcc |
| UB2197_1 | Arabidopsis homeobox protein | tccatgATTAc |
| UB2197_1 | Plant specific NAC [NAM (no apical meristem), ATAF172, CUC2 (cup-shaped cotyledons 2)] transcription factors | agcaggctccatgatTACGccaagctt |
| UB2197_1 | Cell-death specification 2 | ttggcGTAAtc |
| UB2197_1 | Calcium regulated NAC-factors | ccaaGCTTggccactaaggcc |
| UB2197_1 | L1 box, motif for L1layer-specific expression | tagattTAAAttggcct |
| UB2197_1 | Circadian control factors | ccaatttaAATCtac |
| UB2197_1 | Vertebrate TATA binding protein factor | caattTAAAtctactag |
| UB2197_1 | Light responsive element motif, not modulated by different light qualities | aaATCTactag |
| UB2197_2 | E2F-homolog cell cycle regulators | gtaaTTCCcgggatt |
| UB2197_2 | Brassinosteroid (BR) response element | ctgcccCGTGtggccggc |
| UB2197_3 | Core promoter initiator elements | ttTCATtcggt |
| UB2197_3 | Retroviral upstream element | ggcgccatcggTTTCattcgg |
| UB2197_3 | Papillioma virus E2 transcriptional activator | ggaccgatacCGGTagg |
| UB2197_3 | Papillioma virus E2 transcriptional activator | ctaccggtatCGGTccg |
| UB2197_3 | Dehydration responsive element binding factors | caateggaCCGAtaccggtag |
| UB2197_3 | Core promoter motif ten elements | ggccgcaATCGgaccgatacc |
| UB2197_3 | TEF-box | taAAGGgcgaattcgtttaaa |
| UB2197_3 | SBP-domain proteins | ggtcCGTAcagtgttta |
| UB2197_3 | Activator-, mediator- and TBP-dependent core promoter element for RNA polymerase II transcription from TATA-less promoters | ggGTGGtaccg |
| UB2197_3 | SBP-domain proteins | ggccgGTACcacccagc |
| UB2197_3 | Soybean embryo factor 3 | gtaccACCCagcttt |
| UB2197_3 | Arabidopsis homeobox protein | gtaATCAtggc |
| UB2197_3 | Arabidopsis homeobox protein | gccatgATTAc |

TABLE 172-continued lists the spacer region and the transcription factor binding motif present in the region and the nucleotide sequence. Upper case letters denote the motif while surrounding bases indicate examples of sequences that might neighbor the predicted motif but are not necessary for the motif to function in the regulation of transcription

| Spacer ID | Detailed Family Information | Sequence |
|---|---|---|
| UB2197_3 | Plant specific NAC [NAM (no apical meristem), ATAF172, CUC2 (cup-shaped cotyledons 2)] transcription factors | caaagtggccatgatTACGccaagctt |
| UB2197_3 | Cell-death specification 2 | ttggcGTAAtc |
| UB2197_3 | Calcium regulated NAC-factors | ccaaGCTTggccactaaggcc |
| UB2197_3 | L1 box, motif for L1 layer-specific expression | tagattTAAAttggcct |
| UB2197_3 | Circadian control factors | ccaatttaAATCtac |
| UB2197_3 | Vertebrate TATA binding protein factor | caattTAAAtcta ctag |
| UB2197_3 | Light responsive element motif, not modulated by different light qualities | aaATCTactag |
| UB2197_3 | MYB IIG-type binding sites | aatgGGTAggtcatc |
| UB2197_4 | E2F-homolog cell cycle regulators | gtaaTTCCcgggatt |

Of particular note in Table 172 was the surprisingly high number of sequences that contain abscisic acid related transcription factor binding motifs for the construct VC-RTP10690-1qcz_F. Abscisic acid was a plant hormone involved in seed maturation, desiccation, and stress response, see Cutler et al. (2010) for a comprehensive review. Based upon what was known about abscisic acid and its effect on seed maturation, the observed high number of motifs implicated in the regulation of gene expression in response to abscisic acid may have played a role in the observed transcript levels and timing of gene expression for the genes in VC-RTP10690-1qcz_F. In addition to the likely affects on transcription, it is also known in the literature that topography is affected by GC content (see Wachter et al., 2014) and it is prudent to have a GC content in the T-DNA matching that of the host as much as possible. In addition to reducing the possibility of deletions and rearrangements, reducing the amount of repeats would also impact DNA topography and gene regulation (Ramamoorthy et al. 2014). The spacer regions would contribute to the overall impact of the T-DNA upon the local chromatin structure, which in turn will impact how the genes in that region are regulated and transcribed (Parker et al. 2009, Meggendorfer et al. 2010).

Example 24 Gene Expression, Copy Number Determination and Event Detection

Plant material representing wild type, the BiBAC VC-RTP10690-1qcz_F, and the co-transformation constructs: VC-LJB2197-1qcz with VC-LLM337-1qcz rc, VC-LJB2755-2qcz rc with VC-LLM391-2qcz rc and VC-LJB2755-2qcz rc with VC-LTM217-1qcz rc were harvested according to the date after pollination. Construct details (genes and promoters) are found in Table 1, Table 2, Table 4, Table 6, Table 7 and Table 8. Based on the day after pollination, which correlated with developmental stage under the growth conditions employed, the seeds were combined into pools. The pooled seeds were immediately frozen in liquid nitrogen and subsequently stored at −80° C. A third of the frozen immature seeds were homogenized using the Precelly®24-Dual technology in 7 ml tubes and two ceramic beads (6500 Hz, 2-3 times, 20 sec). From each pool three aliquots of 50-70 mg of tissue were used to isolate the RNA. Frozen tissue was ground to a fine powder and extracted following basic procedures familiar to one who was skilled in the art (see Ruuska et al. 2000 and Focks and Benning, 1998 as well as Sambrook et al. 1989 for an overview on RNA extraction from immature seeds and sample and RNA handling). RNA was extracted according to the protocol "SG-MA_0007-2009 RNA isolation" using Spectrum Plant Total RNA-KIT part number STRN50 (SIGMA-ALDRICH GmbH, Munich, Germany). In average the concentration of total RNA was about 450 ng/µl. The 260/280 ratio was at 2.2 and the 260/230 ratio at 2.3.

For cDNA synthesis for qPCR 1 µg of total RNA was treated with DNAsel (DEOXYRIBUNUCLEASE I (AMP-D1, Amplification Grade from SIGMA-Aldrich, GmbH) according to the supplier's protocol. After DNAsel treatment, the reverse transcription reaction was performed with the SuperScript™ III First-Strand Synthesis SuperMix for qRT-PCR (Invitrogen, Cat. No. 11752-250) and with a combination of oligo dT and random hexamers to ensure thorough and even representation of all transcripts, regardless of length.

Quantitative Real Time PCR Protocol

Transcript measurement by quantitative real time PCR was carried out using procedures considered standard to those skilled in the art; see Livak and Schmittgen (2001). The qPCR reactions were done as simplex TaqMan reactions. The endogenous reference gene was isolated in house and used due to predicted stability of the transcript based on the observed stability of the transcript corresponding to the orthologue in Arabidopsis thaliana during development. The canola ortholog was isolated and the gene, SEQ ID, was part of the glycosyl-phosphatidylinositol aminotransferase pathway (GPI). The cDNA reactions, described above, were diluted 1:4. 2 µl cDNA, which corresponded to 25 ng of total RNA, was used per 10 µl qPCR reaction with JumpStart TAQ ReadyMix (P2893-400RXN Sigma-Aldrich, GmbH). Primer/probe concentrations were 900 nmol for forward and reverse primer and 100nmol TaqMan probe. The TaqMan probes for targets of interest were labeled with FAM/BHQ1, and the reference gene was labeled with Yakima Yellow/BHQ1.

Each qPCR assay included a 1:1 dilution curve (5 dilution steps) with cDNA from the pool VC-RTP10690-1qcz_F, a no template control, three-RT controls (VC-RTP10690-1qcz_F, VC-LTM593-1qcz rc (~4 w) and co-transformation VC-LJB2197-1qcz+VC-LLM337-1qcz rc). From each pool three independent aliquots of cDNA were measured as technical repeats. The ABI PRISM@ 7900 sequence detection system (Applied Biosystem) was used with the following PCR Conditions:

Initial denaturation 95° C. for 300 seconds 1 cycle
Amplification 95° C. for 15 seconds/60° C. for 60 seconds repate for 40 cycles The raw data were the Ct values for the target and the endogenous reference gene, respectively.

The dCt values were calculated by subtraction: Ct(GOI)-Ct(Ref). The Reference dCt value was set to equal zero, which was interpreted as meaning that if there was no difference between GPI and the gene of interest (dCt=0) the expression was =1. The fold expression was equal to 2-act (where the dCt=(Ct(GOI)-Ct(Ref)-0)). Three samples from each pool were taken and the geomean as well as the geometric positive and negative deviation were calculated. The slopes of dilution curves were calculated for each gene of interest and the endogenous reference gene (GPI) as a measure for the amplification efficiency. Table 173, Table 174 and Table 175 indicate the probes and primers used to amplify the genes for qPCR assays.

TABLE 173

Probes used in the qPCR reactions

| Target of Interest | Probe | Probe Oligo |
|---|---|---|
| c-o3DES(Pi_GA2) | o3DES-594FAM | CGCTCACTTCTTCGTTGCTGGACTCTC |
| c-o3Des(Pir_GA) | o3DESPIR-198FAM | ATCATCTCTCTCGGAGTTC |
| c-o3Des(Pir_GA) 3' | o3DESPIR-962FAM | CGCTGCTCCTATCATCCCAACTTTCTTCA |
| j-o3DES(PIR_GA)/t-AtPXR | AtPXR-Fam | TCGACCTAGAGGATCCCCGGCC |
| j-BnSETLprom/o3DES(PIR_GA) | BnSETL-1186FAM | CTCTGCCAGCGACCAAATCGAAGC |
| j-o3DES(PIR_GA)/t-BnSETL | BnSETL-Fam | CCTTGTGTTAGTTTAATG |
| c-d5Elo(Ot_GA3) | E011 | TGACAAACAAGCCACCAAGCCCAA |
| c-d4DES(TC_GA) | D4DES-Tc-FAM | TGCTTCCCCAATGTACGTTGCTAGGTTCT |
| c-d4Des(Eg_GA) | D4DES-Eg-FAM | AAGGCACATCCTCC |
| c-d4Des(PI_GA2) | D4DES-PI-770FAM | AGCTTCTTTTCTTGGACGCCCTTGAGC |
| GPI | Exp3-78-YAK | GGATTCGACATTCCATCGGCTTTGA |

TABLE 174

Forward primers used in qPCR

| Target of Interest | Forward Primer | Forward Primer Oligo |
|---|---|---|
| c-o3DES(Pi_GA2) | o3DES-572F | CCGCTGTGGTTATCTCTTTGC |
| c-o3Des(Pir_GA) | o3DESPIR-160F | CTTGGGAGGCTATGTATGTTAGAAGA |
| c-o3Des(Pir_GA) 3' | o3DESPIR-924F | GCTTTCCCTGAGCTTGTTAGGA |
| j-o3DES(PIR_GA)/t-AtPXR | o3DesPir-F | GGAGGCTAAGGCTGCTGCTA |
| j-BnSETLprom/o3DES(PIR_GA) | BnSETL-1164-F | GACCCCCTCTCTCTCGTTGTC |
| j-o3DES(PIR_GA)/t-BnSETL | BnSETL-1164-F | GACCCCCTCTCTCTCGTTGTC |
| c-d5Elo(Ot_GA3) | MA54 | GCAATCGTTGGTAGCCATGA |
| c-d4DES(TC_GA) | D4DES-Tc-F | CAAATCGATGCTGAGTGCAGAT |
| c-d4Des(Eg_GA) | D4DES-EG-F | TGACAAGTAAGCCATCCGTCAGT |
| c-d4Des(PI_GA2) | D4DES-PI-746-F | CTGGTGAGGCTATGTACGCTTTT |
| GPI | Exp 3-52F | GATGAATATCCTCCTGATGCTAACC |

TABLE 175

Reverse primers used for qPCR

| Target of Interest | Reverse Primer | Reverse Primer Oligo |
|---|---|---|
| c-o3DES(Pi_GA2) | o3DES-652R | TCTTAAGTCCCAACTGGAGAGACA |
| c-o3Des(Pir_GA) | o3DESPIR-262R | AAACCAAGGAGCGTCAAGTCTAGA |

TABLE 175-continued

Reverse primers used for qPCR

| Target of Interest | Reverse Primer | Reverse Primer Oligo |
|---|---|---|
| c-o3Des(Pir_GA) 3' | o3DESPIR-1026-R | TCAACAACTCCGTACTTAGCGTACAT |
| j-o3DES(PIR_GA)/t-AtPXR | AtPXR-R | TGCATGTACGTTATATAGTAGGCTTTTG |
| j-BnSETLprom/o3DES(PIR_GA) | o3DESPIR-R | GCAGATGTAGAAGCCATGGTTTG |
| j-o3DES(PIR_GA)/t-BnSETL | o3DESPIR-R | GCAGATGTAGAAGCCATGGTTTG |
| c-d5Elo(Ot_GA3) | MA55 | CGTGTACCACCACGCTTTGT |
| c-d4DES(TC_GA) | D4DES-Tc-988R | AACACGGTCAAAGCCTTCATAATC |
| c-d4Des(Eg_GA) | D4DES-Eg-R | ACTTTTCACCACCGACGAAGTT |
| c-d4Des(PI_GA2) | D4DES-PI-817R | CCTCCCACCTCCAAGCAA |
| GPI | Exp 3-128R | CTTGCATGATGATCAGGAAAGC |

Transcript Analysis of a Time Course for Gene Expression of the BiBAC and Co-Transformations.

Transformants from four constructs were assayed as described above and transcript abundance relative to a single standard was measured as described, following standard protocols known to those skilled in the art as well as instructions provided with the kits employed. The graphs in FIG. 16, FIG. 17, FIG. 18, FIG. 19, FIG. 20 and FIG. 21 represent abundance of the gene listed over time with the error represented by the geometric positive and negative deviation. The time was listed on the abscissa and represents days after pollination and the ordinate contains the expression of the gene of interest relative to an internal standard (canola GPI). Lines with two constructs listed represent co-transformation events.

The gene o3Des(Pi_GA2) driven by the VfUSP promoter with the CaMV35S terminator was present in VC-LJB2755-2qcz, VC-LLM337-1qcz rc and VC-RTP10960-1qcz_F. One observes in FIG. 16 that VC-RTP10960-1qcz_F has relatively low transcript accumulation while the co-transformation combination of VC-LJB2755-2qcz and VC-LLM391-2qcz rc contains the highest accumulation of transcript from the gene o3Des(Pi_GA2). The overall trend for this transcript with the promoter, terminator, intron and spacer region in front of the promoter was to increase over seed development.

The gene d4Des(PI_GA)2 driven by the LuCnl promoter with the AgrOCS 192 bp[LED12] terminator was present in both VC-LTM217-1qcz rc and in VC-RTP10960-1qcz_F. One observes in FIG. 19 for both constructs that the accumulation relative to the GPI reference was in the range of 4-12 fold with gradual accumulation over seed development, with VC-RTP10960-1qcz_F accumulating less than VC-LTM217-1qcz rc.

Figure 17:
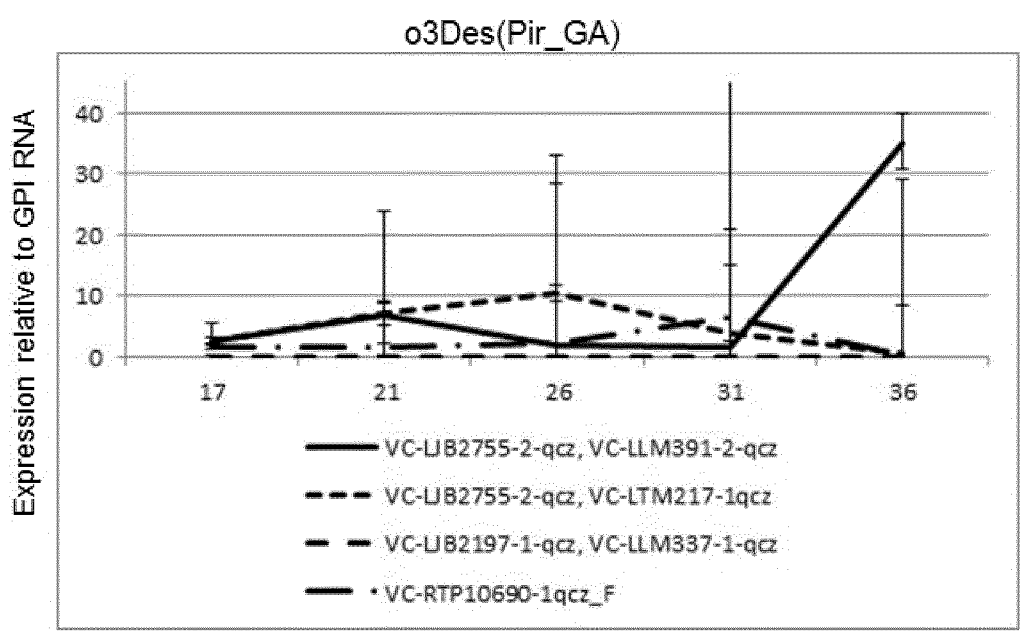
FIG. 17: Comparative transcript analysis of o3Des (Pir_GA) during seed development of single copy event of four different construct combinations. In VC-LJB2755-2qcz and VC-RTP10690-1qcz_F the gene was driven by the LuCnl promoter while in VC-LLM337-1qcz rc the gene was driven by the VfUSP promoter and was expressed at a lower level than the LuCnl o3Des(Pir_GA) combination.
Figure 18:
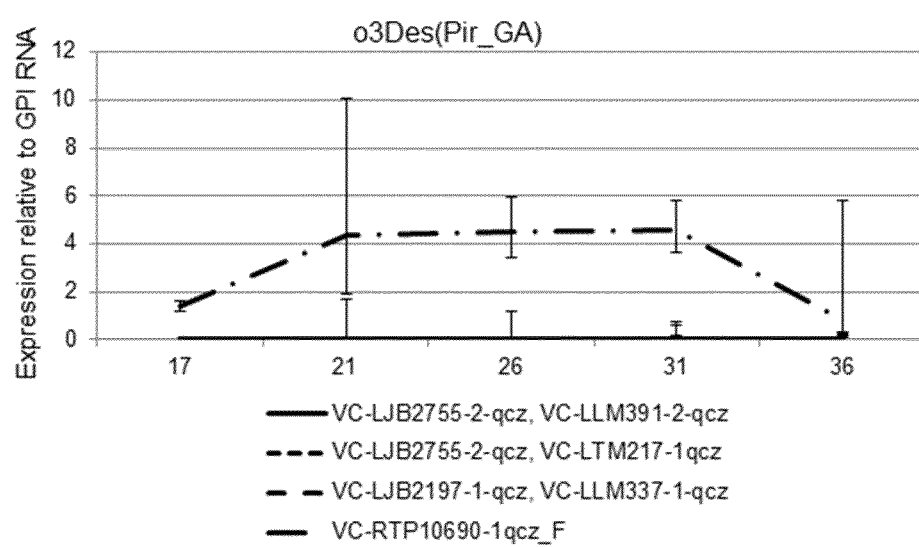
FIG. 18: Comparative transcript analysis of o3Des (Pir_GA) driven by the BnSETL promoter during seed development of single copy event of VC-RTP10690-1qcz_F.
Figure 19:
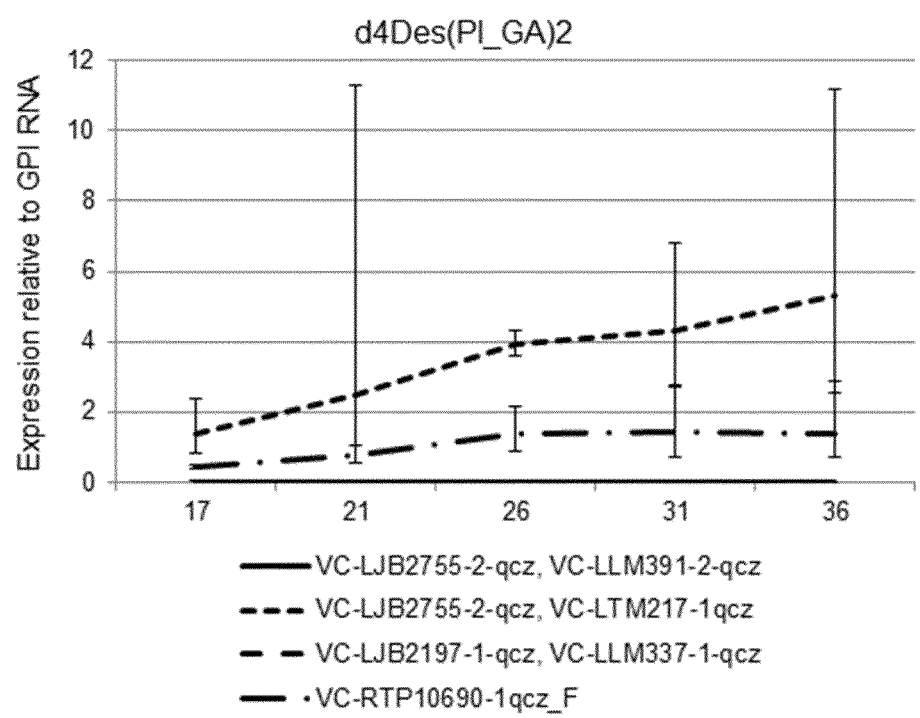
FIG. 19: Comparative transcript analysis of d4Des (PI_GA)2 driven by the LuCnl promoter during seed development of single copy event from VC-RTP10690-1qcz_F and VC-LTM217-1qcz rc, which was present with VC-LJB2755-1qcz. The other constructs lacked this particular d4Des.

The o3Des(Pir_GA) gene was present in VC-LJB2755-2qcz and VC-RTP10960-1qcz_F driven by the LuCnl promoter with the AtPXR 400 bp[LLL823] terminator while it was present in VC-LLM337-1qcz rc driven by the VfSBP_perm3 promoter with the StCATHD-pA terminator. Within error it was difficult to ascribe a pattern to any of the constructs, but as shown in FIG. 17, single copy events of the construct combination VC-LJB2755-2qcz and VC-LLM391-2qcz had a peak towards seed maturation that was not observed with any of the other constructs. An additional copy of the gene driven by the BnSETL promoter and terminated by the BnSETL terminator was present in RTP10960-1qcz_F. However, similar to the d5Des (Tc_GA2) gene controlled by the same set of control elements, the o3Des(Pir_GA) copy under control of the p-BnSETL promoter was expressed at lower levels than the other genes with different control elements (FIG. 18).

Figure 20:
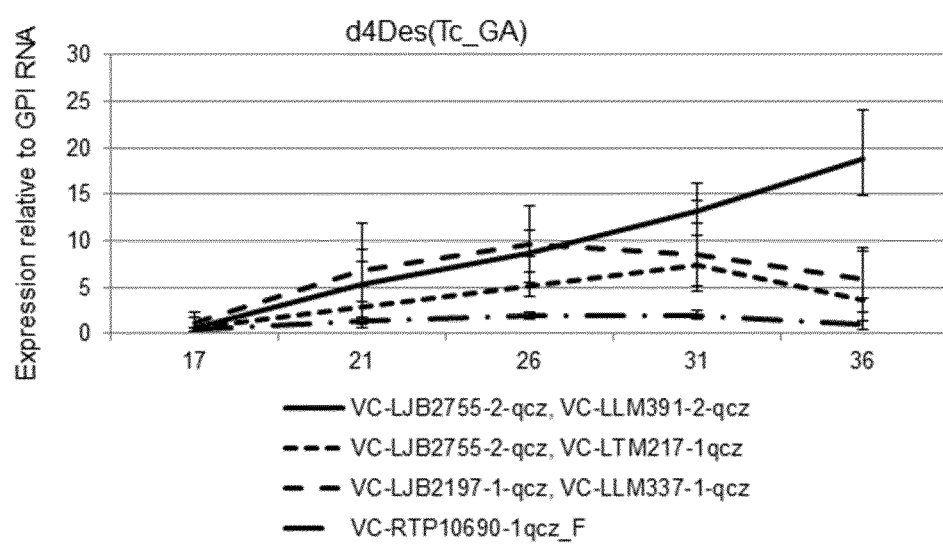
FIG. 20: Comparative transcript analysis of d4Des (Tc_GA) driven by the ARC5 promoter during seed development of single copy event of four different construct combinations.
Figure 21:
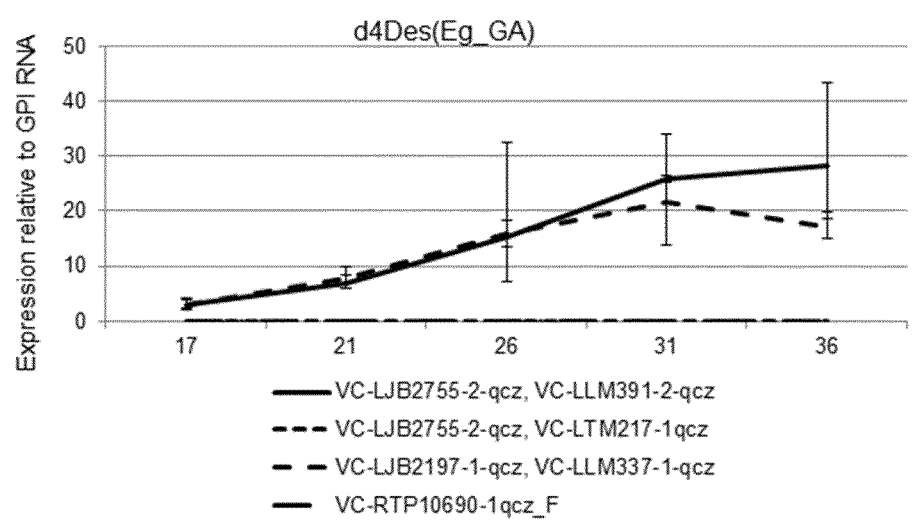
FIG. 21: Comparative transcript analysis of d4Des (Eg_GA) driven by the LuCnl promoter during seed development of single copy event of two different construct combinations; VC-LJB2755-2qcz, VC-LLM391-2qcz rc and VC-LJB2197-1qcz, VC-LLM337-1qcz rc.

The gene d4Des(Tc_GA) was contained in VC-LLM337-1qcz rc, RTP10960-1qcz_F and VC-LTM217-1qcz rc and was driven by the ARC5_perm1 promoter with the pvarc terminator. A single point mutant of this gene; d4Des (Tc_GA)_T564G was contained in VC-LLM391-2qcz rc and regulated by the ARC5_perm1 promoter with the pvarc terminator. The overall trend of expression with this spacer region, promoter and terminator combination was an increase over seed development and then a decrease towards seed maturation, as depicted in FIG. 20. Interestingly, the construct pair VC-LJB2755-2qcz with VC-LLM391-2qcz rc did not adhere to this trend but rather continued to increase over seed development and had a more robust expression than the other constructs and construct combinations. As previously observed VC-RTP10960-1qcz_F had the lowest level of expression.

VC-LLM337-1qcz rc and VC-LLM391-2qcz rc contain d4Des(Eg_GA) driven by the LuCnl promoter with the AgrOCS 192 bp[LED12] terminator. It can be seen in FIG. 21, that similar expression levels that increased during seed development where observed of single copy events containing either one of these two constructs.

Copy Number

To assess whether the entire pathway for PUFA biosynthesis was being brought into the plant and to what extent duplication and/or deletion was occurring in selected events; copy number analysis of certain genes along the T-DNA was carried out.

DNA Extraction

Brown spotted immature seeds from three events were analyzed, in addition to cotyledons of germinating seedlings of two further events. The gDNA was isolated according to standard protocols consistent with Sambrook et al., 1982. To isolate plant tissue DNA the Wizard Magnetic 96 DNA Plant System was used (Promega, Madison, Wis. USA part number FF3760). The supplied protocols were followed with the listed changes being implemented in order to increase the amount of extracted DNA: the volume of the extraction buffer was increased to two hundred microliters and the volume of beads used was increased to ninety microliters with the volume of elution buffer being decreased to twenty microliters.

Duplex qPCR reactions were performed using JumpStart TaqReadyMix for Quantitative PCR (Sigma, D7440). qPCR assays were validated according to standard protocols for qPCR, see Demeke and Jenkins (2010) and Livak and Schmittgen (2001). The genomic copy numbers were calculated with the ddCt method based on the mean of the reference dCt value of a pool of known single copy events. Using the Excel function "frequency", groups of 0, 1, 2, 3, >4 were counted both target and event wise. A Chi-square test was performed for testing the hypothesis the family was segregating for a single T-DNA. The cutoff of P value was set at >0.0499 for a single T-DNA segregation.

PCR for copy number analysis was carried out using the primers and probes listed and according to standard protocols used by those skilled in the art, see Livak and Schmittgen (2001) and Demekes T. and Jenkins R G (2010).

The primer pairs and probes are listed by name below and sequences can be found in the

SEQUENCE LISTING

| Target | Forward Primer | Reverse Primer | Probe |
| --- | --- | --- | --- |
| c-AHAS | c-AHAS_F | c-AHAS_R | c-AHAS_P |
| c-d4Des(Eg_GA) | c-d4Des(Eg_GA)_F | c-d4Des(Eg_GA)_R | c-d4Des(Eg_GA)_P |
| c-d4Des(PI_GA)2 | c-d4Des(PI_GA)2_F | c-d4Des(PI_GA)2_R | c-d4Des(PI_GA)2_P |
| c-d4Des(Tc_GA) | c-d4Des(Tc_GA)_F | c-d4Des(Tc_GA)_R | c-d4Des(Tc_GA)_P |
| c-d5Des(Tc_GA) | c-d5Des(Tc_GA)_F | c-d5Des(Tc_GA)_R | c-d5Des(Tc_GA)_P |
| c-d5Elo(Ot_GA3) | c-d5Elo(Ot_GA3)_F | c-d5Elo(Ot_GA3)_R | c-d5Elo(Ot_GA3)_P |
| c-d6Des(Ot_febit) | c-d6Des(Ot_febit)_F | c-d6Des(Ot_febit)_R | c-d6Des(Ot_febit)_P |
| c-d6Elo(Pp_GA) | c-d6Elo(Pp_GA)_F | c-d6Elo(Pp_GA)_R | c-d6Elo(Pp_GA)_P |
| c-d6Elo(Tp_GA) | c-d6Elo(Tp_GA)_F | c-d6Elo(Tp_GA)_R | c-d6Elo(Tp_GA)_P |
| c-o3Des(Pi_GA) | c-o3Des(Pi_GA)_F | c-o3Des(Pi_GA)_R | c-o3Des(Pi_GA)_P |
| c-o3Des(Pir_GA) | c-o3Des(Pir_GA)_F | c-o3Des(Pir_GA)_R | c-o3Des(Pir_GA)_P |
| j-i-Atss1_c-d5Elo(Ot_GA3) | j-i-Atss1_c-d5Elo(Ot_GA3)_F | j-i-Atss1_c-d5Elo(Ot_GA3)_R | j-i-Atss1_c-d5Elo(Ot_GA3)_P |
| j-i-Atss1_c-d6Elo(Tp_GA2) | j-i-Atss1_c-d6Elo(Tp_GA2)_F | j-i-Atss1_c-d6Elo(Tp_GA2)_R | j-i-Atss1_c-d6Elo(Tp_GA2)_P |
| j-i-Atss14_c-d12Des(Ps_GA) | j-i-Atss14_c-d12Des(Ps_GA)_F | j-i-Atss14_c-d12Des(Ps_GA)_R | j-i-Atss14_c-d12Des(Ps_GA)_P |
| j-i-Atss18_c-d6Elo(Pp_GA2) | j-i-Atss18_c-d6Elo(Pp_GA2)_F | j-i-Atss18_c-d6Elo(Pp_GA2)_R | j-i-Atss18_c-d6Elo(Pp_GA2)_P |
| j-i-Atss18_c-o3Des(Pi_GA2) | j-i-Atss18_c-o3Des(Pi_GA2)_F | j-i-Atss18_c-o3Des(Pi_GA2)_R | j-i-Atss18_c-o3Des(Pi_GA2)_P |
| j-i-Atss2_c-d4Des(Tc_GA3) | j-i-Atss2_c-d4Des(Tc_GA3)_F | j-i-Atss2_c-d4Des(Tc_GA3)_R | j-i-Atss2_c-d4Des(Tc_GA3)_P |
| j-i-Atss2_c-d6Des(Ot febit_GA) | j-i-Atss2_c-d6Des(Ot febit_GA)_F | j-i-Atss2_c-d6Des(Ot febit_GA)_R | j-i-Atss2_c-d6Des(Ot febit_GA)_P |
| j-p-BnFAE_t-PvARC | j-p-BnFAE_t-PvARC_F | j-p-BnFAE_t-PvARC_R | j-p-BnFAE_t-PvARC_P |
| j-p-BnSETL-v1_c-o3Des(Pir_GA) | j-p-BnSETL-v1_c-o3Des(Pir_GA)_F | j-p-BnSETL-v1_c-o3Des(Pir_GA)_R | j-p-BnSETL-v1_c-o3Des(Pir_GA)_P |
| j-p-LuPXR_i-Atss15 | j-p-LuPXR_i-Atss15_F | j-p-LuPXR_i-Atss15_R | j-p-LuPXR_i-Atss15_P |
| j-p-PvARC5_t-BnFAE | j-p-PvARC5_t-BnFAE_F | j-p-PvARC5_t-BnFAE_R | j-p-PvARC5_t-BnFAE_P |
| j-p-PvARC5_t-BnSETL | j-p-PvARC5_t-BnSETL_F | j-p-PvARC5_t-BnSETL_R | j-p-PvARC5_t-BnSETL_P |
| j-t-CaMV_p-LuCnl-2 | j-t-CaMV_p-LuCnl-2_F | j-t-CaMV_p-LuCnl-2_R | j-t-CaMV_p-LuCnl-2_P |
| j-t-E9-p3-2 | j-t-E9-p3-2_F | j-t-E9-p3-2_R | j-t-E9-p3-2_P |
| j-t-PvARC-p-LuCnl | j-t-PvARC-p-LuCnl_F | j-t-PvARC-p-LuCnl_R | j-t-PvARC-p-LuCnl_P |
| j-t-StCAT_p2_p-LuPXR | j-t-StCAT_p2_p-LuPXR_F | j-t-StCAT_p2_p-LuPXR_R | j-t-StCAT_p2_p-LuPXR_P |
| reference (Adh1) | reference (Adh1)_F | reference (Adh1)_R | reference (Adh1)_P |
| c-o3Des(Pi_GA2_SNP) | c-o3Des(Pi_GA2_SNP)_F | c-o3Des(Pi_GA2_SNP)_R | c-o3Des(Pi_GA2_SNP)_P |
| j-t-PvARC-p3 | j-t-PvARC-p3_F | j-t-PvARC-p3_R | j-t-PvARC-p3_P |
| j-i-Atss15_c-o3Des(Pi_GA2) | j-i-Atss15_c-o3Des(Pi_GA2)_F | j-i-Atss15_c-o3Des(Pi_GA2)_R | j-i-Atss15_c-o3Des(Pi_GA2)_P |
| j-p-VfSBPperm3_c-o3Des(Pir_GA) | j-p-VfSBPperm3_c-o3Des(Pir_GA)_F | j-p-VfSBPperm3_c-o3Des(Pir_GA)_R | j-p-VfSBPperm3_c-o3Des(Pir_GA)_P |
| c-d15Des(Ch_ERTp_GA) | c-d15Des(Ch_ERTp_GA)_F | c-d15Des(Ch_ERTp_GA)_R | c-d15Des(Ch_ERTp_GA)_P |
| j-i-Atss2_c-d4Des(PI_GA)-195R) | j-i-Atss2_c-d4Des(PI_GA)-195R)_F | j-i-Atss2_c-d4Des(PI_GA)-195R)_R | j-i-Atss2_c-d4Des(PI_GA)-195R)_P |

Isolation of Genomic Flanking Sequences from Transgenic Events

Genomic DNA sequences flanking each T-DNA insertion in events LANBCH, LBFDGG, LBFDHG, LBFGKN, LBFIHE, LBFLFK, LBFPRA, and LBFDAU were determined. Leaf samples from greenhouse grown plants were harvested and frozen. The leaf tissue was ground and genomic DNA was extracted using standard protocols for plant genomic DNA extraction. An aliquot amount of genomic DNA from each event was then used to isolate flanking sequences by adapter ligation-mediated PCR as described in O'Malley et al. 2007 Nature Protocols 2(1 1):2910-2917. Using this technique, PCR products were generated that contained sequence of the T-DNA border and adjacent genomic DNA. For each event distinct PCR products were obtained corresponding to the left and right border of each T-DNA locus. Individual PCR products were isolated and were sequenced using standard DNA sequencing protocols to determine sequence of the flanking regions. The flanking sequences of event LANBCH are SEQ ID NO: 212, SEQ ID NO: 213, SEQ ID NO: 214, SEQ ID NO: 215, SEQ ID NO: 216, and SEQ ID NO: 217. The flanking sequences of event LBFDGG are SEQ ID NO: 218 and SEQ ID NO: 219. The flanking sequences of event LBFDHG are SEQ ID NO: 220, SEQ ID NO: 221, SEQ ID NO: 222, and SEQ ID NO: 223. The flanking sequences of event LBFGKN are SEQ ID NO: 224 and SEQ ID NO: 225. The flanking sequences for event LBFIHE are SEQ ID NO: 226 and SEQ ID NO: 227. The flanking sequences for event LBFLFK are SEQ ID NO: 228, SEQ ID NO: 229, SEQ ID NO: 230, and SEQ ID NO: 231. The flanking sequences for event LBFPRA are SEQ ID NO: 232, SEQ ID NO: 233, SEQ ID NO: 234, SEQ ID NO: 235, and SEQ ID NO: 236. The flanking sequences for event LBFDAU are SEQ ID NO: 237, SEQ ID NO: 238, SEQ ID NO: 239, and SEQ ID NO: 240. The flanking sequences are useful for determining the genomic location of T-DNA inserts and the integrity of the genomic DNA surrounding the insertion. For example, event LBFGKN contains a single T-DNA insertion of plasmid VC-LTM593-1qcz rc. A DNA sequence alignment of SEQ ID NO: 224 and SEQ ID NO: 3 can be used to reveal the portion of the flanking sequence that corresponds to the T-DNA right border. The portion of the flanking sequence that is not identical to the T-DNA thus corresponds to the genomic DNA that is adjacent to the T-DNA right border. Likewise, the SEQ ID NO: 225 and SEQ ID NO:3 can be aligned to identify the genomic DNA sequence that is adjacent to the T-DNA left border. For event LBFGKN, the genomic DNA fragments adjacent to the right and left border of the T-DNA can be mapped to Chromosome C04 of the *B. napus* Darmor reference genome. Based on annotation of the *B. napus* reference genome, the T-DNA of event LBFGKN is inserted more than 5000 bp away from any predicted genes or coding regions. In addition, the portions of the flanking sequences corresponding to genomic DNA indicate no rearrangements of the genomic DNA around the T-DNA insert.

Thus, in one embodiment, the plant of the invention is a transgenic plant, preferably a transgenic *B. napus* plant of the invention producing EPA and/or DHA, preferably EPA and DHA, comprising one or more T-DNAs for the expression of one or more genes for the production of EPA and/or DHA, whereby each T-DNA copy inserted does not disrupt any gene, e.g. no endogenous or no transgenic gene is disrupted. Preferably, the EPA and DHA content in the bulked seed is 10 mg, 15 mg, 20 mg, 24 mg, 30 mg, 31 mg, 35 mg, 38 mg, or more EPA and DHA/g seed. In one embodiment, the EPA and DHA content in the bulked seed is between 10 mg and 70 mg, between 15 mg and 60 mg, 20 mg and 50 mg, or between 24 mg and 38 mg.

In one embodiment the genetic insertion of the T-DNA is located >5000 base pairs away from any endogenous gene.

The plant of the invention can comprise one or more copies one T-DNA. In one embodiment, the plant is homozygous with one copy of the T-DNA integrated in each of the homozygous loci, in another embodiment, it is homozygous with two copies of the T-DNA integrated in each of the homozygous loci. Further, the plant of the invention can by heterozygous, e.g. one or two copies of the T-DNA are integrated in one herterozygous locus.

Event Specific Detection

The flanking sequences isolated from events LANBCH, LBFDGG, LBFDHG, LBFGKN, LBFIHE, LBFLFK, LBFPRA, and LBFDAU were used for the design of event specific detection assays to test for the presence T-DNA insertions. Specific primer pairs are provided in this example, but the disclosed flanking sequences could be used to design different primer pairs for producing diagnostic amplicons for each locus of each event. Endpoint Taqman qPCR assays for locus detection were developed and are described in this example. Other methods may be known and used by those skilled in the art for the detection of events LANBCH, LBFDGG, LBFDHG, LBFGKN, LBFIHE, LBFLFK, LBFPRA, and LBFDAU. Oligonucleotide primers used for the assays are listed in Table 176. Detection of each locus from LBFDAU and LBFLFK requires the use of a specific combination of forward primer, reverse primer, and probe. The TaqMan probes for targets of interest were labeled with FAM/BHQ1. The method described here is optimized for the Quantstudio™ 12K Flex Real-Time PCR system from Life Technologies, although methods can be adapted to other systems with minor modification known to those skilled in the art. Endpoint Taqman qPCR assays were carried out with JumpStart TaqReadyMix (Sigma, P2893) in a 384-well plate (Life technologies, catalogue number 4309849) in a total volume of 10 microliters per well. Per reaction, 2 µl of template DNA is mixed with 8 microliters of qPCR reaction mixture. The plates were sealed with MicroAmp® Optical Adhesive Film (Life Technologies, catalogue number 4311971).

For event specific detection qPCR reaction mixture was prepared as follows:

| Taqman endpoint qPCR reaction components | |
| --- | --- |
| PCR Component | Amount (µl) per reaction |
| 2X Jumpstart Taq Readymix | 5 |
| 25 mM MgSO4 | 0.4 |
| ROX (Sulforhodamine 101, 12 µM) | 0.1 |
| Forward Primer (10 µM) | 0.9 |
| Reverse Primer (10 µM) | 0.9 |
| Probe (10 µM) | 0.1 |
| gDNA (15-60 ng/µl) | 2 |
| Nuclease free water | 0.6 |
| volume final | 10 µl |

The qPCR reactions were carried out as follows:

| | | Temp | Time |
| --- | --- | --- | --- |
| | step 1 | 95° C. | 5 min |
| 45 cycles | step 2 | 95° C. | 18 sec |
| | step 3 | 60° C. | 1 min |

TABLE 176

Primers and Probes used for event specific detection.

| Event/Locus | Forward Primer | Reverse Primer | Probe |
|---|---|---|---|
| LANBCH locus 1 (N5) | LANBCH locus 1 (N5)_Forward primer | LANBCH locus 1 (N5)_Reverse primer | LANBCH locus 1 (N5)_Probe |
| LANBCH locus 1 (N9) | LANBCH locus 1 (N9)_Forward primer | LANBCH locus 1 (N9)_Reverse primer | LANBCH locus 1 (N9)_Probe |
| LANBCH locus 2 (N5) | LANBCH locus 2 (N5)_Forward primer | LANBCH locus 2 (N5)_Reverse primer | LANBCH locus 2 (N5)_Probe |
| LANBCH locus 2 (N9) | LANBCH locus 2 (N9)_Forward primer | LANBCH locus 2 (N9)_Reverse primer | LANBCH locus 2 (N9)_Probe |
| LBFDAU locus 1 | LBFDAU locus 1_Forward primer | LBFDAU locus 1_Reverse primer | LBFDAU locus 1_Probe |
| LBFDAU locus 2 | LBFDAU locus 2_Forward primer | LBFDAU locus 2_Reverse primer | LBFDAU locus 2_Probe |
| LBFDGG | LBFDGG_Forward primer | LBFDGG_Reverse primer | LBFDGG_Probe |
| LBFDHG locus 1 | LBFDHG locus 1_Forward primer | LBFDHG locus 1_Reverse primer | LBFDHG locus 1_Probe |
| LBFDHG locus 2 | LBFDHG locus 2_Forward primer | LBFDHG locus 2_Reverse primer | LBFDHG locus 2_Probe |
| LBFGKN | LBFGKN_Forward primer | LBFGKN_Reverse primer | LBFGKN_Probe |
| LBFIHE | LBFIHE_Forward primer | LBFIHE_Reverse primer | LBFIHE_Probe |
| LBFLFK locus 1 | LBFLFK locus 1_Forward primer | LBFLFK locus 1_Reverse primer | LBFLFK locus 1_Probe |
| LBFLFK locus 2 | LBFLFK locus 2_Forward primer | LBFLFK locus 2_Reverse primer | LBFLFK locus 2_Probe |
| LBFPRA Locus 1 | LBFPRA Locus 1_Forward primer | LBFPRA Locus 1_Reverse primer | LBFPRA Locus 1_Probe |
| LBFPRA locus 2 | LBFPRA locus 2_Forward primer | LBFPRA locus 2_Reverse primer | LBFPRA locus 2_Probe |
| LBFPRA Locus 3e | LBFPRA Locus 3e_Forward primer | LBFPRA Locus 3e_Reverse primer | LBFPRA Locus 3e_Probe |

Expected amplicon sizes are, given below in base pairs (plus or minus 10 bp):

| Amplicon | Amplicon Size plus or minus 10 bp |
|---|---|
| Amplicon LANBCH locus 1 (N5) | 100 bp |
| Amplicon LANBCH locus 1 (N9) | 150 bp |
| Amplicon LANBCH locus 2 (N5) | 150 bp |
| Amplicon LANBCH locus 2 (N9) | 120 bp |
| Amplicon LBFDAU locus 1 | 110 bp |
| Amplicon LBFDAU locus 2 | 95 bp |
| Amplicon LBFDGG | 100 bp |
| Amplicon LBFDHG locus 1 | 200 bp |
| Amplicon LBFDHG locus 2 | 140 bp |
| Amplicon LBFGKN | 140 bp |
| Amplicon LBFIHE | 110 bp |
| Amplicon LBFLFK locus 1 | 160 bp |
| Amplicon LBFLFK locus 2 | 170 bp |
| Amplicon LBFPRA Locus 1 | 570 bp |
| Amplicon LBFPRA locus 2 | 190 bp |
| Amplicon LBFPRA Locus 3e | 90 bp |

Example 25 Protein Levels

Pooled seed material from four week old siliques was used for protein extraction. To enrich the membrane proteins and reduce the background signal, microsomes isolated from ground seed tissue were used to analyze protein levels for the following enzymes: c-o3Des(Pi_GA2), c-o3Des (Pir_GA), d4Des(Eg), c-d4Des(PI_GA)2, and c-d6Elo (Tp_GA2). For c-o3Des(Pir_GA) and c-d6Elo(Tp_GA2), the microsomes were further extracted with detergent and used for ELISA. The various versions of a given gene (denoted as GA, GA2 etc.) all encoded an identical protein corresponding to the gene listed.

Initially, in a mortar cooled with liquid nitrogen, seeds were ground to a fine powder in Extraction buffer (25 mM Tris, pH 7.4; 140 mM NaCl; 3 mM KCl; 3 mM DTT; 200 mM Sorbitol; and EDTA-free Protease inhibitors (Roche)) at a ratio of 1 g seed/4 ml buffer. The plant cell-debris was removed by centrifugation (5000×g, 10 minutes, 4° C.), re-extracted by grinding a second time as described above with 1.5 ml of Extraction Buffer, and then again separated by centrifugation (5000×g, 10 minutes, 4° C.). The supernatant from these two extractions was combined and represents the cell-free extract (typically 3.5 ml/g seed). Microsomal pellets were obtained from the cell-free extracts by ultra-centrifugation (100,000×g, 60 minutes, 4° C.). For the c-o3Des(Pi_GA2), d4Des(Eg), c-d4Des(PI_GA)2, enzymes the microsomal pellets were suspended in Suspension Buffer (1×TBST+1% TritonX-100). 1×TBST consists of 50 mM Tris, 150 mM NaCl, 0.05% tween 20 detergent with a final pH of 7.6 at 4° C.

For c-o3Des(Pir_GA) and c-d6Elo(Tp_GA2) the microsomal fractions were isolated as described above, and proteins were solubilized with 1×TBST buffer and detergent of choice (For details, please see the table below). For c-d4Des(Tc_GA), c-d5Elo(Ot_GA3), c-d5Des(Tc_GA2), c-d6Des(Ot_febit), c-d6Elo(Pp_GA2), c-d12Des(Ps_GA), the seed powder was further ground in liquid nitrogen and extracted with 1×TBST+1% Triton X100+Protease Inhibitor at 1:3 W/V ratio. The supernatant was cleared at 13,000 g for 20 minutes at 4° C. using a micro-centrifuge and followed by a 10 minute spin at 13,000 g. The clarified supernatant was used for ELISA and total protein assay.

Antibody/antigen hybridization conditions: Plates were blocked with 300 µl/well of freshly made blocking solution. The plates were sealed and incubated for 1 hour with continuous shaking. After 1 hour of incubation, the plates were washed twice with 1×TBST.

The extract from above was used in the ELISA assay. The plate was incubated with 100 µl of standards or sample extract at 4° C. for overnight, without shaking. Standards were serial diluted 1:3. The plates were sealed and incubated overnight at 4° C. After the plates were incubated overnight, the plates were washed five times with 1×TBST. After the wash the plates were incubated with 100 µl of detecting antibody in blocking solution for 1 hour, sealed with continuous shaking. The plates were washed five times with 1×TBST at the end of the one hour incubation step. The plates were then incubated with 100 ml of HRP-conjugated donkey anti-animal of the detecting antibody secondary antibody (1:10,000) in blocking solution for 1 hour, in a sealed plate with continuous shaking. The plates were then washed five times with 1×TBST at the end of the blocking step. 100 µl of 1-step TMB was then added and the plates incubated at room temperature for 20 minutes, sealed with continuous shaking. After the twenty minutes, 100 µl of a 1M HCl solution was added and the plates read at 450 nm.

For c-d6Elo(Tp_GA2) only: all steps were the same as for the other proteins but in place of the HRP conjugated donkey anti-body system used for the others, 100 µl of biotin-conjugated donkey anti-rabbit IgG diluted 1:40,000 in 2% BSA/1×TBST was used. The plate was sealed and shaken continuously during this incubation step, which was done for one hour. The plate was washed five times with 1×TBST at the end of this step. To read this plate, the plate was incubated with 100 µl extravidin-peroxidase diluted 1:40,000 in 2% BSA/1×TBST, sealed and incubated for 1 hour with continuous shaking. The plate was then washed five times with 1×TBST. The plate was read at 450 nm.

TABLE 177

Overview of hybridization for protein detection and quantification. TMB (3,3',5,5'-tetramethylbenzidine) was the substrate for the horse radish peroxidase employed to visualize protein bands, supplied by Sigma-Aldrich T-0565 and used according to the instructions of the manufacturer.

| Coating AB | Blocking Buffer | Sample extraction buffer | Standard ID and dilution | Detecting AB | Secondary AB | TMB |
|---|---|---|---|---|---|---|
| o3Des(Pir) AB212, 1:5,500 | 1% BSA in TBST | 1% Triton X-100, + 1 xTBS, + Protease Inhibitor | 1:3, from 90 ng/ml, full length o3Des(Pir) | AB210 1:1,300, in blocking buffer | 1:10,000 HRP-donkey anti chicken | 1 step TMB, 20 min |
| d4Des(Tc) AB216, 1:15,000 | 1% BSA in TBST | 1% Triton X-100, + 1 xTBS, + Protease Inhibitor | 1:3, from 200 ng/ml, RN121 | AB217, 1:15,000, in blocking buffer | 1:10,000 HRP-donkey anti Rabbit | 1 step TMB, 20 min |
| d5Elo(ot) AB214, 1:1500, | 1% BSA in TBST | 1% Triton X-100, + 1 xTBS, + Protease Inhibitor | 1:3, from 200 ng/ml, RN134 | AB215, 1:1500, in blocking buffer | 1:10,000 HRP-donkey anti chicken | 1 step TMB, 20 min |
| d5Des (Tc) AB90, 1:8000 | 1% BSA in TBST | 1% Triton X-100, + 1 xTBS, + Protease Inhibitor | 1:3, from 100 ng/ml, full tenth d5Des | AB 100, 1:40000, in blocking buffer | 1:10,000 HRP-donkey anti chicken | 1 step TMB, 20 min |
| d6Des(Ot) AB113, 1:500 | 1% BSA in TBST | 1% Triton X-100, + 1 xTBS, + Protease Inhibitor | 1:3, from 100 ng/ml, full length d6Des(Ot) | AB 112 rabbit, 1:10000, in blocking buffer | 1:10,000 HRP-donkey anti rabbit | 1 step TMB, 20 min |
| d6Elo(Pp) AB 107, 1:1000 | 1% BSA in TBST | 1% Triton X-100, + 1 xTBS, + Protease Inhibitor | 1:3, from 110 ng/ml, PA534 | AB 121 chicken, 1:5000 in extraction buffer | 1:10,000 HRP-donkey anti chicken | 1 step TMB, 20 min |
| d6Elo(Tp) AB125, 1:2000, | 2% BSA in TBST | 1 XTBST + 1% DDM + Protease inihibitor | 1:3, from 200 ng/ml, PA678 | AB140, 1:1000, in blocking buffer | 1:40,000 biotin-donkey anti rabbit for 1 hr, then 1:40,000 extravidin-peroxidase | 1 step TMB, 20 min |
| d12Des (Ps) AB128, 1:3000 | 1% BSA in TBST | 1% Triton X-100, + 1 xTBS, + Protease Inhibitor | 1:3, from 200 ng/ml, PA557 | AB 129, 1:3000, in blocking buffer | 1:10,000 HRP-donkey anti Rabbit | 1 step TMB, 20 min |

TABLE 178

Levels of the proteins of interest were expressed as nanograms (ng) per milligram of total protein. The values were the average and standard deviation from three technical measurements of approximately four week old seed material. As one observes the construct VC-RTP10690-1qcz_F had overall less protein for the expressed genes than the combination of VC-LJB2197-1qcz and VC-LLM337-1qcz rc.

| Protein | Wt | LJB2197 + LLM337 | VC-RTP10690-1qcz_F |
|---|---|---|---|
| c-o3Des(Pir_GA), ng/mg total microsomal protein | 9.04 ± 0.5 | 387.5 ± 10.5 | 69.7 ± 1.2 |
| c-d4Des(Tc_GA), ng/mg of total protein | 0.04 ± 0.01 | 0.74 ± 0.03 | 0.1 ± 0.01 |
| c-d5Elo(Ot_GA3), ng/mg of total protein | 0.12 ± 0.01 | 2.85 ± 0.02 | 1.23 ± 0.01 |
| c-d5Des(Tc_GA2), ng/mg of total protein | 0.05 ± 0.01 | 2.03 ± 0.08 | 1.54 ± 0.03 |
| c-d6Des(Ot_febit), ng/mg total protein | 0 ± 0 | 4.1 ± 0.1 | 1.83 ± 0.01 |
| c-d6Elo(Pp_GA2), ng/mg total protein | 0 ± 0 | 3.77 ± 0.3 | 1.1 ± 0.01 |
| c-d6Elo(Tp_GA2), ng/mg of total microsomal protein | 0 ± 0 | 0.33 ± 0.06 | 0.38 ± 0.04 |
| c-d12Des(Ps_GA), ng/mg of total protein | 0.05 ± 01 | 1.5 ± 0.07 | 0.34 ± 0.03 |

Example 26: Desaturase and Elongase Substrate Specificity and Selectivity Observed in Yeast Compared with Fatty Acid Profiles Observed in Canola Events Expressing these Enzymes As shown in Examples 10-18, the engineering of canola to convert endogenous fatty acids, such as oleic acid (18:1n-9) and LA (18:2n-6) to 20:5n-3 and 22:6n-3 requires the introduction of several desaturases and elongases. Although bioinformatics is useful for predicting the function of large, well-studied classes of enzymes, for example a delta-12 desaturase, the precise substrate tolerance of an enzyme must be determined empirically. We therefore, as shown in Examples 21 and 22, determined the substrate tolerance for each desaturase and elongase that was introduced into canola (Examples 10-18). Understanding the substrate profile for each of the introduced enzymes allowed optimal engineering of canola to produce EPA and DHA by:

(1) Conversion of the three most predominant canola endogenous fatty acids (OA, LA, and ALA, see Kumily profiles in Examples 10-18) to EPA and DHA,
(2) Minimizing generation of side reactions, and
(3) Providing a proof-reading mechanism that re-routes side-products back into the biosynthesis of EPA and DHA.

Examples provided herein further detail how the deduced specificity of the introduced desaturases and elongases allowed optimal engineering of canola to produce oil enriched in EPA and DHA.

Delta-6-Desaturase:
Yeast feeding studies (Table 159 and Table 163) show that the delta-6-desaturase (*Ostreococcus tauri*) can readily accept substrates containing, LA (18:2n-6) and ALA (18:3n-3). As shown in Tables 148-152, the resulting GLA (18:3n-6) delta-6-desaturase (*Ostreococcus tauri*) product can be processed by either of the delta-6-elongases (*Physcomitrella patens* or *Thalassiosira pseudonana*), followed by the delta-5-desaturase (*Thraustochytrium* sp. ATCC21685), either of the omega-3-desaturases (*Phytophthora infestans* or *Pythium irregulare*), the delta-5-elongase (*Ostreococcus tauri*) and finally either of the delta-4-desaturases (*Thraustochytrium* sp. and *Pavlova lutheri*) to yield DHA (22:6n-3). The resulting ALA desaturation product, SDA (18:4n-3), can be converted by either of the delta-6-elongases (*Physcomitrella patens* or *Thalassiosira pseudonana*) to a 20:4n-3 containing fatty acid (see Table 160), which can be accepted by the delta-5-desaturase (*Thraustochytrium* sp. ATCC21685) to generate an EPA (20:5n-3) linked fatty acid as shown in Table 162. The fatty acid analysis data presented for the engineered canola lines in Examples (10-18) show significantly lower levels of ALA relative to non-transgenic Kumily controls, consistent with the engineered conversion of ALA to 20:5n-3 and 22:6n-3.

Delta-6-Elongases:
Yeast feeding studies (Table 160 and Table 163) show that both of the delta-6-elongases, *Physcomitrella patens* and *Thalassiosira pseudonana*, accept 18-carbon chain substrates but prefer molecules desaturated at carbon-6 (see GLA (18:3n-6) and SDA (18:4n-3) vs. LA (18:2n-6) and ALA (18:3n-3). The delta-6-elongase from *Thalassiosira pseudonana* is much more stringent than the one from *Physcomitrella patens* in recognizing the delta-6-desaturated fatty acids. In the fatty acid analysis of the engineered canola lines presented in Examples (10-18) 20:2n-6 and 20:3n-3, resulting from desaturation of LA and ALA respectively, are detected. The inclusion of these specific elongases from *Physcomitrella patens* and *Thalassiosira pseudonana* allowed preferred conversion of fatty acids desaturated at carbon-6 thus, providing maximum conversion of of EPA and DHA from GLA and SDA. Fatty acid profiles of the LTM593 (Example 18) line show levels of 20:2n-6 and 20:3n-3 that are about the same as found in wild-type Kumily confirming the specificity of the delta-6 elongases from *Physcomitrella patens* and *Thalassiosira pseudonana* upon introduction into canola.

Delta-5-Desaturase:
Yeast feeding studies (Table 159 and Table 162 and Table 163) show that the delta-5-desaturase (*Thraustochytrium* sp. ATCC21685) accepts DHGLA (20:3n-6) and 20:4n-3. As described above (Example 26 (this section), Delta-6-desaturase), the ability of the delta-5-desaturase (*Thraustochytrium* sp. ATCC21685) to desaturate 20:4n-3 is important for the conversion of ALA and SDA into 20:5n-3 and 22:6n-3.

Omega-3-Desaturases:
Yeast feeding studies show that both omega-3-desaturases, (*Phythophthora infestans* and *Pythium irregulare*) can accept ARA (20:4n-6), DTA (22:4n-6), and DHGLA (20:3n-6). These omega-3-desaturases prefer molecules with 4 double bonds. In the transgenic canola lines described in Examples (10-18), the ability of these omega-3-desaturases to utilize 22:4n-6 as a substrate, as shown in Table 163, allows re-direction of ARA (20:4n-6) that has been elongated by the delta-5-elongase (*Ostreococcus tauri*) back into the pathway as 22:5n-3 (a substrate for the engineered delta-4 desaturases) for synthesis of DHA (22:6n-3). Fatty acid profiles of the LTM593 (Example 18) line show detectable, but low levels of 22:4n-6 consistent with this fatty acid being converted to 22:5n-3 in vivo the described canola that was engineered to synthesize DHA.

Delta-5-Elongase:
Yeast feeding studies show (Table 161 and Table 163) that the delta-5-elongase (*Ostreococcus tauri*) prefers 20-carbon chain substrates, EPA (20:5n-3) and ARA (20:4n-6), but can also extend lipids containing 18-carbon chains, like SDA (18:4n-3) and ALA (18:3n-3). In the engineered canola (Examples 10-18) the presence of the omega-3-desaturases, (*Phythophthora infestans* and *Pythium irregulare*), allows the 22:4n-6 product, resulting from the elongation of ARA, to be converted to 22:5n-3 and which is then desaturated by the delta-4-desaturases (*Thraustochytrium* sp. and *Pavlova lutheri*) to produce the final product, 22:6n-3. Fatty acid analysis of the transgenic canola lines described in Examples 10-18 shows minor levels of 22:4n-6, likely due to the ability of the omega-3 desaturases to redirect this lipid back into the biosynthesis of 22:6n-6. The 20:4n-3 produced from the extension of SDA is a substrate recognized by the delta-5-desaturase (*Thraustochytrium* sp. ATCC21685) and can be converted to 20:5n-3, the preferred substrate of the delta-5-elongase (*Ostreococcus tauri*).

Delta-4-Desaturases:

Yeast feeding studies (Table 159 and Table 163) show that both delta-4-desaturases, (*Thraustochytrium* sp. and *Pavlova lutheri*) can accept 22:5n-3 and DTA (22:4n-6) with a slight preference for 22:5n-3.

Example 27: Using Differentially Labeled Heavy Peptides to Monitor Digestion Efficiency in Quantitative LC-MS The described method provides an avenue for quantitating digestion efficiency in targeted proteomics experiments. In most MRM LC-MS applications, measuring digestion efficiency relies on an indirect measurement which examines a peptide profile of the sample by comparing the number of missed cleavage peptides detected to the number of completely digested peptides detected in a separate LC-MS experiment. While providing an overall perspective of the trypsin efficiency within the experiment, the data does little to address specific digestion of the target sequence being monitored in the MRM experiment. Measuring global digestion efficiency does not address possible sequence specific biases in trypsin activity and may result in misrepresentation of target quantity. Indeed, there was a growing appreciation that trypsin digestion kinetics was strongly influenced by sequence context (Proc J. et al. 2010. Journal of Proteome Res. 9:5422-5437, and Lowenthal M. et al. 2014. Anal Chem. 86:551-558). In order to measure sequence specific digestion efficiency we use two differentially-labeled heavy peptides to obtain a ratio for digestion efficiency (scheme 1). Peptide three includes the correct sequence context for the target by including four amino acids both amino and carboxyl to the two trypsin cleavage sites that generate the native peptide. In general, three amino acids were considered sufficient for trypsin to identify its cleavage site (Makriyannis T. and Y. Clonis. 1997. Biotech Bioeng. 53:49-57) and hydrolysis rates were only affected by the closest two amino acids (Lowenthal M. et al. 2014. Anal Chem. 86:551-558). This scheme allows us to simultaneously assess specific digestion efficiency and also obtain quantitation data for the target molecule. In this design, the two peptides were spiked at equimolar concentrations into the test sample prior to digestion. During sample analysis, transitions were monitored for the target peptide and the two heavy peptide products. Peak intensities obtained from the two heavy peptides were compared to get a ratio for digestion efficiency and the target peptide intensities were used for quantitation.

Scheme 1
Example protein: O3D (Pir)
Sequence:

MASTSAAQDAAPYEFPSLTEIKRALPSECFEASVPLSLYYTARSLALAGS

LAVALSYARALPLVQANALLDATLCTGYVLLQGIVFWGFFTVGHDCGHGA

-continued

FSRSHVLNFSVGTLMHSIILTPFESWKLSHRHHHKNTGNIDKDEIFYPQR

EADSHPVSRHLVMSLGSAWFAYLFAGFPPRTMNHFNPWEAMYVRRVAAVI

ISLGVLFAFAGLYSYLTFVLGFTTMAIYYFGPLFIFATMLVVTTFLHHND

EETPWYADSEWTYVKGNLSSVDRSYGALIDNLSHNIGTHQIHHLFPIIPH

YKLNDATAAFAKAFPELVRKNAAPIIPTFFRMAAMYAKYGVVDTDAKTFT

LKEAKAAAKTKSS target peptide (underlined), native sequence contained in synthetic peptide for digestion efficiency (redouble underlined)

Peptides
DEIFYPQR (native peptide measured from sample)
DEIFYPQ(15N13CR) (for standard curve, and normalization)
NIDKDEIFY(15N13CP)Q(15N13CR)EADS (for digestion efficiency)

Standard peptides (2) (3) were spiked into the test sample at the same concentration prior to proteolysis. After proteolysis the transitions for the product peptides, (2) and DEIFY(15N13CP)Q(15N13CR) were compared in product ion intensity in order to determine the digestion efficiency of the targeted sequence within the context of its native sequence according to the following equation:

$$\% \text{ digestion efficiency} = \frac{\text{peak intensity DEIFY}(15N13CP)Q(15N13CR)}{\text{peak intensity DEIFY } PQ(15N13CR)} * 100$$

The % digestion efficiency is therefore measured in the test sample directly and can be used to assess the impact on detected target concentration.

Example 28: Use of Different Germplasm to Optimize Production of VLC-PUFA

It appears that expression of the same or very similar gene sets in different host plants, such as *Camelina sativa* (Ruiz-Lopez et al., 2014), results in a larger yield of VLC-PUFA than has been attainable in *Brassica napus*. This notion is illustrated by the data in Table 179. Table 179 contains fatty acid data from seeds of transgenic *B. napus* (LBJ1671) and transgenic *C. sativa* (RRes_EPA_line) transformed with nearly identical T-DNAs and the respective wild type controls. The only difference between the constructs used to make the two transgenic lines is that the TDNA used to make the transgenic *B. napus* (LBJ1671) has an extra GFP expression cassette adjacent to the right border. When comparing transgenic *B. napus* (LJB1671) to the WT Kumily control, there is a decrease in the amount of 18:1 and increases in the amounts of 18:2 and 18:3 fatty acids. The 18:2 and 18:3 fatty acids are intermediates of the pathway introduced by LJB1671, and therefore the elongation of 18:2 and 18:3 fatty acids into 20C fatty acids can be considered a bottleneck reaction in *B. napus*. On the other hand, when comparing transgenic *C. sativa* (RRes_EPA_line) to the WT control, there is a decrease in 18:1 and also in 18:2 and 18:3 fatty acids. Therefore, the elongation of 18:2 and 18:3 fatty acids is not a bottleneck in *C. sativa*. The absence of this bottleneck in *C. sativa* results in 10-fold higher 20:5n-3 (EPA) content compared to the transgenic *B. napus*.

The conversion of 18:1 to 18:2 and of 18:2 to 18:3 occurs largely in the phospholipid membrane, while the elongation of 18C fatty acids to 20C fatty acids occurs strictly in the acyl-CoA pool. This difference in substrate specificity means that 18C fatty acids must be released from membrane phospholipids in order to be elongated. This release is apparently a bottleneck in *B. napus*, but not in *C. sativa*. The difference in flux of 18:2 from PC into the CoA pool between these two species could be due to differences in the activities of numerous enzymes, including: 1) phospholipases, 2) acyl-CoA synthetases, 3) lyso-PC acyltransferases, 4) phospholipid-diacylglycerol choline transferases, 5) phospholipid-diacylglycerol acyl transferases, and others. As a consequence of these observations, transforming any of the constructs from example 11 to example 18 into variety of species and germplasms (such as other *Brassica* germplasms in the so called Triangle of U), would result in a preferred embodiment of the present invention (e.g. higher amounts of EPA and DHA, and/or lower amounts of 18:2n-6).

Example 29: Fatty Acid Analysis of Canola Oils and Commercial Oil and Solid Samples (Total FAME Analysis)

Canola Seeds:

10-15 canola seeds were transferred into tubes on a 96-format rack and closed with cap strips. Seeds were ground in a swing mill using 3 mm beads for 2×2 min at 30 Hz. The rack was then centrifuged for 5 min at 4000 rpm to remove powder from the lid. Extraction of oil was carried out by adding 800 μL of methyl tert-butyl ether (MTBE) to the samples followed by extraction in a swing mill for 2×30 sec at 30 Hz. After centrifugation at 4000 rpm for 10 min, 40 μL of the clear supernatant was transferred into a 96-well micro rack and diluted using 260 μL MTBE. Lipids were derivatized into fatty acid methyl esters (FAMEs) by adding 20 μL trimethylsulfonium hydroxide solution (TMSH, 0.2 M in methanol) into each sample. The rack was closed using silicone/PTFE cap mats and incubated for 20 min at room temperature.

TABLE 179

Introduction of a construct that was isogenic for all genes involved in VLC-PUFA synthesis into *Brassica napus* cv Kumily and into *Camelina sativa*. Average fatty acid data of segregating T1 seed of 26 events containing the T-DNA of LJB1671 and wild type (WT) *Brassica napus* cv Kumily are shown in the top two rows of data. For line RRes_EPA, fatty acid profiles of T3 homozygous seeds of selected insertion events, and of the respective WT control, are shown. RRes_EPA line and WT *Camelina sativa* data were taken from supplemental table S1 of Ruiz-Lopez et al., 2014.

| Event | Other | 16:0 | 16:1 n-7 | 16:3 n-3 | 18:0 | 18:1 n-9 | 18:2 n-6 | 18:2 n-9 | 18:3 n-3 | 18:3 n-6 | 18:4 n-3 |
|---|---|---|---|---|---|---|---|---|---|---|---|
| UB1671 introduced into Kumily (n = 26) | 0 | 5 ± 0.5 | 0.2 ± 0.1 | 0.1 ± 0.1 | 2.6 ± 0.6 | 37.8 ± 10.9 | 29.1 ± 4.3 | 0.4 ± 0.4 | 7.8 ± 1.2 | 4.4 ± 5.4 | 2 ± 2.7 |
| WT Kumily greenhouse (n = 46) | 0 | 5 ± 0.1 | 0.4 ± 0 | 0.2 ± 0 | 2.6 ± 0.1 | 66.3 ± 1.7 | 16.8 ± 1.3 | 0 ± 0 | 6.1 ± 0.4 | 0 | 0 |
| RRes_EPA line | 11.9 ± 1.0 | 8.3 ± 0.6 | n.d | n.d | 6.7 ± 0.9 | 5.0 ± 0.8 | 20.6 ± 1.2 | n.d | 15.8 ± 2.9 | 2.4 ± 1.7 | 1.5 ± 1.2 |
| WT Camelina sativa | 11.2 ± 0.1 | 6.5 ± 0.1 | n.d | n.d | 3.4 ± 0.1 | 14.5 ± 0.4 | 19.0 ± 0.6 | n.d | 30.8 ± 0.6 | 0 | 0 |

| Event | 20:0 | 20:1 n-9 | 20:2 n-6 | 20:3 n-6 | 20:3 n-3 | 20:4 n-6 | 20:4 n-3 | 20:5 n-3 | 22:0 | 22:1 n-9 |
|---|---|---|---|---|---|---|---|---|---|---|
| UB1671 introduced into Kumily (n = 26) | 0.9 ± 0.2 | 1.3 ± 0.4 | 1.8 ± 1.8 | 0.6 ± 0.6 | 1.5 ± 1 | 1 ± 0.7 | 0.8 ± 0.5 | 2.1 ± 1.5 | 0.5 ± 0.1 | 0 ± 0 |
| WT Kumily greenhouse (n = 46) | 0.9 ± 0 | 1.2 ± 0 | 0 | 0 | 0 | 0 | 0 | 0 | 0.5 ± 0 | 0 ± 0 |
| RRes_EPA line | n.d | 7.0 ± 0.9 | n.d | n.d | 1.1 ± 0.4 | 3.2 ± 1.1 | 1.6 ± 0.3 | 14.7 ± 2.8 | n.d | n.d |
| WT Camelina sativa | n.d | 14.5 ± 0.1 | n.d | n.d | 0 | 0 | 0 | 0 | n.d | n.d | n.d, not determined.

*Arabidopsis* Seeds:

20 mg of seeds were transferred into tubes on a 96-format rack. The canola seed protocol was followed in all further steps.

Canola Oils and Commercial Oil Samples:

20 µL of oil was transferred into a glass vial and diluted using 1 mL MTBE. 20-80 µL of the sample-solutions were transferred into into a 96-well micro rack and diluted using 260 µL MTBE. Lipids were derivatized into FAMEs by adding 20 µL trimethylsulfonium hydroxide solution (TMSH, 0.2 M in methanol) into each sample. The rack was closed using silicone/PTFE cap mats and incubated for 20 min at room temperature.

Commercial Solid Samples:

Solid samples were lyophilized prior to analysis. 20 mg of solid samples were transferred into tubes on a 96-format rack. The canola seed protocol was followed in all further steps.

An overview on the samples is provided in the following Table.

TABLE 180

Samples description

| Sample Name | Description | Source/Origin |
|---|---|---|
| Transgenic plant samples (T-DNA identity) | | |
| LANBCH oil | *B. napus* (VC-LJB2197-1qcz, VC-LLM337-1qcz rc) | 2014 Field season |
| LANPMZ seeds | *B. napus* (VC-LJB2197-1qcz, VC-LLM337-1qcz rc) | 2012 Field season |
| LAODDN seeds | *B. napus* (VC-LJB2755-2qcz rc, VC-LLM391-2qcz rc) | 2012 Field season |
| LBFDAU oil | *B. napus* (VC-LTM593-1qcz rc) | 2014 Field season |
| LBFGKN seeds | *B. napus* (VC-LTM593-1qcz rc) | 2014 Field season |
| LBFGKN oil | *B. napus* (VC-LTM593-1qcz rc) | 2014 Field season |
| LBFLFK seeds | *B. napus* (VC-LTM593-1qcz rc) | 2014 Field season |
| LBFLFK oil | *B. napus* (VC-LTM593-1qcz rc) | 2014 Field season |
| Arabidopsis seeds | *A. thaliana* (VC-LTM593-1qcz rc) | Greenhouse |
| Non-transgenic plant samples | | |
| Kumily seeds | wild type *B. napus* | 2012 Field season |
| Kumily oil | wild type *B. napus* | 2012 Field season |
| Canola Commodity oil | canola oil blend | |
| Clear Valley 65 oil | canola oil blend (65% oleic acid) | |
| Clear Valley 80 oil | canola oil blend (80% oleic acid) | |
| *Brassica juncea* seeds | wild type *B. juncea* (high erucic acid variety) | |
| Borage oil | oil preparation from plants (*Borago officinalis*) | |
| Echium oil | oil preparation from plants (*Echium plantagineum*) | |
| Primrose oil | oil preparation from plants (*Oenothera*) | |
| Land animal fat samples | | |
| Beef (corned beef) | prepared beef product | |
| Butter 1 | butter from cow milk | |
| Butter 2 | butter from cow milk | |
| Egg yolk from chicken | egg yolk powder from chicken | |
| Fish/Crustacean oil samples | | |
| Menhaden oil | oil preparation from fish (Menhaden) | |
| Salmon oil capsule | oil preparation from fish (Salmon) | |
| Tuna 1 oil | oil preparation from fish (Tuna) | |
| Anchovy 2 oil | oil preparation from fish (Anchovy) | |
| Krill oil capsule | oil preparation from crustacean (Krill) | |
| Algal oil samples | | |
| DHA DHA oil capsule | oil preparation from algae | |
| Omega EPA/DHA oil capsule | oil preparation from algae | |
| Omega-3 EPA & DHA | oil preparation from algae | |
| Omega 3 algae oil | oil preparation from algae | |
| Fungal oil sample | | |
| *Mortierella alpina* ARA-rich oil | oil preparation from fungi | I |

Gc Analysis:

An Agilent 7890A gas chromatograph coupled to Agilent flame ionization detector was used for FAME analysis. Separation of FAMEs was carried out on a DB-225 capillary column (20 m×180 μm×0.2 μm, Agilent) using $H_2$ as carrier gas with a flow rate of 0.8 mL/min. The GC was operated in split mode using a split ratio of 1:50 at an injector temperature of 250° C., injection volume was 1 μL. Oven temperature was held at 190° C. for 3 min and increased to 220° C. with 15° C. min-. Temperature was held at 220° C. for another 6 min. Peak detection and integration was carried out using Agilent GC ChemStation software (Rev. B.04.02 SP1).

TABLE 181

Fatty acids determined by FAME analysis

| Shorthand Name | Trivial Name | Fatty Acid Name (systematic name) | Fatty Acid Souce |
|---|---|---|---|
| 14:0 | Myristic acid | Tetradecanoic acid | Supelco 37 Component FAME Mix |
| 16:0 | Palmitic acid | Hexadecanoic acid | Supelco 37 Component FAME Mix |
| 16:1n-9 | | (Z)-7-Hexadecenoic acid | single standard |
| 16:1n-7 | Palmitoleic acid | (Z)-9-Hexadecenoic acid | Supelco 37 Component FAME Mix |
| 17:0 | Margaric acid | Heptadecanoic Acid | Supelco 37 Component FAME Mix |
| 16:3n-3 | | (Z,Z,Z)-7,10,13-Hexadecatrienoic acid | single standard |
| 18:0 | Stearic acid | Octadecanoic acid | Supelco 37 Component FAME Mix |
| 18:1n-9 | Oleic acid | (Z)-9-Octadecenoic acid | Supelco 37 Component FAME Mix |
| 18:1n-7 | Vaccenic acid | (Z)-11-Octadecenoic acid | single standard |
| 18:2n-9 | | (Z,Z)-6,9-Octadecadienoic acid | single standard |
| 18:2n-6 | Linoleic acid | (Z,Z)-9,12-Octadecadienoic acid | Supelco 37 Component FAME Mix |
| 18:3n-6 | gamma-Linolenic acid | (Z,Z,Z)-6,9,12-Octadecatrienoic acid | Supelco 37 Component FAME Mix |
| 18:3n-3 | alpha-Linolenic acid | (Z,Z,Z)-9,12,15-Octadecatrienoic acid | Supelco 37 Component FAME Mix |
| 18:4n-3 | Stearidonic acid | (Z,Z,Z,Z)-6,9,12,15-Octadecatetraenoic acid | single standard |
| 20:0 | Arachidic acid | Eicosanoic acid | Supelco 37 Component FAME Mix |
| 20:1n-9 | Gondoic acid | (Z)-11-Eicosenoic acid | Supelco 37 Component FAME Mix |
| 20:2n-9 | | (Z,Z)-8,11-Eicosadienoic acid | no standard |
| 20:3n-9 | Mead acid | (Z,Z,Z)-5,8,11-Eicosatrienoic acid | single standard |
| 20:2n-6 | | (Z,Z)-11,14-Eicosadienoic acid | Supelco 37 Component FAME Mix |
| 20:3n-6 | Dihomo-gamma-linolenic acid | (Z,Z,Z)-8,11,14-Eicosatrienoic acid | Supelco 37 Component FAME Mix |
| 20:4n-6 | Arachidonic acid | (Z,Z,Z,Z)-5,8,11,14-Eicosatetraenoic acid | Supelco 37 Component FAME Mix |

TABLE 181-continued

Fatty acids determined by FAME analysis

| Shorthand Name | Trivial Name | Fatty Acid Name (systematic name) | Fatty Acid Souce |
|---|---|---|---|
| 20:3n-3 | | (Z,Z,Z)-11,14,17-Eicosatrienoic acid | Supelco 37 Component FAME Mix |
| 20:4n-3 | | (Z,Z,Z,Z)-8,11,14,17-Eicosatetraenoic acid | single standard |
| 20:5n-3 | Timnodonic acid | (Z,Z,Z,Z,Z)-5,8,11,14,17-Eicosapentaenoic acid | Supelco 37 Component FAME Mix |
| 22:0 | Behenic acid | Docosanoic acid | Supelco 37 Component FAME Mix |
| 22:1n-9 | Erucic acid | (Z)-13-Docosenoic acid | Supelco 37 Component FAME Mix |
| 22:2n-6 | | (Z,Z)-13,16-Docosadienoic acid | Supelco 37 Component FAME Mix |
| 22:4n-6 | Adrenic acid | (Z,Z,Z,Z)-7,10,13,16-Docosatetraenoic acid | single standard |
| 22:5n-6 | Osbond acid | (Z,Z,Z,Z,Z)-4,7,10,13,16-Docosapentaenoic acid | single standard |
| 22:4n-3 | | (Z,Z,Z,Z)-10,13,16,19-Docosatetraenoic acid | no standard |
| 22:5n-3 | Clupanodonic acid | (Z,Z,Z,Z,Z)-7,10,13,16,19-Docosapentaenoic acid | single standard |
| 22:6n-3 | | (Z,Z,Z,Z,Z,Z)-4,7,10,13,16,19-Docosahexaenoic acid | Supelco 37 Component FAME Mix |
| 24:0 | Lignoceric acid | Tetracosanoic Acid | Supelco 37 Component FAME Mix |
| 24:1n-9 | Nervonic acid | Tetracosenoic Acid | Supelco 37 Component FAME Mix |

The commercially available Supelco® 37 Component FAME Mix was used to identify retention times of 22 from 34 target fatty acids, 10 further fatty acids were spiked into the mix or analyzed separately to obtain retention times. For two of the target FAs, no commercial standard was available.

Peak areas of the detected target fatty acids were added up to yield the total peak area. The fatty acid profile and percentage of individual fatty acids was then calculated as peak area percent of total peak area.

The results are shown in the table 182. In all cases, oil data are data from bulk seed collected from field grown plants, rather than from single seed from a greenhouse environment. 20:3 n-6 (DHGLA) ranges from 1.6-3.1% in our transgenic canola samples. However, other EPA DHA containing samples, such as transgenic *Arabidopsis* seeds, fish oil, and algal oil (with more than 1% combined EPA and DHA), do not contain more than 1.1% DHGLA. DHGLA is the product of a delta-6-elongase acting on GLA.

20:3 n-9 (Mead acid) ranges from 0.05-0.23% in our transgenic canola. We also observe 20:3 n-9 in transgenic *Arabidopsis* and in egg yolk. However, other EPA DHA containing samples, such as fish oil and algal oil (with more than 1% combined EPA and DHA), do not contain mead acid. Therefore, the accumulation of mead acid does not always accompany EPA DHA production. The production of mead acid is the result of delta-6-desaturase activity on 18:1 n-9, followed by the activities of the delta-6-elongase and delta-5-desaturase, and it is the combined properties of our enzymes that result in the production of mead acid.

22:5 n-3 (DPA) ranges from 1.9-4.1% in the transgenic canola samples. The amount of DPA does reach 3.3% in one of the algal oil samples, but transgenic *Arabidopsis* only accumulates 0.1% DPA. DPA accumulation is typically below 2% in transgenic *camelina* and canola engineered to produce EPA and DHA (Petrie et al. 2014 PLoS One 9(1) e85061, and WO 2015/089587). DPA accumulation above 2% is only achieved when the delta-4-desaturase has been inactivated (and no DHA is produced) in transgenic *Brassica napus*. In the events examined in this example, there are two copies of the delta-4-desaturase, and we produce DHA, so it is surprising that DPA accumulates.

The total amount of saturated fatty acids in our transgenic canola is low. 16:0 ranges from 4.4 to 5.2% and 18:0 ranges from 2.5 to 2.7%.

18:4 n-3 (SDA) ranges from 0.1 to 0.4% in the transgenic canola samples. This level of SDA is surprisingly low since our delta-6-desaturase has slightly higher activity with ALA than with LA (Table 163).

There are a variety of VLC-PUFA that occur in the transgenic events that do not occur in WT Kumily plants. These fatty acids include 18:2n-9, GLA, SDA, 20:2n-9, 20:3n-9, 20:3 n-6, 20:4n-6, 22:2n-6, 22:5n-6, 22:4n-3, 22:5n-3, and 22:6n-3. The combined amount of these fatty acids ranged from 15.1% to 24.8% in transgenic canola samples.

TABLE 182

(Part A): Fatty acid profile of 34 target fatty acids from total lipids after MTBE extraction, derivatization to FAMES and analysis by GC-FID.

| Sample name | 14:0 | 16:0 | 16:1 n-9 | 16:1 n-7 | 17:0 | 16:3 n-3 | 18:0 | 18:1 n-9 |
|---|---|---|---|---|---|---|---|---|
| LANBCH oil | 0,1 | 4,6 | 0,0 | 0,2 | 0,1 | 0,1 | 2,7 | 26,3 |
| LANPMZ seeds | 0,1 | 4,9 | 0,0 | 0,2 | 0,1 | 0,1 | 2,7 | 29,1 |
| LAODDN seeds | 0,1 | 5,2 | 0,0 | 0,2 | 0,1 | 0,2 | 2,5 | 28,2 |
| LBFDAU oil | 0,1 | 4,6 | 0,0 | 0,2 | 0,0 | 0,1 | 2,7 | 26,9 |
| LBFGKN seeds | 0,1 | 4,5 | 0,0 | 0,2 | 0,1 | 0,1 | 2,5 | 30,9 |
| LBFGKN oil | 0,1 | 4,4 | 0,0 | 0,2 | 0,0 | 0,1 | 2,6 | 32,2 |
| LBFLFK seeds | 0,1 | 4,8 | 0,0 | 0,2 | 0,1 | 0,1 | 2,7 | 26,4 |
| LBFLFKoil | 0,1 | 4,6 | 0,0 | 0,2 | 0,1 | 0,1 | 2,7 | 27,9 |
| Arabidopsis seeds | 0,1 | 7,0 | 0,0 | 0,2 | 0,1 | 0,1 | 5,3 | 8,9 |
| Kumily seeds | 0,1 | 4,7 | 0,0 | 0,3 | 0,1 | 0,1 | 1,9 | 57,1 |
| Bovine fat (corned beef) | 3,7 | 24,6 | 0,3 | 3,7 | 1,2 | 0,0 | 16,9 | 43,9 |
| Butter 1 | 14,2 | 37,7 | 0,3 | 1,9 | 0,7 | 0,0 | 12,7 | 26,8 |
| Butter 2 | 13,4 | 37,4 | 0,3 | 2,0 | 0,7 | 0,0 | 12,3 | 27,5 |
| Egg yolk from chicken | 0,5 | 25,0 | 0,6 | 2,2 | 0,3 | 0,0 | 8,7 | 35,7 |
| Menhaden oil | 8,9 | 17,1 | 0,2 | 12,6 | 2,3 | 0,1 | 3,0 | 7,2 |
| Salmon oil capsule | 7,8 | 17,0 | 0,3 | 8,6 | 1,7 | 0,1 | 3,5 | 9,4 |
| Tuna 1 0525 oil | 3,9 | 19,7 | 0,4 | 5,0 | 1,3 | 0,0 | 5,1 | 14,9 |
| Omevital Anchovy oil | 7,3 | 18,0 | 0,3 | 8,6 | 1,8 | 0,1 | 3,9 | 9,6 |
| Krill oil capsule | 12,7 | 21,3 | 0,1 | 6,8 | 0,3 | 0,1 | 1,2 | 10,9 |
| DHA DHA oil capsule | 5,8 | 16,0 | 0,0 | 0,3 | 0,1 | 0,2 | 1,0 | 15,4 |
| Omega EPA/DHA oil capsule | 1,3 | 16,1 | 0,0 | 0,2 | 0,1 | 0,0 | 1,9 | 26,0 |
| Omega-3 EPA & DHA | 1,9 | 19,2 | 0,0 | 0,3 | 0,5 | 0,0 | 1,7 | 10,2 |
| Omega 3 algae oil | 5,4 | 15,4 | 0,0 | 0,3 | 0,1 | 0,2 | 1,0 | 15,0 |
| Mortierella alpina ARA-rich oil | 0,4 | 6,1 | 0,0 | 0,1 | 0,2 | 0,0 | 6,2 | 5,6 |

| Sample name | 18:1 n-7 | 18:2 n-9 | 18:2 n-6 (LA) | 18:3 n-6 (GLA) | 18:3 n-3 (ALA) | 18:4 n-3 (SDA) | 20:0 | 20:1 n-9 |
|---|---|---|---|---|---|---|---|---|
| LANBCH oil | 3,1 | 0,7 | 31,7 | 1,3 | 5,7 | 0,3 | 0,6 | 0,8 |
| LANPMZ seeds | 2,9 | 0,5 | 33,6 | 0,8 | 4,3 | 0,1 | 0,8 | 0,9 |
| LAODDN seeds | 3,2 | 0,6 | 35,1 | 1,4 | 5,6 | 0,4 | 0,8 | 0,7 |
| LBFDAU oil | 3,1 | 1,0 | 29,5 | 1,6 | 5,8 | 0,3 | 0,6 | 0,7 |
| LBFGKN seeds | 3,7 | 0,5 | 33,2 | 0,9 | 6,8 | 0,2 | 0,6 | 0,8 |
| LBFGKN oil | 2,9 | 0,5 | 33,2 | 0,9 | 6,8 | 0,2 | 0,6 | 0,8 |
| LBFLFK seeds | 3,9 | 0,9 | 30,3 | 1,6 | 5,7 | 0,3 | 0,6 | 0,8 |
| LBFLFKoil | 3,0 | 0,9 | 30,6 | 1,5 | 5,8 | 0,3 | 0,6 | 0,8 |
| Arabidopsis seeds | 1,8 | 0,2 | 22,3 | 0,3 | 16,8 | 0,1 | 3,5 | 17,5 |
| Kumily seeds | 3,8 | 0,0 | 20,1 | 0,0 | 9,3 | 0,0 | 0,6 | 1,1 |
| Bovine fat (corned beef) | 1,9 | 0,5 | 1,6 | 0,2 | 0,7 | 0,1 | 0,1 | 0,2 |
| Butter 1 | 1,4 | 0,8 | 2,0 | 0,0 | 0,6 | 0,0 | 0,2 | 0,1 |
| Butter 2 | 1,6 | 0,8 | 2,4 | 0,0 | 0,5 | 0,0 | 0,2 | 0,1 |
| Egg yolk from chicken | 1,5 | 0,1 | 19,1 | 0,3 | 0,8 | 0,2 | 0,1 | 0,3 |
| Menhaden oil | 3,4 | 0,1 | 1,8 | 0,4 | 1,5 | 3,4 | 0,3 | 1,1 |
| Salmon oil capsule | 3,4 | 0,2 | 1,9 | 0,4 | 1,1 | 2,8 | 0,6 | 1,9 |
| Tuna 1 0525 oil | 2,5 | 0,1 | 2,0 | 0,3 | 0,5 | 1,0 | 0,4 | 1,5 |
| Omevital Anchovy oil | 3,2 | 0,2 | 1,8 | 0,5 | 0,9 | 3,3 | 0,6 | 1,6 |
| Krill oil capsule | 7,0 | 0,2 | 2,3 | 0,3 | 1,3 | 4,2 | 0,1 | 0,7 |
| DHA DHA oil capsule | 0,3 | 0,0 | 1,3 | 0,3 | 0,1 | 0,3 | 0,1 | 0,1 |
| Omega EPA/DHA oil capsule | 0,2 | 0,0 | 2,2 | 0,1 | 0,2 | 0,2 | 0,4 | 0,1 |
| Omega-3 EPA & DHA | 0,2 | 0,0 | 1,4 | 0,1 | 0,1 | 0,2 | 0,4 | 0,1 |
| Omega 3 algae oil | 0,2 | 0,0 | 1,5 | 0,3 | 0,1 | 0,4 | 0,1 | 0,1 |
| Mortierella alpina ARA-rich oil | 0,3 | 0,0 | 7,9 | 2,3 | 0,1 | 0,0 | 0,9 | 0,3 |

Data are mean, n = 2 and FA ex pressed as peak area % from total peak area.

TABLE 182

(Part B): Fatty acid profile of 34 targest fatty acids from total lipids after MTBE extraction, derivatization to FAMES and analysis by GC-FID

| Sample name | 20:2 n-9 | 20:3 n-9 | 20:2 n-6 | 20:3 n-6 (DHGLA) | 20:4 n-6 (ARA) | 20:3 n-3 | 20:4 n-3 (ETA) | 20:5 n-3 (EPA) | 22:0 |
|---|---|---|---|---|---|---|---|---|---|
| LANBCH oil | 0,2 | 0,1 | 0,3 | 1,6 | 3,4 | 0,1 | 1,0 | 7,5 | 0,3 |
| LANPMZ seeds | 0,6 | 0,2 | 0,6 | 2,1 | 3,3 | 0,2 | 1,0 | 5,6 | 0,4 |
| LAODDN seeds | 0,1 | 0,1 | 0,1 | 1,5 | 1,2 | 0,1 | 1,0 | 6,0 | 0,4 |
| LBFDAU oil | 0,3 | 0,1 | 0,1 | 2,9 | 2,2 | 0,1 | 1,9 | 10,1 | 0,3 |
| LBFGKN seeds | 0,2 | 0,1 | 0,2 | 1,8 | 2,0 | 0,1 | 1,1 | 5,7 | 0,3 |
| LBFGKN oil | 0,2 | 0,1 | 0,2 | 1,7 | 1,9 | 0,1 | 1,0 | 5,5 | 0,3 |
| LBFLFK seeds | 0,2 | 0,1 | 0,1 | 2,8 | 2,2 | 0,1 | 1,6 | 8,4 | 0,3 |
| LBFLFKoil | 0,2 | 0,1 | 0,1 | 3,1 | 2,1 | 0,1 | 1,8 | 7,9 | 0,3 |
| Arabidopsis seeds | 0,6 | 0,6 | 1,4 | 0,3 | 0,5 | 1,7 | 0,5 | 5,6 | 0,5 |
| Kumily seeds | 0,0 | 0,0 | 0,1 | 0,0 | 0,0 | 0,0 | 0,0 | 0,0 | 0,3 |
| Bovinefat (corned beef) | 0,0 | 0,0 | 0,0 | 0,1 | 0,2 | 0,0 | 0,0 | 0,0 | 0,0 |
| Butter 1 | 0,0 | 0,0 | 0,0 | 0,1 | 0,2 | 0,0 | 0,0 | 0,1 | 0,1 |
| Butter 2 | 0,0 | 0,0 | 0,0 | 0,1 | 0,2 | 0,0 | 0,0 | 0,1 | 0,1 |
| Egg yolk from chicken | 0,0 | 0,1 | 0,2 | 0,2 | 1,9 | 0,0 | 0,0 | 0,4 | 0,0 |
| Menhaden oil | 0,2 | 0,0 | 0,3 | 0,3 | 1,3 | 0,3 | 1,7 | 16,4 | 0,2 |
| Salmonoil capsule | 0,2 | 0,0 | 0,2 | 0,2 | 1,6 | 0,1 | 1,0 | 19,5 | 0,2 |
| Tuna 1 oil | 0,0 | 0,0 | 0,3 | 0,2 | 2,2 | 0,2 | 0,5 | 7,5 | 0,2 |
| Anchovy 2 oil | 0,2 | 0,0 | 0,2 | 0,2 | 1,4 | 0,1 | 1,0 | 19,5 | 0,2 |
| Krill oil capsule | 0,0 | 0,0 | 0,1 | 0,2 | 0,8 | 0,1 | 0,5 | 18,4 | 0,1 |
| DHA DHA oil capsule | 0,0 | 0,0 | 0,0 | 0,8 | 0,7 | 0,1 | 0,8 | 1,1 | 0,2 |
| Omega EPA/DHA oil capsule | 0,0 | 0,0 | 0,0 | 0,2 | 1,4 | 0,1 | 0,6 | 17,0 | 0,3 |
| Omega-3 EPA & DHA | 0,0 | 0,0 | 0,0 | 0,3 | 1,8 | 0,1 | 0,8 | 19,5 | 0,2 |
| Omega 3 algae oil | 0,0 | 0,0 | 0,0 | 1,1 | 1,0 | 0,1 | 0,9 | 1,3 | 0,3 |
| Mortierella alpina ARA-rich oil | 0,0 | 0,0 | 0,4 | 4,4 | 48,5 | 0,5 | 0,0 | 0,2 | 3,4 |

| Sample name | 22:1 n-9 | 22:2 n-6 | 22:4 n-6 | 22:5 n-6 | 22:4 n-3 | 22:5 n-3 (DPA) | 22:6 n-3 (DHA) | 24:0 | 24:1 |
|---|---|---|---|---|---|---|---|---|---|
| LANBCH oil | 0,0 | 0,1 | 1,5 | 0,0 | 0,4 | 4,1 | 1,3 | 0,1 | 0,1 |
| LANPMZ seeds | 0,0 | 0,1 | 1,3 | 0,0 | 0,4 | 2,5 | 1,0 | 0,2 | 0,2 |
| LAODDN seeds | 0,0 | 0,0 | 1,1 | 0,0 | 0,5 | 2,7 | 0,9 | 0,2 | 0,2 |
| LBFDAU oil | 0,0 | 0,0 | 0,4 | 0,1 | 0,2 | 2,6 | 1,4 | 0,1 | 0,1 |
| LBFGKN seeds | 0,0 | 0,0 | 0,4 | 0,0 | 0,2 | 2,0 | 0,9 | 0,1 | 0,2 |
| LBFGKN oil | 0,0 | 0,0 | 0,4 | 0,0 | 0,1 | 1,9 | 0,9 | 0,1 | 0,1 |
| LBFLFK seeds | 0,0 | 0,0 | 0,7 | 0,1 | 0,4 | 3,3 | 1,3 | 0,1 | 0,2 |
| LBFLFKoil | 0,0 | 0,0 | 0,6 | 0,1 | 0,4 | 3,0 | 1,2 | 0,1 | 0,1 |
| Arabidopsis seeds | 2,0 | 0,0 | 0,7 | 0,0 | 0,0 | 0,1 | 1,3 | 0,2 | 0,4 |
| Kumily seeds | 0,0 | 0,0 | 0,3 | 0,0 | 0,0 | 0,0 | 0,0 | 0,1 | 0,2 |
| Bovinefat (corned beef) | 0,0 | 0,0 | 0,0 | 0,0 | 0,0 | 0,1 | 0,1 | 0,0 | 0,0 |
| Butter 1 | 0,0 | 0,0 | 0,2 | 0,0 | 0,0 | 0,1 | 0,0 | 0,0 | 0,0 |
| Butter 2 | 0,0 | 0,0 | 0,1 | 0,0 | 0,0 | 0,1 | 0,0 | 0,0 | 0,0 |
| Egg yolk from chicken | 0,0 | 0,0 | 0,1 | 0,4 | 0,0 | 0,1 | 1,3 | 0,0 | 0,0 |
| Menhaden oil | 0,2 | 0,0 | 0,3 | 0,6 | 0,1 | 2,8 | 12,1 | 0,2 | 0,3 |
| Salmonoil capsule | 0,3 | 0,0 | 0,2 | 0,4 | 0,1 | 2,5 | 12,7 | 0,1 | 0,6 |
| Tuna 1 oil | 0,2 | 0,0 | 0,3 | 1,8 | 0,1 | 1,3 | 26,6 | 0,2 | 0,6 |
| Anchovy 2 oil | 0,3 | 0,0 | 0,2 | 0,4 | 0,1 | 2,1 | 12,7 | 0,1 | 0,5 |
| Krill oil capsule | 0,5 | 0,0 | 0,0 | 0,2 | 0,0 | 0,4 | 9,2 | 0,1 | 0,1 |
| DHA DHA oil capsule | 0,0 | 0,0 | 0,1 | 15,6 | 0,1 | 0,4 | 38,6 | 0,5 | 0,0 |
| Omega EPA/DHA oil capsule | 0,0 | 0,0 | 0,2 | 1,2 | 0,0 | 3,1 | 26,8 | 0,2 | 0,0 |
| Omega-3 EPA & DHA | 0,1 | 0,0 | 0,3 | 1,9 | 0,0 | 3,3 | 35,6 | 0,1 | 0,0 |

TABLE 182-continued (Part B): Fatty acid profile of 34 targe st fatty acids from total lipids after MTBE extraction, derivatization to FAMES and analysis by GC-FID

| Omega 3 algae oil | 0,0 | 0,0 | 0,1 | 16,0 | 0,1 | 0,6 | 38,2 | 0,5 | 0,0 |
| Mortierella alpina ARA-rich oil | 0,1 | 0,0 | 0,5 | 0,0 | 0,2 | 0,0 | 0,1 | 11,2 | 0,4 |

FID. Data are mean, n = 2 and FA expressed as peak area % from total peak area.

Example 30: Lipid Profiling of Canola Oils and Commercial Oil Samples

Canola Seeds:

12-15 canola seeds were transferred into micro tubes on a 96-format rack and closed with cap strips. Seeds were ground in a swing mill using 3 mm beads for 2×2 min at 30 Hz. The rack was then centrifuged for 5 min at 4000 rpm to remove powder from the lid. Extraction of oil was carried out by adding 800 µL of dichloromethane/methanol (DCM/MeOH, 2:1 v/v to the samples followed by extraction in a swing mill for 2×30 sec at 30 Hz. After centrifugation at 4000 rpm for 10 min, 100 µL of the clear supernatant was transferred into glass vials and dried to remove the solvent.

*Arabidopsis* Seeds:

20 mg of seeds were transferred into tubes on a 96-format rack. The canola seed protocol was followed in all further steps.

Canola Oils and Commercial Oil Samples:

200 µL of oil was transferred into into micro tubes on a 96-format rack and closed with cap strips. Extraction of oil was carried out by adding 800 µL of dichloromethane/methanol (DCM/MeOH, 2:1 v/v to the samples followed by extraction in a swing mill for 2×30 sec at 30 Hz. After centrifugation at 4000 rpm for 10 min, 100 µL of the clear supernatant was transferred into glass vials and dried to remove the solvent.

Normal Phase Fractionation:

The dry residues were resuspended in 100 µL 2,2,4-trimethylpentane and isopropyl alcohol (TMP/IPA (9:1, v/v)) and vortexed thoroughly. The krill oil sample was further diluted 1:30 using TMP/IPA. For triacylglycerol (TAG) isolation, the oil samples were resuspended in 500 µL TMP/IPA prior to fractionation Separation of lipid classes was performed using normal phase HPLC that leads to interaction of lipids and stationary phase based on lipid species (e.g. head group in case of phospholipids) rather than length of fatty acid chain. An Agilent 1200 series HPLC was used that comprised G1322A degasser, G131 1A quaternary pump, G1310A isocratic pump, G1316A thermostatted column compartment (TCC), G1367B HiP autosampler, G1330B FC/ALS Thermostat and G1364 Fraction Collector (all Agilent) coupled to and Alltech 3300 evaporative light scattering detector (ELSD, Grace). A quaternary gradient from TMP, MTBE, acetonitrile (MeCN), DCM, formic acid (FA), ammonium formiate (0.5 M) and water was used for separation of lipid species on a PVA-Sil column (150 mm×3 mm×5 µm, YMC) with an initial flow rate of 0.4 mL/min. The injection volume was 50 µL. Fractions of triacylglycerol (TAG), diacylglycerol (DAG), monoacylglycerol (MAG), phosphatidylcholine (PC), phosphatidylethanolamine (PE) were collected in glass vials. The solvent was removed and the residue was resuspended in 100 µL toluene. Derivatization of lipid species into FAMEs for subsequent fatty acid profiling was carried out using 20 µL TMSH. FAME analysis was performed as described previously for Example 29 with an injection volume of 2 µL.

The results are shown in the tables 183 to 187.

Comparing the data in Table 183, 184, and 185, it is evident that the transgenic canola plants have higher percentages of EPA and DHA in DAG compared to TAG or MAG. For LBFLFK oil, the ratio of EPA in DAG to MAG is 1.6, and in LBFDAU oil the ratio is 1.5. The fact that DAG has more EPA than MAG and TAG is surprising, especially given previous reports showing that EPA and DHA are less likely to be present in the sn-2 position, at least in *camelina* (Ruiz-Lopez et al 2013 The Plant Journal 77, 198-208, and Petrie et al 2014 PLoS One 9(1) e85061). DAG having more EPA DHA than MAG or TAG could be taken to indicate that there is more EPA DHA at the sn-2 position of DAG.

The data in Table 186 and 187 show that PC and PE, respectively, have a higher concentration of DHA than does TAG in transgenic canola. In event LANPMZ there is 8.53% DHA in PC (and 8.5% in PE) compared to just 1% in TAG, whereas for event LBFLFK there is 3.3% DHA in PC compared to 1.2% in TAG. The more efficient accumulation of DHA in TAG relative to PC in the event LBFLFK compared to LANPMZ could be the result of having one delta-4-desaturase that is phospholipid-dependent (d4Des (Tc)) and one that is CoA-dependent (d4Des(PI)) rather than two phospholipid-dependent enzymes in event LANPMZ.

The data in Tables 183 to 187 also show differences in the ratios between DPA and DHA for the transgenic canola samples. For all transgenic canola samples, there is more DPA than DHA in neutral lipids (MAG, DAG, and TAG), while there is more DHA than DPA in polar lipids (PC and PE).

The data in Tables 183 to 187 show that for transgenic canola samples the ratio of EPA to DHA is higher in neutral lipids (MAG, DAG, and TAG) than the ratio of EPA to DHA in polar lipids (PC, PE). There is more EPA than DHA in neutral lipids, but more DHA than EPA in polar lipids.

TABLE 183

(Part A): Fatty acid profile of 34 target fatty acids from monoacylgylcerol (MAG) fraction after DCM/MeOH (2:1) extraction, normal phase fractionation, derivatization to FAMES and analysis by GC-FID.

| sample name | Fraction | 14:0 | 16:0 | 16:1 n-9 | 16:1 n-7 | 17:0 | 16:3 n-3 | 18:0 | 18:1 n-9 | 18:1 n-7 | 18:2 n-9 | 18:2 n-6 (LA) | 18:3 n-6 (GLA) | 18:3 n-3 (ALA) | 18:4 n-3 (SDA) | 20:0 | 20:1 n-9 |
|---|---|---|---|---|---|---|---|---|---|---|---|---|---|---|---|---|---|
| LANBCH oil | MAG | 0,0 | 6,6 | 0,0 | 0,5 | 0,0 | 0,2 | 3,1 | 24,5 | 7,6 | 0,5 | 30,3 | 1,2 | 4,4 | 0,3 | 0,7 | 0,7 |
| LANPMZ seeds | MAG | 0,0 | 10,6 | 0,0 | 1,0 | 0,0 | 0,5 | 4,7 | 23,2 | 17,6 | 0,0 | 26,1 | 0,6 | 2,8 | 0,0 | 0,5 | 0,0 |
| LAODDN seeds | MAG | 0,4 | 12,1 | 0,0 | 1,1 | 0,0 | 0,0 | 6,4 | 22,2 | 15,5 | 0,0 | 25,3 | 1,3 | 4,0 | 0,0 | 1,1 | 0,0 |
| LBFDAU oil | MAG | 0,3 | 6,2 | 0,0 | 0,6 | 0,0 | 0,0 | 2,8 | 24,6 | 7,7 | 0,8 | 28,7 | 1,5 | 5,0 | 0,3 | 0,6 | 0,7 |

TABLE 183-continued (Part A): Fatty acid profile of 34 target fatty acids from monoacylgylcerol (MAG) fraction after DCM/MeOH (2:1) extraction, normal phase fractionation, derivatization to FAMES and analysis by GC-FID.

| sample name | Fraction | 14:0 | 16:0 | 16:1 n-9 | 16:1 n-7 | 17:0 | 16:3 n-3 | 18:0 | 18:1 n-9 | 18:1 n-7 | 18:2 n-9 | 18:2 n-6 (LA) | 18:3 n-6 (GLA) | 18:3 n-3 (ALA) | 18:4 n-3 (SDA) | 20:0 | 20:1 n-9 |
|---|---|---|---|---|---|---|---|---|---|---|---|---|---|---|---|---|---|
| LBFGKN oil | MAG | 0,3 | 6,8 | 0,0 | 0,6 | 0,0 | 0,0 | 3,2 | 28,1 | 7,6 | 0,4 | 28,6 | 0,8 | 4,9 | 0,0 | 0,7 | 0,7 |
| LBFLFK seeds | MAG | 0,0 | 12,7 | 0,0 | 0,9 | 0,0 | 0,0 | 6,8 | 22,8 | 13,2 | 0,3 | 23,7 | 1,1 | 4,3 | 0,0 | 0,9 | 0,0 |
| LBFLFK oil | MAG | 0,2 | 6,7 | 0,0 | 0,6 | 0,0 | 0,2 | 3,0 | 25,3 | 8,2 | 0,7 | 28,9 | 1,4 | 4,7 | 0,2 | 0,6 | 0,7 |
| Kumily oil | MAG | 0,0 | 7,4 | 0,0 | 0,0 | 0,0 | 1,9 | 3,6 | 51,0 | 4,5 | 0,0 | 19,7 | 0,0 | 9,4 | 0,0 | 0,0 | 2,5 |
| Canola Commodity oil | MAG | 0,7 | 7,5 | 0,0 | 0,5 | 0,0 | 2,3 | 3,3 | 47,2 | 5,1 | 0,0 | 20,8 | 0,0 | 8,9 | 0,0 | 0,0 | 3,7 |
| Clear Valley 65 oil | MAG | 0,5 | 13,8 | 0,0 | 2,8 | 0,0 | 1,4 | 2,6 | 28,9 | 31,7 | 0,0 | 14,2 | 0,0 | 0,7 | 0,0 | 0,7 | 2,0 |
| Clear Valley 80 oil | MAG | 0,0 | 5,7 | 0,0 | 0,6 | 0,0 | 3,1 | 3,4 | 65,0 | 5,4 | 0,0 | 9,8 | 0,0 | 3,1 | 0,0 | 0,0 | 4,0 |
| Menhaden oil | MAG | 10,4 | 24,1 | 0,0 | 12,5 | 2,2 | 0,1 | 5,2 | 6,2 | 3,8 | 0,0 | 1,5 | 0,6 | 1,4 | 3,1 | 0,4 | 0,5 |
| Salmon oil capsule | MAG | 8,2 | 22,1 | 0,0 | 8,8 | 1,8 | 0,5 | 6,3 | 8,7 | 3,9 | 0,0 | 1,5 | 0,0 | 0,8 | 2,5 | 0,8 | 1,1 |
| Krill oil capsule | MAG | 5,4 | 21,0 | 0,0 | 3,4 | 0,0 | 1,8 | 3,3 | 7,2 | 6,4 | 0,0 | 1,9 | 0,0 | 0,0 | 2,6 | 0,0 | 1,9 |
| DHA DHA oil capsule | MAG | 7,8 | 24,4 | 0,0 | 1,0 | 0,0 | 0,0 | 3,1 | 10,1 | 0,0 | 0,0 | 3,5 | 0,0 | 0,0 | 0,0 | 0,0 | 0,0 |
| Omega EPA/DHA oil capsule | MAG | 2,2 | 25,8 | 0,0 | 0,0 | 0,0 | 0,0 | 3,3 | 16,0 | 0,0 | 0,0 | 3,2 | 0,0 | 0,0 | 0,0 | 0,0 | 0,0 |
| Omega 3 algae oil | MAG | 5,4 | 29,9 | 0,0 | 0,0 | 0,0 | 0,0 | 3,0 | 6,2 | 0,0 | 0,0 | 2,7 | 0,0 | 0,0 | 0,0 | 0,0 | 0,8 |

Data are mean, n = 2 and FA expressed as peak area % from total peak area

TABLE 183

(part B): Fatty acid profile of 34 target fatty acids from monoacylgylcerol (MAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 20:2n-9 | 20:3n-9 | 20:2n-6 | 20:3n-6 (DHGLA) | 20:4n-6 (ARA) | 20:3n-3 | 20:4n-3 (ETA) | 20:5n-3 (EPA) | 22:0 |
|---|---|---|---|---|---|---|---|---|---|---|
| LANBCH oil | MAG | 0.3 | 0.3 | 0.2 | 1.8 | 2.8 | 0.8 | 1.0 | 5.4 | 0.7 |
| LANPMZ seeds | MAG | 0.0 | 0.0 | 0.0 | 1.9 | 2.8 | 0.0 | 1.4 | 3.9 | 0.0 |
| LAODDN seeds | MAG | 0.0 | 0.0 | 0.0 | 1.0 | 1.0 | 0.0 | 1.3 | 4.1 | 0.0 |
| LBFDAU oil | MAG | 0.3 | 0.2 | 0.2 | 2.8 | 1.9 | 0.0 | 2.0 | 8.0 | 0.0 |
| LBFGKN oil | MAG | 0.0 | 0.3 | 0.2 | 1.7 | 1.7 | 0.7 | 1.0 | 3.9 | 0.0 |
| LBFLFK seeds | MAG | 0.0 | 0.0 | 0.0 | 2.4 | 1.1 | 0.0 | 1.0 | 4.6 | 0.0 |
| LBFLFK oil | MAG | 0.2 | 0.3 | 0.2 | 2.7 | 1.4 | 0.0 | 1.7 | 5.9 | 0.0 |
| Kumily oil | MAG | 0.0 | 0.0 | 0.0 | 0.0 | 0.0 | 0.0 | 0.0 | 0.0 | 0.0 |
| Canola Commodity oil | MAG | 0.0 | 0.0 | 0.0 | 0.0 | 0.0 | 0.0 | 0.0 | 0.0 | 0.0 |
| Clear Valley 65 oil | MAG | 0.0 | 0.0 | 0.0 | 0.0 | 0.0 | 0.0 | 0.0 | 0.0 | 0.0 |
| Clear Valley 80 oil | MAG | 0.0 | 0.0 | 0.0 | 0.0 | 0.0 | 0.0 | 0.0 | 0.0 | 0.0 |
| Menhaden oil | MAG | 0.1 | 0.0 | 0.3 | 0.5 | 1.5 | 0.0 | 1.4 | 12.3 | 0.0 |
| Salmon oil capsule | MAG | 0.0 | 0.0 | 0.0 | 0.4 | 1.6 | 0.0 | 0.0 | 17.2 | 0.0 |
| Krill oil capsule | MAG | 0.0 | 0.0 | 0.0 | 0.0 | 0.0 | 0.0 | 0.0 | 27.7 | 0.0 |
| DHA DHA oil capsule | MAG | 0.0 | 0.0 | 0.0 | 0.0 | 0.0 | 0.0 | 0.0 | 0.0 | 0.0 |
| Omega EPA/DHA oil capsule | MAG | 0.0 | 0.0 | 0.0 | 0.0 | 0.0 | 1.4 | 0.0 | 17.6 | 0.0 |
| Royal Green Omega 3 algae oil | MAG | 0.0 | 0.0 | 0.0 | 0.0 | 1.0 | 0.0 | 0.0 | 0.0 | 0.0 |

| sample name | 22:1n-9 | 22:2n-6 | 22:4n-6 | 22:5n-6 | 22:4n-3 | 22:5n-3 (DPA) | 22:6n-3 (DHA) | 24:0 | 24:0 |
|---|---|---|---|---|---|---|---|---|---|
| LANBCH oil | 0.0 | 0.0 | 1.9 | 0.0 | 0.3 | 2.8 | 1.3 | 0.2 | 0.2 |
| LANPMZ seeds | 0.0 | 0.0 | 0.0 | 0.0 | 0.0 | 1.4 | 1.1 | 0.0 | 0.0 |
| LAODDN seeds | 0.0 | 0.0 | 0.0 | 0.0 | 0.0 | 1.6 | 1.5 | 0.0 | 0.0 |
| LBFDAU oil | 0.0 | 0.0 | 1.3 | 0.0 | 0.0 | 2.2 | 1.4 | 0.0 | 0.0 |
| LBFGKN oil | 0.0 | 0.0 | 4.9 | 0.0 | 0.4 | 1.5 | 1.0 | 0.3 | 0.3 |

TABLE 183-continued (part B): Fatty acid profile of 34 target fatty acids from monoacylgylcerol (MAG) fraction after DCM/MeOH (2:1) extraction, normal phase fractionation, derivatization to FAMES and analysis by GC-FID. Data are mean, n = 2 and FA expressed as peak area % from total peak area

| sample | | | | | | | | | |
|---|---|---|---|---|---|---|---|---|---|
| LBFLFK seeds | 0.0 | 0.0 | 0.7 | 0.0 | 0.4 | 2.0 | 1.3 | 0.0 | 0.0 |
| LBFLFK oil | 0.0 | 0.0 | 2.1 | 0.0 | 0.4 | 2.3 | 1.1 | 0.3 | 0.3 |
| Kumily oil | 0.0 | 0.0 | 0.0 | 0.0 | 0.0 | 0.0 | 0.0 | 0.0 | 0.0 |
| Canola Commodity oil | 0.0 | 0.0 | 0.0 | 0.0 | 0.0 | 0.0 | 0.0 | 0.0 | 0.0 |
| Clear Valley 65 oil | 0.0 | 0.0 | 0.0 | 0.0 | 0.0 | 0.0 | 0.0 | 0.7 | 0.7 |
| Clear Valley 80 oil | 0.0 | 0.0 | 0.0 | 0.0 | 0.0 | 0.0 | 0.0 | 0.0 | 0.0 |
| Menhaden oil | 0.0 | 0.0 | 0.0 | 0.0 | 0.1 | 2.2 | 9.6 | 0.2 | 0.2 |
| Salmon oil capsule | 0.0 | 0.0 | 0.0 | 0.0 | 0.0 | 2.1 | 11.7 | 0.0 | 0.0 |
| Krill oil capsule | 0.0 | 0.0 | 0.0 | 0.0 | 0.0 | 0.0 | 17.4 | 0.0 | 0.0 |
| DHA DHA oil capsule | 0.0 | 0.0 | 0.0 | 12.1 | 0.0 | 0.0 | 38.1 | 0.0 | 0.0 |
| Omega EPA/DHA oil capsule | 0.0 | 0.0 | 0.0 | 0.0 | 0.0 | 3.0 | 27.6 | 0.0 | 0.0 |
| Royal Green Omega 3 algae oil | 0.0 | 0.0 | 0.0 | 14.3 | 0.0 | 0.0 | 36.7 | 0.0 | 0.0 |

TABLE 184

(part A): Fatty acid profile of 34 target fatty acids from diacylgylcerol (DAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LANBCH oil | DAG | 0.0 | 5.4 | 0.0 | 0.0 | 0.0 | 0.0 | 2.6 | 22.0 | 5.0 | 0.8 | 32.7 | 1.4 | 5.8 | 0.0 | 0.0 | 0.0 |
| LBFDAU oil | DAG | 0.0 | 4.7 | 0.0 | 0.0 | 0.0 | 0.0 | 2.3 | 22.4 | 4.9 | 0.5 | 29.9 | 1.7 | 6.3 | 0.0 | 0.0 | 0.0 |
| LBFGKN oil | DAG | 0.0 | 5.9 | 0.0 | 0.0 | 0.0 | 0.0 | 2.6 | 25.8 | 4.9 | 0.0 | 33.2 | 1.1 | 7.2 | 0.0 | 0.0 | 0.0 |
| LBFLFK oil | DAG | 0.0 | 6.1 | 0.0 | 0.0 | 0.0 | 0.0 | 2.5 | 22.9 | 5.1 | 0.8 | 30.7 | 1.7 | 6.4 | 0.0 | 0.0 | 0.0 |
| Canola Commodity oil | DAG | 0.0 | 8.3 | 0.0 | 0.0 | 0.0 | 2.7 | 0.0 | 53.9 | 0.0 | 0.0 | 21.6 | 0.0 | 10.1 | 0.0 | 0.0 | 3.4 |
| Clear Valley 65 oil | DAG | 0.0 | 9.4 | 0.0 | 1.7 | 0.0 | 3.6 | 0.0 | 47.6 | 17.3 | 0.0 | 16.8 | 0.0 | 0.0 | 0.0 | 0.0 | 3.7 |
| Clear Valley 80 oil | DAG | 0.0 | 7.0 | 0.0 | 0.0 | 0.0 | 3.6 | 0.0 | 71.6 | 4.6 | 0.0 | 8.8 | 0.0 | 0.0 | 0.0 | 0.0 | 4.3 |
| Menhaden oil | DAG | 10.4 | 23.6 | 0.0 | 12.6 | 2.4 | 0.0 | 4.9 | 6.4 | 3.8 | 0.0 | 1.5 | 0.0 | 1.5 | 3.6 | 0.0 | 0.8 |
| Salmon oil capsule | DAG | 8.4 | 21.0 | 0.0 | 8.6 | 2.1 | 0.0 | 5.3 | 8.3 | 3.7 | 0.0 | 1.4 | 0.0 | 0.0 | 4.0 | 0.0 | 0.9 |
| DHA DHA oil capsule | DAG | 6.8 | 17.5 | 0.0 | 0.0 | 0.0 | 0.0 | 0.0 | 19.7 | 0.0 | 0.0 | 2.3 | 0.0 | 0.0 | 0.0 | 0.0 | 1.3 |
| Omega EPA/DHA oil capsule | DAG | 2.0 | 16.7 | 0.0 | 0.0 | 0.0 | 0.0 | 3.3 | 32.7 | 0.0 | 0.0 | 2.5 | 0.0 | 0.0 | 0.0 | 0.0 | 1.1 |
| Omega 3 algae oil | DAG | 5.0 | 20.7 | 0.0 | 0.0 | 0.0 | 0.0 | 3.0 | 11.1 | 0.0 | 0.0 | 1.9 | 0.0 | 0.0 | 0.0 | 0.0 | 0.0 |

TABLE 184

(part B): Fatty acid profile of 34 target fatty acids from diacylgylcerol (DAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 20:2n-9 | 20:3n-9 | 20:2n-6 | 20:3n-6 (DHGLA) | 20:4n-6 (ARA) | 20:3n-3 | 20:4n-3 (ETA) | 20:5n-3 (EPA) | 22:0 |
|---|---|---|---|---|---|---|---|---|---|---|
| LANBCH oil | DAG | 0.0 | 0.0 | 0.0 | 2.2 | 4.2 | 0.0 | 1.1 | 8.8 | 0.0 |
| LBFDAU oil | DAG | 0.0 | 0.0 | 0.0 | 3.2 | 2.8 | 0.0 | 2.4 | 11.7 | 0.0 |
| LBFGKN oil | DAG | 0.0 | 0.0 | 0.0 | 2.7 | 2.8 | 0.0 | 0.8 | 7.4 | 0.0 |
| LBFLFK oil | DAG | 0.0 | 0.0 | 0.0 | 3.5 | 2.7 | 0.0 | 2.2 | 9.3 | 0.0 |
| Canola Commodity oil | DAG | 0.0 | 0.0 | 0.0 | 0.0 | 0.0 | 0.0 | 0.0 | 0.0 | 0.0 |
| Clear Valley 65 oil | DAG | 0.0 | 0.0 | 0.0 | 0.0 | 0.0 | 0.0 | 0.0 | 0.0 | 0.0 |
| Clear Valley 80 oil | DAG | 0.0 | 0.0 | 0.0 | 0.0 | 0.0 | 0.0 | 0.0 | 0.0 | 0.0 |
| Menhaden oil | DAG | 0.0 | 0.0 | 0.0 | 0.0 | 1.0 | 0.0 | 1.5 | 13.4 | 0.0 |
| Salmon oil capsule | DAG | 0.0 | 0.0 | 0.0 | 0.0 | 2.4 | 0.0 | 0.0 | 19.6 | 0.0 |
| DHA DHA oil capsule | DAG | 0.0 | 0.0 | 0.0 | 0.0 | 0.0 | 0.0 | 0.0 | 0.0 | 0.0 |
| Omega EPA/DHA oil capsule | DAG | 0.0 | 0.0 | 0.0 | 0.0 | 2.3 | 0.0 | 0.0 | 13.6 | 0.0 |
| Omega 3 algae oil | DAG | 0.0 | 0.0 | 0.0 | 0.0 | 0.0 | 0.0 | 0.0 | 0.0 | 0.0 |

| sample name | 22:1n-9 | 22:2n-6 | 22:4n-6 | 22:5n-6 | 22:4n-3 | 22:5n-3 (DPA) | 22:6n-3 (DHA) | 24:0 | 24:1n-9 |
|---|---|---|---|---|---|---|---|---|---|
| LANBCH oil | 0.0 | 0.0 | 2.1 | 0.0 | 0.0 | 4.1 | 2.0 | 0.0 | 0.0 |
| LBFDAU oil | 0.0 | 0.0 | 2.1 | 0.0 | 0.0 | 2.7 | 2.5 | 0.0 | 0.0 |
| LBFGKN oil | 0.0 | 0.0 | 0.9 | 0.0 | 0.0 | 2.4 | 2.5 | 0.0 | 0.0 |
| LBFLFK oil | 0.0 | 0.0 | 1.4 | 0.0 | 0.0 | 3.2 | 1.7 | 0.0 | 0.0 |
| Canola Commodity oil | 0.0 | 0.0 | 0.0 | 0.0 | 0.0 | 0.0 | 0.0 | 0.0 | 0.0 |
| Clear Valley 65 oil | 0.0 | 0.0 | 0.0 | 0.0 | 0.0 | 0.0 | 0.0 | 0.0 | 0.0 |
| Clear Valley 80 oil | 0.0 | 0.0 | 0.0 | 0.0 | 0.0 | 0.0 | 0.0 | 0.0 | 0.0 |
| Menhaden oil | 0.0 | 0.0 | 0.0 | 0.0 | 0.0 | 2.3 | 10.3 | 0.0 | 1.2 |
| Salmon oil capsule | 0.0 | 0.0 | 0.0 | 0.0 | 0.0 | 1.9 | 12.3 | 0.0 | 0.0 |
| DHA DHA oil capsule | 0.0 | 0.0 | 0.0 | 10.4 | 0.0 | 0.0 | 42.0 | 0.0 | 0.0 |
| Omega EPA/DHA oil capsule | 0.0 | 0.0 | 0.0 | 0.0 | 0.0 | 1.8 | 24.0 | 0.0 | 0.0 |
| Omega 3 algae oil | 0.0 | 0.0 | 0.0 | 13.9 | 0.0 | 0.0 | 44.5 | 0.0 | 0.0 |

TABLE 185

(part A): Fatty acid profile of 34 target fatty acids from triacylgylcerol (TAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LANBCH oil | TAG | 0.1 | 4.5 | 0.0 | 0.2 | 0.1 | 0.1 | 2.8 | 26.2 | 3.1 | 0.7 | 31.5 | 1.3 | 5.6 | 0.2 | 0.7 | 0.8 |
| LANPMZ seeds | TAG | 0.1 | 4.9 | 0.0 | 0.1 | 0.1 | 0.1 | 2.8 | 27.9 | 2.4 | 0.5 | 34.9 | 0.9 | 4.0 | 0.1 | 0.8 | 0.9 |
| LAODDN seeds | TAG | 0.1 | 5.0 | 0.0 | 0.2 | 0.1 | 0.2 | 2.8 | 29.1 | 2.7 | 0.6 | 35.0 | 1.4 | 5.4 | 0.3 | 0.8 | 0.8 |
| LBFDAU oil | TAG | 0.1 | 4.5 | 0.1 | 0.2 | 0.1 | 0.1 | 2.8 | 26.9 | 3.0 | 1.0 | 29.1 | 1.6 | 5.8 | 0.3 | 0.7 | 0.8 |
| LBFGKN oil | TAG | 0.1 | 4.3 | 0.0 | 0.2 | 0.1 | 0.1 | 2.7 | 32.4 | 2.9 | 0.5 | 33.0 | 0.9 | 6.8 | 0.2 | 0.7 | 0.8 |
| LBFLFK seeds | TAG | 0.1 | 4.5 | 0.1 | 0.2 | 0.1 | 0.1 | 2.7 | 28.6 | 3.4 | 0.9 | 30.1 | 1.3 | 5.8 | 0.2 | 0.7 | 0.8 |

TABLE 185-continued (part A): Fatty acid profile of 34 target fatty acids from triacylgylcerol (TAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LBFLFK oil | TAG | 0.1 | 4.5 | 0.0 | 0.2 | 0.1 | 0.1 | 2.8 | 28.0 | 2.9 | 0.9 | 30.3 | 1.5 | 5.7 | 0.2 | 0.7 | 0.8 |
| Arabidopsis seeds | TAG | 0.1 | 6.7 | 0.1 | 0.2 | 0.1 | 0.1 | 5.0 | 7.8 | 1.6 | 0.2 | 21.7 | 0.2 | 17.4 | 0.1 | 3.6 | 18.9 |
| Kumily seeds | TAG | 0.1 | 4.8 | 0.0 | 0.3 | 0.1 | 0.1 | 2.0 | 59.2 | 0.0 | 0.0 | 20.5 | 0.0 | 10.3 | 0.0 | 0.7 | 1.2 |
| Canola Commodity oil | TAG | 0.1 | 3.9 | 0.0 | 0.2 | 0.1 | 0.1 | 1.8 | 60.0 | 2.9 | 0.0 | 19.0 | 0.0 | 9.3 | 0.0 | 0.6 | 1.3 |
| Clear Valley 65 oil | TAG | 0.0 | 4.1 | 0.0 | 0.2 | 0.1 | 0.1 | 1.8 | 69.5 | 2.2 | 0.0 | 17.6 | 0.0 | 0.8 | 0.0 | 0.8 | 1.5 |
| Clear Valley 80 oil | TAG | 0.0 | 2.9 | 0.0 | 0.1 | 0.1 | 0.1 | 2.6 | 80.0 | 0.0 | 0.0 | 8.2 | 0.0 | 2.3 | 0.0 | 0.9 | 1.8 |
| Brassica juncea seeds | TAG | 0.1 | 2.8 | 0.0 | 0.2 | 0.0 | 0.1 | 1.0 | 7.0 | 1.2 | 0.0 | 15.2 | 0.0 | 12.8 | 0.0 | 0.8 | 4.7 |
| Menhaden oil | TAG | 8.7 | 17.0 | 0.0 | 12.8 | 2.3 | 0.1 | 3.1 | 7.0 | 3.5 | 0.1 | 1.7 | 0.4 | 1.5 | 3.7 | 0.0 | 1.1 |
| Salmon oil capsule | TAG | 7.5 | 16.8 | 0.0 | 8.7 | 1.7 | 0.1 | 3.7 | 9.2 | 3.5 | 0.1 | 1.6 | 0.2 | 0.9 | 3.0 | 0.6 | 2.0 |
| Krill oil capsule | TAG | 21.9 | 21.4 | 0.0 | 11.7 | 0.4 | 0.1 | 1.7 | 17.4 | 8.0 | 0.1 | 2.5 | 0.3 | 1.3 | 5.5 | 0.1 | 1.0 |
| DHA DHA oil capsule | TAG | 5.7 | 15.9 | 0.0 | 0.2 | 0.1 | 0.2 | 1.0 | 15.2 | 0.2 | 0.0 | 1.2 | 0.2 | 0.1 | 0.3 | 0.1 | 0.1 |
| Omega EPA/DHA oil capsule | TAG | 1.1 | 15.5 | 0.0 | 0.1 | 0.1 | 0.0 | 1.9 | 25.9 | 0.2 | 0.0 | 2.1 | 0.0 | 0.1 | 0.1 | 0.4 | 0.1 |
| Omega 3 algae oil | TAG | 5.1 | 14.7 | 0.0 | 0.2 | 0.1 | 0.2 | 1.0 | 14.8 | 0.2 | 0.0 | 1.2 | 0.3 | 0.1 | 0.3 | 0.1 | 0.1 |

TABLE 185

(part B): Fatty acid profile of 34 target fatty acids from triacylgylcerol (TAG) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 20:2n-9 | 20:3n-9 | 20:2n-6 | 20:3n-6 (DHGLA) | 20:4n-6 (ARA) | 20:3n-3 | 20:4n-3 (ETA) | 20:5n-3 (EPA) | 22:0 |
|---|---|---|---|---|---|---|---|---|---|---|
| LANBCH oil | TAG | 0.2 | 0.1 | 0.3 | 1.7 | 3.4 | 0.1 | 1.0 | 7.6 | 0.3 |
| LANPMZ seeds | TAG | 0.5 | 0.2 | 0.5 | 2.2 | 3.5 | 0.2 | 1.0 | 5.7 | 0.4 |
| LAODDN seeds | TAG | 0.1 | 0.1 | 0.1 | 1.5 | 1.3 | 0.1 | 0.9 | 6.0 | 0.4 |
| LBFDAU oil | TAG | 0.3 | 0.1 | 0.1 | 3.0 | 2.3 | 0.1 | 1.9 | 10.3 | 0.3 |
| LBFGKN oil | TAG | 0.2 | 0.1 | 0.2 | 1.8 | 1.9 | 0.1 | 1.0 | 5.6 | 0.3 |
| LBFLFK seeds | TAG | 0.3 | 0.1 | 0.1 | 3.1 | 2.0 | 0.1 | 1.7 | 7.7 | 0.3 |
| LBFLFK oil | TAG | 0.3 | 0.1 | 0.1 | 3.2 | 2.1 | 0.1 | 1.8 | 8.0 | 0.3 |
| Arabidopsis seeds | TAG | 0.7 | 0.6 | 1.5 | 0.2 | 0.3 | 1.8 | 0.5 | 6.0 | 0.5 |
| Kumily seeds | TAG | 0.0 | 0.0 | 0.1 | 0.0 | 0.0 | 0.0 | 0.0 | 0.0 | 0.3 |
| Canola Commodity oil | TAG | 0.0 | 0.0 | 0.1 | 0.0 | 0.0 | 0.0 | 0.0 | 0.0 | 0.4 |
| Clear Valley 65 oil | TAG | 0.0 | 0.0 | 0.1 | 0.0 | 0.0 | 0.0 | 0.0 | 0.0 | 0.6 |
| Clear Valley 80 oil | TAG | 0.0 | 0.0 | 0.1 | 0.0 | 0.0 | 0.0 | 0.0 | 0.0 | 0.5 |
| Brassica juncea seeds | TAG | 0.0 | 0.0 | 0.9 | 0.0 | 0.0 | 0.2 | 0.0 | 0.0 | 1.2 |
| Menhaden oil | TAG | 0.2 | 0.0 | 0.3 | 0.3 | 1.3 | 0.2 | 1.8 | 16.7 | 0.2 |
| Salmon oil capsule | TAG | 0.2 | 0.0 | 0.2 | 0.2 | 1.7 | 0.1 | 1.1 | 20.0 | 0.2 |

TABLE 185-continued (part B): Fatty acid profile of 34 target fatty acids from triacylgylcerol (TAG) fraction after DCM/MeOH (2:1) extraction, normal phase fractionation, derivatization to FAMES and analysis by GC-FID. Data are mean, n = 2 and FA expressed as peak area % from total peak area

| | | | | | | | | | |
|---|---|---|---|---|---|---|---|---|---|
| Krilloil capsule | TAG | 0.0 | 0.0 | 0.1 | 0.0 | 0.2 | 0.1 | 0.3 | 3.8 | 0.0 |
| DHA DHA oil capsule | TAG | 0.0 | 0.0 | 0.0 | 0.9 | 0.5 | 0.0 | 0.8 | 0.8 | 0.2 |
| Omega EPA/DHA oil capsule | TAG | 0.0 | 0.0 | 0.0 | 0.3 | 1.4 | 0.1 | 0.6 | 17.1 | 0.3 |
| Omega 3 algae oil | TAG | 0.0 | 0.0 | 0.0 | 1.0 | 0.6 | 0.1 | 0.9 | 1.2 | 0.2 |

| sample name | 22:1n-9 | 22:2n-6 | 22:4n-6 | 22:5n-6 | 22:4n-3 | 22:5n-3 (DPA) | 22:6n-3 (DHA) | 24:0 | 24:1n-9 |
|---|---|---|---|---|---|---|---|---|---|
| LANBCH oil | 0.0 | 0.1 | 1.5 | 0.0 | 0.4 | 4.3 | 1.3 | 0.1 | 0.1 |
| LANPMZ seeds | 0.0 | 0.1 | 1.3 | 0.0 | 0.4 | 2.4 | 1.0 | 0.2 | 0.2 |
| LAODDN seeds | 0.0 | 0.0 | 1.1 | 0.0 | 0.4 | 2.7 | 0.8 | 0.2 | 0.2 |
| LBFDAU oil | 0.0 | 0.0 | 0.3 | 0.0 | 0.2 | 2.7 | 1.4 | 0.1 | 0.1 |
| LBFGKN oil | 0.0 | 0.0 | 0.3 | 0.0 | 0.1 | 1.9 | 0.9 | 0.1 | 0.1 |
| LBFLFK seeds | 0.0 | 0.0 | 0.5 | 0.1 | 0.5 | 3.0 | 1.2 | 0.1 | 0.1 |
| LBFLFK oil | 0.0 | 0.0 | 0.5 | 0.1 | 0.4 | 3.1 | 1.2 | 0.1 | 0.1 |
| Arabidopsis seeds | 2.3 | 0.1 | 0.2 | 0.2 | 0.0 | 0.0 | 1.2 | 0.2 | 0.4 |
| Kumily seeds | 0.0 | 0.0 | 0.3 | 0.0 | 0.0 | 0.0 | 0.0 | 0.2 | 0.2 |
| Canola Commodity oil | 0.0 | 0.0 | 0.1 | 0.0 | 0.0 | 0.0 | 0.0 | 0.2 | 0.2 |
| Clear Valley 65 oil | 0.0 | 0.0 | 0.2 | 0.0 | 0.0 | 0.0 | 0.0 | 0.4 | 0.2 |
| Clear Valley 80 oil | 0.0 | 0.0 | 0.1 | 0.0 | 0.0 | 0.0 | 0.0 | 0.4 | 0.2 |
| Brassica juncea seeds | 49.3 | 1.6 | 0.0 | 0.5 | 0.0 | 0.0 | 0.0 | 0.7 | 2.2 |
| Menhaden oil | 0.2 | 0.0 | 0.3 | 0.6 | 0.1 | 2.9 | 12.1 | 0.1 | 0.4 |
| Salmon oil capsule | 0.4 | 0.0 | 0.2 | 0.5 | 0.1 | 2.6 | 13.0 | 0.1 | 0.6 |
| Krilloil capsule | 0.5 | 0.0 | 0.0 | 0.0 | 0.0 | 0.2 | 1.7 | 0.0 | 0.0 |
| DHA DHA oil capsule | 0.0 | 0.0 | 0.1 | 16.0 | 0.2 | 0.4 | 39.2 | 0.5 | 0.0 |
| Omega EPA/DHA oil capsule | 0.0 | 0.0 | 0.2 | 1.2 | 0.1 | 3.3 | 27.4 | 0.4 | 0.0 |
| Omega 3 algae oil | 0.0 | 0.0 | 0.1 | 16.9 | 0.1 | 0.6 | 39.9 | 0.3 | 0.0 |

TABLE 186

(part A): Fatty acid profile of 34 target fatty acids from phosphatidylcholine (PC) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LANPMZ seeds | PC | 0.0 | 12.7 | 0.6 | 0.3 | 0.1 | 0.1 | 3.4 | 6.6 | 5.8 | 0.0 | 39.2 | 1.8 | 4.5 | 0.3 | 0.0 | 0.0 |
| LAODDN seeds | PC | 0.0 | 11.5 | 0.4 | 0.7 | 0.0 | 0.0 | 3.1 | 9.7 | 5.9 | 0.0 | 37.0 | 4.5 | 10.1 | 1.5 | 0.0 | 0.0 |
| LBFLFK seeds | PC | 0.0 | 8.7 | 0.4 | 0.5 | 0.0 | 0.3 | 2.6 | 10.8 | 7.6 | 0.0 | 39.3 | 1.3 | 6.4 | 0.3 | 0.2 | 0.2 |
| Arabidopsis seeds | PC | 0.0 | 13.2 | 0.9 | 0.7 | 0.0 | 0.0 | 6.6 | 4.1 | 5.2 | 0.0 | 27.9 | 1.2 | 14.4 | 0.6 | 0.9 | 6.8 |
| Kumily seeds | PC | 0.0 | 6.1 | 0.2 | 0.6 | 0.0 | 0.2 | 0.7 | 57.8 | 2.7 | 0.0 | 27.2 | 0.0 | 4.5 | 0.0 | 0.0 | 0.0 |

TABLE 186-continued (part A): Fatty acid profile of 34 target fatty acids from phosphatidylcholine (PC) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| Brassica juncea seeds | PC | 0.0 | 12.3 | 0.0 | 1.8 | 0.0 | 1.1 | 1.5 | 29.4 | 4.6 | 0.0 | 34.4 | 0.0 | 12.0 | 0.0 | 0.0 | 1.9 |
| Krill oil capsule | PC | 3.1 | 26.5 | 0.0 | 1.7 | 0.1 | 0.0 | 1.0 | 4.6 | 5.5 | 0.2 | 2.1 | 0.3 | 1.5 | 3.0 | 0.0 | 0.3 |

TABLE 186

(part B): Fatty acid profile of 34 target fatty acids from phosphatidylcholine (PC) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 20:2n-9 | 20:3n-9 | 20:2n-6 | 20:3n-6 (DHGLA) | 20:4n-6 (ARA) | 20:3n-3 | 20:4n-3 (ETA) | 20:5n-3 (EPA) | 22:0 |
|---|---|---|---|---|---|---|---|---|---|---|
| LANPMZ seeds | PC | 0.0 | 0.0 | 0.0 | 0.7 | 0.0 | 0.3 | 7.0 | 7.3 | 0.0 |
| LAODDN seeds | PC | 0.0 | 0.0 | 0.0 | 0.2 | 0.0 | 0.0 | 6.8 | 3.2 | 0.0 |
| LBFLFK seeds | PC | 0.1 | 0.0 | 0.0 | 0.9 | 0.0 | 0.1 | 10.9 | 4.1 | 0.0 |
| Arabidopsis seeds | PC | 0.0 | 0.0 | 0.0 | 0.0 | 0.0 | 2.8 | 1.0 | 6.3 | 0.0 |
| Kumily seeds | PC | 0.0 | 0.0 | 0.0 | 0.0 | 0.0 | 0.0 | 0.0 | 0.0 | 0.0 |
| Brassica juncea seeds | PC | 0.0 | 0.0 | 0.9 | 0.0 | 0.0 | 0.0 | 0.0 | 0.0 | 0.0 |
| Krill oil capsule | PC | 0.1 | 0.0 | 0.1 | 0.2 | 0.7 | 0.0 | 1.0 | 33.3 | 0.0 |

| sample name | 22:1n-9 | 22:2n-6 | 22:4n-6 | 22:5n-6 | 22:4n-3 | 22:5n-3 (DPA) | 22:6n-3 (DHA) | 24:0 | 24:1n-9 |
|---|---|---|---|---|---|---|---|---|---|
| LANPMZ seeds | 0.0 | 0.0 | 0.0 | 0.0 | 0.0 | 0.4 | 9.0 | 0.0 | 0.0 |
| LAODDN seeds | 0.0 | 0.0 | 0.0 | 0.0 | 0.0 | 0.0 | 5.3 | 0.0 | 0.0 |
| LBFLFK seeds | 0.0 | 0.0 | 0.0 | 0.0 | 0.2 | 1.8 | 3.3 | 0.0 | 0.0 |
| Arabidopsis seeds | 0.0 | 0.0 | 0.0 | 0.0 | 0.0 | 0.0 | 7.2 | 0.0 | 0.0 |
| Kumily seeds | 0.0 | 0.0 | 0.0 | 0.0 | 0.0 | 0.0 | 0.0 | 0.0 | 0.0 |
| Brassica juncea seeds | 0.0 | 0.0 | 0.0 | 0.0 | 0.0 | 0.0 | 0.0 | 0.0 | 0.0 |
| Krill oil capsule | 0.6 | 0.0 | 0.0 | 0.0 | 0.0 | 0.6 | 13.6 | 0.0 | 0.1 |

TABLE 187

(part A): Fatty acid profile of 34 target fatty acids from phosphatidylethanolamine (PE) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LANPMZ seeds | PE | 0.0 | 18.3 | 0.0 | 0.0 | 0.0 | 0.0 | 3.1 | 5.8 | 6.4 | 0.0 | 36.4 | 1.3 | 4.4 | 0.0 | 0.0 | 0.0 |
| LAODDN seeds | PE | 0.0 | 17.7 | 0.0 | 0.0 | 0.0 | 0.0 | 3.3 | 7.9 | 6.0 | 0.0 | 33.6 | 3.0 | 8.5 | 0.0 | 0.0 | 0.0 |

TABLE 187-continued (part A): Fatty acid profile of 34 target fatty acids from phosphatidylethanolamine (PE) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 14:0 | 16:0 | 16:1n-9 | 16:1n-7 | 17:0 | 16:3n-3 | 18:0 | 18:1n-9 | 18:1n-7 | 18:2n-9 | 18:2n-6 (LA) | 18:3n-6 (GLA) | 18:3n-3 (ALA) | 18:4n-3 (SDA) | 20:0 | 20:1n-9 |
|---|---|---|---|---|---|---|---|---|---|---|---|---|---|---|---|---|---|
| LBFLFK seeds | PE | 0.0 | 15.5 | 0.0 | 0.0 | 0.0 | 0.0 | 2.9 | 8.6 | 7.3 | 0.0 | 37.6 | 1.2 | 6.1 | 0.0 | 0.0 | 0.0 |
| Arabidopsis seeds | PE | 0.0 | 18.7 | 0.4 | 0.0 | 0.0 | 0.0 | 5.6 | 2.4 | 4.6 | 0.0 | 27.1 | 0.0 | 13.2 | 0.0 | 0.0 | 4.1 |
| Brassica juncea seeds | PE | 0.0 | 19.1 | 0.0 | 1.1 | 0.0 | 2.1 | 0.0 | 13.4 | 4.5 | 0.0 | 41.4 | 0.0 | 13.3 | 0.0 | 0.0 | 4.1 |
| Krill oil capsule | PE | 1.1 | 16.6 | 0.0 | 0.0 | 0.0 | 2.9 | 0.0 | 4.1 | 13.6 | 0.0 | 0.0 | 0.0 | 0.0 | 0.0 | 0.0 | 4.0 |

TABLE 187

(part B): Fatty acid profile of 34 target fatty acids from phosphatidylethanolamine (PE) fraction after DCM/MeOH (2:1) extraction, normal phase fractionation, derivatization to FAMES and analysis by GC-FID. Data are mean, n = 2 and FA expressed as peak area % from total peak area

| sample name | Fraction | 20:2n-9 | 20:3n-9 | 20:2n-6 | 20:3n-6 (DHGLA) | 20:4n-6 (ARA) | 20:3n-3 | 20:4n-3 (ETA) | 20:5n-3 (EPA) | 22:0 |
|---|---|---|---|---|---|---|---|---|---|---|
| LANPMZ seeds | PE | 0.0 | 0.0 | 0.0 | 1.0 | 6.5 | 0.0 | 4.1 | 4.4 | 0.0 |
| LAODDN seeds | PE | 0.0 | 0.0 | 0.0 | 0.0 | 7.5 | 0.0 | 4.2 | 2.6 | 0.0 |
| LBFLFK seeds | PE | 0.0 | 0.0 | 0.0 | 1.2 | 3.6 | 0.0 | 8.1 | 3.3 | 0.0 |
| Arabidopsis seeds | PE | 0.0 | 0.0 | 0.0 | 0.0 | 11.0 | 0.5 | 0.0 | 4.7 | 0.0 |
| Brassica juncea seeds | PE | 0.0 | 0.0 | 1.0 | 0.0 | 0.0 | 0.0 | 0.0 | 0.0 | 0.0 |
| Krill oil capsule | PE | 0.0 | 0.0 | 0.0 | 0.0 | 2.5 | 0.0 | 0.0 | 24.6 | 0.0 |

| sample name | 22:1n-9 | 22:2n-6 | 22:4n-6 | 22:5n-6 | 22:4n-3 | 22:5n-3 (DPA) | 22:6n-3 (DHA) | 24:0 | 24:1n-9 |
|---|---|---|---|---|---|---|---|---|---|
| LANPMZ seeds | 0.0 | 0.0 | 0.0 | 0.0 | 0.0 | 0.0 | 8.5 | 0.0 | 0.0 |
| LAODDN seeds | 0.0 | 0.0 | 0.0 | 0.0 | 0.0 | 0.0 | 5.9 | 0.0 | 0.0 |
| LBFLFK seeds | 0.0 | 0.0 | 0.0 | 0.0 | 0.0 | 0.9 | 3.6 | 0.0 | 0.0 |
| Arabidopsis seeds | 0.0 | 0.0 | 0.0 | 0.0 | 0.0 | 0.0 | 7.7 | 0.0 | 0.0 |
| Brassica juncea seeds | 0.0 | 0.0 | 0.0 | 0.0 | 0.0 | 0.0 | 0.0 | 0.0 | 0.0 |
| Krill oil capsule | 0.0 | 0.0 | 0.0 | 0.0 | 0.0 | 0.0 | 30.4 | 0.0 | 0.0 |

Example 31: Phospholipid Species Profiling

Diluted extracts from Example 30 were used for phospholipid species analysis

PC Species Profiling

Phosphatidylcholine (PC) species separation was carried out on a 1290 Agilent HPLC coupled to AP15500 triple quadrupole MS (ABSciex). HPLC comprised of G4227A Flex Cube, G4226A autosampler, G1330B thermostat and G4220A binary pump. PC species separation was carried out on a Phenomenex Kinetex C8 column (150 mm×2.1 mm×1.7 µm). The mobile phase consisted of $H_2O$/MeOH/sodium acetate (50 mM) as solvent A and MeOH/sodium acetate (50 mM) as solvent B with a flow rate of 0.5 mL/min. The initial conditions were 40% A followed by a linear gradient to 25% A in a total run time of 7 min. MS was operated in positive ESI mode with a source temperature of 550° C. using scheduled multiple reaction monitoring (sMRM) and an injection volume of 1 µL. Data acquisition was carried out using Analyst 1.5.1 whereas data analysis was done in Multiquant 3.0.1 (AB Sciex). All theoretical $[M+Na]^+$ from phosphatidylcholine species containing C14:0, C16:0, C16:1, C18:0, C18:1, C18:2, C18:3, C20:3, C20:4, C20:5, C22:5 and C22:6 fatty acids were calculated resulting in a total of 78 PC species. In sMRM-mode, the neutral loss of fatty acids was monitored. MRMs of PC species not present in a representative set of test samples from different canola, fish and algae oil sources were removed from the transition list.

All peak areas of target PC species were added to a total peak area. Species with peak areas lower than 10.000 counts were not included in the calculation as they were considered below limit of quantitation having a poor signal-to-noise ratio. PC species profile was then calculated as PC species percent of total PC species.

LPC Species Profiling

Lysophosphatidylcholine (LPC) species separation was carried out on a 1290 Agilent HPLC coupled to AP15500 triple quadrupole MS (ABSciex). HPLC comprised of G4227A Flex Cube, G4226A autosampler, G1330B thermostat and G4220A binary pump. LPC species separation was carried out on a Phenomenex Kinetex C8 column (150 mm×2.1 mm×1.7 µm). The mobile phase consisted of $H_2O$/MeOH/formic as solvent A and MeOH as solvent B with a flow rate of 0.5 mL/min and a linear gradient from 80% A to 0% A over a total run time of 4 min. MS was operated in positive ESI mode with a source temperature of 550° C. using multiple reaction monitoring (MRM) and an injection volume of 1 µL. Data acquisition was carried out using Analyst 1.5.1 whereas data analysis was done in Multiquant 3.0.1 (AB Sciex). All theoretical $[M+H]^+$ from LPC species containing C14:0, C16:0, C16:1, C18:0, C18:1, C18:2, C18:3, C20:3, C20:4, C20:5, C22:5 and C22:6 fatty acids were calculated. In sMRM-mode, the neutral loss of fatty acids was monitored.

All peak areas of target LPC species were added to a total peak area. Species with peak areas lower than 12.500 counts were not included in the calculation as they were considered below limit of quantitation having a poor signal-to-noise ratio. LPC species profile was then calculated as LPC species percent of total LPC species.

PE/LPE Species Profiling

Phosphatidylethanolamine (PE) and lysophosphatidylethanolamine (LPE) species separation was carried out on a 1290 Agilent HPLC coupled to AP15500 triple quadrupole MS (ABSciex). HPLC comprised of G4227A Flex Cube, G4226A autosampler, G1330B thermostat and G4220A binary pump. PE/LPE species separation was carried out on a Phenomenex Kinetex C8 column (150 mm×2.1 mm×1.7 µm). The mobile phase consisted of $H_2O$/MeOH/ammonium formate as solvent A and MeOH/ammonium formate as solvent B with a flow rate of 0.5 mL/min. The initial conditions were 100% A followed by a linear gradient to 0% A over a total run time of 16 min. MS was operated in negative ESI mode with a source temperature of 550° C. using scheduled multiple reaction monitoring (sMRM) and an injection volume of 1 µL. Data acquisition was carried out using Analyst 1.5.1 whereas data analysis was done in Multiquant 3.0.1 (AB Sciex). All theoretical $[M-H]^-$ from PE and LPE species containing C14:0, C16:0, C16:1, C18:0, C18:1, C18:2, C18:3, C20:3, C20:4, C20:5, C22:5 and C22:6 fatty acids were calculated resulting in a total of 78 PE species and 12 LPE species.

MRMs of PE/LPE species not present in a representative set of test samples from different canola, fish and algae oil sources were removed from the transition list.

All peak areas of target PE species and LPE species were added to a total peak area separately. The peak area cut-off for LPE not included into the calculation due to poor signal-to-noise was 2000 counts, for PE it was 5000 counts. PE and LPE species profile were then calculated as PE species percent of total PE species and LPE species percent of total LPE species.

The results are shown in Tables 188 to 191.

Many more phospholipid species were detectable in seed samples than in oil samples. This is probably due to the fact that phospholipids are removed during oil refinement. Tables 186 and 187 showed that for transgenic canola samples PC contains the most DHA of any lipid fraction. For all transgenic canola samples the most abundant PC species containing DHA is PC 18:2 22:6 and the most abundant PC species containing EPA is PC 18:2 20:5 (Table 188). DHA was found in the PC of fish oil and algal oil samples, but only in PC 18:3 22:6. One exception was krill oil, but PC 18:2 22:6 totaled just 0.1% of PC species. The most abundant PE species containing DHA is PE 18:2 22:6 (Table 190).The PC species that decreased the most in transgenic canola samples was PC 18:1 18:1, where PC 18:2 18:2 is the species that increased the most. Accordingly, LPC 18:2 is the most abundant lysoPC species in transgenic canola samples.

TABLE 188

Phosphatidylcholine species profile of occurring PC species comprising 12 target fatty acids from DCM/MeOH (2:1) extracts analyzed by +ESI-HPLC-MS/MS in sMRM mode. Data are mean, n = 2-3 and expressed as relative abundance of species. Species that were not detected in any samples were removed from the table

| Sample Name | LANBCH oil | LANPMZ seeds | LAODDN seeds | LBFDAU oil | LBFGKN seeds | LBFGKN oil | LBFLFK seeds | LBFLFK oil | Arabidopsis seeds | Kumily seeds | Kumily oil |
|---|---|---|---|---|---|---|---|---|---|---|---|
| PC140 161 | 0.0 | 0.0 | 0.0 | 0.0 | 0.0 | 0.0 | 0.0 | 0.0 | 0.0 | 0.0 | 0.0 |
| PC140 181 | 0.0 | 0.0 | 0.0 | 0.0 | 0.0 | 0.0 | 0.0 | 0.0 | 0.0 | 0.0 | 0.0 |
| PC140 182 | 0.0 | 0.0 | 0.0 | 0.0 | 0.0 | 0.0 | 0.0 | 0.0 | 0.0 | 0.0 | 0.0 |
| PC140 183 | 0.0 | 0.0 | 0.0 | 0.0 | 0.0 | 0.0 | 0.0 | 0.0 | 0.0 | 0.0 | 0.0 |
| PC140 204 | 0.0 | 0.0 | 0.0 | 0.0 | 0.0 | 0.0 | 0.0 | 0.0 | 0.0 | 0.0 | 0.0 |
| PC140 205 | 0.0 | 0.0 | 0.0 | 0.0 | 0.0 | 0.0 | 0.0 | 0.0 | 0.0 | 0.0 | 0.0 |
| PC140 225 | 0.0 | 0.0 | 0.0 | 0.0 | 0.0 | 0.0 | 0.0 | 0.0 | 0.0 | 0.0 | 0.0 |
| PC140 226 | 0.0 | 0.0 | 0.0 | 0.0 | 0.0 | 0.0 | 0.0 | 0.0 | 0.0 | 0.0 | 0.0 |
| PC160 160 | 0.5 | 0.7 | 0.4 | 0.4 | 0.3 | 0.0 | 0.4 | 0.9 | 1.0 | 0.0 | 0.0 |
| PC160 161 | 0.0 | 0.0 | 0.0 | 0.0 | 0.0 | 0.0 | 0.0 | 0.0 | 0.0 | 0.0 | 0.0 |
| PC160 180 | 0.0 | 0.3 | 0.2 | 0.0 | 0.2 | 0.0 | 0.3 | 0.0 | 0.7 | 0.0 | 0.0 |
| PC160 181 | 4.9 | 4.8 | 5.2 | 4.6 | 6.6 | 7.5 | 5.8 | 4.5 | 3.7 | 11.5 | 12.9 |
| PC160 182 | 12.4 | 11.7 | 10.3 | 12.6 | 8.8 | 10.1 | 7.6 | 11.5 | 11.6 | 7.5 | 6.7 |
| PC160 183 | 3.9 | 2.3 | 4.7 | 3.5 | 2.0 | 4.8 | 1.8 | 3.4 | 8.2 | 3.2 | 1.9 |
| PC160 203 | 0.0 | 0.0 | 0.0 | 0.0 | 0.0 | 0.0 | 0.0 | 0.0 | 0.0 | 0.0 | 0.0 |
| PC160 205 | 0.0 | 0.0 | 0.0 | 0.0 | 0.0 | 0.0 | 0.0 | 0.0 | 0.0 | 0.0 | 0.0 |
| PC160 225 | 0.0 | 0.0 | 0.0 | 0.0 | 0.0 | 0.0 | 0.0 | 0.0 | 0.0 | 0.0 | 0.0 |
| PC160 226 | 0.0 | 2.7 | 1.5 | 0.0 | 1.3 | 0.0 | 1.2 | 0.0 | 2.4 | 0.0 | 0.0 |
| PC161 161 | 0.0 | 0.0 | 0.0 | 0.0 | 0.0 | 0.0 | 0.0 | 0.0 | 0.0 | 0.0 | 0.0 |

TABLE 188-continued

Phosphatidylcholine species profile of occurring PC species comprising 12 target fatty acids from DCM/MeOH (2:1) extracts analyzed by +ESI-HPLC-MS/MS in sMRM mode. Data are mean, n = 2-3 and expressed as relative abundance of species. Species that were not detected in any samples were removed from the table

| | | | | | | | | | | | |
|---|---|---|---|---|---|---|---|---|---|---|---|
| PC161 180 | 0.0 | 0.0 | 0.0 | 0.0 | 0.0 | 0.0 | 0.0 | 0.0 | 0.0 | 0.0 | 0.0 |
| PC161 181 | 0.0 | 0.3 | 0.4 | 0.0 | 0.4 | 0.0 | 0.5 | 0.0 | 0.7 | 0.7 | 0.0 |
| PC161 182 | 0.0 | 0.8 | 0.7 | 0.0 | 0.5 | 0.0 | 0.4 | 0.0 | 1.7 | 1.1 | 0.0 |
| PC161 183 | 0.0 | 0.3 | 0.7 | 0.0 | 0.3 | 0.0 | 0.4 | 0.0 | 0.6 | 0.5 | 0.0 |
| PC161 203 | 0.0 | 0.0 | 0.0 | 0.0 | 0.0 | 0.0 | 0.0 | 0.0 | 0.0 | 0.0 | 0.0 |
| PC161 205 | 0.0 | 0.0 | 0.0 | 0.0 | 0.0 | 0.0 | 0.0 | 0.0 | 0.0 | 0.0 | 0.0 |
| PC161 226 | 0.0 | 0.0 | 0.0 | 0.0 | 0.0 | 0.0 | 0.0 | 0.0 | 0.0 | 0.0 | 0.0 |
| PC180 181 | 0.0 | 0.5 | 0.6 | 0.0 | 1.4 | 0.0 | 1.2 | 0.0 | 0.8 | 1.8 | 0.0 |
| PC180 182 | 3.6 | 5.2 | 4.3 | 3.7 | 3.8 | 0.0 | 4.0 | 2.9 | 6.6 | 0.2 | 0.2 |
| PC180 183 | 0.0 | 1.0 | 1.8 | 0.0 | 0.7 | 0.0 | 0.8 | 0.0 | 4.1 | 0.0 | 0.0 |
| PC180 205 | 0.0 | 0.0 | 0.0 | 0.0 | 0.0 | 0.0 | 0.0 | 0.0 | 0.0 | 0.0 | 0.0 |
| PC180 226 | 0.0 | 0.8 | 0.6 | 0.0 | 0.4 | 0.0 | 0.3 | 0.0 | 1.3 | 0.0 | 0.0 |
| PC181 181 | 5.8 | 3.4 | 4.2 | 7.0 | 7.8 | 15.5 | 8.0 | 6.6 | 2.3 | 26.8 | 36.1 |
| PC181 182 | 15.8 | 13.5 | 13.1 | 17.8 | 16.7 | 19.4 | 16.0 | 17.6 | 9.3 | 24.4 | 27.4 |
| PC181 183 | 3.4 | 2.7 | 5.1 | 4.1 | 3.5 | 4.3 | 3.8 | 3.9 | 4.4 | 7.0 | 5.0 |
| PC181 204 | 3.0 | 1.9 | 1.8 | 4.9 | 2.6 | 3.5 | 4.6 | 4.2 | 0.4 | 0.0 | 0.0 |
| PC181 205 | 0.0 | 1.2 | 0.7 | 0.0 | 1.2 | 0.0 | 1.3 | 0.0 | 1.2 | 0.0 | 0.0 |
| PC181 226 | 0.0 | 1.4 | 1.0 | 0.0 | 1.1 | 0.0 | 1.2 | 0.0 | 1.3 | 0.0 | 0.0 |
| PC182 182 | 17.8 | 12.5 | 10.7 | 17.4 | 13.8 | 16.8 | 12.4 | 17.2 | 10.8 | 8.4 | 6.8 |
| PC182 183 | 7.6 | 7.2 | 12.4 | 7.4 | 8.6 | 7.6 | 8.4 | 9.1 | 11.6 | 5.9 | 3.1 |
| PC182 203 | 0.0 | 0.0 | 0.0 | 0.0 | 0.0 | 0.0 | 0.0 | 0.0 | 0.0 | 0.0 | 0.0 |
| PC182 204 | 5.7 | 4.7 | 4.5 | 7.2 | 4.9 | 4.0 | 7.3 | 7.9 | 0.7 | 0.0 | 0.0 |
| PC182 205 | 9.7 | 8.6 | 3.0 | 5.8 | 4.5 | 3.3 | 4.1 | 5.3 | 2.9 | 0.0 | 0.0 |
| PC182 226 | 5.9 | 3.9 | 2.2 | 2.4 | 2.2 | 3.3 | 1.4 | 2.2 | 0.0 | 0.0 | 0.0 |
| PC183 183 | 0.0 | 1.6 | 5.2 | 0.0 | 2.3 | 0.0 | 2.2 | 0.6 | 5.9 | 1.2 | 0.0 |
| PC183 205 | 0.0 | 2.4 | 1.9 | 0.0 | 1.7 | 0.0 | 1.6 | 0.7 | 2.6 | 0.0 | 0.0 |
| PC183 226 | 0.0 | 1.4 | 1.8 | 0.0 | 1.0 | 0.0 | 0.7 | 0.0 | 2.0 | 0.0 | 0.0 |
| PC204 204 | 0.0 | 0.7 | 0.7 | 1.3 | 0.8 | 0.0 | 1.9 | 1.4 | 0.0 | 0.0 | 0.0 |
| PC205 205 | 0.0 | 0.7 | 0.1 | 0.0 | 0.3 | 0.0 | 0.4 | 0.0 | 0.4 | 0.0 | 0.0 |
| PC205 225 | 0.0 | 0.0 | 0.0 | 0.0 | 0.0 | 0.0 | 0.0 | 0.0 | 0.0 | 0.0 | 0.0 |
| PC205 226 | 0.0 | 1.0 | 0.3 | 0.0 | 0.4 | 0.0 | 0.3 | 0.0 | 0.9 | 0.0 | 0.0 |
| PC226 226 | 0.0 | 0.4 | 0.1 | 0.0 | 0.1 | 0.0 | 0.0 | 0.0 | 0.0 | 0.0 | 0.0 |

| Sample Name | Canola Commodity oil | Clear Valley 65 oil | Clear Valley 80 oil | Brassica juncea seeds | Salmon oil capsule | Krill oil capsule | DHA DHA oil capsule | Omega EPA/ DHA oil capsule | Omega 3 algea oil |
|---|---|---|---|---|---|---|---|---|---|
| PC140 161 | 0.0 | 0.0 | 0.0 | 0.0 | 0.0 | 0.9 | 0.0 | 0.0 | 0.0 |
| PC140 181 | 0.0 | 0.0 | 0.0 | 0.0 | 0.0 | 1.4 | 0.0 | 0.0 | 0.0 |
| PC140 182 | 0.0 | 0.0 | 0.0 | 0.0 | 0.0 | 1.0 | 0.0 | 0.0 | 0.0 |
| PC140 183 | 0.0 | 0.0 | 0.0 | 0.0 | 0.0 | 0.8 | 0.0 | 0.0 | 0.0 |
| PC140 204 | 0.0 | 0.0 | 0.0 | 0.0 | 0.0 | 0.2 | 0.0 | 0.0 | 0.0 |
| PC140 205 | 0.0 | 0.0 | 0.0 | 0.0 | 0.0 | 8.5 | 0.0 | 0.0 | 0.0 |
| PC140 225 | 0.0 | 0.0 | 0.0 | 0.0 | 0.0 | 0.1 | 0.0 | 0.0 | 0.0 |
| PC140 226 | 0.0 | 0.0 | 0.0 | 0.0 | 0.0 | 1.7 | 0.0 | 0.0 | 0.0 |
| PC160 160 | 0.0 | 0.0 | 0.0 | 0.0 | 0.0 | 0.2 | 0.0 | 0.0 | 0.0 |
| PC160 161 | 0.0 | 0.0 | 0.0 | 0.0 | 0.0 | 2.0 | 0.0 | 0.0 | 0.0 |
| PC160 180 | 0.0 | 0.0 | 0.0 | 0.0 | 0.0 | 0.0 | 0.0 | 0.0 | 0.0 |
| PC160 181 | 12.5 | 15.9 | 9.0 | 11.8 | 0.0 | 10.8 | 3.4 | 6.1 | 6.4 |
| PC160 182 | 7.3 | 7.4 | 0.0 | 11.4 | 0.0 | 3.9 | 14.7 | 12.9 | 20.5 |
| PC160 183 | 1.7 | 0.7 | 0.0 | 8.1 | 0.0 | 1.8 | 0.0 | 0.0 | 0.0 |
| PC160 203 | 0.0 | 0.0 | 0.0 | 0.0 | 0.0 | 0.4 | 0.0 | 0.0 | 0.0 |
| PC160 205 | 0.0 | 0.0 | 0.0 | 0.0 | 0.0 | 13.0 | 0.0 | 0.0 | 0.0 |
| PC160 225 | 0.0 | 0.0 | 0.0 | 0.0 | 0.0 | 0.9 | 0.0 | 0.0 | 0.0 |
| PC160 226 | 0.0 | 0.0 | 0.0 | 0.0 | 0.0 | 8.4 | 0.0 | 0.0 | 0.0 |
| PC161 161 | 0.0 | 0.0 | 0.0 | 0.0 | 0.0 | 0.2 | 0.0 | 0.0 | 0.0 |
| PC161 180 | 0.0 | 0.0 | 0.0 | 0.0 | 0.0 | 0.0 | 0.0 | 0.0 | 0.0 |
| PC161 181 | 0.8 | 0.3 | 0.8 | 0.4 | 0.0 | 0.9 | 0.0 | 0.0 | 0.0 |
| PC161 182 | 0.8 | 0.6 | 0.0 | 1.6 | 0.0 | 0.2 | 0.0 | 0.0 | 0.3 |
| PC161 183 | 0.0 | 0.0 | 0.0 | 1.2 | 0.0 | 2.7 | 0.0 | 0.0 | 0.0 |
| PC161 203 | 0.0 | 0.0 | 0.0 | 0.0 | 0.0 | 0.1 | 0.0 | 0.0 | 0.0 |
| PC161 205 | 0.0 | 0.0 | 0.0 | 0.0 | 0.0 | 4.4 | 0.0 | 0.0 | 0.0 |
| PC161 226 | 0.0 | 0.0 | 0.0 | 0.0 | 0.0 | 0.7 | 0.0 | 0.0 | 0.0 |
| PC180 181 | 0.8 | 0.8 | 0.0 | 1.7 | 0.0 | 0.2 | 0.0 | 0.0 | 1.2 |
| PC180 182 | 0.0 | 0.1 | 0.0 | 0.8 | 0.0 | 0.3 | 3.2 | 3.3 | 6.1 |
| PC180 183 | 0.0 | 0.0 | 0.0 | 0.5 | 0.0 | 0.3 | 0.0 | 0.0 | 0.0 |
| PC180 205 | 0.0 | 0.0 | 0.0 | 0.0 | 0.0 | 2.2 | 0.0 | 0.0 | 0.0 |
| PC180 226 | 0.0 | 0.0 | 0.0 | 0.0 | 0.0 | 1.0 | 0.0 | 0.0 | 0.0 |
| PC181 181 | 28.0 | 32.9 | 66.0 | 15.2 | 29.5 | 4.4 | 9.0 | 18.6 | 7.5 |
| PC181 182 | 27.0 | 28.6 | 19.1 | 18.7 | 0.0 | 2.2 | 19.2 | 16.9 | 24.5 |
| PC181 183 | 6.0 | 1.8 | 4.9 | 7.4 | 0.0 | 0.7 | 0.0 | 0.0 | 0.0 |
| PC181 204 | 0.0 | 0.0 | 0.0 | 0.0 | 0.0 | 0.3 | 0.0 | 0.0 | 0.0 |
| PC181 205 | 0.0 | 0.0 | 0.0 | 0.0 | 0.0 | 7.5 | 0.0 | 0.0 | 0.0 |
| PC181 226 | 0.0 | 0.0 | 0.0 | 0.0 | 0.0 | 4.1 | 0.0 | 0.0 | 0.0 |

TABLE 188-continued

Phosphatidylcholine species profile of occurring PC species comprising 12 target fatty acids from DCM/MeOH (2:1) extracts analyzed by +ESI-HPLC-MS/MS in sMRM mode. Data are mean, n = 2-3 and expressed as relative abundance of species. Species that were not detected in any samples were removed from the table

| | | | | | | | | | |
|---|---|---|---|---|---|---|---|---|---|
| PC182 182 | 10.2 | 10.3 | 0.0 | 8.7 | 32.1 | 0.1 | 49.7 | 35.2 | 33.3 |
| PC182 183 | 4.3 | 0.7 | 0.2 | 9.3 | 0.0 | 0.1 | 0.0 | 0.0 | 0.1 |
| PC182 203 | 0.0 | 0.0 | 0.0 | 0.0 | 0.0 | 0.4 | 0.0 | 0.0 | 0.0 |
| PC182 204 | 0.0 | 0.0 | 0.0 | 0.0 | 0.0 | 0.0 | 0.0 | 0.0 | 0.0 |
| PC182 205 | 0.0 | 0.0 | 0.0 | 0.0 | 0.0 | 1.0 | 0.0 | 0.0 | 0.0 |
| PC182 226 | 0.0 | 0.0 | 0.0 | 0.0 | 0.0 | 0.1 | 0.0 | 0.0 | 0.0 |
| PC183 183 | 0.5 | 0.0 | 0.0 | 3.3 | 0.0 | 0.0 | 0.0 | 0.0 | 0.0 |
| PC183 205 | 0.0 | 0.0 | 0.0 | 0.0 | 0.0 | 0.5 | 0.0 | 0.0 | 0.0 |
| PC183 226 | 0.0 | 0.0 | 0.0 | 0.0 | 38.4 | 0.1 | 0.8 | 7.0 | 0.0 |
| PC204 204 | 0.0 | 0.0 | 0.0 | 0.0 | 0.0 | 0.0 | 0.0 | 0.0 | 0.0 |
| PC205 205 | 0.0 | 0.0 | 0.0 | 0.0 | 0.0 | 4.5 | 0.0 | 0.0 | 0.0 |
| PC205 225 | 0.0 | 0.0 | 0.0 | 0.0 | 0.0 | 0.1 | 0.0 | 0.0 | 0.0 |
| PC205 226 | 0.0 | 0.0 | 0.0 | 0.0 | 0.0 | 3.9 | 0.0 | 0.0 | 0.0 |
| PC226 226 | 0.0 | 0.0 | 0.0 | 0.0 | 0.0 | 0.9 | 0.0 | 0.0 | 0.0 |

TABLE 189

Lysophosphatidylcholine species profile of occurring LPC species comprising 12 target fatty acids from DCM/MeOH (2:1) extracts analyzed by +ESI-HPLC-MS/MS in MRM mode. Data are mean, n = 2-3 and expressed as relative abundance of species. Species that were not detected in any samples were removed from the table

| Sample Name | LANBCH oil | LANPMZ seeds | LAODDN seeds | LBFDAU oil | LBFGKN seeds | LBFGKN oil | LBFLFK seeds | LBFLFK oil | Arabidopsis seeds |
|---|---|---|---|---|---|---|---|---|---|
| LPC 14:0 | 0.0 | 0.1 | 0.1 | 0.0 | 0.0 | 0.0 | 0.0 | 0.0 | 0.2 |
| LPC 16:0 | 2.8 | 14.5 | 14.2 | 2.9 | 11.0 | 2.3 | 11.7 | 1.9 | 18.1 |
| LPC 16:1 | 2.0 | 2.3 | 2.0 | 2.0 | 1.6 | 2.2 | 1.6 | 2.0 | 2.8 |
| LPC 18:0 | 0.8 | 2.5 | 3.1 | 1.0 | 2.2 | 0.6 | 2.5 | 0.5 | 9.1 |
| LPC 18:1 | 13.4 | 16.9 | 16.8 | 15.8 | 22.1 | 26.5 | 21.8 | 14.0 | 13.0 |
| LPC 18:2 | 46.4 | 33.8 | 32.9 | 48.8 | 38.5 | 47.4 | 34.8 | 45.3 | 23.7 |
| LPC 18:3 | 7.0 | 6.7 | 14.7 | 6.8 | 8.2 | 6.7 | 8.0 | 8.9 | 14.0 |
| LPC 20:3 | 1.7 | 0.9 | 0.4 | 1.0 | 0.8 | 0.5 | 1.0 | 0.9 | 3.0 |
| LPC 20:4 | 9.1 | 6.5 | 6.3 | 10.8 | 6.7 | 5.9 | 10.3 | 13.3 | 2.4 |
| LPC 20:5 | 5.6 | 6.7 | 3.5 | 4.0 | 3.8 | 2.6 | 3.7 | 4.8 | 5.6 |
| LPC 22:5 | 1.4 | 0.8 | 0.7 | 1.3 | 0.7 | 0.6 | 1.2 | 3.1 | 0.5 |
| LPC 22:6 | 9.8 | 8.4 | 5.4 | 5.6 | 4.4 | 4.7 | 3.4 | 5.3 | 7.7 |

| Sample Name | Kumily seeds | Menhaden oil | Salmon oil capsule | Krill oil capsule | DHA DHA oil capsule | Omega EPA/ DHA oil capsule | Omega 3 algea oil |
|---|---|---|---|---|---|---|---|
| LPC 14:0 | 0.0 | 0.0 | 0.0 | 4.4 | 0.0 | 0.0 | 0.0 |
| LPC 16:0 | 7.4 | 28.7 | 47.3 | 37.2 | 10.8 | 11.1 | 13.4 |
| LPC 16:1 | 1.3 | 0.0 | 0.0 | 3.2 | 0.0 | 0.0 | 0.0 |
| LPC 18:0 | 0.8 | 48.0 | 0.0 | 1.4 | 5.5 | 11.4 | 5.0 |
| LPC 18:1 | 56.2 | 13.2 | 21.1 | 13.7 | 23.4 | 29.1 | 20.4 |
| LPC 18:2 | 28.9 | 0.0 | 0.0 | 2.2 | 60.4 | 48.4 | 60.9 |
| LPC 18:3 | 5.5 | 0.0 | 0.0 | 1.6 | 0.0 | 0.0 | 0.0 |
| LPC 20:3 | 0.0 | 0.0 | 0.0 | 0.2 | 0.0 | 0.0 | 0.0 |
| LPC 20:4 | 0.0 | 0.0 | 0.0 | 1.0 | 0.0 | 0.0 | 0.0 |
| LPC 20:5 | 0.0 | 10.2 | 21.1 | 22.8 | 0.0 | 0.0 | 0.4 |
| LPC 22:5 | 0.0 | 0.0 | 0.0 | 1.2 | 0.0 | 0.0 | 0.0 |
| LPC 22:6 | 0.0 | 0.0 | 10.5 | 11.1 | 0.0 | 0.0 | 0.0 |

TABLE 190

Phosphatidylethanolamine species profile of occurring PE species comprising 12 target fatty acids from DCM/MeOH (2:1) extracts analyzed by −ESI-HPLC-MS/MS in sMRM mode. Data are mean, n = 2-3 expressed as relative abundance of species. Species that were not detected in any samples were removed from the table

| Sample Name | LANBCH oil | LANPMZ seeds | LAODDN seeds | LBFDAU oil | LBFGKN seeds | LBFGKN oil | LBFLFK seeds | LBFLFK oil | Arabidopsis seeds | Kumily seeds | Kumily oil |
|---|---|---|---|---|---|---|---|---|---|---|---|
| PE140 160 | 0.0 | 0.0 | 0.0 | 0.0 | 0.0 | 0.0 | 0.0 | 0.0 | 0.0 | 0.0 | 0.0 |
| PE140 161 | 0.0 | 0.0 | 0.0 | 0.0 | 0.0 | 0.0 | 0.0 | 0.0 | 0.0 | 0.0 | 0.0 |
| PE140 181 | 0.0 | 0.0 | 0.0 | 0.0 | 0.0 | 0.0 | 0.0 | 0.0 | 0.0 | 0.2 | 0.0 |
| PE140 182 | 0.0 | 1.1 | 0.6 | 0.4 | 0.6 | 0.0 | 0.5 | 0.4 | 0.5 | 0.4 | 0.0 |

TABLE 190-continued

Phosphatidylethanolamine species profile of occurring PE species comprising 12 target fatty acids from DCM/MeOH (2:1) extracts analyzed by −ESI-HPLC-MS/MS in sMRM mode. Data are mean, n = 2-3 expressed as relative abundance of species. Species that were not detected in any samples were removed from the table

| | | | | | | | | | | | |
|---|---|---|---|---|---|---|---|---|---|---|---|
| PE140 183 | 0.0 | 0.1 | 0.2 | 0.0 | 0.1 | 0.0 | 0.1 | 0.0 | 0.2 | 0.1 | 0.0 |
| PE140 203 | 0.0 | 0.0 | 0.0 | 0.0 | 0.0 | 0.0 | 0.0 | 0.0 | 0.0 | 0.0 | 0.0 |
| PE140 204 | 0.0 | 0.0 | 0.0 | 0.0 | 0.0 | 0.0 | 0.0 | 0.0 | 0.0 | 0.0 | 0.0 |
| PE140 205 | 0.0 | 0.0 | 0.0 | 0.0 | 0.0 | 0.0 | 0.0 | 0.0 | 0.0 | 0.0 | 0.0 |
| PE140 226 | 0.0 | 0.0 | 0.0 | 0.0 | 0.0 | 0.0 | 0.0 | 0.0 | 0.0 | 0.0 | 0.0 |
| PE160 160 | 0.3 | 0.1 | 0.1 | 0.2 | 0.1 | 0.0 | 0.1 | 0.1 | 0.1 | 0.0 | 0.0 |
| PE160 161 | 0.5 | 0.5 | 0.4 | 0.0 | 0.4 | 0.0 | 0.4 | 0.5 | 1.1 | 0.3 | 0.0 |
| PE160 180 | 0.0 | 0.0 | 0.0 | 0.0 | 0.0 | 0.0 | 0.0 | 0.0 | 0.0 | 0.0 | 0.0 |
| PE160 181 | 5.0 | 1.9 | 2.4 | 5.4 | 3.0 | 6.6 | 2.6 | 6.0 | 1.8 | 9.7 | 14.7 |
| PE160 182 | 26.6 | 22.2 | 17.9 | 24.7 | 17.6 | 23.2 | 21.2 | 22.0 | 26.0 | 9.8 | 13.5 |
| PE160 183 | 3.0 | 4.6 | 10.4 | 2.9 | 4.7 | 3.7 | 4.8 | 3.7 | 14.6 | 2.4 | 2.4 |
| PE160 203 | 0.0 | 0.0 | 0.0 | 0.0 | 0.0 | 0.0 | 0.0 | 0.0 | 0.0 | 0.0 | 0.0 |
| PE160 204 | 1.4 | 2.0 | 1.1 | 1.4 | 1.6 | 0.0 | 2.3 | 1.6 | 0.5 | 0.0 | 0.0 |
| PE161 161 | 0.0 | 0.0 | 0.0 | 0.0 | 0.0 | 0.0 | 0.0 | 0.0 | 0.2 | 0.1 | 0.0 |
| PE161 180 | 0.0 | 0.0 | 0.0 | 0.0 | 0.0 | 0.0 | 0.0 | 0.0 | 0.0 | 0.0 | 0.0 |
| PE161 181 | 0.2 | 0.2 | 0.3 | 0.3 | 0.5 | 0.0 | 0.4 | 0.5 | 0.5 | 1.0 | 1.0 |
| PE161 182 | 0.9 | 1.1 | 0.9 | 0.8 | 1.2 | 1.0 | 0.9 | 0.9 | 1.6 | 1.5 | 1.0 |
| PE161 204 | 0.0 | 0.0 | 0.0 | 0.0 | 0.1 | 0.0 | 0.1 | 0.0 | 0.0 | 0.0 | 0.0 |
| PE180 181 | 0.0 | 0.1 | 0.1 | 0.1 | 0.1 | 0.0 | 0.1 | 0.0 | 0.0 | 0.0 | 0.0 |
| PE180 182 | 2.6 | 2.5 | 1.8 | 2.7 | 1.7 | 2.0 | 2.2 | 2.5 | 3.6 | 0.4 | 0.7 |
| PE180 183 | 0.0 | 0.3 | 0.7 | 0.2 | 0.4 | 0.0 | 0.4 | 0.0 | 2.3 | 0.1 | 0.0 |
| PE180 226 | 0.0 | 0.1 | 0.1 | 0.0 | 0.1 | 0.0 | 0.0 | 0.0 | 0.4 | 0.0 | 0.0 |
| PE181 181 | 1.9 | 1.0 | 1.2 | 2.4 | 2.8 | 4.6 | 2.0 | 3.4 | 0.6 | 20.6 | 14.1 |
| PE181 182 | 13.7 | 12.8 | 13.5 | 14.2 | 16.3 | 17.0 | 14.8 | 14.5 | 6.9 | 26.7 | 27.6 |
| PE181 183 | 2.2 | 1.9 | 4.8 | 2.6 | 3.3 | 3.2 | 3.7 | 2.9 | 3.8 | 5.2 | 5.6 |
| PE181 204 | 0.8 | 0.5 | 0.5 | 1.8 | 1.3 | 1.0 | 1.9 | 1.4 | 0.0 | 0.0 | 0.0 |
| PE181 226 | 0.5 | 0.6 | 0.5 | 0.2 | 0.7 | 0.0 | 0.6 | 0.4 | 0.5 | 0.0 | 0.0 |
| PE182 182 | 17.8 | 21.0 | 11.6 | 16.0 | 18.8 | 19.0 | 15.7 | 15.7 | 13.5 | 14.6 | 13.3 |
| PE182 183 | 11.0 | 13.1 | 18.2 | 11.5 | 14.1 | 12.3 | 12.0 | 12.0 | 13.7 | 6.3 | 5.6 |
| PE182 203 | 0.7 | 0.4 | 0.0 | 0.6 | 0.4 | 0.0 | 0.5 | 0.5 | 0.4 | 0.0 | 0.0 |
| PE182 204 | 4.7 | 4.9 | 4.4 | 7.1 | 4.0 | 4.7 | 7.0 | 5.7 | 0.2 | 0.0 | 0.0 |
| PE182 225 | 0.0 | 0.0 | 0.0 | 0.0 | 0.1 | 0.0 | 0.0 | 0.3 | 0.0 | 0.0 | 0.0 |
| PE182 226 | 2.1 | 3.3 | 1.4 | 0.9 | 1.6 | 0.0 | 1.1 | 0.6 | 0.9 | 0.0 | 0.0 |
| PE183 183 | 1.8 | 1.1 | 4.0 | 1.6 | 1.9 | 1.7 | 1.4 | 1.9 | 4.6 | 0.8 | 0.6 |
| PE183 204 | 1.0 | 1.0 | 1.7 | 1.4 | 1.5 | 0.0 | 2.2 | 1.7 | 0.4 | 0.0 | 0.0 |
| PE183 226 | 0.7 | 0.9 | 0.9 | 0.3 | 0.6 | 0.0 | 0.4 | 0.3 | 0.8 | 0.0 | 0.0 |
| PE203 205 | 0.0 | 0.0 | 0.0 | 0.0 | 0.0 | 0.0 | 0.0 | 0.0 | 0.0 | 0.0 | 0.0 |
| PE203 226 | 0.0 | 0.0 | 0.0 | 0.0 | 0.0 | 0.0 | 0.0 | 0.0 | 0.0 | 0.0 | 0.0 |
| PE204 205 | 0.3 | 0.2 | 0.1 | 0.3 | 0.3 | 0.0 | 0.2 | 0.3 | 0.0 | 0.0 | 0.0 |
| PE204 226 | 0.0 | 0.3 | 0.2 | 0.1 | 0.2 | 0.0 | 0.2 | 0.0 | 0.0 | 0.0 | 0.0 |
| PE205 205 | 0.2 | 0.1 | 0.1 | 0.1 | 0.1 | 0.0 | 0.1 | 0.1 | 0.1 | 0.0 | 0.0 |
| PE226 226 | 0.0 | 0.1 | 0.0 | 0.0 | 0.0 | 0.0 | 0.0 | 0.0 | 0.0 | 0.0 | 0.0 |

| Sample Name | Canola Commodity oil | Clear Valley 65 oil | Clear Valley 80 oil | Brassica juncea seeds | Menhaden oil | Salmon oil capsule | Krill oil capsule | DHA DHA oil capsule | Omega EPA/ DHA oil capsule | Omega 3 algea oil |
|---|---|---|---|---|---|---|---|---|---|---|
| PE140 160 | 0.0 | 0.0 | 0.0 | 0.0 | 0.0 | 0.0 | 1.4 | 0.0 | 0.0 | 0.0 |
| PE140 161 | 0.0 | 0.0 | 0.0 | 0.0 | 0.0 | 0.0 | 0.4 | 0.0 | 0.0 | 0.0 |
| PE140 181 | 0.0 | 0.3 | 0.0 | 0.0 | 0.0 | 0.0 | 2.1 | 0.0 | 0.0 | 0.0 |
| PE140 182 | 0.4 | 0.5 | 0.0 | 0.5 | 0.0 | 0.0 | 0.0 | 0.0 | 0.0 | 0.0 |
| PE140 183 | 0.0 | 0.0 | 0.0 | 0.2 | 0.0 | 0.0 | 0.1 | 0.0 | 0.0 | 0.0 |
| PE140 203 | 0.0 | 0.0 | 0.0 | 0.0 | 0.0 | 0.0 | 0.2 | 0.0 | 0.0 | 0.0 |
| PE140 204 | 0.0 | 0.0 | 0.0 | 0.0 | 0.0 | 0.0 | 0.0 | 0.0 | 0.0 | 0.0 |
| PE140 205 | 0.0 | 0.0 | 0.0 | 0.0 | 0.0 | 0.0 | 5.7 | 0.0 | 0.0 | 0.0 |
| PE140 226 | 0.0 | 0.0 | 0.0 | 0.0 | 0.0 | 0.0 | 2.9 | 0.0 | 0.0 | 0.0 |
| PE160 160 | 0.0 | 0.0 | 0.0 | 0.0 | 0.0 | 0.0 | 0.9 | 0.0 | 0.0 | 0.3 |
| PE160 161 | 0.0 | 0.0 | 0.0 | 1.0 | 0.0 | 0.0 | 4.2 | 0.0 | 0.0 | 0.0 |
| PE160 180 | 0.0 | 0.0 | 0.0 | 0.0 | 0.0 | 0.0 | 0.1 | 0.0 | 0.0 | 0.0 |
| PE160 181 | 19.0 | 11.4 | 13.0 | 7.2 | 0.0 | 0.0 | 9.9 | 3.1 | 0.0 | 2.5 |
| PE160 182 | 12.9 | 12.3 | 4.9 | 19.5 | 0.0 | 0.0 | 6.9 | 25.7 | 35.7 | 30.0 |
| PE160 183 | 2.0 | 0.3 | 0.0 | 8.4 | 0.0 | 0.0 | 6.1 | 0.0 | 0.0 | 0.0 |
| PE160 203 | 0.0 | 0.0 | 0.0 | 0.0 | 0.0 | 0.0 | 0.4 | 0.0 | 0.0 | 0.0 |
| PE160 204 | 0.0 | 0.0 | 0.0 | 0.0 | 0.0 | 0.0 | 0.3 | 0.0 | 0.0 | 0.0 |
| PE161 161 | 0.0 | 0.0 | 0.0 | 0.1 | 0.0 | 0.0 | 0.0 | 0.0 | 0.0 | 0.0 |
| PE161 180 | 0.0 | 0.0 | 0.0 | 0.0 | 0.0 | 0.0 | 0.0 | 0.0 | 0.0 | 0.0 |
| PE161 181 | 0.8 | 0.8 | 1.8 | 0.9 | 0.0 | 0.0 | 4.0 | 0.0 | 0.0 | 0.0 |
| PE161 182 | 1.1 | 1.1 | 0.0 | 2.1 | 0.0 | 0.0 | 0.5 | 0.0 | 0.0 | 0.0 |
| PE161 204 | 0.0 | 0.0 | 0.0 | 0.0 | 0.0 | 0.0 | 1.2 | 0.0 | 0.0 | 0.0 |
| PE180 181 | 0.0 | 0.3 | 0.0 | 0.2 | 0.0 | 0.0 | 0.0 | 0.0 | 0.0 | 0.0 |
| PE180 182 | 0.4 | 0.4 | 0.0 | 1.0 | 0.0 | 0.0 | 0.0 | 9.5 | 0.0 | 11.6 |
| PE180 183 | 0.0 | 0.0 | 0.0 | 0.3 | 0.0 | 0.0 | 0.0 | 0.0 | 0.0 | 0.0 |
| PE180 226 | 0.0 | 0.0 | 0.0 | 0.0 | 0.0 | 0.0 | 0.0 | 0.0 | 0.0 | 0.0 |
| PE181 181 | 13.2 | 22.3 | 38.9 | 4.9 | 100.0 | 100.0 | 3.4 | 10.0 | 23.0 | 8.7 |

TABLE 190-continued

Phosphatidylethanolamine species profile of occurring PE species comprising 12 target fatty acids from DCM/MeOH (2:1) extracts analyzed by −ESI-HPLC-MS/MS in sMRM mode. Data are mean, n = 2-3 expressed as relative abundance of species. Species that were not detected in any samples were removed from the table

| | | | | | | | | | | |
|---|---|---|---|---|---|---|---|---|---|---|
| PE181 182 | 25.6 | 35.1 | 28.7 | 19.8 | 0.0 | 0.0 | 1.4 | 10.1 | 2.4 | 7.2 |
| PE181 183 | 4.0 | 0.8 | 3.9 | 5.2 | 0.0 | 0.0 | 1.2 | 0.0 | 0.0 | 0.0 |
| PE181 204 | 0.0 | 0.0 | 0.0 | 0.0 | 0.0 | 0.0 | 0.4 | 0.0 | 0.0 | 0.0 |
| PE181 226 | 0.0 | 0.0 | 0.0 | 0.0 | 0.0 | 0.0 | 20.9 | 0.0 | 0.0 | 0.0 |
| PE182 182 | 15.7 | 13.7 | 7.5 | 16.9 | 0.0 | 0.0 | 0.5 | 41.6 | 38.9 | 39.9 |
| PE182 183 | 4.6 | 0.9 | 1.4 | 9.4 | 0.0 | 0.0 | 0.0 | 0.0 | 0.0 | 0.0 |
| PE182 203 | 0.0 | 0.0 | 0.0 | 0.0 | 0.0 | 0.0 | 0.0 | 0.0 | 0.0 | 0.0 |
| PE182 204 | 0.0 | 0.0 | 0.0 | 0.0 | 0.0 | 0.0 | 0.0 | 0.0 | 0.0 | 0.0 |
| PE182 225 | 0.0 | 0.0 | 0.0 | 0.0 | 0.0 | 0.0 | 0.1 | 0.0 | 0.0 | 0.0 |
| PE182 226 | 0.0 | 0.0 | 0.0 | 0.0 | 0.0 | 0.0 | 2.6 | 0.0 | 0.0 | 0.0 |
| PE183 183 | 0.4 | 0.0 | 0.0 | 2.5 | 0.0 | 0.0 | 0.0 | 0.0 | 0.0 | 0.0 |
| PE183 204 | 0.0 | 0.0 | 0.0 | 0.0 | 0.0 | 0.0 | 0.1 | 0.0 | 0.0 | 0.0 |
| PE183 226 | 0.0 | 0.0 | 0.0 | 0.0 | 0.0 | 0.0 | 0.8 | 0.0 | 0.0 | 0.0 |
| PE203 205 | 0.0 | 0.0 | 0.0 | 0.0 | 0.0 | 0.0 | 1.2 | 0.0 | 0.0 | 0.0 |
| PE203 226 | 0.0 | 0.0 | 0.0 | 0.0 | 0.0 | 0.0 | 0.6 | 0.0 | 0.0 | 0.0 |
| PE204 205 | 0.0 | 0.0 | 0.0 | 0.0 | 0.0 | 0.0 | 1.5 | 0.0 | 0.0 | 0.0 |
| PE204 226 | 0.0 | 0.0 | 0.0 | 0.0 | 0.0 | 0.0 | 6.1 | 0.0 | 0.0 | 0.0 |
| PE205 205 | 0.0 | 0.0 | 0.0 | 0.0 | 0.0 | 0.0 | 10.6 | 0.0 | 0.0 | 0.0 |
| PE226 226 | 0.0 | 0.0 | 0.0 | 0.0 | 0.0 | 0.0 | 1.6 | 0.0 | 0.0 | 0.0 |

TABLE 191

Lysophosphatidylethanolamine species profile of occurring LPE species comprising 12 target fatty acids from DCM/MeOH (2:1) extracts analyzed by −ESI-HPLC-MS/MS in sMRM mode. Data are mean, n = 2-3 expressed as relative abundance of species. Species that were not detected in any samples were removed from the table

| Sample Name | LANBCH oil | LANPMZ seeds | LAODDN seeds | LBFDAU oil | LBFGKN seeds | LBFGKN oil | LBFLFK seeds | LBFLFK oil | Arabidopsis seeds | Kumily seeds |
|---|---|---|---|---|---|---|---|---|---|---|
| LPE14:0 | 0.0 | 0.2 | 0.2 | 0.0 | 0.1 | 0.0 | 0.1 | 0.0 | 0.2 | 0.1 |
| LPE16:0 | 1.9 | 18.8 | 20.8 | 2.5 | 14.8 | 1.6 | 14.7 | 1.7 | 22.5 | 9.7 |
| LPE16:1 | 0.6 | 0.7 | 0.6 | 0.6 | 0.5 | 0.7 | 0.5 | 0.7 | 0.8 | 1.1 |
| LPE18:0 | 1.2 | 3.0 | 3.6 | 1.7 | 2.7 | 1.2 | 3.0 | 1.0 | 9.5 | 0.8 |
| LPE18:1 | 7.1 | 15.1 | 16.4 | 9.8 | 19.2 | 13.6 | 19.5 | 7.6 | 12.1 | 42.1 |
| LPE18:2 | 54.5 | 35.7 | 29.7 | 57.8 | 38.1 | 59.8 | 33.8 | 62.3 | 24.3 | 39.6 |
| LPE18:3 | 6.7 | 6.8 | 13.8 | 7.2 | 9.0 | 7.2 | 8.5 | 8.9 | 12.7 | 6.6 |
| LPE20:3 | 0.3 | 0.6 | 0.2 | 0.2 | 0.5 | 0.1 | 0.7 | 0.1 | 1.2 | 0.0 |
| LPE20:4 | 3.4 | 5.1 | 5.9 | 4.6 | 6.2 | 2.7 | 10.6 | 3.5 | 1.5 | 0.0 |
| LPE20:5 | 6.3 | 4.9 | 3.1 | 5.3 | 3.9 | 3.3 | 3.7 | 5.0 | 5.2 | 0.0 |
| LPE22:5 | 0.2 | 0.1 | 0.1 | 0.2 | 0.2 | 0.1 | 0.5 | 0.7 | 0.0 | 0.0 |
| LPE22:6 | 18.0 | 9.0 | 5.6 | 10.1 | 4.8 | 9.6 | 4.3 | 8.4 | 10.2 | 0.0 |

| Sample Name | Canola Commodity oil | Clear Valley 65 oil | Clear Valley 80 oil | Brassica juncea seeds | Salmon oil capsule | Krill oil capsule | DHA DHA oil capsule | Omega EPA/ DHA oil capsule | Omega 3 algea oil |
|---|---|---|---|---|---|---|---|---|---|
| LPE14:0 | 0.1 | 0.1 | 0.0 | 0.1 | 0.0 | 0.6 | 0.0 | 0.0 | 0.0 |
| LPE16:0 | 5.0 | 8.2 | 7.7 | 24.8 | 19.1 | 23.4 | 9.9 | 17.0 | 20.5 |
| LPE16:1 | 0.5 | 0.6 | 0.3 | 1.1 | 0.0 | 1.2 | 0.0 | 0.0 | 0.0 |
| LPE18:0 | 1.4 | 1.7 | 4.6 | 8.6 | 0.0 | 1.9 | 2.5 | 1.2 | 4.2 |
| LPE18:1 | 48.5 | 61.1 | 71.7 | 23.6 | 25.6 | 23.7 | 14.8 | 17.9 | 11.9 |
| LPE18:2 | 40.5 | 27.7 | 14.2 | 32.4 | 42.6 | 1.6 | 72.8 | 64.0 | 63.4 |
| LPE18:3 | 4.0 | 0.6 | 1.5 | 9.4 | 0.0 | 0.7 | 0.0 | 0.0 | 0.0 |
| LPE20:3 | 0.0 | 0.0 | 0.0 | 0.0 | 0.0 | 0.3 | 0.0 | 0.0 | 0.0 |
| LPE20:4 | 0.0 | 0.0 | 0.0 | 0.0 | 0.0 | 2.0 | 0.0 | 0.0 | 0.0 |
| LPE20:5 | 0.0 | 0.0 | 0.0 | 0.0 | 12.8 | 24.8 | 0.0 | 0.0 | 0.0 |
| LPE22:5 | 0.0 | 0.0 | 0.0 | 0.0 | 0.0 | 0.4 | 0.0 | 0.0 | 0.0 |
| LPE22:6 | 0.0 | 0.0 | 0.0 | 0.0 | 0.0 | 19.3 | 0.0 | 0.0 | 0.0 |

Example 32: TAG Species Analysis

Diluted extracts from Example 29 were used for TAG (triacylglycerol) species analysis. TAG species analysis was carried out on a 1290 Agilent HPLC coupled to AP15500 triple quadrupole MS (ABSciex). HPLC comprised of G4227A Flex Cube, G4226A autosampler, G1330B thermostat and G4220A binary pump. TAG species separation was carried out on a Thermo Accucore C30 column (250 mm×2.1 mm×2.6 μm). The mobile phase consisted of MeCN/IPA as solvent A and IPA as solvent B with a flow rate of 0.4 mL/min. Starting conditions were 100% followed by a linear gradient to 20% A with a total run time of 30 min. The Injection volume was 1 μL. The mass spectrometer was operated in positive APCI mode with ion source temperature of 300° C. using scheduled multiple reaction monitoring (sMRM). Data acquisition was carried out using Analyst 1.5.1 whereas data analysis was done in Multiquant 3.0.1 (AB Sciex). All theoretical [M+H]$^+$ from TAG species containing C14:0, C16:0, C16:1, C18:0, C18:1, C18:2, C18:3, C20:3, C20:4, C20:5, C22:5 and C22:6 fatty acids were calculated resulting in a total of 364 TAG species. In MRM-mode, the neutral loss of fatty acids was monitored, therefore all theoretical product ions were calculated as well. The first quadrupole was set to filter only those [M+H]$^+$ of target TAG species that were subsequently fragmented in the second quadrupole which led to the loss of fatty acid. For TAG species containing three different fatty acids, three product ions were monitored in the third quadrupole whereas those species with two different fatty acids led to two product ions. In case of TAG species with only one fatty acid, only one transition could be monitored.

Single and mixed standards of TAGs (16:0/16:0/16:0), (16:1/16:1/16:1), (17:0/17:0/17:0), (18:0/18:0/18:0), (18:1/18:1/18:1), (18:2/18:2/18:2), (18:3/18:3/18:3), (20:5/20:5/20:5), (22:6/22:6/22:6), (16:0/16:0/18:1), (16:0/18:0/18:2), (16:0/18:1/18:1), (16:0/18:2/18:2), (18:0/18:0/18:2), (18:0/18:1/18:1), (18:0/18:1/18:2), (18:1/18:1/18:3) and (18:1/18:2/18:2) were run to identify retention time patterns among TAG species. MRMs of TAG species not present in a representative set of test samples from different canola, fish and algae oil sources were removed from the transition list. For all other species, a retention time was identified to allow for scheduled monitoring of MRM in a given time window which allows for more data points per transition thus leading to a better quality of data.

Baseline separation of all TAG species could not be achieved within a reasonable runtime, therefore peak heights were used instead of peak areas. The sums of all transitions with were used to calculate a total peak height. Species with peak height lower than 1000 counts were not included in the calculation as they were considered below limit of quantitation having a poor signal-to-noise ratio. TAG species profile was then calculated as TAG species percent of total TAG species.

The results are shown in Table 192.

The five most abundant TAG species in Kumily oil are TAG 181 181 183, TAG 181 182 183, TAG 181 181 182, TAG 181 181 181, and TAG 181 182 182. Together, these account for 64.5% of all TAG species. These species are specifically reduced in the transgenic canola samples, where there sum total ranges from 14.3 to 21.2%. Instead, the most abundant single TAG species in the transgenic canola lines is TAG 181 182 205, followed by TAG 181 181 205 and TAG 182 182 205. Together, these three species make up 20.6 to 25.5% of the total TAG species observed in transgenic canola samples. The two most abundant DHA containing TAG species in the transgenic canola samples are TAG 181 182 226 and TAG 182 182 226, which together represent from 1.5 to 3.3% of all TAG species. It is notable that EPA and DHA are found most frequently esterified to TAG together with 18:1 and 18:2. This makeup is likely to be more oxidatively stable that TAG species containing multiple PUFAs. In the transgenic canola samples, the sum of all TAG species with a single EPA, DPA, or DHA is 42.3 to 50.3%, whereas the sum of all TAG species with more than one EPA, DPA, and/or DHA is 3.4 to 6.6%. In fish and algal oils, the sum of all TAG species with more than one EPA, DPA, and/or DHA ranges from 21.1 to 60.3%. Therefore, the transgenic canola samples have the highest proportion of oxidatively stable TAG species. The transgenic canola samples also have a low abundance of TAG 183 183 205 and TAG 183 183 226, with a range of just 0.2 to 0.6% of total TAG species.

TABLE 192

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| Sample name | LANBCH oil | LANPMZ seeds | LAODDN seeds | LANBHC oil | LBFGKN oil | LBFLFK seeds | LBFLFK oil | Arabidopsis seeds | Kumily seeds | Kumily oil | Canola Commodity oil |
|---|---|---|---|---|---|---|---|---|---|---|---|
| TAG 140 140 140 | 0.0 | 0.0 | 0.0 | 0.0 | 0.0 | 0.0 | 0.0 | 0.0 | 0.0 | 0.0 | 0.0 |
| TAG 140 140 160 | 0.0 | 0.0 | 0.0 | 0.0 | 0.0 | 0.0 | 0.0 | 0.0 | 0.0 | 0.0 | 0.0 |
| TAG 140 140 161 | 0.0 | 0.0 | 0.0 | 0.0 | 0.0 | 0.0 | 0.0 | 0.0 | 0.0 | 0.0 | 0.0 |
| TAG 140 140 181 | 0.0 | 0.0 | 0.0 | 0.0 | 0.0 | 0.0 | 0.0 | 0.0 | 0.0 | 0.0 | 0.0 |
| TAG 140 140 183 | 0.0 | 0.0 | 0.0 | 0.0 | 0.0 | 0.0 | 0.0 | 0.0 | 0.0 | 0.0 | 0.0 |
| TAG 140 140 205 | 0.0 | 0.0 | 0.0 | 0.0 | 0.0 | 0.0 | 0.0 | 0.0 | 0.0 | 0.0 | 0.0 |
| TAG 140 140 225 | 0.0 | 0.0 | 0.0 | 0.0 | 0.0 | 0.0 | 0.0 | 0.0 | 0.0 | 0.0 | 0.0 |
| TAG 140 140 226 | 0.0 | 0.0 | 0.0 | 0.0 | 0.0 | 0.0 | 0.0 | 0.0 | 0.0 | 0.0 | 0.0 |
| TAG 140 160 161 | 0.0 | 0.0 | 0.0 | 0.0 | 0.0 | 0.0 | 0.0 | 0.0 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| TAG | | | | | | | | | | | |
|---|---|---|---|---|---|---|---|---|---|---|---|
| TAG 140 160 181 | 0.0 | 0.0 | 0.0 | 0.0 | 0.0 | 0.0 | 0.0 | 0.0 | 0.0 | 0.0 | 0.0 |
| TAG 140 160 182 | 0.0 | 0.0 | 0.0 | 0.0 | 0.0 | 0.0 | 0.0 | 0.0 | 0.0 | 0.0 | 0.0 |
| TAG 140 160 205 | 0.0 | 0.0 | 0.0 | 0.0 | 0.0 | 0.0 | 0.0 | 0.0 | 0.0 | 0.0 | 0.0 |
| TAG 140 160 226 | 0.0 | 0.0 | 0.0 | 0.0 | 0.0 | 0.0 | 0.0 | 0.0 | 0.0 | 0.0 | 0.0 |
| TAG 140 161 161 | 0.0 | 0.0 | 0.0 | 0.0 | 0.0 | 0.0 | 0.0 | 0.0 | 0.0 | 0.0 | 0.0 |
| TAG 140 161 183 | 0.0 | 0.0 | 0.0 | 0.0 | 0.0 | 0.0 | 0.0 | 0.0 | 0.0 | 0.0 | 0.0 |
| TAG 140 161 205 | 0.0 | 0.0 | 0.0 | 0.0 | 0.0 | 0.0 | 0.0 | 0.0 | 0.0 | 0.0 | 0.0 |
| TAG 140 161 226 | 0.0 | 0.0 | 0.0 | 0.0 | 0.0 | 0.0 | 0.0 | 0.0 | 0.0 | 0.0 | 0.0 |
| TAG 140 181 181 | 0.0 | 0.0 | 0.0 | 0.0 | 0.0 | 0.0 | 0.0 | 0.0 | 0.0 | 0.0 | 0.0 |
| TAG 140 205 205 | 0.0 | 0.0 | 0.0 | 0.0 | 0.0 | 0.0 | 0.0 | 0.0 | 0.0 | 0.0 | 0.0 |
| TAG 140 205 226 | 0.0 | 0.0 | 0.0 | 0.0 | 0.0 | 0.0 | 0.0 | 0.0 | 0.0 | 0.0 | 0.0 |
| TAG 160 160 181 | 0.1 | 0.1 | 0.2 | 0.1 | 0.1 | 0.1 | 0.0 | 0.1 | 0.2 | 0.2 | 0.1 |
| TAG 160 160 182 | 0.5 | 0.3 | 0.3 | 0.5 | 0.4 | 0.3 | 0.4 | 1.1 | 0.4 | 0.2 | 0.4 |
| TAG 160 160 183 | 0.3 | 0.2 | 0.2 | 0.3 | 0.3 | 0.3 | 0.3 | 2.4 | 0.8 | 0.5 | 0.5 |
| TAG 160 160 205 | 0.2 | 0.2 | 0.2 | 0.2 | 0.1 | 0.3 | 0.2 | 0.6 | 0.0 | 0.0 | 0.0 |
| TAG 160 160 225 | 0.0 | 0.0 | 0.0 | 0.0 | 0.0 | 0.0 | 0.0 | 0.0 | 0.0 | 0.0 | 0.0 |
| TAG 160 160 226 | 0.0 | 0.0 | 0.0 | 0.0 | 0.0 | 0.0 | 0.0 | 0.0 | 0.0 | 0.0 | 0.0 |
| TAG 160 161 161 | 0.0 | 0.0 | 0.0 | 0.0 | 0.0 | 0.0 | 0.0 | 0.0 | 0.0 | 0.0 | 0.0 |
| TAG 160 161 181 | 0.0 | 0.0 | 0.0 | 0.0 | 0.0 | 0.0 | 0.0 | 0.0 | 0.0 | 0.0 | 0.0 |
| TAG 160 161 205 | 0.0 | 0.0 | 0.0 | 0.0 | 0.0 | 0.0 | 0.0 | 0.0 | 0.0 | 0.0 | 0.0 |
| TAG 160 161 225 | 0.0 | 0.0 | 0.0 | 0.0 | 0.0 | 0.0 | 0.0 | 0.0 | 0.0 | 0.0 | 0.0 |
| TAG 160 161 226 | 0.0 | 0.0 | 0.0 | 0.0 | 0.0 | 0.0 | 0.0 | 0.0 | 0.0 | 0.0 | 0.0 |
| TAG 160 180 181 | 0.1 | 0.1 | 0.1 | 0.1 | 0.1 | 0.1 | 0.1 | 0.3 | 0.2 | 0.2 | 0.2 |
| TAG 160 180 182 | 0.1 | 0.2 | 0.3 | 0.1 | 0.1 | 0.1 | 0.1 | 0.5 | 0.1 | 0.1 | 0.1 |
| TAG 160 180 183 | 0.2 | 0.2 | 0.2 | 0.2 | 0.2 | 0.2 | 0.1 | 2.6 | 0.3 | 0.2 | 0.2 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | | | |
|---|---|---|---|---|---|---|---|---|---|---|---|
| TAG 160 180 205 | 0.0 | 0.1 | 0.1 | 0.0 | 0.0 | 0.1 | 0.0 | 0.7 | 0.0 | 0.0 | 0.0 |
| TAG 160 180 225 | 0.0 | 0.0 | 0.0 | 0.0 | 0.0 | 0.0 | 0.0 | 0.0 | 0.0 | 0.0 | 0.0 |
| TAG 160 180 226 | 0.0 | 0.0 | 0.0 | 0.0 | 0.0 | 0.0 | 0.0 | 0.0 | 0.0 | 0.0 | 0.0 |
| TAG 160 181 181 | 0.7 | 2.4 | 0.8 | 0.7 | 0.9 | 0.8 | 1.0 | 0.5 | 3.4 | 5.1 | 2.5 |
| TAG 160 181 182 | 2.6 | 1.9 | 3.4 | 2.6 | 2.7 | 3.2 | 2.3 | 2.0 | 4.8 | 2.8 | 3.7 |
| TAG 160 181 183 | 1.3 | 1.8 | 0.0 | 1.3 | 1.8 | 1.5 | 0.0 | 3.1 | 6.6 | 5.1 | 6.1 |
| TAG 160 181 205 | 1.5 | 1.3 | 1.2 | 1.5 | 1.2 | 2.0 | 2.2 | 1.3 | 0.0 | 0.0 | 0.0 |
| TAG 160 181 225 | 0.7 | 0.4 | 0.7 | 0.7 | 0.4 | 0.7 | 0.5 | 0.0 | 0.0 | 0.0 | 0.0 |
| TAG 160 182 182 | 4.1 | 4.9 | 4.3 | 4.1 | 2.9 | 3.2 | 2.1 | 4.1 | 1.8 | 1.6 | 0.0 |
| TAG 160 182 183 | 2.4 | 2.5 | 3.1 | 2.4 | 2.6 | 2.3 | 1.5 | 9.2 | 5.8 | 3.7 | 3.5 |
| TAG 160 182 205 | 4.3 | 3.3 | 3.1 | 4.3 | 1.7 | 3.8 | 2.4 | 7.6 | 0.0 | 0.0 | 0.0 |
| TAG 160 182 225 | 1.7 | 1.6 | 2.1 | 1.7 | 0.8 | 1.4 | 1.4 | 0.0 | 0.0 | 0.0 | 0.0 |
| TAG 160 183 183 | 0.3 | 0.3 | 0.5 | 0.3 | 0.6 | 0.4 | 0.4 | 4.6 | 1.1 | 1.2 | 0.0 |
| TAG 160 183 205 | 0.7 | 0.4 | 0.5 | 0.7 | 0.6 | 0.6 | 0.7 | 2.8 | 0.0 | 0.0 | 0.0 |
| TAG 160 184 205 | 0.0 | 0.0 | 0.0 | 0.0 | 0.0 | 0.0 | 0.0 | 0.0 | 0.0 | 0.0 | 0.0 |
| TAG 160 205 205 | 0.4 | 0.2 | 0.2 | 0.4 | 0.3 | 0.4 | 0.3 | 1.6 | 0.0 | 0.0 | 0.0 |
| TAG 160 205 225 | 0.0 | 0.0 | 0.0 | 0.0 | 0.0 | 0.0 | 0.0 | 0.0 | 0.0 | 0.0 | 0.0 |
| TAG 160 205 226 | 0.0 | 0.0 | 0.0 | 0.0 | 0.0 | 0.0 | 0.0 | 0.5 | 0.0 | 0.0 | 0.0 |
| TAG 160 225 226 | 0.0 | 0.0 | 0.0 | 0.0 | 0.0 | 0.0 | 0.0 | 0.0 | 0.0 | 0.0 | 0.0 |
| TAG 160 226 226 | 0.0 | 0.0 | 0.0 | 0.0 | 0.0 | 0.0 | 0.0 | 0.0 | 0.0 | 0.0 | 0.0 |
| TAG 161 161 181 | 0.0 | 0.0 | 0.0 | 0.0 | 0.0 | 0.0 | 0.0 | 0.0 | 0.0 | 0.0 | 0.0 |
| TAG 161 161 205 | 0.0 | 0.0 | 0.0 | 0.0 | 0.0 | 0.0 | 0.0 | 0.0 | 0.0 | 0.0 | 0.0 |
| TAG 161 181 181 | 0.0 | 0.0 | 0.0 | 0.0 | 0.0 | 0.0 | 0.0 | 0.0 | 0.3 | 0.2 | 0.1 |
| TAG 161 181 183 | 0.0 | 0.0 | 0.0 | 0.0 | 0.0 | 0.0 | 0.0 | 0.0 | 0.3 | 0.0 | 0.0 |
| TAG 161 181 205 | 0.0 | 0.0 | 0.0 | 0.0 | 0.0 | 0.0 | 0.0 | 0.0 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | | | |
|---|---|---|---|---|---|---|---|---|---|---|---|
| TAG 161 182 183 | 0.0 | 0.0 | 0.0 | 0.0 | 0.0 | 0.0 | 0.0 | 0.0 | 0.0 | 0.0 | 0.0 |
| TAG 161 205 205 | 0.0 | 0.0 | 0.0 | 0.0 | 0.0 | 0.0 | 0.0 | 0.0 | 0.0 | 0.0 | 0.0 |
| TAG 161 205 226 | 0.0 | 0.0 | 0.0 | 0.0 | 0.0 | 0.0 | 0.0 | 0.0 | 0.0 | 0.0 | 0.0 |
| TAG 161 226 226 | 0.0 | 0.0 | 0.0 | 0.0 | 0.0 | 0.0 | 0.0 | 0.0 | 0.0 | 0.0 | 0.0 |
| TAG 180 180 180 | 0.0 | 0.0 | 0.0 | 0.0 | 0.0 | 0.0 | 0.0 | 0.0 | 0.0 | 0.0 | 2.4 |
| TAG 180 180 181 | 0.1 | 0.1 | 0.1 | 0.1 | 0.2 | 0.1 | 0.1 | 0.4 | 0.2 | 0.2 | 0.1 |
| TAG 180 180 182 | 0.1 | 0.1 | 0.1 | 0.1 | 0.1 | 0.1 | 0.1 | 0.5 | 0.0 | 0.0 | 0.1 |
| TAG 180 180 183 | 0.0 | 0.0 | 0.0 | 0.0 | 0.1 | 0.0 | 0.0 | 0.6 | 0.0 | 0.0 | 0.0 |
| TAG 180 181 181 | 0.2 | 0.3 | 0.2 | 0.2 | 0.3 | 0.2 | 0.2 | 0.2 | 0.8 | 0.6 | 0.3 |
| TAG 180 181 182 | 0.5 | 0.8 | 0.4 | 0.5 | 0.6 | 0.5 | 0.4 | 0.8 | 0.7 | 0.9 | 0.9 |
| TAG 180 181 183 | 0.9 | 0.4 | 0.4 | 0.9 | 0.8 | 0.4 | 0.4 | 1.4 | 2.0 | 0.9 | 0.9 |
| TAG 180 181 203 | 0.0 | 0.0 | 0.0 | 0.0 | 0.0 | 0.0 | 0.0 | 0.0 | 0.0 | 0.0 | 0.2 |
| TAG 180 181 205 | 0.8 | 0.4 | 0.4 | 0.8 | 0.4 | 0.9 | 0.5 | 0.0 | 0.0 | 0.0 | 0.0 |
| TAG 180 181 225 | 0.2 | 0.1 | 0.1 | 0.2 | 0.1 | 0.1 | 0.1 | 0.0 | 0.0 | 0.0 | 0.0 |
| TAG 180 182 182 | 0.9 | 0.8 | 1.0 | 0.9 | 0.9 | 0.8 | 0.6 | 1.7 | 0.0 | 0.0 | 0.0 |
| TAG 180 182 183 | 0.8 | 0.6 | 0.8 | 0.8 | 0.7 | 0.7 | 0.6 | 5.0 | 0.6 | 0.5 | 0.6 |
| TAG 180 182 205 | 0.7 | 0.4 | 0.4 | 0.7 | 0.6 | 0.7 | 0.7 | 1.7 | 0.0 | 0.0 | 0.0 |
| TAG 180 182 225 | 0.6 | 0.3 | 0.5 | 0.6 | 0.3 | 0.9 | 0.5 | 0.0 | 0.0 | 0.0 | 0.0 |
| TAG 180 183 183 | 0.0 | 0.0 | 0.0 | 0.0 | 0.0 | 0.0 | 0.0 | 3.6 | 0.3 | 0.3 | 0.0 |
| TAG 180 183 205 | 0.0 | 0.0 | 0.0 | 0.0 | 0.0 | 0.0 | 0.0 | 1.2 | 0.0 | 0.0 | 0.0 |
| TAG 180 205 205 | 0.0 | 0.0 | 0.0 | 0.0 | 0.0 | 0.0 | 0.0 | 0.4 | 0.0 | 0.0 | 0.0 |
| TAG 180 205 226 | 0.0 | 0.0 | 0.0 | 0.0 | 0.0 | 0.0 | 0.0 | 0.0 | 0.0 | 0.0 | 0.0 |
| TAG 180 226 226 | 0.0 | 0.0 | 0.0 | 0.0 | 0.0 | 0.0 | 0.0 | 0.0 | 0.0 | 0.0 | 0.0 |
| TAG 181 181 181 | 1.2 | 1.4 | 1.1 | 1.2 | 2.9 | 1.3 | 2.6 | 0.5 | 12.4 | 8.2 | 0.0 |
| TAG 181 181 182 | 2.1 | 3.8 | 4.6 | 2.1 | 3.7 | 3.5 | 2.6 | 0.5 | 10.8 | 9.1 | 17.1 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | | | |
|---|---|---|---|---|---|---|---|---|---|---|---|
| TAG 181 181 183 | 0.0 | 0.0 | 0.0 | 0.0 | 0.0 | 0.0 | 0.0 | 0.0 | 0.0 | 23.1 | 18.4 |
| TAG 181 181 203 | 0.6 | 0.0 | 0.5 | 0.6 | 0.7 | 1.0 | 1.1 | 0.0 | 0.0 | 0.0 | 4.6 |
| TAG 181 181 204 | 1.5 | 0.0 | 0.0 | 1.5 | 1.7 | 0.0 | 1.2 | 0.0 | 0.0 | 0.0 | 0.0 |
| TAG 181 181 205 | 5.3 | 6.6 | 7.5 | 5.3 | 6.9 | 4.9 | 7.6 | 0.0 | 0.0 | 0.0 | 0.0 |
| TAG 181 181 225 | 1.9 | 2.5 | 1.5 | 1.9 | 1.0 | 1.4 | 1.2 | 0.0 | 0.0 | 0.0 | 0.0 |
| TAG 181 181 226 | 0.5 | 0.7 | 0.3 | 0.5 | 1.0 | 0.8 | 0.8 | 0.0 | 0.0 | 0.0 | 0.0 |
| TAG 181 182 182 | 5.2 | 8.0 | 9.9 | 5.2 | 8.1 | 6.1 | 4.9 | 0.0 | 13.5 | 5.5 | 5.0 |
| TAG 181 182 183 | 5.7 | 5.8 | 4.6 | 5.7 | 6.5 | 5.8 | 6.0 | 3.1 | 16.4 | 18.6 | 13.3 |
| TAG 181 182 203 | 0.9 | 1.6 | 1.6 | 0.9 | 1.3 | 2.0 | 1.6 | 0.0 | 0.0 | 0.0 | 1.9 |
| TAG 181 182 205 | 10.1 | 10.2 | 10.5 | 10.1 | 7.5 | 12.4 | 10.9 | 0.0 | 0.0 | 0.0 | 0.0 |
| TAG 181 182 225 | 4.2 | 3.0 | 3.8 | 4.2 | 2.7 | 3.5 | 3.8 | 0.0 | 0.0 | 0.0 | 0.0 |
| TAG 181 182 226 | 1.4 | 0.9 | 0.8 | 1.4 | 1.2 | 2.1 | 1.4 | 0.0 | 0.0 | 0.0 | 0.0 |
| TAG 181 183 183 | 0.0 | 0.0 | 0.0 | 0.0 | 0.0 | 0.0 | 0.0 | 2.9 | 8.0 | 4.1 | 4.5 |
| TAG 181 183 203 | 0.0 | 0.0 | 0.0 | 0.0 | 0.0 | 0.0 | 0.0 | 0.0 | 0.0 | 0.0 | 3.2 |
| TAG 181 204 205 | 1.2 | 0.0 | 0.0 | 1.2 | 1.2 | 0.0 | 0.0 | 0.0 | 0.0 | 0.0 | 0.0 |
| TAG 181 205 205 | 1.1 | 0.8 | 1.0 | 1.1 | 1.2 | 1.8 | 1.3 | 0.9 | 0.0 | 0.0 | 0.0 |
| TAG 181 205 225 | 0.6 | 0.4 | 0.4 | 0.6 | 0.5 | 0.8 | 0.8 | 0.0 | 0.0 | 0.0 | 0.0 |
| TAG 181 205 226 | 0.4 | 0.3 | 0.1 | 0.4 | 0.1 | 0.2 | 0.2 | 0.6 | 0.0 | 0.0 | 0.0 |
| TAG 181 226 226 | 0.0 | 0.0 | 0.0 | 0.0 | 0.0 | 0.0 | 0.0 | 0.0 | 0.0 | 0.0 | 0.0 |
| TAG 182 182 182 | 4.2 | 6.4 | 5.5 | 4.0 | 3.0 | 3.5 | 6.0 | 0.8 | 2.4 | 1.7 | 0.0 |
| TAG 182 182 183 | 3.3 | 3.5 | 5.7 | 3.3 | 5.3 | 3.4 | 3.9 | 1.9 | 2.9 | 2.7 | 3.4 |
| TAG 182 182 203 | 1.0 | 0.0 | 0.0 | 1.0 | 0.8 | 0.0 | 1.9 | 0.0 | 0.0 | 0.0 | 0.7 |
| TAG 182 182 205 | 5.3 | 8.1 | 3.6 | 5.3 | 7.3 | 5.1 | 6.9 | 2.7 | 0.0 | 0.0 | 0.0 |
| TAG 182 182 225 | 2.6 | 2.1 | 2.5 | 2.6 | 2.1 | 2.6 | 1.4 | 0.0 | 0.0 | 0.0 | 0.0 |
| TAG 182 182 226 | 1.2 | 1.1 | 0.6 | 1.2 | 1.5 | 1.2 | 1.4 | 0.9 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | | | |
|---|---|---|---|---|---|---|---|---|---|---|---|
| TAG 182 183 183 | 1.5 | 1.0 | 1.5 | 1.5 | 2.3 | 1.4 | 1.1 | 2.8 | 2.0 | 2.1 | 2.0 |
| TAG 182 183 203 | 0.0 | 0.0 | 0.0 | 0.0 | 0.0 | 0.0 | 0.0 | 1.6 | 0.0 | 0.0 | 2.4 |
| TAG 182 183 205 | 2.7 | 2.0 | 2.8 | 2.7 | 2.7 | 3.4 | 3.5 | 4.8 | 0.0 | 0.0 | 0.0 |
| TAG 182 183 225 | 1.6 | 1.0 | 1.3 | 1.6 | 0.7 | 0.0 | 0.9 | 0.0 | 0.0 | 0.0 | 0.0 |
| TAG 182 183 226 | 0.9 | 0.0 | 0.0 | 0.9 | 1.1 | 0.0 | 0.8 | 2.7 | 0.0 | 0.0 | 0.0 |
| TAG 182 205 205 | 0.9 | 0.5 | 0.6 | 0.9 | 0.7 | 1.1 | 1.7 | 2.1 | 0.0 | 0.0 | 0.0 |
| TAG 182 205 225 | 1.1 | 0.5 | 0.4 | 1.1 | 0.5 | 1.1 | 1.0 | 0.0 | 0.0 | 0.0 | 0.0 |
| TAG 182 205 226 | 0.0 | 0.3 | 0.2 | 0.0 | 0.0 | 0.4 | 0.0 | 0.8 | 0.0 | 0.0 | 0.0 |
| TAG 182 225 226 | 0.2 | 0.1 | 0.1 | 0.2 | 0.1 | 0.2 | 0.2 | 0.0 | 0.0 | 0.0 | 0.0 |
| TAG 183 183 183 | 0.1 | 0.0 | 0.2 | 0.1 | 0.3 | 0.2 | 0.1 | 0.7 | 0.6 | 0.5 | 0.0 |
| TAG 183 183 203 | 0.0 | 0.0 | 0.0 | 0.0 | 0.0 | 0.0 | 0.0 | 0.0 | 0.0 | 0.0 | 0.5 |
| TAG 183 183 205 | 0.4 | 0.2 | 0.4 | 0.4 | 0.3 | 0.5 | 0.4 | 2.0 | 0.0 | 0.0 | 0.0 |
| TAG 183 183 226 | 0.1 | 0.1 | 0.1 | 0.1 | 0.1 | 0.1 | 0.1 | 1.3 | 0.0 | 0.0 | 0.0 |
| TAG 183 205 205 | 0.4 | 0.1 | 0.2 | 0.4 | 0.3 | 0.5 | 0.3 | 1.5 | 0.0 | 0.0 | 0.0 |
| TAG 183 205 226 | 0.0 | 0.1 | 0.1 | 0.0 | 0.0 | 0.2 | 0.0 | 0.8 | 0.0 | 0.0 | 0.0 |
| TAG 205 205 205 | 0.2 | 0.1 | 0.1 | 0.2 | 0.1 | 0.2 | 0.1 | 0.7 | 0.0 | 0.0 | 0.0 |
| TAG 205 205 226 | 0.0 | 0.0 | 0.0 | 0.0 | 0.0 | 0.0 | 0.0 | 0.3 | 0.0 | 0.0 | 0.0 |
| TAG 205 226 226 | 0.0 | 0.0 | 0.0 | 0.0 | 0.0 | 0.0 | 0.0 | 0.0 | 0.0 | 0.0 | 0.0 |
| TAG 226 226 226 | 0.0 | 0.0 | 0.0 | 0.0 | 0.0 | 0.0 | 0.0 | 0.0 | 0.0 | 0.0 | 0.0 |

| Sample name | Clear Valley 65 oil | Clear Valley 80 oil | Brassica juncea seeds | Menhaden oil | Salmon oil capsule | Krill oil capsule | DHA DHA oil capsule | Omega EPA/ DHA oil capsule | Omega 3 algea oil |
|---|---|---|---|---|---|---|---|---|---|
| TAG 140 140 140 | 0.0 | 0.0 | 0.0 | 0.0 | 0.0 | 0.1 | 0.0 | 0.0 | 0.1 |
| TAG 140 140 160 | 0.0 | 0.0 | 0.0 | 0.0 | 0.0 | 0.0 | 0.1 | 0.0 | 0.1 |
| TAG 140 140 161 | 0.0 | 0.0 | 0.0 | 0.8 | 0.7 | 10.8 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | |
|---|---|---|---|---|---|---|---|---|---|
| TAG 140 140 181 | 0.0 | 0.0 | 0.0 | 0.5 | 0.4 | 10.5 | 0.0 | 0.0 | 0.0 |
| TAG 140 140 183 | 0.0 | 0.0 | 0.0 | 0.6 | 0.2 | 2.1 | 0.0 | 0.0 | 0.0 |
| TAG 140 140 205 | 0.0 | 0.0 | 0.0 | 6.7 | 7.0 | 3.3 | 0.3 | 0.4 | 0.4 |
| TAG 140 140 225 | 0.0 | 0.0 | 0.0 | 0.0 | 0.0 | 0.0 | 3.5 | 0.0 | 2.7 |
| TAG 140 140 226 | 0.0 | 0.0 | 0.0 | 2.4 | 2.0 | 1.2 | 10.5 | 1.0 | 10.4 |
| TAG 140 160 161 | 0.0 | 0.0 | 0.0 | 1.0 | 0.6 | 15.4 | 0.0 | 0.0 | 0.0 |
| TAG 140 160 181 | 0.0 | 0.0 | 0.0 | 0.6 | 1.4 | 15.7 | 0.0 | 0.0 | 0.0 |
| TAG 140 160 182 | 0.0 | 0.0 | 0.0 | 0.2 | 0.0 | 2.5 | 0.0 | 0.0 | 0.0 |
| TAG 140 160 205 | 0.0 | 0.0 | 0.0 | 8.3 | 10.1 | 8.8 | 0.0 | 2.0 | 0.0 |
| TAG 140 160 226 | 0.0 | 0.0 | 0.0 | 5.1 | 4.4 | 2.5 | 23.9 | 3.7 | 21.2 |
| TAG 140 161 161 | 0.0 | 0.0 | 0.0 | 1.5 | 0.7 | 2.4 | 0.0 | 0.0 | 0.0 |
| TAG 140 161 183 | 0.0 | 0.0 | 0.0 | 0.6 | 0.3 | 0.0 | 0.0 | 0.0 | 0.0 |
| TAG 140 161 205 | 0.0 | 0.0 | 0.0 | 8.4 | 7.0 | 2.9 | 0.0 | 0.0 | 0.0 |
| TAG 140 161 226 | 0.0 | 0.0 | 0.0 | 3.7 | 1.7 | 0.0 | 0.0 | 0.0 | 0.4 |
| TAG 140 181 181 | 0.0 | 0.0 | 0.0 | 0.5 | 0.4 | 5.0 | 0.0 | 0.0 | 0.0 |
| TAG 140 205 205 | 0.0 | 0.0 | 0.0 | 3.6 | 3.4 | 0.0 | 0.1 | 1.2 | 0.2 |
| TAG 140 205 226 | 0.0 | 0.0 | 0.0 | 1.4 | 2.2 | 0.0 | 1.3 | 3.6 | 1.1 |
| TAG 160 160 181 | 0.3 | 0.2 | 0.5 | 0.2 | 0.3 | 0.9 | 0.0 | 0.0 | 0.0 |
| TAG 160 160 182 | 0.3 | 0.2 | 2.3 | 0.0 | 0.0 | 0.0 | 0.0 | 0.0 | 0.0 |
| TAG 160 160 183 | 0.0 | 0.0 | 7.3 | 0.0 | 0.0 | 0.0 | 0.0 | 0.0 | 0.0 |
| TAG 160 160 205 | 0.0 | 0.0 | 0.0 | 2.9 | 3.6 | 1.4 | 0.0 | 5.9 | 0.0 |
| TAG 160 160 225 | 0.0 | 0.0 | 0.0 | 0.0 | 0.0 | 0.0 | 0.0 | 1.7 | 0.0 |
| TAG 160 160 226 | 0.0 | 0.0 | 0.0 | 3.1 | 2.6 | 0.0 | 11.3 | 12.6 | 8.8 |
| TAG 160 161 161 | 0.0 | 0.0 | 0.0 | 1.8 | 0.8 | 0.0 | 0.0 | 0.0 | 0.0 |
| TAG 160 161 181 | 0.0 | 0.0 | 0.0 | 1.4 | 0.7 | 3.3 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| TAG | | | | | | | | | |
|---|---|---|---|---|---|---|---|---|---|
| TAG 160 161 205 | 0.0 | 0.0 | 0.0 | 6.1 | 8.3 | 1.5 | 0.0 | 0.0 | 0.0 |
| TAG 160 161 225 | 0.0 | 0.0 | 0.0 | 0.7 | 1.0 | 0.0 | 0.0 | 0.0 | 0.0 |
| TAG 160 161 226 | 0.0 | 0.0 | 0.0 | 5.7 | 0.0 | 0.0 | 1.1 | 0.3 | 0.7 |
| TAG 160 180 181 | 0.3 | 0.5 | 0.4 | 0.1 | 0.1 | 0.1 | 0.1 | 0.1 | 0.1 |
| TAG 160 180 182 | 0.1 | 0.0 | 0.6 | 0.0 | 0.0 | 0.0 | 0.0 | 0.0 | 0.0 |
| TAG 160 180 183 | 0.0 | 0.1 | 1.9 | 0.0 | 0.0 | 0.0 | 0.0 | 0.0 | 0.0 |
| TAG 160 180 205 | 0.0 | 0.0 | 0.0 | 0.5 | 0.5 | 0.0 | 0.0 | 0.8 | 0.0 |
| TAG 160 180 225 | 0.0 | 0.0 | 0.0 | 0.0 | 0.0 | 0.0 | 0.0 | 0.3 | 0.0 |
| TAG 160 180 226 | 0.0 | 0.0 | 0.0 | 0.0 | 0.0 | 0.0 | 0.0 | 1.0 | 0.0 |
| TAG 160 181 181 | 4.7 | 12.5 | 1.7 | 0.2 | 0.4 | 1.3 | 0.8 | 2.0 | 1.1 |
| TAG 160 181 182 | 8.4 | 3.0 | 4.0 | 0.0 | 0.0 | 0.0 | 0.0 | 0.0 | 0.0 |
| TAG 160 181 183 | 1.0 | 3.4 | 9.8 | 0.0 | 0.0 | 0.0 | 0.0 | 0.0 | 0.0 |
| TAG 160 181 205 | 0.0 | 0.0 | 0.0 | 4.9 | 8.1 | 3.0 | 0.0 | 0.0 | 0.0 |
| TAG 160 181 225 | 0.0 | 0.0 | 0.0 | 0.0 | 0.0 | 0.0 | 0.0 | 0.0 | 0.0 |
| TAG 160 182 182 | 1.9 | 0.0 | 5.0 | 0.0 | 0.0 | 0.0 | 0.0 | 0.0 | 0.0 |
| TAG 160 182 183 | 0.5 | 0.4 | 15.4 | 0.0 | 0.0 | 0.0 | 0.0 | 0.0 | 0.0 |
| TAG 160 182 205 | 0.0 | 0.0 | 0.0 | 0.0 | 0.0 | 0.0 | 0.0 | 0.0 | 0.0 |
| TAG 160 182 225 | 0.0 | 0.0 | 0.0 | 0.0 | 0.0 | 0.0 | 0.0 | 0.0 | 0.0 |
| TAG 160 183 183 | 0.0 | 0.0 | 10.2 | 0.0 | 0.0 | 0.0 | 0.0 | 0.0 | 0.0 |
| TAG 160 183 205 | 0.0 | 0.0 | 0.0 | 0.0 | 0.0 | 0.0 | 0.0 | 0.0 | 0.0 |
| TAG 160 184 205 | 0.0 | 0.0 | 0.0 | 1.7 | 2.9 | 2.0 | 0.0 | 0.0 | 0.0 |
| TAG 160 205 205 | 0.0 | 0.0 | 0.0 | 2.8 | 3.6 | 0.9 | 0.0 | 8.0 | 0.0 |
| TAG 160 205 225 | 0.0 | 0.0 | 0.0 | 0.0 | 0.0 | 0.0 | 0.0 | 3.1 | 0.0 |
| TAG 160 205 226 | 0.0 | 0.0 | 0.0 | 2.4 | 3.8 | 0.0 | 0.0 | 13.4 | 0.0 |
| TAG 160 225 226 | 0.0 | 0.0 | 0.0 | 0.0 | 0.0 | 0.0 | 13.0 | 1.2 | 16.5 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | |
|---|---|---|---|---|---|---|---|---|---|
| TAG 160 226 226 | 0.0 | 0.0 | 0.0 | 1.0 | 1.1 | 0.0 | 21.2 | 12.0 | 20.1 |
| TAG 161 161 181 | 0.0 | 0.0 | 0.0 | 0.4 | 0.3 | 0.0 | 0.0 | 0.0 | 0.0 |
| TAG 161 161 205 | 0.0 | 0.0 | 0.0 | 4.9 | 3.4 | 0.0 | 0.0 | 0.0 | 0.0 |
| TAG 161 181 181 | 0.7 | 0.6 | 0.0 | 0.1 | 0.2 | 0.7 | 0.0 | 0.0 | 0.0 |
| TAG 161 181 183 | 0.0 | 0.0 | 0.0 | 0.0 | 0.0 | 0.0 | 0.0 | 0.0 | 0.0 |
| TAG 161 181 205 | 0.0 | 0.0 | 0.0 | 2.0 | 3.1 | 0.0 | 0.0 | 0.0 | 0.0 |
| TAG 161 182 183 | 0.0 | 0.0 | 2.3 | 0.0 | 0.0 | 0.0 | 0.0 | 0.0 | 0.0 |
| TAG 161 205 205 | 0.0 | 0.0 | 0.0 | 2.6 | 1.7 | 0.0 | 0.0 | 0.0 | 0.0 |
| TAG 161 205 226 | 0.0 | 0.0 | 0.0 | 2.1 | 0.0 | 0.0 | 0.0 | 0.0 | 0.0 |
| TAG 161 226 226 | 0.0 | 0.0 | 0.0 | 0.3 | 0.3 | 0.0 | 0.6 | 0.1 | 0.5 |
| TAG 180 180 180 | 0.0 | 0.0 | 0.0 | 0.0 | 0.0 | 0.0 | 0.0 | 0.0 | 0.0 |
| TAG 180 180 181 | 0.3 | 0.7 | 0.2 | 0.0 | 0.0 | 0.0 | 0.1 | 0.1 | 0.1 |
| TAG 180 180 182 | 0.0 | 0.1 | 0.3 | 0.0 | 0.0 | 0.0 | 0.0 | 0.0 | 0.0 |
| TAG 180 180 183 | 0.0 | 0.0 | 0.3 | 0.0 | 0.0 | 0.0 | 0.0 | 0.0 | 0.0 |
| TAG 180 181 181 | 1.4 | 2.8 | 0.0 | 0.0 | 0.0 | 0.0 | 0.4 | 0.6 | 0.4 |
| TAG 180 181 182 | 1.3 | 1.7 | 0.0 | 0.0 | 0.0 | 0.0 | 0.0 | 0.2 | 0.0 |
| TAG 180 181 183 | 0.0 | 0.9 | 0.0 | 0.0 | 0.0 | 0.0 | 0.0 | 0.0 | 0.0 |
| TAG 180 181 203 | 0.0 | 0.0 | 0.0 | 0.0 | 0.0 | 0.0 | 0.0 | 0.0 | 0.0 |
| TAG 180 181 205 | 0.0 | 0.0 | 0.0 | 0.0 | 0.5 | 0.0 | 0.0 | 0.0 | 0.0 |
| TAG 180 181 225 | 0.0 | 0.0 | 0.0 | 0.1 | 0.2 | 0.0 | 0.0 | 0.0 | 0.0 |
| TAG 180 182 182 | 0.0 | 0.0 | 0.0 | 0.0 | 0.0 | 0.0 | 0.0 | 0.0 | 0.0 |
| TAG 180 182 183 | 0.0 | 0.0 | 2.0 | 0.0 | 0.0 | 0.0 | 0.0 | 0.0 | 0.0 |
| TAG 180 182 205 | 0.0 | 0.0 | 0.0 | 0.0 | 0.0 | 0.0 | 0.0 | 0.0 | 0.0 |
| TAG 180 182 225 | 0.0 | 0.0 | 0.0 | 0.0 | 0.0 | 0.0 | 0.0 | 0.0 | 0.0 |
| TAG 180 183 183 | 0.0 | 0.0 | 1.4 | 0.0 | 0.0 | 0.0 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | |
|---|---|---|---|---|---|---|---|---|---|
| TAG 180 183 205 | 0.0 | 0.0 | 0.0 | 0.0 | 0.0 | 0.0 | 0.0 | 0.0 | 0.0 |
| TAG 180 205 205 | 0.0 | 0.0 | 0.0 | 0.3 | 0.7 | 0.0 | 0.0 | 0.0 | 0.0 |
| TAG 180 205 226 | 0.0 | 0.0 | 0.0 | 0.3 | 0.9 | 0.0 | 0.0 | 0.7 | 0.0 |
| TAG 180 226 226 | 0.0 | 0.0 | 0.0 | 0.1 | 0.2 | 0.0 | 0.5 | 0.4 | 0.4 |
| TAG 181 181 181 | 20.9 | 29.9 | 0.3 | 0.1 | 0.2 | 0.3 | 3.3 | 5.0 | 3.3 |
| TAG 181 181 182 | 33.1 | 18.8 | 1.7 | 0.0 | 0.0 | 0.0 | 0.7 | 1.1 | 0.4 |
| TAG 181 181 183 | 6.2 | 13.3 | 0.0 | 0.0 | 0.0 | 0.0 | 0.0 | 0.0 | 0.0 |
| TAG 181 181 203 | 0.0 | 0.0 | 0.0 | 0.0 | 0.0 | 0.0 | 0.0 | 0.0 | 0.0 |
| TAG 181 181 204 | 0.0 | 0.0 | 0.0 | 0.0 | 0.0 | 0.0 | 0.0 | 0.0 | 0.0 |
| TAG 181 181 205 | 0.0 | 0.0 | 0.0 | 0.4 | 1.3 | 0.0 | 0.0 | 0.0 | 0.0 |
| TAG 181 181 225 | 0.0 | 0.0 | 0.0 | 0.1 | 0.1 | 0.0 | 0.0 | 0.0 | 0.0 |
| TAG 181 181 226 | 0.0 | 0.0 | 0.0 | 0.6 | 0.8 | 0.0 | 0.0 | 0.0 | 0.0 |
| TAG 181 182 182 | 13.1 | 4.9 | 0.0 | 0.0 | 0.0 | 0.0 | 0.5 | 0.6 | 0.3 |
| TAG 181 182 183 | 3.6 | 3.8 | 8.7 | 0.0 | 0.0 | 0.0 | 0.0 | 0.0 | 0.0 |
| TAG 181 182 203 | 0.0 | 0.0 | 0.0 | 0.0 | 0.0 | 0.0 | 0.0 | 0.0 | 0.0 |
| TAG 181 182 205 | 0.0 | 0.0 | 0.0 | 0.0 | 0.0 | 0.0 | 0.0 | 0.0 | 0.0 |
| TAG 181 182 225 | 0.0 | 0.0 | 0.0 | 0.0 | 0.0 | 0.0 | 0.0 | 0.0 | 0.0 |
| TAG 181 182 226 | 0.0 | 0.0 | 0.0 | 0.0 | 0.0 | 0.0 | 0.0 | 0.0 | 0.0 |
| TAG 181 183 183 | 0.0 | 1.3 | 4.4 | 0.0 | 0.0 | 0.0 | 0.0 | 0.0 | 0.0 |
| TAG 181 183 203 | 0.0 | 0.0 | 0.0 | 0.0 | 0.0 | 0.0 | 0.0 | 0.0 | 0.0 |
| TAG 181 204 205 | 0.0 | 0.0 | 0.0 | 0.0 | 0.0 | 0.0 | 0.0 | 0.0 | 0.0 |
| TAG 181 205 205 | 0.0 | 0.0 | 0.0 | 0.8 | 1.2 | 0.3 | 0.0 | 0.0 | 0.0 |
| TAG 181 205 225 | 0.0 | 0.0 | 0.0 | 0.2 | 0.3 | 0.0 | 0.0 | 0.0 | 0.0 |
| TAG 181 205 226 | 0.0 | 0.0 | 0.0 | 0.9 | 1.6 | 0.0 | 0.0 | 0.0 | 0.0 |
| TAG 181 226 226 | 0.0 | 0.0 | 0.0 | 0.5 | 0.3 | 0.0 | 0.0 | 0.0 | 0.0 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | |
|---|---|---|---|---|---|---|---|---|---|
| TAG 182 182 182 | 1.6 | 0.3 | 2.0 | 0.0 | 0.0 | 0.0 | 0.3 | 0.5 | 0.6 |
| TAG 182 182 183 | 0.3 | 0.4 | 8.4 | 0.0 | 0.0 | 0.0 | 0.0 | 0.0 | 0.0 |
| TAG 182 182 203 | 0.0 | 0.0 | 0.0 | 0.0 | 0.0 | 0.0 | 0.0 | 0.0 | 0.0 |
| TAG 182 182 205 | 0.0 | 0.0 | 0.0 | 0.0 | 0.0 | 0.0 | 0.0 | 0.0 | 0.0 |
| TAG 182 182 225 | 0.0 | 0.0 | 0.0 | 0.0 | 0.0 | 0.0 | 0.0 | 0.0 | 0.0 |
| TAG 182 182 226 | 0.0 | 0.0 | 0.0 | 0.0 | 0.0 | 0.0 | 0.0 | 0.0 | 0.0 |
| TAG 182 183 183 | 0.0 | 0.2 | 7.5 | 0.0 | 0.0 | 0.0 | 0.0 | 0.0 | 0.0 |
| TAG 182 183 203 | 0.0 | 0.0 | 0.0 | 0.0 | 0.0 | 0.0 | 0.0 | 0.0 | 0.0 |
| TAG 182 183 205 | 0.0 | 0.0 | 0.0 | 0.0 | 0.0 | 0.0 | 0.0 | 0.0 | 0.0 |
| TAG 182 183 225 | 0.0 | 0.0 | 0.0 | 0.0 | 0.0 | 0.0 | 0.0 | 0.0 | 0.0 |
| TAG 182 183 226 | 0.0 | 0.0 | 0.0 | 0.0 | 0.0 | 0.0 | 0.0 | 0.0 | 0.0 |
| TAG 182 205 205 | 0.0 | 0.0 | 0.0 | 0.0 | 0.0 | 0.0 | 0.0 | 0.0 | 0.0 |
| TAG 182 205 225 | 0.0 | 0.0 | 0.0 | 0.0 | 0.0 | 0.0 | 0.0 | 0.0 | 0.0 |
| TAG 182 205 226 | 0.0 | 0.0 | 0.0 | 0.0 | 0.0 | 0.0 | 0.0 | 0.0 | 0.0 |
| TAG 182 225 226 | 0.0 | 0.0 | 0.0 | 0.0 | 0.0 | 0.0 | 0.0 | 0.0 | 0.0 |
| TAG 183 183 183 | 0.0 | 0.0 | 1.3 | 0.0 | 0.0 | 0.0 | 0.0 | 0.0 | 0.0 |
| TAG 183 183 203 | 0.0 | 0.0 | 0.0 | 0.0 | 0.0 | 0.0 | 0.0 | 0.0 | 0.0 |
| TAG 183 183 205 | 0.0 | 0.0 | 0.0 | 0.0 | 0.0 | 0.0 | 0.0 | 0.0 | 0.0 |
| TAG 183 183 226 | 0.0 | 0.0 | 0.0 | 0.0 | 0.0 | 0.0 | 0.0 | 0.0 | 0.0 |
| TAG 183 205 205 | 0.0 | 0.0 | 0.0 | 0.2 | 0.4 | 0.0 | 0.0 | 0.0 | 0.0 |
| TAG 183 205 226 | 0.0 | 0.0 | 0.0 | 0.0 | 0.0 | 0.0 | 0.0 | 0.0 | 0.0 |
| TAG 205 205 205 | 0.0 | 0.0 | 0.0 | 0.6 | 0.9 | 0.4 | 0.0 | 2.5 | 0.0 |
| TAG 205 205 226 | 0.0 | 0.0 | 0.0 | 0.5 | 0.8 | 0.2 | 0.5 | 5.1 | 0.8 |

TABLE 192-continued

Triacylglycerol sspecies profile of occurring TAG species comprising 12 target fatty acids from MTBE extracts analyzed by +APCI-HPLC-MS/MS in sMRM mode. Data are mean. n = 2 expressed as relative abundance of species. Species that were not detected in any samples were removed from the table

| | | | | | | | | | |
|---|---|---|---|---|---|---|---|---|---|
| TAG 205 226 226 | 0.0 | 0.0 | 0.0 | 0.2 | 0.5 | 0.0 | 1.0 | 5.3 | 1.5 |
| TAG 226 226 226 | 0.0 | 0.0 | 0.0 | 0.0 | 0.1 | 0.0 | 4.7 | 3.8 | 7.7 |

Sequences of the Invention

Table 193 shows the sequences of the invention by their name, and the associated SEQ-ID number of the sequence listing. Further sequences of the present invention are included in the sequence listing.

TABLE 193

Association of sequence names to SEQ-IDs in the sequence listing.

| SEQ ID NO: | Sequence Name |
|---|---|
| 1 | RTP10690-1qcz_F |
| 2 | RTP10691-2qcz |
| 3 | VC-LTM593-1qcz |
| 4 | VC-LTM595-1qcz |
| 5 | VC-LJB2197-1qcz |
| 6 | VC-LJB2755-2qcz |
| 7 | VC-LLM306-1qcz |
| 8 | VC-LLM337-1qcz |
| 9 | VC-LLM338-3qcz |
| 10 | VC-LLM391-2qcz |
| 11 | VC-LLM217-1qcz |
| 12 | o3DES-594FAM |
| 13 | o3DESPIR-198FAM |
| 14 | o3DESPIR-962FAM |
| 15 | AtPXR-Fam |
| 16 | BnSETL-1186FAM |
| 17 | BnSETL-Fam |
| 18 | E011 |
| 19 | D4DES-Tc-FAM |
| 20 | D4DES-Eg-FAM |
| 21 | D4DES-Pl-770FAM |
| 22 | Exp3-78-YAK |
| 23 | o3DES-572F |
| 24 | o3DESPIR-160F |
| 25 | o3DESPIR-924F |
| 26 | o3DesPir-F |
| 27 | BnSETL-1164-F |
| 28 | MA54 |
| 29 | D4DES-Tc-F |
| 30 | D4DES-EG-F |
| 31 | D4DES-Pl-746-F |
| 32 | Exp 3-52F |
| 33 | o3DES-652R |
| 34 | o3DESPIR-262R |
| 35 | o3DESPIR-1026-R |
| 36 | AtPXR-R |
| 37 | o3DESPIR-R |
| 38 | MA55 |
| 39 | D4DES-Tc-988R |
| 40 | D4DES-Eg-R |
| 41 | D4DES-Pl-817R |
| 42 | Exp 3-128R |
| 43 | RTP10690_1 |
| 44 | RTP10690_2 |
| 45 | RTP10690_3 |
| 46 | RTP10690_4 |
| 47 | RTP10690_5 |
| 48 | RTP10690_6 |
| 49 | RTP10690_7 |
| 50 | RTP10690_8 |
| 51 | RTP10690_9 |

TABLE 193-continued

Association of sequence names to SEQ-IDs in the sequence listing.

| SEQ ID NO: | Sequence Name |
|---|---|
| 52 | RTP10690_10 |
| 53 | RTP10690_11 |
| 54 | RTP10690_12 |
| 55 | RTP10690_5' |
| 56 | t-AtAHASL |
| 57 | LJB2197_5' |
| 58 | LJB2197_1 |
| 59 | LJB2197_2 |
| 60 | LJB2197_3 |
| 61 | LJB2197_4 |
| 62 | c-AHAS_F |
| 63 | c-d4Des(Eg_GA)_F |
| 64 | c-d4Des(Pl_GA)2_F |
| 65 | c-d4Des(Tc_GA)_F |
| 66 | c-d5Des(Tc_GA)_F |
| 67 | c-d5Elo(Ot_GA3)_F |
| 68 | c-d6Des(Ot_febit)_F |
| 69 | c-d6Elo(Pp_GA)_F |
| 70 | c-d6Elo(Tp_GA)_F |
| 71 | c-o3Des(Pi_GA)_F |
| 72 | c-o3Des(Pir_GA)_F |
| 73 | j-i-Atss1_c-d5Elo(Ot_GA3)_F |
| 74 | j-i-Atss1_c-d6Elo(Tp_GA2)_F |
| 75 | j-i-Atss14_c-d12Des(Ps_GA)_F |
| 76 | j-i-Atss18_c-d6Elo(Pp_GA2)_F |
| 77 | j-i-Atss18_c-o3Des(Pi_GA2)_F |
| 78 | j-i-Atss2_c-d4Des(Tc_GA3)_F |
| 79 | j-i-Atss2_c-d6Des(Ot febit_GA)_F |
| 80 | j-p-BnFAE_ t-PvARC_F |
| 81 | j-p-BnSETL-v1_c-o3Des(Pir_GA)_F |
| 82 | j-p-LuPXR_i-Atss15_F |
| 83 | j-p-PvARC5_t-BnFAE_F |
| 84 | j-p-PvARC5_t-BnSETL_F |
| 85 | j-t-CaMV_p-LuCnl-2_F |
| 86 | j-t-E9-p3-2_F |
| 87 | j-t-PvARC-p-LuCnl_F |
| 88 | j-t-StCAT_p2_p-LuPXR_F |
| 89 | reference (Adh1)_F |
| 90 | c-AHAS_R |
| 91 | c-d4Des(Eg_GA)_R |
| 92 | c-d4Des(Pl_GA)2_R |
| 93 | c-d4Des(Tc_GA)_R |
| 94 | c-d5Des(Tc_GA)_R |
| 95 | c-d5Elo(Ot_GA3)_R |
| 96 | c-d6Des(Ot_febit)_R |
| 97 | c-d6Elo(Pp_GA)_R |
| 98 | c-d6Elo(Tp_GA)_R |
| 99 | c-o3Des(Pi_GA)_R |
| 100 | c-o3Des(Pir_GA)_R |
| 101 | j-i-Atss1_c-d5Elo(Ot_GA3)_R |
| 102 | j-i-Atss1_c-d6Elo(Tp_GA2)_R |
| 103 | j-i-Atss14_c-d12Des(Ps_GA)_R |
| 104 | j-i-Atss18_c-d6Elo(Pp_GA2)_R |
| 105 | j-i-Atss18_c-o3Des(Pi_GA2)_R |
| 106 | j-i-Atss2_c-d4Des(Tc_GA3)_R |
| 107 | j-i-Atss2_c-d6Des(Ot febit_GA)_R |
| 108 | j-p-BnFAE_ t-PvARC_R |
| 109 | j-p-BnSETL-v1_c-o3Des(Pir_GA)_R |
| 110 | j-p-LuPXR_i-Atss15_R |

TABLE 193-continued

Association of sequence names to SEQ-IDs in the sequence listing.

| SEQ ID NO: | Sequence Name |
|---|---|
| 111 | j-p-PvARC5_t-BnFAE_R |
| 112 | j-p-PvARC5_t-BnSETL_R |
| 113 | j-t-CaMV_p-LuCnl-2_R |
| 114 | j-t-E9-p3-2_R |
| 115 | j-t-PvARC-p-LuCnl_R |
| 116 | j-t-StCAT_p2_p-LuPXR_R |
| 117 | reference (Adh1)_R |
| 118 | c-AHAS_P |
| 119 | c-d4Des(Eg_GA)_P |
| 120 | c-d4Des(PI_GA)2_P |
| 121 | c-d4Des(Tc_GA)_P |
| 122 | c-d5Des(Tc_GA)_P |
| 123 | c-d5Elo(Ot_GA3)_P |
| 124 | c-d6Des(Ot_febit)_P |
| 125 | c-d6Elo(Pp_GA)_P |
| 126 | c-d6Elo(Tp_GA)_P |
| 127 | c-o3Des(Pi_GA)_P |
| 128 | c-o3Des(Pir_GA)_P |
| 129 | j-i-Atss1_c-d5Elo(Ot_GA3)_P |
| 130 | j-i-Atss1_c-d6Elo(Tp_GA2)_P |
| 131 | j-i-Atss14_c-d12Des(Ps_GA)_P |
| 132 | j-i-Atss18_c-d6Elo(Pp_GA2)_P |
| 133 | j-i-Atss18_c-o3Des(Pi_GA2)_P |
| 134 | j-i-Atss2_c-d4Des(Tc_GA3)_P |
| 135 | j-i-Atss2_c-d6Des(Ot febit_GA)_P |
| 136 | j-p-BnFAE_ t-PvARC_P |
| 137 | j-p-BnSETL-v1_c-o3Des(Pir_GA)_P |
| 138 | j-p-LuPXR_i-Atss15_P |
| 139 | j-p-PvARC5_t-BnFAE_P |
| 140 | j-p-PvARC5_t-BnSETL_P |
| 141 | j-t-CaMV_p-LuCnl-2_P |
| 142 | j-t-E9-p3-2_P |
| 143 | j-t-PvARC-p-LuCnl_P |
| 144 | j-t-StCAT_p2_p-LuPXR_P |
| 145 | reference (Adh1)_P |
| 146 | c-o3Des(Pi_GA2_SNP)_F |
| 147 | j-t-PvARC-p3_F |
| 148 | j-i-Atss15_c-o3Des(Pi_GA2)_F |
| 149 | j-p-VfSBPperm3_c-o3Des(Pir_GA)_F |
| 150 | c-d15Des(Ch_ERTp_GA)_F |
| 151 | j-i-Atss2_c-d4Des(PI_GA)-195R)_F |
| 152 | c-o3Des(Pi_GA2_SNP)_R |
| 153 | j-t-PvARC-p3_R |
| 154 | j-i-Atss15_c-o3Des(Pi_GA2)_R |
| 155 | j-p-VfSBPperm3_c-o3Des(Pir_GA)_R |
| 156 | c-d15Des(Ch_ERTp_GA)_R |
| 157 | j-i-Atss2_c-d4Des(PI_GA)-195R)_R |
| 158 | c-o3Des(Pi_GA2_SNP)_P |
| 159 | j-t-PvARC-p3_P |
| 160 | j-i-Atss15_c-o3Des(Pi_GA2)_P |
| 161 | j-p-VfSBPperm3_c-o3Des(Pir_GA)_P |
| 162 | c-d15Des(Ch_ERTp_GA)_P |
| 163 | j-i-Atss2_c-d4Des(PI_GA)-195R)_P |
| 164 | LANBCH locus 1 (N5) Forward primer |
| 165 | LANBCH locus 1 (N9) Forward primer |
| 166 | LANBCH locus 2 (N5) Forward primer |
| 167 | LANBCH locus 2 (N9) Forward primer |
| 168 | LBFDAU locus 1 Forward primer |
| 169 | LBFDAU locus 2 Forward primer |
| 170 | LBFDGG Forward primer |
| 171 | LBFDHG locus 1 Forward primer |
| 172 | LBFDHG locus 2 Forward primer |
| 173 | LBFGKN Forward primer |
| 174 | LBFIHE Forward primer |
| 175 | LBFLFK locus 1 Forward primer |
| 176 | LBFLFK locus 2 Forward primer |
| 177 | LBFPRA Locus 1 Forward primer |
| 178 | LBFPRA locus 2 Forward primer |
| 179 | LBFPRA Locus 3e Forward primer |
| 180 | LANBCH locus 1 (N5) Reverse primer |
| 181 | LANBCH locus 1 (N9) Reverse primer |
| 182 | LANBCH locus 2 (N5) Reverse primer |
| 183 | LANBCH locus 2 (N9) Reverse primer |
| 184 | LBFDAU locus 1 Reverse primer |
| 185 | LBFDAU locus 2 Reverse primer |
| 186 | LBFDGG Reverse primer |
| 187 | LBFDHG locus 1 Reverse primer |
| 188 | LBFDHG locus 2 Reverse primer |
| 189 | LBFGKN Reverse primer |
| 190 | LBFIHE Reverse primer |
| 191 | LBFLFK locus 1 Reverse primer |
| 192 | LBFLFK locus 2 Reverse primer |
| 193 | LBFPRA Locus 1 Reverse primer |
| 194 | LBFPRA locus 2 Reverse primer |
| 195 | LBFPRA Locus 3e Reverse primer |
| 196 | LANBCH locus 1 (N5) Probe sequence |
| 197 | LANBCH locus 1 (N9) Probe sequence |
| 198 | LANBCH locus 2 (N5) Probe sequence |
| 199 | LANBCH locus 2 (N9) Probe sequence |
| 200 | LBFDAU locus 1 Probe sequence |
| 201 | LBFDAU locus 2 Probe sequence |
| 202 | LBFDGG Probe sequence |
| 203 | LBFDHG locus 1 Probe sequence |
| 204 | LBFDHG locus 2 Probe sequence |
| 205 | LBFGKN Probe sequence |
| 206 | LBFIHE Probe sequence |
| 207 | LBFLFK locus 1 Probe sequence |
| 208 | LBFLFK locus 2 Probe sequence |
| 209 | LBFPRA Locus 1 Probe sequence |
| 210 | LBFPRA locus 2 Probe sequence |
| 211 | LBFPRA Locus 3e Probe sequence |
| 212 | VC-LJB2197-1qcz LANBCH RB6 Locus 1 |
| 213 | VC-LJB2197-1qcz LANBCH LB2 Locus 1 |
| 214 | VC-LLM337-1qcz LANBCH RB2 Locus 1 |
| 215 | VC-LLM337-1qcz LANBCH LB1 Locus 1 |
| 216 | VC-LJB2197-1qcz LANBCH RB3 Locus 2 |
| 217 | VC-LLM337-1qcz LANBCH RB1 Locus 2 |
| 218 | VC-LTM593-1qcz LBFDGG RB |
| 219 | VC-LTM593-1qcz LBFDGG LB |
| 220 | VC-LTM593-1qcz LBFDHG RB Locus 1 |
| 221 | VC-LTM593-1qcz LBFDHG LB Locus 1 |
| 222 | VC-LTM593-1qcz LBFDHG RB Locus 2 |
| 223 | VC-LTM593-1qcz LBFDHG LB Locus 2 |
| 224 | VC-LTM593-1qcz LBFGKN RB1 |
| 225 | VC-LTM593-1qcz LBFGKN LB1 |
| 226 | VC-LTM593-1qcz LBFIHE RB1 |
| 227 | VC-LTM593-1qcz LBFIHE LB1 |
| 228 | VC-LTM593-1qcz LBFLFK RB1 Locus 1 |
| 229 | VC-LTM593-1qcz LBFLFK LB1 Locus 1 |
| 230 | VC-LTM593-1qcz LBFLFK RB2 Locus 2 |
| 231 | VC-LTM593-1qcz LBFLFK LB2 Locus 2 |
| 232 | VC-LTM593-1qcz LBFPRA RB1 Locus 1 |
| 233 | VC-LTM593-1qcz LBFPRA LB1 Locus 1 |
| 234 | VC-LTM593-1qcz LBFPRA RB3 Locus 2 |
| 235 | VC-LTM593-1qcz LBFPRA L1 Locus 2 |
| 236 | VC-LTM593-1qcz LBFPRA Locus 3e |
| 237 | VC-LTM593-1qcz LBFDAU RB1 Locus 1 |
| 238 | VC-LTM593-1qcz LBFDAU LB1 Locus 1 |
| 239 | VC-LTM593-1qcz LBFDAU R Locus 2 |
| 240 | VC-LTM593-1qcz LBFDAU L Locus 2 |
| 241 | Amplicon LANBCH locus 1 (N5) |
| 242 | Amplicon LANBCH locus 1 (N9) |
| 243 | Amplicon LANBCH locus 2 (N5) |
| 244 | Amplicon LANBCH locus 2 (N9) |
| 245 | Amplicon LBFDAU locus 1 |
| 246 | Amplicon LBFDAU locus 2 |
| 247 | Amplicon LBFDGG |
| 248 | Amplicon LBFDHG locus 1 |
| 249 | Amplicon LBFDHG locus 2 |
| 250 | Amplicon LBFGKN |
| 251 | Amplicon LBFIHE |
| 252 | Amplicon LBFLFK locus 1 |
| 253 | Amplicon LBFLFK Locus 2 |
| 254 | Amplicon LBFPRA Locus 1 |
| 255 | Amplicon LBFPRA locus 2 |
| 256 | Amplicon LBFPRA Locus 3e |

REFERENCE LIST

Arondel, V., Lemieux, B., Hwang, I., Gibson, S., Goodman, H. M., and Somerville, C. R. (1992). Map-based cloning of a gene controlling omega-3 fatty acid desaturation in *Arabidopsis*. Science 258, 1353-1355.

Bafor, M., Smith, M. A., Jonsson, L., Stobart, K., and Stymne, S. Biochem J. (1991). Ricinoleic acid biosynthesis and triacylglycerol assembly in microsomal preparations from developing castor-bean (*Ricinus communis*) endosperm. 280, 507-514.

Bernert, J. T and Sprecher, H. (1977). Analysis of Partial Reactions in the Overall Chain Elongation of Saturated and Unsaturated Fatty Acids by Rat Liver Microsomes. J. Biol. Chem. 252, 6736-6744.

Banas, A., Bafor, M., Wiberg, E., Lenman, M., Stahl, U., Stymne, 5. (1997). Biosynthesis of an Acetylenic Fatty Acid in Microsomal Preparations from Developing Seeds of *Crepis alpina*. In: *Physiology, Biochemistry and Molecular Biology of Plant Lipids* (Williams, J. P., Kahn, M. U., Lem, N. W., eds.) pp. 57-59. Kluwer Academic Press, Dordrecht.

Bates P D, Fatihi A, Snapp A R, Carlsson A S, Browse J, Lu C (2012) Acyl Editing and Headgroup Exchange Are the Major Mechanisms That Direct Polyunsaturated Fatty Acid Flux into Triacylglycerols. Plant Physiology 160: 1530-1 539

Bligh, E. G., and Dyer, J. J. (1959). A rapid method for total lipid extraction and purification. Can J. Biochem. Physiol. 37:911-918 Broadwater, J. A., Whittle, E., and Shanklin, J. (2002). Desaturation and hydroxylation. Residues 148 and 324 of *Arabidopsis* FAD2, in addition to substrate chain length, exert a major influence in partitioning of catalytic specificity. J. Biol. Chem. 277, 15613-15620.

Broun, P., Shanklin, J., Whittle, E., and Somerville, C. (1998b). Catalytic plasticity of fatty acid modification enzymes underlying chemical diversity of plant lipids. Science 282, 1315-1317.

Calvo, A. M., Gardner, H. W., and Keller, N. P. (2001). Genetic connection between fatty acid metabolism and sporulation in *Aspergillus nidulans*. J. Biol. Chem. 276, 25766-25774.

Brown A J., Sweeney B., Mainwaring D O. and James D C. (2014) Synthetic Promoters for CHO Cell Engineering. Biotechnology and Bioengineering, 111, 8:1638-1647.

Cutler S R., Rodriguez P L., Finkelstein R R., and Abrams S R. (2010) Abscisic Acid: Emergence of a Core Signaling Network. Annual Review of Plant Biology 61:651-679.

Demekes T. and Jenkins R G. (2010) Influence of DNA extraction methods, PCR inhibitors and quantification methods on real-time PCR assay of biotechnology-derived traits. Analytical and Bioanalytical Chemistry 396, 1977-1990.

Domergue, F. Abbadi, A., Ott, C., Zank, T. K., Zahringer, U., and Heinz, E. (2003) Acyl Carriers Used as Substrates by the Desaturases and Elongases Involved in Very Long-chain Polyunsaturated Fatty Acids Biosynthesis Reconstituted in Yeast. J. Biol. Chem. 278, 35115-35126

Domergue, F., Abbadi, A., Zähringer, U., Moreau, H., Heinz, E. (2005) In vivo characterization of the first acyl-CoA D6-desaturase from a member of the plant kingdom, the microalga *Ostreococcus tauri*. Biochem. J. 389, 483-490.

Dubos C., Kelemen Z., Sebastian A., Bülow L., Huep G., Xu W., Grain D., Salsac F., Brousse C., Lepiniec L, Weisshaar B., Contreras-Moreira B. and Hehl R. BMC Genomics 15:317.

Focks N. and Benning C. (1998) wrinkled1: A novel, low-seed-oil mutant of *Arabidopsis* with a deficiency in the seed-specific regulation of carbohydrate metabolism. Plant Physiology 118, 1:91-101.

Ganas et al in Physiology, Biochemistry and Molecular Biology of Plant Lipids, Eds Williams, J. P., Khan, M. U. and Lem, N. W., Kluwer Academic Publishers, N L, 1996, 57-59

Griffiths, G., Stobart, A. K., and Stymne, S. (1988). Δ6- and Δ12-desaturase activities and phosphatidic acid formation in microsomal preparations from the developing cotyledons of common borage (*Borago officinalis*). Biochem. J. 252, 641-647

Hamilton C M (1997) A binary-BAC system for plant transformation with high-molecular-weight DNA. Gene 200: 107-116

Hattori T., Totsuka M., Hobo T., Kagaya Y., Yamamota-Toyoda A. (2002) Experimentally determined sequence requirement of ACGT containing abscisic acid response element. Plant and Cell Physiology 43, 1:136-140.

Higo K., Ugawa Y., Iwamoto M., Korenaga T. (1999) Plant Cis-acting regulatory DNA elements (PLACE) database: 1999. Nucleic Acids Research 27, 1:297-300.

Hinnebusch A. (2014) The Scanning Mechanism of Eukaryotic Translation Initiation. Annual Review of Biochemistry 83, 779-812

Jain, S., Stanford, N., Bhagwat, N., Seiler, B., Costanzo, M., Boone, C. and Peter, P. (2007). Identification of a Novel Lysophospholipid Acyltransferase in *Saccaromyces cerevisiae*. J. Biol. Chem. 282, 30562-30569.

Kargiotidou A., Deli D., Galanopoulou D., Tsaftaris A. and Farmaki T. (2008) Low temperature and light regulate delta 12 fatty acid desaturases (FAD2) at a transcriptional level in cotton (*Gossypium hirsutum*) Journal of Experimental Botany, 59, 8:2043-2056

Keller W., Konig P. and Richmond T J. (1995) Crystal Structure of a bZIP/DNA Complex at 2.2 Å: Determinants of DNA Specific Recognition. Journal of Molecular Biology 254, 657-667.

Kim W-C., Reca I-B., Kim Y S. Park S., Thomashow M F. Keegstra K. Han K-H. (2014) Transcription factors that directly regulate the expression of CSLA9 encoding mannan synthase in *Arabidopsis thaliana*. Plant Molecular Biology 84, 577-587

Knutzon, D. S., Thurmond, J. M., Huang, Y. S., Chaudhary, S., Bobik, E. G., Jr., Chan, G. M., Kirchner, S. J., and Mukerji, P. (1998). Identification of Delta5-dehydratase from *Mortierella alpina* by heterologous expression in Bakers' yeast and canola. J. Biol. Chem. 273, 29360-29366.

Komori, T., Imayama, T., Kato, N., Ishida, N., Ueki, j., and Komari, T. (2007). Current Status of Binary Vectors and Superbinary Vectors. Plant Physiology 145(4), 1155-1160, doi: http://dx.doi. org/10.1104/pp. 107.105734

Kong F., Yamasaki T. and Ohama T. (2014) Expression levels of domestic cDNA cassettes integrated in the nuclear genomes of various Ch/amydomonas *reinhardtii* strains. Journal of Bioscience and Bioengineering 117, 5:613-616.

Kozak M. Initiation of translation in prokaryotes and eukaryotes (1999) Gene 234, 187-208.

Livak K. and Schmittgen T D. (2001) Analysis of Relative Gene Expression Data Using Real-Time Quantitative PCR and the 2-deltadeltaCT Method. Methods 25, 402-408.

López Y., Patil A., Nakai K. (2013) Identification of novel motif patterns to decipher the promoter architecture of co-expressed genes in *Arabidopsis thaliana*. BMC Systems Biology 7(Suppl 3):S10

Lowenthal, M., Liang, Y., Phinney, K. W., and Stein, S. E. (2014) Quantitative Bottom-Up Proteomics Depends on Digestion Conditions. Anal Chem. 86:551-558

Machens F., Becker M., Umrath F., Hehl R. (2014) Identification of a novel type of WRKY transcription factor binding site in elicitor-responsive cis-sequences from *Arabidopsis thaliana*. Plant Molecular Biology 84,371-385

Mantle, P. G. and Nisbet, L. J. (1976). Differentiation of *Claviceps purpurea* in axenic culture. J. Gen. Microbiol. 93, 321-334.

Makriyannis T, Clonis Y D. (1997) Design and study of peptide-ligand affinity chromatography adsorbents: application to the case of trypsin purification from bovine pancreas. Biotech Bioeng.; 53: 49-57.

Meggendorfer M., Weierich C., Wolff H., Brack-Werner R., Cremer T. (2010) Functional nuclear topography of transcriptionally inducible extra-chromosomal transgene clusters. Chromosome Research 18, 401-417.

Meesapyodsuk, D., Qui, X. (2012). The Front-end Desaturase: Structure, Function, Evolution and Biotechnological Use Lipids 47, 227-237

Mendel, J. G. (1866). *Versuche über Pflanzenhybriden* Verhandlungen des naturforschenden Vereines in BrOnn, Bd. IV fOr das Jahr, 1865 Abhandlungen:3-47.

Mey, G., Oeser, B., Lebrun, M. H., and Tudzynski, P. (2002). The biotrophic, non-appressorium-forming grass pathogen *Claviceps purpurea* needs a Fus3/Pmk1 homologous mitogen-activated protein kinase for colonization of rye ovarian tissue. Mol. Plant Microbe Interact. 15, 303-312.

Muino J M., Smaczniak C., Angenent G C., Kaufmann K. and van Dijk A D J. (2014) Structural determinants of DNA recognition by plant MADS-domain transcription factors. Nucleic Acids Research 42, 4:2138-2146.

Murashige T. and Skoog F. (1962) A Revised Medium for Rapid Growth and Bio Assays with Tobacco Tissue Cultures. Physiologia *Plantarum* 15, 3:473-497

Nakagawa S., Niimura Y., Gojobori T., Tanaka H., and Miura K-I. (2008) Diversity of preferred nucleotide sequences around the translation initiation codon in eukaryote genomes. Nucleic Acids Research 36, 3:861-871

Nishikata K., Cox R S III., Shimoyama S., Yoshida Y., Matsui M., Makita Y. and Toyoda T. (2013) Database Construction for PromoterCAD: Synthetic Promoter Design for Mammals and Plants ACS Synthetic Biology 3, 192-196.

Okayasu, T.; Nagao, M.; Ishibashi, T.; and Imai, Y. (1981) Purification and Parial Characterization of Linoleoyl-CoA Desaturase from Rat Liver Microsomes Arch. Biochem. Biophys. 206, 21-28.

Okuley, J., Lightner, J., Feldmann, K., Yadav, N., Lark, E., and Browse, J. (1994). *Arabidopsis* FAD2 gene encodes the enzyme that was essential for polyunsaturated lipid synthesis. Plant Cell 6, 147-158.

Parker S. C. J., Hansen L., Abaan H. O, Tullius T. D., Margulies E. H. (2009) Local DNA Topography Correlates with Functional Noncoding Regions of the Human Genome. Science 324, 389-392.

Paul, S., Gable, K., Beaudoin, F., Cahoon, E. Jaworski, J., Napier, J. A., and Dunn, T. M. (2006). Members of the *Arabidopsis* FAE1-like 3-Ketoacyl-CoA Synthase Gene Family Substitute for the Elop Proteins of *Saccharomyces cerevisiae*. J. Biol. Chem. 281, 9018-9029.

Proc, J. L., Kuzyk, M. A., Hardie, D. B., Yang, J., Smith, D. S., Jackson, A. M. Parker, C. E., and Borchers, C. H. (2010) A quantitative study of the effects of chaotropic agents, surfactants, and solvents on the digestion efficiency of human plasma proteins by trypsin. J. Proteome Res. 9, 5422-5437.

Qi, B., Fraser, T., Mugford, S., Dobson, G., Sayanova, O., Butler, J., Napier, J. A., Stobart, A. K., and Lazarus, C. M. (2004). Production of very long chain polyunsaturated omega-3 and omega-6 fatty acids in plants. Nat. Biotechnol. 22, 739-745.

Ramamoorthy S., Garapati H. S., Mishra R. K. (2014) Length and sequence dependent accumulation of simple sequence repeats in vertebrates: Potential role in genome organization and regulation. Gene 551,167-175.

Riekhof, W. R., Wu, J., Gij6n, M. A., Zarini, S., Murphy, R. C. and Voelker, D. R. Lysophosphatidylcholine Metabolism in *Saccaromyces cerevisiae*: The Role of P-Type ATPases In Transport and A Broad Specificity Acyltransferase in Acylation. J. Biol. Chem. 2007, 282:36853-36861.

Ruiz-Lopez N., Haslam R P., Napier J A. and Sayanova O. (2014) Successful high-level accumulation of fish oil omega-3 long-chain polyunsaturated fatty acids in a transgenic oilseed crop. The Plant Journal 77, 198-208.

Ruuska S A., Girke T., Benning C., and John B. Ohlrogge. Contrapuntal Networks of Gene Expression during *Arabidopsis* Seed Filling The Plant Cell 14, 6:1191-1206.

Sánchez-Garcia A. Mancha M., Heinz E., Martinez-Rivas J. M. (2004) Differential temperature regulation of three sunflower microsomal oleate desaturase (FAD2) isoforms overexpressed in *Saccharomyces cerevisiae* European Journal of Lipid Science and Technology 106, 583-590

Sarkar A K. and Lahiri A. (2013) Specificity determinants for the abscisic acid response element. FEBS Open Bio 3, 101-105.

Schwender J., Goffman F., Ohlrogge J. B., and Shachar-Hill Y (2004) Rubisco without the Calvin cycle improves the carbon efficiency of developing green seeds. Nature 432, 779-782

Shanklin J, Somerville C. (1991) Stearoyl-acyl-carrier-protein desaturase from higher plants was structurally unrelated to the animal and fungal homologs. Proc Natl Acad Sci USA 88, 2510-2514.

Shanklin, J. and Cahoon, E. B. (1998). DESATURATION AND RELATED MODIFICATIONS OF FATTY ACIDS1. Annu. Rev. Plant Physiol Plant Mol. Biol. 49,611-641.

Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985). Measurement of protein using bicinchonic acid. Anal. Biochem. 150, 76-85.

Strittmatter, P.; Spatz, L.; Corcoran, D.; Rogers, M. J.; Setlow, B.; and Redline, R. (1974) Purification and properties of rat liver microsomal stearyl coenzyme A desaturase. Proc. Nat. Acad. Sci. USA 71, 4565-4569.

Stymne, S. and Stobart, A. K. (1986) Biosynthesis of y-linolenic acid in cotyledons and microsomal preparations of the developing seeds of common borage (*Borago officina/is*). Biochem. J. 240, 385-393.

Tamaki, H., Shimada, A., Ito, Y., Ohya, M., Takase, J., Miyashita, M., Miyagawa, H., Nozaki, H., Nakayama, R. and Hidehiko Kumagai (2007) LPT1 Encodes a Membrane-bound O-Acyltransferase Involved in the Acylation of Lysophospholipids in the Yeast *Saccharomyces cerevisiae*. J. Biol. Chem. 282, 34288-34298.

Tang G-Q., Novitzky W P., Griffin H C., Huber S C., and Dewey R E. (2005) Oleate desaturase enzymes of soybean: evidence of regulation through differential stability and phosphorylation. The Plant Journal 44, 433-446.

Tudzynski, P., Correia, T., and Keller, U. (2001). Biotechnology and genetics of ergot alkaloids. Appl. Microbiol. Biotechnol. 57, 593-605.

Wachter E., Quante T., Merusi C., Arczewska A., Stewart F., Webb S., Bird A. (2014) Synthetic CpG islands reveal DNA sequence determinants of chromatin structure. eLIFE e03397. DOI: 10.7554/eLife.03397.

Wijesundra C. (2008) The influence of triacylglycerol structure on the oxidative stability of polyunsaturated oils. Lipid Technology 20,199-202.

Xiao G., Zhang Z Q., Yin C F., Liu R Y., Wu X M., Tan T L., Chen S Y., Lu C M. and Guan C Y. (2014) Characterization of the promoter and 5'-UTR intron of oleic acid desaturase (FAD2) gene in Brassica napus. Gene 545, 45-55.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11613761B1). An electronic copy of the "Sequence Listing" will also be available from the USPTO upon request and payment of the fee set forth in 37 CFR 1.19(b)(3).

The invention claimed is:

1. A plant comprising one or more T-DNA comprising one or more expression cassettes encoding for one or more delta-5-desaturase (d5Des), one or more delta-6-elongase (d6Elo), one or more delta-6-desaturase (d6Des), one or more omega-3-desaturase (o3Des), one or more delta-5-elongase (d5Elo) and at least one CoA-dependent delta-4-desaturase (d4Des) and at least one phospholipid dependent delta-4-desaturase (d4Des), wherein, when the plant is grown to obtain oil-containing seeds, the seeds produce oil having DHA and EPA, wherein the plant has a higher delta-4 desaturase conversion efficiency than a second transgenic plant differing from the plant only by comprising one or more expression cassettes encoding for at least two phospholipid dependent delta-4-desaturases and encoding no CoA-dependent delta-4-desaturase, and wherein the plant is a plant of the genus Brassica.

2. The plant or seed or part thereof of claim 1 comprising one or more T-DNAs encoding for at least two d6Des, at least two d6Elo and/or, at least two o3Des.

3. The plant, seed or part thereof of claim 1 further encoding for one or more d12Des.

4. The plant, seed or part thereof of claim 1, wherein the T-DNA is integrated in the genome of the plant, seed or part thereof.

5. The plant, seed or part thereof of claim 1, wherein the T-DNA measured from left to right border element has a length of at least 30000 bp.

6. The plant, seed or part thereof of claim 1, wherein the T-DNA comprises the expression cassettes for the desaturases and elongases of the vector VC-LTM593-1qcz which has a sequence shown in SEQ ID NO: 3.

7. A method of plant oil production, comprising the steps of i) growing a plant to obtain oil-containing seeds thereof, wherein the plant comprises one or more T-DNA comprising one or more expression cassettes encoding for one or more delta-5-desaturase (d5Des), one or more delta-6-elongase (d6Elo), one or more delta-6-desaturase (d6Des), one or more omega-3-desaturase (o3Des), one or more delta-5-elongase (d5Elo) and at least one CoA-dependent delta-4-desaturase (d4Des) and at least one phospholipid dependent delta-4-desaturase (d4Des), ii) harvesting said seeds, and iii) extracting oil from said seeds harvested in step ii), wherein the oil has DHA and EPA, wherein the plant is a plant of the genus Brassica, and wherein the plant has a higher delta-4 desaturase conversion efficiency than a second transgenic plant differing from the plant only by comprising one or more expression cassettes encoding for at least two phospholipid dependent delta-4-desaturases and encoding no CoA-dependent delta-4-desaturase.

8. The plant of claim 1, wherein, when the plant is grown to obtain oil-containing seeds, the seeds produce oil having an EPA content of between 2% and 15% by weight based on the total lipid content.

9. The plant of claim 1, wherein, when the plant is grown to obtain oil-containing seeds, the seeds produce oil having an EPA content of between 5% and 10% by weight based on the total lipid content.

10. A seed comprising one or more T-DNA comprising one or more expression cassettes encoding for one or more delta-5-desaturase (d5Des), one or more delta-6-elongase (d6Elo), one or more delta-6-desaturase (d6Des), one or more omega-3-desaturase (o3Des), one or more delta-5-elongase (d5Elo) and at least one CoA-dependent delta-4-desaturase (d4Des) and at least one phospholipid dependent delta-4-desaturase (d4Des), wherein the seed comprises oil having DHA and EPA wherein the seed is a seed of a plant of the genus Brassica, and wherein the seed has a higher delta-4 desaturase conversion efficiency than seed from a second transgenic plant differing from the seed only by comprising one or more expression cassettes encoding for at least two phospholipid dependent delta-4-desaturases and encoding no CoA-dependent delta-4-desaturase.

11. The seed of claim 10, wherein the seed comprises oil having an EPA content of between 2% and 15% by weight based on the total lipid content.

12. The seed of claim 10, wherein the seed comprises oil having an EPA content of between 5% and 10% by weight based on the total lipid content.

* * * * *